(12) United States Patent
Kim et al.

(10) Patent No.: US 11,261,186 B2
(45) Date of Patent: Mar. 1, 2022

(54) BIARYL DERIVATIVE AS GPR120 AGONIST

(71) Applicant: LG CHEM, LTD., Seoul (KR)

(72) Inventors: Young Kwan Kim, Daejeon (KR); Sang Yun Park, Daejeon (KR); Hyun Woo Joo, Daejeon (KR); Eun Sil Choi, Daejeon (KR); Seung Yup Paek, Daejeon (KR); Seung Wan Kang, Daejeon (KR); Byung Gyu Kim, Daejeon (KR); Chang Seok Lee, Daejeon (KR); Sung Wook Kim, Daejeon (KR); Sang Dae Lee, Daejeon (KR)

(73) Assignee: LG CHEM. LTD., Seoul (KR)

( * ) Notice: Subject to any disclaimer, the term of this patent is extended or adjusted under 35 U.S.C. 154(b) by 0 days.

(21) Appl. No.: 15/539,310

(22) PCT Filed: Dec. 23, 2015

(86) PCT No.: PCT/KR2015/014178
§ 371 (c)(1),
(2) Date: Jun. 23, 2017

(87) PCT Pub. No.: WO2016/105118
PCT Pub. Date: Jun. 30, 2016

(65) Prior Publication Data
US 2017/0349594 A1    Dec. 7, 2017

(30) Foreign Application Priority Data
Dec. 24, 2014    (KR) .................. 10-2014-0188399

(51) Int. Cl.
| | | |
|---|---|---|
| C07D 239/34 | (2006.01) | |
| C07D 401/10 | (2006.01) | |
| C07D 403/10 | (2006.01) | |
| C07D 471/04 | (2006.01) | |
| C07D 487/04 | (2006.01) | |
| C07D 401/04 | (2006.01) | |
| A61K 31/4725 | (2006.01) | |
| C07C 59/31 | (2006.01) | |
| C07C 229/42 | (2006.01) | |

(Continued)

(52) U.S. Cl.
CPC ........ *C07D 487/04* (2013.01); *A61K 31/4725* (2013.01); *C07C 59/31* (2013.01); *C07C 229/42* (2013.01); *C07C 229/44* (2013.01); *C07C 317/22* (2013.01); *C07D 207/06* (2013.01); *C07D 209/08* (2013.01); *C07D 211/34* (2013.01); *C07D 213/30* (2013.01); *C07D 213/64* (2013.01); *C07D 213/70* (2013.01); *C07D 231/56* (2013.01); *C07D 235/16* (2013.01); *C07D 239/34* (2013.01); *C07D 241/18* (2013.01); *C07D 261/08* (2013.01); *C07D 277/34* (2013.01); *C07D 307/42* (2013.01); *C07D 307/80* (2013.01); *C07D 311/58* (2013.01); *C07D 317/46* (2013.01); *C07D 317/72* (2013.01); *C07D 333/16* (2013.01); *C07D 401/04* (2013.01); *C07D 401/10* (2013.01); *C07D 401/12* (2013.01); *C07D 401/14* (2013.01); *C07D 405/04* (2013.01); *C07D 405/12* (2013.01); *C07D 405/14* (2013.01); *C07D 407/04* (2013.01); *C07D 409/04* (2013.01); *C07D 409/10* (2013.01); *C07D 409/14* (2013.01); *C07D 413/10* (2013.01); *C07D 413/12* (2013.01); *C07D 417/10* (2013.01); *C07C 2601/04* (2017.05); *C07C 2601/08* (2017.05)

(58) Field of Classification Search
None
See application file for complete search history.

(56) References Cited

U.S. PATENT DOCUMENTS

| | | | | |
|---|---|---|---|---|
| 6,448,205 B1 * | 9/2002 | Schafer | .................. | A01N 43/40 504/244 |
| 8,846,910 B2 * | 9/2014 | Sattigeri | .............. | C07D 401/06 544/180 |

(Continued)

FOREIGN PATENT DOCUMENTS

| | | |
|---|---|---|
| EP | 1309575 B1 | 6/2005 |
| EP | 1798224 A1 | 6/2007 |

(Continued)

OTHER PUBLICATIONS

RN 1082231-32-0 in STN Registry 2008.*

(Continued)

*Primary Examiner* — Brian E McDowell
(74) *Attorney, Agent, or Firm* — Rothwell, Figg, Ernst & Manbeck, P.C.

(57) ABSTRACT

Compounds having the chemical formula 1,

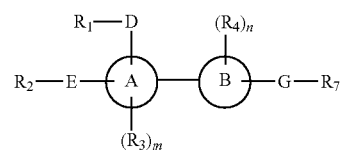

a method for producing the compounds of chemical formula 1, a pharmaceutical composition comprising same, and use thereof as a GPR120 agonist for prevention or treatment of inflammation or metabolic diseases such as diabetes, complications from diabetes, obesity, non-alcoholic fatty liver disease, fatty liver disease, and osteoporosis.

2 Claims, No Drawings

(51) Int. Cl.

| | |
|---|---|
| C07C 229/44 | (2006.01) |
| C07C 317/22 | (2006.01) |
| C07D 207/06 | (2006.01) |
| C07D 209/08 | (2006.01) |
| C07D 211/34 | (2006.01) |
| C07D 213/30 | (2006.01) |
| C07D 213/64 | (2006.01) |
| C07D 213/70 | (2006.01) |
| C07D 231/56 | (2006.01) |
| C07D 235/16 | (2006.01) |
| C07D 241/18 | (2006.01) |
| C07D 261/08 | (2006.01) |
| C07D 277/34 | (2006.01) |
| C07D 307/42 | (2006.01) |
| C07D 307/80 | (2006.01) |
| C07D 311/58 | (2006.01) |
| C07D 317/46 | (2006.01) |
| C07D 317/72 | (2006.01) |
| C07D 333/16 | (2006.01) |
| C07D 401/12 | (2006.01) |
| C07D 401/14 | (2006.01) |
| C07D 405/04 | (2006.01) |
| C07D 405/12 | (2006.01) |
| C07D 405/14 | (2006.01) |
| C07D 407/04 | (2006.01) |
| C07D 409/04 | (2006.01) |
| C07D 409/10 | (2006.01) |
| C07D 409/14 | (2006.01) |
| C07D 413/10 | (2006.01) |
| C07D 413/12 | (2006.01) |
| C07D 417/10 | (2006.01) |

(56) References Cited

U.S. PATENT DOCUMENTS

| | | | |
|---|---|---|---|
| 8,877,791 B2 | 11/2014 | Cantley et al. | |
| 9,073,895 B2* | 7/2015 | Berry | C07D 239/42 |
| 9,771,326 B2* | 9/2017 | Peng | C07D 211/62 |
| 2003/0134885 A1 | 7/2003 | Bernardon et al. | |
| 2008/0194617 A1 | 8/2008 | Tawaraishi et al. | |
| 2008/0319037 A1 | 12/2008 | Woo et al. | |
| 2010/0022592 A1 | 1/2010 | Epple et al. | |
| 2014/0256706 A1 | 9/2014 | Wang et al. | |

FOREIGN PATENT DOCUMENTS

| | | |
|---|---|---|
| JP | H08-501318 A | 2/1996 |
| JP | 2001-524465 A | 12/2001 |
| JP | 2003-506317 A | 2/2003 |
| JP | 2004-500383 A | 1/2004 |
| JP | 2004-505958 A | 2/2004 |
| JP | 2005-535583 A | 11/2005 |
| JP | 2006-504761 A | 2/2006 |
| JP | 2006-522118 A | 9/2006 |
| JP | 2006-526590 A | 11/2006 |
| JP | 2007-536290 A | 12/2007 |
| JP | 2008-515866 A | 5/2008 |
| JP | 2008-531494 A | 8/2008 |
| JP | 2009-504597 A | 2/2009 |
| JP | 2009-051827 A | 3/2009 |
| JP | 2009-542680 A | 12/2009 |
| JP | 2011-506421 A | 3/2011 |
| JP | 2012-510496 A | 5/2012 |
| JP | 2012-528107 A | 11/2012 |
| JP | 2014-501720 A | 1/2014 |
| JP | 2014-503534 A | 2/2014 |
| KR | 10-2009-0113382 A | 10/2009 |
| WO | 1994/012461 A1 | 6/1994 |
| WO | 9718188 A1 | 5/1997 |
| WO | 99/009000 A2 | 2/1999 |
| WO | 99/26921 A1 | 6/1999 |
| WO | 00/59864 A1 | 10/2000 |
| WO | 2001/060806 A2 | 8/2001 |
| WO | 02/089738 A2 | 11/2002 |
| WO | 2003/066629 A2 | 8/2003 |
| WO | 2003/070686 A1 | 8/2003 |
| WO | 03/093237 A1 | 11/2003 |
| WO | 2004/039764 A1 | 5/2004 |
| WO | 2004/071447 A2 | 8/2004 |
| WO | 2004/089885 A1 | 10/2004 |
| WO | 2004/110974 A1 | 12/2004 |
| WO | 2005/019184 A1 | 3/2005 |
| WO | 2005/105724 A1 | 11/2005 |
| WO | 2006/037982 A2 | 4/2006 |
| WO | 2006/038606 A1 | 4/2006 |
| WO | 2006/090235 A1 | 8/2006 |
| WO | 2007/017289 A2 | 2/2007 |
| WO | 2008103500 A1 | 8/2008 |
| WO | 2008103501 A1 | 8/2008 |
| WO | 2008/127728 A1 | 10/2008 |
| WO | 2009/074829 A1 | 6/2009 |
| WO | 2010008831 A2 | 1/2010 |
| WO | 2010/051176 A1 | 5/2010 |
| WO | 2010/063666 A1 | 6/2010 |
| WO | 2010/070076 A1 | 6/2010 |
| WO | 2010/123016 A1 | 10/2010 |
| WO | 2010/136474 A2 | 12/2010 |
| WO | 2011-159297 A1 | 12/2011 |
| WO | 2012/052540 A1 | 4/2012 |
| WO | 2012/065956 A1 | 5/2012 |
| WO | 2012/082853 A1 | 6/2012 |
| WO | 2012126181 A1 | 9/2012 |
| WO | 2013-139341 A1 | 9/2013 |
| WO | 2013-185766 A1 | 12/2013 |
| WO | 2014-059232 A2 | 4/2014 |
| WO | 2014081756 A1 | 5/2014 |
| WO | 2014/159794 A2 | 10/2014 |
| WO | 2014-209034 A1 | 12/2014 |
| WO | 2016038540 A1 | 3/2016 |
| WO | 2016040222 A1 | 3/2016 |
| WO | 2016/052928 A1 | 4/2016 |

OTHER PUBLICATIONS

RN 779328-98-2 in STN Registry 2004.*
RN 1008744-32-8 in STN Registry, 2008.*
Search Report issued for International Application No. PCT/KR2015/014178 dated Aug. 23, 2016 (4 pages).
T. Luker et al., "Switching between agonists and antagonists at CRTh2 in a series of highly potent and selective biaryl phenoxyacetic acids," Bioorganic & Medicinal Chemistry Letters, 2011, vol. 21, pp. 3616-3621.
J.W. Tilley et al., "Identification of N-acyl 4-(3-pyridonyl)phenylalanine derivatives and their orally active prodrug esters as dual acting 41 and 47 receptor antagonists," Bioorganic & Medicinal Chemistry Letters, 2013, vol. 23, pp. 1036-1040.
R. Frei et al., "Expedient construction of small molecule macroarrays via sequential palladium- and copper-mediated reactions and their ex situ biological testing" Chemical Science, 2012, vol. 3, pp. 1555-1561.
Geiger et al., "Sythesis and Spectroscopic Characterization of Chiral Biphenyl-Cholesterol Gels", Langmuir, 2014, 30, pp. 13979-13986.
Extended Search Report cited in European Application No. 15873645.4 dated May 2, 2018, 9 pages.
RN 1183368-13-8, 1182259-89-7, 1182253-77-5, 1182241-89-9, 1182222-48-5, 1182210-78-1, 1182115-71-4, 1182071-56-2, 1182071-50-6, Database Registry [Online] Retrieved from STN, Chemical Catalog, Supplier: Otava, Sep. 10, 2009, 8 pages.
RN 1181808-09-2, 1181808-06-2, 1181785-63-6, 181767-75-8, 1181764-42-0, 1181764-41-9, 1181763-30-3, 1181723-13-6, 1181723-09-0, 1181723-08-9, 1181705-41-8, 1181664-74-3, 1181664-76-5, 1181662-49-6, 1181660-5-7 Database Registry [Online] Retrieved from STN, Chemical Catalog, Supplier: Otava, Sep. 9, 2009, 8 pages.

(56) References Cited

OTHER PUBLICATIONS

B.Q. Chen et al., "New Combined Liquid Crystalline Polymers from Polyaddition of Biphenol Diglycidyl Ether and Trimeric esters," Macromolecules, 1999, vol. 32, pp. 6485-6492.

J.Y. Nioche et al., "Synthesis and structure-activity relationships of new ACAT inhibitors," European Journal of Medicinal Chemistry, 1995, vol. 30, pp. 377-385.

B. Hirani et al., "Liquid crystallinity of newly synthesized glucose derivatives with mesogenic side chains", Liquid Crystals, 1997, vol. 23, pp. 59-67.

M. Manickam et al., "Design and Synthesis of Novel Calamitic and Discotic Materials Based on the Photorefractive Carbazole Unit", Molecular Crystals and Liquid Crystals, 2010, vol. 518, pp. 84-100.

Examination Report issued for Australian Patent Application No. 2019203429 dated Aug. 28, 2019, 6 pages.

Fortes, M.P. et al., A convenient eco-friendly system for the synthesis of 5-sulfenyl tetrazole derivatives of indoles and pyrroles employing CeCh-7H20 in PEG-400, Rsc Advances (2014), 4(65), pp. 34519-34530.

CAS RN 1629618-39-8, 3-[(2'-methoxy[1,T-binaphthalen]-2-yl)thio]-propanenitrile, STN Entry Date Oct. 21, 2014.

CAS RN 1541040-80-5, 6-chloro-2-(1-methyl-1H-benzimidazol-5-yl)-4-pyrimidineacetic acid, STN Entry Date Feb. 10, 2014.

CAS RN 1521829-31-1, B-methyl-4-(5-methyl-2-furanyl)-1H-Indole-3-propanoic acid, STN Entry Date Jan. 16, 2014.

Mavunkel, B., et al., "Pyrimidine-based inhibitors of CaMKIIδ", Bioorganic & Medical Chemistry Letters, 2008, vol. 18, pp. 2404-2408.

Chen, L., et al., "p53- alpha-Helix mimetics antagonize p53/MDM2 interaction and activate p53", Mol Chacer Ther, 2005, vol. 4, No. 6, pp. 1019-1025.

Registry(STN)[online] May 14, 2014 CAS Registration No. 1605018-87-8, Mar. 7, 2014 CAS Registration No. 1564013-51-9, Feb. 11, 2014 CAS Registration No. 1541490-95-2, Jul. 5, 2011 CAS Registration Tumber 1311279-35-2, Jul. 5, 2014 CAS Registration No. 1311278-83-7, Sep. 12, 2014 CAS Registration No. 1622655-64-4, Sep. 12, 2014 CAS Regisliation No. 1622575-13-6, Sep. 12, 2014 CAS Regisliation No. 1622496-18-7 (date of search: Oct. 15, 2020) (2 pages).

Yang, S.S., et al., "Synthesis of 2,4'-disubstituted biphenyls via regioselective electrophilic and nucleophilic addition to the (η5-cyclo-hexadienylidene)2[Cr(CO)3]2 dianion", Tetrahedron Letters, 1991, vol. 32, No. 28, pp. 3341-3344.

Ernst, J.T., et al., "Design of a protein surface antagonist based on alpha-helix mimicry: inhibition of gp41 assembly and viral fusion", Angew. Chem. Int. Ed., 2002, vol. 41, No. 2, pp. 278-281.

Registry (STN) [online] Jul. 5, 2011 CAS Registration No. 1311278-61-1, Jun. 13, 2011 CAS Registration No. 1309267-82-0, Jun. 6, 2014 CAS Regisliation No. 1609751-07-6 (date of search: Oct. 15, 2020) (1 page).

* cited by examiner

BIARYL DERIVATIVE AS GPR120 AGONIST

CROSS-REFERENCE TO RELATED APPLICATIONS

This application is a 35 U.S.C. § 371 National Phase Entry Application from PCT/KR2015/014178, filed on Dec. 23, 2015, and designating the United States, which claims priority under 35 U.S.C. § 119 to Korean Patent Application No. 10-2014-0188399 filed on Dec. 24, 2014 with the Korean Intellectual Property Office, the disclosures of which are herein incorporated by reference in their entirety.

TECHNICAL FIELD

The present invention relates to novel compound derivatives as GPR120 agonists, a method for preparing the same, a pharmaceutical composition comprising the same as active ingredients and use thereof. Herein a GPR120 agonist means a compound which can be effectively used for preventing or treating metabolic diseases such as diabetes, complications of diabetes, obesity, non-alcoholic fatty liver, steatohepatitis and osteoporosis, or inflammation, by promoting GLP-1 in the gastrointestinal tract and anti-inflammatory action.

BACKGROUND ART

Diabetes is largely divided into two types—i.e., insulin-dependent type 1 diabetes and insulin-independent (insulin-resistant) type 2 diabetes which is found in 90% or more of diabetic patients.

GPR120 agonists, which are noted for possible treatment of type 2 diabetes, are known to have (1) an antidiabetic effect caused by the actions of increasing incretin hormone in intestinal cells, (2) anti-inflammatory action in macrophages, and (3) an action of improvement on insulin resistance in lipocytes. They are also known as a possible treatment of type 1 diabetes due to the improvement on proliferation of pancreas cells by anti-inflammatory action.

G protein-coupled receptor 120 (GPR120) is expressed copiously in the intestines, lungs, adipose tissue, and macrophages which induce inflammation, and is activated by long-chain free fatty acid (FFA). GPR120 stimulates the secretion of glucagon-like peptide-1 (GLP-1) by FFA. GLP-1, an incretin hormone, is known to stimulate the secretion of insulin in the pancreas dependently on blood glucose level, and also to have the effect of improvement of insulin resistance, proliferation of β-cells, appetite loss and increase of satiety. Recently, GPR120 is known to relate with improvement of insulin resistance and anti-inflammatory effect, and therefore, it is regarded as a target for developing a drug to effectively improve insulin resistance, type 2 diabetes and obesity involving low-level chronic inflammation. Furthermore, in animal experiments of type 1 diabetes, GPR120 agonists are reported to improve the secretion of insulin by the action of proliferation of β-cells.

Since GPR 120 agonists also have anti-inflammatory action, they are reported to be a possible treatment of inflammation-related diseases—for example, steatohepatitis, rheumatoid arthritis, etc.

Considering the above, researches on GPR120 agonists are actively in progress. In the representative compounds presented as GPR120 agonists, two aryl groups are connected with a center bridge structure, and the characteristic feature is that one of two aryl groups is substituted by carboxylic acid. GPR120 agonist compounds are disclosed in WO 2013/185766, WO 2013/139341, WO 2011/159297, WO 2010/080537, WO 2010/104195, WO 2010/048207, WO 2009/147990, WO 2008/066131, WO 2008/103500 and WO 2008/139879.

DISCLOSURE OF INVENTION

Technical Problem

The object of the present invention is to provide a novel biaryl derivative as a GPR120 agonist.

Another object of the present invention is to provide a method for preparing the biaryl derivative.

Still another object of the present invention is to provide a pharmaceutical composition for the prevention or treatment of metabolic disease such as diabetes, complications of diabetes, obesity, non-alcoholic fatty liver, steatohepatitis and osteoporosis, or inflammation which comprises the biaryl derivative as an active ingredient, and a method for preparing the composition.

A still further object of the present invention is to provide a method for preventing and treating metabolic disease such as diabetes, complications of diabetes, obesity, non-alcoholic fatty liver, steatohepatitis and osteoporosis, or inflammation which uses the biaryl derivative as an active ingredient.

Solution to Problem

To accomplish the object, the present invention provides a biaryl derivative of Formula 1, or a pharmaceutically acceptable salt or isomer thereof:

[Formula 1]

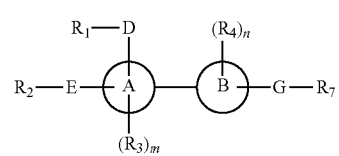

wherein,

A and B represent independently aryl or heteroaryl;

D and E may independently not exist, or represent independently C, CH, $CH_2$, N, NH, O or S;

$R_1$ and $R_2$ may independently not exist, or represent independently hydrogen, halogen, alkyl, cycloalkyl, heterocycloalkyl, oxo, alkylcycloalkyl, cycloalkylalkyl, haloalkyl, alkoxy, alkoxyalkyl, alkoxyaryl, cycloalkoxy, cycloalkylalkoxy, alkylheterocycloalkyl, aryl, alkylaryl, aralkyl, haloaryl, heteroaryl, alkylheteroaryl or haloalkylaryl;

$R_1$ and $R_2$ may be connected each other, or with D and/or E to form a ring, or may form a fused ring with A; the ring is optionally substituted with alkyl, halogen, alkoxycarbonyl, cycloalkylalkyl, haloaryl or alkylaryl; and when D and E represent C, CH or N, $R_1$ and $R_2$ can represent two or three alkyl, oxo, cycloalkyl, alkoxy, alkylcycloalkyl, aryl or alkylaryl which may be the same or different;

$R_3$ and $R_4$ represent independently hydrogen, halogen, alkyl, cycloalkyl, heterocycloalkyl, alkoxy, nitrile, oxo, cycloalkoxy, aryloxy, heteroaryloxy, aminoalkyl, aminocycloalkyl, aminoaryl, alkylamine, cycloalkylamine, aminoheteroaryl, thioalkyl, thioaryl or thioheteroaryl;

m and n represent independently an integer of 0 to 5;

G represents —$(CR_5R_6)_p$-J-$(CR_5R_6)_q$, wherein J represents $CH_2$, O, N, NH, S or a double bond; $R_5$ and $R_6$ represent independently hydrogen, halogen, alkyl or cycloalkyl, hydroxy or amine, or may be connected each other to form cycloalkyl, and when J is N, each of $R_5$ and $R_6$ at two $(CR_5R_6)$s may be connected to form a ring, or may be substituted with alkyl; and p and q represent independently an integer of 0 to 6; and $R_7$ represents carboxylic acid or carboxylic acid isostere.

The compound of Formula 1 according to the present invention may form a pharmaceutically acceptable salt, which includes an acid-addition salt which is formed from an inorganic acid such as hydrochloric acid, sulfuric acid, nitric acid, phosphoric acid, hydrobromic acid and hydroiodic acid; an organic acid such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acid such as methanesulfonic acid, ethanesulfonic acid, benzenesulfonic acid and p-toluenesulfonic acid, which form non-toxic acid-addition salt including pharmaceutically acceptable anion. In addition, a pharmaceutically acceptable carboxylic acid salt includes the salt with alkali metal or alkali earth metal such as lithium, sodium, potassium, calcium and magnesium; salts with amino acid such as lysine, arginine and guanidine; an organic salt such as dicyclohexylamine, N-methyl-D-glucamine, tris(hydroxymethyl)methylamine, diethanolamine, choline and triethylamine. The compound of Formula 1 according to the present invention may be converted into their salts by conventional methods.

Meanwhile, since the compound of Formula 1 according to the present invention can have an asymmetric carbon center and asymmetric axis or plane, they can exist as E- or Z-isomer, R- or S-isomer, racemic mixtures or diastereoisomer mixtures and each diastereoisomer, all of which are within the scope of the present invention.

Herein, unless indicated otherwise, the term "the compound of Formula 1" is used to mean all the compounds of Formula 1, including the pharmaceutically acceptable salts and isomers thereof.

Herein, the following concepts defined to the substituents are used to define the compound of Formula 1.

The term "halogen" or "halo" means fluoride (F), chlorine (Cl), bromine (Br) or iodine (I).

The term "carboxylic acid isostere" includes, but is not limited to, isoxazolol, pyrazolol, isothiazolol, thiazolidinedione, pyrrolidinedione, oxazolidinedione, imidazolidinedione, thiazolidinedione, imidazoledione, pyrroledione, phenol, pyridinol, dioxothiadiazolidineone, tetrazole, triazole, imidazole, sulfonic acid, sulfonamide, acetamide, nitrile, hydroxyacetamidine, oxadiazoleone, oxadiazolethione and the like.

The term "alkyl" means straight or branched hydrocarbons, may include a single bond, a double bond and a triple bond, and is preferably $C_1$-$C_{10}$-alkyl. Examples of alkyl include, but are not limited to, methyl, ethyl, n-propyl, i-propyl, n-butyl, i-butyl, tert-butyl, acetylene, vinyl, trifluoromethyl and the like.

The term "cycloalkyl" means partially or fully saturated single or fused ring hydrocarbons, and is preferably $C_3$-$C_{10}$-cycloalkyl. Examples of cycloalkyl include, but are not limited to, cyclopropyl, cyclobutyl, cyclopentyl, cyclohexyl, cyclohexenyl and the like.

Unless otherwise defined, the term "alkoxy" means alkyloxy having 1 to 10 carbon atoms.

Unless otherwise defined, the term "cycloalkoxy" means cycloalkyloxy having 3 to 10 carbon atoms.

Aryl means aromatic hydrocarbons, preferably $C_5$-$C_{12}$-aryl, more preferably $C_6$-$C_{10}$-aryl, and includes, but is not limited to, phenyl, naphthyl and the like.

Heteroaryl means 3- to 12-membered, more preferably 5- to 10-membered aromatic hydrocarbons which form a single or fused ring—which may be fused with benzo or C3-C8 cycloalkyl—including at least one heteroatom selected from N, O and S as a ring member. Examples of heteroaryl include, but are not limited to, pyridinyl, pyrimidinyl, pyridazinyl, pyrazinyl, oxadiazolyl, isoxadiazolyl, tetrazolyl, triazolyl, indolyl, indazolyl, isoxazolyl, oxazolyl, thiazolyl, isothiazolyl, furanyl, benzofuranyl, imidazolyl, thiophenyl, benzthiazole, benzimidazole, quinolinyl, indolinyl, 1,2,3,4-tetrahydroisoquinolyl, 3,4-dihydroisoquinolinyl, thiazolopyridyl, 2,3-dihydrobenzofuran, 2,3-dihydrothiophene, 2,3-dihydroindole, benzo[1,3]dioxin, chroman, thiochroman, 1,2,3,4-tetrahydroquinoline, 4H-benzo[1,3]dioxin, 2,3-dihydrobenzo[1,4]-dioxin, 6,7-dihydro-5H-cyclopenta[d]pyrimidine and the like.

Heterocyclyl means partially or fully saturated hydrocarbons which form a single or fused ring including at least one heteroatom selected from N, O and S, and is preferably 3- to 12-membered heterocyclyl. Examples of heterocyclyl include, but are not limited to, pyrrolidinyl, piperidinyl, morpholinyl, imidazolinyl, piperazinyl, tetrahydrofuran, tetrahydrothiofuran and the like.

Aralkyl, alkylaryl and heteroarylalkyl mean groups which are formed by the combination of the above-mentioned aryl with alkyl or heteroaryl with alkyl. Examples include, but are not limited to, benzyl, thiophene methyl, pyrimidine methyl and the like.

The above-mentioned amine, alkyl, cycloalkyl, aryl, heteroaryl, heterocyclyl, aralkyl and heteroarylalkyl may be substituted by at least one group selected from the following groups: alkyl, cycloalkyl, heterocyclyl, aryl, heteroaryl, aralkyl, heteroarylalkyl, heterocyclylalkyl, oxo, cyano, halo, nitro, —OR, —OC(O)R, —OC(O)OR, —SR, —S(O)R, —S(O)$_2$R, —C(O)R, —C(O)OR, —C(S)R, —C(O)NRR, —NR$_2$, —NRCHO, —NRC(O)R, —NRC(O)NRR, —C(S)NRR, —NRC(S)R and —NRC(S)NRR, wherein R is independently selected from hydrogen, alkyl, cycloalkyl, heterocyclyl, aryl, heteroaryl, aralkyl and heteroarylalkyl, and when two Rs are substituted, they may be connected to form cycloalkyl or heterocyclyl.

According to one embodiment of the present invention, in the above Formula 1

A and B represent independently $C_5$-$C_{12}$ aryl or 3- to 12-membered heteroaryl having at least one heteroatom selected from N, O and S;

D and E may independently not exist, or represent independently C, CH, CH$_2$, N, NH, O or S;

$R_1$ and $R_2$ may independently not exist, or represent independently hydrogen, halogen, $C_1$-$C_{10}$ alkyl, $C_3$-$C_{10}$ cycloalkyl, 3- to 12-membered heterocycloalkyl, oxo, $C_1$-$C_{10}$ alkyl-$C_3$-$C_{10}$ cycloalkyl, $C_3$-$C_{10}$ cycloalkyl-$C_1$-$C_{10}$ alkyl, halo-$C_1$-$C_{10}$ alkyl, $C_1$-$C_{10}$ alkoxy, $C_1$-$C_{10}$ alkoxy-$C_1$-$C_{10}$ alkyl, $C_1$-$C_{10}$ alkoxy-$C_5$-$C_{12}$ aryl, $C_3$-$C_{10}$ cycloalkoxy, $C_3$-$C_{10}$ cycloalkyl-$C_1$-$C_{10}$ alkoxy, $C_1$-$C_{10}$ alkyl-3- to 12-membered heterocycloalkyl, $C_5$-$C_{12}$ aryl, $C_1$-$C_{10}$ alkyl-$C_5$-$C_{12}$ aryl, $C_5$-$C_{12}$ aryl-$C_1$-$C_{10}$ alkyl, halo-$C_5$-$C_{12}$ aryl, 3- to 12-membered heteroaryl, $C_1$-$C_{10}$ alkyl-3- to 12-membered heteroaryl or halo-$C_1$-$C_{10}$ alkyl-$C_5$-$C_{12}$ aryl, wherein the heterocycloalkyl and heteroaryl have at least one heteroatom selected from N, O and S;

$R_1$ and $R_2$ may be connected each other, or with D and/or E to form $C_3$-$C_{10}$ cycloalkyl, $C_5$-$C_{12}$ aryl or 3- to 12-membered heterocycloalkyl having at least one heteroatom selected from N, O and S, or may form 3- to 15-membered heterocycle or heteroaryl having at least one heteroatom selected from N, O and S, fused with A; the cycloalkyl, aryl, heterocycloalkyl, heterocycle or heteroaryl is optionally substituted with $C_1$-$C_{10}$ alkyl, halogen, $C_1$-$C_{10}$ alkoxycarbonyl, $C_3$-$C_{10}$ cycloalkyl-$C_1$-$C_{10}$ alkyl, halo-$C_5$-$C_{12}$ aryl or $C_1$-$C_{10}$ alkyl-$C_5$-$C_{12}$ aryl; and when D and E represent C, CH or N, $R_1$ and $R_2$ can represent two or three $C_1$-$C_{10}$ alkyl, oxo, $C_3$-$C_{10}$ cycloalkyl, $C_1$-$C_{10}$ alkoxy, $C_1$-$C_{10}$ alkyl-$C_3$-$C_{10}$ cycloalkyl, $C_5$-$C_{12}$ aryl or $C_1$-$C_{10}$ alkyl-$C_5$-$C_{12}$ aryl which may be the same or different;

$R_3$ and $R_4$ represent independently hydrogen, halogen, $C_1$-$C_{10}$ alkyl, $C_3$-$C_{10}$ cycloalkyl, 3- to 12-membered heterocycloalkyl, $C_1$-$C_{10}$ alkoxy, nitrile, oxo, $C_3$-$C_{10}$ cycloalkoxy, $C_5$-$C_{12}$ aryloxy, 3- to 12 membered heteroaryloxy, amino-$C_1$-$C_{10}$ alkyl, amino-$C_3$-$C_{10}$ cycloalkyl, amino-$C_5$-$C_{12}$ aryl, $C_1$-$C_{10}$ alkylamine, $C_3$-$C_{10}$ cycloalkylamine, amino-3- to 12-membered heteroaryl, thio-$C_1$-$C_{10}$ alkyl, thio-$C_5$-$C_{12}$ aryl or thio-3 to 12-membered heteroaryl;

m and n represent independently an integer of 0 to 3;

G represents —$(CR_5R_6)_p$-J-$(CR_5R_6)_q$, wherein J represents $CH_2$, O, N, NH, S or double bond; $R_5$ and $R_6$ represent independently hydrogen, halogen, $C_1$-$C_{10}$ alkyl or $C_3$-$C_{10}$ cycloalkyl, hydroxy or amine, or may be connected each other to form $C_3$-$C_{10}$ cycloalkyl, and when J is N, each of $R_5$ and $R_6$ at two $(CR_5R_6)$s may be connected to form 3- to 12-membered heteroaryl or 3- to 12-membered heterocycloalkyl having 1 or 2 N atoms, or may be substituted with $C_1$-$C_{10}$ alkyl; and p and q represent independently an integer of 0 to 6; and $R_7$ represents carboxylic acid or carboxylic acid isostere.

According to another embodiment of the present invention, A and B represent independently $C_6$-$C_{10}$ aryl or 5- to 10-membered heteroaryl having 1 to 3 heteroatoms selected from N, O and S.

According to still another embodiment of the present invention, $R_1$ and $R_2$ may independently not exist, or represent independently hydrogen, halogen, $C_1$-$C_8$ alkyl, $C_3$-$C_8$ cycloalkyl, 3- to 10 membered heterocycloalkyl, oxo, $C_1$-$C_8$ alkyl-$C_3$-$C_8$ cycloalkyl, $C_3$-$C_8$ cycloalkyl-$C_1$-$C_8$ alkyl, halo-$C_1$-$C_8$ alkyl, $C_1$-$C_8$ alkoxy, $C_1$-$C_8$ alkoxy-$C_1$-$C_8$ alkyl, $C_1$-$C_8$ alkoxy-$C_6$-$C_{10}$ aryl, $C_3$-$C_8$ cycloalkoxy, $C_3$-$C_8$ cycloalkyl-$C_1$-$C_8$ alkoxy, $C_1$-$C_8$ alkyl-3- to 10-membered heterocycloalkyl, $C_6$-$C_{10}$ aryl, $C_1$-$C_8$ alkyl-$C_6$-$C_{10}$ aryl, $C_6$-$C_{10}$ aryl-$C_1$-$C_8$ alkyl, halo-$C_6$-$C_{10}$ aryl, 5- to 10-membered heteroaryl, $C_1$-$C_8$ alkyl-5- to 10-membered heteroaryl or halo-$C_1$-$C_8$ alkyl-$C_6$-$C_{10}$ aryl, wherein the heterocycloalkyl and heteroaryl have 1 to 3 heteroatoms selected from N, O and S;

$R_1$ and $R_2$ may be connected each other, or with D and/or E to form $C_3$-$C_8$ cycloalkyl, $C_6$-$C_{10}$ aryl or 3- to 12-membered heterocycloalkyl having 1 to 3 heteroatoms selected from N, O and S, or may form 3- to 14-membered heterocycle or heteroaryl having 1 to 4 heteroatoms selected from N, O and S, fused with A; the cycloalkyl, aryl, heterocycloalkyl, heterocycle or heteroaryl is optionally substituted with $C_1$-$C_8$ alkyl, halogen, $C_1$-$C_8$ alkoxycarbonyl, $C_3$-$C_8$ cycloalkyl-$C_1$-$C_8$ alkyl, halo-$C_6$-$C_{10}$ aryl or $C_1$-$C_8$ alkyl-$C_6$-$C_{10}$ aryl; and when D and E represent C, CH or N, $R_1$ and $R_2$ can represent two or three $C_1$-$C_8$ alkyl, oxo, $C_3$-$C_8$ cycloalkyl, $C_1$-$C_8$ alkoxy, $C_1$-$C_8$ alkyl-$C_3$-$C_8$ cycloalkyl, $C_6$-$C_{10}$ aryl or $C_1$-$C_8$ alkyl-$C_6$-$C_{10}$ aryl which may be the same or different.

According to still another embodiment of the present invention, $R_3$ and $R_4$ represent independently hydrogen, halogen, $C_1$-$C_{10}$ alkyl, $C_3$-$C_{10}$ cycloalkyl, 3- to 12-membered heterocycloalkyl, $C_1$-$C_{10}$ alkoxy, nitrile, oxo or $C_3$-$C_{10}$ cycloalkoxy.

According to still another embodiment of the present invention, G represents —$(CR_5R_6)_p$-J-$(CR_5R_6)_q$, wherein J represents $CH_2$, O, N, NH, S or a double bond; $R_5$ and $R_6$ represent independently hydrogen, halogen, $C_1$-$C_8$ alkyl or $C_3$-$C_8$ cycloalkyl, hydroxy or amine, or may be connected each other to form $C_3$-$C_8$ cycloalkyl, and when J is N, each of $R_5$ and $R_6$ at two $(CR_5R_6)$s may be connected to form 3- to 10-membered heteroaryl or 3- to 12-membered heterocycloalkyl having 1 or 2 N atoms, or may be substituted with $C_1$-$C_8$ alkyl; and p and q represent independently an integer of 0 to 5.

Representative compounds of Formula 1 according to the present invention include, but are not limited to, the following compounds:

3-[6-(2-isopropylsulfanyl-pyridin-3-yl)-quinolin-2-yl]-propionic acid,

3-[6-(6-isopropylsulfanyl-pyridin-2-yl)-quinolin-2-yl]-propionic acid,

[6-(6-cyclopentyloxy-pyridin-2-yl)-naphthalen-2-yloxy]-acetic acid,

[6-(2-cyclopentyloxy-pyridin-3-yl)-naphthalen-2-yloxy]-acetic acid,

4-[6-(2-isopropylsulfanyl-pyridin-3-yl)-naphthalen-2-yloxy]-butyric acid,

4-[6-(6-isopropylsulfanyl-pyridin-2-yl)-naphthalen-2-yloxy]-butyric acid,

3-[6-(2-isopropylsulfanyl-pyridin-3-yl)-chroman-2-yl]-propionic acid,

3-[6-(6-isopropylsulfanyl-pyridin-2-yl)-chroman-2-yl]-propionic acid,

3-[6-(6-cyclopentyloxy-pyridin-2-yl)-chroman-2-yl]-propionic acid,

3-[6-(2-cyclopentyloxy-pyridin-3-yl)-chroman-2-yl]-propionic acid,

3-[6-(6-cyclopentyloxy-pyridin-2-yl)-1,2,3,4-tetrahydro-quinolin-2-yl]-propionic acid, 3-[6-(6-cyclopentyloxy-pyridin-2-yl)-1-methyl-1,2,3,4-tetrahydro-quinolin-2-yl]-propionic acid,

[6-(2-isopropylsulfanyl-pyridin-3-yl)-1-oxo-3,4-dihydro-1H-isoquinolin-2-yl]-acetic acid,

[6-(6-isopropylsulfanyl-pyridin-2-yl)-1-oxo-3,4-dihydro-1H-isoquinolin-2-yl]-acetic acid, 3-[6-(2-cyclopentyloxy-pyridin-3-yl)-1-oxo-3,4-dihydro-1H-isoquinolin-2-yl]-propionic acid, 3-[6-(2-isopropylsulfanyl-pyridin-3-yl)-1-oxo-3,4-dihydro-1H-isoquinolin-2-yl]-propionic acid, 4-(3'-benzyloxy-3,5-difluoro-biphenyl-4-yloxy)-butyric acid, 4-(3,5-difluoro-3'-isopropoxy-biphenyl-4-yloxy)-butyric acid, 4-(3,5-difluoro-3'-propoxy-biphenyl-4-yloxy)-butyric acid, 4-(3'-cyclopropylmethoxy-3,5-difluoro-biphenyl-4-yloxy)-butyric acid, 4-(3'-cyclobutoxy-3,5-difluoro-biphenyl-4-yloxy)-butyric acid, 4-[4-(2,2-dimethyl-2,3-dihydro-benzofuran-7-yl)-2,6-difluoro-phenoxy]-butyric acid, 4-[4-(2,2-dimethyl-benzo[1,3]dioxol-4-yl)-2,6-difluoro-phenoxy]-butyric acid, 4-[4-(2-cyclobutylsulfanyl-3-pyridyl)-2,6-difluoro-phenoxy]butanenitrile, 2-cyclobutylsulfanyl-3-{3,5-difluoro-4-[3-(1H-tetrazol-5-yl)propoxy]phenyl}pyridine, 2-cyclobutylsulfanyl-3-{4-[3-(1H-tetrazol-5-yl)propyl]phenyl}pyridine, 5-[4-(2-cyclobutylsulfanyl-3-pyridyl)phenyl]pentanoic acid, 5-[4-(6-cyclopentylsulfanyl-2-pyridyl)phenyl]pentanoic acid, 5-[4-(2-cyclopentylsulfanyl-3-pyridyl)phenyl]pentanoic acid,
2-cyclobutylsulfanyl-3-[3,5-difluoro-4-(1H-tetrazol-5-yl-methoxy)phenyl]pyridine,
5-[2,6-difluoro-4-(2-propylsulfanyl-3-pyridyl)phenyl]pentanoic acid,
5-[4-(6-cyclobutoxy-2-pyridyl)-2,6-difluoro-phenyl]pentanoic acid,
5-[4-(6-cyclopentoxy-2-pyridyl)-2,6-difluoro-phenyl]pentanoic acid,
5-[4-(2,2-difluoro-benzo[1,3]dioxol-4-yl)-2,6-difluoro-phenyl]pentanoic acid,
5-[4-(2-cyclobutylsulfanyl-3-pyridyl)-2,6-difluoro-phenyl]pentanoic acid,
5-[4-(2-cyclopentylsulfanyl-3-pyridyl)-2,6-difluoro-phenyl]pentanoic acid,
5-[4-(2-cyclopentoxy-3-pyridyl)-2,6-difluoro-phenyl]pentanoic acid,
{2-[4-(2-cyclobutylsulfanyl-3-pyridyl)-2,6-difluoro-phenyl]ethoxy}acetic acid,
5-[4-(2-cyclobutylsulfanyl-3-pyridyl)phenyl]hexanoic acid,
5-[4-(6-cyclobutoxy-2-pyridyl)-phenyl]hexanoic acid,
5-[4-(6-cyclobutoxy-2-pyridyl)-2,6-difluoro-phenyl]hexanoic acid,
5-[4-(2-ethylsulfanyl-3-pyridyl)-2,6-difluoro-phenyl]hexanoic acid,
5-[2,6-difluoro-4-(2-propylsulfanyl-3-pyridyl)-phenyl]hexanoic acid,
4-[1-methyl-5-(2-phenoxyphenyl)benzimidazol-2-yl]butanoic acid,
3-[1-methyl-5-(2-phenoxyphenyl)benzimidazol-2-yl]propanoic acid,
5-[2,6-difluoro-4-(2-isopropoxy-3-pyridyl)phenyl]hexanoic acid,
5-(2'-cyclopentylamino-3,5-difluoro-bisphenyl-4-yl)hexanoic acid,
5-[4-(2-cyclobutylsulfanyl-3-pyridyl)-2,6-difluoro-phenyl]hexanoic acid,
5-[4-(2-cyclopentylsulfanyl-3-pyridyl)-2,6-difluoro-phenyl]hexanoic acid,
5-[2,6-difluoro-4-(2-isopropylsulfanyl-3-pyridyl)-phenyl]hexanoic acid,
5-[4-(2-cyclopentoxy-3-pyridyl)-2,6-difluoro-phenyl]hexanoic acid,
5-(3'-cyclopentylamino-3,5-difluoro-biphenyl-4-yl)-hexanoic acid,
5-[2,6-difluoro-4-(6-isopropylsulfanyl-2-pyridyl)-phenyl]hexanoic acid,
5-[4-(6-cyclopentylsulfanyl-2-pyridyl)-2,6-difluoro-phenyl]hexanoic acid,
5-[2,6-difluoro-4-(6-propylsulfanyl-2-pyridyl)phenyl]hexanoic acid,
5-[4-(6-cyclopentoxy-2-pyridyl)-2,6-difluoro-phenyl]hexanoic acid,
4-[4-(2-isopropoxy-3-pyridyl)phenyl]butanoic acid,
5-[2,6-difluoro-4-(2-hydroxy-3-pyridyl)phenyl]hexanoic acid,
5-[4-(2-cyclobutoxy-3-pyridyl)-2,6-difluoro-phenyl]hexanoic acid,
5-[4-(2-cyclopropylmethoxy-3-pyridyl)-2,6-difluoro-phenyl]hexanoic acid,
5-[[4-(2-cyclobutylsulfanyl-3-pyridyl)-2,6-difluoro-phenoxy]methyl]isoxazol-3-ol,
N-hydroxy-4-[4-(2-propylsulfanyl-3-pyridyl)phenyl]butaneamidine,
3-[3-[4-(2-propylsulfanyl-3-pyridyl)phenyl]propyl]-4H-1,2,4-oxadiazol-5-one,
3-[3-[4-(2-propylsulfanyl-3-pyridyl)phenyl]propyl]-4H-1,2,4-oxadiazol-5-thione,
5-[[4-(2-cyclopentylsulfanyl-3-pyridyl)-2,6-difluoro-phenoxy]methyl]isoxazol-3-ol,
5-[[2,6-difluoro-4-(2-propylsulfanyl-3-pyridyl)phenoxy]methyl]isoxazol-3-ol,
5-[[4-[2-(cyclopentoxy)-3-pyridyl]-2,6-difluoro-phenoxy]methyl]isoxazol-3-ol,
5-[[2,6-difluoro-4-(2-isopropylsulfanyl-3-pyridyl)phenoxy]methyl]isoxazol-3-ol,
5-[[2,6-difluoro-4-(2-isopropoxy-3-pyridyl)phenoxy]methyl]isoxazol-3-ol,
5-[[2,6-difluoro-4-(6-isopropylsulfanyl-2-pyridyl)phenoxy]methyl]isoxazol-3-ol,
5-[[2,6-difluoro-4-(6-isopropoxy-2-pyridyl)phenoxy]methyl]isoxazol-3-ol,
5-[[4-[6-(cyclopropylmethoxy)-2-pyridyl]-2,6-difluoro-phenoxy]methyl]isoxazol-3-ol,
5-[[2,6-difluoro-4-(6-propoxy-2-pyridyl)phenoxy]methyl]is oxazol-3-ol,
5-[[2,6-difluoro-4-(2-propoxy-3-pyridyl)phenoxy]methyl]isoxazol-3-ol,
5-[(E)-3-[4-(2-cyclobutylsulfanyl-3-pyridyl)-2,6-difluoro-phenyl]allyl]thiazolidin-2,4-dione,
5-[[4-[2-(cyclobutoxy)-3-pyridyl]-2,6-difluoro-phenoxy]methyl]isoxazol-3-ol,
5-[[4-[2-(cyclobutylmethoxy)-3-pyridyl]-2,6-difluoro-phenoxy]methyl]isoxazol-3-ol,
5-[[4-[2-(cyclopentoxy)-3-pyridyl]anilino]methyl]isoxazol-3-ol,
5-[[4-[2-(cyclopentoxy)-3-pyridyl]-2,6-difluoro-phenoxy]methyl]pyridin-2-ol,
4-[[4-[2-(cyclopentoxy)-3-pyridyl]-2,6-difluoro-phenoxy]methyl]pyridin-2-ol,
5-[[4-[2-(cyclopentoxy)-3-pyridyl]phenyl]sulfanylmethyl]isoxazol-3-ol,
5-[(E)-3-[4-[2-(cyclopentoxy)-3-pyridyl]-2,6-difluoro-phenyl]allyl]-1,1-dioxo-1,2,5-thiadiazolidin-3-one,
5-[[4-[2-(cyclopentoxy)-3-pyridyl]-2,6-difluoro-phenyl]sulfanylmethyl]isoxazol-3-ol,
5-[[4-[2-(cyclopentoxy)-3-pyridyl]-2,6-difluoro-anilino]methyl]isoxazol-3-ol,
5-[3-[4-[2-(cyclopentoxy)-3-pyridyl]-2,6-difluoro-phenyl]propyl]-1,1-dioxo-1,2,5-thiadiazolidin-3-one,
5-[[4-[2-(cyclopentoxy)-3-pyridyl]-N-methyl-anilino]methyl]isoxazol-3-ol,
5-[2-[4-[2-(cyclopentoxy)-3-pyridyl]-2,6-difluoro-phenyl]ethyl]isoxazol-3-ol,
5-[2-[4-[2-(cyclopentoxy)-3-pyridyl]-2,6-difluoro-phenyl]propyl]isoxazol-3-ol,
5-[2-[4-[2-(cyclopentoxy)-3-pyridyl]-2,6-difluoro-phenoxy]ethyl]isoxazol-3-ol,
5-[2-[4-[2-(cyclopentoxy)-3-pyridyl]-2,6-difluoro-anilino]ethyl]isoxazol-3-ol,
2-[1-[5-(6-isopropylsulfanyl-2-pyridyl)-2-pyridyl]-3-piperidyl]acetic acid,
4-[[5-(6-isopropylsulfanyl-2-pyridyl)-2-pyridyl]amino]butanoic acid,
2-[1-[4-(2-cyclobutylsulfanyl-3-pyridyl)phenyl]pyrazol-4-yl]acetic acid,
5-[4-[2-(cyclopentoxy)-3-pyridyl]-2,6-difluoro-anilino]pentanoic acid,
5-[4-[2-(cyclopentoxy)-3-pyridyl]-N-ethyl-2,6-difluoro-anilino]pentanoic acid,
5-[2,6-difluoro-4-(6-isopropylsulfanyl-2-pyridyl)anilino]pentanoic acid, 5-[2,6-difluoro-4-(2-isopropylsulfanyl-3-pyridyl)anilino]
pentanoic acid,
5-[4-[6-(cyclopropylmethoxy)-2-pyridyl]-2,6-difluoro-anilino]pentanoic acid,
5-[4-[2-(cyclopropylmethoxy)-3-pyridyl]-2,6-difluoro-anilino]pentanoic acid,
2-[1-[4-(2-cyclopentylsulfanyl-3-pyridyl)-2,6-difluoro-phenyl]-4-piperidyl]acetic acid,
5-[4-[6-(cyclopropylmethoxy)-2-pyridyl]-2,6-difluoro-N-methyl-anilino]pentanoic acid,
2-[1-[4-[2-(cyclopentoxy)-3-pyridyl]-2,6-difluoro-phenyl]-4-piperidyl]acetic acid,
2-[1-[2,6-difluoro-4-(2-tetrahydrofuran-3-yloxy-3-pyridyl)phenyl]-4-piperidyl]acetic acid,
2-[1-[2,6-difluoro-4-(2-isopropylsulfanyl-3-pyridyl)phenyl]-4-piperidyl]acetic acid,
2-[1-[2,6-difluoro-4-(6-isopropylsulfanyl-2-pyridyl)phenyl]-4-piperidyl]acetic acid,
2-[1-[4-[6-(cyclopropylmethoxy)-2-pyridyl]-2,6-difluoro-phenyl]-4-piperidyl]acetic acid,
2-[1-[2,6-difluoro-4-(6-isopropylsulfanyl-2-pyridyl)phenyl]-3-piperidyl]acetic acid,
2-[1-[2,6-difluoro-4-(2-isopropylsulfanyl-3-pyridyl)phenyl]-3-piperidyl]acetic acid,
2-[1-[2,6-difluoro-4-(2-isopropylsulfanyl-3-pyridyl)phenyl]azetidin-3-yl]acetic acid,
6-[2,6-difluoro-4-(2-isopropylsulfanyl-3-pyridyl)phenyl]-6-azaspiro[2.5]octan-2-carboxylic acid,
6-[2,6-difluoro-4-(6-isopropylsulfanyl-2-pyridyl)phenyl]-6-azaspiro[2.5]octan-2-carboxylic acid,
2-[1-[4-(2-cyclopentylsulfanyl-3-pyridyl)-2,6-difluoro-phenyl]azetidin-3-yl]acetic acid,
2-[1-[4-[2-(cyclopentoxy)-3-pyridyl]-2,6-difluoro-phenyl]azetidin-3-yl]acetic acid,
2-[1-[2,6-difluoro-4-(6-isopropylsulfanyl-2-pyridyl)phenyl]azetidin-3-yl]acetic acid,
2-[1-[2,6-difluoro-4-(6-isopropoxy-2-pyridyl)phenyl]azetidin-3-yl]acetic acid,
2-[1-[4-[6-(cyclopentoxy)-2-pyridyl]-2,6-difluoro-phenyl]azetidin-3-yl]acetic acid,
2-[1-[2,6-difluoro-4-(2-propylsulfanyl-3-pyridyl)phenyl]-4-piperidyl]acetic acid,
2-[1-[4-(2-cyclobutylsulfanyl-3-pyridyl)-2,6-difluoro-phenyl]-4-piperidyl]acetic acid,
2-[1-[2,6-difluoro-4-(2-isopropoxy-3-pyridyl)phenyl]-4-piperidyl]acetic acid,
2-[1-[2,6-difluoro-4-(2-propoxy-3-pyridyl)phenyl]-4-piperidyl]acetic acid,
2-[1-[4-[2-(cyclopropylmethoxy)-3-pyridyl]-2,6-difluoro-phenyl]-4-piperidyl]acetic acid,
2-[1-[2,6-difluoro-4-(2-isopropylsulfanyl-3-pyridyl)phenyl]pyrazol-4-yl]acetic acid,
2-[1-[2,6-difluoro-4-(6-isopropylsulfanyl-2-pyridyl)phenyl]pyrazol-4-yl]acetic acid,
2-[1-[2,6-difluoro-4-(2-isopropylsulfanyl-3-pyridyl)phenyl]pyrrolidin-3-yl]acetic acid,
2-[1-[2,6-difluoro-4-(6-isopropylsulfanyl-2-pyridyl)phenyl]pyrrolidin-3-yl]acetic acid,
3-[1-[2,6-difluoro-4-(2-isopropylsulfanyl-3-pyridyl)phenyl]-4-piperidyl]propanoic acid,
3-[1-[2,6-difluoro-4-(6-isopropylsulfanyl-2-pyridyl)phenyl]-4-piperidyl]propanoic acid,
2-[2-[4-(2-cyclopentylsulfanyl-3-pyridyl)-2,6-difluoro-anilino]ethyl]cyclopropane carboxylic acid,
2-[1-[2,6-difluoro-4-(2-isopropylsulfanyl-3-pyridyl)phenyl]-3-piperidyl]acetamide,
2-[4-[2,6-difluoro-4-(2-isopropylsulfanyl-3-pyridyl)phenyl]piperazin-1-yl]acetic acid,
3-[1-[2,6-difluoro-4-(2-isopropylsulfanyl-3-pyridyl)phenyl]pyrazol-4-yl]propanoic acid,
4-[5-(2-cyclopentylsulfanyl-3-pyridyl)indolin-1-yl]butanoic acid,
3-[1-[2,6-difluoro-4-(2-isopropylsulfanyl-3-pyridyl)phenyl]azetidin-3-yl]propanoic acid,
2-[(3R)-1-[2,6-difluoro-4-(2-isopropylsulfanyl-3-pyridyl)phenyl]pyrrolidin-3-yl]acetic acid,
2-[(3R)-1-[4-[2-(cyclopentoxy)-3-pyridyl]-2,6-difluoro-phenyl]pyrrolidin-3-yl]acetic acid,
2-[(3 S)-1-[2,6-difluoro-4-(2-isopropylsulfanyl-3-pyridyl)phenyl]pyrrolidin-3-yl]acetic acid,
2-[(3 S)-1-[4-[2-(cyclopentoxy)-3-pyridyl]-2,6-difluoro-phenyl]pyrrolidin-3-yl]acetic acid,
2-[1-[2-fluoro-4-(2-isopropylsulfanyl-3-pyridyl)phenyl]-4-piperidyl]acetic acid,
2-[1-[4-[2-(cyclopentoxy)-3-pyridyl]-2-fluoro-phenyl]-4-piperidyl]acetic acid,
3-[6-(6-isopropylsulfanyl-pyridin-2-yl)-naphthalen-2-yl]-propanoic acid,
3-[6-(6-phenoxy-pyridin-2-yl)-naphthalen-2-yl]-propanoic acid,
3-[6-(2-phenoxy-phenyl)-naphthalen-2-yl]-propanoic acid,
3-[6-(6-cyclopentylsulfanyl-pyridin-2-yl)-naphthalen-2-yl]-propanoic acid,
3-[6-(2-phenoxy-pyridin-3-yl)-naphthalen-2-yl]-propanoic acid,
3-[6-(3-phenoxy-phenyl)-naphthalen-2-yl]-propanoic acid,
3-[6-(3-isopropoxy-phenyl)-naphthalen-2-yl]-propanoic acid,
3-[6-(3-cyclobutoxy-phenyl)-naphthalen-2-yl]-propanoic acid,
3-[6-(6-cyclobutoxy-pyridin-2-yl)-naphthalen-2-yl]-propanoic acid,
3-[6-(2-isopropoxy-pyridin-3-yl)-naphthalen-2-yl]-propanoic acid,
3-[6-(2-cyclopentyloxy-pyridin-3-yl)-naphthalen-2-yl]-propanoic acid,
3-{6-[2-(2-fluoro-phenoxy)-phenyl]-naphthalen-2-yl}-propanoic acid,
3-{6-[6-(2-fluoro-phenoxy)-pyridin-2-yl]-naphthalen-2-yl}-propanoic acid,
4-[4-(2,2-difluoro-benzo[1,3]dioxol-4-yl)-2,6-difluoro-phenylsulfanyl]-butyric acid,
4-[4-(2,2-difluoro-benzo[1,3]dioxol-4-yl)-2-fluoro-phenylsulfanyl]-butyric acid,
4-[4-(2,2-difluoro-benzo[1,3]dioxol-4-yl)-phenylsulfanyl]-butyric acid,
4-(4-spiro[1,3-benzodioxol-2,1'-cyclopentan]-4-ylphenyl)sulfanylbutanoic acid,
4-(2-fluoro-4-spiro[1,3-benzodioxol-2,1'-cyclopentan]-4-yl-phenyl)sulfanylbutanoic acid,
5-[4-(2-isopropoxy-pyridin-3-yl)-phenyl]-5-methyl-hexanoic acid,
5-[4-(2-isopropylsulfanyl-pyridin-3-yl)-phenyl]-5-methyl-hexanoic acid,
5-[4-(2-cyclopentyloxy-pyridin-3-yl)-phenyl]-5-methyl-hexanoic acid,
5-[4-(2-cyclopentyloxy-pyridin-3-yl)-2-fluoro-phenyl]-5-methyl-hexanoic acid,
5-[4-(2-cyclopentyloxy-pyridin-3-yl)-2,6-difluoro-phenyl]-5-methyl-hexanoic acid,
5-[4-(2-cyclopentylsulfanyl-pyridin-3-yl)-phenyl]-5-methyl-hexanoic acid, 5-[4-(2-cyclobutylsulfanyl-pyridin-3-yl)-2,6-difluoro-phenyl]-5-methyl-hexanoic acid,
5-[4-(2-cyclobutylsulfanyl-pyridin-3-yl)-phenyl]-5-methyl-hexanoic acid,
4-{1-[4-(2-cyclopentyloxy-pyridin-3-yl)-2,6-difluoro-phenyl]-cyclopropyl}-butyric acid,
4-{1-[4-(2-cyclobutylsulfanyl-pyridin-3-yl)-2,6-difluoro-phenyl]-cyclopropyl}-butyric acid,
4-{1-[4-(6-cyclobutoxy-pyridin-2-yl)-2,6-difluoro-phenyl]-cyclopropyl}-butyric acid,
4-{1-[4-(2-cyclobutylmethoxy-pyridin-3-yl)-2,6-difluoro-phenyl]-cyclopropyl}-butyric acid,
4-{1-[4-(6-cyclopropylmethoxy-pyridin-2-yl)-2,6-difluoro-phenyl]-cyclopropyl}-butyric acid,
5-[4-(2,2-difluoro-benzo[1,3]dioxol-4-yl)-2,6-difluoro-phenyl]-hexanoic acid,
{2-[4-(2-cyclopentyloxy-pyridin-3-yl)-phenyl]-2,2-difluoro-ethoxy}-acetic acid,
{2-[4-(2-cyclobutylsulfanyl-pyridin-3-yl)-phenyl]-2,2-difluoro-ethoxy}-acetic acid,
{2-[4-(6-cyclobutoxy-pyridin-2-yl)-phenyl]-2,2-difluoro-ethoxy}-acetic acid,
3-{2-[4-(2-cyclopentyloxy-pyridin-3-yl)-2,6-difluoro-phenyl]-cyclopropyl}-propanoic acid,
3-{2-[4-(2-cyclobutylsulfanyl-pyridin-3-yl)-2,6-difluoro-phenyl]-cyclopropyl}-propanoic acid,
5-[4-(2-cyclopentyloxy-pyridin-3-yl)-phenyl]-5,5-difluoro-pentanoic acid,
5-[4-(2-cyclobutylsulfanyl-pyridin-3-yl)-phenyl]-5,5-difluoro-pentanoic acid,
3-{2-[2,6-difluoro-4-(2-propylsulfanyl-pyridin-3-yl)-phenyl]-cyclopropyl}-propanoic acid,
3-{2-[4-(6-cyclobutoxy-pyridin-2-yl)-2,6-difluoro-phenyl]-cyclopropyl}-propanoic acid,
5-[4-(2-cyclopropylmethoxy-pyridin-3-yl)-phenyl]-5,5-difluoro-pentanoic acid,
3-{2-[4-(2-cyclopentylsulfanyl-pyridin-3-yl)-2,6-difluoro-phenyl]-cyclopropyl}-propanoic acid,
3-{2-[4-(2-cyclopentylamino-pyridin-3-yl)-2,6-difluoro-phenyl]-cyclopropyl}-propanoic acid,
5-[4-(2-cyclopentylsulfanyl-pyridin-3-yl)-phenyl]-5,5-difluoro-pentanoic acid,
5-[4-(2-cyclobutoxy-pyridin-3-yl)-phenyl]-5,5-difluoro-pentanoic acid,
5-[4-(6-cyclobutoxy-pyridin-2-yl)-phenyl]-5,5-difluoro-pentanoic acid,
{4-[4-(2-cyclopentyloxy-pyridin-3-yl)-2-fluoro-phenyl]-cyclohexyl}-acetic acid,
3-{2-[4-(2-cyclobutoxy-pyridin-3-yl)-2,6-difluoro-phenyl]-cyclopropyl}-propanoic acid,
3-{2-[4-(2-cyclobutylmethoxy-pyridin-3-yl)-2,6-difluoro-phenyl]-cyclopropyl}-propanoic acid,
3-(2-{2,6-difluoro-4-[2-(tetrahydro-pyran-4-yloxy)-pyridin-3-yl]-phenyl}-cyclopropyl)-propanoic acid,
3-{2-[4-(6-cyclopropylmethoxy-pyridin-2-yl)-2,6-difluoro-phenyl]-cyclopropyl}-propanoic acid,
5,5-difluoro-5-[4-(6-isopropylsulfanyl-pyridin-2-yl)-phenyl]-pentanoic acid,
4-[4-(2,2-dimethyl-2,3-dihydro-benzofuran-4-yl)-phenoxy]-butyric acid,
4-[4-(2,2-dimethyl-2,3-dihydro-benzofuran-4-yl)-2-fluoro-phenoxy]-butyric acid,
4-{[4-(2-cyclobutylsulfanyl-pyridin-3-yl)-2,6-difluoro-phenyl]-methyl-amino}-butyric acid,
4-{[4-(2-cyclopentyloxy-pyridin-3-yl)-2,6-difluoro-phenyl]-methyl-amino}-butyric acid,
4-{[4-(2-cyclopentylsulfanyl-pyridin-3-yl)-2,6-difluoro-phenyl]-methyl-amino}-butyric acid,
4-{[2,6-difluoro-4-(2-isopropylsulfanyl-pyridin-3-yl)-phenyl]-methyl-amino}-butyric acid,
4-[(3'-cyclobutoxy-3,5-difluoro-biphenyl-4-yl)-methyl-amino]-butyric acid,
4-[5-(2-cyclopentylsulfanyl-pyridin-3-yl)-indol-1-yl]-butyric acid,
4-[(3,5-difluoro-3'-pyrrolidin-1-yl-biphenyl-4-yl)-methyl-amino]-butyric acid,
4-{[4-(6-cyclobutylsulfanyl-pyridin-2-yl)-2,6-difluoro-phenyl]-methyl-amino}-butyric acid,
4-{[4-(2,2-difluoro-benzo[1,3]dioxol-4-yl)-2,6-difluoro-phenyl]-methyl-amino}-butyric acid,
4-{[4-(6-cyclopentyloxy-pyridin-2-yl)-2,6-difluoro-phenyl]-methyl-amino}-butyric acid,
4-{[4-(6-cyclobutoxy-pyridin-2-yl)-2,6-difluoro-phenyl]-methyl-amino}-butyric acid,
4-{[4-(2-cyclobutoxy-pyridin-3-yl)-2,6-difluoro-phenyl]-methyl-amino}-butyric acid,
4-{[2,6-difluoro-4-(2-propylsulfanyl-pyridin-3-yl)-phenyl]-methyl-amino}-butyric acid,
4-{[4-(2-ethylsulfanyl-pyridin-3-yl)-2,6-difluoro-phenyl]-methyl-amino}-butyric acid,
4-{[4-(2-cyclobutylsulfanyl-pyridin-3-yl)-2-fluoro-phenyl]-methyl-amino}-butyric acid,
2-{[4-(2-cyclopentylsulfanyl-pyridin-3-yl)-2,6-difluoro-phenylamino]-methyl}-cyclopropane carboxylic acid,
2-{[4-(2-cyclopentylsulfanyl-pyridin-3-yl)-phenylamino]-methyl}-cyclopropane carboxylic acid,
4-{[2-fluoro-4-(2-isopropylsulfanyl-pyridin-3-yl)-phenyl]-methyl-amino}-butyric acid,
4-{[4-(2-cyclopentylsulfanyl-pyridin-3-yl)-2-fluoro-phenyl]-methyl-amino}-butyric acid,
4-{[2,6-difluoro-4-(2-isopropoxy-pyridin-3-yl)-phenyl]-methyl-amino}-butyric acid,
4-[(2'-cyclopentylamino-3,5-difluoro-biphenyl-4-yl)-methyl-amino]-butyric acid,
4-[methyl-(3,5,5'-trifluoro-2'-isopropoxy-biphenyl-4-yl)-amino]-butyric acid,
4-{[4-(2-cyclopentyloxy-5-methyl-pyridin-3-yl)-2,6-difluoro-phenyl]-methyl-amino}-butyric acid,
4-{[4-(2-cyclobutylmethoxy-pyridin-3-yl)-2,6-difluoro-phenyl]-methyl-amino}-butyric acid,
4-{[2,6-difluoro-4-(2-methoxy-pyridin-3-yl)-phenyl]-methyl-amino}-butyric acid,
4-({2,6-difluoro-4-[2-(tetrahydro-furan-3-yloxy)-pyridin-3-yl]-phenyl}-methyl-amino)-butyric acid,
4-[(3,5-difluoro-2'-pyrrolidin-1-yl-biphenyl-4-yl)-methyl-amino]-butyric acid,
4-[(3,5-difluoro-2'-methylamino-biphenyl-4-yl)-methyl-amino]-butyric acid,
4-{[3,5-difluoro-2'-(isopropyl-methyl-amino)-biphenyl-4-yl]-methyl-amino}-butyric acid,
4-{[4-(2-cyclobutylsulfanyl-pyridin-3-yl)-2,6-difluoro-phenyl]-ethyl-amino}-butyric acid,
4-{[4-(2-cyclobutylmethoxy-pyridin-3-yl)-2,6-difluoro-phenyl]-ethyl-amino}-butyric acid,
4-{[2,6-difluoro-4-(2-isopropoxy-pyridin-3-yl)-phenyl]-ethyl-amino}-butyric acid,
(R)-5-[4-(2-cyclobutylsulfanyl-pyridin-3-yl)-2,6-difluoro-phenyl]-hexanoic acid,
(E)-(R)-5-[4-(2-cyclobutylsulfanyl-pyridin-3-yl)-2,6-difluoro-phenyl]-hex-2-enoic acid,
(S)-5-[4-(2-cyclobutylsulfanyl-pyridin-3-yl)-2,6-difluoro-phenyl]-hexanoic acid, 5-{2,6-difluoro-4-[2-(tetrahydro-furan-3-yloxy)-pyridin-3-yl]-phenyl}-hexanoic acid,
5-{2,6-difluoro-4-[2-(tetrahydro-pyran-4-yloxy)-pyridin-3-yl]-phenyl}-hexanoic acid,
5-{2,6-difluoro-4-[2-(oxetan-3-yloxy)-pyridin-3-yl]-phenyl}-hexanoic acid,
4-[4-(2-cyclobutoxy-pyridin-3-yl)-2-fluoro-phenoxy]-butyric acid,
4-[4-(2-cyclopentyloxy-pyridin-3-yl)-2-fluoro-phenoxy]-butyric acid,
4-[4-(2-cyclobutylsulfanyl-pyridin-3-yl)-2-fluoro-phenoxy]-butyric acid,
4-[4-(2-cyclopentylsulfanyl-pyridin-3-yl)-2-fluoro-phenoxy]-butyric acid,
6-[4-(2-cyclopentyloxy-pyridin-3-yl)-2,6-difluoro-phenyl]-heptanoic acid,
6-[4-(2-cyclopentylsulfanyl-pyridin-3-yl)-2,6-difluoro-phenyl]-heptanoic acid,
4-[4-(2-cyclopropylmethoxy-pyridin-3-yl)-2-fluoro-phenylsulfanyl]-butyric acid,
4-[4-(2-cyclopropylmethoxy-pyridin-3-yl)-2-fluoro-phenoxy]-butyric acid,
4-[4-(2-cyclobutylmethoxy-pyridin-3-yl)-2-fluoro-phenoxy]-butyric acid,
4-[3-(6-cyclopentyloxy-pyridin-2-yl)-phenoxy]-butyric acid,
4-[3-(2-cyclopentyloxy-pyridin-3-yl)-phenoxy]-butyric acid,
5-[4-(2-cyclopentyloxy-pyridin-3-yl)-2-fluoro-phenyl]-pentanoic acid,
5-[4-(2-cyclobutoxy-pyridin-3-yl)-2-fluoro-phenyl]-pentanoic acid,
5-[4-(2-cyclobutylmethoxy-pyridin-3-yl)-2-fluoro-phenyl]-pentanoic acid,
5-[4-(2-cyclopropylmethoxy-pyridin-3-yl)-2-fluoro-phenyl]-pentanoic acid,
5-[4-(2-cyclopentylsulfanyl-pyridin-3-yl)-2-fluoro-phenyl]-pentanoic acid,
5-[4-(2-cyclobutylsulfanyl-pyridin-3-yl)-2-fluoro-phenyl]-pentanoic acid,
5-[4-(2-cyclobutylmethoxy-pyridin-3-yl)-2,6-difluoro-phenyl]-pentanoic acid,
5-[4-(2-cyclobutoxy-pyridin-3-yl)-2,6-difluoro-phenyl]-pentanoic acid,
5-[4-(2-cyclopropylmethoxy-pyridin-3-yl)-2,6-difluoro-phenyl]-pentanoic acid,
4-[4-(5-chloro-2,2-dimethyl-2,3-dihydro-benzofuran-7-yl)-2,6-difluoro-phenoxy]-butyric acid,
4-[4-(5-chloro-2,2-dimethyl-2,3-dihydro-benzofuran-7-yl)-2,6-difluoro-phenylsulfanyl]-butyric acid,
4-{[4-(5-chloro-2,2-dimethyl-2,3-dihydro-benzofuran-7-yl)-2,6-difluoro-phenyl]-methyl-amino}-butyric acid,
5-[4-(5-chloro-2,2-dimethyl-2,3-dihydro-benzofuran-7-yl)-2,6-difluoro-phenyl]-hexanoic acid,
4-[2,6-difluoro-4-(7-methoxy-2,2-dimethyl-2,3-dihydro-benzofuran-4-yl)-phenoxy]-butyric acid,
4-[2,6-difluoro-4-(7-methoxy-2,2-dimethyl-2,3-dihydro-benzofuran-4-yl)-phenylsulfanyl]-butyric acid,
4-{[2,6-difluoro-4-(7-methoxy-2,2-dimethyl-2,3-dihydro-benzofuran-4-yl)-phenyl]-methyl-amino}-butyric acid,
5-[2,6-difluoro-4-(7-methoxy-2,2-dimethyl-2,3-dihydro-benzofuran-4-yl-phenyl]-hexanoic acid,
4-(2,6-difluoro-4-spiro[3H-benzofuran-2,1'-cyclopentan]-7-yl-phenoxy)-butyric acid,
4-(2,6-difluoro-4-spiro[3H-benzofuran-2,1'-cyclopentan]-7-yl-phenylsulfanyl)-butyric acid,
4-(2,6-difluoro-N-methyl-4-spiro[3H-benzofuran-2,1'-cyclopentan]-7-yl-anilino)-butyric acid,
5-(2,6-difluoro-4-spiro[3H-benzofuran-2,1'-cyclopentan]-7-yl-phenyl)-hexanoic acid,
7-[4-(3-carboxy-propoxy)-3,5-difluoro-phenyl]-5-fluoro-2,2-dimethyl-2,3-dihydro-indol-1-carboxylic acid methyl ester,
4-[2,6-difluoro-4-(5-fluoro-2,2-dimethyl-2,3-dihydro-1H-indol-7-yl)-phenoxy]-butyric acid,
4-[4-(3-carboxy-propoxy)-3,5-difluoro-phenyl]-5-fluoro-2,2-dimethyl-2,3-dihydro-indol-1-carboxylic acid methyl ester,
4-[2,6-difluoro-4-(5-fluoro-2,2-dimethyl-2,3-dihydro-1H-indol-4-yl)-phenoxy]-butyric acid,
4-[2,6-difluoro-4-(5-fluoro-2,2-dimethyl-2,3-dihydro-1H-indol-7-yl)-phenylsulfanyl]-butyric acid,
3-[6-(2-isopropylsulfanyl-pyridin-3-yl)-thiochroman-2-yl]-propionic acid,
3-[6-(2-cyclopentoxy-pyridin-3-yl)-thiochroman-2-yl]-propionic acid,
3-[6-(2-cyclobutylsulfanyl-pyridin-3-yl)-chroman-2-yl]-propionic acid,
3-[6-(7-methoxy-2,2-dimethyl-2,3-dihydro-benzofuran-4-yl)-chroman-2-yl]-propionic acid,
3-[6-(7-methoxy-2,2-dimethyl-2,3-dihydro-benzofuran-4-yl)-thiochroman-2-yl]-propionic acid,
3-[6-(2-cyclobutylsulfanyl-pyridin-3-yl)-thiochroman-2-yl]-propionic acid,
3-[6-(2-cyclopropylmethoxy-pyridin-3-yl)-chroman-2-yl]-propionic acid,
3-[6-(2-cyclobutoxy-pyridin-3-yl)-chroman-2-yl]-propionic acid,
3-[6-(2-cyclobutoxy-pyridin-3-yl)-thiochroman-2-yl]-propionic acid,
3-[6-(2-cyclopropylmethoxy-pyridin-3-yl)-thiochroman-2-yl]-propionic acid,
3-[6-(2-cyclopentylsulfanyl-pyridin-3-yl)-chroman-2-yl]-propionic acid,
3-[6-(2-cyclopentylsulfanyl-pyridin-3-yl)-thiochroman-2-yl]-propionic acid,
3-[6-(5-chloro-2,2-dimethyl-2,3-dihydro-benzofuran-7-yl)-thiochroman-2-yl]-propionic acid,
3-(6-spiro[3H-benzofuran-2,1'-cyclopentan]-7-yl-thiochroman-2-yl)-propionic acid,
3-{6-[2-(tetrahydro-pyran-4-yloxy)-pyridin-3-yl]-thiochroman-2-yl}-propionic acid,
{1-[2,6-difluoro-4-(7-methoxy-2,2-dimethyl-2,3-dihydro-benzofuran-4-yl)-phenyl]-azetidin-3-yl}-acetic acid,
3-[6-(6-isopropylsulfanyl-pyridin-2-yl)]-propionic acid,
4-(2,6-difluoro-4-spiro[1,3-benzodioxol-2,1'-cyclopentan]-4-yl-phenoxy)butanoic acid,
4-(4-spiro[1,3-benzodioxol-2,1'-cyclopentan]-4-ylphenoxy)butanoic acid,
4-(2-fluoro-4-spiro[1,3-benzodioxol-2,1'-cyclopentan]-4-yl-phenoxy)butanoic acid,
4-[4-(2,2-difluoro-benzo[1,3]dioxol-4-yl)-2,6-difluoro-phenoxy]-butyric acid,
4-[4-(2,2-dimethyl-2,3-dihydro-benzofuran-4-yl)-2,6-difluoro-phenoxy]-butyric acid,
4-[4-(2-cyclohexylsulfanyl-pyridin-3-yl)-2,6-difluoro-phenoxy]-butyric acid,
3-[4-(2-cyclopentyloxy-pyridin-3-yl)-benzylsulfanyl]-propionic acid,
2-[1-[4-[6-(cyclobutoxy)-2-pyridyl]-2,6-difluoro-phenyl]-4-piperidyl]acetic acid,
2-[1-[2,6-difluoro-4-(6-propoxy-2-pyridyl)phenyl]-4-piperidyl]acetic acid, 2-[1-[2,6-difluoro-4-(6-isopropoxy-2-pyridyl)phenyl]-4-piperidyl]acetic acid,
2-[1-[4-(6-cyclobutylsulfanyl-2-pyridyl)-2,6-difluoro-phenyl]-4-piperidyl]acetic acid,
2-[1-[2,6-difluoro-4-(6-propylsulfanyl-2-pyridyl)phenyl]-4-piperidyl]acetic acid,
2-[1-[4-[6-(cyclopentoxy)-2-pyridyl]-2,6-difluoro-phenyl]-4-piperidyl]acetic acid,
2-[1-[4-[3-(cyclobutoxy)phenyl]-2,6-difluoro-phenyl]-4-piperidyl]acetic acid,
2-[1-[4-[3-(cyclopropylmethoxy)phenyl]-2,6-difluoro-phenyl]-4-piperidyl]acetic acid,
2-[1-[2,6-difluoro-4-[3-(isopropoxymethyl)phenyl]phenyl]-4-piperidyl]acetic acid,
2-[1-[4-[3-(ethoxymethyl)phenyl]-2,6-difluoro-phenyl]-4-piperidyl]acetic acid,
2-[1-[4-[3-(cyclobutoxy)-4-fluoro-phenyl]-2,6-difluoro-phenyl]-4-piperidyl]acetic acid,
2-[1-[4-[3-(cyclobutoxy)-4-methoxy-phenyl]-2,6-difluoro-phenyl]-4-piperidyl]acetic acid,
2-[1-[4-[3-(cyclobutoxy)-5-fluoro-phenyl]-2,6-difluoro-phenyl]-4-piperidyl]acetic acid,
2-[1-[2-chloro-4-[6-(cyclopropylmethoxy)-2-pyridyl]-6-fluoro-phenyl]-4-piperidyl]acetic acid,
2-[1-[4-[6-(cyclobutylmethoxy)-2-pyridyl]-2,6-difluoro-phenyl]-4-piperidyl]acetic acid,
2-[1-[4-(6-tert-butoxy-2-pyridyl)-2,6-difluoro-phenyl]-4-piperidyl]acetic acid,
2-[1-[4-[3-(cyclobutoxy)-2-methyl-phenyl]-2,6-difluoro-phenyl]-4-piperidyl]acetic acid,
2-[1-[4-[5-chloro-6-(cyclobutoxy)-2-pyridyl]-2,6-difluoro-phenyl]-4-piperidyl]acetic acid,
2-[1-[4-[6-(cyclopropanecarbonyl)-2-pyridyl]-2,6-difluoro-phenyl]-4-piperidyl]acetic acid,
2-[1-[4-[6-(cyclobutoxymethyl)-2-pyridyl]-2,6-difluoro-phenyl]-4-piperidyl]acetic acid,
2-[1-[4-(6-ethoxy-2-pyridyl)-2,6-difluoro-phenyl]-4-piperidyl]acetic acid,
2-[1-[2,6-difluoro-4-[6-(2,2,2-trifluoroethoxy)-2-pyridyl]phenyl]-4-piperidyl]acetic acid,
2-[1-[2,6-difluoro-4-[6-(2,2,2-trifluoro-1-methyl-ethoxy)-2-pyridyl]phenyl]-4-piperidyl]acetic acid,
2-[1-[4-(6-cyclopentyl-2-pyridyl)-2,6-difluoro-phenyl]-4-piperidyl]acetic acid,
2-[1-[4-[6-[cyclopropyl(methoxy)methyl]-2-pyridyl]-2,6-difluoro-phenyl]-4-piperidyl]acetic acid,
2-[1-[2-chloro-4-[6-(cyclobutoxy)-2-pyridyl]-6-fluoro-phenyl]-4-piperidyl]acetic acid,
2-[1-[4-[6-(cyclobutoxy)-2-pyridyl]-2-fluoro-phenyl]-4-piperidyl]acetic acid,
2-[1-[4-[6-(cyclobutoxy)-2-pyridyl]-2,6-difluoro-phenyl]azetidin-3-yl]acetic acid,
2-[1-[4-[6-(cyclopropylmethoxy)-2-pyridyl]-2,6-difluoro-phenyl]azetidin-3-yl]acetic acid,
2-[1-[4-[4-(cyclobutoxy)-6-methyl-pyrimidin-2-yl]-2,6-difluoro-phenyl]-4-piperidyl]acetic acid,
2-[1-[4-(6-butoxy-2-pyridyl)-2,6-difluoro-phenyl]-4-piperidyl]acetic acid,
2-[1-[4-[2-(cyclobutoxy)-6-methyl-pyrimidin-4-yl]-2,6-difluoro-phenyl]-4-piperidyl]acetic acid,
2-[1-[4-[2-(cyclobutoxy)thiazol-4-yl]-2,6-difluoro-phenyl]-4-piperidyl]acetic acid,
2-[1-[4-[6-(cyclobutoxy)-4-methyl-2-pyridyl]-2,6-difluoro-phenyl]-4-piperidyl]acetic acid,
2-[1-[4-[4-(cyclobutoxy)-6-methyl-pyrimidin-2-yl]-2,6-difluoro-phenyl]azetidin-3-yl]acetic acid,
2-[1-[4-[6-(cyclobutoxy)pyrazin-2-yl]-2,6-difluoro-phenyl]-4-piperidyl]acetic acid,
2-[1-[4-[4-(cyclobutoxy)pyrimidin-2-yl]-2,6-difluoro-phenyl]-4-piperidyl]acetic acid,
2-[1-[4-[4-(cyclopropylmethoxy)-6-methyl-pyrimidin-2-yl]-2,6-difluoro-phenyl]-4-piperidyl]acetic acid,
2-[1-[4-[4-(cyclopropylmethoxy)pyrimidin-2-yl]-2,6-difluoro-phenyl]-4-piperidyl]acetic acid,
2-[1-[4-[6-(cyclopropylmethoxy)pyrazin-2-yl]-2,6-difluoro-phenyl]-4-piperidyl]acetic acid,
2-[1-[4-[6-(cyclobutoxy)pyrazin-2-yl]-2,6-difluoro-phenyl]azetidin-3-yl]acetic acid,
2-[1-[4-[6-(cyclopropylmethoxy)pyrazin-2-yl]-2,6-difluoro-phenyl]azetidin-3-yl]acetic acid,
2-[1-[4-[4-(cyclobutoxy)pyrimidin-2-yl]-2,6-difluoro-phenyl]azetidin-3-yl]acetic acid,
2-[1-[4-[4-(cyclopropylmethoxy)pyrimidin-2-yl]-2,6-difluoro-phenyl]azetidin-3-yl]acetic acid,
2-[1-[4-(6-ethoxypyrazin-2-yl)-2,6-difluoro-phenyl]-4-piperidyl]acetic acid,
2-[1-[2,6-difluoro-4-(6-isopropoxypyrazin-2-yl)phenyl]-4-piperidyl]acetic acid,
2-[1-[2,6-difluoro-4-(6-methoxypyrazin-2-yl)phenyl]-4-piperidyl]acetic acid,
2-[1-[2,6-difluoro-4-(6-propoxypyrazin-2-yl)phenyl]-4-piperidyl]acetic acid,
2-[1-[2,6-difluoro-4-(6-isobutoxypyrazin-2-yl)phenyl]-4-piperidyl]acetic acid,
2-[1-[4-(6-butoxypyrazin-2-yl)-2,6-difluoro-phenyl]-4-piperidyl]acetic acid,
2-[1-[4-[6-(cyclopentoxy)pyrazin-2-yl]-2,6-difluoro-phenyl]-4-piperidyl]acetic acid,
2-[1-[4-(4-ethoxypyrimidin-2-yl)-2,6-difluoro-phenyl]-4-piperidyl]acetic acid,
2-[1-[2,6-difluoro-4-(4-isopropoxypyrimidin-2-yl)phenyl]-4-piperidyl]acetic acid,
2-[1-[2,6-difluoro-4-(4-propoxypyrimidin-2-yl)phenyl]-4-piperidyl]acetic acid,
2-[1-[2,6-difluoro-4-(4-isobutoxypyrimidin-2-yl)phenyl]-4-piperidyl]acetic acid,
2-[1-[4-(4-ethoxy-6-methyl-pyrimidin-2-yl)-2,6-difluoro-phenyl]-4-piperidyl]acetic acid,
2-[1-[2,6-difluoro-4-(4-isopropoxy-6-methyl-pyrimidin-2-yl)phenyl]-4-piperidyl]acetic acid,
2-[1-[2,6-difluoro-4-(4-methyl-6-propoxy-pyrimidin-2-yl)phenyl]-4-piperidyl]acetic acid,
2-[1-[2,6-difluoro-4-(4-isobutoxy-6-methyl-pyrimidin-2-yl)phenyl]-4-piperidyl]acetic acid,
2-[1-[2,6-difluoro-4-(6-pyrrolidin-1-ylpyrazin-2-yl)phenyl]-4-piperidyl]acetic acid,
2-[1-[2,6-difluoro-4-[6-(isopropylamino)pyrazin-2-yl]phenyl]-4-piperidyl]acetic acid,
2-[1-[4-[6-(diethylamino)pyrazin-2-yl]-2,6-difluoro-phenyl]-4-piperidyl]acetic acid,
2-[1-[2,6-difluoro-4-[6-(isobutylamino)pyrazin-2-yl]phenyl]-4-piperidyl]acetic acid,
2-[1-[4-[6-(cyclopentylamino)pyrazin-2-yl]-2,6-difluoro-phenyl]-4-piperidyl]acetic acid,
2-[1-[4-[6-(cyclopentylamino)-2-pyridyl]-2,6-difluoro-phenyl]-4-piperidyl]acetic acid,
2-[1-[4-[6-(dimethylamino)pyrazin-2-yl]-2,6-difluoro-phenyl]-4-piperidyl]acetic acid,
2-[1-[2,6-difluoro-4-[4-(isobutylamino)pyrimidin-2-yl]phenyl]-4-piperidyl]acetic acid,
2-[1-[4-[6-(cyclobutoxy)-5-methyl-pyrazin-2-yl]-2,6-difluoro-phenyl]-4-piperidyl]acetic acid, 2-[1-[2,6-difluoro-4-(6-phenylpyrazin-2-yl)phenyl]-4-piperidyl]acetic acid,
2-[1-[4-(6-cyclopentylpyrazin-2-yl)-2,6-difluoro-phenyl]-4-piperidyl]acetic acid,
2-[1-[2,6-difluoro-4-(6-isobutylpyrazin-2-yl)phenyl]-4-piperidyl]acetic acid,
2-[1-[2,6-difluoro-4-(4-isobutylpyrimidin-2-yl)phenyl]-4-piperidyl]acetic acid,
2-[1-[4-[5-(cyclobutoxy)-3-methyl-isothiazol-4-yl]-2,6-difluoro-phenyl]-4-piperidyl]acetic acid,
{1-[4-(4-ethoxy-thiazol-2-yl)-2,6-difluoro-phenyl]-piperidin-4-yl}acetic acid,
{1-[4-(4-ethoxy-5-methyl-thiazol-2-yl)-2,6-difluoro-phenyl]-piperidin-4-yl}acetic acid,
2-[1-[4-(6-butylpyrazin-2-yl)-2,6-difluoro-phenyl]-4-piperidyl]acetic acid,
2-[1-[2,6-difluoro-4-(6-isopentylpyrazin-2-yl)phenyl]-4-piperidyl]acetic acid,
2-[1-[4-[4-(cyclobutoxy)-5-fluoro-pyrimidin-2-yl]-2,6-difluoro-phenyl]-4-piperidyl]acetic acid,
2-[1-[4-[4-(cyclopropylmethoxy)-5-fluoro-pyrimidin-2-yl]-2,6-difluoro-phenyl]-4-piperidyl]acetic acid,
2-[1-[4-(6-cyclobutyl-2-pyridyl)-2,6-difluoro-phenyl]-4-piperidyl]acetic acid,
2-[1-[4-(6-cyclobutylpyrazin-2-yl)-2,6-difluoro-phenyl]-4-piperidyl]acetic acid,
2-[1-[4-[6-(cyclobutylmethyl)-2-pyridyl]-2,6-difluoro-phenyl]-4-piperidyl]acetic acid,
2-[1-[4-[6-(cyclopentylmethyl)-2-pyridyl]-2,6-difluoro-phenyl]-4-piperidyl]acetic acid,
{1-[4-(4-cyclopropylmethoxy-thiazol-2-yl)-2,6-difluoro-phenyl]-piperidin-4-yl}acetic acid,
(1-{2,6-difluoro-4-[4-(4-fluoro-phenyl)-thiazol-2-yl]-phenyl}-piperidin-4-yl)-acetic acid,
{1-[4-(4-cyclobutoxy-thiazol-2-yl)-2,6-difluoro-phenyl]-piperidin-4-yl}acetic acid,
{1-[4-(4-butoxy-thiazol-2-yl)-2,6-difluoro-phenyl]-piperidin-4-yl}acetic acid,
2-(1-{2,6-difluoro-4-[7-(propan-2-yl)-7H-pyrrolo[2,3-d]pyrimidin-4-yl]phenyl}piperidin-4-yl)acetic acid,
2-[1-[4-(6,7-dihydro-5H-cyclopenta[d]pyrimidin-4-yl)-2,6-difluoro-phenyl]-4-piperidyl]acetic acid,
2-[1-[4-[4-(cyclobutoxy)-6,7-dihydro-5H-cyclopenta[d]pyrimidin-2-yl]-2,6-difluoro-phenyl]-4-piperidyl]acetic acid,
2-[1-[4-[4-(cyclobutoxy)-5,6-dimethyl-pyrimidin-2-yl]-2,6-difluoro-phenyl]-4-piperidyl]acetic acid,
4-[2-chloro-4-[6-(cyclobutoxy)-2-pyridyl]-6-fluoro-phenoxy]butanoic acid,
4-[2,6-dichloro-4-[6-(cyclobutoxy)-2-pyridyl]phenoxy]butanoic acid,
4-[4-[3-(cyclopropylmethoxymethyl)-2-furyl]-2,6-difluoro-phenoxy]butanoic acid,
4-[4-[6-(cyclopropylmethoxymethyl)-2-pyridyl]-2,6-difluoro-phenoxy]butanoic acid,
4-[2-chloro-4-[3-(cyclobutoxy)-5-fluoro-phenyl]-6-fluoro-phenoxy]butanoic acid,
4-[4-[3-(cyclopropylmethoxymethyl)-5-methyl-isoxazol-4-yl]-2,6-difluoro-phenoxy]butanoic acid,
4-[2-chloro-4-[4-(cyclobutoxy)-6-methyl-pyrimidin-2-yl]-6-fluoro-phenoxy]butanoic acid,
4-[2-chloro-4-[2-(cyclobutoxy)-6-methyl-pyrimidin-4-yl]-6-fluoro-phenoxy]butanoic acid,
4-[4-[6-chloro-4-(cyclobutoxy)-2-pyridyl]-2,6-difluoro-phenoxy]butanoic acid,
4-[4-[2-(cyclobutoxy)thiazol-4-yl]-2,6-difluoro-phenoxy]butanoic acid,
4-[4-[6-(cyclobutoxy)-4-methyl-2-pyridyl]-2,6-difluoro-phenoxy]butanoic acid,
4-[2-chloro-4-[4-(cyclopropylmethoxy)-6-methyl-pyrimidin-2-yl]-6-fluoro-phenoxy]butanoic acid,
4-[4-[2-(cyclopropylmethoxy)thiazol-4-yl]-2,6-difluoro-phenoxy]butanoic acid,
4-[4-[6-(cyclobutoxy)pyrazin-2-yl]-2,6-difluoro-phenoxy]butanoic acid,
5-[4-[6-(cyclobutoxy)pyrazin-2-yl]-2,6-difluoro-phenyl]hexanoic acid,
4-[2-chloro-4-(6-cyclopentyloxy-pyridin-2-yl)-6-fluoro-phenoxy]-butyric acid,
4-[2-chloro-4-(6-cyclopropylmethoxy-pyridin-2-yl)-6-fluoro-phenoxy]-butyric acid,
4-[2-chloro-6-fluoro-4-(6-isopropoxy-pyridin-2-yl)-phenoxy]-butyric acid,
4-[2-chloro-4-(6-cyclobutylsulfanyl-pyridin-2-yl)-6-fluoro-phenoxy]-butyric acid,
4-[2-chloro-6-fluoro-4-(6-isopropylsulfanyl-pyridin-2-yl)-phenoxy]-butyric acid,
4-(5-chloro-3'-cyclobutoxy-3-fluoro-biphenyl-4-yloxy)-butyric acid,
4-(5-chloro-3'-cyclopropylmethoxy-3-fluoro-biphenyl-4-yloxy)-butyric acid,
4-(5-chloro-3'-cyclopropylmethoxy-3-fluoro-4'-methoxy-biphenyl-4-yloxy)-butyric acid,
4-(5-chloro-3'-cyclopropylmethoxy-3,4'-difluoro-biphenyl-4-yloxy)-butyric acid,
4-(3'-cyclobutylsulfanyl-3,5-difluoro-biphenyl-4-yloxy)-butyric acid,
5-(3'-cyclobutoxy-3,5-difluoro-biphenyl-4-yl)-hexanoic acid,
5-(5'-cyclobutoxy-3,5,3'-trifluoro-biphenyl-4-yl)-hexanoic acid,
5-(3'-cyclopropylmethoxy-3,5-difluoro-4'-methoxy-biphenyl-4-yl)-hexanoic acid,
5-(3'-cyclopropylmethoxy-3,5-difluoro-biphenyl-4-yl)-hexanoic acid,
5-(5'-cyclobutoxy-3'-fluoro-biphenyl-4-yl)-5,5-difluoropentanoic acid,
5-[4-(5-chloro-6-cyclobutoxy-pyridin-2-yl)-2,6-difluoro-phenyl]-hexanoic acid,
4-(3'-cyclobutanesulfonyl-3,5-difluoro-biphenyl-4-yloxy)-butyric acid,
5-({[4-(6-cyclobutoxy-pyridin-2-yl)-phenyl]-methyl-amino}-methyl)-isoxazol-3-ol,
5-[4-(2-cyclobutoxy-6-methyl-pyrimidin-4-yl)-2,6-difluoro-phenyl]-hexanoic acid,
5-[4-(4-cyclobutoxy-6-methyl-pyrimidin-2-yl)-2,6-difluoro-phenyl]-hexanoic acid,
4-[4-(4-cyclobutoxy-pyrimidin-2-yl)-2,6-difluoro-phenoxy]-butyric acid,
4-[4-(2-cyclobutoxy-pyrimidin-4-yl)-2,6-difluoro-phenoxy]-butyric acid,
4-[2-chloro-4-(4-cyclobutoxy-pyrimidin-2-yl)-6-fluoro-phenoxy]-butyric acid,
4-[2-chloro-4-(2-cyclobutoxy-pyrimidin-4-yl)-6-fluoro-phenoxy]-butyric acid,
4-[2-chloro-4-(6-chloro-4-cyclobutoxy-pyridin-2-yl)-6-fluoro-phenoxy]-butyric acid,
4-[4-(4-cyclobutoxy-6-methyl-pyrimidin-2-yl)-2,6-difluoro-phenoxy]-butyric acid,
4-[2-chloro-4-(2-cyclobutoxy-thiazol-4-yl)-6-fluoro-phenoxy]-butyric acid,
4-[2-chloro-4-(2-cyclopropylmethoxy-thiazol-4-yl)-6-fluoro-phenoxy]-butyric acid, 4-[2-chloro-4-(4-cyclopropylmethoxy-pyrimidin-2-yl)-6-fluoro-phenoxy]-butyric acid,
4-[2-chloro-4-(6-cyclobutoxy-4-methyl-pyridin-2-yl)-6-fluoro-phenoxy]-butyric acid,
4-[2-chloro-4-(6-cyclobutoxy-pyrazin-2-yl)-6-fluoro-phenoxy]-butyric acid,
4-[2-chloro-4-(6-cyclopropylmethoxy-pyrazin-2-yl)-6-fluoro-phenoxy]-butyric acid,
4-[4-(4-cyclopropylmethoxy-6-methyl-pyrimidin-2-yl)-2,6-difluoro-phenoxy]-butyric acid,
4-[4-(4-cyclopropylmethoxy-pyrimidin-2-yl)-2,6-difluoro-phenoxy]-butyric acid,
4-[4-(6-cyclopropylmethoxy-pyrazin-2-yl)-2,6-difluoro-phenoxy]-butyric acid,
4-[2-chloro-4-(6-cyclopropylmethoxy-4-methyl-pyridin-2-yl)-6-fluoro-phenoxy]-butyric acid,
4-[2-chloro-6-fluoro-4-(6-isopropoxy-pyrazin-2-yl)-phenoxy]-butyric acid,
4-[2-chloro-4-(6-ethoxy-pyrazin-2-yl)-6-fluoro-phenoxy]-butyric acid,
{(R)-1-[4-(6-cyclopropylmethoxy-pyridin-2-yl)-2,6-difluoro-phenyl]-pyrrolidin-3-yl}-acetic acid,
{1-[4-(2,2-difluoro-benzo[1,3]dioxol-4-yl)-2,6-difluoro-phenyl]-piperidin-4-yl}-acetic acid,
3-[8-fluoro-6-(2-isopropylsulfanyl-3-pyridyl)thiochroman-2-yl]propanoic acid,
3-[6-[6-(cyclobutoxy)-2-pyridyl]thiochroman-2-yl]propanoic acid,
3-[2-[2,6-difluoro-4-(7-methoxy-2,2-dimethyl-3H-benzofuran-4-yl)phenyl]cyclopropyl]propanoic acid,
3-[2-(2,6-difluoro-4-spiro[3H-benzofuran-2,1'-cyclopentan]-7-yl-phenyl)cyclopropyl]propanoic acid,
3-[6-[6-(cyclobutoxy)-2-pyridyl]chroman-2-yl]propanoic acid,
3-[6-[6-(cyclopropylmethoxy)-2-pyridyl]chroman-2-yl]propanoic acid,
4-[4-(2,3-dimethoxyphenyl)-2,6-difluoro-phenoxy]butanoic acid,
3-[6-[3-(cyclopropylmethoxy)phenyl]chroman-2-yl]propanoic acid,
3-[6-[3-(cyclopentoxy)phenyl]chroman-2-yl]propanoic acid,
4-(2,6-difluoro-N-methyl-4-spiro[1,3-benzodioxol-2,1'-cyclopentan]-4-yl-anilino)butanoic acid,
5-(2,6-difluoro-4-spiro[1,3-benzodioxol-2,1'-cyclopentan]-4-yl-phenyl)hexanoic acid,
3-[6-(6-tert-butylsulfanyl-2-pyridyl)chroman-2-yl]propanoic acid,
3-[6-(6-isopropoxy-2-pyridyl)chroman-2-yl]propanoic acid,
2-[1-(2,6-difluoro-4-spiro[1,3-benzodioxol-2,1'-cyclopentan]-4-yl-phenyl)-4-piperidyl]acetic acid,
4-[4-(2,3-dipropoxyphenyl)-2,6-difluoro-phenoxy]butanoic acid,
4-[4-[6-(cyclobutoxy)-5-methoxy-2-pyridyl]-2,6-difluoro-phenoxy]butanoic acid,
4-[4-[6-(cyclobutoxy)-5-methoxy-2-pyridyl]-2,6-difluoro-N-methyl-anilino]butanoic acid,
2-[1-[4-[6-(cyclobutoxy)-5-methoxy-2-pyridyl]-2,6-difluoro-phenyl]-4-piperidyl]acetic acid,
2-[1-[4-(2,3-dipropoxyphenyl)-2,6-difluoro-phenyl]-4-piperidyl]acetic acid,
4-[4-[6-(cyclopropylmethoxy)-5-methoxy-2-pyridyl]-2,6-difluoro-phenoxy]butanoic acid,
4-[4-(2,3-dipropoxyphenyl)-2,6-difluoro-N-methyl-anilino]butanoic acid,
4-[4-[6-(cyclopropylmethoxy)-5-methoxy-2-pyridyl]-2,6-difluoro-N-methyl-anilino]butanoic acid, 2-[1-[4-[6-(cyclopropylmethoxy)-5-methoxy-2-pyridyl]-2,6-difluoro-phenyl]-4-piperidyl]acetic acid,
4-[4-(6-chloroindol-1-yl)-2,6-difluoro-phenoxy]butanoic acid,
5-[4-[6-(cyclobutoxy)-5-methoxy-2-pyridyl]phenyl]-5,5-difluoro-pentanoic acid,
4-[2,6-difluoro-4-(5-fluoroindol-1-yl)phenoxy]butanoic acid,
4-[4-[3-(cyclopropylmethylamino)phenyl]-2,6-difluoro-N-methyl-anilino]butanoic acid,
4-[2,6-difluoro-N-methyl-4-(6-pyrrolidin-1-yl-2-pyridyl)anilino]butanoic acid,
4-[2,6-difluoro-4-(5-methoxyindol-1-yl)phenoxy]butanoic acid,
4-[4-(5-cyanoindol-1-yl)-2,6-difluoro-phenoxy]butanoic acid,
4-[4-[3-(cyclopropylmethoxymethyl)-2-furyl]-2,6-difluoro-N-methyl-anilino]butanoic acid,
4-[2,6-difluoro-4-(4-fluoroindol-1-yl)phenoxy]butanoic acid,
4-[4-(7-chloroindol-1-yl)-2,6-difluoro-phenoxy]butanoic acid,
4-[4-[5-(cyclopropylmethoxymethyl)-2-furyl]-2,6-difluoro-N-methyl-anilino]butanoic acid,
4-[4-[6-(cyclopropylmethoxy)indol-1-yl]-2,6-difluoro-phenoxy]butanoic acid,
4-[4-(7-chloroindol-1-yl)-2,6-difluoro-N-methyl-anilino]butanoic acid,
4-[4-[6-(cyclobutoxy)indol-1-yl]-2,6-difluoro-phenoxy]butanoic acid,
4-[4-[5-(cyclobutoxy)indol-1-yl]-2,6-difluoro-phenoxy]butanoic acid,
4-[2,6-difluoro-4-(4-methoxyindol-1-yl)phenoxy]butanoic acid,
4-[2,6-difluoro-4-(7-methoxyindol-1-yl)phenoxy]butanoic acid,
4-[2,6-difluoro-4-[5-(methoxymethyl)indazol-1-yl]phenoxy]butanoic acid,
2-[1-[4-(7-chloroindol-1-yl)-2,6-difluoro-phenyl]-4-piperidyl]acetic acid,
4-[4-[6-(cyclobutoxy)indazol-1-yl]-2,6-difluoro-phenoxy]butanoic acid,
4-[2-chloro-4-[6-(cyclobutoxy)indazol-1-yl]-6-fluoro-phenoxy]butanoic acid,
4-[4-[4-(cyclobutoxy)-6-methyl-pyrimidin-2-yl]-2,6-difluoro-N-methyl-anilino]butanoic acid,
4-[4-[4-(cyclobutoxy)pyrimidin-2-yl]-2,6-difluoro-N-methyl-anilino]butanoic acid,
4-[4-[2-(cyclobutoxy)thiazol-4-yl]-2,6-difluoro-N-methyl-anilino]butanoic acid,
2-[1-[4-[6-(cyclobutoxy)indazol-1-yl]-2,6-difluoro-phenyl]-4-piperidyl]acetic acid,
4-[4-[6-(cyclobutoxy)pyrazin-2-yl]-2,6-difluoro-N-methyl-anilino]butanoic acid,
4-[4-[4-(cyclopropylmethoxy)-6-methyl-pyrimidin-2-yl]-2,6-difluoro-N-methyl-anilino]butanoic acid,
4-[4-[4-(cyclopropylmethoxy)pyrimidin-2-yl]-2,6-difluoro-N-methyl-anilino]butanoic acid,
4-[4-[6-(cyclopropylmethoxy)pyrazin-2-yl]-2,6-difluoro-N-methyl-anilino]butanoic acid,
4-[4-[6-(cyclobutoxy)indazol-1-yl]-2,6-difluoro-N-methyl-anilino]butanoic acid,
4-[4-[6-(cyclopropylmethoxy)-2-pyridyl]-2,6-difluoro-N-methyl-anilino]butanoic acid,
2-[1-[4-[6-(cyclobutoxy)indazol-1-yl]-2,6-difluoro-phenyl]pyrrolidin-3-yl]acetic acid, 2-{1-[2,6-difluoro-4-(6-propoxy-pyrazin-2-yl)phenyl]pyrrolidin-3-yl}acetic acid,
2-{1-[2,6-difluoro-4-(6-isobutoxy-pyrazin-2-yl)phenyl]pyrrolidin-3-yl}acetic acid,
2-{1-[2,6-difluoro-4-(6-cyclopentoxy-pyrazin-2-yl)phenyl]pyrrolidin-3-yl}acetic acid,
2-{1-[2,6-difluoro-4-(6-butoxy-pyrazin-2-yl)phenyl]pyrrolidin-3-yl}acetic acid,
2-{1-[2,6-difluoro-4-(4-propoxy-pyrimidin-2-yl)phenyl]pyrrolidin-3-yl}acetic acid,
2-{1-[2,6-difluoro-4-(4-isopropoxy-pyrimidin-2-yl)phenyl]pyrrolidin-3-yl}acetic acid,
2-{1-[2,6-difluoro-4-(4-ethoxy-pyrimidin-2-yl)phenyl]pyrrolidin-3-yl}acetic acid,
2-{1-[2,6-difluoro-4-(4-isobutoxy-pyrimidin-2-yl)phenyl]pyrrolidin-3-yl}acetic acid,
2-{1-[2,6-difluoro-4-(6-isobutylamino-pyrazin-2-yl)phenyl]pyrrolidin-3-yl}acetic acid,
2-{1-[2,6-difluoro-4-(6-cyclopentylamino-pyrazin-2-yl)phenyl]pyrrolidin-3-yl}acetic acid,
2-{1-[2,6-difluoro-4-(6-isopropylamino-pyrazin-2-yl)phenyl]pyrrolidin-3-yl}acetic acid,
2-{1-[2,6-difluoro-4-(6-diethylamino-pyrazin-2-yl)phenyl]pyrrolidin-3-yl}acetic acid,
3-[6-(6-cyclobutoxy-pyrazin-2-yl)-thiochroman-2-yl]-propionic acid,
2-[1-[4-[4-(4-chlorophenoxy)pyrimidin-2-yl]-2,6-difluorophenyl]-4-piperidyl]acetic acid,
2-[1-[4-[4-(4-chlorophenoxy)pyrimidin-2-yl]-2,6-difluorophenyl]-pyrrolidin-3-yl]acetic acid,
2-[1-[4-[4-phenoxy-pyrimidin-2-yl]-2,6-difluoro-phenyl]-4-piperidyl]acetic acid,
2-[1-[4-[4-(4-fluorophenoxy)pyrimidin-2-yl]-2,6-difluorophenyl]-4-piperidyl]acetic acid,
2-[1-[4-[4-(4-pyridin-3-yloxy-pyrimidin-2-yl]-2,6-difluorophenyl]-4-piperidyl]acetic acid,
2-[1-[2,6-difluoro-4-[6-(4-fluorophenoxy)pyrazin-2-yl]phenyl]-4-piperidyl]acetic acid,
2-[1-[4-[4-(4-methoxyphenoxy)pyrimidin-2-yl]-2,6-difluoro-phenyl]-4-piperidyl]acetic acid,
2-[1-[2,6-difluoro-4-[4-(4-fluorophenoxy)-6-methyl-pyrimidin-2-yl]phenyl]-4-piperidyl]acetic acid,
2-[1-[4-[4-(p-tolyloxy)pyrimidin-2-yl]-2,6-difluoro-phenyl]-4-piperidyl]acetic acid,
2-[1-[4-[4-(3,4-difluorophenoxy)pyrimidin-2-yl]-2,6-difluoro-phenyl]-4-piperidyl]acetic acid,
4-[4-(5-chloro-2-methyl-benzofuran-7-yl)-2,6-difluoro-phenoxy]-butyric acid,
5-[4-(5-chloro-2-methyl-benzofuran-7-yl)-2,6-difluoro-phenyl]-hexanoic acid,
4-[(3'-cyclobutylmethoxy-3,5-difluoro-biphenyl-4-yl)-methyl-amino]-butyric acid,
4-(3'-cyclobutylmethoxy-3,5-difluoro-biphenyl-4-yloxy)-butyric acid,
4-{[4-(6-cyclobutylmethoxy-pyridin-2-yl)-2,6-difluoro-phenyl]-methyl-amino}-butyric acid,
4-[4-(6-cyclobutylmethoxy-pyridin-2-yl)-2,6-difluoro-phenoxy]-butyric acid,
4-[(3'-cyclopropylmethoxy-3,5-difluoro-biphenyl-4-yl)-methyl-amino]-butyric acid,
4-[(3'-cyclopentyloxy-3,5-difluoro-biphenyl-4-yl)-methyl-amino]-butyric acid,
4-(3'-cyclopropylmethoxy-3,5-difluoro-4'-methoxy-biphenyl-4-yloxy)-butyric acid,
4-(3'-cyclopropylmethoxy-3,5,4'-trifluoro-biphenyl-4-yloxy)-butyric acid,
4-(5'-cyclobutoxy-3,5,3'-trifluoro-biphenyl-4-yloxy)-butyric acid,
4-[(5'-cyclobutylmethoxy-3,5-difluoro-2'-methyl-biphenyl-4-yl)-methyl-amino]-butyric acid,
4-(5'-cyclobutylmethoxy-3,5-difluoro-2'-methyl-biphenyl-4-yloxy)-butyric acid,
4-{[4-(5-chloro-6-cyclobutoxy-pyridin-2-yl)-2,6-difluoro-phenyl]-methyl-amino}-butyric acid,
4-(3'-cyclopropylmethoxy-3,5-difluoro-4'-methyl-biphenyl-4-yloxy)-butyric acid,
4-[4-(5-chloro-6-cyclobutoxy-pyridin-2-yl)-2,6-difluoro-phenoxy]-butyric acid,
4-(4'-chloro-3'-cyclopropylmethoxy-3,5-difluoro-biphenyl-4-yloxy)-butyric acid,
5-(5'-cyclobutoxy-3,3'-difluoro-biphenyl-4-yl)-pentanoic acid,
4-(5'-cyclobutoxy-3,3'-difluoro-biphenyl-4-yloxy)-butyric acid,
5-[4-(6-cyclobutoxy-pyridin-2-yl)-2-fluoro-phenyl]-pentanoic acid,
4-[4-(6-cyclobutoxy-pyridin-2-yl)-2-fluoro-phenoxy]-butyric acid,
4-[4-(6-cyclobutylmethoxy-pyridin-2-yl)-2-fluoro-phenoxy]-butyric acid,
4-[4-(6-cyclobutylsulfanyl-pyridin-2-yl)-2-fluoro-phenoxy]-butyric acid,
2-(3'-cyclobutoxy-3,5,5'-trifluoro-biphenyl-4-yloxymethyl)-cyclopropane carboxylic acid,
2-[4-(4-cyclobutoxy-6-methyl-pyrimidin-2-yl)-2,6-difluoro-phenoxymethyl]-cyclopropane carboxylic acid,
2-[4-(4-cyclobutoxy-pyrimidin-2-yl)-2,6-difluoro-phenoxymethyl]-cyclopropane carboxylic acid,
2-[4-(6-cyclobutoxy-pyridin-2-yl)-2,6-difluoro-phenoxymethyl]-cyclopropane carboxylic acid,
2-[4-(4-cyclopropylmethoxy-pyrimidin-2-yl)-2,6-difluoro-phenoxymethyl]-cyclopropane carboxylic acid,
2-[4-(4-cyclopropylmethoxy-6-methyl-pyrimidin-2-yl)-2,6-difluoro-phenoxymethyl]-cyclopropane carboxylic acid,
2-[4-(6-cyclopropylmethoxy-pyrazin-2-yl)-2,6-difluoro-phenoxymethyl]-cyclopropane carboxylic acid,
2-[4-(6-cyclobutoxy-4-methyl-pyridin-2-yl)-2,6-difluoro-phenoxymethyl]-cyclopropane carboxylic acid,
2-[4-(6-cyclopropylmethoxy-pyridin-2-yl)-2,6-difluoro-phenoxymethyl]-cyclopropane carboxylic acid,
2-[4-(6-cyclobutoxy-pyrazin-2-yl)-2,6-difluoro-phenoxymethyl]-cyclopropane carboxylic acid,
2-[4-(2-cyclobutoxy-thiazol-4-yl)-2,6-difluoro-phenoxymethyl]-cyclopropane carboxylic acid,
2-[2-chloro-4-(6-cyclopropylmethoxy-pyridin-2-yl)-6-fluoro-phenoxymethyl]-cyclopropane carboxylic acid,
2-[2-chloro-4-(4-cyclobutoxy-6-methyl-pyrimidin-2-yl)-6-fluoro-phenoxymethyl]-cyclopropane carboxylic acid,
2-[2-chloro-4-(6-cyclobutoxy-pyridin-2-yl)-6-fluoro-phenoxymethyl]-cyclopropane carboxylic acid,
3-[6-(3-cyclobutoxy-phenyl)-chroman-2-yl]-propionic acid,
3-[6-(6-propoxy-pyridin-2-yl)-chroman-2-yl]-propionic acid,
4-[2,6-difluoro-4-(1H-indol-6-yl)-phenoxy]-butanoic acid,
4-[2,6-difluoro-4-(1-isopropyl-1H-indol-6-yl)-phenoxy]-butanoic acid,
4-[4-(1-cyclopropylmethyl-1H-indol-6-yl)-2,6-difluoro-phenoxy]-butanoic acid
{1-[4-(6-cyclopropylmethoxy-pyridin-2-yl)-2,6-difluoro-phenyl]-pyrrolidin-3-yl}-acetic acid,
{1-[4-(6-cyclobutoxy-pyridin-2-yl)-2,6-difluoro-phenyl]-pyrrolidin-3-yl}-acetic acid, 4-[4-(3-chloro-1-isopropyl-1H-indol-6-yl)-2,6-difluoro-phenoxy]-butanoic acid,
{1-[2,6-difluoro-4-(6-isopropoxy-pyridin-2-yl)-phenyl]-pyrrolidin-3-yl}-acetic acid,
{1-[4-(6-cyclobutylmethoxy-pyridin-2-yl)-2,6-difluoro-phenyl]-pyrrolidin-3-yl}-acetic acid,
4-[4-(5-cyclopropylmethoxymethyl-thiophen-2-yl)-2,6-difluoro-phenoxy]-butanoic acid,
4-[4-(5-cyclopropylmethoxymethyl-thiophen-3-yl)-2,6-difluoro-phenoxy]-butanoic acid,
{1-[4-(5-cyclopropylmethoxymethyl-thiophen-3-yl)-2,6-difluoro-phenyl]-piperidin-4-yl}-acetic acid,
4-[4-(4-cyclopropylmethoxymethyl-2-methyl-thiazol-5-yl)-2,6-difluoro-phenoxy]-butanoic acid,
{1-[4-(5-cyclomethoxymethyl-thiophen-2-yl)-2,6-difluoro-phenyl]-piperidin-4-yl}-acetic acid,
{1-[4-(4-cyclopropylmethoxymethyl-2-methyl-thiazol-5-yl)-2,6-difluoro-phenyl]-piperidin-4-yl}-acetic acid,
4-[4-(5-cyclobutylmethoxymethyl-thiophen-3-yl)-2,6-difluoro-phenoxy]-butanoic acid,
4-[2,6-difluoro-4-(5-isobutoxymethyl-thiophen-3-yl)-phenoxy]-butanoic acid,
4-[4-(5-cyclobutoxymethyl-thiophen-3-yl)-2,6-difluoro-phenoxy]-butanoic acid,
4-[4-(3-cyclopropylmethoxymethyl-thiophen-2-yl)-2,6-difluoro-phenoxy]-butanoic acid,
{1-[4-(4-cyclobutoxy-6-methyl-pyrimidin-2-yl)-2,6-difluoro-phenyl]-pyrrolidin-3-yl}-acetic acid,
{1-[4-(4-cyclopropylmethoxy-6-methyl-pyrimidin-2-yl)-2,6-difluoro-phenyl]-pyrrolidin-3-yl}-acetic acid,
{1-[4-(6-cyclobutoxy-4-methyl-pyridin-2-yl)-2,6-difluoro-phenyl]-pyrrolidin-3-yl}-acetic acid,
{1-[4-(6-cyclobutoxy-pyrazin-2-yl)-2,6-difluoro-phenyl]-pyrrolidin-3-yl}-acetic acid,
{1-[4-(4-cyclobutoxy-pyrimidin-2-yl)-2,6-difluoro-phenyl]-pyrrolidin-3-yl}-acetic acid,
{1-[4-(6-cyclopropylmethoxy-pyrazin-2-yl)-2,6-difluoro-phenyl]-pyrrolidin-3-yl}-acetic acid,
{1-[4-(4-cyclopropylmethoxy-pyrimidin-2-yl)-2,6-difluoro-phenyl]-pyrrolidin-3-yl}-acetic acid,
{1-[4-(2-cyclobutoxy-thiazol-4-yl)-2,6-difluoro-phenyl]-pyrrolidin-3-yl}-acetic acid,
{1-[4-(2-cyclopropylmethoxy-thiazol-4-yl)-2,6-difluoro-phenyl]-pyrrolidin-3-yl}-acetic acid,
{1-[2,6-difluoro-4-(6-methoxy-pyrazin-2-yl)-phenyl]-pyrrolidin-3-yl}-acetic acid,
{1-[4-(6-ethoxy-pyrazin-2-yl)-2,6-difluoro-phenyl]-pyrrolidin-3-yl}-acetic acid,
{1-[2,6-difluoro-4-(6-isopropoxy-pyrazin-2-yl)-phenyl]-pyrrolidin-3-yl}-acetic acid,
{1-[2,6-difluoro-4-(4-isopropoxy-6-methyl-pyrimidin-2-yl)-phenyl]-pyrrolidin-3-yl}-acetic acid,
{1-[2,6-difluoro-4-(4-isobutoxy-6-methyl-pyrimidin-2-yl)-phenyl]-pyrrolidin-3-yl}-acetic acid,
{1-[2,6-difluoro-4-(4-methyl-6-propoxy-pyrimidin-2-yl)-phenyl]-pyrrolidin-3-yl}-acetic acid,
{1-[4-(4-ethoxy-6-methyl-pyrimidin-2-yl)-2,6-difluoro-phenyl]-pyrrolidin-3-yl}-acetic acid,
{1-[4-(5-cyclobutoxy-3-methyl-isothiazol-4-yl)-2,6-difluoro-phenyl]-pyrrolidin-3-yl}-acetic acid,
{1-[4-(4-cyclobutoxy-5-fluoro-pyrimidin-2-yl)-2,6-difluoro-phenyl]-pyrrolidin-3-yl}-acetic acid,
{1-[4-(4-cyclopropylmethoxy-5-fluoro-pyrimidin-2-yl)-2,6-difluoro-phenyl]-pyrrolidin-3-yl}-acetic acid,
{1-[2,6-difluoro-4-(5-fluoro-4-isobutoxy-pyrimidin-2-yl)-phenyl]-pyrrolidin-3-yl}-acetic acid,
(1-{2,6-difluoro-4-[6-(3-methoxy-propoxy)-pyridin-2-yl]-phenyl}-pyrrolidin-3-yl)-acetic acid,
(1-{2,6-difluoro-4-[6-(tetrahydro-thiopyran-4-yloxy-pyridin-2-yl]-phenyl}-pyrrolidin-3-yl)-acetic acid,
{1-[2,6-difluoro-4-(5-fluoro-4-isobutoxy-pyrimidin-2-yl)-phenyl]-piperidin-4-yl}-acetic acid,
{1-[2,6-difluoro-4-(5-fluoro-4-propoxy-pyrimidin-2-yl)-phenyl]-piperidin-4-yl}-acetic acid,
(1-{2,6-difluoro-4-[4-(3-methyl-butoxy)-pyrimidin-2-yl]-phenyl}-piperidin-4-yl)-acetic acid,
(1-{2,6-difluoro-4-[4-(3-methoxy-propoxy)-pyrimidin-2-yl]-phenyl}-piperidin-4-yl)-acetic acid,
(1-{2,6-difluoro-4-[4-(3-methoxy-propoxy)-6-methyl-pyrimidin-2-yl]-phenyl}-piperidin-4-yl)-acetic acid,
(1-{2,6-difluoro-4-[4-(2-methoxy-ethoxy)-6-methyl-pyrimidin-2-yl]-phenyl}-piperidin-4-yl)-acetic acid,
(1-{2,6-difluoro-4-[6-(3-methoxy-propoxy)-pyridin-2-yl]-phenyl}-piperidin-4-yl)-acetic acid,
{(S)-1-[4-(6-cyclopropylmethoxy-pyridin-2-yl)-2,6-difluoro-phenyl]-pyrrolidin-3-yl}-acetic acid,
2-[1-[2,6-difluoro-4-[4-[(6-methyl-3-pyridyl)oxy]pyrimidin-2-yl]phenyl]-4-piperidyl]acetic acid,
2-[1-[2,6-difluoro-4-[6-(4-ethylphenoxy)pyrimidin-2-yl]phenyl]-4-piperidyl]acetic acid,
2-[1-[4-[4-(3-fluorophenoxy)pyrimidin-2-yl]-2,6-difluoro-phenyl]-4-piperidyl]acetic acid,
2-[1-[2,6-difluoro-4-[4-(3,4-fluorophenoxy)-6-methyl-pyrimidin-2-yl]phenyl]-4-piperidyl]acetic acid,
2-[1-[2,6-difluoro-4-[4-(2-pyridyloxy)pyrimidin-2-yl]phenyl]-4-piperidyl]acetic acid,
2-[1-[2,6-difluoro-4-[4-[4-(trifluoromethyl)phenoxy]pyrimidin-2-yl]phenyl]-4-piperidyl]acetic acid,
2-[1-[2,6-difluoro-4-[4-[3-(trifluoromethyl)phenoxy]pyrimidin-2-yl]phenyl]-4-piperidyl]acetic acid,
2-[1-[2,6-difluoro-4-[4-methyl-6-[4-(trifluoromethyl)phenoxy]pyrimidin-2-yl]phenyl]-4-piperidyl]acetic acid,
2-[1-[2,6-difluoro-4-[4-methyl-6-[3-(trifluoromethyl)phenoxy]pyrimidin-2-yl]phenyl]-4-piperidyl]acetic acid,
{1-[4-(6-cyclobutoxy-4-trifluoromethyl-pyridin-2-yl)-2,6-difluoro-phenyl]-piperidin-4-yl}-acetic acid,
(1-{2,6-difluoro-4-[2-(4-fluoro-phenyl)-benzo[b]thiophen-4-yl]-phenyl}-piperidin-4-yl)-acetic acid,
{1-[2,6-difluoro-4-(2-m-tolyl-benzo[b]thiophen-4-yl)-phenyl]-piperidin-4-yl}-acetic acid,
{1-[4-(4-cyclobutoxy-6-trifluoromethyl-pyrimidin-2-yl)-2,6-difluoro-phenyl]-piperidin-4-yl}-acetic acid,
{1-[2,6-difluoro-4-(4-propoxy-6-trifluoromethyl-pyrimidin-2-yl)-phenyl]-piperidin-4-yl}-acetic acid,
(1-{2,6-difluoro-4-[4-(4-fluoro-phenoxy)-6-trifluoromethyl-pyrimidin-2-yl]-phenyl}-piperidin-4-yl)-acetic acid,
3-{1-[2,6-difluoro-4-(6-propoxy-pyridin-2-yl)-phenyl]-piperidin-4-yl}-propionic acid,
3-{1-[4-(6-cyclobutyl-pyridin-2-yl)-2,6-difluoro-phenyl]-piperidin-4-yl}-propionic acid, and
3-{1-[4-(6-ethoxy-pyridin-2-yl)-2,6-difluoro-phenyl]-piperidin-4-yl}-propionic acid.

The terms and abbreviations used herein retain their original meanings unless indicated otherwise.

The present invention also provides a method for preparing the compound of Formula 1. Hereinafter, the method for preparing the compound of Formula 1 is explained based on exemplary reactions in order to illustrate the present invention. However, a person skilled in the art could prepare the compound of Formula 1 by various methods based on the structure of Formula 1, and such methods should be interpreted as being within the scope of the present invention. That is, the compound of Formula 1 may be prepared by the methods described herein or by combining various methods disclosed in the prior art, which should be interpreted as being within the scope of the present invention. Accordingly, a method for preparing the compound of Formula 1 is not limited to the following methods.

As represented in the following Reaction Scheme 1, the compound of Formula 1 according to the present invention can be prepared by C—C coupling reaction of Compound 2 and Compound 3 in the presence of a conventional metal catalyst, and, if necessary, additional hydrolysis.

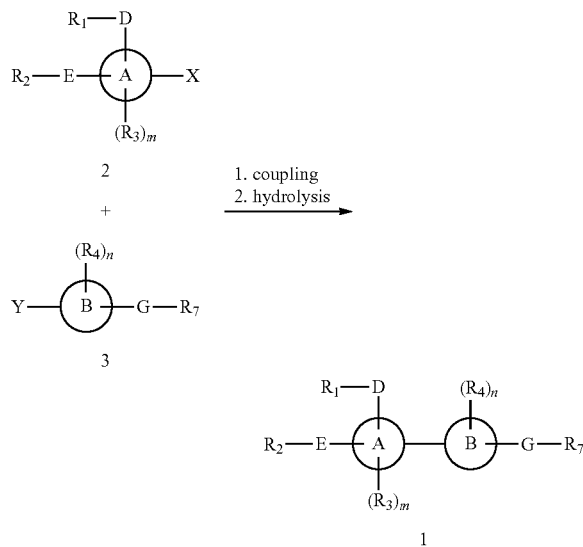

[Reaction Scheme 1]

In addition, the compound of Formula 1 according to the present invention can be prepared by coupling reaction of Compound 4 and Compound 5, Compound 6 or Compound 7 in the presence of conventional base or coupling reagents and, if necessary, additional hydrolysis, as represented in the following Reaction Scheme 2. In the Reaction Scheme 2, $Z$—$R_7$ and J of Compounds 4 and 7 represent independently halogen, OH, SH or O-alkyl. When $Z$—$R_7$ is O-alkyl, it is converted to OH by dealkylation reaction before being subjected to coupling reaction.

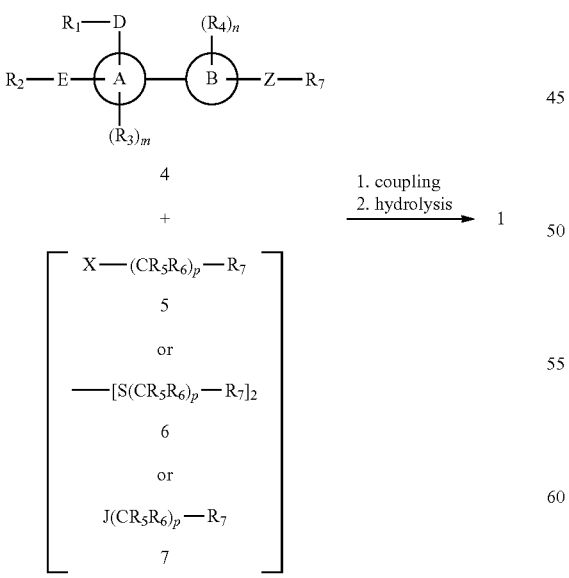

[Reaction Scheme 2]

Furthermore, the compound of Formula 1 according to the present invention can be prepared by reacting Compound 8 substituted with J radical with Compound 9 or Compound 10 in the presence of conventional base, metal catalysts or coupling reagents, as represented in the following Reaction Scheme 3. In Reaction Scheme 3, J and Y represent independently halogen, OH, SH or $NH_2$. When J is amine, "reductive-amination reaction" can be carried out with Compound 11.

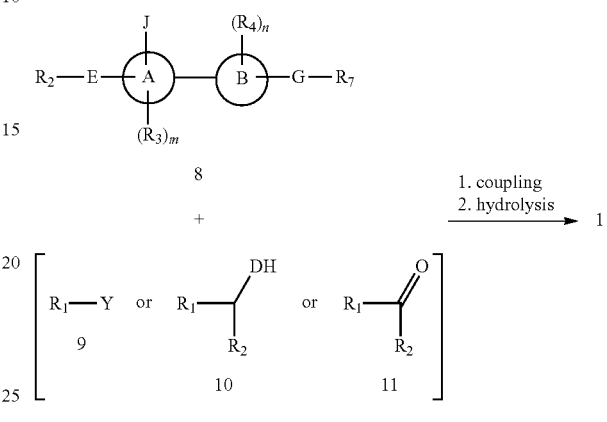

[Reaction Scheme 3]

In Reaction Scheme 1, Compound 2 can be obtained by the coupling reaction of Compound 12 and Compound 13 in the presence of conventional acid, base or coupling reagent, as represented in the following Reaction Scheme 4.

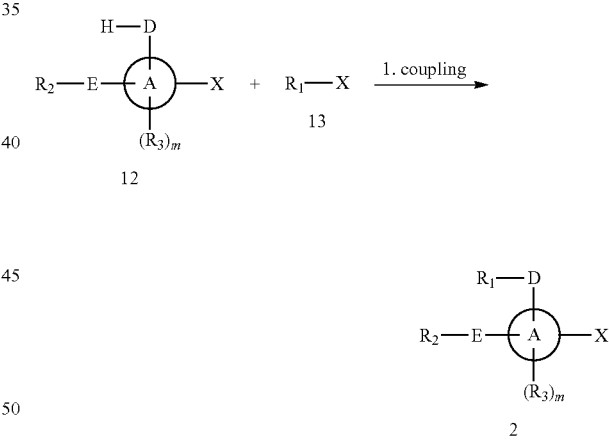

[Reaction Scheme 4]

In addition, Compound 2 can be prepared by the coupling reaction of Compound 14 and Compound 10 in the presence of conventional base and metal catalyst, as represented in the following Reaction Scheme 5.

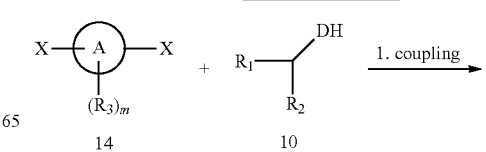

[Reaction Scheme 5]

Furthermore, Compound 2 in which $R_1$ and $R_2$ form a ring with D and E can be prepared in the presence of conventional acid, as represented in the following Reaction Scheme 6.

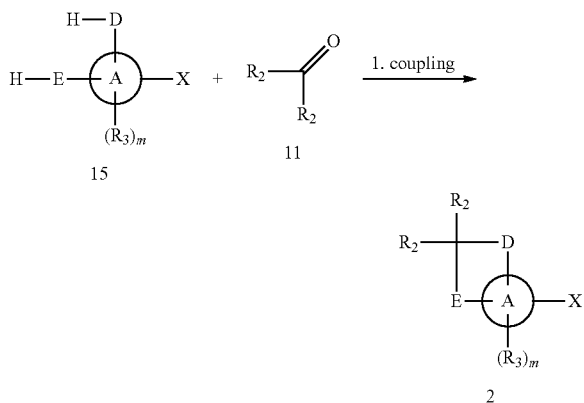

Meanwhile, Compound 3 can be prepared by the coupling reaction of Compound 16 and Compound 17 in the presence of conventional base or coupling reagent, as represented in the following Reaction Scheme 7.

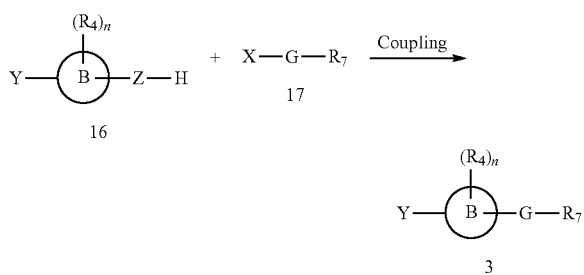

In the above Reaction Schemes 1 to 7,

X represents halogen or $-OSO_2CF_3$,

Y represents boronic acid or boronic acid ester, and

A, B, D, E, G, $R_1$, $R_2$, $R_3$, $R_4$, $R_7$, m, n and p are the same as in the above Formula 1.

In the above reaction, transition metal such as palladium (Pd) can be used as a conventional metal catalyst. The above reactions can be carried out in conventional solvents which do not have an adverse effect on the reactions. Preferable solvents include, but are not limited to, one or more selected from dimethylformamide, dimethylacetamide, tetrahydrofuran, acetonitrile, methanol, ethanol, water, 1,2-dichloroethane, dimethylsulfoxide, ethylether, methyl tert-butylether, methylene chloride and chloroform.

In the above reactions, unexplained compounds are known compounds or compounds easily obtainable from known compounds by known methods or similar methods.

The compound of Formula 1 obtained by the above methods can be separated or purified from the reaction products by conventional methods such as recrystallization, ionospheresis, silica gel column chromatography or ion-exchange chromatography.

As explained above, the compounds according to the present invention, starting materials or intermediates for the preparation thereof can be prepared by a variety of methods, which should be interpreted as being within the scope of the present invention.

The compound of Formula 1 according to the present invention has the effect of GPR120 agonist. Accordingly, the present invention provides a pharmaceutical composition as a GPR120 agonist comprising the compound of Formula 1, a pharmaceutically acceptable salt or isomer thereof as an active ingredient. Various kinds of prodrugs, which are converted into the compound of Formula I in vivo, are also within the scope of the present invention.

Exemplary diseases which can be prevented or treated by the pharmaceutical composition according to the present invention as a GPR120 agonist include, but are not limited to, metabolic diseases such as diabetes, complications of diabetes, obesity, non-alcoholic fatty liver, steatohepatitis, osteoporosis and the like, and inflammation. The complications of diabetes include, but are not limited to, neurogenic disease, hyperlipidemia, hypertension, retinosis and renal failure.

In addition, the present invention provides a method for preparing the composition for preventing or treating metabolic diseases such as diabetes, complications of diabetes, obesity, non-alcoholic fatty liver, steatohepatitis, osteoporosis and the like, and inflammation which comprises the step of mixing the compound of Formula 1, a pharmaceutically acceptable salt or isomer thereof as an active ingredient and a pharmaceutically acceptable carrier.

In the present invention, a "pharmaceutical composition" or a "composition for lowering blood glucose level" may include other components such as carriers, diluents, excipients, etc., in addition to the active ingredient of the present invention. Accordingly, the pharmaceutical composition may include pharmaceutically acceptable carriers, diluents, excipients or combinations thereof, if necessary. The pharmaceutical composition facilitates the administration of compounds into the body. Various methods for administering the compounds include, but are not limited to, oral, injection, aerosol, parenteral and local administration.

Herein, a "carrier" means a compound that facilitates the addition of compounds into the cell or tissue. For example, dimethylsulfoxide (DMSO) is a conventional carrier facilitating the administration of many organic compounds into living cells or tissues.

Herein, a "diluent" means a compound that not only stabilizes a biologically active form but is diluted in solvent dissolving the compounds. A dissolved salt in buffer is used as a diluent in this field. A conventionally used buffer is a phosphate buffer saline mimicking salt form in body fluid. Since a buffer solution can control the pH of the solution at low concentration, a buffer diluent hardly modifies the biological activity of compounds.

Herein, "pharmaceutically acceptable" means such property that does not impair the biological activity and physical property of compounds.

The compounds according to the present invention can be formulated as various pharmaceutically administered dosage forms. In the preparation of the pharmaceutical composition of the present invention, an active component—specifically, the compound of Formula 1 or a pharmaceutically acceptable salt or isomer thereof—is mixed with selected pharmaceutically acceptable carriers considering the dosage form to be prepared. For example, the pharmaceutical composition of the present invention can be formulated as injections, oral preparations and the like, as needed.

The compound of the present invention can be formulated by conventional methods using known pharmaceutical carriers and excipients, and inserted into a unit or multi-unit containers. The formulations may be solution, suspension or emulsion in oil or aqueous solvent and include conventional dispersing agents, suspending agents or stabilizing agents. In addition, the compound may be, for example, dry powder form which is dissolved in sterilized pyrogen-free water before use. The compound of the present invention can be formulated into suppositories by using a conventional suppository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the compounds of the present invention with at least one carrier selected from inert diluents such as sucrose, lactose or starch, lubricants such as magnesium stearate, disintegrating agents, binders and the like.

The compound or a pharmaceutical composition comprising the same according to the present invention can be administered in combination with other drugs—for example, other antidiabetics—as required.

The dose of the compound of Formula 1 according to the present invention is determined by a physician's prescription considering the patient's body weight, age and disease condition. A typical dose for adults is in the range of about 0.3 to 500 mg per day according to the frequency and intensity of administration. A typical daily dose of intramuscular or intravenous administration for adults is in the range of about 1 to 300 mg per day which can be administered in divided unit dosages. Some patients need a higher daily dose.

The present invention also provides a method for preventing or treating diseases by using an effective amount of the compound of Formula 1 or a pharmaceutically acceptable salt or isomer thereof as an active ingredient of GPR120 agonist. Representative diseases to be treated by GPR120 agonist include, but are not limited to, metabolic diseases such as the above-mentioned diabetes, complications of diabetes, obesity, non-alcoholic fatty liver, steatohepatitis and osteoporosis, and inflammatory diseases. Herein, the term "treatment" is used to mean deterring, delaying or ameliorating the progress of diseases in a subject exhibiting symptoms of diseases. The term "prevention" is used to mean deterring, delaying or ameliorating the sign of diseases in a subject at risk of exhibiting symptoms of diseases, even if he or she does not exhibit the symptoms.

Effects of the Invention

The biaryl derivative of Formula 1 according to the present invention as a GPR120 agonist promotes GLP-1 formation in the gastrointestinal tract and improve insulin resistance in the liver or in muscle due to anti-inflammatory action in macrophages, lipocytes, etc., and can accordingly be effectively used for preventing or treating metabolic diseases such as diabetes, complications of diabetes, obesity, non-alcoholic fatty liver, steatohepatitis, osteoporosis and the like, and inflammatory diseases.

MODES FOR THE INVENTION

The present invention is explained in more detail by the following Examples. However, these Examples seek to illustrate the present invention only, and the scope of the present invention is not limited by them.

Hereinafter, M means molar concentration and N means normal concentration. In addition, abbreviations used in the following Preparation Examples and Examples are as follows:

AcCl: acetyl chloride
AcOH: acetic acid
$BBr_3$: boron tribromide
BINAP: 2,2'-bis(diphenylphosphino)-1,1'-binaphthyl
$Br_2$: bromine
$Bu_4NI$: tetrabutylammonium iodide
CSA: camphosulfonic acid
$CH_3CN$: acetonitrile
$Cs_2CO_3$: cesium carbonate
DBU: 1,8-diazabicyclo[5.4.0]undec7-ene
DCE: 1,2-dichloroethane
DCM: dichloromethane
DIBAL-H: diisobutylaluminum hydride
DIPEA: N,N-diisopropylethylamine
DME: 1,2-dimethoxyethane
DMF: N,N-dimethylformamide
DMS: dimethyl sulfide
DMSO: dimethyl sulfoxide
DPPF: 1,1'-bis(diphenylphosphino)ferrocene
EtOAc: ethyl acetate
EtOH: ethanol
$Et_2O$: diethyl ether
$Fe(acac)_3$: iron(III)acetylacetonate
HCl: hydrochloric acid
Hex: n-hexane
IBX: 2-iodoxybenzoic acid
$K_2CO_3$: potassium carbonate
KOAc: potassium acetate
LAH: lithium aluminum hydride
LiHMDS: bis(trimethylsilyl)amide lithium
MC: methylene chloride
mCPBA: 3-chloroperbenzoic acid
MeOH: methanol
$MgSO_4$: magnesium sulfate
MsCl: methanesulfonyl chloride
MTBE: tert-butyl methyl ether
$NaBH_4$: sodium borohydride
NaCl: sodium chloride
$Na_2CO_3$: sodium carbonate
NaH: sodium hydride
NaOAc: sodium acetate
NaOEt: sodium ethoxide
NaOH: sodium hydroxide
NBS: N-bromosuccinimide
n-BuLi: butyl lithium
NCS: N-chlorosuccinimide
NMM: 4-methylmorpholine
NMP: 1-methylpyrrolidin-2-one
Pd/C: palladium/carbon
$PdCl_2$(dppf)-DCM: 1,1'-bis(diphenylphosphino)ferrocene-palladium(II) dichloride dichloromethane
$PdCl_2(PPh_3)_2$: bis(triphenylphosphine)palladium(II) dichloride
$Pd_2(dba)_3$: tris(dibenzylideneacetone)dipalladium(0)

Pd(OAc)$_2$: palladium(II) acetate
Pd(PPh$_3$)$_4$: tetrakis(triphenylphosphine)palladium(0)
PtO$_2$: platinum(IV)oxide
SOCl$_2$: thionyl chloride
SPhos: 2-dicyclohexylphosphino-2',6'-dimethoxybiphenyl
TBAB: tetrabutylammonium bromide
TEA: triethylamine
TFA: trifluoroacetic acid
THF: tetrahydrofuran
TMEDA: N,N,N',N'-tetramethylethylenediamine
TMSCl: chlorotrimethylsilane Preparation Example 1: 3-[6-(4,4,5,5-tetramethyl-[1,3,2]dioxaborolan-2-yl)-quinolin-2-yl]-propionic acid ethyl ester Step A: 6-bromo-2-methyl-quinoline 4-Bromo-phenylamine (3.0 g, 17.44 mmol) was dissolved in 30 mL of 6N HCl. Crotonaldehyde (2.44 g, 34.88 mmol) was slowly added thereto, and the reaction mixture was stirred at 100° C. for 16 hours. The mixture was cooled to 0° C., neutralized with aqueous ammonia, extracted with EtOAc and purified by column chromatography to obtain the title compound (2 g, 52%).
$^1$H-NMR (CDCl$_3$) δ 8.02~7.92 (2H, m), 7.89 (1H, d), 7.73 (1H, d), 7.32 (1H, d), 1.60 (3H, s)

Step B: 6-bromo-quinolin-2-carbaldehyde

6-Bromo-2-methyl-quinoline (1.0 g, 4.50 mmol) obtained in Step A was dissolved in 1,4-dioxane. Selenium dioxide (0.65 g, 5.85 mmol) was added thereto, and the reaction mixture was stirred at 80° C. for 3 hours. The mixture was filtered through Celite and solidified with Et$_2$O to obtain the title compound (0.93 g, 88%).
$^1$H-NMR (CDCl$_3$) δ 10.20 (1H, s), 8.22 (1H, d), 8.15~8.02 (3H, m), 7.90 (1H, d)

Step C: (E)-3-(6-bromo-quinolin-2-yl)-acrylic acid ethyl ester

6-Bromo-quinolin-2-carbaldehyde (0.93 g, 3.95 mmol) obtained in Step B was dissolved in THF. NaH (60%)(0.17 g, 4.35 mmol) was slowly added thereto at 0° C., and the reaction mixture was stirred for 30 minutes. Triethyl phosphonoacetate (0.97 g, 4.35 mmol) was added dropwise, and the reaction mixture was stirred at room temperature for 16 hours. The reaction solution was extracted with EtOAc and purified by column chromatography to obtain the title compound (0.86 g, 72%).
$^1$H-NMR (CDCl$_3$) δ 8.10 (1H, d), 8.00~7.92 (2H, m), 7.82~7.70 (2H, m), 7.63 (1H, d), 6.97 (1H, d), 4.30 (2H, q), 1.36 (3H, t)

Step D: (E)-3-[6-(4,4,5,5-tetramethyl-[1,3,2]dioxaborolan-2-yl)-quinolin-2-yl]-acrylic acid ethyl ester (E)-3-(6-bromo-quinolin-2-yl)-acrylic acid ethyl ester (0.86 g, 2.82 mmol) obtained in Step C, bis(pinacolato)diboron (0.86 g, 3.39 mmol), potassium acetate (0.83 g, 8.47 mmol) and DPPF (0.11 g, 0.2 mol) were dissolved in 10 mL of 1,4-dioxane and charged with N$_2$ gas for 5 minutes. PdCl$_2$(dppf)-DCM (0.16 g, 0.2 mmol) was added thereto, and the reaction mixture was stirred at 80° C. for 4 hours. The reaction solution was filtered through Celite and purified by column chromatography to obtain the title compound (0.84 g, 86%).
$^1$H-NMR (CDCl$_3$) δ 8.31 (1H, s), 8.20 (1H, d), 8.10~8.05 (2H, m), 7.89 (1H, d), 7.60 (1H, d), 6.98 (1H, d), 4.30 (2H, q), 1.35 (12H, s), 1.25 (3H, t)

Step E: 3-[6-(4,4,5,5-tetramethyl-[1,3,2]dioxaborolan-2-yl)-quinolin-2-yl]-propionic acid ethyl ester (E)-3-[6-(4,4,5,5-tetramethyl-[1,3,2]dioxaborolan-2-yl)-quinolin-2-yl]-acrylic acid ethyl ester (0.83 g, 2.35 mmol) obtained in Step D was dissolved in MeOH. 10% Pd/C (0.08 g) was added thereto, and the reaction mixture was stirred at room temperature for 2 hours under hydrogen atmosphere. After termination of the reaction, the mixture was filtered through Celite and concentrated under reduced pressure to obtain the title compound (0.83 g, 99%).
$^1$H-NMR (CDCl$_3$) δ 8.29 (1H, s), 8.10~7.90 (3H, m), 7.33 (1H, d), 4.17 (2H, q), 3.32 (2H, t), 2.94 (2H, t), 1.39 (12H, s), 1.25 (3H, t)

Preparation Example 2: [6-(4,4,5,5-tetramethyl-[1,3,2]dioxaborolan-2-yl)-naphthalen-2-yloxy]-acetic acid ethyl ester Step A: (6-bromo-naphthalen-2-yloxy)-acetic acid ethyl ester 6-Bromo-naphthalen-2-ol (1.0 g, 4.48 mmol) was dissolved in 20 mL of DMF and cooled to 0° C. Cs$_2$CO$_3$ (1.75 g, 5.38 mmol) and bromoacetic acid ethyl ester (0.75 g, 4.48 mmol) were added thereto, and the mixture was stirred at room temperature for 16 hours. Water was added to the reaction solution, and the solution was extracted with EtOAc to separate an organic layer. The organic layer was dried with MgSO$_4$ and purified by column chromatography to obtain the title compound (1.3 g, 94%).
$^1$H-NMR (CDCl$_3$) δ 7.93 (1H, s), 7.70 (1H, d), 7.60 (1H, d), 7.50 (1H, d), 7.24 (1H, d), 7.04 (1H, s), 4.72 (2H, s), 4.29 (2H, q), 1.29 (3H, t)

Step B: [6-(4,4,5,5-tetramethyl-[1,3,2]dioxaborolan-2-yl)-naphthalen-2-yloxy]-acetic acid ethyl ester (6-Bromo-naphthalen-2-yloxy)-acetic acid ethyl ester (0.5 g, 1.62 mmol) obtained in Step A was reacted in the same manner as in Step D of Preparation Example 1 to obtain the title compound (0.48 g, 83%).
$^1$H-NMR (CDCl$_3$) δ 8.29 (1H, s), 7.80 (2H, d), 7.68 (1H, d), 7.21 (1H, d), 7.06 (1H, s), 4.74 (2H, s), 4.31 (2H, q), 1.38 (12H, s), 1.29 (3H, t)

Preparation Example 3: 4-[6-(4,4,5,5-tetramethyl-[1,3,2]dioxaborolan-2-yl)-naphthalen-2-yloxy]-butyric acid ethyl ester Step A: 4-(6-bromo-naphthalen-2-yloxy)-butyric acid ethyl ester 6-Bromo-naphthalen-2-ol (1.0 g, 4.48 mmol) and 4-bromo-butyric acid ethyl ester (0.87 g, 4.48 mmol) were reacted in the same manner as in Step A of Preparation Example 2 to obtain the title compound (1.5 g, 94%).
$^1$H-NMR (CDCl$_3$) δ 7.91 (1H, s), 7.65 (1H, d), 7.57 (1H, d), 7.48 (1H, d), 7.15 (1H, d), 7.08 (1H, s), 4.20~4.10 (4H, m), 2.55 (2H, t), 2.18 (2H, t), 1.25 (3H, t)

Step B: 4-[6-(4,4,5,5-tetramethyl-[1,3,2]dioxaborolan-2-yl)-naphthalen-2-yloxy]-butyric acid ethyl ester 4-(6-Bromo-naphthalen-2-yloxy)-butyric acid ethyl ester (1 g, 2.96 mmol) obtained in Step A were reacted in the same manner as in Step D of Preparation Example 1 to obtain the title compound (0.8 g, 70%).
$^1$H-NMR (CDCl$_3$) δ 8.27 (1H, s), 7.78~7.75 (2H, m), 7.69 (1H, d), 7.12~7.08 (2H, m), 4.18~4.10 (4H, m), 2.55 (2H, t), 2.18 (2H, t), 1.33 (12H, s), 1.25 (3H, t)

Preparation Example 4: 3-[6-(4,4,5,5-tetramethyl-[1,3,2]dioxaborolan-2-yl)-chroman-2-yl]-propionic acid ethyl ester

Step A: chroman-2-carboxylic acid

4-Oxo-4H-chromene-2-carboxylic acid (4.0 g, 21.03 mmol) was dissolved in 20 mL of acetic acid. 10% Pd/C (0.4 g) was added thereto and stirred at room temperature for 16 hours under 60 psi of hydrogen. The reaction solution was filtered through Celite, diluted with EtOAc, and extracted with sodium bicarbonate aqueous solution. The water layer was again acidified with 6N HCl and extracted with EtOAc. The organic layer was dried with MgSO$_4$ and concentrated under reduced pressure to obtain the title compound (3.0 g, 80%).
$^1$H-NMR (CDCl$_3$) δ 7.13 (1H, t), 7.05 (1H, d), 6.95~6.85 (2H, m), 4.75 (1H, m), 3.00~2.80 (2H, m), 2.40 (1H, m), 2.20 (1H, m)

Step B: chroman-2-yl-methanol

Chroman-2-carboxylic acid (1.0 g, 5.61 mmol) obtained in Step A was dissolved in 20 mL of THF and cooled to −20° C. Isobutyl chloroformate (0.84 g, 6.17 mmol) and NMM (0.65 g, 6.45 mmol) were added thereto and the mixture was stirred at the same temperature for 1 hour. NaBH$_4$ (0.42 g, 11.22 mmol) was dissolved in THF at another reactor and cooled to −78° C. The above reaction solution was filtered through Celite, added to another reactor, and the mixture was stirred at room temperature for 2 hours. The reaction solution was extracted with EtOAc, dried with MgSO$_4$ and purified by column chromatography to obtain the title compound (0.8 g, 87%).
$^1$H-NMR (CDCl$_3$) δ 7.15~7.05 (2H, m), 6.90~6.80 (2H, m), 4.15 (1H, m), 3.85~3.70 (2H, m), 2.95~2.75 (2H, m), 2.10~1.80 (3H, m)

Step C: (E)-3-chroman-2-yl-acrylic acid ethyl ester

Oxalyl chloride (1.16 g, 9.13 mmol) was added to 30 mL of DCM and cooled to −78° C. DMSO (1.19 g, 15.22 mmol) was slowly added thereto and stirred for 0.5 hour. The solution in with chroman-2-yl-methanol (1.0 g, 6.09 mmol) obtained in Step B was dissolved in 5 mL of DCM and TEA (2.46 g, 24.36 mmol) were sequentially and slowly added. The mixture was stirred at room temperature for 1 hour, and (carbethoxymethylene)triphenylphosphorane (2.54 g, 7.30 mmol) was then added thereto and the reaction of the mixture was carried out at room temperature for 16 hours. Water was added to the reaction solution, and this solution was extracted with DCM to separate an organic layer. The organic layer was dried with MgSO$_4$ and purified by column chromatography to obtain the title compound (1.47 g, 69%).
$^1$H-NMR (CDCl$_3$) δ 7.20~7.00 (3H, m), 6.90~6.80 (2H, m), 6.18 (1H, m), 4.75 (1H, m), 4.24 (2H, q), 2.95~2.70 (2H, m), 2.15 (1H, m), 1.85 (1H, m), 1.26 (3H, t)

Step D: 3-chroman-2-yl-propionic acid ethyl ester (E)-3-chroman-2-yl-acrylic acid ethyl ester (0.53 g, 2.28 mmol) obtained in Step C was dissolved in MeOH. 10% Pd/C (0.05 g) was added thereto, and the reaction mixture was stirred at room temperature for 16 hours under hydrogen atmosphere. After termination of the reaction, the mixture was filtered through Celite and concentrated under reduced pressure to obtain the title compound (0.51 g, 96%).
$^1$H-NMR (CDCl$_3$) δ 7.12~7.00 (2H, m), 6.84~6.77 (2H, m), 4.16 (2H, q), 4.01 (1H, m), 2.90~2.70 (2H, m), 2.68~2.51 (2H, m), 2.05~1.95 (3H, m), 1.75 (1H, m), 1.22 (3H, t)

Step E: 3-(6-bromo-chroman-2-yl)-propionic acid ethyl ester

3-Chroman-2-yl-propionic acid ethyl ester (0.2 g, 0.85 mmol) obtained in Step D was dissolved in 15 mL of DMF. NBS (0.15 g, 0.85 mmol) was added thereto at 0° C., and the reaction mixture was stirred at room temperature for 24 hours. The reaction solution was concentrated and 50 mL of water was added thereto. The reaction solution was extracted with Et$_2$O, dried with MgSO$_4$ and purified by column chromatography to obtain the title compound (0.21 g, 80%).
$^1$H-NMR (CDCl$_3$) δ 7.17~7.10 (2H, m), 6.65 (1H, d), 4.16 (2H, q), 3.97 (1H, m), 2.90~2.70 (2H, m), 2.65~2.50 (2H, m), 2.05~1.95 (3H, m), 1.72 (1H, m), 1.26 (3H, t)

Step F: 3-[6-(4,4,5,5-tetramethyl-[1,3,2]dioxaborolan-2-yl)-chroman-2-yl]-propionic acid ethyl ester 3-(6-Bromo-chroman-2-yl)-propionic acid ethyl ester (0.21 g, 0.67 mmol) obtained in Step E was reacted in the same manner as in Step D of Preparation Example 1 to obtain the title compound (0.19 g, 79%).
$^1$H-NMR (CDCl$_3$) δ 7.56~7.52 (2H, m), 6.76 (1H, d), 4.14 (2H, q), 4.04 (1H, m), 2.90~2.75 (2H, m), 2.65~2.50 (2H, m), 2.08~1.97 (3H, m), 1.75 (1H, m), 1.32 (12H, s), 1.26 (3H, t)

Preparation Example 5: 3-[6-(4,4,5,5-tetramethyl-[1,3,2]dioxaborolan-2-yl)-thiochroman-2-yl]-propionic acid ethyl ester

Step A: 6-bromo-4-oxo-thiochroman-2-carboxylic acid 4-bromo-benzenethiol (5.0 g, 26.45 mmol) and furan-2,5-dione (2.6 g, 26.45 mmol) were dissolved in 50 mL of toluene and heated to 50° C. TEA (0.1 mL) was slowly added thereto and the reaction mixture was stirred at 50° C. for 1 hour. The reaction solution was concentrated under reduced pressure, dissolved in 50 mL of DCM, and cooled to 0° C. AlCl$_3$ (5.3 g, 39.67 mmol) was added thereto, and the reaction solution was stirred at room temperature for 1 hours, slowly added dropwise to cold concentrated HCl solution, and extracted with DCM. The organic solvent was dried with MgSO$_4$, concentrated under reduced pressure and solidified with Et$_2$O to obtain the title compound (4.3 g, 57%).

¹H-NMR (CDCl₃) δ 7.98 (1H, d), 7.65 (1H, dd), 7.31 (1H, d), 4.31 (1H, t), 3.09 (2H, m)

Step B: 6-bromo-4-oxo-thiochroman-2-carboxylic acid methyl ester

6-Bromo-4-oxo-thiochroman-2-carboxylic acid (4.3 g, 14.97 mmol) obtained in Step A was dissolved in 50 mL of methanol. Concentrated sulfuric acid (0.8 mL) was added thereto, and the mixture was stirred for 18 hours under reflux. The reaction solution was concentrated under reduced pressure, extracted with EtOAc, dried with MgSO₄ and purified by column chromatography to obtain the title compound (4.2 g, 93%).
¹H-NMR (CDCl₃) δ 8.24 (1H, d), 7.51 (1H, dd), 7.13 (1H, d), 4.13 (1H, t), 3.74 (3H, s), 3.17 (2H, d)

Step C: 6-bromo-thiochroman-2-carboxylic acid methyl ester

6-Bromo-4-oxo-thiochroman-2-carboxylic acid methyl ester (2.0 g, 6.64 mmol) obtained in Step B was dissolved in 20 mL of TFA. Triethylsilane (2.1 mL, 13.28 mmol) was added thereto, and the mixture was stirred at room temperature for 3 hours. The reaction solution was concentrated under reduced pressure, extracted with EtOAc, dried with MgSO₄ and purified by column chromatography to obtain the title compound (1.5 g, 78%).
¹H-NMR (CDCl₃) δ 7.22 (2H, m), 7.00 (1H, d), 4.02 (1H, m), 3.76 (3H, s), 2.96~2.72 (2H, m), 2.33~2.18 (2H, m)

Step D: 6-bromo-thiochroman-2-carboxylic acid

6-Bromo-thiochroman-2-carboxylic acid methyl ester (1.5 g, 5.22 mmol) obtained in Step C was dissolved in each 15 mL of THF, MeOH and 1N NaOH aqueous solution, and the mixture was stirred at room temperature for 2 hours. The organic solvent was removed, and adjusted to pH 3 by the use of 1N HCl aqueous solution, and extracted with EtOAc to separate the organic layer. The organic layer was dried with MgSO₄ and concentrated under reduced pressure to obtain the title compound (1.4 g, 98%).

Step E: (6-bromo-thiochroman-2-yl)-methanol

6-Bromo-thiochroman-2-carboxylic acid (1.4 g, 5.13 mmol) obtained in Step D was dissolved in 50 mL of THF and cooled to −20° C. Isobutyl chloroformate (0.74 mL, 5.64 mmol) and NMM (0.71 mL, 6.48 mmol) were added thereto, and the mixture was stirred at the same temperature for 1.5 hours. NaBH₄ (0.38 g, 10.26 mmol) was dissolved in 20 mL of THF and 5 mL of MeOH at another reactor and cooled to −78° C. The above reaction solution was filtered through Celite and added to another reactor, and the mixture was stirred at room temperature for 2 hours. The reaction solution was extracted with EtOAc, dried with MgSO₄ and purified by column chromatography to obtain the title compound (1.3 g, 98%).
¹H-NMR (CDCl₃) δ 7.19 (2H, m), 7.00 (1H, d), 3.78~3.66 (2H, m), 3.49 (1H, m), 2.83~2.71 (2H, m), 2.22 (1H, m), 1.88~1.78 (2H, m)

Step F: (E)-3-(6-bromo-thiochroman-2-yl)-acrylic acid ethyl ester

Oxalyl chloride (0.64 mL, 7.53 mmol) was added to 30 mL of DCM and cooled to −78° C. DMSO (0.9 mL, 12.55 mmol) was slowly added, and the mixture was stirred for 0.5 hour. The solution in which (6-bromo-thiochroman-2-yl)-methanol (1.3 g, 5.02 mmol) obtained in Step E was dissolved in 5 mL of DCM and TEA (2.8 mL, 20.08 mmol) were sequentially added thereto. The mixture was stirred at room temperature for 1 hour. (Carbethoxymethylene)triphenylphosphorane (2.1 g, 6.02 mmol) was added thereto, and the reaction was carried out at room temperature for 18 hours. Water was added to the reaction solution, and the mixture was extracted with DCM to separate an organic layer. The organic layer was dried with MgSO₄ and purified by column chromatography to obtain the title compound (0.90 g, 55%).
¹H-NMR (CDCl₃) δ 7.20 (2H, m), 6.97 (1H, m), 6.90 (1H, m), 6.00 (1H, d), 4.20 (2H, q), 4.02 (1H, m), 2.81 (2H, m), 2.28 (1H, m), 1.92 (1H, m), 1.28 (3H, t)

Step G: 3-(6-bromo-thiochroman-2-yl)-propionic acid ethyl ester (E)-3-(6-bromo-thiochroman-2-yl)-acrylic acid ethyl ester (0.90 g, 2.75 mmol) obtained in Step F was dissolved in 30 mL of DME. p-Toluenesulfonyl hydrazide (3.60 g, 19.25 nmol) was added little by little and heated to 90° C. Sodium acetate (2.26 g, 27.50 mmol, 1.4 M aqueous solution) was added thereto, and the mixture was stirred for 18 hours under reflux. Water was added to the reaction solution and the mixture was extracted with DCM. The organic layer was dried with MgSO₄ and purified by column chromatography to obtain the title compound (0.80 g, 88%).
¹H-NMR (CDCl₃) δ 7.16 (2H, m), 6.93 (1H, d), 4.14 (2H, q), 3.29 (1H, m), 2.80 (2H, m), 2.49 (2H, m), 2.20 (1H, m), 2.02 (1H, m), 1.92 (1H, m), 1.77 (1H, m), 1.25 (3H, t)

Step H: 3-[6-(4,4,5,5-tetramethyl-[1,3,2]dioxaborolan-2-yl)-thiochroman-2-yl]-propionic acid ethyl ester 3-(6-Bromo-thiochroman-2-yl)-propionic acid ethyl ester (0.80 g, 2.43 mmol) obtained in Step G was reacted in the same manner as in Step D of Preparation Example 1 to obtain the title compound (0.68 g, 74%).
¹H-NMR (CDCl₃) δ 7.47 (2H, m), 7.08 (1H, d), 4.14 (2H, q), 3.32 (1H, m), 2.84 (2H, m), 2.49 (2H, m), 2.22 (1H, m), 2.00 (2H, m), 1.81 (1H, m), 1.32 (12H, s), 1.25 (3H, t)

Preparation Example 6: 3-[6-(4,4,5,5-tetramethyl-[1,3,2]dioxaborolan-2-yl)-1,2,3,4-tetrahydro-quinolin-2-yl]-propionic acid ethyl ester

Step A: 3-(1,2,3,4-tetrahydro-quinolin-2-yl)-propionic acid ethyl ester

Quinolin-2-carbaldehyde (1 g, 6.36 mmol) was dissolved in THE NaH (60%)(0.28 g, 7.00 mmol) was slowly added thereto at 0° C., and the mixture was stirred for 30 minutes. Triethyl phosphonoacetate (1.57 g, 7.00 mmol) was added dropwise, and the mixture was stirred at room temperature for 16 hours. The reaction solution was extracted with EtOAc, purified by column chromatography and dissolved in 30 mL of methanol. 10% PtO₂ (0.1 g) was added thereto, and the mixture was stirred at room temperature for 16 hours under hydrogen atmosphere. After termination of the reaction, the reaction product was filtered through Celite and concentrated under reduced pressure to obtain the title compound (0.7 g, 47%).

¹H-NMR (CDCl₃) δ 7.00~6.90 (2H, m), 6.62 (1H, t), 6.46 (1H, d), 4.15 (2H, q), 3.85 (1H, brs), 3.32 (1H, m), 2.84~2.70 (2H, m), 2.45 (2H, m), 1.97~1.80 (3H, m), 1.65 (1H, m), 1.24 (3H, t)

Step B: 3-(6-bromo-1,2,3,4-tetrahydro-quinolin-2-yl)-propionic acid ethyl ester 3-(1,2,3,4-Tetrahydro-quinolin-2-yl)-propionic acid ethyl ester (0.7 g, 3.00 mmol) obtained in Step A was dissolved in 15 mL of DMF. NBS (0.53 g, 3.00 mmol) was added thereto at 0° C., and the mixture was stirred at room temperature for 24 hours. The reaction solution was concentrated, and 50 mL of water was added thereto. The mixture was extracted with Et₂O, dried with MgSO₄ and purified by column chromatography to obtain the title compound (0.85 g, 91%).
¹H-NMR (CDCl₃) δ 7.08~7.00 (2H, m), 6.37 (1H, d), 4.12 (2H, q), 3.30 (1H, m), 2.80~2.65 (2H, m), 2.41 (2H, m), 1.95~1.80 (3H, m), 1.50 (1H, m), 1.25 (3H, t)

Step C: 3-[6-(4,4,5,5-tetramethyl-[1,3,2]dioxaborolan-2-yl)-1,2,3,4-tetrahydro-quinolin-2-yl]-propionic acid ethyl ester 3-(6-Bromo-1,2,3,4-tetrahydro-quinolin-2-yl)-propionic acid ethyl ester (0.33 g, 1.07 mmol) obtained in Step B was reacted in the same manner as in Step D of Preparation Example 1 to obtain the title compound (0.11 g, 29%).
¹H-NMR (CDCl₃) δ 7.42 (2H, m), 6.44 (1H, d), 4.20~4.05 (3H, m), 3.34 (1H, m), 2.80~2.70 (2H, m), 2.50~2.35 (2H, m), 1.95~1.80 (3H, m), 1.75 (1H, m), 1.31 (12H, s), 1.24 (3H, t)

Preparation Example 7: [1-oxo-6-(4,4,5,5-tetramethyl-[1,3,2]dioxaborolan-2-yl)-3,4-dihydro-1H-isoquinolin-2-yl]-acetic acid ethyl ester Step A: 6-bromo-3,4-dihydro-2H-isoquinolin-1-one 5-bromo-indan-1-one (2.35 g, 11.13 mmol) was dissolved in 10 mL of DCM and 10 mL of methanesulfonic acid and cooled to 0° C. Sodium azide (1.45 g, 22.27 mmol) was added thereto, and the mixture was stirred at room temperature for 16 hours. The reaction solution was cooled to 0° C., neutralized with NaOH and extracted with EtOAc. The extract was dried with MgSO₄ and purified by column chromatography to obtain the title compound (1.14 g, 45%).
¹H-NMR (CDCl₃) δ 7.92 (1H, d), 7.48 (1H, d), 7.39 (1H, s), 6.10 (1H, brs), 3.57 (2H, t), 2.99 (2H, t)

Step B: (6-bromo-1-oxo-3,4-dihydro-1H-isoquinolin-2-yl)-acetic acid ethyl ester

6-Bromo-3,4-dihydro-2H-isoquinolin-1-one (0.4 g, 1.77 mmol) obtained in Step A was dissolved in 10 mL of THF and cooled to 0° C. NaH (60%)(0.14 g, 3.54 mmol) was added thereto, and the mixture was stirred at room temperature 0.5 hour. Ethyl bromoacetate (0.44 g, 2.65 mmol) was added to the reaction solution, and the mixture was stirred for 2 hours under reflux. The reaction solution was extracted with EtOAc, dried with MgSO₄ and purified by column chromatography to obtain the title compound (0.49 g, 89%).
¹H-NMR (CDCl₃) δ 7.93 (1H, d), 7.47 (1H, d), 7.37 (1H, s), 4.32 (2H, s), 4.23 (2H, q), 3.66 (2H, t), 3.05 (2H, t), 1.29 (3H, t)

Step C: [1-oxo-6-(4,4,5,5-tetramethyl-[1,3,2]dioxaborolan-2-yl)-3,4-dihydro-1H-isoquinolin-2-yl]-acetic acid ethyl ester (6-Bromo-1-oxo-3,4-dihydro-1H-isoquinolin-2-yl)-acetic acid ethyl ester (0.79 g, 1.57 mmol) obtained in Step B was reacted in the same manner as in Step D of Preparation Example 1 to obtain the title compound (0.54 g, 96%).
¹H-NMR (CDCl₃) δ 8.06 (1H, d), 7.76 (1H, d), 7.64 (1H, s), 4.34 (2H, s), 4.21 (2H, q), 3.65 (2H, t), 3.07 (2H, t), 1.30 (12H, s), 1.26 (3H, t)

Preparation Example 8: 3-[1-oxo-6-(4,4,5,5-tetramethyl-[1,3,2]dioxaborolan-2-yl)-3,4-dihydro-1H-isoquinolin-2-yl]-propionic acid methyl ester Step A: 3-(6-bromo-1-oxo-3,4-dihydro-1H-isoquinolin-2-yl)-propionic acid methyl ester 6-Bromo-3,4-dihydro-2H-isoquinolin-1-one (0.3 g, 1.32 mmol) obtained in Step A of Preparation Example 7 was dissolved in 10 mL of THF and cooled to 0° C. NaH (60%)(0.11 g, 2.65 mmol) was added thereto, and the mixture was stirred at room temperature for 0.5 hour. 3-Bromo-propionic acid methyl ester (0.33 g, 2.00 mmol) was added to the reaction solution, and the mixture was stirred for 2 hours under reflux. The reaction solution was extracted with EtOAc, dried with MgSO₄ and purified by column chromatography to obtain the title compound (0.38 g, 92%).
¹H-NMR (CDCl₃) δ 7.90 (1H, d), 7.47 (1H, d), 7.34 (1H, s), 3.80 (2H, t), 3.69 (3H, s), 3.63 (2H, t), 2.94 (2H, t), 2.73 (2H, t)

Step B: 3-[1-oxo-6-(4,4,5,5-tetramethyl-[1,3,2]dioxaborolan-2-yl)-3,4-dihydro-1H-isoquinolin-2-yl]-propionic acid methyl ester 3-(6-Bromo-1-oxo-3,4-dihydro-1H-isoquinolin-2-yl)-propionic acid methyl ester (0.38 g, 1.22 mmol) obtained in Step A was reacted in the same manner as in Step D of Preparation Example 1 to obtain the title compound (0.36 g, 82%).
¹H-NMR (CDCl₃) δ 8.03 (1H, d), 7.77 (1H, d), 7.61 (1H, s), 3.82 (2H, t), 3.68 (3H, s), 3.63 (2H, t), 2.98 (2H, t), 2.72 (2H, t), 1.35 (12H, s)

Preparation Example 9: 3-iodo-2-isopropylsulfanyl-pyridine

2-Fluoro-3-iodo-pyridine (0.3 g, 1.34 mmol), Cs₂CO₃ (0.66 g, 1.34 mmol) and propane-2-thiol (0.125 mL, 1.34 mmol) were added to a reactor, and the mixture was stirred at room temperature for 8 hours. Water was added to the reaction solution and the mixture was extracted with EtOAc. An organic layer was separated, and the separated organic layer was dried with MgSO₄ and purified by column chromatography to obtain the title compound (0.21 g, 56%).
¹H-NMR (CDCl₃) δ 8.40 (1H, m), 7.92 (1H, m), 6.69 (1H, m), 3.95 (1H, m), 1.39 (6H, d)

Preparation Example 10: 2-chloro-6-isopropylsulfanyl-pyridine 2,6-Dichloropyridine (3.0 g, 20.3 mmol) and propane-2-thiol (1.88 mL, 20.3 mmol) were reacted in the same manner as in Preparation Example 9 to obtain the title compound (3.63 g, 95%).

¹H-NMR (CDCl₃) δ 7.40 (1H, t), 7.05 (1H, t), 6.98 (1H, t), 4.00 (1H, m), 1.40 (6H, d)

Preparation Example 11: 2-cyclopentyloxy-3-iodo-pyridine

Cyclopentanol (0.038 g, 0.44 mmol) and 2-fluoro-3-iodo-pyridine (0.10 g, 0.44 mmol) were reacted in the same manner as in Preparation Example 34 to obtain the title compound (0.091 g, 70%).

¹H-NMR (CDCl₃) δ 8.09 (1H, m), 7.99 (1H, m), 6.59 (1H, m), 5.43 (1H, m), 2.00 (2H, m), 1.94 (4H, m), 1.66 (2H, m)

Preparation Example 12: 2-chloro-6-cyclopentyloxy-pyridine

6-Chloro-2-pyridinol (1.95 g, 15 mmol) and K₂CO₃ (4.16 g, 30 mmol) were dissolved in 50 mL of DMF. Cyclopentyl bromide (1.94 mL, 18 mmol) was added thereto, and the mixture was stirred at 80° C. for 24 hours. Solids were removed, and the filtrate was concentrated to obtain the title compound (2.92 g, 98%).

¹H NMR (CDCl₃) δ 7.47 (1H, t), 6.84 (1H, d), 6.51 (1H, d), 5.38 (1H, m), 1.97 (2H, m), 1.79 (4H, m), 1.62 (2H, m)

Preparation Example 13: 2-cyclobutylsulfanyl-3-iodo-pyridine

Step A: Cyclobutane Thiol

Magnesium (0.99 g, 40.74 mmol) was dissolved in THF (20 mL). Cyclobutyl bromide (5.0 g, 37.03 mmol) was dissolved in THF (5 mL) at 50° C. and added thereto, and the mixture was stirred for 2 hours under reflux. Sulfur (1.06 g, 33.33 mmol) was slowly added thereto at 0° C., and the mixture was stirred at 50° C. for 2 hours. LAH (0.843 g, 22.22 mmol) was slowly added thereto at 0° C., and the mixture was stirred for 30 minutes under reflux stirred. After termination of the reaction by the use of ammoniumchloride aqueous solution (20 mL) and 1N HCl (20 mL) at 0° C., an organic layer was separated and extracted with Et₂O (30 mL×3). The organic layer was dried with MgSO₄ and used for the next step.

Step B: 2-cyclobutylsulfanyl-3-iodo-pyridine

Cyclobutane thiol (0.069 g, 0.782 mmol) obtained in Step A and 2-fluoro-3-iodo-pyridine (0.1 g, 0.43 mmol) were dissolved in DMF (3 mL). Cs₂CO₃ (0.26 g, 0.86 mmol) was added thereto, and the mixture was heated to 80° C. and stirred. NaCl aqueous solution was added to the reaction solution, and the mixture was extracted with EtOAc. The organic layer was dried with MgSO₄ and purified by column chromatography (eluent, EtOAc/Hex=1/4) to obtain the title compound (0.115 g, 91%).

¹H-NMR (CDCl₃) δ 8.36 (1H, m), 7.90 (1H, m), 6.69 (1H, m), 4.33 (1H, m), 2.54 (2H, m), 2.14 (2H, m), 2.05 (2H, m)

Preparation Example 14: 2-chloro-6-cyclopentylsulfanyl-pyridine 2,6-Dichloropyridine (3.08 g, 20.7 mmol) and Cs₂CO₃ (6.8 g, 20.7 mmol) were dissolved in 40 mL of DMF. Cyclopentylthiol (2.17 mL, 20.7 mmol) was added thereto, and the mixture was stirred at 80° C. for 16 hours. Solids were filtered, and the filtrate was concentrated to obtain the title compound (4.24 g, 95%).

¹H NMR (CDCl₃) δ 7.40 (1H, t), 7.06 (1H, d), 6.97 (1H, d), 4.01 (1H, m), 2.22 (2H, m), 1.76 (2H, m), 1.64 (4H, m)

Preparation Example 15: 2-cyclopentylsulfanyl-3-iodo-pyridine

2-Fluoro-3-iodo-pyridine (0.065 g, 0.29 mmol), Cs₂CO₃ (0.19 g, 0.58 mmol) and cyclopentylthiol (0.03 g, 0.291 mmol) were dissolved in 2 mL of DMF, and the mixture was stirred at 80° C. for 2 hours. NaCl aqueous solution was added to the reaction solution, and the mixture was extracted with EtOAc to separate an organic layer. The organic layer was dried with MgSO₄ and purified by column chromatography (eluent, EtOAc/Hex=1/4) to obtain the title compound (0.053 g, 65%).

¹H-NMR (CDCl₃) δ 8.38 (1H, m), 7.89 (1H, m), 6.68 (1H, m), 4.00 (1H, m), 2.22 (2H, m), 1.80 (2H, m), 1.66 (4H, m)

Preparation Example 16: 4-[2,6-difluoro-4-(4,4,5,5-tetramethyl-1,3,2-dioxaborolan-2-yl)phenoxy]butyric acid ethyl ester

Step A: 4-bromo-2,6-difluoro-phenol 2,6-Difluorophenol (1.02 g, 7.8 mmol) was dissolve in 15 mL of DMF. NBS (1.40 g, 7.84 mmol) was added thereto at 0° C., and the mixture was stirred at room temperature for 24 hours. The reaction solution was concentrated, and 50 mL of water was added thereto. The reaction solution was extracted with Et₂O and dried with MgSO₄ to obtain the title compound (1.41 g, 86%).

¹H NMR (CDCl₃) δ 7.08 (2H, m), 5.42 (1H, brs)

Step B: 2,6-difluoro-4-(4,4,5,5-tetramethyl-1,3,2-dioxaborolan-2-yl)phenol

4-Bromo-2,6-difluoro-phenol (1.414 g, 6.76 mmol) obtained in Step A, bis(pinacolato)diboron (1.8 g, 7.09 mmol), potassium acetate (2.66 g, 27 mmol) and DPPF (0.19 g, 0.34 mmol) were dissolved in 23 mL of 1,4-dioxane. The mixture was charged with N₂ gas for 5 minutes, and PdCl₂ (dppf)-DCM (0.27 g, 0.34 mmol) was added thereto. The mixture was stirred at 80° C. for 3 hours, filtered through Celite and purified by column chromatography to obtain the title compound (1.366 g, 79%).

¹H NMR (CDCl₃) δ 7.33 (2H, m), 5.25 (1H, s), 1.32 (12H, s)

Step C: 4-[2,6-difluoro-4-(4,4,5,5-tetramethyl-1,3,2-dioxaborolan-2-yl)phenoxy]butyric acid ethyl ester 2,6-Difluoro-4-(4,4,5,5-tetramethyl-1,3,2-dioxaborolan-2-yl)phenol (1.87 g, 7.3 mmol) obtained in Step B, Cs₂CO₃ (4.76 g, 14.6 mmol) and 4-bromo-butyric acid ethyl ester (1.42 g, 7.3 mmol) were dissolved in 24 mL of DMF. The mixture was stirred at room temperature for 24 hours. Solids were filtered and purified by column chromatography to obtain the title compound (1.66 g, 61%).

¹H NMR (CDCl₃) δ 7.29 (2H, m), 4.21 (2H, t), 4.14 (2H, q), 2.56 (2H, t), 2.07 (2H, m), 1.32 (12H, s), 1.25 (3H, t)

Preparation Example 17: 1-benzyloxy-3-iodo-benzene

3-Iodo phenol (0.5 g, 2.27 mmol) was dissolved in acetonitrile (5 mL). Cs₂CO₃ (2.22 g, 6.81 mmol) and bromomethylbenzene (0.27 mL, 2.27 mmol) were sequentially added thereto. The mixture was stirred at 80-85° C. for 2 hours. After termination of the reaction, the reactions solution was cooled and filtered through Celite. The filtrate was concentrated under reduced pressure and purified by column chromatography (eluent, EtOAc/Hex=1/10) to obtain the title compound (0.7 g, 99%).

$^1$H NMR (400 MHz, CDCl$_3$) δ 7.39-7.23 (m, 7H), 6.97-6.87 (m, 2H), 4.95 (s, 2H)

Preparation Example 18: 1-iodo-3-isopropoxy-benzene

3-Iodo phenol (0.5 g, 2.27 mmol) and 2-bromo-propane (0.21 mL, 2.27 mmol) were reacted in the same manner as in Preparation Example 17 to obtain the title compound (0.59 g, 99%).

$^1$H NMR (400 MHz, CDCl$_3$) δ 7.27-7.22 (m, 2H), 6.96 (t, 1H), 6.86-6.81 (m, 1H), 4.54-4.44 (m, 1H), 1.31 (d, 6H)

Preparation Example 19: 1-iodo-3-propoxy-benzene

3-Iodo phenol (0.5 g, 2.27 mmol) and 1-bromo-propane (0.21 mL, 2.27 mmol) were reacted in the same manner as in Preparation Example 17 to obtain the title compound (0.58 g, 97%).

$^1$H NMR (400 MHz, CDCl$_3$) δ 7.28-7.23 (m, 2H), 6.97 (t, 1H), 6.87-6.82 (m, 1H), 3.85 (t, 2H), 1.83-1.71 (m, 2H), 1.02 (t, 3H)

Preparation Example 20: 1-cyclopropylmethoxy-3-iodo-benzene

3-Iodo phenol (0.5 g, 2.27 mmol) and bromomethyl-cyclopropane (0.22 mL, 2.27 mmol) were reacted in the same manner as in Preparation Example 17 to obtain the title compound (0.59 g, 95%).

$^1$H NMR (400 MHz, CDCl$_3$) δ 7.26-7.20 (m, 2H), 6.93 (t, 1H), 6.84-6.80 (m, 1H), 3.71 (d, 2H), 1.28-1.15 (m, 1H), 0.63-0.57 (m, 2H), 0.33-0.28 (m, 2H)

Preparation Example 21: 1-cyclobutoxy-3-iodo-benzene

3-Iodo phenol (0.5 g, 2.27 mmol) was dissolved in acetonitrile (5 mL). Cs$_2$CO$_3$ (2.22 g, 6.81 mmol) and bromocyclobutane (0.21 mL, 2.27 mmol) were sequentially added thereto. The mixture was stirred at 80-85° C. for 10 hours, and the reaction solution was cooled and filtered through Celite. The filtrate was concentrated under reduced pressure and purified by column chromatography (eluent, EtOAc/Hex=1/10) to obtain the title compound (0.45 g, 72%).

$^1$H NMR (400 MHz, CDCl$_3$) δ 7.25-7.20 (m, 1H), 7.17-7.13 (m, 1H), 6.92 (t, 1H), 6.77-6.72 (m, 1H), 4.59-4.50 (m, 1H), 2.44-2.33 (m, 2H), 2.19-2.05 (m, 2H), 1.88-1.77 (m, 1H), 1.70-1.57 (m, 1H)

Preparation Example 22: 7-iodo-2,2-dimethyl-2,3-dihydro-benzofuran

Step A: 1-iodo-2-(2-methyl-allyloxy)-benzene

2-Iodo phenol (0.93 g, 4.23 mmol) was dissolved in DMF (5 mL). K$_2$CO$_3$ (0.82 g, 5.92 mmol) and 3-chloro-2-methyl-propene (0.5 mL, 5.08 mmol) were sequentially added thereto. The mixture was stirred at 70-75° C. for 12 hours. After termination of the reaction, the reactions solution was cooled. Water was added to the reaction solution, and the reaction solution was extracted with EtOAc to separate an organic layer. The organic layer was concentrated under reduced pressure and purified by column chromatography (eluent, EtOAc/Hex=1/10) to obtain the title compound (1.05 g, 91%).

$^1$H NMR (500 MHz, CDCl$_3$) δ 7.77 (d, 1H), 7.27 (t, 1H), 6.79 (d, 1H), 6.70 (t, 1H), 5.19 (s, 1H), 5.02 (s, 1H), 4.48 (s, 2H), 1.87 (s, 3H)

Step B: 2-iodo-6-(2-methyl-allyl)-phenol

1-Iodo-2-(2-methyl-allyloxy)-benzene (1.05 g, 3.83 mmol) obtained in Step A was added to a seal tube, and NMP (5 mL) was then added thereto. The mixture was stirred at 200° C. for 12 hours. After termination of the reaction, the reactions solution was cooled. Water was added to the reaction solution, and the reaction solution was extracted with EtOAc to separate an organic layer. The organic layer was concentrated under reduced pressure and purified by column chromatography (eluent, EtOAc/Hex=1/10) to obtain the title compound (0.25 g, 24%).

$^1$H NMR (500 MHz, CDCl$_3$) δ 7.46-6.54 (m, 3H), 3.11 (s, 1H), 3.01 (s, 1H), 1.50 (s, 2H), 1.47 (s, 3H)

Step C: 7-iodo-2,2-dimethyl-2,3-dihydro-benzofuran

HCOOH (5 mL) and water (0.5 mL) were added to 2-iodo-6-(2-methyl-allyl)-phenol (0.25 g, 0.91 mmol) obtained in Step B. The mixture was stirred for 12 hours under reflux. After termination of the reaction, the reactions solution was cooled. Water was added to the reaction solution, and the reaction solution was extracted with EtOAc to separate an organic layer. The organic layer was concentrated under reduced pressure and purified by column chromatography (eluent, EtOAc/Hex=1/10) to obtain the title compound (0.07 g, 24%).

$^1$H NMR (500 MHz, CDCl$_3$) δ 7.44 (d, 1H), 7.06 (d, 1H), 6.56 (t, 1H), 3.11 (s, 2H), 1.50 (s, 6H)

Preparation Example 23: 4-iodo-2,2-dimethyl-benzo[1,3]dioxol

Step A: 1-iodo-2,3-dimethoxy-benzene

THF (5 mL) was added to 1,2-dimethoxy-benzene (0.5 g, 3.62 mmol) and cooled to 0-5° C. n-BuLi (1.6 mL, 3.98 mmol) was slowly added dropwise thereto, and the mixture was stirred at 0-5° C. for 2 hours. The reaction solution was cooled to −78° C., and I$_2$ (1.01 g, 3.98 mmol)/THF (5 mL) solution was added thereto. The temperature was increased to room temperature, and the reaction solution was stirred for 2 hours. After termination of the reaction, the reaction solution was concentrated under reduced pressure. Saturated NaHCO$_3$ solution was added to the reaction solution, and extracted with DCM to separate an organic layer. The organic layer was concentrated under reduced pressure and purified by column chromatography (eluent, EtOAc/Hex=1/10) to obtain the title compound (0.62 g, 65%).

$^1$H NMR (500 MHz, CDCl$_3$) δ 7.36-7.32 (m, 1H), 6.90-6.86 (m, 1H), 6.79 (t, 1H), 3.85 (s, 3H), 3.83 (s, 3H)

Step B: 3-iodo-benzene-1,2-diol

1-Iodo-2,3-dimethoxy-benzene (0.62 g, 2.35 mmol) obtained in Step A was dissolved in DCM (23 mL) and cooled to 0-5° C. 1M BBr$_3$ (0.276 mL, 7.05 mmol) was slowly added thereto, and the mixture was stirred at room temperature for 3 hours. After termination of the reaction, the reaction solution was cooled to −20° C. and diluted by slowly adding ethanol. The mixture was stirred at room temperature for 30 minutes, and saturated NaHCO$_3$ aqueous solution was added thereto. The mixture was extracted with DCM. The organic layer was dried with MgSO$_4$, concentrated under reduced pressure and purified by column chromatography (eluent, EtOAc/Hex=1/4) to obtain the title compound (0.12 g, 22%).

$^1$H NMR (500 MHz, CDCl$_3$) δ 7.18 (d, 1H), 6.87 (d, 1H), 6.60 (t, 1H), 5.64 (s, br, 2H)

Step C: 4-iodo-2,2-dimethyl-benzo[1,3]dioxol

Benzene (5 mL) was added to 3-iodo-benzene-1,2-diol (50 mg, 0.21 mmol) obtained in Step B. 2,2-Dimethoxypropane (0.052 mL, 0.42 mmol) and p-TsOH.H$_2$O (catalytic amount) were added thereto, and the mixture was stirred for 2 hours under reflux. After termination of the reaction, the reaction solution was cooled, and saturated NaHCO$_3$ solution was added thereto. The reaction solution was extracted with EtOAc to separate an organic layer. The organic layer was concentrated under reduced pressure and purified by column chromatography (eluent, EtOAc/Hex=1/10) to obtain the title compound (40 mg, 58%).

$^1$H NMR (500 MHz, CDCl$_3$) δ 7.08 (d, 1H), 6.68 (d, 1H), 6.55 (t, 1H), 1.71 (s, 6H)

Preparation Example 24: 4-(2-cyclobutylsulfanyl-pyridin-3-yl)-2,6-difluoro-phenol 2-Cyclobutylsulfanyl-3-iodo-pyridine (0.193 g, 0.66 mmol) obtained in Preparation Example 13 and 2,6-difluoro-4-(4,4,5,5-tetramethyl-1,3,2-dioxaborolan-2-yl)phenol (0.254 g, 0.992 mmol) obtained in Step B of Preparation Example 16 were reacted in the same manner as in Step A of Example 1 to obtain the title compound (0.078 g, 40%).

$^1$H-NMR (CDCl$_3$) δ 8.39 (1H, m), 7.30 (1H, m), 6.98 (3H, m), 5.15 (1H, s), 4.40 (1H, m), 2.49 (2H, m), 2.02 (4H, m)

Preparation Example 25: 4-[4-(4,4,5,5-tetramethyl-[1,3,2]dioxaborolan-2-yl)phenyl]butanenitrile Step A: 3-(4-bromophenyl)propan-1-ol 3-(4-Bromophenyl)propanoic acid (1.41 g, 6.16 mmol) was dissolved in THF (20 mL). Borane-THF 1.0 M solution (18.5 mL, 18.5 mmol) was slowly added dropwise at 0° C. The mixture was stirred at room temperature for 16 hours. After termination of the reaction, the reaction solution was diluted with water at 0° C. and washed with 1N HCl. The reaction solution was extracted with EtOAc, and the organic layer was dried with anhydrous magnesium sulfate and purified by column chromatography (eluent, EtOAc/Hex=1/5) to obtain the title compound (1.31 g, 99%).

NMR: $^1$H-NMR (CDCl$_3$) δ 7.39 (2H, m), 7.09 (2H, m), 3.67 (2H, m), 2.67 (2H, t), 1.87 (2H, m)

Step B: 3-(4-bromophenyl)propyl methanesulfonate 3-(4-Bromophenyl)propan-1-ol (1.07 g, 4.97 mmol) obtained in Step A was dissolved in DCM (12 mL). TEA (1.04 mL, 7.46 mmol) was added thereto, and methanesulfonyl chloride (0.46 mL, 5.96 mmol) was then slowly added thereto at 0° C. The mixture was stirred for 2 hours. After termination of the reaction, the reaction solution was diluted with water at 0° C., washed with 1N HCl and extracted with DCM. The organic layer was dried with anhydrous magnesiumsulfate to obtain 1.4 g of the title compound, which was used in the next step without purification.

Step C: 4-(4-bromophenyl)butanenitrile 3-(4-Bromophenyl)propyl methanesulfonate (0.557 g, 1.899 mmol) obtained in Step B was dissolved in DMF (9 mL). Sodium cyanide (0.372 g, 7.599 mmol) was added thereto, and the reaction was carried out at 70° C. for 16 hours. After termination of the reaction, the reaction solution was diluted with sodium bicarbonate solution and extracted with EtOAc. The organic layer was dried with anhydrous magnesiumsulfate and purified by column chromatography (eluent, EtOAc/Hex=1/10) to obtain the title compound (0.273 g, 64%).

NMR: $^1$H-NMR (CDCl$_3$) δ 7.43 (2H, m), 7.05 (2H, m), 2.73 (2H, t), 2.31 (2H, t), 1.95 (2H, m)

Step D: 4-[4-(4,4,5,5-tetramethyl-[1,3,2]dioxaborolan-2-yl)phenyl]butanenitrile 4-(4-bromophenyl)butanenitrile (0.273 g, 1.299 mmol) obtained in Step C, bis(pinacolato)diboron (0.346 g, 1.364 mmol), potassium acetate (0.51 g, 5.196 mmol) and DPPF (0.036 g, 0.065 mmol) were dissolved in 1,4-dioxane (10 mL). The mixture was charged with N$_2$ gas for 5 minutes, and PdCl$_2$(dppf)-DCM (0.053 g, 0.065 mmol) was added thereto. The reaction solution was stirred at 80° C. for 16 hours, filtered through Celite, diluted with water and extracted with ethyl acetate. The organic layer was dried with anhydrous magnesiumsulfate and purified by column chromatography (eluent, EtOAc/Hex=1/10) to obtain the title compound (0.203 g, 57%).

NMR: $^1$H-NMR (CDCl$_3$) δ 7.74 (2H, m), 7.19 (2H, m), 2.78 (2H, t), 2.29 (2H, t), 1.97 (2H, m), 1.33 (12H, s)

Preparation Example 26: 5-[4-(4,4,5,5-tetramethyl-[1,3,2]dioxaborolan-2-yl)phenyl]pentanoic acid ethyl ester Step A: 3-(4-bromophenyl)propanal Oxalyl chloride (0.599 mL, 6.973 mmol) was dissolved in DCM (15 mL), and DMSO (0.99 mL, 13.94 mmol) dissolved in DCM (10 mL) was slowly added thereto at −78° C. The mixture was stirred for 15 minutes, and 3-(4-bromophenyl)propan-1-ol (1.0 g, 4.64 mmol) dissolved in DCM (10 mL) was slowly added thereto at −78° C. The mixture was stirred for 30 minutes, and TEA (1.96 mL) was slowly added thereto at −78° C. The temperature was slowly increased to room temperature, and the reaction solution was stirred for 3 hours. After termination of the reaction, the reaction solution was diluted with water and extracted with DCM. The organic layer was dried with anhydrous magnesiumsulfate and purified by column chromatography (eluent, EtOAc/Hex=1/5) to obtain the title compound (0.859 g, 86%).

NMR: $^1$H-NMR (CDCl$_3$) δ 9.81 (1H, s), 7.40 (2H, d), 7.07 (2H, d), 2.91 (2H, m), 2.77 (2H, t)

Step B: (E)-5-(4-bromophenyl)pent-2-enoic acid ethyl ester 3-(4-Bromophenyl)propanal (0.859 g, 4.031 mmol) obtained in Step A and (1-ethoxycarbonylethylidene)triphenylphosphorane (1.685 g, 4.837 mmol) were dissolved in benzene (15 mL), and the mixture was stirred at 60° C. for 16 hours. After termination of the reaction, the solvent was distilled under reduced pressure and purified by column chromatography (eluent, EtOAc/Hex=1/10) to obtain the title compound (0.903 g, 79%).

NMR: $^1$H-NMR (CDCl$_3$) δ 7.40 (2H, m), 7.06 (2H, m), 6.94 (1H, m), 5.82 (1H, m), 4.18 (2H, q), 2.72 (2H, m), 2.49 (2H, m), 1.28 (3H, t)

Step C: (E)-5-[4-(4,4,5,5-tetramethyl-[1,3,2]dioxaborolan-2-yl)phenyl]pent-2-enoic acid ethyl ester (E)-5-(4-bromophenyl)pent-2-enoic acid ethyl ester (0.903 g, 3.18 mmol) obtained in Step B was reacted in the same manner as in Step D of Preparation Example 25 to obtain the title compound (0.429 g, 40%).

NMR: $^1$H-NMR (CDCl$_3$) δ 7.73 (2H, m), 7.18 (2H, m), 6.97 (1H, m), 5.82 (1H, m), 4.16 (2H, q), 2.76 (2H, m), 2.51 (2H, m), 1.33 (12H, s), 1.28 (3H, t)

Step D: 5-[4-(4,4,5,5-tetramethyl-[1,3,2]dioxaborolan-2-yl)phenyl]pentanoic acid ethyl ester (E)-5-[4-(4,4,5,5-tetramethyl-[1,3,2]dioxaborolan-2-yl)phenyl]pent-2-enoic acid ethyl ester (0.429 g, 1.29 mmol) and Pd/C (0.05 g) were dissolved in methanol (13 mL). The mixture was charged with H$_2$ gas and stirred at room temperature for 8 hours. After termination of the reaction, the reaction product was filtered through Celite to obtain the title compound (0.425 g, 99%).

NMR: $^1$H-NMR (CDCl$_3$) δ 7.74 (2H, m), 7.19 (2H, m), 4.10 (2H, q), 2.63 (2H, m), 2.30 (2H, m), 1.64 (4H, m), 1.34 (12H, s), 1.25 (3H, t)

Preparation Example 27: 5-[2,6-difluoro-4-(4,4,5,5-tetramethyl-[1,3,2]dioxaborolan-2-yl)phenyl]pentanoic acid ethyl ester Step A: 3-(4-bromo-2,6-difluoro-phenyl)prop-2-enal 4-bromo-2,6-difluoro-benzaldehyde (1.21 g, 5.47 mmol) and ethyl(triphenylphosphoranylidene)acetaldehyde (1.83 g, 6.022 mmol) were dissolved in benzene (11 mL), and the mixture was stirred at 70° C. for 16 hours. After termination of the reaction, the reaction product was concentrated under reduced pressure and purified by column chromatography (eluent, EtOAc/Hex=1/20) to obtain the title compound (1.27 g, 93%).

NMR: $^1$H-NMR (CDCl$_3$) δ 9.67 (1H, m), 7.51 (1H, m), 7.18 (2H, m), 6.95 (1H, m)

Step B: (E)-5-(4-bromo-2,6-difluoro-phenyl)penta-2,4-dienoic acid ethyl ester 3-(4-Bromo-2,6-difluoro-phenyl)prop-2-enal (1.27 g, 5.14 mmol) obtained in Step A and (1-ethoxycarbonylethylidene)triphenylphosphorane (2.15 g, 6.168 mmol) were dissolved in benzene (11 mL), and the mixture was stirred at 70° C. for 16 hours. After termination of the reaction, the reaction product was concentrated under reduced pressure and purified by column chromatography (eluent EtOAc/Hex=1/20) to obtain the title compound (1.61 g, 98%).

NMR: $^1$H-NMR (CDCl$_3$) δ 7.40 (1H, m), 7.15 (3H, m), 6.83 (1H, d), 6.03 (1H, d), 4.22 (2H, q), 1.30 (3H, t)

Step C: (E)-5-[2,6-difluoro-4-(4,4,5,5-tetramethyl-[1,3,2]dioxaborolan-2-yl)phenyl]penta-2,4-dienoic acid ethyl ester (E)-5-(4-bromo-2,6-difluoro-phenyl)penta-2,4-dienoic acid ethyl ester (0.09 g, 0.283 mmol) obtained in Step B was dissolved in DME (4 mL), and bis(pinacolato)diboron (0.086 g, 0.034 mmol), potassium acetate (0.083 g, 0.85 mmol) and PdCl$_2$(PPh$_3$)$_2$ (0.012 g, 0.014 mmol) were added thereto. The mixture was stirred at 80° C. for 16 hours, filtered through Celite, diluted with water, and extracted with ethyl acetate. The organic layer was dried with anhydrous magnesiumsulfate and purified by column chromatography (eluent, EtOAc/Hex=1/7) to obtain the title compound (0.068 g, 66%).

NMR: $^1$H-NMR (CDCl$_3$) δ 7.43 (1H, m), 7.30-7.20 (3H, m), 6.95 (1H, d), 6.03 (1H, d), 4.23 (2H, q), 1.32 (15H, m)

Step D: 5-[2,6-difluoro-4-(4,4,5,5-tetramethyl-[1,3,2]dioxaborolan-2-yl)phenyl]pentanoic acid ethyl ester (E)-5-[2,6-difluoro-4-(4,4,5,5-tetramethyl-[1,3,2]dioxaborolan-2-yl)phenyl]penta-2,4-dienoic acid ethyl ester (0.068 g, 0.18 mmol) obtained in Step C and Pd/C (0.01 g) were dissolve in methanol (3 mL). The mixture was charged with H$_2$ gas and stirred at room temperature for 8 hours. After termination of the reaction, the reaction product was filtered through Celite to obtain the title compound (0.063 g, 92%).

NMR: $^1$H-NMR (CDCl$_3$) δ 7.25 (2H, m), 4.10 (2H, q), 2.69 (2H, m), 2.30 (2H, t), 1.70-1.60 (4H, m), 1.32 (12H, s), 1.23 (3H, t)

Preparation Example 28: 3-iodo-2-propylsulfanyl-pyridine

After addition of 31 mL of CH$_3$CN to 2-fluoro-3-iodopyridine (2.08 g, 9.3 mmol) and propane-1-thiol (0.89 mL, 9.8 mmol), Cs$_2$CO$_3$ (3.33 g, 10.2 mmol) was added thereto, and the mixture was stirred for 5 hours under reflux. The reaction solution was cooled to room temperature. Solids were filtered, and the filtrate was purified by column chromatography to obtain the title compound (1.58 g, 60%).

1H-NMR (CDCl$_3$) δ 8.40 (1H, m), 7.92 (1H, m), 6.71 (1H, m), 3.13 (2H, t), 1.75 (2H, m), 1.06 (3H, t)

Preparation Example 29: 2-chloro-6-cyclobutoxy-pyridine 5 mL of DMF was added to 6-chloro-2-pyridone (0.2 g, 1.5 mmol), bromocyclobutane (0.26 g, 1.8 mmol) and K$_2$CO$_3$ (0.43 g. 3 mmol), and the mixture was stirred at 80° C. for 16 hours. The reaction solution was concentrated under reduced pressure and purified by column chromatography to obtain the title compound (0.28 g, 98%).

$^1$H NMR (CDCl$_3$) δ 7.49 (1H, t), 6.86 (1H, d), 6.59 (1H, d), 5.16 (1H, m), 2.46 (2H, m), 2.13 (2H, m), 1.83 (1H, m), 1.66 (1H, m)

Preparation Example 30: {2-[2,6-difluoro-4-(4,4,5,5-tetramethyl-[1,3,2]dioxaborolan-2-yl)-phenyl]ethoxy}acetic acid tert-butyl ester Step A: [2-(4-bromo-2,6-difluoro-phenyl)ethoxy]acetic acid tert-butyl ester 2-(4-bromo-2,6-difluoro-phenyl)ethanol (0.116 g, 0.489 mmol), tert-butyl bromoacetate (0.57 mL, 3.91 mmol), tert-butyl ammonium hydrogen sulfate (0.133 g, 0.391 mmol) were dissolved in toluene (2.5 mL). 6N NaOH (8 mL) was added thereto, and the mixture was stirred for 5 hours. After termination of the reaction, the reaction solution was diluted with water, extracted with EtOAc. The organic layer was dried with anhydrous magnesiumsulfate and purified by column chromatography (eluent, EtOAc/Hex=1/8) to obtain the title compound (0.15 g, 77%).
NMR: $^1$H-NMR (CDCl$_3$) δ 7.06 (2H, m), 3.95 (2H, s), 3.69 (2H, t), 2.96 (2H, t), 1.46 (9H, s)

Step B: {2-[2,6-difluoro-4-(4,4,5,5-tetramethyl-[1,3,2]dioxaborolan-2-yl)-phenyl]ethoxy}acetic acid tert-butyl ester

[2-(4-Bromo-2,6-difluoro-phenyl)ethoxy]acetic acid tert-butyl ester (0.15 g, 0.42 mmol) obtained in Step A was reacted in the same manner as in Step C of Preparation Example 27 to obtain the title compound (0.09 g, 53%).
NMR: $^1$H-NMR (CDCl$_3$) δ 7.26 (2H, m), 3.96 (2H, s), 3.70 (2H, t), 3.03 (2H, t), 1.49 (9H, s), 1.33 (12H, s)

Preparation Example 31: 5-[4-(4,4,5,5-tetramethyl-[1,3,2]dioxaborolan-2-yl)phenyl]hexanoic acid ethyl ester Step A: 3-(4-bromophenyl)but-2-enoic acid ethyl ester NaH (60%) was dissolved in THF (20 mL), and 2-diethoxyphosphoryl acetic acid ethyl ester (3.29 mL, 16.57 mmol) was slowly added thereto at 0° C. After 30 minutes, 1-(4-bromophenyl)ethanone (2.0 g, 10.04 mmol) dissolved in THF (10 mL) was slowly added thereto. The mixture was stirred at room temperature for 16 hours. After termination of the reaction, the reaction solution was diluted with water and extracted with Et$_2$O. The organic layer was dried with anhydrous magnesiumsulfate and purified by column chromatography (eluent, EtOAc/Hex=1/10) to obtain the title compound (1.89 g, 70%).
NMR: $^1$H-NMR (CDCl$_3$) δ 7.51 (2H, m), 7.35 (2H, m), 6.11 (1H, s), 4.22 (2H, q), 2.55 (3H, s), 1.32 (3H, t)

Step B: 3-(4-bromophenyl)butan-1-ol 3-(4-Bromophenyl)but-2-enoic acid ethyl ester (1.89 g, 7.02 mmol) obtained in Step A was dissolved in THF (22 mL), and LAH (0.48 g, 12.86 mmol) was added little by little thereto at 0° C. The mixture was stirred at room temperature for 16 hours. After termination of the reaction, the reaction solution was diluted with 1N HCl at 0° C. and extracted with DCM. The organic layer was dried with anhydrous magnesiumsulfate and purified by column chromatography (eluent, Et$_2$O/Hex=1/2) to obtain the title compound (0.437 g, 25%).
NMR: $^1$H-NMR (CDCl$_3$) δ 7.41 (2H, m), 7.08 (2H, m), 3.58 (2H, m), 2.88 (1H, m), 1.85 (2H, t), 1.28 (3H, d), 0.88 (1H, t)

Step C: 3-(4-bromophenyl)butanal 3-(4-Bromophenyl)butan-1-ol (0.437 g, 1.90 mmol) obtained in Step B was reacted in the same manner as in Step A of Preparation Example 26 to obtain the title compound (0.386 g, 89%).
NMR: $^1$H-NMR (CDCl$_3$) δ 9.70 (1H, s), 7.42 (2H, m), 7.10 (2H, m), 3.33 (1H, m), 2.68 (2H, m), 1.30 (3H, d)

Step D: (E)-5-(4-bromophenyl)hex-2-enoic acid ethyl ester 3-(4-Bromophenyl)butanal (0.386 g, 1.69 mmol) obtained in Step C was reacted in the same manner as in Step B of Preparation Example 26 to obtain the title compound (0.508 g, 99%).
NMR: $^1$H-NMR (CDCl$_3$) δ 7.41 (2H, m), 7.06 (2H, m), 6.83 (1H, m), 5.76 (1H, d), 4.15 (2H, q), 2.87 (1H, m), 2.45 (2H, m), 1.27 (6H, m)

Step E: (E)-5-[4-(4,4,5,5-tetramethyl-[1,3,2]dioxaborolan-2-yl)phenyl]hex-2-enoic acid ethyl ester (E)-5-(4-bromophenyl)hex-2-enoic acid ethyl ester (0.508 g, 1.70 mmol) obtained in Step D were reacted in the same manner as in Step C of Preparation Example 26 to obtain the title compound (0.214 g, 42%).
NMR: $^1$H-NMR (CDCl$_3$) δ 7.75 (2H, m), 7.20 (2H, m), 6.85 (1H, m), 5.79 (1H, d), 4.15 (2H, q), 2.89 (1H, m), 2.49 (2H, m), 1.34 (12H, s), 1.27 (6H, m)

Step F: 5-[4-(4,4,5,5-tetramethyl-[1,3,2]dioxaborolan-2-yl)phenyl]hexanoic acid ethyl ester (E)-5-[4-(4,4,5,5-tetramethyl-[1,3,2]dioxaborolan-2-yl)phenyl]hex-2-enoic acid ethyl ester (0.314 g, 0.825 mmol) obtained in Step E and Pd/C (0.035 g) were dissolved in methanol (6 mL). The mixture was charged with H$_2$ gas and stirred at room temperature for 8 hours. After termination of the reaction, the reaction product was filtered through Celite to obtain the title compound (0.314 g, 99%).
NMR: $^1$H-NMR (CDCl$_3$) δ 7.74 (2H, m), 7.19 (2H, m), 4.09 (2H, q), 2.71 (1H, m), 2.24 (2H, m), 1.60 (3H, m), 1.40 (1H), 1.34 (12H, s), 1.25 (6H, m)

Preparation Example 32: 5-[2,6-difluoro-4-(4,4,5,5-tetramethyl-[1,3,2]dioxaborolan-2-yl)phenyl] hexanoic acid ethyl ester Step A: (E)-4-diethoxyphosphorylbut-2-enoic acid ethyl ester (75%)

(E)-4-bromobut-2-enoic acid ethyl ester (75%)(10 g, 51.80 mmol) and triethyl-phosphate (8.88 mL, 51.80 mmol) were stirred at 130° C. for 16 hours. The reaction product was washed with toluene and distilled under reduced pressure. The obtained title compound was used for the next step without purification.

Step B: (4-bromo-2,6-difluoro-phenyl)-trimethyl-silane

Diisopropylamine (16.11 mL, 113.99 mL) was dissolved in THF (100 mL), and 2.3 M n-BuLi (50 mL) was slowly added thereto at −100° C. The mixture was stirred for 20 minutes, and 1-bromo-3,5-difluoro-benzene (20 g, 103.63 mmol) was dissolved in THF (30 mL) at −100° C. and slowly added thereto. The mixture was stirred for 2 hours. TMSCl was dissolved in THF (20 mL) at −100° C. and slowly added thereto. The mixture was stirred at room temperature for 16 hours. After termination of the reaction, the reaction solution was diluted with water at 0° C. and extracted with Et$_2$O. The organic layer was dried with anhydrous magnesiumsulfate and distilled under reduced pressure at 30° C. or below. The obtained title compound was used for the next step without purification.

NMR: $^1$H-NMR (CDCl$_3$) δ 6.98 (2H, m), 0.35 (9H, s)

Step C: 1-(4-bromo-2,6-difluoro-phenyl)ethanone

AlCl$_3$ (16.89 g, 126.7 mmol) was dissolved in DCM (130 mL), and AcCl (9 mL, 126.7 mmol) was added thereto at 0° C. The mixture was stirred for 1 hour. (4-Bromo-2,6-difluoro-phenyl)-trimethyl-silane (27.48 g, 105.59 mmol) obtained in Step B was dissolved in DCM (70 mL) and slowly added thereto at −80° C. The mixture was stirred for 16 hours. After termination of the reaction, the reaction solution was diluted with ammonium chloride aqueous solution at 0° C. and extracted with Et$_2$O. The organic layer was dried with anhydrous magnesiumsulfate and purified by column chromatography (eluent, EtOAc/Hex=1/10) to obtain the title compound (19.89 g, 74%).

NMR: $^1$H-NMR (CDCl$_3$) δ 7.16 (2H, m), 2.58 (3H, s)

Step D: (2E,4E)-5-(4-bromo-2,6-difluoro-phenyl)hexa-2,4-dienoic acid ethyl ester (E)-4-diethoxyphosphorylbut-2-enoic acid ethyl ester (75%) (9.21 g, 36.806 mmol) obtained in Step A was dissolved in THF (70 mL), and LiHMDS (37 mL, 36.80 mmol) was slowly added thereto at −78° C. The mixture was stirred for 30 minutes and cooled to −78° C. 1-(4-Bromo-2,6-difluoro-phenyl)ethanone (7.16 g, 28.31 mmol) obtained in Step C was dissolved in THF (25 mL) and slowly added thereto. The mixture was stirred at room temperature for 16 hours. The reaction solution was diluted with ammonium chloride aqueous solution at 0° C. and extracted with Et$_2$O. The organic layer was dried with anhydrous magnesiumsulfate and purified by column chromatography (eluent, EtOAc/Hex=1/20) to obtain the title compound (7.95 g, 84%).

NMR: $^1$H-NMR (CDCl$_3$) δ 7.67 (1H, m), 7.12 (2H, m), 6.26 (1H, d), 5.96 (1H, d), 4.23 (2H, q), 2.20 (3H, m), 1.31 (3H, t)

Step E: (E)-5-[2,6-difluoro-4-(4,4,5,5-tetramethyl-[1,3,2]dioxaborolan-2-yl)phenyl]hexa-2,4-dienoic acid ethyl ester (2E,4E)-5-(4-bromo-2,6-difluoro-phenyl)hexa-2,4-dienoic acid ethyl ester (7.95 g, 24.0 mmol) obtained in Step D was dissolved in 1,4-dioxane (80 mL) and was reacted in the same manner as in Step C of Preparation Example 27 to obtain the title compound (7.25 g, 79%).

NMR: $^1$H-NMR (CDCl$_3$) δ 7.69 (1H, m), 7.34 (2H, m), 6.29 (1H, d), 5.92 (1H, d), 4.22 (2H, q), 2.20 (3H, m), 1.35 (15H, m)

Step F: 5-[2,6-difluoro-4-(4,4,5,5-tetramethyl-[1,3,2]dioxaborolan-2-yl)phenyl]hexanoic acid ethyl ester (E)-5-[2,6-difluoro-4-(4,4,5,5-tetramethyl-[1,3,2]dioxaborolan-2-yl)phenyl]hexa-2,4-dienoic acid ethyl ester (7.25 g, 19.16 mmol), Pd/C (0.70 g) obtained in Step E was dissolved in methanol (100 mL), charged with H$_2$ gas and stirred at room temperature for 8 hours. After termination of the reaction, the reaction solution was filtered through Celite to obtain the title compound (7.16 g, 97%).

NMR: $^1$H-NMR (CDCl$_3$) δ 7.22 (2H, m), 4.08 (2H, q), 3.21 (1H, m), 2.24 (2H, m), 1.80 (1H, m), 1.65 (1H, m), 1.60 (1H, m), 1.45 (1H, m), 1.30 (15H, m), 1.20 (3H, t)

Preparation Example 33:
2-ethylsulfanyl-3-iodo-pyridine

2-Fluoro-3-iodo-pyridine (0.475 g, 2.13 mmol), Cs$_2$CO$_3$ (3.47 g, 10.65 mmol), ethanethiol (0.239 mL, 3.19 mmol) were reacted in the same manner as in Preparation Example 28 to obtain the title compound (0.512 g, 90%).

$^1$H-NMR (CDCl$_3$) δ 8.40 (1H, m), 7.92 (1H, m), 6.72 (1H, m), 3.16 (2H, q), 1.39 (3H, t)

Preparation Example 34:
3-iodo-2-isopropoxy-pyridine

Isopropyl alcohol (0.043 g, 717 mmol) was dissolved in dry DMF (3 mL). NaH (60%)(0.03 g, 0.71 mmol) was slowly added dropwise thereto at 0° C., and the mixture was stirred for 30 minutes. The mixture was slowly added to a flask containing 2-fluoro-3-iodo-pyridine (0.10 g, 0.44 mmol) and stirred at room temperature for 1 hour. NH$_4$Cl aqueous solution was added to the reaction solution, and the reaction solution was extracted with EtOAc to separate an organic layer. The organic layer was dried with anhydrous MgSO$_4$ and purified by column chromatography (eluent, EtOAc/Hex=1/4) to obtain the title compound (0.029 g, 24%).

$^1$H-NMR (CDCl$_3$) δ 8.08 (1H, m), 8.00 (1H, m), 6.59 (1H, m), 5.27 (1H, m), 1.38 (6H, d)

Preparation Example 35:
N-cyclopentyl-2-iodo-aniline

2-Iodoaniline (0.39 g, 1.78 mmol) was dissolved in 6 mL of dichloroethane. Cyclopentanone (0.15 g, 1.78 mmol) and acetic acid (0.11 mL, 1.96 mmol) were added thereto, and the mixture was stirred at room temperature for 16 hours. Sodium triacetoxyborohydride (0.56 g, 2.67 mmol) added thereto, and the mixture was stirred for 5 hours. The reaction solution was diluted with water and extracted with DCM to separate an organic layer. The organic layer was dried with MgSO$_4$ and purified by column chromatography to obtain the title compound (0.12 g, 23%).

1H-NMR (CDCl$_3$) δ 7.64 (1H, d), 7.18 (1H, t), 6.60 (1H, d), 6.40 (1H, t), 4.14 (1H, brs), 3.80 (1H, m), 2.02 (2H, m), 1.76 (2H, m), 1.63 (2H, m), 1.53 (2H, m)

Preparation Example 36:
3-bromo-N-cyclopentyl-aniline

3-Bromoaniline (0.306 g, 1.78 mmol) and cyclopentanone (0.15 g, 1.78 mmol) were reacted in the same manner as in Preparation Example 35 to obtain the title compound (0.347 g, 81%).

1H-NMR (CDCl$_3$) δ 6.98 (1H, t), 6.77 (1H, d), 6.72 (1H, m), 6.49 (1H, m), 3.77 (2H, m), 2.02 (2H, m) 1.72 (2H, m), 1.62 (2H, m), 1.45 (2H, m)

Preparation Example 37:
2-bromo-6-propylsulfanyl-pyridine 2,6-Dibromopyridine (0.2 g, 0.84 mmol), Cs$_2$CO$_3$ (0.412 g, 1.27 mmol) and propanethiol (0.076 mL, 0.84 mmol) were reacted in the same manner as in Preparation Example 28 to obtain the title compound (0.184 g, 93%).

1H-NMR (CDCl$_3$) δ 7.27 (1H, t), 7.11 (2H, m), 3.13 (2H, t), 1.74 (2H, m), 1.04 (3H, t)

Preparation Example 38: 4-[4-(4,4,5,5-tetramethyl-[1,3,2]dioxaborolan-2-yl)phenyl]butanoic acid methyl ester

Step A: 4-(4-bromophenyl)butanoic acid methyl ester 4-(4-Aminophenyl)butanoic acid (0.5 g, 2.87 mmol) was dissolved in HBr (2 mL) at 0° C. and stirred for 10 minutes. Sodium nitrite (0.192 g, 2.78 mmol) was dissolved in water (1.3 mL) at 0° C. and added thereto. CuBr (0.22 g, 1.53 mmol) was dissolved in HBr (2 mL) at 0° C. and added thereto. The mixture was stirred at 80° C. for 4 hours. After termination of the reaction, the reaction solvent was diluted with methanol at 0° C. and extracted with ethyl acetate. The organic layer was dried with anhydrous magnesiumsulfate, and without purification diazomethane (6 mL) was added thereto. The solvent was distilled under reduced pressure and purified by column chromatography (eluent, EtOAc/Hex=1/4) to obtain the title compound (0.139 g, 19%).

NMR: $^1$H-NMR (CDCl$_3$) δ 7.42 (2H, m), 7.04 (2H, m), 3.66 (3H, s), 2.59 (2H, t), 2.31 (2H, m), 1.93 (2H, m)

Step B: 4-[4-(4,4,5,5-tetramethyl-[1,3,2]dioxaborolan-2-yl)phenyl]butanoic acid methyl ester 4-(4-Bromophenyl)butanoic acid methyl ester (0.165 g, 0.64 mmol) obtained in Step A was reacted in the same manner as in Step C of Preparation Example 27 to obtain the title compound (0.039 g, 57%).

NMR: $^1$H-NMR (CDCl$_3$) δ 7.72 (2H, m), 7.19 (2H, m), 3.66 (3H, s), 2.67 (2H, t), 2.32 (2H, t), 1.96 (2H, m), 1.34 (12H, s)

Preparation Example 39: 2-cyclobutoxy-3-iodo-pyridine

Cyclobutanol (0.064 g, 1.34 mmol) and 2-fluoro-3-iodo-pyridine (0.2 g, 0.89 mmol) were reacted in the same manner as in Preparation Example 34 to obtain the title compound (0.16 g, 66%).

1H-NMR (CDCl$_3$) δ 8.07 (1H, m), 8.00 (1H, m), 6.61 (1H, m), 5.18 (1H, m), 2.47 (2H, m), 2.20 (2H, m), 1.84 (1H, m), 1.67 (1H, m)

Preparation Example 40: 2-cyclopropylmethoxy-3-iodo-pyridine

Cyclopropyl-methanol (0.089 g, 1.23 mmol) was dissolved in anhydrous DMF (2 mL), and NaH (60%)(0.054 g, 1.35 mmol) was slowly added dropwise thereto at 0° C. The mixture was stirred for 30 minutes. The mixture was slowly added to a flask containing 2-fluoro-3-iodo-pyridine (0.137 g, 0.617 mmol) and stirred at room temperature for 1 hour. NH$_4$Cl aqueous solution was added to the reaction solution, and the reaction solution was extracted with EtOAc to separate an organic layer. The organic layer was dried with MgSO$_4$ and purified by column chromatography (eluent, EtOAc/Hex=1/5) to obtain the title compound (0.141 g, 83%).

$^1$H-NMR (CDCl$_3$) δ 8.07 (1H, m), 8.00 (1H, m), 6.61 (1H, m), 4.20 (2H, d), 1.32 (1H, m), 0.60 (2H, m), 0.39 (2H, m)

Preparation Example 41: 2-cyclobutoxy-3-iodo-pyridine

Cyclobutanol (0.064 g, 1.34 mmol) and 2-fluoro-3-iodo-pyridine (0.2 g, 0.89 mmol) were reacted in the same manner as in Preparation Example 34 to obtain the title compound (0.16 g, 66%).

1H-NMR (CDCl$_3$) δ 8.07 (1H, m), 8.00 (1H, m), 6.61 (1H, m), 5.18 (1H, m), 2.47 (2H, m), 2.20 (2H, m), 1.84 (1H, m), 1.67 (1H, m)

Preparation Example 42: 2-bromo-6-isopropoxy-pyridine

Propan-2-ol (0.065 mL, 0.84 mmol) and 2,6-dibromopyridine (0.2 g, 0.84 mmol) were reacted in the same manner as in Preparation Example 34 to obtain the title compound (0.027 g, 14%).

1H-NMR (CDCl$_3$) δ 7.37 (1H, t), 7.00 (1H, d), 6.60 (1H, d), 5.27 (1H, m), 1.33 (6H, d)

Preparation Example 43: 2-chloro-6-cyclopropylmethoxy-pyridine

6-Chloro-2-pyridone (1.0 g, 7.7 mmol), K$_2$CO$_3$ (2.13 g, 15.4 mmol) and (bromomethyl)cyclopropane (1.1 g, 8.1 mmol) were added to 15 mL of DMF, and the mixture was stirred at 80° C. for 16 hours. The reaction solution was concentrated under reduced pressure and purified by column chromatography to obtain the title compound (0.65 g, 45%).

$^1$H NMR (CDCl$_3$) δ 7.50 (1H, t), 6.87 (1H, d), 6.67 (1H, d), 4.12 (2H, d), 1.26 (1H, m), 0.62 (2H, m), 0.36 (2H, m)

Preparation Example 44: 2-bromo-6-cyclopropylmethoxy-pyridine

Cyclopropylmethanol (0.068 mL, 0.84 mmol) and 2,6-dibromopyridine (0.2 g, 0.84 mmol) were reacted in the same manner as in Preparation Example 34 to obtain the title compound (0.1 g, 53%).

1H-NMR (CDCl$_3$) δ 7.39 (1H, t), 7.03 (1H, d), 6.70 (1H, d), 4.12 (2H, d), 1.24 (1H, m), 0.59 (2H, m), 0.35 (2H, m)

Preparation Example 45: 2-bromo-6-propoxy-pyridine

Propanol (0.07 mL, 0.92 mmol) and 2,6-dibromopyridine (0.2 g, 0.84 mmol) were reacted in the same manner as in Preparation Example 34 to obtain the title compound (0.067 g, 36%).

1H-NMR (CDCl$_3$) δ 7.39 (1H, t), 7.03 (1H, d), 6.65 (1H, d), 4.23 (2H, t), 1.76 (2H, m), 1.00 (3H, t)

Preparation Example 46: 2-chloro-6-isopropoxy-pyridine

Isopropanol (0.97 g, 16.1 mmol) was dissolved in 45 mL of THF and cooled to 0° C. NaH (55% in mineral oil, 0.7 g, 16 mmol) was added thereto, and the mixture was stirred at room temperature for 1 hour. 2,6-Dichloropyridine (2.0 g, 13.5 mmol) was added thereto, and the mixture was stirred for 16 hours under reflux. The reaction solution was cooled to room temperature, diluted with 20 mL of water and extracted with EtOAc. The separated organic layer was dried with MgSO$_4$ and purified by column chromatography to obtain the title compound (1.917 g, 82%).

¹H NMR (CDCl₃) δ 7.48 (1H, t), 6.83 (1H, d), 6.58 (1H, d), 5.29 (1H, m), 1.34 (6H, d)

Preparation Example 47: 3-iodo-2-propoxy-pyridine

Propanol (0.1 mL, 1.34 mmol) and 2-fluoro-3-iodo-pyridine (0.2 g, 0.89 mmol) were reacted in the same manner as in Preparation Example 34 to obtain the title compound (0.11 g, 46%).
1H-NMR (CDCl₃) δ 8.08 (1H, m), 8.00 (1H, m), 6.61 (1H, m), 4.28 (2H, t), 1.82 (2H, m), 1.04 (3H, t)

Preparation Example 48:
2-cyclobutylmethoxy-3-iodo-pyridine

Cyclobutyl-methanol (0.37 g, 4.31 mmol) and 2-fluoro-3-iodo-pyridine (0.60 g, 2.69 mmol) were reacted in the same manner as in Preparation Example 34 to obtain the title compound (0.75 g, 96%).
¹H-NMR (CDCl₃) δ 8.08 (1H, m), 8.02 (1H, m), 6.63 (1H, m), 4.29 (2H, d), 2.79 (1H, m), 2.12 (2H, m), 1.96 (4H, m)

Preparation Example 49:
3-iodo-2-(tetrahydro-furan-3-yloxy)-pyridine

Tetrahydro-furan-3-ol (0.39 g, 4.44 mmol) and 2-fluoro-3-iodo-pyridine (0.66 g, 2.96 mmol) were reacted in the same manner as in Preparation Example 34 to obtain the title compound (0.68 g, 80%).
¹H-NMR (CDCl₃) δ 8.08 (1H, m), 8.03 (1H, m), 6.65 (1H, m), 5.53 (1H, m), 4.12 (1H, m), 4.06 (1H, m), 3.94 (2H, m), 2.23 (2H, m)

Preparation Example 50:
3-iodo-2-(tetrahydro-pyran-4-yloxy)-pyridine

Tetrahydro-pyran-4-ol (0.45 g, 4.44 mmol) and 2-fluoro-3-iodo-pyridine (0.66 g, 2.96 mmol) were reacted in the same manner as in Preparation Example 34 to obtain the title compound (0.80 g, 89%).
¹H-NMR (CDCl₃) δ 8.07 (1H, d), 8.01 (1H, d), 6.63 (1H, m), 5.30 (1H, m), 4.01 (2H, m), 3.68 (2H, m), 2.04 (2H, m), 1.85 (2H, m)

Preparation Example 51:
N-cyclopentyl-3-iodo-pyridin-2-amine

2-Fluoro-3-iodo-pyridine (0.3 g, 1.34 mmol), cyclopentylamine (0.34 g, 4 mmol) and diisopropylethylamine (0.46 mL, 2.68 mmol) were dissolved in 3.3 mL of CH₃CN and the mixture was stirred at 110° C. for 2 hours by the use of microwave. The reaction solution was concentrated under reduced pressure and purified by column chromatography to obtain the title compound (0.155 g, 40%).
¹H-NMR (CDCl₃) δ 8.07 (1H, d), 7.80 (1H, d), 6.28 (1H, m), 4.88 (1H, brs), 4.30 (1H, m), 2.10 (2H, m), 1.75 (2H, m), 1.65 (2H, m), 1.48 (2H, m)

Preparation Example 52:
2-bromo-6-cyclobutylsulfanyl-pyridine

Cyclobutylthiol (0.074 g, 0.84 mmol) and 2,6-dibromopyridine (0.2 g, 0.84 mmol) were reacted in the same manner as in Preparation Example 34 to obtain the title compound (0.047 g, 22%).

¹H-NMR (CDCl₃) δ 7.27 (1H, t), 7.11 (1H, d), 7.00 (1H, d), 4.28 (1H, m), 2.53 (2H, m), 2.08 (4H, m)

Preparation Example 53:
1-(3-bromophenyl)pyrrolidine 1,3-Dibromobenzene (1.0 g, 4.24 mmol), pyrrolidine (0.43 mL, 5.0 mmol), sodium tert-butoxide (1.14 g, 11.87 mmol) and BINAP (0.2 g, 0.32 mmol) were dissolved in 17 mL of toluene. Pd₂(dba)₃ (0.097 g, 0.1 mmol) was added thereto, and the mixture was stirred 4 hours under reflux. Solids were filtered through Celite and purified by column chromatography to obtain the title compound (0.52 g, 54%).
1H-NMR (CDCl₃) δ 7.05 (1H, t), 6.75 (1H, d), 6.67 (1H, m), 6.45 (1H, m), 3.26 (4H, m), 2.00 (4H, m)

Preparation Example 54:
2-chloro-6-phenoxy-pyridine 2,6-Dichloropyridine (2.0 g, 13.5 mmol) and phenol (1.4 mL, 14.9 mmol) were reacted in the same manner as in Preparation Example 34 to obtain the title compound (3.5 g, 84%).
¹H-NMR (CDCl₃) δ 7.62 (1H, t), 7.41 (2H, m), 7.21 (1H, t), 7.14 (2H, d), 6.74 (2H, d)

Preparation Example 55:
2-bromo-4-fluoro-1-isopropoxy-benzene

2-Bromo-4-fluoro-phenol (0.3 g, 1.57 mmol), 2-bromopropane (0.22 mL) and Cs₂CO₃ (1.53 g) were reacted in the same manner as in Preparation Example 28 to obtain the title compound (0.33 g, 89%).
1H-NMR (CDCl₃) δ 7.28 (1H, m), 6.94 (1H, m), 6.88 (1H, m), 4.44 (1H, m), 1.32 (6H, d).

Preparation Example 56:
3-bromo-5-methyl-pyridin-2-ol

5-Methyl-pyridin-2-ol (1 g, 9.16 mmol) was dissolved in 4 mL of CS₂. Br₂ (0.47 mL) was added thereto, and the mixture was stirred at room temperature for 2 hours. Sodium thiosulfate (Na₂S₂O₃) aqueous solution was added thereto, and the reaction solution was extracted with EtOAc. The separated organic layer was dried with MgSO₄ and concentrated under reduced pressure to obtain the title compound (1.7 g, 98%) in a solid form.
1H-NMR (CDCl₃) δ 7.73 (1H, s), 7.22 (1H, s), 2.10 (3H, s).

Preparation Example 57:
3-bromo-2-cyclopentyloxy-5-methyl-pyridine

3-Bromo-5-methyl-pyridin-2-ol (0.5 g, 2.66 mmol) obtained in Preparation Example 56, bromo-cyclopentan (0.43 mL) and Cs₂CO₃ (2.6 g) were reacted in the same manner as in Preparation Example 28 to obtain the title compound (0.25 g, 37%).
H-NMR (CDCl₃) δ 7.86 (1H, s), 7.60 (1H, s), 5.38 (1H, m), 2.21 (3H, s), 1.93 (2H, m), 1.82 (4H, m), 1.61 (2H, m).

Preparation Example 58: 3-[(4-methoxyphenyl)methoxy]isoxazol-5-carboxylic acid methyl ester 3-Hydroxyisoxazol-5-carboxylic acid methyl ester (4.73 g, 33 mmol) was dissolved in 66 mL of DMF. K₂CO₃ (5.0 g, 36.3 mmol) and 4-methoxybenzyl chloride (4.5 mL, 33 mmol) were added thereto at 0° C., and the mixture was stirred at 60° C. for 10 hours. The reaction solution was concentrated under reduced pressure, diluted with water and extracted with EtOAc. The organic layer was dried with MgSO$_4$ and purified by column chromatography to obtain the title compound (4.06 g, 47%).

$^1$H-NMR (CDCl$_3$) δ 7.39 (2H, d), 6.92 (2H, d), 6.54 (1H, s), 5.24 (2H, s), 3.95 (3H, s), 3.81 (3H, s)

Preparation Example 59: [3-[(4-methoxyphenyl)methoxy]isoxazol-5-yl]methanol

3-[(4-Methoxyphenyl)methoxy]isoxazol-5-carboxylic acid methyl ester (4.06 g, 15.4 mmol) obtained in Preparation Example 58 was dissolved in 51 mL of MeOH. NaBH$_4$ (0.87 g, 23 mmol) was added thereto, and the mixture was stirred for 4 hours under reflux. The reaction solution was diluted with water and extracted with EtOAc. The organic layer was dried with MgSO$_4$ and purified by column chromatography to obtain the title compound (2.58 g, 71%).

$^1$H-NMR (CDCl$_3$) δ 7.38 (2H, d), 6.92 (2H, d), 5.89 (1H, s), 5.19 (2H, s), 4.66 (2H, d), 3.82 (3H, s), 1.95 (1H, t)

Preparation Example 60: [3-[(4-methoxyphenyl)methoxy]isoxazol-5-yl]methyl methanesulfonate

[3-[(4-Methoxyphenyl)methoxy]isoxazol-5-yl]methanol (0.19 g, 0.82 mmol) obtained in Preparation Example 59 was dissolved in 4 mL of DCM. DIPEA (0.29 mL, 1.64 mmol) and methanesulfonyl chloride (0.07 mL, 0.9 mmol) were sequentially added thereto at 0° C., and the mixture was stirred at room temperature for 80 minutes. The reaction solution was diluted with water and extracted with EtOAc. The organic layer was dried with MgSO$_4$ and used for the next reaction without purification.

$^1$H-NMR (CDCl$_3$) δ 7.38 (2H, d), 6.93 (2H, d), 6.08 (1H, s), 5.21 (2H, s), 5.18 (2H, s), 3.82 (3H, s), 3.06 (3H, s)

Preparation Example 61: 3-[(4-methoxyphenyl)methoxy]isoxazol-5-carbaldehyde

[3-[(4-Methoxyphenyl)methoxy]isoxazol-5-yl]methanol (0.4 g, 1.7 mmol) obtained in Preparation Example 59 was dissolved in 8 mL of DCM. Pyridinium chlorochromate (0.74 g, 3.4 mmol) was added thereto, and the mixture was stirred at room temperature for 16 hours. The reaction product was filtered through silica gel to obtain the title compound (0.22 g, 55%).

$^1$H-NMR (CDCl$_3$) δ 9.84 (1H, s), 7.39 (2H, d), 6.93 (2H, d), 6.57 (1H, s), 5.27 (2H, s), 3.83 (3H, s)

Preparation Example 62: 5-[[2,6-difluoro-4-(4,4,5,5-tetramethyl-1,3,2-dioxaborolan-2-yl)phenoxy]methyl]-3-[(4-methoxyphenyl)methoxy]isoxazol To 2,6-difluoro-4-(4,4,5,5-tetramethyl-1,3,2-dioxaborolan-2-yl)phenol (2.42 g, 9.43 mmol) obtained in Step B of Preparation Example 16, [3-[(4-methoxyphenyl)methoxy]isoxazol-5-yl]methanol (2.19 g, 9.31 mmol) obtained in Preparation Example 59 and triphenylphosphine (2.44 g, 9.31 mmol) 93 mL of THF was added and cooled to 0° C. Diisopropyl azodicarboxylate (1.83 mL, 9.31 mmol) was added thereto, and the mixture was stirred at room temperature for 16 hours. The reaction solution was concentrated under reduced pressure and purified by column chromatography to obtain the title compound (3.07 g, 70%).

$^1$H-NMR (CDCl$_3$) δ 7.37 (2H, d), 7.32 (2H, m), 6.91 (2H, d), 6.00 (1H, s), 5.18 (2H, s), 5.17 (2H, s), 3.82 (3H, s), 1.33 (12H, s)

Preparation Example 63: 3-[(4-methoxyphenyl)methoxy]-5-methyl-isoxazole

5-Methylisoxazol-3-ol (0.64 g, 6.46 mmol) was dissolved in 13 mL of DMF. K$_2$CO$_3$ (0.98 g, 7.1 mmol) and 4-methoxybenzyl chloride (0.88 mL, 6.46 mmol) were added thereto, and the mixture was stirred at 60° C. for 4 hours. The filtrate obtained by filtering solids was purified by column chromatography to obtain the title compound (0.53 g, 40%).

$^1$H-NMR (CDCl$_3$) δ 7.37 (2H, d), 6.91 (2H, d), 5.62 (1H, s), 5.17 (2H, s), 3.82 (3H, s), 2.33 (3H, s)

Preparation Example 64: 4-[2-(cyclopentoxy)-3-pyridyl]aniline

2-Cyclopentoxy-3-iodo-pyridine (0.3 g, 1 mmol) obtained in Preparation Example 11 and 4-(4,4,5,5-tetramethyl-1,3,2-dioxaborolan-2-yl)aniline (0.22 g, 1 mmol) were reacted in the same manner as in Step A of Example 1 to obtain the title compound (0.18 g, 72%).

$^1$H-NMR (CDCl$_3$) δ 8.06 (1H, m), 7.56 (1H, m), 7.39 (2H, d), 6.89 (1H, m), 6.72 (2H, d), 5.50 (1H, m), 3.73 (2H, brs), 1.95 (2H, m), 1.83 (2H, m), 1.75 (2H, m), 1.62 (2H, m)

Preparation Example 65: 4-[2-(cyclopentoxy)-3-pyridyl]benzenethiol

Catalytic amount of copper chloride (I) was added to 12 mL of water. SOCl$_2$ (0.2 mL, 2.58 mmol) was added thereto at 0° C., and the mixture was stirred at room temperature for 16 hours. 4-[2-(Cyclopentoxy)-3-pyridyl]aniline (0.18 g, 0.71 mmol) obtained in Preparation Example 64 was prepared in another reaction vessel, and 7.1 mL of 3 M HCl aqueous solution was added thereto. Sodium nitrite (0.054 g, 0.78 mmol, 5 M aqueous solution) was slowly added thereto at −5° C., and the mixture was stirred at 0° C. for 1 hour, and slowly added to the mixture solution of copper chloride (I) and SOCl$_2$. The reaction solution was stirred at 0° C. for 3 hours and extracted with EtOAc. The organic layer was MgSO$_4$, and 20 mL of THF was added thereto and cooled to 0° C. Triphenylphosphine (0.27 g, 1 mmol) was added thereto, and the mixture was stirred. After 15 minutes, 20 mL of water was added thereto, and the reaction solution was stirred at room temperature for 16 hours and extracted with EtOAc. The organic layer was dried with MgSO$_4$ and purified by column chromatography to obtain the title compound (0.022 g, 11%).

$^1$H-NMR (CDCl$_3$) δ 8.12 (1H, m), 7.56 (1H, m), 7.44 (2H, d), 7.30 (2H, d), 6.91 (1H, m), 5.50 (1H, m), 1.94 (2H, m), 1.80 (2H, m), 1.72 (2H, m), 1.62 (2H, m)

Preparation Example 66: 2,6-difluoro-4-(4,4,5,5-tetramethyl-1,3,2-dioxaborolan-2-yl)aniline 2,6-Difluoro-4-iodo-aniline (9.35 g, 36.7 mmol) was reacted in the same manner as in Step D of Preparation Example 1 to obtain the title compound (6.46 g, 69%).

$^1$H-NMR (CDCl$_3$) δ 7.24 (2H, m), 3.93 (2H, brs), 1.31 (12H, s)

Preparation Example 67: 4-[2-(cyclopentoxy)-3-pyridyl]-2,6-difluoro-aniline

2-Cyclopentoxy-3-iodo-pyridine (1.09 g, 3.8 mmol) obtained in Preparation Example 11 and 2,6-difluoro-4-(4, 4,5,5-tetramethyl-1,3,2-dioxaborolan-2-yl)aniline (0.925 g, 3.62 mmol) obtained in Preparation Example 66 were reacted in the same manner as in Step A of Example 1 to obtain the title compound (0.6 g, 57%).

$^1$H-NMR (CDCl$_3$) δ 8.10 (1H, m), 7.54 (1H, m), 7.11 (2H, m), 6.90 (1H, m), 5.51 (1H, m), 3.78 (2H, brs), 1.95 (2H, m), 1.83 (2H, m), 1.76 (2H, m), 1.65 (2H, m)

Preparation Example 68: 4-[2-(cyclopentoxy)-3-pyridyl]-2,6-difluoro-benzenethiol 4-[2-(Cyclopentoxy)-3-pyridyl]-2,6-difluoro-aniline (0.42 g, 1.47 mmol) obtained in Preparation Example 67 was reacted in the same manner as in Preparation Example 65 to obtain the title compound (0.046 g, 10%).

$^1$H-NMR (CDCl$_3$) δ 8.20 (1H, m), 7.61 (1H, m), 7.22 (2H, m), 7.00 (1H, m), 5.56 (1H, m), 1.99 (2H, m), 1.86 (2H, m), 1.80 (2H, m), 1.70 (2H, m)

Preparation Example 69: 2,6-difluoro-4-(4,4,5,5-tetramethyl-1,3,2-dioxaborolan-2-yl)benzoic acid methyl ester

Step A: 4-bromo-2,6-difluoro-benzoic acid 70 mL of THF was cooled to −78° C., and diisopropylamine (4 mL, 28.5 mmol) and butyllithium (13 mL, 27.2 mmol, 2.1 M hexane solution) were sequentially added thereto. The mixture was stirred at −78° C. for 1 hour, and 1-bromo-3,5-difluorobenzene (5.0 g, 25.9 mmol) dissolved in 15 mL was slowly added thereto. The mixture was stirred at −78° C. for 45 minutes, and the reaction solution was transferred to a beaker containing solid carbon dioxide and stirred at room temperature for 16 hours. The reaction solution was adjusted to pH 3 by the addition of 1N HCl aqueous solution and extracted with EtOAc. The organic layer was collected and dried with MgSO$_4$ to obtain the title compound (5.15 g, 84%).

$^1$H-NMR (CDCl$_3$) δ 7.20 (2H, m)

Step B: 4-bromo-2,6-difluoro-benzoic acid methyl ester

4-Bromo-2,6-difluoro-benzoic acid (5.15 g, 21.7 mmol) obtained in Step A was dissolve in 54 mL of MeOH. SOCl$_2$ (2.4 mL, 32.6 mmol) was added thereto, and the mixture was stirred for 3 hours under reflux. The reaction solution was concentrated under reduced pressure, diluted with sodium bicarbonate aqueous solution, and extracted with EtOAc. The organic layer was collected and dried with MgSO$_4$ to obtain the title compound (2.9 g, 53%).

$^1$H-NMR (CDCl$_3$) δ 7.16 (2H, m), 3.95 (3H, s)

Step C: 2,6-difluoro-4-(4,4,5,5-tetramethyl-1,3,2-dioxaborolan-2-yl)benzoic acid methyl ester 4-Bromo-2,6-difluoro-benzoic acid methyl ester (1.27 g, 5.0 mmol) obtained in Step B was reacted in the same manner as in Step D of Preparation Example 1 to obtain the title compound (1.20 g, 80%).

$^1$H-NMR (CDCl$_3$) δ 7.34 (2H, m), 3.95 (3H, s), 1.34 (12H, s)

Preparation Example 70: 3-[4-(chloromethyl)-3,5-difluoro-phenyl]-2-(cyclopentoxy)pyridine

Step A: 4-[2-(cyclopentoxy)-3-pyridyl]-2,6-difluoro-benzoic acid methyl ester 2-Cyclopentoxy-3-iodo-pyridine (0.96 g, 3.3 mmol) obtained in Preparation Example 11 and 2,6-difluoro-4-(4,4,5,5-tetramethyl-1,3,2-dioxaborolan-2-yl)benzoic acid methyl ester (1.04 g, 3.5 mmol) obtained in Preparation Example 69 were reacted in the same manner as in Step A of Example 1 to obtain the title compound (0.47 g, 42%).

$^1$H-NMR (CDCl$_3$) δ 8.20 (1H, m), 7.61 (1H, m), 7.21 (2H, m), 6.95 (1H, m), 5.53 (1H, m), 3.97 (3H, s), 1.95 (2H, m), 1.81 (2H, m), 1.74 (2H, m), 1.65 (2H, m)

Step B: [4-[2-(cyclopentoxy)-3-pyridyl]-2,6-difluoro-phenyl]methanol

4-[2-(Cyclopentoxy)-3-pyridyl]-2,6-difluoro-benzoic acid methyl ester (0.47 g, 1.41 mmol) obtained in Step A was dissolved in 7 mL of THF. Diisobutylaluminum hydride (1.32 mL, 2.1 mmol, 1.6 M toluene solution) was slowly added thereto at −78° C. The reaction solution was stirred at −78° C. for 2 hours and additionally stirred at room temperature for 1 hour. After termination of the reaction, the reaction solution was cooled to −78° C., and MeOH was added thereto. After addition of HCl aqueous solution at 0° C., the reaction solution was stirred for 1 hour. Solids were filtered through Celite, and water was added to the filtrate. The filtrate was extracted with EtOAc. The organic layer was dried with MgSO$_4$ to obtain the title compound (0.38 g, 90%).

$^1$H-NMR (CDCl$_3$) δ 8.17 (1H, m), 7.58 (1H, m), 7.16 (2H, m), 6.95 (1H, m), 5.53 (1H, m), 4.82 (2H, d), 1.95 (2H, m), 1.89 (1H, t, OH), 1.82 (2H, m), 1.75 (2H, m), 1.64 (2H, m)

Step C: 3-[4-(chloromethyl)-3,5-difluoro-phenyl]-2-(cyclopentoxy)pyridine

[4-[2-(Cyclopentoxy)-3-pyridyl]-2,6-difluoro-phenyl]methanol (0.38 g, 1.27 mmol) obtained in Step B was dissolved in 6.4 mL of CH$_3$CN, and SOCl$_2$ (0.19 mL, 2.54 mmol) was slowly added thereto. The mixture was stirred at room temperature for 90 minutes. The reaction solution was concentrated under reduced pressure and water was added thereto. The reaction solution was extracted with EtOAc, and the organic layer was dried with MgSO$_4$ to obtain the title compound (0.40 g, 99%).

$^1$H-NMR (CDCl$_3$) δ 8.19 (1H, m), 7.59 (1H, m), 7.18 (2H, m), 6.99 (1H, m), 5.53 (1H, m), 4.71 (2H, s), 1.96 (2H, m), 1.82-1.63 (6H, m)

Preparation Example 71: 4-[4-(4,4,5,5-tetramethyl-1,3,2-dioxaborolan-2-yl)phenyl]butanenitrile

Step A: 3-(4-bromophenyl)propan-1-ol 3-(4-Bromophenyl)propanoic acid (1.67 g, 7.3 mmol) was dissolved in 24 mL of THF and cooled to 0° C. Borane-THF (22 mL, 22 mmol, 1.0 M THF solution) was added thereto, and the mixture was stirred at room temperature for 16 hours. The reaction solution was cooled to 0° C., and water and 1N HCl aqueous solution were sequentially added thereto. The reaction solution was extracted with EtOAc, and the organic layer was dried with MgSO$_4$ and purified by column chromatography to obtain the title compound (1.46 g, 93%).

$^1$H-NMR (CDCl$_3$) δ 7.40 (2H, d), 7.08 (2H, d), 3.66 (2H, m), 2.67 (2H, m), 1.86 (2H, m), 1.26 (1H, t, OH)

Step B: 3-(4-bromophenyl)propyl methanesulfonate 3-(4-Bromophenyl)propan-1-ol (1.46 g, 6.79 mmol) obtained in Step A was reacted in the same manner as in Preparation Example 60 to obtain the title compound (1.87 g, 93%).

$^1$H-NMR (CDCl$_3$) δ 7.42 (2H, d), 7.07 (2H, d), 4.22 (2H, t), 3.00 (3H, s), 2.72 (2H, t), 2.05 (2H, m)

Step C: 4-(4-bromophenyl)butanenitrile 3-(4-Bromophenyl)propyl methanesulfonate (1.04 g, 3.55 mmol) obtained in Step B was reacted in the same manner as in Step E of Preparation Example 81 to obtain the title compound (0.73 g, 99%).

$^1$H-NMR (CDCl$_3$) δ 7.44 (2H, d), 7.07 (2H, d), 2.74 (2H, t), 2.32 (2H, t), 1.96 (2H, m)

Step D: 4-[4-(4,4,5,5-tetramethyl-1,3,2-dioxaborolan-2-yl)phenyl]butanenitrile 4-(4-Bromophenyl)butanenitrile (0.73 g, 3.5 mmol) obtained in Step C was reacted in the same manner as in Step D of Preparation Example 1 to obtain the title compound (0.7 g, 73%).

$^1$H-NMR (CDCl$_3$) δ 7.70 (2H, d), 7.20 (2H, d), 2.79 (2H, t), 2.30 (2H, t), 1.99 (2H, m), 1.34 (12H, s)

Preparation Example 72: 5-[[2,6-difluoro-4-(4,4,5,5-tetramethyl-1,3,2-dioxaborolan-2-yl)phenoxy]methyl]-2-[(4-methoxyphenyl)methoxy]pyridine Step A: 6-[(4-methoxyphenyl)methoxy]pyridin-3-carboxylic acid (4-Methoxyphenyl)methanol (2.6 mL, 21 mmol) was dissolved in 47 mL of DMF. NaH (1.23 g, 28.1 mmol, 55 wt % in mineral oil) was added thereto at 0° C., and the mixture was stirred for 30 minutes. 6-Chloropyridin-3-carboxylic acid (2.22 g, 14 mmol) was added thereto, and the mixture was stirred at 80° C. for 7 hours. The reaction solution was concentrated under reduced pressure and water was added thereto. The reaction solution was adjusted to pH 3 by the use of 1 N HCl aqueous solution. The precipitate was filtered and dried to obtain the title compound (1.67 g, 45%).

$^1$H-NMR (CDCl$_3$) δ 8.92 (1H, s), 8.20 (1H, m), 7.41 (2H, d), 6.92 (2H, d), 6.82 (1H, m), 5.40 (2H, s), 3.82 (3H, s)

Step B: 6-[(4-methoxyphenyl)methoxy]pyridin-3-carboxylic acid ethyl ester

6-[(4-Methoxyphenyl)methoxy]pyridin-3-carboxylic acid (1.67 g, 6.4 mmol) obtained in Step A was dissolved in 13 mL of THF. 1,1-Carbonyldiimidazole (1.03 g, 6.4 mmol) was added thereto, and the mixture was stirred at room temperature for 1 hour. 13 mL of anhydrous ethanol was added thereto, and the mixture was stirred at room temperature for 16 hours. The reaction solution was concentrated under reduced pressure and purified by column chromatography to obtain the title compound (1.49 g, 80%).

$^1$H-NMR (CDCl$_3$) δ 8.85 (1H, m), 8.15 (1H, m), 7.40 (2H, d), 6.93 (2H, d), 6.79 (1H, m), 5.37 (2H, s), 4.38 (2H, q), 3.83 (3H, s), 1.39 (3H, t)

Step C: [6-[(4-methoxyphenyl)methoxy]-3-pyridyl]methanol

6-[(4-Methoxyphenyl)methoxy]pyridin-3-carboxylic acid ethyl ester (1.48 g, 5.18 mmol) obtained in Step B was reacted in the same manner as in Step B of Preparation Example 70 to obtain the title compound (0.96 g, 76%).

$^1$H-NMR (CDCl$_3$) δ 8.15 (1H, m), 7.62 (1H, m), 7.39 (2H, d), 6.92 (2H, d), 6.79 (1H, m), 5.31 (2H, s), 4.63 (2H, s), 3.81 (3H, s)

Step D: 5-[[2,6-difluoro-4-(4,4,5,5-tetramethyl-1,3,2-dioxaborolan-2-yl)phenoxy]methyl]-2-[(4-methoxyphenyl)methoxy]pyridine

[6-[(4-Methoxyphenyl)methoxy]-3-pyridyl]methanol (0.144 g, 0.58 mmol) obtained in Step C and 2,6-difluoro-4-(4,4,5,5-tetramethyl-1,3,2-dioxaborolan-2-yl)phenol (0.15 g, 0.58 mmol) obtained in Step B of Preparation Example 16 were reacted in the same manner as in Preparation Example 62 to obtain the title compound (0.155 g, 55%).

$^1$H-NMR (CDCl$_3$) δ 8.15 (1H, m), 7.70 (1H, m), 7.38 (2H, d), 7.28 (2H, m), 6.90 (2H, d), 6.76 (1H, m), 5.29 (2H, s), 5.13 (2H, s), 3.80 (3H, s), 1.32 (12H, s)

Preparation Example 73: 4-[[2,6-difluoro-4-(4,4,5,5-tetramethyl-1,3,2-dioxaborolan-2-yl)phenoxy]methyl]-2-[(4-methoxyphenyl)methoxy]pyridine Step A: 2-[(4-methoxyphenyl)methoxy]pyridin-4-carboxylic acid 2-Chloropyridin-4-carboxylic acid (2.22 g, 14 mmol) and (4-methoxyphenyl)methanol (2.6 mL, 21 mmol) were reacted in the same manner as in Step A of Preparation Example 72 to obtain the title compound (1.86 g, 51%).

$^1$H-NMR (CDCl$_3$) δ 8.33 (1H, m), 7.45 (1H, m), 7.39 (3H, m), 6.92 (2H, d), 5.35 (2H, s), 3.82 (3H, s)

Step B: 2-[(4-methoxyphenyl)methoxy]pyridin-4-carboxylic acid ethyl ester

2-[(4-Methoxyphenyl)methoxy]pyridin-4-carboxylic acid (0.51 g, 1.97 mmol) obtained in Step A was reacted in the same manner as in Step B of Preparation Example 72 to obtain the title compound (0.39 g, 68%).

$^1$H-NMR (CDCl$_3$) δ 8.28 (1H, m), 7.38 (4H, m), 6.92 (2H, d), 5.36 (2H, s), 4.42 (2H, q), 3.88 (3H, s), 1.38 (3H, t)

Step C: [2-[(4-methoxyphenyl)methoxy]-4-pyridyl]methanol

2-[(4-Methoxyphenyl)methoxy]pyridin-4-carboxylic acid ethyl ester (0.39 g, 1.34 mmol) obtained in Step B was reacted in the same manner as in Step C of Preparation Example 72 to obtain the title compound (0.25 g, 75%).

$^1$H-NMR (CDCl$_3$) δ 8.14 (1H, m), 7.39 (2H, d), 6.90 (4H, m), 5.32 (2H, s), 4.69 (2H, s), 3.81 (3H, s)

Step D: 4-[[2,6-difluoro-4-(4,4,5,5-tetramethyl-1,3,2-dioxaborolan-2-yl)phenoxy]methyl]-2-[(4-methoxyphenyl)methoxy]pyridine

[2-[(4-Methoxyphenyl)methoxy]-4-pyridyl]methanol (0.25 g, 1 mmol) obtained in Step C and 2,6-difluoro-4-(4, 4,5,5-tetramethyl-1,3,2-dioxaborolan-2-yl)phenol (0.26 g, 1 mmol) obtained in Step B of Preparation Example 16 were reacted in the same manner as in Preparation Example 62 to obtain the title compound (0.09 g, 18%).

$^1$H-NMR (CDCl$_3$) δ 8.15 (1H, m), 7.40 (2H, d), 7.28 (2H, m), 6.96 (1H, m), 6.90 (3H, m), 5.30 (2H, s), 5.17 (2H, s), 3.81 (3H, s), 1.32 (12H, s)

Preparation Example 74: 3-[4-(1-chloroethyl)-2,6-difluoro-phenyl]-2-(cyclopentoxy)pyridine Step A: 1-[2,6-difluoro-4-(4,4,5,5-tetramethyl-1,3,2-dioxaborolan-2-yl)phenyl]ethaneone 1-(4-Bromo-2,6-difluoro-phenyl)ethaneone (0.97 g, 4.13 mmol) obtained in Step C of Preparation Example 32 was reacted in the same manner as in Step D of Preparation Example 1 to obtain the title compound (0.9 g, 77%).

$^1$H-NMR (CDCl$_3$) δ 7.35 (2H, m), 2.59 (3H, s), 1.34 (12H, s)

Step B: 1-[4-[2-(cyclopentoxy)-3-pyridyl]-2,6-difluoro-phenyl]ethaneone

1-[2,6-Difluoro-4-(4,4,5,5-tetramethyl-1,3,2-dioxaborolan-2-yl)phenyl]ethaneone (0.24 g, 0.89 mmol) obtained in Step A and 2-cyclopentoxy-3-iodo-pyridine (0.024 g, 0.84 mmol) obtained in Preparation Example 11 were reacted in the same manner as in Step A of Example 1 to obtain the title compound (0.13 g, 48%).

$^1$H-NMR (CDCl$_3$) δ 8.20 (1H, m), 7.60 (1H, m), 7.21 (2H, m), 6.95 (1H, m), 5.54 (1H, m), 2.64 (3H, s), 1.96 (2H, m), 1.82 (2H, m), 1.75 (2H, m), 1.65 (2H, m)

Step C: 1-[4-[2-(cyclopentoxy)-3-pyridyl]-2,6-difluoro-phenyl]ethanol

1-[4-[2-(cyclopentoxy)-3-pyridyl]-2,6-difluoro-phenyl]ethaneone (0.13 g, 0.41 mmol) obtained in Step B was dissolved in 2 mL of MeOH. NaBH$_4$ (0.031 g, 0.82 mmol) was added thereto, and the mixture was stirred at room temperature for 16 hours. After addition of water, the reaction solution was extracted with EtOAc. The organic layer was dried with MgSO$_4$ to obtain the title compound (0.12 g, 92%).

$^1$H-NMR (CDCl$_3$) δ 8.16 (1H, m), 7.58 (1H, m), 7.12 (2H, m), 6.93 (1H, m), 5.53 (1H, m), 5.28 (1H, m), 2.22 (1H, d, OH), 1.96 (2H, m), 1.80 (4H, m), 1.68 (5H, m)

Step D: 3-[4-(1-chloroethyl)-2,6-difluoro-phenyl]-2-(cyclopentoxy)pyridine

1-[4-[2-(cyclopentoxy)-3-pyridyl]-2,6-difluoro-phenyl]ethanol (0.12 g, 0.37 mmol) obtained in Step C was dissolved in 3.5 mL of chloroform. SOCl$_2$ (0.055 mL, 0.75 mmol) was added thereto, and the mixture was stirred at 60° C. for 3 hours. The reaction solution was concentrated under reduced pressure to obtain the title compound (0.12 g, 98%).

$^1$H-NMR (CDCl$_3$) δ 8.34 (1H, m), 7.86 (1H, m), 7.18 (1H, m), 7.11 (2H, m), 5.87 (1H, m), 5.48 (1H, m), 2.16 (2H, m), 1.99 (3H, d), 1.89 (2H, m), 1.74 (4H, m)

Preparation Example 75: 2-[[(E)-3-[4-[2-(cyclopentoxy)-3-pyridyl]-2,6-difluoro-phenyl]allyl]-sulfamoyl-amino]acetic acid ethyl ester Step A: (E)-3-[2,6-difluoro-4-(4,4,5,5-tetramethyl-1,3,2-dioxaborolan-2-yl)phenyl]prop-2-enoic acid ethyl ester (E)-3-(4-bromo-2,6-difluoro-phenyl)prop-2-enoic acid ethyl ester (3.8 g, 13 mmol) obtained in Step A of Preparation Example 195 was reacted in the same manner as in Step D of Preparation Example 1 to obtain the title compound (2.16 g, 49%).

$^1$H-NMR (CDCl$_3$) δ 7.79 (1H, d), 7.33 (2H, m), 6.78 (1H, d), 4.27 (2H, q), 1.34 (15H, m)

Step B: (E)-3-[4-[2-(cyclopentoxy)-3-pyridyl]-2,6-difluoro-phenyl]prop-2-enoic acid ethyl ester (E)-3-[2,6-difluoro-4-(4,4,5,5-tetramethyl-1,3,2-dioxaborolan-2-yl)phenyl]prop-2-enoic acid ethyl ester (0.67 g, 1.98 mmol) obtained in Step A and 2-cyclopentoxy-3-iodo-pyridine (0.55 g, 1.89 mmol) obtained in Preparation Example 11 were reacted in the same manner as in Step A of Example 1 to obtain the title compound (0.56 g, 80%).

$^1$H-NMR (CDCl$_3$) δ 8.19 (1H, m), 7.82 (1H, d), 7.61 (1H, m), 7.21 (2H, m), 6.96 (1H, m), 6.76 (1H, d), 5.54 (1H, m), 4.28 (2H, q), 1.96 (2H, m), 1.75 (4H, m), 1.66 (2H, m), 1.35 (3H, t)

Step C: (E)-3-[4-[2-(cyclopentoxy)-3-pyridyl]-2,6-difluoro-phenyl]prop-2-en-1-ol (E)-3-[4-[2-(cyclopentoxy)-3-pyridyl]-2,6-difluoro-phenyl]prop-2-enoic acid ethyl ester (0.4 g, 1.07 mmol) obtained in Step B was reacted in the same manner as in Step B of Preparation Example 70 to obtain the title compound (0.28 g, 78%).

$^1$H-NMR (CDCl$_3$) δ 8.17 (1H, m), 7.60 (1H, m), 7.15 (2H, m), 6.93 (1H, m), 6.72 (2H, m), 5.53 (1H, m), 4.40 (2H, m), 1.95 (2H, m), 1.83 (2H, m), 1.76 (2H, m), 1.65 (2H, m), 1.50 (1H, t, OH)

Step D: [(E)-3-[4-[2-(cyclopentoxy)-3-pyridyl]-2,6-difluoro-phenyl]allyl]methanesulfonate (E)-3-[4-[2-(cyclopentoxy)-3-pyridyl]-2,6-difluoro-phenyl]prop-2-en-1-ol (0.28 g, 0.84 mmol) obtained in Step C was reacted in the same manner as in Preparation Example 60 to obtain the title compound (0.28 g, 83%).

$^1$H-NMR (CDCl$_3$) δ 8.18 (1H, m), 7.61 (1H, m), 7.17 (2H, m), 6.94 (1H, m), 6.81 (1H, d), 6.67 (1H, m), 5.53 (1H, m), 4.93 (2H, d), 3.07-2.80 (3H, s), 1.95 (2H, m), 1.85 (2H, m), 1.76 (2H, m), 1.66 (2H, m)

Step E: 2-[[(E)-3-[4-[2-(cyclopentoxy)-3-pyridyl]-2,6-difluoro-phenyl]allyl]amino]acetic acid ethyl ester

[(E)-3-[4-[2-(cyclopentoxy)-3-pyridyl]-2,6-difluoro-phenyl]allyl]methanesulfonate (0.28 g, 0.7 mmol) obtained in Step D was dissolved in 3.5 mL of THF. Hydrochloric acid salt of glycine ethyl ester (0.098 g, 0.7 mmol) and TEA (0.58 mL, 4.2 mmol) was added thereto, and the mixture was stirred for 16 hours under reflux. The reaction solution was concentrated under reduced pressure and purified by column chromatography to obtain the title compound (0.076 g, 26%).

$^1$H-NMR (CDCl$_3$) δ 8.15 (1H, m), 7.60 (1H, m), 7.13 (2H, m), 6.92 (1H, m), 6.60 (2H, m), 5.52 (1H, m), 4.20 (2H, q), 3.50 (2H, d), 3.47 (2H, s), 1.95 (2H, m), 1.82 (2H, m), 1.76 (2H, m), 1.65 (2H, m), 1.30 (3H, t)

Step F: 2-[[(E)-3-[4-[2-(cyclopentoxy)-3-pyridyl]-2,6-difluoro-phenyl]allyl]-sulfamoyl-amino]acetic acid ethyl ester Chlorosulfonyl isocyanate (0.024 mL, 0.27 mmol) was dissolved in 1 mL of DCM and cooled to 0° C. Tert-butyl alcohol (0.02 g, 0.27 mmol) was added thereto, and the mixture was stirred at room temperature for 1 hour. 2-[[(E)-3-[4-[2-(cyclopentoxy)-3-pyridyl]-2,6-difluoro-phenyl]allyl]amino]acetic acid ethyl ester (0.076 g, 0.18 mmol, 0.2M DCM solution) obtained in Step E and TEA (0.05 mL, 0.36 mmol) were added thereto, and the mixture was stirred at room temperature for 90 minutes. After addition of water, the reaction solution was extracted with EtOAc and purified by column chromatography to obtain the title compound (0.038 g, 28%).

$^1$H-NMR (CDCl$_3$) δ 8.17 (1H, m), 7.59 (1H, m), 7.15 (2H, m), 6.93 (1H, m), 6.61 (2H, m), 5.53 (1H, m), 4.68 (2H, brs), 4.22 (2H, q), 4.14 (2H, d), 4.11 (2H, s), 1.95 (2H, m), 1.82 (2H, m), 1.75 (2H, m), 1.65 (2H, m), 1.28 (3H, t)

Preparation Example 76: [(E)-3-[4-(2-cyclobutylsulfanyl-3-pyridyl)-2,6-difluoro-phenyl]allyl]methanesulfonate Step A: (E)-3-[4-(2-cyclobutylsulfanyl-3-pyridyl)-2,6-difluoro-phenyl]prop-2-enoic acid ethyl ester (E)-3-[2,6-difluoro-4-(4,4,5,5-tetramethyl-1,3,2-dioxaborolan-2-yl)phenyl]prop-2-enoic acid ethyl ester (0.19 g, 0.57 mmol) obtained in Step A of Preparation Example 75 and 3-iodo-2-cyclobutylsulfanyl-pyridine (0.15 g, 0.51 mmol) obtained in Preparation Example 13 were reacted in the same manner as in Step A of Example 1 to obtain the title compound (0.15 g, 80%).

$^1$H-NMR (CDCl$_3$) δ 8.44 (1H, m), 7.80 (1H, d), 7.36 (1H, m), 7.05 (3H, m), 6.79 (1H, d), 4.44 (1H, m), 4.29 (2H, q), 2.51 (2H, m), 2.05 (4H, m), 1.36 (3H, t)

Step B: (E)-3-[4-(2-cyclobutylsulfanyl-3-pyridyl)-2,6-difluoro-phenyl]prop-2-en-1-ol (E)-3-[4-(2-cyclobutylsulfanyl-3-pyridyl)-2,6-difluoro-phenyl]prop-2-enoic acid ethyl ester (0.15 g, 0.41 mmol) obtained in Step A was reacted in the same manner as in Step B of Preparation Example 70 to obtain the title compound (0.13 g, 99%).

$^1$H-NMR (CDCl$_3$) δ 8.43 (1H, m), 7.35 (1H, m), 7.04 (1H, m), 6.99 (2H, m), 6.73 (2H, m), 4.41 (3H, m), 2.51 (2H, m), 2.04 (4H, m)

Step C: [(E)-3-[4-(2-cyclobutylsulfanyl-3-pyridyl)-2,6-difluoro-phenyl]allyl]methanesulfonate (E)-3-[4-(2-cyclobutylsulfanyl-3-pyridyl)-2,6-difluoro-phenyl]prop-2-en-1-ol (0.13 g, 0.4 mmol) obtained in Step B was reacted in the same manner as in Preparation Example 60 to obtain the title compound (0.14 g, 87%).

$^1$H-NMR (CDCl$_3$) δ 8.43 (1H, m), 7.36 (1H, m), 7.02 (3H, m), 6.81 (1H, d), 6.68 (1H, m), 4.94 (2H, d), 4.44 (1H, m), 3.08 (3H, s), 2.52 (2H, m), 2.04 (4H, m)

Preparation Example 77: 5-[2-[tert-butyl(diphenyl)silyl]oxyethyl]isoxazol-3-ol

Hydroxylamine hydrochloride (0.63 g, 9 mmol) was dissolved in 13 mL of MeOH, and NaOH (0.96 g, 24 mmol, 10% aqueous solution) was added thereto. 5-[Tert-butyl(diphenyl)silyl]oxypent-2-ynoic acid methyl ester (2.77 g, 7.5 mmol, 1.0 M MeOH solution) was added thereto, and the mixture was stirred at room temperature for 48 hours. The reaction solution was adjusted to pH 2 by the use of 6 M HCl aqueous solution, extracted with Et$_2$O and purified by column chromatography to obtain the title compound (1.0 g, 36%).

$^1$H-NMR (CDCl$_3$) δ 7.62 (4H, m), 7.43 (6H, m), 5.76 (1H, s), 3.91 (2H, t), 2.87 (2H, t), 1.03 (9H, s)

Preparation Example 78: tert-butyl-[2-[3-[(4-methoxyphenyl)methoxy]isoxazol-5-yl]ethoxy]-diphenyl-silane 5-[2-[Tert-butyl(diphenyl)silyl]oxyethyl]isoxazol-3-ol (0.28 g, 0.76 mmol) obtained in Preparation Example 77 was dissolved in 2.5 mL of DMF. K$_2$CO$_3$ (0.21 g, 1.52 mmol) and 4-methoxybenzyl chloride (0.1 mL, 0.76 mmol) were added thereto, and the mixture was stirred at 60° C. for 10 hours. The reaction solution was concentrated under reduced pressure. After addition of water, the reaction solution was extracted with EtOAc. The organic layer was dried with MgSO$_4$ and purified by column chromatography to obtain the title compound (0.26 g, 70%).

$^1$H-NMR (CDCl$_3$) δ 7.72-7.37 (12H, m), 6.91 (2H, d), 5.71 (1H, s), 5.17 (2H, s), 3.89 (2H, t), 3.81 (3H, s), 2.87 (2H, t), 1.02 (9H, s)

Preparation Example 79: 2-[3-[(4-methoxyphenyl)methoxy]isoxazol-5-yl]ethanol

Tert-butyl-[2-[3-[(4-methoxyphenyl)methoxy]isoxazol-5-yl]ethoxy]-diphenyl-silane (0.26 g, 0.53 mmol) obtained in Preparation Example 78 was dissolved in 10 mL of THF. Tetrabutylammonium fluoride (0.53 mL, 0.53 mmol, 1.0 M THF solution) was slowly added thereto at 0° C., and the mixture was stirred for 30 minutes. After addition of ammonium chloride aqueous solution, the reaction solution was extracted with EtOAc. The organic layer was dried with MgSO$_4$ and purified by column chromatography to obtain the title compound (0.075 g, 56%).

$^1$H-NMR (CDCl$_3$) δ 7.38 (2H, d), 6.90 (2H, d), 5.75 (1H, s), 5.17 (2H, s), 3.93 (2H, m), 3.82 (3H, s), 2.92 (2H, t), 1.70 (1H, brs)

Preparation Example 80: 2-fluoro-5-(6-isopropylsulfanyl-2-pyridyl)pyridine

Step A: 2-fluoro-5-(4,4,5,5-tetramethyl-1,3,2-dioxaborolan-2-yl)pyridine

5-Bromo-2-fluoropyridine (2.0 g, 11.3 mmol), K$_2$CO$_3$ (4.46 g, 45 mmol) and bis(pinacolato)diboron (3.17 g, 12.4 mmol) were dissolved in 38 mL of DMF and charged with nitrogen gas for 5 minutes. After addition of catalytic amount of PdCl$_2$(dppf)-DCM, the mixture was stirred at 80° C. for 3 hours. Solids were filtered and purified by column chromatography to obtain the title compound (1.59 g, 60%).

$^1$H-NMR (DMSO-d$_6$) δ 8.45 (1H, d), 8.16 (1H, m), 7.20 (1H, dd), 1.30 (12H, s)

Step B: 2-fluoro-5-(6-isopropylsulfanyl2-pyridyl)pyridine

2-Chloro-6-isopropylsulfanyl-pyridine (0.14 g, 0.7 mmol) obtained in Preparation Example 10 and 2-fluoro-5-(4,4,5,5-tetramethyl-1,3,2-dioxaborolan-2-yl)pyridine (0.2 g, 0.9 mmol) obtained in Step A were dissolved in 1.1 mL of 2 M Na$_2$CO$_3$ aqueous solution and 5 mL 1,4-dioxane, and charged with nitrogen gas for 5 minutes. After addition of Pd(PPh$_3$)$_4$ (43 mg, 0.04 mmol), the mixture was stirred for 4 hours under reflux. The reaction solution was diluted with water and extracted with EtOAc to separate an organic layer. The organic layer was dried with MgSO₄ and purified by column chromatography to obtain the title compound (0.114 g, 62%).

¹H-NMR (CDCl₃) δ 8.84 (1H, d), 8.43 (1H, m), 7.56 (1H, t), 7.39 (1H, d), 7.13 (1H, d), 7.04 (1H, dd), 4.13 (1H, m), 1.46 (6H, d)

Preparation Example 81: 2-[1-[4-(4,4,5,5-tetramethyl-1,3,2-dioxaborolan-2-yl)phenyl]pyrazol-4-yl] acetic acid methyl ester Step A: 1-(4-bromophenyl)pyrazole 1H-pyrazole (1.0 g, 14.7 mmol) and 4-bromofluorobenzene (5.14 g, 29.4 mmol) were dissolved in 80 mL of DMF. Potassium phosphate (15.6 g, 73.5 mmol) was added thereto, and the mixture was stirred at 150° C. for 27 hours. After addition of 150 mL of water, the reaction solution was extracted with Et₂O to obtain the title compound (3.45 g, 99%).

¹H-NMR (CDCl₃) δ 7.90 (1H, m), 7.72 (1H, m), 7.58 (4H, m), 6.48 (1H, m)

Step B: 1-(4-bromophenyl)pyrazol-4-carbaldehyde 50 mL of DMF was cooled to 0° C., and POCl₃ was added thereto. The mixture was stirred for 15 minutes. 1-(4-Bromophenyl)pyrazole (3.45 g, 14.7 mmol) obtained in Step A was slowly added thereto, and the mixture was stirred at 110° C. for 3 hours. After cooling to room temperature, sodium bicarbonate aqueous solution was added thereto, and the mixture was stirred for 30 minutes. The reaction solution was extracted with Et₂O and purified by column chromatography to obtain the title compound (0.45 g, 12%).

¹H-NMR (CDCl₃) δ 9.97 (1H, s), 8.42 (1H, s), 8.17 (1H, s), 7.62 (4H, m)

Step C: [1-(4-bromophenyl)pyrazol-4-yl]methanol 1-(4-Bromophenyl)pyrazol-4-carbaldehyde (0.45 g, 1.79 mmol) obtained in Step B was dissolved in 3 mL of THF and 3.6 mL of MeOH. NaBH₄ (0.14 g, 3.76 mmol) was slowly added thereto, and the mixture was stirred for 90 minutes. The adjusted to pH 1 at 0° C. After addition of 1 M NaOH aqueous solution (4 mL, 4 mmol), the reaction solution was extracted with EtOAc to obtain the title compound (0.39 g, 87%).

¹H-NMR (CDCl₃) δ 7.91 (1H, s), 7.72 (1H, s), 7.57 (4H, m), 4.68 (2H, m), 1.60 (1H, brs)

Step D: 1-(4-bromophenyl)-4-(chloromethyl)pyrazole

[1-(4-Bromophenyl)pyrazol-4-yl]methanol (0.39 g, 1.55 mmol) obtained in Step C was dissolved in 8 mL of DCM. DIPEA (0.4 mL, 2.3 mmol) and methanesulfonyl chloride (0.13 mL, 1.7 mmol) were sequentially added thereto at 0° C., and the mixture was stirred at room temperature for 90 minutes. After addition of water, the organic layer extracted with DCM was purified by column chromatography to obtain the title compound (0.25 g, 58%).

¹H-NMR (CDCl₃) δ 7.92 (1H, s), 7.73 (1H, s), 7.57 (4H, m), 4.60 (2H, s)

Step E: 2-[1-(4-bromophenyl)pyrazol-4-yl]acetonitrile 1-(4-Bromophenyl)-4-(chloromethyl)pyrazole (0.25 g, 0.9 mmol) obtained in Step D was dissolved in 4.5 mL of DMSO. Sodium cyanide (0.18 g, 3.6 mmol) was added thereto, and the mixture was stirred at room temperature. After addition of water, the reaction solution was extracted with EtOAc to obtain the title compound (0.19 g, 80%).

¹H-NMR (CDCl₃) δ 7.93 (1H, s), 7.67 (1H, s), 7.58 (4H, m), 3.68 (2H, s)

Step F: 2-[1-(4-bromophenyl)pyrazol-4-yl]acetic acid

2-[1-(4-Bromophenyl)pyrazol-4-yl]acetonitrile (0.19 g, 0.76 mmol) obtained in Step E was dissolved in 0.45 mL of water and 0.4 mL of concentrated sulfuric acid, and the mixture was stirred for 3 hours under reflux. The precipitate formed by the addition of water was dried to obtain the title compound (0.2 g, 98%).

¹H-NMR (DMSO-d₆) δ 8.39 (1H, s), 7.76 (2H, d), 7.67 (3H, m), 3.50 (2H, s)

Step G: 2-[1-(4-bromophenyl)pyrazol-4-yl]acetic acid methyl ester

2-[1-(4-Bromophenyl)pyrazol-4-yl]acetic acid (0.2 g, 0.71 mmol) obtained in Step F was dissolved in 2.4 mL of THE Diazomethane (3 mL, 0.78 mmol, 0.25 M Et₂O solution) was added thereto, and the mixture was stirred for 20 minutes. The reaction solution was concentrated under reduced pressure to obtain the title compound (0.21 g, 99%).

¹H-NMR (CDCl₃) δ 7.89 (1H, s), 7.64 (1H, s), 7.55 (4H, m), 3.73 (3H, s), 3.73 (2H, s)

Step H: 2-[1-[4-(4,4,5,5-tetramethyl-1,3,2-dioxaborolan-2-yl)phenyl]pyrazol-4-yl]acetic acid methyl ester 2-[1-(4-Bromophenyl)pyrazol-4-yl]acetic acid methyl ester (0.21 g, 0.71 mmol) obtained in Step G, bis(pinacolato)diboron (0.19 g, 0.74 mmol) and DPPF (0.02 g, 0.035 mmol) were dissolved in 3.6 mL of 1,4-dioxane and charged with nitrogen gas. PdCl₂(dppf)-DCM (0.03 g, 0.035 mmol) was added thereto, and the mixture was stirred for 1 hour under reflux. Solids were filtered through Celite, and the filtrate was concentrated under reduced pressure and purified by column chromatography to obtain the title compound (0.096 g, 40%).

¹H-NMR (CDCl₃) δ 7.97 (1H, s), 7.88 (2H, d), 7.67 (3H, m), 3.73 (3H, s), 3.59 (2H, s), 1.36 (12H, s)

Preparation Example 82: benzyl N-[2,6-difluoro-4-(4,4,5,5-tetramethyl-1,3,2-dioxaborolan-2-yl)phenyl] carbamate Benzyl N-(4-bromo-2,6-difluoro-phenyl)carbamate (1.61 g, 4.7 mmol) was reacted in the same manner as in Step D of Preparation Example 1 to obtain the title compound (1.5 g, 82%).

¹H-NMR (CDCl₃) δ 7.36 (7H, m), 6.20 (1H, brs), 5.21 (2H, s), 1.33 (12H, s)

Preparation Example 83: 5-[2,6-difluoro-4-(4,4,5,5-tetramethyl-1,3,2-dioxaborolan-2-yl)anilino]pentanoic acid ethyl ester

Step A: 5-[N-benzyloxycarbonyl-2,6-difluoro-4-(4,4,5,5-tetramethyl-1,3,2-dioxaborolan-2-yl)anilino]pentanoic acid ethyl ester Benzyl N-[2,6-difluoro-4-(4,4,5,5-tetramethyl-1,3,2-dioxaborolan-2-yl)phenyl]carbamate (0.79 g, 2 mmol) obtained in Preparation Example 82 was dissolved in 6.7 mL of DMF. NaH (0.18 g, 55 wt % in mineral oil, 4 mmol) and 5-bromopentanoic acid ethyl ester (0.44 g, 2.1 mmol) were sequentially added thereto at 0° C., and the mixture was stirred at room temperature for 16 hours. The reaction solution was concentrated under reduced pressure. After addition of ammonium chloride aqueous solution, the reaction solution was extracted with EtOAc. The organic layer was collected, dried with $MgSO_4$ and purified by column chromatography to obtain the title compound (0.447 g, 45%).

$^1$H-NMR ($CDCl_3$) δ 7.40-7.18 (7H, m), 5.10 (2H, s), 4.08 (2H, q), 3.64 (2H, t), 2.28 (2H, t), 1.62 (2H, m), 1.54 (2H, m), 1.33 (12H, s), 1.21 (3H, t)

Step B: 5-[2,6-difluoro-4-(4,4,5,5-tetramethyl-1,3,2-dioxaborolan-2-yl)anilino]pentanoic acid ethyl ester 5-[N-benzyloxycarbonyl-2,6-difluoro-4-(4,4,5,5-tetramethyl-1,3,2-dioxaborolan-2-yl)anilino]pentanoic acid ethyl ester (0.46 g, 0.89 mmol) obtained in Step A was dissolved in 5 mL of MeOH. 10 wt % Pd/C (0.05 g) was added thereto, and the mixture was stirred for 16 hours under hydrogen atmosphere. Solids were filtered through Celite, and the filtrate was concentrated under reduced pressure to obtain the title compound (0.35 g, 99%).

$^1$H-NMR ($CDCl_3$) δ 7.21 (2H, m), 4.12 (2H, q), 3.39 (2H, t), 2.33 (2H, t), 1.71 (2H, m), 1.62 (2H, m), 1.32 (12H, s), 1.25 (3H, t)

Preparation Example 84: 2-[1-[2,6-difluoro-4-(4,4,5,5-tetramethyl-1,3,2-dioxaborolan-2-yl)phenyl]-4-piperidyl]acetic acid methyl ester

Step A: 2-[1-(2,6-difluoro-4-nitro-phenyl)-4-piperidyl]acetic acid methyl ester 3,4,5-Trifluoronitrobenzene (1.68 g, 9.43 mmol) was dissolved in 24 mL of DMF. Hydrochloric acid salt of (4-piperidyl)acetic acid methyl ester (2.02 g, 10.4 mmol) and DIPEA (4.1 mL, 23.5 mmol) were sequentially added, and the mixture was stirred at room temperature for 16 hours. The reaction solution was concentrated under reduced pressure. After addition of water, the reaction solution was extracted with EtOAc. The organic layer was collected and dried with $MgSO_4$ to obtain the title compound (3.0 g, 99%), which was used for the next step without purification.

$^1$H-NMR ($CDCl_3$) δ 7.74 (2H, m), 3.69 (3H, s), 3.50 (2H, m), 3.20 (2H, m), 2.31 (2H, d), 2.01 (1H, m), 1.80 (2H, m), 1.42 (2H, m)

Step B: 2-[1-(4-amino-2,6-difluoro-phenyl)-4-piperidyl]acetic acid methyl ester To 2-[1-(2,6-difluoro-4-nitro-phenyl)-4-piperidyl]acetic acid methyl ester (1.1 g, 3.5 mmol) obtained in Step A, each 12 mL of THF, MeOH and water were added. Ammonium chloride (1.31 g, 24.5 mmol) and iron (1.37 g, 24.5 mmol) were added thereto, and the mixture was stirred for 2 hours under reflux. After termination of the reaction, solids were filtered through Celite. After addition of water, the filtrate was extracted with EtOAc. The organic layer was collected and dried with $MgSO_4$ to obtain the title compound (0.82 g, 80%), which was used for the next step without purification.

$^1$H-NMR ($CDCl_3$) δ 6.15 (2H, m), 3.68 (3H, s), 3.04 (4H, m), 2.28 (2H, d), 1.90 (1H, m), 1.82 (2H, m), 1.43 (2H, m)

Step C: 2-[1-(4-bromo-2,6-difluoro-phenyl)-4-piperidyl]acetic acid methyl ester $CuBr_2$ (0.75 g, 3.36 mmol) was dissolved in 7 mL of $CH_3CN$. Tert-butyl nitrite (0.5 mL, 4.2 mmol) was added thereto, and the mixture was stirred at room temperature for 5 minutes. 2-[1-(4-Amino-2,6-difluoro-phenyl)-4-piperidyl]acetic acid methyl ester (0.8 g, 2.8 mmol) obtained in Step B was dissolved in 1.5 mL of $CH_3CN$ and added thereto. The reaction solution was stirred at room temperature for 1 hour and concentrated under reduced pressure. After addition of water, and reaction solution was extracted with EtOAc. The organic layer was purified by column chromatography to obtain the title compound (0.61 g, 60%).

$^1$H-NMR ($CDCl_3$) δ 7.00 (2H, m), 3.68 (3H, s), 3.19 (2H, m), 3.09 (2H, m), 2.29 (2H, d), 1.93 (1H, m), 1.75 (2H, m), 1.42 (2H, m)

Step D: 2-[1-[2,6-difluoro-4-(4,4,5,5-tetramethyl-1,3,2-dioxaborolan-2-yl)phenyl]-4-piperidyl]acetic acid methyl ester 2-[1-(4-Bromo-2,6-difluoro-phenyl)-4-piperidyl]acetic acid methyl ester (0.61 g, 1.7 mmol) obtained in Step C was reacted in the same manner as in Step D of Preparation Example 1 to obtain the title compound (0.52 g, 77%).

$^1$H-NMR ($CDCl_3$) δ 7.22 (2H, m), 3.68 (3H, s), 3.31 (2H, m), 3.10 (2H, m), 2.29 (2H, d), 1.95 (1H, m), 1.74 (2H, m), 1.43 (2H, m), 1.32 (12H, s)

Preparation Example 85: 2-[2-[2,6-difluoro-4-(4,4,5,5-tetramethyl-1,3,2-dioxaborolan-2-yl)anilino]ethyl]cyclopropanecarboxylic acid ethyl ester

Step A: (E)-5-(1,3-dioxoisoindolin-2-yl)pent-2-enoic acid ethyl ester 3-(1,3-Dioxoisoindolin-2-yl)propanal (2.5 g, 12.3 mmol) was dissolved in 80 mL of DCM. (1-Ethoxycarbonylethylidene)triphenylphosphorane (4.50 g, 12.9 mmol) was added thereto, and the mixture was stirred at room temperature for 2 hours. The reaction solution was concentrated under reduced pressure and purified by column chromatography to obtain the title compound (2.99 g, 89%).

$^1$H-NMR ($CDCl_3$) δ 7.83 (2H, m), 7.72 (2H, m), 6.91 (1H, m), 5.90 (1H, d), 4.16 (2H, q), 3.83 (2H, t), 2.60 (2H, m), 1.26 (3H, t)

Step B: 2-[2-(1,3-dioxoisoindolin-2-yl)ethyl]cyclopropanecarboxylic acid ethyl ester (E)-5-(1,3-dioxoisoindolin-2-yl)pent-2-enoic acid ethyl ester (2.0 g, 7.32 mmol) obtained in Step A was dissolved in 10 mL of THF. Diazomethane (88 mL, 22 mmol, 0.25M $Et_2O$ solution) was added thereto, and palladium (II) acetate (0.18 g, 0.8 mmol) was then slowly added thereto. The mixture was stirred at room temperature for 16 hours, and water was added thereto. The reaction solution was extracted with EtOAc and purified by column chromatography to obtain the title compound (1.72 g, 82%).

$^1$H-NMR (CDCl$_3$) δ 7.84 (2H, m), 7.72 (2H, m), 4.10 (2H, q), 3.79 (2H, m), 1.69 (2H, m), 1.38 (2H, m), 1.23 (3H, t), 1.17 (1H, m), 0.72 (1H, m)

Step C: 2-[2-(2,6-difluoro-4-nitro-anilino)ethyl]cyclopropanecarboxylic acid ethyl ester 2-[2-(1,3-Dioxoisoindolin-2-yl)ethyl]cyclopropanecarboxylic acid ethyl ester (1.72 g, 6 mmol) obtained in Step B was dissolved in 40 mL of EtOH. Hydrazine hydrate (1.4 mL, 30 mmol) was added thereto, and the mixture was stirred at room temperature for 3 hours. To the precipitate formed by the addition of Et$_2$O 20 mL of DMF, 3,4,5-trifluoronitrobenzene (1.06 g, 6 mmol) and DIPEA (1.57 mL, 9 mmol) were sequentially added, and the mixture was stirred at room temperature for 72 hours. The reaction solution was concentrated under reduced pressure, and water was added thereto. The organic layer extracted with EtOAc was purified by column chromatography to obtain the title compound (1.1 g, 58%).

$^1$H-NMR (CDCl$_3$) δ 7.78 (2H, m), 4.42 (1H, brs), 4.12 (2H, q), 3.62 (2H, m), 1.65 (2H, m), 1.42 (2H, m), 1.27 (3H, t), 1.22 (1H, m), 0.73 (1H, m)

Step D: 2-[2-(4-amino-2,6-difluoro-anilino)ethyl]cyclopropanecarboxylic acid ethyl ester 2-[2-(2,6-Difluoro-4-nitro-anilino)ethyl]cyclopropanecarboxylic acid ethyl ester (1.1 g, 3.5 mmol) obtained in Step C was reacted in the same manner as in Step B of Preparation Example 84 to obtain the title compound (0.88 g, 88%).

$^1$H-NMR (CDCl$_3$) δ 6.20 (2H, m), 4.12 (2H, q), 3.22 (2H, t), 1.58 (1H, m), 1.49 (1H, m), 1.40 (2H, m), 1.26 (3H, t), 1.18 (1H, m), 0.72 (1H, m)

Step E: 2-[2-(4-bromo-2,6-difluoro-anilino)ethyl]cyclopropanecarboxylic acid ethyl ester 2-[2-(4-Amino-2,6-difluoro-anilino)ethyl]cyclopropanecarboxylic acid ethyl ester (0.88 g, 3.09 mmol) obtained in Step D was reacted in the same manner as in Step C of Preparation Example 84 to obtain the title compound (0.085 g, 8%).

$^1$H-NMR (CDCl$_3$) δ 6.97 (2H, m), 4.10 (2H, q), 3.66 (1H, brs), 3.41 (2H, m), 1.56 (2H, m), 1.39 (2H, m), 1.27 (3H, t), 1.19 (1H, m), 0.72 (1H, m)

Step F: 2-[2-[2,6-difluoro-4-(4,4,5,5-tetramethyl-1,3,2-dioxaborolan-2-yl)anilino]ethyl]cyclopropanecarboxylic acid ethyl ester 2-[2-(4-Bromo-2,6-difluoro-anilino)ethyl]cyclopropanecarboxylic acid ethyl ester (0.085 g, 0.24 mmol) obtained in Step E was reacted in the same manner as in Step D of Preparation Example 1 to obtain the title compound (0.05 g, 50%).

$^1$H-NMR (CDCl$_3$) δ 7.22 (2H, m), 4.10 (2H, q), 3.92 (1H, brs), 3.48 (2H, t), 1.58 (2H, m), 1.40 (2H, m), 1.31 (12H, s), 1.26 (3H, t), 1.20 (1H, m), 0.71 (1H, m)

Preparation Example 86: 2-[1-[2,6-difluoro-4-(4,4,5,5-tetramethyl-1,3,2-dioxaborolan-2-yl)phenyl]-3-piperidyl]acetonitrile

Step A: tert-butyl 3-(hydroxymethyl)piperidin-1-carboxylate

3-Piperidinemethanol (0.91 g, 7.9 mmol) was dissolved in 13 mL of 1,4-dioxane and 8 mL of water. Di-tert-butyl dicarbonate (1.81 g, 8.3 mmol) and 8 mL of 1N NaOH aqueous solution were added thereto. The mixture was stirred at room temperature for 5 hours. After addition of water, the reaction solution was extracted with EtOAc. The organic layer was separated and dried with MgSO$_4$ to obtain the title compound (1.5 g, 90%).

$^1$H-NMR (DMSO-d$_6$) δ 4.51 (1H, t), 3.94 (1H, brs), 3.78 (1H, m), 3.36 (1H, m), 3.29 (1H, m), 3.19 (1H, m), 2.69 (1H, m), 1.67 (1H, m), 1.59 (1H, m), 1.46 (1H, m), 1.38 (9H, s), 1.29 (1H, m), 1.09 (1H, m)

Step B: tert-butyl 3-(methylsulfonyloxymethyl)piperidin-1-carboxylate

Tert-butyl 3-(hydroxymethyl)piperidin-1-carboxylate (0.31 g, 1.4 mmol) obtained in Step A was dissolved in 7 mL of DCM and cooled to 0° C. DIPEA (0.57 mL, 3.3 mmol) and methanesulfonyl chloride (0.12 mL, 1.54 mmol) were added thereto, and the mixture was stirred for 3 hours. After addition of water, the reaction solution was extracted with EtOAc to separate an organic layer. The organic layer was dried with MgSO$_4$ to obtain the title compound (0.41 g, 98%).

$^1$H-NMR (CDCl$_3$) δ 4.10 (2H, m), 3.95 (1H, m), 3.80 (1H, m), 3.02 (3H, s), 2.93 (1H, m), 2.79 (1H, m), 1.96 (1H, m), 1.82 (1H, m), 1.66 (1H, m), 1.49 (1H, m), 1.45 (9H, s), 1.33 (1H, m)

Step C: tert-butyl 3-(cyanomethyl)piperidin-1-carboxylate

Tert-butyl 3-(methylsulfonyloxymethyl)piperidin-1-carboxylate (0.41 g, 1.4 mmol) obtained in Step B was dissolved in 7 mL of DMF. Sodium cyanide (0.075 g, 1.54 mmol) was added thereto, and the mixture was stirred at 60° C. for 16 hours. The reaction solution was concentrated under reduced pressure, diluted with water, and extracted with EtOAc. The organic layer was separated and dried with MgSO$_4$ to obtain the title compound (0.29 g, 93%).

$^1$H-NMR (CDCl$_3$) δ 3.90 (1H, m), 3.82 (1H, m), 2.92 (2H, m), 2.30 (2H, m), 1.92 (2H, m), 1.68 (1H, m), 1.49 (1H, m), 1.46 (9H, s), 1.35 (1H, m)

Step D: 2-(3-piperidyl)acetonitrile hydrochloride

Tert-butyl 3-(cyanomethyl)piperidin-1-carboxylate (0.292 g, 1.3 mmol) obtained in Step C was dissolved in 13 mL of DCM and cooled to 0° C. HCl (1.3 mL, 5.6 mmol, 4 M 1,4-dioxane solution) was slowly added thereto. After stirring at 0° C. for 1 hour, the reaction solution was concentrated under reduced pressure to obtain the title compound (0.18 g, 86%).

$^1$H-NMR (DMSO-d$_6$) δ 9.16 (2H, brs), 3.21 (2H, t), 2.73 (1H, m), 2.61 (3H, m), 2.11 (1H, m), 1.81 (2H, m), 1.69 (1H, m), 1.27 (1H, m)

Step E: 2-[1-(2,6-difluoro-4-nitro-phenyl)-3-piperidyl]acetonitrile 2-(3-Piperidyl)acetonitrile hydrochloride (1.67 g, 10.4 mmol) obtained in Step D and 3,4,5-trifluoronitrobenzene (1.67 g, 9.45 mmol) were reacted in the same manner as in Step A of Preparation Example 84 to obtain the title compound (2.53 g, 95%).

$^1$H-NMR (CDCl$_3$) δ 7.76 (2H, m), 3.50 (1H, m), 3.40 (1H, m), 3.17 (1H, m), 3.04 (1H, m), 2.42 (2H, d), 2.16 (1H, m), 2.00 (1H, m), 1.82 (1H, m), 1.74 (1H, m), 1.44 (1H, m)

Step F: 2-[1-(4-bromo-2,6-difluoro-phenyl)-3-piperidyl]acetonitrile

2-[1-(2,6-Difluoro-4-nitro-phenyl)-3-piperidyl]acetonitrile (2.53 g, 9 mmol) obtained in Step E was reacted in the same manner as in Steps B and C of Preparation Example 84 to obtain the title compound (1.16 g, 41%).

$^1$H-NMR (CDCl$_3$) δ 7.00 (2H, m), 3.25 (1H, m), 3.13 (1H, m), 3.02 (1H, m), 2.90 (1H, m), 2.44 (2H, m), 2.13 (1H, m), 1.90 (1H, m), 1.76 (1H, m), 1.70 (1H, m), 1.42 (1H, m)

Step G: 2-[1-[2,6-difluoro-4-(4,4,5,5-tetramethyl-1,3,2-dioxaborolan-2-yl)phenyl]-3-piperidyl]acetonitrile 2-[1-(4-Bromo-2,6-difluoro-phenyl)-3-piperidyl]acetonitrile (1.16 g, 3.7 mmol) obtained in Step F was reacted in the same manner as in Step D of Preparation Example 1 to obtain the title compound (0.91 g, 68%).

$^1$H-NMR (CDCl$_3$) δ 7.23 (2H, m), 3.34 (1H, m), 3.22 (1H, m), 3.07 (1H, m), 2.94 (1H, m), 2.44 (2H, m), 2.13 (1H, m), 1.92 (1H, m), 1.76 (1H, m), 1.70 (1H, m), 1.43 (1H, m), 1.32 (12H, s)

Preparation Example 87: 5-[N-benzyloxycarbonyl-4-[2-(cyclopentoxy)-3-pyridyl]-2,6-difluoro-anilino]pentanoic acid ethyl ester

Step A: benzyl N-[4-[2-(cyclopentoxy)-3-pyridyl]-2,6-difluoro-phenyl]carbamate 2-Cyclopentoxy-3-iodo-pyridine (0.42 g, 1.47 mmol) obtained in Preparation Example 11 and benzyl N-[2,6-difluoro-4-(4,4,5,5-tetramethyl-1,3,2-dioxaborolan-2-yl)phenyl]carbamate (0.063 g, 1.61 mmol) obtained in Preparation Example 82 were reacted in the same manner as in Step A of Example 1 to obtain the title compound (0.5 g, 80%).

$^1$H-NMR (CDCl$_3$) δ 8.16 (1H, m), 7.58 (1H, m), 7.37 (5H, m), 7.19 (2H, m), 6.93 (1H, m), 6.18 (1H, brs), 5.52 (1H, m), 5.24 (2H, s), 1.96 (2H, m), 1.81 (2H, m), 1.76 (2H, m), 1.63 (2H, m)

Step B: 5-[N-benzyloxycarbonyl-4-[2-(cyclopentoxy)-3-pyridyl]-2,6-difluoro-anilino]pentanoic acid ethyl ester Benzyl N-[4-[2-(cyclopentoxy)-3-pyridyl]-2,6-difluoro-phenyl]carbamate (0.23 g, 0.54 mmol) obtained in Step A and 5-bromopentanoic acid ethyl ester (0.12 g, 0.57 mmol) were dissolved in 3.6 mL of DMF. NaH (0.032 g, 0.81 mmol, 55% in mineral oil) was added thereto, and the mixture was stirred at room temperature for 4 hours. The reaction solution was concentrated under reduced pressure. After addition of water and 1N HCl aqueous solution, the reaction solution was extracted with EtOAc. The organic layer was dried with MgSO$_4$ and purified by column chromatography to obtain the title compound (0.14 g, 47%).

$^1$H-NMR (CDCl$_3$) δ 8.17 (1H, m), 7.59 (1H, m), 7.40-7.20 (7H, m), 6.95 (1H, m), 5.53 (1H, m), 5.13 (2H, s), 4.09 (2H, q), 3.67 (2H, t), 2.33 (2H, t), 1.97 (2H, m), 1.80-1.60 (10H, m), 1.23 (3H, t)

Preparation Example 88: 2-[1-[2,6-difluoro-4-(4,4,5,5-tetramethyl-1,3,2-dioxaborolan-2-yl)phenyl]azetidin-3-yl]acetic acid ethyl ester

Step A: 1-(2,6-difluoro-4-nitro-phenyl)azetidin-3-ol 3,4,5-Trifluoronitrobenzene (5.58 g, 31.5 mmol) and hydrochloric acid salt of 3-hydroxyazetidine (3.8 g, 34.7 mmol) were reacted in the same manner as in Step A of Preparation Example 84 to obtain the title compound (7.25 g, 99%).

$^1$H-NMR (CDCl$_3$) δ 7.71 (2H, m), 4.80 (1H, m), 4.65 (2H, m), 4.27 (2H, m), 1.85 (1H, brs)

Step B: 2-[1-(2,6-difluoro-4-nitro-phenyl)azetidin-3-ylidene]acetic acid ethyl ester Oxalyl chloride (1.68 mL, 19.6 mmol) was added to 130 mL of DCM and cooled to −78° C. DMSO (2.77 mL, 39 mmol) was added thereto, and the mixture was stirred for 10 minutes. 1-(2,6-Difluoro-4-nitro-phenyl)azetidin-3-ol (3 g, 13 mmol) obtained in Step A was slowly added thereto, and the mixture was stirred at −78° C. for 15 minutes. TEA (8.88 mL, 63.7 mmol) was added thereto, and the mixture was stirred at −78° C. for 40 minutes and additionally stirred at room temperature for 30 minutes. (1-ethoxycarbonylethylidene)triphenylphosphorane (4.53 g, 13 mmol) was added thereto, and the mixture was stirred at room temperature for 16 hours. After addition of water, the reaction solution was extracted with DCM and purified by column chromatography to obtain the title compound (2.84 g, 73%).

$^1$H-NMR (CDCl$_3$) δ 7.74 (2H, m), 5.81 (1H, m), 5.33 (2H, m), 5.10 (2H, m), 4.21 (2H, q), 1.30 (3H, t)

Step C: 2-[1-(4-amino-2,6-difluoro-phenyl)azetidin-3-yl]acetic acid ethyl ester 2-[1-(2,6-Difluoro-4-nitro-phenyl)azetidin-3-ylidene]acetic acid ethyl ester (2.84 g, 9.52 mmol) obtained in Step B was dissolved in 80 mL of MeOH and 40 mL of THF. After addition of 0.5 g of 10 wt % Pd/C, the mixture was stirred for 16 hours under hydrogen atmosphere. Solids were filtered through Celite to obtain the title compound (2.36 g, 92%).

$^1$H-NMR (CDCl$_3$) δ 6.14 (2H, m), 4.21 (2H, m), 4.13 (2H, q), 3.72 (2H, m), 3.44 (2H, brs), 2.95 (1H, m), 2.66 (2H, d), 1.26 (3H, t)

Step D: 2-[1-(4-bromo-2,6-difluoro-phenyl)azetidin-3-yl]acetic acid ethyl ester 2-[1-(4-Amino-2,6-difluoro-phenyl)azetidin-3-yl]acetic acid ethyl ester (2.36 g, 8.7 mmol) obtained in Step C were reacted in the same manner as in Step C of Preparation Example 84 to obtain the title compound (1.04 g, 36%).

$^1$H-NMR (CDCl$_3$) δ 6.89 (2H, m), 4.34 (2H, m), 4.15 (2H, q), 3.84 (2H, m), 3.01 (1H, m), 2.67 (2H, d), 1.26 (3H, t)

Step E: 2-[1-[2,6-difluoro-4-(4,4,5,5-tetramethyl-1,3,2-dioxaborolan-2-yl)phenyl]azetidin-3-yl]acetic acid ethyl ester 2-[1-(4-Bromo-2,6-difluoro-phenyl)azetidin-3-yl]acetic acid ethyl ester (1.04 g, 3.11 mmol) obtained in Step D was reacted in the same manner as in Step D of Preparation Example 1 to obtain the title compound (0.62 g, 51%).

¹H-NMR (CDCl₃) δ 7.15 (2H, m), 4.41 (2H, m), 4.14 (2H, q), 3.91 (2H, m), 3.05 (1H, m), 2.68 (2H, d), 1.31 (12H, s), 1.27 (3H, t)

Preparation Example 89: 6-[2,6-difluoro-4-(4,4,5,5-tetramethyl-1,3,2-dioxaborolan-2-yl)phenyl]-6-azaspiro[2.5]octan-2-carboxylic acid ethyl ester Step A: 1-(2,6-difluoro-4-nitro-phenyl)piperidin-4-one 3,4,5-Trifluoronitrobenzene (4.0 g, 22.6 mmol) and piperidin-4-one hydrochloride (3.37 g, 24.8 mmol) were reacted in the same manner as in Step A of Preparation Example 84 to obtain the title compound (5.38 g, 93%).

¹H-NMR (CDCl₃) δ 7.82 (2H, m), 3.66 (4H, m), 2.62 (4H, m)

Step B: 2-[1-(2,6-difluoro-4-nitro-phenyl)-4-piperidylidene]acetic acid ethyl ester 190 mL of THF was cooled to 0° C., and NaH (1.83 g, 42 mmol, 55 wt % in mineral oil) was added thereto. Triethyl phosphonoacetate (9.7 g, 43.3 mmol) was added thereto, and the mixture was stirred at room temperature for 30 minutes. 1-(2,6-Difluoro-4-nitro-phenyl)piperidin-4-one (5.38 g, 21 mmol) obtained in Step A was added thereto, and the mixture was stirred at room temperature for 2 hours. EtOAc was added thereto, and the reaction solution was adjusted to pH 4 by the addition of 1N HCl aqueous solution. The organic layer extracted with EtOAc was purified by column chromatography to obtain the title compound (6.85 g, 99%).

¹H-NMR (CDCl₃) δ 7.78 (2H, m), 5.75 (1H, s), 4.17 (2H, q), 3.45 (2H, t), 3.42 (2H, t), 3.12 (2H, t), 2.45 (2H, t), 1.31 (3H, t)

Step C: 6-(2,6-difluoro-4-nitro-phenyl)-6-azaspiro [2.5]octan-2-carboxylic acid ethyl ester 2-[1-(2,6-Difluoro-4-nitro-phenyl)-4-piperidylidene]acetic acid ethyl ester (0.55 g, 1.68 mmol) obtained in Step B was dissolved in 5.6 mL of THF. After addition of iazomethane (40 mL, 10 mmol, 0.25 M Et₂O solution), catalytic amount of palladium(II) acetate was added thereto, and the mixture was stirred at room temperature. After termination of the reaction, the reaction solution was concentrated and purified by column chromatography to obtain the title compound (0.4 g, 65%).

¹H-NMR (CDCl3) δ 7.77 (2H, m), 4.15 (2H, q), 3.45-3.24 (4H, m), 1.88 (2H, m), 1.59 (3H, m), 1.30 (3H, t), 1.23 (1H, m), 0.97 (1H, m)

Step D: 6-(4-bromo-2,6-difluoro-phenyl)-6-azaspiro [2.5]octan-2-carboxylic acid ethyl ester 6-(2,6-Difluoro-4-nitro-phenyl)-6-azaspiro[2.5]octan-2-carboxylic acid ethyl ester (0.4 g, 1.1 mmol) obtained in Step C was reacted in the same manner as in Steps B and C of Preparation Example 84 to obtain the title compound (0.22 g, 52%).

¹H-NMR (CDCl₃) δ 7.00 (2H, m), 4.16 (2H, q), 3.21-3.04 (4H, m), 1.84 (2H, m), 1.56 (3H, m), 1.28 (3H, t), 1.18 (1H, m), 0.94 (1H, m)

Step E: 6-[2,6-difluoro-4-(4,4,5,5-tetramethyl-1,3,2-dioxaborolan-2-yl)phenyl]-6-azaspiro[2.5]octan-2-carboxylic acid ethyl ester 6-(4-Bromo-2,6-difluoro-phenyl)-6-azaspiro[2.5]octan-2-carboxylic acid ethyl ester (0.22 g, 0.58 mmol) obtained in Step D was reacted in the same manner as in Step D of Preparation Example 1 to obtain the title compound (0.15 g, 60%).

¹H-NMR (CDCl₃) δ 7.22 (2H, m), 4.14 (2H, q), 3.32-3.10 (4H, m), 1.84 (2H, m), 1.55 (3H, m), 1.30 (12H, s), 1.27 (3H, t), 1.18 (1H, m), 0.94 (1H, m)

Preparation Example 90: 2-[1-[2,6-difluoro-4-(4,4,5,5-tetramethyl-1,3,2-dioxaborolan-2-yl)phenyl]pyrazol-4-yl]acetic acid methyl ester Step A: 1-(2,6-difluoro-4-nitro-phenyl)pyrazol-4-carboxylic acid ethyl ester 3,4,5-Trifluoronitrobenzene (3.17 g, 17.9 mmol) and 4-pyrazolcarboxylic acid ethyl ester (2.50 g, 17.9 mmol) were reacted in the same manner as in Step A of Preparation Example 84 to obtain the title compound (3.70 g, 70%).

¹H-NMR (CDCl₃) δ 8.25 (1H, s), 8.23 (1H, s), 8.05 (2H, m), 4.36 (2H, q), 1.38 (3H, t)

Step B: 1-(4-bromo-2,6-difluoro-phenyl)pyrazol-4-carboxylic acid ethyl ester 1-(2,6-Difluoro-4-nitro-phenyl)pyrazol-4-carboxylic acid ethyl ester (3.7 g, 12.4 mmol) obtained in Step A was reacted in the same manner as in Steps B and C of Preparation Example 84 to obtain the title compound (3.0 g, 74%).

¹H-NMR (CDCl₃) δ 8.17 (1H, s), 8.14 (1H, s), 7.31 (2H, m), 4.34 (2H, q), 1.37 (3H, t)

Step C: [1-(4-bromo-2,6-difluoro-phenyl)pyrazol-4-yl]methanol 1-(4-Bromo-2,6-difluoro-phenyl)pyrazol-4-carboxylic acid ethyl ester (3.0 g, 9.16 mmol) obtained in Step B was dissolved in 46 mL of Et₂O and cooled to −78° C. Diisobutylaluminum hydride (15.2 mL, 23 mmol, 1.5 M toluene solution) was slowly added thereto, and the mixture was stirred at room temperature for 16 hours. Solids, which were formed by the sequential addition of MeOH and potassium sodium tartrate aqueous solution, were filtered through Celite. The filtrate was dried with MgSO₄ to obtain the title compound (2.6 g, 99%).

¹H-NMR (CDCl₃) δ 7.81 (1H, s), 7.64 (1H, s), 7.28 (2H, m), 4.70 (2H, d), 1.60 (1H, t)

Step D: 1-(4-bromo-2,6-difluoro-phenyl)-4-(chloromethyl)pyrazol

[1-(4-Bromo-2,6-difluoro-phenyl)pyrazol-4-yl]methanol (2.6 g, 9.16 mmol) obtained in Step C was reacted in the same manner as in Step D of Preparation Example 81 to obtain the title compound (1.5 g, 53%).

¹H-NMR (CDCl₃) δ 7.82 (1H, s), 7.67 (1H, s), 7.28 (2H, m), 4.61 (2H, s)

Step E: 2-[1-(4-bromo-2,6-difluoro-phenyl)pyrazol-4-yl]acetonitrile 1-(4-Bromo-2,6-difluoro-phenyl)-4-(chloromethyl)pyrazol (1.5 g, 4.9 mmol) obtained in Step D was reacted in the same manner as in Step E of Preparation Example 81 to obtain the title compound (0.66 g, 45%).

¹H-NMR (CDCl₃) δ 7.76 (1H, s), 7.67 (1H, s), 7.30 (2H, m), 3.69 (2H, s)

Step F: 2-[1-(4-bromo-2,6-difluoro-phenyl)pyrazol-4-yl]acetic acid

2-[1-(4-Bromo-2,6-difluoro-phenyl)pyrazol-4-yl]acetonitrile (0.66 g, 2.21 mmol) obtained in Step E was reacted in the same manner as in Step F of Preparation Example 81 to obtain the title compound (0.58 g, 82%).

¹H-NMR (CDCl₃) δ 7.76 (1H, s), 7.66 (1H, s), 7.27 (2H, m), 3.65 (2H, s)

Step G: 2-[1-(4-bromo-2,6-difluoro-phenyl)pyrazol-4-yl]acetic acid methyl ester 2-[1-(4-Bromo-2,6-difluoro-phenyl)pyrazol-4-yl]acetic acid (0.58 g, 1.83 mmol) obtained in Step F was dissolved in 6 mL of THE Diazomethane (13 mL, 3.25 mmol, 0.25 M Et₂O solution) was added thereto, and the mixture was stirred at room temperature for 40 minutes. The reaction solution was concentrated under reduced pressure to obtain the title compound (0.6 g, 99%).

¹H-NMR (CDCl₃) δ 7.74 (1H, s), 7.65 (1H, s), 7.27 (2H, m), 3.74 (3H, s), 3.60 (2H, s)

Step H: 2-[1-[2,6-difluoro-4-(4,4,5,5-tetramethyl-1,3,2-dioxaborolan-2-yl)phenyl]pyrazol-4-yl]acetic acid methyl ester 2-[1-(4-Bromo-2,6-difluoro-phenyl)pyrazol-4-yl]acetic acid methyl ester (0.6 g, 1.82 mmol) obtained in Step G was reacted in the same manner as in Step D of Preparation Example 1 to obtain the title compound (0.52 g, 76%).

¹H-NMR (CDCl₃) δ 7.75 (1H, s), 7.69 (1H, s), 7.46 (2H, m), 3.74 (3H, s), 3.60 (2H, s), 1.35 (12H, s)

Preparation Example 91: 2-[1-[2,6-difluoro-4-(4,4,5,5-tetramethyl-1,3,2-dioxaborolan-2-yl)phenyl]pyrrolidin-3-yl]acetic acid ethyl ester

Step A: tert-butyl 3-hydroxypyrrolidin-1-carboxylate

3-Pyrrolidinol (4.66 g, 53 mmol) was dissolved in 90 mL of DCM. Dimethylaminopyridine (0.65 g, 5.3 mmol) and TEA (8.1 mL, 58.3 mmol) were added thereto. The reaction solution was cooled to 0° C., and di-tert-butyl dicarbonate (12.84 g, 58.8 mmol) was added thereto. The mixture was stirred at room temperature for 48 hours. 1 M NaOH aqueous solution (53 mL, 53 mmol) was added thereto, and the mixture was stirred for 10 minutes. After addition of water, the reaction solution was extracted with DCM and dried with MgSO₄. The organic layer was purified by column chromatography to obtain the title compound (8.98 g, 90%).

¹H-NMR (CDCl₃) δ 4.45 (1H, m), 3.46 (3H, m), 3.33 (1H, m), 1.97 (2H, m), 1.42 (9H, s)

Step B: tert-butyl 3-oxopyrrolidin-1-carboxylate

Oxalyl chloride (6.0 mL, 70.5 mmol) was added to 300 mL of DCM and cooled to −78° C. DMSO (9.9 mL, 139 mmol) was added thereto, and the mixture was stirred for 15 minutes. Tert-butyl 3-hydroxypyrrolidin-1-carboxylate (8.98 g, 48 mmol) obtained in Step A was added thereto, and the mixture was stirred for 20 minutes. TEA (32 mL, 0.23 mol) was added thereto, and the mixture was stirred at −78° C. for 1 hour and additionally stirred at room temperature for 1 hour. After addition of water, the reaction solution was extracted with DCM. The organic layer was dried with MgSO₄ and purified by column chromatography to obtain the title compound (7.92 g, 89%).

¹H-NMR (CDCl₃) δ 3.77 (4H, m), 2.59 (2H, t), 1.48 (9H, s)

Step C: tert-butyl 3-(2-ethoxy-2-oxo-ethylidene)pyrrolidin-1-carboxylate

Tert-butyl 3-oxopyrrolidin-1-carboxylate (1.82 g, 9.82 mmol) obtained in Step B was dissolved in 49 mL of DCM. (1-Ethoxycarbonylethylidene)triphenylphosphorane (3.59 g, 10.3 mmol) was added thereto, and the mixture was stirred for 72 hours under reflux. The reaction solution was concentrated under reduced pressure and purified by column chromatography to obtain the title compound (2.0 g, 80%).

¹H-NMR (CDCl₃) δ 5.81 (1H, s), 4.42-4.13 (2H, m), 4.18 (2H, q), 3.56 (2H, m), 3.12-2.74 (2H, t), 1.46 (9H, s), 1.28 (3H, t)

Step D: tert-butyl 3-(2-ethoxy-2-oxo-ethyl)pyrrolidin-1-carboxylate

Tert-butyl 3-(2-ethoxy-2-oxo-ethylidene)pyrrolidin-1-carboxylate (2.0 g, 7.83 mmol) obtained in Step C was dissolved in 40 mL of EtOH. 0.2 g of 10 wt % Pd/C was added thereto, and the mixture was stirred for 24 hours under hydrogen atmosphere. Solids were filtered and concentrated under reduced pressure to obtain the title compound (1.95 g, 97%).

¹H-NMR (CDCl₃) δ 4.14 (2H, q), 3.58 (1H, m), 3.45 (1H, m), 3.29 (1H, m), 2.92 (1H, m), 2.56 (1H, m), 2.38 (2H, d), 2.07 (1H, m), 1.51 (1H, m), 1.46 (9H, s), 1.26 (3H, t)

Step E: 2-[1-(2,6-difluoro-4-nitro-phenyl)pyrrolidin-3-yl]acetic acid ethyl ester Tert-butyl 3-(2-ethoxy-2-oxo-ethyl)pyrrolidin-1-carboxylate (1.95 g, 7.57 mmol) obtained in Step D was dissolved in 7 mL of DCM. HCl (7.8 mL, 30 mmol, 4 M 1,4-dioxane solution) was added thereto, and the mixture was stirred at room temperature for 90 minutes. The reaction solution was concentrated under reduced pressure to obtain hydrochloric acid salt of 2-pyrrolidin-3-ylacetic acid ethyl ester. The obtained hydrochloric acid salt of 2-pyrrolidin-3-ylacetic acid ethyl ester and 3,4,5-trifluoronitrobenzene (1.34 g, 7.57 mmol) were reacted in the same manner as in Step A of Preparation Example 84 to obtain the title compound (2.24 g, 94%).

¹H-NMR (CDCl₃) δ 7.72 (2H, m), 4.17 (2H, q), 3.89 (1H, m), 3.81 (1H, m), 3.76 (1H, m), 3.47 (1H, m), 2.62 (1H, m), 2.46 (2H, d), 2.16 (1H, m), 1.65 (1H, m), 1.27 (3H, t)

Step F: 2-[1-(4-bromo-2,6-difluoro-phenyl)pyrrolidin-3-yl]acetic acid ethyl ester 2-[1-(2,6-Difluoro-4-nitro-phenyl)pyrrolidin-3-yl]acetic acid ethyl ester (2.24 g, 7.12 mmol) obtained in Step E was reacted in the same manner as in Steps B and C of Preparation Example 84 to obtain the title compound (0.92 g, 37%).

¹H-NMR (CDCl₃) δ 6.93 (2H, m), 4.15 (2H, q), 3.60 (2H, m), 3.49 (1H, m), 3.24 (1H, m), 2.62 (1H, m), 2.44 (2H, d), 2.13 (1H, m), 1.63 (1H, m), 1.26 (3H, t)

Step G: 2-[1-[2,6-difluoro-4-(4,4,5,5-tetramethyl-1,3,2-dioxaborolan-2-yl)phenyl]pyrrolidin-3-yl]acetic acid ethyl ester 2-[1-(4-Bromo-2,6-difluoro-phenyl)pyrrolidin-3-yl]acetic acid ethyl ester (0.92 g, 2.64 mmol) obtained in Step F was reacted in the same manner as in Step D of Preparation Example 1 to obtain the title compound (0.82 g, 79%).
¹H-NMR (CDCl₃) δ 7.18 (2H, m), 4.15 (2H, q), 3.70 (2H, m), 3.59 (1H, m), 3.35 (1H, m), 2.60 (1H, m), 2.44 (2H, m), 2.14 (1H, m), 1.61 (1H, m), 1.36 (12H, s), 1.27 (3H, t)

Preparation Example 92: 3-[1-[2,6-difluoro-4-(4,4,5,5-tetramethyl-1,3,2-dioxaborolan-2-yl)phenyl]-4-piperidyl]propanoic acid ethyl ester Step A: tert-butyl 4-[(E)-3-ethoxy-3-oxo-prop-1-enyl]piperidin-1-carboxylate Tert-butyl 4-(hydroxymethyl)piperidin-1-carboxylate (4.0 g, 18.6 mmol) was reacted in the same manner as in Step B of Preparation Example 88 to obtain the title compound (4.36 g, 83%).
¹H-NMR (CDCl₃) δ 6.89 (1H, dd), 5.78 (1H, d), 4.21 (2H, q), 4.12 (2H, m), 2.76 (2H, m), 2.28 (1H, m), 1.72 (2H, m), 1.45 (9H, s), 1.33 (2H, m), 1.28 (3H, t)

Step B: (E)-3-[1-(2,6-difluoro-4-nitro-phenyl)-4-piperidyl]prop-2-enoic acid ethyl ester Tert-butyl 4-[(E)-3-ethoxy-3-oxo-prop-1-enyl]piperidin-1-carboxylate (4.33 g, 15.1 mmol) obtained in Step A was dissolved in HCl (15 mL, 60 mmol, 4 M 1,4-dioxane solution) and stirred at 60° C. for 90 minutes. After addition of Et₂O, the reaction solution was concentrated under reduced pressure to obtain hydrochloric acid salt of (E)-3-(4-piperidyl)prop-2-enoic acid ethyl ester. The obtained hydrochloric acid salt of (E)-3-(4-piperidyl)prop-2-enoic acid ethyl ester and 3,4,5-trifluoronitrobenzene (2.67 g, 15.1 mmol) were reacted in the same manner as in Step A of Preparation Example 84 to obtain the title compound (5.1 g, 99%).
¹H-NMR (CDCl₃) δ 7.75 (2H, m), 6.94 (1H, dd), 5.86 (1H, d), 4.20 (2H, q), 3.54 (2H, m), 3.22 (2H, m), 2.36 (1H, m), 1.84 (2H, m), 1.64 (2H, m), 1.30 (3H, t)

Step C: (E)-3-[1-(4-bromo-2,6-difluoro-phenyl)-4-piperidyl]prop-2-enoic acid ethyl ester (E)-3-[1-(2,6-difluoro-4-nitro-phenyl)-4-piperidyl]prop-2-enoic acid ethyl ester (5.1 g, 15 mmol) obtained in Step B were reacted in the same manner as in Steps B and C of Preparation Example 84 to obtain the title compound (2.45 g, 43%).
¹H-NMR (CDCl₃) δ 7.00 (2H, m), 6.95 (1H, dd), 5.84 (1H, d), 4.20 (2H, q), 3.23 (2H, m), 3.10 (2H, m), 2.29 (1H, m), 1.78 (2H, m), 1.61 (2H, m), 1.30 (3H, t)

Step D: 3-[1-(4-bromo-2,6-difluoro-phenyl)-4-piperidyl]propanoic acid ethyl ester (E)-3-[1-(4-bromo-2,6-difluoro-phenyl)-4-piperidyl]prop-2-enoic acid ethyl ester (2.45 g, 6.54 mmol) obtained in Step C was dissolved in 70 mL of DME. p-Toluenesulfonyl hydrazide (8.52 g, 45.6 nmol) was added thereto little by little, and the mixture was heated to 90° C. Sodium acetate (5.36 g, 65.4 mmol, 1.4 M aqueous solution) was added thereto, and the mixture was stirred for 9 hours under reflux. After addition of water, the reaction solution was extracted with DCM. The organic layer was dried with MgSO₄ to obtain the title compound (2.46 g, 99%).
¹H-NMR (CDCl₃) δ 6.99 (2H, m), 4.13 (2H, q), 3.18 (2H, m), 3.01 (2H, m), 2.34 (2H, m), 1.71 (2H, m), 1.63 (2H, m), 1.37 (3H, m), 1.26 (3H, t)

Step E: 3-[1-[2,6-difluoro-4-(4,4,5,5-tetramethyl-1,3,2-dioxaborolan-2-yl)phenyl]-4-piperidyl]propanoic acid ethyl ester 3-[1-(4-Bromo-2,6-difluoro-phenyl)-4-piperidyl]propanoic acid ethyl ester (2.46 g, 6.54 mmol) obtained in Step D was reacted in the same manner as in Step D of Preparation Example 1 to obtain the title compound (2.02 g, 73%).
¹H-NMR (CDCl₃) δ 7.23 (2H, m), 4.14 (2H, q), 3.31 (2H, m), 3.05 (2H, m), 2.34 (2H, m), 1.71 (2H, m), 1.62 (2H, m), 1.36 (3H, m), 1.32 (12H, s), 1.25 (3H, t)

Preparation Example 93: 2-[4-[2,6-difluoro-4-(4,4,5,5-tetramethyl-1,3,2-dioxaborolan-2-yl)phenyl]piperazin-1-yl]acetic acid ethyl ester Step A: 4-(2-ethoxy-2-oxo-ethyl)piperazin-1-carboxylic acid benzyl ester 1-Piperazincarboxylic acid benzyl ester (3.12 g, 14.2 mmol) was dissolved in 47 mL of THF. Bromoacetic acid ethyl ester (1.73 mL, 15.6 mmol) and TEA (5.92 mL, 42.5 mmol) were sequentially added thereto, and the mixture was stirred for 90 minutes under reflux. The reaction solution was cooled to at room temperature. Solids were filtered, and water was added thereto. The organic layer extracted with EtOAc was dried with MgSO₄ to obtain the title compound (4.3 g, 99%).
¹H-NMR (CDCl₃) δ 7.35 (5H, m), 5.13 (2H, s), 4.19 (2H, q), 3.56 (4H, m), 3.22 (2H, s), 2.55 (4H, m), 1.27 (3H, t)

Step B: 2-piperazin-1-ylacetic acid ethyl ester 4-(2-Ethoxy-2-oxo-ethyl)piperazin-1-carboxylic acid benzyl ester (4.30 g, 14.0 mmol) obtained in Step A was dissolved in 70 mL of MeOH. 0.43 g of 10 wt % Pd/C was added thereto, and the mixture was stirred for 24 hours under hydrogen atmosphere. Solids were filtered through Celite to obtain the title compound (2.40 g, 99%).
¹H-NMR (CDCl₃) δ 4.19 (2H, q), 3.20 (2H, s), 2.94 (4H, m), 2.57 (4H, m), 1.28 (3H, t)

Step C: 2-[4-(2,6-difluoro-4-nitro-phenyl)piperazin-1-yl]acetic acid ethyl ester 2-Piperazin-1-ylacetic acid ethyl ester (2.40 g, 13.9 mmol) obtained in Step B, 3,4,5-trifluoronitrobenzene (2.35 g, 13.3 mmol) and DIPEA (3.50 mL, 13.9 mmol) were dissolved in 33 mL of DMF and stirred at room temperature for 16 hours. The reaction solution was concentrated under reduced pressure. After addition of water, the reaction solution was extracted with EtOAc to obtain the title compound (4.37 g, 99%).

¹H-NMR (CDCl₃) δ 7.78 (2H, m), 4.22 (2H, q), 3.50 (4H, m), 3.38 (2H, s), 2.85 (4H, m), 1.30 (3H, t)

Step D: 2-[4-(4-bromo-2,6-difluoro-phenyl)piperazin-1-yl]acetic acid ethyl ester 2-[4-(2,6-Difluoro-4-nitro-phenyl)piperazin-1-yl]acetic acid ethyl ester (4.34 g, 13.2 mmol) obtained in Step C was reacted in the same manner as in Steps B and C of Preparation Example 84 to obtain the title compound (0.27 g, 6%).
¹H-NMR (CDCl₃) δ 7.00 (2H, m), 4.20 (2H, q), 3.26 (2H, s), 3.24 (4H, m), 2.70 (4H, m), 1.27 (3H, t)

Step E: 2-[4-[2,6-difluoro-4-(4,4,5,5-tetramethyl-1,3,2-dioxaborolan-2-yl)phenyl]piperazin-1-yl]acetic acid ethyl ester 2-[4-(4-Bromo-2,6-difluoro-phenyl)piperazin-1-yl]acetic acid ethyl ester (0.27 g, 0.74 mmol) obtained in Step D was reacted in the same manner as in Step D of Preparation Example 1 to obtain the title compound (0.12 g, 39%).
¹H-NMR (CDCl₃) δ 7.23 (2H, m), 4.20 (2H, q), 3.30 (4H, m), 3.25 (2H, s), 2.70 (4H, m), 1.33 (12H, s), 1.28 (3H, t)

Preparation Example 94: 3-[1-[2,6-difluoro-4-(4,4,5,5-tetramethyl-1,3,2-dioxaborolan-2-yl)phenyl]pyrazol-4-yl]propanoic acid ethyl ester Step A: tert-butyl 4-(hydroxymethyl)pyrazol-1-carboxylate 4-Pyrazolcarboxylic acid ethyl ester (4.45 g, 31.7 mmol) was dissolved in 30 mL of THE Dimethylaminopyridine (0.19 g, 1.59 mmol), TEA (5.3 mL, 38.1 mmol) and di-tert-butyl dicarbonate (8.31 g, 38.1 mmol) were sequentially added thereto, and the mixture was stirred at room temperature for 1 hour. After addition of water, the reaction solution was extracted with EtOAc. The organic layer was dried with MgSO₄, and 140 mL of Et₂O was added thereto. After cooling to −78° C., the mixture was reacted in the same manner as in Step C of Preparation Example 90 to obtain the title compound (1.42 g, 22%)

¹H-NMR (CDCl₃) δ 8.02 (1H, s), 7.68 (1H, s), 4.60 (2H, s), 1.63 (9H, s)

Step B: tert-butyl 4-formylpyrazol-1-carboxylate

Tert-butyl 4-(hydroxymethyl)pyrazol-1-carboxylate (1.42 g, 7.1 mmol) obtained in Step A was dissolved in 40 mL of DCM. MgSO₄ (1.2 g, 9.9 mmol) and manganese dioxide (4.32 g, 50 mmol) were added thereto, and the mixture was stirred at room temperature for 16 hours. Solids were filtered and purified by column chromatography to obtain the title compound (1.03 g, 74%).
¹H-NMR (CDCl₃) δ 9.96 (1H, s), 8.61 (1H, s), 8.13 (1H, s), 1.67 (9H, s)

Step C: tert-butyl 4-[(E)-3-ethoxy-3-oxo-prop-1-enyl]pyrazol-1-carboxylate

Tert-butyl 4-formylpyrazol-1-carboxylate (1.0 g, 5.28 mmol) obtained in Step B was reacted in the same manner as in Step A of Preparation Example 85 to obtain the title compound (1.05 g, 74%).

¹H-NMR (CDCl₃) δ 8.21 (1H, s), 7.89 (1H, s), 7.54 (1H, d), 6.29 (1H, d), 4.25 (2H, q), 1.66 (9H, s), 1.31 (3H, t)

Step D: (E)-3-[1-(2,6-difluoro-4-nitro-phenyl)pyrazol-4-yl]prop-2-enoic acid ethyl ester Tert-butyl 4-[(E)-3-ethoxy-3-oxo-prop-1-enyl]pyrazol-1-carboxylate (0.88 g, 3.3 mmol) obtained in Step C was dissolved in 22 mL of DCM. 11 mL of TFA was added thereto, and the mixture was stirred at room temperature for 6 hours. After addition of Et₂O, the reaction solution was concentrated under reduced pressure to obtain solids. 11 mL of DMSO, 3,4,5-trifluoronitrobenzene (0.58 g, 3.3 mmol) and K₂CO₃ (1.37 g, 9.9 mmol) were sequentially added to the solids, and the mixture was stirred at 90° C. for 16 hours. After addition of water, the reaction solution was extracted with EtOAc. The organic layer was dried with MgSO₄ and purified by column chromatography to obtain the title compound (0.73 g, 41%).
¹H-NMR (CDCl₃) δ 8.04 (3H, m), 7.92 (1H, s), 7.62 (1H, d), 6.32 (1H, d), 4.27 (2H, q), 1.33 (3H, t)

Step E: 3-[1-(4-bromo-2,6-difluoro-phenyl)pyrazol-4-yl]propanoic acid ethyl ester (E)-3-[1-(2,6-difluoro-4-nitro-phenyl)pyrazol-4-yl]prop-2-enoic acid ethyl ester (0.71 g, 2.2 mmol) obtained in Step D was reacted in the same manner as in Steps C and D of Preparation Example 88 to obtain the title compound (0.68 g, 86%).
¹H-NMR (CDCl₃) δ 7.66 (1H, s), 7.47 (1H, s), 7.26 (2H, m), 4.14 (2H, q), 2.88 (2H, t), 2.62 (2H, t), 1.25 (3H, t)

Step F: 3-[1-[2,6-difluoro-4-(4,4,5,5-tetramethyl-1,3,2-dioxaborolan-2-yl)phenyl]pyrazol-4-yl]propanoic acid ethyl 3-[1-(4-Bromo-2,6-difluoro-phenyl)pyrazol-4-yl]propanoic acid ethyl ester (0.075 g, 0.21 mmol) obtained in Step E was reacted in the same manner as in Step D of Preparation Example 1 to obtain the title compound (0.03 g, 36%).
¹H-NMR (CDCl₃) δ 7.66 (1H, s). 7.52 (1H, m), 7.47 (2H, m), 4.15 (2H, q), 2.89 (2H, t), 2.63 (2H, t), 1.35 (12H, s), 1.24 (3H, t)

Preparation Example 95: 4-[5-(4,4,5,5-tetramethyl-1,3,2-dioxaborolan-2-yl)indolin-1-yl]butanoic acid ethyl ester Step A: 5-bromoindoline 10 mL of acetic acid was added to 5-bromoindole (2.5 g, 12.8 mmol) and cooled to 0° C. Sodium triacetoxyborohydride (2.38 g, 37.9 mmol) was added thereto, and the mixture was stirred at room temperature for 16 hours. After addition of water, the reaction solution was extracted with Et₂O, and the organic layer washed with sodium bicarbonate aqueous solution. The organic layer was dried with MgSO₄ and purified by column chromatography to obtain the title compound (0.95 g, 38%).
¹H-NMR (CDCl₃) δ 7.19 (1H, d), 7.09 (1H, dd), 6.50 (1H, d), 3.74 (1H, brs), 3.56 (2H, t), 3.02 (2H, t)

Step B: 4-(5-bromoindolin-1-yl)butanoic acid ethyl ester

5-Bromoindoline (0.95 g, 4.8 mmol) obtained in Step A was dissolved in 16 mL of DMF. K₂CO₃ (1.32 g, 9.6 mmol)

and 4-bromobutanoic acid ethyl ester (0.94 g, 4.8 mmol) were added thereto, and the mixture was stirred at 70° C. for 24 hours. The reaction solution was concentrated under reduced pressure and purified by column chromatography to obtain the title compound (0.59 g, 39%).

$^1$H-NMR (CDCl$_3$) δ 7.12 (2H, m), 6.30 (1H, d), 4.11 (2H, q), 3.35 (2H, t), 3.06 (2H, t), 2.94 (2H, t), 2.39 (2H, t), 1.91 (2H, m), 1.24 (3H, t)

Step C: 4-[5-(4,4,5,5-tetramethyl-1,3,2-dioxaborolan-2-yl)indolin-1-yl]butanoic acid ethyl ester 4-(5-Bromoindolin-1-yl)butanoic acid ethyl ester (0.59 g, 1.88 mmol) obtained in Step B was reacted in the same manner as in Step D of Preparation Example 1 to obtain the title compound (0.48 g, 70%).

$^1$H-NMR (CDCl$_3$) δ 7.55 (1H, dd), 7.49 (1H, m), 6.41 (1H, d), 4.11 (2H, q), 3.40 (2H, t), 3.15 (2H, t), 2.96 (2H, t), 2.39 (2H, t), 1.92 (2H, m), 1.31 (12H, s), 1.25 (3H, t)

Preparation Example 96: 3-[1-[2,6-difluoro-4-(4,4,5,5-tetramethyl-1,3,2-dioxaborolan-2-yl)phenyl]azetidin-3-yl]propanoic acid ethyl ester Step A: 1-tert-butoxycarbonylazetidin-3-carboxylic acid 60 mL of THF and 60 mL of 0.5 M NaOH aqueous solution were added to azetidin-3-carboxylic acid (3 g, 30 mmol). Di-tert-butyl dicarbonate (6.8 g, 31.1 mmol) was slowly added thereto, and the mixture was stirred at room temperature for 24 hours. The reaction solution was concentrated under reduced pressure. The reaction solution was adjusted to pH 4 by the addition of water and HCl aqueous solution, and extracted with EtOAc. The organic layer was dried with MgSO$_4$ to obtain the title compound (4.5 g, 73%).

$^1$H-NMR (CDCl$_3$) δ 4.12 (4H, m), 3.38 (1H, m), 1.44 (9H, s)

Step B: (E)-3-[1-(2,6-difluoro-4-nitro-phenyl)azetidin-3-yl]prop-2-enoic acid ethyl ester 1-Tert-butoxycarbonylazetidin-3-carboxylic acid (3.5 g, 17.4 mmol) obtained in Step A was sequentially reacted in the same manner as in Step A of Preparation Example 71, Step E of Preparation Example 86 and Step B of Preparation Example 88 to obtain the title compound (0.5 g, 9%).

$^1$H-NMR (CDCl$_3$) δ 7.70 (2H, m), 7.14 (1H, m), 5.93 (1H, d), 4.62 (2H, m), 4.28 (2H, m), 4.22 (2H, q), 3.60 (1H, m), 1.30 (3H, t)

Step C: 3-[1-(4-bromo-2,6-difluoro-phenyl)azetidin-3-yl]propanoic acid ethyl ester (E)-3-[1-(2,6-difluoro-4-nitro-phenyl)azetidin-3-yl]prop-2-enoic acid ethyl ester (0.66 g, 2.1 mmol) obtained in Step B was sequentially reacted in the same manner as in Step C of Preparation Example 88 and Step C of Preparation Example 84 to obtain the title compound (0.14 g, 19%).

$^1$H-NMR (CDCl$_3$) δ 6.88 (2H, m), 4.25 (2H, m), 4.14 (2H, q), 3.78 (2H, m), 2.67 (1H, m), 2.29 (2H, t), 1.96 (2H, m), 1.26 (3H, t)

Step D: 3-[1-[2,6-difluoro-4-(4,4,5,5-tetramethyl-1,3,2-dioxaborolan-2-yl)phenyl]azetidin-3-yl]propanoic acid ethyl ester 3-[1-(4-Bromo-2,6-difluoro-phenyl)azetidin-3-yl]propanoic acid ethyl ester (0.13 g, 0.38 mmol) obtained in Step C was reacted in the same manner as in Step D of Preparation Example 1 to obtain the title compound (0.032 g, 21%).

$^1$H-NMR (CDCl$_3$) δ 7.15 (2H, m), 4.32 (2H, m), 4.12 (2H, q), 3.85 (2H, m), 2.67 (1H, m), 2.29 (2H, t), 1.97 (2H, m), 1.32 (12H, s), 1.27 (3H, t)

Preparation Example 97: 2-[(3S)-1-[2,6-difluoro-4-(4,4,5,5-tetramethyl-1,3,2-dioxaborolan-2-yl)phenyl]pyrrolidin-3-yl]acetic acid methyl ester Step A: 2-[(3S)-1-tert-butoxycarbonylpyrrolidin-3-yl]propanedioic acid ethyl ester (3S)-3-hydroxypyrrolidin-1-carboxylic acid tert-butyl ester (1.5 g, 8 mmol) was dissolved in 16 mL of toluene and cooled to −10° C. TEA (1.7 mL, 12 mmol) and methanesulfonyl chloride (0.8 mL, 10.1 mmol) were slowly added thereto. The mixture was stirred at room temperature for 80 minutes, and solids were filtered. The filtrate was washed with sodium bicarbonate aqueous solution, dried with MgSO$_4$ and concentrated under reduced pressure to obtain (3S)-3-methylsulfonyloxypyrrolidin-1-carboxylic acid tert-butyl ester. 27 mL of EtOH and malonic acid ethyl ester (2.62 g, 16.4 mmol) were prepared in another flask, and sodium (0.37 g, 16 mmol) was added thereto little by little. The mixture was stirred at room temperature for 30 minutes. (3S)-3-methylsulfonyloxypyrrolidin-1-carboxylic acid tert-butyl ester was added thereto, and the mixture was stirred for 16 hours under reflux. The reaction solution was cooled to room temperature and adjusted to pH 4 by the addition of water and 1N HCl aqueous solution. The reaction solution was extracted with MTBE to obtain the title compound (2.08 g, 79%).

$^1$H-NMR (CDCl$_3$) δ 4.22 (2H, q), 3.64 (1H, m), 3.50 (1H, m), 3.28 (2H, m), 3.03 (1H, m), 2.81 (1H, m), 2.08 (1H, m), 1.63 (1H, m), 1.45 (9H, s), 1.27 (6H, t)

Step B: 2-[(3S)-1-tert-butoxycarbonylpyrrolidin-3-yl]propanedioic acid

2-[(3S)-1-tert-butoxycarbonylpyrrolidin-3-yl]propanedioic acid ethyl ester (2.08 g, 6.3 mmol) obtained in Step A was dissolved in 9 mL of THF 44 wt % KOH aqueous solution (5 g, 39 mmol) was added thereto, and the mixture was stirred at 45° C. for 24 hours. The reaction solution was cooled to room temperature and washed with MTBE. The water layer was adjusted to pH 4 and extracted with EtOAc. The organic layer was dried with MgSO$_4$ to obtain the title compound (1.42 g, 83%).

$^1$H-NMR (CD$_3$OD) δ 3.63 (1H, m), 3.45 (1H, m), 3.30 (2H, m), 3.05 (1H, m), 2.74 (1H, m), 2.10 (1H, m), 1.71 (1H, m), 1.45 (9H, s)

Step C: 2-[(3S)-1-tert-butoxycarbonylpyrrolidin-3-yl]acetic acid

2-[(3S)-1-tert-butoxycarbonylpyrrolidin-3-yl]propanedioic acid (1.42 g, 5.22 mmol) obtained in Step B was dissolved in 15 mL of toluene and 0.2 mL of DMSO, and stirred for 16 hours under reflux. The reaction solution was cooled to room temperature. After addition of water, the reaction solution was extracted with MTBE. The organic layer was dried with MgSO$_4$ to obtain the title compound (1.05 g, 87%).

¹H-NMR (CD₃OD) δ 3.58 (1H, m), 3.43 (1H, m), 3.27 (1H, m), 2.93 (1H, m), 2.52 (1H, m), 2.40 (2H, d), 2.08 (1H, m), 1.58 (1H, m), 1.45 (9H, s)

Step D: 2-[(3S)-1-(2,6-difluoro-4-nitro-phenyl)pyrrolidin-3-yl]acetic acid methyl ester 2-[(3S)-1-tert-butoxycarbonylpyrrolidin-3-yl]acetic acid (1.05 g, 4.58 mmol) obtained in Step C was dissolved in 15 mL of THF. Diazomethane (0.25 M Et₂O solution, 27 mL, 6.87 mmol) was added thereto, and the mixture was stirred at room temperature for 40 minutes. The reaction solution was concentrated under reduced pressure. After addition of 15 mL of DCM and HCl (4 M 1,4-dioxane solution, 4.6 mL), the reaction solution was stirred at room temperature for 90 minutes. The reaction solution was concentrated under reduced pressure and dissolved in 15 mL of DMF. TEA (1.6 mL, 11.5 mmol) and 3,4,5-trifluoronitrobenzene (0.81 g, 4.58 mmol) were sequentially added thereto, and the mixture was stirred at room temperature for 48 hours. The reaction solution was concentrated under reduced pressure. After addition of water, the reaction solution was extracted with EtOAc to obtain the title compound (1.33 g, 97%).
¹H-NMR (CDCl₃) δ 7.72 (2H, m), 3.89 (1H, m), 3.82 (1H, m), 3.76 (1H, m), 3.71 (3H, s), 3.47 (1H, m), 2.63 (1H, m), 2.49 (2H, d), 2.18 (1H, m), 1.64 (1H, m)

Step E: 2-[(3S)-1-(4-bromo-2,6-difluoro-phenyl)pyrrolidin-3-yl]acetic acid methyl ester 2-[(3S)-1-(2,6-difluoro-4-nitro-phenyl)pyrrolidin-3-yl]acetic acid methyl ester (1.33 g, 4.43 mmol) obtained in Step D was sequentially reacted in the same manner as in Steps B and C of Preparation Example 84 to obtain the title compound (0.38 g, 25%).
¹H-NMR (CDCl₃) δ 6.93 (2H, m), 3.69 (3H, s), 3.60 (2H, m), 3.48 (1H, m), 3.24 (1H, m), 2.63 (1H, m), 2.45 (2H, d), 2.13 (1H, m), 1.62 (1H, m)

Step F: 2-[(3S)-1-[2,6-difluoro-4-(4,4,5,5-tetramethyl-1,3,2-dioxaborolan-2-yl)phenyl]pyrrolidin-3-yl]acetic acid methyl ester 2-[(3S)-1-(4-bromo-2,6-difluoro-phenyl)pyrrolidin-3-yl]acetic acid methyl ester (0.37 g, 1.1 mmol) obtained in Step E was reacted in the same manner as in Step D of Preparation Example 1 to obtain the title compound (0.18 g, 43%).
¹H-NMR (CDCl₃) δ 7.17 (2H, m), 3.70 (5H, m), 3.59 (1H, m), 3.35 (1H, m), 2.61 (1H, m), 2.46 (2H, m), 2.12 (1H, m), 1.62 (1H, m), 1.31 (12H, s)

Preparation Example 98: 2-[(3R)-1-[2,6-difluoro-4-(4,4,5,5-tetramethyl-1,3,2-dioxaborolan-2-yl)phenyl]pyrrolidin-3-yl]acetic acid methyl ester (3R)-3-hydroxypyrrolidin-1-carboxylic acid tert-butyl ester (1.0 g, 5.34 mmol) was reacted in the same manner as in Steps A, B, C, D, E and F of Preparation Example 97 to obtain the title compound (0.14 g, 7%).
¹H-NMR (CDCl₃) δ 7.17 (2H, m), 3.70 (5H, m), 3.59 (1H, m), 3.35 (1H, m), 2.61 (1H, m), 2.46 (2H, m), 2.12 (1H, m), 1.62 (1H, m), 1.31 (12H, s)

Preparation Example 99: 2-[1-[2-fluoro-4-(4,4,5,5-tetramethyl-1,3,2-dioxaborolan-2-yl)phenyl]-4-piperidyl]acetic acid ethyl ester Step A: 1-(2-fluoro-4-nitro-phenyl)piperidin-4-one 1,2-Difluoro-4-nitro-benzene (1.50 g, 9.42 mmol) was dissolved in 31 mL of DMF. TEA (3.3 mL, 23.5 mmol) and hydrate of 4-piperidone hydrochloride (1.52 g, 9.9 mmol) were sequentially added thereto, and the mixture was stirred at room temperature for 48 hours. The reaction solution was concentrated under reduced pressure. After addition of water, the reaction solution was extracted with EtOAc. The organic layer was dried with MgSO₄ to obtain the title compound (2.03 g, 91%).
¹H-NMR (CDCl₃) δ 8.02 (1H, m), 7.96 (1H, m), 6.98 (1H, t), 3.65 (4H, t), 2.65 (4H, t)

Step B: 2-[1-(2-fluoro-4-nitro-phenyl)-4-piperidylidene]acetic acid ethyl ester 1-(2-Fluoro-4-nitro-phenyl)piperidin-4-one (2.03 g, 8.55 mmol) obtained in Step A was reacted in the same manner as in Step B of Preparation Example 89 to obtain the title compound (2.65 g, 99%).
¹H-NMR (CDCl₃) δ 7.95 (1H, m), 7.92 (1H, m), 6.91 (1H, m), 5.76 (1H, s), 4.17 (2H, q), 3.43 (2H, m), 3.38 (2H, m), 3.16 (2H, m), 2.50 (2H, m), 1.30 (3H, t)

Step C: 2-[1-(4-bromo-2-fluoro-phenyl)-4-piperidyl]acetic acid ethyl ester

2-[1-(2-Fluoro-4-nitro-phenyl)-4-piperidylidene]acetic acid ethyl ester (2.65 g, 8.6 mmol) obtained in Step B was sequentially reacted in the same manner as in Step C of Preparation Example 88 and Step C of Preparation Example 84 to obtain the title compound (0.72 g, 24%).
¹H-NMR (CDCl₃) δ 7.15 (2H, m), 6.81 (1H, t), 4.14 (2H, q), 3.38 (2H, m), 2.67 (2H, m), 2.29 (2H, d), 1.92 (1H, m), 1.82 (2H, m), 1.48 (2H, m), 1.26 (3H, t)

Step D: 2-[1-[2-fluoro-4-(4,4,5,5-tetramethyl-1,3,2-dioxaborolan-2-yl)phenyl]-4-piperidyl]acetic acid ethyl ester 2-[1-(4-Bromo-2-fluoro-phenyl)-4-piperidyl]acetic acid ethyl ester (0.22 g, 0.64 mmol) obtained in Step C was reacted in the same manner as in Step D of Preparation Example 1 to obtain the title compound (0.20 g, 80%).
¹H-NMR (CDCl₃) δ 7.48 (1H, m), 7.41 (1H, m), 6.92 (1H, t), 4.14 (2H, q), 3.52 (2H, m), 2.72 (2H, m), 2.29 (2H, d), 1.94 (1H, m), 1.83 (2H, m), 1.50 (2H, m), 1.32 (12H, s), 1.27 (3H, t)

Preparation Example 100: 1-(6-bromo-naphthalen-2-yl)-ethaneone

2-Bromo-naphthalene (0.5 g, 2.41 mmol), AlCl₃ (0.338 g, 2.53 mmol) and AcCl (0.172 mL, 2.41 mmol) were dissolved in 3.4 mL of nitrobenzene, and stirred at 100° C. for 4 hours under reflux. After addition of water, the reaction solution extracted with EtOAc. The organic layer was separated, dried with MgSO₄ and purified by column chromatography to obtain the title compound (0.3 g, 49%).
¹H-NMR (CDCl₃) δ 8.43 (1H, s), 8.06 (2H, m), 7.82 (2H, t), 7.63 (1H, m), 2.72 (3H, s).

Preparation Example 101: 6-bromo-naphthalen-2-carboxylic acid 1-(6-Bromo-naphthalen-2-yl)-ethaneone (0.22 g, 0.88 mmol) obtained in Preparation Example 100 was dissolved in 3 mL of 1,4-dioxane. NaOH (0.353 g, 8.8 mmol) dissolved in 3 mL of water and 9-11% NaOCl solution (1.67 mL, 2.64 mmol) were added thereto, and the mixture was heated to 70° C. and stirred for 4 hours. After addition of NaHSO$_3$ aqueous solution and water, the reaction solution was extracted with ether. 1N HCl was added thereto, and the organic layer was separated, dried with MgSO$_4$ and purified by column chromatography to obtain the title compound (0.156 g, 70%).

$^1$H-NMR (CDCl$_3$) δ 8.56 (1H, s), 8.05 (2H, m), 7.79 (2H, m), 7.58 (1H, m).

Preparation Example 102:
(6-bromo-naphthalen-2-yl)-methanol

6-Bromo-naphthalen-2-carboxylic acid (0.42 g, 1.67 mmol) obtained in Preparation Example 101 was reacted in the same manner as in Step B of Preparation Example 31 to obtain the title compound (0.307 g, 77%).

$^1$H-NMR (CDCl$_3$) δ 8.00 (1H, s), 7.83-7.69 (3H, m), 7.57-7.52 (2H, m), 4.85 (2H, m), 1.75 (1H, t).

Preparation Example 103:
2-bromo-6-chloromethyl-naphthalene (6-Bromo-naphthalen-2-yl)-methanol (0.307 g, 1.29 mmol) obtained in Preparation Example 102 was dissolved in 5 mL of acetonitrile. Thionyl-chloride (0.188 mL, 2.59 mmol) was added thereto at 0° C., and the mixture was stirred at room temperature for 1 hour. The reaction solution was distilled under reduced pressure and purified by column chromatography to obtain the title compound (0.248 g, 75%).

$^1$H-NMR (CDCl$_3$) δ 8.00 (1H, s), 7.83-7.68 (3H, m), 7.58-7.53 (2H, m), 4.73 (2H, s).

Preparation Example 104:
2-(6-bromo-naphthalen-2-ylmethyl)-malonic acid dimethyl ester NaH (60% in mineral oil, 0.058 g, 1.45 mmol) was dissolved in 3 mL of DMF. Dimethyl malonate (0.166 mL, 1.45 mmol) was added thereto, and the mixture was stirred for 15 minutes. 2-Bromo-6-chloromethyl-naphthalene (0.248 g, 0.97 mmol) obtained in Preparation Example 103 was added thereto, and the mixture was heated to 60° C. and stirred for 4 hours. After addition of water, the reaction solution was extracted with EtOAc. The organic layer was separated, dried with MgSO$_4$ and purified by column chromatography to obtain the title compound (0.26 g, 76%).

$^1$H-NMR (CDCl$_3$) δ 7.96 (1H, s), 7.71-7.62 (3H, m), 7.52 (1H, m), 7.36 (1H, m), 3.75 (1H, m), 3.69 (6H, s), 3.87 (2H, d).

Preparation Example 105:
3-(6-bromo-naphthalen-2-yl)-propionic acid 2-(6-Bromo-naphthalen-2-ylmethyl)-malonic acid dimethyl ester (0.26 g, 0.74 mmol) obtained in Preparation Example 104 was dissolved in 12 mL of ethanol and 12 mL of THF. 6 mL of 4N KOH was added thereto, and the mixture was heated to 60° C. and stirred for 1 hour. The reaction solution was distilled under reduced pressure. Solids obtained by the addition of 2N HCl were dissolved in 6 mL of pyridine, heated to 60° C. and stirred for 1 hour. The reaction solution was distilled under reduced pressure. After addition of 2N HCl and water, the reaction solution was extracted with EtOAc. The organic layer was separated, dried with MgSO$_4$ and purified by column chromatography to obtain the title compound (0.055 g, 26%).

$^1$H-NMR (CDCl$_3$) δ 7.96 (1H, s), 7.70-7.62 (3H, m), 7.53 (1H, m), 7.36 (1H, m), 3.11 (2H, t), 2.77 (2H, t).

Preparation Example 106:
3-(6-bromo-naphthalen-2-yl)-propionic acid methyl ester 3-(6-Bromo-naphthalen-2-yl)-propionic acid (0.055 g, 0.2 mmol) obtained in Preparation Example 105 was reacted in the same manner as in Step G of Preparation Example 81 to obtain the title compound (0.052 g, 91%).

$^1$H-NMR (CDCl$_3$) δ 7.96 (1H, s), 7.70-7.61 (3H, m), 7.53 (1H, m), 7.36 (1H, m), 3.67 (3H, s), 3.10 (2H, t), 2.72 (2H, t).

Preparation Example 107: 3-[6-(4,4,5,5-tetramethyl-[1,3,2]dioxaborolan-2-yl)-naphthalen-2-yl]-propionic acid methyl ester 3-(6-Bromo-naphthalen-2-yl)-propionic acid methyl ester (0.085 g, 0.29 mmol) obtained in Preparation Example 106 was reacted in the same manner as in Step D of Preparation Example 1 to obtain the title compound (0.083 g, 84%).

$^1$H-NMR (CDCl$_3$) δ 8.32 (1H, s), 7.80 (2H, d), 7.75 (1H, d), 7.62 (1H, s), 7.32 (1H, d), 3.67 (3H, s), 3.12 (2H, t), 2.73 (2H, t), 1.39 (12H, s).

Preparation Example 108: 6-(4,4,5,5-tetramethyl-[1,3,2]dioxaborolan-2-yl)-naphthalen-2-carboxylic acid methyl ester 6-Bromo-naphthalen-2-carboxylic acid methyl ester (1 g, 3.77 mmol) was reacted in the same manner as in Step D of Preparation Example 1 to obtain the title compound (0.824 g, 70%).

$^1$H-NMR (CDCl$_3$) δ 8.59 (1H, s), 8.39 (1H, s), 8.05 (1H, d), 7.92 (3H, m), 3.98 (3H, s), 1.40 (12H, s).

Preparation Example 109:
6-(6-phenoxy-pyridin-2-yl)-naphthalen-2-carboxylic acid methyl ester 6-(4,4,5,5-Tetramethyl-[1,3,2]dioxaborolan-2-yl)-naphthalen-2-carboxylic acid methyl ester (0.2 g, 0.64 mmol) obtained in Preparation Example 108 and 2-chloro-6-phenoxy-pyridine (0.132 g, 0.64 mmol) obtained in Preparation Example 54 were reacted in the same manner as in Step A of Example 1 to obtain the title compound (0.17 g, 74%).

$^1$H-NMR (CDCl$_3$) δ 8.58 (1H, s), 8.45 (1H, s), 8.06 (2H, m), 7.93 (2H, m), 7.78 (1H, t), 7.63 (1H, d), 7.44 (2H, m), 7.24 (3H, m), 6.82 (1H, d), 3.98 (3H, s).

Preparation Example 110: 2-[6-(6-phenoxy-pyridin-2-yl)-naphthalen-2-ylmethyl]-malonic acid dimethyl ester 6-(6-Phenoxy-pyridin-2-yl)-naphthalen-2-carboxylic acid methyl ester (0.17 g, 0.48 mmol) obtained in Preparation Example 109 was sequentially reacted in the same manner as in Preparation Examples 102, 103 and 104 to obtain the title compound (0.125 g, 59%).

$^1$H-NMR (CDCl$_3$) δ 8.39 (1H, s), 8.02 (1H, m), 7.82-7.74 (3H, m), 7.61 (2H, m), 7.43 (2H, m), 7.32 (1H, m), 7.23 (3H, m), 6.78 (1H, d), 3.78 (1H, t), 3.69 (6H, s), 3.38 (2H, d).

Preparation Example 111: 6-(2-phenoxy-phenyl)-naphthalen-2-carboxylic acid methyl ester 6-(4,4,5,5-Tetramethyl-[1,3,2]dioxaborolan-2-yl)-naphthalen-2-carboxylic acid methyl ester (0.62 g, 2.34 mmol) obtained in Preparation Example 108 and 2-phenoxyphenylboronic acid (0.5 g, 2.34 mmol) were reacted in the same manner as in Step A of Example 1 to obtain the title compound (0.8 g, 96%).
$^1$H-NMR (CDCl$_3$) δ 8.57 (1H, s), 8.03 (2H, m), 7.92 (1H, d), 7.86 (1H, d), 7.77 (1H, m), 7.56 (1H, m), 7.35 (1H, m), 7.24 (3H, m), 7.05 (2H, m), 6.94 (2H, m), 3.98 (3H, s).

Preparation Example 112: 2-[6-(2-phenoxy-phenyl)-naphthalen-2-ylmethyl]-malonic acid dimethyl ester 6-(2-Phenoxy-phenyl)-naphthalen-2-carboxylic acid methyl ester (0.8 g, 2.26 mmol) obtained in Preparation Example 111 was sequentially reacted in the same manner as in Preparation Examples 102, 103 and 104 to obtain the title compound (0.64 g, 64%).
$^1$H-NMR (CDCl$_3$) δ 7.95 (1H, s), 7.74 (2H, m), 7.68 (1H, m), 7.61 (1H, m), 7.55 (1H, m), 7.32 (2H, m), 7.25 (3H, m), 7.04 (2H, m), 6.94 (2H, m), 3.79 (1H, m), 3.68 (6H, s), 3.38 (2H, d).

Preparation Example 113: 6-(6-cyclopentylsulfanyl-pyridin-2-yl)-naphthalen-2-carboxylic acid methyl ester 6-(4,4,5,5-Tetramethyl-[1,3,2]dioxaborolan-2-yl)-naphthalen-2-carboxylic acid methyl ester (0.2 g, 0.64 mmol) obtained in Preparation Example 108 and 2-chloro-6-cyclopentylsulfanyl-pyridine (0.136 g, 0.64 mmol) obtained in Preparation Example 14 were reacted as in Step A of Example 1 to obtain the title compound (0.03 g, 13%).
$^1$H-NMR (CDCl$_3$) δ 8.62 (1H, s), 8.52 (1H, s), 8.25 (1H, m), 8.08 (1H, m), 8.03 (1H, d), 7.97 (1H, d), 7.58 (2H, m), 7.15 (1H, m), 4.25 (1H, m), 4.00 (3H, s), 2.30 (2H, m), 1.84-1.73 (6H, m).

Preparation Example 114: 2-[6-(6-cyclopentylsulfanyl-pyridin-2-yl)-naphthalen-2-ylmethyl]-malonic acid dimethyl ester 6-(6-Cyclopentylsulfanyl-pyridin-2-yl)-naphthalen-2-carboxylic acid methyl ester (0.03 g, 0.08 mmol) obtained in Preparation Example 113 was sequentially reacted in the same manner as in Preparation Examples 102, 103 and 104 to obtain the title compound (0.019 g, 51%).
$^1$H-NMR (CDCl$_3$) δ 8.45 (1H, s), 8.16 (1H, m), 7.86 (2H, m), 7.68 (1H, s), 7.55 (2H, m), 7.35 (1H, m), 7.13 (1H, m), 4.25 (1H, m), 3.80 (1H, t), 3.70 (6H, s), 3.41 (2H, d), 2.31 (2H, m), 1.73-1.60 (6H, m).

Preparation Example 115: 6-(2-phenoxy-pyridin-3-yl)-naphthalen-2-carboxylic acid methyl ester Step A: 3-chloro-2-phenoxy-pyridine 2,3-Dichloro-pyridine (0.3 g, 2.03 mmol), phenol (0.286 g, 3.04 mmol), Cu (0.257 g, 4.05 mmol) and Cs$_2$CO$_3$ (1.98 g, 6.08 mmol) were reacted in the same manner as in Preparation Example 17 to obtain the title compound (0.193 g, 77%).

Step B: 6-(2-phenoxy-pyridin-3-yl)-naphthalen-2-carboxylic acid methyl ester 6-(4,4,5,5-Tetramethyl-[1,3,2]dioxaborolan-2-yl)-naphthalen-2-carboxylic acid methyl ester (0.242 g, 0.78 mmol) obtained in Preparation Example 108 and 3-chloro-2-phenoxy-pyridine (0.16 g, 0.78 mmol) obtained in Step A were reacted in the same manner as in Step A of Example 1 to obtain the title compound (0.06 g, 22%).
$^1$H-NMR (CDCl$_3$) δ 8.63 (1H, s), 8.20 (1H, m), 8.12 (1H, s), 8.08 (1H, m), 7.92 (1H, m), 7.86 (2H, m), 7.39 (2H, m), 7.20-7.13 (4H, m), 6.80 (1H, m), 4.00 (3H, s).

Preparation Example 116: [6-(2-phenoxy-pyridin-3-yl)-naphthalen-2-yl]-methanol 6-(2-Phenoxy-pyridin-3-yl)-naphthalen-2-carboxylic acid methyl ester (0.06 g, 0.17 mmol) obtained in Preparation Example 115 was reacted in the same manner as in Step B of Preparation Example 31 to obtain the title compound (0.024 g, 43%).
$^1$H-NMR (CDCl$_3$) δ 8.18 (1H, m), 8.08 (1H, s), 7.88 (3H, m), 7.82 (2H, m), 7.51 (1H, d), 7.38 (2H, t), 7.19-7.12 (4H, m), 4.87 (2H, d), 1.78 (1H, t).

Preparation Example 117: 6-(3-phenoxy-phenyl)-naphthalen-2-carboxylic acid methyl ester 6-(4,4,5,5-Tetramethyl-[1,3,2]dioxaborolan-2-yl)-naphthalen-2-carboxylic acid methyl ester (0.125 g, 0.40 mmol) obtained in Preparation Example 108 and 1-bromo-3-phenoxy-benzene (0.1 g, 0.40 mmol) were reacted in the same manner as in Step A of Example 1 to obtain the title compound (0.032 g, 22%).
$^1$H-NMR (CDCl$_3$) δ 8.62 (1H, s), 8.09-8.00 (3H, m), 7.92 (1H, d), 7.76 (1H, m), 7.46 (2H, m), 7.37 (3H, m), 7.10 (4H, m), 3.99 (3H, s).

Preparation Example 118: [6-(3-phenoxy-phenyl)-naphthalen-2-yl]-methanol 6-(3-Phenoxy-phenyl)-naphthalen-2-carboxylic acid methyl ester (0.032 g, 0.09 mmol) obtained in Preparation Example 117 was reacted in the same manner as in Step B of Preparation Example 31 to obtain the title compound (0.029 g, 98%).
$^1$H-NMR (CDCl$_3$) δ 8.01 (1H, s), 7.88 (3H, m), 7.71 (1H, m), 7.52-7.34 (6H, m), 7.14-7.03 (4H, m), 4.88 (2H, d), 1.75 (1H, t).

Preparation Example 119: 6-(3-isopropoxy-phenyl)-naphthalen-2-carboxylic acid methyl ester Step A: 1-bromo-3-isopropoxy-benzene 3-Bromo phenol (0.2 g, 1.16 mmol) and 2-bromo-propane (0.163 mL, 1.73 mmol) were reacted in the same manner as in Preparation Example 17 to obtain the title compound (0.193 g, 77%).

Step B: 6-(3-isopropoxy-phenyl)-naphthalen-2-carboxylic acid methyl ester 6-(4,4,5,5-Tetramethyl-[1,3,2]dioxaborolan-2-yl)-naphthalen-2-carboxylic acid methyl ester (0.280 g, 0.89 mmol) obtained in Preparation Example 108 and 1-bromo-3-isopropoxy-benzene (0.193 g, 1.39 mmol) obtained in Step A were reacted in the same manner as in Step A of Example 1 to obtain the title compound (0.078 g, 27%).
$^1$H-NMR (CDCl$_3$) δ 8.63 (1H, s), 8.10-8.00 (3H, m), 7.92 (1H, m), 7.80 (1H, m), 7.39 (1H, m), 7.26 (2H, m), 6.93 (1H, m), 4.66 (1H, m), 3.99 (3H, s), 1.39 (6H, d).

Preparation Example 120: [6-(3-isopropoxy-phenyl)-naphthalen-2-yl]-methanol 6-(3-Isopropoxy-phenyl)-naphthalen-2-carboxylic acid methyl ester (0.305 g, 0.9 mmol) obtained in Preparation Example 119 was reacted in the same manner as in Step B of Preparation Example 31 to obtain the title compound (0.196 g, 70%).
$^1$H-NMR (CDCl$_3$) δ 8.03 (1H, s), 7.88 (3H, m), 7.73 (1H, m), 7.50 (1H, m), 7.36 (1H, m), 7.26 (2H, m), 6.91 (1H, m), 4.88 (2H, d), 4.66 (1H, m), 1.77 (1H, t), 1.39 (6H, d).

Preparation Example 121: 6-(3-cyclobutoxy-phenyl)-naphthalen-2-carboxylic acid methyl ester

Step A: 1-bromo-3-cyclobutoxy-benzene

3-Bromo phenol (0.2 g, 1.16 mmol) and bromocyclobutane (0.163 mL, 1.73 mmol) were reacted in the same manner as in Preparation Example 17 to obtain the title compound (0.262 g, 100%).

Step B: 6-(3-cyclobutoxy-phenyl)-naphthalen-2-carboxylic acid methyl ester 6-(4,4,5,5-Tetramethyl-[1,3,2]dioxoborolan-2-yl)-naphthalen-2-carboxylic acid methyl ester (0.435 g, 1.39 mmol) obtained in Preparation Example 108 and 1-bromo-3-cyclobutoxy-benzene (0.317 g, 1.39 mmol) obtained in Step A were reacted in the same manner as in Step A of Example 1 to obtain the title compound (0.305 g, 65%).
$^1$H-NMR (CDCl$_3$) δ 8.63 (1H, s), 8.10-8.00 (3H, m), 7.92 (1H, m), 7.79 (1H, m), 7.38 (1H, m), 7.26 (1H, m), 7.17 (1H, s), 6.86 (1H, m), 4.74 (1H, m), 3.99 (3H, s), 2.50 (2H, m), 2.24 (2H, m), 1.90 (1H, m), 1.72 (1H, m).

Preparation Example 122: [6-(3-cyclobutoxy-phenyl)-naphthalen-2-yl]-methanol 6-(3-Cyclobutoxy-phenyl)-naphthalen-2-carboxylic acid methyl ester (0.305 g, 0.9 mmol) obtained in Preparation Example 121 was reacted in the same manner as in Step B of Preparation Example 31 to obtain the title compound (0.196 g, 70%).
$^1$H-NMR (CDCl$_3$) δ 8.02 (1H, s), 7.88 (3H, m), 7.74 (1H, m), 7.50 (1H, m), 7.36 (1H, m), 7.26 (1H, m), 7.17 (1H, s), 6.83 (1H, m), 4.88 (2H, d), 4.74 (1H, m), 2.50 (2H, m), 2.23 (2H, m), 1.90 (1H, m), 1.73 (2H, m).

Preparation Example 123: 6-(6-cyclobutoxy-pyridin-2-yl)-naphthalen-2-carboxylic acid methyl ester 6-(4,4,5,5-Tetramethyl-[1,3,2]dioxaborolan-2-yl)-naphthalen-2-carboxylic acid methyl ester (0.39 g, 1.25 mmol) obtained in Preparation Example 108 and 2-chloro-6-cyclobutoxy-pyridine (0.23 g, 1.25 mmol) obtained in Preparation Example 29 were reacted in the same manner as in Step A of Example 1 to obtain the title compound (0.21 g, 50%).
$^1$H-NMR (CDCl$_3$) δ 8.62 (1H, s), 8.51 (1H, s), 8.22 (1H, m), 8.10-7.91 (3H, m), 7.68 (1H, t), 7.48 (1H, m), 6.70 (1H, d), 5.35 (1H, m), 3.98 (3H, s), 2.60 (2H, m), 2.24 (2H, m), 1.89 (1H, m), 1.76 (1H, m).

Preparation Example 124: [6-(6-cyclobutoxy-pyridin-2-yl)-naphthalen-2-yl]-methanol 6-(6-Cyclobutoxy-pyridin-2-yl)-naphthalen-2-carboxylic acid methyl ester (0.21 g, 0.6 mmol) obtained in Preparation Example 123 was reacted in the same manner as in Step B of Preparation Example 31 to obtain the title compound (0.155 g, 80%).
$^1$H-NMR (CDCl$_3$) δ 8.47 (1H, s), 8.17 (1H, m), 7.93 (2H, m), 7.84 (1H, s), 7.66 (1H, t), 7.48 (2H, m), 6.67 (1H, d), 5.35 (1H, m), 4.89 (2H, d), 2.57 (2H, m), 2.24 (2H, m), 1.89 (1H, m), 1.78 (2H, m).

Preparation Example 125: 6-(2-isopropoxy-pyridin-3-yl)-naphthalen-2-carboxylic acid methyl ester 6-(4,4,5,5-Tetramethyl-[1,3,2]dioxaborolan-2-yl)-naphthalen-2-carboxylic acid methyl ester (0.144 g, 0.46 mmol) obtained in Preparation Example 108 and 3-iodo-2-isopropoxy-pyridine (0.124 g, 0.46 mmol) obtained in Preparation Example 34 were reacted in the same manner as in Step A of Example 1 to obtain the title compound (0.092 g, 62%).
$^1$H-NMR (CDCl$_3$) δ 8.62 (1H, s), 8.18 (1H, m), 8.06 (2H, m), 7.97 (1H, d), 7.89 (1H, d), 7.80 (1H, m), 7.72 (1H, m), 6.97 (1H, m), 5.45 (1H, m), 3.99 (3H, s), 1.36 (6H, d).

Preparation Example 126: 6-(2-cyclopentyloxy-pyridin-3-yl)-naphthalen-2-carboxylic acid methyl ester 6-(4,4,5,5-Tetramethyl-[1,3,2]dioxaborolan-2-yl)-naphthalen-2-carboxylic acid methyl ester (0.223 g, 0.7 mmol) obtained in Preparation Example 108 and 2-cyclopentyloxy-3-iodo-pyridine (0.207 g, 0.7 mmol) obtained in Preparation Example 11 were reacted in the same manner as in Step A of Example 1 to obtain the title compound (0.123 g, 49%).
$^1$H-NMR (CDCl$_3$) δ 8.62 (1H, s), 8.19 (1H, m), 8.08 (1H, m), 8.03 (1H, s), 7.96 (1H, d), 7.89 (1H, d), 7.77 (1H, m), 7.73 (1H, m), 6.97 (1H, m), 5.57 (1H, m), 4.00 (3H, s), 1.95 (2H, m), 1.85 (2H, m), 1.73 (2H, m), 1.63 (2H, m).

Preparation Example 127: 2-chloro-6-(2-fluoro-phenoxy)-pyridine 2,6-Dichloropyridine (0.2 g, 1.35 mmol) and 2-fluorophenol (0.151 g, 1.35 mmol) were reacted in the same manner as in Preparation Example 12 to obtain the title compound (0.045 g, 15%).
$^1$H-NMR (CDCl$_3$) δ 7.64 (1H, m), 7.27 (2H, m), 7.20 (2H, m), 7.05 (1H, d), 6.85 (1H, d).

Preparation Example 128: 3-[6-(2-bromo-phenyl)-naphthalen-2-yl]-propionic acid methyl ester 3-(6-Bromo-naphthalen-2-yl)-propionic acid methyl ester (0.1 g, 0.34 mmol) obtained in Preparation Example 106 and 2-bromophenylboronic acid (0.068 g, 0.34 mmol) were reacted in the same manner as in Step A of Example 1 to obtain the title compound (0.012 g, 9%).

$^1$H-NMR (CDCl$_3$) δ 7.81-7.23 (9H, m), 7.10 (1H, m), 3.70 (3H, s), 3.07 (2H, t), 2.72 (2H, t).

Preparation Example 129: 3-{6-[2-(2-fluoro-phenoxy)-phenyl]-naphthalen-2-yl}-propionic acid methyl ester 3-[6-(2-Bromo-phenyl)-naphthalen-2-yl]-propionic acid methyl ester (0.012 g, 0.03 mmol) obtained in Preparation Example 128 was dissolved in 1 mL of 1,4-dioxane. CuI (0.001 g, 0.006 mmol), Cs$_2$CO$_3$ (0.021 g, 0.06 mmol) and 2-fluoro-phenol (0.006 mL, 0.06 mmol) were added thereto, and the mixture was stirred for 18 hours under reflux. The reaction solution was filtered through Celite and purified by column chromatography to obtain the title compound (0.012 g, 92%).

$^1$H-NMR (CDCl$_3$) δ 7.82-7.35 (4H, m), 7.20-7.04 (8H, m), 6.80 (2H, m) 3.67 (3H, s), 3.06 (2H, t), 2.70 (2H, t).

Preparation Example 130: 2-(4-bromo-phenyl)-2-methyl-propionic acid ethyl ester (4-Bromo-phenyl)-acetic acid ethyl ester (0.1 g, 0.41 mmol) was dissolved in 1 mL of THF t-BuOK (0.092 g, 0.82 mmol) was added thereto, and iodomethane (0.051 mL, 0.82 mmol) was added thereto at 0° C. The mixture was stirred at room temperature for 18 hours. After addition of 1N HCl and water, the reaction solution was extracted with EtOAc. The organic layer was separated, dried with MgSO$_4$ and purified by column chromatography to obtain the title compound (0.047 g, 42%).

$^1$H-NMR (CDCl$_3$) δ 7.42 (2H, d), 7.21 (2H, d), 4.11 (2H, q), 1.54 (6H, s), 1.18 (3H, t).

Preparation Example 131: 2-(4-bromo-phenyl)-2-methyl-propan-1-ol 2-(4-Bromo-phenyl)-2-methyl-propionic acid ethyl ester (0.236 g, 0.87 mmol) obtained in Preparation Example 130 was reacted in the same manner as in Step B of Preparation Example 31 to obtain the title compound (0.17 g, 85%).

$^1$H-NMR (CDCl$_3$) δ 7.45 (2H, d), 7.26 (2H, d), 3.61 (2H, d), 1.55 (1H, m), 1.31 (6H, s).

Preparation Example 132: 2-(4-bromo-phenyl)-2-methyl-propionaldehyde 2-(4-Bromo-phenyl)-2-methyl-propan-1-ol (0.17 g, 0.74 mmol) obtained in Preparation Example 131 was dissolved in 2.5 mL of MC and 0.5 mL of DMSO. IBX (0.249 g, 0.89 mmol) was added thereto at 0° C., and the mixture was stirred at room temperature for 4 hours. After addition of water, the reaction solution was extracted with MC. The organic layer was separated, dried with MgSO$_4$ and purified by column chromatography to obtain the title compound (0.052 g, 30%).

$^1$H-NMR (CDCl$_3$) δ 9.46 (1H, s), 7.50 (2H, d), 7.13 (2H, d), 1.44 (6H, s)

Preparation Example 133: 3-(4-bromo-phenyl)-3-methyl-butyraldehyde 2-(4-Bromo-phenyl)-2-methyl-propionaldehyde (0.33 g, 1.45 mmol) obtained in Preparation Example 132 was reacted in the same manner as in Preparation Example 152 to obtain the title compound (0.275 g, 78%).

$^1$H-NMR (CDCl$_3$) δ 9.52 (1H, m), 7.45 (2H, d), 7.24 (2H, d), 2.66 (2H, m), 1.44 (6H, s).

Preparation Example 134: (E)-5-(4-bromo-phenyl)-5-methyl-hex-2-enoic acid ethyl ester 3-(4-Bromo-phenyl)-3-methyl-butyraldehyde (0.275 g, 1.14 mmol) obtained in Preparation Example 133 was reacted in the same manner as in Step A of Preparation Example 85 to obtain the title compound (0.348 g, 98%).

$^1$H-NMR (CDCl$_3$) δ 7.42 (2H, d), 7.19 (2H, d), 6.69 (1H, m), 5.74 (1H, d), 4.15 (2H, q), 2.48 (2H, d), 1.32 (6H, s), 1.25 (3H, t).

Preparation Example 135: (E)-5-methyl-5-[4-(4,4,5,5-tetramethyl-[1,3,2]dioxaborolan-2-yl)-phenyl]-hex-2-enoic acid ethyl ester (E)-5-(4-bromo-phenyl)-5-methyl-hex-2-enoic acid ethyl ester (0.348 g, 1.12 mmol) obtained in Preparation Example 134 was reacted in the same manner as in Step D of Preparation Example 1 to obtain the title compound (0.291 g, 72%).

$^1$H-NMR (CDCl$_3$) δ 7.75 (2H, d), 7.34 (2H, d), 6.70 (1H, m), 5.76 (1H, d), 4.12 (2H, q), 2.50 (2H, d), 1.33 (18H, s), 1.24 (3H, t).

Preparation Example 136: 5-methyl-5-[4-(4,4,5,5-tetramethyl-[1,3,2]dioxaborolan-2-yl)-phenyl]-hexanoic acid ethyl ester (E)-5-methyl-5-[4-(4,4,5,5-tetramethyl-[1,3,2]dioxaborolan-2-yl)-phenyl]-hex-2-enoic acid ethyl ester (0.291 g, 0.81 mmol) obtained in Preparation Example 135 was reacted in the same manner as in Step E of Preparation Example 1 to obtain the title compound (0.248 g, 84%).

$^1$H-NMR (CDCl$_3$) δ 7.75 (2H, d), 7.33 (2H, d), 4.08 (2H, q), 2.17 (2H, t), 1.65 (2H, m), 1.35 (20H, m), 1.22 (3H, t).

Preparation Example 137: 2-(4-bromo-2-fluoro-phenyl)-2-methyl-propionitrile

Step A: (4-bromo-2-fluoro-phenyl)-acetonitrile

4-Bromo-1-bromomethyl-2-fluoro-benzene (0.5 g, 1.87 mmol) was reacted in the same manner as in Preparation Example 149 to obtain the title compound (0.386 g, 96%).

Step B: 2-(4-bromo-2-fluoro-phenyl)-2-methyl-propionitrile (4-Bromo-2-fluoro-phenyl)-acetonitrile (0.24 g, 1.12 mmol) obtained in Step A was reacted in the same manner as in Preparation Example 143 to obtain the title compound (0.235 g, 86%).

$^1$H-NMR (CDCl$_3$) δ 7.40-7.26 (3H, m), 1.78 (6H, s).

Preparation Example 138: 2-(4-bromo-2-fluoro-phenyl)-2-methyl-propionaldehyde 2-(4-Bromo-2-fluoro-phenyl)-2-methyl-propionitrile (0.235 g, 0.97 mmol) obtained in Preparation Example 137 was reacted in the same manner as in Preparation Example 151 to obtain the title compound (0.2 g, 84%).

¹H-NMR (CDCl₃) δ 9.61 (1H, m), 7.34 (1H, m), 7.26 (1H, m), 7.16 (1H, t), 1.44 (6H, s).

Preparation Example 139: 3-(4-bromo-2-fluoro-phenyl)-3-methyl-butyraldehyde 2-(4-Bromo-2-fluoro-phenyl)-2-methyl-propionaldehyde (0.2 g, 0.82 mmol) obtained in Preparation Example 138 was reacted in the same manner as in Preparation Example 152 to obtain the title compound (0.067 g, 31%).
¹H-NMR (CDCl₃) δ 9.51 (1H, t), 7.25-7.16 (3H, m), 2.81 (2H, s), 1.43 (6H, s).

Preparation Example 140: (E)-5-(4-bromo-2-fluoro-phenyl)-5-methyl-hex-2-enoic acid ethyl ester 3-(4-Bromo-2-fluoro-phenyl)-3-methyl-butyraldehyde (0.067 g, 0.26 mmol) obtained in Preparation Example 139 was reacted in the same manner as in Step A of Preparation Example 85 to obtain the title compound (0.072 g, 84%).
¹H-NMR (CDCl₃) δ 7.20 (2H, m), 7.08 (1H, t), 6.66 (1H, m), 5.79 (1H, d), 4.14 (2H, q), 2.62 (2H, d), 1.37 (6H, s), 1.25 (3H, t).

Preparation Example 141: (E)-5-[2-fluoro-4-(4,4,5,5-tetramethyl-[1,3,2]dioxaborolan-2-yl)-phenyl]-5-methyl-hex-2-enoic acid ethyl ester (E)-5-(4-bromo-2-fluoro-phenyl)-5-methyl-hex-2-enoic acid ethyl ester (0.072 g, 0.22 mmol) obtained in Preparation Example 140 was reacted in the same manner as in Step D of Preparation Example 1 to obtain the title compound (0.045 g, 54%).
¹H-NMR (CDCl₃) δ 7.47 (1H, d), 7.42 (1H, d), 7.23 (1H, t), 6.66 (1H, m), 5.75 (1H, d), 4.11 (2H, q), 2.65 (2H, d), 1.32 (18H, s), 1.23 (3H, t).

Preparation Example 142: 5-[2-fluoro-4-(4,4,5,5-tetramethyl-[1,3,2]dioxaborolan-2-yl)-phenyl]-5-methyl-hexanoic acid ethyl ester (E)-5-[2-fluoro-4-(4,4,5,5-tetramethyl-[1,3,2]dioxaborolan-2-yl)-phenyl]-5-methyl-hex-2-enoic acid ethyl ester (0.045 g, 0.12 mmol) obtained in Preparation Example 141 was reacted in the same manner as in Step E of Preparation Example 1 to obtain the title compound (0.02 g, 44%).
¹H-NMR (CDCl₃) δ 7.47 (1H, d), 7.38 (1H, d), 7.23 (1H, t), 4.06 (2H, q), 2.19 (2H, t), 1.75 (2H, m), 1.35 (20H, m), 1.21 (3H, t).

Preparation Example 143: 2-(4-bromo-2,6-difluoro-phenyl)-2-methyl-propionitrile (4-Bromo-2,6-difluoro-phenyl)-acetonitrile (0.4 g, 1.72 mmol) obtained in Preparation Example 149 was dissolved in 2 mL of DMF and 2 mL of THF. NaH (60% in mineral oil, 0.152 g, 3.79 mmol) and iodomethane (0.236 mL, 3.79 mmol) were added thereto at 0° C., and the mixture was stirred at room temperature for 3 hours. After addition of water, the reaction solution was extracted with EtOAc. The organic layer was separated, dried with MgSO₄ and purified by column chromatography to obtain the title compound (0.372 g, 83%).
¹H-NMR (CDCl₃) δ 7.12 (2H, m), 1.86 (6H, s).

Preparation Example 144: 2-(4-bromo-2,6-difluoro-phenyl)-2-methyl-propionaldehyde 2-(4-Bromo-2,6-difluoro-phenyl)-2-methyl-propionitrile (0.372 g, 1.43 mmol) obtained in Preparation Example 143 was reacted in the same manner as in Preparation Example 151 to obtain the title compound (0.328 g, 87%).
¹H-NMR (CDCl₃) δ 9.60 (1H, m), 7.08 (2H, m), 1.50 (6H, s).

Preparation Example 145: 3-(4-bromo-2,6-difluoro-phenyl)-3-methyl-butyraldehyde 2-(4-Bromo-2,6-difluoro-phenyl)-2-methyl-propionaldehyde (0.328 g, 1.25 mmol) obtained in Preparation Example 144 was reacted in the same manner as in Preparation Example 152 to obtain the title compound (0.16 g, 46%).
¹H-NMR (CDCl₃) δ 9.61 (1H, s), 7.01 (2H, m), 2.86 (2H, s), 1.54 (6H, s).

Preparation Example 146: (E)-5-(4-bromo-2,6-difluoro-phenyl)-5-methyl-hex-2-enoic acid ethyl ester 3-(4-Bromo-2,6-difluoro-phenyl)-3-methyl-butyraldehyde (0.16 g, 0.58 mmol) obtained in Preparation Example 145 was reacted in the same manner as in Step A of Preparation Example 85 to obtain the title compound (0.17 g, 85%).
¹H-NMR (CDCl₃) δ 6.98 (2H, m), 6.74 (1H, m), 5.78 (1H, d), 4.14 (2H, q), 2.64 (2H, d), 1.46 (6H, s), 1.25 (3H, t).

Preparation Example 147: 5-(4-bromo-2,6-difluoro-phenyl)-5-methyl-hexanoic acid ethyl ester (E)-5-(4-bromo-2,6-difluoro-phenyl)-5-methyl-hex-2-enoic acid ethyl ester (0.17 g, 0.49 mmol) obtained in Preparation Example 146 was reacted in the same manner as in Preparation Example 174 to obtain the title compound (0.15 g, 87%).
¹H-NMR (CDCl₃) δ 6.96 (2H, m), 4.08 (2H, q), 2.23 (2H, t), 1.72 (2H, m), 1.43 (8H, m), 1.22 (3H, t).

Preparation Example 148: 5-[2,6-difluoro-4-(4,4,5,5-tetramethyl-[1,3,2]dioxaborolan-2-yl)-phenyl]-5-methyl-hexanoic acid ethyl ester 5-(4-Bromo-2,6-difluoro-phenyl)-5-methyl-hexanoic acid ethyl ester (0.15 g, 0.43 mmol) obtained in Preparation Example 147 was reacted in the same manner as in Step D of Preparation Example 1 to obtain the title compound (0.07 g, 41%).
¹H-NMR (CDCl₃) δ 7.20 (2H, m), 4.08 (2H, q), 2.21 (2H, t), 1.75 (2H, m), 1.46 (8H, m), 1.32 (12H, s), 1.21 (3H, t).

Preparation Example 149: (4-bromo-2,6-difluoro-phenyl)-acetonitrile

5-Bromo-2-bromomethyl-1,3-difluoro-benzene (1.1 g, 3.85 mmol) was dissolved in 6 mL of ethanol and 2 mL of water. KCN (0.268 g, 4.12 mmol) was added thereto and heated to 60° C., and the mixture was stirred for 2 hours. After addition of water, the reaction solution was extracted with EtOAc. The organic layer was separated, dried with MgSO₄ and purified by column chromatography to obtain the title compound (0.8 g, 89%).
¹H-NMR (CDCl₃) δ 7.17 (2H, m), 3.69 (2H, s).

Preparation Example 150: 1-(4-bromo-2,6-difluoro-phenyl)-cyclopropanecarbonitrile (4-Bromo-2,6-difluoro-phenyl)-acetonitrile (0.4 g, 1.72 mmol) obtained in Preparation Example 149 was dissolved in 1 mL of toluene and 1.7 mL of 50% NaOH aqueous solution. 1-Bromo-2-chloroethane (0.287 mL, 3.44 mmol) and benzyltriethylammonium chloride (0.098 g, 0.43 mmol) were added thereto at 0° C., the mixture was heated to 40° C. and stirred for 18 hours. After addition of water, the reaction solution was extracted with EtOAc. The organic layer was separated, dried with $MgSO_4$ and purified by column chromatography to obtain the title compound (0.27 g, 60%).

$^1$H-NMR ($CDCl_3$) δ 7.12 (2H, m), 1.76 (2H, m), 1.36 (2H, m).

Preparation Example 151: 1-(4-bromo-2,6-difluoro-phenyl)-cyclopropanecarbaldehyde 1-(4-Bromo-2,6-difluoro-phenyl)-cyclopropanecarbonitrile (0.270 g, 1.05 mmol) obtained in Preparation Example 150 was dissolved in 5 mL of MC. DIBAL-H (0.77 mL, 1.15 mmol) was added thereto at −78° C., and the mixture was stirred for 2 hours and additionally stirred at room temperature for 1 hour. After addition of 1N HCl and KNa tartrate aqueous solution, the reaction solution was extracted with MC. The organic layer was separated, dried with $MgSO_4$ and purified by column chromatography to obtain the title compound (0.216 g, 79%).

$^1$H-NMR ($CDCl_3$) δ 8.83 (1H, s), 7.10 (2H, m), 1.70 (2H, m), 1.46 (2H, m).

Preparation Example 152: [1-(4-bromo-2,6-difluoro-phenyl)-cyclopropyl]-acetaldehyde (Methoxymethyl)triphenylphosphonium chloride (0.425 g, 1.24 mmol) was dissolved in 3 mL of THF. LiHMDS (1.24 mL, 1.24 mmol) were added thereto at 0° C., and the mixture was stirred for 15 minutes. 1-(4-Bromo-2,6-difluoro-phenyl)-cyclopropanecarbaldehyde (0.216 g, 0.83 mmol) obtained in Preparation Example 151 was added thereto 0° C., and the mixture was stirred at room temperature for 18 hours. After addition of water, the reaction solution was extracted with EtOAc. The organic layer was separated, dried with $MgSO_4$ and purified by column chromatography. The purified organic layer was dissolved in 2N HCl (0.2 M) and THF (0.1 M), and heated to 70° C., the mixture was stirred for 18 hours. After addition of water, the reaction solution was extracted with EtOAc. The organic layer was separated, dried with $MgSO_4$ and purified by column chromatography to obtain the title compound (0.375 g, 84%).

$^1$H-NMR ($CDCl_3$) δ 9.77 (1H, s), 7.02 (2H, m), 2.49 (2H, d), 0.99 (4H, m).

Preparation Example 153: (E)-4-[1-(4-bromo-2,6-difluoro-phenyl)-cyclopropyl]-but-2-enoic acid ethyl ester

[1-(4-Bromo-2,6-difluoro-phenyl)-cyclopropyl]-acetaldehyde (0.375 g, 1.36 mmol) obtained in Preparation Example 152 was reacted in the same manner as in Step A of Preparation Example 85 to obtain the title compound (0.443 g, 94%).

$^1$H-NMR ($CDCl_3$) δ 7.00 (2H, m), 6.90 (1H, m), 5.72 (1H, d), 4.15 (2H, q), 2.37 (2H, d), 1.27 (3H, t), 0.87 (4H, m).

Preparation Example 154: 4-[1-(4-bromo-2,6-difluoro-phenyl)-cyclopropyl]-butyric acid ethyl ester (E)-4-[1-(4-bromo-2,6-difluoro-phenyl)-cyclopropyl]-but-2-enoic acid ethyl ester (0.443 g, 1.28 mmol) obtained in Preparation Example 153 was reacted in the same manner as in Preparation Example 174 to obtain the title compound (0.414 g, 93%).

$^1$H-NMR ($CDCl_3$) δ 7.02 (2H, m), 4.10 (2H, q), 2.26 (2H, t), 1.63 (2H, m), 1.50 (2H, m), 1.24 (3H, t), 0.79 (4H, s).

Preparation Example 155: 4-{1-[2,6-difluoro-4-(4,4,5,5-tetramethyl-[1,3,2]dioxaborolan-2-yl)-phenyl]-cyclopropyl}-butyric acid ethyl ester 4-[1-(4-Bromo-2,6-difluoro-phenyl)-cyclopropyl]-butyric acid ethyl ester (0.414 g, 1.19 mmol) obtained in Preparation Example 154 was reacted in the same manner as in Step D of Preparation Example 1 to obtain the title compound (0.322 g, 70%).

$^1$H-NMR ($CDCl_3$) δ 7.20 (2H, m), 4.08 (2H, q), 2.24 (2H, t), 1.62 (2H, m), 1.54 (2H, m), 1.32 (12H, s), 1.20 (3H, t), 0.80 (4H, m).

Preparation Example 156: 1-bromo-4-(2-bromo-1,1-difluoro-ethyl)-benzene

2-Bromo-1-(4-bromo-phenyl)-ethaneone (0.5 g, 1.8 mmol) was dissolved in 4 mL of MC. DAST (diethylaminosulfur trifluoride, 0.58 g, 3.6 mmol) was added thereto at 0° C., and the mixture was stirred at 0° C. for 1 hour, at room temperature for 2 hours, and at 40° C. for 4 hours. After addition of water, the reaction solution was extracted with MC. The organic layer was separated, dried with $MgSO_4$ and purified by column chromatography to obtain the title compound (0.345 g, 64%).

$^1$H-NMR ($CDCl_3$) δ 7.60 (2H, d), 7.38 (2H, d), 3.72 (2H, t).

Preparation Example 157: acetic acid 2-(4-bromo-phenyl)-2,2-difluoro-ethyl ester 1-Bromo-4-(2-bromo-1,1-difluoro-ethyl)-benzene (0.324 g, 1.08 mmol) obtained in Preparation Example 156 was dissolved in 4 mL of DMF. KOAc (0.424 g, 4.32 mmol) and 18-crown-6 (0.028 g, 0.11 mmol) were added thereto and heated to 80° C., and the mixture was stirred for 18 hours. After addition of water, the reaction solution was extracted with ether. The organic layer was separated, dried with $MgSO_4$ and purified by column chromatography to obtain the title compound (0.216 g, 71%).

$^1$H-NMR ($CDCl_3$) δ 7.59 (2H, d), 7.38 (2H, d), 4.44 (2H, t), 2.06 (3H, s).

Preparation Example 158: 2-(4-bromo-phenyl)-2,2-difluoro-ethanol

Acetic acid 2-(4-bromo-phenyl)-2,2-difluoro-ethyl ester (0.21 g, 0.77 mmol) obtained in Preparation Example 157 was dissolved in 4 mL of ethanol and 1 mL of water. NaOH (0.062 g, 1.55 mmol) was added thereto, and the mixture was stirred at room temperature for 2 hours. The reaction solution was concentrated under reduced pressure. After addition of water, the reaction solution was extracted with EtOAc. The organic layer was separated, dried with $MgSO_4$ and purified by column chromatography to obtain the title compound (0.176 g, 96%).

$^1$H-NMR ($CDCl_3$) δ 7.59 (2H, d), 7.40 (2H, d), 3.96 (2H, m), 1.87 (1H, m).

Preparation Example 159: [2-(4-bromo-phenyl)-2,2-difluoro-ethoxy]-acetic acid ethyl ester 2-(4-Bromo-phenyl)-2,2-difluoro-ethanol (0.24 g, 1.01 mmol) obtained in Preparation Example 158 was reacted in the same manner as in Preparation Example 164 to obtain the title compound (0.24 g, 70%).
$^1$H-NMR (CDCl$_3$) δ 7.57 (2H, d), 7.42 (2H, d), 4.20 (2H, q), 4.18 (2H, s), 3.99 (2H, t), 1.26 (3H, t).

Preparation Example 160: {2,2-difluoro-2-[4-(4,4,5,5-tetramethyl-[1,3,2]dioxaborolan-2-yl)-phenyl]-ethoxy}-acetic acid ethyl ester

[2-(4-Bromo-phenyl)-2,2-difluoro-ethoxy]-acetic acid ethyl ester (0.24 g, 0.74 mmol) obtained in Preparation Example 159 was reacted in the same manner as in Step D of Preparation Example 1 to obtain the title compound (0.22 g, 80%).
$^1$H-NMR (CDCl$_3$) δ 7.86 (2H, d), 7.51 (2H, d), 4.20 (2H, q), 4.14 (2H, s), 4.00 (2H, t), 1.34 (12H, s), 1.25 (3H, t).

Preparation Example 161: (E)-4-(4-bromo-phenyl)-4,4-difluoro-but-2-enoic acid ethyl ester 2-(4-Bromo-phenyl)-2,2-difluoro-ethanol (0.5 g, 2.11 mmol) obtained in Preparation Example 158 was reacted in the same manner as in Step C of Preparation Example 4 to obtain the title compound (0.42 g, 65%).
$^1$H-NMR (CDCl$_3$) δ 7.59 (2H, d), 7.35 (2H, d), 6.95 (1H, m), 6.26 (1H, d), 4.23 (2H, q), 1.28 (3H, t).

Preparation Example 162: 4-(4-bromo-phenyl)-4,4-difluoro-butyric acid ethyl ester (E)-4-(4-bromo-phenyl)-4,4-difluoro-but-2-enoic acid ethyl ester (0.42 g, 1.38 mmol) obtained in Preparation Example 161 was reacted in the same manner as in Preparation Example 174 to obtain the title compound (0.24 g, 57%).
$^1$H-NMR (CDCl$_3$) δ 7.56 (2H, d), 7.34 (2H, d), 4.11 (2H, q), 2.47 (4H, m), 1.22 (3H, t).

Preparation Example 163: 4-(4-bromo-phenyl)-4,4-difluoro-butan-1-ol 4-(4-Bromo-phenyl)-4,4-difluoro-butyric acid ethyl ester (0.244 g, 0.79 mmol) obtained in Preparation Example 162 was reacted in the same manner as in Step C of Preparation Example 90 to obtain the title compound (0.2 g, 95%).
$^1$H-NMR (CDCl$_3$) δ 7.56 (2H, d), 7.34 (2H, d), 3.66 (2H, m), 2.20 (2H, m), 1.70 (2H, m), 1.26 (1H, m).

Preparation Example 164: 4-(4-bromo-phenylsulfanyl)-butyric acid ethyl ester

4-Bromo-benzenethiol (0.5 g, 2.64 mmol) was dissolved in 5 mL of THF and cooled to 0° C. NaH (60% in mineral oil, 0.11 g, 2.64 mmol) was added thereto, and the mixture was stirred for 30 minutes. 4-Bromo-butyric acid ethyl ester (0.42 mL, 2.91 mmol) was added thereto, and the mixture was stirred at room temperature for 4 hours. After addition of ammonium chloride aqueous solution, the reaction solution was extracted with EtOAc. The organic layer was separated, dried with MgSO$_4$ and purified by column chromatography to obtain the title compound (0.80 g, 99%).
$^1$H-NMR (CDCl$_3$) δ 7.38 (2H, d), 7.19 (2H, d), 4.13 (2H, q), 2.93 (2H, t), 2.43 (2H, t), 1.93 (2H, m), 1.24 (3H, t).

Preparation Example 165: methanesulfonic acid 4-(4-bromo-phenyl)-4,4-difluoro-butyl ester 4-(4-Bromo-phenyl)-4,4-difluoro-butan-1-ol (0.263 g, 0.99 mmol) obtained in Preparation Example 163 was reacted in the same manner as in Step B of Preparation Example 25 to obtain the title compound (0.28 g, 82%).
$^1$H-NMR (CDCl$_3$) δ 7.56 (2H, d), 7.32 (2H, d), 4.26 (2H, t), 3.00 (3H, s), 2.23 (2H, m), 1.94 (2H, m).

Preparation Example 166: 5-(4-bromo-phenyl)-5,5-difluoro-pentanenitrile

Methanesulfonic acid 4-(4-bromo-phenyl)-4,4-difluoro-butyl ester (0.28 g, 0.82 mmol) obtained in Preparation Example 165 was reacted in the same manner as in Step C of Preparation Example 25 to obtain the title compound (0.21 g, 94%).
$^1$H-NMR (CDCl$_3$) δ 7.58 (2H, d), 7.34 (2H, d), 2.42 (2H, t), 2.24 (2H, m), 1.87 (2H, m).

Preparation Example 167: 5-(4-bromo-phenyl)-5,5-difluoro-pentanoic acid 5-(4-Bromo-phenyl)-5,5-difluoro-pentanenitrile (0.21 g, 0.77 mmol) obtained in Preparation Example 166 was dissolved in 2 mL of ethanol and 2 mL of water. NaOH (0.107 g, 2.68 mmol) was added thereto, and the mixture was stirred for 3 hours under reflux. After addition of 1N HCl, the reaction solution was extracted with EtOAc. The organic layer was separated, dried with MgSO$_4$ and purified by column chromatography to obtain the title compound (0.26 g, 48%).
$^1$H-NMR (CDCl$_3$) δ 7.56 (2H, d), 7.34 (2H, d), 2.41 (2H, t), 2.15 (2H, m), 1.78 (2H, m).

Preparation Example 168: 5-(4-bromo-phenyl)-5,5-difluoro-pentanoic acid methyl ester 5-(4-Bromo-phenyl)-5,5-difluoro-pentanoic acid (0.212 g, 0.72 mmol) obtained in Preparation Example 167 was reacted in the same manner as in Step G of Preparation Example 81 to obtain the title compound (0.19 g, 85%).
$^1$H-NMR (CDCl$_3$) δ 7.57 (2H, d), 7.34 (2H, d), 3.66 (3H, s), 2.35 (2H, t), 2.15 (2H, m), 1.76 (2H, m).

Preparation Example 169: 5,5-difluoro-5-[4-(4,4,5,5-tetramethyl-[1,3,2]dioxaborolan-2-yl)-phenyl]-pentanoic acid methyl ester 5-(4-Bromo-phenyl)-5,5-difluoro-pentanoic acid methyl ester (0.190 g, 0.62 mmol) obtained in Preparation Example 168 was reacted in the same manner as in Step D of Preparation Example 1 to obtain the title compound (0.13 g, 59%).
$^1$H-NMR (CDCl$_3$) δ 7.85 (2H, d), 7.46 (2H, d), 3.65 (3H, s), 2.34 (2H, t), 2.16 (2H, m), 1.76 (2H, m), 1.35 (12H, s).

Preparation Example 170: (E)-3-(4-bromo-2,6-difluoro-phenyl)-acrylic acid ethyl ester 4-Bromo-2,6-difluoro-benzaldehyde (1.52 g, 6.88 mmol) was reacted in the same manner as in Step A of Preparation Example 85 to obtain the title compound (1.3 g, 65%).
$^1$H-NMR (CDCl$_3$) δ 7.66 (1H, d), 7.13 (2H, m), 6.70 (1H, d), 4.27 (2H, q), 1.32 (3H, t).

Preparation Example 171: 2-(4-bromo-2,6-difluoro-phenyl)-cyclopropanecarboxylic acid ethyl ester Trimethylsulfoxonium iodide (0.462 g, 2.10 mmol) was dissolved in 5 mL of DMSO. NaH (60% in mineral oil, 0.084 g, 2.10 mmol) was added thereto, and the mixture was stirred for 30 minutes. After cooling to 0° C., (E)-3-(4-bromo-2,6-difluoro-phenyl)-acrylic acid ethyl ester (0.51 g, 1.75 mmol) obtained in Preparation Example 170 was added thereto, and the mixture was stirred at room temperature for 4 hours. After addition of water, the reaction solution was extracted with EtOAc. The organic layer was separated, dried with MgSO$_4$ and purified by column chromatography to obtain the title compound (0.26 g, 48%).

$^1$H-NMR (CDCl$_3$) δ 7.02 (2H, m), 4.19 (2H, q), 2.42 (1H, m), 2.14 (1H, m), 1.54 (2H, m), 1.28 (3H, t).

Preparation Example 172: [2-(4-bromo-2,6-difluoro-phenyl)-cyclopropyl]-methanol 2-(4-Bromo-2,6-difluoro-phenyl)-cyclopropanecarboxylic acid ethyl ester (0.26 g, 0.85 mmol) obtained in Preparation Example 171 was reacted in the same manner as in Step C of Preparation Example 90 to obtain the title compound (0.17 g, 76%).

$^1$H-NMR (CDCl$_3$) δ 7.00 (2H, m), 3.70 (1H, m), 3.57 (1H, m), 1.66 (2H, m), 1.45 (1H, t), 1.19 (1H, m), 0.93 (1H, m).

Preparation Example 173: (E)-3-[2-(4-bromo-2,6-difluoro-phenyl)-cyclopropyl]-acrylic acid ethyl ester

[2-(4-Bromo-2,6-difluoro-phenyl)-cyclopropyl]-methanol (0.314 g, 1.19 mmol) obtained in Preparation Example 172 was reacted in the same manner as in Step C of Preparation Example 4 to obtain the title compound (0.36 g, 91%).

$^1$H-NMR (CDCl$_3$) δ 7.00 (2H, m), 6.56 (1H, m), 5.93 (1H, d), 4.19 (2H, q), 2.04 (2H, m), 1.63 (1H, m), 1.28 (4H, m).

Preparation Example 174: 3-[2-(4-bromo-2,6-difluoro-phenyl)-cyclopropyl]-propionic acid ethyl ester (E)-3-[2-(4-bromo-2,6-difluoro-phenyl)-cyclopropyl]-acrylic acid ethyl ester (0.228 g, 0.69 mmol) obtained in Preparation Example 173 was dissolved in 5 mL of DME. p-Toluenesulfonhydrazide (0.897 g, 4.82 mmol) were added thereto, and the mixture was stirred for 5 minutes under reflux. 4.9 mL of 1.4 M NaOAc solution was added thereto, and the mixture was stirred for 18 hours under reflux. The reaction solution was diluted with water and extracted with DCM to separate an organic layer. The organic layer was dried with MgSO$_4$ and purified by column chromatography to obtain the title compound (0.19 g, 82%).

$^1$H-NMR (CDCl$_3$) δ 6.99 (2H, m), 4.12 (2H, q), 2.48 (2H, t), 1.77 (1H, m), 1.67 (1H, m), 1.53 (1H, m), 1.32 (1H, m), 1.26 (3H, t), 1.12 (1H, m), 0.80 (1H, m).

Preparation Example 175: 3-{2-[2,6-difluoro-4-(4,4,5,5-tetramethyl-[1,3,2]dioxaborolan-2-yl)-phenyl]-cyclopropyl}-propionic acid ethyl ester 3-[2-(4-Bromo-2,6-difluoro-phenyl)-cyclopropyl]-propionic acid ethyl ester (0.190 g, 0.57 mmol) obtained in Preparation Example 174 was reacted in the same manner as in Step D of Preparation Example 1 to obtain the title compound (0.183 g, 84%).

$^1$H-NMR (CDCl$_3$) δ 7.18 (2H, m), 4.14 (2H, q), 2.49 (2H, t), 1.77 (1H, m), 1.68 (2H, m), 1.38 (1H, m), 1.32 (12H, s), 1.24 (4H, m), 0.81 (1H, m).

Preparation Example 176: 8-(4-bromo-2-fluoro-phenyl)-1,4-dioxa-spiro[4.5]dec-7-ene 4-Bromo-2-fluoro-1-iodo-benzene (0.68 g, 2.25 mmol) and 8-(4,4,5,5-tetramethyl-[1,3,2]dioxaborolan-2-yl)-1,4-dioxa-spiro[4.5]dec-7-ene (0.5 g, 1.88 mmol) were reacted in the same manner as in Step A of Example 1 to obtain the title compound (0.4 g, 68%).

$^1$H-NMR (CDCl$_3$) δ 7.20 (2H, m), 7.12 (1H, t), 5.84 (1H, m), 4.01 (4H, s), 2.58 (2H, m), 2.44 (2H, m), 1.88 (2H, t).

Preparation Example 177: 8-[2-fluoro-4-(4,4,5,5-tetramethyl-[1,3,2]dioxaborolan-2-yl)-phenyl]-1,4-dioxa-spiro[4.5]dec-7-ene 8-(4-Bromo-2-fluoro-phenyl)-1,4-dioxa-spiro[4.5]dec-7-ene (0.27 g, 0.86 mmol) obtained in Preparation Example 176 was reacted in the same manner as in Step D of Preparation Example 1 to obtain the title compound (0.2 g, 64%).

$^1$H-NMR (CDCl$_3$) δ 7.50 (1H, m), 7.43 (1H, m), 7.27 (1H, m), 5.89 (1H, m), 4.02 (4H, s), 2.64 (2H, m), 2.48 (2H, m), 1.90 (2H, t), 1.34 (12H, s).

Preparation Example 178: 8-[2-fluoro-4-(4,4,5,5-tetramethyl-[1,3,2]dioxaborolan-2-yl)-phenyl]-1,4-dioxa-spiro[4.5]decane 8-[2-Fluoro-4-(4,4,5,5-tetramethyl-[1,3,2]dioxaborolan-2-yl)-phenyl]-1,4-dioxa-spiro[4.5]dec-7-ene (0.2 g, 0.55 mmol) obtained in Preparation Example 177 was reacted in the same manner as in Step E of Preparation Example 1 to obtain the title compound (0.17 g, 84%).

$^1$H-NMR (CDCl$_3$) δ 7.52 (1H, m), 7.43 (1H, m), 7.28 (1H, m), 3.98 (4H, s), 2.94 (1H, m), 1.87-1.68 (8H, m), 1.33 (12H, s).

Preparation Example 179: 2-cyclopentyloxy-3-[4-(1,4-dioxa-spiro[4.5]dec-8-yl)-3-fluoro-phenyl]-pyridine 8-[2-Fluoro-4-(4,4,5,5-tetramethyl-[1,3,2]dioxaborolan-2-yl)-phenyl]-1,4-dioxa-spiro[4.5]decane (0.17 g, 0.47 mmol) obtained in Preparation Example 178 and 2-cyclopentyloxy-3-iodo-pyridine (0.2 g, 0.7 mmol) obtained in Preparation Example 11 were reacted in the same manner as in Step A of Example 1 to obtain the title compound (0.113 g, 60%).

$^1$H-NMR (CDCl$_3$) δ 8.12 (1H, m), 7.58 (1H, m), 7.28 (3H, m), 6.90 (1H, m), 3.99 (4H, s), 2.94 (1H, m), 1.89-1.72 (14H, m), 1.54 (2H, m).

Preparation Example 180: 4-[4-(2-cyclopentyloxy-pyridin-3-yl)-2-fluoro-phenyl]-cyclohexanone 2-Cyclopentyloxy-3-[4-(1,4-dioxa-spiro[4.5]dec-8-yl)-3-fluoro-phenyl]-pyridine (0.113 g, 0.28 mmol) obtained in Preparation Example 179 was added to 1N HCl (0.15 mL) dissolved in 3 mL of THF and stirred at room temperature for 16 hours. The reaction solution was diluted with sodium bicarbonate solution and extracted with EtOAc. The organic layer was separated, dried with MgSO$_4$ and purified by column chromatography to obtain the title compound (0.048 g, 48%).

¹H-NMR (CDCl₃) δ 8.14 (1H, m), 7.58 (1H, m), 7.30 (2H, m), 7.25 (1H, m), 6.92 (1H, m), 5.51 (1H, m), 3.37 (1H, m), 2.53 (4H, m), 2.25 (2H, m), 1.97 (4H, m), 1.75 (4H, m), 1.62 (2H, m).

Preparation Example 181: {4-[4-(2-cyclopentyloxy-pyridin-3-yl)-2-fluoro-phenyl]-cyclohexylidene}-acetic acid ethyl ester 4-[4-(2-Cyclopentyloxy-pyridin-3-yl)-2-fluoro-phenyl]-cyclohexanone (0.045 g, 0.13 mmol) obtained in Preparation Example 180 was reacted in the same manner as in Step C of Preparation Example 1 to obtain the title compound (0.045 g, 83%).
¹H-NMR (CDCl₃) δ 8.13 (1H, m), 7.59 (1H, m), 7.29 (2H, m), 7.20 (1H, m), 6.91 (1H, m), 5.70 (1H, s), 5.52 (1H, m), 4.16 (2H, q), 4.00 (1H, m), 3.17 (1H, m), 2.42 (2H, m), 2.10 (3H, m), 1.95 (2H, m), 1.84-1.62 (8H, m), 1.30 (3H, t).

Preparation Example 182: {4-[4-(2-cyclopentyloxy-pyridin-3-yl)-2-fluoro-phenyl]-cyclohexyl}-acetic acid ethyl ester {4-[4-(2-Cyclopentyloxy-pyridin-3-yl)-2-fluoro-phenyl]-cyclohexylidene}-acetic acid ethyl ester (0.045 g, 0.11 mmol) obtained in Preparation Example 181 was reacted in the same manner as in Step E of Preparation Example 1 to obtain the title compound (0.045 g, 99%).
¹H-NMR (CDCl₃) δ 8.13 (1H, m), 7.60 (1H, m), 7.27 (3H, m), 6.91 (1H, m), 5.51 (1H, m), 4.15 (2H, q), 2.85 (1H, m), 2.49-2.25 (2H, m), 1.95-1.59 (16H, m), 1.26 (3H, t), 1.22 (1H, m).

Preparation Example 183: 4-{[2,6-difluoro-4-(4,4,5,5-tetramethyl-[1,3,2]dioxaborolan-2-yl)-phenyl]-methyl-amino}-butyric acid methyl ester 3,4,5-Trifluoronitrobenzene (9.4 g, 53 mmol) and hydrochloric acid salt of 4-methylamino-butyric acid methyl ester (8.9 g, 53 mmol) were reacted in the same manner as in Preparation Example 84 to obtain the title compound (10 g, 51%).
¹H-NMR (CDCl₃) δ 7.24 (2H, d), 3.64 (3H, s), 3.16 (2H, t), 2.88 (3H, m), 2.36 (2H, t), 1.85 (2H, m), 1.31 (12H, s)

Preparation Example 184: 4-[5-(4,4,5,5-tetramethyl-[1,3,2]dioxaborolan-2-yl)-indol-1-yl]-butyric acid ethyl ester 5-Bromo-1H-indole (0.10 g, 0.51 mmol) and 4-bromobutyric acid ethyl ester (0.10 g, 0.51 mmol) were reacted in the same manner as in Preparation Example 3 to obtain the title compound (0.060 g, 33%).
¹H-NMR (CDCl₃) δ 8.15 (1H, s), 7.65 (1H, d), 7.34 (1H, d), 7.07 (1H, d), 6.51 (1H, d), 4.21 (2H, t), 4.11 (2H, m), 2.25 (2H, t), 2.14 (2H, m), 1.36 (12H, s), 1.24 (3H, t)

Preparation Example 185: 2-bromo-6-cyclopentyloxy-pyridine

Cyclopentanol (0.077 mL, 0.84 mmol) and 2,6-dibromopyridine (0.2 g, 0.84 mmol) were reacted in the same manner as in Preparation Example 34 to obtain the title compound (0.09 g, 44%).
¹H-NMR (CDCl₃) δ 7.36 (1H, t), 7.00 (1H, d), 6.60 (1H, d), 5.36 (1H, m), 1.98 (2H, m), 1.77 (4H, m), 1.61 (2H, m)

Preparation Example 186: 2-bromo-6-cyclobutoxy-pyridine

Cyclobutanol (0.06 mL, 0.84 mmol) and 2,6-dibromopyridine (0.2 g, 0.84 mmol) were reacted in the same manner as in Preparation Example 34 to obtain the title compound (0.06 g, 31%).
¹H-NMR (CDCl₃) δ 7.39 (1H, t), 7.01 (1H, d), 6.61 (1H, d), 5.14 (1H, m), 2.45 (2H, m), 2.11 (2H, m), 1.82 (1H, m), 1.65 (1H, m)

Preparation Example 187: 4-{[2-fluoro-4-(4,4,5,5-tetramethyl-[1,3,2]dioxaborolan-2-yl)-phenyl]-methyl-amino}-butyric acid methyl ester 3,4-Difluoronitrobenzene (1.30 g, 8.17 mmol) and hydrochloric acid salt of 4-methylamino-butyric acid methyl ester (1.64 g, 9.81 mmol) were reacted in the same manner as in Preparation Example 84 to obtain the title compound (0.25 g, 8.7%).
¹H-NMR (CDCl₃) δ 7.45 (1H, m), 7.40 (1H, m), 6.83 (1H, m), 3.65 (3H, s), 3.25 (2H, t), 2.86 (3H, s), 2.36 (2H, t), 1.91 (2H, m), 1.31 (12H, s)

Preparation Example 188: 4-(2-cyclopentylsulfanyl-pyridin-3-yl)-2,6-difluoro-phenylamine 2-Cyclopentylsulfanyl-3-iodo-pyridine (0.70 g, 2.29 mmol) obtained in Preparation Example 15 and 2,6-difluoro-4-(4,4,5,5-tetramethyl-1,3,2-dioxaborolan-2-yl)aniline (0.59 g, 2.29 mmol) obtained in Preparation Example 66 were reacted in the same manner as in Preparation Example 67 to obtain the title compound (0.40 g, 57%).
¹H-NMR (CDCl₃) δ 8.40 (1H, m), 7.31 (1H, m), 6.99 (1H, m), 6.93 (2H, m), 4.07 (1H, m), 3.82 (2H, s), 2.19 (2H, m), 1.71 (2H, m), 1.61 (4H, m)

Preparation Example 189: 4-(2-cyclopentylsulfanyl-pyridin-3-yl)-phenylamine

2-Cyclopentylsulfanyl-3-iodo-pyridine (1.2 g, 3.9 mmol) obtained in Preparation Example 15 and 4-(4,4,5,5-tetramethyl-1,3,2-dioxaborolan-2-yl)aniline (0.86 g, 3.9 mmol) were reacted in the same manner as in Preparation Example 67 to obtain the title compound (1.0 g, 94%).
¹H-NMR (CDCl₃) δ 8.37 (1H, m), 7.33 (1H, m), 7.23 (2H, d), 7.00 (1H, m), 6.74 (2H, d), 4.08 (1H, m), 3.76 (2H, s), 2.19 (2H, m), 1.70 (2H, m), 1.59 (4H, m)

Preparation Example 190: 4-{[2,6-difluoro-4-(2-fluoro-pyridin-3-yl)-phenyl]-methyl-amino}-butyric acid methyl ester 2-Fluoro-3-iodo-pyridine (0.20 g, 0.90 mmol) and 4-{[2,6-difluoro-4-(4,4,5,5-tetramethyl-[1,3,2]dioxaborolan-2-yl)-phenyl]-methyl-amino}-butyric acid methyl ester (0.33 g, 0.90 mmol) obtained in Preparation Example 183 were reacted in the same manner as in Step A of Example 1 to obtain the title compound (0.25 g, 82%).
¹H-NMR (CDCl₃) δ 8.20 (1H, m), 7.82 (1H, m), 7.28 (1H, m), 7.09 (2H, m), 3.66 (3H, s), 3.18 (2H, t), 2.90 (3H, s), 2.40 (2H, t), 1.88 (2H, m), 1.59 (4H, m)

Preparation Example 191: 1-(2-iodo-phenyl)-pyrrolidine

Step A: 2-pyrrolidin-1-yl-phenylamine

Fluoro-2-nitro-benzene (0.70 g, 4.96 mmol) and pyrrolidine (0.42 g, 5.95 mmol) were sequentially reacted in the same manner as in Steps A and B of Preparation Example 84 to obtain the title compound (0.70 g, 87%).

Step B: 1-(2-iodo-phenyl)-pyrrolidine

2-Pyrrolidin-1-yl-phenylamine (0.70 g, 4.31 mmol) obtained in Step A 에 was added to 19 mL of water and cooled to 0° C. 5 mL of sulfuric acid 5 mL was added, and sodium nitrite (0.30 g, 4.31 mmol) dissolved in water was then slowly added thereto. While maintaining the temperature, the mixture was stirred for 30 minutes. Potassium iodide (0.93 g, 5.60 mmol) dissolved in 10 mL of water was added thereto. The temperature was increased to 60° C., and the mixture was stirred for 3 hours. After addition of water, the reaction solution was extracted with EtOAc. The organic layer was purified by column chromatography to obtain the title compound (0.18 g, 12%).
$^1$H-NMR (CDCl$_3$) δ 7.83 (1H, m), 7.25 (1H, m), 6.95 (1H, m), 6.67 (1H, m), 3.29 (4H, m), 1.94 (4H, m)

Preparation Example 192: (2-iodo-phenyl)-methyl-amine

Fluoro-2-nitro-benzene (1.00 g, 7.09 mmol) and methylamine hydrochloride (0.57 g, 8.50 mmol) were reacted in the same manner as in Preparation Example 191 to obtain the title compound (0.35 g, 21%).
$^1$H-NMR (CDCl$_3$) δ 7.65 (1H, m), 7.25 (1H, m), 6.57 (1H, m), 6.46 (1H, m), 4.20 (1H, s), 2.89 (3H, d)

Preparation Example 193: (2-iodo-phenyl)-isopropyl-methyl-amine

Fluoro-2-nitro-benzene (1.30 g, 9.21 mmol) and isopropyl-methyl-amine (0.81 g, 11.1 mmol) were reacted in the same manner as in Preparation Example 191 to obtain the title compound (0.35 g, 14%).
$^1$H-NMR (CDCl$_3$) δ 7.85 (1H, m), 7.28 (1H, m), 7.06 (1H, m), 6.77 (1H, m), 3.48 (1H, m), 2.62 (3H, s), 1.12 (6H, d)

Preparation Example 194: 4-{[2,6-difluoro-4-(4,4,5,5-tetramethyl-[1,3,2]dioxaborolan-2-yl)-phenyl]-ethyl-amino}-butyric acid methyl ester 3,4,5-Trifluoronitrobenzene (0.68 g, 3.84 mmol) and hydrochloric acid salt of 4-ethylamino-butyric acid methyl ester (0.58 g, 3.20 mmol) were reacted in the same manner as in Preparation Example 84 to obtain the title compound (0.38 g, 31%).
$^1$H-NMR (CDCl$_3$) δ 7.25 (2H, m), 3.63 (3H, s), 3.18 (4H, m), 2.35 (2H, t), 1.74 (2H, m), 1.32 (12H, s), 1.02 (3H, t)

Preparation Example 195: (R)-5-[2,6-difluoro-4-(4,4,5,5-tetramethyl-[1,3,2]dioxaborolan-2-yl)-phenyl]-hexanoic acid ethyl ester Step A: (E)-3-(4-bromo-2,6-difluoro-phenyl)prop-2-enoic acid ethyl ester 4-Bromo-2,6-difluoro-benzaldehyde (2.0 g, 13.6 mmol) and (1-ethoxycarbonylethylidene)triphenylphosphorane (5.7 g, 16.3 mmol) were reacted in the same manner as in Step B of Preparation Example 27 to obtain the title compound (3.9 g, 99%).

Step B: (E)-3-(4-bromo-2,6-difluoro-phenyl)-acrylic acid (E)-3-(4-bromo-2,6-difluoro-phenyl)prop-2-enoic acid ethyl ester (1.13 g, 3.88 mmol) obtained in Step A was reacted in the same manner as in Step B of Example 1 to obtain the title compound (1.0 g, 98%).

Step C: (R)-3-[(E)-3-(4-bromo-2,6-difluoro-phenyl)-acryloyl]-4-phenyl-oxazolidin-2-one (E)-3-(4-bromo-2,6-difluoro-phenyl)-acrylic acid (0.50 g, 1.9 mmol) obtained in Step B was dissolved in 10 mL of THF and cooled to −78° C. Trimethylacetyl chloride (0.29 g, 2.4 mmol) was added thereto, and the mixture was stirred for 15 minutes. (R)-4-phenyl-oxazolidin-2-one (0.42 g, 2.6 mmol) was dissolved in 10 mL of THF and cooled to −78° C., and n-butyllithium (1.16 mL, 2.7 mmol) was then added thereto. This solution was added to the first solution by the use of a cannula. While maintaining the temperature, the mixture was stirred for 1.5 hours. The temperature was increased to room temperature, and the mixture was stirred for 16 hours. After termination of the reaction by the use of saturated ammonium chloride solution, the reaction solution was extracted with EtOAc. The organic layer was separated, dried with MgSO$_4$ and purified by column chromatography to obtain the title compound (0.50 g, 64%).

Step D: (R)-3-[(R)-3-(4-bromo-2,6-difluoro-phenyl)-butyryl]-4-phenyl-oxazolidin-2-one CuBr-DMS (1.18 g, 5.7 mmol) was added to 10 mL of THF and stirred at −40 OC for 30 minutes. DMS (3.38 g, 54.4 mmol) and methylmagnesium bromide (1.74 mL, 5.2 mmol) was added thereto, and the mixture was stirred for 30 minutes. The temperature was increased to −20° C., and (R)-3-[(E)-3-(4-bromo-2,6-difluoro-phenyl)-acryloyl]-4-phenyl-oxazolidin-2-one (0.52 g, 1.3 mmol) obtained in Step C was dissolved in 3 mL of THF and slowly added thereto. While maintaining the temperature, the mixture was stirred for 2.5 hours. The temperature was slowly increased to room temperature, and the mixture was stirred at room temperature for 72 hours. After termination of the reaction by the use of saturated ammonium chloride solution, the reaction solution was extracted with EtOAc. The organic layer was separated, dried with MgSO$_4$ and purified by column chromatography to obtain the title compound (0.33 g, 61%).

Step E: (E)-(R)-5-(4-bromo-2,6-difluoro-phenyl)-hex-2-enoic acid ethyl ester (R)-3-[(R)-3-(4-bromo-2,6-difluoro-phenyl)-butyryl]-4-phenyl-oxazolidin-2-one (0.33 g, 0.78 mmol) obtained in Step D was sequentially reacted in the same manner as in Preparation Example 151 and Step A of Preparation Example 85 to obtain the title compound (0.11 g, 42%).

Step F: (R)-5-[2,6-difluoro-4-(4,4,5,5-tetramethyl-[1,3,2]dioxaborolan-2-yl)-phenyl]-hexanoic acid ethyl ester (E)-(R)-5-(4-bromo-2,6-difluoro-phenyl)-hex-2-enoic acid ethyl ester (0.15 g, 0.45 mmol) obtained in Step E was sequentially reacted in the same manner as in Steps G and H of Preparation Example 5 to obtain the title compound (0.070 g, 40%).
NMR: $^1$H-NMR (CDCl$_3$) δ 7.22 (2H, m), 4.08 (2H, q), 3.21 (1H, m), 2.24 (2H, m), 1.80 (1H, m), 1.65 (1H, m), 1.60 (1H, m), 1.45 (1H, m), 1.30 (15H, m), 1.20 (3H, t)

Preparation Example 196: (E)-(R)-5-[2,6-difluoro-4-(4,4,5,5-tetramethyl-[1,3,2]dioxaborolan-2-yl)-phenyl]-hex-2-enoic acid ethyl ester (E)-(R)-5-(4-bromo-2,6-difluoro-phenyl)-hex-2-enoic acid ethyl ester (0.11 g, 0.33 mmol) obtained in Step E of Preparation Example 195 was reacted in the same manner as in Step D of Preparation Example 1 to obtain the title compound (0.10 g, 80%).

¹H-NMR (CDCl₃) δ 7.24 (2H, m), 6.84 (1H, m), 5.80 (1H, m), 4.15 (2H, m), 3.40 (1H, m), 2.66 (2H, m), 1.30 (18H, m)

Preparation Example 197: (S)-5-[2,6-difluoro-4-(4,4,5,5-tetramethyl-[1,3,2]dioxaborolan-2-yl)-phenyl]-hexanoic acid ethyl ester

Step A: (S)-3-[(E)-3-(4-bromo-2,6-difluoro-phenyl)-acryloyl]-4-phenyl-oxazolidin-2-one (E)-3-(4-bromo-2,6-difluoro-phenyl)-acrylic acid (1.03 g, 3.9 mmol) obtained in Step B of Preparation Example 195 and (S)-4-phenyl-oxazolidin-2-one (0.86 g, 5.3 mmol) were reacted in the same manner as in Step C of Preparation Example 195 to obtain the title compound (1.30 g, 81%).

Step B: (S)-3-[(S)-3-(4-bromo-2,6-difluoro-phenyl)-butyryl]-4-phenyl-oxazolidin-2-one (S)-3-[(E)-3-(4-bromo-2,6-difluoro-phenyl)-acryloyl]-4-phenyl-oxazolidin-2-one (1.30 g, 3.2 mmol) obtained in Step A of Preparation Example 197 was reacted in the same manner as in Step D of Preparation Example 195 to obtain the title compound (1.0 g, 74%).

Step C: (E)-(S)-5-(4-bromo-2,6-difluoro-phenyl)-hex-2-enoic acid ethyl ester (S)-3-[(S)-3-(4-bromo-2,6-difluoro-phenyl)-butyryl]-4-phenyl-oxazolidin-2-one (0.70 g, 1.6 mmol) obtained in Step B Preparation Example 197 was reacted in the same manner as in Step E of Preparation Example 195 to obtain the title compound (0.50 g, 91%).

Step D: (S)-5-[2,6-difluoro-4-(4,4,5,5-tetramethyl-[1,3,2]dioxaborolan-2-yl)-phenyl]-hexanoic acid ethyl ester ((E)-(S)-5-(4-bromo-2,6-difluoro-phenyl)-hex-2-enoic acid ethyl ester (0.37 g, 1.12 mmol) obtained in Step C of Preparation Example 197 was reacted in the same manner as in Step F of Preparation Example 195 to obtain the title compound (0.16 g, 37%)

NMR: ¹H-NMR (CDCl₃) δ 7.22 (2H, m), 4.08 (2H, q), 3.21 (1H, m), 2.24 (2H, m), 1.80 (1H, m), 1.65 (1H, m), 1.60 (1H, m), 1.45 (1H, m), 1.30 (15H, m), 1.20 (3H, t)

Preparation Example 198: 4-[2-fluoro-4-(4,4,5,5-tetramethyl-1,3,2-dioxaborolan-2-yl)phenoxy]butyric acid ethyl ester

Step A: 2-fluoro-4-(4,4,5,5-tetramethyl-1,3,2-dioxaborolan-2-yl)phenol

4-Bromo-2-fluorophenol (1.9 g, 9.9 mmol), bis(pinacolato)diboron (2.9 g, 11.4 mmol), potassium acetate (3.90 g, 39.7 mmol) and DPPF (0.27 g, 0.49 mmol) were dissolved in 32 mL of 1,4-dioxane, and charged with N₂ gas for 5 minutes. PdCl₂(dppf)-DCM (0.4 g, 0.49 mmol) was added thereto, and the mixture was stirred for 4 hours under reflux stirred. The reaction solution was filtered through Celite and purified by column chromatography to obtain the title compound (2.2 g, 93%).

¹H NMR (CDCl₃) δ 7.49 (2H, m), 6.98 (1H, t), 5.31 (1H, brs), 1.33 (12H, s)

Step B: 4-[2-fluoro-4-(4,4,5,5-tetramethyl-1,3,2-dioxaborolan-2-yl)phenoxy]butyric acid ethyl ester 2-Fluoro-4-(4,4,5,5-tetramethyl-1,3,2-dioxaborolan-2-yl)phenol (0.56 g, 2.3 mmol) obtained in Step A, 4-bromobutyric acid ethyl ester (0.34 mL, 2.3 mmol) and Cs₂CO₃ (0.92 g, 2.8 mmol) were dissolved in 8 mL of DMF, and stirred at room temperature for 16 hours. The reaction solution was concentrated and purified by column chromatography to obtain the title compound (0.52 g, 63%).

¹H NMR (CDCl₃) δ 7.49 (2H, m), 6.93 (1H, t), 4.15 (2H, t), 4.10 (2H, q), 2.53 (2H, t), 2.15 (2H, m), 1.33 (12H, s), 1.25 (3H, t)

Preparation Example 199: 6-[2,6-difluoro-4-(4,4,5,5-tetramethyl-[1,3,2]dioxaborolan-2-yl)-phenyl]-heptanoic acid ethyl ester 1-(4-Bromo-2,6-difluoro-phenyl)ethaneone (2.50 g, 10.6 mmol) obtained in Step C of Preparation Example 32 and (methoxymethyl)triphenylphosphonium chloride (4.38 g, 12.8 mmol) were sequentially reacted in the same manner as in Preparation Example 152, Step A of Preparation Example 85, Step B of Preparation Example 70, Step C of Preparation Example 4, Step C of Preparation Example 26 and Step D of Preparation Example 26 to obtain the title compound (0.50 g, 13%).

¹H-NMR (CDCl₃) δ 7.23 (2H, m), 4.09 (2H, m), 3.22 (1H, m), 2.22 (2H, t), 1.77 (1H, m), 1.61 (5H, m), 1.33 (18H, s)

Preparation Example 200: 4-[3-(4,4,5,5-tetramethyl-[1,3,2]dioxaborolan-2-yl)-phenoxy]-butyric acid ethyl ester 3-Bromo-phenol (0.75 g, 4.34 mmol) and 4-bromo-butyric acid ethyl ester (1.01 g, 5.20 mmol) were reacted in the same manner as in Preparation Example 3 to obtain the title compound (1.1 g, 76%).

¹H-NMR (CDCl₃) δ 7.37 (1H, d), 7.31 (2H, m), 6.99 (1H, m), 4.14 (2H, m), 4.03 (2H, t), 2.52 (2H, t), 2.11 (2H, m), 1.33 (12H, s), 1.27 (3H, t)

Preparation Example 201: 5-[2-fluoro-4-(4,4,5,5-tetramethyl-[1,3,2]dioxaborolan-2-yl)-phenyl]-pentanoic acid ethyl ester 4-Bromo-2-fluoro-benzaldehyde (0.40 g, 1.97 mmol) and ethyl(triphenylphosphoranylidene)acetaldehyde (0.66 g, 2.17 mmol) were reacted in the same manner as in Preparation Example 27 to obtain the title compound (0.35 g, 51%).

¹H-NMR (CDCl₃) δ 7.48 (1H, d), 7.42 (1H, d), 7.17 (1H, t), 4.12 (2H, m), 2.68 (2H, t), 2.33 (2H, t), 1.67 (4H, m), 1.34 (12H, s), 1.25 (3H, t)

Preparation Example 202: 4-[4-(4,4,5,5-tetramethyl-[1,3,2]dioxaborolan-2-yl)-phenylsulfanyl]-butyric acid ethyl ester 4-(4-Bromo-phenylsulfanyl)-butyric acid ethyl ester (0.83 g, 2.7 mmol) obtained in Preparation Example 164 and bis(pinacolato)diboron (0.76 g, 3.0 mmol) were reacted in the same manner as in Step D of Preparation Example 1 to obtain the title compound (0.73 g, 75%).
$^1$H-NMR (CDCl$_3$) δ 7.70 (2H, d), 7.27 (2H, d), 4.11 (2H, q), 2.99 (2H, t), 2.44 (2H, t), 1.96 (2H, m), 1.32 (12H, s), 1.24 (3H, t).

Preparation Example 203: 4-bromo-2-fluoro-benzenethiol

Step A: 4-bromo-2-fluoro-benzenesulfonyl chloride

4-Bromo-2-fluoroaniline (1 g, 5.26 mmol) was reacted in the same manner as in Step A of Preparation Example 206 to obtain the title compound (0.49 g, 34%).
$^1$H-NMR (CDCl$_3$) δ 7.85 (1H, m), 7.55 (2H, m).

Step B: 4-bromo-2-fluoro-benzenethiol

4-Bromo-2-fluoro-benzenesulfonyl chloride (0.49 g, 1.79 mmol) obtained in Step A was reacted in the same manner as in Step B of Preparation Example 206 to obtain the title compound (0.37 g, 99%).
$^1$H-NMR (CDCl$_3$) δ 7.23 (1H, m), 7.16 (2H, m), 3.57 (1H, s).

Preparation Example 204: 4-(4-bromo-2-fluoro-phenylsulfanyl)-butyric acid ethyl ester 4-Bromo-2-fluoro-benzenethiol (0.37 g, 1.81 mmol) obtained in Preparation Example 203, NaH (60% in mineral oil, 0.07 g, 1.81 mmol) and 4-bromo-butyric acid ethyl ester (0.28 mL, 1.99 mmol) were reacted in the same manner as in Preparation Example 164 to obtain the title compound (0.43 g, 75%).
$^1$H-NMR (CDCl$_3$) δ 7.23 (3H, m), 4.12 (2H, q), 2.92 (2H, t), 2.44 (2H, t), 1.90 (2H, m), 1.25 (3H, t).

Preparation Example 205: 4-[2-fluoro-4-(4,4,5,5-tetramethyl-[1,3,2]dioxaborolan-2-yl)-phenylsulfanyl]-butyric acid ethyl ester 4-(4-Bromo-2-fluoro-phenylsulfanyl)-butyric acid ethyl ester (0.43 g, 1.36 mmol) obtained in Preparation Example 204 and bis(pinacolato)diboron (0.34 g, 1.50 mmol) were reacted in the same manner as in Step D of Preparation Example 1 to obtain the title compound (0.27 g, 53%).
1H-NMR (CDCl$_3$) δ 7.50 (1H, d), 7.43 (1H, d), 7.32 (1H, t), 4.11 (2H, q), 2.98 (2H, t), 2.45 (2H, t), 1.93 (2H, m), 1.33 (12H, s), 1.24 (3H, t).

Preparation Example 206: 4-bromo-2,6-difluoro-benzenethiol

Step A: 4-bromo-2,6-difluoro-benzenesulfonyl chloride

CuCl$_2$ (0.77 g, 5.77 mmol) was dissolved in 200 mL of water. SOCl$_2$ (29 mL, 0.40 mol) was added thereto at 0° C., and the mixture was stirred at room temperature for 18 hours. 4-Bromo-2,6-difluoroaniline (20 g, 0.096 mol) was dissolved in 240 mL of HCl and 900 mL of water, and the solution in which NaNO$_2$ (7 g, 0.10 mol) was dissolved in 200 mL of water was added thereto at 0° C. The above thionyl chloride solution was added thereto, and the reaction was carried out at room temperature for 1 hour to obtain the title compound (24 g, 85%) in a solid form.

Step B: 4-bromo-2,6-difluoro-benzenethiol

4-Bromo-2,6-difluoro-benzenesulfonyl chloride (24 g, 0.08 mol) obtained in Step A was dissolved in 270 mL of THE PPh$_3$ (75 g, 0.28 mol) was added thereto, and the mixture was stirred at room temperature for 15 minutes. After addition of water, the mixture was stirred at room temperature for 18 hours. After addition of water, the reaction solution was extracted with EtOAc. The organic layer was separated, dried with MgSO$_4$ and purified by column chromatography to obtain the title compound (15 g, 83%).
$^1$H-NMR (CDCl$_3$) δ 7.10 (2H, d), 3.58 (1H, s).

Preparation Example 207: 4-(4-bromo-2,6-difluoro-phenylsulfanyl)-butyric acid ethyl ester 4-Bromo-2,6-difluoro-benzenethiol (15 g, 0.066 mol) obtained in Preparation Example 206, NaH (60% in mineral oil, 2.6 g, 0.066 mol) and 4-bromo-butyric acid ethyl ester (10 mL, 0.073 mol) were reacted in the same manner as in Preparation Example 164 to obtain the title compound (18.56 g, 82%).
$^1$H-NMR (CDCl$_3$) δ 7.11 (2H, d), 4.11 (2H, q), 2.90 (2H, t), 2.43 (2H, t), 1.82 (2H, m), 1.24 (3H, t).

Preparation Example 208: 4-[2,6-difluoro-4-(4,4,5,5-tetramethyl-[1,3,2]dioxaborolan-2-yl)-phenylsulfanyl]-butyric acid ethyl ester 4-(4-Bromo-2,6-difluoro-phenylsulfanyl)-butyric acid ethyl ester (11.6 g, 0.034 mol) obtained in Preparation Example 207 and bis(pinacolato)diboron (9.5 g, 0.038 mol) were reacted in the same manner as in Step D of Preparation Example 1 to obtain the title compound (10.6 g, 80%).
$^1$H-NMR (CDCl$_3$) δ 7.30 (2H, d), 4.09 (2H, q), 2.94 (2H, t), 2.43 (2H, t), 1.83 (2H, m), 1.33 (12H, s), 1.22 (3H, t).

Preparation Example 209: 3-iodo-2-(oxetan-3-yloxy)-pyridine

Oxetan-3-ol (0.93 g, 12.6 mmol) and 2-fluoro-3-iodo-pyridine (1.40 g, 6.30 mmol) were reacted in the same manner as in Preparation Example 34 to obtain the title compound (1.60 g, 92%).
$^1$H-NMR (CDCl$_3$) δ 8.05 (2H, m), 6.67 (1H, m), 5.61 (1H, m), 5.01 (2H, t), 4.79 (2H, m)

Preparation Example 210: 7-bromo-5-chloro-2,2-dimethyl-2,3-dihydro-benzofuran The title compound was obtained by the method disclosed in WO 2009/119088 A1.
$^1$H NMR (CDCl$_3$) δ 7.25 (2H, s), 7.02 (1H, m), 3.06 (2H, s), 1.50 (6H, s)

Preparation Example 211: 4-bromo-7-methoxy-2,2-dimethyl-2,3-dihydro-benzofuran The title compound was obtained by the method disclosed in WO 2005/075456 A1.

¹H NMR (CDCl₃) δ 6.94 (1H, d), 6.67 (1H, d), 3.88 (3H, s), 3.08 (2H, s), 1.57 (6H, s)

Preparation Example 212: 7-bromospiro[3H-benzofuran-2,1'-cyclopentan]

The title compound was obtained by the method disclosed in WO 2011/159297 A1.
¹H NMR (CDCl₃) δ 7.23 (1H, d), 7.04 (1H, d), 6.67 (1H, t), 3.23 (2H, s), 2.14 (2H, m), 1.93 (2H, m), 1.72 (4H, m)

Preparation Example 213: 5-fluoro-7-iodo-2,2-dimethyl-2,3-dihydro-indol-1-carboxylic acid methyl ester Step A: 5-fluoro-2,2-dimethyl-2,3-dihydro-indol-1-carboxylic acid methyl ester The title compound was obtained by the method disclosed in US 2013/0109734 A1.
¹H-NMR (CDCl₃) δ 7.71 (1H, brs), 6.83 (2H, m), 3.84 (3H, s), 2.99 (2H, s), 1.55 (6H, s)

Step B: 5-fluoro-7-iodo-2,2-dimethyl-2,3-dihydro-indol-1-carboxylic acid methyl ester 5-fluoro-2,2-dimethyl-2,3-dihydro-indol-1-carboxylic acid methyl ester (0.1 g, 0.45 mmol) obtained in Step A was dissolved in 3 mL of THF and cooled to −78° C. 1.7M tert-butyllithium pentane solution (0.7 mL, 1.16 mmol) was added dropwise thereto, and the mixture was stirred at −78° C. for 1 hour. 1,2-Diiodo-ethane (0.38 g, 1.35 mmol) was dissolved in 1 mL of THF and slowly added dropwise thereto, and the mixture was stirred at −78° C. for 30 minutes. The temperature was increased to room temperature, and the mixture was additionally stirred for 1 hour. After termination of the reaction by the addition of sodium thiosulfate aqueous solution and sodium bicarbonate aqueous solution, the reaction solution was extracted with ethyl acetate to separate an organic layer. The organic layer was dried with MgSO₄ and purified by column chromatography to obtain the title compound (0.074 g, 47%).
¹H-NMR (CDCl₃) δ 7.78 (1H, brs), 6.89 (1H, t), 3.88 (3H, s), 3.00 (2H, s), 1.61 (6H, s)

Preparation Example 214: 5-fluoro-4-iodo-2,2-dimethyl-2,3-dihydro-indol-1-carboxylic acid methyl ester 5-Fluoro-2,2-dimethyl-2,3-dihydro-indol-1-carboxylic acid methyl ester (0.26 g, 1.16 mmol) obtained in Step A of Preparation Example 213 was dissolved in 10 mL of THF. TMEDA (0.8 mL, 5.22 mmol) was added dropwise thereto and cooled to −78° C. 1.4M sec-BuLi hexane solution (2.5 mL, 3.49 mmol) was added dropwise thereto, and the mixture was stirred at −78° C. for 1 hour. 1,2-Diiodo-ethane (0.38 g, 1.35 mmol) was dissolved in 5 mL of THF and slowly added dropwise thereto. The mixture was stirred at −78° C. for 30 minutes. The temperature was increased to room temperature, and the mixture was additionally stirred for 1.5 hours. After termination of the reaction by the addition of sodium thiosulfate aqueous solution and sodium bicarbonate aqueous solution, the reaction solution was extracted with ethyl acetate to separate an organic layer. The organic layer was dried with MgSO₄ and purified by column chromatography to obtain the title compound (0.170 g, 42%).

¹H-NMR (CDCl₃) δ 7.35 (1H, dd), 6.86 (1H, dd), 3.81 (3H, s), 2.96 (2H, s), 1.48 (6H, s)

Preparation Example 215: 4-iodospiro[1,3-benzodioxol-2,1'-cyclopentan]

Step A: 1-iodo-2,3-dimethoxy-benzene 1,2-Dimethoxybenzene (500 mg, 3.62 mmol) was dissolved in THF (5 mL) and cooled to 0-5° C. n-BuLi (2.5 M in Hexane, 1.6 mL, 3.98 mmol) was slowly added dropwise thereto, and the mixture was stirred at 0-5° C. for 2 hours and cooled to −78° C. I₂ (1.01 g, 3.98 mmol)/THF (5 mL) solution was slowly added thereto, and the mixture was stirred at room temperature for 2 hours and concentrated under reduced pressure. The concentrated solution was diluted with saturated NaHCO₃ solution, extracted with DCM and separated. The extract solution was concentrated under reduced pressure and purified by column chromatography (eluent, EtOAc/Hex=1/10) to obtain the title compound (620 mg, 65% yield).
¹H NMR (500 MHz, CDCl₃) δ 7.36-7.32 (m, 1H), 6.90-6.86 (m, 1H), 6.79 (dd, 1H), 3.85 (s, 3H), 3.83 (s, 3H)

Step B: 3-iodo-benzene-1,2-diol

1-Iodo-2,3-dimethoxy-benzene (0.62 g, 2.35 mmol) obtained in Step A was dissolved in DCM (3 mL) and cooled to 0-5° C. 1M BBr₃ (7.04 mL, 7.05 mmol) was added thereto, and the mixture was stirred at room temperature for 3 hours stirred. After termination of the reaction, the reaction solution was cooled to −20° C. and diluted by slowly adding ethanol. The mixture was stirred at room temperature for 30 minutes. Saturated NaHCO₃ aqueous solution was added thereto, and the reaction solution was extracted with DCM. The organic layer was dried with anhydrous magnesiumsulfate, concentrated under reduced pressure and purified by column chromatography (eluent, EtOAc/Hex=1/4) to obtain the title compound (0.12 g, 22% yield).
¹H NMR (500 MHz, CDCl₃) δ 7.18 (d, 1H), 6.87 (d, 1H), 6.60 (dd, 1H), 5.64 (s, br, 2H)

Step C: 4-iodospiro[1,3-benzodioxol-2,1'-cyclopentane]

Toluene (5 mL) was added to 3-iodo-benzene-1,2-diol (60 mg, 0.254 mmol) obtained in Step B. Cyclopentanone (0.025 mL, 0.28 mmol) and p-TsOH.H₂O (catalytic amount) were added thereto, and the mixture was stirred at 130-140° C. for 12 hours by the use of a Dean-Stark apparatus. After termination of the reaction, the reaction solution was cooled. After addition of saturated NaHCO₃ solution, the reaction solution was extracted with EtOAc to separate an organic layer. The organic layer was concentrated under reduced pressure and purified by column chromatography (eluent, EtOAc/Hex=1/4) to obtain the title compound (25 mg, 33%).
¹H NMR (500 MHz, CDCl₃) δ 7.08 (d, 1H), 6.68 (d, 1H), 6.55 (dd, 1H), 2.20-2.06 (m, 4H), 1.90-1.79 (m, 4H)

Preparation Example 216: 2-bromo-3-iodophenol

Step A: 2-bromo-3-methoxy-phenylamine

2-Bromo-1-methoxy-3-nitrobenzene (1 g, 4.31 mmol), Fe (1.68 g, 30.17 mmol) and NH₄Cl (1.61 g, 30.17 mmol) were dissolved in THF (4 mL)/MeOH (4 mL)/H₂O (2 mL)

solution and stirred for 1 hour under reflux. After termination of the reaction, the reaction solution was cooled to room temperature, diluted with saturated NaHCO$_3$ solution and extracted with EtOAc. The extract solution was concentrated under reduced pressure and purified by column chromatography (eluent, EtOAc/Hex=1/5) to obtain the title compound (0.83 g, 95% yield).

$^1$H NMR (500 MHz, CDCl$_3$) δ 7.05 (dd, 1H), 6.42 (d, 1H), 6.31 (d, 1H), 3.86 (s, 3H)

Step B: 2-bromo-1-iodo-3-methoxybenzene

35% HCl (3 mL) and ice (3 g) were added to 2-bromo-3-methoxy-phenylamine (0.83 g, 4.11 mmol) obtained in Step A, and cooled to 0-5° C. NaNO$_2$ (0.31 g, 4.52 mmol)/H$_2$O (2 mL) solution was slowly added thereto, and the mixture was stirred at 0-5° C. for 20 minutes. Pre-prepared KI (6.82 g, 41.1 mmol)/H$_2$O (10 mL) solution was slowly added dropwise to the reaction solution, and the reaction was carried out at room temperature for 12 hours. After termination of the reaction, NaOH solution was added thereto, and the reaction solution was extracted with DCM. The organic layer was washed with saturated NaHCO$_3$ aqueous solution and water. The extracted organic layer was concentrated under reduced pressure and purified by column chromatography (eluent, EtOAc/Hex=1/10) to obtain the title compound (0.88 g, 68%).

$^1$H NMR (500 MHz, CDCl$_3$) δ 7.48 (d, 1H), 7.00 (dd, 1H), 6.85 (d, 1H), 3.87 (s, 3H)

Step C: 2-bromo-3-iodophenol

2-Bromo-1-iodo-3-methoxybenzene (0.88 g, 2.81 mmol) obtained in Step B was dissolved in DCM (4 mL) and cooled to 0-5° C. 1M BBr$_3$ (8.4 mL, 8.43 mmol) was slowly added dropwise thereto, and the mixture was stirred at 0-5° C. for 1 hour and additionally stirred at room temperature for 1 hour. After termination of the reaction, the reaction solution was cooled to −20° C. and diluted by slowly adding methanol. The mixture was stirred at room temperature for 30 minutes. After addition of saturated NaHCO$_3$ aqueous solution, the reaction solution was extracted with DCM. The organic layer was dried with anhydrous magnesiumsulfate, concentrated under reduced pressure and purified by column chromatography (eluent, EtOAc/Hex=1/5) to obtain the title compound (0.723 g, 86%).

1H NMR (500 MHz, CDCl3) δ 7.43-7.39 (m, 1H), 7.02-6.92 (m, 2H), 5.61 (s, 1H)

Preparation Example 217: 4-bromo-2,6-difluoro-benzenethiol

Step A: 4-bromo-2,6-difluoro-benzenesulfonyl chloride

CuCl$_2$ (0.77 g, 5.77 mmol) was dissolved in 200 mL of water. SOCl$_2$ (29 mL, 0.40 mol) was added thereto at 0° C., and the mixture was stirred at room temperature for 18 hours. 4-Bromo-2,6-difluoroaniline (20 g, 0.096 mol) was dissolved in 240 mL of HCl and 900 mL of water, and the solution in which NaNO$_2$ (7 g, 0.10 mol) was dissolved in 200 mL of water was added thereto at 0° C. The above thionyl chloride solution was added thereto, and the reaction was carried out at room temperature for 1 hour to obtain the title compound (24 g, 85%) in a solid form.

Step B: 4-bromo-2,6-difluoro-benzenethiol

4-Bromo-2,6-difluoro-benzenesulfonyl chloride (24 g, 0.08 mol) obtained in Step A was dissolved in 270 mL of THF. PPh$_3$ (75 g, 0.28 mol) was added thereto, and the mixture was stirred at room temperature for 15 minutes. After addition of water, the mixture was stirred at room temperature for 18 hours. After addition of water, the reaction solution was extracted with EtOAc. The organic layer was separated, dried with MgSO$_4$ and purified by column chromatography to obtain the title compound (15 g, 83%).

$^1$H-NMR (CDCl$_3$) δ 7.10 (2H, d), 3.58 (1H, s).

Preparation Example 218: 4-(4-bromo-2,6-difluoro-phenylsulfanyl)-butyric acid ethyl ester 4-Bromo-2,6-difluoro-benzenethiol (15 g, 0.066 mol) obtained in Preparation Example 217, NaH (60% in mineral oil, 2.6 g, 0.066 mol) and 4-bromo-butyric acid ethyl ester (10 mL, 0.073 mol) were reacted in the same manner as in Preparation Example 34 to obtain the title compound (18.56 g, 82%).

$^1$H-NMR (CDCl$_3$) δ 7.11 (2H, d), 4.11 (2H, q), 2.90 (2H, t), 2.43 (2H, t), 1.82 (2H, m), 1.24 (3H, t).

Preparation Example 219: 4-[2,6-difluoro-4-(4,4,5,5-tetramethyl-[1,3,2]dioxaborolan-2-yl)-phenylsulfanyl]-butyric acid ethyl ester 4-(4-Bromo-2,6-difluoro-phenylsulfanyl)-butyric acid ethyl ester (11.6 g, 0.034 mol) obtained in Preparation Example 218, bis(pinacolo)diboron (9.5 g, 0.038 mol), potassium acetate (8.4 g, 0.085 mol) and dichloro[1,1'-bis(diphenylphosphino)ferrocene]palladium(II) (2.5 g, 0.003 mol) were reacted in the same manner as in Step D of Example 1 to obtain the title compound (10.6 g, 80%).

$^1$H-NMR (CDCl$_3$) δ 7.30 (2H, d), 4.09 (2H, q), 2.94 (2H, t), 2.43 (2H, t), 1.83 (2H, m), 1.33 (12H, s), 1.22 (3H, t).

Preparation Example 220: 2-[1-[2,6-difluoro-4-(4,4,5,5-tetramethyl-1,3,2-dioxaborolan-2-yl)phenyl]-4-piperidyl]acetic acid ethyl ester Step A: 2-[1-(4-bromo-2,6-difluoro-phenyl)-4-piperidyl]acetic acid ethyl ester 2-[1-(2,6-Difluoro-4-nitro-phenyl)-4-piperidylidene]acetic acid ethyl ester (11.44 g, 35 mmol) obtained in Step B of Preparation Example 89 was dissolved in 100 mL of MeOH and 50 mL of DCM. 0.7 g of 10 wt % Pd/C was added thereto, and the mixture was stirred for 20 minutes under 40 psi of hydrogen atmosphere. Solids were filtered through Celite and concentrated under reduced pressure to obtain 2-[1-(4-amino-2,6-difluoro-phenyl)-4-piperidyl]acetic acid ethyl ester. This compound was reacted in the same manner as in Step C of Preparation Example 84 to obtain the title compound (6.53 g, 52%).

$^1$H-NMR (CDCl$_3$) δ 6.99 (2H, m), 4.14 (2H, q), 3.18 (2H, m), 3.08 (2H, m), 2.28 (2H, d), 1.93 (1H, m), 1.75 (2H, m), 1.46 (2H, m), 1.27 (3H, m)

Step B: 2-[1-[2,6-difluoro-4-(4,4,5,5-tetramethyl-1,3,2-dioxaborolan-2-yl)phenyl]-4-piperidyl]acetic acid ethyl ester 2-[1-(4-Bromo-2,6-difluoro-phenyl)-4-piperidyl]acetic acid ethyl ester (6.53 g, 18 mmol) obtained in Step A was reacted in the same manner as in Step D of Preparation Example 84 to obtain the title compound (4.68 g, 63%).

¹H-NMR (CDCl₃) δ 7.22 (2H, m), 4.14 (2H, q), 3.31 (2H, m), 3.10 (2H, m), 2.28 (2H, d), 1.96 (1H, m), 1.74 (2H, m), 1.42 (2H, m), 1.32 (12H, s), 1.26 (3H, t)

Preparation Example 221: 4-[2-chloro-6-fluoro-4-(4,4,5,5-tetramethyl-1,3,2-dioxaborolan-2-yl)phenoxy]butanoic acid ethyl ester Step A: 4-(4-bromo-2-chloro-6-fluoro-phenoxy)butanoic acid ethyl ester After addition of 15 mL of DMF, 4-bromo-2-chloro-6-fluoro-phenol (2.25 g, 10.0 mmol), K₂CO₃ (2.07 g, 15.0 mmol) and 4-bromobutanoic acid ethyl ester (1.95 g, 10.0 mmol) were stirred at 80° C. for 5 hours. The reaction solution was cooled to room temperature. After addition of water, the reaction solution was extracted with EtOAc. The organic layer was dried with anhydrous magnesium sulfate and purified by column chromatography to obtain the title compound (3.29 g, 97%).
¹H-NMR (CDCl₃) δ 7.32 (1H, m), 7.18 (1H, m), 4.12 (4H, m), 2.60 (2H, t), 2.10 (2H, m), 1.27 (3H, t)

Step B: 4-[2-chloro-6-fluoro-4-(4,4,5,5-tetramethyl-1,3,2-dioxaborolan-2-yl)phenoxy]butanoic acid ethyl ester 4-(4-Bromo-2-chloro-6-fluoro-phenoxy)butanoic acid ethyl ester (1.45 g, 4.27 mmol) Step A obtained in Step A was reacted in the same manner as in Step D of Preparation Example 1 to obtain the title compound (1.42 g, 86%).
¹H-NMR (CDCl₃) δ 7.58 (1H, m), 7.41 (1H, m), 4.16 (4H, m), 2.60 (2H, t), 2.10 (2H, m), 1.32 (12H, s), 1.26 (3H, t)

Preparation Example 222: 4-[2,6-dichloro-4-(4,4,5,5-tetramethyl-1,3,2-dioxaborolan-2-yl)phenoxy]butanoic acid ethyl ester Step A: 4-(4-bromo-2,6-dichloro-phenoxy)butanoic acid ethyl ester After addition of 15 mL of DMF 4-bromo-2,6-dichloro-phenol (2.42 g, 10.0 mmol), K₂CO₃ (2.07 g, 15.0 mmol) and 4-bromobutanoic acid ethyl ester (1.95 g, 10.0 mmol) were stirred at 80° C. for 5 hours. The reaction solution was cooled to room temperature. After addition of water, the reaction solution was extracted with EtOAc and purified by column chromatography to obtain the title compound (3.10 g, 87%).
¹H-NMR (CDCl₃) δ 7.44 (2H, s), 4.16 (2H, q), 4.04 (2H, t), 2.63 (2H, t), 2.16 (2H, m), 1.27 (3H, t)

Step B: 4-[2,6-dichloro-4-(4,4,5,5-tetramethyl-1,3,2-dioxaborolan-2-yl)phenoxy]butanoic acid ethyl ester 4-(4-Bromo-2,6-dichloro-phenoxy)butanoic acid ethyl ester (1.20 g, 3.37 mmol) obtained in Step A was reacted in the same manner as in Step D of Preparation Example 1 to obtain the title compound (0.825 g, 61%).
¹H-NMR (CDCl₃) δ 7.70 (2H, s), 4.16 (2H, q), 4.07 (2H, t), 2.65 (2H, t), 2.16 (2H, m), 1.33 (12H, s), 1.27 (3H, t)

Preparation Example 223: 2-[1-[2,6-difluoro-4-(3-hydroxyphenyl)phenyl]-4-piperidyl]acetic acid ethyl ester 3-Iodophenol (0.17 g, 0.77 mmol) and 2-[1-[2,6-difluoro-4-(4,4,5,5-tetramethyl-1,3,2-dioxaborolan-2-yl)phenyl]-4-piperidyl]acetic acid ethyl ester (0.35 g, 0.85 mmol) obtained in Preparation Example 220 was reacted in the same manner as in Step A of Example 1 to obtain the title compound (0.21 g, 75%).
¹H-NMR (CDCl₃) δ 7.30 (1H, m), 7.06 (3H, m), 6.97 (1H, m), 6.81 (1H, m), 4.88 (1H, brs), 4.15 (2H, q), 3.27 (2H, m), 3.13 (2H, m), 2.29 (2H, d), 1.96 (1H, m), 1.77 (2H, m), 1.47 (2H, m), 1.27 (3H, t)

Preparation Example 224: [1-(2,6-difluoro-4-thiocarbamoyl-phenyl)-piperidin-4-yl]-acetic acid ethyl ester Step A: [1-(4-cyano-2,6-difluoro-phenyl)-piperidin-4-yl]-acetic acid ethyl ester 3,4,5-Trifluorobenzonitrile (3.14 g, 20 mmol) and hydrochloric acid salt of 2-(4-piperidin)acetic acid ethyl ester (4.15 g, 20 mmol) were reacted in the same manner as in Step A of Preparation Example 84 to obtain the title compound (4.80 g, 78%).
¹H-NMR (CDCl₃) δ 7.16 (2H, m), 4.19 (2H, q), 3.45 (2H, m), 3.19 (2H, m), 2.32 (2H, d), 2.03 (1H, m), 1.82 (2H, m), 1.43 (2H, m), 1.31 (3H, t)

Step B: [1-(2,6-difluoro-4-thiocarbamoyl-phenyl)-piperidin-4-yl]-acetic acid ethyl ester

[1-(4-Cyano-2,6-difluoro-phenyl)-piperidin-4-yl]-acetic acid ethyl ester (1.54 g, 5.0 mmol) obtained in Step A, magnesium dichloride hexahydrate (4.07 g, 40.0 mmol) and sodium thiolate hydrate (3.70 g, 50.0 mmol) were dissolved in DMF (20 mL) and stirred for 3 hours. After addition of water, the reaction solution was extracted with EtOAc. The organic layer was washed with sodium chloride aqueous solution, dried with anhydrous magnesium sulfate and purified by column chromatography to obtain the title compound (1.41 g, 82%).
¹H-NMR (CDCl₃) δ 7.64 (1H, s), 7.45 (2H, m), 7.16 (1H, s), 4.19 (2H, q), 3.42 (2H, m), 3.17 (2H, m), 2.32 (2H, d), 2.00 (1H, m), 1.80 (2H, m), 1.46 (2H, m), 1.31 (3H, t)

Preparation Example 225: 2-chloro-6-fluoro-4-(4,4,5,5-tetramethyl-1,3,2-dioxaborolan-2-yl)aniline Step A: 4-bromo-2-chloro-6-fluoro-aniline 4-Bromo-2-fluoro-aniline (5.0 g, 26 mmol) was dissolved in 52 mL of CH₃CN. N-chlorosuccinimide (4.37 g, 33 mmol) was added thereto, and the mixture was stirred for 3 hours under reflux. The reaction solution was cooled to room temperature. After addition of NaHCO₃ aqueous solution, the reaction solution was extracted with DCM. The organic layer was dried with anhydrous magnesium sulfate and purified by column chromatography to obtain the title compound (4.41 g, 75%).
¹H-NMR (CDCl₃) δ 7.21 (1H, m), 7.09 (1H, m), 4.08 (2H, brs)

Step B: 2-chloro-6-fluoro-4-(4,4,5,5-tetramethyl-1,3,2-dioxaborolan-2-yl)aniline 4-Bromo-2-chloro-6-fluoro-aniline (4.4 g, 20 mmol) obtained in Step A was reacted in the same manner as in Step D of Preparation Example 1 to obtain the title compound (3.68 g, 67%).

¹H-NMR (CDCl₃) δ 7.50 (1H, m), 7.32 (1H, m), 4.28 (2H, brs), 1.33 (12H, s)

Preparation Example 226: 4-chloro-2-(cyclopropyl-methoxy)-6-methyl-pyrimidine 20 mL of THF was added to cyclopropylmethanol (0.36 g, 5.0 mmol) and cooled to 0° C. NaH (60 wt % in mineral oil, 0.24 g, 6.0 mmol) was added thereto, and the mixture was stirred for 30 minutes. 2,6-Dichloro-4-methyl-pyrimidine (0.815 g, 5.0 mmol) was added thereto, and the mixture was stirred at room temperature for 16 hours. After addition of water, the reaction solution was extracted with EtOAc. The organic layer was purified by column chromatography to obtain the title compound (0.37 g, 37%).

¹H-NMR (CDCl₃) δ 6.83 (1H, s), 4.19 (2H, d), 2.43 (3H, s), 1.31 (1H, m), 0.61 (2H, m), 0.37 (2H, m)

Preparation Example 227: 2-chloro-4-(cyclopropyl-methoxy)-6-methyl-pyrimidine 20 mL of THF was added to cyclopropylmethanol (0.36 g, 5.0 mmol) and cooled to 0° C. NaH (60 wt % in mineral oil, 0.24 g, 6.0 mmol) was added thereto, and the mixture was stirred for 30 minutes. After addition of 2,6-dichloro-4-methyl-pyrimidine (0.815 g, 5.0 mmol), the mixture was stirred at room temperature for 16 hours. After addition of water, the reaction solution was extracted with EtOAc. The organic layer was purified by column chromatography to obtain the title compound (0.41 g, 41%).

¹H-NMR (CDCl₃) δ 6.54 (1H, s), 4.23 (2H, d), 2.46 (3H, s), 1.30 (1H, m), 0.56 (2H, m), 0.40 (2H, m)

Preparation Example 228: 2-chloro-4-(cyclobutoxy)-6-methyl-pyrimidine 2,6-Dichloro-4-methyl-pyrimidine (0.815 g, 5.0 mmol) and cyclobutanol (0.36 g, 5.0 mmol) were reacted in the same manner as in Preparation Example 226 to obtain the title compound (0.455 g, 46%).

¹H-NMR (CDCl₃) δ 6.44 (1H, s), 5.21 (1H, m), 2.45 (2H, m), 2.41 (3H, s), 2.14 (2H, m), 1.85 (1H, m), 1.67 (1H, m)

Preparation Example 229: 4-chloro-2-(cyclobutoxy)-6-methyl-pyrimidine 2,6-Dichloro-4-methyl-pyrimidine (0.815 g, 5.0 mmol) and cyclobutanol (0.36 g, 5.0 mmol) were reacted in the same manner as in Preparation Example 226 to obtain the title compound (0.455 g, 46%).

¹H-NMR (CDCl₃) δ 6.81 (1H, s), 5.21 (1H, m), 2.45 (2H, m), 2.41 (3H, s), 2.14 (2H, m), 1.85 (1H, m), 1.67 (1H, m)

Preparation Example 230: 2-chloro-4-(cyclobutoxy)pyrimidine

Cyclobutanol (0.58 g, 8.05 mmol) and 2,4-dichloropyrimidine (1 g, 6.71 mmol) were reacted in the same manner as in Preparation Example 226 to obtain the title compound (0.4 g, 32%) and the by-product, 4-chloro-2-cyclobutoxy-pyrimidine (0.4 g, 32%).

¹H-NMR (CDCl₃) δ 8.27 (1H, d), 6.61 (1H, d), 5.26 (1H, m), 2.48 (2H, m), 2.16 (2H, m), 1.88 (1H, m), 1.70 (1H, m).

Preparation Example 231: 2-chloro-4-(cyclopropylmethoxy)pyrimidine

Cyclopropylmethanol (0.72 g, 10.0 mmol) and 2,4-dichloropyrimidine (1.49 g, 10.0 mmol) were reacted in the same manner as in Preparation Example 226 to obtain the title compound (0.78 g, 42%).

¹H-NMR (CDCl₃) δ 8.32 (1H, m), 6.71 (1H, m), 4.26 (2H, d), 1.30 (1H, m), 0.68 (2H, m), 0.42 (2H, m)

Preparation Example 232: 2-chloro-6-(cyclobutoxy)pyrazine

Cyclobutanol (0.36 g, 5.0 mmol) and 2,6-dichloropyrazine (0.745 g, 5.0 mmol) were reacted in the same manner as in Preparation Example 226 to obtain the title compound (0.53 g, 57%).

¹H-NMR (CDCl₃) δ 8.15 (1H, s), 8.11 (1H, s), 5.22 (1H, m), 2.53 (2H, m), 2.20 (2H, m), 1.91 (1H, m), 1.73 (1H, m)

Preparation Example 233: 2-chloro-6-(cyclopropylmethoxy)pyrazine

Cyclopropylmethanol (0.72 g, 10.0 mmol) and 2,6-dichloropyrazine (1.49 g, 10.0 mmol) were reacted in the same manner as in Preparation Example 226 to obtain the title compound (1.49 g, 81%).

¹H-NMR (CDCl₃) δ 8.18 (1H, s), 8.16 (1H, s), 4.21 (2H, d), 1.33 (1H, m), 0.68 (2H, m), 0.42 (2H, m)

Preparation Example 234: 2-chloro-6-methoxy-pyrazine

MeOH (0.27 mL, 6.7 mmol) was dissolve in 15 mL of THF. NaH (60 wt % in mineral oil, 0.32 g, 8.0 mmol) was added thereto, and the mixture was stirred at room temperature for 30 minutes. 2,6-Dichloropyrazine (1.0 g, 6.7 mmol) dissolved in 20 mL of THF was slowly added thereto, and the mixture was stirred at room temperature for 16 hours. After addition of ammonium chloride aqueous solution, the reaction solution was extracted with Et₂O. The organic layer was dried with anhydrous magnesium sulfate and purified by column chromatography to obtain the title compound (0.71 g, 73%).

¹H-NMR (CDCl₃) δ 8.14 (1H, s), 8.13 (1H, s), 3.99 (3H, s)

Preparation Example 235: 2-chloro-6-propoxy-pyrazine

Propan-1-ol (0.4 g, 6.7 mmol) was dissolved in 15 mL of THF. NaH (60 wt % in mineral oil, 0.32 g, 8.0 mmol) was added thereto, and the mixture was stirred at room temperature for 30 minutes. 2,6-Dichloropyrazine (1.0 g, 6.7 mmol) dissolved in 20 mL of THF was slowly added thereto, and the mixture was stirred at room temperature for 16 hours. After addition of ammonium chloride aqueous solution, the reaction solution was extracted with Et₂O. The organic layer was dried with anhydrous magnesium sulfate and purified by column chromatography to obtain the title compound (0.77 g, 66%).

¹H-NMR (CDCl₃) δ 8.12 (1H, s), 8.11 (1H, s), 4.29 (2H, t), 1.82 (2H, m), 1.03 (3H, t)

Preparation Example 236: 2-butoxy-6-chloro-pyrazine

Butan-1-ol (0.5 g, 6.7 mmol) was dissolved in 15 mL of THF. NaH (60 wt % in mineral oil, 0.32 g, 8.0 mmol) was added thereto, and the mixture was stirred at room temperature for 30 minutes. 2,6-Dichloropyrazine (1.0 g, 6.7 mmol) dissolved in 20 mL of THF was slowly added thereto, and the mixture was stirred at room temperature for 16 hours. After addition of ammonium chloride aqueous solution, the reaction solution was extracted with Et$_2$O. The organic layer was dried with anhydrous magnesium sulfate and purified by column chromatography to obtain the title compound (1.15 g, 92%).

$^1$H-NMR (CDCl$_3$) δ 8.11 (1H, s), 8.10 (1H, s), 4.33 (2H, t), 1.78 (2H, m), 1.48 (2H, m), 0.98 (3H, t)

Preparation Example 237:
2-chloro-6-isobutoxy-pyrazine

2-Methylpropan-1-ol (0.5 g, 6.7 mmol) was dissolved in 15 mL of THF. NaH (60 wt % in mineral oil, 0.32 g, 8.0 mmol) was added thereto, and the mixture was stirred at room temperature for 30 minutes. 2,6-Dichloropyrazine (1.0 g, 6.7 mmol) dissolved in 20 mL of THF was slowly added thereto, and the mixture was stirred at room temperature for 16 hours. After addition of ammonium chloride aqueous solution, the reaction solution was extracted with Et$_2$O. The organic layer was dried with anhydrous magnesium sulfate and purified by column chromatography to obtain the title compound (1.04 g, 83%).

$^1$H-NMR (CDCl$_3$) δ 8.12 (2H, s), 4.10 (2H, d), 2.11 (1H, m), 1.03 (6H, d)

Preparation Example 238:
2-chloro-6-(cyclopentoxy)pyrazine

Cyclopentanol (0.58 g, 6.7 mmol) was dissolved in 15 mL of THF. NaH (60 wt % in mineral oil, 0.32 g, 8.0 mmol) was added thereto, and the mixture was stirred at room temperature for 30 minutes. 2,6-Dichloropyrazine (1.0 g, 6.7 mmol) dissolved in 20 mL of THF was slowly added thereto, and the mixture was stirred at room temperature for 16 hours. After addition of ammonium chloride aqueous solution, the reaction solution was extracted with Et$_2$O. The organic layer was dried with anhydrous magnesium sulfate and purified by column chromatography to obtain the title compound (1.07 g, 80%).

$^1$H-NMR (CDCl$_3$) δ 8.09 (1H, s), 8.05 (1H, s), 5.40 (1H, m), 1.98 (2H, m), 1.80 (4H, m), 1.65 (2H, m)

Preparation Example 239:
2-chloro-4-ethoxy-pyrimidine 2,4-Dichloropyrimidine (3.0 g, 20.1 mmol) was dissolved in 40 mL of EtOH. NaOEt (1.0 M in EtOH, 20 mL, 20 mmol) was added thereto, and the mixture was stirred at room temperature for 16 hours. The reaction solution was concentrated under reduced pressure. After addition of water, the reaction solution was extracted with Et$_2$O. The organic layer was dried with anhydrous magnesium sulfate and purified by column chromatography to obtain the title compound (1.41 g, 44%).

$^1$H-NMR (CDCl$_3$) δ 8.27 (1H, d), 6.64 (1H, d), 4.45 (2H, q), 1.40 (3H, t)

Preparation Example 240:
2-chloro-4-isopropoxy-pyrimidine

Cs$_2$CO$_3$ (7.15 g, 21.9 mmol) and 50 mL of propan-2-ol were added to 2,4-dichloropyrimidine (3.0 g, 20.1 mmol), and the mixture was stirred for 24 hours under reflux. After filtering solids, the filtrate was purified by column chromatography to obtain the title compound (2.24 g, 65%).

$^1$H-NMR (CDCl$_3$) δ 8.25 (1H, d), 6.58 (1H, d), 5.40 (1H, m), 1.37 (6H, d)

Preparation Example 241:
2-chloro-4-propoxy-pyrimidine

Propan-1-ol (1.33 g, 22.1 mmol) was dissolved in 60 mL of THF. NaH (60 wt % in mineral oil, 0.96 g, 24.1 mmol) was added thereto, and the mixture was stirred at room temperature for 30 minutes. 2,4-Dichloropyrimidine (3.0 g, 22.1 mmol) was added thereto, and the mixture was stirred at room temperature for 24 hours. After addition of ammonium chloride aqueous solution, the reaction solution was extracted with Et$_2$O. The organic layer was dried with anhydrous magnesium sulfate and purified by column chromatography to obtain the title compound (2.06 g, 59%).

$^1$H-NMR (CDCl$_3$) δ 8.27 (1H, d), 6.65 (1H, d), 4.34 (2H, t), 1.81 (2H, m), 1.03 (3H, t)

Preparation Example 242:
2-chloro-4-isobutoxy-pyrimidine

2-Methylpropan-1-ol (1.64 g, 22.1 mmol) was dissolved in 60 mL of THF. NaH (60 wt % in mineral oil, 0.96 g, 24.1 mmol) was added thereto, and the mixture was stirred at room temperature for 30 minutes. 2,4-Dichloropyrimidine (3.0 g, 22.1 mmol) was added thereto, and the mixture was stirred at room temperature for 24 hours. After addition of ammonium chloride aqueous solution, the reaction solution was extracted with Et$_2$O. The organic layer was dried with anhydrous magnesium sulfate and purified by column chromatography to obtain the title compound.

$^1$H-NMR (CDCl$_3$) δ 8.27 (1H, d), 6.65 (1H, d), 4.15 (2H, d), 2.09 (1H, m), 1.00 (6H,

Preparation Example 243:
2-chloro-4-ethoxy-6-methyl-pyrimidine

Cs$_2$CO$_3$ (6.6 g, 20.2 mmol) and 46 mL of EtOH were added to 2,4-dichloro-6-methyl-pyrimidine (3.0 g, 18.4 mmol), and the mixture was stirred for 48 hours under reflux. After filtering solids, the filtrate was purified by column chromatography to obtain the title compound (1.88 g, 59%).

$^1$H-NMR (CDCl$_3$) δ 6.47 (1H, s), 4.41 (2H, q), 2.42 (3H, s), 1.39 (3H, t)

Preparation Example 244:
2-chloro-4-isopropoxy-6-methyl-pyrimidine

Cs$_2$CO$_3$ (6.6 g, 20.2 mmol) and 46 mL of propan-2-ol were added to 2,4-dichloro-6-methyl-pyrimidine (3.0 g, 18.4 mmol), and the mixture was stirred for 16 hours under reflux. After filtering solids, the filtrate was purified by column chromatography to obtain the title compound (1.18 g, 34%).

$^1$H-NMR (CDCl$_3$) δ 6.41 (1H, s), 5.38 (1H, m), 2.40 (3H, s), 1.34 (6H, d)

Preparation Example 245:
2-chloro-4-methyl-6-propoxy-pyrimidine

Cs$_2$CO$_3$ (6.6 g, 20.2 mmol) and 46 mL of propan-1-ol were added to 2,4-dichloro-6-methyl-pyrimidine (3.0 g, 18.4 mmol), and the mixture was stirred for 16 hours under reflux. After filtering solids, the filtrate was purified by column chromatography to obtain the title compound (1.72 g, 50%).

$^1$H-NMR (CDCl$_3$) δ 6.48 (1H, s), 4.31 (2H, t), 2.42 (3H, s), 1.79 (2H, m), 1.00 (3H, t)

Preparation Example 246:
2-chloro-4-isobutoxy-6-methyl-pyrimidine

2-Methylpropan-1-ol (3.5 g, 21.4 mmol) was dissolved in 50 mL of THF. NaH (60 wt % in mineral oil, 1.03 g, 25.7 mmol) was added thereto, and the mixture was stirred at room temperature for 30 minutes. 2,4-Dichloro-6-methyl-pyrimidine (3.0 g, 18.4 mmol) dissolved in 20 mL of THF was added thereto, and the mixture was stirred at room temperature for 16 hours. After addition of ammonium chloride aqueous solution, the reaction solution was extracted with Et$_2$O. The organic layer was dried with anhydrous magnesium sulfate and purified by column chromatography to obtain the title compound (1.75 g, 41%).

$^1$H-NMR (CDCl$_3$) δ 6.49 (1H, s), 4.13 (2H, d), 2.42 (3H, s), 2.07 (1H, m), 1.00 (6H, d)

Preparation Example 247:
2-chloro-4-(2-methoxyethoxy)-6-methyl-pyrimidine 2,6-Dichloro-4-methyl-pyrimidine (1.63 g, 10.0 mmol) and 2-methoxyethanol (0.76 g, 10.0 mmol) were reacted in the same manner as in Preparation Example 226 to obtain the title compound (1.03 g, 51%).

$^1$H-NMR (CDCl$_3$) δ 6.59 (1H, s), 4.56 (2H, m), 3.75 (2H, m), 3.45 (3H, s), 2.45 (3H, s)

Preparation Example 248:
2-chloro-4-(3-methoxy-propoxy)-6-methyl-pyrimidine 2,6-Dichloro-4-methyl-pyrimidine (1.63 g, 10.0 mmol) and 3-methoxypropanol (0.90 g, 10.0 mmol) were reacted in the same manner as in Preparation Example 226 to obtain the title compound (1.05 g, 48%).

$^1$H-NMR (CDCl$_3$) δ 6.52 (1H, s), 4.47 (2H, t), 3.54 (2H, t), 3.38 (3H, s), 2.48 (3H, s), 2.06 (2H, m)

Preparation Example 249:
2-chloro-6-pyrrolidin-1-yl-pyrazine 2,6-Dichloropyrazine (2.0 g, 13.4 mmol) was dissolved in 13 mL of DMSO. Pyrrolidine (1.05 g, 14.7 mmol) and DIPEA (2.92 mL, 16.7 mmol) were sequentially added thereto, and the mixture was stirred at room temperature for 24 hours. The reaction solution was diluted with water, extracted with EtOAc and purified by column chromatography to obtain the title compound (2.36 g, 96%).

$^1$H-NMR (CDCl$_3$) δ 7.74 (1H, s), 7.71 (1H, s), 3.49 (4H, m), 2.03 (4H, m)

Preparation Example 250:
6-chloro-N-isopropyl-pyrazin-2-amine

Propan-2-amine (1.7 mL, 20.1 mmol), 1 mL of TEA and 2 mL of THF were added to 2,6-dichloropyrazine (2.0 g, 13.4 mmol), and the mixture was stirred at 60° C. for 24 hours. After filtering solids, the filtrate was purified by column chromatography to obtain the title compound (1.35 g, 59%).

$^1$H-NMR (CDCl$_3$) δ 7.75 (1H, s), 7.71 (1H, s), 4.61 (1H, brs), 4.00 (1H, m), 1.26 (6H, d)

Preparation Example 251:
6-chloro-N-isobutyl-pyrazin-2-amine

2-Methylpropan-1-amine (2 mL, 20.1 mmol), 1 mL of TEA and 3 mL of THF were added to 2,6-dichloropyrazine (2.0 g, 13.4 mmol), and the mixture was stirred at 60° C. for 24 hours. After filtering solids, the filtrate was purified by column chromatography to obtain the title compound (1.95 g, 78%).

$^1$H-NMR (CDCl$_3$) δ 7.77 (1H, s), 7.75 (1H, s), 4.97 (1H, brs), 3.17 (2H, m), 1.90 (1H, m), 0.99 (6H, d)

Preparation Example 252:
6-chloro-N-cyclopentyl-pyrazin-2-amine

Cyclopentanamine (1.48 g, 17.4 mmol), 1 mL of TEA and 3 mL of THF were added to 2,6-dichloropyrazine (2.0 g, 13.4 mmol), and the mixture was stirred at 60° C. for 24 hours. After filtering solids, the filtrate was purified by column chromatography to obtain the title compound (1.84 g, 69%).

$^1$H-NMR (CDCl$_3$) δ 7.77 (1H, s), 7.74 (1H, s), 4.80 (1H, brs), 4.09 (1H, m), 2.07 (2H, m), 1.74 (2H, m), 1.67 (2H, m), 1.48 (2H, m)

Preparation Example 253:
6-chloro-N,N-diethyl-pyrazin-2-amine 2,6-Dichloropyrazine (2.0 g, 13.4 mmol) was dissolved in 13 mL of DMSO. Diethylamine (1.53 mL, 14.7 mmol) and DIPEA (2.92 mL, 16.7 mmol) were sequentially added thereto, and the mixture was stirred at room temperature for 24 hours. The reaction solution was diluted with water, extracted with EtOAc and purified by column chromatography to obtain the title compound (1.44 g, 58%).

$^1$H-NMR (CDCl$_3$) δ 7.80 (1H, s), 7.70 (1H, s), 3.51 (4H, q), 1.21 (6H, t)

Preparation Example 254:
6-chloro-N,N-dimethyl-pyrazin-2-amine 2,6-Dichloropyrazine (2.0 g, 13.4 mmol) was dissolved in 13 mL of DMSO. Dimethylamine hydrochloride (1.31 g, 16.08 mmol) and DIPEA (5.2 mL, 30 mmol) were sequentially added thereto, and the mixture was stirred at room temperature for 24 hours. The reaction solution was diluted with water, extracted with EtOAc and purified by column chromatography to obtain the title compound (1.82 g, 86%).

$^1$H-NMR (CDCl$_3$) δ 7.87 (1H, s), 7.77 (1H, s), 3.13 (6H, s)

Preparation Example 255:
2-chloro-N-isobutyl-pyrimidin-4-amine 15 mL of THF, 2-methylpropan-1-amine (2.6 mL, 26.1 mmol) and DIPEA (5.3 mL, 30 mmol) were added to 2,4-dichloropyrimidin (3.0 g, 20.1 mmol), the mixture was stirred at 65° C. for 16 hours. The reaction solution was concentrated under reduced pressure and purified by column chromatography to obtain the title compound (2.57 g, 69%).

$^1$H-NMR (CDCl$_3$) δ 8.03 (1H, m), 6.23 (1H, d), 5.40 (1H, brs), 3.07 (2H, m), 1.89 (1H, m), 0.98 (6H, d)

Preparation Example 256: 5-chloro-3-(cyclobutoxy)-2-methyl-pyrazine

Step A: 3,5-dichloro-2-methyl-pyrazine 110 mL of THF was added to 2,2,6,6-tetramethylpiperidine (3.3 mL, 20 mmol) and cooled to −78° C. n-BuLi (2.5 M hexane solution, 8 mL, 20 mmol) was added thereto, and the mixture was stirred at −78° C. for 30 minutes. 2,6-Dichloropyrazine (2.0 g, 13.4 mmol) dissolved in 20 mL was added thereto, and the mixture was stirred at −78° C. for 90 minutes. Iodomethane (3.8 mL, 60 mmol) was added thereto, and the mixture was stirred at room temperature for 3 hours. Solids were removed by filtration, and the filtrate was purified by column chromatography to obtain the title compound (0.77 g, 35%).

$^1$H-NMR (CDCl$_3$) δ 8.41 (1H, s), 2.65 (3H, s)

Step B: 5-chloro-3-(cyclobutoxy)-2-methyl-pyrazine 3,5-Dichloro-2-methyl-pyrazine (0.62 g, 3.8 mmol) obtained in Step A and cyclobutanol (0.3 g, 4.18 mmol) was reacted in the same manner as in Preparation Example 226 to obtain the title compound (0.54 g, 71%).

$^1$H-NMR (CDCl$_3$) δ 7.98 (1H, s), 5.20 (1H, m), 2.48 (2H, m), 2.43 (3H, s), 2.15 (2H, m), 1.86 (1H, m), 1.70 (1H, m)

Preparation Example 257: 2-chloro-6-isobutyl-pyrazine 50 mL of THF, 5 mL of NMP and Fe(acac)$_3$ (0.24 g, 0.67 mmol) were added to 2,6-dichloropyrazine (2.0 g, 13.4 mmol), and the mixture was cooled to 0° C. Isobutylmagnesium bromide (2.0 M Et$_2$O solution, 12 mL, 24 mmol) was slowly added thereto. The reaction solution was stirred at room temperature for 24 hours. After addition of water, the reaction solution was extracted with Et$_2$O. The organic layer was dried with anhydrous magnesium sulfate and purified by column chromatography to obtain the title compound (0.32 g, 14%).

$^1$H-NMR (CDCl$_3$) δ 8.43 (1H, s), 8.31 (1H, s), 2.66 (2H, d), 2.13 (1H, m), 0.95 (6H, d)

Preparation Example 258: 2-chloro-6-cyclopentyl-pyrazine 13 mL of toluene, SPhos (1.37 g, 3.3 mmol) and Pd(OAc)$_2$ (0.38 g, 1.67 mmol) were added to 2,6-dichloropyrazine (1.0 g, 6.7 mmol). Cyclopentylzinc bromide (0.5 M THF solution, 20 mL, 10 mmol) was added thereto, and the mixture was stirred at room temperature for 16 hours. After addition of ammonium chloride aqueous solution, the reaction solution was extracted with EtOAc. The organic layer was purified by column chromatography to obtain the title compound (0.19 g, 15%).

$^1$H-NMR (CDCl$_3$) δ 8.39 (1H, s), 8.36 (1H, s), 3.18 (1H, m), 2.10 (2H, m), 1.85 (4H, m), 1.71 (2H, m)

Preparation Example 259: 2-chloro-4-isobutyl-pyrimidine 40 mL of THF, Pd(PPh$_3$)$_4$ (1.0 g, 0.9 mmol) and triisobutylaluminum (1.0 M hexane solution, 16 mL, 16 mmol) were added to 2,4-dichloropyrimidine (2.0 g, 13.4 mmol), and the mixture was stirred for 20 hours under reflux. After cooling and addition of water, the reaction solution was extracted with Et$_2$O. The organic layer was purified by column chromatography to obtain the title compound (0.32 g, 14%).

$^1$H-NMR (CDCl$_3$) δ 8.49 (1H, d), 7.08 (1H, d), 2.63 (2H, d), 2.14 (1H, m), 0.95 (6H, d)

Preparation Example 260: 2-butyl-6-chloro-pyrazine 50 mL of THF, 5 mL of NMP and Fe(acac)$_3$ (0.24 g, 0.67 mmol) were added to 2,6-dichloropyrazine (2.0 g, 13.4 mmol), and the mixture was cooled to 0° C. Butylmagnesium chloride (0.9 M THF solution, 16 mL, 14.4 mmol) was slowly added thereto. The reaction solution was stirred at room temperature for 24 hours. After addition of water, the reaction solution was extracted with Et$_2$O. The organic layer was dried with anhydrous magnesium sulfate and purified by column chromatography to obtain the title compound (0.38 g, 17%).

$^1$H-NMR (CDCl$_3$) δ 8.42 (1H, s), 8.35 (1H, s), 2.79 (2H, t), 1.73 (2H, m), 1.39 (2H, m), 0.95 (3H, t)

Preparation Example 261: 2-chloro-6-isopentyl-pyrazine 50 mL of THF, 5 mL of NMP and Fe(acac)$_3$ (0.24 g, 0.67 mmol) were added to 2,6-dichloropyrazine (2.0 g, 13.4 mmol), and the mixture was cooled to 0° C. Isopentylmagnesium bromide (0.9 M THF solution, 16 mL, 14.4 mmol) was slowly added thereto. The reaction solution was stirred at room temperature for 24 hours. After addition of water, the reaction solution was extracted with Et$_2$O. The organic layer was dried with anhydrous magnesium sulfate and purified by column chromatography to obtain the title compound (0.36 g, 15%).

$^1$H-NMR (CDCl$_3$) δ 8.41 (1H, s), 8.35 (1H, s), 2.79 (2H, m), 1.62 (3H, m), 0.95 (6H, d)

Preparation Example 262: 2-chloro-6-cyclobutyl-pyrazine

Magnesium (0.326 g, 13.4 mL) and 13.4 mL of THF were added to a dried flask. Bromocyclobutane (1.81 g, 13.4 mmol) was slowly added thereto, and the mixture was stirred for 1 hour under reflux. The reaction solution was cooled to 0° C. Fe(acac)$_3$ (0.24 g, 16 mmol) dissolved in 2 mL of THF was added thereto, and the mixture was stirred for 5 minutes. 2,6-Dichloropyrazine (2.0 g, 13.4 mmol) dissolved in 20 mL of THF and 2 mL of NMP was added thereto, and the mixture was stirred for 2 hours. After addition of ammonium chloride aqueous solution, the reaction solution was extracted with Et$_2$O and purified by column chromatography to obtain the title compound (0.05 g, 2%).

$^1$H-NMR (CDCl$_3$) δ 8.40 (1H, s), 8.33 (1H, s), 3.68 (1H, m), 2.38 (4H, m), 2.10 (1H, m), 1.96 (1H, m)

Preparation Example 263: 4-chloro-6,7-dihydro-5H-cyclopenta[d]pyrimidine

Step A: 2-aminocyclopentene-1-carboxylic acid methyl ester

2-Oxocyclopentancarboxylic acid methyl ester (9.86 g, 69.3 mmol) was dissolved in 140 mL of MeOH. Ammonium formate (21.9 g, 350 mmol) was added thereto, and the mixture was stirred for 24 hours under reflux. The reaction solution was cooled to room temperature. Small amount of SiO$_2$ was added, and the reaction solution was concentrated under reduced pressure and purified by column chromatography to obtain the title compound (9.49 g, 97%).

$^1$H-NMR (DMSO-$d_6$) δ 6.76 (2H, brs), 3.53 (3H, s), 2.39 (4H, m), 1.70 (2H, m)

Step B: 2-formamidocyclopentene-1-carboxylic acid methyl ester 21 mL of formic acid was cooled to 0° C. 30 mL of acetic anhydride was added, and 2-aminocyclopentene-1-carboxylic acid methyl ester (4.76 g, 33.7 mmol) obtained in Step A was then added thereto little by little. The reaction solution was stirred at room temperature for 16 hours. The organic layer extracted with EtOAc was purified by column chromatography to obtain the title compound (4.95 g, 87%).

$^1$H-NMR (DMSO-$d_6$) δ 10.28 (0.5H, brs), 9.72 (0.5H, brs), 8.57 (0.5H, brs), 8.28 (0.5H, brs), 3.68 (3H, s), 3.05 (1H, m), 2.88 (1H, m), 2.46 (2H, m), 1.86 (2H, m)

Step C: 6,7-dihydro-5H-cyclopenta[d]pyrimidin-4-ol

Ammonium formate (9.94 g, 157 mmol) was dissolved in 15 mL of formamide. 2-Formamidocyclopentene-1-carboxylic acid methyl ester (4.94 g, 29.2 mmol) obtained in Step B was added thereto, and the mixture was stirred at 150° C. for 4 hours. After cooling to room temperature, the reaction solution was stirred for 16 hours. The formed precipitate was dried to obtain the title compound (1.56 g, 39%).

$^1$H-NMR (DMSO-$d_6$) δ 12.28 (1H, brs), 8.02 (1H, s), 2.75 (2H, t), 2.62 (2H, t), 1.95 (2H, m)

Step D: 4-chloro-6,7-dihydro-5H-cyclopenta[d]pyrimidine 11 mL of phosphorus oxychloride was added to 6,7-dihydro-5H-cyclopenta[d]pyrimidin-4-ol (1.56 g, 11.4 mmol) obtained in Step C, and the mixture was stirred for 4 hours under reflux. The reaction solution was cooled to room temperature. DCM was added thereto, and water was then added thereto. The water layer was extracted with DCM, and the organic layer was purified by column chromatography to obtain the title compound (1.67 g, 95%).

$^1$H-NMR (DMSO-$d_6$) δ 8.78 (1H, s), 3.03 (2H, t), 2.99 (2H, t), 2.10 (2H, m)

Preparation Example 264: 2-chloro-4-(cyclobutoxy)-6,7-dihydro-5H-cyclopenta[d]pyrimidine

Step A: 2,4-dichloro-6,7-dihydro-5H-cyclopenta[d]pyrimidine 12 mL of EtOH and 0.6 mL of concentrated HCl were added to 2-oxocyclopentancarboxylic acid methyl ester (5.2 g, 36.6 mmol) and urea (2.42 g, 40.2 mmol), and the mixture was stirred for 3 hours under reflux. The reaction solution was cooled to room temperature. The formed solids were dissolved in 12 mL of 5% NaOH aqueous solution, and the reaction solution was stirred for 2 hours under reflux. The reaction solution was cooled to 0° C. and adjusted to pH 3. The formed solids were filtered to obtain 6,7-dihydro-5H-cyclopenta[d]pyrimidin-2,4-diol (3.34 g, 60%). This compound was dissolved in 7 mL of phosphorus oxychloride, and the mixture was stirred for 4 hours under reflux. The reaction solution was cooled to room temperature. After addition of cold water, the reaction solution was extracted with DCM to obtain the title compound (0.98 g, 24%).

$^1$H-NMR (CDCl$_3$) δ 3.08 (2H, t), 2.99 (2H, t), 2.22 (2H, m)

Step B: 2-chloro-4-(cyclobutoxy)-6,7-dihydro-5H-cyclopenta[d]pyrimidine

Cyclobutanol (0.34 g, 4.75 mmol) was dissolved in 30 mL of THF and cooled to 0° C. NaH (60 wt % in mineral oil, 0.21 g, 5.18 mmol) was added thereto, and the mixture was stirred for 30 minutes. 2,4-Dichloro-6,7-dihydro-5H-cyclopenta[d]pyrimidine (0.82 g, 4.32 mmol) obtained in Step A was dissolved in 13 mL of THF and added thereto. The mixture was stirred at room temperature for 16 hours. After addition of water, the reaction solution was extracted with EtOAc. The organic layer was purified by column chromatography to obtain the title compound (0.59 g, 61%).

$^1$H-NMR (CDCl$_3$) δ 5.28 (1H, m), 2.93 (2H, m), 2.82 (2H, m), 2.48 (2H, m), 2.13 (4H, m), 1.84 (1H, m), 1.67 (1H, m)

Preparation Example 265: 2-chloro-4-(cyclobutoxy)-5,6-dimethyl-pyrimidine

Step A: 2,4-dichloro-5,6-dimethyl-pyrimidine 5,6-Dimethyl-1H-pyrimidin-2,4-dione (2.5 g, 17.8 mmol) was dissolved in 12 mL of phosphorus oxychloride, and the mixture was stirred for 4 hours under reflux. The reaction solution was cooled to at room temperature and added to cold water. The formed precipitate was dried to obtain the title compound (3.08 g, 98%).

$^1$H-NMR (DMSO-$d_6$) δ 2.51 (3H, s), 2.30 (3H, s)

Step B: 2-chloro-4-(cyclobutoxy)-5,6-dimethyl-pyrimidine

Cyclobutanol (0.45 g, 6.21 mmol) was dissolved in 40 mL of THF and cooled to 0° C. NaH (60 wt % in mineral oil, 0.27 g, 6.77 mmol) was added thereto, and the mixture was stirred for 30 minutes. 2,4-Dichloro-5,6-dimethyl-pyrimidine (1.0 g, 5.64 mmol) obtained in Step A was dissolved in 15 mL of THF and added thereto. The mixture was stirred at room temperature for 16 hours. After addition of water, the reaction solution was extracted with EtOAc. The organic layer was purified by column chromatography to obtain the title compound (0.84 g, 70%).

$^1$H-NMR (CDCl$_3$) δ 5.24 (1H, m), 2.48 (2H, m), 2.40 (3H, s), 2.13 (2H, m), 2.08 (3H, s), 1.84 (1H, m), 1.68 (1H, m)

Preparation Example 266: (6-bromo-2-pyridyl)methanol

6-Bromopyridin-2-carbaldehyde (1.86 g, 10.0 mmol) was dissolved in 30 mL of MeOH and cooled to 0° C. NaBH$_4$ (0.38 g, 10.0 mmol) was slowly added thereto, and the mixture was stirred at room temperature for 30 minutes. After addition of water, the organic layer extracted with EtOAc was purified by column chromatography to obtain the title compound (1.86 g, 99%).

$^1$H-NMR (CDCl$_3$) δ 7.56 (1H, t), 7.40 (1H, m), 7.28 (1H, m), 4.75 (2H, d), 3.02 (1H, t)

Preparation Example 267: 2-bromo-6-(cyclopropylmethoxymethyl)pyridine (6-Bromo-2-pyridyl)methanol (0.376 g, 2.0 mmol) obtained in Preparation Example 266 was dissolved in 8 mL of THF. NaH (60 wt % in mineral oil, 0.088 g, 2.2 mmol)

was added thereto, and the mixture was stirred at room temperature for 30 minutes. Bromomethylcyclopropane (0.297 g, 2.2 mmol) and Bu$_4$NI (0.074 g, 0.2 mmol) were sequentially added thereto, and the mixture was stirred at room temperature. The reaction solution was adjusted to pH 4 by the addition of water. The organic layer extracted with DCM was purified by column chromatography to obtain the title compound (0.283 g, 58%).

$^1$H-NMR (CDCl$_3$) δ 7.56 (1H, t), 7.47 (1H, m), 7.37 (1H, m), 4.63 (2H, s), 3.41 (2H, d), 1.10 (1H, m), 0.56 (2H, m), 0.24 (2H, m)

Preparation Example 268:
(6-bromo-2-pyridyl)-cyclopropyl-methanol

6-Bromopyridin-2-carbaldehyde (0.93 g, 5.0 mmol) was dissolved in 20 mL of THF. Cyclopropyl magnesium bromide (0.5 M in THF, 11 mL, 5.5 mmol) was slowly added thereto, and the mixture was stirred at room temperature for 15 minutes. After addition of ammonium chloride aqueous solution, the organic layer extracted with DCM was purified by column chromatography to obtain the title compound (1.09 g, 96%).

$^1$H-NMR (CDCl$_3$) δ 7.55 (1H, t), 7.40 (1H, d), 7.37 (1H, d), 4.09 (1H, m), 3.62 (1H, d), 1.12 (1H, m), 0.55 (4H, m)

Preparation Example 269:
2-bromo-6-(cyclobutoxymethyl)pyridine (6-Bromo-2-pyridyl)methanol (0.38 g, 2.0 mmol) obtained in Preparation Example 266 was dissolved in 5 mL of DCM. 2-Bromo-6-(chloromethyl)pyridine obtained by the addition of 1.2 mL of SOCl$_2$ and cyclobutanol (0.145 g, 2.0 mmol) were reacted in the same manner as in Preparation Example 267 to obtain the title compound (0.365 g, 75%).

$^1$H-NMR (CDCl$_3$) δ 7.55 (1H, t), 7.43 (1H, d), 7.38 (1H, d), 4.51 (2H, s), 4.06 (1H, m), 2.23 (2H, m), 2.00 (2H, m), 1.73 (1H, m), 3.53 (1H, m)

Preparation Example 270:
2,6-dichloro-4-(cyclobutoxy)pyridine

2-Chloro-6-cyclobutoxy-pyridine (0.88 g, 4.8 mmol) was dissolved in 50 mL of DCM. mCPBA (4.45 g, 17.8 mmol) was added thereto, and the mixture was stirred at room temperature for 3 days. The precipitate was removed by filtration, and the filtrate was washed with 1N NaOH aqueous solution and extracted with chloroform. The organic layer was dried with anhydrous magnesium sulfate for concentration. 15 mL of POCl$_3$ was added thereto, and the mixture was stirred at 90° C. for 3 hours. The reaction solution was concentrated under reduced pressure. Cold water and 1N NaOH aqueous solution were sequentially added thereto, and the reaction solution was extracted with DCM. The organic layer was dried with anhydrous magnesium sulfate and purified by column chromatography to obtain the title compound (0.956 g, 91%).

$^1$H-NMR (CDCl$_3$) δ 6.67 (2H, s), 4.66 (1H, m), 2.46 (2H, m), 2.19 (2H, m), 1.90 (1H, m), 1.70 (1H, m)

Preparation Example 271:
2-chloro-6-(cyclobutoxy)-4-methyl-pyridine

Step A: 2-(cyclobutoxy)-4-methyl-pyridine

2-Chloro-4-methyl-pyridine (0.89 g, 7.0 mmol) and cyclobutanol (0.05 g, 7.0 mmol) were reacted in the same manner as in Preparation Example 226 to obtain the title compound (0.827 g, 72%).

$^1$H-NMR (CDCl$_3$) δ 8.03 (1H, m), 6.71 (1H, m), 6.54 (1H, m), 5.19 (1H, m), 2.49 (2H, m), 2.32 (3H, s), 2.16 (2H, m), 1.86 (1H, m), 1.70 (1H, m)

Step B: 2-chloro-6-(cyclobutoxy)-4-methyl-pyridine 2-(Cyclobutoxy)-4-methyl-pyridine (0.0827 g, 5.07 mmol) obtained in Step A was reacted in the same manner as in Preparation Example 270 to obtain the title compound (0.405 g, 40%).

$^1$H-NMR (CDCl$_3$) δ 6.75 (1H, m), 6.44 (1H, m), 5.18 (1H, m), 2.49 (2H, m), 2.30 (3H, s), 2.12 (2H, m), 1.85 (1H, m), 1.70 (1H, m)

Preparation Example 272:
2-tert-butoxy-6-chloro-pyridine 45 mL of toluene and potassium tert-butoxide (2.77 g, 24.6 mmol) were added to 2,6-dichloropyridine (3.04 g, 20.5 mmol), and the mixture was stirred for 24 hours under reflux. Solids were filtered through Celite, and the filtrate was purified by column chromatography to obtain the title compound (1.57 g, 41%).

$^1$H-NMR (CDCl$_3$) δ 7.44 (1H, t), 6.82 (1H, d), 6.54 (1H, d), 1.58 (9H, s)

Preparation Example 273:
2-chloro-6-ethoxy-pyridine

EtOH (2.8 mL, 47 mmol) was added to 80 mL of THF, and the mixture was cooled to 0° C. Sodium (0.57 g, 25 mmol) was slowly added thereto, and the mixture was stirred at 40° C. for 30 minutes. 2,6-Dichloropyridine (3.51 g, 23.7 mmol) was added thereto, and the mixture was stirred at 50° C. for 16 hours. After addition of water, the reaction solution was extracted with Et$_2$O and purified by column chromatography to obtain the title compound (2.27 g, 61%).

$^1$H-NMR (CDCl$_3$) δ 7.50 (1H, t), 6.87 (1H, d), 6.62 (1H, d), 4.36 (2H, q), 1.38 (3H, t)

Preparation Example 274:
2-chloro-6-(2,2,2-trifluoroethoxy)pyridine 2,2,2-Trifluoroethanol (2.42 g, 24 mmol) was dissolved in 67 mL of THF. NaH (55 wt % in mineral oil, 1.06 g, 24 mmol) was added thereto, and the mixture was stirred at room temperature for 45 minutes. 2,6-Dichloropyridine (3.0 g, 20 mmol) was added thereto, and the mixture was stirred at 70° C. for 16 hours. After addition of water, the reaction solution was extracted with Et$_2$O and purified by column chromatography to obtain the title compound (2.17 g, 51%).

$^1$H-NMR (CDCl$_3$) δ 7.60 (1H, t), 7.00 (1H, d), 6.79 (1H, d), 4.73 (2H, m)

Preparation Example 275: 2-chloro-6-(2,2,2-trifluoro-1-methyl-ethoxy)pyridine 1,1,1-Trifluoro-2-propanol (2.76 g, 24 mmol) was dissolved in 67 mL of THF. NaH (55 wt % in mineral oil, 1.06 g, 24 mmol) was added thereto, and the mixture was stirred at room temperature for 45 minutes. 2,6-Dichloropyridine (3.0 g, 20 mmol) was added thereto, and the mixture was stirred at 70° C. for 16 hours. After addition of water, the reaction solution was extracted with Et$_2$O and purified by column chromatography to obtain the title compound (3.58 g, 79%).

¹H-NMR (CDCl₃) δ 7.57 (1H, t), 6.97 (1H, d), 6.73 (1H, d), 5.72 (1H, m), 1.50 (3H, d)

Preparation Example 276:
2-butoxy-6-chloro-pyridine

Butan-1-ol (1.87 g, 25.2 mmol) was dissolved in 50 mL of DMF and cooled to 0° C. NaH (55 wt % in mineral oil, 1.10 g, 25.2 mmol) was added thereto, and the mixture was stirred at room temperature for 45 minutes. 2,6-dichloro-pyridine (3.55 g, 24.0 mmol) was added thereto, and the mixture was stirred for 16 hours. After addition of ammonium chloride aqueous solution, the reaction solution was extracted with Et₂O and purified by column chromatography to obtain the title compound (4.05 g, 91%).
¹H-NMR (CDCl₃) δ 7.50 (1H, t), 6.87 (1H, d), 6.63 (1H, d), 4.28 (2H, t), 1.74 (2H, m), 1.46 (2H, m), 0.97 (3H, t)

Preparation Example 277:
2-chloro-6-cyclobutyl-pyridine 2,6-Dichloropyridine (1.98 g, 13.4 mmol) and Fe(acac)₃ (0.24 g, 0.67 mmol) were dissolved in 49 mL of THF and 5 mL of NMP, and cooled to 0° C. Cyclobutylmagnesium bromide (0.9 M THF solution, 18 mL, 16 mmol) was slowly added thereto, and the mixture was stirred at 0° C. for 6 hours. After termination of the reaction by the addition of ammonium chloride aqueous solution, the reaction solution was extracted with Et₂O. The organic layer was dried with anhydrous magnesiumsulfate and purified by column chromatography to obtain the title compound (0.43 g, 19%).
¹H-NMR (CDCl₃) δ 7.54 (1H, t), 7.12 (1H, d), 7.08 (1H, d), 3.63 (1H, m), 2.33 (4H, m), 2.05 (1H, m), 1.90 (1H, m)

Preparation Example 278:
2-bromo-6-(cyclobutylidenemethyl)pyridine 35 mL of THF was added to 2-bromo-6-(diethoxyphosphorylmethyl)pyridine (2.2 g, 7.14 mmol), and the mixture was cooled to 0° C. LiHMDS (1.0 M THF solution, 8.6 mL, 8.6 mmol) was added thereto, and the mixture was stirred at 0° C. for 30 minutes. Cyclobutanone (0.50 g, 7.14 mmol) was added thereto, and the mixture was stirred at room temperature for 16 hours. After addition of ammonium chloride aqueous solution, the reaction solution was extracted with EtOAc and purified by column chromatography to obtain the title compound (1.02 g, 64%).
¹H-NMR (CDCl₃) δ 7.42 (1H, t), 7.20 (1H, d), 7.04 (1H, d), 6.19 (1H, m), 3.13 (2H, m), 2.91 (2H, m), 2.14 (2H, m)

Preparation Example 279:
2-bromo-6-(cyclopentylidenemethyl)pyridine 35 mL of THF was added to 2-bromo-6-(diethoxyphosphorylmethyl)pyridine (2.2 g, 7.14 mmol), and the mixture was cooled to 0° C. LiHMDS (1.0 M THF solution, 8.6 mL, 8.6 mmol) was added thereto, and the mixture was stirred at 0° C. for 30 minutes. Cyclopentanone (0.6 g, 7.14 mmol) was added thereto, and the mixture was stirred at room temperature for 16 hours. After addition of ammonium chloride aqueous solution, the reaction solution was extracted with EtOAc and purified by column chromatography to obtain the title compound (1.17 g, 69%).
¹H-NMR (CDCl₃) δ 7.43 (1H, t), 7.20 (1H, d), 7.13 (1H, d), 6.41 (1H, m), 2.73 (2H, m), 2.52 (2H, m), 1.81 (2H, m), 1.68 (2H, m)

Preparation Example 280:
1-bromo-3-(cyclopropylmethoxy)benzene

3-Bromophenol (0.865 g, 5.0 mmol) and bromomethylcyclopropane (1.01 g, 7.5 mmol) were reacted in the same manner as in Preparation Example 12 to obtain the title compound (1.09 g, 96%).
¹H-NMR (CDCl₃) δ 7.13 (1H, m), 7.06 (2H, m), 6.88 (1H, m), 3.82 (2H, d), 1.28 (1H, m), 0.65 (2H, m), 0.35 (2H, m)

Preparation Example 281:
1-bromo-3-(cyclobutoxy)benzene

3-Bromophenol (0.865 g, 5.0 mmol) and bromocyclobutane (1.01 g, 7.5 mmol) were reacted in the same manner as in Preparation Example 12 to obtain the title compound (1.04 g, 91%).
¹H-NMR (CDCl₃) δ 7.10 (1H, t), 7.05 (1H, m), 6.95 (1H, m), 6.74 (1H, m), 4.60 (1H, m), 2.44 (2H, m), 2.14 (2H, m), 1.85 (1H, m), 1.69 (1H, m)

Preparation Example 282:
4-bromo-2-(cyclopropylmethoxy)-1-methoxy-benzene 20 mL of DMF was added to 5-bromo-2-methoxy-phenol (1.8 g, 8.87 mmol), bromomethylcyclopropane (1.44 g, 10.7 mmol), K₂CO₃ (1.84 g, 13.3 mmol) and Bu₄NI (0.33 g, 0.88 mmol), and the mixture was stirred at 80° C. After termination of the reaction, the reaction solution was cooled to room temperature. After addition of water, the reaction solution was extracted with EtOAc. The organic layer was dried with anhydrous magnesium sulfate and purified by column chromatography to obtain the title compound (2.21 g, 97%).
¹H-NMR (CDCl₃) δ 7.02 (1H, m), 6.97 (1H, d), 6.74 (1H, d), 3.85 (3H, s), 3.82 (2H, d), 1.33 (1H, m), 0.65 (2H, m), 0.35 (2H, m)

Preparation Example 283:
4-bromo-2-(cyclopropylmethoxy)-1-fluoro-benzene

5-Bromo-2-fluoro-phenol (0.955 g, 5.0 mmol) and bromomethylcyclopropane (0.81 g, 6.0 mmol) were reacted in the same manner as in Preparation Example 12 to obtain the title compound (1.22 g, 99%).
¹H-NMR (CDCl₃) δ 7.06 (1H, m), 6.95 (2H, m), 3.85 (2H, d), 1.30 (1H, m), 0.66 (2H, m), 0.36 (2H, m)

Preparation Example 284:
1-bromo-3-(cyclobutoxy)-5-fluoro-benzene

3-Bromo-5-fluoro-phenol (0.955 g, 5.0 mmol) and bromocyclobutane (0.81 g, 6.0 mmol) were reacted in the same manner as in Preparation Example 12 to obtain the title compound (1.19 g, 97%).
¹H-NMR (CDCl₃) δ 6.84 (1H, m), 6.76 (1H, m), 6.46 (1H, m), 4.57 (1H, m), 2.44 (2H, m), 2.15 (2H, m), 1.88 (1H, m), 1.70 (1H, m)

Preparation Example 285:
1-bromo-3-cyclobutylsulfonyl-benzene 20 mL of THF and 20 mL of MeOH were added to 1-bromo-3-cyclobutylsulfanyl-benzene (0.73 g, 3.0 mmol) obtained in Preparation Example 293. Oxone (9.2 g, 30 mmol) dissolved in 40 mL of water was added thereto, and the mixture was stirred at room temperature for 5 hours.

After termination of the reaction, water was added thereto, and the reaction solution was extracted with EtOAc. The organic layer was dried with anhydrous magnesium sulfate and purified by column chromatography to obtain the title compound (0.81 g, 98%).

$^1$H-NMR (CDCl$_3$) δ 8.01 (1H, d), 7.79 (2H, m), 7.44 (1H, t), 3.85 (1H, m), 2.60 (2H, m), 2.20 (2H, m), 1.98 (2H, m)

Preparation Example 286:
1-bromo-3-(isopropoxymethyl)benzene 10 mL of 2-propanol and iron(II) sulfate heptahydrate (2.78 g, 6 mmol) were added to 1-bromo-3-(bromomethyl)benzene (2.5 g, 10 mmol), and the mixture was stirred for 36 hours under reflux. Solids were filtered through Celite and purified by column chromatography to obtain the title compound (1.5 g, 65%).

$^1$H-NMR (CDCl$_3$) δ 7.50 (1H, m), 7.39 (1H, m), 7.27 (1H, m), 7.19 (1H, t), 4.47 (2H, s), 3.67 (1H, m), 1.22 (6H, d)

Preparation Example 287:
1-bromo-3-(ethoxymethyl)benzene 10 mL of EtOH and iron(II) sulfate heptahydrate (2.78 g, 6 mmol) were added to 1-bromo-3-(bromomethyl)benzene (2.5 g, 10 mmol) and the mixture was stirred for 36 hours under reflux. Solids were filtered through Celite and purified by column chromatography to obtain the title compound (1.54 g, 71%).

$^1$H-NMR (CDCl$_3$) δ 7.50 (1H, m), 7.40 (1H, m), 7.26 (1H, m), 7.21 (1H, t), 4.47 (2H, s), 3.53 (2H, q), 1.26 (3H, t)

Preparation Example 288:
1-bromo-3-(cyclobutoxy)-2-methyl-benzene

Step A: 3-bromo-2-methyl-phenol 31 mL of 1N sulfuric acid aqueous solution was added to 3-bromo-2-methyl-aniline (4.04 g, 21.7 mmol), and the mixture was cooled to 0° C. Sodium nitrite (6.0 M aqueous solution, 4.3 mL) was slowly added thereto. After 15 minutes, 10 mL of sulfuric acid was added thereto, and the mixture was stirred for 1 hour under reflux. The reaction solution was cooled to room temperature. After addition of water, the reaction solution was extracted with Et$_2$O. The organic layer was dried with anhydrous magnesium sulfate and purified by column chromatography to obtain the title compound (2.34 g, 58%).

$^1$H-NMR (CDCl$_3$) δ 7.14 (1H, d), 6.92 (1H, t), 6.71 (1H, d), 4.83 (1H, brs), 2.34 (3H, s)

Step B: 1-bromo-3-(cyclobutoxy)-2-methyl-benzene

3-Bromo-2-methyl-phenol (0.2 g, 1 mmol) obtained in Step A was dissolved in 3.6 mL of DMF. Bromocyclobutane (0.17 g, 1.28 mmol) and Cs$_2$CO$_3$ (0.7 g, 2.14 mmol) were added thereto, and the mixture was stirred at 50° C. for 24 hours. The reaction solution was concentrated under reduced pressure and purified by column chromatography to obtain the title compound (0.2 g, 83%).

$^1$H-NMR (CDCl$_3$) δ 7.12 (1H, d), 6.95 (1H, t), 6.61 (1H, d), 4.60 (1H, m), 2.44 (2H, m), 2.30 (3H, s), 2.16 (2H, m), 1.86 (1H, m), 1.69 (1H, m)

Preparation Example 289:
4-bromo-2-(cyclobutoxy)thiazole

Cyclobutanol (0.065 g, 0.9 mmol) was dissolved in 8 mL of THF. NaH (55 wt % in mineral oil, 0.04 g, 0.9 mmol) was added thereto, and the mixture was stirred at room temperature for 30 minutes. 2,4-Dibromothiazole (0.2 g, 0.82 mmol) was added thereto, and the mixture was stirred for 16 hours. After addition of ammonium chloride aqueous solution, the reaction solution was extracted with EtOAc and purified by column chromatography to obtain the title compound (0.13 g, 68%).

$^1$H-NMR (CDCl$_3$) δ 6.56 (1H, s), 5.17 (1H, m), 2.48 (2H, m), 2.20 (2H, m), 1.84 (1H, m), 1.65 (1H, m)

Preparation Example 290:
4-bromo-2-(cyclopropylmethoxy)thiazole

Cyclopropylmethanol (0.14 g, 2.0 mmol) was dissolved in 16 mL of THF. NaH (55 wt % in mineral oil, 0.086 g, 2.0 mmol) was added thereto, and the mixture was stirred at room temperature for 30 minutes. 2,4-Dibromothiazole (0.4 g, 1.64 mmol) was added thereto, and the mixture was stirred for 24 hours. After addition of ammonium chloride aqueous solution, the reaction solution was extracted with Et$_2$O and purified by column chromatography to obtain the title compound (0.23 g, 60%).

$^1$H-NMR (CDCl$_3$) δ 6.57 (1H, s), 4.25 (2H, d), 1.30 (1H, m), 0.65 (2H, m), 0.37 (2H, m)

Preparation Example 291: 4-bromo-3-(cyclopropyl-methoxymethyl)-5-methyl-isoxazole Step A:
3-(cyclopropylmethoxymethyl)-5-methyl-isoxazole 5-Methylisoxazol-3-carboxylic acid methyl ester (1.5 g, 10.5 mmol) was dissolved in 27 mL of EtOH. NaBH$_4$ (0.8 g, 21 mmol) was slowly added thereto, and the mixture was stirred at room temperature for 16 hours. The reaction solution was neutralized by the addition of HCl aqueous solution, extracted with EtOAc and dried with anhydrous magnesium sulfate for concentration. The obtained concentrate was dissolved in 20 mL of DCM. 1.4 mL of SOCl$_2$ was added thereto, and the mixture was stirred at room temperature for 16 hours and concentrated. The mixed solution of cyclopropylmethanol (0.31 g, 4.2 mmol), NaH (55 wt % in mineral oil, 0.19 g, 4.2 mmol) and DMF (20 mL) was added thereto, and the mixture was stirred at room temperature for 72 hours. The reaction solution was concentrated under reduced pressure. After addition of ammonium chloride aqueous solution, the reaction solution was extracted with EtOAc and purified by column chromatography to obtain the title compound (0.074 g, 4%).

$^1$H-NMR (CDCl$_3$) δ 6.05 (1H, s), 4.56 (2H, s), 3.31 (2H, d), 2.42 (3H, s), 1.07 (1H, m), 0.55 (2H, m), 0.21 (2H, m)

Step B: 4-bromo-3-(cyclopropylmethoxymethyl)-5-methyl-isoxazole 3-(Cyclopropylmethoxymethyl)-5-methyl-isoxazole (0.074 g, 0.44 mmol) obtained in Step A was dissolved in 1.5 mL of DMF. N-bromosuccinimide (0.078 g, 0.44 mmol) was added thereto, and the mixture was stirred at room temperature for 48 hours. The reaction solution was concentrated under reduced pressure. After addition of water, the reaction solution was extracted with Et$_2$O and purified by column chromatography to obtain the title compound (0.069 g, 55%).

$^1$H-NMR (CDCl$_3$) δ 4.57 (2H, s), 3.35 (2H, d), 2.42 (3H, s), 1.10 (1H, m), 0.54 (2H, m), 0.23 (2H, m)

Preparation Example 292: 4-bromo-5-(cyclobutoxy)-3-methyl-isothiazole

Cyclobutanol (0.32 g, 4.4 mmol) and 4,5-dibromo-3-methyl-isothiazole (1.03 g, 4.0 mmol, WO2013 132376A1) were reacted in the same manner as in Preparation Example 226 to obtain the title compound (0.120 g, 12%).
$^1$H-NMR (CDCl$_3$) δ 4.68 (1H, m), 2.52 (2H, m), 2.45 (3H, s), 2.35 (2H, m), 1.94 (1H, m), 1.72 (1H, m)

Preparation Example 293: 1-bromo-3-cyclobutylsulfanyl-benzene

3-Bromo-benzenethiol (3 g, 15.87 mmol) and bromocyclobutane (2.25 mL, 23.80 mmol) were reacted in the same manner as in Preparation Example 17 to obtain the title compound (3.36 g, 87%).
$^1$H-NMR (CDCl$_3$) δ 7.33 (1H, s), 7.26 (1H, m), 7.12 (2H, m), 3.89 (1H, m), 2.47 (2H, m), 2.07 (3H, m), 2.04 (1H, m).

Preparation Example 294: 4-(4,4,5,5-tetramethyl-[1,3,2]dioxaborolan-2-yl)-phenylamine 4-Bromo-phenylamine (1 g, 5.81 mmol), bis(pinacolato)diboron (1.6 g, 6.39 mmol) and potassium acetate (1.43 g, 14.53 mmol) were dissolved in 20 mL of 1,4-dioxane and charged with N$_2$ gas for 5 minutes. PdCl$_2$(dppf)-DCM (0.425 g, 0.58 mmol) was added thereto, and the mixture was stirred at 80° C. for 16 hours. The reaction solution was filtered through Celite, diluted with water and extracted with ethyl acetate. The organic layer was dried with anhydrous magnesiumsulfate and purified by column chromatography to obtain the title compound (0.764 g, 60%).
$^1$H-NMR (CDCl$_3$) δ 7.60 (2H, d), 6.66 (2H, d), 3.82 (2H, br), 1.31 (12H, s).

Preparation Example 295: 4-(6-cyclobutoxy-pyridin-2-yl)-phenylamine

2-Bromo-6-cyclobutoxy-pyridine (0.251 g, 1.37 mmol) obtained in Preparation Example 186 and 4-(4,4,5,5-tetramethyl-[1,3,2]dioxaborolan-2-yl)-phenylamine (0.2 g, 0.91 mmol) obtained in Preparation Example 294 were reacted in the same manner as in Step A of Example 1 to obtain the title compound (0.17 g, 77%).
$^1$H-NMR (CDCl$_3$) δ 7.85 (2H, d), 7.55 (1H, t), 7.21 (1H, d), 6.72 (2H, d), 6.51 (1H, d), 5.26 (1H, m), 3.79 (2H, br), 2.51 (2H, m), 2.18 (2H, m), 1.86 (1H, m), 1.72 (1H, m).

Preparation Example 296: 4-(6-cyclobutoxy-pyridin-2-yl)-phenyl]-[3-(4-methoxy-phenoxy)-isoxazol-5-ylmethyl]-amine 4-(6-Cyclobutoxy-pyridin-2-yl)-phenylamine (0.17 g, 0.71 mmol) obtained in Preparation Example 295 and 3-[(4-methoxyphenyl)methoxy]isoxazol-5-carbaldehyde (0.122 g, 0.71 mmol) obtained in Preparation Example 61 were dissolved in 2.3 mL of DCE. Sodium triacetoxyborohydride (0.225 g, 1.06 mmol) was added thereto, and the mixture was stirred at room temperature for 16 hours. After addition of sodium bicarbonate aqueous solution, the reaction solution was extracted with DCM and purified by column chromatography. The obtained compound was dissolved in 2 ml of methanol. NaBH$_4$ (0.053 g, 1.41 mmol) was added thereto, and the mixture was stirred at room temperature for 16 hours. The reaction solution was diluted with water and extracted with ethyl acetate. The organic layer was dried with anhydrous magnesiumsulfate and purified by column chromatography to obtain the title compound (0.1 g, 30%).
$^1$H-NMR (CDCl$_3$) δ 7.87 (2H, d), 7.54 (1H, t), 7.34 (2H, d), 7.20 (1H, d), 6.90 (2H, d), 6.69 (2H, d), 6.53 (1H, d), 5.81 (1H, s), 5.25 (1H, m), 4.40 (2H, d), 3.80 (3H, s), 2.52 (2H, m), 2.18 (2H, m), 1.83 (1H, m), 1.72 (1H, m).

Preparation Example 297: 1-bromo-3-(cyclopentoxy)benzene

The title compound was obtained by the method disclosed in WO 2014/209034 A1.
$^1$H NMR (CDCl$_3$) δ 7.11 (1H, t), 7.02 (2H, m), 6.80 (1H, dd), 4.72 (1H, m), 1.94-1.73 (6H, m), 1.62 (2H, m)

Preparation Example 298: 3,6-dichloro-2-cyclobutoxy-pyridine

Step A: 6-chloro-2-cyclobutoxy-3-nitro-pyrimidine 2,6-Dichloro-3-nitro-pyrimidine (1.93 g, 10.0 mmol) and cyclobutanol (0.645 g, 9.0 mmol) were reacted in the same manner as in Preparation Example 227 to obtain the title compound (1.92 g, 93%).
$^1$H-NMR (CDCl$_3$) δ 8.27 (1H, d), 7.04 (2H, t), 5.39 (1H, m), 2.56 (2H, m), 2.30 (2H, m), 1.93 (1H, m), 1.78 (1H, m)

Step B: 3,6-dichloro-2-cyclobutoxy-pyrimidine

Methanol (60 mL) was added to nickel(II) chloride hexahydrate (NiCl$_2$ 6H$_2$O)(1.0 g, 4.21 mmol), and sodium borohydride (0.30 g, 7.93 mmol) was then added thereto little by little. The mixture was stirred for 30 minutes, and 6-chloro-2-cyclobutoxy-3-nitro-pyrimidine (1.92 g, 8.40 mmol) obtained in Step A was added thereto. Sodium borohydride (0.65 g, 17.2 mmol) was slowly added thereto for 10 minutes, and the mixture was stirred for 30 minutes. The reaction product was filtered through Celite, and the filtrate was concentrated under reduced pressure and extracted with water and EtOAc. The organic layer was dried with anhydrous magnesiumsulfate and purified by column chromatography to obtain 6-chloro-2-cyclobutoxy-pyridin-3-ylamine (1.37 g, 82%).
6-Chloro-2-cyclobutoxy-pyridin-3-ylamine (0.60 g, 3.0 mmol), copper chloride(II) (0.484 g, 3.6 mmol) and tBuONO (0.464 g, 4.5 mmol) were reacted in the same manner as in Step C of Preparation Example 84 to obtain the title compound (0.341 g, 52%).
$^1$H-NMR (CDCl$_3$) δ 7.58 (1H, d), 6.87 (1H, d), 5.26 (1H, m), 2.53 (2H, m), 2.24 (2H, m), 1.88 (1H, m), 1.74 (1H, m)

Preparation Example 299: 2-chloro-6-cyclobutylsulfanyl-pyridine

The title compound was obtained by the method disclosed in WO 2014/209034 A1.
$^1$H NMR (CDCl$_3$) δ 7.40 (1H, t), 6.98 (2H, m), 4.30 (1H, m), 2.56 (2H, m), 2.08 (4H, m)

Preparation Example 300: 2-chloro-6-cyclopropylmethoxy-4-methyl-pyridine

Cyclopropylmethanol (0.979 g, 13.58 mmol) and 2,6-dichloro-4-methyl-pyridine (2 g, 12.34 mmol) were reacted in the same manner as in Preparation Example 226 to obtain the title compound (1.62 g, 66%).

¹H-NMR (CDCl₃) δ 6.75 (1H, s), 6.43 (1H, s), 5.18 (1H, m), 2.48 (2H, m), 2.30 (3H, s), 2.14 (2H, m), 1.84 (1H, m), 1.68 (1H, m).

Preparation Example 301:
2-chloro-6-isopropoxy-pyrazine

Isopropanol (1.85 ml, 24.16 mmol) and 2,6-dichloropyrazine (3 g, 20.13 mmol) were reacted in the same manner as in Preparation Example 226 to obtain the title compound (2.77 g, 79%).
¹H-NMR (CDCl₃) δ 8.04-8.09 (2H, d), 5.28 (1H, m), 1.36 (6H, d).

Preparation Example 302:
2-chloro-6-ethoxy-pyrazine

Ethanol (1.17 ml, 24.16 mmol) and 2,6-dichloropyrazine (3 g, 20.13 mmol) were reacted in the same manner as in Preparation Example 226 to obtain the title compound (2.63 g, 82%).
¹H-NMR (CDCl₃) δ 8.12 (2H, d), 4.39 (2H, q), 1.40 (3H, t).

Preparation Example 303: {(R)-1-[2,6-difluoro-4-(4,4,5,5-tetramethyl-[1,3,2]dioxaborolan-2-yl)-phenyl]-pyrrolidin-3-yl}-acetic acid methyl ester Step A: 2-((R)-1-tert-butoxycarbonyl-pyrrolidin-3-yl)-malonic acid diethyl ester (R)-3-hydroxy-pyrrolidin-1-carboxylic acid tert-butyl ester (1 g, 5.34 mmol) was dissolved in 18 mL of MC. Et₃N (2.22 ml, 16.02 mmol) was added thereto at 0° C., and MsCl (0.62 ml, 8.01 mmol) was then added thereto. The mixture was stirred at room temperature for 16 hours. The reaction solution was diluted with water and extracted with MC. The organic layer was dried with anhydrous magnesiumsulfate and purified by column chromatography to obtain (R)-3-methanesulfonyloxy-pyrrolidin-1-carboxylic acid tert-butyl ester. At another flask, diethyl malonate (1.7 ml, 11.3 mmol) was dissolved in 10 ml of ethanol. NaOEt (21% wt, 4.2 ml, 11.3 mmol) was added thereto, and the mixture was stirred at 40° C. for 1 hour. The obtained (R)-3-methanesulfonyloxy-pyrrolidin-1-carboxylic acid tert-butyl ester (1.5 g, 5.65 mmol) was dissolved in 8 ml of ethanol and added thereto. The mixture was stirred at 80° C. for 16 hours. The reaction solution was adjusted to pH 2 by the use of 6N HCl aqueous solution and extracted with ether. The organic layer was dried with anhydrous magnesiumsulfate and purified by column chromatography to obtain the title compound (0.785 g, 44%).
¹H-NMR (CDCl₃) δ 4.21 (4H, m), 3.63 (1H, m), 3.47 (1H, m), 3.25 (2H, m), 3.01 (1H, m), 2.80 (1H, m), 2.06 (1H, m), 1.62 (1H, m), 1.42 (9H, s), 1.26 (6H, m).

Step B:
(R)-3-carboxymethyl-pyrrolidin-1-carboxylic acid tert-butyl ester 2-((R)-1-tert-butoxycarbonyl-pyrrolidin-3-yl)-malonic acid diethyl ester (0.785 g, 2.38 mmol) obtained in Step A was dissolved in 8 mL of THF. 6N NaOH (2 ml, 11.9 mmol) was added thereto, and the mixture was stirred at 40° C. for 16 hours. The reaction solution was adjusted to pH 2 by the use of 6N HCl aqueous solution and extracted with EtOAc. The organic layer was dried with anhydrous magnesiumsulfate and concentrated under reduced pressure to obtain 2-((R)-1-tert-butoxycarbonyl-pyrrolidin-3-yl)-malonic acid. The obtained compound was dissolved in 4.5 ml of toluene. 0.06 ml of DMSO was added thereto, and the mixture was stirred for 4 hours under reflux. After addition of 10% citric acid, the reaction solution was extracted with EtOAc. The organic layer was dried with anhydrous magnesiumsulfate and purified by column chromatography to obtain the title compound (0.29 g, 53%).
¹H-NMR (CDCl₃) δ 3.62 (1H, m), 3.45 (1H, m), 3.29 (1H, m), 2.96 (1H, m), 2.56 (1H, m), 2.44 (2H, d), 2.07 (1H, m), 1.57 (1H, m), 1.44 (9H, s).

Step C: (R)-1-(2,6-difluoro-4-nitro-phenyl)-pyrrolidin-3-yl-acetic acid methyl ester (R)-3-carboxymethyl-pyrrolidin-1-carboxylic acid tert-butyl ester (0.29 g, 1.26 mmol) obtained in Step B was dissolved in 10 ml of MC. 0.25 M CH₂N₂ (10 ml, 2.53 mmol) was was added thereto at 0° C., and the mixture was stirred at room temperature for 3 hours. The reaction solution was concentrated under reduced pressure to obtain (R)-3-methoxycarbonylmethyl-pyrrolidin-1-carboxylic acid tert-butyl ester. The obtained compound was dissolved in 5 ml of MC. HCl (1.58 mL, 6.32 mmol, 4 M 1,4-dioxane solution) was added thereto at 0° C., and the mixture was stirred at room temperature for 2 hours. The reaction solution was concentrated under reduced pressure to obtain hydrochloric acid salt of (R)-pyrrolidin-3-yl-acetic acid methyl ester. The obtained compound and 3,4,5-trifluoronitrobenzene (0.163 ml, 1.42 mmol) were reacted in the same manner as in Step A of Preparation Example 84 to obtain the title compound (0.38 g, 98%).
¹H-NMR (CDCl₃) δ 7.73 (2H, m), 3.91-3.75 (3H, m), 3.71 (3H, s), 3.48 (1H, m), 2.64 (1H, m), 2.48 (2H, m), 2.18 (1H, m), 1.65 (1H, m).

Step D: [(R)-1-(4-amino-2,6-difluoro-phenyl)-pyrrolidin-3-yl]-acetic acid methyl ester (R)-1-(2,6-difluoro-4-nitro-phenyl)-pyrrolidin-3-yl]-acetic acid methyl ester (0.38 g, 1.26 mmol) obtained in Step C was dissolved in 4 mL of EtOAc. 0.04 g of 10 wt % Pd/C was added thereto, and the mixture was stirred for 24 hours under hydrogen atmosphere. Solids were filtered and concentrated under reduced pressure to obtain the title compound (0.315 g, 92%).
¹H-NMR (CDCl₃) δ 6.17 (2H, m), 3.66 (3H, s), 3.41 (1H, m), 3.28 (2H, m), 2.98 (1H, m), 2.66 (1H, m), 2.45 (2H, m), 2.13 (1H, m), 1.60 (1H, m).

Step E: [(R)-1-(4-bromo-2,6-difluoro-phenyl)-pyrrolidin-3-yl]-acetic acid methyl ester

[(R)-1-(4-amino-2,6-difluoro-phenyl)-pyrrolidin-3-yl]-acetic acid methyl ester (0.315 g, 1.16 mmol) obtained in Step D was dissolved in 3 mL of CH₃CN. CSA (0.345 g, 1.40 mmol), tert-butyl nitrite (0.166 mL, 1.40 mmol), TBAB (0.751 g, 2.33 mmol) and CuBr₂ (0.003 g, 0.01 mmol) were added thereto, and the mixture was stirred at room temperature for 16 hours. Solids were filtered and concentrated under reduced pressure. After addition of water, the reaction solution was extracted with EtOAc. The organic layer was dried with anhydrous magnesiumsulfate and purified by column chromatography to obtain the title compound (0.2 g, 51%).

¹H-NMR (CDCl₃) δ 6.93 (2H, m), 3.68 (3H, s), 3.59 (2H, m), 3.47 (1H, m), 3.23 (1H, m), 2.61 (1H, m), 2.45 (2H, m), 2.11 (1H, m), 1.59 (1H, m).

Step F: {(R)-1-[2,6-difluoro-4-(4,4,5,5-tetramethyl-[1,3,2]dioxaborolan-2-yl)-phenyl]-pyrrolidin-3-yl}-acetic acid methyl ester

[(R)-1-(4-bromo-2,6-difluoro-phenyl)-pyrrolidin-3-yl]-acetic acid methyl ester (0.225 g, 0.67 mmol) obtained in Step E was reacted in the same manner as in Preparation Example 294 to obtain the title compound (0.09 g, 33%).
¹H-NMR (CDCl₃) δ 7.16 (2H, m), 3.71 (5H, m), 3.60 (1H, m), 3.32 (1H, m), 2.61 (1H, m), 2.44 (2H, d), 2.11 (1H, m), 1.61 (1H, m), 1.30 (12H, s)

Preparation Example 304: 3-[8-fluoro-6-(4,4,5,5-tetramethyl-1,3,2-dioxaborolan-2-yl)thiochroman-2-yl]propanoic acid ethyl ester Step A: 4-bromo-2-fluoro-benzenethiol The title compound was obtained by the method disclosed in WO 2006/21759 A1.
¹H NMR (CDCl₃) δ 7.24 (2H, m), 7.16 (2H, m), 3.58 (1H, s)

Step B: 6-bromo-8-fluoro-4-oxo-thiochroman-2-carboxylic acid

4-Bromo-2-fluoro-benzenethiol (3.0 g, 14.48 mmol) and furan-2,5-dione (1.4 g, 14.48 mmol) were dissolved in 50 mL of toluene and heated to 50° C. TEA (0.1 ml) was slowly added thereto, and the mixture was stirred at 50° C. for 1 hour. The reaction solution was concentrated under reduced pressure, dissolved in 50 mL of DCM and cooled to 0° C. AlCl₃ (2.9 g, 21.73 mmol) was added thereto, and the mixture was stirred at room temperature for 1 hour. After slowly adding cold concentrated HCl solution dropwise, the reaction solution was extracted with DCM. The organic solvent was dried with MgSO₄, concentrated under reduced pressure and solidified with Et₂O to obtain the title compound (2.3 g, 52%).
¹H-NMR (DMSO-d₆) δ 7.89 (2H, m), 4.55 (1H, t), 3.14 (2H, m)

Step C: 6-bromo-8-fluoro-4-oxo-thiochroman-2-carboxylic acid methyl ester

6-Bromo-8-fluoro-4-oxo-thiochroman-2-carboxylic acid (2.3 g, 7.54 mmol) obtained in Step B was dissolved in 50 mL of methanol. Concentrated sulfuric acid (0.8 mL) was added thereto, and the mixture was stirred for 18 hours under reflux. The reaction solution was concentrated under reduced pressure, extracted with EtOAc, dried with MgSO₄ and purified by column chromatography to obtain the title compound (1.5 g, 62%).
¹H-NMR (CDCl₃) δ 8.08 (1H, m), 7.37 (1H, dd), 4.15 (1H, t), 3.76 (3H, s), 3.18 (2H, d)

Step D: 6-bromo-8-fluoro-thiochroman-2-carboxylic acid methyl ester

6-Bromo-8-fluoro-4-oxo-thiochroman-2-carboxylic acid methyl ester (1.5 g, 4.70 mmol) obtained in Step C was dissolved in 20 mL of TFA. Triethylsilane (1.5 mL, 9.40 mmol) was added thereto, and the mixture was stirred at room temperature for 3 hours. The reaction solution was concentrated under reduced pressure, extracted with EtOAc, dried with MgSO₄ and purified by column chromatography to obtain the title compound (0.34 g, 24%).
¹H-NMR (CDCl₃) δ 7.06 (2H, m), 4.01 (1H, m), 3.78 (3H, s), 3.01-2.93 (1H, m), 2.84-2.77 (1H, m), 2.34-2.20 (2H, m)

Step E: 6-bromo-8-fluoro-thiochroman-2-carboxylic acid

6-Bromo-8-fluoro-thiochroman-2-carboxylic acid methyl ester (0.340 g, 1.11 mmol) obtained in Step D was dissolved in each 5 mL of THF, MeOH and 1N NaOH aqueous solution, and the mixture was stirred at room temperature for 2 hours. After removing of organic solvent, the reaction solution was adjusted to pH 3 by the use of 1N HCl aqueous solution and extracted with EtOAc to separate an organic layer. The organic layer was dried with MgSO₄ and concentrated under reduced pressure to obtain the title compound (0.280 g, 86%).

Step F: (6-bromo-8-fluoro-thiochroman-2-yl)-methanol

6-Bromo-8-fluoro-thiochroman-2-carboxylic acid (0.28 g, 0.96 mmol) obtained in Step E was dissolved in 10 mL of THF and cooled to −20° C. Isobutyl chloroformate (0.14 mL, 1.06 mmol) and NMM (0.12 mL, 1.10 mmol) was added thereto, and the mixture was stirred at the same temperature for 1.5 hours. At another reactor, NaBH₄ (0.073 g, 1.92 mmol) was dissolved in 4 mL of THF and 1 mL of MeOH and cooled to −78° C. The above reaction solution was filtered through Celite and added thereto. The mixture was stirred at room temperature for 2 hours. The reaction solution was extracted with EtOAc, dried with MgSO₄ and purified by column chromatography to obtain the title compound (0.175 g, 66%).
¹H-NMR (CDCl₃) δ 7.06 (2H, m), 3.77 (2H, m), 3.49 (1H, m), 2.90-2.73 (2H, m), 2.22 (1H, m), 1.88 (2H, m)

Step G: (E)-3-(6-bromo-8-fluoro-thiochroman-2-yl)prop-2-enoic acid ethyl ester

Oxalyl chloride (0.1 mL, 0.95 mmol) was added to 5 mL of DCM and cooled to −78° C. DMSO (0.11 ml, 1.57 mmol) was slowly added thereto, and the mixture was stirred for 0.5 hour. The solution in which (6-bromo-8-fluoro-thiochroman-2-yl)-methanol (0.175 g, 0.63 mmol) obtained in Step F was dissolved in 2 mL of DCM, and TEA (0.35 mL, 2.52 mmol) were sequentially added thereto, and the mixture was stirred at room temperature for 1 hour. (Carbethoxymethylene)triphenylphosphorane (0.263 g, 0.76 mmol) was added thereto, and the mixture was stirred at room temperature for 18 hours. After addition of water, the reaction solution was extracted with DCM to separate an organic layer. The organic layer was dried with MgSO₄ and purified by column chromatography to obtain the title compound (0.180 g, 83%).
¹H-NMR (CDCl₃) δ 7.06 (2H, m), 6.91 (1H, m), 6.03 (1H, d), 4.19 (2H, q), 4.01 (1H, m), 2.82 (2H, m), 2.28 (1H, m), 1.95 (1H, m), 1.28 (3H, t)

Step H: 3-(6-bromo-8-fluoro-thiochroman-2-yl)propanoic acid ethyl ester (E)-3-(6-bromo-8-fluoro-thiochroman-2-yl)-acetic acid ethyl ester (0.180 g, 0.52 mmol) obtained in Step G was dissolved in 10 mL of DME. p-Toluenesulfonyl hydrazide (0.680 g, 3.65 nmol) was added thereto little by little and heated to 90° C. Sodium acetate (0.427 g, 5.20 mmol, 1.4 M aqueous solution) was added thereto, and the mixture was stirred for 18 hours under reflux. After addition of water, the reaction solution was extracted with DCM. The organic layer was dried with MgSO$_4$ and purified by column chromatography to obtain the title compound (0.030 g, 17%).

$^1$H-NMR (CDCl$_3$) δ 7.02 (2H, m), 4.14 (2H, q), 3.29 (1H, m), 2.83 (2H, m), 2.49 (2H, m), 2.21 (1H, m), 2.03 (1H, m), 1.94 (1H, m), 1.78 (1H, m), 1.25 (3H, t)

Step I: 3-[8-fluoro-6-(4,4,5,5-tetramethyl-1,3,2-dioxaborolan-2-yl)thiochroman-2-yl]propanoic acid ethyl ester 3-(6-Bromo-8-fluoro-thiochroman-2-yl)-propionic acid ethyl ester (0.070 mg, 0.21 mmol) obtained in Step H was reacted in the same manner as in Step D of Preparation Example 1 to obtain the title compound (0.046 g, 57%).

$^1$H-NMR (CDCl$_3$) δ 7.27 (2H, m), 4.14 (2H, q), 3.30 (1H, m), 2.88 (2H, m), 2.51 (2H, m), 2.22 (1H, m), 2.00 (2H, m), 1.82 (1H, m), 1.32 (12H, s), 1.26 (3H, t)

Preparation Example 305:
1-iodo-2,3-dipropoxy-benzene 7 mL of DMF was added to 3-iodo benzene-1,2-diol (0.28 g, 1.18 mmol), 1-iodopropane (0.3 mL, 2.96 mmol) and K$_2$CO$_3$ (0.49 g. 3.54 mmol), and the mixture was stirred at 80° C. for 16 hours. The reaction solution was concentrated under reduced pressure and purified by column chromatography to obtain the title compound (0.24 g, 64%).

$^1$H-NMR (CDCl$_3$) δ 7.32 (1H, m), 6.85 (1H, m), 6.74 (1H, t), 3.94 (4H, m), 1.83 (4H, m), 1.07 (6H, m)

Preparation Example 306:
2-(cyclopropylmethoxy)-6-iodo-3-methoxy-pyridine

Step A: 2-bromo-6-iodo-3-methoxy-pyridine

The title compound was obtained by the method disclosed in WO 2006/21759 A1.

$^1$H-NMR (MeOH-d$_4$) δ 7.64 (1H, d), 7.08 (1H, d), 3.83 (3H, s)

Step B:
2-(cyclopropylmethoxy)-6-iodo-3-methoxy-pyridine

Cyclopropyl methanol (0.54 mL, 6.62 mmol) was dissolved in dry DMF (5 mL). NaH (60%)(0.248 g, 6.21 mmol) was slowly added dropwise thereto at 0° C., and the mixture was stirred for 30 minutes. 2-Bromo-6-iodo-3-methoxy-pyridine (1.3 g, 4.14 mmol) obtained in Step A was added thereto, and the mixture was stirred at room temperature for 16 hours. After addition of water, the reaction solution was extracted with EtOAc. The organic layer was purified by column chromatography to obtain the title compound (0.89 g, 70%).

$^1$H-NMR (CDCl$_3$) δ 7.20 (1H, d), 6.73 (1H, d), 4.19 (2H, d), 3.84 (3H, s), 1.31 (1H, m), 0.60 (2H, m), 0.38 (2H, m)

Preparation Example 307:
2-(cyclobutoxy)-6-iodo-3-methoxy-pyridine

2-Bromo-6-iodo-3-methoxy-pyridine (1.5 g, 4.78 mmol) and cyclobutanol (0.6 mL, 7.17 mmol) were reacted in the same manner as in Preparation Example 306 to obtain the title compound (0.92 g, 63%).

$^1$H-NMR (CDCl$_3$) δ 7.19 (1H, d), 6.72 (1H, d), 5.22 (1H, m), 3.83 (3H, s), 2.48 (2H, m), 2.21 (2H, m), 1.83 (1H, m), 1.67 (1H, m)

Preparation Example 308:
6-(cyclobutoxy)-1H-indole 1H-indol-6-ol (0.1 g, 0.75 mmol) and bromocyclobutane (0.203 g, 1.50 mmol) were reacted in the same manner as in Preparation Example 12 to obtain the title compound (0.068 g, 28%).

$^1$H-NMR (CDCl$_3$) δ 7.99 (1H, brs), 7.48 (1H, d), 7.07 (1H, m), 6.77 (1H, m), 6.73 (1H, m), 6.46 (1H, m), 4.66 (1H, m), 2.46 (2H, m), 2.20 (2H, m), 1.85 (1H, m), 1.70 (1H, m)

Preparation Example 309:
6-(cyclobutoxy)-1H-indazole 1H-indazol-6-ol (0.5 g, 3.72 mmol) and bromocyclobutane (0.7 mL, 1.50 mmol) were reacted in the same manner as in Preparation Example 12 to obtain the title compound (0.4 g, 57%).

$^1$H-NMR (CDCl$_3$) δ 10.07 (1H, brs), 7.96 (1H, m), 7.60 (1H, m), 6.78 (1H, m), 6.73 (1H, m), 4.68 (1H, m), 2.50 (2H, m), 2.22 (2H, m), 1.89 (1H, m), 1.74 (1H, m)

Preparation Example 310:
5-(cyclobutoxy)-1H-indole 1H-indol-5-ol (0.1 g, 0.75 mmol) and bromocyclobutane (0.203 g, 1.50 mmol) were reacted in the same manner as in Preparation Example 12 to obtain the title compound (0.021 g, 19%).

$^1$H-NMR (CDCl$_3$) δ 8.06 (1H, s), 7.27 (1H, m), 7.16 (1H, t), 7.00 (1H, m), 6.81 (1H, m), 6.45 (1H, m), 4.66 (1H, m), 2.47 (2H, m), 2.19 (2H, m), 1.85 (1H, m), 1.69 (1H, m)

Preparation Example 311:
6-(cyclopropylmethoxy)-1H-indole 1H-indol-6-ol (0.05 g, 0.38 mmol) and bromomethylcyclopropane (0.061 g, 0.45 mmol) were reacted in the same manner as in Preparation Example 12 to obtain the title compound (0.018 g, 24%).

$^1$H-NMR (CDCl$_3$) δ 7.99 (1H, s), 7.50 (1H, d), 7.09 (1H, m), 6.89 (1H, m), 6.81 (1H, m), 6.47 (1H, m), 3.83 (2H, d), 1.31 (1H, m), 0.64 (2H, m), 0.36 (2H, m)

Preparation Example 312:
2-chloro-4-(4-chloro-phenoxy)-pyrimidine 2,4-Dichloro-pyrimidine (1.16 g, 7.78 mmol) and 4-chloro-phenol (1.0 g, 7.78 mmol) were reacted in the same manner as in Preparation Example 226 to obtain the title compound (0.735 g, 39%).

$^1$H-NMR (CDCl$_3$) δ 8.45 (1H, d), 7.40 (2H, m), 7.10 (2H, m), 6.83 (1H, d)

Preparation Example 313:
2-chloro-4-phenoxy-pyrimidine 2,4-Dichloro-pyrimidine (1.6 g, 10.62 mmol) and phenol (1.0 g, 10.62 mmol) were reacted in the same manner as in Preparation Example 226 to obtain the title compound (1.9 g, 86%).

¹H-NMR (CDCl₃) δ 8.43 (1H, d), 7.46 (2H, m), 7.31 (1H, m), 7.15 (2H, m), 6.77 (1H, d)

Preparation Example 314:
2-chloro-4-(4-fluoro-phenoxy)-pyrimidine 2,4-Dichloro-pyrimidine (1.3 g, 8.92 mmol) and 4-fluoro-phenol (1.0 g, 8.92 mmol) were reacted in the same manner as in Preparation Example 226 to obtain the title compound (1.1 g, 55%).
¹H-NMR (CDCl₃) δ 8.44 (1H, d), 7.12 (4H, d), 6.81 (1H, d)

Preparation Example 315:
2-chloro-4-(4-pyridin-3-yloxy)-pyrimidine 2,4-Dichloro-pyrimidine (1.57 g, 10.51 mmol) and pyridin-3-ol (1.0 g, 10.51 mmol) were reacted in the same manner as in Preparation Example 226 to obtain the title compound (0.52 g, 24%).
¹H-NMR (CDCl₃) δ 8.56 (1H, dd), 8.53 (1H, d), 8.50 (1H, d), 7.57 (1H, m), 7.40 (1H, m), 6.93 (1H, d)

Preparation Example 316:
2-chloro-4-(4-fluoro-phenoxy)-pyrazine 2,6-Dichloro-pyrazine (1.3 g, 8.92 mmol) and 4-fluoro-phenol (1.0 g, 8.92 mmol) were reacted in the same manner as in Preparation Example 226 to obtain the title compound (1.1 g, 55%).
¹H-NMR (CDCl₃) δ 8.29 (2H, s), 7.12 (4H, m)

Preparation Example 317:
2-chloro-4-(4-methoxy-phenoxy)-pyrimidine 2,4-Dichloro-pyrimidine (1.2 g, 8.05 mmol) and 4-methoxy-phenol (1.0 g, 8.05 mmol) were reacted in the same manner as in Preparation Example 226 to obtain the title compound (1.5 g, 79%).
¹H-NMR (CDCl₃) δ 8.41 (1H, d), 7.07 (2H, m), 6.94 (2H, m), 6.74 (1H, d), 3.83 (3H, s)

Preparation Example 318:
2-chloro-4-(4-fluoro-phenoxy)-6-methyl-pyrimidine 2,4-Dichloro-6-methyl-pyrimidine (1.45 g, 8.92 mmol) and 4-fluoro-phenol (1.0 g, 8.92 mmol) were reacted in the same manner as in Preparation Example 226 to obtain the title compound (1.7 g, 80%).
¹H-NMR (CDCl₃) δ 7.11 (4H, m), 6.61 (1H, d)

Preparation Example 319:
2-chloro-4-p-tolyloxypyrimidine 2,4-Dichloro-pyrimidine (1.38 g, 9.24 mmol) and 4-methyl-phenol (1.0 g, 9.24 mmol) were reacted in the same manner as in Preparation Example 226 to obtain the title compound (1.4 g, 69%).
¹H-NMR (CDCl₃) δ 8.41 (1H, d), 7.24 (2H, m), 7.05 (2H, m), 6.75 (1H, d), 2.38 (3H, s)

Preparation Example 320:
2-chloro-4-(3,4-difluoro-phenoxy)-pyrimidine 2,4-Dichloro-pyrimidine (1.14 g, 7.69 mmol) and 3,4-difluoro-phenol (1.0 g, 7.69 mmol) were reacted in the same manner as in Preparation Example 226 to obtain the title compound (0.8 g, 43%).

¹H-NMR (CDCl₃) δ 8.47 (1H, d), 7.24 (1H, m), 7.04 (1H, m), 6.93 (1H, m), 6.85 (1H, d)

Preparation Example 321: 2-[2,6-difluoro-4-(4,4,5,5-tetramethyl-[1,3,2]dioxaborolan-2-yl)-phenoxymethyl]-cyclopropanecarboxylic acid ethyl ester 2,6-Difluoro-4-(4,4,5,5-tetramethyl-1,3,2-dioxaborolan-2-yl)phenol (0.2 g, 0.78 mmol) obtained in Step B of Preparation Example 16, 2-hydroxymethyl-cyclopropanecarboxylic acid ethyl ester (0.17 g, 1.17 mmol), triphenylphosphine (0.51 g, 1.95 mmol) and diisopropyl azodicarboxylate (0.39 g, 1.95 mmol) were reacted in the same manner as in Preparation Example 62 to obtain the title compound (0.25 g, 84%).
¹H-NMR (CDCl₃) δ 7.30 (2H, m), 4.13 (3H, m), 4.03 (1H, m), 1.86 (1H, m), 1.64 (1H, m), 1.32 (12H, s), 1.26 (4H, m), 0.93 (1H, m)

Preparation Example 322: 2-[2-chloro-6-fluoro-4-(4,4,5,5-tetramethyl-[1,3,2]dioxaborolan-2-yl)-phenoxymethyl]-cyclopropanecarboxylic acid ethyl ester 2-Chloro-6-fluoro-4-(4,4,5,5-tetramethyl-1,3,2-dioxaborolan-2-yl)phenol (0.75 g, 2.8 mmol), 2-hydroxymethyl-cyclopropanecarboxylic acid ethyl ester (0.48 g, 6.9 mmol), triphenylphosphine (1.80 g, 6.9 mmol) and diisopropyl azodicarboxylate (1.39 g, 6.9 mmol) were reacted in the same manner as in Preparation Example 62 to obtain the title compound (0.82 g, 75%).
¹H-NMR (CDCl₃) δ 7.58 (1H, s), 7.41 (1H, d), 4.13 (3H, m), 3.99 (1H, m), 1.89 (1H, m), 1.65 (1H, m), 1.32 (12H, s), 1.25 (4H, m), 0.95 (1H, m)

Preparation Example 323:
1-bromo-3-cyclobutylmethoxy-benzene

3-Bromo-phenol (1.2 g, 6.94 mmol), Cs₂CO₃ (4.52 g, 13.9 mmol) and bromomethyl-cyclobutane (0.86 mL, 7.63 mmol) were reacted in the same manner as in Preparation Example 28 to obtain the title compound (1.70 g, 99%).
¹H-NMR (CDCl₃) δ 7.12 (1H, m), 7.06 (2H, m), 6.83 (1H, m), 3.90 (2H, d), 2.76 (1H, m), 2.14 (2H, m), 1.96 (4H, m)

Preparation Example 324:
2-chloro-6-cyclobutylmethoxy-pyridine

6-Chloro-pyridin-2-ol (2.0 g, 15.4 mmol), K₂CO₃ (4.27 g, 30.1 mmol) and bromomethyl-cyclobutane (1.91 mL, 17.0 mmol) were reacted in the same manner as in Preparation Example 12 to obtain the title compound (2.30 g, 75%).
¹H-NMR (CDCl₃) δ 7.50 (1H, t), 6.87 (1H, d), 6.64 (1H, d), 4.26 (2H, d), 2.76 (1H, m), 2.12 (2H, m), 1.94 (4H, m)

Preparation Example 325:
2-bromo-4-cyclobutylmethoxy-1-methyl-benzene

3-Bromo-4-methyl-phenol (0.5 g, 2.67 mmol), Cs₂CO₃ (1.74 g, 5.35 mmol) and bromomethyl-cyclobutane (0.33 mL, 2.94 mmol) were reacted in the same manner as in Preparation Example 28 to obtain the title compound (0.65 g, 95%).
¹H-NMR (CDCl₃) δ 7.09 (2H, m), 6.76 (1H, m), 3.88 (2H, d), 2.76 (1H, m), 2.31 (3H, s), 2.13 (2H, m), 1.95 (4H, m)

Preparation Example 326:
4-bromo-1-chloro-2-cyclopropylmethoxy-benzene

5-Bromo-2-chloro-phenol (0.5 g, 2.41 mmol), Cs$_2$CO$_3$ (1.60 g, 4.82 mmol) and bromomethyl-cyclopropane (0.26 mL, 2.65 mmol) were reacted in the same manner as in Preparation Example 28 to obtain the title compound (0.60 g, 95%).

$^1$H-NMR (CDCl$_3$) δ 7.22 (1H, d), 7.02 (2H, m), 3.87 (2H, d), 1.32 (1H, m), 0.67 (2H, m), 0.40 (2H, m)

Preparation Example 327:
4-bromo-2-cyclopropylmethoxy-1-methyl-benzene

5-Bromo-2-methyl-phenol (0.5 g, 2.67 mmol), Cs$_2$CO$_3$ (1.70 g, 5.35 mmol) and bromomethyl-cyclopropane (0.29 mL, 2.94 mmol) were reacted in the same manner as in Preparation Example 28 to obtain the title compound (0.63 g, 98%).

$^1$H-NMR (CDCl$_3$) δ 6.97 (2H, m), 6.89 (1H, s), 3.79 (2H, d), 2.18 (3H, s), 1.26 (1H, m), 0.63 (2H, m), 0.35 (2H, m)

Preparation Example 328:
7-bromo-5-chloro-2-methyl-benzofuran

Step A: 2-bromo-4-chloro-1-prop-2-ynyloxy-benzene

2-Bromo-4-chloro-phenol (1.0 g, 4.82 mmol), 3-bromopropyne (0.79 g, 5.30 mmol) and K$_2$CO$_3$ (1.47 g, 10.6 mmol) were reacted in the same manner as in Preparation Example 12 to obtain the title compound (1.1 g, 93%).

$^1$H-NMR (CDCl$_3$) δ 7.55 (1H, d), 7.24 (1H, m), 6.99 (1H, d), 4.76 (2H, d), 2.55 (1H, t)

Step B: 7-bromo-5-chloro-2-methyl-benzofuran

2-Bromo-4-chloro-1-prop-2-ynyloxy-benzene (1.1 g, 4.48 mmol) obtained in Step A and cesium fluoride (0.95 g, 6.27 mmol) were dissolved in 7.5 mL of diethyl-phenyl-amine, and stirred at 210° C. for 4 hours. The reaction solution was cooled to room temperature and diluted with hexane. After washing with 1N HCl three times, the organic layer was separated. The organic layer was dried with MgSO$_4$ and purified by column chromatography to obtain the title compound (0.65 g, 59%).

$^1$H-NMR (CDCl$_3$) δ 7.37 (2H, d), 6.39 (1H, s), 2.49 (3H, s)

Preparation Example 329:
2-chloro-4-cyclobutoxy-5-fluoro-pyrimidine 2,4-Dichloro-5-fluoro-pyrimidine (0.50 g, 2.99 mmol) and cyclobutanol (0.26 ml, 3.29 mmol) were reacted in the same manner as in Preparation Example 226 to obtain the title compound (0.57 g, 89%).

$^1$H-NMR (400 MHz, CDCl$_3$); δ 8.17 (d, 1H), 5.37-5.29 (m, 1H), 2.55-2.48 (m, 2H), 2.30-2.20 (m, 2H), 1.94-1.86 (m, 1H), 1.77-1.67 (m, 1H)

Preparation Example 330:
2-chloro-4-cyclopropylmethoxy-5-fluoro-pyrimidine 2,4-Dichloro-5-fluoro-pyrimidine (0.50 g, 2.99 mmol) and cyclopropylmethanol (0.27 ml, 3.29 mmol) were reacted in the same manner as in Preparation Example 226 to obtain the title compound (0.52 g, 81%).

$^1$H-NMR (400 HMz, CDCl$_3$); δ 8.19-8.18 (d, 1H), 4.32-4.31 (d, 2H), 1.37-1.30 (m, 1H), 0.70-0.65 (m, 2H), 0.43-0.39 (m, 2H)

Preparation Example 331:
2-chloro-5-fluoro-4-isobutoxy-pyrimidine 2,4-Dichloro-5-fluoro-pyrimidine (0.50 g, 2.99 mmol) and 2-methyl-propan-1-ol (0.30 ml, 3.29 mmol) were reacted in the same manner as in Preparation Example 226 to obtain the title compound (0.51 g, 79%).

$^1$H-NMR (400 HMz, CDCl$_3$); δ 8.18 (d, 1H), 4.25-4.10 (d, 2H), 2.21-2.11 (m, 1H), 1.05-1.03 (d, 6H)

Preparation Example 332:
2-chloro-6-(3-methoxy-propoxy)-pyridine 2,6-Dichloropyridine (0.50 g, 3.38 mmol) and 3-methoxy-propan-1ol (0.40 ml, 4.05 mmol) were reacted in the same manner as in Preparation Example 226 to obtain the title compound (0.37 g, 51%).

$^1$H-NMR (400 HMz, CDCl$_3$); δ 8.18 (d, 1H), 4.25-4.10 (d, 2H), 2.21-2.11 (m, 1H), 1.05-1.03 (d, 6H)

Preparation Example 333:
2-chloro-6-(tetrahydro-thiopyran-4-yloxy)-pyridine 2,6-Dichloropyridine (0.50 g, 3.38 mmol) and tetrahydro-2H-thiopyran-4-ol (0.44 g, 3.72 mmol) were reacted in the same manner as in Preparation Example 226 to obtain the title compound (0.36 g, 44%).

$^1$H-NMR (400 HMz, CDCl$_3$); δ 8.18 (d, 1H), 4.25-4.10 (d, 2H), 2.21-2.11 (m, 1H), 1.05-1.03 (d, 6H)

Preparation Example 334:
2-chloro-5-fluoro-4-propoxy-pyrimidine 2,4-Dichloro-5-fluoro-pyrimidine (0.40 g, 2.40 mmol) and propan-1-ol (0.20 ml, 2.64 mmol) were reacted in the same manner as in Preparation Example 226 to obtain the title compound (0.35 g, 77%).

$^1$H-NMR (500 HMz, CDCl$_3$); δ 8.17-8.16 (d, 1H), 4.43-4.41 (t, 2H), 1.89-1.82 (m, 1H), 1.05-1.02 (t, 3H)

Preparation Example 335:
2-chloro-4-(3-methyl-butoxy)-pyrimidine 2,4-Dichloropyrimidine (0.50 g, 3.36 mmol) and 3-methylbutan-1-ol (0.40 ml, 3.69 mmol) were reacted in the same manner as in Preparation Example 226 to obtain the title compound (0.59 g, 87%).

$^1$H-NMR (500 HMz, CDCl$_3$); δ 8.27-8.25 (d, 1H), 6.63-6.62 (d, 1H), 4.41-4.39 (t, 2H), 1.80-1.75 (m, 1H), 1.70-1.65 (q, 2H), 0.96-0.94 (d, 6H)

Preparation Example 336:
2-chloro-4-(3-methoxy-propoxy)-pyrimidine 2,4-Dichloropyrimidine (0.50 g, 3.36 mmol) and 3-methoxypropan-1-ol (0.35 ml, 3.69 mmol) were reacted in the same manner as in Preparation Example 226 to obtain the title compound (0.34 g, 50%).

$^1$H-NMR (500 HMz, CDCl$_3$); δ 8.28-8.27 (d, 1H), 6.65-6.64 (d, 1H), 4.48-4.45 (t, 2H), 3.52-3.50 (t, 2H), 3.34 (s, 3H), 2.05-2.02 (m, 2H)

Preparation Example 337: 5-bromo-4-cyclopropyl-methoxymethyl-2-methyl-thiazole Step A: 4-cyclopropylmethoxymethyl-2-methyl-thiazole Cyclopropyl-methanol (0.65 ml, 7.93 mmol) and 4-chloromethyl-2-methyl-thiazole (0.78 g, 5.28 mmol) were reacted in the same manner as in Preparation Example 226 to obtain the title compound (0.83 g, 80%).

$^1$H-NMR (400 HMz CDCl$_3$); δ 7.06 (s, 1H), 4.61 (s, 2H), 3.46-3.40 (d, 2H), 2.71 (s, 3H), 1.15-1.09 (m, 1H), 0.58-0.53 (m, 2H), 0.25-0.21 (m, 2H)

Step B: 5-bromo-4-cyclopropylmethoxymethyl-2-methyl-thiazole

4-Cyclopropylmethoxymethyl-2-methyl-thiazole (0.52 g, 2.64 mmol) and 1,3-dibromo-5,5-dimethyl-imidazolin-2,4-dione (0.74 g, 2.64 mmol) were reacted in the same manner as in Step B of Preparation Example 6 to obtain the title compound (0.66 g, 96%).

$^1$H-NMR (400 HMz CDCl$_3$); δ 4.46 (s, 2H), 3.39-3.38 (d, 2H), 2.66 (s, 3H), 1.16-1.09 (m, 1H), 0.57-0.53 (m, 2H), 0.25-0.22 (m, 2H)

Preparation Example 338: 4-bromo-2-cyclobutoxymethyl-thiophene

4-Bromo-2-chloromethyl-thiophene (0.30 g, 1.42 mmol) and cyclobutanol (0.14 ml, 1.84 mmol) were reacted in the same manner as in Preparation Example 226 to obtain the title compound (0.065 g, 19%).

$^1$H-NMR (400 HMz CDCl$_3$); δ 7.17-7.16 (d, 1H), 6.90 (d, 1H), 4.52 (s, 2H), 4.06-3.99 (m, 1H), 2.24-2.16 (m, 2H), 2.01-1.92 (m, 2H), 1.75-1.68 (m, 1H), 1.52-1.47 (m, 1H)

Preparation Example 339: 4-(4-bromo-2,6-difluoro-phenoxy)-butanoic acid ethyl ester 4-Bromo-2,6-difluoro-phenol (19.5 g, 93.3 mmol) obtained in Step A of Preparation Example 16 and 4-bromo-butyric acid ethyl ester (21.82 g, 112 mmol) were reacted in the same manner as in Step C of Preparation Example 16 to obtain the title compound (30.0 g, 99%).

$^1$H-NMR (CDCl$_3$) δ 7.09 (2H, m), 4.16 (4H, m), 2.57 (2H, t), 2.08 (2H, m), 1.28 (3H, t)

Preparation Example 340: 2-chloro-4-(6-methyl-pyridin-3-yloxy)-pyrimidine 2,4-Dichloro-pyrimidine (1.36 g, 9.16 mmol) and 6-methyl-pyridin-3-ol (1.0 g, 9.16 mmol) were reacted in the same manner as in Preparation Example 226 to obtain the title compound (0.850 g, 42%).

$^1$H-NMR (CDCl$_3$) δ 8.47 (1H, d), 8.38 (1H, d), 7.44 (1H, m), 7.24 (1H, m), 6.89 (1H, d)

Preparation Example 341: 2-chloro-4-(4-ethyl-phenoxy)-pyrimidine 2,4-Dichloro-pyrimidine (1.22 g, 8.18 mmol) and 4-ethyl-phenol (1.0 g, 8.18 mmol) were reacted in the same manner as in Preparation Example 226 to obtain the title compound (1.5 g, 78%).

$^1$H-NMR (CDCl$_3$) δ 8.41 (1H, d), 7.26 (2H, m), 7.06 (2H, m), 6.74 (1H, d), 2.67 (2H, q), 1.27 (3H, t)

Preparation Example 342: 2-chloro-4-(3-fluoro-phenoxy)-pyrimidine 2,4-Dichloro-pyrimidine (1.3 g, 8.92 mmol) and 3-fluoro-phenol (1.0 g, 8.92 mmol) were reacted in the same manner as in Preparation Example 226 to obtain the title compound (1.2 g, 59%).

$^1$H-NMR (CDCl$_3$) δ 8.47 (1H, d), 7.40 (1H, m), 7.04-6.91 (3H, m), 6.84 (1H, d)

Preparation Example 343: 2-chloro-4-(3,4-difluoro-phenoxy)-6-methyl-pyrimidine 2,4-Dichloro-6-methyl-pyrimidine (1.25 g, 7.69 mmol) and 3,4-difluoro-phenol (1.0 g, 7.69 mmol) were reacted in the same manner as in Preparation Example 226 to obtain the title compound (1.1 g, 55%).

$^1$H-NMR (CDCl$_3$) δ 7.22 (1H, q), 7.03 (1H, m), 6.90 (1H, m), 6.67 (1H, s), 2.51 (3H, s)

Preparation Example 344: 2-chloro-4-(pyridin-2-yloxy)-pyrimidine 2,4-Dichloro-pyrimidine (1.57 g, 10.51 mmol) and pyridin-2-ol (1.0 g, 10.51 mmol) were reacted in the same manner as in Preparation Example 226 to obtain the title compound (0.1 g, 4%).

$^1$H-NMR (CDCl$_3$) δ 8.52 (1H, d), 8.38 (1H, m), 7.85 (1H, m), 7.25 (1H, m), 7.15 (1H, d), 7.03 (1H, d)

Preparation Example 345: 2-chloro-4-[4-(trifluoromethyl)phenoxy]pyrimidine 2,4-Dichloropyrimidine (2.0 g, 13.4 mmol) and 4-(trifluoromethyl)phenol (2.17 g, 13.4 mmol) were reacted in the same manner as in Preparation Example 226 to obtain the title compound (2.62 g, 71%).

$^1$H-NMR (CDCl$_3$) δ 8.50 (1H, d), 7.72 (2H, d), 7.30 (2H, d), 6.89 (1H, d)

Preparation Example 346: 2-chloro-4-[3-(trifluoromethyl)phenoxy]pyrimidine 2,4-Dichloropyrimidine (2.0 g, 13.4 mmol) and 3-(trifluoromethyl)phenol (2.17 g, 13.4 mmol) were reacted in the same manner as in Preparation Example 226 to obtain the title compound (2.7 g, 73%).

$^1$H-NMR (CDCl$_3$) δ 8.50 (1H, d), 7.57 (2H, m), 7.44 (1H, m), 7.38 (1H, m), 6.88 (1H, d)

Preparation Example 347: 2-chloro-4-methyl-6-[4-(trifluoromethyl)phenoxy]pyrimidine 2,6-Dichloro-4-methyl-pyrimidine (3.0 g, 18.4 mmol) and 4-(trifluoromethyl)phenol (2.98 g, 18.4 mmol) were reacted in the same manner as in Preparation Example 226 to obtain the title compound (3.2 g, 62%).

$^1$H-NMR (CDCl$_3$) δ 7.70 (2H, d), 7.27 (2H, d), 6.70 (1H, s), 2.52 (3H, s)

Preparation Example 348: 2-chloro-4-methyl-6-[3-(trifluoromethyl)phenoxy]pyrimidine 2,6-Dichloro-4-methyl-pyrimidine (3.0 g, 18.4 mmol) and 3-(trifluoromethyl)phenol (2.98 g, 18.4 mmol) were reacted in the same manner as in Preparation Example 226 to obtain the title compound (3.0 g, 57%).

$^1$H-NMR (CDCl$_3$) δ 7.56 (2H, m), 7.42 (1H, m), 7.36 (1H, m), 6.69 (1H, s), 2.52 (3H, s)

Preparation Example 349: 2-chloro-4-cyclobutoxy-6-trifluoromethyl-pyrimidine 2,6-Dichloro-6-trifluoromethyl-pyrimidine (0.40 g, 1.85 mmol) and cyclobutanol (0.17 ml, 2.22 mmol) were reacted in the same manner as in Preparation Example 226 to obtain the title compound (0.40 g, 86%).

$^1$H-NMR (400 HMz CDCl$_3$); δ 7.08 (s, 1H), 6.83 (s, 1H), 5.24-5.15 (m, 1H), 2.52 (m, 2H), 2.17-2.11 (m, 2H), 1.87-1.84 (m, 1H), 1.73-1.65 (m, 1H)

Preparation Example 350: 4-bromo-benzo[b]thiophene

3-Bromo-benzenethiol (0.5 g, 2.64 mmol) was dissolved in 8 mL of DMF. Bromoacetaldehyde diethyl acetal (0.52 g, 2.64 mmol) and K$_2$CO$_3$ (0.548 g, 3.97 mmol) were added thereto, and the mixture was stirred at room temperature for 16 hours. After addition of water, the reaction solution was extracted with EtOAc. The organic layer was dried with anhydrous magnesiumsulfate and concentrated under reduced pressure to obtain 1-bromo-3-(2,2-diethoxy-ethylsulfanyl)-benzene. The obtained compound was dissolved in 8 ml of MC. 0.7 g of PPA (polyphosphoric acid) was added thereto, and the mixture was stirred for 4 hours under reflux. After addition of Na$_2$CO$_3$ aqueous solution, the reaction solution was extracted with MC. The organic layer was dried with anhydrous magnesiumsulfate and purified by column chromatography to obtain the mixture of 4-bromo-benzo[b]thiophene and 6-bromo-benzo[b]thiophene (1:1, 0.33 g, 58%).

$^1$H-NMR (CDCl$_3$) δ 8.01 (1H, s), 7.80 (1H, d), 7.66 (1H, d), 7.50 (4H, m), 7.41 (1H, d), 7.29 (1H, d), 7.19 (1H, t)

Preparation Example 351: [1-(4-benzo[b]thiophen-4-yl-2,6-difluoro-phenyl)-piperidin-4-yl]-acetic acid ethyl ester The mixture of 4-bromo-benzo[b]thiophene and 6-bromo-benzo[b]thiophene (0.19 g, 0.89 mmol) obtained in Preparation Example 350 and 2-[1-[2,6-difluoro-4-(4,4,5,5-tetramethyl-1,3,2-dioxaborolan-2-yl)phenyl]-4-piperidyl]acetic acid ethyl ester (0.365 g, 0.89 mmol) obtained in Preparation Example 220 were reacted in the same manner as in Step A of Example 1 to obtain the title compound (0.11 g, 29%).

$^1$H-NMR (CDCl$_3$) δ 7.87 (1H, d), 7.46 (2H, s), 7.39 (1H, t), 7.29 (1H, d), 7.04 (2H, m), 4.14 (2H, q), 3.32 (2H, m), 3.16 (2H, m), 2.29 (2H, d), 1.96 (1H, m), 1.77 (2H, m), 1.46 (2H, m), 1.26 (3H, t)

Preparation Example 352: 2-chloro-4-cyclobutoxy-6-trifluoromethyl-pyrimidine Cyclobutanol (0.365 g, 5.07 mmol) and 2,4-dichloro-6-trifluoromethyl-pyrimidine (1 g, 4.61 mmol) were reacted in the same manner as in Preparation Example 226 to obtain the title compound (0.603 g, 51%).

$^1$H-NMR (CDCl$_3$) δ 6.93 (1H, s), 5.30 (1H, m), 2.50 (2H, m), 2.18 (2H, m), 1.87 (1H, m), 1.71 (1H, m)

Preparation Example 353: 2-chloro-4-propoxy-6-trifluoromethyl-pyrimidine

Propanol (0.304 g, 5.07 mmol) and 2,4-dichloro-6-trifluoromethyl-pyrimidine (1 g, 4.61 mmol) were reacted in the same manner as in Preparation Example 226 to obtain the title compound (0.602 g, 54%).

$^1$H-NMR (CDCl$_3$) δ 6.97 (1H, s), 4.41 (2H, t), 1.83 (2H, m), 1.02 (3H, t)

Preparation Example 354: 2-chloro-4-(4-fluoro-phenoxy)-6-trifluoromethyl-pyrimidine 4-Fluoro-phenol (0.568 g, 5.07 mmol) and 2,4-dichloro-6-trifluoromethyl-pyrimidine (1 g, 4.61 mmol) were reacted in the same manner as in Preparation Example 226 to obtain the title compound (1.07 g, 79%).

$^1$H-NMR (CDCl$_3$) δ 7.15 (5H, m)

Example 1: 3-[6-(2-isopropylsulfanyl-pyridin-3-yl)-quinolin-2-yl]-propionic acid

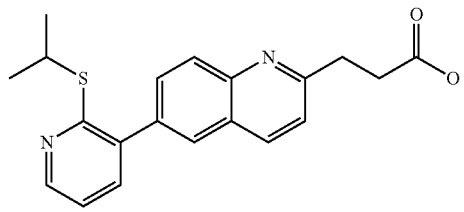 [SMILES: CC(C)Sc1ncccc1-c1ccc2nc(CCC(=O)O)ccc2c1]

Step A: 3-[6-(2-isopropylsulfanyl-pyridin-3-yl)-quinolin-2-yl]-propionic acid ethyl ester

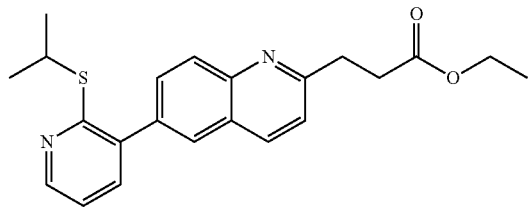 [SMILES: CCOC(=O)CCc1ccc2cc(-c3cccnc3SC(C)C)ccc2n1]

3-[6-(4,4,5,5-Tetramethyl-[1,3,2]dioxaborolan-2-yl)-quinolin-2-yl]-propionic acid ethyl ester (0.06 g, 0.17 mmol) obtained in Preparation Example 1 and 3-iodo-2-isopropylsulfanyl-pyridine (0.047 g, 0.17 mmol) obtained in Preparation Example 9 were dissolved in 0.25 mL of 2M sodium carbonate and 2 mL of DME, and charged with nitrogen for 5 minutes. PdCl$_2$(PPh$_3$)$_2$ (0.006 g, 0.008 mmol) was added thereto, and the mixture was stirred for 4 hours under reflux. After addition of water, the reaction solution was extracted with EtOAc to separate an organic layer. The organic layer was dried with MgSO$_4$ and purified by column chromatography to obtain the title compound (0.040 g, 63%).

$^1$H-NMR (CDCl$_3$) δ 8.53 (1H, d), 8.15-8.08 (2H, m), 7.82 (1H, s), 7.78 (1H, d), 7.50 (1H, d), 7.39 (1H, d), 7.12 (1H, m), 4.15-4.10 (3H, m), 3.34 (2H, t), 2.97 (2H, t), 1.40 (6H, d), 1.30 (3H, t)

Step B: 3-[6-(2-isopropylsulfanyl-pyridin-3-yl)-quinolin-2-yl]-propionic acid 3-[6-(2-Isopropylsulfanyl-pyridin-3-yl)-quinolin-2-yl]-propionic acid ethyl ester (0.040 g, 0.10 mmol) obtained in Step A was dissolved in each 0.3 mL of THF, MeOH and 1N NaOH aqueous solution, and the mixture was stirred at room temperature for 2 hours. After removing organic solvent, the reaction solution was adjusted to pH 3 by the use of 1N HCl aqueous solution and extracted with EtOAc to separate an organic layer. The organic layer was dried with MgSO$_4$ and concentrated under reduced pressure to obtain the title compound (0.030 g, 86%).

$^1$H-NMR (CDCl$_3$) δ 8.51 (1H, d), 8.26 (1H, d), 8.11 (1H, d), 7.92-7.80 (2H, m), 7.46 (1H, d), 7.40 (1H, d), 7.10 (1H, m), 4.15 (1H, m), 3.38 (2H, t), 2.98 (2H, t), 1.35 (6H, d)

Example 2: 3-[6-(6-isopropylsulfanyl-pyridin-2-yl)-quinolin-2-yl]-propionic acid

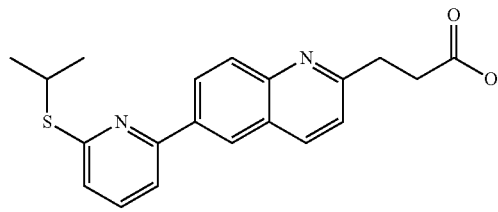 [SMILES: CC(C)Sc1cccc(-c2ccc3nc(CCC(=O)O)ccc3c2)n1]

Step A: 3-[6-(6-isopropylsulfanyl-pyridin-2-yl)-quinolin-2-yl]-propionic acid ethyl ester

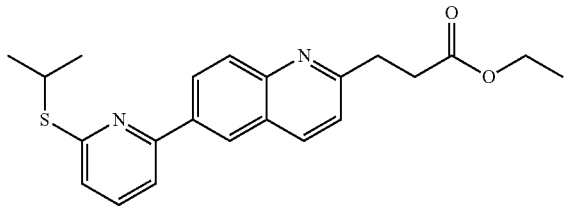 [SMILES: CCOC(=O)CCc1ccc2cc(-c3cccc(SC(C)C)n3)ccc2n1]

3-[6-(4,4,5,5-Tetramethyl-[1,3,2]dioxaborolan-2-yl)-quinolin-2-yl]-propionic acid ethyl ester (0.06 g, 0.17 mmol) obtained in Preparation Example 1 and 2-chloro-6-isopropylsulfanyl-pyridine (0.032 g, 0.17 mmol) obtained in Preparation Example 10 were reacted in the same manner as in Step A of Example 1 to obtain the title compound (0.021 g, 33%).

$^1$H-NMR (CDCl$_3$) δ 8.50 (1H, s), 8.43 (1H, d), 8.20 (1H, d), 8.14 (1H, d), 7.65-7.60 (2H, m), 7.40 (1H, d), 7.16 (1H, m), 4.31-4.17 (3H, m), 3.34 (2H, t), 2.96 (2H, t), 1.54 (6H, d), 1.29 (3H, t)

Step B: 3-[6-(6-isopropylsulfanyl-pyridin-2-yl)-quinolin-2-yl]-propionic acid 3-[6-(6-Isopropylsulfanyl-pyridin-2-yl)-quinolin-2-yl]-propionic acid ethyl ester (0.021 g, 0.06 mmol) obtained in Step A was reacted in the same manner as in Step B of Example 1 to obtain the title compound (0.016 g, 83%).

$^1$H-NMR (CDCl$_3$) δ 8.51-8.46 (2H, m), 8.32 (1H, d), 8.11 (1H, d), 7.65-7.55 (2H, m), 7.41 (1H, d), 7.15 (1H, m), 4.20 (1H, m), 3.39 (2H, t), 2.98 (2H, t), 1.50 (6H, d)

Example 3: [6-(6-cyclopentyloxy-pyridin-2-yl)-naphthalen-2-yloxy]-acetic acid

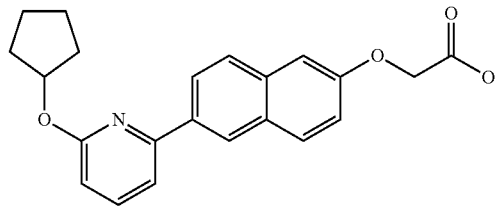 [SMILES: O=C(O)COc1ccc2cc(-c3cccc(OC4CCCC4)n3)ccc2c1]

Step A: [6-(6-cyclopentyloxy-pyridin-2-yl)-naphthalen-2-yloxy]-acetic acid ethyl ester

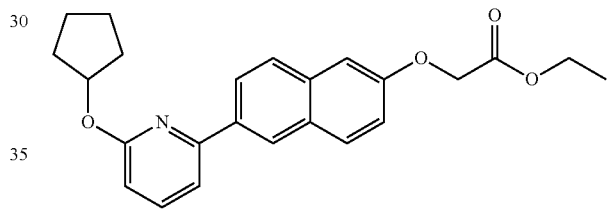

[6-(4,4,5,5-Tetramethyl-[1,3,2]dioxaborolan-2-yl)-naphthalen-2-yloxy]-acetic acid ethyl ester (0.06 g, 0.17 mmol) obtained in Preparation Example 2 and 2-chloro-6-cyclopentyloxy-pyridine (0.033 g, 0.17 mmol) obtained in Preparation Example 12 were reacted in the same manner as in Step A of Example 1 to obtain the title compound (0.013 g, 20%).

$^1$H-NMR (CDCl$_3$) δ 8.43 (1H, s), 8.17 (1H, d), 7.86 (1H, d), 7.77 (1H, t), 7.62 (1H, d), 7.42 (1H, d), 7.25 (1H, d), 7.12 (1H, s), 6.63 (1H, d), 5.60 (1H, m), 4.75 (2H, s), 4.30 (2H, q), 2.20-1.60 (8H, m), 1.22 (3H, t)

Step B: [6-(6-cyclopentyloxy-pyridin-2-yl)-naphthalen-2-yloxy]-acetic acid

[6-(6-cyclopentyloxy-pyridin-2-yl)-naphthalen-2-yloxy]-acetic acid ethyl ester (0.013 g, 0.03 mmol) obtained in Step A was reacted in the same manner as in Step B of Example 1 to obtain the title compound (0.010 g, 83%).

$^1$H-NMR (CDCl$_3$) δ 8.48 (1H, s), 8.22 (1H, d), 7.94 (1H, d), 7.83 (1H, d), 7.70 (1H, t), 7.47 (1H, d), 7.25 (1H, d), 7.20 (1H, s), 6.70 (1H, d), 5.63 (1H, m), 4.87 (2H, s), 2.20-1.70 (8H, m)

Example 4: [6-(2-cyclopentyloxy-pyridin-3-yl)-naphthalen-2-yloxy]-acetic acid

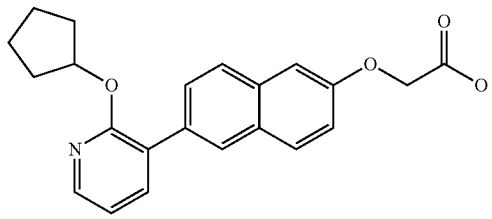 [SMILES: O=C(O)COc1ccc2cc(-c3cccnc3OC3CCCC3)ccc2c1]

Step A: [6-(2-cyclopentyloxy-pyridin-3-yl)-naphthalen-2-yloxy]-acetic acid ethyl ester

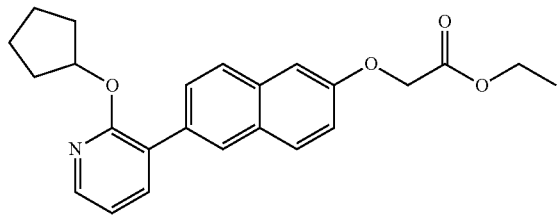 [SMILES: CCOC(=O)COc1ccc2cc(-c3cccnc3OC3CCCC3)ccc2c1]

[6-(4,4,5,5-Tetramethyl-[1,3,2]dioxaborolan-2-yl)-naphthalen-2-yloxy]-acetic acid ethyl ester (0.06 g, 0.17 mmol) obtained in Preparation Example 2 and 2-cyclopentyloxy-3-iodo-pyridine (0.049 g, 0.17 mmol) obtained in Preparation Example 11 were reacted in the same manner as in Step A of Example 1 to obtain the title compound (0.030 g, 45%).
$^1$H-NMR (CDCl$_3$) δ 8.21 (1H, d), 8.00 (1H, s), 7.85-7.70 (4H, m), 7.24 (1H, d), 7.18 (1H, s), 6.99 (1H, t), 5.60 (1H, m), 4.80 (2H, s), 4.36 (2H, q), 2.10-1.60 (8H, m), 1.35 (3H, t)

Step B: [6-(2-cyclopentyloxy-pyridin-3-yl)-naphthalen-2-yloxy]-acetic acid

[6-(2-Cyclopentyloxy-pyridin-3-yl)-naphthalen-2-yloxy]-acetic acid ethyl ester (0.030 g, 0.08 mmol) obtained in Step A was reacted in the same manner as in Step B of Example 1 to obtain the title compound (0.018 g, 67%).
$^1$H-NMR (CDCl$_3$) δ 8.24 (1H, d), 7.97 (1H, s), 7.85-7.70 (4H, m), 7.30 (1H, d), 7.20 (1H, s), 7.00 (1H, t), 5.57 (1H, m), 4.87 (2H, s), 2.10-1.65 (8H, m)

Example 5: 4-[6-(2-isopropylsulfanyl-pyridin-3-yl)-naphthalen-2-yloxy]-butyric acid

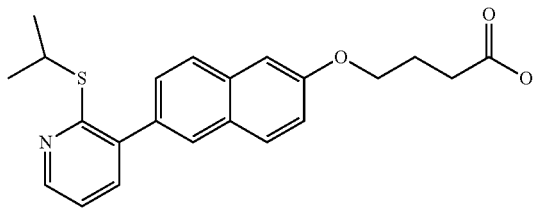 [SMILES: CC(C)Sc1ncccc1-c1ccc2cc(OCCCC(=O)O)ccc2c1]

Step A: 4-[6-(2-isopropylsulfanyl-pyridin-3-yl)-naphthalen-2-yloxy]-butyric acid ethyl ester

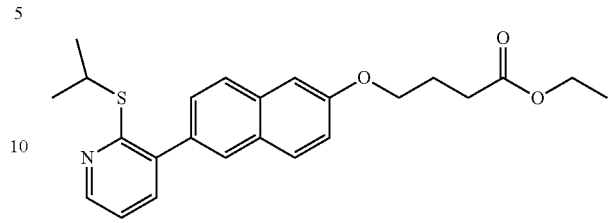

4-[6-(4,4,5,5-Tetramethyl-[1,3,2]dioxaborolan-2-yl)-naphthalen-2-yloxy]-butyric acid ethyl ester (0.05 g, 0.13 mmol) obtained in Preparation Example 3 and 3-iodo-2-isopropylsulfanyl-pyridine (0.036 g, 0.13 mmol) obtained in Preparation Example 9 were reacted in the same manner as in Step A of Example 1 to obtain the title compound (0.035 g, 66%).
$^1$H-NMR (CDCl$_3$) δ 8.50 (1H, d), 7.82-7.75 (3H, m), 7.62-7.48 (2H, m), 7.20 (2H, m), 7.10 (1H, m), 4.25-4.05 (5H, m), 2.63 (2H, t), 2.22 (2H, t), 1.39 (6H, d), 1.30 (3H, t)

Step B: 4-[6-(2-isopropylsulfanyl-pyridin-3-yl)-naphthalen-2-yloxy]-butyric acid 4-[6-(2-Isopropylsulfanyl-pyridin-3-yl)-naphthalen-2-yloxy]-butyric acid ethyl ester (0.035 g, 0.09 mmol) obtained in Step A was reacted in the same manner as in Step B of Example 1 to obtain the title compound (0.025 g, 78%).
$^1$H-NMR (CDCl$_3$) δ 8.46 (1H, d), 7.80-7.75 (3H, m), 7.52 (1H, d), 7.45 (1H, d), 7.15 (2H, m), 7.05 (1H, m), 4.18 (2H, t), 4.07 (1H, m), 2.65 (2H, t), 2.22 (2H, t), 1.34 (6H, d)

Example 6: 4-[6-(6-isopropylsulfanyl-pyridin-2-yl)-naphthalen-2-yloxy]-butyric acid

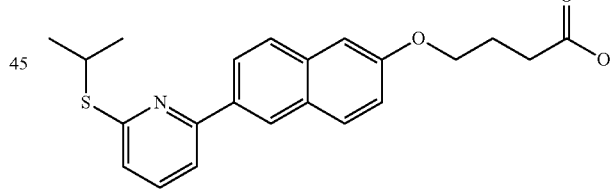

Step A: 4-[6-(6-isopropylsulfanyl-pyridin-2-yl)-naphthalen-2-yloxy]-butyric acid ethyl ester

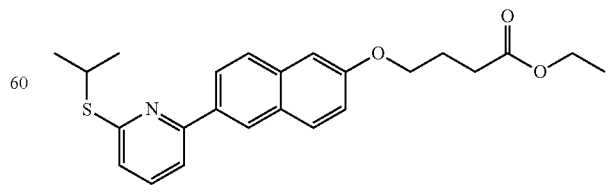

4-[6-(4,4,5,5-Tetramethyl-[1,3,2]dioxaborolan-2-yl)-naphthalen-2-yloxy]-butyric acid ethyl ester (0.05 g, 0.13 mmol) obtained in Preparation Example 3 and 2-chloro-6-isopropylsulfanyl-pyridine (0.024 g, 0.13 mmol) obtained in Preparation Example 10 were reacted in the same manner as in Step A of Example 1 to obtain the title compound (0.012 g, 23%).

$^1$H-NMR (CDCl$_3$) δ 8.46 (1H, s), 8.20 (1H, d), 7.90-7.80 (2H, m), 7.60 (2H, m), 7.22-7.12 (3H, m), 4.35-4.15 (5H, m), 2.61 (2H, t), 2.22 (2H, t), 1.54 (6H, d), 1.30 (3H, t)

Step B: 4-[6-(6-isopropylsulfanyl-pyridin-2-yl)-naphthalen-2-yloxy]-butyric acid 4-[6-(6-Isopropylsulfanyl-pyridin-2-yl)-naphthalen-2-yloxy]-butyric acid ethyl ester (0.012 g, 0.03 mmol) obtained in Step A was reacted in the same manner as in Step B of Example 1 to obtain the title compound (0.010 g, 88%).

$^1$H-NMR (CDCl$_3$) δ 8.41 (1H, s), 8.15 (1H, d), 7.84-7.77 (2H, m), 7.53 (2H, m), 7.16-7.12 (2H, m), 7.09 (1H, d), 4.24-4.12 (3H, m), 2.65 (2H, t), 2.21 (2H, t), 1.49 (6H, d)

Example 7: 3-[6-(2-isopropylsulfanyl-pyridin-3-yl)-chroman-2-yl]-propionic acid

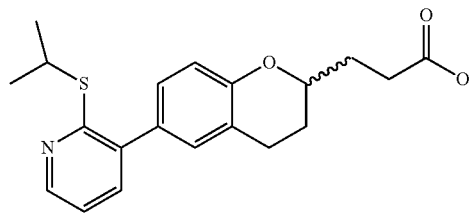 [SMILES: CC(C)Sc1ncccc1-c1ccc2c(c1)CCC(CCC(=O)O)O2]

Step A: 3-[6-(2-isopropylsulfanyl-pyridin-3-yl)-chroman-2-yl]-propionic acid ethyl ester

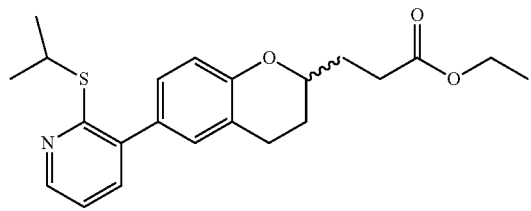 [SMILES: CCOC(=O)CCC1CCc2cc(-c3cccnc3SC(C)C)ccc2O1]

3-[6-(4,4,5,5-Tetramethyl-[1,3,2]dioxaborolan-2-yl)-chroman-2-yl]-propionic acid ethyl ester (0.06 g, 0.16 mmol) obtained in Preparation Example 4 and 3-iodo-2-isopropylsulfanyl-pyridine (0.046 g, 0.16 mmol) obtained in Preparation Example 9 were reacted in the same manner as in Step A of Example 1 to obtain the title compound (0.040 g, 66%).

$^1$H-NMR (CDCl$_3$) δ 8.40 (1H, d), 7.35 (1H, d), 7.18 (1H, d), 7.08 (1H, s), 7.00 (1H, t), 6.82 (1H, d), 4.17 (2H, q), 4.15-4.00 (2H, m), 2.95-2.80 (2H, m), 2.70-2.50 (2H, m), 2.05 (3H, m), 1.80 (1H, m), 1.35 (6H, d), 1.28 (3H, t)

Step B: 3-[6-(2-isopropylsulfanyl-pyridin-3-yl)-chroman-2-yl]-propionic acid

3-[6-(2-Isopropylsulfanyl-pyridin-3-yl)-chroman-2-yl]-propionic acid ethyl ester (0.040 g, 0.10 mmol) obtained in Step A was reacted in the same manner as in Step B of Example 1 to obtain the title compound (0.028 g, 76%).

$^1$H-NMR (CDCl$_3$) δ 8.38 (1H, d), 7.33 (1H, d), 7.14 (1H, d), 7.07 (1H, s), 7.00 (1H, t), 6.83 (1H, d), 4.15-4.00 (2H, m), 2.95-2.75 (2H, m), 2.70-2.50 (2H, m), 2.05-1.90 (3H, m), 1.80 (1H, m), 1.34 (6H, d)

Example 8: 3-[6-(6-isopropylsulfanyl-pyridin-2-yl)-chroman-2-yl]-propionic acid

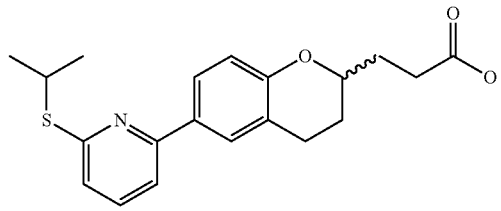 [SMILES: CC(C)Sc1cccc(-c2ccc3c(c2)CCC(CCC(=O)O)O3)n1]

Step A: 3-[6-(6-isopropylsulfanyl-pyridin-2-yl)-chroman-2-yl]-propionic acid ethyl ester

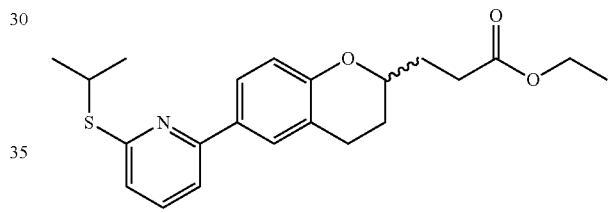

3-[6-(4,4,5,5-Tetramethyl-[1,3,2]dioxaborolan-2-yl)-chroman-2-yl]-propionic acid ethyl ester (0.06 g, 0.16 mmol) obtained in Preparation Example 4 and 2-chloro-6-isopropylsulfanyl-pyridine (0.031 g, 0.16 mmol) obtained in Preparation Example 10 were reacted in the same manner as in Step A of Example 1 to obtain the title compound (0.020 g, 33%).

$^1$H-NMR (CDCl$_3$) δ 7.79-7.72 (2H, m), 7.49 (1H, t), 7.33 (1H, d), 7.02 (1H, d), 6.84 (1H, d), 4.20-4.05 (4H, m), 2.97-2.80 (2H, m), 2.70-2.50 (2H, m), 2.10-2.00 (3H, m), 1.82 (1H, m), 1.45 (6H, d), 1.26 (3H, t)

Step B: 3-[6-(6-isopropylsulfanyl-pyridin-2-yl)-chroman-2-yl]-propionic acid

3-[6-(6-Isopropylsulfanyl-pyridin-2-yl)-chroman-2-yl]-propionic acid ethyl ester (0.020 g, 0.05 mmol) obtained in Step A was reacted in the same manner as in Step B of Example 1 to obtain the title compound (0.014 g, 75%).

$^1$H-NMR (CDCl$_3$) δ 7.78-7.73 (2H, m), 7.46 (1H, t), 7.32 (1H, d), 7.01 (1H, d), 6.85 (1H, d), 4.14-4.07 (2H, m), 2.97-2.82 (2H, m), 2.75-2.60 (2H, m), 2.08-2.00 (3H, m), 1.80 (1H, m), 1.45 (6H, m)

Example 9: 3-[6-(6-cyclopentyloxy-pyridin-2-yl)-chroman-2-yl]-propionic acid

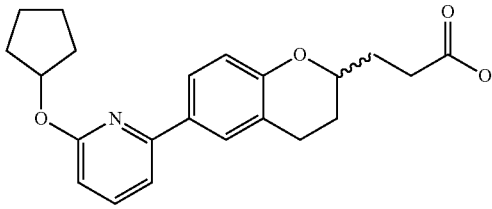

Step A: 3-[6-(6-cyclopentyloxy-pyridin-2-yl)-chroman-2-yl]-propionic acid ethyl ester

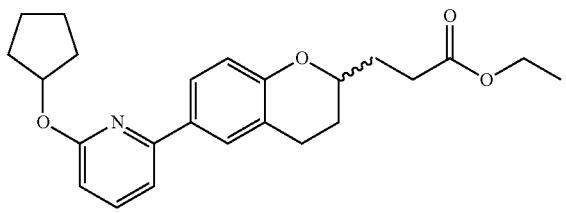 [SMILES: CCOC(=O)CCC1CCc2cc(-c3cccc(OC4CCCC4)n3)ccc2O1]

3-[6-(4,4,5,5-Tetramethyl-[1,3,2]dioxaborolan-2-yl)-chroman-2-yl]-propionic acid ethyl ester (0.06 g, 0.16 mmol) obtained in Preparation Example 4 and 2-chloro-6-cyclopentyloxy-pyridine (0.033 g, 0.16 mmol) obtained in Preparation Example 12 were reacted in the same manner as in Step A of Example 1 to obtain the title compound (0.013 g, 21%).

$^1$H-NMR (CDCl$_3$) δ 7.77-7.70 (2H, m), 7.54 (1H, t), 7.20 (1H, d), 6.85 (1H, d), 6.54 (1H, d), 5.50 (1H, m), 4.13 (2H, q), 4.08 (1H, m), 3.00-2.50 (4H, m), 2.10-1.55 (12H, m), 1.24 (3H, t)

Step B: 3-[6-(6-cyclopentyloxy-pyridin-2-yl)-chroman-2-yl]-propionic acid

3-[6-(6-Cyclopentyloxy-pyridin-2-yl)-chroman-2-yl]-propionic acid ethyl ester (0.013 g, 0.03 mmol) obtained in Step A was reacted in the same manner as in Step B of Example 1 to obtain the title compound (0.010 g, 83%).

$^1$H-NMR (CDCl$_3$) δ 7.72-7.65 (2H, m), 7.45 (1H, t), 7.11 (1H, d), 6.79 (1H, d), 6.49 (1H, d), 5.45 (1H, m), 4.04 (1H, m), 2.95-2.50 (4H, m), 2.10-1.65 (12H, m)

Example 10: 3-[6-(2-cyclopentyloxy-pyridin-3-yl)-chroman-2-yl]-propionic acid

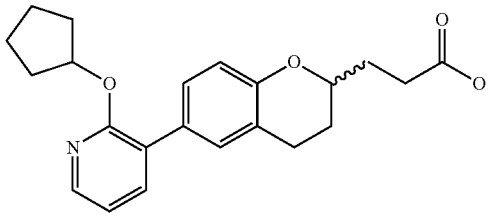 [SMILES: O=C(O)CCC1CCc2cc(-c3cccnc3OC3CCCC3)ccc2O1]

Step A: 3-[6-(2-cyclopentyloxy-pyridin-3-yl)-chroman-2-yl]-propionic acid ethyl ester

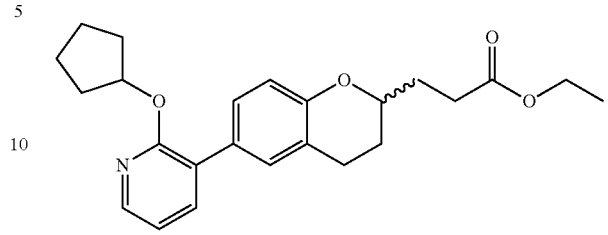

3-[6-(4,4,5,5-Tetramethyl-[1,3,2]dioxaborolan-2-yl)-chroman-2-yl]-propionic acid ethyl ester (0.06 g, 0.16 mmol) obtained in Preparation Example 4 and 2-cyclopentyloxy-3-iodo-pyridine (0.049 g, 0.16 mmol) obtained in Preparation Example 11 were reacted in the same manner as in Step A of Example 1 to obtain the title compound (0.030 g, 48%).

$^1$H-NMR (CDCl$_3$) δ 8.07 (1H, d), 7.56 (1H, d), 7.32-7.26 (2H, m), 6.85 (1H, t), 6.80 (1H, d), 5.49 (1H, m), 4.15 (2H, q), 4.10 (1H, m), 2.95-2.55 (4H, m), 2.10-1.55 (12H, m), 1.26 (3H, t)

Step B: 3-[6-(2-cyclopentyloxy-pyridin-3-yl)-chroman-2-yl]-propionic acid

3-[6-(2-Cyclopentyloxy-pyridin-3-yl)-chroman-2-yl]-propionic acid ethyl ester (0.030 g, 0.08 mmol) obtained in Step A was reacted in the same manner as in Step B of Example 1 to obtain the title compound (0.018 g, 67%).

$^1$H-NMR (CDCl$_3$) δ 8.09 (1H, d), 7.56 (1H, d), 7.31-7.26 (2H, m), 6.88 (1H, t), 6.81 (1H, d), 5.49 (1H, m), 4.08 (1H, m), 2.95-2.60 (4H, m), 2.10-1.65 (12H, m)

Example 11: 3-[6-(6-cyclopentyloxy-pyridin-2-yl)-1,2,3,4-tetrahydro-quinolin-2-yl]-propionic acid

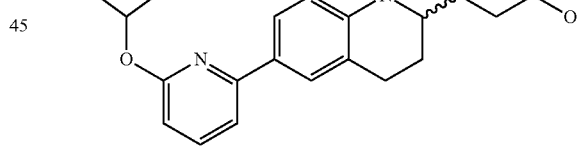

Step A: 3-[6-(6-cyclopentyloxy-pyridin-2-yl)-1,2,3,4-tetrahydro-quinolin-2-yl]-propionic acid ethyl ester

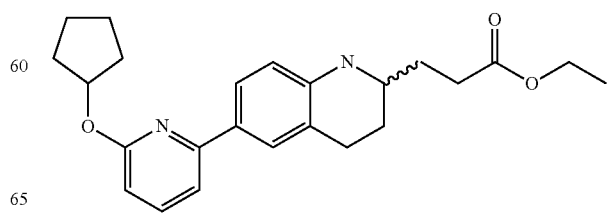

3-[6-(4,4,5,5-Tetramethyl-[1,3,2]dioxaborolan-2-yl)-1,2,3,4-tetrahydro-quinolin-2-yl]-propionic acid ethyl ester (0.1 g, 0.30 mmol) obtained in Preparation Example 6 and 2-chloro-6-cyclopentyloxy-pyridine (0.06 g, 0.30 mmol) obtained in Preparation Example 12 were reacted in the same manner as in Step A of Example 1 to obtain the title compound (0.035 g, 30%).

$^1$H-NMR (CDCl$_3$) δ 7.68 (2H, m), 7.51 (1H, t), 7.15 (1H, d), 6.56-6.48 (2H, m), 5.51 (1H, m), 4.16 (2H, q), 4.05 (1H, brs), 3.40 (1H, m), 2.90-2.80 (2H, m), 2.55-2.40 (2H, m), 2.10-1.60 (12H, m), 1.25 (3H, t)

Step B: 3-[6-(6-cyclopentyloxy-pyridin-2-yl)-1,2,3,4-tetrahydro-quinolin-2-yl]-propionic acid 3-[6-(6-Cyclopentyloxy-pyridin-2-yl)-1,2,3,4-tetrahydro-quinolin-2-yl]-propionic acid ethyl ester (0.012 g, 0.03 mmol) obtained in Step A was reacted in the same manner as in Step B of Example 1 to obtain the title compound (0.010 g, 91%).

$^1$H-NMR (CDCl$_3$) δ 7.68 (2H, m), 7.52 (1H, t), 7.16 (1H, d), 6.60-6.48 (2H, m), 5.52 (1H, m), 3.42 (1H, m), 2.90-2.80 (2H, m), 2.60-2.50 (2H, m), 2.05-1.60 (12H, m)

Example 12: 3-[6-(6-cyclopentyloxy-pyridin-2-yl)-1-methyl-1,2,3,4-tetrahydro-quinolin-2-yl]-propionic acid

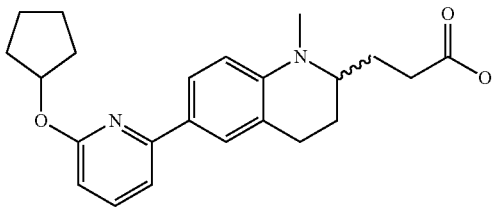 [SMILES: O=C(O)CCC1CCc2cc(-c3cccc(OC4CCCC4)n3)ccc2N1]

Step A: 3-[6-(6-cyclopentyloxy-pyridin-2-yl)-1-methyl-1,2,3,4-tetrahydro-quinolin-2-yl]-propionic acid ethyl ester

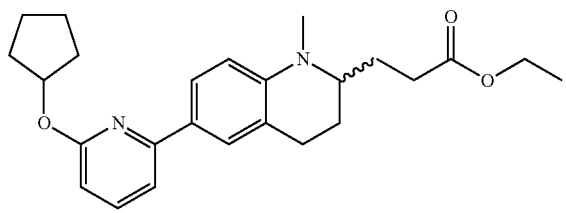 [SMILES: CCOC(=O)CCC1CCc2cc(-c3cccc(OC4CCCC4)n3)ccc2N1C]

3-[6-(6-Cyclopentyloxy-pyridin-2-yl)-1,2,3,4-tetrahydro-quinolin-2-yl]-propionic acid ethyl ester (0.012 g, 0.03 mmol) obtained in Step A of Example 11 was dissolved in 5 mL of DCE. Formaldehyde (0.005 g, 0.06 mmol) and acetic acid (0.002 g, 0.036 mmol) were added thereto, and the mixture was stirred at room temperature for 1 hour. Sodium triacetoxyborohydride (0.013 g, 0.06 mmol) was added to the reaction solution, and the reaction was carried out at room temperature for 16 hours. After addition of 50 mL of water, the reaction solution was extracted with DCM, dried with MgSO$_4$ and purified by column chromatography to obtain the title compound (0.007 g, 58%).

$^1$H-NMR (CDCl$_3$) δ 7.79 (1H, d), 7.68 (1H, s), 7.54 (1H, t), 7.16 (1H, d), 6.61 (1H, d), 6.47 (1H, d), 5.52 (1H, m), 4.13 (2H, q), 3.32 (1H, m), 3.01 (3H, s), 2.95-2.75 (2H, m), 2.50-2.30 (2H, m), 2.10-1.60 (12H, m), 1.24 (3H, t)

Step B: 3-[6-(6-cyclopentyloxy-pyridin-2-yl)-1-methyl-1,2,3,4-tetrahydro-quinolin-2-yl]-propionic acid 3-[6-(6-Cyclopentyloxy-pyridin-2-yl)-1-methyl-1,2,3,4-tetrahydro-quinolin-2-yl]-propionic acid ethyl ester (0.007 g, 0.02 mmol) obtained in Step A was reacted in the same manner as in Step B of Example 1 to obtain the title compound (0.006 g, 92%).

$^1$H-NMR (CDCl$_3$) δ 7.80 (1H, d), 7.68 (1H, s), 7.54 (1H, t), 7.18 (1H, d), 6.65 (1H, d), 6.47 (1H, d), 5.52 (1H, m), 3.36 (1H, m), 3.02 (3H, s), 2.95-2.70 (2H, m), 2.55-2.30 (2H, m), 2.10-1.60 (12H, m)

Example 13: [6-(2-isopropylsulfanyl-pyridin-3-yl)-1-oxo-3,4-dihydro-1H-isoquinolin-2-yl]-acetic acid

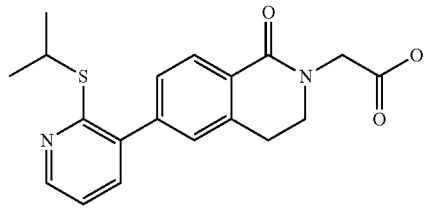 [SMILES: CC(C)Sc1ncccc1-c1ccc2c(c1)CCN(CC(=O)O)C2=O]

Step A: [6-(2-isopropylsulfanyl-pyridin-3-yl)-1-oxo-3,4-dihydro-1H-isoquinolin-2-yl]-acetic acid ethyl ester

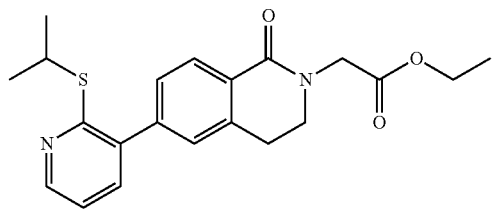 [SMILES: CCOC(=O)CN1CCc2cc(-c3cccnc3SC(C)C)ccc2C1=O]

[1-Oxo-6-(4,4,5,5-tetramethyl-[1,3,2]dioxaborolan-2-yl)-3,4-dihydro-1H-isoquinolin-2-yl]-acetic acid ethyl ester (0.06 g, 0.16 mmol) obtained in Preparation Example 7 and 3-iodo-2-isopropylsulfanyl-pyridine (0.047 g, 0.16 mmol) obtained in Preparation Example 9 were reacted in the same manner as in Step A of Example 1 to obtain the title compound (0.020 g, 33%).

$^1$H-NMR (CDCl$_3$) δ 8.46 (1H, d), 8.15 (1H, d), 7.41-7.35 (2H, m), 7.25 (1H, d), 7.04 (1H, t), 4.36 (2H, s), 4.22 (2H, q), 4.07 (1H, m), 3.73 (2H, t), 3.10 (2H, t), 1.37 (6H, d), 1.26 (3H, t)

Step B: [6-(2-isopropylsulfanyl-pyridin-3-yl)-1-oxo-3,4-dihydro-1H-isoquinolin-2-yl]-acetic acid

[6-(2-Isopropylsulfanyl-pyridin-3-yl)-1-oxo-3,4-dihydro-1H-isoquinolin-2-yl]-acetic acid ethyl ester (0.020 g, 0.05 mmol) obtained in Step A was reacted in the same manner as in Step B of Example 1 to obtain the title compound (0.012 g, 63%).

$^1$H-NMR (CDCl$_3$) δ 8.47 (1H, d), 8.13 (1H, d), 7.43-7.35 (2H, m), 7.25 (1H, d), 7.05 (1H, t), 4.40 (2H, s), 4.13 (1H, m), 3.74 (2H, t), 3.13 (2H, t), 1.36 (6H, d)

Example 14: [6-(6-isopropylsulfanyl-pyridin-2-yl)-1-oxo-3,4-dihydro-1H-isoquinolin-2-yl]-acetic acid

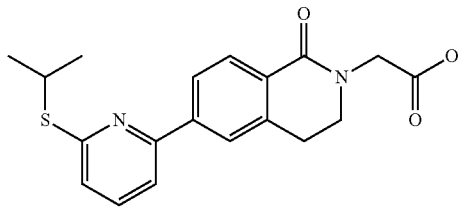 [SMILES: CC(C)Sc1cccc(-c2ccc3c(c2)CCN(CC(=O)O)C3=O)n1]

Step A: [6-(6-isopropylsulfanyl-pyridin-2-yl)-1-oxo-3,4-dihydro-1H-isoquinolin-2-yl]-acetic acid ethyl ester

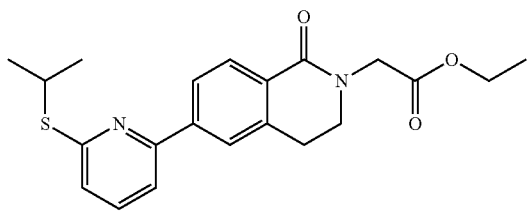 [SMILES: CCOC(=O)CN1CCc2cc(-c3cccc(SC(C)C)n3)ccc2C1=O]

[1-Oxo-6-(4,4,5,5-tetramethyl-[1,3,2]dioxaborolan-2-yl)-3,4-dihydro-1H-isoquinolin-2-yl]-acetic acid ethyl ester (0.06 g, 0.16 mmol) obtained in Preparation Example 7 and 2-chloro-6-isopropylsulfanyl-pyridine (0.031 g, 0.16 mmol) obtained in Preparation Example 10 were reacted in the same manner as in Step A of Example 1 to obtain the title compound (0.014 g, 23%).

$^1$H-NMR (CDCl$_3$) δ 8.17 (1H, d), 7.98 (1H, d), 7.89 (1H, s), 7.55 (1H, t), 7.47 (1H, d), 7.12 (1H, d), 4.36 (2H, s), 4.30-4.15 (3H, m), 3.72 (2H, t), 3.17 (2H, t), 1.47 (6H, d), 1.28 (3H, t)

Step B: [6-(6-isopropylsulfanyl-pyridin-2-yl)-1-oxo-3,4-dihydro-1H-isoquinolin-2-yl]-acetic acid

[6-(6-Isopropylsulfanyl-pyridin-2-yl)-1-oxo-3,4-dihydro-1H-isoquinolin-2-yl]-acetic acid ethyl ester (0.014 g, 0.04 mmol) obtained in Step A was reacted in the same manner as in Step B of Example 1 to obtain the title compound (0.010 g, 78%).

$^1$H-NMR (CDCl$_3$) δ 8.17 (1H, d), 7.98 (1H, d), 7.89 (1H, s), 7.53 (1H, t), 7.45 (1H, d), 7.12 (1H, d), 4.40 (2H, s), 4.15 (1H, m), 3.75 (2H, t), 3.16 (2H, t), 1.48 (6H, d)

Example 15: 3-[6-(2-cyclopentyloxy-pyridin-3-yl)-1-oxo-3,4-dihydro-1H-isoquinolin-2-yl]-propionic acid

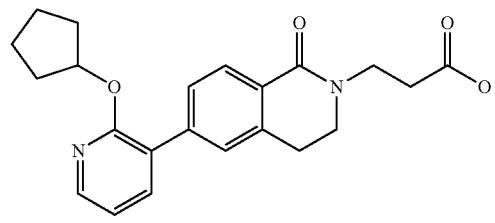 [SMILES: O=C(O)CCN1CCc2cc(-c3cccnc3OC3CCCC3)ccc2C1=O]

Step A: 3-[6-(2-cyclopentyloxy-pyridin-3-yl)-1-oxo-3,4-dihydro-1H-isoquinolin-2-yl]-propionic acid methyl ester

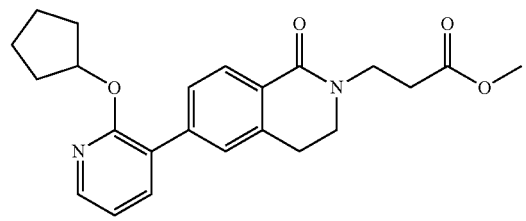 [SMILES: COC(=O)CCN1CCc2cc(-c3cccnc3OC3CCCC3)ccc2C1=O]

3-[1-Oxo-6-(4,4,5,5-tetramethyl-[1,3,2]dioxaborolan-2-yl)-3,4-dihydro-1H-isoquinolin-2-yl]-propionic acid methyl ester (0.06 g, 0.16 mmol) obtained in Preparation Example 8 and 2-cyclopentyloxy-3-iodo-pyridine (0.048 g, 0.16 mmol) obtained in Preparation Example 11 were reacted in the same manner as in Step A of Example 1 to obtain the title compound (0.015 g, 23%).

$^1$H-NMR (CDCl$_3$) δ 8.17 (1H, d), 8.09 (1H, d), 7.62 (1H, d), 7.53 (1H, d), 7.37 (1H, s), 6.93 (1H, t), 5.53 (1H, m), 3.85 (2H, t), 3.77-3.70 (5H, m), 3.00 (2H, t), 2.74 (2H, t), 2.00-1.60 (8H, m)

Step B: 3-[6-(2-cyclopentyloxy-pyridin-3-yl)-1-oxo-3,4-dihydro-1H-isoquinolin-2-yl]-propionic acid 3-[6-(2-Cyclopentyloxy-pyridin-3-yl)-1-oxo-3,4-dihydro-1H-isoquinolin-2-yl]-propionic acid methyl ester (0.015 g, 0.04 mmol) obtained in Step A was reacted in the same manner as in Step B of Example 1 to obtain the title compound (0.020 g, 56%).

$^1$H-NMR (CDCl$_3$) δ 8.17 (1H, d), 8.06 (1H, d), 7.62 (1H, d), 7.52 (1H, d), 7.37 (1H, s), 6.93 (1H, t), 5.52 (1H, m), 3.85 (2H, t), 3.71 (2H, t), 3.05 (2H, t), 2.82 (2H, t), 2.00-1.60 (8H, m)

Example 16: 3-[6-(2-isopropylsulfanyl-pyridin-3-yl)-1-oxo-3,4-dihydro-1H-isoquinolin-2-yl]-propionic acid

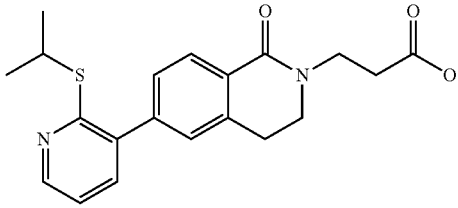 [SMILES: CC(C)Sc1ncccc1-c1ccc2c(c1)CCN(CCC(=O)O)C2=O]

Step A: 3-[6-(2-isopropylsulfanyl-pyridin-3-yl)-1-oxo-3,4-dihydro-1H-isoquinolin-2-yl]-propionic acid methyl ester

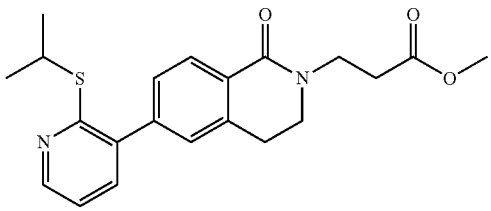 [SMILES: COC(=O)CCN1CCc2cc(-c3cccnc3SC(C)C)ccc2C1=O]

3-[1-Oxo-6-(4,4,5,5-tetramethyl-[1,3,2]dioxaborolan-2-yl)-3,4-dihydro-1H-isoquinolin-2-yl]-propionic acid methyl ester (0.06 g, 0.16 mmol) obtained in Preparation Example 8 and 3-iodo-2-isopropylsulfanyl-pyridine (0.047 g, 0.16 mmol) obtained in Preparation Example 9 were reacted in the same manner as in Step A of Example 1 to obtain the title compound (0.030 g, 46%).

$^1$H-NMR (CDCl$_3$) δ 8.46 (1H, d), 8.11 (1H, d), 7.45-7.35 (2H, m), 7.25 (1H, d), 7.03 (1H, t), 4.07 (1H, m), 3.85 (2H, t), 3.75-3.65 (5H, m), 3.05 (2H, t), 2.75 (2H, t), 1.35 (6H, d)

Step B: 3-[6-(2-isopropylsulfanyl-pyridin-3-yl)-1-oxo-3,4-dihydro-1H-isoquinolin-2-yl]-propionic acid 3-[6-(2-Isopropylsulfanyl-pyridin-3-yl)-1-oxo-3,4-dihydro-1H-isoquinolin-2-yl]-propionic acid methyl ester (0.030 g, 0.08 mmol) obtained in Step A was reacted in the same manner as in Step B of Example 1 to obtain the title compound (0.020 g, 69%).

$^1$H-NMR (CDCl$_3$) δ 8.46 (1H, d), 8.10 (1H, d), 7.45-7.35 (2H, m), 7.25 (1H, d), 7.05 (1H, t), 4.05 (1H, m), 3.90 (2H, t), 3.75 (2H, t), 3.05 (2H, t), 2.80 (2H, t), 1.34 (6H, d)

Example 17: 4-(3'-benzyloxy-3,5-difluoro-biphenyl-4-yloxy)-butyric acid

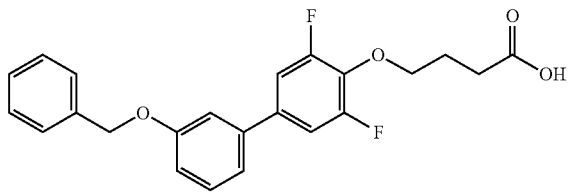 [SMILES: O=C(O)CCCOc1c(F)cc(-c2cccc(OCc3ccccc3)c2)cc1F]

Step A: 4-(3'-benzyloxy-3,5-difluoro-biphenyl-4-yloxy)-butyric acid ethyl ester 2N Na$_2$CO$_3$ (0.5 mL) and 1,4-dioxane (5 mL) were added to 1-benzyloxy-3-iodo-benzene (42 mg, 0.135 mmol) obtained in Preparation Example 17, 4-[2,6-difluoro-4-(4,4,5,5-tetramethyl-1,3,2-dioxaborolan-2-yl)phenoxy]butyric acid ethyl ester (50 mg, 0.135 mmol) obtained in Preparation Example 16 and PdCl$_2$(dppf)-DCM (5.5 mg, 0.0068 mmol), and the mixture was stirred 2 hours under reflux. After termination of the reaction, the reaction solution was cooled and filtered through Celite. After addition of water, the reaction solution was extracted with EtOAc to separate an organic layer. The organic layer was dried with MgSO$_4$, concentrated under reduced pressure and purified by column chromatography (eluent, EtOAc/Hex=1/10) to obtain the title compound (20 mg, 35%).

$^1$H NMR (400 MHz, CDCl$_3$) δ 7.48-7.43 (m, 2H), 7.43-7.37 (m, 2H), 7.37-7.31 (m, 2H), 7.13-7.06 (m, 4H), 6.99-6.95 (m, 1H), 4.12 (s, 2H), 4.21 (t, 2H), 4.16 (q, 2H), 2.58 (t, 2H), 2.15-2.06 (m, 2H), 1.27 (t, 3H)

Step B: 4-(3'-benzyloxy-3,5-difluoro-biphenyl-4-yloxy)-butyric acid 4-(3'-Benzyloxy-3,5-difluoro-biphenyl-4-yloxy)-butyric acid ethyl ester (20 mg, 0.047 mmol) obtained in Step A was reacted in the same manner as in Step B of Example 1 to obtain the title compound (18 mg, 96%).

$^1$H NMR (400 MHz, CDCl$_3$) δ 7.48-7.43 (m, 2H), 7.43-7.36 (m, 2H), 7.37-7.31 (m, 2H), 7.13-7.06 (m, 4H), 6.99-6.95 (m, 1H), 4.12 (s, 2H), 4.21 (t, 2H), 4.16 (q, 2H), 2.66 (t, 2H), 2.15-2.05 (m, 2H), 1.27 (t, 3H)

Example 18: 4-(3,5-difluoro-3'-isopropoxy-biphenyl-4-yloxy)-butyric acid

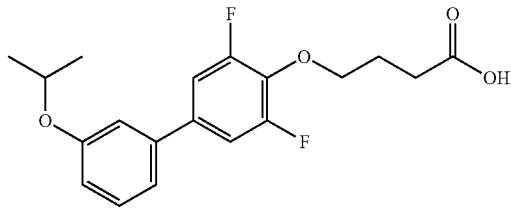 [SMILES: CC(C)Oc1cccc(-c2cc(F)c(OCCCC(=O)O)c(F)c2)c1]

Step A: 4-(3,5-difluoro-3'-isopropoxy-biphenyl-4-yloxy)-butyric acid ethyl ester 2 N Na$_2$CO$_3$ (0.5 mL) and 1,4-dioxane (5 mL) were added to 1-iodo-3-isopropoxy-benzene (35 mg, 0.135 mmol) obtained in Preparation Example 18, 4-[2,6-difluoro-4-(4,4,5,5-tetramethyl-1,3,2-dioxaborolan-2-yl)phenoxy]butyric acid ethyl ester (50 mg, 0.135 mmol) obtained in Preparation Example 16 and PdCl$_2$(dppf)-DCM (5.5 mg, 0.0068 mmol), and the mixture was stirred for 2 hours under reflux. After termination of the reaction, the reaction solution was cooled and filtered through Celite. After addition of water, the reaction solution was extracted with EtOAc to separate an organic layer. The organic layer was dried with MgSO$_4$, concentrated under reduced pressure and purified by column chromatography (eluent, EtOAc/Hex=1/10) to obtain the title compound (32 mg, 63%).

¹H NMR (400 MHz, CDCl₃) δ 7.40-7.34 (m, 1H), 7.29-6.97 (m, 4H), 6.96-7.182 (m, 1H), 4.70-4.52 (m, 1H), 4.28-4.08 (m, 4H), 2.69-2.52 (m, 2H), 2.20-2.03 (m, 2H), 1.37 (d, 6H), 1.25 (t, 3H)

Step B: 4-(3,5-difluoro-3'-isopropoxy-biphenyl-4-yloxy)-butyric acid 4-(3,5-Difluoro-3'-isopropoxy-biphenyl-4-yloxy)-butyric acid ethyl ester (32 mg, 0.085 mmol) obtained in Step A was reacted in the same manner as in Step B of Example 1 to obtain the title compound (28 mg, 95%).

¹H NMR (400 MHz, CDCl₃) δ 7.32 (t, 1H), 7.15-7.07 (m, 2H), 7.07-7.03 (m, 1H), 7.03-7.00 (m, 1H), 6.91-6.86 (m, 1H), 4.66-4.56 (m, 1H), 4.22 (t, 2H), 2.67 (t, 2H), 2.16-2.07 (m, 2H), 1.36 (d, 6H)

Example 19: 4-(3,5-difluoro-3'-propoxy-biphenyl-4-yloxy)-butyric acid

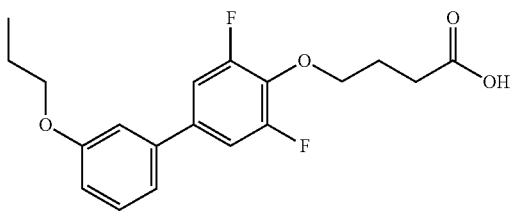 [SMILES: CCCOc1cccc(-c2cc(F)c(OCCCC(=O)O)c(F)c2)c1]

Step A: 4-(3,5-difluoro-3'-propoxy-biphenyl-4-yloxy)-butyric acid ethyl ester

1-Iodo-3-propoxy-benzene (35 mg, 0.135 mmol) obtained in Preparation Example 19, 4-[2,6-difluoro-4-(4,4,5,5-tetramethyl-1,3,2-dioxaborolan-2-yl)phenoxy]butyric acid ethyl ester (50 mg, 0.135 mmol) obtained in Preparation Example 16 and PdCl₂(dppf)-DCM (5.5 mg, 0.0068 mmol) were reacted in the same manner as in Step A of Example 18 to obtain the title compound (42 mg, 83%).

¹H NMR (400 MHz, CDCl₃) δ 7.32 (t, 1H), 7.16-7.09 (m, 2H), 7.09-7.04 (m, 1H), 7.04-7.00 (m, 1H), 6.92-6.87 (m, 1H), 4.20 (t, 2H), 4.16 (q, 2H), 3.97 (t, 2H), 2.57 (t, 2H), 2.15-2.04 (m, 2H), 1.89-1.78 (m, 2H), 1.28 (t, 3H), 1.06 (t, 3H)

Step B: 4-(3,5-difluoro-3'-propoxy-biphenyl-4-yloxy)-butyric acid 4-(3,5-Difluoro-3'-propoxy-biphenyl-4-yloxy)-butyric acid ethyl ester (42 mg, 0.11 mmol) obtained in Step A was reacted in the same manner as in Step B of Example 1 to obtain the title compound (37 mg, 95%).

¹H NMR (400 MHz, CDCl₃) δ 7.32 (t, 1H), 7.16-7.09 (m, 2H), 7.09-7.00 (m, 2H), 6.93-6.87 (m, 1H), 4.22 (t, 2H), 3.97 (t, 2H), 2.67 (t, 2H), 2.19-2.06 (m, 2H), 1.89-1.78 (m, 2H), 1.05 (t, 3H)

Example 20: 4-(3'-cyclopropylmethoxy-3,5-difluoro-biphenyl-4-yloxy)-butyric acid

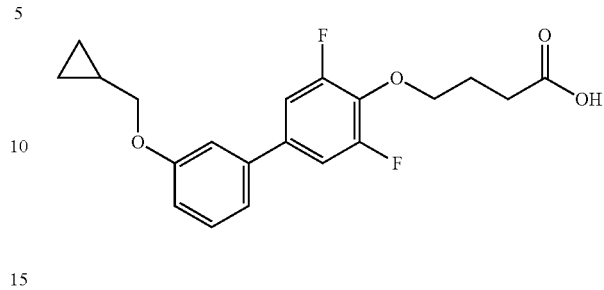

Step A: 4-(3'-cyclopropylmethoxy-3,5-difluoro-biphenyl-4-yloxy)-butyric acid ethyl ester 1-Cyclopropylmethoxy-3-iodo-benzene (37 mg, 0.135 mmol) obtained in Preparation Example 20, 4-[2,6-difluoro-4-(4,4,5,5-tetramethyl-1,3,2-dioxaborolan-2-yl)phenoxy]butyric acid ethyl ester (50 mg, 0.135 mmol) obtained in Preparation Example 16 and PdCl₂(dppf)-DCM (5.5 mg, 0.0068 mmol) were reacted in the same manner as in Step A of Example 18 to obtain the title compound (20 mg, 38%).

¹H NMR (400 MHz, CDCl₃) δ 7.32 (t, 1H), 7.16-7.09 (m, 2H), 7.09-7.05 (m, 1H), 7.05-7.02 (m, 1H), 6.92-6.87 (m, 1H), 4.20 (t, 2H), 4.16 (q, 2H), 3.85 (d, 2H), 2.59 (t, 2H), 2.15-2.05 (m, 2H), 1.35-1.21 (m, 1H), 1.27 (t, 3H), 0.71-0.62 (m, 2H), 0.41-0.34 (m, 2H)

Step B: 4-(3'-cyclopropylmethoxy-3,5-difluoro-biphenyl-4-yloxy)-butyric acid 4-(3'-Cyclopropylmethoxy-3,5-difluoro-biphenyl-4-yloxy)-butyric acid ethyl ester (20 mg, 0.05 mmol) obtained in Step A was reacted in the same manner as in Step B of Example 1 to obtain the title compound (18.4 mg, 99%).

¹H NMR (400 MHz, CDCl₃) δ 7.32 (t, 1H), 7.15-7.09 (m, 2H), 7.09-7.05 (m, 1H), 7.05-7.02 (m, 1H), 6.92-6.87 (m, 1H), 4.22 (t, 2H), 3.85 (d, 2H), 2.67 (t, 2H), 2.15-2.06 (m, 2H), 1.33-1.21 (m, 1H), 0.70-0.62 (m, 2H), 0.41-0.33 (m, 2H)

Example 21: 4-(3'-cyclobutoxy-3,5-difluoro-biphenyl-4-yloxy)-butyric acid

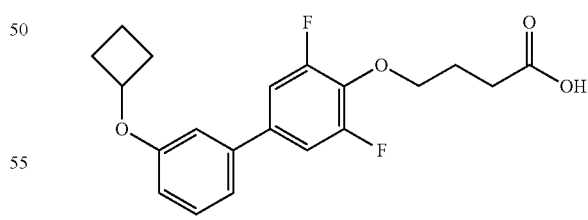

Step A: 4-(3'-cyclobutoxy-3,5-difluoro-biphenyl-4-yloxy)-butyric acid ethyl ester 1-Cyclobutoxy-3-iodo-benzene (37 mg, 0.135 mmol) obtained in Preparation Example 21, 4-[2,6-difluoro-4-(4,4,5,5-tetramethyl-1,3,2-dioxaborolan-2-yl)phenoxy]butyric acid ethyl ester (50 mg, 0.135 mmol) obtained in Preparation Example 16 and PdCl₂(dppf)-DCM (5.5 mg, 0.0068 mmol)

were reacted in the same manner as in Step A of Example 18 to obtain the title compound (30 mg, 57%).

$^1$H NMR (400 MHz, CDCl$_3$) δ 7.31 (t, 1H), 7.14-7.07 (m, 2H), 7.07-7.04 (m, 1H), 6.96-6.92 (m, 1H), 6.83-6.79 (m, 1H), 4.73-4.64 (m, 1H), 4.20 (t, 2H), 4.16 (q, 2H), 2.59 (t, 2H), 2.52-2.41 (m, 2H), 2.26-2.13 (m, 2H), 2.13-2.04 (m, 2H), 1.93-1.82 (m, 1H), 1.78-1.67 (m, 1H), 1.28 (t, 3H)

Step B: 4-(3'-cyclobutoxy-3,5-difluoro-biphenyl-4-yloxy)-butyric acid 4-(3'-Cyclobutoxy-3,5-difluoro-biphenyl-4-yloxy)-butyric acid ethyl ester (30 mg, 0.077 mmol) obtained in Step A was reacted in the same manner as in Step B of Example 1 to obtain the title compound (27 mg, 97%).

$^1$H NMR (400 MHz, CDCl$_3$) δ 7.31 (t, 1H), 7.14-7.08 (m, 2H), 7.08-7.03 (m, 1H), 6.96-6.92 (m, 1H), 6.83-6.78 (m, 1H), 4.73-4.64 (m, 1H), 4.22 (t, 2H), 2.67 (t, 2H), 2.51-2.42 (m, 2H), 2.28-2.17 (m, 2H), 2.17-2.07 (m, 2H), 1.92-1.82 (m, 1H), 1.78-1.64 (m, 1H)

Example 22: 4-[4-(2,2-dimethyl-2,3-dihydro-benzofuran-7-yl)-2,6-difluoro-phenoxy]-butyric acid

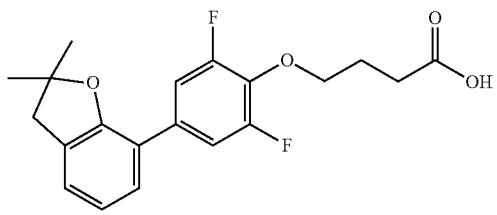 [SMILES: CC1(C)Cc2cccc(-c3cc(F)c(OCCCC(=O)O)c(F)c3)c2O1]

Step A: 4-[4-(2,2-dimethyl-2,3-dihydro-benzofuran-7-yl)-2,6-difluoro-phenoxy]-butyric acid ethyl ester 7-Iodo-2,2-dimethyl-2,3-dihydro-benzofuran (35 mg, 0.13 mmol) obtained in Preparation Example 22, 4-[2,6-difluoro-4-(4,4,5,5-tetramethyl-1,3,2-dioxaborolan-2-yl)phenoxy]butyric acid ethyl ester (47 mg, 0.13 mmol) obtained in Preparation Example 16 and PdCl$_2$(dppf)-DCM (5.2 mg, 0.0065 mmol) were reacted in the same manner as in Step A of Example 18 to obtain the title compound (20 mg, 40%).

$^1$H NMR (400 MHz, CDCl$_3$) δ 7.35-7.27 (m, 2H), 7.20 (d, 1H), 7.11 (d, 1H), 6.88 (t, 1H), 4.23-4.12 (m, 4H), 3.04 (s, 2H), 2.58 (t, 2H), 2.14-2.04 (m, 2H), 1.51 (s, 6H), 1.26 (t, 3H)

Step B: 4-[4-(2,2-dimethyl-2,3-dihydro-benzofuran-7-yl)-2,6-difluoro-phenoxy]-butyric acid 4-[4-(2,2-Dimethyl-2,3-dihydro-benzofuran-7-yl)-2,6-difluoro-phenoxy]-butyric acid ethyl ester (20 mg, 0.051 mmol) obtained in Step A was reacted in the same manner as in Step B of Example 1 to obtain the title compound (17 mg, 92%).

$^1$H NMR (400 MHz, CDCl$_3$) δ 7.34-7.27 (m, 2H), 7.20 (d, 1H), 7.11 (d, 1H), 6.88 (t, 1H), 4.20 (t, 2H), 3.04 (s, 2H), 2.67 (t, 2H), 2.14-2.06 (m, 2H), 1.51 (s, 6H)

Example 23: 4-[4-(2,2-dimethyl-benzo[1,3]dioxol-4-yl)-2,6-difluoro-phenoxy]-butyric acid

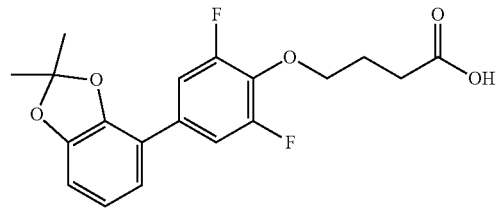 [SMILES: CC1(C)Oc2cccc(-c3cc(F)c(OCCCC(=O)O)c(F)c3)c2O1]

Step A: 4-[4-(2,2-dimethyl-benzo[1,3]dioxol-4-yl)-2,6-difluoro-phenoxy]-butyric acid ethyl ester 4-Iodo-2,2-dimethyl-benzo[1,3]dioxole (40 mg, 0.145 mmol) obtained in Preparation Example 23, 4-[2,6-difluoro-4-(4,4,5,5-tetramethyl-1,3,2-dioxaborolan-2-yl)phenoxy] butyric acid ethyl ester (53.6 mg, 0.145 mmol) obtained in Preparation Example 16 and PdCl$_2$(dppf)-DCM (5.9 mg, 0.0073 mmol) were reacted in the same manner as in Step A of Example 18 to obtain the title compound (19 mg, 33%).

$^1$H NMR (400 MHz, CDCl$_3$) δ 7.32-7.24 (m, 2H), 6.94-6.81 (m, 2H), 6.74-6.70 (m, 1H), 4.20 (t, 2H), 4.15 (q, 2H), 2.58 (t, 2H), 2.13-2.05 (m, 2H), 1.72 (s, 6H), 1.26 (t, 3H)

Step B: 4-[4-(2,2-dimethyl-benzo[1,3]dioxol-4-yl)-2,6-difluoro-phenoxy]-butyric acid 4-[4-(2,2-Dimethyl-benzo[1,3]dioxol-4-yl)-2,6-difluoro-phenoxy]-butyric acid ethyl ester (19 mg, 0.048 mmol) obtained in Step A was reacted in the same manner as in Step B of Example 1 to obtain the title compound (16 mg, 91%).

$^1$H NMR (400 MHz, CDCl$_3$) δ 7.32-7.22 (m, 2H), 6.94-6.78 (m, 2H), 6.74-6.68 (m, 1H), 4.21 (t, 2H), 2.65 (t, 2H), 2.14-2.03 (m, 2H), 1.72 (s, 6H)

Example 24: 4-[4-(2-cyclobutylsulfanyl-3-pyridyl)-2,6-difluoro-phenoxy]butanenitrile

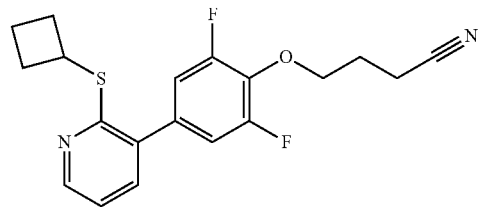 [SMILES: N#CCCCOc1c(F)cc(-c2cccnc2SC2CCC2)cc1F]

4-(2-Cyclobutylsulfanyl-pyridin-3-yl)-2,6-difluoro-phenol (0.06 g, 0.204 mmol) obtained in Preparation Example 24 was dissolved in DMF (3 mL), and 4-bromobutanenitrile (0.02 mL, 0.204 mmol) was added thereto. Cs$_2$CO$_3$ (0.133 g, 0.108 mmol) was added thereto, and the mixture was stirred at room temperature for 16 hours. After addition of brine aqueous solution, the reaction solution was extracted with EtOAc. The organic layer was dried with anhydrous magnesium sulfate and purified by column chromatography (eluent, EtOAc/Hex=1/2.5) to obtain the title compound (0.056 g, 76%).

NMR: $^1$H-NMR (CDCl$_3$) δ 8.41 (1H, m), 7.32 (1H, m), 7.01 (3H, m), 4.43 (1H, m), 4.30 (2H, t), 2.69 (2H, t), 2.52 (2H, m), 2.15 (2H, m), 2.04 (4H, m)

Example 25: 2-cyclobutylsulfanyl-3-{3,5-difluoro-4-[3-(1H-tetrazol-5-yl)propoxy]phenyl}pyridin

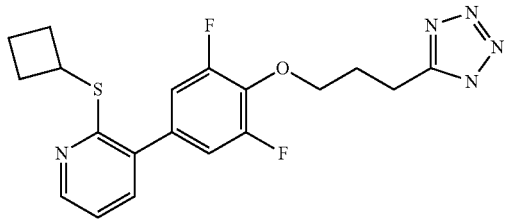 [SMILES: Fc1cc(-c2cccnc2SC2CCC2)cc(F)c1OCCCc1nnn[nH]1]

4-[4-(2-Cyclobutylsulfanyl-3-pyridyl)-2,6-difluoro-phenoxy]butanenitrile (0.056 g, 0.155 mmol) obtained in Example 24, sodium azide (0.029 g, 0.434 mmol) and ammonium chloride (0.024 g, 0.434 mmol) were dissolved in DMF (3 mL), and the mixture was stirred at 120° C. for 16 hours. After termination of the reaction, the reaction solution was diluted with water and extracted with EtOAc. The organic layer was dried with anhydrous magnesium sulfate and purified by column chromatography (eluent, MeOH/DCM=1/20) to obtain the title compound (0.004 g, 7.2%).

NMR: $^1$H-NMR (CDCl$_3$) δ 8.42 (1H, m), 7.32 (1H, m), 7.03 (3H, m), 4.43 (1H, m), 4.31 (2H, t), 3.34 (2H, t), 2.53 (2H, m), 2.32 (2H, m), 2.06 (4H, m)

Example 26: 2-cyclobutylsulfanyl-3-{4-[3-(1H-tetrazol-5-yl)propyl]phenyl}pyridine

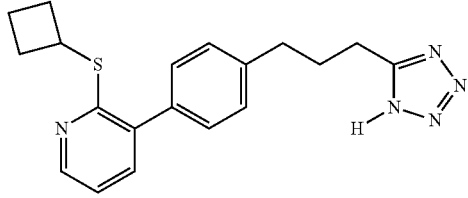 [SMILES: c1cnc(SC2CCC2)c(-c2ccc(CCCc3nnn[nH]3)cc2)c1]

Step A: 4-[4-(2-cyclobutylsulfanyl-3-pyridyl)phenyl]butanenitrile

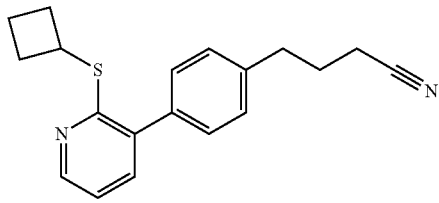 [SMILES: N#CCCCc1ccc(-c2cccnc2SC2CCC2)cc1]

2-Cyclobutylsulfanyl-3-iodo-pyridine (0.038 g, 0.177 mmol) obtained in Preparation Example 13 and 4-[4-(4,4,5,5-tetramethyl-[1,3,2]dioxaborolan-2-yl)phenyl]butanenitrile (0.045 g, 0.166 mmol) obtained in Preparation Example 25 were reacted in the same manner as in Step A of Example 1 to obtain the title compound (0.03 g, 55%).

NMR: $^1$H-NMR (CDCl$_3$) δ 8.39 (1H, m), 7.34 (3H, m), 7.26 (2H, m), 7.00 (1H, m), 4.22 (1H, m), 2.83 (2H, t), 2.48 (2H, m), 2.37 (2H, t), 2.03 (6H, m)

Step B: 2-cyclobutylsulfanyl-3-{4-[3-(1H-tetrazol-5-yl)propyl]phenyl}pyridine

4-[4-(2-Cyclobutylsulfanyl-pyridin-3-yl)phenyl]butanenitrile (0.03 g, 0.097 mmol) obtained in Step A was reacted in the same manner as in Example 25 to obtain the title compound (0.001 g, 4.6%).

NMR: $^1$H-NMR (CDCl$_3$) δ 8.39 (1H, m), 7.34 (3H, m), 7.26 (2H, m), 7.03 (1H, m), 4.41 (1H, m), 3.00 (2H, t), 2.77 (2H, m), 2.49 (2H, m), 2.20 (2H, m), 2.01 (4H, m)

Example 27: 5-[4-(2-cyclobutylsulfanyl-3-pyridyl)phenyl]pentanoic acid

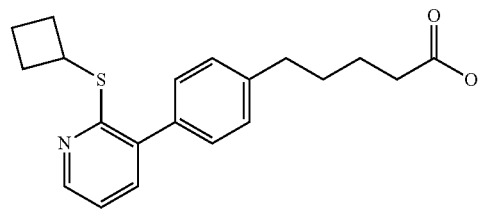 [SMILES: O=C(O)CCCCc1ccc(-c2cccnc2SC2CCC2)cc1]

Step A: 5-[4-(2-cyclobutylsulfanyl-3-pyridyl)phenyl]pentanoic acid ethyl ester

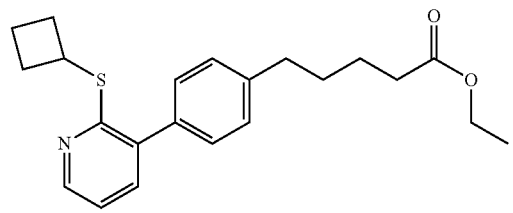 [SMILES: CCOC(=O)CCCCc1ccc(-c2cccnc2SC2CCC2)cc1]

2-Cyclobutylsulfanyl-3-iodo-pyridine (0.08 g, 0.27 mmol) obtained in Preparation Example 13 and 5-[4-(4,4,5,5-tetramethyl-[1,3,2]dioxaborolan-2-yl)phenyl]pentanoic acid ethyl ester (0.085 g, 0.25 mmol) obtained in Preparation Example 26 were reacted in the same manner as in Step A of Example 1 to obtain the title compound (0.063 g, 62%).

NMR: $^1$H-NMR (CDCl$_3$) δ 8.37 (1H, m), 7.33 (3H, m), 7.26 (2H, m), 7.00 (1H, m), 4.41 (1H, m), 4.12 (2H, q), 2.68 (2H, m), 2.48 (2H, m), 2.33 (2H, m), 1.99 (4H, m), 1.71 (4H, m), 1.24 (3H, t)

Step B: 5-[4-(2-cyclobutylsulfanyl-3-pyridyl)phenyl]pentanoic acid

5-[4-(2-Cyclobutylsulfanyl-3-pyridyl)phenyl]pentanoic acid ethyl ester (0.063 g, 0.17 mmol) obtained in Step A was dissolved in EtOH (2 mL). 1N NaOH (1 mL) was added thereto, and the mixture was stirred at room temperature for 3 hours. After termination of the reaction, the reaction solution was concentrated under reduced pressure, and residues were diluted with water. The water layer was adjusted to pH 2-3 by the use of 1N HCl and extracted with ethyl acetate. The organic layer was dried with anhydrous magnesium sulfate and purified by column chromatography (eluent, EtOAc/Hex=1/2) to obtain the title compound (0.044 g, 75%).

NMR: $^1$H-NMR (CDCl$_3$) δ 8.37 (1H, m), 7.31 (3H, m), 7.26 (2H, m), 7.00 (1H, m), 4.41 (1H, m), 2.68 (2H, m), 2.48 (2H, m), 2.40 (2H, m), 1.99 (4H, m), 1.72 (4H, m)

Example 28: 5-[4-(6-cyclopentylsulfanyl-2-pyridyl) phenyl]pentanoic acid

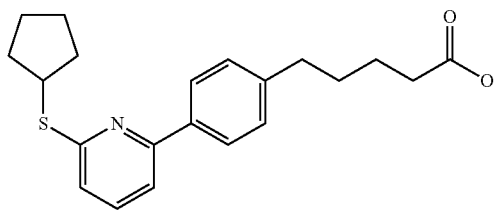 [SMILES: O=C(O)CCCCc1ccc(-c2cccc(SC3CCCC3)n2)cc1]

2-Chloro-6-cyclopentylsulfanyl-pyridine (0.042 g, 0.196 mmol) obtained in Preparation Example 14 and 5-[4-(4,4,5,5-tetramethyl-[1,3,2]dioxaborolan-2-yl)phenyl]pentanoic acid ethyl ester (0.061 g, 0.183 mmol) obtained in Preparation Example 26 were reacted in the same manner as in Example 1 to obtain the title compound (0.015 g, 21%).

NMR: $^1$H-NMR (CDCl$_3$) δ 7.94 (2H, m), 7.49 (1H, m), 7.38 (1H, m), 7.26 (2H, m), 7.06 (1H, m), 4.18 (1H, m), 2.68 (2H, m), 2.38 (2H, m), 2.24 (2H, m), 1.76 (2H, m), 1.72-1.60 (8H, m)

Example 29: 5-[4-(2-cyclopentylsulfanyl-3-pyridyl) phenyl]pentanoic acid

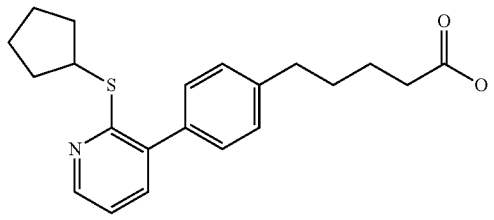 [SMILES: O=C(O)CCCCc1ccc(-c2cccnc2SC2CCCC2)cc1]

2-Cyclopentylsulfanyl-3-iodo-pyridine (0.03 g, 0.14 mmol) obtained in Preparation Example 15 and 5-[4-(4,4,5,5-tetramethyl-[1,3,2]dioxaborolan-2-yl)phenyl]pentanoic acid ethyl ester (0.044 g, 0.131 mmol) obtained in Preparation Example 26 were reacted in the same manner as in Example 1 to obtain the title compound (0.017 g, 34%).

NMR: $^1$H-NMR (CDCl$_3$) δ 8.39 (1H, m), 7.33 (3H, m), 7.26 (2H, m), 7.01 (1H, m), 4.07 (1H, m), 2.67 (2H, m), 2.39 (2H, m), 2.17 (2H, m), 1.70 (6H, m), 1.65 (4H, m)

Example 30: 2-cyclobutylsulfanyl-3-[3,5-difluoro-4-(1H-tetrazol-5-ylmethoxy)phenyl]pyridine

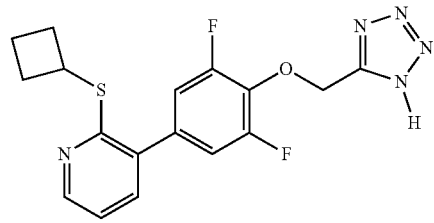 [SMILES: Fc1cc(-c2cccnc2SC2CCC2)cc(F)c1OCc1nnn[nH]1]

Step A: 2-[4-(2-cyclobutylsulfanyl-3-pyridyl)-2,6-difluoro-phenoxy]acetonitrile

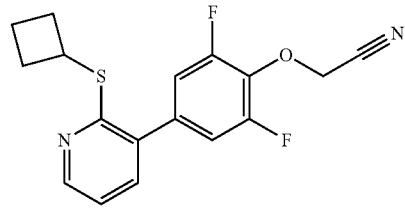 [SMILES: N#CCOc1c(F)cc(-c2cccnc2SC2CCC2)cc1F]

4-(2-Cyclobutylsulfanyl-pyridin-3-yl)-2,6-difluoro-phenol (0.103 g, 0.351 mmol) obtained in Preparation Example 24 was dissolved in acetone (5 mL). Bromoacetonitrile (0.03 mL, 0.421 mmol) and K$_2$CO$_3$ (0.058 g, 0.421 mmol) were added thereto, and the mixture was stirred at 70° C. for 2 hours, and stirred at room temperature for 16 hours. After termination of the reaction, the reaction solution was diluted with water and extracted with EtOAc. The organic layer was dried with anhydrous magnesiumsulfate and purified by column chromatography (eluent, MeOH/DCM=1/21) to obtain the title compound (0.104 g, 89%).

$^1$H-NMR (CDCl$_3$) δ 8.43 (1H, m), 7.33 (1H, m), 7.05 (3H, m), 4.91 (2H, s), 4.41 (1H, m), 2.52 (2H, m), 2.05 (4H, m)

Step B: 2-cyclobutylsulfanyl-3-[3,5-difluoro-4-(1H-tetrazol-5-ylmethoxy)phenyl]pyridine 2-[4-(2-Cyclobutylsulfanyl-3-pyridyl)-2,6-difluoro-phenoxy]acetonitrile (0.104 g, 0.312 mmol) obtained in Step A was reacted in the same manner as in Example 25 to obtain the title compound (0.024 g, 20%).

NMR: $^1$H-NMR (CDCl$_3$) δ 8.43 (1H, m), 7.31 (1H, m), 7.04 (3H, m), 5.63 (2H, s), 4.41 (1H, m), 2.50 (2H, m), 2.03 (4H, m)

Example 31: 5-[2,6-difluoro-4-(2-propylsulfanyl-3-pyridyl)phenyl]pentanoic acid

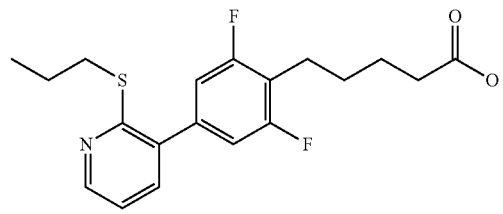 [SMILES: CCCSc1ncccc1-c1cc(F)c(CCCCC(=O)O)c(F)c1]

3-Iodo-2-propylsulfanyl-pyridine (0.082 g, 0.293 mmol) obtained in Preparation Example 28 and 5-[2,6-difluoro-4-(4,4,5,5-tetramethyl-[1,3,2]dioxaborolan-2-yl)phenyl]pentanoic acid ethyl ester (0.10 g, 0.274 mmol) obtained in Preparation Example 27 were reacted in the same manner as in Example 1 to obtain the title compound (0.057 g, 48%).

NMR: $^1$H-NMR (CDCl$_3$) δ 8.44 (1H, m), 7.35 (1H, m), 7.04 (1H, m), 6.94 (2H, m), 3.14 (2H, t), 2.74 (2H, t), 2.42 (2H, t), 1.70 (6H, m), 1.00 (3H, t)

Example 32: 5-[4-(6-cyclobutoxy-2-pyridyl)-2,6-difluoro-phenyl]pentanoic acid

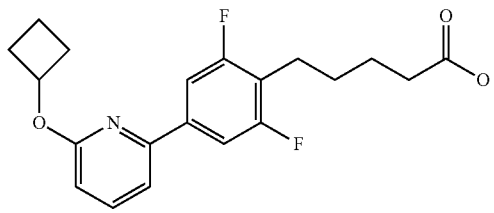 [SMILES: O=C(O)CCCCc1c(F)cc(-c2cccc(OC3CCC3)n2)cc1F]

2-Chloro-6-cyclobutoxy-pyridine (0.017 g, 0.091 mmol) obtained in Preparation Example 29 and 5-[2,6-difluoro-4-(4,4,5,5-tetramethyl-[1,3,2]dioxaborolan-2-yl)phenyl]pentanoic acid ethyl ester (0.031 g, 0.085 mmol) obtained in Preparation Example 27 were reacted in the same manner as in Example 1 to obtain the title compound (0.015 g, 49%).

NMR: $^1$H-NMR (CDCl$_3$) δ 7.60 (1H, t), 7.50 (2H, m), 7.28 (1H, m), 6.66 (1H, d), 5.27 (1H, m), 2.73 (2H, t), 2.52 (2H, m), 2.41 (2H, t), 2.19 (2H, m), 1.85 (1H, m), 1.72 (5H, m)

Example 33: 5-[4-(6-cyclopentoxy-2-pyridyl)-2,6-difluoro-phenyl]pentanoic acid

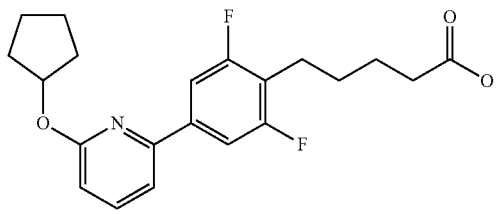 [SMILES: O=C(O)CCCCc1c(F)cc(-c2cccc(OC3CCCC3)n2)cc1F]

2-Chloro-6-cyclopentyloxy-pyridine (0.018 g, 0.091 mmol) obtained in Preparation Example 12 and 5-[2,6-difluoro-4-(4,4,5,5-tetramethyl-[1,3,2]dioxaborolan-2-yl)phenyl]pentanoic acid ethyl ester (0.031 g, 0.085 mmol) obtained in Preparation Example 27 were reacted in the same manner as in Example 1 to obtain the title compound (0.017 g, 47%).

NMR: $^1$H-NMR (CDCl$_3$) δ 7.49 (1H, t), 7.52 (2H, m), 7.22 (1H, m), 6.64 (1H, d), 5.51 (1H, m), 2.73 (2H, t), 2.40 (2H, t), 2.05 (2H, m), 1.82-1.60 (10H, m)

Example 34: 5-[4-(2,2-difluoro-benzo[1,3]dioxol-4-yl)-2,6-difluoro-phenyl]pentanoic acid

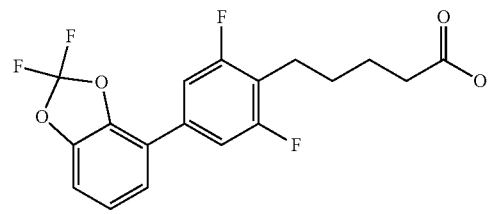 [SMILES: O=C(O)CCCCc1c(F)cc(-c2cccc3c2OC(F)(F)O3)cc1F]

4-Bromo-2,2-difluoro-benzo[1,3]dioxole (0.059 g, 0.248 mmol) and 5-[2,6-difluoro-4-(4,4,5,5-tetramethyl-[1,3,2]dioxaborolan-2-yl)phenyl]pentanoic acid ethyl ester (0.086 g, 0.232 mmol) obtained in Preparation Example 27 were reacted in the same manner as in Example 1 to obtain the title compound (0.038 g, 44%).

NMR: $^1$H-NMR (CDCl$_3$) δ 7.26-7.17 (3H, m), 7.07 (1H, m), 7.05 (1H, m), 2.75 (2H, m), 2.41 (2H, m), 1.71-1.60 (4H, m)

Example 35: 5-[4-(2-cyclobutylsulfanyl-3-pyridyl)-2,6-difluoro-phenyl]pentanoic acid

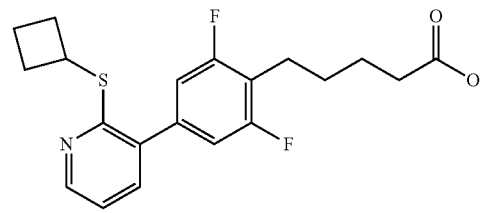 [SMILES: O=C(O)CCCCc1c(F)cc(-c2cccnc2SC2CCC2)cc1F]

2-Cyclobutylsulfanyl-3-iodo-pyridine (0.025 g, 0.084 mmol) obtained in Preparation Example 13 and 5-[2,6-difluoro-4-(4,4,5,5-tetramethyl-[1,3,2]dioxaborolan-2-yl)phenyl]pentanoic acid ethyl ester (0.029 g, 0.078 mmol) obtained in Preparation Example 27 were reacted in the same manner as in Example 1 to obtain the title compound (0.01 g, 34%).

NMR: $^1$H-NMR (CDCl$_3$) δ 8.41 (1H, m), 7.33 (1H, m), 7.03 (1H, m), 6.93 (2H, m), 4.42 (1H, m), 2.73 (2H, t), 2.49 (2H, m), 2.42 (2H, t), 2.10-1.95 (4H, m), 1.73 (4H, m)

Example 36: 5-[4-(2-cyclopentylsulfanyl-3-pyridyl)-2,6-difluoro-phenyl]pentanoic acid

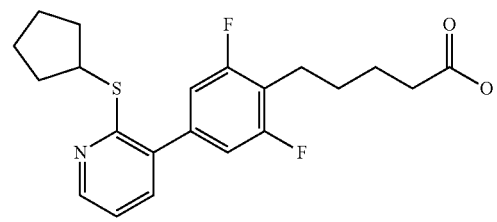 [SMILES: O=C(O)CCCCc1c(F)cc(-c2cccnc2SC2CCCC2)cc1F]

2-Cyclopentylsulfanyl-3-iodo-pyridine (0.034 g, 0.159 mmol) obtained in Preparation Example 15 and 5-[2,6-difluoro-4-(4,4,5,5-tetramethyl-[1,3,2]dioxaborolan-2-yl)

phenyl]pentanoic acid ethyl ester (0.044 g, 0.12 mmol) obtained in Preparation Example 27 were reacted in the same manner as in Example 1 to obtain the title compound (0.015 g, 33%).

NMR: $^1$H-NMR (CDCl$_3$) δ 8.43 (1H, m), 7.33 (1H, m), 7.03 (1H, m), 6.94 (2H, m), 4.09 (1H, m), 2.73 (2H, t), 2.42 (2H, m), 2.21 (2H, m), 1.71-1.57 (10H, m)

Example 37: 5-[4-(2-cyclopentoxy-3-pyridyl)-2,6-difluoro-phenyl]pentanoic acid

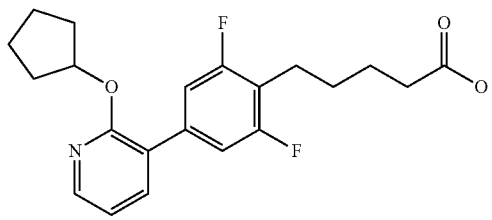 [SMILES: O=C(O)CCCCc1c(F)cc(-c2cccnc2OC2CCCC2)cc1F]

2-cyclopentyloxy-3-iodo-pyridine (0.026 g, 0.089 mmol) obtained in Preparation Example 11 and 5-[2,6-difluoro-4-(4,4,5,5-tetramethyl-[1,3,2]dioxaborolan-2-yl)phenyl]pentanoic acid ethyl ester (0.03 g, 0.084 mmol) obtained in Preparation Example 27 were reacted in the same manner as in Example 1 to obtain the title compound (0.014 g, 44%).

NMR: $^1$H-NMR (CDCl$_3$) δ 8.15 (1H, m), 7.58 (1H, m), 7.09 (2H, m), 6.93 (1H, m), 5.52 (1H, m), 2.73 (2H, t), 2.42 (2H, m), 1.95 (2H, m), 1.71-1.57 (10H, m)

Example 38: {2-[4-(2-cyclobutylsulfanyl-3-pyridyl)-2,6-difluoro-phenyl]ethoxy}acetic acid

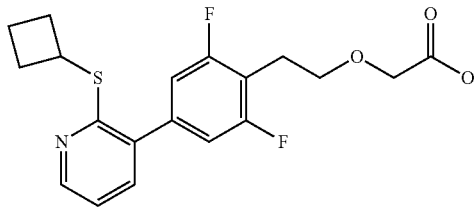 [SMILES: O=C(O)COCCc1c(F)cc(-c2cccnc2SC2CCC2)cc1F]

Step A: {2-[4-(2-cyclobutylsulfanyl-3-pyridyl)-2,6-difluoro-phenyl]ethoxy}acetic acid tert-butyl ester

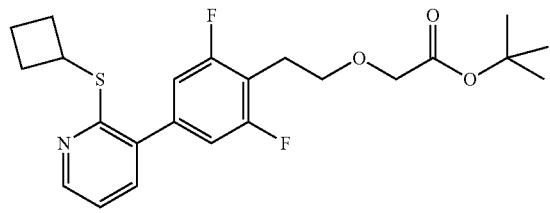 [SMILES: CC(C)(C)OC(=O)COCCc1c(F)cc(-c2cccnc2SC2CCC2)cc1F]

2-Cyclobutylsulfanyl-3-iodo-pyridine (0.031 g, 0.107 mmol) obtained in Preparation Example 13 and {2-[2,6-difluoro-4-(4,4,5,5-tetramethyl-[1,3,2]dioxaborolan-2-yl)phenyl]ethoxy}acetic acid tert-butyl ester (0.04 g, 0.10 mmol) obtained in Preparation Example 30 were reacted in the same manner as in Step A of Example 1 to obtain the title compound (0.025 g, 58%).

Step B: {2-[4-(2-cyclobutylsulfanyl-3-pyridyl)-2,6-difluoro-phenyl]ethoxy}acetic acid {2-[4-(2-Cyclobutylsulfanyl-3-pyridyl)-2,6-difluoro-phenyl]ethoxy}acetic acid tert-butyl ester (0.025 g, 0.057 mmol) obtained in Step A was dissolved in DCM (3 mL). TFA (1 mL) was added thereto, and the mixture was stirred for 4 hours. After termination of the reaction, the reaction solution was concentrated under reduced pressure and washed with Et$_2$O and DCM. The reaction product was dried with anhydrous magnesium sulfate and purified by column chromatography (eluent, EtOAc/Hex=1/2) to obtain the title compound (0.016 g, 76%).

NMR: $^1$H-NMR (CDCl$_3$) δ 8.41 (1H, m), 7.33 (1H, m), 7.03 (1H, m), 6.97 (2H, m), 4.42 (1H, m), 4.13 (2H, s), 3.83 (2H, t), 3.07 (2H, m), 2.51 (2H, m), 2.10-1.95 (4H, m)

Example 39: 5-[4-(2-cyclobutylsulfanyl-3-pyridyl)phenyl]hexanoic acid

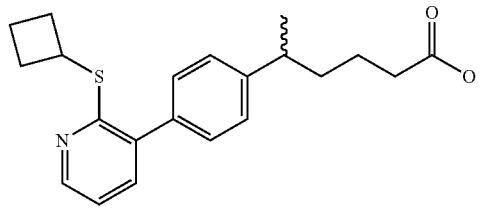 [SMILES: CC(CCCC(=O)O)c1ccc(-c2cccnc2SC2CCC2)cc1]

2-Cyclobutylsulfanyl-3-iodo-pyridine (0.033 g, 0.111 mmol) obtained in Preparation Example 13 and 5-[4-(4,4,5,5-tetramethyl-[1,3,2]dioxaborolan-2-yl)phenyl]hexanoic acid ethyl ester (0.04 g, 0.104 mmol) obtained in Preparation Example 31 were reacted in the same manner as in Example 1 to obtain the title compound (0.021 g, 51%).

NMR: $^1$H-NMR (CDCl$_3$) δ 8.38 (1H, m), 7.36 (3H, m), 7.26 (2H, m), 7.01 (1H, m), 4.42 (1H, m), 2.75 (1H, m), 2.49 (2H, m), 2.36 (2H, m), 2.10-2.00 (4H, m), 1.67-1.50 (4H, m), 1.30 (3H, d)

Example 40: 5-[4-(6-cyclobutoxy-2-pyridyl)-phenyl]hexanoic acid

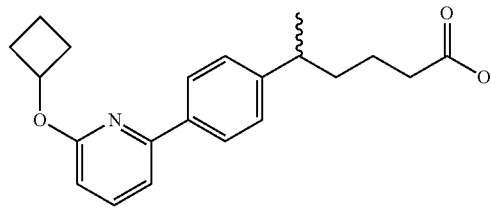 [SMILES: CC(CCCC(=O)O)c1ccc(-c2cccc(OC3CCC3)n2)cc1]

2-Chloro-6-cyclobutoxy-pyridine (0.038 g, 0.206 mmol) obtained in Preparation Example 29 and 5-[4-(4,4,5,5-tetramethyl-[1,3,2]dioxaborolan-2-yl)phenyl]hexanoic acid ethyl ester (0.051 g, 0.147 mmol) obtained in Preparation Example 31 were reacted in the same manner as in Example 1 to obtain the title compound (0.032 g, 63%).

NMR: ¹H-NMR (CDCl₃) δ 7.94 (2H, d), 7.59 (1H, m), 7.23 (3H, m), 6.61 (1H, d), 5.29 (1H, m), 2.76 (1H, m), 2.53 (2H, m), 2.33 (2H, m), 2.20 (2H, m), 1.90 (1H, m), 1.80-1.50 (5H, m), 1.28 (3H, d)

Example 41: 5-[4-(6-cyclobutoxy-2-pyridyl)-2,6-difluoro-phenyl]hexanoic acid

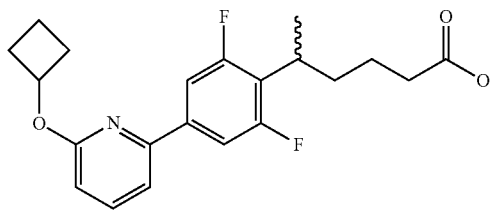 [SMILES: CC(CCCC(=O)O)c1c(F)cc(-c2cccc(OC3CCC3)n2)cc1F]

2-Chloro-6-cyclobutoxy-pyridine (0.068 g, 0.371 mmol) obtained in Preparation Example 29 and 5-[2,6-difluoro-4-(4,4,5,5-tetramethyl-[1,3,2]dioxaborolan-2-yl)-phenyl] hexanoic acid ethyl ester (0.062 g, 0.337 mmol) obtained in Preparation Example 32 were reacted in the same manner as in Example 1 to obtain the title compound (0.030 g, 23%).
NMR: ¹H-NMR (CDCl₃) δ 7.61 (1H, t), 7.49 (2H, d), 7.23 (1H, m), 6.66 (1H, d), 5.27 (1H, m), 3.24 (1H, m), 2.54 (2H, m), 2.35 (2H, t), 2.20 (2H, m), 1.87 (2H, m), 1.74 (2H, m), 1.70-1.45 (2H, m), 1.25 (3H, d)

Example 42: 5-[4-(2-ethylsulfanyl-3-pyridyl)-2,6-difluoro-phenyl]hexanoic acid

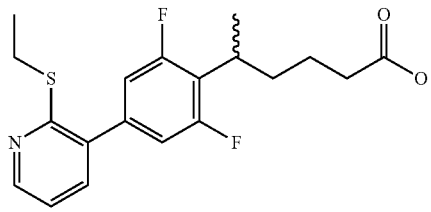 [SMILES: CCSc1ncccc1-c1cc(F)c(C(C)CCCC(=O)O)c(F)c1]

2-Ethylsulfanyl-3-iodo-pyridine (0.041 g, 0.154 mmol) obtained in Preparation Example 33 and 5-[2,6-difluoro-4-(4,4,5,5-tetramethyl-[1,3,2]dioxaborolan-2-yl)phenyl] hexanoic acid ethyl ester (0.047 g, 0.144 mmol) obtained in Preparation Example 32 were reacted in the same manner as in Example 1 to obtain the title compound (0.011 g, 21%).
NMR: ¹H-NMR (CDCl₃) δ 8.44 (1H, m), 7.37 (1H, m), 7.04 (1H, m), 6.93 (2H, d), 3.27 (1H, m), 3.18 (2H, q), 2.37 (2H, t), 1.85 (1H, m), 1.80-1.50 (3H, m), 1.40-1.30 (6H, m)

Example 43: 5-[2,6-difluoro-4-(2-propylsulfanyl-3-pyridyl)-phenyl]hexanoic acid

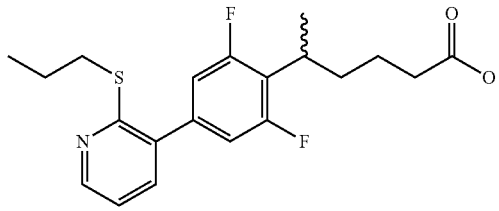 [SMILES: CCCSc1ncccc1-c1cc(F)c(C(C)CCCC(=O)O)c(F)c1]

3-Iodo-2-propylsulfanyl-pyridine (0.040 g, 0.143 mmol) obtained in Preparation Example 28 and 5-[2,6-difluoro-4-(4,4,5,5-tetramethyl-[1,3,2]dioxaborolan-2-yl)phenyl] hexanoic acid ethyl ester (0.044 g, 0.133 mmol) obtained in Preparation Example 32 were reacted in the same manner as in Example 1 to obtain the title compound (0.01 g, 18%).
NMR: ¹H-NMR (CDCl₃) δ 8.44 (1H, m), 7.35 (1H, m), 7.04 (1H, m), 6.94 (2H, d), 3.24 (1H, m), 3.14 (2H, t), 2.38 (2H, t), 1.85 (1H, m), 1.75-1.60 (5H, m), 1.38 (3H, d), 1.02 (3H, t)

Example 44: 4-[1-methyl-5-(2-phenoxyphenyl)benzimidazol-2-yl]butanoic acid

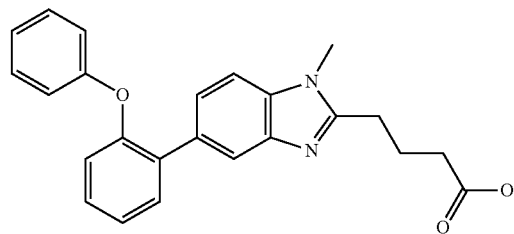 [SMILES: Cn1c(CCCC(=O)O)nc2cc(-c3ccccc3Oc3ccccc3)ccc21]

Step A: 5-[(2-amino-4-bromo-N-methyl-anilino)-5-oxo-pentanoic acid ethyl ester

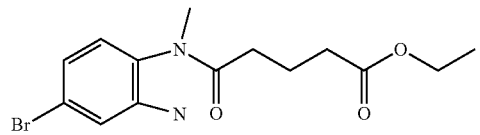 [SMILES: CCOC(=O)CCCC(=O)N(C)c1ccc(Br)cc1N]

4-Bromo-N,N-dimethylaniline (0.341 g, 1.69 mmol) was dissolved in DCM (8 mL). 5-Chloro-5-oxo-pentanoic acid ethyl ester (0.217 mL, 1.54 mmol) was slowly added thereto at 0° C. TEA (0.472 mL, 3.39 mmol) was added thereto at 0° C., and the mixture was stirred at room temperature for 16 hours. After termination of the reaction, the reaction solution was diluted with water and extracted with DCM. The organic layer was dried with anhydrous magnesium sulfate and used for the next step without purification.

Step B: 4-(5-bromo-1-methyl-benzimidazol-2-yl)butanoic acid

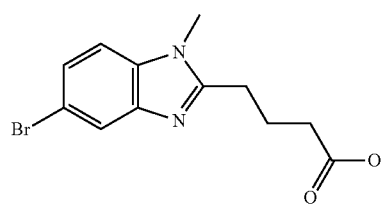 [SMILES: Cn1c(CCCC(=O)O)nc2cc(Br)ccc21]

5-[(2-Amino-4-bromo-N-methyl-anilino)-5-oxo-pentanoic acid ethyl ester obtained in Step A was dissolved in AcOH (4 mL) and stirred at 75° C. for 16 hours. The solvent was distilled under reduced pressure, and the reaction product was washed with toluene and distilled under reduced pressure. The obtained product was used for the next step without purification.

Step C:
4-(5-bromo-1-methyl-benzimidazol-2-yl)butanoic acid methyl ester

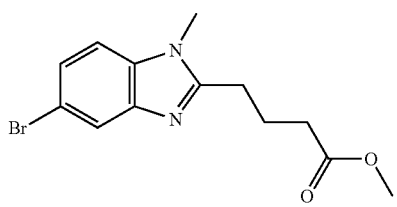 [SMILES: COC(=O)CCCc1nc2cc(Br)ccc2n1C]

Diazomethane (2.5 mL) was added to 4-(5-bromo-1-methyl-benzimidazol-2-yl)butanoic acid (0.091 g, 0.30 mmol) obtained in Step B, and the solvent was distilled under reduced pressure to obtain the title compound (0.58 g, 63%).
NMR: $^1$H-NMR (CDCl$_3$) δ 7.84 (1H, s), 7.35 (1H, d), 7.17 (1H, d), 3.74 (3H, s), 3.67 (3H, s), 2.95 (2H, t), 2.52 (2H, t), 2.21 (2H, m)

Step D: 4-[1-methyl-5-(2-phenoxyphenyl)benzimidazol-2-yl]butanoic acid methyl ester

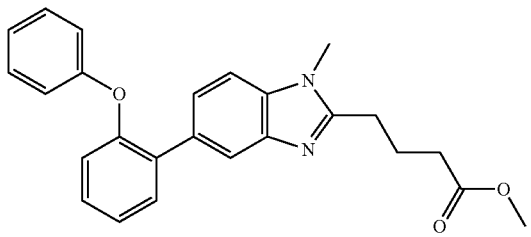 [SMILES: COC(=O)CCCc1nc2cc(-c3ccccc3Oc3ccccc3)ccc2n1C]

2-Phenoxyphenylboronic acid (0.058 g, 0.269 mmol) and 4-(5-bromo-1-methyl-benzimidazol-2-yl)butanoic acid methyl ester (0.04 g, 0.134 mmol) obtained in Step C were dissolved in DME (3 mL) and water (0.3 mL), and charged with N$_2$ gas for 5 minutes. Tetrakis(triphenylphosphine) palladium(0) (0.005 g, 0.004 mmol) and Cs$_2$CO$_3$ (0.175 g, 0.538 mmol) were added thereto, and the mixture was stirred at 80° C. for 8 hours. After termination of the reaction, the reaction solution was diluted with water and extracted with EtOAc. The organic layer was dried with anhydrous magnesium sulfate and purified by column chromatography (eluent, EtOAc/Hex=1/1) to obtain the title compound (0.023 g, 21%).
NMR: $^1$H-NMR (CDCl$_3$) δ 7.88 (1H, m), 7.70-7.60 (5H, m), 7.20 (4H, m), 7.10 (1H, m), 6.90 (1H, m), 3.74 (3H, s), 3.64 (3H, s), 2.95 (2H, t), 2.51 (2H, t), 2.19 (2H, m)

Step E: 4-[1-methyl-5-(2-phenoxyphenyl)benzimidazol-2-yl]butanoic acid

4-[1-Methyl-5-(2-phenoxyphenyl)benzimidazol-2-yl]butanoic acid methyl ester (0.023 g, 0.057 mmol) obtained in Step D was reacted in the same manner as in Step B of Example 1 to obtain the title compound (0.003 g, 14%).

NMR: 1H-NMR (MeOD) δ 7.74 (1H, m), 7.53 (1H, m), 7.45 (2H, s), 7.35 (1H, m), 7.29 (1H, m), 7.21 (2H, m), 7.06 (1H, m), 6.95 (1H, m), 6.85 (2H, d), 3.82 (3H, s), 3.02 (2H, t), 2.42 (2H, t), 2.13 (2H, m)

Example 45: 3-[1-methyl-5-(2-phenoxyphenyl)benzimidazol-2-yl]propanoic acid

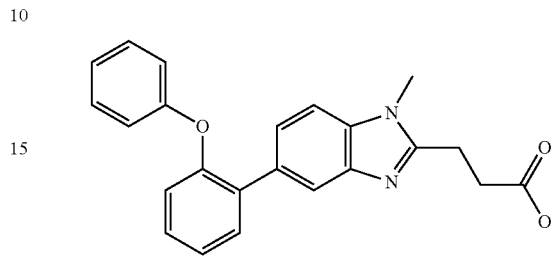

Step A: 4-(2-amino-4-bromo-N-methyl-anilino)-4-oxo-butanoic acid ethyl ester

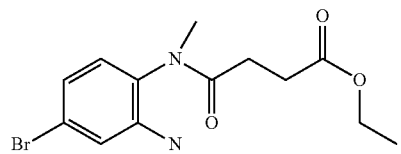 [SMILES: CCOC(=O)CCC(=O)N(C)c1ccc(Br)cc1N]

4-Bromo-N,N-dimethylaniline (0.196 g, 0.974 mmol) was dissolved in DCM (8 mL). 3-Chlorocarbonyl-propionic acid ethyl ester (0.125 mL, 0.886 mmol) was slowly added thereto at 0° C. TEA (0.273 mL, 1.955 mmol) was added thereto at 0° C., and the mixture was stirred at room temperature for 16 hours. After termination of the reaction, the reaction solution was diluted with water and extracted with DCM. The organic layer was dried with anhydrous magnesium sulfate and used for the next step with simple filter purification.

Step B:
3-(5-bromo-1-methyl-benzimidazol-2-yl)propanoic acid ethyl ester

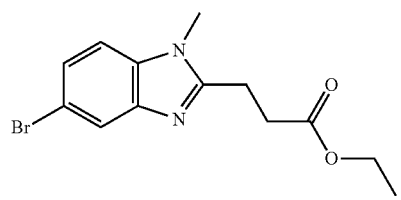 [SMILES: CCOC(=O)CCc1nc2cc(Br)ccc2n1C]

4-(2-Amino-4-bromo-N-methyl-anilino)-4-oxo-butanoic acid ethyl ester (0.238 g, 0.722 mmol) obtained in Step A was dissolved in AcOH (5 mL) and stirred at 75° C. for 16 hours. The solvent was distilled under reduced pressure, and the product was washed with toluene and distilled under reduced pressure. The obtained product was used for the next step with simple filter purification.

NMR: ¹H-NMR (CDCl₃) δ 7.83 (1H, s), 7.34 (1H, d), 7.17 (1H, d), 4.14 (2H, q), 3.76 (3H, s), 3.15 (2H, t), 3.01 (2H, t), 1.26 (2H, t)

Step C: 3-[1-methyl-5-(2-phenoxyphenyl)benzimidazol-2-yl]propanoic acid

2-Phenoxyphenylboronic acid (0.109 g, 0.507 mmol) and 3-(5-bromo-1-methyl-benzimidazol-2-yl)propanoic acid ethyl ester (0.079 g, 0.253 mmol) obtained in Step B were sequentially reacted in the same manner as in Step D of Example 44 and Step B of Example 1 to obtain the title compound (0.011 g, 11%).
NMR: 1H-NMR (MeOD) δ 7.74 (1H, m), 7.53 (1H, m), 7.47 (2H, s), 7.36 (1H, m), 7.33 (1H, m), 7.23 (2H, m), 7.05 (1H, m), 7.03 (1H, m), 6.84 (2H, d), 3.83 (3H, s), 3.19 (2H, t), 2.92 (2H, t)

Example 46: 5-[2,6-difluoro-4-(2-isopropoxy-3-pyridyl)phenyl]hexanoic acid

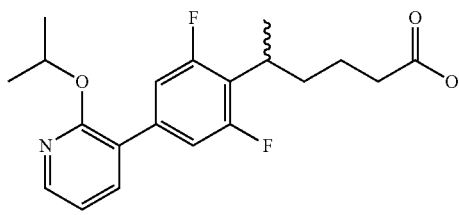

3-Iodo-2-isopropoxy-pyridine (0.052 g, 0.197 mmol) obtained in Preparation Example 34 and 5-[2,6-difluoro-4-(4,4,5,5-tetramethyl-[1,3,2]dioxaborolan-2-yl)phenyl]hexanoic acid ethyl ester (0.071 g, 0.184 mmol) obtained in Preparation Example 32 were reacted in the same manner as in Example 1 to obtain the title compound (0.039 g, 57%).
NMR: ¹H-NMR (CDCl₃) δ 8.14 (1H, m), 7.59 (1H, m), 7.10 (2H, m), 6.92 (1H, m), 5.42 (1H, m), 3.23 (1H, m), 2.37 (2H, t), 1.85 (1H, m), 1.80-1.50 (3H, m), 1.37 (9H, m)

Example 47: 5-(2'-cyclopentylamino-3,5-difluoro-bisphenyl-4-yl)hexanoic acid

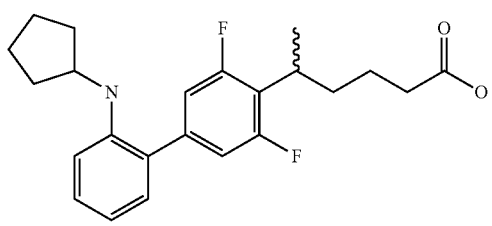 [SMILES: CC(CCCC(=O)O)c1c(F)cc(-c2ccccc2NC2CCCC2)cc1F]

N-cyclopentyl-2-iodo-aniline (0.056 g, 0.195 mmol) obtained in Preparation Example 35 and 5-[2,6-difluoro-4-(4,4,5,5-tetramethyl-[1,3,2]dioxaborolan-2-yl)phenyl]hexanoic acid ethyl ester (0.07 g, 0.182 mmol) obtained in Preparation Example 32 were reacted in the same manner as in Example 1 to obtain the title compound (0.035 g, 50%).
NMR: ¹H-NMR (CDCl₃) δ 7.25 (1H, m), 7.03 (1H, m), 6.90 (2H, d), 6.70 (2H, m), 4.12 (1H, m), 3.23 (1H, m), 2.38 (2H, t), 2.00 (2H, m), 1.85 (1H, m), 1.80-1.50 (8H, m), 1.50-1.40 (5H, m)

Example 48: 5-[4-(2-cyclobutylsulfanyl-3-pyridyl)-2,6-difluoro-phenyl]hexanoic acid

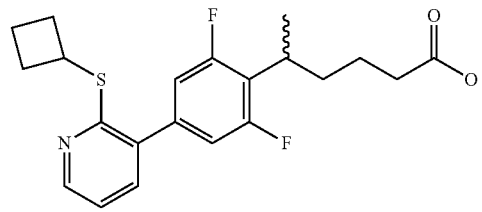

2-Cyclobutylsulfanyl-3-iodo-pyridine (0.047 g, 0.161 mmol) obtained in Preparation Example 13 and 5-[2,6-difluoro-4-(4,4,5,5-tetramethyl-[1,3,2]dioxaborolan-2-yl)-phenyl]hexanoic acid ethyl ester (0.049 g, 0.128 mmol) obtained in Preparation Example 32 were reacted in the same manner as in Example 1 to obtain the title compound (0.018 g, 39%).
NMR: ¹H-NMR (CDCl₃) δ 8.42 (1H, m), 7.34 (1H, m), 7.03 (1H, m), 6.93 (2H, d), 4.43 (1H, m), 3.25 (1H, m), 2.52 (2H, m), 2.38 (2H, t), 2.12-2.00 (4H, m), 1.85 (1H, m), 1.75 (2H, m), 1.58 (1H, m), 1.38 (3H, d)

Example 49: 5-[4-(2-cyclopentylsulfanyl-3-pyridyl)-2,6-difluoro-phenyl]hexanoic acid

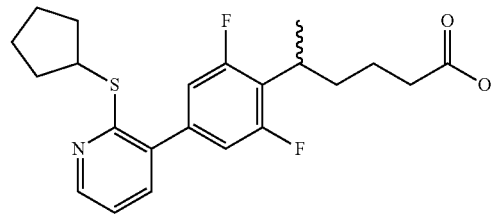

2-Cyclopentylsulfanyl-3-iodo-pyridine (0.03 g, 0.14 mmol) obtained in Preparation Example 15 and 5-[2,6-difluoro-4-(4,4,5,5-tetramethyl-[1,3,2]dioxaborolan-2-yl)-phenyl]hexanoic acid ethyl ester (0.043 g, 0.131 mmol) obtained in Preparation Example 32 were reacted in the same manner as in Example 1 to obtain the title compound (0.015 g, 28%).
NMR: ¹H-NMR (CDCl₃) δ 8.43 (1H, m), 7.33 (1H, m), 7.02 (1H, m), 6.92 (2H, d), 4.08 (1H, m), 3.23 (1H, m), 2.37 (2H, t), 2.20 (2H, m), 1.80 (1H, m), 1.80-1.50 (9H, m), 1.36 (3H, d)

Example 50: 5-[2,6-difluoro-4-(2-isopropylsulfanyl-3-pyridyl)-phenyl]hexanoic acid

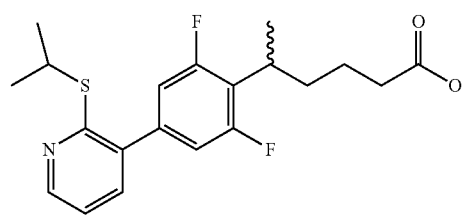 [SMILES: CC(C)Sc1ncccc1-c1cc(F)c(C(C)CCCC(=O)O)c(F)c1]

3-Iodo-2-isopropylsulfanyl-pyridine (0.039 g, 0.139 mmol) obtained in Preparation Example 9 and 5-[2,6-difluoro-4-(4,4,5,5-tetramethyl-[1,3,2]dioxaborolan-2-yl)phenyl]hexanoic acid ethyl ester (0.043 g, 0.131 mmol) obtained in Preparation Example 32 were reacted in the same manner as in Example 1 to obtain the title compound (0.013 g, 28%).

NMR: $^1$H-NMR (CDCl$_3$) δ 8.44 (1H, m), 7.35 (1H, m), 7.04 (1H, m), 6.92 (2H, d), 4.06 (1H, m), 3.25 (1H, m), 2.38 (2H, t), 1.83 (1H, m), 1.74 (2H, m), 1.58 (1H, m), 1.36 (9H, m)

Example 51: 5-[4-(2-cyclopentoxy-3-pyridyl)-2,6-difluoro-phenyl]hexanoic acid

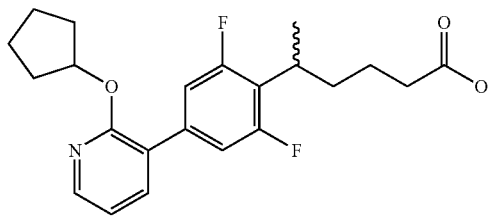 [SMILES: CC(CCCC(=O)O)c1c(F)cc(-c2cccnc2OC2CCCC2)cc1F]

2-Cyclopentyloxy-3-iodo-pyridine (0.049 g, 0.169 mmol) obtained in Preparation Example 11 and 5-[2,6-difluoro-4-(4,4,5,5-tetramethyl-[1,3,2]dioxaborolan-2-yl)phenyl]hexanoic acid ethyl ester (0.052 g, 0.158 mmol) obtained in Preparation Example 32 were reacted in the same manner as in Example 1 to obtain the title compound (0.026 g, 40%).

NMR: $^1$H-NMR (CDCl$_3$) δ 8.15 (1H, m), 7.59 (1H, m), 7.09 (2H, d), 6.92 (1H, m), 5.52 (1H, m), 3.23 (1H, m), 2.37 (2H, t), 1.96 (2H, m), 1.80-1.50 (10H, m), 1.37 (3H, d)

Example 52: 5-(3'-cyclopentylamino-3,5-difluoro-biphenyl-4-yl)-hexanoic acid

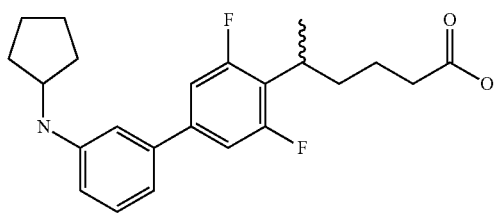 [SMILES: CC(CCCC(=O)O)c1c(F)cc(-c2cccc(NC3CCCC3)c2)cc1F]

3-Bromo-N-cyclopentyl-aniline (0.043 g, 0.178 mmol) obtained in Preparation Example 36 and 5-[2,6-difluoro-4-(4,4,5,5-tetramethyl-[1,3,2]dioxaborolan-2-yl)phenyl]hexanoic acid ethyl ester (0.062 g, 0.162 mmol) obtained in Preparation Example 32 were reacted in the same manner as in Example 1 to obtain the title compound (0.03 g, 47%).

NMR: $^1$H-NMR (CDCl$_3$) δ 7.20 (1H, m), 7.02 (2H, d), 6.80 (1H, m), 6.70 (1H, m), 6.60 (1H, m), 3.80 (1H, m), 3.20 (1H, m), 2.35 (2H, m), 2.10 (2H, m), 1.85 (1H, m), 1.80-1.42 (9H, m), 1.35 (3H, d)

Example 53: 5-[2,6-difluoro-4-(6-isopropylsulfanyl-2-pyridyl)-phenyl]hexanoic acid

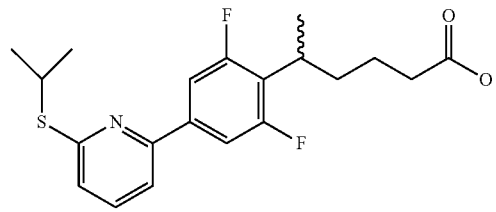 [SMILES: CC(C)Sc1cccc(-c2cc(F)c(C(C)CCCC(=O)O)c(F)c2)n1]

2-Chloro-6-isopropylsulfanyl-pyridine (0.025 g, 0.134 mmol) obtained in Preparation Example 10 and 5-[2,6-difluoro-4-(4,4,5,5-tetramethyl-[1,3,2]dioxaborolan-2-yl)phenyl]hexanoic acid ethyl ester (0.048 g, 0.125 mmol) obtained in Preparation Example 32 were reacted in the same manner as in Example 1 to obtain the title compound (0.019 g, 38%).

NMR: $^1$H-NMR (CDCl$_3$) δ 7.53 (3H, m), 7.35 (1H, m), 7.10 (1H, m), 4.15 (1H, m), 3.24 (1H, m), 2.36 (2H, t), 1.83 (1H, m), 1.70-1.60 (3H, m), 1.47 (6H, d), 1.37 (3H, d)

Example 54: 5-[4-(6-cyclopentylsulfanyl-2-pyridyl)-2,6-difluoro-phenyl]hexanoic acid

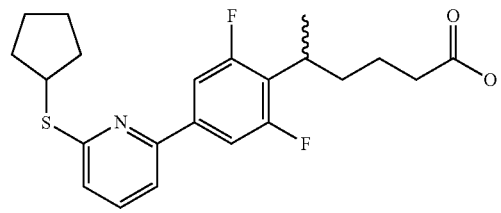 [SMILES: CC(CCCC(=O)O)c1c(F)cc(-c2cccc(SC3CCCC3)n2)cc1F]

2-Chloro-6-cyclopentylsulfanyl-pyridine (0.03 g, 0.142 mmol) obtained in Preparation Example 14 and 5-[2,6-difluoro-4-(4,4,5,5-tetramethyl-[1,3,2]dioxaborolan-2-yl)phenyl]hexanoic acid ethyl ester (0.051 g, 0.133 mmol) obtained in Preparation Example 32 were reacted in the same manner as in Example 1 to obtain the title compound (0.015 g, 29%).

NMR: $^1$H-NMR (CDCl$_3$) δ 7.52 (3H, m), 7.33 (1H, m), 7.11 (1H, m), 4.18 (1H, m), 3.26 (1H, m), 2.37 (2H, t), 2.26 (2H, m), 1.90-1.60 (10H, m), 1.36 (3H, d)

Example 55: 5-[2,6-difluoro-4-(6-propylsulfanyl-2-pyridyl)phenyl]hexanoic acid

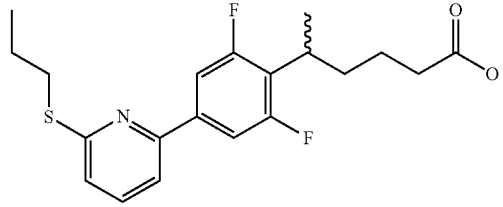 [SMILES: CCCSc1cccc(-c2cc(F)c(C(C)CCCC(=O)O)c(F)c2)n1]

2-Bromo-6-propylsulfanyl-pyridine (0.046 g, 0.195 mmol) obtained in Preparation Example 37 and 5-[2,6- difluoro-4-(4,4,5,5-tetramethyl-[1,3,2]dioxaborolan-2-yl)phenyl]hexanoic acid ethyl ester (0.07 g, 0.183 mmol) obtained in Preparation Example 32 were reacted in the same manner as in Example 1 to obtain the title compound (0.034 g, 49%).

NMR: $^1$H-NMR (CDCl$_3$) δ 7.52 (3H, m), 7.33 (1H, m), 7.13 (1H, m), 3.23 (3H, m), 2.34 (2H, t), 1.84 (3H, m), 1.70-1.60 (3H, m), 1.35 (3H, d), 1.09 (3H, t)

Example 56: 5-[4-(6-cyclopentoxy-2-pyridyl)-2,6-difluoro-phenyl]hexanoic acid

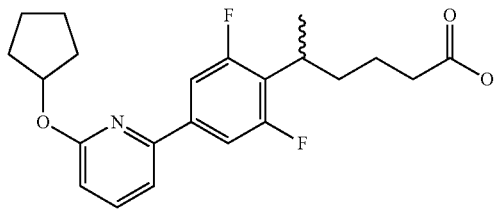

2-Chloro-6-cyclopentyloxy-pyridine (0.035 g, 0.176 mmol) obtained in Preparation Example 12 and 5-[2,6-difluoro-4-(4,4,5,5-tetramethyl-[1,3,2]dioxaborolan-2-yl)phenyl]hexanoic acid ethyl ester (0.063 g, 0.164 mmol) obtained in Preparation Example 32 were reacted in the same manner as in Example 1 to obtain the title compound (0.024 g, 37%).

NMR: $^1$H-NMR (CDCl$_3$) δ 7.59 (1H, t), 7.49 (2H, m), 7.21 (1H, d), 6.64 (1H, d), 5.50 (1H, m), 3.22 (1H, m), 2.33 (2H, t), 2.03 (2H, m), 1.84 (4H, m), 1.75-1.40 (6H, m), 1.34 (3H, d)

Example 57: 4-[4-(2-isopropoxy-3-pyridyl)phenyl]butanoic acid

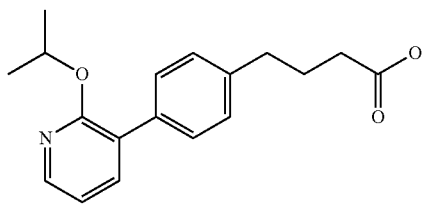 [SMILES: CC(C)Oc1ncccc1-c1ccc(CCCC(=O)O)cc1]

3-Iodo-2-isopropoxy-pyridine (0.066 g, 0.249 mmol) obtained in Preparation Example 34 and 4-[4-(4,4,5,5-tetramethyl-[1,3,2]dioxaborolan-2-yl)phenyl]butanoic acid methyl ester (0.069 g, 0.226 mmol) obtained in Preparation Example 38 were reacted in the same manner as in Example 1 to obtain the title compound (0.01 g, 15%).

NMR: $^1$H-NMR (CDCl$_3$) δ 8.11 (1H, m), 7.60 (1H, m), 7.51 (2H, m), 7.23 (2H, m), 6.90 (1H, m), 5.40 (1H, m), 2.72 (2H, t), 2.43 (2H, m), 2.02 (2H, m), 1.34 (6H, d)

Example 58: 5-[2,6-difluoro-4-(2-hydroxy-3-pyridyl)phenyl]hexanoic acid

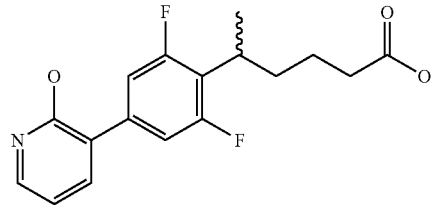 [SMILES: CC(CCCC(=O)O)c1c(F)cc(-c2cccnc2O)cc1F]

Step A: 3-iodo-2-(4-methoxy-benzyloxy)-pyridine

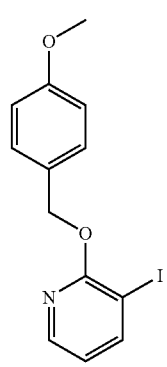 [SMILES: COc1ccc(COc2ncccc2I)cc1]

(4-Methoxy-phenyl)-methanol (0.34 g, 2.46 mmol) was dissolved in DMF (7.5 mL). NaH (60%)(0.107 g, 2.69 mmol) was added thereto at 0° C., and the mixture was stirred. 2-Fluoro-3-iodo-pyridine (0.5 g, 2.24 mmol) was added thereto, and the mixture was stirred for 16 hours. After termination of the reaction, the reaction solution was diluted with water and extracted with Et$_2$O. The organic layer was dried with anhydrous magnesium sulfate and purified by column chromatography (eluent, EtOAc/Hex=1/10) to obtain the title compound (0.726 g, 95%).

NMR: $^1$H-NMR (CDCl$_3$) δ 8.12 (1H, d), 8.03 (1H, d), 7.44 (2H, d), 6.91 (2H, d), 6.65 (1H, m), 5.37 (2H, s), 3.82 (3H, s)

Step B: 5-{2,6-difluoro-4-[2-(4-methoxy-benzyloxy)-pyridin-3-yl]phenyl}hexanoic acid methyl ester

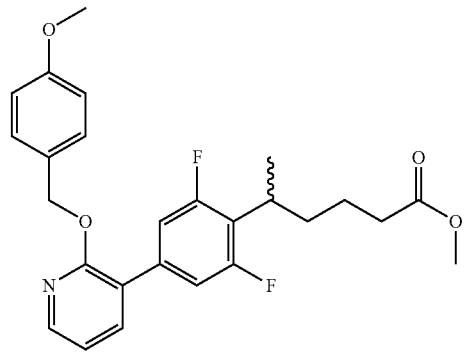 [SMILES: COC(=O)CCCC(C)c1c(F)cc(-c2cccnc2OCc2ccc(OC)cc2)cc1F]

3-Iodo-2-(4-methoxy-benzyloxy)-pyridine (0.102 g, 0.299 mmol) obtained in Step A and 5-[2,6-difluoro-4-(4,4,5,5-tetramethyl-[1,3,2]dioxaborolan-2-yl)phenyl]hexanoic acid ethyl ester (0.107 g, 0.279 mmol) obtained in Preparation Example 32 were reacted in the same manner as in Step A of Example 1 to obtain the title compound (0.099 g, 75%).

NMR: $^1$H-NMR (CDCl$_3$) δ 8.18 (1H, d), 7.62 (1H, d), 7.37 (2H, d), 7.09 (2H, d), 6.98 (1H, m), 6.89 (2H, d), 5.43 (2H, s), 4.11 (2H, q), 3.81 (3H, s), 3.21 (1H, m), 2.30 (2H, t), 1.81 (1H, m), 1.66-1.55 (3H, m), 1.35 (3H, d), 1.24 (3H, t)

Step C: 5-[2,6-difluoro-4-(2-hydroxy-3-pyridyl)phenyl]hexanoic acid methyl ester

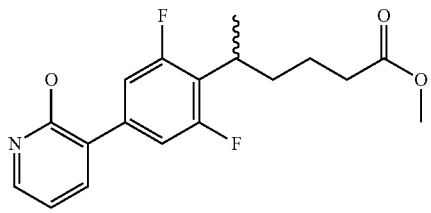 [SMILES: COC(=O)CCCC(C)c1c(F)cc(-c2cccnc2O)cc1F]

5-{2,6-Difluoro-4-[2-(4-methoxy-benzyloxy)-pyridin-3-yl]phenyl}hexanoic acid methyl ester (0.099 g, 0.21 mmol) obtained in Step B was dissolved in TFA/DCM (1/1) and stirred for 2 hours. The solvent was distilled under reduced pressure, and the product was washed with Et$_2$O and used for the next step without purification.

Step D: 5-[2,6-difluoro-4-(2-hydroxy-3-pyridyl)phenyl]hexanoic acid

5-[2,6-Difluoro-4-(2-hydroxy-3-pyridyl)phenyl]hexanoic acid methyl ester (0.039 g, 0.116 mmol) obtained in Step C was reacted in the same manner as in Step B of Example 1 to obtain the title compound (0.029 g, 78%).

NMR: 1H-NMR (MeOD) δ 7.81 (1H, m), 7.46 (1H, m), 7.44 (2H, d), 6.50 (1H, t), 3.25 (1H, m), 2.27 (2H, t), 1.80 (1H, m), 1.75 (1H, m), 1.70-1.40 (2H, m), 1.36 (3H, d)

Example 59: 5-[4-(2-cyclobutoxy-3-pyridyl)-2,6-difluoro-phenyl]hexanoic acid

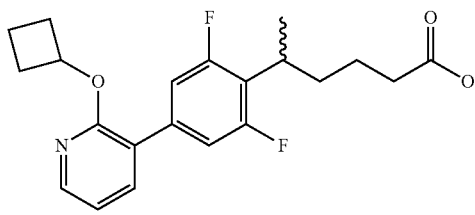

2-Cyclobutoxy-3-iodo-pyridine (0.06 g, 0.218 mmol) obtained in Preparation Example 39 and 5-[2,6-difluoro-4-(4,4,5,5-tetramethyl-[1,3,2]dioxaborolan-2-yl)phenyl]hexanoic acid ethyl ester (0.078 g, 0.203 mmol) obtained in Preparation Example 32 were reacted in the same manner as in Example 1 to obtain the title compound (0.043 g, 56%).

NMR: $^1$H-NMR (CDCl$_3$) δ 8.12 (1H, m), 7.59 (1H, m), 7.12 (2H, d), 6.93 (1H, d), 5.28 (1H, m), 3.24 (1H, m), 2.47 (2H, m), 2.37 (2H, t), 2.15 (2H, m), 1.90 (2H, m), 1.70-1.50 (4H, m), 1.37 (3H, d)

Example 60: 5-[4-(2-cyclopropylmethoxy-3-pyridyl)-2,6-difluoro-phenyl]hexanoic acid

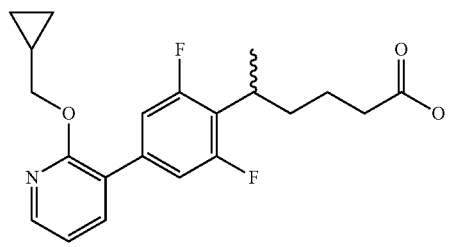 [SMILES: CC(CCCC(=O)O)c1c(F)cc(-c2cccnc2OCC2CC2)cc1F]

2-Cyclopropylmethoxy-3-iodo-pyridine (0.062 g, 0.225 mmol) obtained in Preparation Example 40 and 5-[2,6-difluoro-4-(4,4,5,5-tetramethyl-[1,3,2]dioxaborolan-2-yl)phenyl]hexanoic acid ethyl ester (0.080 g, 0.21 mmol) obtained in Preparation Example 32 were reacted in the same manner as in Example 1 to obtain the title compound (0.036 g, 47%).

NMR: $^1$H-NMR (CDCl$_3$) δ 8.13 (1H, m), 7.61 (1H, m), 7.14 (2H, d), 6.95 (1H, d), 4.23 (2H, d), 3.24 (1H, m), 2.37 (2H, t), 1.85 (1H, m), 1.84-1.50 (3H, m), 1.40-1.30 (4H, m), 0.61 (2H, m), 0.36 (2H, m)

Example 61: 5-[[4-(2-cyclobutylsulfanyl-3-pyridyl)-2,6-difluoro-phenoxy]methyl]isoxazol-3-ol

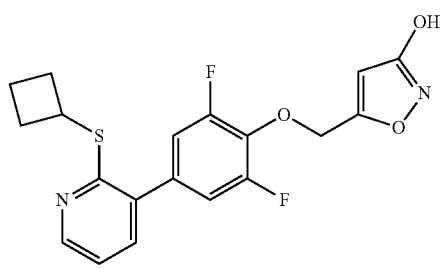 [SMILES: Oc1cc(COc2c(F)cc(-c3cccnc3SC3CCC3)cc2F)on1]

Step A: 5-[[4-(2-cyclobutylsulfanyl-3-pyridyl)-2,6-difluoro-phenoxy]methyl]-3-[(4-methoxyphenyl)methoxy]isoxazole 5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.21 g, 0.45 mmol) obtained in Preparation Example 62 and 3-iodo-2-cyclobutylsulfanyl-pyridine (0.12 g, 0.41 mmol) obtained in Preparation Example 13 were reacted in the same manner as in Step A of Example 1 to obtain the title compound (0.14 g, 65%).

$^1$H-NMR (CDCl$_3$) δ 8.42 (1H, m), 7.39 (2H, d), 7.32 (1H, m), 7.03 (3H, m), 6.92 (2H, d), 6.07 (1H, s), 5.21 (2H, s), 5.20 (2H, s), 4.41 (1H, m), 3.82 (3H, s), 2.50 (2H, m), 2.05 (4H, m)

Step B: 5-[[4-(2-cyclobutylsulfanyl-3-pyridyl)-2,6-difluoro-phenoxy]methyl]isoxazol-3-ol 5-[[4-(2-Cyclobutylsulfanyl-3-pyridyl)-2,6-difluoro-phenoxy]methyl]-3-[(4-methoxyphenyl)methoxy]isoxazole (0.1 g, 0.19 mmol) obtained in Step A was dissolved in 1.3 mL of DCM. 0.6 mL of TFA and 0.15 mL of anisole were added thereto, and the mixture was stirred at room temperature for 5 hours. The reaction solution was concentrated under reduced pressure. After addition of sodium bicarbonate aqueous solution, the reaction solution was extracted with EtOAc. The organic layer was dried with MgSO$_4$ and purified by column chromatography to obtain the title compound (0.053 g, 73%).

$^1$H-NMR (CDCl$_3$) δ 8.42 (1H, m), 7.33 (1H, m), 7.03 (3H, m), 6.13 (1H, s), 5.20 (2H, s), 4.41 (1H, m), 2.52 (2H, m), 2.06 (4H, m)

Example 62: N'-hydroxy-4-[4-(2-propylsulfanyl-3-pyridyl)phenyl]butaneamidine

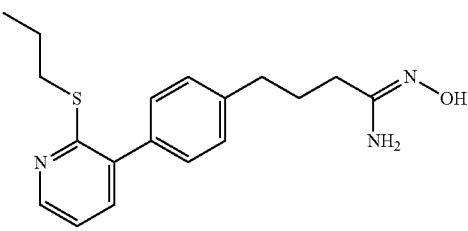 [SMILES: CCCSc1ncccc1-c1ccc(CCC/C(N)=N/O)cc1]

Step A: 4-[4-(2-propylsulfanyl-3-pyridyl)phenyl]butanenitrile

4-[4-(4,4,5,5-Tetramethyl-1,3,2-dioxaborolan-2-yl)phenyl]butanenitrile (0.52 g, 1.9 mmol) obtained in Preparation Example 71 and 3-iodo-2-propylsulfanyl-pyridine (0.5 g, 1.79 mmol) obtained in Preparation Example 28 were reacted in the same manner as in Step A of Example 1 to obtain the title compound (0.31 g, 56%).

$^1$H-NMR (CDCl$_3$) δ 8.42 (1H, m), 7.36 (3H, m), 7.26 (2H, d), 7.03 (1H, m), 3.13 (2H, t), 2.82 (2H, t), 2.38 (2H, t), 2.04 (2H, m), 1.70 (2H, m), 1.01 (3H, t)

Step B: N-hydroxy-4-[4-(2-propylsulfanyl-3-pyridyl)phenyl]butaneamidine

4-[4-(2-Propylsulfanyl-3-pyridyl)phenyl]butanenitrile (0.31 g, 1 mmol) obtained in Step A was dissolved in 0.6 mL of EtOH. 0.3 mL of 50 wt % hydroxylamine aqueous solution was added thereto, and the mixture was stirred for 16 hours under reflux. The reaction solution was concentrated under reduced pressure and extracted with EtOAc to obtain the title compound (0.32 g, 99%).

$^1$H-NMR (CDCl$_3$) δ 8.42 (1H, m), 7.36 (3H, m), 7.26 (2H, d), 7.04 (1H, m), 4.53 (2H, brs), 3.13 (2H, t), 2.71 (2H, t), 2.22 (2H, t), 1.95 (2H, m), 1.70 (2H, m), 1.00 (3H, t)

Example 63: 3-[3-[4-(2-propylsulfanyl-3-pyridyl)phenyl]propyl]-4H-1,2,4-oxadiazol-5-one

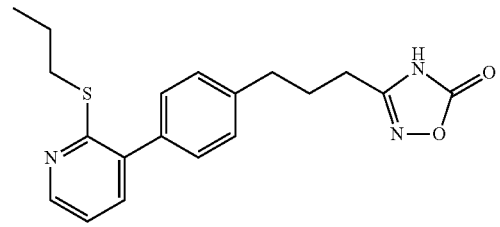 [SMILES: CCCSc1ncccc1-c1ccc(CCCc2noc(=O)[nH]2)cc1]

N-hydroxy-4-[4-(2-propylsulfanyl-3-pyridyl)phenyl]butaneamidine (0.08 g, 0.24 mmol) obtained in Example 62 was dissolved in 1 mL of pyridine. Chloroformic acid ethyl ester (0.023 mL, 0.24 mmol) was added thereto at 0° C., and the mixture was stirred at 100° C. for 2 hours. The reaction solution was concentrated under reduced pressure. After addition of water, the reaction solution was extracted with EtOAc. The organic layer was dried with MgSO$_4$ and purified by column chromatography to obtain the title compound (0.018 g, 21%).

$^1$H-NMR (CDCl$_3$) δ 8.42 (1H, m), 7.36 (3H, m), 7.25 (2H, d), 7.05 (1H, m), 3.12 (2H, t), 2.77 (2H, t), 2.61 (2H, t), 2.08 (2H, m), 1.68 (2H, m), 1.01 (3H, t)

Example 64: 3-[3-[4-(2-propylsulfanyl-3-pyridyl)phenyl]propyl]-4H-1,2,4-oxadiazol-5-thione

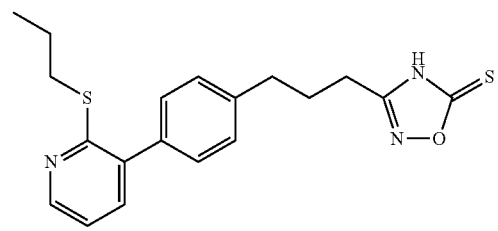 [SMILES: CCCSc1ncccc1-c1ccc(CCCc2noc(=S)[nH]2)cc1]

N-hydroxy-4-[4-(2-propylsulfanyl-3-pyridyl)phenyl]butaneamidine (0.11 g, 0.33 mmol) obtained in Example 62 was dissolved in 1.1 mL of CH$_3$CN. 1,1'-Thiocarbonyldiimidazole (0.079 g, 0.4 mmol) and DBU (0.064 g, 0.43 mmol) were added thereto, and the mixture was stirred at room temperature for 48 hours. The reaction solution was concentrated under reduced pressure and purified by column chromatography to obtain the title compound (0.005 g, 4%).

$^1$H-NMR (CDCl$_3$) δ 8.36 (1H, m), 7.26 (3H, m), 7.15 (2H, m), 6.95 (1H, m), 3.06 (2H, t), 2.64 (2H, m), 2.58 (2H, m), 1.99 (2H, m), 1.68 (2H, m), 0.94 (3H, t)

Example 65: 5-[[4-(2-cyclopentylsulfanyl-3-pyridyl)-2,6-difluoro-phenoxy]methyl]isoxazol-3-ol

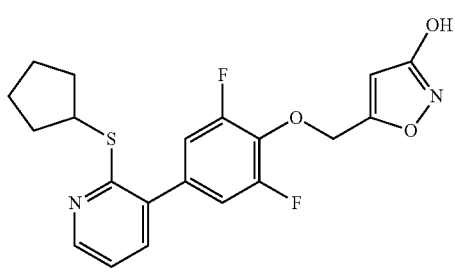

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.087 g, 0.18 mmol) obtained in Preparation Example 62 and 2-cyclopentylsulfanyl-3-iodo-pyridine (0.056 g, 0.18 mmol) obtained in Preparation Example 15 were reacted in the same manner as in Example 61 to obtain the title compound (0.027 g, 34%).

$^1$H-NMR (CDCl$_3$) δ 8.45 (1H, m), 7.34 (1H, m), 7.04 (3H, m), 6.15 (1H, s), 5.19 (2H, s), 4.10 (1H, m), 2.21 (2H, m), 1.73 (2H, m), 1.60 (4H, m)

Example 66: 5-[[2,6-difluoro-4-(2-propylsulfanyl-3-pyridyl)phenoxy]methyl]isoxazol-3-ol

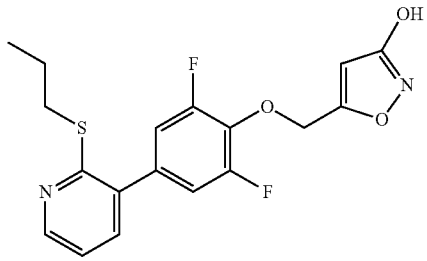

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.12 g, 0.25 mmol) obtained in Preparation Example 62 and 3-iodo-2-propylsulfanyl-pyridine (0.064 g, 0.23 mmol) obtained in Preparation Example 28 were reacted in the same manner as in Example 61 to obtain the title compound (0.017 g, 20%).

$^1$H-NMR (CDCl$_3$) δ 8.44 (1H, m), 7.34 (1H, m), 7.04 (3H, m), 6.12 (1H, s), 5.19 (2H, s), 1.44 (2H, t), 1.69 (2H, m), 1.02 (3H, t)

Example 67: 5-[[4-[2-(cyclopentoxy)-3-pyridyl]-2,6-difluoro-phenoxy]methyl]isoxazol-3-ol

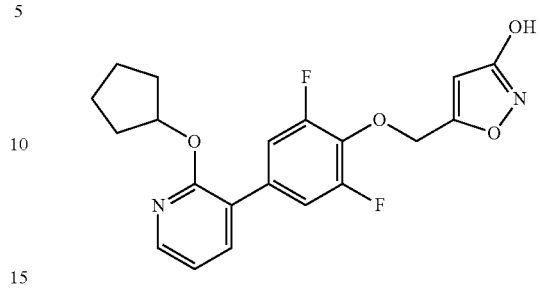

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.2 g, 0.42 mmol) obtained in Preparation Example 62 and 2-cyclopentoxy-3-iodo-pyridine (0.1 g, 0.35 mmol) obtained in Preparation Example 11 were reacted in the same manner as in Example 61 to obtain the title compound (0.06 g, 50%).

$^1$H-NMR (CDCl$_3$) δ 8.15 (1H, m), 7.56 (1H, m), 7.18 (2H, m), 6.92 (1H, m), 6.10 (1H, s), 5.52 (1H, m), 5.18 (2H, s), 1.97 (2H, m), 1.93 (2H, m), 1.74 (2H, m), 1.65 (2H, m)

Example 68: 5-[[2,6-difluoro-4-(2-isopropylsulfanyl-3-pyridyl)phenoxy]methyl]isoxazol-3-ol

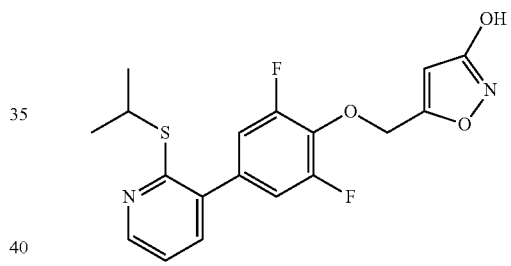

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.2 g, 0.43 mmol) obtained in Preparation Example 62 and 3-iodo-2-isopropylsulfanyl-pyridine (0.11 g, 0.39 mmol) obtained in Preparation Example 9 were reacted in the same manner as in Example 61 to obtain the title compound (0.033 g, 22%).

$^1$H-NMR (CDCl$_3$) δ 8.45 (1H, m), 7.34 (1H, m), 7.03 (3H, m), 6.12 (1H, s), 5.19 (2H, s), 4.06 (1H, m), 1.37 (6H, d)

Example 69: 5-[[2,6-difluoro-4-(2-isopropoxy-3-pyridyl)phenoxy]methyl]isoxazol-3-ol

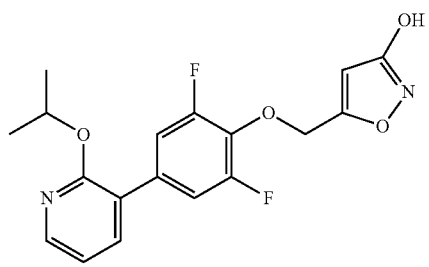 [SMILES: CC(C)Oc1ncccc1-c1cc(F)c(OCc2cc(O)no2)c(F)c1]

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.06 g, 0.13 mmol) obtained in Preparation Example 62 and 3-iodo-2-isopropoxy-pyridine (0.03 g, 0.11 mmol) obtained in Preparation Example 34 were reacted in the same manner as in Example 61 to obtain the title compound (0.005 g, 12%).

$^1$H-NMR (CDCl$_3$) δ 8.14 (1H, m), 7.55 (1H, m), 7.20 (2H, m), 6.92 (1H, m), 6.12 (1H, s), 5.41 (1H, m), 5.18 (2H, s), 1.35 (6H, d)

Example 70: 5-[[2,6-difluoro-4-(6-isopropylsulfanyl-2-pyridyl)phenoxy]methyl]isoxazol-3-ol

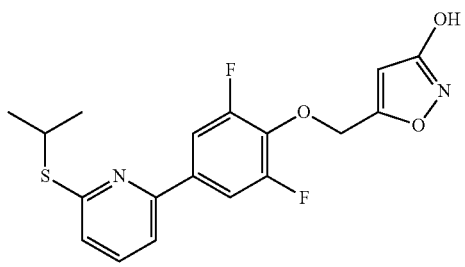 [SMILES: CC(C)Sc1cccc(-c2cc(F)c(OCc3cc(O)no3)c(F)c2)n1]

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.093 g, 0.2 mmol) obtained in Preparation Example 62 and 2-chloro-6-isopropylsulfanyl-pyridine (0.034 g, 0.18 mmol) obtained in Preparation Example 10 were reacted in the same manner as in Example 61 to obtain the title compound (0.013 g, 19%).

$^1$H-NMR (CDCl$_3$) δ 7.59 (2H, m), 7.53 (1H, t), 7.32 (1H, d), 7.10 (1H, d), 6.10 (1H, s), 5.18 (2H, s), 4.13 (1H, m), 1.46 (6H, d)

Example 71: 5-[[2,6-difluoro-4-(6-isopropoxy-2-pyridyl)phenoxy]methyl]isoxazol-3-ol

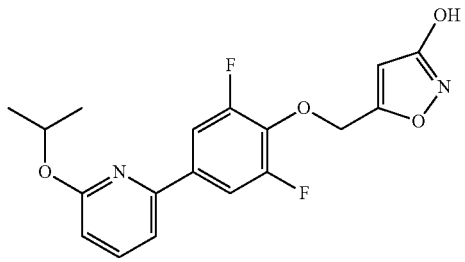 [SMILES: CC(C)Oc1cccc(-c2cc(F)c(OCc3cc(O)no3)c(F)c2)n1]

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.12 g, 0.24 mmol) obtained in Preparation Example 62 and 2-bromo-6-isopropoxy-pyridine (0.053 g, 0.24 mmol) obtained in Preparation Example 42 were reacted in the same manner as in Example 61 to obtain the title compound (0.035 g, 40%).

$^1$H-NMR (CDCl$_3$) δ 7.58 (3H, m), 7.20 (1H, d), 6.65 (1H, d), 6.10 (1H, s), 5.44 (1H, m), 5.18 (2H, s), 1.40 (6H, d)

Example 72: 5-[[4-[6-(cyclopropylmethoxy)-2-pyridyl]-2,6-difluoro-phenoxy]methyl]isoxazol-3-ol

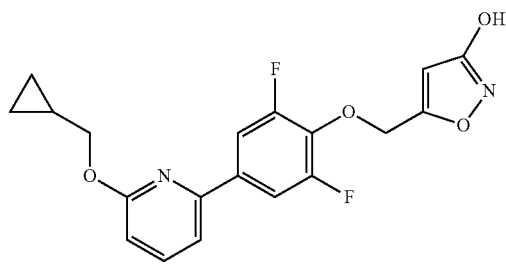 [SMILES: Oc1cc(COc2c(F)cc(-c3cccc(OCC4CC4)n3)cc2F)on1]

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.094 g, 0.2 mmol) obtained in Preparation Example 62 and 2-bromo-6-(cyclopropylmethoxy)pyridine (0.038 g, 0.16 mmol) obtained in Preparation Example 44 were reacted in the same manner as in Example 61 to obtain the title compound (0.006 g, 10%).

$^1$H-NMR (CDCl$_3$) δ 7.61 (3H, m), 7.22 (1H, d), 6.74 (1H, d), 6.10 (1H, s), 5.18 (2H, s), 4.23 (2H, d), 1.35 (1H, m), 0.64 (2H, m), 0.39 (2H, m)

Example 73: 5-[[2,6-difluoro-4-(6-propoxy-2-pyridyl)phenoxy]methyl]isoxazol-3-ol

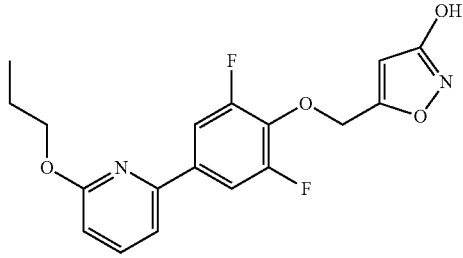 [SMILES: CCCOc1cccc(-c2cc(F)c(OCc3cc(O)no3)c(F)c2)n1]

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.094 g, 0.2 mmol) obtained in Preparation Example 62 and 2-bromo-6-propoxy-pyridine (0.036 g, 0.16 mmol) obtained in Preparation Example 45 were reacted in the same manner as in Example 61 to obtain the title compound (0.006 g, 10%).

$^1$H-NMR (CDCl$_3$) δ 7.60 (3H, m), 7.22 (1H, d), 6.70 (1H, d), 6.10 (1H, s), 5.18 (2H, s), 4.36 (2H, t), 1.85 (2H, m), 1.06 (3H, t)

Example 74: 5-[[2,6-difluoro-4-(2-propoxy-3-pyridyl)phenoxy]methyl]isoxazol-3-ol

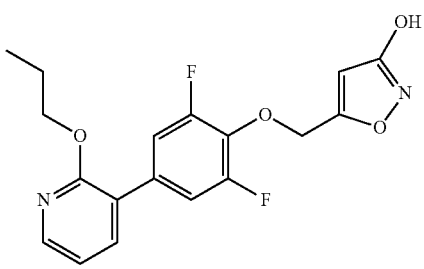 [SMILES: CCCOc1ncccc1-c1cc(F)c(OCc2cc(O)no2)c(F)c1]

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.094 g, 0.2 mmol) obtained in Preparation Example 62 and 3-iodo-2-propoxy-pyridine (0.044 g, 0.16 mmol) obtained in Preparation Example 47 were reacted in the same manner as in Example 61 to obtain the title compound (0.023 g, 38%).

$^1$H-NMR (CDCl$_3$) δ 8.15 (1H, m), 7.57 (1H, m), 7.19 (2H, m), 6.95 (1H, m), 6.11 (1H, s), 5.18 (2H, s), 4.33 (2H, t), 1.80 (2H, m), 1.01 (3H, t)

Example 75: 5-[(E)-3-[4-(2-cyclobutylsulfanyl-3-pyridyl)-2,6-difluoro-phenyl]allyl]thiazolidin-2,4-dione

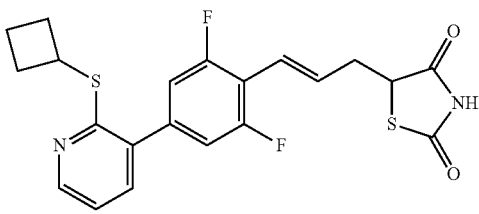 [SMILES: O=C1NC(=O)C(C/C=C/c2c(F)cc(-c3cccnc3SC3CCC3)cc2F)S1]

Thiazolidinedione (0.041 g, 0.35 mmol) was dissolved in 1.4 mL of THF and cooled to −78° C. Butyllithium (0.36 mL, 0.73 mmol, 2.0 M hexane solution) was added thereto, and the mixture was stirred at 0° C. for 30 minutes. The reaction solution was cooled to −78° C., and [(E)-3-[4-(2-cyclobutylsulfanyl-3-pyridyl)-2,6-difluoro-phenyl]allyl]methanesulfonate (0.14 g, 0.35 mmol) obtained in Preparation Example 76 was added thereto, and the mixture was stirred at room temperature for 4 hours. After addition of ammonium chloride aqueous solution, the reaction solution was extracted with EtOAc and purified by column chromatography to obtain the title compound (0.025 g, 16%).

$^1$H-NMR (CDCl$_3$) δ 8.43 (1H, m), 7.95 (1H, brs), 7.34 (1H, m), 7.05 (1H, m), 6.99 (2H, m), 6.63 (1H, d), 6.53 (1H, m), 4.48 (1H, m), 4.43 (1H, m), 3.14 (1H, m), 2.90 (1H, m), 2.51 (2H, m), 2.04 (4H, m)

Example 76: 5-[[4-[2-(cyclobutoxy)-3-pyridyl]-2,6-difluoro-phenoxy]methyl]isoxazol-3-ol

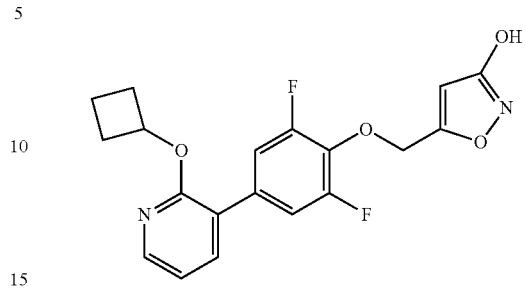

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.06 g, 0.12 mmol) obtained in Preparation Example 62 and 2-cyclobutoxy-3-iodo-pyridine (0.032 g, 0.11 mmol) obtained in Preparation Example 41 were reacted in the same manner as in Example 61 to obtain the title compound (0.01 g, 23%).

$^1$H-NMR (CDCl$_3$) δ 8.14 (1H, m), 7.58 (1H, m), 7.22 (2H, m), 6.95 (1H, m), 6.12 (1H, s), 5.27 (1H, m), 5.18 (2H, s), 2.47 (2H, m), 2.13 (2H, m), 1.84 (1H, m), 1.69 (1H, m)

Example 77: 5-[[4-[2-(cyclobutylmethoxy)-3-pyridyl]-2,6-difluoro-phenoxy]methyl]isoxazol-3-ol

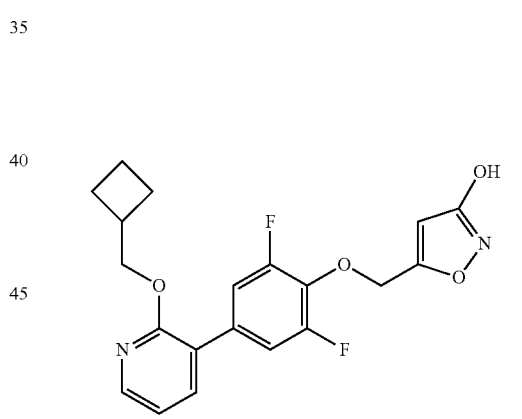

5-[[2,6-Difluoro-4-(4,4,5,5-tetramethyl-1,3,2-dioxaborolan-2-yl)phenoxy]methyl]-3-[(4-methoxyphenyl)methoxy]isoxazole (0.06 g, 0.12 mmol) obtained in Preparation Example 62 and 2-cyclobutylmethoxy-3-iodo-pyridine (0.033 g, 0.11 mmol) obtained in Preparation Example 48 were reacted in the same manner as in Example 61 to obtain the title compound (0.011 g, 26%).

$^1$H-NMR (CDCl$_3$) δ 8.15 (1H, m), 7.58 (1H, m), 7.21 (2H, m), 6.96 (1H, m), 6.11 (1H, s), 5.19 (2H, s), 4.32 (2H, d), 2.78 (1H, m), 2.11 (2H, m), 1.95-1.85 (4H, m)

Example 78: 5-[[4-[2-(cyclopentoxy)-3-pyridyl]anilino]methyl]isoxazol-3-ol

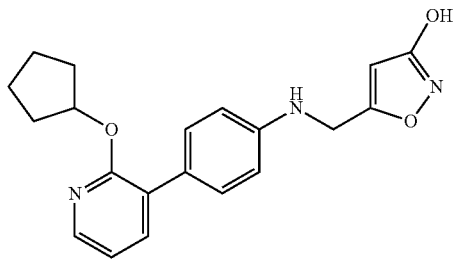

Step A: 4-[2-(cyclopentoxy)-3-pyridyl]-N-[[3-[(4-methoxyphenyl)methoxy]isoxazol-5-yl]methyl]aniline 4-[2-(Cyclopentoxy)-3-pyridyl]-aniline (0.11 g, 0.45 mmol) obtained in Preparation Example 64 and 3-[(4-methoxyphenyl)methoxy]isoxazol-5-carbaldehyde (0.10 g, 0.45 mmol) obtained in Preparation Example 61 were dissolved in 4.5 mL of DCE. Sodium triacetoxyborohydride (0.14 g, 0.68 mmol) was added thereto, and the mixture was stirred at room temperature for 16 hours. After addition of sodium bicarbonate aqueous solution, the reaction solution was extracted with DCM and purified by column chromatography to obtain the title compound (0.09 g, 43%).

$^1$H-NMR (CDCl$_3$) δ 8.07 (1H, m), 7.54 (1H, m), 7.43 (2H, d), 7.35 (2H, d), 6.92 (2H, d), 6.88 (1H, m), 6.87 (2H, d), 5.84 (1H, s), 5.50 (1H, m), 5.17 (2H, s), 4.40 (2H, d), 4.20 (1H, t, NH), 3.82 (3H, s), 1.93 (2H, m), 1.82 (2H, m), 1.73 (2H, m), 1.61 (2H, m)

Step B: 5-[[4-[2-(cyclopentoxy)-3-pyridyl]anilino]methyl]isoxazol-3-ol

4-[2-(Cyclopentoxy)-3-pyridyl]-N-[[3-[(4-methoxyphenyl)methoxy]isoxazol-5-yl]methyl]aniline (0.033 g, 0.07 mmol) obtained in Step A was reacted in the same manner as in Step B of Example 61 to obtain the title compound (0.02 g, 84%).

$^1$H-NMR (CDCl$_3$) δ 8.07 (1H, m), 7.56 (1H, m), 7.45 (2H, d), 6.88 (1H, m), 6.67 (2H, d), 5.90 (1H, s), 5.49 (1H, m), 4.41 (2H, s), 1.95 (2H, m), 1.83 (2H, m), 1.75 (2H, m), 1.62 (2H, m)

Example 79: 5-[[4-[2-(cyclopentoxy)-3-pyridyl]-2,6-difluoro-phenoxy]methyl]pyridin-2-ol

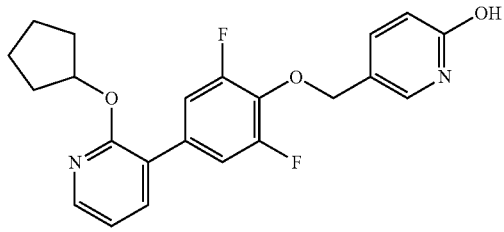 [SMILES: Oc1ccc(COc2c(F)cc(-c3cccnc3OC3CCCC3)cc2F)cn1]

2-Cyclopentoxy-3-iodo-pyridine (0.08 g, 0.28 mmol) obtained in Preparation Example 11 and 5-[[2,6-difluoro-4-(4,4,5,5-tetramethyl-1,3,2-dioxaborolan-2-yl)phenoxy]methyl]-2-[(4-methoxyphenyl)methoxy]pyridine (0.14 g, 0.3 mmol) obtained in Preparation Example 72 were reacted in the same manner as in Example 61 to obtain the title compound (0.018 g, 16%).

$^1$H-NMR (CDCl$_3$) δ 12.8 (1H, brs), 8.14 (1H, m), 7.66 (1H, m), 7.55 (1H, m), 7.41 (1H, m), 7.15 (2H, m), 6.92 (1H, m), 6.62 (1H, m), 5.50 (1H, m), 4.96 (2H, s), 1.94 (2H, m), 1.78 (2H, m), 1.73 (2H, m), 1.65 (2H, m)

Example 80: 4-[[4-[2-(cyclopentoxy)-3-pyridyl]-2,6-difluoro-phenoxy]methyl]pyridin-2-ol

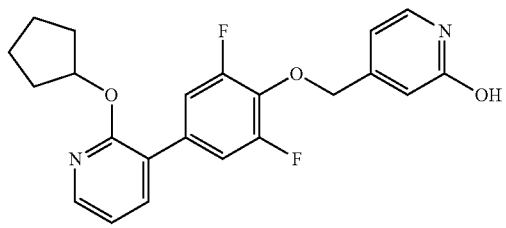 [SMILES: Oc1cc(COc2c(F)cc(-c3cccnc3OC3CCCC3)cc2F)ccn1]

2-Cyclopentoxy-3-iodo-pyridine (0.05 g, 0.18 mmol) obtained in Preparation Example 11 and 4-[[2,6-difluoro-4-(4,4,5,5-tetramethyl-1,3,2-dioxaborolan-2-yl)phenoxy]methyl]-2-[(4-methoxyphenyl)methoxy]pyridine (0.08 g, 0.18 mmol) obtained in Preparation Example 73 were reacted in the same manner as in Example 61 to obtain the title compound (0.018 g, 16%).

$^1$H-NMR (CDCl$_3$) δ 12.2 (1H, brs), 8.15 (1H, m), 7.54 (1H, m), 7.38 (1H, m), 7.14 (2H, m), 6.90 (1H, m), 6.73 (1H, m), 6.48 (1H, m), 5.50 (1H, m), 5.07 (2H, s), 1.94 (2H, m), 1.81 (2H, m), 1.74 (2H, m), 1.65 (2H, m)

Example 81: 5-[[4-[2-(cyclopentoxy)-3-pyridyl]phenyl]sulfanylmethyl]isoxazol-3-ol

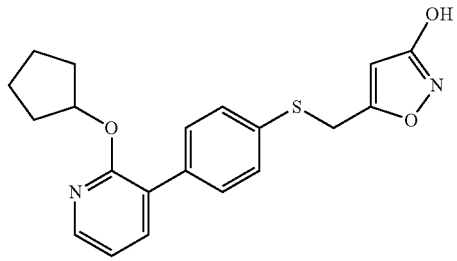 [SMILES: Oc1cc(CSc2ccc(-c3cccnc3OC3CCCC3)cc2)on1]

4-[2-(Cyclopentoxy)-3-pyridyl]benzenethiol (0.022 g, 0.08 mmol) obtained in Preparation Example 65 and [3-[(4-methoxyphenyl)methoxy]isoxazol-5-yl]methyl methanesulfonate (0.03 g, 0.1 mmol) obtained in Preparation Example 60 were dissolved in 0.8 mL of DMF. K$_2$CO$_3$ (0.022 g, 0.16 mmol) was added thereto, and the mixture was stirred at room temperature for 5 hours. The reaction solution was concentrated under reduced pressure, and solids were filtered by the addition of EtOAc. The filtrate was purified by column chromatography to obtain 5-[[4-[2-(cyclopentoxy)-3-pyridyl]phenyl]sulfanylmethyl]-3-[(4-methoxyphenyl)methoxy]isoxazol. The obtained compound was reacted in the same manner as in Step B of Example 61 to obtain the title compound (0.01 g, 36%).

¹H-NMR (CDCl₃) δ 8.14 (1H, m), 7.58 (1H, m), 7.52 (2H, d), 7.38 (2H, d), 6.93 (1H, m), 5.78 (1H, s), 5.50 (1H, m), 4.05 (2H, s), 1.93 (2H, m), 1.81 (2H, m), 1.72 (2H, m), 1.63 (2H, m)

Example 82: 5-[(E)-3-[4-[2-(cyclopentoxy)-3-pyridyl]-2,6-difluoro-phenyl]allyl]-1,1-dioxo-1,2,5-thiadiazolidin-3-one

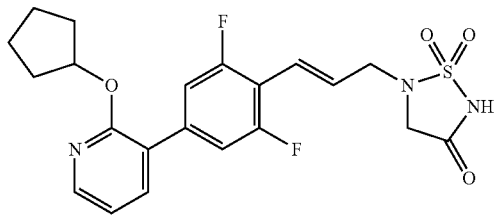 [SMILES: O=C1CN(C/C=C/c2c(F)cc(-c3cccnc3OC3CCCC3)cc2F)S(=O)(=O)N1]

2-[[(E)-3-[4-[2-(cyclopentoxy)-3-pyridyl]-2,6-difluoro-phenyl]allyl]-sulfamoyl-amino]acetic acid ethyl ester (0.038 g, 0.08 mmol) obtained in Preparation Example 75 was dissolved in 0.8 mL of THF. NaH (0.005 g, 0.11 mmol, 55 wt % in mineral oil) was added thereto, and the mixture was stirred at room temperature for 16 hours. After addition of ammonium chloride aqueous solution, the reaction solution was extracted with EtOAc. The organic layer was purified by column chromatography to obtain the title compound (0.022 g, 65%).

¹H-NMR (CDCl₃) δ 8.17 (1H, m), 7.90 (1H, brs), 7.60 (1H, m), 7.15 (2H, m), 6.94 (1H, m), 6.64 (1H, d), 6.47 (1H, m), 5.53 (1H, m), 4.20 (2H, d), 3.97 (2H, s), 1.95 (2H, m), 1.80 (2H, m), 1.75 (2H, m), 1.66 (2H, m)

Example 83: 5-[[4-[2-(cyclopentoxy)-3-pyridyl]-2,6-difluoro-phenyl]sulfanylmethyl]isoxazol-3-ol

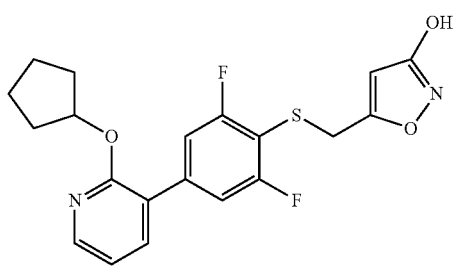 [SMILES: Oc1cc(CSc2c(F)cc(-c3cccnc3OC3CCCC3)cc2F)on1]

Step A: 5-[[4-[2-(cyclopentoxy)-3-pyridyl]-2,6-difluoro-phenyl]sulfanylmethyl]-3-[(4-methoxyphenyl)methoxy]isoxazole 4-[2-(Cyclopentoxy)-3-pyridyl]-2,6-difluoro-benzenethiol (0.077 g, 0.25 mmol) obtained in Preparation Example 68 and [3-[(4-methoxyphenyl)methoxy]isoxazol-5-yl]methyl methanesulfonate (0.08 g, 0.25 mmol) obtained in Preparation Example 60 were dissolved in 1.5 mL of DMF. K₂CO₃ (0.042 g, 0.3 mmol) was added thereto, and the mixture was stirred at room temperature for 16 hours. After addition of water, the reaction solution was extracted with EtOAc and purified by column chromatography to obtain the title compound (0.1 g, 80%).

¹H-NMR (CDCl₃) δ 8.18 (1H, m), 7.60 (1H, m), 7.35 (2H, d), 7.18 (2H, m), 6.96 (1H, m), 6.89 (2H, d), 5.76 (1H, s), 5.53 (1H, m), 5.14 (2H, s), 4.04 (2H, s), 3.80 (3H, s), 1.97 (2H, m), 1.81 (2H, m), 1.75 (2H, m), 1.63 (2H, m)

Step B: 5-[[4-[2-(cyclopentoxy)-3-pyridyl]-2,6-difluoro-phenyl]sulfanylmethyl]isoxazol-3-ol 5-[[4-[2-(Cyclopentoxy)-3-pyridyl]-2,6-difluoro-phenyl]sulfanylmethyl]-3-[(4-methoxyphenyl)methoxy]isoxazole (0.1 g, 0.2 mmol) obtained in Step A was reacted in the same manner as in Step B of Example 61 to obtain the title compound (0.067 g, 85%).

¹H-NMR (CDCl₃) δ 8.18 (1H, m), 7.60 (1H, m), 7.19 (2H, m), 6.93 (1H, m), 5.76 (1H, s), 5.52 (1H, m), 4.01 (2H, s), 1.96 (2H, m), 1.81 (2H, m), 1.75 (2H, m), 1.63 (2H, m)

Example 84: 5-[[4-[2-(cyclopentoxy)-3-pyridyl]-2,6-difluoro-anilino]methyl]isoxazol-3-ol

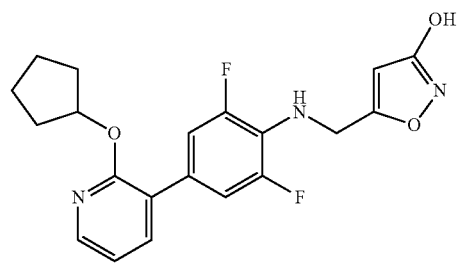 [SMILES: Oc1cc(CNc2c(F)cc(-c3cccnc3OC3CCCC3)cc2F)on1]

Step A: 4-[2-(cyclopentoxy)-3-pyridyl]-2,6-difluoro-N-[[3-[(4-methoxyphenyl)methoxy]isoxazol-5-yl]methyl]aniline 4-[2-(Cyclopentoxy)-3-pyridyl]-2,6-difluoro-aniline (0.17 g, 0.6 mmol) obtained in Preparation Example 67 and 3-[(4-methoxyphenyl)methoxy]isoxazol-5-carbaldehyde (0.14 g, 0.6 mmol) obtained in Preparation Example 61 were dissolved in 6 mL of DCE. Sodium triacetoxyborohydride (0.25 g, 1.2 mmol) was added thereto, and the mixture was stirred at room temperature for 16 hours. After addition of sodium bicarbonate aqueous solution, the reaction solution was extracted with DCM and purified by column chromatography to obtain the title compound (0.013 g, 4%).

¹H-NMR (CDCl₃) δ 8.11 (1H, m), 7.54 (1H, m), 7.34 (2H, d), 7.10 (2H, m), 6.90 (3H, m), 5.81 (1H, s), 5.51 (1H, m), 5.16 (2H, s), 4.55 (2H, d), 4.12 (1H, m, NH), 3.81 (3H, s), 1.95 (2H, m), 1.78 (4H, m), 1.64 (2H, m)

Step B: 5-[[4-[2-(cyclopentoxy)-3-pyridyl]-2,6-difluoro-anilino]methyl]isoxazol-3-ol 4-[2-(cyclopentoxy)-3-pyridyl]-2,6-difluoro-N-[[3-[(4-methoxyphenyl)methoxy]isoxazol-5-yl]methyl]aniline (0.013 g, 0.026 mmol) obtained in Step A was reacted in the same manner as in Step B of Example 61 to obtain the title compound (0.007 g, 65%).

¹H-NMR (CDCl₃) δ 8.11 (1H, m), 7.55 (1H, m), 7.12 (2H, m), 6.90 (1H, m), 5.86 (1H, s), 5.51 (1H, m), 4.54 (2H, s), 4.10 (1H, brs), 1.95 (2H, m), 1.78 (4H, m), 1.63 (2H, m)

Example 85: 5-[3-[4-[2-(cyclopentoxy)-3-pyridyl]-2,6-difluoro-phenyl]propyl]-1,1-dioxo-1,2,5-thiadiazolidin-3-one

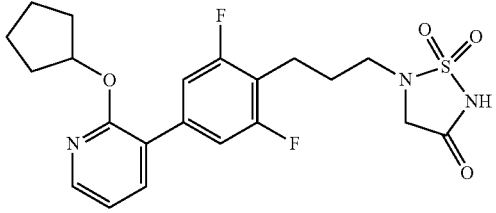 [SMILES: O=C1CN(CCCc2c(F)cc(-c3cccnc3OC3CCCC3)cc2F)S(=O)(=O)N1]

5-[(E)-3-[4-[2-(cyclopentoxy)-3-pyridyl]-2,6-difluoro-phenyl]allyl]-1,1-dioxo-1,2,5-thiadiazolidin-3-one (0.016 g, 0.035 mmol) obtained in Example 82 was dissolved in 0.4 mL of MeOH. Catalytic amount of 10 wt % Pd/C was added thereto, and the mixture was stirred for 16 hours under hydrogen atmosphere. Solids were filtered through Celite, and the filtrate was concentrated to obtain the title compound (0.015 g, 94%).

$^1$H-NMR (CDCl$_3$) δ 8.16 (1H, m), 7.65 (1H, brs), 7.58 (1H, m), 7.12 (2H, m), 6.93 (1H, m), 5.52 (1H, m), 3.94 (2H, s), 3.47 (2H, t), 2.74 (2H, t), 1.96 (2H, m), 1.92 (2H, m), 1.78 (2H, m), 1.75 (2H, m), 1.65 (2H, m)

Example 86: 5-[[4-[2-(cyclopentoxy)-3-pyridyl]-N-methyl-anilino]methyl]isoxazol-3-ol

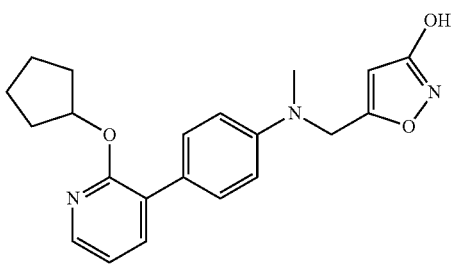 [SMILES: CN(Cc1cc(O)no1)c1ccc(-c2cccnc2OC2CCCC2)cc1]

4-[2-(Cyclopentoxy)-3-pyridyl]-N-[[3-[(4-methoxyphenyl)methoxy]isoxazol-5-yl]methyl]aniline (0.057 g, 0.12 mmol) obtained in Step A of Example 78 was dissolved in 1.2 mL of DMF. NaH (0.008 g, 0.18 mmol, 55 wt % in mineral oil) was added thereto at 0° C., and the mixture was stirred for 30 minutes. Iodomethane (0.01 g, 0.13 mmol) was added thereto, and the mixture was stirred at room temperature for 72 hours. The reaction solution was concentrated under reduced pressure. After addition of water, the reaction solution was extracted with EtOAc and purified by column chromatography to obtain 4-[2-(cyclopentoxy)-3-pyridyl]-N-[[3-[(4-methoxyphenyl)methoxy]isoxazol-5-yl]methyl]-N-methyl-aniline (0.023 g, 39%). The obtained compound was reacted in the same manner as in Step B of Example 61 to obtain the title compound (0.001 g, 6%).

$^1$H-NMR (CDCl$_3$) δ 8.08 (1H, m), 7.57 (1H, m), 7.51 (2H, d), 6.90 (1H, m), 6.79 (2H, d), 5.78 (1H, s), 5.50 (1H, m), 4.52 (2H, s), 3.08 (3H, s), 1.95 (2H, m), 1.83 (2H, m), 1.75 (2H, m), 1.63 (2H, m)

Example 87: 5-[2-[4-[2-(cyclopentoxy)-3-pyridyl]-2,6-difluoro-phenyl]ethyl]isoxazol-3-ol

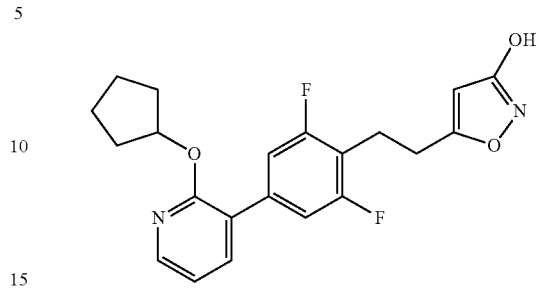

Diisopropylamine (0.13 mL, 0.92 mmol) was dissolved in 3.3 mL of THF. Butyllithium (0.35 mL, 0.87 mmol, 2.5 M hexane solution) was added thereto at −78° C., and the mixture was stirred for 15 minutes. 5-Methylisoxazol-3-ol (0.033 g, 0.33 mmol) was added thereto, and the mixture was stirred at −78° C. for 2 hours. 3-[4-(Chloromethyl)-3,5-difluoro-phenyl]-2-(cyclopentoxy)pyridine (0.16 g, 0.5 mmol) obtained in Preparation Example 70 was added thereto, and the mixture was stirred at room temperature for 2 hours. The reaction solution was diluted with Et$_2$O and cooled to 0° C. The reaction solution was adjusted to pH 3 and extracted with EtOAc. The product was dried with MgSO$_4$ and purified by column chromatography to obtain the title compound (0.032 g, 26%).

$^1$H-NMR (CDCl$_3$) δ 8.16 (1H, m), 7.58 (1H, m), 7.11 (2H, m), 6.92 (1H, m), 5.71 (1H, s), 5.52 (1H, m), 3.06 (2H, m), 2.98 (2H, m), 1.95 (2H, m), 1.82 (2H, m), 1.75 (2H, m), 1.65 (2H, m)

Example 88: 5-[2-[4-[2-(cyclopentoxy)-3-pyridyl]-2,6-difluoro-phenyl]propyl]isoxazol-3-ol

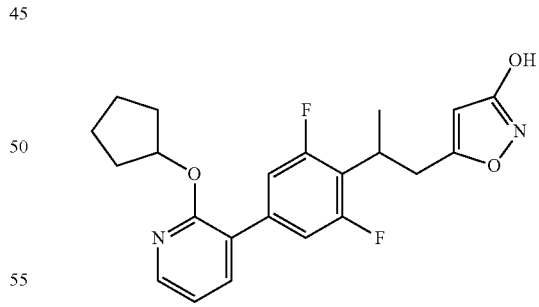

5-Methylisoxazol-3-ol (0.028 g, 0.28 mmol) and 3-[4-(1-chloroethyl)-3,5-difluoro-phenyl]-2-(cyclopentoxy)pyridine (0.12 g, 0.37 mmol) obtained in Preparation Example 74 were reacted in the same manner as in Example 87 to obtain the title compound (0.007 g, 6%).

$^1$H-NMR (CDCl$_3$) δ 8.16 (1H, m), 7.59 (1H, m), 7.08 (2H, m), 6.92 (1H, m), 5.61 (1H, s), 5.52 (1H, m), 3.64 (1H, m), 3.14 (1H, m), 3.07 (1H, m), 1.95 (2H, m), 1.83-1.63 (6H, m), 1.43 (3H, d)

Example 89: 5-[2-[4-[2-(cyclopentoxy)-3-pyridyl]-2,6-difluoro-phenoxy]ethyl]isoxazol-3-ol

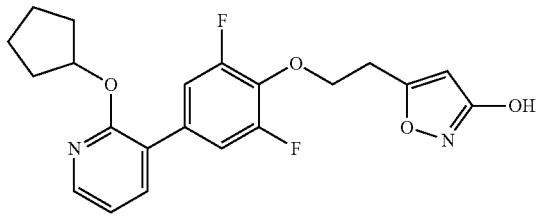 [SMILES: Oc1cc(CCOc2c(F)cc(-c3cccnc3OC3CCCC3)cc2F)on1]

Step A: 5-[2-[4-[2-(cyclopentoxy)-3-pyridyl]-2,6-difluoro-phenoxy]ethyl]-3-[(4-methoxyphenyl)methoxy]isoxazole 4-[2-(Cyclopentoxy)-3-pyridyl]-2,6-difluoro-phenol (0.087 g, 0.3 mmol) and 2-[3-[(4-methoxyphenyl)methoxy]isoxazol-5-yl]ethanol (0.075 g, 0.3 mmol) were reacted in the same manner as in Preparation Example 62 to obtain the title compound (0.065 g, 40%).

$^1$H-NMR (CDCl$_3$) δ 8.14 (1H, m), 7.56 (1H, m), 7.39 (2H, d), 7.16 (2H, m), 6.92 (3H, m), 5.90 (1H, s), 5.52 (1H, m), 5.19 (2H, s), 4.43 (2H, t), 3.82 (3H, s), 3.16 (2H, t), 1.95 (2H, m), 1.82 (2H, m), 1.76 (2H, m), 1.64 (2H, m)

Step B: 5-[2-[4-[2-(cyclopentoxy)-3-pyridyl]-2,6-difluoro-phenoxy]ethyl]isoxazol-3-ol 5-[2-[4-[2-(Cyclopentoxy)-3-pyridyl]-2,6-difluoro-phenoxy]ethyl]-3-[(4-methoxyphenyl)methoxy]isoxazole (0.065 g, 0.12 mmol) obtained in Step A was reacted in the same manner as in Step B of Example 61 to obtain the title compound (0.038 g, 79%).

$^1$H-NMR (CDCl$_3$) δ 8.14 (1H, m), 7.55 (1H, m), 7.17 (2H, m), 6.92 (1H, m), 5.95 (1H, s), 5.52 (1H, m), 4.44 (2H, t), 3.16 (2H, t), 1.95 (2H, m), 1.82 (2H, m), 1.74 (2H, m), 1.65 (2H, m)

Example 90: 5-[2-[4-[2-(cyclopentoxy)-3-pyridyl]-2,6-difluoro-anilino]ethyl]isoxazol-3-ol

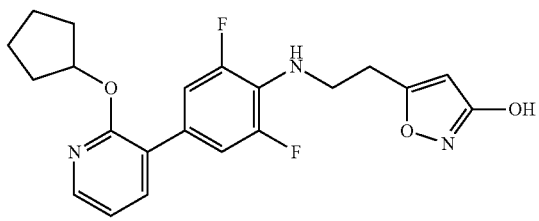 [SMILES: Oc1cc(CCNc2c(F)cc(-c3cccnc3OC3CCCC3)cc2F)on1]

Step A: N-[4-[2-(cyclopentoxy)-3-pyridyl]-2,6-difluoro-phenyl]-2-(3-hydroxyisoxazol-5-yl)acetamide 4-[2-(Cyclopentoxy)-3-pyridyl]-2,6-difluoro-aniline (0.17 g, 0.58 mmol) obtained in Preparation Example 67 and N,N'-dicyclohexylcarbodiimide (0.13 g, 0.61 mmol) were dissolved in 2 mL of THF. 2-(3-Hydroxyisoxazol-5-yl)acetic acid (0.083 g, 0.58 mmol) was added thereto, and the mixture was stirred at room temperature for 72 hours. 2-(3-Hydroxyisoxazol-5-yl)acetic acid (0.040 g, 0.28 mmol) was additionally added thereto, and the mixture was stirred at 70° C. for 90 minutes. The reaction solution was cooled to room temperature, and solids were filtered. The filtrate was purified by column chromatography to obtain the title compound (0.067 g, 28%).

$^1$H-NMR (CDCl$_3$) δ 8.17 (1H, m), 7.57 (1H, m), 7.22 (2H, m), 7.00 (1H, brs), 6.93 (1H, m), 6.07 (1H, s), 5.52 (1H, m), 3.89 (1H, brs), 2.33 (2H, s), 1.94 (2H, m), 1.81 (2H, m), 1.74 (2H, m), 1.65 (2H, m)

Step B: 5-[2-[4-[2-(cyclopentoxy)-3-pyridyl]-2,6-difluoro-anilino]ethyl]isoxazol-3-ol N-[4-[2-(cyclopentoxy)-3-pyridyl]-2,6-difluoro-phenyl]-2-(3-hydroxyisoxazol-5-yl)acetamide (0.066 g, 0.16 mmol) Obtained in Step A was dissolved in 1.6 mL of THF. Borane-dimethyl sulfide (0.14 mL, 0.67 mmol, 5.0 M Et$_2$O solution) was added thereto, and the mixture was stirred at room temperature for 4 hours. The reaction solution was concentrated under reduced pressure. After sequential addition of MeOH and 1 N HCl aqueous solution, the reaction solution was concentrated under reduced pressure. After addition of water, the reaction solution was extracted with EtOAc. The organic layer was purified by column chromatography to obtain the title compound (0.02 g, 31%).

$^1$H-NMR (CDCl$_3$) δ 8.11 (1H, m), 7.56 (1H, m), 7.12 (2H, m), 6.89 (1H, m), 5.77 (1H, s), 5.52 (1H, m), 3.71 (2H, m), 2.96 (2H, m), 1.97 (2H, m), 1.83 (2H, m), 1.77 (2H, m), 1.65 (2H, m)

Example 91: 2-[1-[5-(6-isopropylsulfanyl-2-pyridyl)-2-pyridyl]-3-piperidyl]acetic acid

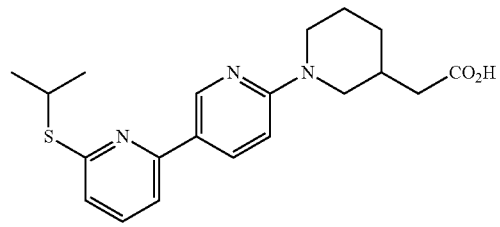 [SMILES: CC(C)Sc1cccc(-c2ccc(N3CCCC(CC(=O)O)C3)nc2)n1]

Step A: 2-[1-[5-(6-isopropylsulfanyl-2-pyridyl)-2-pyridyl]-3-piperidyl]acetonitrile 2-Fluoro-5-(6-isopropylsulfanyl-2-pyridyl)pyridine (0.025 g, 0.1 mmol) obtained in Step B of Preparation Example 80 and hydrochloric acid salt of 2-(3-piperidyl)acetonitrile (0.06 g, 0.37 mmol) obtained in Step D of Preparation Example 86 were dissolved in 0.5 mL of DMF. Cs$_2$CO$_3$ (0.165 g, 0.5 mmol) was added thereto, and the mixture was stirred at 50° C. for 4 hours. After removing solids, the product was purified by column chromatography to obtain the title compound (0.015 g, 42%).

$^1$H-NMR (CDCl$_3$) δ 8.86 (1H, d), 8.14 (1H, dd), 7.47 (1H, t), 7.30 (1H, d), 7.01 (1H, d), 6.75 (1H, d), 4.38 (1H, m), 4.17 (1H, m), 4.10 (1H, m), 3.09 (1H, m), 2.91 (1H, m), 2.39 (2H, m), 2.05 (2H, m), 1.82 (1H, m), 1.67 (1H, m), 1.50 (1H, m), 1.44 (6H, d)

Step B: 2-[1-[5-(6-isopropylsulfanyl-2-pyridyl)-2-pyridyl]-3-piperidyl]acetic acid 0.4 mL of EtOH and 6 N NaOH aqueous solution (0.04 mL, 0.25 mmol) were added to 2-[1-[5-(6-isopropylsulfanyl-2-pyridyl)-2-pyridyl]-3-piperidyl]acetonitrile (0.015 g, 0.042 mmol) obtained in Step A, and the mixture was stirred for 16 hours under reflux. The reaction solution was concentrated under reduced pressure and adjusted to pH 5 by the use of 1 N HCl aqueous solution. The reaction solution was extracted with EtOAc and purified by column chromatography to obtain the title compound (0.005 g, 32%).

$^1$H-NMR (CDCl$_3$) δ 8.76 (1H, d), 8.18 (1H, m), 7.47 (1H, t), 7.29 (1H, m), 7.01 (1H, d), 6.78 (1H, d), 4.14 (1H, m), 3.84 (1H, m), 3.76 (1H, m), 3.60 (1H, m), 3.48 (1H, m), 2.49 (1H, m), 2.30 (1H, m), 2.23 (1H, m), 1.98 (1H, m), 1.68 (2H, m), 1.50 (1H, m), 1.44 (6H, d)

Example 92: 4-[[5-(6-isopropylsulfanyl-2-pyridyl)-2-pyridyl]amino]butanoic acid

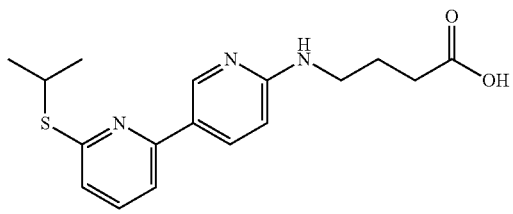 [SMILES: CC(C)Sc1cccc(-c2ccc(NCCCC(=O)O)nc2)n1]

Step A: 4-[[5-(6-isopropylsulfanyl-2-pyridyl)-2-pyridyl]amino]butanoic acid ethyl ester 3 mL of acetone was added to 2-fluoro-5-(6-isopropylsulfanyl-2-pyridyl)pyridine (0.088 g, 0.35 mmol) obtained in Step B of Preparation Example 80, hydrochloric acid salt of 4-aminobutanoic acid ethyl ester (0.065 g, 0.39 mmol) and K$_2$CO$_3$ (0.147 g, 1.06 mmol), and the mixture was stirred at 70° C. for 16 hours. The reaction solution was concentrated under reduced pressure and purified by column chromatography to obtain the title compound (0.02 g, 16%).

$^1$H-NMR (CDCl$_3$) δ 8.78 (1H, m), 8.09 (1H, m), 7.46 (1H, t), 7.27 (1H, d), 7.00 (1H, d), 6.47 (1H, d), 4.88 (1H, brs), 4.14 (3H, m), 3.42 (2H, m), 2.44 (2H, t), 2.00 (2H, m), 1.45 (6H, d), 1.25 (3H, t)

Step B: 4-[[5-(6-isopropylsulfanyl-2-pyridyl)-2-pyridyl]amino]butanoic acid

4-[[5-(6-Isopropylsulfanyl-2-pyridyl)-2-pyridyl]amino] butanoic acid ethyl ester (0.02 g, 0.055 mmol) obtained in Step A was reacted in the same manner as in Step B of Example 1 to obtain the title compound (0.01 g, 55%).

$^1$H-NMR (MeOH-d$_4$) δ 8.63 (1H, m), 8.16 (1H, m), 7.55 (1H, t), 7.40 (1H, d), 7.03 (1H, d), 6.70 (1H, d), 4.07 (1H, m), 3.39 (2H, t), 2.40 (2H, t), 1.92 (2H, m), 1.41 (6H, d)

Example 93: 2-[1-[4-(2-cyclobutylsulfanyl-3-pyridyl)phenyl]pyrazol-4-yl]acetic acid

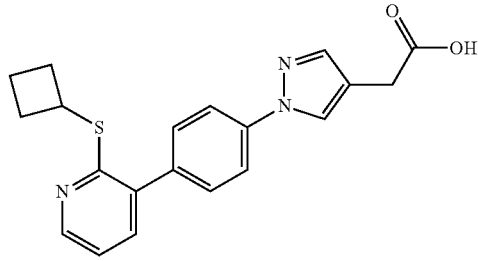 [SMILES: O=C(O)Cc1cnn(-c2ccc(-c3cccnc3SC3CCC3)cc2)c1]

Step A: 2-[1-[4-(2-cyclobutsulfanyl-3-pyridyl)phenyl]pyrazol-4-yl]acetic acid methyl ester 2-[1-[4-(4,4,5,5-Tetramethyl-1,3,2-dioxaborolan-2-yl) phenyl]pyrazol-4-yl]acetic acid methyl ester (0.04 g, 0.11 mmol) obtained in Preparation Example 81 and 3-iodo-2-cyclobutylsulfanyl-pyridine (0.034 g, 0.11 mmol) obtained in Preparation Example 13 were reacted in the same manner as in Step A of Example 1 to obtain the title compound (0.021 g, 47%).

$^1$H-NMR (CDCl$_3$) δ 8.41 (1H, m), 7.97 (1H, s), 7.75 (2H, d), 7.67 (1H, s), 7.50 (2H, d), 7.40 (1H, m), 7.05 (1H, m), 4.43 (1H, m), 3.74 (3H, s), 3.60 (2H, s), 2.51 (2H, m), 2.03 (4H, m)

Step B: 2-[1-[4-(2-cyclobutylsulfanyl-3-pyridyl) phenyl]pyrazol-4-yl]acetic acid 2-[1-[4-(2-Cyclobutylsulfanyl-3-pyridyl)phenyl]pyrazol-4-yl]acetic acid methyl ester (0.021 g, 0.05 mmol) obtained in Step A was reacted in the same manner as in Step B of Example 1 to obtain the title compound (0.006 g, 30%).

$^1$H-NMR (CDCl$_3$) δ 8.42 (1H, m), 7.99 (1H, s), 7.76 (2H, d), 7.70 (1H, s), 7.51 (2H, d), 7.40 (1H, m), 7.06 (1H, m), 4.43 (1H, m), 3.67 (2H, s), 2.51 (2H, m), 2.03 (4H, m)

Example 94: 5-[4-[2-(cyclopentoxy)-3-pyridyl]-2,6-difluoro-anilino]pentanoic acid

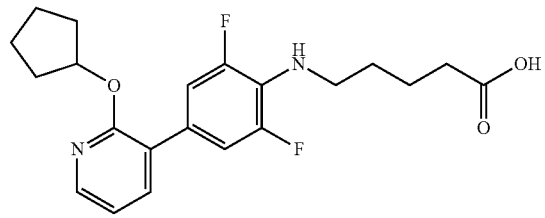 [SMILES: O=C(O)CCCCNc1c(F)cc(-c2cccnc2OC2CCCC2)cc1F]

Step A: 5-[4-[2-(cyclopentoxy)-3-pyridyl]-2,6-difluoro-anilino]-5-oxo-pentanoic acid ethyl ester 4-[2-(cyclopentoxy)-3-pyridyl]-2,6-difluoro-aniline (0.09 g, 0.31 mmol) obtained in Preparation Example 67 was dissolved in 1.6 mL of DCM. DIPEA (0.054 mL, 0.31 mmol) and ethyl glutaryl chloride (0.05 mL, 0.31 mmol) were added thereto, and the mixture was stirred at room temperature for 2 hours. After addition of water, the reaction solution was extracted with EtOAc. The organic layer was dried with MgSO$_4$ and purified by column chromatography to obtain the title compound (0.09 g, 67%).

$^1$H-NMR (CDCl$_3$) δ 8.17 (1H, m), 7.57 (1H, m), 7.20 (2H, m), 7.00 (1H, brs), 6.93 (1H, m), 5.52 (1H, m), 4.15 (2H, q), 2.54 (2H, m), 2.46 (2H, m), 2.08 (2H, m), 1.93 (2H, m), 1.79 (2H, m), 1.74 (2H, m), 1.63 (2H, m), 1.27 (3H, t)

Step B: 5-[4-[2-(cyclopentoxy)-3-pyridyl]-2,6-difluoro-anilino]pentanoic acid ethyl ester 5-[4-[2-(Cyclopentoxy)-3-pyridyl]-2,6-difluoro-anilino]-5-oxo-pentanoic acid ethyl ester (0.06 g, 0.14 mmol) obtained in Step A was dissolved in 1.4 mL of THF. Borane-dimethyl sulfide (0.06 mL, 0.28 mmol, 5.0 M Et$_2$O solution) was added thereto, and the mixture was stirred at room temperature for 16 hours. The reaction solution was concentrated under reduced pressure. After addition of water, the reaction solution was extracted with EtOAc. The organic layer was dried with MgSO$_4$ and purified by column chromatography to obtain the title compound (0.009 g, 15%).

$^1$H-NMR (CDCl$_3$) δ 8.09 (1H, m), 7.54 (1H, m), 7.10 (2H, m), 6.88 (1H, m), 5.52 (1H, m), 4.13 (2H, q), 3.65 (1H, brs), 3.38 (2H, t), 2.35 (2H, t), 1.96 (2H, m), 1.83 (2H, m), 1.75 (4H, m), 1.65 (4H, m), 1.25 (3H, t)

Step C: 5-[4-[2-(cyclopentoxy)-3-pyridyl]-2,6-difluoro-anilino]pentanoic acid

5-[4-[2-(Cyclopentoxy)-3-pyridyl]-2,6-difluoro-anilino]pentanoic acid ethyl ester (0.009 g, 0.021 mmol) obtained in Step B was reacted in the same manner as in Step B of Example 1 to obtain the title compound (0.004 g, 48%).

$^1$H-NMR (CDCl$_3$) δ 8.10 (1H, m), 7.55 (1H, m), 7.12 (2H, m), 6.99 (1H, m), 5.51 (1H, m), 3.39 (2H, t), 2.41 (2H, t), 1.95 (2H, m), 1.83 (2H, m), 1.75 (4H, m), 1.65 (4H, m)

Example 95: 5-[4-[2-(cyclopentoxy)-3-pyridyl]-N-ethyl-2,6-difluoro-anilino]pentanoic acid

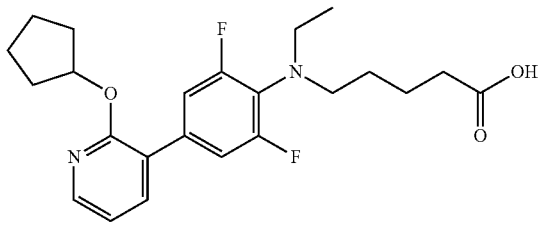 [SMILES: CCN(CCCCC(=O)O)c1c(F)cc(-c2cccnc2OC2CCCC2)cc1F]

Step A: 5-[N-acetyl-4-[2-(cyclopentoxy)-3-pyridyl]-2,6-difluoro-anilino]pentanoic acid ethyl ester 5-[N-benzyloxycarbonyl-4-[2-(cyclopentoxy)-3-pyridyl]-2,6-difluoro-anilino]pentanoic acid ethyl ester (0.14 g, 0.25 mmol) obtained in Preparation Example 87 was dissolved in 1.3 mL of MeOH. Catalytic amount of 10 wt % Pd/C was added thereto, and the mixture was stirred for 16 hours under hydrogen atmosphere. Solids were filtered to obtain 5-[4-[2-(cyclopentoxy)-3-pyridyl]-2,6-difluoro-anilino]pentanoic acid ethyl ester (0.11 g, 99%). The obtained compound (0.09 g, 0.21 mmol) was dissolved in 2.1 mL of DCM. DIPEA (0.04 mL, 0.23 mmol) and acetyl chloride (0.015 mL, 0.21 mmol) were added thereto, and the mixture was stirred at room temperature for 72 hours. After addition of water, the reaction solution was extracted with EtOAc and purified by column chromatography to obtain the title compound (0.064 g, 66%).

$^1$H-NMR (CDCl$_3$) δ 8.20 (1H, m), 7.62 (1H, m), 7.28 (2H, m), 6.96 (1H, m), 5.55 (1H, m), 4.10 (2H, q), 3.69 (2H, t), 2.31 (2H, t), 1.99 (2H, m), 1.92 (3H, s), 1.83 (2H, m), 1.76 (2H, m), 1.66 (4H, m), 1.57 (2H, m), 1.24 (3H, t)

Step B: 5-[4-[2-(cyclopentoxy)-3-pyridyl]-N-ethyl-2,6-difluoro-anilino]pentanoic acid ethyl ester 5-[N-acetyl-4-[2-(cyclopentoxy)-3-pyridyl]-2,6-difluoro-anilino]pentanoic acid ethyl ester (0.06 g, 0.13 mmol) obtained in Step A was reacted in the same manner as in Step B of Example 94 to obtain the title compound (0.019 g, 33%).

$^1$H-NMR (CDCl$_3$) δ 8.14 (1H, m), 7.58 (1H, m), 7.12 (2H, m), 6.92 (1H, m), 5.52 (1H, m), 4.11 (2H, q), 3.16 (4H, m), 2.29 (2H, t), 1.97 (2H, m), 1.83 (2H, m), 1.76 (2H, m), 1.65 (4H, m), 1.50 (2H, m), 1.23 (3H, t), 1.05 (3H, t)

Step C: 5-[4-[2-(cyclopentoxy)-3-pyridyl]-N-ethyl-2,6-difluoro-anilino]pentanoic acid 5-[4-[2-(Cyclopentoxy)-3-pyridyl]-N-ethyl-2,6-difluoro-anilino]pentanoic acid ethyl ester (0.019 g, 0.04 mmol) obtained in Step B was reacted in the same manner as in Step B of Example 1 to obtain the title compound (0.018 g, 99%).

$^1$H-NMR (CDCl$_3$) δ 8.14 (1H, m), 7.59 (1H, m), 7.12 (2H, m), 6.92 (1H, m), 5.52 (1H, m), 3.17 (4H, m), 2.35 (2H, t), 1.97 (2H, m), 1.83 (2H, m), 1.76 (2H, m), 1.68 (4H, m), 1.53 (2H, m), 1.05 (3H, t)

Example 96: 5-[2,6-difluoro-4-(6-isopropylsulfanyl-2-pyridyl)anilino]pentanoic acid

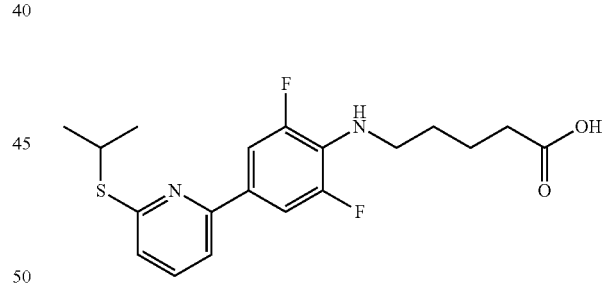

Step A: 5-[2,6-difluoro-4-(6-isopropylsulfanyl-2-pyridyl)anilino]pentanoic acid ethyl ester 0.7 mL of dimethoxyethane and 2M Na$_2$CO$_3$ (0.3 mL, 0.6 mmol) were added to 5-[2,6-difluoro-4-(4,4,5,5-tetramethyl-1,3,2-dioxaborolan-2-yl)anilino]pentanoic acid ethyl ester (0.087 g, 0.23 mmol) obtained in Preparation Example 83 and 2-chloro-6-isopropylsulfanyl-pyridine (0.038 g, 0.2 mmol) obtained in Preparation Example 10, and charged with nitrogen for 5 minutes. Pd(PPh$_3$)$_4$ (12 mg, 0.01 mmol) was added thereto, and the mixture was stirred for 16 hours under reflux. The reaction solution was cooled to room temperature, and solids were filtered through Celite. The filtrate was purified by column chromatography to obtain the title compound (0.057 g, 70%).

¹H-NMR (CDCl₃) δ 7.53 (2H, m), 7.47 (1H, t), 7.26 (1H, d), 7.02 (1H, d), 4.14 (3H, m), 3.77 (1H, brs), 3.41 (2H, m), 2.35 (2H, t), 1.74 (2H, m), 1.65 (2H, m), 1.45 (6H, d), 1.26 (3H, t)

Step B: 5-[2,6-difluoro-4-(6-isopropylsulfanyl-2-pyridyl)anilino]pentanoic acid

5-[2,6-Difluoro-4-(6-isopropylsulfanyl-2-pyridyl)anilino]pentanoic acid ethyl ester (0.057 g, 0.14 mmol) Obtained in Step A was reacted in the same manner as in Step B of Example 1 to obtain the title compound (0.037 g, 69%).

¹H-NMR (CDCl₃) δ 7.53 (2H, m), 7.47 (1H, t), 7.26 (1H, d), 7.02 (1H, d), 4.13 (1H, m), 3.42 (2H, m), 2.41 (2H, t), 1.75 (2H, m), 1.68 (2H, m), 1.46 (6H, d)

Example 97: 5-[2,6-difluoro-4-(2-isopropylsulfanyl-3-pyridyl)anilino]pentanoic acid

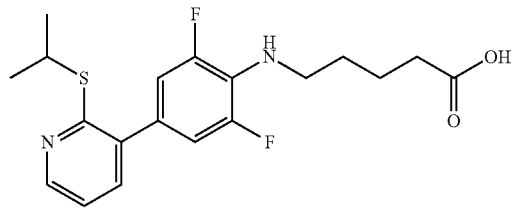 [SMILES: CC(C)Sc1ncccc1-c1cc(F)c(NCCCCC(=O)O)c(F)c1]

5-[2,6-Difluoro-4-(4,4,5,5-tetramethyl-1,3,2-dioxaborolan-2-yl)anilino]pentanoic acid ethyl ester (0.087 g, 0.23 mmol) obtained in Preparation Example 83 and 3-iodo-2-isopropylsulfanyl-pyridine (0.038 g, 0.2 mmol) obtained in Preparation Example 9 were reacted in the same manner as in Example 1 to obtain the title compound (0.043 g, 56%).

¹H-NMR (CDCl₃) δ 8.41 (1H, m), 7.32 (1H, m), 7.02 (1H, m), 6.90 (2H, m), 4.05 (1H, m), 3.41 (2H, m), 2.43 (2H, t), 1.77 (2H, m), 1.69 (2H, m), 1.37 (6H, d)

Example 98: 5-[4-[6-(cyclopropylmethoxy)-2-pyridyl]-2,6-difluoro-anilino]pentanoic acid

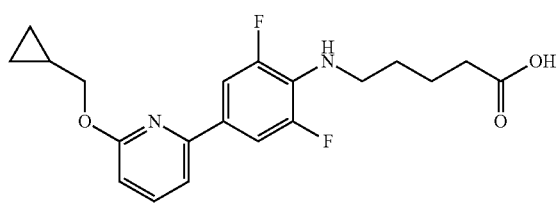

5-[2,6-Difluoro-4-(4,4,5,5-tetramethyl-1,3,2-dioxaborolan-2-yl)anilino]pentanoic acid ethyl ester (0.087 g, 0.23 mmol) obtained in Preparation Example 83 and 2-chloro-6-cyclopropylmethoxy-pyridine (0.037 g, 0.2 mmol) obtained in Preparation Example 43 were reacted in the same manner as in Example 1 to obtain the title compound (0.046 g, 61%).

¹H-NMR (CDCl₃) δ 7.58 (1H, m), 7.52 (2H, m), 7.16 (1H, d), 6.65 (1H, d), 4.23 (2H, d), 3.41 (2H, m), 2.42 (2H, t), 1.76 (2H, m), 1.67 (2H, m), 1.33 (1H, m), 0.63 (2H, m), 0.38 (2H, m)

Example 99: 5-[4-[2-(cyclopropylmethoxy)-3-pyridyl]-2,6-difluoro-anilino]pentanoic acid

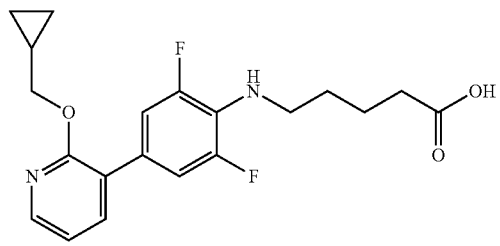 [SMILES: O=C(O)CCCCNc1c(F)cc(-c2cccnc2OCC2CC2)cc1F]

5-[2,6-Difluoro-4-(4,4,5,5-tetramethyl-1,3,2-dioxaborolan-2-yl)anilino]pentanoic acid ethyl ester (0.087 g, 0.23 mmol) obtained in Preparation Example 83 and 2-cyclopropylmethoxy-3-iodo-pyridine (0.055 g, 0.2 mmol) obtained in Preparation Example 40 were reacted in the same manner as in Example 1 to obtain the title compound (0.042 g, 57%).

¹H-NMR (CDCl₃) δ 8.08 (1H, m), 7.57 (1H, m), 7.17 (2H, m), 6.92 (1H, m), 4.22 (2H, d), 3.40 (2H, m), 2.42 (2H, t), 1.77 (2H, m), 1.68 (2H, m), 1.30 (1H, m), 0.60 (2H, m), 0.35 (2H, m)

Example 100: 2-[1-[4-(2-cyclopentylsulfanyl-3-pyridyl)-2,6-difluoro-phenyl]-4-piperidyl]acetic acid

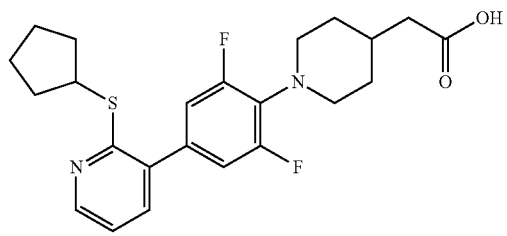

Step A: 2-[1-[4-(2-cyclopentylsulfanyl-3-pyridyl)-2,6-difluoro-phenyl]-4-piperidyl]acetic acid methyl ester 2-[1-[2,6-Difluoro-4-(4,4,5,5-tetramethyl-1,3,2-dioxaborolan-2-yl)phenyl]-4-piperidyl]acetic acid methyl ester (0.082 g, 0.21 mmol) obtained in Preparation Example 84 and 2-cyclopentylsulfanyl-3-iodo-pyridine (0.053 g, 0.19 mmol) obtained in Preparation Example 15 were reacted in the same manner as in Step A of Example 1 to obtain the title compound (0.052 g, 66%).

¹H-NMR (CDCl₃) δ 8.41 (1H, m), 7.32 (1H, m), 7.01 (1H, m), 6.93 (2H, m), 4.08 (1H, m), 3.69 (3H, s), 3.31 (2H, m), 3.14 (2H, m), 2.31 (2H, d), 2.03 (2H, m), 1.95 (1H, m), 1.77 (4H, m), 1.72 (4H, m), 1.45 (2H, m)

Step B: 2-[1-[4-(2-cyclopentylsulfanyl-3-pyridyl)-2,6-difluoro-phenyl]-4-piperidyl]acetic acid 2-[1-[4-(2-Cyclopentylsulfanyl-3-pyridyl)-2,6-difluoro-phenyl]-4-piperidyl]acetic acid methyl ester (0.052 g, 0.12 mmol) obtained in Step A was reacted in the same manner as in Step B of Example 1 to obtain the title compound (0.024 g, 48%).

$^1$H-NMR (CDCl$_3$) δ 8.41 (1H, m), 7.30 (1H, m), 7.01 (1H, m), 6.92 (2H, m), 4.08 (1H, m), 3.33 (2H, m), 3.15 (2H, m), 2.36 (2H, d), 2.20 (2H, m), 1.95 (1H, m), 1.82 (2H, m), 1.72 (2H, m), 1.62-1.48 (6H, m)

Example 101: 5-[4-[6-(cyclopropylmethoxy)-2-pyridyl]-2,6-difluoro-N-methyl-anilino]pentanoic acid

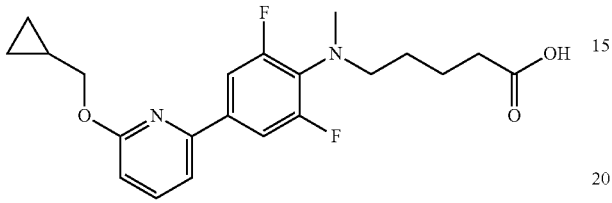

5-[4-[6-(Cyclopropylmethoxy)-2-pyridyl]-2,6-difluoro-anilino]pentanoic acid (0.023 g, 0.06 mmol) obtained in Example 98 was dissolved in 3 mL of DMF. NaH (0.008 g, 55 wt % in mineral oil, 0.18 mmol) and iodomethane (0.011 mL, 0.18 mmol) were sequentially added thereto, and the mixture was stirred at room temperature for 1 hour. After addition of ammonium chloride aqueous solution, the reaction solution was extracted with EtOAc. The organic layer was dried with anhydrous magnesium sulfate and reacted in the same manner as in Step B of Example 1 to obtain the title compound (0.013 g, 54%).

$^1$H-NMR (CDCl$_3$) δ 7.60 (1H, t), 7.50 (2H, m), 7.21 (1H, d), 6.70 (1H, d), 4.24 (2H, d), 3.14 (2H, t), 2.90 (3H, s), 2.35 (2H, t), 1.67 (2H, m), 1.59 (2H, m), 1.33 (1H, m), 0.63 (2H, m), 0.39 (2H, m)

Example 102: 2-[1-[4-[2-(cyclopentoxy)-3-pyridyl]-2,6-difluoro-phenyl]-4-piperidyl]acetic acid

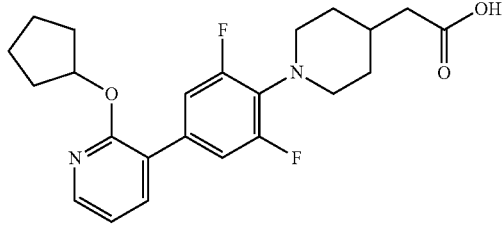 [SMILES: O=C(O)CC1CCN(c2c(F)cc(-c3cccnc3OC3CCCC3)cc2F)CC1]

2-[1-[2,6-Difluoro-4-(4,4,5,5-tetramethyl-1,3,2-dioxa-borolan-2-yl)phenyl]-4-piperidyl]acetic acid methyl ester (0.082 g, 0.21 mmol) obtained in Preparation Example 84 and 2-cyclopentoxy-3-iodo-pyridine (0.055 g, 0.19 mmol) obtained in Preparation Example 11 were reacted in the same manner as in Example 1 to obtain the title compound (0.04 g, 42%).

$^1$H-NMR (CDCl$_3$) δ 8.12 (1H, m), 7.55 (1H, m), 7.08 (2H, m), 6.90 (1H, m), 5.51 (1H, m), 3.32 (2H, m), 3.15 (2H, m), 2.36 (2H, d), 1.95 (3H, m), 1.84 (6H, m), 1.50 (2H, m), 1.47 (2H, m)

Example 103: 2-[1-[2,6-difluoro-4-(2-tetrahydro-furan-3-yloxy-3-pyridyl)phenyl]-4-piperidyl]acetic acid

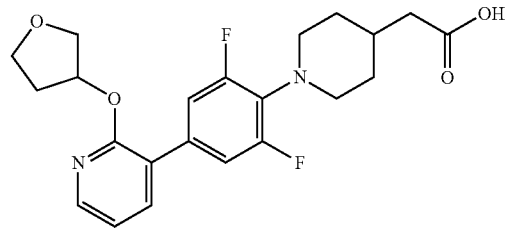 [SMILES: O=C(O)CC1CCN(c2c(F)cc(-c3cccnc3OC3CCOC3)cc2F)CC1]

2-[1-[2,6-Difluoro-4-(4,4,5,5-tetramethyl-1,3,2-dioxa-borolan-2-yl)phenyl]-4-piperidyl]acetic acid methyl ester (0.082 g, 0.21 mmol) obtained in Preparation Example 84 and 3-iodo-2-(tetrahydro-furan-3-yloxy)-pyridine (0.055 g, 0.19 mmol) obtained in Preparation Example 49 were reacted in the same manner as in Example 1 to obtain the title compound (0.036 g, 46%).

$^1$H-NMR (CDCl$_3$) δ 8.10 (1H, m), 7.58 (1H, m), 7.10 (2H, m), 6.96 (1H, m), 5.64 (1H, m), 4.13 (1H, m), 3.93 (3H, m), 3.32 (2H, m), 3.15 (2H, m), 2.36 (2H, d), 2.25 (1H, m), 2.13 (1H, m), 1.98 (1H, m), 1.82 (2H, m), 1.50 (2H, m)

Example 104: 2-[1-[2,6-difluoro-4-(2-isopropylsulfanyl-3-pyridyl)phenyl]-4-piperidyl]acetic acid

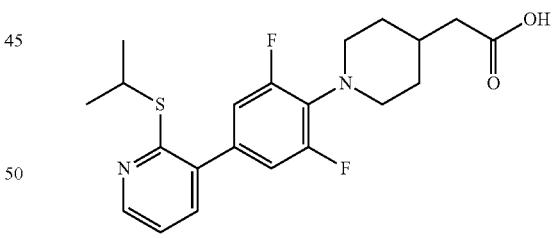

2-[1-[2,6-Difluoro-4-(4,4,5,5-tetramethyl-1,3,2-dioxa-borolan-2-yl)phenyl]-4-piperidyl]acetic acid methyl ester (0.082 g, 0.21 mmol) obtained in Preparation Example 84 and 3-iodo-2-isopropylsulfanyl-pyridine (0.05 g, 0.19 mmol) obtained in Preparation Example 9 were reacted in the same manner as in Example 1 to obtain the title compound (0.024 g, 32%).

$^1$H-NMR (CDCl$_3$) δ 8.42 (1H, m), 7.33 (1H, m), 7.02 (1H, m), 6.91 (2H, m), 4.06 (1H, m), 3.32 (2H, m), 3.16 (2H, m), 2.36 (2H, d), 1.98 (1H, m), 1.83 (2H, m), 1.51 (2H, m), 1.37 (6H, d)

Example 105: 2-[1-[2,6-difluoro-4-(6-isopropylsulfanyl-2-pyridyl)phenyl]-4-piperidyl]acetic acid

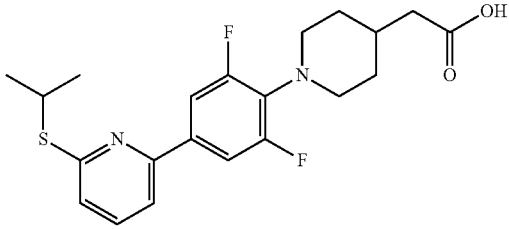

2-[1-[2,6-Difluoro-4-(4,4,5,5-tetramethyl-1,3,2-dioxaborolan-2-yl)phenyl]-4-piperidyl]acetic acid methyl ester (0.082 g, 0.21 mmol) obtained in Preparation Example 84 and 2-chloro-6-isopropylsulfanyl-pyridine (0.035 g, 0.19 mmol) obtained in Preparation Example 10 were reacted in the same manner as in Example 1 to obtain the title compound (0.024 g, 31%).

$^1$H-NMR (CDCl$_3$) δ 7.53 (3H, m), 7.27 (1H, d), 7.05 (1H, d), 4.13 (1H, m), 3.32 (2H, m), 3.17 (2H, m), 2.37 (2H, d), 1.98 (1H, m), 1.97 (2H, m), 1.49 (8H, m)

Example 106: 2-[1-[4-[6-(cyclopropylmethoxy)-2-pyridyl]-2,6-difluoro-phenyl]-4-piperidyl]acetic acid

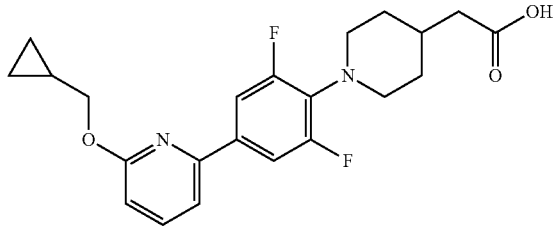 [SMILES: O=C(O)CC1CCN(c2c(F)cc(-c3cccc(OCC4CC4)n3)cc2F)CC1]

2-[1-[2,6-Difluoro-4-(4,4,5,5-tetramethyl-1,3,2-dioxaborolan-2-yl)phenyl]-4-piperidyl]acetic acid methyl ester (0.082 g, 0.21 mmol) obtained in Preparation Example 84 and 2-chloro-6-cyclopropylmethoxy-pyridine (0.035 g, 0.19 mmol) obtained in Preparation Example 43 were reacted in the same manner as in Example 1 to obtain the title compound (0.027 g, 35%).

$^1$H-NMR (CDCl$_3$) δ 7.60 (1H, t), 7.51 (2H, m), 7.20 (1H, d), 6.70 (1H, d), 4.23 (2H, d), 3.32 (2H, m), 3.16 (2H, m), 2.35 (2H, d), 1.98 (1H, m), 1.82 (2H, m), 1.50 (2H, m), 1.34 (1H, m), 0.64 (2H, m), 0.40 (2H, m)

Example 107: 2-[1-[2,6-difluoro-4-(6-isopropylsulfanyl-2-pyridyl)phenyl]-3-piperidyl]acetic acid

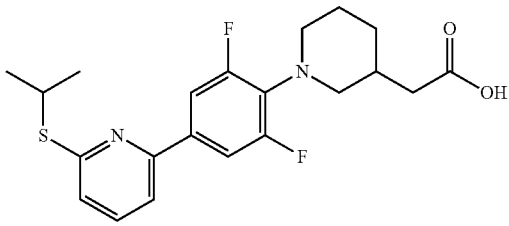 [SMILES: CC(C)Sc1cccc(-c2cc(F)c(N3CCCC(CC(=O)O)C3)c(F)c2)n1]

Step A: 2-[1-[2,6-difluoro-4-(6-isopropylsulfanyl-2-pyridyl)phenyl]-3-piperidyl]acetonitrile 2-[1-[2,6-Difluoro-4-(4,4,5,5-tetramethyl-1,3,2-dioxaborolan-2-yl)phenyl]-3-piperidyl]acetonitrile (0.12 g, 0.33 mmol) obtained in Preparation Example 86 and 2-chloro-6-isopropylsulfanyl-pyridine (0.056 g, 0.3 mmol) obtained in Preparation Example 10 were reacted in the same manner as in Step A of Example 1 to obtain the title compound (0.081 g, 70%).

$^1$H-NMR (CDCl$_3$) δ 7.52 (3H, m), 7.30 (1H, d), 7.07 (1H, d), 4.13 (1H, m), 3.36 (1H, m), 3.25 (1H, m), 3.11 (1H, m), 2.98 (1H, m), 2.47 (2H, m), 2.17 (1H, m), 1.93 (1H, m), 1.80 (1H, m), 1.73 (1H, m), 1.47 (7H, m)

Step B: 2-[1-[2,6-difluoro-4-(6-isopropylsulfanyl-2-pyridyl)phenyl]-3-piperidyl]acetic acid 2-[1-[2,6-Difluoro-4-(6-isopropylsulfanyl-2-pyridyl)phenyl]-3-piperidyl]acetonitrile (0.081 g, 0.21 mmol) obtained in Step A was reacted in the same manner as in Step B of Example 91 to obtain the title compound (0.046 g, 54%).

$^1$H-NMR (CDCl$_3$) δ 7.50 (3H, m), 7.28 (1H, d), 7.05 (1H, d), 4.13 (1H, m), 3.35 (1H, m), 3.25 (1H, m), 3.07 (1H, m), 2.90 (1H, m), 2.46 (1H, m), 2.35 (1H, m), 2.45 (1H, m), 1.90 (1H, m), 1.75 (2H, m), 1.46 (6H, d), 1.25 (1H, m)

Example 108: 2-[1-[2,6-difluoro-4-(2-isopropylsulfanyl-3-pyridyl)phenyl]-3-piperidyl]acetic acid

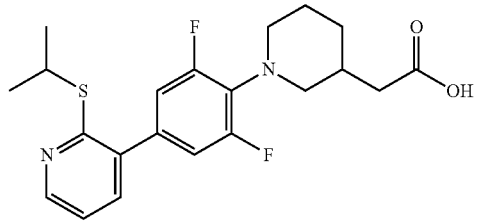 [SMILES: CC(C)Sc1ncccc1-c1cc(F)c(N2CCCC(CC(=O)O)C2)c(F)c1]

Step A: 2-[1-[2,6-difluoro-4-(2-isopropylsulfanyl-3-pyridyl)phenyl]-3-piperidyl]acetonitrile 2-[1-[2,6-Difluoro-4-(4,4,5,5-tetramethyl-1,3,2-dioxaborolan-2-yl)phenyl]-3-piperidyl]acetonitrile (0.12 g, 0.33 mmol) obtained in Preparation Example 86 and 3-iodo-2-isopropylsulfanyl-pyridine (0.084 g, 0.3 mmol) obtained in Preparation Example 9 were reacted in the same manner as in Step A of Example 1 to obtain the title compound (0.072 g, 63%).

$^1$H-NMR (CDCl$_3$) δ 8.43 (1H, m), 7.32 (1H, m), 7.02 (1H, m), 6.95 (2H, m), 4.07 (1H, m), 3.36 (1H, m), 3.24 (1H, m), 3.10 (1H, m), 2.98 (1H, m), 2.47 (2H, m), 2.16 (1H, m), 1.92 (1H, m), 1.80 (1H, m), 1.73 (1H, m), 1.43 (1H, m), 1.36 (6H, d)

Step B: 2-[1-[2,6-difluoro-4-(2-isopropylsulfanyl-3-pyridyl)phenyl]-3-piperidyl]acetic acid 2-[1-[2,6-Difluoro-4-(2-isopropylsulfanyl-3-pyridyl)phenyl]-3-piperidyl]acetonitrile (0.072 g, 0.19 mmol) obtained in Step A was reacted in the same manner as in Step B of Example 91 to obtain the title compound (0.023 g, 30%).

¹H-NMR (CDCl₃) δ 8.41 (1H, m), 7.33 (1H, m), 7.02 (1H, m), 6.92 (2H, m), 4.06 (1H, m), 3.35 (1H, m), 3.24 (1H, m), 3.07 (1H, m), 2.90 (1H, m), 2.45 (1H, m), 2.35 (1H, m), 2.24 (1H, m), 1.89 (1H, m), 1.73 (2H, m), 1.36 (6H, d), 1.26 (1H, m)

Example 109: 2-[1-[2,6-difluoro-4-(2-isopropylsulfanyl-3-pyridyl)phenyl]azetidin-3-yl]acetic acid

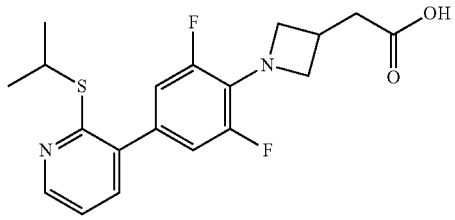 [SMILES: CC(C)Sc1ncccc1-c1cc(F)c(N2CC(CC(=O)O)C2)c(F)c1]

Step A: 2-[1-[2,6-difluoro-4-(2-isopropylsulfanyl-3-pyridyl)phenyl]azetidin-3-yl]acetic acid ethyl ester 2-[1-[2,6-Difluoro-4-(4,4,5,5-tetramethyl-1,3,2-dioxaborolan-2-yl)phenyl]azetidin-3-yl]acetic acid ethyl ester (0.076 g, 0.2 mmol) obtained in Preparation Example 88 and 3-iodo-2-isopropylsulfanyl-pyridine (0.05 g, 0.18 mmol) obtained in Preparation Example 9 were reacted in the same manner as in Step A of Example 1 to obtain the title compound (0.046 g, 63%).

¹H-NMR (CDCl₃) δ 8.39 (1H, m), 7.31 (1H, m), 7.00 (1H, m), 6.84 (2H, m), 4.40 (2H, m), 4.15 (2H, q), 4.05 (1H, m), 3.92 (2H, m), 3.05 (1H, m), 2.71 (2H, d), 1.37 (6H, d), 1.27 (3H, t)

Step B: 2-[1-[2,6-difluoro-4-(2-isopropylsulfanyl-3-pyridyl)phenyl]azetidin-3-yl]acetic acid 2-[1-[2,6-Difluoro-4-(2-isopropylsulfanyl-3-pyridyl)phenyl]azetidin-3-yl]acetic acid ethyl ester (0.046 g, 0.11 mmol) obtained in Step A was reacted in the same manner as in Step B of Example 1 to obtain the title compound (0.016 g, 40%).

¹H-NMR (CDCl₃) δ 8.41 (1H, m), 7.31 (1H, m), 7.00 (1H, m), 6.86 (2H, m), 4.42 (2H, m), 4.03 (1H, m), 3.93 (2H, m), 3.07 (1H, m), 2.78 (2H, d), 1.36 (6H, d)

Example 110: 6-[2,6-difluoro-4-(2-isopropylsulfanyl-3-pyridyl)phenyl]-6-azaspiro[2.5]octan-2-carboxylic acid

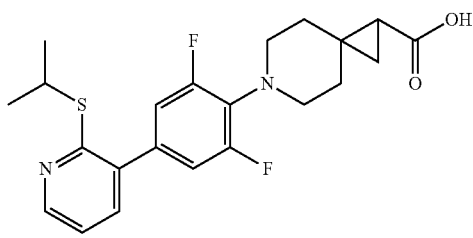 [SMILES: CC(C)Sc1ncccc1-c1cc(F)c(N2CCC3(CC2)CC3C(=O)O)c(F)c1]

Step A: 6-[2,6-difluoro-4-(2-isopropylsulfanyl-3-pyridyl)phenyl]-6-azaspiro[2.5]octan-2-carboxylic acid ethyl ester 6-[2,6-Difluoro-4-(4,4,5,5-tetramethyl-1,3,2-dioxaborolan-2-yl)phenyl]-6-azaspiro[2.5]octan-2-carboxylic acid ethyl ester (0.092 g, 0.21 mmol) obtained in Preparation Example 89 and 3-iodo-2-isopropylsulfanyl-pyridine (0.053 g, 0.19 mmol) obtained in Preparation Example 9 were reacted in the same manner as in Step A of Example 1 to obtain the title compound (0.061 g, 72%).

¹H-NMR (CDCl₃) δ 8.42 (1H, m), 7.33 (1H, m), 7.02 (1H, m), 6.92 (2H, m), 4.17 (2H, q), 4.06 (1H, m), 3.32-3.11 (4H, m), 1.86 (2H, m), 1.59 (3H, m), 1.34 (6H, d), 1.30 (3H, t), 1.20 (1H, m), 0.96 (1H, m)

Step B: 6-[2,6-difluoro-4-(2-isopropylsulfanyl-3-pyridyl)phenyl]-6-azaspiro[2.5]octan-2-carboxylic acid 6-[2,6-Difluoro-4-(2-isopropylsulfanyl-3-pyridyl)phenyl]-6-azaspiro[2.5]octan-2-carboxylic acid ethyl ester (0.061 g, 0.13 mmol) obtained in Step A was reacted in the same manner as in Step B of Example 1 to obtain the title compound (0.04 g, 70%).

¹H-NMR (CDCl₃+MeOH-d₄) δ 8.42 (1H, m), 7.34 (1H, m), 7.04 (1H, m), 6.94 (2H, m), 4.05 (1H, m), 3.40-3.10 (4H, m), 1.90 (2H, m), 1.60 (3H, m), 1.36 (6H, d), 1.19 (1H, m), 0.99 (1H, m)

Example 111: 6-[2,6-difluoro-4-(6-isopropylsulfanyl-2-pyridyl)phenyl]-6-azaspiro[2.5]octan-2-carboxylic acid

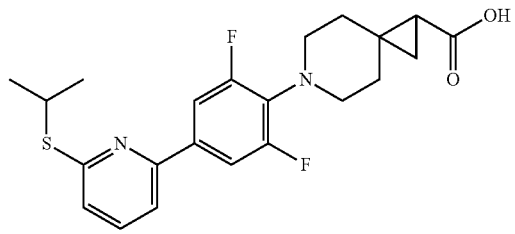 [SMILES: CC(C)Sc1cccc(-c2cc(F)c(N3CCC4(CC3)CC4C(=O)O)c(F)c2)n1]

6-[2,6-Difluoro-4-(4,4,5,5-tetramethyl-1,3,2-dioxaborolan-2-yl)phenyl]-6-azaspiro[2.5]octan-2-carboxylic acid ethyl ester (0.092 g, 0.21 mmol) obtained in Preparation Example 89 and 2-chloro-6-isopropylsulfanyl-pyridine (0.036 g, 0.19 mmol) obtained in Preparation Example 10 were reacted in the same manner as in Example 1 to obtain the title compound (0.045 g, 57%).

¹H-NMR (CDCl₃) δ 7.51 (3H, m), 7.30 (1H, m), 7.07 (1H, m), 4.12 (1H, m), 3.30-3.19 (4H, m), 1.93 (2H, m), 1.62 (3H, m), 1.46 (6H, d), 1.26 (1H, m), 1.05 (1H, m)

Example 112: 2-[1-[4-(2-cyclopentylsulfanyl-3-pyridyl)-2,6-difluoro-phenyl]azetidin-3-yl]acetic acid

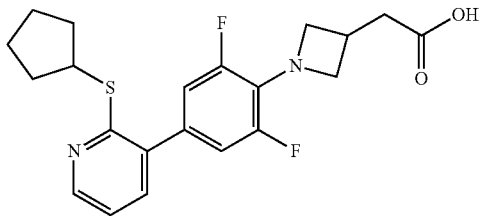 [SMILES: O=C(O)CC1CN(c2c(F)cc(-c3cccnc3SC3CCCC3)cc2F)C1]

2-[1-[2,6-Difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 and 2-cyclopentylsulfanyl-3-iodo-pyridine (0.072 g, 0.24 mmol) obtained in Preparation Example 15 were reacted in the same manner as in Example 1 to obtain the title compound (0.045 g, 46%).
$^1$H-NMR (CDCl$_3$) δ 8.39 (1H, m), 7.29 (1H, m), 6.99 (1H, m), 6.85 (2H, m), 4.42 (2H, m), 4.07 (1H, m), 3.94 (2H, m), 3.05 (1H, m), 2.78 (2H, d), 2.20 (2H, m), 1.74 (2H, m), 1.56 (4H, m)

Example 113: 2-[1-[4-[2-(cyclopentoxy)-3-pyridyl]-2,6-difluoro-phenyl]azetidin-3-yl]acetic acid

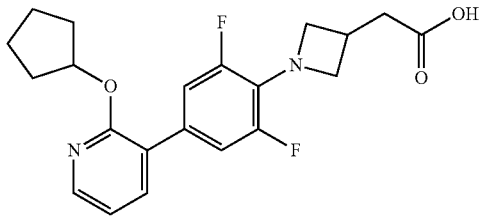 [SMILES: O=C(O)CC1CN(c2c(F)cc(-c3cccnc3OC3CCCC3)cc2F)C1]

2-[1-[2,6-Difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 and 2-cyclopentoxy-3-iodo-pyridine (0.070 g, 0.24 mmol) obtained in Preparation Example 11 were reacted in the same manner as in Example 1 to obtain the title compound (0.035 g, 37%).
$^1$H-NMR (CDCl$_3$) δ 8.10 (1H, m), 7.54 (1H, m), 7.05 (2H, m), 6.89 (1H, m), 5.50 (1H, m), 4.41 (2H, m), 3.93 (2H, m), 3.05 (1H, m), 2.80 (2H, d), 1.95 (2H, m), 1.83 (2H, m), 1.77 (2H, m), 1.64 (2H, m)

Example 114: 2-[1-[2,6-difluoro-4-(6-isopropylsulfanyl-2-pyridyl)phenyl]azetidin-3-yl]acetic acid

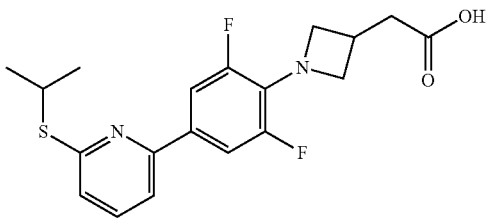 [SMILES: CC(C)Oc1cccc(-c2cc(F)c(N3CC(CC(=O)O)C3)c(F)c2)n1]

2-[1-[2,6-Difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 and 2-chloro-6-isopropylsulfanyl-pyridine (0.045 g, 0.24 mmol) obtained in Preparation Example 10 were reacted in the same manner as in Example 1 to obtain the title compound (0.048 g, 52%).
$^1$H-NMR (CDCl$_3$) δ 7.46 (3H, m), 7.25 (1H, d), 7.00 (1H, d), 4.43 (2H, m), 4.12 (1H, m), 3.95 (2H, m), 3.05 (1H, m), 2.79 (2H, d), 1.46 (6H, d)

Example 115: 2-[1-[2,6-difluoro-4-(6-isopropoxy-2-pyridyl)phenyl]azetidin-3-yl]acetic acid

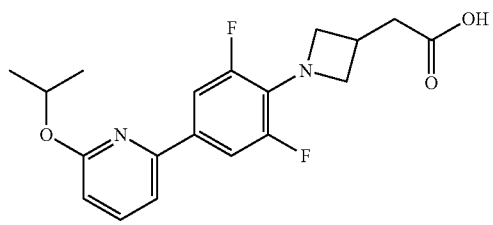

2-[1-[2,6-Difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 and 2-chloro-6-isopropoxy-pyridine (0.041 g, 0.24 mmol) obtained in Preparation Example 46 were reacted in the same manner as in Example 1 to obtain the title compound (0.012 g, 13%).
$^1$H-NMR (CDCl$_3$) δ 7.54 (1H, t), 7.45 (2H, m), 7.12 (1H, d), 6.56 (1H, d), 5.44 (1H, m), 4.42 (2H, m), 3.94 (2H, m), 3.05 (1H, m), 2.79 (2H, d), 1.39 (6H, d)

Example 116: 2-[1-[4-[6-(cyclopentoxy)-2-pyridyl]-2,6-difluoro-phenyl]azetidin-3-yl]acetic acid

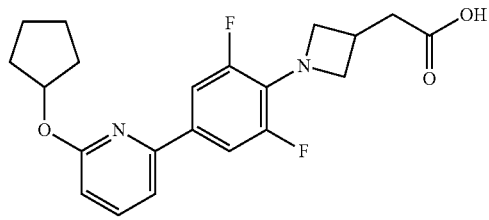 [SMILES: O=C(O)CC1CN(c2c(F)cc(-c3cccc(OC4CCCC4)n3)cc2F)C1]

2-[1-[2,6-Difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 and 2-chloro-6-cyclopentoxy-pyridine (0.047 g, 0.24 mmol) obtained in Preparation Example 12 were reacted in the same manner as in Example 1 to obtain the title compound (0.012 g, 12%).
$^1$H-NMR (CDCl$_3$) δ 7.54 (1H, t), 7.47 (2H, m), 7.12 (1H, d), 6.56 (1H, d), 5.50 (1H, m), 4.42 (2H, m), 3.95 (2H, m), 3.05 (1H, m), 2.79 (2H, d), 2.05 (2H, m), 1.83 (4H, m), 1.65 (2H, m)

Example 117: 2-[1-[2,6-difluoro-4-(2-propylsulfa-nyl-3-pyridyl)phenyl]-4-piperidyl]acetic acid

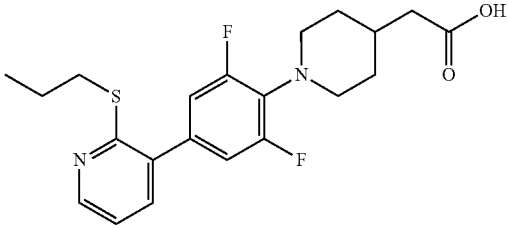 [SMILES: CCCSc1ncccc1-c1cc(F)c(N2CCC(CC(=O)O)CC2)c(F)c1]

2-[1-[2,6-Difluoro-4-(4,4,5,5-tetramethyl-1,3,2-dioxaborolan-2-yl)phenyl]-4-piperidyl]acetic acid methyl ester (0.11 g, 0.28 mmol) obtained in Preparation Example 84 and 3-iodo-2-propylsulfanyl-pyridine (0.071 g, 0.25 mmol) obtained in Preparation Example 28 were reacted in the same manner as in Example 1 to obtain the title compound (0.038 g, 37%).

$^1$H-NMR (CDCl$_3$) δ 8.42 (1H, m), 7.33 (1H, m), 7.02 (1H, m), 6.95 (2H, m), 3.32 (2H, m), 3.14 (4H, m), 2.37 (2H, d), 1.98 (1H, m), 1.83 (2H, m), 1.70 (2H, m), 1.50 (2H, m), 1.01 (3H, t)

Example 118: 2-[1-[4-(2-cyclobutylsulfanyl-3-pyridyl)-2,6-difluoro-phenyl]-4-piperidyl]acetic acid

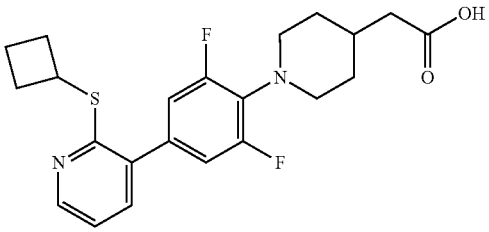 [SMILES: O=C(O)CC1CCN(c2c(F)cc(-c3cccnc3SC3CCC3)cc2F)CC1]

2-[1-[2,6-Difluoro-4-(4,4,5,5-tetramethyl-1,3,2-dioxaborolan-2-yl)phenyl]-4-piperidyl]acetic acid methyl ester (0.11 g, 0.28 mmol) obtained in Preparation Example 84 and 3-iodo-2-cyclobutylsulfanyl-pyridine (0.075 g, 0.25 mmol) obtained in Preparation Example 13 were reacted in the same manner as in Example 1 to obtain the title compound (0.031 g, 29%).

$^1$H-NMR (CDCl$_3$) δ 8.39 (1H, m), 7.31 (1H, m), 7.01 (1H, m), 6.93 (2H, m), 4.42 (1H, m), 3.32 (2H, m), 3.15 (2H, m), 2.50 (2H, m), 2.37 (2H, d), 2.05 (5H, m), 1.83 (2H, m), 1.50 (2H, m)

Example 119: 2-[1-[2,6-difluoro-4-(2-isopropoxy-3-pyridyl)phenyl]-4-piperidyl]acetic acid

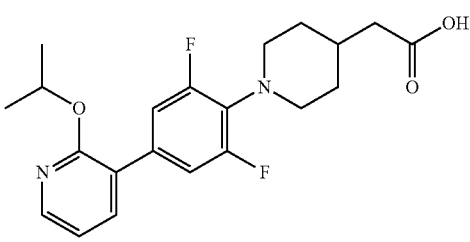

2-[1-[2,6-Difluoro-4-(4,4,5,5-tetramethyl-1,3,2-dioxaborolan-2-yl)phenyl]-4-piperidyl]acetic acid methyl ester (0.11 g, 0.28 mmol) obtained in Preparation Example 84 and 3-iodo-2-isopropoxy-pyridine (0.067 g, 0.25 mmol) obtained in Preparation Example 34 were reacted in the same manner as in Example 1 to obtain the title compound (0.046 g, 47%).

$^1$H-NMR (CDCl$_3$) δ 8.11 (1H, m), 7.55 (1H, m), 7.11 (2H, m), 6.90 (1H, m), 5.40 (1H, m), 3.31 (2H, m), 3.15 (2H, m), 2.37 (2H, d), 1.97 (1H, m), 1.82 (2H, m), 1.50 (2H, m), 1.36 (6H, d)

Example 120: 2-[1-[2,6-difluoro-4-(2-propoxy-3-pyridyl)phenyl]-4-piperidyl]acetic acid

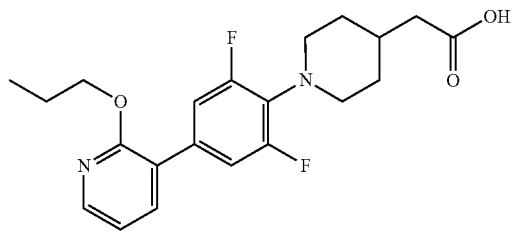 [SMILES: CCCOc1ncccc1-c1cc(F)c(N2CCC(CC(=O)O)CC2)c(F)c1]

2-[1-[2,6-Difluoro-4-(4,4,5,5-tetramethyl-1,3,2-dioxaborolan-2-yl)phenyl]-4-piperidyl]acetic acid methyl ester (0.11 g, 0.28 mmol) obtained in Preparation Example 84 and 3-iodo-2-propoxy-pyridine (0.067 g, 0.25 mmol) obtained in Preparation Example 47 were reacted in the same manner as in Example 1 to obtain the title compound (0.032 g, 33%).

$^1$H-NMR (CDCl$_3$) δ 8.12 (1H, m), 7.57 (1H, m), 7.10 (2H, m), 6.93 (1H, m), 4.32 (2H, t), 3.31 (2H, m), 3.15 (2H, m), 2.37 (2H, d), 1.97 (1H, m), 1.82 (4H, m), 1.50 (2H, m), 1.02 (3H, t)

Example 121: 2-[1-[4-[2-(cyclopropylmethoxy)-3-pyridyl]-2,6-difluoro-phenyl]-4-piperidyl]acetic acid

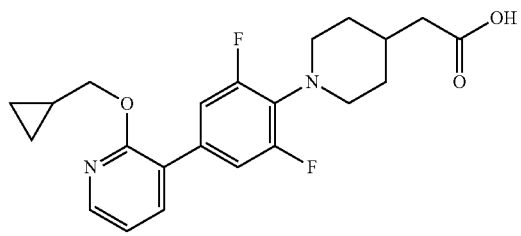 [SMILES: O=C(O)CC1CCN(c2c(F)cc(-c3cccnc3OCC3CC3)cc2F)CC1]

2-[1-[2,6-Difluoro-4-(4,4,5,5-tetramethyl-1,3,2-dioxaborolan-2-yl)phenyl]-4-piperidyl]acetic acid methyl ester (0.11 g, 0.28 mmol) obtained in Preparation Example 84 and 2-cyclopropylmethoxy-3-iodo-pyridine (0.07 g, 0.25 mmol) obtained in Preparation Example 40 were reacted in the same manner as in Example 1 to obtain the title compound (0.046 g, 45%).

$^1$H-NMR (CDCl$_3$) δ 8.10 (1H, m), 7.58 (1H, m), 7.16 (2H, m), 6.93 (1H, m), 4.22 (2H, d), 3.31 (2H, m), 3.15 (2H, m), 2.37 (2H, d), 1.98 (1H, m), 1.82 (2H, m), 1.50 (2H, m), 1.30 (1H, m), 0.59 (2H, m), 0.35 (2H, m)

Example 122: 2-[1-[2,6-difluoro-4-(2-isopropylsulfanyl-3-pyridyl)phenyl]pyrazol-4-yl]acetic acid

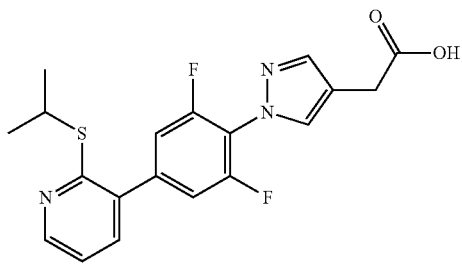 [SMILES: CC(C)Sc1ncccc1-c1cc(F)c(-n2cc(CC(=O)O)cn2)c(F)c1]

Step A: 2-[1-[2,6-difluoro-4-(2-isopropylsulfanyl-3-pyridyl)phenyl]pyrazol-4-yl]acetic acid methyl ester 2-[1-[2,6-Difluoro-4-(4,4,5,5-tetramethyl-1,3,2-dioxaborolan-2-yl)phenyl]pyrazol-4-yl]acetic acid methyl ester (0.1 g, 0.26 mmol) obtained in Preparation Example 90 and 3-iodo-2-isopropylsulfanyl-pyridine (0.066 g, 0.23 mmol) obtained in Preparation Example 9 were reacted in the same manner as in Step A of Example 1 to obtain the title compound (0.065 g, 70%).

$^1$H-NMR (CDCl$_3$) δ 8.48 (1H, m), 7.77 (1H, s), 7.72 (1H, s), 7.39 (1H, m), 7.16 (2H, m), 7.07 (1H, m), 4.10 (1H, m), 3.75 (3H, s), 3.63 (2H, s), 1.38 (6H, d)

Step B: 2-[1-[2,6-difluoro-4-(2-isopropylsulfanyl-3-pyridyl)phenyl]pyrazol-4-yl]acetic acid 2-[1-[2,6-Difluoro-4-(2-isopropylsulfanyl-3-pyridyl)phenyl]pyrazol-4-yl]acetic acid methyl ester (0.065 g, 0.16 mmol) obtained in Step A was reacted in the same manner as in Step B of Example 1 to obtain the title compound (0.021 g, 33%).

$^1$H-NMR (CDCl$_3$) δ 8.48 (1H, m), 7.80 (1H, s), 7.74 (1H, s), 7.40 (1H, m), 7.16 (2H, m), 7.08 (1H, m), 4.09 (1H, m), 3.67 (2H, s), 1.38 (6H, d)

Example 123: 2-[1-[2,6-difluoro-4-(6-isopropylsulfanyl-2-pyridyl)phenyl]pyrazol-4-yl]acetic acid

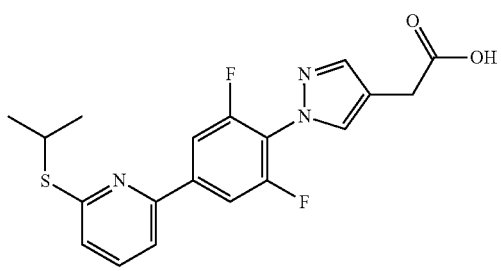 [SMILES: CC(C)Sc1cccc(-c2cc(F)c(-n3cc(CC(=O)O)cn3)c(F)c2)n1]

2-[1-[2,6-Difluoro-4-(4,4,5,5-tetramethyl-1,3,2-dioxaborolan-2-yl)phenyl]pyrazol-4-yl]acetic acid methyl ester (0.1 g, 0.26 mmol) obtained in Preparation Example 90 and 2-chloro-6-isopropylsulfanyl-pyridine (0.044 g, 0.23 mmol) obtained in Preparation Example 10 were reacted in the same manner as in Example 1 to obtain the title compound (0.032 g, 37%).

$^1$H-NMR (CDCl$_3$) δ 7.80 (1H, s), 7.75 (2H, m), 7.74 (1H, s), 7.57 (1H, t), 7.41 (1H, d), 7.16 (1H, d), 4.14 (1H, m), 3.68 (2H, s), 1.48 (6H, d)

Example 124: 2-[1-[2,6-difluoro-4-(2-isopropylsulfanyl-3-pyridyl)phenyl]pyrrolidin-3-yl]acetic acid

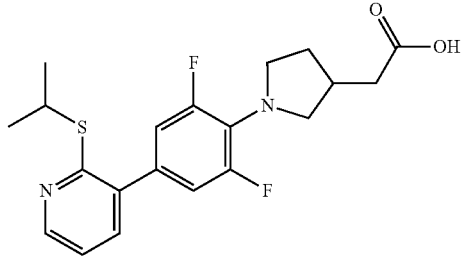 [SMILES: CC(C)Sc1ncccc1-c1cc(F)c(N2CCC(CC(=O)O)C2)c(F)c1]

Step A: 2-[1-[2,6-difluoro-4-(2-isopropylsulfanyl-3-pyridyl)phenyl]pyrrolidin-3-yl]acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.105 g, 0.26 mmol) obtained in Preparation Example 91 and 3-iodo-2-isopropylsulfanyl-pyridine (0.062 g, 0.22 mmol) obtained in Preparation Example 9 were reacted in the same manner as in Step A of Example 1 to obtain the title compound (0.055 g, 59%).

$^1$H-NMR (CDCl$_3$) δ 8.40 (1H, m), 7.32 (1H, m), 7.01 (1H, m), 6.88 (2H, m), 4.16 (2H, q), 4.05 (1H, m), 3.72 (1H, m), 3.67 (1H, m), 3.60 (1H, m), 3.33 (1H, m), 2.64 (1H, m), 2.46 (2H, m), 2.13 (1H, m), 1.63 (1H, m), 1.36 (6H, d), 1.27 (3H, t)

Step B: 2-[1-[2,6-difluoro-4-(2-isopropylsulfanyl-3-pyridyl)phenyl]pyrrolidin-3-yl]acetic acid 2-[1-[2,6-Difluoro-4-(2-isopropylsulfanyl-3-pyridyl)phenyl]pyrrolidin-3-yl]acetic acid ethyl ester (0.055 g, 0.13 mmol) obtained in Step A was reacted in the same manner as in Step B of Example 1 to obtain the title compound (0.038 g, 74%).

$^1$H-NMR (CDCl$_3$) δ 8.39 (1H, m), 7.32 (1H, m), 7.01 (1H, m), 6.89 (2H, m), 4.04 (1H, m), 3.74 (1H, m), 3.66 (1H, m), 3.60 (1H, m), 3.35 (1H, m), 2.65 (1H, m), 2.53 (2H, m), 2.18 (1H, m), 1.65 (1H, m), 1.36 (6H, d)

Example 125: 2-[1-[2,6-difluoro-4-(6-isopropylsulfanyl-2-pyridyl)phenyl]pyrrolidin-3-yl]acetic acid

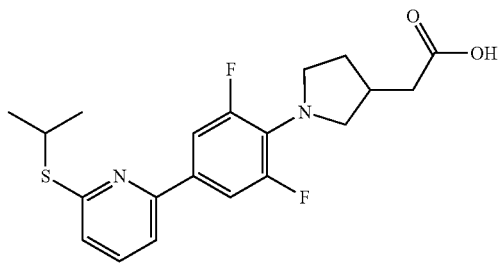

2-[1-[2,6-Difluoro-4-(4,4,5,5-tetramethyl-1,3,2-dioxaborolan-2-yl)phenyl]pyrrolidin-3-yl]acetic acid ethyl ester (0.105 g, 0.26 mmol) obtained in Preparation Example 91 and 2-chloro-6-isopropylsulfanyl-pyridine (0.042 g, 0.22 mmol) obtained in Preparation Example 10 were reacted in the same manner as in Example 1 to obtain the title compound (0.04 g, 46%).

¹H-NMR (CDCl₃) δ 7.48 (3H, m), 7.26 (1H, d), 7.02 (1H, d), 4.13 (1H, m), 3.76 (1H, m), 3.70 (1H, m), 3.62 (1H, m), 3.38 (1H, m), 2.66 (1H, m), 2.54 (2H, m), 2.20 (1H, m), 1.66 (1H, m), 1.46 (6H, d)

Example 126: 3-[1-[2,6-difluoro-4-(2-isopropylsulfanyl-3-pyridyl)phenyl]-4-piperidyl]propanoic acid

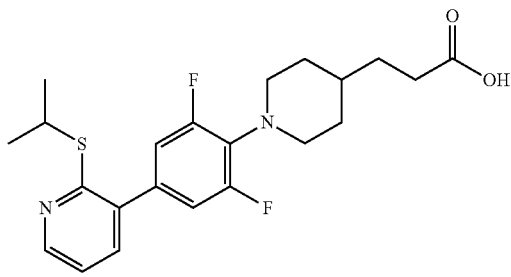 [SMILES: CC(C)Sc1ncccc1-c1cc(F)c(N2CCC(CCC(=O)O)CC2)c(F)c1]

Step A: 3-[1-[2,6-difluoro-4-(2-isopropylsulfanyl-3-pyridyl)phenyl]-4-piperidyl]propanoic acid ethyl ester 3-[1-[2,6-Difluoro-4-(4,4,5,5-tetramethyl-1,3,2-dioxaborolan-2-yl)phenyl]-4-piperidyl]propanoic acid ethyl ester (0.11 g, 0.26 mmol) obtained in Preparation Example 92 and 3-iodo-2-isopropylsulfanyl-pyridine (0.062 g, 0.22 mmol) obtained in Preparation Example 9 were reacted in the same manner as in Step A of Example 1 to obtain the title compound (0.069 g, 69%).

¹H-NMR (CDCl₃) δ 8.42 (1H, m), 73.2 (1H, m), 7.02 (1H, m), 6.92 (2H, m), 4.15 (2H, q), 4.06 (1H, m), 3.31 (2H, m), 3.10 (2H, m), 2.36 (2H, m), 1.74 (2H, m), 1.65 (2H, m), 1.41 (3H, m), 1.36 (6H, d), 1.27 (3H, t)

Step B: 3-[1-[2,6-difluoro-4-(2-isopropylsulfanyl-3-pyridyl)phenyl]-4-piperidyl]propanoic acid 3-[1-[2,6-Difluoro-4-(2-isopropylsulfanyl-3-pyridyl)phenyl]-4-piperidyl]propanoic acid ethyl ester (0.069 g, 0.15 mmol) obtained in Step A was reacted in the same manner as in Step B of Example 1 to obtain the title compound (0.04 g, 62%).

¹H-NMR (CDCl₃) δ 8.42 (1H, m), 7.33 (1H, m), 7.02 (1H, m), 6.91 (2H, m), 4.06 (1H, m), 3.32 (2H, m), 3.10 (2H, m), 2.43 (2H, m), 1.75 (2H, m), 1.67 (2H, m), 1.45 (3H, m), 1.35 (6H, d)

Example 127: 3-[1-[2,6-difluoro-4-(6-isopropylsulfanyl-2-pyridyl)phenyl]-4-piperidyl]propanoic acid

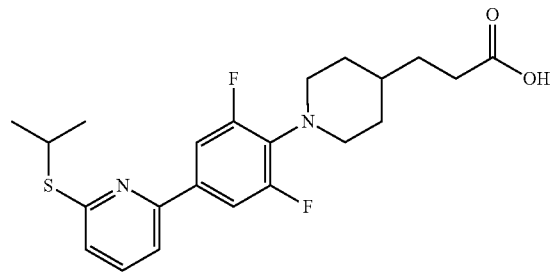 [SMILES: CC(C)Sc1cccc(-c2cc(F)c(N3CCC(CCC(=O)O)CC3)c(F)c2)n1]

3-[1-[2,6-Difluoro-4-(4,4,5,5-tetramethyl-1,3,2-dioxaborolan-2-yl)phenyl]-4-piperidyl]propanoic acid ethyl ester (0.11 g, 0.26 mmol) obtained in Preparation Example 92 and 2-chloro-6-isopropylsulfanyl-pyridine (0.042 g, 0.22 mmol) obtained in Preparation Example 10 were reacted in the same manner as in Example 1 to obtain the title compound (0.052 g, 56%).

¹H-NMR (CDCl₃) δ 7.51 (3H, m), 7.29 (1H, d), 7.06 (1H, d), 4.13 (1H, m), 3.33 (2H, m), 3.10 (2H, m), 2.43 (2H, m), 1.75 (2H, m), 1.68 (2H, m), 1.45 (9H, m)

Example 128: 2-[2-[4-(2-cyclopentylsulfanyl-3-pyridyl)-2,6-difluoro-anilino]ethyl]cyclopropanecarboxylic acid

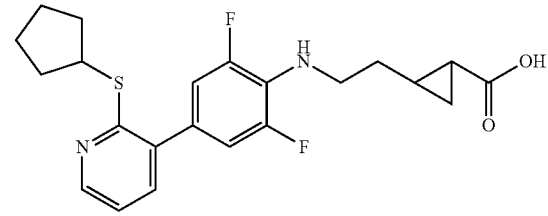 [SMILES: O=C(O)C1CC1CCNc1c(F)cc(-c2cccnc2SC2CCCC2)cc1F]

2-[2-[2,6-Difluoro-4-(4,4,5,5-tetramethyl-1,3,2-dioxaborolan-2-yl)anilino]ethyl]cyclopropanecarboxylic acid ethyl ester (0.04 g, 0.1 mmol) obtained in Preparation Example 85 and 2-cyclopentylsulfanyl-3-iodo-pyridine (0.031 g, 0.1 mmol) obtained in Preparation Example 15 were reacted in the same manner as in Example 1 to obtain the title compound (0.021 g, 50%).

¹H-NMR (CDCl₃) δ 8.40 (1H, m), 7.31 (1H, m), 7.00 (1H, m), 6.91 (2H, m), 4.08 (1H, m), 3.49 (2H, t), 2.20 (2H, m), 1.72-1.45 (9H, m), 1.36 (2H, m), 0.85 (1H, m)

Example 129: 2-[1-[2,6-difluoro-4-(2-isopropylsulfanyl-3-pyridyl)phenyl]-3-piperidyl]acetamide

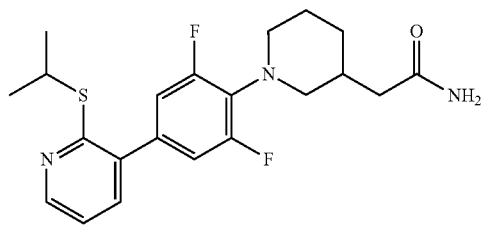 [SMILES: CC(C)Sc1ncccc1-c1cc(F)c(N2CCCC(CC(N)=O)C2)c(F)c1]

1.9 mL of EtOH and 0.19 mL of 6 M NaOH aqueous solution were added to 2-[1-[2,6-difluoro-4-(2-isopropylsulfanyl-3-pyridyl)phenyl]-3-piperidyl]acetonitrile (0.072 g, 0.18 mmol) obtained in Step A of Example 108, and the mixture was stirred for 24 hours under reflux. The reaction solution was concentrated under reduced pressure. After addition of water, the reaction solution was adjusted to pH 5 by the use of 1 N HCl aqueous solution and extracted with EtOAc. The organic layer was dried with MgSO$_4$ and purified by column chromatography to obtain the title compound (0.025 g, 33%).

$^1$H-NMR (CDCl$_3$) δ 8.42 (1H, m), 7.32 (1H, m), 7.02 (1H, m), 6.92 (2H, m), 5.56 (1H, brs), 5.51 (1H, brs), 4.06 (1H, m), 3.33 (1H, m), 3.24 (1H, m), 3.08 (1H, m), 2.89 (1H, m), 2.37 (1H, m), 2.26-2.18 (2H, m), 1.89 (1H, m), 1.74 (2H, m), 1.37 (6H, d), 1.30 (1H, m)

Example 130: 2-[4-[2,6-difluoro-4-(2-isopropylsulfanyl-3-pyridyl)phenyl]piperazin-1-yl]acetic acid

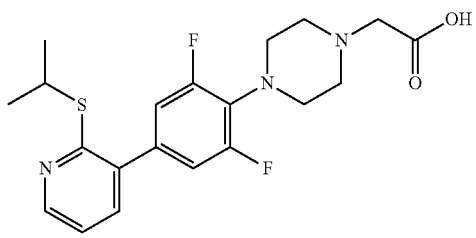 [SMILES: CC(C)Sc1ncccc1-c1cc(F)c(N2CCN(CC(=O)O)CC2)c(F)c1]

2-[4-[2,6-Difluoro-4-(4,4,5,5-tetramethyl-1,3,2-dioxaborolan-2-yl)phenyl]piperazin-1-yl]acetic acid ethyl ester (0.12 g, 0.29 mmol) obtained in Preparation Example 93 and 3-iodo-2-isopropylsulfanyl-pyridine (0.074 g, 0.26 mmol) obtained in Preparation Example 9 were reacted in the same manner as in Example 1 to obtain the title compound (0.002 g, 2%).

$^1$H-NMR (MeOH-d$_4$) δ 8.47 (1H, m), 7.56 (1H, m), 7.19 (1H, m), 7.07 (2H, m), 3.99 (1H, m), 3.17 (4H, m), 2.74 (2H, s), 2.57 (4H, m), 1.30 (6H, d)

Example 131: 3-[1-[2,6-difluoro-4-(2-isopropylsulfanyl-3-pyridyl)phenyl]pyrazol-4-yl]propanoic acid

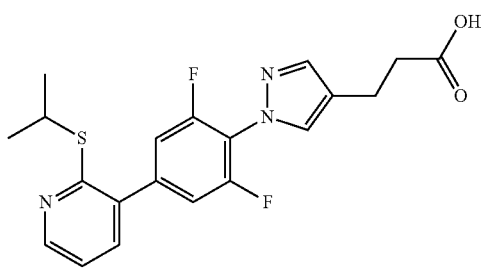 [SMILES: CC(C)Sc1ncccc1-c1cc(F)c(-n2cc(CCC(=O)O)cn2)c(F)c1]

3-[1-[2,6-Difluoro-4-(4,4,5,5-tetramethyl-1,3,2-dioxaborolan-2-yl)phenyl]pyrazol-4-yl]propanoic acid ethyl ester (0.03 g, 0.07 mmol) obtained in Preparation Example 94 and 3-iodo-2-isopropylsulfanyl-pyridine (0.019 g, 0.066 mmol) obtained in Preparation Example 9 were reacted in the same manner as in Example 1 to obtain the title compound (0.013 g, 49%).

$^1$H-NMR (CDCl$_3$) δ 8.48 (1H, m), 7.70 (1H, s), 7.57 (1H, m), 7.38 (1H, m), 7.15 (2H, m), 7.06 (1H, m), 4.10 (1H, m), 2.92 (2H, t), 2.71 (2H, t), 1.38 (6H, d)

Example 132: 4-[5-(2-cyclopentylsulfanyl-3-pyridyl)indolin-1-yl]butanoic acid

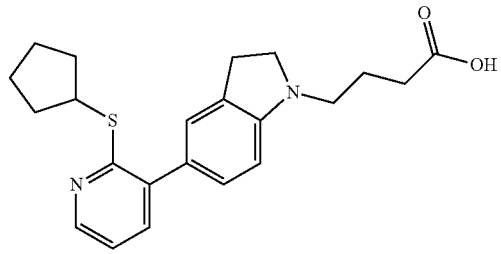 [SMILES: O=C(O)CCCN1CCc2cc(-c3cccnc3SC3CCCC3)ccc21]

Step A: 4-[5-(2-cyclopentylsulfanyl-3-pyridyl)indolin-1-yl]butanoic acid ethyl ester

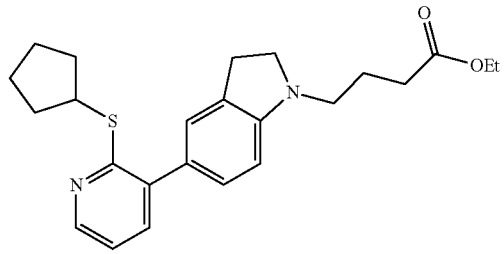 [SMILES: CCOC(=O)CCCN1CCc2cc(-c3cccnc3SC3CCCC3)ccc21]

4-[5-(4,4,5,5-Tetramethyl-1,3,2-dioxaborolan-2-yl)indolin-1-yl]butanoic acid ethyl ester (0.11 g, 0.26 mmol) obtained in Preparation Example 95 and 2-cyclopentylsulfanyl-3-iodo-pyridine (0.074 g, 0.24 mmol) obtained in Preparation Example 15 were reacted in the same manner as in Step A of Example 1 to obtain the title compound (0.05 g, 50%).

$^1$H-NMR (CDCl$_3$) δ 8.35 (1H, m), 7.32 (1H, m), 7.11 (2H, m), 6.98 (1H, m), 6.47 (1H, m), 4.14 (2H, q), 4.06 (1H, m), 3.42 (2H, t), 3.14 (2H, t), 3.01 (2H, t), 2.43 (2H, t), 2.20 (2H, m), 1.97 (2H, m), 1.72-1.65 (6H, m), 1.24 (3H, t)

Step B: 4-[5-(2-cyclopentylsulfanyl-3-pyridyl)indolin-1-yl]butanoic acid

4-[5-(2-Cyclopentylsulfanyl-3-pyridyl)indolin-1-yl]butanoic acid ethyl ester (0.05 g, 0.12 mmol) obtained in Step A was reacted in the same manner as in Step B of Example 1 to obtain the title compound (0.034 g, 74%).

$^1$H-NMR (CDCl$_3$) δ 8.35 (1H, m), 7.32 (1H, m), 7.13 (2H, m), 6.99 (1H, m), 6.50 (1H, m), 4.06 (1H, m), 3.42 (2H, t), 3.17 (2H, t), 3.02 (2H, t), 2.51 (2H, t), 2.20 (2H, m), 1.98 (2H, m), 1.71-1.52 (6H, m)

Example 133: 3-[1-[2,6-difluoro-4-(2-isopropylsulfanyl-3-pyridyl)phenyl]azetidin-3-yl]propanoic acid

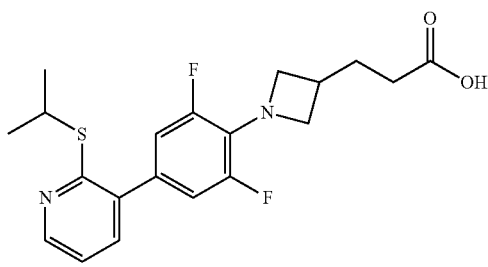 [SMILES: CC(C)Sc1ncccc1-c1cc(F)c(N2CC(CCC(=O)O)C2)c(F)c1]

3-[1-[2,6-Difluoro-4-(4,4,5,5-tetramethyl-1,3,2-dioxaborolan-2-yl)phenyl]azetidin-3-yl]propanoic acid ethyl ester (0.032 g, 0.08 mmol) obtained in Preparation Example 96 and 3-iodo-2-isopropylsulfanyl-pyridine (0.023 g, 0.08 mmol) obtained in Preparation Example 9 were reacted in the same manner as in Example 1 to obtain the title compound (0.002 g, 6%).

$^1$H-NMR (CDCl$_3$) δ 8.34 (1H, m), 7.32 (1H, m), 7.01 (1H, m), 6.85 (2H, m), 4.35 (2H, m), 4.05 (1H, m), 3.87 (2H, m), 2.74 (1H, m), 2.37 (2H, m), 2.01 (2H, m), 1.35 (6H, d)

Example 134: 2-[(3R)-1-[2,6-difluoro-4-(2-isopropylsulfanyl-3-pyridyl)phenyl]pyrrolidin-3-yl]acetic acid

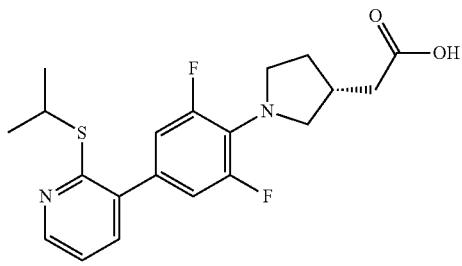

2-[(3R)-1-[2,6-difluoro-4-(4,4,5,5-tetramethyl-1,3,2-dioxaborolan-2-yl)phenyl]pyrrolidin-3-yl]acetic acid methyl ester (0.07 g, 0.18 mmol) obtained in Preparation Example 98 and 3-iodo-2-isopropylsulfanyl-pyridine (0.046 g, 0.16 mmol) obtained in Preparation Example 9 were reacted in the same manner as in Example 1 to obtain the title compound (0.031 g, 49%).

$^1$H-NMR (CDCl$_3$) δ 8.39 (1H, m), 7.32 (1H, m), 7.01 (1H, m), 6.89 (2H, m), 4.04 (1H, m), 3.74 (1H, m), 3.66 (1H, m), 3.60 (1H, m), 3.35 (1H, m), 2.65 (1H, m), 2.53 (2H, m), 2.18 (1H, m), 1.65 (1H, m), 1.36 (6H, d)

Example 135: 2-[(3R)-1-[4-[2-(cyclopentoxy)-3-pyridyl]-2,6-difluoro-phenyl]pyrrolidin-3-yl]acetic acid

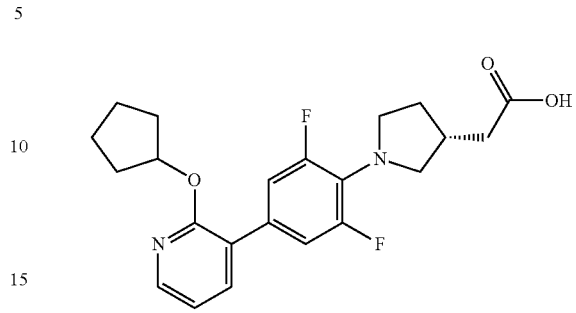

2-[(3R)-1-[2,6-difluoro-4-(4,4,5,5-tetramethyl-1,3,2-dioxaborolan-2-yl)phenyl]pyrrolidin-3-yl]acetic acid methyl ester (0.07 g, 0.18 mmol) obtained in Preparation Example 98 and 2-cyclopentoxy-3-iodo-pyridine (0.048 g, 0.16 mmol) obtained in Preparation Example 11 were reacted in the same manner as in Example 1 to obtain the title compound (0.032 g, 50%).

$^1$H-NMR (CDCl$_3$) δ 8.10 (1H, m), 7.55 (1H, m), 7.10 (2H, m), 6.89 (1H, m), 5.51 (1H, m), 3.73 (1H, m), 3.66 (1H, m), 3.59 (1H, m), 3.35 (1H, m), 2.66 (1H, m), 2.54 (2H, m), 2.18 (1H, m), 1.95 (2H, m), 1.84-1.75 (4H, m), 1.65 (3H, m)

Example 136: 2-[(3S)-1-[2,6-difluoro-4-(2-isopropylsulfanyl-3-pyridyl)phenyl]pyrrolidin-3-yl]acetic acid

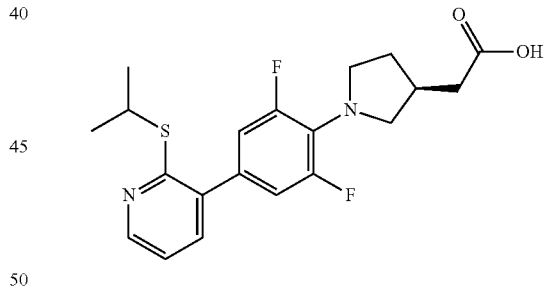

2-[(3S)-1-[2,6-difluoro-4-(4,4,5,5-tetramethyl-1,3,2-dioxaborolan-2-yl)phenyl]pyrrolidin-3-yl]acetic acid methyl ester (0.085 g, 0.22 mmol) obtained in Preparation Example 97 and 3-iodo-2-isopropylsulfanyl-pyridine (0.056 g, 0.2 mmol) obtained in Preparation Example 9 were reacted in the same manner as in Example 1 to obtain the title compound (0.042 g, 54%).

$^1$H-NMR (CDCl$_3$) δ 8.39 (1H, m), 7.32 (1H, m), 7.01 (1H, m), 6.89 (2H, m), 4.04 (1H, m), 3.74 (1H, m), 3.66 (1H, m), 3.60 (1H, m), 3.35 (1H, m), 2.65 (1H, m), 2.53 (2H, m), 2.18 (1H, m), 1.65 (1H, m), 1.36 (6H, d)

Example 137: 2-[(3S)-1-[4-[2-(cyclopentoxy)-3-pyridyl]-2,6-difluoro-phenyl]pyrrolidin-3-yl]acetic acid

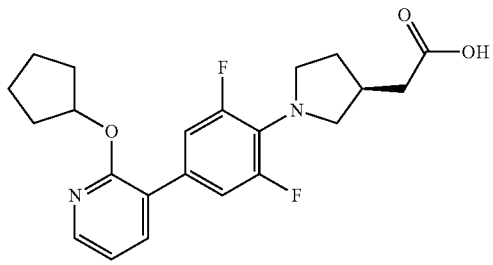 [SMILES: O=C(O)C[C@@H]1CCN(c2c(F)cc(-c3cccnc3OC3CCCC3)cc2F)C1]

2-[(3S)-1-[2,6-difluoro-4-(4,4,5,5-tetramethyl-1,3,2-dioxaborolan-2-yl)phenyl]pyrrolidin-3-yl]acetic acid methyl ester (0.085 g, 0.22 mmol) obtained in Preparation Example 97 and 2-cyclopentoxy-3-iodo-pyridine (0.059 g, 0.2 mmol) obtained in Preparation Example 11 were reacted in the same manner as in Example 1 to obtain the title compound (0.032 g, 40%).
$^1$H-NMR (CDCl$_3$) δ 8.10 (1H, m), 7.55 (1H, m), 7.10 (2H, m), 6.89 (1H, m), 5.51 (1H, m), 3.73 (1H, m), 3.66 (1H, m), 3.59 (1H, m), 3.35 (1H, m), 2.66 (1H, m), 2.54 (2H, m), 2.18 (1H, m), 1.95 (2H, m), 1.84-1.75 (4H, m), 1.65 (3H, m)

Example 138: 2-[1-[2-fluoro-4-(2-isopropylsulfanyl-3-pyridyl)phenyl]-4-piperidyl]acetic acid

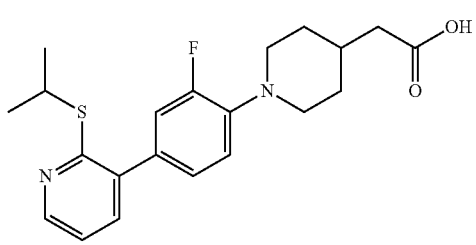 [SMILES: CC(C)Sc1ncccc1-c1ccc(N2CCC(CC(=O)O)CC2)c(F)c1]

Step A: 2-[1-[2-fluoro-4-(2-isopropylsulfanyl-3-pyridyl)phenyl]-4-piperidyl]acetic acid ethyl ester

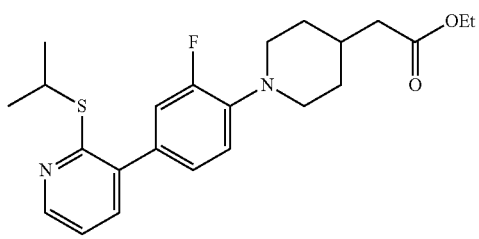 [SMILES: CCOC(=O)CC1CCN(c2ccc(-c3cccnc3SC(C)C)cc2F)CC1]

2-[1-[2-Fluoro-4-(4,4,5,5-tetramethyl-1,3,2-dioxaborolan-2-yl)phenyl]-4-piperidyl]acetic acid ethyl ester (0.10 g, 0.25 mmol) obtained in Preparation Example 99 and 3-iodo-2-isopropylsulfanyl-pyridine (0.063 g, 0.227 mmol) obtained in Preparation Example 9 were reacted in the same manner as in Step A of Example 1 to obtain the title compound (0.07 g, 74%).

$^1$H-NMR (CDCl$_3$) δ 8.40 (1H, m), 7.35 (1H, m), 7.12 (2H, m), 7.01 (2H, m), 4.14 (2H, q), 4.04 (1H, m), 3.51 (2H, m), 2.75 (2H, m), 2.31 (2H, d), 1.96 (1H, m), 1.85 (2H, m), 1.50 (2H, m), 1.36 (6H, d), 1.27 (3H, t)

Step B: 2-[1-[2-fluoro-4-(2-isopropylsulfanyl-3-pyridyl)phenyl]-4-piperidyl]acetic acid 2-[1-[2-Fluoro-4-(2-isopropylsulfanyl-3-pyridyl)phenyl]-4-piperidyl]acetic acid ethyl ester (0.07 g, 0.17 mmol) obtained in Step A was reacted in the same manner as in Step B of Example 1 to obtain the title compound (0.044 g, 68%).
$^1$H-NMR (CDCl$_3$) δ 8.42 (1H, m), 7.34 (1H, m), 7.11 (2H, m), 7.00 (2H, m), 4.05 (1H, m), 3.52 (2H, m), 2.76 (2H, m), 2.37 (2H, d), 1.97 (1H, m), 1.91 (2H, m), 1.55 (2H, m), 1.35 (6H, d)

Example 139: 2-[1-[4-[2-(cyclopentoxy)-3-pyridyl]-2-fluoro-phenyl]-4-piperidyl]acetic acid

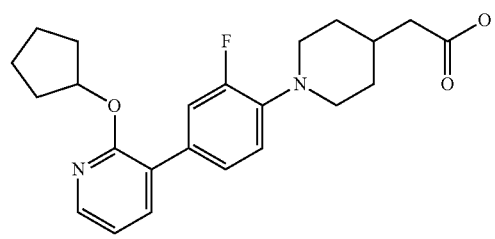 [SMILES: O=C(O)CC1CCN(c2ccc(-c3cccnc3OC3CCCC3)cc2F)CC1]

Step A: 2-[1-[4-[2-(cyclopentoxy)-3-pyridyl]-2-fluoro-phenyl]-4-piperidyl]acetic acid ethyl ester

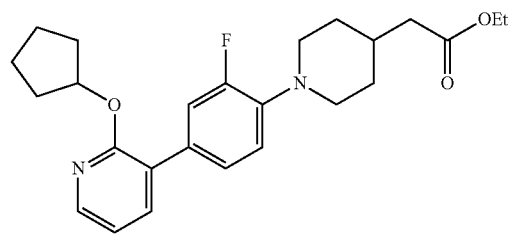 [SMILES: CCOC(=O)CC1CCN(c2ccc(-c3cccnc3OC3CCCC3)cc2F)CC1]

2-[1-[2-Fluoro-4-(4,4,5,5-tetramethyl-1,3,2-dioxaborolan-2-yl)phenyl]-4-piperidyl]acetic acid ethyl ester (0.10 g, 0.25 mmol) obtained in Preparation Example 99 and 2-cyclopentoxy-3-iodo-pyridine (0.066 g, 0.227 mmol) obtained in Preparation Example 11 were reacted in the same manner as in Step A of Example 1 to obtain the title compound (0.072 g, 74%).
$^1$H-NMR (CDCl$_3$) δ 8.10 (1H, m), 7.57 (1H, m), 7.32 (1H, m), 7.25 (1H, m), 6.97 (1H, t), 6.90 (1H, m), 5.51 (1H, m), 4.16 (2H, q), 3.51 (2H, m), 2.74 (2H, m), 2.30 (2H, d), 1.95 (3H, m), 1.87-1.72 (6H, m), 1.64-1.47 (4H, m), 1.28 (3H, t)

Step B: 2-[1-[4-[2-(cyclopentoxy)-3-pyridyl]-2-fluoro-phenyl]-4-piperidyl]acetic acid 2-[1-[4-[2-(Cyclopentoxy)-3-pyridyl]-2-fluoro-phenyl]-4-piperidyl]acetic acid ethyl ester (0.072 g, 0.17 mmol) obtained in Step A was reacted in the same manner as in Step B of Example 1 to obtain the title compound (0.043 g, 64%).

¹H-NMR (CDCl₃) δ 8.11 (1H, m), 7.57 (1H, m), 7.31 (1H, m), 7.25 (1H, m), 6.97 (1H, t), 6.90 (1H, m), 5.50 (1H, m), 3.51 (2H, m), 2.75 (2H, m), 2.38 (2H, d), 2.00-1.88 (5H, m), 1.86-1.72 (4H, m), 1.68-1.52 (4H, m)

Example 140: 3-[6-(6-isopropylsulfanyl-pyridin-2-yl)-naphthalen-2-yl]-propanoic acid

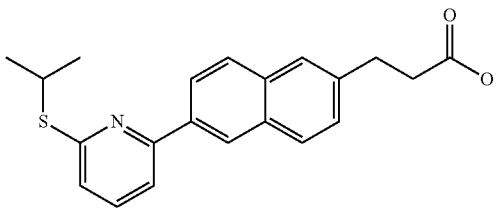 [SMILES: CC(C)Sc1cccc(-c2ccc3cc(CCC(=O)O)ccc3c2)n1]

3-[6-(4,4,5,5-Tetramethyl-[1,3,2]dioxoborolan-2-yl)-naphthalen-2-yl]-propanoic acid methyl ester (0.082 g, 0.24 mmol) obtained in Preparation Example 107 and 2-chloro-6-isopropylsulfanyl-pyridine (0.045 g, 0.24 mmol) obtained in Preparation Example 10 were sequentially reacted in the same manner as in Steps A and B of Example 1 to obtain the title compound (0.003 g, 3%).
¹H-NMR (CDCl₃) δ 8.46 (1H, s), 8.18 (1H, dd), 7.87 (2H, m), 7.68 (1H, s), 7.56 (2H, m), 7.38 (1H, m), 7.11 (1H, m), 4.22 (1H, m), 3.15 (2H, t), 2.80 (2H, t), 1.50 (6H, d).

Example 141: 3-[6-(6-phenoxy-pyridin-2-yl)-naphthalen-2-yl]-propanoic acid

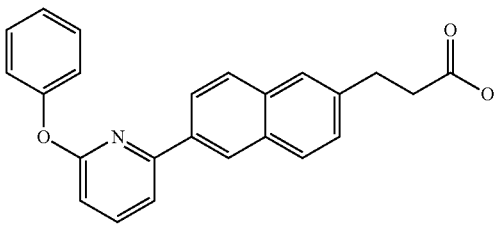 [SMILES: O=C(O)CCc1ccc2cc(-c3cccc(Oc4ccccc4)n3)ccc2c1]

2-[6-(6-Phenoxy-pyridin-2-yl)-naphthalen-2-ylmethyl]-malonic acid dimethyl ester (0.125 g, 0.28 mmol) obtained in Preparation Example 110 was reacted in the same manner as in Preparation Example 105 to obtain the title compound (0.039 g, 37%).
¹H-NMR (CDCl₃) δ 8.40 (1H, s), 8.03 (1H, dd), 7.85-7.73 (3H, m), 7.64-7.59 (2H, m), 7.43 (2H, m), 7.34 (1H, dd), 7.25 (3H, m), 6.78 (1H, d), 3.13 (2H, t), 2.78 (2H, t).

Example 142: 3-[6-(2-phenoxy-phenyl)-naphthalen-2-yl]-propanoic acid

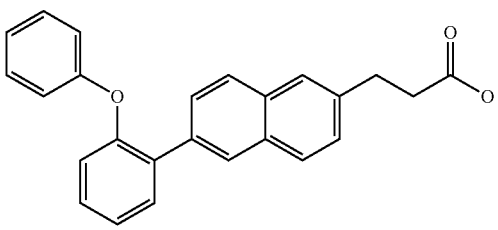

2-[6-(2-Phenoxy-phenyl)-naphthalen-2-ylmethyl]-malonic aciddimethyl ester (0.640 g, 1.45 mmol) obtained in Preparation Example 112 was reacted in the same manner as in Preparation Example 105 to obtain the title compound (0.126 g, 23%).
¹H-NMR (CDCl₃) δ 7.94 (1H, s), 7.76-7.73 (2H, m), 7.68 (1H, dd), 7.61 (1H, s), 7.54 (1H, dd), 7.33-7.29 (2H, m), 7.26-7.21 (3H, m), 7.04-6.98 (2H, m), 6.93 (2H, m), 3.10 (2H, t), 2.75 (2H, t).

Example 143: 3-[6-(6-cyclopentylsulfanyl-pyridin-2-yl)-naphthalen-2-yl]-propanoic acid

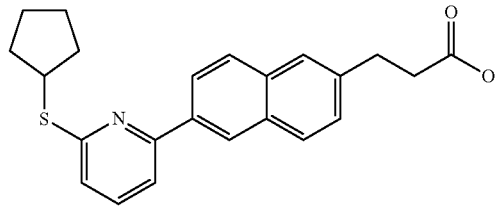 [SMILES: O=C(O)CCc1ccc2cc(-c3cccc(SC4CCCC4)n3)ccc2c1]

2-[6-(6-Cyclopentylsulfanyl-pyridin-2-yl)-naphthalen-2-ylmethyl]-malonic acid dimethyl ester (0.019 g, 0.04 mmol) obtained in Preparation Example 114 was reacted in the same manner as in Preparation Example 105 to obtain the title compound (0.005 g, 33%).
¹H-NMR (CDCl₃) δ 8.46 (1H, s), 8.16 (1H, dd), 7.86 (2H, q), 7.67 (1H, s), 7.56 (2H, m), 7.37 (1H, dd), 7.12 (1H, m), 4.23 (1H, m), 3.15 (2H, t), 2.80 (2H, t), 2.31 (2H, m), 1.83-1.72 (6H, m).

Example 144: 3-[6-(2-phenoxy-pyridin-3-yl)-naphthalen-2-yl]-propanoic acid

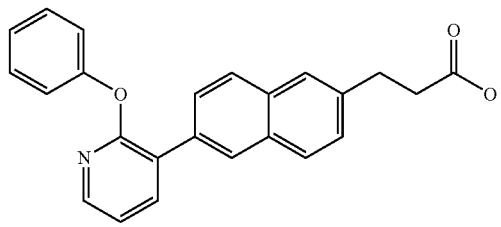 [SMILES: O=C(O)CCc1ccc2cc(-c3cccnc3Oc3ccccc3)ccc2c1]

[6-(2-Phenoxy-pyridin-3-yl)-naphthalen-2-yl]-methanol (0.024 g, 0.07 mmol) obtained in Preparation Example 116 was sequentially reacted in the same manner as in Preparation Examples 103, 104 and 105 to obtain the title compound (0.009 g, 33%).
¹H-NMR (CDCl₃) δ 8.17 (1H, m), 8.04 (1H, s), 7.87-7.77 (4H, m), 7.67 (1H, s), 7.39-7.37 (3H, m), 7.18-7.11 (4H, m), 3.13 (2H, t), 2.77 (2H, t).

Example 145: 3-[6-(3-phenoxy-phenyl)-naphthalen-2-yl]-propanoic acid

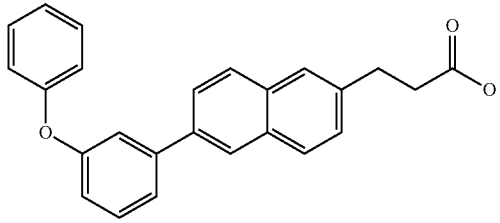 [SMILES: O=C(O)CCc1ccc2cc(-c3cccc(Oc4ccccc4)c3)ccc2c1]

[6-(3-Phenoxy-phenyl)-naphthalen-2-yl]-methanol (0.029 g, 0.09 mmol) obtained in Preparation Example 118 was sequentially reacted in the same manner as in Preparation Examples 103, 104 and 105 to obtain the title compound (0.013 g, 40%).
$^1$H-NMR (CDCl$_3$) δ 7.97 (1H, s), 7.82 (2H, m), 7.69-7.66 (2H, m), 7.42 (2H, m), 7.35 (4H, m), 7.13-7.07 (3H, m), 6.99 (1H, m), 3.13 (2H, t), 2.78 (2H, t).

Example 146: 3-[6-(3-isopropoxy-phenyl)-naphthalen-2-yl]-propanoic acid

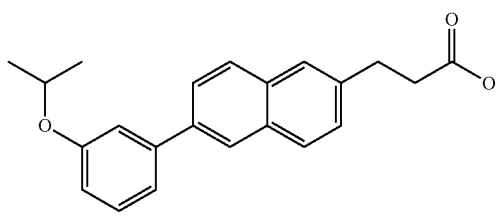 [SMILES: CC(C)Oc1cccc(-c2ccc3cc(CCC(=O)O)ccc3c2)c1]

[6-(3-Isopropoxy-phenyl)-naphthalen-2-yl]-methanol (0.054 g, 0.18 mmol) obtained in Preparation Example 120 was sequentially reacted in the same manner as in Preparation Examples 103, 104 and 105 to obtain the title compound (0.013 g, 20%).
$^1$H-NMR (CDCl$_3$) δ 7.99 (1H, s), 7.82 (2H, m), 7.70 (2H, m), 7.37 (2H, m), 7.26 (2H, m), 6.89 (1H, dd), 4.65 (1H, m), 3.14 (2H, t), 2.78 (2H, t), 1.38 (6H, d).

Example 147: 3-[6-(3-cyclobutoxy-phenyl)-naphthalen-2-yl]-propanoic acid

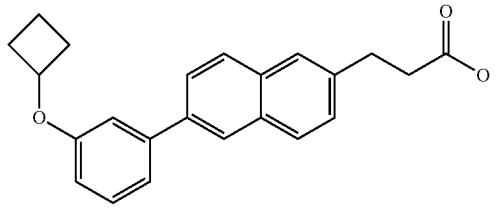 [SMILES: O=C(O)CCc1ccc2cc(-c3cccc(OC4CCC4)c3)ccc2c1]

[6-(3-Cyclobutoxy-phenyl)-naphthalen-2-yl]-methanol (0.196 g, 0.64 mmol) obtained in Preparation Example 122 was sequentially reacted in the same manner as in Preparation Examples 103, 104 and 105 to obtain the title compound (0.03 g, 13%).
$^1$H-NMR (CDCl$_3$) δ 8.00 (1H, s), 7.86-7.82 (2H, m), 7.74-7.67 (2H, m), 7.35 (2H, m), 7.26 (1H, m), 7.15 (1H, s), 6.82 (1H, m), 4.73 (1H, m), 3.15 (2H, t), 2.78 (2H, t), 2.50 (2H, m), 2.20 (2H, m), 1.89 (1H, m), 1.70 (1H, m).

Example 148: 3-[6-(6-cyclobutoxy-pyridin-2-yl)-naphthalen-2-yl]-propanoic acid

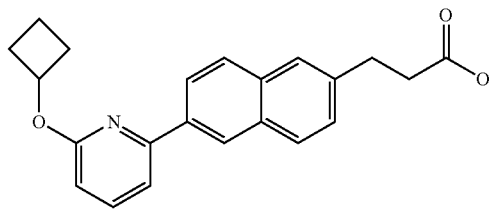 [SMILES: O=C(O)CCc1ccc2cc(-c3cccc(OC4CCC4)n3)ccc2c1]

[6-(6-Cyclobutoxy-pyridin-2-yl)-naphthalen-2-yl]-methanol (0.155 g, 0.5 mmol) obtained in Preparation Example 124 was sequentially reacted in the same manner as in Preparation Examples 103, 104 and 105 to obtain the title compound (0.012 g, 7%).
$^1$H-NMR (CDCl$_3$) δ 8.43 (1H, s), 8.14 (1H, m), 7.86 (2H, m), 7.64 (2H, m), 7.44 (1H, m), 7.36 (1H, m), 6.65 (1H, d), 5.34 (1H, m), 3.14 (2H, t), 2.80 (2H, t), 2.57 (2H, m), 2.24 (2H, m), 1.87 (1H, m), 1.77 (1H, m).

Example 149: 3-[6-(2-isopropoxy-pyridin-3-yl)-naphthalen-2-yl]-propanoic acid

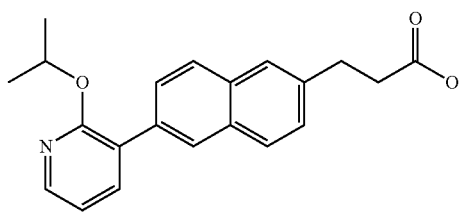 [SMILES: CC(C)Oc1ncccc1-c1ccc2cc(CCC(=O)O)ccc2c1]

6-(2-Isopropoxy-pyridin-3-yl)-naphthalen-2-carboxylic acid methyl ester (0.092 g, 0.29 mmol) obtained in Preparation Example 125 was sequentially reacted in the same manner as in Preparation Examples 102, 103, 104 and 105 to obtain the title compound (0.033 g, 34%).
$^1$H-NMR (CDCl$_3$) δ 8.15 (1H, m), 7.96 (1H, s), 7.80 (2H, d), 7.72-7.68 (3H, m), 7.36 (1H, d), 6.95 (1H, m), 5.42 (1H, m), 3.15 (2H, t), 2.79 (2H, t), 1.34 (6H, d).

Example 150: 3-[6-(2-cyclopentyloxy-pyridin-3-yl)-naphthalen-2-yl]-propanoic acid

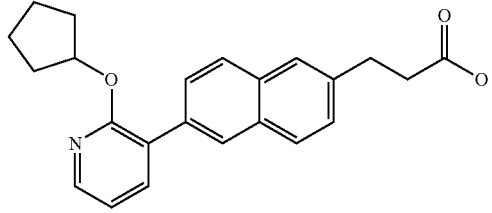 [SMILES: O=C(O)CCc1ccc2cc(-c3cccnc3OC3CCCC3)ccc2c1]

6-(2-Cyclopentyloxy-pyridin-3-yl)-naphthalen-2-carboxylic acid methyl ester (0.123 g, 0.35 mmol) obtained in Preparation Example 126 was sequentially reacted in the same manner as in Preparation Example 102, 103, 104 and 105 to obtain the title compound (0.043 g, 33%).

¹H-NMR (CDCl₃) δ 8.16 (1H, m), 7.96 (1H, s), 7.80 (2H, d), 7.71-7.67 (3H, m), 7.36 (1H, m), 6.96 (1H, m), 5.55 (1H, m), 3.15 (2H, t), 2.80 (2H, t), 1.93 (2H, m), 1.73 (2H, m), 1.62 (2H, m), 1.36 (2H, m).

Example 151: 3-{6-[2-(2-fluoro-phenoxy)-phenyl]-naphthalen-2-yl}-propanoic acid

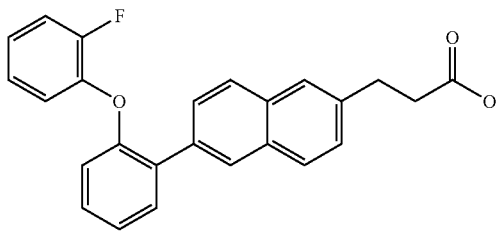 [SMILES: O=C(O)CCc1ccc2cc(-c3ccccc3Oc3ccccc3F)ccc2c1]

3-{6-[2-(2-Fluoro-phenoxy)-phenyl]-naphthalen-2-yl}-propanoic acid methyl ester (0.012 g, 0.03 mmol) obtained in Preparation Example 129 was reacted in the same manner as in Step B of Example 1 to obtain the title compound (0.005 g, 45%).

¹H-NMR (CDCl₃) δ 7.64-7.29 (10H, m), 7.23 (1H, m), 7.10 (2H, m), 7.03 (1H, m), 3.09 (2H, t), 2.75 (2H, t).

Example 152: 3-{6-[6-(2-fluoro-phenoxy)-pyridin-2-yl]-naphthalen-2-yl}-propanoic acid

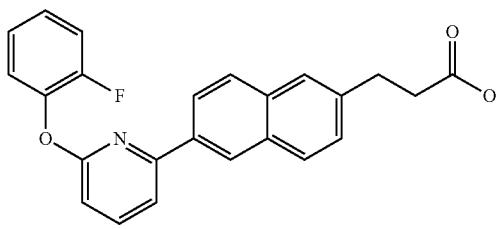 [SMILES: O=C(O)CCc1ccc2cc(-c3cccc(Oc4ccccc4F)n3)ccc2c1]

3-[6-(4,4,5,5-Tetramethyl-[1,3,2]dioxaborolan-2-yl)-naphthalen-2-yl]-propanoic acid methyl ester (0.067 g, 0.2 mmol) obtained in Preparation Example 107 and 2-chloro-6-(2-fluoro-phenoxy)-pyridine (0.045 g, 0.2 mmol) obtained in Preparation Example 127 were sequentially reacted in the same manner as in Steps A and B of Example 1 to obtain the title compound (0.001 g, 1%).

¹H-NMR (CDCl₃) δ 8.48 (1H, s), 8.10 (1H, m), 7.93 (2H, m), 7.79-7.60 (6H, m), 7.40-7.24 (3H, m), 3.15 (2H, t), 2.80 (2H, t).

Example 153: 4-[4-(2,2-difluoro-benzo[1,3]dioxol-4-yl)-2,6-difluoro-phenylsulfanyl]-butyric acid

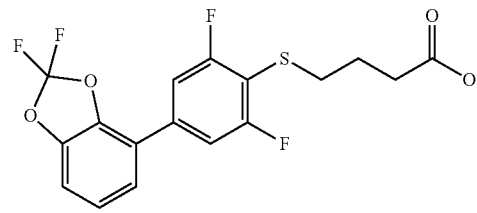 [SMILES: O=C(O)CCCSc1c(F)cc(-c2cccc3c2OC(F)(F)O3)cc1F]

4-[2,6-Difluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 208 and 4-bromo-2,2-difluoro-benzo[1,3]dioxole (0.034 g, 0.14 mmol) were sequentially reacted in the same manner as in Steps A and B of Example 1 to obtain the title compound (0.027 g, 54%).

¹H-NMR (CDCl₃) δ 7.30 (2H, m), 7.25 (1H, m), 7.17 (1H, t), 7.09 (1H, d), 2.98 (2H, t), 2.55 (2H, t), 1.90 (2H, m).

Example 154: 4-[4-(2,2-difluoro-benzo[1,3]dioxol-4-yl)-2-fluoro-phenylsulfanyl]-butyric acid

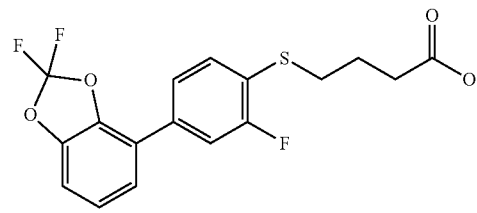 [SMILES: O=C(O)CCCSc1ccc(-c2cccc3c2OC(F)(F)O3)cc1F]

4-[2-Fluoro-4-(4,4,5,5-tetramethyl-[1,3,2]dioxaborolan-2-yl)-phenylsulfanyl]-butyric acid ethyl ester (0.1 g, 0.27 mmol) obtained in Preparation Example 205 and 4-bromo-2,2-difluoro-benzo[1,3]dioxole (0.07 g, 0.3 mmol) were sequentially reacted in the same manner as in Steps A and B of Example 1 to obtain the title compound (0.035 g, 35%).

¹H-NMR (CDCl₃) δ 7.46-7.40 (3H, m), 7.25 (1H, m), 7.14 (1H, t), 7.05 (1H, d), 3.02 (2H, t), 2.56 (2H, t), 1.99 (2H, m).

Example 155: 4-[4-(2,2-difluoro-benzo[1,3]dioxol-4-yl)-phenylsulfanyl]-butyric acid

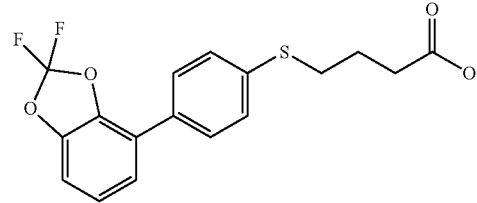 [SMILES: O=C(O)CCCSc1ccc(-c2cccc3c2OC(F)(F)O3)cc1]

4-[4-(4,4,5,5-Tetramethyl-[1,3,2]dioxaborolan-2-yl)-phenylsulfanyl]-butyric acid ethyl ester (0.1 g, 0.28 mmol) obtained in Preparation Example 202 and 4-bromo-2,2-difluoro-benzo[1,3]dioxole (0.074 g, 0.31 mmol) were sequentially reacted in the same manner as in Steps A and B of Example 1 to obtain the title compound (0.022 g, 22%).

¹H-NMR (CDCl₃) δ 7.62 (2H, d), 7.40 (2H, d), 7.25 (1H, m), 7.12 (1H, t), 7.02 (1H, d), 3.03 (2H, t), 2.55 (2H, t), 2.00 (2H, m).

Example 156: 4-(4-spiro[1,3-benzodioxol-2,1'-cyclopentane]-4-ylphenyl)sulfanylbutanoic acid

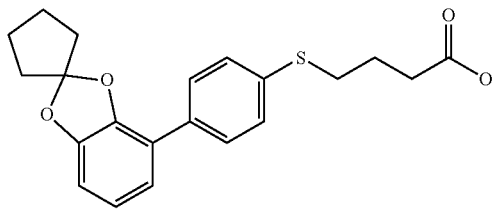 [SMILES: O=C(O)CCCSc1ccc(-c2cccc3c2OC2(CCCC2)O3)cc1]

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 202 and 4-iodospiro[1,3-benzodioxol-2,1'-cyclopentane] (0.047 g, 0.16 mmol) obtained in Preparation Example 215 were sequentially reacted in the same manner as in Steps A and B of Example 1 to obtain the title compound (0.027 g, 51%).

¹H-NMR (CDCl₃) δ 7.65 (2H, d), 7.38 (2H, d), 6.97 (1H, d), 6.84 (1H, t), 6.71 (1H, d), 3.01 (2H, t), 2.54 (2H, t), 2.11 (4H, m), 1.99 (2H, m), 1.84 (4H, m).

Example 157: 4-(2-fluoro-4-spiro[1,3-benzodioxol-2,1'-cyclopentan]-4-yl-phenyl)sulfanylbutanoic acid

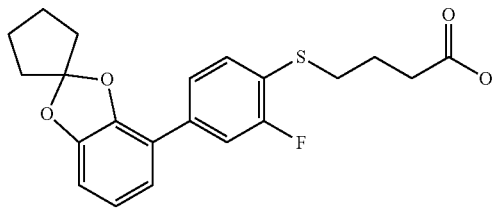 [SMILES: O=C(O)CCCSc1ccc(-c2cccc3c2OC2(CCCC2)O3)cc1F]

4-[2-Fluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 205 and 4-iodospiro[1,3-benzodioxol-2,1'-cyclopentane] (0.045 g, 0.15 mmol) obtained in Preparation Example 215 were sequentially reacted in the same manner as in Steps A and B of Example 1 to obtain the title compound (0.024 g, 45%).

¹H-NMR (CDCl₃) δ 7.48-7.41 (3H, m), 6.96 (1H, d), 6.85 (1H, t), 6.73 (1H, d), 2.99 (2H, t), 2.55 (2H, t), 2.13 (4H, m), 1.96 (2H, m), 1.85 (4H, m).

Example 158: 5-[4-(2-isopropoxy-pyridin-3-yl)-phenyl]-5-methyl-hexanoic acid

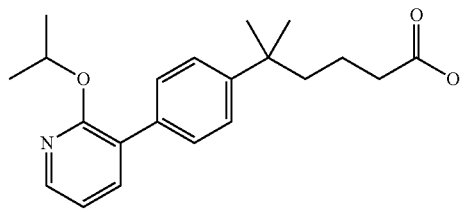 [SMILES: CC(C)Oc1ncccc1-c1ccc(C(C)(C)CCCC(=O)O)cc1]

5-Methyl-5-[4-(4,4,5,5-tetramethyl-[1,3,2]dioxaborolan-2-yl)-phenyl]-hexanoic acid ethyl ester (0.05 g, 0.14 mmol) obtained in Preparation Example 136 and 3-iodo-2-isopropoxy-pyridine (0.055 g, 0.21 mmol) obtained in Preparation Example 34 were sequentially reacted in the same manner as in Steps A and B of Example 1 to obtain the title compound (0.017 g, 36%).

¹H-NMR (CDCl₃) δ 8.10 (1H, m), 7.61 (1H, m), 7.53 (2H, d), 7.35 (2H, d), 6.90 (1H, m), 5.39 (1H, m), 2.30 (2H, t), 1.67 (2H, m), 1.47 (2H, m), 1.34 (12H, m).

Example 159: 5-[4-(2-isopropylsulfanyl-pyridin-3-yl)-phenyl]-5-methyl-hexanoic acid

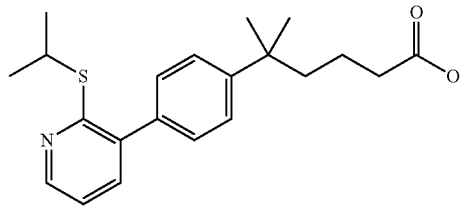 [SMILES: CC(C)Sc1ncccc1-c1ccc(C(C)(C)CCCC(=O)O)cc1]

5-Methyl-5-[4-(4,4,5,5-tetramethyl-[1,3,2]dioxaborolan-2-yl)-phenyl]-hexanoic acid ethyl ester (0.05 g, 0.14 mmol) obtained in Preparation Example 136 and 3-iodo-2-isopropylsulfanyl-pyridine (0.058 g, 0.21 mmol) obtained in Preparation Example 9 were sequentially reacted in the same manner as in Steps A and B of Example 1 to obtain the title compound (0.022 g, 44%).

¹H-NMR (CDCl₃) δ 8.42 (1H, m), 7.36 (5H, m), 7.02 (1H, m), 4.06 (1H, m), 2.26 (2H, t), 1.68 (2H, m), 1.48 (2H, m), 1.31 (12H, m).

Example 160: 5-[4-(2-cyclopentyloxy-pyridin-3-yl)-phenyl]-5-methyl-hexanoic acid

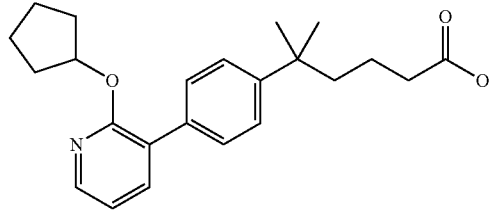 [SMILES: CC(C)(CCCC(=O)O)c1ccc(-c2cccnc2OC2CCCC2)cc1]

5-Methyl-5-[4-(4,4,5,5-tetramethyl-[1,3,2]dioxaborolan-2-yl)-phenyl]-hexanoic acid ethyl ester (0.05 g, 0.14 mmol)

obtained in Preparation Example 136 and 2-cyclopentyloxy-3-iodo-pyridine (0.06 g, 0.21 mmol) obtained in Preparation Example 11 were sequentially reacted in the same manner as in Steps A and B of Example 1 to obtain the title compound (0.026 g, 47%).

$^1$H-NMR (CDCl$_3$) δ 8.12 (1H, m), 7.62 (1H, m), 7.52 (2H, d), 7.36 (2H, d), 6.91 (1H, m), 5.50 (1H, m), 2.27 (2H, t), 1.94 (2H, m), 1.83-1.60 (8H, m), 1.46 (2H, m), 1.35 (6H, s).

Example 161: 5-[4-(2-cyclopentyloxy-pyridin-3-yl)-2-fluoro-phenyl]-5-methyl-hexanoic acid

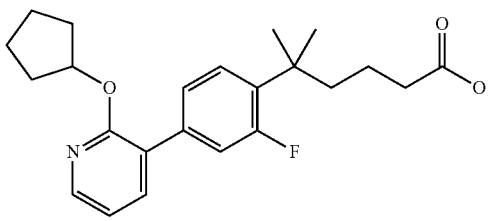 [SMILES: CC(C)(CCCC(=O)O)c1ccc(-c2cccnc2OC2CCCC2)cc1F]

5-[2-Fluoro-4-(4,4,5,5-tetramethyl-[1,3,2]dioxaborolan-2-yl)-phenyl]-5-methyl-hexanoic acid ethyl ester (0.02 g, 0.05 mmol) obtained in Preparation Example 142 and 2-cyclopentyloxy-3-iodo-pyridine (0.023 g, 0.08 mmol) obtained in Preparation Example 11 were sequentially reacted in the same manner as in Steps A and B of Example 1 to obtain the title compound (0.011 g, 50%).

$^1$H-NMR (CDCl$_3$) δ 8.14 (1H, m), 7.61 (1H, m), 7.27 (3H, m), 6.91 (1H, m), 5.52 (1H, m), 2.30 (2H, t), 1.97 (2H, m), 1.82-1.73 (6H, m), 1.63 (2H, m), 1.44 (2H, m), 1.40 (6H, s).

Example 162: 5-[4-(2-cyclopentyloxy-pyridin-3-yl)-2,6-difluoro-phenyl]-5-methyl-hexanoic acid

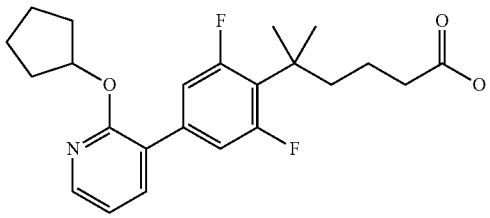 [SMILES: CC(C)(CCCC(=O)O)c1c(F)cc(-c2cccnc2OC2CCCC2)cc1F]

5-[2,6-Difluoro-4-(4,4,5,5-tetramethyl-[1,3,2]dioxaborolan-2-yl)-phenyl]-5-methyl-hexanoic acid ethyl ester (0.035 g, 0.09 mmol) obtained in Preparation Example 148 and 2-cyclopentyloxy-3-iodo-pyridine (0.038 g, 0.13 mmol) obtained in Preparation Example 11 were sequentially reacted in the same manner as in Steps A and B of Example 1 to obtain the title compound (0.022 g, 62%).

$^1$H-NMR (CDCl$_3$) δ 8.14 (1H, m), 7.60 (1H, m), 7.07 (2H, m), 6.92 (1H, m), 5.51 (1H, m), 2.31 (2H, t), 1.95 (2H, m), 1.87-1.72 (6H, m), 1.63 (2H, m), 1.52 (2H, m), 1.49 (6H, s).

Example 163: 5-[4-(2-cyclopentylsulfanyl-pyridin-3-yl)-phenyl]-5-methyl-hexanoic acid

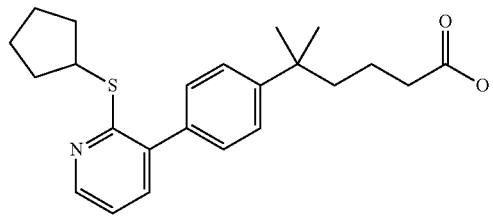 [SMILES: CC(C)(CCCC(=O)O)c1ccc(-c2cccnc2SC2CCCC2)cc1]

5-Methyl-5-[4-(4,4,5,5-tetramethyl-[1,3,2]dioxaborolan-2-yl)-phenyl]-hexanoic acid ethyl ester (0.05 g, 0.14 mmol) obtained in Preparation Example 136 and 2-cyclopentylsulfanyl-3-iodo-pyridine (0.063 g, 0.21 mmol) obtained in Preparation Example 15 were sequentially reacted in the same manner as in Steps A and B of Example 1 to obtain the title compound (0.032 g, 60%).

$^1$H-NMR (CDCl$_3$) δ 8.40 (1H, m), 7.37 (5H, m), 7.01 (1H, m), 4.07 (1H, m), 2.28 (2H, t), 2.18 (2H, m), 1.69-1.46 (10H, m), 1.34 (6H, s).

Example 164: 5-[4-(2-cyclobutylsulfanyl-pyridin-3-yl)-2,6-difluoro-phenyl]-5-methyl-hexanoic acid

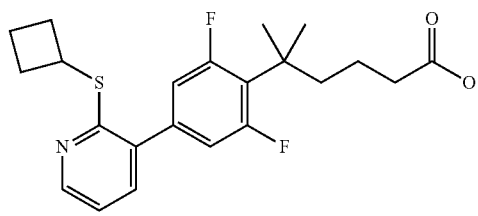 [SMILES: CC(C)(CCCC(=O)O)c1c(F)cc(-c2cccnc2SC2CCC2)cc1F]

5-[2,6-Difluoro-4-(4,4,5,5-tetramethyl-[1,3,2]dioxaborolan-2-yl)-phenyl]-5-methyl-hexanoic acid ethyl ester (0.035 g, 0.09 mmol) obtained in Preparation Example 148 and 2-cyclobutylsulfanyl-3-iodo-pyridine (0.038 g, 0.13 mmol) obtained in Preparation Example 13 were sequentially reacted in the same manner as in Steps A and B of Example 1 to obtain the title compound (0.025 g, 71%).

$^1$H-NMR (CDCl$_3$) δ 8.40 (1H, m), 7.33 (1H, m), 7.02 (1H, m), 6.90 (2H, m), 4.42 (1H, m), 2.50 (2H, m), 2.32 (2H, t), 2.07-2.00 (4H, m), 1.80 (2H, m), 1.54 (2H, m), 1.49 (6H, s).

Example 165: 5-[4-(2-cyclobutylsulfanyl-pyridin-3-yl)-phenyl]-5-methyl-hexanoic acid

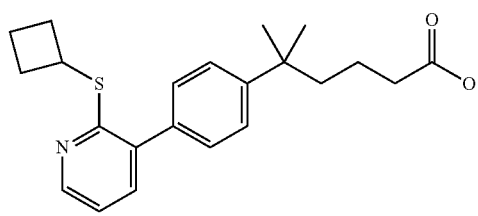 [SMILES: CC(C)(CCCC(=O)O)c1ccc(-c2cccnc2SC2CCC2)cc1]

5-Methyl-5-[4-(4,4,5,5-tetramethyl-[1,3,2]dioxaborolan-2-yl)-phenyl]-hexanoic acid ethyl ester (0.05 g, 0.14 mmol)

obtained in Preparation Example 136 and 2-cyclobutylsulfanyl-3-iodo-pyridine (0.06 g, 0.21 mmol) obtained in Preparation Example 13 were sequentially reacted in the same manner as in Steps A and B of Example 1 to obtain the title compound (0.035 g, 68%).

¹H-NMR (CDCl₃) δ 8.38 (1H, m), 7.36 (5H, m), 7.01 (1H, m), 4.41 (1H, m), 2.49 (2H, m), 2.27 (2H, t), 2.06-1.98 (4H, m), 1.67 (2H, m), 1.48 (2H, m), 1.34 (6H, s).

Example 166: 4-{1-[4-(2-cyclopentyloxy-pyridin-3-yl)-2,6-difluoro-phenyl]-cyclopropyl}-butyric acid

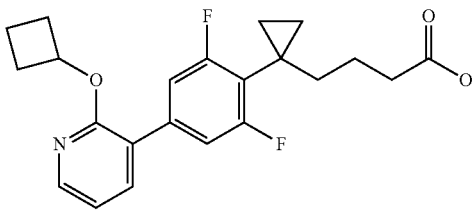 [SMILES: O=C(O)CCCC1(c2c(F)cc(-c3cccnc3OC3CCC3)cc2F)CC1]

4-{1-[2,6-Difluoro-4-(4,4,5,5-tetramethyl-[1,3,2]dioxaborolan-2-yl)-phenyl]-cyclopropyl}-butyric acid ethyl ester (0.05 g, 0.13 mmol) obtained in Preparation Example 155 and 2-cyclopentyloxy-3-iodo-pyridine (0.055 g, 0.19 mmol) obtained in Preparation Example 11 were sequentially reacted in the same manner as in Steps A and B of Example 1 to obtain the title compound (0.014 g, 27%).

¹H-NMR (CDCl₃) δ 8.15 (1H, m), 7.58 (1H, m), 7.08 (2H, m), 6.91 (1H, m), 5.51 (1H, m), 2.31 (2H, t), 1.95 (2H, m), 1.82-1.57 (10H, m), 0.87-0.81 (4H, m).

Example 167: 4-{1-[4-(2-cyclobutylsulfanyl-pyridin-3-yl)-2,6-difluoro-phenyl]-cyclopropyl}-butyric acid

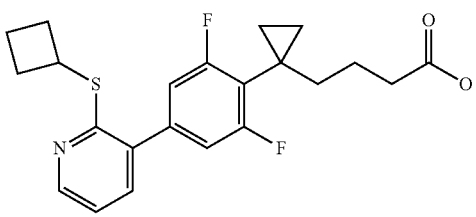 [SMILES: O=C(O)CCCC1(c2c(F)cc(-c3cccnc3SC3CCC3)cc2F)CC1]

4-{1-[2,6-Difluoro-4-(4,4,5,5-tetramethyl-[1,3,2]dioxaborolan-2-yl)-phenyl]-cyclopropyl}-butyric acid ethyl ester (0.05 g, 0.13 mmol) obtained in Preparation Example 155 and 2-cyclobutylsulfanyl-3-iodo-pyridine (0.055 g, 0.19 mmol) obtained in Preparation Example 13 were sequentially reacted in the same manner as in Steps A and B of Example 1 to obtain the title compound (0.016 g, 31%).

¹H-NMR (CDCl₃) δ 8.41 (1H, m), 7.33 (1H, m), 7.01 (1H, m), 6.92 (2H, m), 4.42 (1H, m), 2.49 (2H, m), 2.36 (2H, t), 2.07-2.00 (4H, m), 1.71 (2H, m), 1.58 (2H, m), 0.88-0.82 (4H, m).

Example 168: 4-{1-[4-(6-cyclobutoxy-pyridin-2-yl)-2,6-difluoro-phenyl]-cyclopropyl}-butyric acid

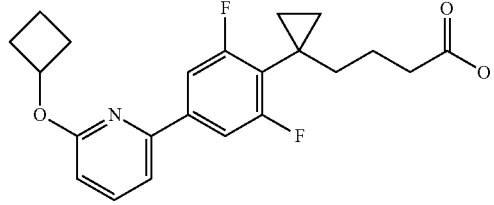 [SMILES: O=C(O)CCCC1(c2c(F)cc(-c3cccc(OC4CCC4)n3)cc2F)CC1]

4-{1-[2,6-Difluoro-4-(4,4,5,5-tetramethyl-[1,3,2]dioxaborolan-2-yl)-phenyl]-cyclopropyl}-butyric acid ethyl ester (0.05 g, 0.13 mmol) obtained in Preparation Example 155 and 2-chloro-6-cyclobutoxy-pyridine (0.035 g, 0.19 mmol) obtained in Preparation Example 29 were sequentially reacted in the same manner as in Steps A and B of Example 1 to obtain the title compound (0.007 g, 14%).

¹H-NMR (CDCl₃) δ 7.60 (1H, t), 7.46 (2H, m), 7.23 (1H, d), 6.66 (1H, d), 5.26 (1H, m), 2.52 (2H, m), 2.33 (2H, t), 2.18 (2H, m), 1.85 (1H, m), 1.80-1.69 (3H, m), 1.58 (2H, m), 0.86-0.82 (4H, m).

Example 169: 4-{1-[4-(2-cyclobutylmethoxy-pyridin-3-yl)-2,6-difluoro-phenyl]-cyclopropyl}-butyric acid

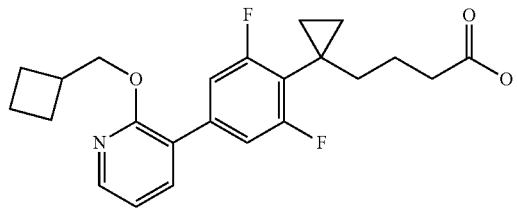 [SMILES: O=C(O)CCCC1(c2c(F)cc(-c3cccnc3OCC3CCC3)cc2F)CC1]

4-{1-[2,6-Difluoro-4-(4,4,5,5-tetramethyl-[1,3,2]dioxaborolan-2-yl)-phenyl]-cyclopropyl}-butyric acid ethyl ester (0.05 g, 0.13 mmol) obtained in Preparation Example 155 and 2-cyclobutylmethoxy-3-iodo-pyridine (0.055 g, 0.19 mmol) obtained in Preparation Example 48 were sequentially reacted in the same manner as in Steps A and B of Example 1 to obtain the title compound (0.012 g, 23%).

¹H-NMR (CDCl₃) δ 8.14 (1H, m), 7.59 (1H, m), 7.09 (2H, m), 6.94 (1H, m), 4.32 (2H, d), 2.79 (1H, m), 2.35 (2H, t), 2.11 (2H, m), 2.0-1.85 (4H, m), 1.70 (2H, m), 1.58 (2H, m), 0.86-0.81 (4H, m).

Example 170: 4-{1-[4-(6-cyclopropylmethoxy-pyridin-2-yl)-2,6-difluoro-phenyl]-cyclopropyl}-butyric acid

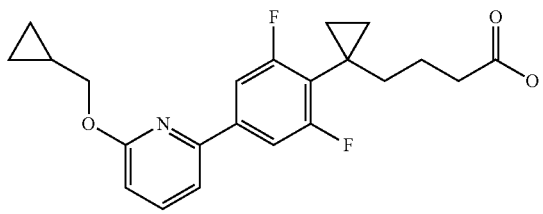 [SMILES: O=C(O)CCCC1(c2c(F)cc(-c3cccc(OCC4CC4)n3)cc2F)CC1]

4-{1-[2,6-Difluoro-4-(4,4,5,5-tetramethyl-[1,3,2]dioxaborolan-2-yl)-phenyl]-cyclopropyl}-butyric acid ethyl ester (0.09 g, 0.23 mmol) obtained in Preparation Example 155 and 2-chloro-6-cyclopropylmethoxy-pyridine (0.063 g, 0.34 mmol) obtained in Preparation Example 43 were sequentially reacted in the same manner as in Steps A and B of Example 1 to obtain the title compound (0.018 g, 20%).

¹H-NMR (CDCl₃) δ 7.61 (1H, t), 7.48 (2H, m), 7.24 (1H, d), 6.73 (1H, d), 4.22 (2H, d), 2.33 (2H, t), 1.69 (2H, m), 1.58 (2H, m), 1.32 (1H, m), 0.89-0.81 (4H, m), 0.62 (2H, m), 0.38 (2H, m).

Example 171: 5-[4-(2,2-difluoro-benzo[1,3]dioxol-4-yl)-2,6-difluoro-phenyl]-hexanoic acid

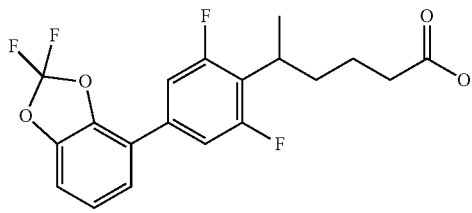 [SMILES: CC(CCCC(=O)O)c1c(F)cc(-c2cccc3c2OC(F)(F)O3)cc1F]

5-[2,6-Difluoro-4-(4,4,5,5-tetramethyl-[1,3,2]dioxaborolan-2-yl)phenyl]hexanoic acid ethyl ester (0.05 g, 0.13 mmol) obtained in Preparation Example 32 and 4-bromo-2,2-difluoro-benzo[1,3]dioxole (0.027 g, 0.2 mmol) were sequentially reacted in the same manner as in Steps A and B of Example 1 to obtain the title compound (0.022 g, 44%).

¹H-NMR (CDCl₃) δ 7.25-7.12 (4H, m), 7.06 (1H, d), 3.24 (1H, m), 2.35 (2H, t), 1.84 (1H, m), 1.74 (1H, m), 1.64 (1H, m), 1.53 (1H, m), 1.35 (3H, d).

Example 172: {2-[4-(2-cyclopentyloxy-pyridin-3-yl)-phenyl]-2,2-difluoro-ethoxy}-acetic acid

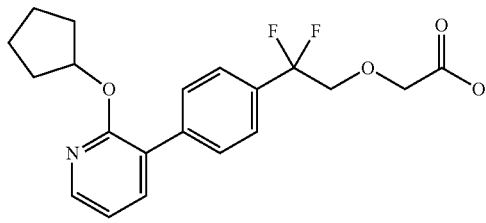 [SMILES: O=C(O)COCC(F)(F)c1ccc(-c2cccnc2OC2CCCC2)cc1]

{2,2-Difluoro-2-[4-(4,4,5,5-tetramethyl-[1,3,2]dioxaborolan-2-yl)-phenyl]-ethoxy}-acetic acid ethyl ester (0.05 g, 0.13 mmol) obtained in Preparation Example 160 and 2-cyclopentyloxy-3-iodo-pyridine (0.058 g, 0.2 mmol) obtained in Preparation Example 11 were sequentially reacted in the same manner as in Steps A and B of Example 1 to obtain the title compound (0.008 g, 15%).

¹H-NMR (CDCl₃) δ 8.17 (1H, m), 7.63 (3H, m), 7.55 (2H, d), 6.93 (1H, m), 5.51 (1H, m), 4.28 (2H, s), 4.05 (2H, t), 1.93 (2H, m), 1.81 (2H, m), 1.71 (2H, m), 1.62 (2H, m).

Example 173: {2-[4-(2-cyclobutylsulfanyl-pyridin-3-yl)-phenyl]-2,2-difluoro-ethoxy}-acetic acid

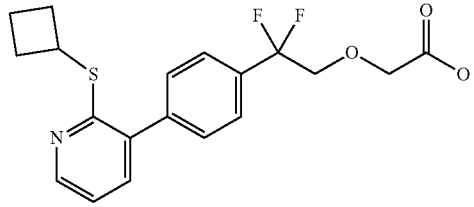 [SMILES: O=C(O)COCC(F)(F)c1ccc(-c2cccnc2SC2CCC2)cc1]

{2,2-Difluoro-2-[4-(4,4,5,5-tetramethyl-[1,3,2]dioxaborolan-2-yl)-phenyl]-ethoxy}-acetic acid ethyl ester (0.05 g, 0.13 mmol) obtained in Preparation Example 160 and 2-cyclobutylsulfanyl-3-iodo-pyridine (0.059 g, 0.2 mmol) obtained in Preparation Example 13 were sequentially reacted in the same manner as in Steps A and B of Example 1 to obtain the title compound (0.005 g, 10%).

¹H-NMR (CDCl₃) δ 8.40 (1H, m), 7.55 (2H, d), 7.46 (2H, d), 7.30 (1H, m), 7.00 (1H, m), 4.39 (1H, m), 4.21 (2H, s), 4.02 (2H, t), 2.47 (2H, m), 1.99 (4H, m).

Example 174: {2-[4-(6-cyclobutoxy-pyridin-2-yl)-phenyl]-2,2-difluoro-ethoxy}-acetic acid

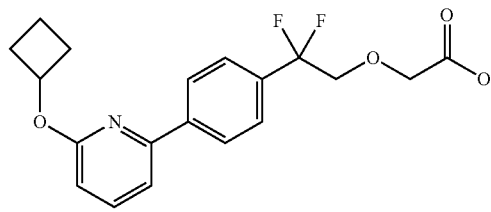 [SMILES: O=C(O)COCC(F)(F)c1ccc(-c2cccc(OC3CCC3)n2)cc1]

{2,2-Difluoro-2-[4-(4,4,5,5-tetramethyl-[1,3,2]dioxaborolan-2-yl)-phenyl]-ethoxy}-acetic acid ethyl ester (0.05 g, 0.13 mmol) obtained in Preparation Example 160 and 2-chloro-6-cyclobutoxy-pyridine (0.037 g, 0.2 mmol) obtained in Preparation Example 29 were sequentially reacted in the same manner as in Steps A and B of Example 1 to obtain the title compound (0.008 g, 16%).

¹H-NMR (CDCl₃) δ 8.01 (2H, d), 7.57-7.51 (3H, m), 7.26 (1H, m), 6.64 (1H, d), 5.24 (1H, m), 4.18 (2H, s), 4.00 (2H, t), 2.49 (2H, m), 2.16 (2H, m), 1.84 (1H, m), 1.70 (1H, m).

Example 175: 3-{2-[4-(2-cyclopentyloxy-pyridin-3-yl)-2,6-difluoro-phenyl]-cyclopropyl}-propanoic acid

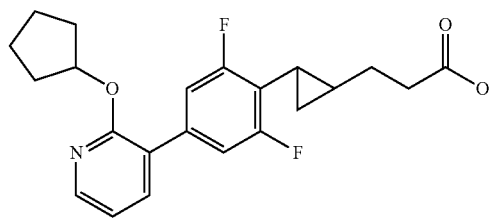 [SMILES: O=C(O)CCC1CC1c1c(F)cc(-c2cccnc2OC2CCCC2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.05 g, 0.13 mmol) obtained in Preparation Example 175 and 2-cyclopentyloxy-3-iodo-pyridine (0.057 g, 0.2 mmol) obtained in Preparation Example 11 were sequentially reacted in the same manner as in Steps A and B of Example 1 to obtain the title compound (0.024 g, 47%).

¹H-NMR (CDCl$_3$) δ 8.14 (1H, m), 7.55 (1H, m), 7.06 (2H, m), 6.91 (1H, m), 5.51 (1H, m), 2.58 (2H, t), 1.96 (2H, m), 1.83-1.63 (9H, m), 1.42 (1H, m), 1.24 (1H, m), 0.82 (1H, m).

Example 176: 3-{2-[4-(2-cyclobutylsulfanyl-pyridin-3-yl)-2,6-difluoro-phenyl]-cyclopropyl}-propanoic acid

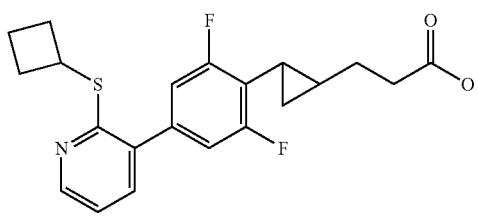 [SMILES: O=C(O)CCC1CC1c1c(F)cc(-c2cccnc2SC2CCC2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.05 g, 0.13 mmol) obtained in Preparation Example 175 and 2-cyclobutylsulfanyl-3-iodo-pyridine (0.057 g, 0.2 mmol) obtained in Preparation Example 13 were sequentially reacted in the same manner as in Steps A and B of Example 1 to obtain the title compound (0.024 g, 47%).

¹H-NMR (CDCl$_3$) δ 8.41 (1H, m), 7.32 (1H, m), 7.02 (1H, m), 6.90 (2H, m), 4.42 (1H, m), 2.59 (2H, t), 2.50 (2H, m), 2.09-2.00 (4H, m), 1.82 (1H, m), 1.73-1.63 (2H, m), 1.43 (1H, m), 1.26 (1H, m), 0.83 (1H, m).

Example 177: 5-[4-(2-cyclopentyloxy-pyridin-3-yl)-phenyl]-5,5-difluoro-pentanoic acid

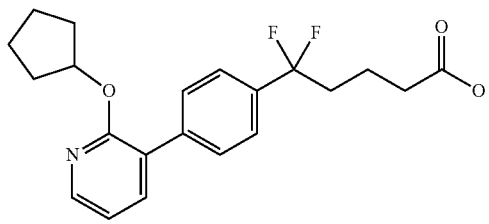 [SMILES: O=C(O)CCCC(F)(F)c1ccc(-c2cccnc2OC2CCCC2)cc1]

5,5-Difluoro-5-[4-(4,4,5,5-tetramethyl-[1,3,2]dioxaborolan-2-yl)-phenyl]-pentanoic acid methyl ester (0.05 g, 0.14 mmol) obtained in Preparation Example 169 and 2-cyclopentyloxy-3-iodo-pyridine (0.061 g, 0.21 mmol) obtained in Preparation Example 11 were sequentially reacted in the same manner as in Steps A and B of Example 1 to obtain the title compound (0.03 g, 56%).

¹H-NMR (CDCl$_3$) δ 8.16 (1H, m), 7.62-7.59 (3H, m), 7.49 (2H, m), 6.93 (1H, m), 5.51 (1H, m), 2.44 (2H, t), 2.22 (2H, m), 1.97-1.61 (10H, m).

Example 178: 5-[4-(2-cyclobutylsulfanyl-pyridin-3-yl)-phenyl]-5,5-difluoro-pentanoic acid

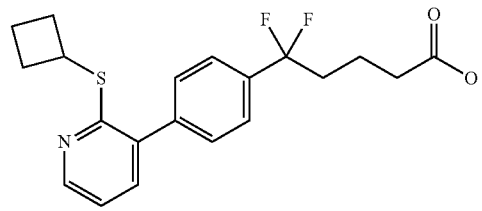 [SMILES: O=C(O)CCCC(F)(F)c1ccc(-c2cccnc2SC2CCC2)cc1]

5,5-Difluoro-5-[4-(4,4,5,5-tetramethyl-[1,3,2]dioxaborolan-2-yl)-phenyl]-pentanoic acid methyl ester (0.05 g, 0.14 mmol) obtained in Preparation Example 169 and 2-cyclobutylsulfanyl-3-iodo-pyridine (0.061 g, 0.21 mmol) obtained in Preparation Example 13 were sequentially reacted in the same manner as in Steps A and B of Example 1 to obtain the title compound (0.025 g, 47%).

¹H-NMR (CDCl$_3$) δ 8.42 (1H, m), 7.55-7.47 (4H, m), 7.35 (1H, m), 7.04 (1H, m), 4.43 (1H, m), 2.51-2.43 (4H, m), 2.25 (2H, m), 2.09-1.98 (4H, m), 1.87 (2H, m).

Example 179: 3-{2-[2,6-difluoro-4-(2-propylsulfanyl-pyridin-3-yl)-phenyl]-cyclopropyl}-propanoic acid

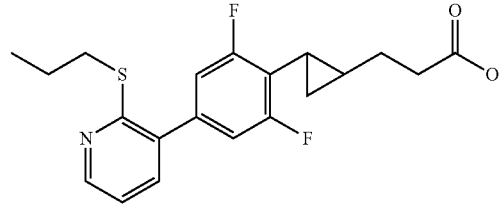 [SMILES: CCCSc1ncccc1-c1cc(F)c(C2CC2CCC(=O)O)c(F)c1]

3-{2-[2,6-Difluoro-4-(4,4,5,5-tetramethyl-[1,3,2]dioxaborolan-2-yl)-phenyl]-cyclopropyl}-propanoic acid ethyl ester (0.04 g, 0.1 mmol) obtained in Preparation Example 175 and 3-iodo-2-propylsulfanyl-pyridine (0.044 g, 0.16 mmol) obtained in Preparation Example 28 were sequentially reacted in the same manner as in Steps A and B of Example 1 to obtain the title compound (0.016 g, 40%).

¹H-NMR (CDCl$_3$) δ 8.43 (1H, m), 7.33 (1H, m), 7.03 (1H, m), 6.91 (2H, m), 3.14 (2H, t), 2.59 (2H, t), 1.84 (1H, m), 1.73-1.63 (4H, m), 1.43 (1H, m), 1.26 (1H, m), 1.01 (3H, t), 0.85 (1H, m).

Example 180: 3-{2-[4-(6-cyclobutoxy-pyridin-2-yl)-2,6-difluoro-phenyl]-cyclopropyl}-propanoic acid

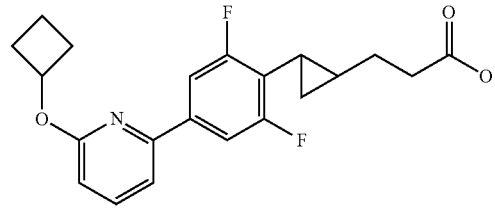 [SMILES: O=C(O)CCC1CC1c1c(F)cc(-c2cccc(OC3CCC3)n2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.05 g, 0.13 mmol) obtained in Preparation Example 175 and 2-chloro-6-cyclobutoxy-pyridine (0.036 g, 0.2 mmol) obtained in Preparation Example 29 were sequentially reacted in the same manner as in Steps A and B of Example 1 to obtain the title compound (0.005 g, 10%).

¹H-NMR (CDCl₃) δ 7.61 (1H, t), 7.43 (2H, m), 7.25 (1H, d), 6.65 (1H, d), 5.25 (1H, m), 2.59 (2H, t), 2.52 (2H, m), 2.18 (2H, m), 1.85 (2H, m), 1.69-1.62 (3H, m), 1.39 (1H, m), 1.24 (1H, m), 0.84 (1H, m).

Example 181: 5-[4-(2-cyclopropylmethoxy-pyridin-3-yl)-phenyl]-5,5-difluoro-pentanoic acid

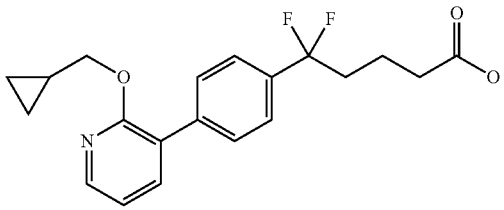 [SMILES: O=C(O)CCCC(F)(F)c1ccc(-c2cccnc2OCC2CC2)cc1]

5,5-Difluoro-5-[4-(4,4,5,5-tetramethyl-[1,3,2]dioxaborolan-2-yl)-phenyl]-pentanoic acid methyl ester (0.027 g, 0.08 mmol) obtained in Preparation Example 169 and 2-cyclopropylmethoxy-3-iodo-pyridine (0.031 g, 0.11 mmol) obtained in Preparation Example 40 were sequentially reacted in the same manner as in Steps A and B of Example 1 to obtain the title compound (0.015 g, 55%).

¹H-NMR (CDCl₃) δ 8.14 (1H, m), 7.67 (2H, d), 7.62 (1H, m), 7.52 (2H, d), 6.95 (1H, m), 4.22 (2H, d), 2.43 (2H, t), 2.24 (2H, m), 1.86 (2H, m), 1.26 (1H, m), 0.56 (2H, m), 0.32 (2H, m).

Example 182: 3-{2-[4-(2-cyclopentylsulfanyl-pyridin-3-yl)-2,6-difluoro-phenyl]-cyclopropyl}-propanoic acid

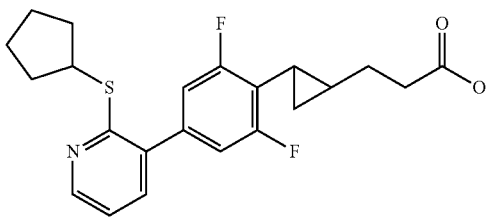 [SMILES: O=C(O)CCC1CC1c1c(F)cc(-c2cccnc2SC2CCCC2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.027 g, 0.07 mmol) obtained in Preparation Example 175 and 2-cyclopentylsulfanyl-3-iodo-pyridine (0.032 g, 0.11 mmol) obtained in Preparation Example 15 were sequentially reacted in the same manner as in Steps A and B of Example 1 to obtain the title compound (0.007 g, 25%).

¹H-NMR (CDCl₃) δ 8.42 (1H, m), 7.29 (1H, m), 7.02 (1H, m), 6.87 (2H, m), 4.07 (1H, m), 2.57 (2H, t), 2.19 (2H, m), 1.81 (1H, m), 1.72-1.53 (8H, m), 1.42 (1H, m), 1.25 (1H, m), 0.82 (1H, m).

Example 183: 3-{2-[4-(2-cyclopentylamino-pyridin-3-yl)-2,6-difluoro-phenyl]-cyclopropyl}-propanoic acid

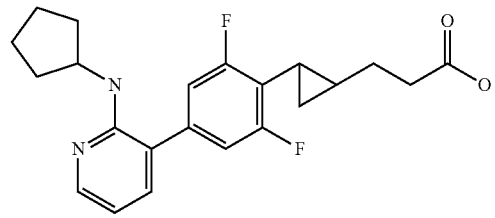 [SMILES: O=C(O)CCC1CC1c1c(F)cc(-c2cccnc2NC2CCCC2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.027 g, 0.07 mmol) obtained in Preparation Example 175 and N-cyclopentyl-3-iodo-pyridin-2-amine (0.031 g, 0.11 mmol) obtained in Preparation Example 51 were sequentially reacted in the same manner as in Steps A and B of Example 1 to obtain the title compound (0.005 g, 18%).

¹H-NMR (CDCl₃) δ 8.13 (1H, m), 7.17 (1H, m), 6.84 (2H, m), 6.59 (1H, m), 4.49 (1H, br), 4.33 (1H, m), 2.58 (2H, t), 2.04 (2H, m), 1.83 (1H, m), 1.74-1.58 (6H, m), 1.43 (1H, m), 1.33 (2H, m), 1.24 (1H, m), 0.84 (1H, m).

Example 184: 5-[4-(2-cyclopentylsulfanyl-pyridin-3-yl)-phenyl]-5,5-difluoro-pentanoic acid

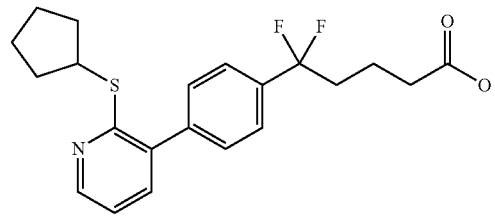 [SMILES: O=C(O)CCCC(F)(F)c1ccc(-c2cccnc2SC2CCCC2)cc1]

5,5-Difluoro-5-[4-(4,4,5,5-tetramethyl-[1,3,2]dioxaborolan-2-yl)-phenyl]-pentanoic acid methyl ester (0.04 g, 0.11 mmol) obtained in Preparation Example 169 and 2-cyclopentylsulfanyl-3-iodo-pyridine (0.052 g, 0.17 mmol) obtained in Preparation Example 15 were sequentially reacted in the same manner as in Steps A and B of Example 1 to obtain the title compound (0.016 g, 36%).

¹H-NMR (CDCl₃) δ 8.44 (1H, m), 7.54-7.47 (4H, m), 7.35 (1H, m), 7.05 (1H, m), 4.11 (1H, m), 2.45 (2H, t), 2.31-2.20 (4H, m), 1.87 (2H, m), 1.70-1.52 (6H, m).

Example 185: 5-[4-(2-cyclobutoxy-pyridin-3-yl)-phenyl]-5,5-difluoro-pentanoic acid

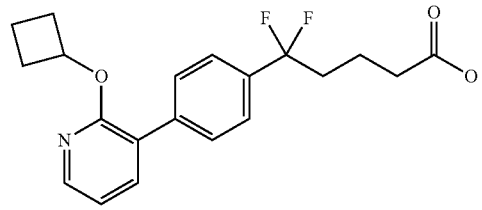 [SMILES: O=C(O)CCCC(F)(F)c1ccc(-c2cccnc2OC2CCC2)cc1]

5,5-Difluoro-5-[4-(4,4,5,5-tetramethyl-[1,3,2]dioxaborolan-2-yl)-phenyl]-pentanoic acid methyl ester (0.04 g, 0.11 mmol) obtained in Preparation Example 169 and 2-cyclobutoxy-3-iodo-pyridine (0.046 g, 0.17 mmol) obtained in Preparation Example 41 were sequentially reacted in the same manner as in Steps A and B of Example 1 to obtain the title compound (0.017 g, 42%).

$^1$H-NMR (CDCl$_3$) δ 8.13 (1H, m), 7.65 (2H, d), 7.59 (1H, m), 7.51 (2H, d), 6.94 (1H, m), 5.27 (1H, m), 2.45 (4H, m), 2.24 (2H, m), 2.11 (2H, m), 1.87-1.79 (3H, m), 1.67 (1H, m).

Example 186: 5-[4-(6-cyclobutoxy-pyridin-2-yl)-phenyl]-5,5-difluoro-pentanoic acid

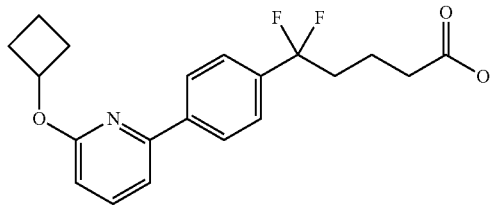 [SMILES: O=C(O)CCCC(F)(F)c1ccc(-c2cccc(OC3CCC3)n2)cc1]

5,5-Difluoro-5-[4-(4,4,5,5-tetramethyl-[1,3,2]dioxaborolan-2-yl)-phenyl]-pentanoic acid methyl ester (0.04 g, 0.11 mmol) obtained in Preparation Example 169 and 2-chloro-6-cyclobutoxy-pyridine (0.03 g, 0.17 mmol) obtained in Preparation Example 29 were sequentially reacted in the same manner as in Steps A and B of Example 1 to obtain the title compound (0.004 g, 10%).

$^1$H-NMR (CDCl$_3$) δ 8.06 (2H, d), 7.63 (1H, t), 7.54 (2H, d), 7.33 (1H, d), 6.66 (1H, d), 5.28 (1H, m), 2.54 (2H, m), 2.42 (2H, t), 2.22 (4H, m), 1.88-1.71 (4H, m).

Example 187: {4-[4-(2-cyclopentyloxy-pyridin-3-yl)-2-fluoro-phenyl]-cyclohexyl}-acetic acid

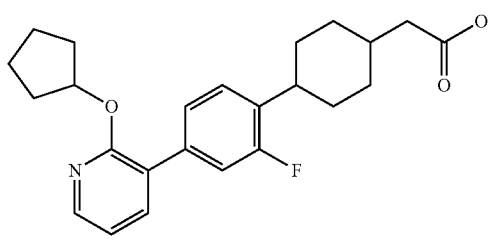 [SMILES: O=C(O)CC1CCC(c2ccc(-c3cccnc3OC3CCCC3)cc2F)CC1]

{4-[4-(2-Cyclopentyloxy-pyridin-3-yl)-2-fluoro-phenyl]-cyclohexyl}-acetic acid ethyl ester (0.045 g, 0.11 mmol) obtained in Preparation Example 182 was reacted in the same manner as in Step B of Example 1 to obtain the title compound (0.039 g, 92%).

$^1$H-NMR (CDCl$_3$) δ 8.13 (1H, m), 7.60 (1H, m), 7.27 (3H, m), 6.91 (1H, m), 5.51 (1H, m), 2.87 (1H, m), 2.56-2.33 (2H, m), 1.95-1.54 (16H, m), 1.26 (1H, m).

Example 188: 3-{2-[4-(2-cyclobutoxy-pyridin-3-yl)-2,6-difluoro-phenyl]-cyclopropyl}-propanoic acid

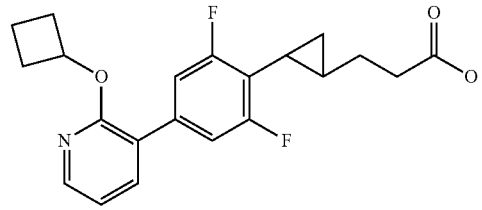 [SMILES: O=C(O)CCC1CC1c1c(F)cc(-c2cccnc2OC2CCC2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.04 g, 0.1 mmol) obtained in Preparation Example 175 and 2-cyclobutoxy-3-iodo-pyridine (0.043 g, 0.16 mmol) obtained in Preparation Example 41 were sequentially reacted in the same manner as in Steps A and B of Example 1 to obtain the title compound (0.018 g, 46%).

$^1$H-NMR (CDCl$_3$) δ 8.11 (1H, m), 7.54 (1H, m), 7.06 (2H, m), 6.92 (1H, m), 5.25 (1H, m), 2.60 (2H, t), 2.45 (2H, m), 2.12 (2H, m), 1.82 (2H, m), 1.68 (3H, m), 1.41 (1H, m), 1.24 (1H, m), 0.83 (1H, m).

Example 189: 3-{2-[4-(2-cyclobutylmethoxy-pyridin-3-yl)-2,6-difluoro-phenyl]-cyclopropyl}-propanoic acid

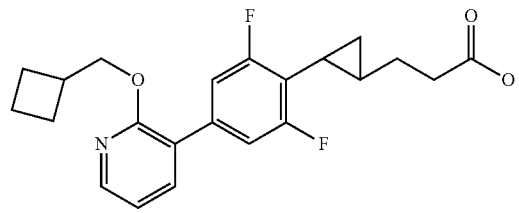 [SMILES: O=C(O)CCC1CC1c1c(F)cc(-c2cccnc2OCC2CCC2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.04 g, 0.1 mmol) obtained in Preparation Example 175 and 2-cyclobutylmethoxy-3-iodo-pyridine (0.046 g, 0.16 mmol) obtained in Preparation Example 48 were sequentially reacted in the same manner as in Steps A and B of Example 1 to obtain the title compound (0.025 g, 62%).

$^1$H-NMR (CDCl$_3$) δ 8.12 (1H, m), 7.57 (1H, m), 7.07 (2H, m), 6.93 (1H, m), 4.30 (2H, d), 2.78 (1H, m), 2.58 (2H, t), 2.11 (2H, m), 1.99-1.78 (5H, m), 1.71-1.62 (2H, m), 1.40 (1H, m), 1.23 (1H, m), 0.83 (1H, m).

Example 190: 3-(2-{2,6-difluoro-4-[2-(tetrahydro-pyran-4-yloxy)-pyridin-3-yl]-phenyl}-cyclopropyl)-propanoic acid

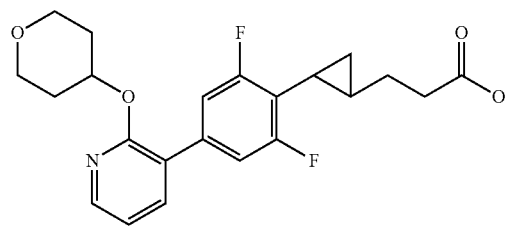 [SMILES: O=C(O)CCC1CC1c1c(F)cc(-c2cccnc2OC2CCOCC2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.04 g, 0.1 mmol) obtained in Preparation Example 175 and 3-iodo-2-(tetrahydro-pyran-4-yloxy)-pyridine (0.048 g, 0.16 mmol) obtained in Preparation Example 50 were sequentially reacted in the same manner as in Steps A and B of Example 1 to obtain the title compound (0.024 g, 57%).

$^1$H-NMR (CDCl$_3$) δ 8.11 (1H, m), 7.57 (1H, m), 7.06 (2H, m), 6.92 (1H, m), 5.36 (1H, m), 3.89 (2H, m), 3.63 (2H, m), 2.58 (2H, t), 2.05 (2H, m), 1.82 (3H, m), 1.73-1.62 (2H, m), 1.41 (1H, m), 1.24 (1H, m), 0.83 (1H, m).

Example 191: 3-{2-[4-(6-cyclopropylmethoxy-pyridin-2-yl)-2,6-difluoro-phenyl]-cyclopropyl}-propanoic acid

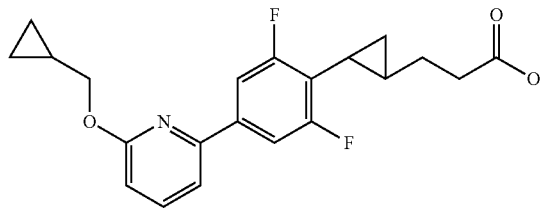 [SMILES: O=C(O)CCC1CC1c1c(F)cc(-c2cccc(OCC3CC3)n2)cc1F]

3-{2-[2,6-Difluoro-4-(4,4,5,5-tetramethyl-[1,3,2]dioxaborolan-2-yl)-phenyl]-cyclopropyl}-propanoic acid ethyl ester (0.04 g, 0.1 mmol) obtained in Preparation Example 175 and 2-chloro-6-cyclopropylmethoxy-pyridine (0.03 g, 0.16 mmol) obtained in Preparation Example 43 were sequentially reacted in the same manner as in Steps A and B of Example 1 to obtain the title compound (0.0045 g, 11%).

$^1$H-NMR (CDCl$_3$) δ 7.60 (1H, t), 7.45 (2H, m), 7.23 (1H, d), 6.71 (1H, d), 4.22 (2H, d), 2.57 (2H, t), 1.82 (1H, m), 1.65 (2H, m), 1.38 (1H, m), 1.31 (1H, m), 1.22 (1H, m), 0.83 (1H, m), 0.63 (2H, m), 0.38 (2H, m).

Example 192: 5,5-difluoro-5-[4-(6-isopropylsulfanyl-pyridin-2-yl)-phenyl]-pentanoic acid

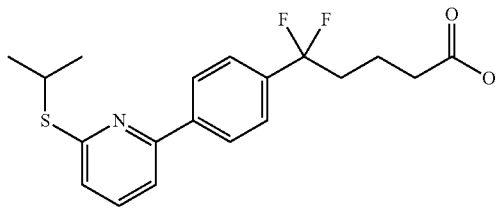 [SMILES: CC(C)Sc1cccc(-c2ccc(C(F)(F)CCCC(=O)O)cc2)n1]

5,5-Difluoro-5-[4-(4,4,5,5-tetramethyl-[1,3,2]dioxaborolan-2-yl)-phenyl]-pentanoic acid methyl ester (0.04 g, 0.11 mmol) obtained in Preparation Example 169 and 2-chloro-6-isopropylsulfanyl-pyridine (0.03 g, 0.17 mmol) obtained in Preparation Example 10 were sequentially reacted in the same manner as in Steps A and B of Example 1 to obtain the title compound (0.005 g, 13%).

$^1$H-NMR (CDCl$_3$) δ 8.10 (2H, d), 7.54 (3H, m), 7.43 (1H, d), 7.10 (1H, d), 4.15 (1H, m), 2.43 (2H, t), 2.23 (2H, m), 1.82 (2H, m), 1.47 (6H, d).

Example 193: 4-[4-(2,2-dimethyl-2,3-dihydro-benzofuran-4-yl)-phenoxy]-butyric acid

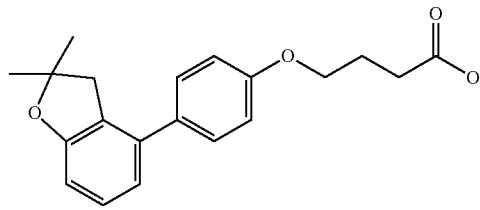 [SMILES: CC1(C)Cc2c(cccc2-c2ccc(OCCCC(=O)O)cc2)O1]

Step A: 4-[3'-hydroxy-2'-(2-methyl-propenyl)-biphenyl-4-yloxy]-butyric acid ethyl ester 4-(2'-Bromo-3'-hydroxy-biphenyl-4-yloxy)-butyric acid ethyl ester (36 mg, 0.095 mmol) and 4,4,5,5-tetramethyl-2-(2-methyl-propenyl)-[1,3,2]dioxaborolane (35 mg, 0.19 mmol) were dissolved in 0.5 mL of 1 M sodium carbonate and 4 mL of dimethoxyethane, and charged with nitrogen for 5 minutes. PdCl$_2$(PPh$_3$)$_2$ (3.3 mg, 0.00475 mmol) was added thereto, and the mixture was stirred for 4 hours under refluxs. The reaction solution was cooled to room temperature. After addition of water, the reaction solution extracted with EtOAc to separate an organic layer. The organic layer was dried with anhydrous magnesium sulfate and purified by column chromatography (eluent, EtOAc/Hex=1/4) to obtain the title compound (17 mg, 51% yield).

$^1$H NMR (400 MHz, CDCl$_3$) δ 7.23-7.17 (m, 3H), 6.93-6.89 (m, 1H), 6.89-6.84 (m, 3H), 5.85 (s, 1H), 5.36 (s, 1H), 4.16 (q, 2H), 4.03 (t, 2H), 2.53 (t, 2H), 2.17-2.08 (m, 2H), 1.84 (s, 3H), 1.58 (s, 3H), 1.27 (t, 3H)

Step B: 4-[4-(2,2-dimethyl-2,3-dihydro-benzofuran-4-yl)-phenoxy]-butyric acid ethyl ester 4-[3'-Hydroxy-2'-(2-methyl-propenyl)-biphenyl-4-yloxy]-butyric acid ethyl ester (17 mg, 0.048 mmol) obtained in Step A and Amberlyst 15 resin (17 mg) were reacted in the same manner as in Step C of Example 291 to obtain the title compound (10 mg, 59% yield).

Step C: 4-[4-(2,2-dimethyl-2,3-dihydro-benzofuran-4-yl)-phenoxy]-butyric acid

4-[4-(2,2-Dimethyl-2,3-dihydro-benzofuran-4-yl)-phenoxy]-butyric acid ethyl ester (10 mg, 0.028 mmol) obtained in Step B was reacted in the same manner as in Step B of Example 287 to obtain the title compound (7 mg, 76% yield).

$^1$H NMR (500 MHz, CDCl$_3$) δ 7.37 (d, 2H), 7.16 (dd, 1H), 6.93 (d, 2H), 6.87 (d, 1H), 6.70 (d, 1H), 4.06 (t, 2H), 3.09 (s, 2H), 2.61 (t, 2H), 2.20-2.10 (m, 2H), 1.46 (s, 6H)

Example 194: 4-[4-(2,2-dimethyl-2,3-dihydro-benzofuran-4-yl)-2-fluoro-phenoxy]-butyric acid

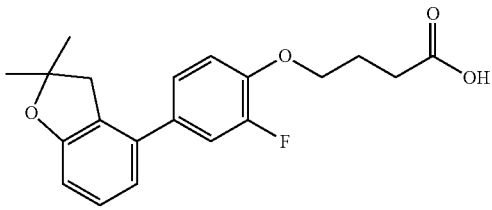 [SMILES: CC1(C)Cc2c(cccc2-c2ccc(OCCCC(=O)O)c(F)c2)O1]

Step A: 4-[3-fluoro-3'-hydroxy-2'-(2-methyl-propenyl)-biphenyl-4-yloxy]-butyric acid ethyl ester 4-(2'-Bromo-3-fluoro-3'-hydroxy-biphenyl-4-yloxy)-butyric acid ethyl ester (140 mg, 0.35 mmol) and 4,4,5,5-tetramethyl-2-(2-methyl-propenyl)-[1,3,2]dioxaborolane (141 mg, 0.77 mmol) were dissolved in 1 mL of 1 M sodium carbonate and 6 mL of dimethoxyethane, and charged with nitrogen for 5 minutes. PdCl$_2$(PPh$_3$)$_2$ (12 mg, 0.0175 mmol) was added thereto, and the mixture was reacted in the same manner as in Step A of Example 193 to obtain the title compound (70 mg, 53% yield).

$^1$H NMR (500 MHz, CDCl$_3$) δ 7.20 (dd, 1H), 7.04-6.99 (m, 1H), 6.99-6.95 (m, 1H), 6.95-6.89 (m, 2H), 6.84 (d, 1H), 5.83 (s, 1H), 5.42 (s, 1H), 4.15 (q, 2H), 4.10 (t, 2H), 2.55 (t, 2H), 2.19-2.12 (m, 2H), 1.85 (s, 3H), 1.57 (s, 3H), 1.26 (t, 3H)

Step B: 4-[4-(2,2-dimethyl-2,3-dihydro-benzofuran-4-yl)-2-fluoro-phenoxy]-butyric acid ethyl ester 4-[3-Fluoro-3'-hydroxy-2'-(2-methyl-propenyl)-biphenyl-4-yloxy]-butyric acid ethyl ester (70 mg, 0.188 mmol) obtained in Step A and Amberlyst 15 resin (70 mg) were reacted in the same manner as in Step C of Example 291 to obtain the title compound (40 mg, 57% yield).

$^1$H NMR (500 MHz, CDCl$_3$) δ 7.20-7.11 (m, 3H), 7.00 (dd, 1H), 6.85 (d, 1H), 6.72 (d, 1H), 4.15 (q, 2H), 4.11 (t, 2H), 3.08 (s, 2H), 2.56 (t, 2H), 2.20-2.12 (m, 2H), 1.47 (s, 6H), 1.26 (t, 3H)

Step C: 4-[4-(2,2-dimethyl-2,3-dihydro-benzofuran-4-yl)-2-fluoro-phenoxy]-butyric acid 4-[4-(2,2-Dimethyl-2,3-dihydro-benzofuran-4-yl)-2-fluoro-phenoxy]-butyric acid ethyl ester (40 mg, 0.107 mmol) obtained in Step B was reacted in the same manner as in Step B of Example 287 to obtain the title compound (36 mg, 97% yield).

$^1$H NMR (500 MHz, CDCl$_3$) δ 7.20-7.11 (m, 3H), 6.99 (dd, 1H), 6.85 (d, 1H), 6.72 (d, 1H), 4.13 (t, 2H), 3.08 (s, 2H), 2.64 (t, 2H), 2.21-2.14 (m, 2H), 1.47 (s, 6H)

Example 195: 4-{[4-(2-cyclobutylsulfanyl-pyridin-3-yl)-2,6-difluoro-phenyl]-methyl-amino}-butyric acid

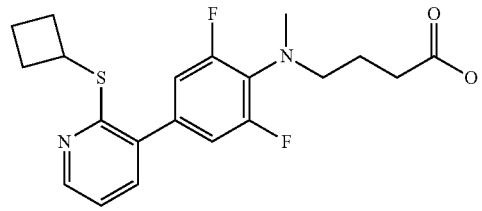

2-Cyclobutylsulfanyl-3-iodo-pyridine (0.045 g, 0.15 mmol) obtained in Preparation Example 13 and 4-{[2,6-difluoro-4-(4,4,5,5-tetramethyl-[1,3,2]dioxaborolan-2-yl)-phenyl]-methyl-amino}-butyric acid methyl ester (0.057 g, 0.15 mmol) obtained in Preparation Example 183 were reacted in the same manner as in Example 1 to obtain the title compound (0.040 g, 66%).

$^1$H-NMR (CDCl$_3$) δ 8.40 (1H, m), 7.32 (1H, m), 7.02 (1H, m), 6.94 (2H, m), 4.44 (1H, m), 3.18 (2H, t), 2.89 (3H, s), 2.50 (4H, m), 2.05 (4H, m), 1.90 (2H, m)

Example 196: 4-{[4-(2-cyclopentyloxy-pyridin-3-yl)-2,6-difluoro-phenyl]-methyl-amino}-butyric acid

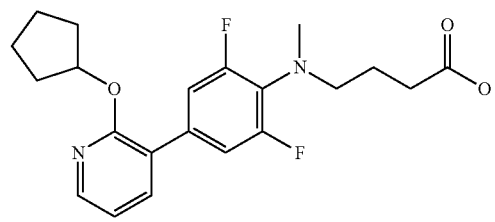 [SMILES: CN(CCCC(=O)O)c1c(F)cc(-c2cccnc2OC2CCCC2)cc1F]

2-Cyclopentyloxy-3-iodo-pyridine (0.030 g, 0.10 mmol) obtained in Preparation Example 11 and 4-{[2,6-difluoro-4-(4,4,5,5-tetramethyl-[1,3,2]dioxaborolan-2-yl)-phenyl]-methyl-amino}-butyric acid methyl ester (0.038 g, 0.10 mmol) obtained in Preparation Example 183 were reacted in the same manner as in Example 1 to obtain the title compound (0.015 g, 37%).

$^1$H-NMR (CDCl$_3$) δ 8.14 (1H, m), 7.57 (1H, m), 7.11 (2H, m), 6.92 (1H, m), 5.52 (1H, m), 3.19 (2H, t), 2.88 (3H, s), 2.48 (2H, t), 1.95 (2H, m), 1.89 (6H, m), 1.64 (2H, m)

Example 197: 4-{[4-(2-cyclopentylsulfanyl-pyridin-3-yl)-2,6-difluoro-phenyl]-methyl-amino}-butyric acid

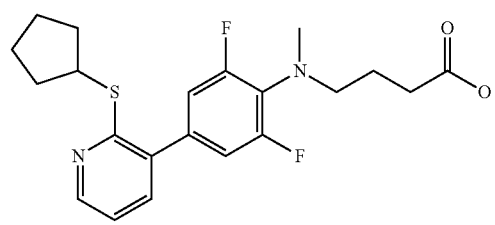 [SMILES: CN(CCCC(=O)O)c1c(F)cc(-c2cccnc2SC2CCCC2)cc1F]

2-Cyclopentylsulfanyl-3-iodo-pyridine (0.037 g, 0.12 mmol) obtained in Preparation Example 15 and 4-{[2,6-difluoro-4-(4,4,5,5-tetramethyl-[1,3,2]dioxaborolan-2-yl)-phenyl]-methyl-amino}-butyric acid methyl ester (0.045 g, 0.12 mmol) obtained in Preparation Example 183 were reacted in the same manner as in Example 1 to obtain the title compound (0.015 g, 30%).

¹H-NMR (CDCl₃) δ 8.42 (1H, m), 7.31 (1H, m), 7.03 (1H, m), 6.95 (2H, m), 4.10 (1H, m), 3.20 (2H, t), 2.89 (3H, s), 2.50 (2H, t), 2.20 (2H, m), 1.90 (2H, m), 1.62 (6H, m)

Example 198: 4-{[2,6-difluoro-4-(2-isopropylsulfanyl-pyridin-3-yl)-phenyl]-methyl-amino}-butyric acid

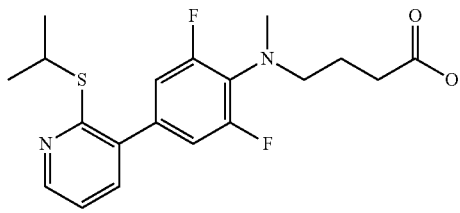 [SMILES: CC(C)Sc1ncccc1-c1cc(F)c(N(C)CCCC(=O)O)c(F)c1]

3-Iodo-2-isopropylsulfanyl-pyridine (0.030 g, 0.11 mmol) obtained in Preparation Example 9 and 4-{[2,6-difluoro-4-(4,4,5,5-tetramethyl-[1,3,2]dioxaborolan-2-yl)-phenyl]-methyl-amino}-butyric acid methyl ester (0.040 g, 0.11 mmol) obtained in Preparation Example 183 were reacted in the same manner as in Example 1 to obtain the title compound (0.025 g, 61%).

¹H-NMR (CDCl₃) δ 8.43 (1H, m), 7.34 (1H, m), 7.02 (1H, m), 6.94 (2H, m), 4.09 (1H, m), 3.19 (2H, t), 2.89 (3H, s), 2.49 (2H, t), 1.90 (2H, m), 1.37 (6H, d)

Example 199: 4-[(3'-cyclobutoxy-3,5-difluoro-biphenyl-4-yl)-methyl-amino]-butyric acid

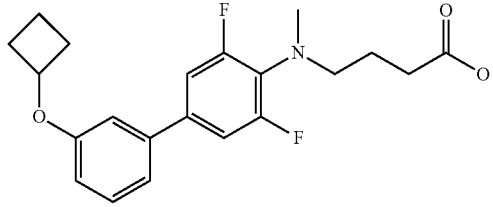

1-Cyclobutoxy-3-iodo-benzene (0.035 g, 0.13 mmol) obtained in Preparation Example 21 and 4-{[2,6-difluoro-4-(4,4,5,5-tetramethyl-[1,3,2]dioxaborolan-2-yl)-phenyl]-methyl-amino}-butyric acid methyl ester (0.047 g, 0.13 mmol) obtained in Preparation Example 183 were reacted in the same manner as in Example 1 to obtain the title compound (0.030 g, 62%).

¹H-NMR (CDCl₃) δ 7.31 (1H, t), 7.07 (3H, m), 6.94 (1H, m), 6.81 (1H, m), 4.70 (1H, m), 3.16 (2H, t), 2.91 (3H, s), 2.47 (4H, m), 2.21 (2H, m), 1.88 (3H, m), 1.71 (1H, m)

Example 200: 4-[5-(2-cyclopentylsulfanyl-pyridin-3-yl)-indol-1-yl]-butyric acid

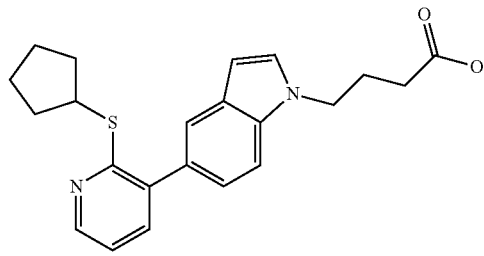 [SMILES: O=C(O)CCCn1ccc2cc(-c3cccnc3SC3CCCC3)ccc21]

2-Cyclopentylsulfanyl-3-iodo-pyridine (0.010 g, 0.03 mmol) obtained in Preparation Example 15 and 4-[5-(4,4,5,5-tetramethyl-[1,3,2]dioxaborolan-2-yl)-indol-1-yl]-butyric acid ethyl ester (0.012 g, 0.03 mmol) obtained in Preparation Example 184 were reacted in the same manner as in Example 1 to obtain the title compound (0.006 g, 48%).

¹H-NMR (CDCl₃) δ 7.31 (1H, t), 7.07 (3H, m), 6.94 (1H, m), 6.81 (1H, m), 4.70 (1H, m), 3.16 (2H, t), 2.91 (3H, s), 2.47 (4H, m), 2.21 (2H, m), 1.88 (3H, m), 1.71 (1H, m)

¹H-NMR (CDCl₃) δ 8.41 (1H, m), 7.65 (1H, s), 7.41 (2H, m), 7.28 (1H, m), 7.13 (1H, m), 7.03 (1H, m), 6.54 (1H, d), 4.25 (2H, t), 4.10 (1H, m), 2.40 (2H, t), 2.22 (4H, m), 1.68 (2H, m), 1.60 (4H, m)

Example 201: 4-[(3,5-difluoro-3'-pyrrolidin-1-yl-biphenyl-4-yl)-methyl-amino]-butyric acid

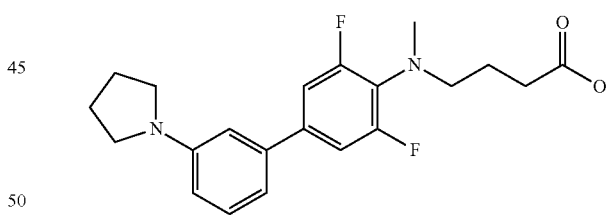

1-(3-Bromophenyl)pyrrolidine (0.030 g, 0.13 mmol) obtained in Preparation Example 53 and 4-{[2,6-difluoro-4-(4,4,5,5-tetramethyl-[1,3,2]dioxaborolan-2-yl)-phenyl]-methyl-amino}-butyric acid methyl ester (0.049 g, 0.13 mmol) obtained in Preparation Example 183 were reacted in the same manner as in Example 1 to obtain the title compound (0.025 g, 50%).

¹H-NMR (CDCl₃) δ 7.25 (1H, m), 7.06 (2H, m), 6.78 (1H, d), 6.62 (1H, s), 6.56 (1H, m), 3.33 (4H, m), 3.17 (2H, t), 2.86 (3H, s), 2.46 (2H, m), 2.03 (4H, m), 1.86 (2H, m)

Example 202: 4-{[4-(6-cyclobutylsulfanyl-pyridin-2-yl)-2,6-difluoro-phenyl]-methyl-amino}-butyric acid

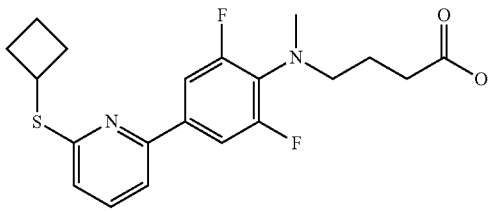 [SMILES: CN(CCCC(=O)O)c1c(F)cc(-c2cccc(SC3CCC3)n2)cc1F]

2-Bromo-6-cyclobutylsulfanyl-pyridine (0.025 g, 0.10 mmol) obtained in Preparation Example 52 and 4-{[2,6-difluoro-4-(4,4,5,5-tetramethyl-[1,3,2]dioxaborolan-2-yl)-phenyl]-methyl-amino}-butyric acid methyl ester (0.038 g, 0.10 mmol) obtained in Preparation Example 183 were reacted in the same manner as in Example 1 to obtain the title compound (0.026 g, 65%).

$^{1}$H-NMR (CDCl$_{3}$) δ 7.54 (3H, m), 7.30 (1H, d), 7.09 (1H, d), 4.17 (1H, m), 3.21 (2H, t), 2.90 (3H, s), 2.46 (2H, t), 2.26 (2H, m), 1.89 (2H, m), 1.70 (4H, m)

Example 203: 4-{[4-(2,2-difluoro-benzo[1,3]dioxol-4-yl)-2,6-difluoro-phenyl]-methyl-amino}-butyric acid

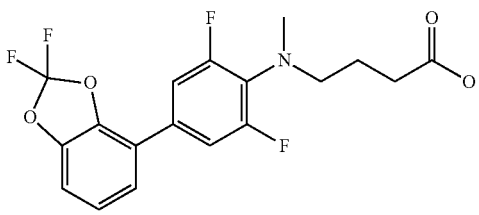 [SMILES: CN(CCCC(=O)O)c1c(F)cc(-c2cccc3c2OC(F)(F)O3)cc1F]

4-Bromo-2,2-difluoro-1,3-benzodioxole (0.025 g, 0.11 mmol) and 4-{[2,6-difluoro-4-(4,4,5,5-tetramethyl-[1,3,2]dioxaborolan-2-yl)-phenyl]-methyl-amino}-butyric acid methyl ester (0.039 g, 0.11 mmol) obtained in Preparation Example 183 were reacted in the same manner as in Example 1 to obtain the title compound (0.025 g, 61%).

$^{1}$H-NMR (CDCl$_{3}$) δ 7.22 (3H, m), 7.15 (1H, t), 7.04 (1H, d), 3.21 (2H, t), 2.90 (3H, s), 2.47 (2H, t), 1.89 (2H, m)

Example 204: 4-{[4-(6-cyclopentyloxy-pyridin-2-yl)-2,6-difluoro-phenyl]-methyl-amino}-butyric acid

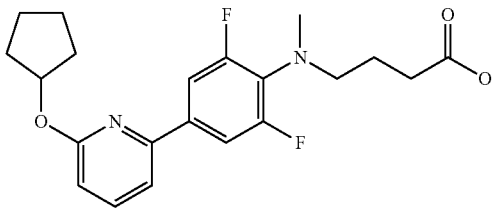 [SMILES: CN(CCCC(=O)O)c1c(F)cc(-c2cccc(OC3CCCC3)n2)cc1F]

2-Bromo-6-cyclopentyloxy-pyridine (0.030 g, 0.12 mmol) obtained in Preparation Example 185 and 4-{[2,6-difluoro-4-(4,4,5,5-tetramethyl-[1,3,2]dioxaborolan-2-yl)-phenyl]-methyl-amino}-butyric acid methyl ester (0.046 g, 0.12 mmol) obtained in Preparation Example 183 were reacted in the same manner as in Example 1 to obtain the title compound (0.025 g, 52%).

$^{1}$H-NMR (CDCl$_{3}$) δ 7.58 (1H, t), 7.53 (2H, m), 7.19 (1H, d), 6.63 (1H, d), 5.51 (1H, m), 3.20 (2H, t), 2.89 (3H, s), 2.47 (2H, t), 2.03 (2H, m), 1.88 (6H, m), 1.65 (2H, m)

Example 205: 4-{[4-(6-cyclobutoxy-pyridin-2-yl)-2,6-difluoro-phenyl]-methyl-amino}-butyric acid

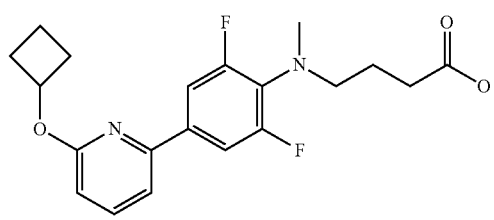 [SMILES: CN(CCCC(=O)O)c1c(F)cc(-c2cccc(OC3CCC3)n2)cc1F]

2-Bromo-6-cyclobutoxy-pyridine (0.030 g, 0.13 mmol) obtained in Preparation Example 186 and 4-{[2,6-difluoro-4-(4,4,5,5-tetramethyl-[1,3,2]dioxaborolan-2-yl)-phenyl]-methyl-amino}-butyric acid methyl ester (0.049 g, 0.13 mmol) obtained in Preparation Example 183 were reacted in the same manner as in Example 1 to obtain the title compound (0.020 g, 41%).

$^{1}$H-NMR (CDCl$_{3}$) δ 7.61 (1H, t), 7.51 (2H, m), 7.21 (1H, d), 6.64 (1H, d), 5.27 (1H, m), 3.20 (2H, t), 2.89 (3H, s), 2.51 (2H, m), 2.47 (2H, t), 2.20 (2H, m), 1.88 (3H, m), 1.75 (1H, m)

Example 206: 4-{[4-(2-cyclobutoxy-pyridin-3-yl)-2,6-difluoro-phenyl]-methyl-amino}-butyric acid

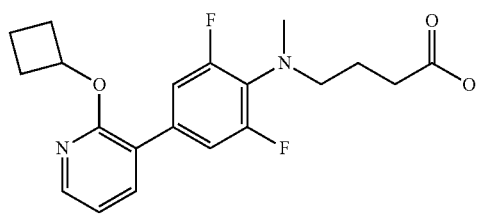

2-Cyclobutoxy-3-iodo-pyridine (0.030 g, 0.11 mmol) obtained in Preparation Example 41 and 4-{[2,6-difluoro-4-(4,4,5,5-tetramethyl-[1,3,2]dioxaborolan-2-yl)-phenyl]-methyl-amino}-butyric acid methyl ester (0.040 g, 0.11 mmol) obtained in Preparation Example 183 were reacted in the same manner as in Example 1 to obtain the title compound (0.022 g, 54%).

$^{1}$H-NMR (CDCl$_{3}$) δ 8.11 (1H, m), 7.58 (1H, m), 7.15 (2H, m), 6.94 (1H, m), 5.29 (1H, m), 3.20 (2H, t), 2.89 (3H, s), 2.50 (4H, m), 2.16 (2H, m), 1.90 (3H, m), 1.69 (1H, m)

Example 207: 4-{[2,6-difluoro-4-(2-propylsulfanyl-pyridin-3-yl)-phenyl]-methyl-amino}-butyric acid

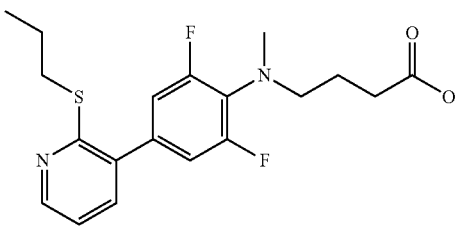 [SMILES: CCCSc1ncccc1-c1cc(F)c(N(C)CCCC(=O)O)c(F)c1]

3-Iodo-2-propylsulfanyl-pyridine (0.030 g, 0.11 mmol) obtained in Preparation Example 28 and 4-{[2,6-difluoro-4-(4,4,5,5-tetramethyl-[1,3,2]dioxaborolan-2-yl)-phenyl]-methyl-amino}-butyric acid methyl ester (0.040 g, 0.11 mmol) obtained in Preparation Example 183 were reacted in the same manner as in Example 1 to obtain the title compound (0.021 g, 51%).
$^1$H-NMR (CDCl$_3$) δ 8.43 (1H, m), 7.34 (1H, m), 7.02 (1H, m), 6.96 (2H, m), 3.19 (2H, t), 3.14 (2H, t), 2.89 (3H, s), 2.50 (2H, m), 1.91 (2H, m), 1.72 (2H, m), 1.03 (3H, t)

Example 208: 4-{[4-(2-ethylsulfanyl-pyridin-3-yl)-2,6-difluoro-phenyl]-methyl-amino}-butyric acid

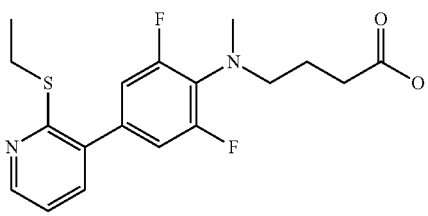 [SMILES: CCSc1ncccc1-c1cc(F)c(N(C)CCCC(=O)O)c(F)c1]

2-Ethylsulfanyl-3-iodo-pyridine (0.030 g, 0.11 mmol) obtained in Preparation Example 33 and 4-{[2,6-difluoro-4-(4,4,5,5-tetramethyl-[1,3,2]dioxaborolan-2-yl)-phenyl]-methyl-amino}-butyric acid methyl ester (0.042 g, 0.11 mmol) obtained in Preparation Example 183 were reacted in the same manner as in Example 1 to obtain the title compound (0.018 g, 43%).
$^1$H-NMR (CDCl$_3$) δ 8.43 (1H, m), 7.35 (1H, m), 7.05 (1H, m), 6.96 (2H, m), 3.19 (4H, m), 2.93 (3H, s), 2.49 (2H, t), 1.92 (2H, m), 1.35 (3H, t)

Example 209: 4-{[4-(2-cyclobutylsulfanyl-pyridin-3-yl)-2-fluoro-phenyl]-methyl-amino}-butyric acid

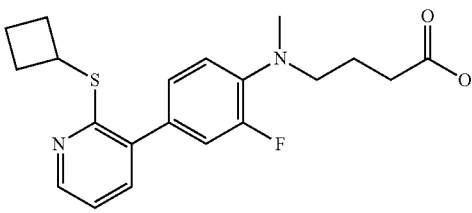 [SMILES: CN(CCCC(=O)O)c1ccc(-c2cccnc2SC2CCC2)cc1F]

2-Cyclobutylsulfanyl-3-iodo-pyridine (0.040 g, 0.14 mmol) obtained in Preparation Example 13 and 4-{[2-fluoro-4-(4,4,5,5-tetramethyl-[1,3,2]dioxaborolan-2-yl)-phenyl]-methyl-amino}-butyric acid methyl ester (0.048 g, 0.14 mmol) obtained in Preparation Example 187 were reacted in the same manner as in Example 1 to obtain the title compound (0.025 g, 48%).
$^1$H-NMR (CDCl$_3$) δ 8.38 (1H, m), 7.34 (1H, m), 7.12 (2H, m), 7.01 (2H, m), 4.43 (1H, m), 3.25 (2H, t), 2.87 (3H, s), 2.51 (4H, m), 2.01 (6H, m)

Example 210: 2-{[4-(2-cyclopentylsulfanyl-pyridin-3-yl)-2,6-difluoro-phenylamino]-methyl}-cyclopropanecarboxylic acid

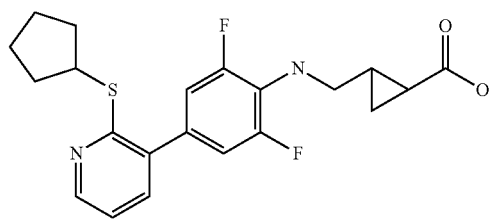 [SMILES: O=C(O)C1CC1CNc1c(F)cc(-c2cccnc2SC2CCCC2)cc1F]

4-(2-Cyclopentylsulfanyl-pyridin-3-yl)-2,6-difluoro-phenylamine (0.050 g, 0.16 mmol) obtained in Preparation Example 188 and 2-formyl-cyclopropanecarboxylic acid ethyl ester (0.026 g, 0.18 mmol) were sequentially reacted in the same manner as in Preparation Example 35 and Step B of Example 1 to obtain the title compound (0.009 g, 14%).
$^1$H-NMR (CDCl$_3$) δ 8.40 (1H, m), 7.30 (1H, m), 7.00 (1H, m), 6.92 (2H, m), 4.09 (1H, m), 3.37 (2H, d), 2.20 (2H, m), 1.82 (1H, m), 1.72 (2H, m), 1.62 (5H, m), 1.32 (2H, m), 0.98 (1H, m)

Example 211: 2-{[4-(2-cyclopentylsulfanyl-pyridin-3-yl)-phenylamino]-methyl}-cyclopropanecarboxylic acid

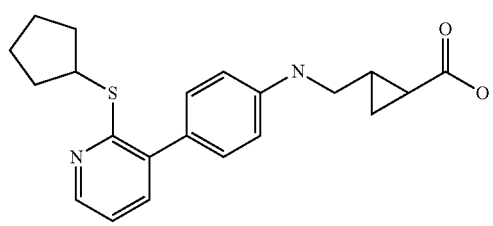 [SMILES: O=C(O)C1CC1CNc1ccc(-c2cccnc2SC2CCCC2)cc1]

Step A: 2-{[4-(2-cyclopentylsulfanyl-pyridin-3-yl)-phenylamino]-methyl}-cyclopropanecarboxylic acid ethyl ester 4-(2-Cyclopentylsulfanyl-pyridin-3-yl)-phenylamine (0.140 g, 0.52 mmol) obtained in Preparation Example 189 and 2-formyl-cyclopropanecarboxylic acid ethyl ester (0.081 g, 0.57 mmol) were reacted in the same manner as in Preparation Example 35 to obtain the title compound (0.150 g, 73%).

Step B: 2-{[4-(2-cyclopentylsulfanyl-pyridin-3-yl)-phenylamino]-methyl}-cyclopropanecarboxylic acid 2-{[4-(2-Cyclopentylsulfanyl-pyridin-3-yl)-phenylamino]-methyl}-cyclopropanecarboxylic acid ethyl ester (0.030 g, 0.08 mmol) obtained in Step A was reacted in the same manner as in Step B of Example 1 to obtain the title compound (0.025 g, 90%).

$^1$H-NMR (CDCl$_3$) δ 8.37 (1H, m), 7.34 (1H, m), 7.26 (2H, d), 7.00 (1H, m), 6.66 (2H, d), 4.09 (1H, m), 3.20 (1H, m), 3.09 (1H, m), 2.19 (2H, m), 1.84 (1H, m), 1.72 (2H, m), 1.60 (5H, m), 1.35 (1H, m), 0.99 (1H, m)

Example 212: 4-{[2-fluoro-4-(2-isopropylsulfanyl-pyridin-3-yl)-phenyl]-methyl-amino}-butyric acid

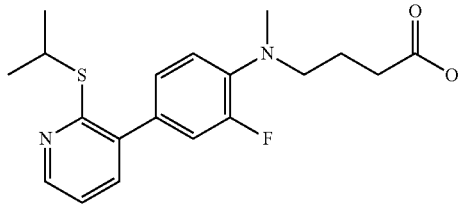 [SMILES: CC(C)Sc1ncccc1-c1ccc(N(C)CCCC(=O)O)c(F)c1]

3-Iodo-2-isopropylsulfanyl-pyridine (0.030 g, 0.11 mmol) obtained in Preparation Example 9 and 4-{[2-fluoro-4-(4,4,5,5-tetramethyl-[1,3,2]dioxaborolan-2-yl)-phenyl]-methyl-amino}-butyric acid methyl ester (0.038 g, 0.11 mmol) obtained in Preparation Example 187 were reacted in the same manner as in Example 1 to obtain the title compound (0.021 g, 54%).

$^1$H-NMR (CDCl$_3$) δ 8.41 (1H, m), 7.35 (1H, m), 7.11 (2H, m), 7.01 (2H, m), 4.06 (1H, m), 3.25 (2H, t), 2.87 (3H, s), 2.51 (2H, t), 1.97 (2H, m), 1.36 (6H, d)

Example 213: 4-{[4-(2-cyclopentylsulfanyl-pyridin-3-yl)-2-fluoro-phenyl]-methyl-amino}-butyric acid

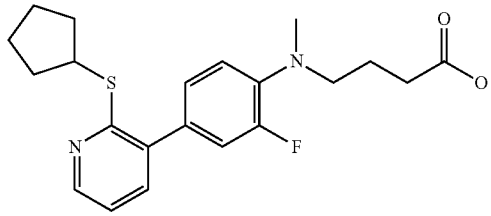 [SMILES: CN(CCCC(=O)O)c1ccc(-c2cccnc2SC2CCCC2)cc1F]

2-Cyclopentylsulfanyl-3-iodo-pyridine (0.030 g, 0.10 mmol) obtained in Preparation Example 15 and 4-{[2-fluoro-4-(4,4,5,5-tetramethyl-[1,3,2]dioxaborolan-2-yl)-phenyl]-methyl-amino}-butyric acid methyl ester (0.035 g, 0.10 mmol) obtained in Preparation Example 187 were reacted in the same manner as in Example 1 to obtain the title compound (0.017 g, 45%).

$^1$H-NMR (CDCl$_3$) δ 8.40 (1H, m), 7.34 (1H, m), 7.12 (2H, m), 7.01 (2H, m), 4.09 (1H, m), 3.25 (2H, t), 2.87 (3H, s), 2.51 (2H, t), 2.20 (2H, m), 1.97 (2H, m), 1.63 (6H, m)

Example 214: 4-{[2,6-difluoro-4-(2-isopropoxy-pyridin-3-yl)-phenyl]-methyl-amino}-butyric acid

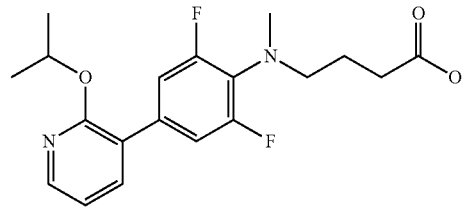

3-Iodo-2-isopropoxy-pyridine (0.030 g, 0.11 mmol) obtained in Preparation Example 34 and 4-{[2,6-difluoro-4-(4,4,5,5-tetramethyl-[1,3,2]dioxaborolan-2-yl)-phenyl]-methyl-amino}-butyric acid methyl ester (0.042 g, 0.11 mmol) obtained in Preparation Example 183 were reacted in the same manner as in Example 1 to obtain the title compound (0.022 g, 55%).

$^1$H-NMR (CDCl$_3$) δ 8.11 (1H, m), 7.55 (1H, m), 7.10 (2H, m), 6.90 (1H, m), 5.41 (1H, m), 3.14 (2H, t), 2.88 (3H, s), 2.41 (2H, t), 1.86 (2H, m), 1.37 (6H, d)

Example 215: 4-[(2'-cyclopentylamino-3,5-difluoro-biphenyl-4-yl)-methyl-amino]-butyric acid

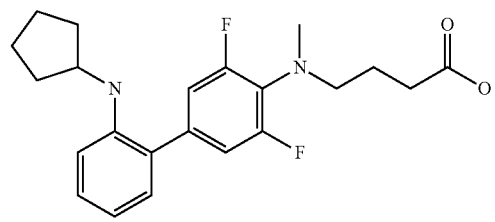 [SMILES: CN(CCCC(=O)O)c1c(F)cc(-c2ccccc2NC2CCCC2)cc1F]

N-cyclopentyl-2-iodo-aniline (0.030 g, 0.10 mmol) obtained in Preparation Example and 4-{[2,6-difluoro-4-(4,4,5,5-tetramethyl-[1,3,2]dioxaborolan-2-yl)-phenyl]-methyl-amino}-butyric acid methyl ester (0.039 g, 0.10 mmol) obtained in Preparation Example 183 were reacted in the same manner as in Example 1 to obtain the title compound (0.015 g, 37%).

$^1$H-NMR (CDCl$_3$) δ 7.23 (1H, m), 7.01 (1H, m), 6.93 (2H, m), 6.72 (2H, m), 3.77 (1H, m), 3.19 (2H, t), 2.88 (3H, s), 2.49 (2H, t), 2.01 (2H, m), 1.90 (2H, m), 1.67 (4H, m), 1.43 (2H, m)

Example 216: 4-[methyl-(3,5,5'-trifluoro-2'-isopropoxy-biphenyl-4-yl)-amino]-butyric acid

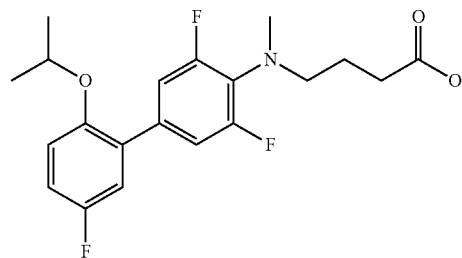 [SMILES: CC(C)Oc1ccc(F)cc1-c1cc(F)c(N(C)CCCC(=O)O)c(F)c1]

2-Bromo-4-fluoro-1-isopropoxy-benzene (0.030 g, 0.13 mmol) obtained in Preparation Example 55 and 4-{[2,6-difluoro-4-(4,4,5,5-tetramethyl-[1,3,2]dioxaborolan-2-yl)-phenyl]-methyl-amino}-butyric acid methyl ester (0.048 g, 0.13 mmol) obtained in Preparation Example 183 were reacted in the same manner as in Example 1 to obtain the title compound (0.030 g, 61%).

$^1$H-NMR (CDCl$_3$) δ 7.08 (2H, m), 6.98 (2H, m), 6.91 (1H, m), 4.37 (1H, m), 3.16 (2H, t), 2.88 (3H, s), 2.47 (2H, t), 1.87 (2H, m), 1.25 (6H, d)

Example 217: 4-{[4-(2-cyclopentyloxy-5-methyl-pyridin-3-yl)-2,6-difluoro-phenyl]-methyl-amino}-butyric acid

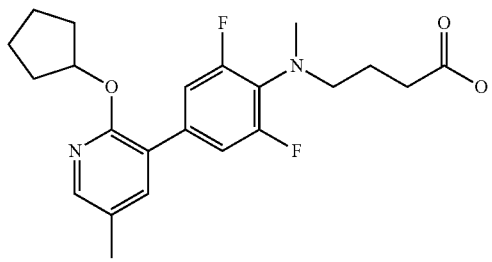 [SMILES: Cc1cnc(OC2CCCC2)c(-c2cc(F)c(N(C)CCCC(=O)O)c(F)c2)c1]

3-Bromo-2-cyclopentyloxy-5-methyl-pyridine (0.030 g, 0.12 mmol) obtained in Preparation Example 57 and 4-{[2,6-difluoro-4-(4,4,5,5-tetramethyl-[1,3,2]dioxaborolan-2-yl)-phenyl]-methyl-amino}-butyric acid methyl ester (0.043 g, 0.12 mmol) obtained in Preparation Example 183 were reacted in the same manner as in Example 1 to obtain the title compound (0.025 g, 53%).

$^1$H-NMR (CDCl$_3$) δ 7.94 (1H, m), 7.40 (1H, m), 7.13 (2H, m), 5.47 (1H, m), 3.19 (2H, t), 2.88 (3H, s), 2.50 (2H, t), 2.27 (3H, s), 1.94 (2H, m), 1.89 (2H, m), 1.78 (4H, m), 1.63 (2H, m)

Example 218: 4-{[4-(2-cyclobutylmethoxy-pyridin-3-yl)-2,6-difluoro-phenyl]-methyl-amino}-butyric acid

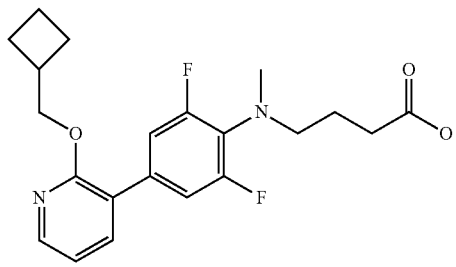 [SMILES: CN(CCCC(=O)O)c1c(F)cc(-c2cccnc2OCC2CCC2)cc1F]

4-{[2,6-Difluoro-4-(2-fluoro-pyridin-3-yl)-phenyl]-methyl-amino}-butyric acid methyl ester (0.050 g, 0.15 mmol) obtained in Preparation Example 190 and cyclobutyl-methanol (0.026 g, 0.30 mmol) were reacted in the same manner as in Preparation Example 34 to obtain the title compound (0.020 g, 35%).

$^1$H-NMR (CDCl$_3$) δ 8.13 (1H, m), 7.59 (1H, m), 7.14 (2H, m), 6.95 (1H, m), 4.32 (2H, d), 3.17 (2H, t), 2.88 (3H, s), 2.80 (1H, m), 2.48 (2H, t), 2.10 (2H, m), 1.89 (6H, m)

Example 219: 4-{[2,6-difluoro-4-(2-methoxy-pyridin-3-yl)-phenyl]-methyl-amino}-butyric acid

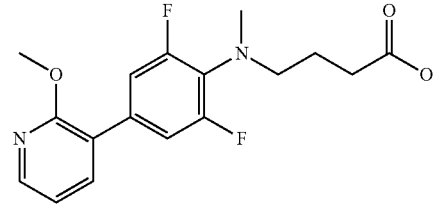 [SMILES: COc1ncccc1-c1cc(F)c(N(C)CCCC(=O)O)c(F)c1]

In the synthesis process of Example 218, the title compound (5 mg, 10%) was obtained as a by-product.

$^1$H-NMR (CDCl$_3$) δ 8.16 (1H, m), 7.58 (1H, m), 7.11 (2H, m), 6.98 (1H, m), 3.98 (3H, s), 3.19 (2H, t), 2.87 (3H, s), 2.48 (2H, t), 1.90 (2H, m)

Example 220: 4-({2,6-difluoro-4-[2-(tetrahydro-furan-3-yloxy)-pyridin-3-yl]-phenyl}-methyl-amino)-butyric acid

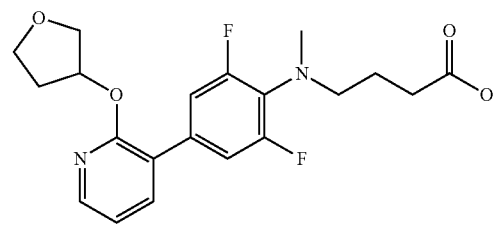 [SMILES: CN(CCCC(=O)O)c1c(F)cc(-c2cccnc2OC2CCOC2)cc1F]

4-{[2,6-Difluoro-4-(2-fluoro-pyridin-3-yl)-phenyl]-methyl-amino}-butyric acid methyl ester (0.050 g, 0.15 mmol) obtained in Preparation Example 190 and tetrahydro-furan-3-ol (0.026 g, 0.30 mmol) were reacted in the same manner as in Preparation Example 34 to obtain the title compound (0.023 g, 40%).

$^1$H-NMR (CDCl$_3$) δ 8.11 (1H, m), 7.59 (1H, m), 7.09 (2H, m), 6.97 (1H, m), 5.64 (1H, m), 4.06 (1H, m), 3.94 (3H, m), 3.19 (2H, t), 2.89 (3H, s), 2.46 (2H, t), 2.26 (1H, m), 2.16 (1H, m), 1.88 (2H, m)

Example 221: 4-[(3,5-difluoro-2'-pyrrolidin-1-yl-biphenyl-4-yl)-methyl-amino]-butyric acid

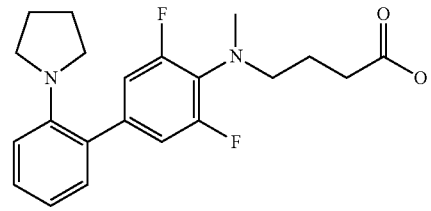 [SMILES: CN(CCCC(=O)O)c1c(F)cc(-c2ccccc2N2CCCC2)cc1F]

1-(2-Iodo-phenyl)-pyrrolidine (0.030 g, 0.11 mmol) obtained in Preparation Example 191 and 4-{[2,6-difluoro-4-(4,4,5,5-tetramethyl-[1,3,2]dioxaborolan-2-yl)-phenyl]-methyl-amino}-butyric acid methyl ester (0.041 g, 0.11 mmol) obtained in Preparation Example 183 were reacted in the same manner as in Example 1 to obtain the title compound (0.020 g, 48%).

¹H-NMR (CDCl₃) δ 7.26 (1H, m), 7.12 (1H, m), 6.97 (2H, m), 6.84 (2H, m), 3.16 (2H, t), 2.94 (4H, m), 2.87 (3H, s), 2.48 (2H, t), 1.88 (2H, m), 1.80 (4H, m)

Example 222: 4-[(3,5-difluoro-2'-methylamino-biphenyl-4-yl)-methyl-amino]-butyric acid

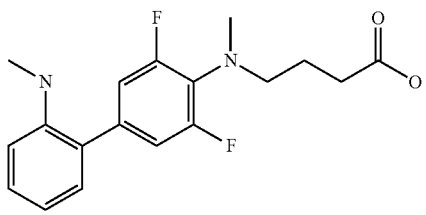 [SMILES: CNc1ccccc1-c1cc(F)c(N(C)CCCC(=O)O)c(F)c1]

(2-Iodo-phenyl)-methyl-amine (0.030 g, 0.13 mmol) obtained in Preparation Example 192 and 4-{[2,6-difluoro-4-(4,4,5,5-tetramethyl-[1,3,2]dioxaborolan-2-yl)-phenyl]-methyl-amino}-butyric acid methyl ester (0.048 g, 0.13 mmol) obtained in Preparation Example 183 were reacted in the same manner as in Example 1 to obtain the title compound (0.023 g, 54%).

¹H-NMR (CDCl₃) δ 7.27 (1H, m), 7.04 (1H, m), 6.93 (2H, m), 6.76 (1H, t), 6.69 (1H, d), 3.18 (2H, t), 2.88 (3H, s), 2.81 (3H, s), 2.48 (2H, t), 2.00 (2H, m)

Example 223: 4-{[3,5-difluoro-2'-(isopropyl-methyl-amino)-biphenyl-4-yl]-methyl-amino}-butyric acid

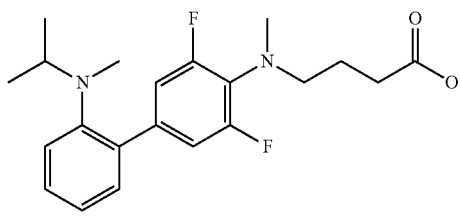 [SMILES: CC(C)N(C)c1ccccc1-c1cc(F)c(N(C)CCCC(=O)O)c(F)c1]

(2-Iodo-phenyl)-isopropyl-methyl-amine (0.030 g, 0.11 mmol) obtained in Preparation Example 193 and 4-{[2,6-difluoro-4-(4,4,5,5-tetramethyl-[1,3,2]dioxaborolan-2-yl)-phenyl]-methyl-amino}-butyric acid methyl ester (0.040 g, 0.11 mmol) obtained in Preparation Example 183 were reacted in the same manner as in Example 1 to obtain the title compound (0.020 g, 48%).

¹H-NMR (CDCl₃) δ 7.25 (1H, m), 7.16 (1H, m), 7.12 (2H, m), 7.05 (2H, m), 3.18 (3H, m), 2.87 (3H, s), 2.58 (3H, s), 2.50 (2H, t), 1.87 (2H, m), 0.85 (6H, d)

Example 224: 4-{[4-(2-cyclobutylsulfanyl-pyridin-3-yl)-2,6-difluoro-phenyl]-ethyl-amino}-butyric acid

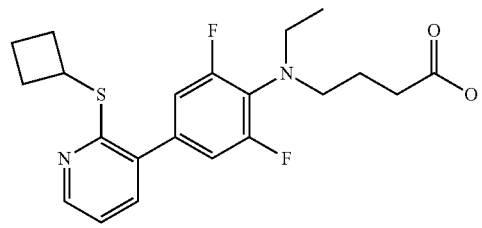 [SMILES: CCN(CCCC(=O)O)c1c(F)cc(-c2cccnc2SC2CCC2)cc1F]

2-Cyclobutylsulfanyl-3-iodo-pyridine (0.050 g, 0.17 mmol) obtained in Preparation Example 13 and 4-{[2,6-difluoro-4-(4,4,5,5-tetramethyl-[1,3,2]dioxaborolan-2-yl)-phenyl]-ethyl-amino}-butyric acid methyl ester (0.066 g, 0.17 mmol) obtained in Preparation Example 194 were reacted in the same manner as in Example 1 to obtain the title compound (0.026 g, 38%).

¹H-NMR (CDCl₃) δ 8.41 (1H, m), 7.35 (1H, m), 7.02 (1H, m), 6.96 (2H, m), 4.44 (1H, m), 3.24 (2H, t), 3.18 (2H, m), 2.49 (4H, m), 2.04 (4H, m), 1.83 (2H, m), 1.08 (3H, t)

Example 225: 4-{[4-(2-cyclobutylmethoxy-pyridin-3-yl)-2,6-difluoro-phenyl]-ethyl-amino}-butyric acid

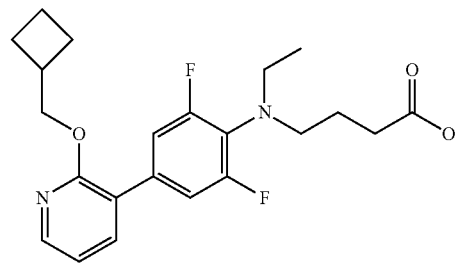 [SMILES: CCN(CCCC(=O)O)c1c(F)cc(-c2cccnc2OCC2CCC2)cc1F]

2-Cyclobutylmethoxy-3-iodo-pyridine (0.050 g, 0.17 mmol) obtained in Preparation Example 48 and 4-{[2,6-difluoro-4-(4,4,5,5-tetramethyl-[1,3,2]dioxaborolan-2-yl)-phenyl]-ethyl-amino}-butyric acid methyl ester (0.066 g, 0.17 mmol) obtained in Preparation Example 194 were reacted in the same manner as in Example 1 to obtain the title compound (0.025 g, 35%).

¹H-NMR (CDCl₃) δ 8.14 (1H, m), 7.61 (1H, m), 7.15 (2H, m), 6.96 (1H, m), 4.33 (2H, d), 3.20 (4H, m), 2.81 (1H, m), 2.48 (2H, t), 2.12 (2H, m), 1.88 (4H, m), 1.79 (2H, m), 1.06 (3H, t)

Example 226: 4-{[2,6-difluoro-4-(2-isopropoxy-pyridin-3-yl)-phenyl]-ethyl-amino}-butyric acid

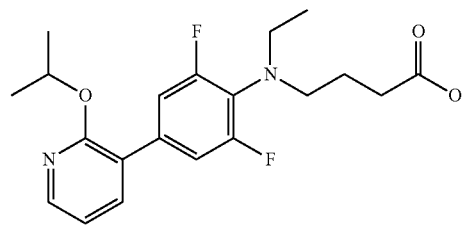 [SMILES: CCN(CCCC(=O)O)c1c(F)cc(-c2cccnc2OC(C)C)cc1F]

3-Iodo-2-isopropoxy-pyridine (0.050 g, 0.19 mmol) obtained in Preparation Example 34 and 4-{[2,6-difluoro-4-(4,4,5,5-tetramethyl-[1,3,2]dioxaborolan-2-yl)-phenyl]-ethyl-amino}-butyric acid methyl ester (0.073 g, 0.19 mmol) obtained in Preparation Example 194 were reacted in the same manner as in Example 1 to obtain the title compound (0.027 g, 37%).

$^1$H-NMR (CDCl$_3$) δ 8.13 (1H, m), 7.57 (1H, m), 7.14 (2H, m), 6.92 (1H, m), 5.42 (1H, m), 3.20 (4H, m), 2.48 (2H, t), 1.82 (2H, m), 1.37 (6H, d), 1.06 (3H, t)

Example 227: (R)-5-[4-(2-cyclobutylsulfanyl-pyridin-3-yl)-2,6-difluoro-phenyl]-hexanoic acid

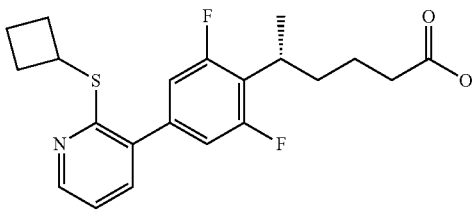

2-Cyclobutylsulfanyl-3-iodo-pyridine (0.050 g, 0.17 mmol) obtained in Preparation Example 13 and (R)-5-[2,6-difluoro-4-(4,4,5,5-tetramethyl-[1,3,2]dioxaborolan-2-yl)-phenyl]-hexanoic acid ethyl ester (0.066 g, 0.17 mmol) obtained in Preparation Example 195 were reacted in the same manner as in Example 1 to obtain the title compound (0.038 g, 56%).

$^1$H-NMR (CDCl$_3$) δ 8.42 (1H, m), 7.36 (1H, m), 7.04 (1H, m), 6.93 (2H, m), 4.44 (1H, m), 3.25 (1H, m), 2.51 (2H, m), 2.38 (2H, t), 2.09 (4H, m), 1.85 (1H, m), 1.70 (2H, m), 1.55 (1H, m), 1.38 (3H, d)

Example 228: (E)-(R)-5-[4-(2-cyclobutylsulfanyl-pyridin-3-yl)-2,6-difluoro-phenyl]-hex-2-enoic acid

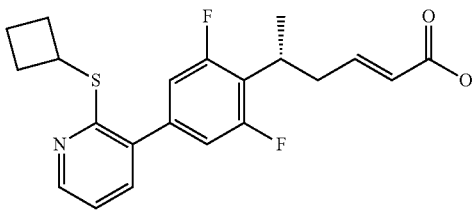 [SMILES: C[C@H](C/C=C/C(=O)O)c1c(F)cc(-c2cccnc2SC2CCC2)cc1F]

2-Cyclobutylsulfanyl-3-iodo-pyridine (0.015 g, 0.05 mmol) obtained in Preparation Example 13 and (E)-(R)-5-[2,6-difluoro-4-(4,4,5,5-tetramethyl-[1,3,2]dioxaborolan-2-yl)-phenyl]-hex-2-enoic acid ethyl ester (0.020 g, 0.05 mmol) obtained in Preparation Example 196 were reacted in the same manner as in Example 1 to obtain the title compound (0.010 g, 50%).

$^1$H-NMR (CDCl$_3$) δ 8.41 (1H, m), 7.35 (1H, m), 7.03 (4H, m), 5.87 (1H, d), 4.43 (1H, m), 3.42 (1H, m), 2.70 (2H, m), 2.52 (2H, m), 2.05 (4H, m), 1.39 (3H, d)

Example 229: (S)-5-[4-(2-cyclobutylsulfanyl-pyridin-3-yl)-2,6-difluoro-phenyl]-hexanoic acid

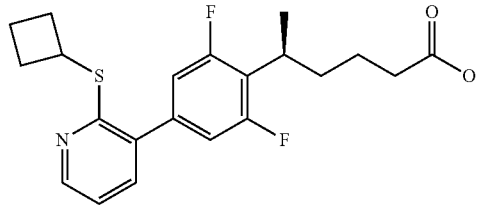

2-Cyclobutylsulfanyl-3-iodo-pyridine (0.040 g, 0.14 mmol) obtained in Preparation Example 13 and (S)-5-[2,6-difluoro-4-(4,4,5,5-tetramethyl-[1,3,2]dioxaborolan-2-yl)-phenyl]-hexanoic acid ethyl ester (0.049 g, 0.13 mmol) obtained in Preparation Example 197 were reacted in the same manner as in Example 1 to obtain the title compound (0.020 g, 39%).

$^1$H-NMR (CDCl$_3$) δ 8.42 (1H, m), 7.36 (1H, m), 7.04 (1H, m), 6.93 (2H, m), 4.44 (1H, m), 3.25 (1H, m), 2.51 (2H, m), 2.38 (2H, t), 2.09 (4H, m), 1.85 (1H, m), 1.70 (2H, m), 1.55 (1H, m), 1.38 (3H, d)

Example 230: 5-{2,6-difluoro-4-[2-(tetrahydro-furan-3-yloxy)-pyridin-3-yl]-phenyl}-hexanoic acid

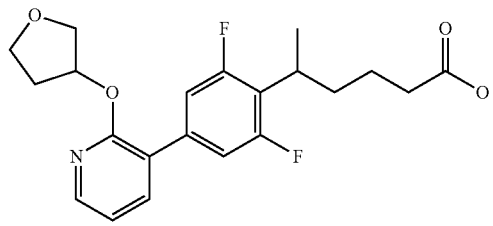

3-Iodo-2-(tetrahydro-furan-3-yloxy)-pyridine (0.040 g, 0.14 mmol) obtained in Preparation Example 49 and 5-[2,6-difluoro-4-(4,4,5,5-tetramethyl-[1,3,2]dioxaborolan-2-yl)phenyl]hexanoic acid ethyl ester (0.049 g, 0.13 mmol) obtained in Preparation Example 32 were reacted in the same manner as in Example 1 to obtain the title compound (0.030 g, 56%).

$^1$H-NMR (CDCl$_3$) δ 8.13 (1H, m), 7.62 (1H, m), 7.07 (2H, m), 6.98 (1H, m), 5.65 (1H, m), 4.07 (1H, m), 3.95 (3H, m), 3.23 (1H, m), 2.36 (3H, m), 2.17 (1H, m), 1.83 (1H, m), 1.72 (2H, m), 1.55 (1H, m), 1.36 (3H, d)

Example 231: 5-{2,6-difluoro-4-[2-(tetrahydro-pyran-4-yloxy)-pyridin-3-yl]-phenyl}-hexanoic acid

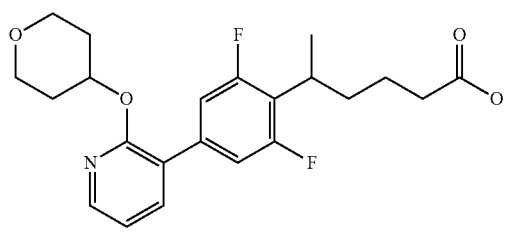 [SMILES: CC(CCCC(=O)O)c1c(F)cc(-c2cccnc2OC2CCOCC2)cc1F]

3-Iodo-2-(tetrahydro-pyran-4-yloxy)-pyridine (0.040 g, 0.13 mmol) obtained in Preparation Example 50 and 5-[2,6-difluoro-4-(4,4,5,5-tetramethyl-[1,3,2]dioxaborolan-2-yl)phenyl]hexanoic acid ethyl ester (0.050 g, 0.13 mmol) obtained in Preparation Example 32 were reacted in the same manner as in Example 1 to obtain the title compound (0.020 g, 43%).

$^1$H-NMR (CDCl$_3$) δ 8.13 (1H, m), 7.62 (1H, m), 7.10 (2H, m), 6.95 (1H, m), 5.38 (1H, m), 3.91 (2H, m), 3.64 (2H, m), 3.24 (1H, m), 2.37 (2H, m), 2.09 (2H, m), 1.85 (3H, m), 1.70 (2H, m), 1.55 (1H, m), 1.37 (3H, d)

Example 232: 5-{2,6-difluoro-4-[2-(oxetan-3-yloxy)-pyridin-3-yl]-phenyl}-hexanoic acid

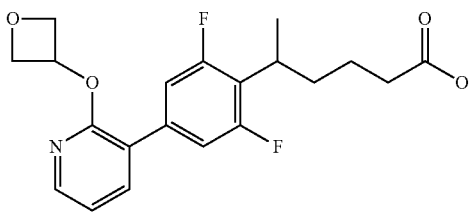 [SMILES: CC(CCCC(=O)O)c1c(F)cc(-c2cccnc2OC2COC2)cc1F]

3-Iodo-2-(oxetan-3-yloxy)-pyridine (0.030 g, 0.11 mmol) obtained in Preparation Example 209 and 5-[2,6-difluoro-4-(4,4,5,5-tetramethyl-[1,3,2]dioxaborolan-2-yl)phenyl]hexanoic acid ethyl ester (0.041 g, 0.11 mmol) obtained in Preparation Example 32 were reacted in the same manner as in Example 1 to obtain the title compound (0.013 g, 32%).

$^1$H-NMR (CDCl$_3$) δ 8.07 (1H, m), 7.64 (1H, m), 7.12 (2H, m), 7.01 (1H, m), 5.66 (1H, m), 5.02 (2H, m), 4.76 (2H, m), 3.25 (1H, m), 2.36 (2H, m), 1.85 (1H, m), 1.73 (2H, m), 1.54 (1H, m), 1.37 (3H, d)

Example 233: 4-[4-(2-cyclobutoxy-pyridin-3-yl)-2-fluoro-phenoxy]-butyric acid

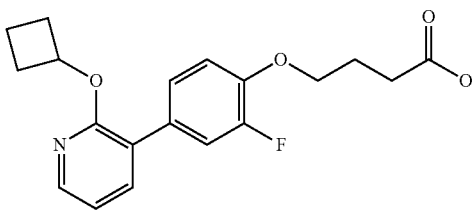 [SMILES: O=C(O)CCCOc1ccc(-c2cccnc2OC2CCC2)cc1F]

2-Cyclobutoxy-3-iodo-pyridine (0.030 g, 0.11 mmol) obtained in Preparation Example 41 and 4-[2-fluoro-4-(4,4,5,5-tetramethyl-1,3,2-dioxaborolan-2-yl)phenoxy]butyric acid ethyl ester (0.038 g, 0.11 mmol) obtained in Preparation Example 198 were reacted in the same manner as in Example 1 to obtain the title compound (0.025 g, 66%).

$^1$H-NMR (CDCl$_3$) δ 8.09 (1H, m), 7.55 (1H, m), 7.40 (1H, m), 7.26 (1H, m), 7.00 (1H, m), 6.92 (1H, m), 5.29 (1H, m), 4.15 (2H, t), 2.64 (2H, t), 2.46 (2H, m), 2.20 (4H, m), 1.82 (1H, m), 1.68 (1H, m)

Example 234: 4-[4-(2-cyclopentyloxy-pyridin-3-yl)-2-fluoro-phenoxy]-butyric acid

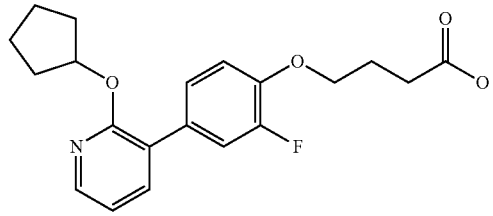

2-Cyclopentyloxy-3-iodo-pyridine (0.030 g, 0.10 mmol) obtained in Preparation Example 11 and 4-[2-fluoro-4-(4,4,5,5-tetramethyl-1,3,2-dioxaborolan-2-yl)phenoxy]butyric acid ethyl ester (0.037 g, 0.10 mmol) obtained in Preparation Example 198 were reacted in the same manner as in Example 1 to obtain the title compound (0.024 g, 64%).

$^1$H-NMR (CDCl$_3$) δ 8.12 (1H, m), 7.56 (1H, m), 7.36 (1H, m), 7.25 (1H, m), 6.97 (1H, m), 6.90 (1H, m), 5.50 (1H, m), 4.14 (2H, t), 2.64 (2H, t), 2.21 (2H, m), 1.93 (2H, m), 1.81 (4H, m), 1.62 (2H, m)

Example 235: 4-[4-(2-cyclobutylsulfanyl-pyridin-3-yl)-2-fluoro-phenoxy]-butyric acid

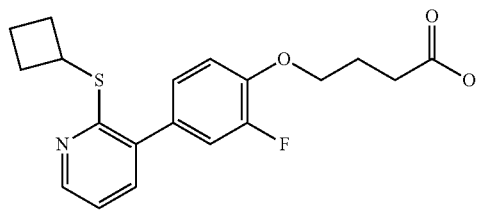

2-Cyclobutylsulfanyl-3-iodo-pyridine (0.030 g, 0.10 mmol) obtained in Preparation Example 13 and 4-[2-fluoro-4-(4,4,5,5-tetramethyl-1,3,2-dioxaborolan-2-yl)phenoxy]butyric acid ethyl ester (0.036 g, 0.10 mmol) obtained in Preparation Example 198 were reacted in the same manner as in Example 1 to obtain the title compound (0.022 g, 59%).

$^1$H-NMR (CDCl$_3$) δ 8.39 (1H, m), 7.32 (1H, m), 7.18 (2H, m), 7.02 (2H, m), 4.42 (1H, m), 4.16 (2H, t), 2.65 (2H, t), 2.49 (2H, m), 2.20 (2H, m), 2.01 (4H, m)

Example 236: 4-[4-(2-cyclopentylsulfanyl-pyridin-3-yl)-2-fluoro-phenoxy]-butyric acid

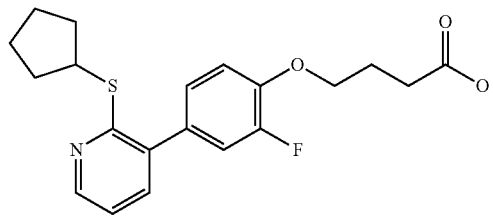 [SMILES: O=C(O)CCCOc1ccc(-c2cccnc2SC2CCCC2)cc1F]

2-Cyclopentylsulfanyl-3-iodo-pyridine (0.030 g, 0.10 mmol) obtained in Preparation Example 15 and 4-[2-fluoro-4-(4,4,5,5-tetramethyl-1,3,2-dioxaborolan-2-yl)phenoxy]

butyric acid ethyl ester (0.035 g, 0.10 mmol) obtained in Preparation Example 198 were reacted in the same manner as in Example 1 to obtain the title compound (0.020 g, 54%).

¹H-NMR (CDCl₃) δ 8.41 (1H, m), 7.33 (1H, m), 7.16 (1H, m), 7.12 (1H, m), 7.02 (2H, m), 4.15 (2H, t), 4.07 (1H, m), 2.63 (2H, t), 2.19 (4H, m), 1.70 (2H, m), 1.61 (4H, m)

Example 237: 6-[4-(2-cyclopentyloxy-pyridin-3-yl)-2,6-difluoro-phenyl]-heptanoic acid

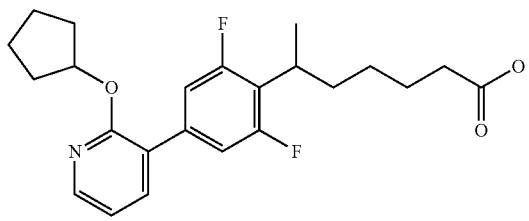 [SMILES: CC(CCCCC(=O)O)c1c(F)cc(-c2cccnc2OC2CCCC2)cc1F]

2-Cyclopentyloxy-3-iodo-pyridine (0.040 g, 0.14 mmol) obtained in Preparation Example 11 and 6-[2,6-difluoro-4-(4,4,5,5-tetramethyl-[1,3,2]dioxaborolan-2-yl)-phenyl]-heptanoic acid ethyl ester (0.055 g, 0.14 mmol) obtained in Preparation Example 199 were reacted in the same manner as in Example 1 to obtain the title compound (0.028 g, 50%).

¹H-NMR (CDCl₃) δ 8.15 (1H, m), 7.60 (1H, m), 7.09 (2H, m), 6.93 (1H, m), 5.52 (1H, m), 3.23 (1H, m), 2.33 (2H, t), 1.97 (2H, m), 1.85 (5H, m), 1.64 (5H, m), 1.35 (4H, m), 1.25 (1H, m)

Example 238: 6-[4-(2-cyclopentylsulfanyl-pyridin-3-yl)-2,6-difluoro-phenyl]-heptanoic acid

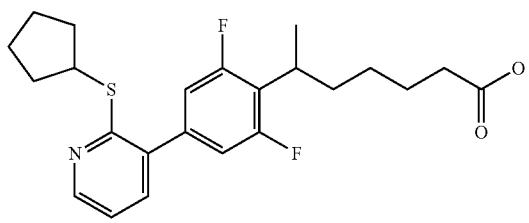

2-Cyclopentylsulfanyl-3-iodo-pyridine (0.040 g, 0.13 mmol) obtained in Preparation Example 15 and 6-[2,6-difluoro-4-(4,4,5,5-tetramethyl-[1,3,2]dioxaborolan-2-yl)-phenyl]-heptanoic acid ethyl ester (0.052 g, 0.13 mmol) obtained in Preparation Example 199 were reacted in the same manner as in Example 1 to obtain the title compound (0.025 g, 45%).

¹H-NMR (CDCl₃) δ 8.43 (1H, m), 7.33 (1H, m), 7.03 (1H, m), 6.93 (2H, m), 4.15 (1H, m), 3.24 (1H, m), 2.34 (2H, t), 2.20 (2H, m), 1.82 (1H, m), 1.64 (10H, m), 1.36 (3H, d), 1.25 (1H, m)

Example 239: 4-[4-(2-cyclopropylmethoxy-pyridin-3-yl)-2-fluoro-phenylsulfanyl]-butyric acid

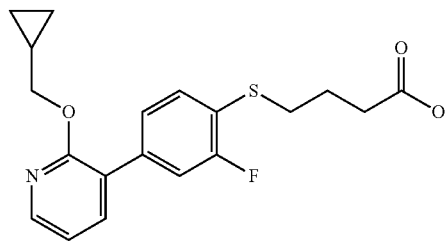

4-[2-Fluoro-4-(4,4,5,5-tetramethyl-[1,3,2]dioxaborolan-2-yl)-phenylsulfanyl]-butyric acid ethyl ester (0.04 g, 0.11 mmol) obtained in Preparation Example 205 and 2-cyclopropylmethoxy-3-iodo-pyridine (0.03 g, 0.11 mmol) obtained in Preparation Example 40 were sequentially reacted in the same manner as in Steps A and B of Example 1 to obtain the title compound (0.020 g, 51%).

¹H-NMR (CDCl₃) δ 8.14 (1H, m), 7.63 (1H, m), 7.44 (3H, m), 6.97 (1H, m), 4.23 (2H, d), 3.04 (2H, t), 2.58 (2H, t), 2.02 (2H, m), 1.29 (1H, m), 0.61 (2H, m), 0.36 (2H, m)

Example 240: 4-[4-(2-cyclopropylmethoxy-pyridin-3-yl)-2-fluoro-phenoxy]-butyric acid

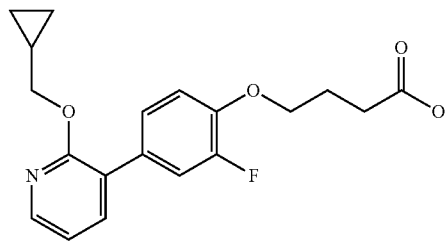 [SMILES: O=C(O)CCCOc1ccc(-c2cccnc2OCC2CC2)cc1F]

2-Cyclopropylmethoxy-3-iodo-pyridine (0.030 g, 0.11 mmol) obtained in Preparation Example 40 and 4-[2-fluoro-4-(4,4,5,5-tetramethyl-1,3,2-dioxaborolan-2-yl)phenoxy] butyric acid ethyl ester (0.038 g, 0.11 mmol) obtained in Preparation Example 198 were reacted in the same manner as in Example 1 to obtain the title compound (0.018 g, 48%).

¹H-NMR (CDCl₃) δ 8.15 (1H, m), 7.64 (1H, m), 7.49 (1H, d), 7.36 (1H, d), 7.07 (1H, t), 7.00 (1H, m), 4.27 (2H, d), 4.21 (2H, t), 2.71 (2H, t), 2.27 (2H, m), 1.34 (1H, m), 0.65 (2H, m), 0.40 (2H, m)

Example 241: 4-[4-(2-cyclobutylmethoxy-pyridin-3-yl)-2-fluoro-phenoxy]-butyric acid

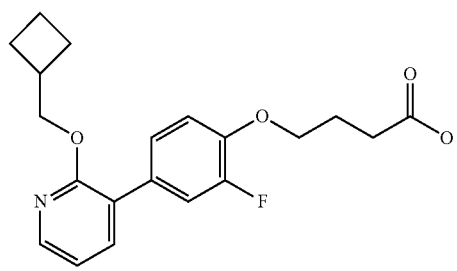 [SMILES: O=C(O)CCCOc1ccc(-c2cccnc2OCC2CCC2)cc1F]

2-Cyclobutylmethoxy-3-iodo-pyridine (0.030 g, 0.10 mmol) obtained in Preparation Example 48 and 4-[2-fluoro-4-(4,4,5,5-tetramethyl-1,3,2-dioxaborolan-2-yl)phenoxy]butyric acid ethyl ester (0.037 g, 0.10 mmol) obtained in Preparation Example 198 were reacted in the same manner as in Example 1 to obtain the title compound (0.022 g, 59%).

$^1$H-NMR (CDCl$_3$) δ 8.16 (1H, m), 7.64 (1H, m), 7.45 (1H, m), 7.32 (1H, m), 7.05 (2H, m), 4.37 (2H, d), 4.21 (2H, t), 2.85 (1H, m), 2.71 (2H, t), 2.26 (2H, m), 2.12 (2H, m), 1.98 (4H, m)

Example 242: 4-[3-(6-cyclopentyloxy-pyridin-2-yl)-phenoxy]-butyric acid

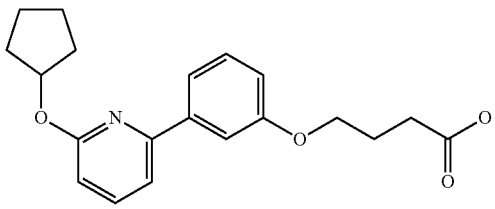 [SMILES: O=C(O)CCCOc1cccc(-c2cccc(OC3CCCC3)n2)c1]

2-Chloro-6-cyclopentyloxy-pyridine (0.030 g, 0.15 mmol) obtained in Preparation Example 12 and 4-[3-(4,4,5,5-tetramethyl-[1,3,2]dioxaborolan-2-yl)-phenoxy]-butyric acid ethyl ester (0.051 g, 0.15 mmol) obtained in Preparation Example 200 were reacted in the same manner as in Example 1 to obtain the title compound (0.035 g, 68%).

$^1$H-NMR (CDCl$_3$) δ 7.60 (3H, m), 7.34 (1H, m), 7.27 (1H, m), 6.92 (1H, m), 6.63 (1H, m), 5.53 (1H, m), 4.12 (2H, t), 2.63 (2H, t), 2.17 (2H, m), 2.04 (2H, m), 1.84 (2H, m), 1.65 (4H, m)

Example 243: 4-[3-(2-cyclopentyloxy-pyridin-3-yl)-phenoxy]-butyric acid

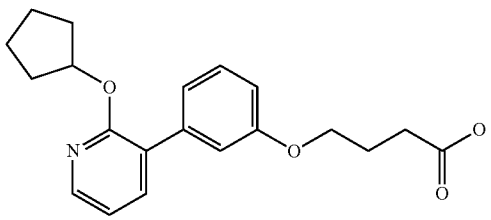 [SMILES: O=C(O)CCCOc1cccc(-c2cccnc2OC2CCCC2)c1]

2-Cyclopentyloxy-3-iodo-pyridine (0.030 g, 0.10 mmol) obtained in Preparation Example 11 and 4-[3-(4,4,5,5-tetramethyl-[1,3,2]dioxaborolan-2-yl)-phenoxy]-butyric acid ethyl ester (0.035 g, 0.10 mmol) obtained in Preparation Example 200 were reacted in the same manner as in Example 1 to obtain the title compound (0.015 g, 42%).

$^1$H-NMR (CDCl$_3$) δ 8.13 (1H, m), 7.61 (1H, m), 7.29 (1H, m), 7.12 (2H, m), 6.92 (1H, m), 6.87 (1H, m), 5.51 (1H, m), 4.07 (2H, t), 2.61 (2H, t), 2.15 (2H, m), 1.98 (2H, m), 1.82 (2H, m), 1.70 (4H, m)

Example 244: 5-[4-(2-cyclopentyloxy-pyridin-3-yl)-2-fluoro-phenyl]-pentanoic acid

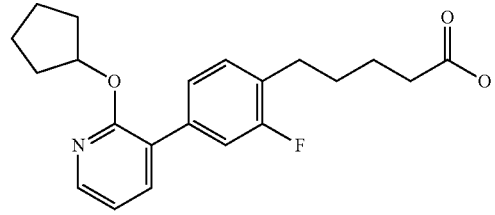 [SMILES: O=C(O)CCCCc1ccc(-c2cccnc2OC2CCCC2)cc1F]

2-Cyclopentyloxy-3-iodo-pyridine (0.030 g, 0.10 mmol) obtained in Preparation Example 11 and 5-[2-fluoro-4-(4,4,5,5-tetramethyl-[1,3,2]dioxaborolan-2-yl)-phenyl]-pentanoic acid ethyl ester (0.036 g, 0.10 mmol) obtained in Preparation Example 201 were reacted in the same manner as in Example 1 to obtain the title compound (0.021 g, 57%).

$^1$H-NMR (CDCl$_3$) δ 8.14 (1H, m), 7.58 (1H, m), 7.25 (2H, m), 7.20 (1H, m), 6.91 (1H, m), 5.51 (1H, m), 2.71 (2H, t), 2.43 (2H, t), 1.95 (2H, m), 1.82 (2H, m), 1.74 (5H, m), 1.66 (3H, m)

Example 245: 5-[4-(2-cyclobutoxy-pyridin-3-yl)-2-fluoro-phenyl]-pentanoic acid

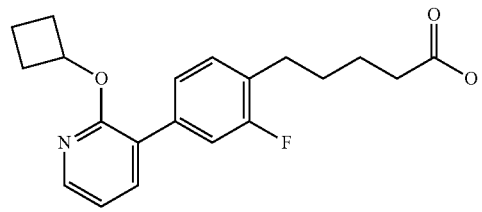 [SMILES: O=C(O)CCCCc1ccc(-c2cccnc2OC2CCC2)cc1F]

2-Cyclobutoxy-3-iodo-pyridine (0.030 g, 0.10 mmol) obtained in Preparation Example 41 and 5-[2-fluoro-4-(4,4,5,5-tetramethyl-[1,3,2]dioxaborolan-2-yl)-phenyl]-pentanoic acid ethyl ester (0.036 g, 0.10 mmol) obtained in Preparation Example 201 were reacted in the same manner as in Example 1 to obtain the title compound (0.021 g, 57%).

$^1$H-NMR (CDCl$_3$) δ 8.11 (1H, m), 7.59 (1H, m), 7.29 (3H, m), 6.94 (1H, m), 5.28 (1H, m), 2.71 (2H, t), 2.45 (4H, m), 2.15 (2H, m), 1.74 (6H, m)

Example 246: 5-[4-(2-cyclobutylmethoxy-pyridin-3-yl)-2-fluoro-phenyl]-pentanoic acid

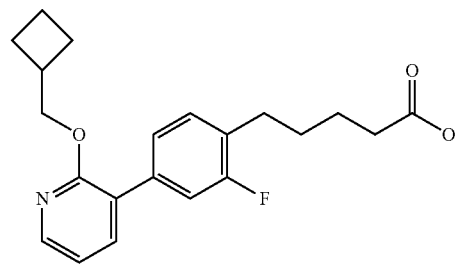 [SMILES: O=C(O)CCCCc1ccc(-c2cccnc2OCC2CCC2)cc1F]

2-Cyclobutylmethoxy-3-iodo-pyridine (0.030 g, 0.10 mmol) obtained in Preparation Example 48 and 5-[2-fluoro-4-(4,4,5,5-tetramethyl-[1,3,2]dioxaborolan-2-yl)-phenyl]-pentanoic acid ethyl ester (0.036 g, 0.10 mmol) obtained in Preparation Example 201 were reacted in the same manner as in Example 1 to obtain the title compound (0.022 g, 59%).

$^1$H-NMR (CDCl$_3$) δ 8.13 (1H, m), 7.62 (1H, m), 7.26 (2H, m), 7.20 (1H, m), 7.95 (1H, m), 4.32 (2H, m), 2.77 (1H, t), 2.71 (2H, t), 2.42 (2H, t), 2.10 (2H, m), 1.88 (4H, m), 1.72 (4H, m)

Example 247: 5-[4-(2-cyclopropylmethoxy-pyridin-3-yl)-2-fluoro-phenyl]-pentanoic acid

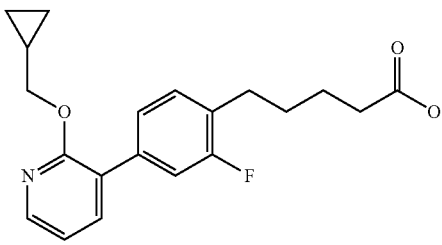 [SMILES: O=C(O)CCCCc1ccc(-c2cccnc2OCC2CC2)cc1F]

2-Cyclopropylmethoxy-3-iodo-pyridine (0.030 g, 0.11 mmol) obtained in Preparation Example 40 and 5-[2-fluoro-4-(4,4,5,5-tetramethyl-[1,3,2]dioxaborolan-2-yl)-phenyl]-pentanoic acid ethyl ester (0.038 g, 0.11 mmol) obtained in Preparation Example 201 were reacted in the same manner as in Example 1 to obtain the title compound (0.020 g, 53%).

$^1$H-NMR (CDCl$_3$) δ 8.11 (1H, m), 7.60 (1H, m), 7.30 (2H, m), 7.21 (1H, m), 6.95 (1H, m), 4.22 (2H, d), 2.71 (2H, t), 2.43 (2H, m), 1.73 (4H, m), 1.29 (1H, m), 0.58 (2H, m), 0.34 (2H, m)

Example 248: 5-[4-(2-cyclopentylsulfanyl-pyridin-3-yl)-2-fluoro-phenyl]-pentanoic acid

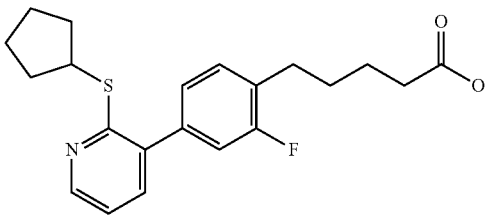

2-Cyclopentylsulfanyl-3-iodo-pyridine (0.030 g, 0.10 mmol) obtained in Preparation Example 15 and 5-[2-fluoro-4-(4,4,5,5-tetramethyl-[1,3,2]dioxaborolan-2-yl)-phenyl]-pentanoic acid ethyl ester (0.034 g, 0.10 mmol) obtained in Preparation Example 201 were reacted in the same manner as in Example 1 to obtain the title compound (0.023 g, 63%).

$^1$H-NMR (CDCl$_3$) δ 8.42 (1H, m), 7.35 (1H, m), 7.25 (1H, m), 7.13 (2H, m), 7.02 (1H, m), 4.09 (1H, m), 2.72 (2H, t), 2.43 (2H, t), 2.19 (2H, m), 1.73 (6H, m), 1.69 (4H, m)

Example 249: 5-[4-(2-cyclobutylsulfanyl-pyridin-3-yl)-2-fluoro-phenyl]-pentanoic acid

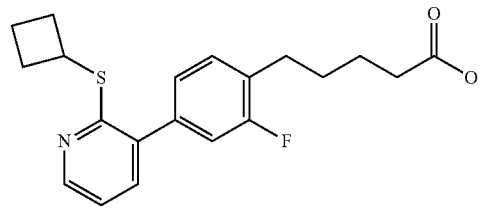

2-Cyclobutylsulfanyl-3-iodo-pyridine (0.030 g, 0.10 mmol) obtained in Preparation Example 13 and 5-[2-fluoro-4-(4,4,5,5-tetramethyl-[1,3,2]dioxaborolan-2-yl)-phenyl]-pentanoic acid ethyl ester (0.039 g, 0.10 mmol) obtained in Preparation Example 201 were reacted in the same manner as in Example 1 to obtain the title compound (0.024 g, 65%).

$^1$H-NMR (CDCl$_3$) δ 8.41 (1H, m), 7.34 (1H, m), 7.25 (1H, m), 7.13 (2H, m), 7.02 (1H, m), 4.43 (1H, m), 2.72 (2H, t), 2.50 (2H, m), 2.42 (2H, t), 2.06 (4H, m), 1.74 (4H, m)

Example 250: 5-[4-(2-cyclobutylmethoxy-pyridin-3-yl)-2,6-difluoro-phenyl]-pentanoic acid

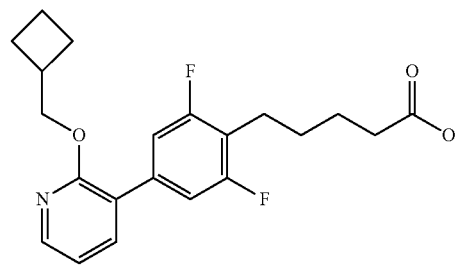 [SMILES: O=C(O)CCCCc1c(F)cc(-c2cccnc2OCC2CCC2)cc1F]

2-Cyclobutylmethoxy-3-iodo-pyridine (0.030 g, 0.10 mmol) obtained in Preparation Example 48 and 5-[2,6-difluoro-4-(4,4,5,5-tetramethyl-[1,3,2]dioxaborolan-2-yl)phenyl]pentanoic acid ethyl ester (0.038 g, 0.10 mmol) obtained in Preparation Example 27 were reacted in the same manner as in Example 1 to obtain the title compound (0.024 g, 62%).

$^1$H-NMR (CDCl$_3$) δ 8.15 (1H, m), 7.61 (1H, m), 7.12 (2H, m), 6.96 (1H, m), 4.29 (2H, d), 2.78 (3H, m), 2.42 (2H, t), 2.11 (2H, m), 1.88 (4H, m), 1.71 (4H, m)

Example 251: 5-[4-(2-cyclobutoxy-pyridin-3-yl)-2,6-difluoro-phenyl]-pentanoic acid

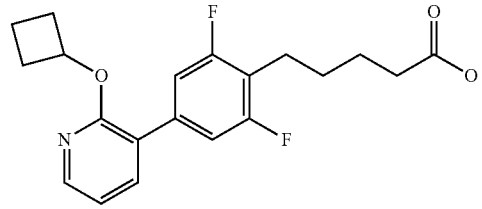

2-Cyclobutoxy-3-iodo-pyridine (0.030 g, 0.11 mmol) obtained in Preparation Example 41 and 5-[2,6-difluoro-4-(4,4,5,5-tetramethyl-[1,3,2]dioxaborolan-2-yl)phenyl]pentanoic acid ethyl ester (0.040 g, 0.11 mmol) obtained in Preparation Example 27 were reacted in the same manner as in Example 1 to obtain the title compound (0.021 g, 53%).

$^1$H-NMR (CDCl$_3$) δ 8.13 (1H, m), 7.59 (1H, m), 7.13 (2H, m), 6.94 (1H, m), 5.28 (1H, m), 2.74 (2H, t), 2.46 (4H, m), 2.15 (2H, m), 1.88 (1H, m), 1.71 (5H, m)

Example 252: 5-[4-(2-cyclopropylmethoxy-pyridin-3-yl)-2,6-difluoro-phenyl]-pentanoic acid

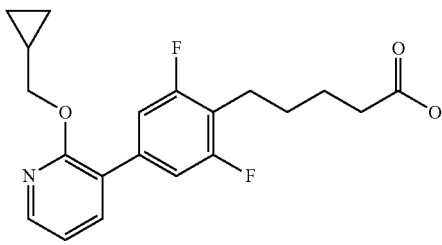 [SMILES: O=C(O)CCCCc1c(F)cc(-c2cccnc2OCC2CC2)cc1F]

2-Cyclopropylmethoxy-3-iodo-pyridine (0.030 g, 0.11 mmol) obtained in Preparation Example 40 and 5-[2,6-difluoro-4-(4,4,5,5-tetramethyl-[1,3,2]dioxaborolan-2-yl)phenyl]pentanoic acid ethyl ester (0.040 g, 0.11 mmol) obtained in Preparation Example 27 were reacted in the same manner as in Example 1 to obtain the title compound (0.026 g, 66%).

$^1$H-NMR (CDCl$_3$) δ 8.13 (1H, m), 7.61 (1H, m), 7.16 (2H, m), 6.96 (1H, m), 4.22 (2H, d), 2.74 (2H, t), 2.43 (2H, t), 1.72 (4H, m), 1.31 (1H, m), 0.60 (2H, m), 0.36 (2H, m)

Example 253: 4-[4-(5-chloro-2,2-dimethyl-2,3-dihydro-benzofuran-7-yl)-2,6-difluoro-phenoxy]-butyric acid

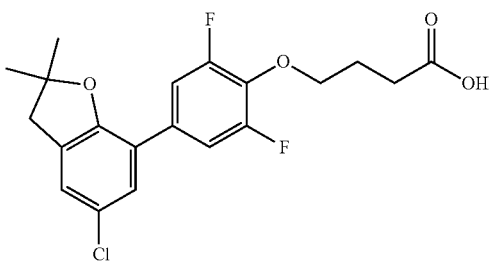 [SMILES: CC1(C)Cc2cc(Cl)cc(-c3cc(F)c(OCCCC(=O)O)c(F)c3)c2O1]

7-Bromo-5-chloro-2,2-dimethyl-2,3-dihydro-benzofuran (0.093 g, 0.36 mmol) obtained in Preparation Example 210 and 4-[2,6-difluoro-4-(4,4,5,5-tetramethyl-1,3,2-dioxaborolan-2-yl)phenoxy]butyric acid ethyl ester (89 mg, 0.24 mmol) obtained in Preparation Example 16 were reacted in the same manner as in Example 1 to obtain the title compound (0.053 g, 56%).

$^1$H-NMR (CDCl$_3$) δ 7.27 (2H, m), 7.18 (1H, m), 7.07 (1H, m), 4.21 (2H, t), 3.02 (2H, s), 2.66 (2H, t), 2.10 (2H, m), 1.50 (6H, s)

Example 254: 4-[4-(5-chloro-2,2-dimethyl-2,3-dihydro-benzofuran-7-yl)-2,6-difluoro-phenylsulfanyl]-butyric acid

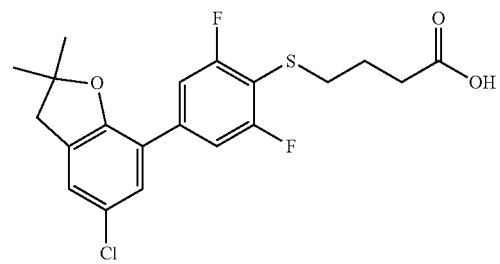 [SMILES: CC1(C)Cc2cc(Cl)cc(-c3cc(F)c(SCCCC(=O)O)c(F)c3)c2O1]

7-Bromo-5-chloro-2,2-dimethyl-2,3-dihydro-benzofuran (0.098 g, 0.37 mmol) obtained in Preparation Example 210 and 4-[2,6-difluoro-4-(4,4,5,5-tetramethyl-[1,3,2]-dioxaborolan-2-yl)-phenylsulfanyl]butyric acid ethyl ester (0.096 g, 0.25 mmol) obtained in Preparation Example 219 were reacted in the same manner as in Example 1 to obtain the title compound (0.024 g, 23%).

$^1$H-NMR (CDCl$_3$) δ 7.31 (2H, m), 7.23 (1H, m), 7.10 (1H, m), 3.03 (2H, s), 2.95 (2H, t), 2.56 (2H, t), 1.89 (2H, m), 1.51 (6H, s)

Example 255: 4-{[4-(5-chloro-2,2-dimethyl-2,3-dihydro-benzofuran-7-yl)-2,6-difluoro-phenyl]-methyl-amino}-butyric acid

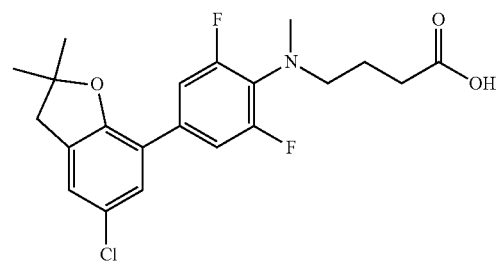 [SMILES: CN(CCCC(=O)O)c1c(F)cc(-c2cc(Cl)cc3c2OC(C)(C)C3)cc1F]

7-bromo-5-chloro-2,2-dimethyl-2,3-dihydro-benzofuran (0.101 g, 0.39 mmol) obtained in Preparation Example 210 and 4-{[2,6-difluoro-4-(4,4,5,5-tetramethyl-[1,3,2]dioxaborolan-2-yl)-phenyl]-methyl-amino}-butyric acid methyl ester (0.160 g, 0.42 mmol) obtained in Preparation Example 183 were reacted in the same manner as in Example 1 to obtain the title compound (0.101 g, 63%).

$^1$H-NMR (CDCl$_3$) δ 7.24 (1H, m), 7.21 (1H, m), 7.19 (1H, m), 7.05 (1H, m), 3.16 (2H, t), 3.02 (2H, s), 2.87 (3H, s), 2.45 (2H, t), 1.86 (2H, m), 1.51 (6H, s)

Example 256: 5-[4-(5-chloro-2,2-dimethyl-2,3-dihydro-benzofuran-7-yl)-2,6-difluoro-phenyl]-hexanoic acid

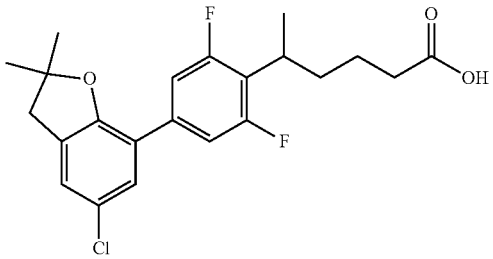

7-Bromo-5-chloro-2,2-dimethyl-2,3-dihydro-benzofuran (0.082 g, 0.31 mmol) obtained in Preparation Example 210 and 5-[2,6-difluoro-4-(4,4,5,5-tetramethyl-[1,3,2]dioxaborolan-2-yl)phenyl]hexanoic acid ethyl ester (0.130 g, 0.34 mmol) obtained in Preparation Example 32 were reacted in the same manner as in Example 1 to obtain the title compound (0.094 g, 74%).

$^1$H-NMR (CDCl$_3$) δ 7.22 (2H, m), 7.19 (1H, m), 7.07 (1H, m), 3.22 (1H, m), 3.02 (2H, s), 2.35 (2H, t), 1.84 (1H, m), 1.68 (2H, m), 1.52 (1H, m), 1.51 (6H, s), 1.34 (3H, d)

Example 257: 4-[2,6-difluoro-4-(7-methoxy-2,2-dimethyl-2,3-dihydro-benzofuran-4-yl)-phenoxy]-butyric acid

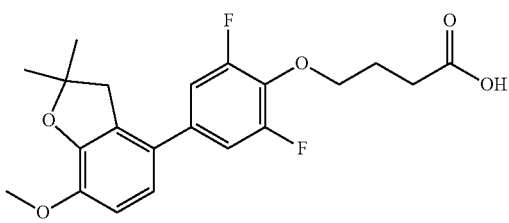 [SMILES: COc1ccc(-c2cc(F)c(OCCCC(=O)O)c(F)c2)c2c1OC(C)(C)C2]

4-Bromo-7-methoxy-2,2-dimethyl-2,3-dihydro-benzofuran (0.083 g, 0.32 mmol) obtained in Preparation Example 211 and 4-[2,6-difluoro-4-(4,4,5,5-tetramethyl-1,3,2-dioxaborolan-2-yl)phenoxy]butyric acid ethyl ester (0.133 g, 0.36 mmol) obtained in Preparation Example 16 were reacted in the same manner as in Example 17 to obtain the title compound (0.097 g, 79%).

$^1$H-NMR (CDCl$_3$) δ 6.94 (2H, m), 6.81 (2H, s), 4.21 (2H, t), 3.90 (3H, s), 3.11 (2H, s), 2.67 (2H, t), 2.11 (2H, m), 1.52 (6H, s)

Example 258: 4-[2,6-difluoro-4-(7-methoxy-2,2-dimethyl-2,3-dihydro-benzofuran-4-yl)-phenylsulfanyl]-butyric acid

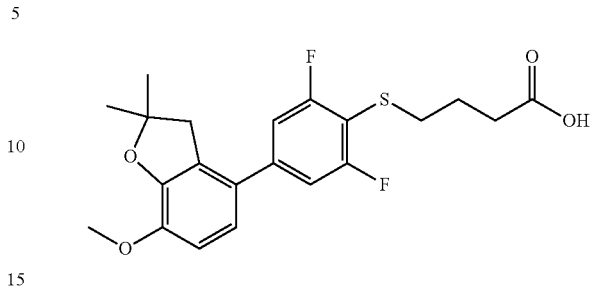

4-Bromo-7-methoxy-2,2-dimethyl-2,3-dihydro-benzofuran (0.061 g, 0.24 mmol) obtained in Preparation Example 211 and 4-[2,6-difluoro-4-(4,4,5,5-tetramethyl-[1,3,2]-dioxaborolan-2-yl)-phenylsulfanyl]butyric acid ethyl ester (0.100 g, 0.26 mmol) obtained in Preparation Example 219 were reacted in the same manner as in Example 17 to obtain the title compound (0.047 g, 48%).

$^1$H-NMR (CDCl$_3$) δ 6.98 (2H, m), 6.84 (2H, m), 3.91 (3H, s), 3.14 (2H, s), 2.96 (2H, t), 2.55 (2H, t), 1.88 (2H, m), 1.53 (6H, s)

Example 259: 4-{[2,6-difluoro-4-(7-methoxy-2,2-dimethyl-2,3-dihydro-benzofuran-4-yl)-phenyl]-methyl-amino}-butyric acid

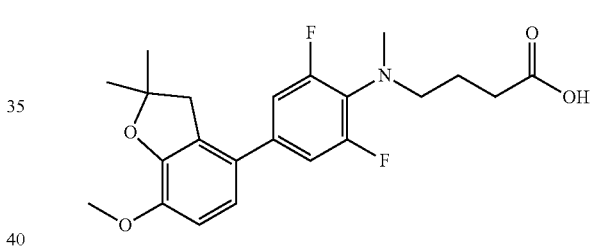

4-Bromo-7-methoxy-2,2-dimethyl-2,3-dihydro-benzofuran (0.061 g, 0.24 mmol) obtained in Preparation Example 211 and 4-{[2,6-difluoro-4-(4,4,5,5-tetramethyl-[1,3,2]dioxaborolan-2-yl)-phenyl]-methyl-amino}-butyric acid methyl ester (0.100 g, 0.26 mmol) obtained in Preparation Example 183 were reacted in the same manner as in Example 17 to obtain the title compound (0.107 g, 100%).

$^1$H-NMR (CDCl$_3$) δ 6.89 (2H, m), 6.81 (2H, s), 3.90 (3H, s), 3.15 (2H, t), 3.13 (2H, s), 2.46 (2H, t), 1.86 (2H, m), 1.52 (6H, s)

Example 260: 5-[2,6-difluoro-4-(7-methoxy-2,2-dimethyl-2,3-dihydro-benzofuran-4-yl-phenyl]-hexanoic acid

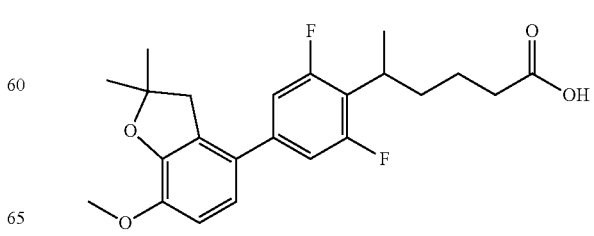

4-Bromo-7-methoxy-2,2-dimethyl-2,3-dihydro-benzofuran (0.061 g, 0.24 mmol) obtained in Preparation Example 211 and 5-[2,6-difluoro-4-(4,4,5,5-tetramethyl-[1,3,2]dioxaborolan-2-yl)phenyl]hexanoic acid ethyl ester (0.099 g, 0.26 mmol) obtained in Preparation Example 32 were reacted in the same manner as in Example 17 to obtain the title compound (0.077 g, 79%).

$^1$H-NMR (CDCl$_3$) δ 6.88 (2H, m), 6.82 (2H, m), 3.90 (3H, s), 3.21 (1H, m), 3.14 (2H, s), 2.35 (2H, t), 1.83 (1H, m), 1.68 (2H, m), 1.53 (1H, m), 1.52 (6H, s), 1.35 (3H, d)

Example 261: 4-(2,6-difluoro-4-spiro[3H-benzofuran-2,1'-cyclopentan]-7-yl-phenoxy)-butyric acid

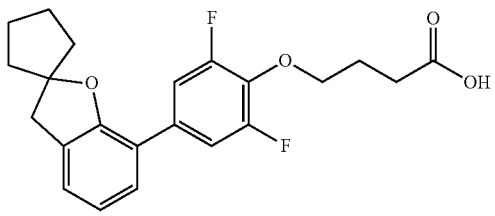 [SMILES: O=C(O)CCCOc1c(F)cc(-c2cccc3c2OC2(CCCC2)C3)cc1F]

7-Bromospiro[3H-benzofuran-2,1'-cyclopentane] (0.062 g, 0.24 mmol) obtained in Preparation Example 212 and 4-[2,6-difluoro-4-(4,4,5,5-tetramethyl-1,3,2-dioxaborolan-2-yl)phenoxy]butyric acid ethyl ester (0.100 g, 0.27 mmol) obtained in Preparation Example 16 were reacted in the same manner as in Example 1 to obtain the title compound (0.087 g, 93%).

$^1$H-NMR (CDCl$_3$) δ 7.32 (2H, m), 7.21 (1H, d), 7.12 (1H, m), 6.88 (1H, t), 4.21 (2H, t), 3.20 (2H, s), 2.67 (2H, t), 2.11 (4H, m), 1.92 (2H, m), 1.75 (4H, m)

Example 262: 4-(2,6-difluoro-4-spiro[3H-benzofuran-2,1'-cyclopentan]-7-yl-phenylsulfanyl)-butyric acid

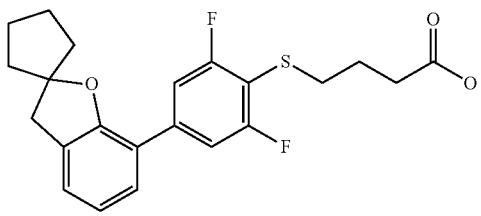 [SMILES: O=C(O)CCCSc1c(F)cc(-c2cccc3c2OC2(CCCC2)C3)cc1F]

7-Bromospiro[3H-benzofuran-2,1'-cyclopentane] (0.067 g, 0.26 mmol) obtained in Preparation Example 212 and 4-[2,6-difluoro-4-(4,4,5,5-tetramethyl-[1,3,2]-dioxaborolan-2-yl)-phenylsulfanyl]butyric acid ethyl ester (0.112 g, 0.29 mmol) obtained in Preparation Example 219 were reacted in the same manner as in Example 1 to obtain the title compound (0.053 g, 50%).

$^1$H-NMR (CDCl$_3$) δ 7.36 (2H, m), 7.25 (1H, d), 7.15 (1H, m), 6.89 (1H, t), 3.21 (2H, s), 2.94 (2H, t), 2.56 (2H, t), 2.11 (2H, m), 1.89 (4H, m), 1.75 (4H, m)

Example 263: 4-(2,6-difluoro-N-methyl-4-spiro[3H-benzofuran-2,1'-cyclopentan]-7-yl-anilino)-butyric acid

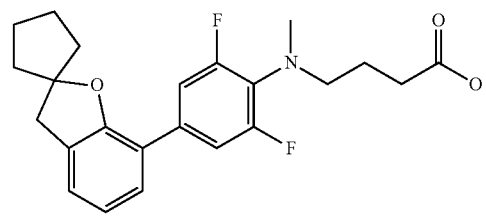 [SMILES: CN(CCCC(=O)O)c1c(F)cc(-c2cccc3c2OC2(CCCC2)C3)cc1F]

7-Bromospiro[3H-benzofuran-2,1'-cyclopentane] (0.067 g, 0.26 mmol) obtained in Preparation Example 212 and 4-{[2,6-difluoro-4-(4,4,5,5-tetramethyl-[1,3,2]dioxaborolan-2-yl)-phenyl]-methyl-amino}-butyric acid methyl ester (0.111 g, 0.29 mmol) obtained in Preparation Example 183 were reacted in the same manner as in Example 1 to obtain the title compound (0.064 g, 61%).

$^1$H-NMR (CDCl$_3$) δ 7.28 (2H, m), 7.22 (1H, d), 7.11 (1H, m), 6.87 (1H, t), 3.20 (2H, s), 3.17 (2H, t), 2.87 (3H, s), 2.47 (2H, t), 2.13 (2H, m), 1.90 (4H, m), 1.75 (4H, m)

Example 264: 5-(2,6-difluoro-4-spiro[3H-benzofuran-2,1'-cyclopentan]-7-yl-phenyl)-hexanoic acid

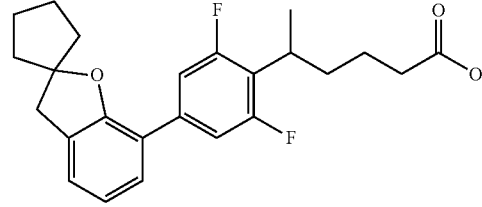 [SMILES: CC(CCCC(=O)O)c1c(F)cc(-c2cccc3c2OC2(CCCC2)C3)cc1F]

7-Bromospiro[3H-benzofuran-2,1'-cyclopentane] (0.067 g, 0.26 mmol) obtained in Preparation Example 212 and 5-[2,6-difluoro-4-(4,4,5,5-tetramethyl-[1,3,2]dioxaborolan-2-yl)phenyl]hexanoic acid ethyl ester (0.100 g, 0.26 mmol) obtained in Preparation Example 32 were reacted in the same manner as in Example 1 to obtain the title compound (0.039 g, 37%).

$^1$H-NMR (CDCl$_3$) δ 7.26 (2H, m), 7.23 (1H, m), 7.12 (1H, m), 6.88 (1H, t), 3.22 (1H, m), 3.20 (2H, s), 2.35 (2H, t), 2.15 (2H, m), 1.93 (2H, m), 1.90-1.52 (8H, m), 1.32 (3H, d)

Example 265: 7-[4-(3-carboxy-propoxy)-3,5-difluoro-phenyl]-5-fluoro-2,2-dimethyl-2,3-dihydro-indol-1-carboxylic acid methyl ester

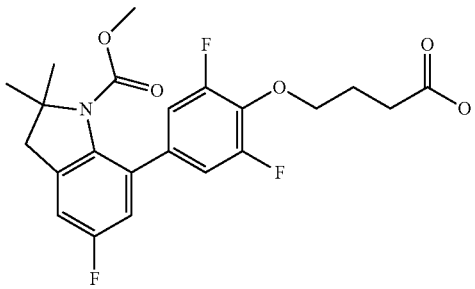 [SMILES: COC(=O)N1c2c(cc(F)cc2-c2cc(F)c(OCCCC(=O)O)c(F)c2)CC1(C)C]

Step A: 7-[4-(3-ethoxycarbonyl-propoxy)-3,5-difluoro-phenyl]-5-fluoro-2,2-dimethyl-2,3-dihydro-indol-1-carboxylic acid methyl ester

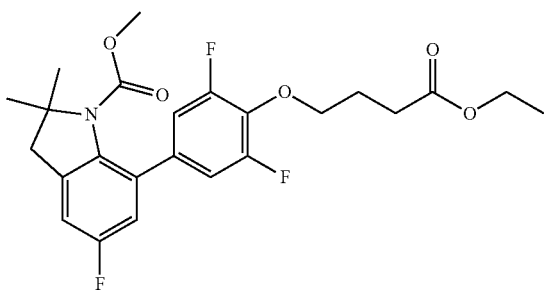 [SMILES: CCOC(=O)CCCOc1c(F)cc(-c2cc(F)cc3c2N(C(=O)OC)C(C)(C)C3)cc1F]

5-Fluoro-7-iodo-2,2-dimethyl-2,3-dihydro-indol-1-carboxylic acid methyl ester (0.074 g, 0.21 mmol) obtained in Preparation Example 213 and 4-[2,6-difluoro-4-(4,4,5,5-tetramethyl-1,3,2-dioxaborolan-2-yl)phenoxy]butyric acid ethyl ester (0.063 g, 0.17 mmol) obtained in Preparation Example 16 were reacted in the same manner as in Step A of Example 1 to obtain the title compound (0.045 g, 46%).

$^1$H-NMR (CDCl$_3$) δ 7.73 (1H, brs), 6.96 (1H, t), 6.91 (2H, m), 4.23 (2H, t), 4.15 (2H, q), 3.86 (3H, s), 2.91 (2H, s), 2.59 (2H, t), 2.11 (2H, m), 1.53 (6H, s), 1.27 (3H, t)

Step B: 7-[4-(3-carboxy-propoxy)-3,5-difluoro-phenyl]-5-fluoro-2,2-dimethyl-2,3-dihydro-indol-1-carboxylic acid methyl ester 7-[4-(3-ethoxycarbonyl-propoxy)-3,5-difluoro-phenyl]-5-fluoro-2,2-dimethyl-2,3-dihydro-indol-1-carboxylic acid methyl ester (0.010 g, 0.021 mmol) obtained in Step A was reacted in the same manner as in Step B of Example 1 to obtain the title compound (0.006 g, 64%).

$^1$H-NMR (CDCl$_3$) δ 7.73 (1H, brs), 6.97 (1H, t), 6.90 (2H, m), 4.25 (2H, t), 3.86 (3H, s), 2.91 (2H, s), 2.67 (2H, t), 2.13 (2H, m), 1.53 (6H, s)

Example 266: 4-[2,6-difluoro-4-(5-fluoro-2,2-dimethyl-2,3-dihydro-1H-indol-7-yl)-phenoxy]-butyric acid

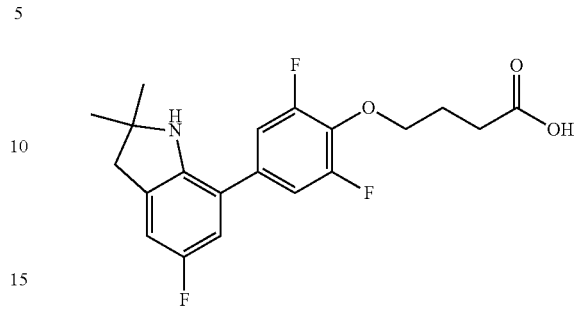

7-[4-(3-Carboxy-propoxy)-3,5-difluoro-phenyl]-5-fluoro-2,2-dimethyl-2,3-dihydro-indol-1-carboxylic acid methyl ester (0.030 g, 0.07 mmol) obtained in Example 265 was dissolved in 3 mL of MeOH and 1 mL of 6N NaOH aqueous solution, and the mixture was stirred at 80° C. for 24 hours under reflux. After removing organic solvent, the reaction solution was adjusted to pH 3 by the use of 6N HCl aqueous solution and extracted with EtOAc to separate an organic layer. The organic layer was dried with MgSO$_4$ and concentrated under reduced pressure to obtain the title compound (0.002 g, 8%).

$^1$H-NMR (CDCl$_3$) δ 6.97 (2H, m), 6.85 (1H, m), 6.52 (1H, m), 4.28 (2H, t), 2.83 (2H, s), 2.71 (2H, t), 2.17 (2H, m), 1.35 (6H, s)

Example 267: 4-[4-(3-carboxy-propoxy)-3,5-difluoro-phenyl]-5-fluoro-2,2-dimethyl-2,3-dihydro-indol-1-carboxylic acid methyl ester

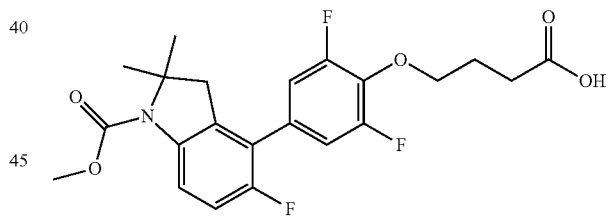

Step A: 4-[4-(3-ethoxycarbonyl-propoxy)-3,5-difluoro-phenyl]-5-fluoro-2,2-dimethyl-2,3-dihydro-indol-1-carboxylic acid methyl ester

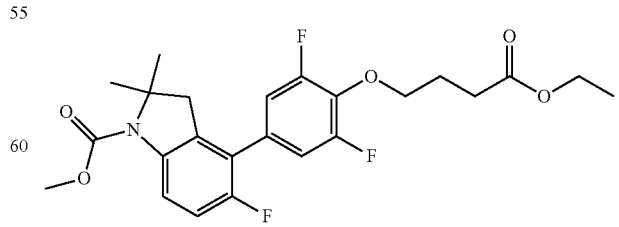

5-Fluoro-4-iodo-2,2-dimethyl-2,3-dihydro-indol-1-carboxylic acid methyl ester (0.085 g, 0.24 mmol) obtained in Preparation Example 214 and 4-[2,6-difluoro-4-(4,4,5,5- tetramethyl-1,3,2-dioxaborolan-2-yl)phenoxy]butyric acid ethyl ester (0.089 g, 0.24 mmol) obtained in Preparation Example 16 were reacted in the same manner as in Step A of Example 1 to obtain the title compound (0.050 g, 45%).

¹H-NMR (CDCl₃) δ 6.89-6.77 (4H, m), 4.18 (2H, q), 4.17 (2H, t), 3.11 (3H, s), 2.97 (2H, s), 2.57 (2H, t), 2.08 (2H, m), 1.57 (6H, s), 1.27 (3H, t)

Step B: 4-[4-(3-carboxy-propoxy)-3,5-difluoro-phenyl]-5-fluoro-2,2-dimethyl-2,3-dihydro-indol-1-carboxylic acid methyl ester 4-[4-(3-Ethoxycarbonyl-propoxy)-3,5-difluoro-phenyl]-5-fluoro-2,2-dimethyl-2,3-dihydro-indol-1-carboxylic acid methyl ester (0.010 g, 0.021 mmol) obtained in Step A was reacted in the same manner as in Step B of Example 1 to obtain the title compound (0.009 g, 100%).

¹H-NMR (CDCl₃) δ 6.87-6.78 (4H, m), 4.20 (2H, t), 3.12 (3H, s), 2.97 (2H, s), 2.65 (2H, t), 2.11 (2H, m), 1.57 (6H, s)

Example 268: 4-[2,6-difluoro-4-(5-fluoro-2,2-dimethyl-2,3-dihydro-1H-indol-4-yl)-phenoxy]-butyric acid

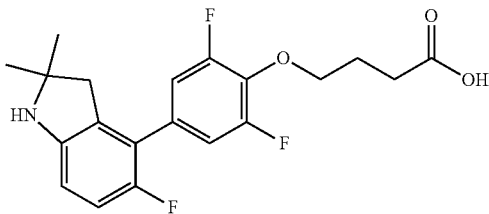 [SMILES: CC1(C)Cc2c(ccc(F)c2-c2cc(F)c(OCCCC(=O)O)c(F)c2)N1]

4-[4-(3-Ethoxycarbonyl-propoxy)-3,5-difluoro-phenyl]-5-fluoro-2,2-dimethyl-2,3-dihydro-indol-1-carboxylic acid methyl ester (0.04 g, 0.085 mmol) obtained in Step A of Example 267 was each 2 mL of MeOH and 6N NaOH aqueous solution, and the mixture was stirred at 80° C. for 48 hours under reflux. After removing organic solvent, the reaction solution was adjusted to pH 3 by the use of 6N HCl aqueous solution and extracted with EtOAc to separate an organic layer. The organic layer was dried with MgSO₄ and concentrated under reduced pressure to obtain the title compound (0.001 g, 3%).

¹H-NMR (CDCl₃) δ 7.08 (2H, m), 6.78 (1H, m), 6.71 (1H, m), 4.21 (2H, t), 2.86 (2H, s), 2.66 (2H, t), 2.11 (2H, m), 1.31 (6H, s)

Example 269: 4-[2,6-difluoro-4-(5-fluoro-2,2-dimethyl-2,3-dihydro-1H-indol-7-yl)-phenylsulfanyl]-butyric acid

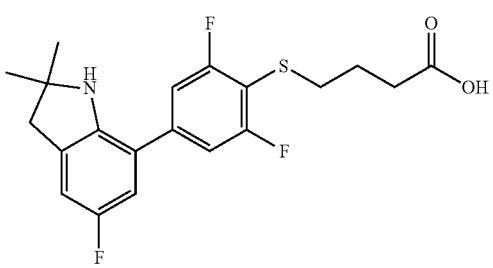 [SMILES: CC1(C)Cc2cc(F)cc(-c3cc(F)c(SCCCC(=O)O)c(F)c3)c2N1]

Step A: 7-[4-(3-ethoxycarbonyl-propylsulfanyl)-3,5-difluoro-phenyl]-5-fluoro-2,2-dimethyl-2,3-dihydro-indol-1-carboxylic acid methyl ester

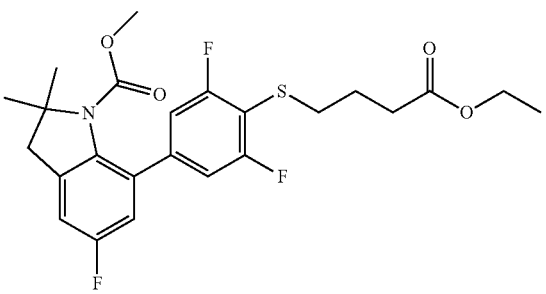 [SMILES: CCOC(=O)CCCSc1c(F)cc(-c2cc(F)cc3c2N(C(=O)OC)C(C)(C)C3)cc1F]

5-Fluoro-7-iodo-2,2-dimethyl-2,3-dihydro-indol-1-carboxylic acid methyl ester (0.148 g, 0.42 mmol) obtained in Preparation Example 213 and 4-[2,6-difluoro-4-(4,4,5,5-tetramethyl-[1,3,2]-dioxaborolan-2-yl)-phenylsulfanyl]butyric acid ethyl ester (0.162 g, 0.42 mmol) obtained in Preparation Example 219 were reacted in the same manner as in Step A of Example 17 to obtain the title compound (0.135 g, 67%).

¹H-NMR (CDCl₃) δ 7.79 (1H, brs), 7.02 (1H, t), 6.98 (2H, m), 4.17 (2H, q), 3.90 (2H, s), 3.02 (2H, t), 2.97 (2H, s), 2.54 (2H, t), 1.96 (2H, m), 1.59 (6H, s), 1.29 (3H, t)

Step B: 4-[2,6-difluoro-4-(5-fluoro-2,2-dimethyl-2,3-dihydro-1H-indol-7-yl)-phenylsulfanyl]-butyric acid 7-[4-(3-Ethoxycarbonyl-propylsulfanyl)-3,5-difluoro-phenyl]-5-fluoro-2,2-dimethyl-2,3-dihydro-indol-1-carboxylic acid methyl ester (0.065 g, 0.134 mmol) obtained in Step A was reacted in the same manner as in Example 266 to obtain the title compound (0.005 g, 9%).

¹H-NMR (CDCl₃) δ 6.96 (2H, m), 6.81 (1H, m), 6.50 (1H, m), 2.95 (2H, t), 2.80 (2H, s), 2.54 (2H, t), 1.90 (2H, m), 1.30 (6H, s)

Example 270: 3-[6-(2-isopropylsulfanyl-pyridin-3-yl)-thiochroman-2-yl]-propionic acid

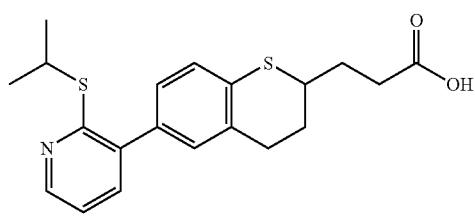 [SMILES: CC(C)Sc1ncccc1-c1ccc2c(c1)CCC(CCC(=O)O)S2]

3-Iodo-2-isopropylsulfanyl-pyridine (0.060 g, 0.21 mmol) obtained in Preparation Example 9 and 3-[6-(4,4,5,5-tetramethyl-[1,3,2]dioxaborolan-2-yl)-thiochroman-2-yl]-propionic acid ethyl ester (0.079 g, 0.21 mmol) obtained in Preparation Example 5 were reacted in the same manner as in Example 17 to obtain the title compound (0.050 g, 64%).

¹H-NMR (CDCl₃) δ 8.40 (1H, m), 7.34 (1H, m), 7.13 (2H, s), 7.06 (1H, s), 7.01 (1H, m), 4.04 (1H, m), 3.37 (1H, m), 2.89 (2H, m), 2.59 (2H, m), 2.25 (1H, m), 2.06 (1H, m), 1.99 (1H, m), 1.86 (1H, m), 1.35 (6H, d)

Example 271: 3-[6-(2-cyclopentoxy-pyridin-3-yl)-thiochroman-2-yl]-propionic acid

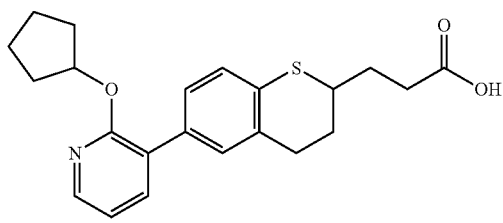 [SMILES: O=C(O)CCC1CCc2cc(-c3cccnc3OC3CCCC3)ccc2S1]

2-Cyclopentyloxy-3-iodo-pyridine (0.072 g, 0.25 mmol) obtained in Preparation Example 11 and 3-[6-(4,4,5,5-tetramethyl-[1,3,2]dioxaborolan-2-yl)-thiochroman-2-yl]-propionic acid ethyl ester (0.095 g, 0.25 mmol) obtained in Preparation Example 5 were reacted in the same manner as in Example 17 to obtain the title compound (0.071 g, 74%).

$^1$H-NMR (CDCl$_3$) δ 8.09 (1H, m), 7.56 (1H, m), 7.27 (1H, m), 7.10 (1H, d), 6.89 (1H, m), 5.49 (1H, m), 3.37 (1H, m), 2.87 (2H, m), 2.59 (2H, m), 2.25 (1H, m), 2.11-1.58 (11H, m)

Example 272: 3-[6-(2-cyclobutylsulfanyl-pyridin-3-yl)-chroman-2-yl]-propionic acid

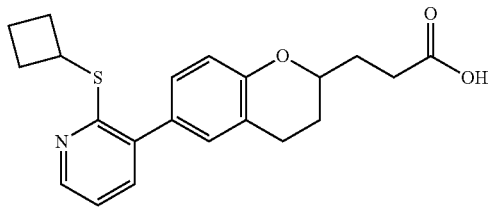

2-Cyclobutylsulfanyl-3-iodo-pyridine (0.050 g, 0.17 mmol) obtained in Preparation Example 13 and 3-[6-(4,4,5,5-tetramethyl-[1,3,2]dioxaborolan-2-yl)-chroman-2-yl]-propionic acid ethyl ester (0.061 g, 0.17 mmol) obtained in Preparation Example 4 were reacted in the same manner as in Example 17 to obtain the title compound (0.038 g, 61%).

$^1$H-NMR (CDCl$_3$) δ 8.36 (1H, m), 7.33 (1H, dd), 7.14 (1H, dd), 6.99 (1H, m), 6.85 (1H, d), 4.42 (1H, t), 4.10 (1H, m), 2.91 (1H, m), 2.80 (1H, m), 2.68 (2H, m), 2.51 (2H, m), 2.01 (7H, m), 1.81 (1H, m)

Example 273: 3-[6-(7-methoxy-2,2-dimethyl-2,3-dihydro-benzofuran-4-yl)-chroman-2-yl]-propionic acid

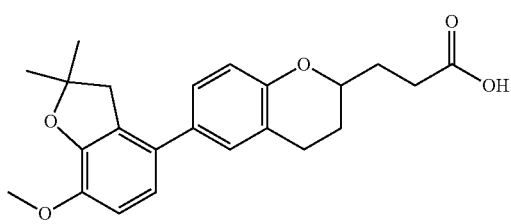 [SMILES: COc1ccc(-c2ccc3c(c2)CCC(CCC(=O)O)O3)c2c1OC(C)(C)C2]

4-Bromo-7-methoxy-2,2-dimethyl-2,3-dihydro-benzofuran (0.068 g, 0.26 mmol) obtained in Preparation Example 211 and 3-[6-(4,4,5,5-tetramethyl-[1,3,2]dioxaborolan-2-yl)-chroman-2-yl]-propionic acid ethyl ester (0.094 g, 0.26 mmol) obtained in Preparation Example 4 were reacted in the same manner as in Example 17 to obtain the title compound (0.054 g, 54%).

$^1$H-NMR (CDCl$_3$) δ 7.13 (1H, m), 7.08 (1H, m), 6.80 (3H, m), 4.08 (1H, m), 3.88 (3H, s), 3.11 (2H, d), 2.88 (1H, m), 2.80 (1H, m), 2.65 (2H, m), 2.02 (3H, m), 1.78 (1H, m), 1.50 (6H, d)

Example 274: 3-[6-(7-methoxy-2,2-dimethyl-2,3-dihydro-benzofuran-4-yl)-thiochroman-2-yl]-propionic acid

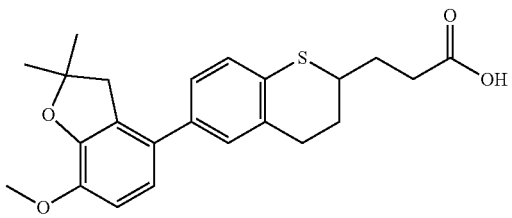

4-Bromo-7-methoxy-2,2-dimethyl-2,3-dihydro-benzofuran (0.068 g, 0.26 mmol) obtained in Preparation Example 211 and 3-[6-(4,4,5,5-tetramethyl-[1,3,2]dioxaborolan-2-yl)-thiochroman-2-yl]-propionic acid ethyl ester (0.098 g, 0.26 mmol) obtained in Preparation Example 5 were reacted in the same manner as in Example 17 to obtain the title compound (0.038 g, 37%).

$^1$H-NMR (CDCl$_3$) δ 7.10 (3H, m), 6.80 (2H, m), 3.88 (3H, s), 3.36 (1H, m), 3.11 (2H, s), 2.89 (2H, m), 2.59 (2H, m), 2.26 (1H, m), 2.06 (1H, m), 1.98 (1H, m), 1.84 (1H, m), 1.50 (6H, s)

Example 275: 3-[6-(2-cyclobutylsulfanyl-pyridin-3-yl)-thiochroman-2-yl]-propionic acid

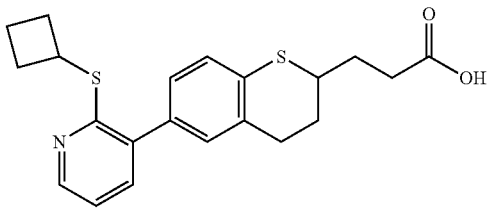 [SMILES: O=C(O)CCC1CCc2cc(-c3cccnc3SC3CCC3)ccc2S1]

2-Cyclobutylsulfanyl-3-iodo-pyridine (0.060 g, 0.20 mmol) obtained in Preparation Example 13 and 3-[6-(4,4,5,5-tetramethyl-[1,3,2]dioxaborolan-2-yl)-thiochroman-2-yl]-propionic acid ethyl ester (0.075 g, 0.20 mmol) obtained in Preparation Example 5 were reacted in the same manner as in Example 17 to obtain the title compound (0.051 g, 66%).

$^1$H-NMR (CDCl$_3$) δ 8.38 (1H, m), 7.34 (1H, dd), 7.14 (2H, s), 7.09 (1H, s), 7.00 (1H, m), 4.41 (1H, m), 3.38 (1H, m), 2.91 (2H, m), 2.63 (2H, m), 2.49 (2H, m), 2.26 (1H, m), 2.13~1.98 (6H, m), 1.87 (1H, m)

Example 276: 3-[6-(2-cyclopropylmethoxy-pyridin-3-yl)-chroman-2-yl]-propionic acid

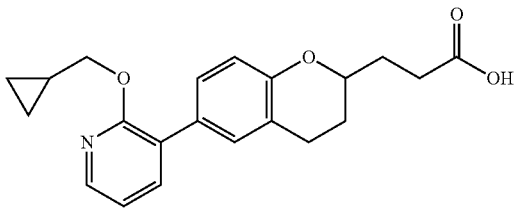 [SMILES: O=C(O)CCC1CCc2cc(-c3cccnc3OCC3CC3)ccc2O1]

2-Cyclopropylmethoxy-3-iodo-pyridine (0.062 g, 0.23 mmol) obtained in Preparation Example 40 and 3-[6-(4,4,5,5-tetramethyl-[1,3,2]dioxaborolan-2-yl)-chroman-2-yl]-propionic acid ethyl ester (0.083 g, 0.23 mmol) obtained in Preparation Example 4 were reacted in the same manner as in Example 17 to obtain the title compound (0.057 g, 70%).

$^1$H-NMR (CDCl$_3$) δ 8.07 (1H, m), 7.58 (1H, dd), 7.36 (1H, m), 7.33 (1H, s), 6.91 (1H, m), 6.84 (1H, d), 4.20 (2H, d), 4.09 (1H, m), 2.92 (1H, m), 2.82 (1H, m), 2.65 (2H, m), 2.04 (3H, m), 1.81 (1H, m), 1.29 (1H, m), 0.56 (2H, m), 0.35 (2H, m)

Example 277: 3-[6-(2-cyclobutoxy-pyridin-3-yl)-chroman-2-yl]-propionic acid

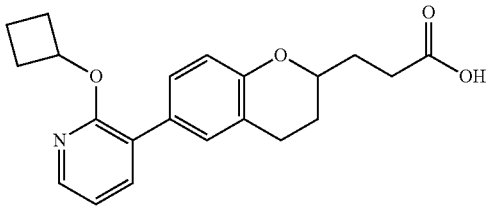 [SMILES: O=C(O)CCC1CCc2cc(-c3cccnc3OC3CCC3)ccc2O1]

2-Cyclobutoxy-3-iodo-pyridine (0.062 g, 0.22 mmol) obtained in Preparation Example 41 and 3-[6-(4,4,5,5-tetramethyl-[1,3,2]dioxaborolan-2-yl)-chroman-2-yl]-propionic acid ethyl ester (0.083 g, 0.22 mmol) obtained in Preparation Example 4 were reacted in the same manner as in Example 17 to obtain the title compound (0.054 g, 69%).

$^1$H-NMR (CDCl$_3$) δ 8.06 (1H, m), 7.55 (1H, dd), 7.35 (1H, dd), 7.28 (1H, m), 6.90 (1H, m), 6.84 (1H, d), 5.25 (1H, m), 4.11 (1H, m), 2.91 (1H, m), 2.81 (1H, m), 2.65 (2H, m), 2.46 (2H, m), 2.12 (2H, m), 2.02 (3H, m), 1.80 (2H, m), 1.67 (1H, m)

Example 278: 3-[6-(2-cyclobutoxy-pyridin-3-yl)-thiochroman-2-yl]-propionic acid

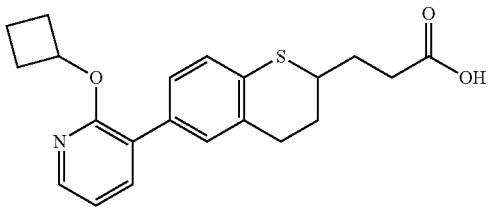 [SMILES: O=C(O)CCC1CCc2cc(-c3cccnc3OC3CCC3)ccc2S1]

2-Cyclobutoxy-3-iodo-pyridine (0.062 g, 0.22 mmol) obtained in Preparation Example 41 and 3-[6-(4,4,5,5-tetramethyl-[1,3,2]dioxaborolan-2-yl)-thiochroman-2-yl]-propionic acid ethyl ester (0.083 g, 0.22 mmol) obtained in Preparation Example 5 were reacted in the same manner as in Example 17 to obtain the title compound (0.051 g, 62%).

$^1$H-NMR (CDCl$_3$) δ 8.08 (1H, m), 7.57 (1H, dd), 7.34 (1H, dd), 7.28 (1H, m), 7.13 (1H, d), 6.91 (1H, m), 5.26 (1H, m), 3.38 (1H, m), 2.91 (2H, m), 2.62 (2H, m), 2.46 (2H, m), 2.26 (1H, m), 2.13-1.98 (4H, m), 1.85 (2H, m), 1.68 (1H, m)

Example 279: 3-[6-(2-cyclopropylmethoxy-pyridin-3-yl)-thiochroman-2-yl]-propionic acid

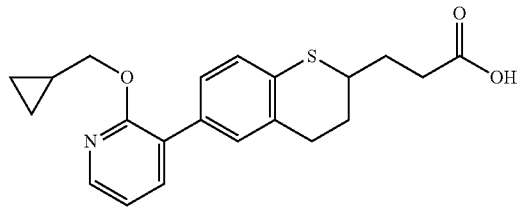 [SMILES: O=C(O)CCC1CCc2cc(-c3cccnc3OCC3CC3)ccc2S1]

2-Cyclopropylmethoxy-3-iodo-pyridine (0.065 g, 0.24 mmol) obtained in Preparation Example 40 and 3-[6-(4,4,5,5-tetramethyl-[1,3,2]dioxaborolan-2-yl]-thiochroman-2-yl]-propionic acid ethyl ester (0.090 g, 0.24 mmol) obtained in Preparation Example 5 were reacted in the same manner as in Example 17 to obtain the title compound (0.053 g, 59%).

$^1$H-NMR (CDCl$_3$) δ 8.08 (1H, dd), 7.58 (1H, dd), 7.34 (2H, m), 7.13 (1H, d), 6.92 (1H, m), 4.20 (2H, d), 3.38 (1H, m), 2.91 (2H, m), 2.61 (2H, m), 2.29 (1H, m), 2.06 (2H, m), 1.88 (2H, m), 1.28 (1H, m), 0.56 (2H, m), 0.34 (2H, m)

Example 280: 3-[6-(2-cyclopentylsulfanyl-pyridin-3-yl)-chroman-2-yl]-propionic acid

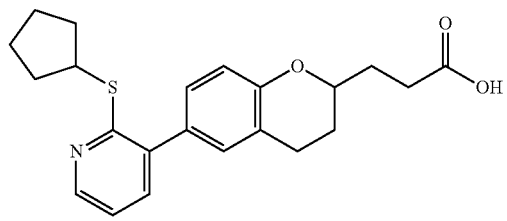 [SMILES: O=C(O)CCC1CCc2cc(-c3cccnc3SC3CCCC3)ccc2O1]

2-Cyclopentylsulfanyl-3-iodo-pyridine (0.068 g, 0.22 mmol) obtained in Preparation Example 15 and 3-[6-(4,4,5,5-tetramethyl-[1,3,2]dioxaborolan-2-yl)-chroman-2-yl]-propionic acid ethyl ester (0.079 g, 0.22 mmol) obtained in Preparation Example 4 were reacted in the same manner as in Example 17 to obtain the title compound (0.057 g, 67%).

$^1$H-NMR (CDCl$_3$) δ 8.39 (1H, dd), 7.33 (1H, dd), 7.15 (1H, dd), 7.09 (1H, s), 7.00 (1H, m), 6.84 (1H, d), 4.08 (2H, m), 2.93 (1H, m), 2.75 (1H, m), 2.66 (2H, m), 2.19 (2H, m), 2.03 (3H, m), 1.85-1.52 (7H, m)

Example 281: 3-[6-(2-cyclopentylsulfanyl-pyridin-3-yl)-thiochroman-2-yl]-propionic acid

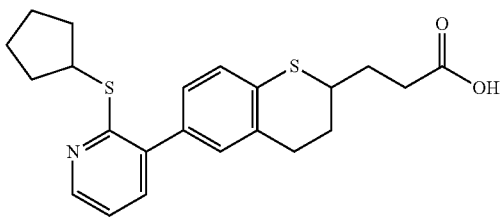

2-Cyclopentylsulfanyl-3-iodo-pyridine (0.072 g, 0.23 mmol) obtained in Preparation Example 15 and 3-[6-(4,4,5,5-tetramethyl-[1,3,2]dioxaborolan-2-yl)-thiochroman-2-yl]-propionic acid ethyl ester (0.087 g, 0.23 mmol) obtained in Preparation Example 5 were reacted in the same manner as in Example 17 to obtain the title compound (0.074 g, 80%).

$^1$H-NMR (CDCl$_3$) δ 8.40 (1H, dd), 7.32 (1H, dd), 7.14 (2H, m), 7.09 (1H, m), 7.00 (1H, m), 4.07 (1H, m), 3.38 (1H, m), 2.89 (2H, m), 2.59 (2H, m), 2.20 (3H, m), 2.03 (2H, m), 1.85 (2H, m), 1.75-1.49 (5H, m)

Example 282: 3-[6-(5-chloro-2,2-dimethyl-2,3-dihydro-benzofuran-7-yl)-thiochroman-2-yl]-propionic acid

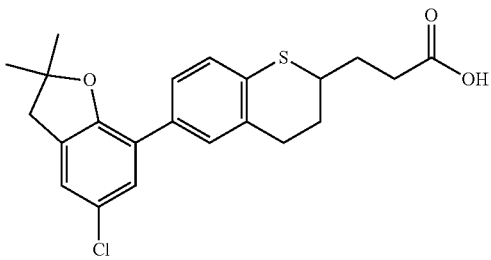 [SMILES: CC1(C)Cc2cc(Cl)cc(-c3ccc4c(c3)CCC(CCC(=O)O)S4)c2O1]

7-Bromo-5-chloro-2,2-dimethyl-2,3-dihydro-benzofuran (0.063 g, 0.24 mmol) obtained in Preparation Example 210 and 3-[6-(4,4,5,5-tetramethyl-[1,3,2]dioxaborolan-2-yl)-thiochroman-2-yl]-propionic acid ethyl ester (0.090 g, 0.24 mmol) obtained in Preparation Example 5 were reacted in the same manner as in Example 17 to obtain the title compound (0.076 g, 78%).

$^1$H-NMR (CDCl$_3$) δ 7.41 (1H, dd), 7.33 (1H, s), 7.20 (1H, s), 7.11 (1H, d), 7.02 (1H, s), 3.36 (1H, m), 3.01 (2H, s), 2.90 (2H, m), 2.59 (2H, m), 2.26 (1H, m), 2.02 (1H, m), 1.85 (1H, m), 1.48 (6H, s)

Example 283: 3-(6-spiro[3H-benzofuran-2,1'-cyclopentan]-7-yl-thiochroman-2-yl)-propionic acid

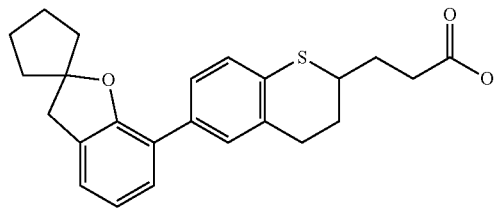 [SMILES: O=C(O)CCC1CCc2cc(-c3cccc4c3OC3(CCCC3)C4)ccc2S1]

7-Bromospiro[3H-benzofuran-2,1'-cyclopentane] (0.058 g, 0.23 mmol) obtained in Preparation Example 212 and 3-[6-(4,4,5,5-tetramethyl-[1,3,2]dioxaborolan-2-yl)-thiochroman-2-yl]-propionic acid ethyl ester (0.090 g, 0.23 mmol) obtained in Preparation Example 5 were reacted in the same manner as in Example 17 to obtain the title compound (0.047 g, 52%).

$^1$H-NMR (CDCl$_3$) δ 7.46 (1H, dd), 7.23 (1H, m), 7.11 (1H, d), 7.08 (1H, dd), 6.86 (1H, m), 3.36 (1H, m), 3.19 (2H, s), 2.90 (2H, m), 2.59 (2H, m), 2.26 (1H, m), 2.11 (3H, m), 1.97 (1H, m), 1.87 (3H, m), 1.73 (4H, m)

Example 284: 3-{6-[2-(tetrahydro-pyran-4-yloxy)-pyridin-3-yl]-thiochroman-2-yl}-propionic acid

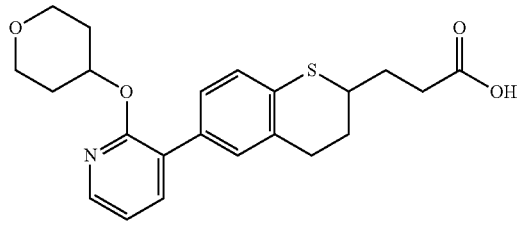 [SMILES: O=C(O)CCC1CCc2cc(-c3cccnc3OC3CCOCC3)ccc2S1]

3-Iodo-2-(tetrahydro-pyran-4-yloxy)-pyridine (0.080 g, 0.26 mmol) obtained in Preparation Example 50 and 3-[6-(4,4,5,5-tetramethyl-[1,3,2]dioxaborolan-2-yl)-thiochroman-2-yl]-propionic acid ethyl ester (0.098 g, 0.26 mmol) obtained in Preparation Example 5 were reacted in the same manner as in Example 17 to obtain the title compound (0.090 g, 86%).

$^1$H-NMR (CDCl$_3$) δ 8.08 (1H, dd), 7.59 (1H, dd), 7.30 (2H, m), 7.13 (1H, d), 6.92 (1H, m), 5.35 (1H, m), 3.91 (2H, m), 3.63 (2H, m), 3.38 (1H, m), 2.90 (2H, m), 2.58 (2H, m), 2.28 (1H, m), 2.04 (4H, m), 1.82 (3H, m)

Example 285: {1-[2,6-difluoro-4-(7-methoxy-2,2-dimethyl-2,3-dihydro-benzofuran-4-yl)-phenyl]-azetidin-3-yl}-acetic acid

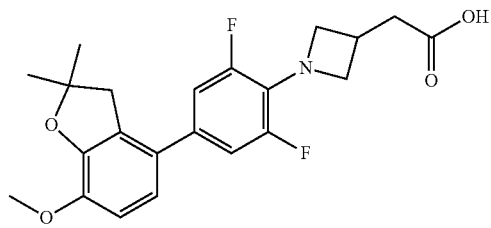 [SMILES: COc1ccc(-c2cc(F)c(N3CC(CC(=O)O)C3)c(F)c2)c2c1OC(C)(C)C2]

4-Bromo-7-methoxy-2,2-dimethyl-2,3-dihydro-benzofuran (0.083 g, 0.32 mmol) obtained in Preparation Example 211 and 2-[1-[2,6-difluoro-4-(4,4,5,5-tetramethyl-1,3,2-dioxaborolan-2-yl)phenyl]azetidin-3-yl]acetic acid ethyl ester (0.121 g, 0.32 mmol) obtained in Preparation Example 88 were reacted in the same manner as in Example 17 to obtain the title compound (0.047 g, 36%).

$^1$H-NMR (CDCl$_3$) δ 6.82 (2H, m), 6.78 (2H, s), 4.39 (2H, m), 3.89 (2H, m), 3.88 (3H, s), 3.11 (2H, s), 3.03 (1H, m), 2.78 (2H, d), 1.51 (6H, s)

Example 286: 3-[6-(6-isopropylsulfanyl-pyridin-2-yl)-thiochroman-2-yl]-propionic acid

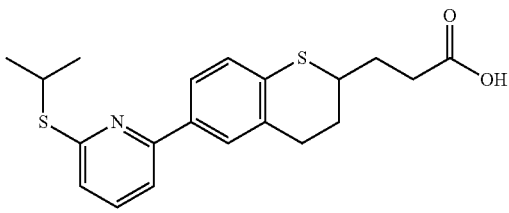 [SMILES: CC(C)Sc1cccc(-c2ccc3c(c2)CCC(CCC(=O)O)S3)n1]

2-Chloro-6-isopropylsulfanyl-pyridine (0.028 g, 0.15 mmol) obtained in Preparation Example 10, 3-[6-(4,4,5,5-tetramethyl-[1,3,2]dioxaborolan-2-yl)-thiochroman-2-yl]-propionic acid ethyl ester (0.057 g, 0.15 mmol) obtained in Preparation Example 5 and Pd(PPh$_3$)$_4$ were reacted in the same manner as in Example 17 to obtain the title compound (0.010 g, 18%).

$^1$H-NMR (CDCl$_3$) δ 7.72 (2H, m), 7.48 (1H, m), 7.34 (1H, d), 7.15 (1H, d), 7.03 (1H, d), 4.13 (1H, m), 3.39 (1H, m), 2.96 (2H, m), 2.62 (2H, m), 2.28 (1H, m), 2.05 (2H, m), 1.86 (1H, m), 1.45 (6H, d)

Example 287: 4-(2,6-difluoro-4-spiro[1,3-benzodioxol-2,1'-cyclopentan]-4-yl-phenoxy)butanoic acid

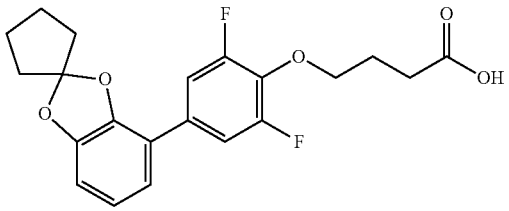 [SMILES: O=C(O)CCCOc1c(F)cc(-c2cccc3c2OC2(CCCC2)O3)cc1F]

Step A: ethyl 4-(2,6-difluoro-4-spiro[1,3-benzodioxol-2,1'-cyclopentan]-4-yl-phenoxy)butanoate 4-Iodospiro[1,3-benzodioxol-2,1'-cyclopentane] (25 mg, 0.083 mmol) obtained in Step C of Preparation Example 215 and 4-[2,6-difluoro-4-(4,4,5,5-tetramethyl-1,3,2-dioxaborolan-2-yl)phenoxy]butyric acid ethyl ester (30.6 mg, 0.083 mmol) were dissolved in 0.2 mL of 2 M sodium carbonate and 2 mL of 1,4-dioxane, and charged with nitrogen for 5 minutes. PdCl$_2$(dppf) (3.4 mg, 0.004 mmol) was added thereto, and the mixture was stirred for 1 hour under reflux. The reaction solution was cooled to room temperature. After addition of water, the reaction solution was extracted with EtOAc to separate an organic layer. The organic layer was dried with anhydrous magnesium sulfate and purified by column chromatography (eluent, EtOAc/Hex=1/4) to obtain the title compound (9 mg, 26% yield).

$^1$H NMR (500 MHz, CDCl$_3$) δ 7.32-7.24 (m, 2H), 6.93-6.90 (m, 1H), 6.84 (dd, 1H), 6.74-6.70 (m, 1H), 4.20 (t, 2H), 4.15 (q, 2H), 2.58 (t, 2H), 2.17-2.11 (m, 4H), 2.10-2.05 (m, 2H), 1.90-1.81 (m, 4H), 1.26 (t, 3H)

Step B: 4-(2,6-difluoro-4-spiro[1,3-benzodioxol-2,1'-cyclopentan]-4-yl-phenoxy)butanoic acid Ethyl 4-(2,6-difluoro-4-spiro[1,3-benzodioxol-2,1'-cyclopentane]-4-yl-phenoxy)butanoate (9 mg, 0.022 mmol) obtained in Step A was dissolved in THF/MeOH/H$_2$O (2:2:1, 1 mL). LiOH (5.15 mg, 0.22 mmol) was added thereto, and the mixture was stirred at room temperature for 4 hours. After termination of the reaction, the reaction solution was concentrated under reduced pressure, adjusted to pH 3 by the use of 1N HCl aqueous solution and extracted with EtOAc. The organic layer was dried with anhydrous magnesium sulfate and concentrated under reduced pressure to obtain the title compound (8.3 mg, 95% yield).

$^1$H NMR (500 MHz, CDCl$_3$) δ 7.32-7.24 (m, 2H), 6.93-6.90 (m, 1H), 6.84 (dd, 1H), 6.74-6.70 (m, 1H), 4.21 (t, 2H), 2.67 (t, 2H), 2.18-2.05 (m, 6H), 1.90-1.81 (m, 4H)

Example 288: 4-(4-spiro[1,3-benzodioxol-2,1'-cyclopentan]-4-ylphenoxy)butanoic acid

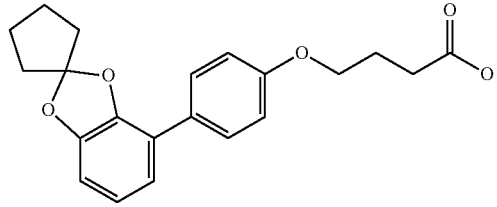 [SMILES: O=C(O)CCCOc1ccc(-c2cccc3c2OC2(CCCC2)O3)cc1]

Step A: 4-spiro[1,3-benzodioxol-2,1'-cyclopentan]-4-ylphenol

4-Iodospiro[1,3-benzodioxol-2,1'-cyclopentane] (50 mg, 0.166 mmol) obtained in Step C of Preparation Example 215, 4-hydroxyphenylboronic acid (23 mg, 0.166 mmol) and K$_2$CO$_3$ (46 mg, 0.33 mmol) were dissolved in 1,4-dioxane/H$_2$O (4:1, 2 mL), and charged with nitrogen gas for 5 minutes. Pd(PPh$_3$)$_4$ (9.6 mg, 0.0083 mmol) was added thereto, and the mixture was stirred for 1 hour under reflux. After termination of the reaction, the reaction solution was diluted with water and extracted with EtOAc to separate an organic layer. The organic layer was concentrated under reduced pressure and purified by column chromatography (eluent, EtOAc/Hex=1/2) to obtain the title compound (41 mg, 92% yield).

$^1$H NMR (500 MHz, CDCl$_3$) δ 7.61 (d, 2H), 6.95 (d, 1H), 6.88 (d, 2H), 6.83 (dd, 1H), 6.68 (d, 1H), 2.17-2.08 (m, 4H), 1.88-1.80 (m, 4H)

Step B: ethyl 4-(4-spiro[1,3-benzodioxol-2,1'-cyclopentan]4-ylphenoxy)butanoate

4-Spiro[1,3-benzodioxol-2,1'-cyclopentan]-4-ylphenol (41 mg, 0.153 mmol) obtained in Step A was dissolved in AN (5 mL), and Cs$_2$CO$_3$ (124 mg, 0.38 mmol) was added thereto. 4-Bromo-butyric acid ethyl ester (26 μL, 0.18 mmol) was added thereto, and the mixture was stirred for 1 hour under reflux. The reaction solution was cooled to room temperature. The reaction solution was concentrated under reduced pressure and purified by column chromatography (eluent, EtOAc/Hex=1/10) to obtain the title compound (28 mg, 48% yield).

$^1$H NMR (500 MHz, CDCl$_3$) δ 7.65 (d, 2H), 6.98-6.92 (m, 3H), 6.83 (dd, 1H), 6.68 (d, 1H), 4.15 (q, 2H), 4.04 (t, 2H), 2.53 (t, 2H), 2.16-2.08 (m, 6H), 1.88-1.80 (m, 4H), 1.26 (t, 3H)

Step C: 4-(4-spiro[1,3-benzodioxol-2,1'-cyclopentan]4-ylphenoxy)butanoic acid

Ethyl 4-(4-spiro[1,3-benzodioxol-2,1'-cyclopentan]4-ylphenoxy)butanoate (28 mg, 0.073 mmol) obtained in Step B was reacted in the same manner as in Step B of Example 287 to obtain the title compound (25 mg, 96% yield).

$^1$H NMR (500 MHz, CDCl$_3$) δ 7.65 (d, 2H), 6.98-6.92 (m, 3H), 6.83 (dd, 1H), 6.68 (d, 1H), 4.04 (t, 2H), 2.62 (t, 2H), 2.17-2.09 (m, 6H), 1.88-1.80 (m, 4H)

Example 289: 4-(2-fluoro-4-spiro[1,3-benzodioxol-2,1'-cyclopentan]-4-yl-phenoxy)butanoic acid

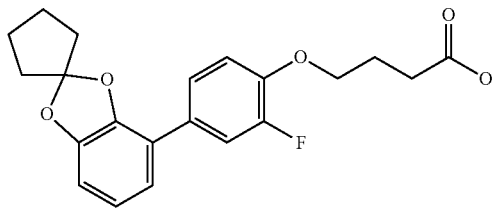 [SMILES: O=C(O)CCCOc1ccc(-c2cccc3c2OC2(CCCC2)O3)cc1F]

Step A: ethyl 4-(2-fluoro-4-spiro[1,3-benzodioxol-2,1'-cyclopentan]-4-yl-phenoxy)butanoate 2-Fluoro-4-spiro[1,3-benzodioxol-2,1'-cyclopentan]-4-yl-phenol (28 mg, 0.098 mmol) was reacted in the same manner as in Step B of Example 288 to obtain the title compound (37 mg, 94% yield).

$^1$H NMR (500 MHz, CDCl$_3$) δ 7.50 (dd, 1H), 7.44-7.40 (m, 1H), 7.00 (dd, 1H), 6.95 (d, 1H), 6.83 (dd, 1H), 6.70 (d, 1H), 4.18-4.09 (m, 4H), 2.55 (t, 2H), 2.19-2.09 (m, 6H), 1.89-1.80 (m, 4H), 1.26 (t, 3H)

Step B: 4-(2-fluoro-4-spiro[1,3-benzodioxol-2,1'-cyclopentan]-4-yl-phenoxy)butanoic acid Ethyl 4-(2-fluoro-4-spiro[1,3-benzodioxol-2,1'-cyclopentan]-4-yl-phenoxy)butanoate (28 mg, 0.073 mmol) obtained in Step A was reacted in the same manner as in Step B of Example 287 to obtain the title compound (25 mg, 96% yield).

$^1$H NMR (500 MHz, CDCl$_3$) δ 7.50 (dd, 1H), 7.44-7.40 (m, 1H), 7.00 (dd, 1H), 6.95 (d, 1H), 6.83 (dd, 1H), 6.70 (d, 1H), 4.12 (t, 2H), 2.64 (t, 2H), 2.19-2.09 (m, 6H), 1.89-1.80 (m, 4H)

Example 290: 4-[4-(2,2-difluoro-benzo[1,3]dioxol-4-yl)-2,6-difluoro-phenoxy]-butyric acid

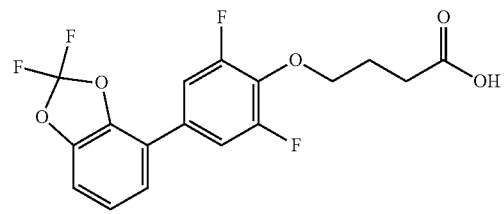 [SMILES: O=C(O)CCCOc1c(F)cc(-c2cccc3c2OC(F)(F)O3)cc1F]

Step A: 4-[4-(2,2-difluoro-benzo[1,3]dioxol-4-yl)-2,6-difluoro-phenoxy]-butyric acid ethyl ester 4-Bromo-2,2-difluoro-benzo[1,3]dioxole (50 mg, 0.21 mmol), 4-[2,6-difluoro-4-(4,4,5,5-tetramethyl-1,3,2-dioxaborolan-2-yl)phenoxy]butyric acid ethyl ester (78 mg, 0.21 mmol) obtained in Preparation Example 16 and NaOH (25 mg, 0.63 mmol) were dissolved in 1,4-dioxane/H$_2$O (4:1, 5 mL), and charged with nitrogen for 5 minutes. Pd(PPh$_3$)$_4$ (12 mg, 0.0105 mmol) was added thereto, and the mixture was stirred for 1 hour under reflux. After termination of the reaction, the reaction solution was diluted with water and extracted with EtOAc to separate an organic layer. The organic layer was concentrated under reduced pressure and purified by column chromatography (eluent, EtOAc/Hex=1/3) to obtain the title compound (20 mg, 24% yield).

$^1$H NMR (500 MHz, CDCl$_3$) δ 7.29-7.22 (m, 2H), 7.21-7.17 (m, 1H), 7.14 (dd, 1H), 7.07-7.03 (m, 1H), 4.23 (t, 2H), 4.15 (q, 2H), 2.58 (t, 2H), 2.15-2.06 (m, 2H), 1.26 (t, 3H)

Step B: 4-[4-(2,2-difluoro-benzo[1,3]dioxol-4-yl)-2,6-difluoro-phenoxy]-butyric acid 4-[4-(2,2-Difluoro-benzo[1,3]dioxol-4-yl)-2,6-difluoro-phenoxy]-butyric acid ethyl ester (20 mg, 0.045 mmol) obtained in Step A was reacted in the same manner as in Step B of Example 287 to obtain the title compound (16 mg, 86% yield).

$^1$H NMR (500 MHz, CDCl$_3$) δ 7.29-7.23 (m, 2H), 7.21-7.17 (m, 1H), 7.14 (dd, 1H), 7.06-7.03 (dd, 1H), 4.25 (t, 2H), 2.67 (t, 2H), 2.16-2.07 (m, 2H)

Example 291: 4-[4-(2,2-dimethyl-2,3-dihydro-benzofuran-4-yl)-2,6-difluoro-phenoxy]-butyric acid

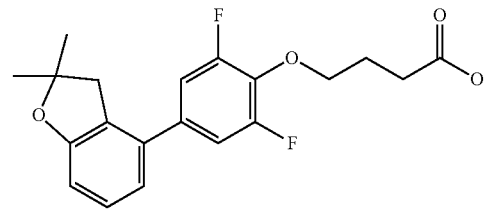 [SMILES: CC1(C)Cc2c(cccc2-c2cc(F)c(OCCCC(=O)O)c(F)c2)O1]

Step A: 4-(2'-bromo-3,5-difluoro-3'-hydroxy-biphenyl-4-yloxy)-butyric acid ethyl ester 2-Bromo-3-iodophenol (100 mg, 0.335 mmol) obtained in Step C of Preparation Example 216 and 4-[2,6-difluoro-4-

(4,4,5,5-tetramethyl-1,3,2-dioxaborolan-2-yl)phenoxy]butyric acid ethyl ester (124 mg, 0.335 mmol) obtained in Preparation Example 16 were dissolved in 0.4 mL of 2 M sodium carbonate and 4 mL of 1,4-dioxane, and charged with nitrogen gas for 5 minutes. PdCl$_2$(dppf) (14 mg, 0.0168 mmol) was added thereto, and the mixture was stirred for 1 hour under reflux. The reaction solution was cooled to room temperature. After addition of water, the reaction solution was extracted with EtOAc to separate an organic layer. The organic layer was dried with anhydrous magnesium sulfate and purified by column chromatography (eluent, EtOAc/Hex=1/4) to obtain the title compound (70 mg, 50% yield).

$^1$H NMR (500 MHz, CDCl$_3$) δ 7.24 (dd, 1H), 7.03 (d, 1H), 6.97-6.88 (m, 2H), 6.83 (d, 1H), 5.85 (s, 1H), 4.23 (t, 2H), 4.15 (q, 2H), 2.59 (t, 2H), 2.15-2.07 (m, 2H), 1.27 (t, 3H)

Step B: 4-[3,5-difluoro-3'-hydroxy-2'-(2-methyl-propenyl)-biphenyl-4-yloxy]-butyric acid ethyl ester 4-(2'-Bromo-3,5-difluoro-3'-hydroxy-biphenyl-4-yloxy)-butyric acid ethyl ester (70 mg, 0.169 mmol) obtained in Step A and 4,4,5,5-tetramethyl-2-(2-methyl-propenyl)-[1,3,2]dioxaborolan (93 mg, 0.507 mmol) were dissolved in 0.4 mL of 2 M sodium carbonate and 4 mL of 1,4-dioxane, and charged with nitrogen for 5 minutes. PdCl$_2$(dppf) (7 mg, 0.0085 mmol) was added thereto, and the mixture was stirred for 12 hours under reflux. The reaction solution was cooled to room temperature. After addition of water and EtOAc, the reaction solution was stirred for 30 minutes and filtered through Celite. Separation of the layers was carried out to separate an organic layer. The organic layer was dried with anhydrous magnesium sulfate and purified by column chromatography (eluent, EtOAc/Hex=1/3) to obtain the title compound (17 mg, 26% yield).

$^1$H NMR (500 MHz, CDCl$_3$) δ 7.21 (dd, 1H), 6.94 (d, 1H), 6.86-6.78 (m, 3H), 5.83 (s, 1H), 5.36 (s, 1H), 4.19 (t, 2H), 4.15 (q, 2H), 2.58 (t, 2H), 2.13-2.06 (m, 2H), 1.87 (s, 3H), 1.57 (s, 3H), 1.26 (t, 3H)

Step C: 4-[4-(2,2-dimethyl-2,3-dihydro-benzofuran-4-yl)-2,6-difluoro-phenoxy]-butyric acid ethyl ester 4-[3,5-Difluoro-3'-hydroxy-2'-(2-methyl-propenyl)-biphenyl-4-yloxy]-butyric acid ethyl ester (17 mg, 0.044 mmol) obtained in Step B was dissolved in toluene (2 mL). Amberlyst 15 resin (17 mg) was added thereto, and the mixture was stirred for 4 hours under reflux. The reaction solution was cooled to room temperature, filtered, concentrated under reduced pressure and purified by column chromatography (eluent, EtOAc/Hex=1/4) to obtain the title compound (9 mg, 53% yield).

$^1$H NMR (500 MHz, CDCl$_3$) δ 7.17 (dd, 1H), 7.01-6.93 (m, 2H), 6.82 (d, 1H), 6.74 (d, 1H), 4.20 (t, 2H), 4.15 (q, 2H), 3.08 (s, 2H), 2.58 (t, 2H), 2.13-2.06 (m, 2H), 1.48 (s, 6H), 1.27 (t, 3H)

Step D: 4-[4-(2,2-dimethyl-2,3-dihydro-benzofuran-4-yl)-2,6-difluoro-phenoxy]-butyric acid 4-[4-(2,2-Dimethyl-2,3-dihydro-benzofuran-4-yl)-2,6-difluoro-phenoxy]-butyric acid ethyl ester (9 mg, 0.023 mmol) obtained in Step C was reacted in the same manner as in Step B of Example 287 to obtain the title compound (8.2 mg, 98% yield).

$^1$H NMR (500 MHz, CDCl$_3$) δ 7.17 (dd, 1H), 7.01-6.94 (m, 2H), 6.82 (d, 1H), 6.74 (d, 1H), 4.22 (t, 2H), 3.08 (s, 2H), 2.67 (t, 2H), 2.15-2.07 (m, 2H), 1.48 (s, 6H)

Example 292: 4-[4-(2-cyclohexylsulfanyl-pyridin-3-yl)-2,6-difluoro-phenoxy]-butyric acid

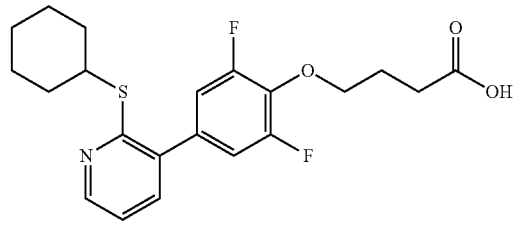 [SMILES: O=C(O)CCCOc1c(F)cc(-c2cccnc2SC2CCCCC2)cc1F]

Step A: 4-[4-(2-cyclohexylsulfanyl-pyridin-3-yl)-2,6-difluoro-phenoxy]-butyric acid ethyl ester 4-[2,6-Difluoro-4-(2-fluoro-pyridin-3-yl)-phenoxy]-butyric acid ethyl ester (50 mg, 0.147 mmol), Cs$_2$CO$_3$ (192 mg, 0.588 mmol) and cyclohexanethiol (36 μL, 0.294 mmol) were reacted in the same manner as in Step B of Example 288 to obtain the title compound (5 mg, 8% yield).

$^1$H NMR (500 MHz, CDCl$_3$) δ 8.42 (d, 1H), 7.32 (d, 1H), 7.03-6.93 (m, 3H), 4.23 (t, 2H), 4.16 (q, 2H), 3.95-3.86 (m, 1H), 2.59 (t, 2H), 2.14-2.07 (m, 2H), 2.07-2.01 (m, 2H), 1.78-1.69 (m, 2H), 1.66-1.57 (m, 1H), 1.49-1.36 (m, 4H), 1.35-1.23 (m, 1H), 1.27 (t, 3H)

Step B: 4-[4-(2-cyclohexylsulfanyl-pyridin-3-yl)-2,6-difluoro-phenoxy]-butyric acid 4-[4-(2-Cyclohexylsulfanyl-pyridin-3-yl)-2,6-difluoro-phenoxy]-butyric acid ethyl ester (5 mg, 0.0115 mmol) obtained in Step A was reacted in the same manner as in Step B of Example 287 to obtain the title compound (4.2 mg, 90% yield).

$^1$H NMR (500 MHz, CDCl$_3$) δ 8.84 (d, 1H), 7.67 (d, 1H), 7.51-7.45 (m, 1H), 7.02-6.93 (m, 2H), 4.29 (t, 2H), 3.32-3.23 (m, 1H), 2.65 (t, 2H), 2.17-1.98 (m, 4H), 1.90-1.81 (m, 1H), 1.68-1.23 (m, 7H)

Example 293: 3-[4-(2-cyclopentyloxy-pyridin-3-yl)-benzylsulfanyl]-propionic acid

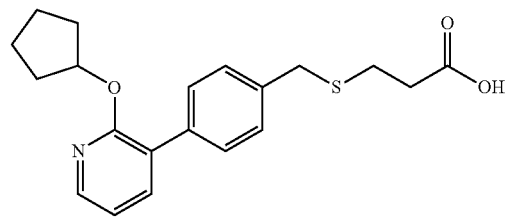 [SMILES: O=C(O)CCSCc1ccc(-c2cccnc2OC2CCCC2)cc1]

Step A: [4-(2-cyclopentyloxy-pyridin-3-yl)-phenyl]-methanol

2-Cyclopentyloxy-3-iodo-pyridine (100 mg, 0.346 mmol), [4-(hydroxymethyl)-phenyl]boronic acid (52.6 mg, 0.346 mmol) and K₂CO₃ (96 mg, 0.692 mmol) were dissolved in 1,4-dioxane/H₂O (4:1, 4 mL), and charged with nitrogen for 5 minutes. Pd(PPh₃)₄ (20 mg, 0.0173 mmol) was added thereto, and the mixture was stirred for 1 hour under reflux. After termination of the reaction, the reaction solution was diluted with water and extracted with EtOAc to separate an organic layer. The organic layer was concentrated under reduced pressure and purified by column chromatography (eluent, EtOAc/Hex=1/4) to obtain the title compound (88 mg, 94% yield).

¹H NMR (500 MHz, CDCl₃) δ 8.12 (dd, 1H), 7.58 (dd, 1H), 7.54 (d, 2H), 7.39 (d, 2H), 6.90 (dd, 1H), 5.53-5.47 (m, 1H), 4.72 (s, 2H), 2.09 (s, 1H), 1.98-1.88 (m, 2H), 1.85-1.76 (m, 2H), 1.76-1.67 (m, 2H), 1.65-1.55 (m, 2H)

Step B: 3-(4-bromomethyl-phenyl)-2-cyclopentyloxy-pyridin

[4-(2-Cyclopentyloxy-pyridin-3-yl)-phenyl]-methanol (70 mg, 0.26 mmol) was dissolved in DCM. NBS (69 mg, 0.39 mmol) and triphenylphosphine (102 mg, 0.39 mmol) were added thereto, and the mixture was stirred at room temperature for 2 hours. After termination of the reaction, the reaction solution was diluted with water and extracted with DCM to separate an organic layer. The organic layer was concentrated under reduced pressure and purified by column chromatography (eluent, EtOAc/Hex=1/10) to obtain the title compound (80 mg, 93% yield).

¹H NMR (500 MHz, CDCl₃) δ 8.14 (dd, 1H), 7.59 (dd, 1H), 7.54 (d, 2H), 7.42 (d, 2H), 6.91 (dd, 1H), 5.55-5.50 (m, 1H), 4.54 (s, 2H), 2.00-1.90 (m, 2H), 1.85-1.77 (m, 2H), 1.76-1.68 (m, 2H), 1.67-1.57 (m, 2H)

Step C: 3-[4-(2-cyclopentyloxy-pyridin-3-yl)-benzylsulfanyl]-propionic acid

EtOH (2 mL) and NaOH (19 mg, 0.48 mmol) were added to 3-mercapto-propionic acid (21 µL, 0.24 mmol), and the mixture was stirred at room temperature for 15 minutes. 3-(4-Bromomethyl-phenyl)-2-cyclopentyloxy-pyridine (80 mg, 0.24 mmol) obtained in Step B was dissolved in EtOH (2 mL) and THF (0.5 mL), and slowly added dropwise to the above solution. The mixture was stirred at room temperature for 3 hours. The reaction solution was adjusted to pH 3 by the use of 1N HCl aqueous solution and extracted with EtOAc. The organic layer was dried with anhydrous magnesium sulfate and concentrated under reduced pressure to obtain the title compound (83 mg, 97% yield).

¹H NMR (500 MHz, CDCl₃) δ 8.14 (dd, 1H), 7.60 (dd, 1H), 7.50 (d, 2H), 7.34 (d, 2H), 6.92 (dd, 1H), 5.53-5.46 (m, 1H), 3.78 (s, 2H), 2.72 (t, 2H), 2.62 (t, 2H), 1.98-1.88 (m, 2H), 1.84-1.75 (m, 2H), 1.75-1.65 (m, 2H), 1.65-1.55 (m, 2H)

Example 294: 2-[1-[4-[6-(cyclobutoxy)-2-pyridyl]-2,6-difluoro-phenyl]-4-piperidyl]acetic acid

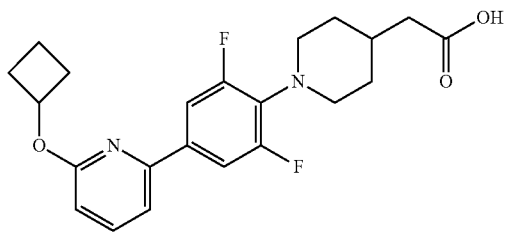 [SMILES: O=C(O)CC1CCN(c2c(F)cc(-c3cccc(OC4CCC4)n3)cc2F)CC1]

2-Chloro-6-cyclobutoxy-pyridine (0.062 g, 0.33 mmol) obtained in Preparation Example 29 and 2-[1-[2,6-difluoro-4-(4,4,5,5-tetramethyl-1,3,2-dioxaborolan-2-yl)phenyl]-4-piperidyl]acetic acid methyl ester (0.147 g, 0.37 mmol) obtained in Preparation Example 84 were reacted in the same manner as in Step A of Example 96 and Step B of Example 1 to obtain the title compound (0.058 g, 44%).

¹H-NMR (CDCl₃) δ 7.57 (1H, t), 7.49 (2H, m), 7.20 (1H, d), 6.62 (1H, d), 5.26 (1H, m), 3.32 (2H, m), 3.16 (2H, m), 2.52 (2H, m), 2.36 (2H, d), 2.19 (2H, m), 1.98 (1H, m), 1.84 (3H, m), 1.75 (1H, m), 1.48 (2H, m)

Example 295: 2-[1-[2,6-difluoro-4-(6-propoxy-2-pyridyl)phenyl]-4-piperidyl]acetic acid

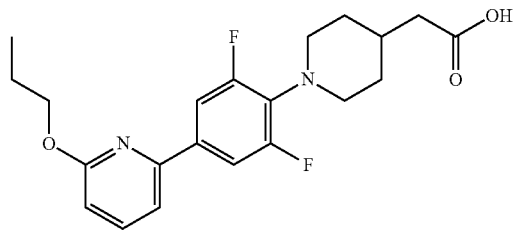 [SMILES: CCCOc1cccc(-c2cc(F)c(N3CCC(CC(=O)O)CC3)c(F)c2)n1]

2-Chloro-6-propoxy-pyridine (0.057 g, 0.33 mmol) and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.097 g, 75%).

¹H-NMR (CDCl₃) δ 7.60 (1H, t), 7.50 (2H, m), 7.19 (1H, d), 6.66 (1H, d), 4.35 (2H, t), 3.31 (2H, m), 3.15 (2H, m), 2.36 (2H, d), 1.98 (1H, m), 1.83 (4H, m), 1.49 (2H, m), 1.05 (3H, t)

Example 296: 2-[1-[2,6-difluoro-4-(6-isopropoxy-2-pyridyl)phenyl]-4-piperidyl]acetic acid

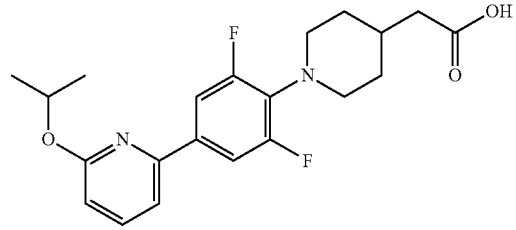 [SMILES: CC(C)Oc1cccc(-c2cc(F)c(N3CCC(CC(=O)O)CC3)c(F)c2)n1]

2-Chloro-6-isopropoxy-pyridine (0.057 g, 0.33 mmol) obtained in Preparation Example 46 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.097 g, 75%).

¹H-NMR (CDCl₃) δ 7.58 (1H, t), 7.49 (2H, m), 7.16 (1H, d), 6.61 (1H, d), 5.44 (1H, m), 3.31 (2H, m), 3.14 (2H, m), 2.36 (2H, d), 1.98 (1H, m), 1.82 (2H, m), 1.50 (2H, m), 1.39 (6H, d)

Example 297: 2-[1-[4-(6-cyclobutylsulfanyl-2-pyridyl)-2,6-difluoro-phenyl]-4-piperidyl]acetic acid

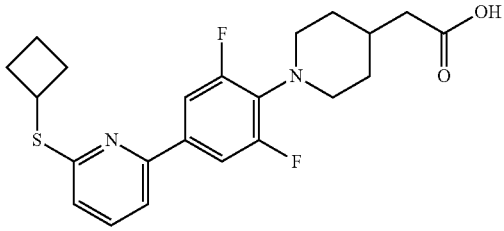

2-Chloro-6-cyclobutylsulfanyl-pyridine (0.066 g, 0.33 mmol) and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.036 g, 26%).

$^1$H-NMR (CDCl$_3$) δ 7.52 (3H, m), 7.29 (1H, d), 7.01 (1H, d), 4.42 (1H, m), 3.34 (2H, m), 3.18 (2H, m), 2.60 (2H, m), 2.37 (2H, d), 2.15 (4H, m), 1.99 (1H, m), 1.82 (2H, m), 1.50 (2H, m)

Example 298: 2-[1-[2,6-difluoro-4-(6-propylsulfanyl-2-pyridyl)phenyl]-4-piperidyl]acetic acid

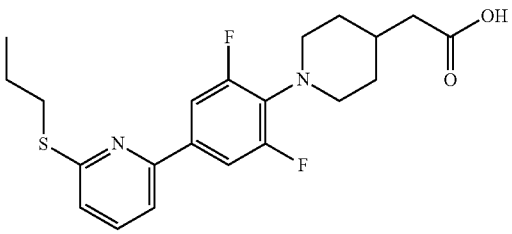

2-Chloro-6-propylsulfanyl-pyridine (0.077 g, 0.33 mmol) and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.032 g, 24%).

$^1$H-NMR (CDCl$_3$) δ 7.51 (3H, m), 7.29 (1H, d), 7.09 (1H, d), 3.33 (2H, m), 3.23 (2H, t), 3.15 (2H, m), 2.37 (2H, d), 1.99 (1H, m), 1.82 (4H, m), 1.50 (2H, m), 1.08 (3H, t)

Example 299: 2-[1-[4-[6-(cyclopentoxy)-2-pyridyl]-2,6-difluoro-phenyl]-4-piperidyl]acetic acid

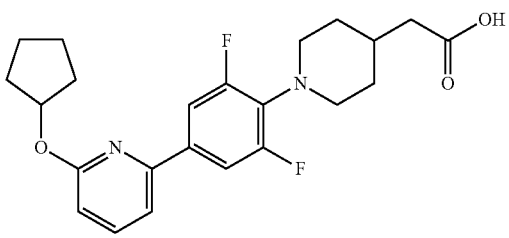 [SMILES: O=C(O)CC1CCN(c2c(F)cc(-c3cccc(OC4CCCC4)n3)cc2F)CC1]

2-Chloro-6-cyclopentyloxy-pyridine (0.066 g, 0.33 mmol) obtained in Preparation Example 12 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.099 g, 72%).

$^1$H-NMR (CDCl$_3$) δ 7.57 (1H, t), 7.51 (2H, m), 7.17 (1H, d), 6.61 (1H, d), 5.51 (1H, m), 3.32 (2H, m), 3.15 (2H, m), 2.37 (2H, d), 2.05 (3H, m), 1.84 (6H, m), 1.65 (2H, m), 1.49 (2H, m)

Example 300: 2-[1-[4-[3-(cyclobutoxy)phenyl]-2,6-difluoro-phenyl]-4-piperidyl]acetic acid

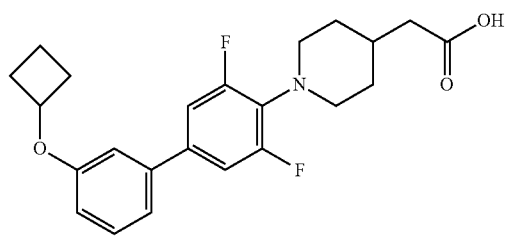 [SMILES: O=C(O)CC1CCN(c2c(F)cc(-c3cccc(OC4CCC4)c3)cc2F)CC1]

Step A: 2-[1-[4-[3-(cyclobutoxy)phenyl]-2,6-difluoro-phenyl]-4-piperidyl]acetic acid ethyl ester 2-[1-[2,6-Difluoro-4-(3-hydroxyphenyl)phenyl]-4-piperidyl]acetic acid ethyl ester (0.095 g, 0.25 mmol) obtained in Preparation Example 223 was dissolved in 0.85 mL of DMF. K$_2$CO$_3$ (0.07 g, 0.5 mmol) and bromocyclobutane (0.037 g, 0.27 mmol) were added thereto, and the mixture was stirred at 60° C. for 16 hours. The reaction solution was concentrated under reduced pressure. Solids were filtered, and the filtrate was purified by column chromatography to obtain the title compound (0.049 g, 44%).

$^1$H-NMR (CDCl$_3$) δ 7.30 (1H, t), 7.05 (3H, m), 6.94 (1H, m), 6.79 (1H, m), 4.68 (1H, m), 4.15 (2H, q), 3.27 (2H, m), 3.13 (2H, m), 2.45 (2H, m), 2.29 (2H, d), 2.19 (2H, m), 1.96 (1H, m), 1.88 (1H, m), 1.77 (2H, m), 1.70 (1H, m), 1.45 (2H, m), 1.27 (3H, t)

Step B: 2-[1-[4-[3-(cyclobutoxy)phenyl]-2,6-difluoro-phenyl]-4-piperidyl]acetic acid 2-[1-[4-[3-(Cyclobutoxy)phenyl]-2,6-difluoro-phenyl]-4-piperidyl]acetic acid ethyl ester (0.049 g, 0.11 mmol) obtained in Step A was reacted in the same manner as in Step B of Example 1 to obtain the title compound (0.033 g, 75%).

$^1$H-NMR (CDCl$_3$) δ 7.30 (1H, t), 7.05 (3H, m), 6.94 (1H, m), 6.78 (1H, m), 4.68 (1H, m), 3.27 (2H, m), 3.14 (2H, m), 2.47 (2H, m), 2.35 (2H, d), 2.19 (2H, m), 1.96 (1H, m), 1.86 (1H, m), 1.82 (2H, m), 1.71 (1H, m), 1.49 (2H, m)

Example 301: 2-[1-[4-[3-(cyclopropylmethoxy)phenyl]-2,6-difluoro-phenyl]-4-piperidyl]acetic acid

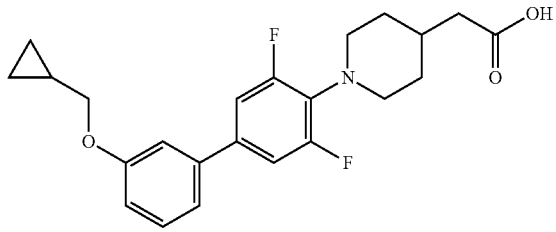

Step A: 2-[1-[4-[3-(cyclopropylmethoxy)phenyl]-2,6-difluoro-phenyl]-4-piperidyl]acetic acid ethyl ester 2-[1-[2,6-Difluoro-4-(3-hydroxyphenyl)phenyl]-4-piperidyl]acetic acid ethyl ester (0.095 g, 0.25 mmol) obtained in Preparation Example 223 was dissolved in 0.85 mL of DMF. $K_2CO_3$ (0.07 g, 0.5 mmol) and bromomethylcyclopropane (0.037 g, 0.27 mmol) were added thereto, and the mixture was stirred at 60° C. for 16 hours. The reaction solution was concentrated under reduced pressure. Solids were filtered, and the filtrate was purified by column chromatography to obtain the title compound (0.059 g, 55%).

$^1$H-NMR (CDCl$_3$) δ 7.31 (1H, t), 7.05 (4H, m), 6.88 (1H, m), 4.15 (2H, q), 3.85 (2H, d), 3.27 (2H, m), 3.13 (2H, m), 2.29 (2H, d), 1.96 (1H, m), 1.77 (2H, m), 1.45 (2H, m), 1.27 (4H, m), 0.67 (2H, m), 0.37 (2H, m)

Step B: 2-[1-[4-[3-(cyclopropylmethoxy)phenyl]-2,6-difluoro-phenyl]-4-piperidyl]acetic acid 2-[1-[4-[3-(Cyclopropylmethoxy)phenyl]-2,6-difluoro-phenyl]-4-piperidyl]acetic acid ethyl ester (0.059 g, 0.14 mmol) obtained in Step A was reacted in the same manner as in Step B of Example 1 to obtain the title compound (0.055 g, 99%).

$^1$H-NMR (CDCl$_3$) δ 7.31 (1H, t), 7.05 (4H, m), 6.88 (1H, m), 3.85 (2H, d), 3.28 (2H, m), 3.14 (2H, m), 2.36 (2H, d), 1.97 (1H, m), 1.82 (2H, m), 1.50 (2H, m), 1.29 (1H, m), 0.67 (2H, m), 0.36 (2H, m)

Example 302: 2-[1-[2,6-difluoro-4-[3-(isopropoxymethyl)phenyl]phenyl]-4-piperidyl]acetic acid

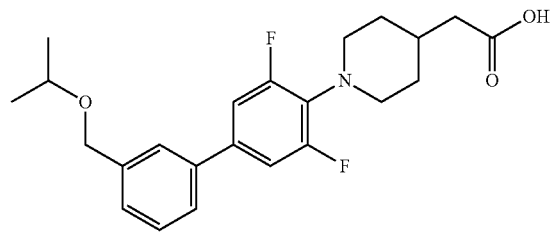 [SMILES: CC(C)OCc1cccc(-c2cc(F)c(N3CCC(CC(=O)O)CC3)c(F)c2)c1]

1-Bromo-3-(isopropoxymethyl)benzene (0.076 g, 0.33 mmol) obtained in Preparation Example 286 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.09 g, 68%).

$^1$H-NMR (CDCl$_3$) δ 7.49 (1H, m), 7.41 (2H, m), 7.33 (1H, m), 7.08 (2H, m), 4.55 (2H, s), 3.72 (1H, m), 3.28 (2H, m), 3.14 (2H, m), 2.36 (2H, d), 1.97 (1H, m), 1.82 (2H, m), 1.49 (2H, m), 1.23 (6H, d)

Example 303: 2-[1-[4-[3-(ethoxymethyl)phenyl]-2,6-difluoro-phenyl]-4-piperidyl]acetic acid

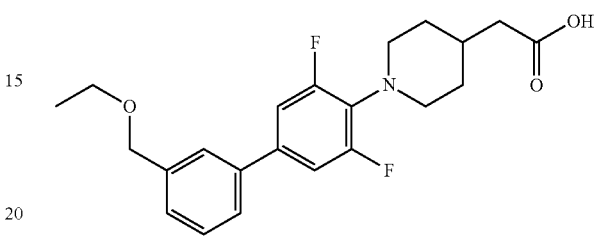

1-Bromo-3-(ethoxymethyl)benzene (0.072 g, 0.33 mmol) obtained in Preparation Example 287 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.07 g, 54%).

$^1$H-NMR (CDCl$_3$) δ 7.49 (1H, m), 7.41 (2H, m), 7.32 (1H, m), 7.08 (2H, m), 4.55 (2H, s), 3.58 (2H, q), 3.28 (2H, m), 3.15 (2H, m), 2.37 (2H, d), 1.97 (1H, m), 1.83 (2H, m), 1.50 (2H, m), 1.27 (3H, t)

Example 304: 2-[1-[4-[3-(cyclobutoxy)-4-fluoro-phenyl]-2,6-difluoro-phenyl]-4-piperidyl]acetic acid

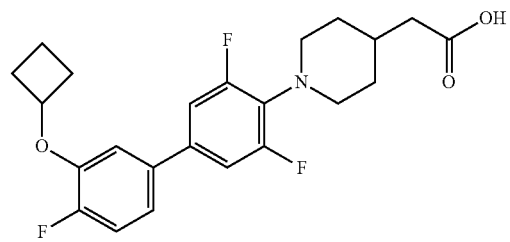 [SMILES: O=C(O)CC1CCN(c2c(F)cc(-c3ccc(F)c(OC4CCC4)c3)cc2F)CC1]

Step A: 2-[1-[2,6-difluoro-4-(4-fluoro-3-hydroxyphenyl)phenyl]-4-piperidyl]acetic acid ethyl ester 5-Bromo-2-fluoro-phenol (0.127 g, 0.66 mmol) and 2-[1-[2,6-difluoro-4-(4,4,5,5-tetramethyl-1,3,2-dioxaborolan-2-yl)phenyl]-4-piperidyl]acetic acid ethyl ester (0.30 g, 0.73 mmol) obtained in Preparation Example 220 were reacted in the same manner as in Step A of Example 96 to obtain the title compound (0.19 g, 73%).

$^1$H-NMR (CDCl$_3$) δ 7.12 (2H, m), 6.99 (3H, m), 5.22 (1H, brs), 4.14 (2H, q), 3.26 (2H, m), 3.13 (2H, m), 2.30 (2H, d), 1.96 (1H, m), 1.77 (2H, m), 1.45 (2H, m), 1.27 (3H, t)

Step B: 2-[1-[4-[3-(cyclobutoxy)-4-fluoro-phenyl]-2,6-difluoro-phenyl]-4-piperidyl]acetic acid ethyl ester 1 mL of DMF, bromocyclobutane (0.032 g, 0.23 mmol) and Cs$_2$CO$_3$ (0.136 g, 0.42 mmol) were added to 2-[1-[2,6- difluoro-4-(4-fluoro-3-hydroxy-phenyl)phenyl]-4-piperidyl]acetic acid ethyl ester (0.084 g, 0.21 mmol) obtained in Step A, and the mixture was stirred at 50° C. for 16 hours. Solids were filtered, and the filtrate was purified by column chromatography to obtain the title compound (0.068 g, 72%).

¹H-NMR (CDCl₃) δ 7.10 (1H, m), 6.98 (3H, m), 6.92 (1H, m), 4.73 (1H, m), 4.14 (2H, q), 3.26 (2H, m), 3.13 (2H, m), 2.48 (2H, m), 2.39 (4H, m), 1.97 (1H, m), 1.88 (1H, m), 1.77 (2H, m), 1.70 (1H, m), 1.45 (2H, m), 1.26 (3H, t)

Step C: 2-[1-[4-[3-(cyclobutoxy)-4-fluoro-phenyl]-2,6-difluoro-phenyl]-4-piperidyl]acetic acid 2-[1-[4-[3-(Cyclobutoxy)-4-fluoro-phenyl]-2,6-difluoro-phenyl]-4-piperidyl]acetic acid ethyl ester (0.068 g, 0.15 mmol) obtained in Step B was reacted in the same manner as in Step B of Example 1 to obtain the title compound (0.03 g, 71%).

¹H-NMR (CDCl₃) δ 7.10 (1H, m), 6.98 (3H, m), 6.92 (1H, m), 4.73 (1H, m), 3.27 (2H, m), 3.14 (2H, m), 2.47 (2H, m), 2.36 (2H, d), 2.26 (2H, m), 1.97 (1H, m), 1.89 (1H, m), 1.82 (2H, m), 1.70 (1H, m), 1.50 (2H, m)

Example 305: 2-[1-[4-[3-(cyclobutoxy)-4-methoxy-phenyl]-2,6-difluoro-phenyl]-4-piperidyl]acetic acid

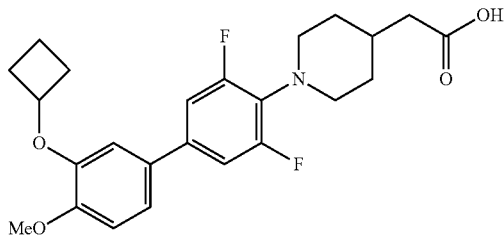

Step A: 2-[1-[2,6-difluoro-4-(3-hydroxy-4-methoxy-phenyl)phenyl]-4-piperidyl]acetic acid ethyl ester 5-Bromo-2-methoxy-phenol (0.135 g, 0.66 mmol) and 2-[1-[2,6-difluoro-4-(4,4,5,5-tetramethyl-1,3,2-dioxaborolan-2-yl)phenyl]-4-piperidyl]acetic acid ethyl ester (0.30 g, 0.73 mmol) obtained in Preparation Example 220 were reacted in the same manner as in Step A of Example 96 to obtain the title compound (0.167 g, 62%).

¹H-NMR (CDCl₃) δ 7.09 (1H, m), 7.01 (3H, m), 6.89 (1H, m), 5.64 (1H, brs), 4.16 (2H, q), 3.92 (3H, s), 3.25 (2H, m), 3.14 (2H, m), 2.29 (2H, d), 1.97 (1H, m), 1.77 (2H, m), 1.46 (2H, m), 1.27 (3H, t)

Step B: 2-[1-[4-[3-(cyclobutoxy)-4-methoxy-phenyl]-2,6-difluoro-phenyl]-4-piperidyl]acetic acid ethyl ester 1 mL of DMF, bromocyclobutane (0.032 g, 0.23 mmol) and Cs₂CO₃ (0.136 g, 0.42 mmol) were added to 2-[1-[2,6-difluoro-4-(3-hydroxy-4-methoxy-phenyl)phenyl]-4-piperidyl]acetic acid ethyl ester (0.08 g, 0.2 mmol) obtained in Step A, and the mixture was stirred at 50° C. for 16 hours. Solids were filtered, and the filtrate was purified by column chromatography to obtain the title compound (0.045 g, 49%).

¹H-NMR (CDCl₃) δ 7.04 (1H, m), 6.93 (2H, m), 6.90 (1H, m), 6.85 (1H, m), 4.72 (1H, m), 4.14 (2H, q), 3.90 (3H, s), 3.2 (2H, m), 3.13 (2H, m), 2.50 (2H, m), 2.30 (4H, m), 1.95 (1H, m), 1.88 (1H, m), 1.76 (2H, m), 1.70 (1H, m), 1.47 (2H, m), 1.27 (3H, t)

Step C: 2-[1-[4-[3-(cyclobutoxy)-4-methoxy-phenyl]-2,6-difluoro-phenyl]-4-piperidyl]acetic acid 2-[1-[4-[3-(Cyclobutoxy)-4-methoxy-phenyl]-2,6-difluoro-phenyl]-4-piperidyl]acetic acid ethyl ester (0.045 g, 0.10 mmol) obtained in Step B was reacted in the same manner as in Step B of Example 1 to obtain the title compound (0.04 g, 94%).

¹H-NMR (CDCl₃) δ 7.04 (1H, m), 6.99 (2H, m), 6.90 (1H, m), 6.86 (1H, m), 4.72 (1H, m), 3.90 (3H, s), 3.26 (2H, m), 3.14 (2H, m), 2.50 (2H, m), 2.36 (2H, d), 2.30 (2H, m), 1.96 (1H, m), 1.88 (1H, m), 1.82 (2H, m), 1.71 (1H, m), 1.50 (2H, m)

Example 306: 2-[1-[4-[3-(cyclobutoxy)-5-fluoro-phenyl]-2,6-difluoro-phenyl]-4-piperidyl]acetic acid

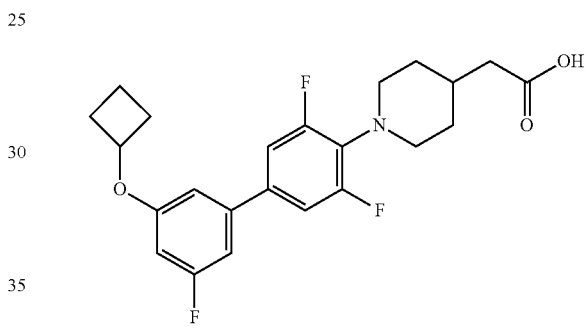

Step A: 2-[1-[2,6-difluoro-4-(3-fluoro-5-hydroxy-phenyl)phenyl]-4-piperidyl]acetic acid ethyl ester 3-Bromo-5-fluoro-phenol (0.127 g, 0.66 mmol) and 2-[1-[2,6-difluoro-4-(4,4,5,5-tetramethyl-1,3,2-dioxaborolan-2-yl)phenyl]-4-piperidyl]acetic acid ethyl ester (0.30 g, 0.73 mmol) obtained in Preparation Example 220 were reacted in the same manner as in Step A of Example 96 to obtain the title compound (0.24 g, 85%).

¹H-NMR (CDCl₃) δ 7.02 (2H, m), 6.79 (1H, m), 6.75 (1H, m), 6.55 (1H, m), 5.02 (1H, brs), 4.14 (2H, q), 3.28 (2H, m), 3.13 (2H, m), 2.30 (2H, d), 1.95 (1H, m), 1.77 (2H, m), 1.45 (2H, m), 1.27 (3H, t)

Step B: 2-[1-[4-[3-(cyclobutoxy)-5-fluoro-phenyl]-2,6-difluoro-phenyl]-4-piperidyl]acetic acid ethyl ester 2 mL of DMF, bromocyclobutane (0.058 g, 0.43 mmol) and Cs₂CO₃ (0.25 g, 0.76 mmol) were added to 2-[1-[2,6-difluoro-4-(3-fluoro-5-hydroxy-phenyl)phenyl]-4-piperidyl]acetic acid ethyl ester (0.15 g, 0.39 mmol) obtained in Step A, and the mixture was stirred at 50° C. for 16 hours. Solids were filtered, and the filtrate was purified by column chromatography to obtain the title compound (0.072 g, 41%).

¹H-NMR (CDCl₃) δ 7.01 (2H, m), 6.76 (1H, m), 6.73 (1H, m), 6.48 (1H, m), 4.64 (1H, m), 4.14 (2H, q), 3.28 (2H, m), 3.13 (2H, m), 2.47 (2H, m), 2.28 (2H, d), 2.18 (2H, m), 1.96 (1H, m), 1.88 (1H, m), 1.77 (2H, m), 1.70 (1H, m), 1.47 (2H, m), 1.27 (3H, t)

Step C: 2-[1-[4-[3-(cyclobutoxy)-5-fluoro-phenyl]-2,6-difluoro-phenyl]-4-piperidyl]acetic acid 2-[1-[4-[3-(Cyclobutoxy)-5-fluoro-phenyl]-2,6-difluoro-phenyl]-4-piperidyl]acetic acid ethyl ester (0.072 g, 0.16 mmol) obtained in Step B was reacted in the same manner as in Step B of Example 1 to obtain the title compound (0.037 g, 55%).
$^1$H-NMR (CDCl$_3$) δ 7.00 (2H, m), 6.77 (1H, m), 6.73 (1H, m), 6.49 (1H, m), 4.65 (1H, m), 3.29 (2H, m), 3.14 (2H, m), 2.47 (2H, m), 2.35 (2H, d), 2.18 (2H, m), 1.96 (1H, m), 1.88 (1H, m), 1.82 (2H, m), 1.71 (1H, m), 1.48 (2H, m)

Example 307: 2-[1-[2-chloro-4-[6-(cyclopropyl-methoxy)-2-pyridyl]-6-fluoro-phenyl]-4-piperidyl]acetic acid

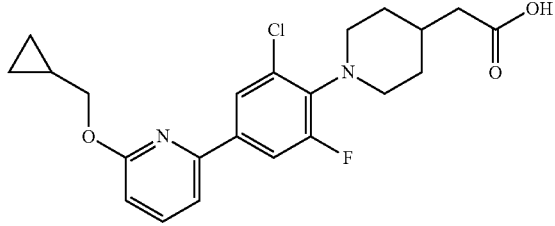

Step A: 2-chloro-4-[6-(cyclopropylmethoxy)-2-pyridyl]-6-fluoro-aniline

2-Chloro-6-cyclopropylmethoxy-pyridine (0.23 g, 1.25 mmol) obtained in Preparation Example 43 and 2-chloro-6-fluoro-4-(4,4,5,5-tetramethyl-1,3,2-dioxaborolan-2-yl)aniline (0.37 g, 1.37 mmol) obtained in Preparation Example 225 were reacted in the same manner as in Step A of Example 96 to obtain the title compound (0.28 g, 77%).
$^1$H-NMR (CDCl$_3$) δ 7.74 (1H, m), 7.64 (1H, m), 7.58 (1H, m), 7.18 (1H, m), 6.65 (1H, m), 4.22 (2H, d), 4.21 (2H, brs), 1.33 (1H, m), 0.64 (2H, m), 0.39 (2H, m)

Step B: 2-(4-bromo-3-chloro-5-fluoro-phenyl)-6-(cyclopropylmethoxy)pyridine

2-Chloro-4-[6-(cyclopropylmethoxy)-2-pyridyl]-6-fluoro-aniline (0.27 g, 0.95 mmol) obtained in Step A was reacted in the same manner as in Step C of Preparation Example 84 to obtain the title compound (0.146 g, 43%).
$^1$H-NMR (CDCl$_3$) δ 7.90 (1H, m), 7.71 (1H, m), 7.65 (1H, m), 7.28 (1H, m), 6.78 (1H, m), 4.23 (2H, d), 1.32 (1H, m), 0.64 (2H, m), 0.40 (2H, m)

Step C: 2-[1-[2-chloro-4-[6-(cyclopropylmethoxy)-2-pyridyl]-6-fluoro-phenyl]-4-piperidyl]acetic acid ethyl ester 2.7 mL of 1,4-dioxane was added to 2-(4-bromo-3-chloro-5-fluoro-phenyl)-6-(cyclopropylmethoxy)pyridine (0.145 g, 0.4 mmol) obtained in Step B, hydrochloric acid salt of 2-(4-piperidyl)acetic acid ethyl ester (0.084 g, 0.4 mmol), 2-dicyclohexylphosphino-2', 6'-dimethoxybiphenyl (0.041 g, 0.1 mmol) and Cs$_2$CO$_3$ (0.52 g, 1.6 mmol), and charged with nitrogen gas for 5 minutes. Pd$_2$(dba)$_3$ (0.036 g, 0.04 mmol) was added thereto, and the mixture was stirred at 70° C. for 16 hours. Solids were filtered through Celite, and the filtrate was purified by column chromatography to obtain the title compound (0.015 g, 8%).
$^1$H-NMR (CDCl$_3$) δ 7.79 (1H, m), 7.60 (2H, m), 7.21 (1H, m), 6.71 (1H, m), 4.23 (2H, d), 4.14 (2H, q), 3.22 (2H, m), 3.15 (2H, m), 2.31 (2H, d), 1.96 (1H, m), 1.76 (2H, m), 1.49 (2H, m), 1.32 (1H, m), 1.27 (3H, t), 0.64 (2H, m), 0.40 (2H, m)

Step D: 2-[1-[2-chloro-4-[6-(cyclopropylmethoxy)-2-pyridyl]-6-fluoro-phenyl]-4-piperidyl]acetic acid 2-[1-[2-Chloro-4-[6-(cyclopropylmethoxy)-2-pyridyl]-6-fluoro-phenyl]-4-piperidyl]acetic acid ethyl ester (0.015 g, 0.033 mmol) obtained in Step C was reacted in the same manner as in Step B of Example 1 to obtain the title compound (0.014 g, 99%).
$^1$H-NMR (CDCl$_3$) δ 7.79 (1H, m), 7.60 (2H, m), 7.21 (1H, m), 6.71 (1H, m), 4.23 (2H, d), 3.23 (2H, m), 3.16 (2H, m), 2.38 (2H, d), 2.00 (1H, m), 1.82 (2H, m), 1.51 (2H, m), 1.32 (1H, m), 0.64 (2H, m), 0.40 (2H, m)

Example 308: 2-[1-[4-[6-(cyclobutylmethoxy)-2-pyridyl]-2,6-difluoro-phenyl]-4-piperidyl]acetic acid

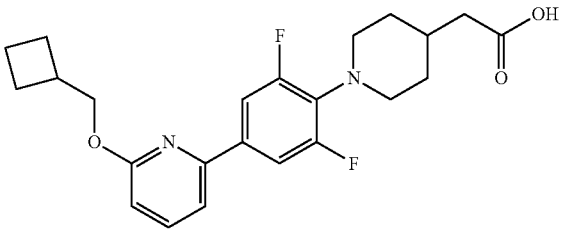 [SMILES: O=C(O)CC1CCN(c2c(F)cc(-c3cccc(OCC4CCC4)n3)cc2F)CC1]

2-Chloro-6-(cyclobutylmethoxy)pyridine (0.066 g, 0.33 mmol) obtained in Preparation Example 324 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.11 g, 80%).
$^1$H-NMR (CDCl$_3$) δ 7.59 (1H, t), 7.51 (2H, m), 7.19 (1H, m), 6.66 (1H, m), 4.36 (2H, d), 3.32 (2H, m), 3.16 (2H, m), 2.80 (1H, m), 2.37 (2H, d), 2.14 (2H, m), 1.93 (5H, m), 1.82 (2H, m), 1.51 (2H, m)

Example 309: 2-[1-[4-(6-tert-butoxy-2-pyridyl)-2,6-difluoro-phenyl]-4-piperidyl]acetic acid

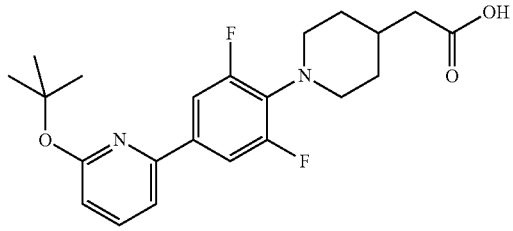 [SMILES: CC(C)(C)Oc1cccc(-c2cc(F)c(N3CCC(CC(=O)O)CC3)c(F)c2)n1]

2-Tert-butoxy-6-chloro-pyridine (0.062 g, 0.33 mmol) obtained in Preparation Example 272 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.10 g, 78%).

$^1$H-NMR (CDCl$_3$) δ 7.55 (1H, t), 7.45 (2H, m), 7.17 (1H, m), 6.58 (1H, m), 3.32 (2H, m), 3.15 (2H, m), 2.37 (2H, d), 1.97 (1H, m), 1.83 (2H, m), 1.65 (9H, s), 1.50 (2H, m)

Example 310: 2-[1-[4-[3-(cyclobutoxy)-2-methyl-phenyl]-2,6-difluoro-phenyl]-4-piperidyl]acetic acid

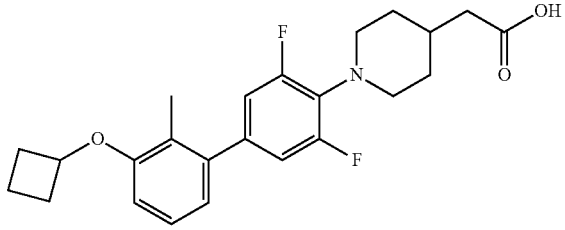 [SMILES: Cc1c(OC2CCC2)cccc1-c1cc(F)c(N2CCC(CC(=O)O)CC2)c(F)c1]

1-Bromo-3-(cyclobutoxy)-2-methyl-benzene (0.08 g, 0.33 mmol) obtained in Preparation Example 288 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.055 g, 40%).

$^1$H-NMR (CDCl$_3$) δ 7.12 (1H, t), 6.77 (3H, m), 6.68 (1H, m), 4.65 (1H, m), 3.29 (2H, m), 3.15 (2H, m), 2.46 (2H, m), 2.36 (2H, d), 2.19 (2H, m), 2.12 (3H, s), 1.97 (1H, m), 1.85 (3H, m), 1.70 (1H, m), 1.50 (2H, m)

Example 311: 2-[1-[4-[5-chloro-6-(cyclobutoxy)-2-pyridyl]-2,6-difluoro-phenyl]-4-piperidyl]acetic acid

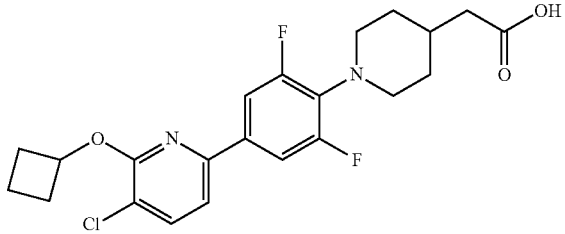 [SMILES: O=C(O)CC1CCN(c2c(F)cc(-c3ccc(Cl)c(OC4CCC4)n3)cc2F)CC1]

3,6-Dichloro-2-(cyclobutoxy)pyridine (0.080 g, 0.36 mmol) obtained in Preparation Example 298 and 2-[1-[2,6-difluoro-4-(4,4,5,5-tetramethyl-1,3,2-dioxaborolan-2-yl)phenyl]-4-piperidyl]acetic acid ethyl ester (0.16 g, 0.39 mmol) obtained in Preparation Example 220 were reacted in the same manner as in Step A of Example 96 and Step B of Example 1 to obtain the title compound (0.02 g, 13%).

$^1$H-NMR (CDCl$_3$) δ 7.63 (1H, d), 7.46 (2H, m), 7.15 (1H, d), 5.32 (1H, m), 3.32 (2H, m), 3.15 (2H, m), 2.54 (2H, m), 2.37 (2H, d), 2.26 (2H, m), 1.98 (1H, m), 1.80 (4H, m), 1.48 (2H, m)

Example 312: 2-[1-[4-[6-(cyclopropanecarbonyl)-2-pyridyl]-2,6-difluoro-phenyl]-4-piperidyl]acetic acid

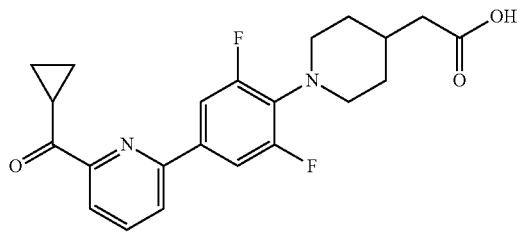 [SMILES: O=C(O)CC1CCN(c2c(F)cc(-c3cccc(C(=O)C4CC4)n3)cc2F)CC1]

Step A: 2-[1-[4-[6-[cyclopropyl](hydroxy)methyl]-2-pyridyl]-2,6-difluoro-phenyl]-4-piperidyl]acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.205 g, 0.50 mmol) obtained in Preparation Example 220 and (6-bromo-2-pyridyl)-cyclopropyl-methanol (0.125 g, 0.55 mmol) obtained in Preparation Example 268 were reacted in the same manner as in Step A of Example 96 to obtain the title compound (0.165 g, 77%).

$^1$H-NMR (CDCl$_3$) δ 7.77 (1H, m), 7.58 (2H, m), 7.36 (2H, m), 4.58 (1H, m), 4.14 (2H, m), 3.33 (2H, m), 3.16 (2H, m), 2.30 (2H, m), 1.97 (1H, m), 1.79 (2H, m), 1.46 (2H, m), 1.32 (3H, t), 1.15 (1H, m), 0.60 (4H, m)

Step B: 2-[1-[4-[6-(cyclopropanecarbonyl)-2-pyridyl]-2,6-difluoro-phenyl]-4-piperidyl]acetic acid 4 mL of DMSO was added to 2-[1-[4-[6-[cyclopropyl](hydroxy)methyl]-2-pyridyl]-2,6-difluoro-phenyl]-4-piperidyl]acetic acid ethyl ester (0.053 g, 0.123 mmol) obtained in Step A. IBX (0.103 g, 0.368 mmol) was added thereto, and the mixture was stirred at room temperature to obtain 2-[1-[4-[6-(cyclopropanecarbonyl)-2-pyridyl]-2,6-difluoro-phenyl]-4-piperidyl]acetic acid ethyl ester (0.05 g, 95%). The obtained compound was reacted in the same manner as in Step B of Example 1 to obtain the title compound (0.038 g, 81%).

$^1$H-NMR (CDCl$_3$) δ 7.98 (1H, d), 7.95 (1H, t), 7.81 (1H, d), 7.66 (2H, m), 3.67 (1H, m), 3.36 (2H, m), 3.18 (2H, m), 2.37 (2H, d), 2.00 (1H, m), 1.85 (2H, m), 1.50 (2H, m), 1.29 (2H, m), 1.17 (2H, m)

Example 313: 2-[1-[4-[6-(cyclobutoxymethyl)-2-pyridyl]-2,6-difluoro-phenyl]-4-piperidyl]acetic acid

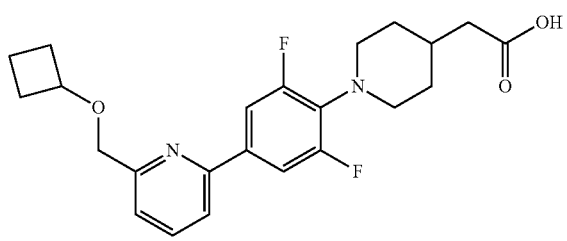 [SMILES: O=C(O)CC1CCN(c2c(F)cc(-c3cccc(COC4CCC4)n3)cc2F)CC1]

2-[1-[2,6-Difluoro-4-(4,4,5,5-tetramethyl-1,3,2-dioxaborolan-2-yl)phenyl]-4-piperidyl]acetic acid ethyl ester (0.082 g, 0.20 mmol) obtained in Preparation Example 220 and 2-bromo-6-(cyclobutoxymethyl)pyridine (0.053 g, 0.22 mmol) obtained in Preparation Example 269 were reacted in the same manner as in Step A of Example 96 and Step B of Example 1 to obtain the title compound (0.039 g, 47%).

$^1$H-NMR (CDCl$_3$) δ 7.72 (1H, t), 7.49 (3H, m), 7.39 (1H, d), 4.58 (2H, s), 4.10 (1H, m), 3.31 (2H, m), 3.14 (2H, m), 2.35 (2H, d), 2.25 (2H, m), 2.02 (3H, m), 1.81 (2H, m), 1.73 (1H, m), 1.48 (3H, m)

Example 314: 2-[1-[4-(6-ethoxy-2-pyridyl)-2,6-difluoro-phenyl]-4-piperidyl]acetic acid

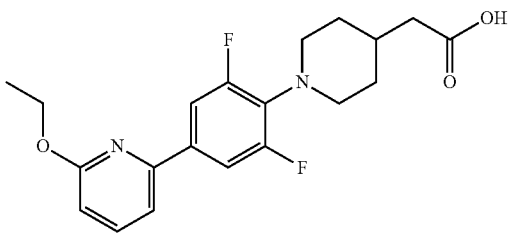

2-Chloro-6-ethoxy-pyridine (0.053 g, 0.33 mmol) obtained in Preparation Example 273 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.10 g, 80%).

$^1$H-NMR (CDCl$_3$) δ 7.60 (1H, t), 7.51 (2H, m), 7.20 (1H, d), 6.65 (1H, d), 4.45 (2H, q), 3.31 (2H, m), 3.15 (2H, m), 2.37 (2H, d), 1.97 (1H, m), 1.82 (2H, m), 1.50 (2H, m), 1.43 (3H, t)

Example 315: 2-[1-[2,6-difluoro-4-[6-(2,2,2-trifluoroethoxy)-2-pyridyl]phenyl]-4-piperidyl]acetic acid

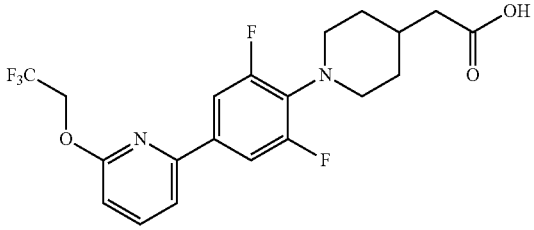 [SMILES: O=C(O)CC1CCN(c2c(F)cc(-c3cccc(OCC(F)(F)F)n3)cc2F)CC1]

2-Chloro-6-(2,2,2-trifluoroethoxy)pyridine (0.071 g, 0.33 mmol) obtained in Preparation Example 274 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) 220 were reacted in the same manner as in Step A of Example 96 and Step B of Example 1 to obtain the title compound (0.082 g, 58%).

$^1$H-NMR (CDCl$_3$) δ 7.69 (1H, t), 7.46 (2H, m), 7.31 (1H, d), 6.80 (1H, d), 4.84 (2H, q), 3.33 (2H, m), 3.16 (2H, m), 2.37 (2H, d), 1.98 (1H, m), 1.83 (2H, m), 1.50 (2H, m)

Example 316: 2-[1-[2,6-difluoro-4-[6-(2,2,2-trifluoro-1-methyl-ethoxy)-2-pyridyl]phenyl]-4-piperidyl]acetic acid

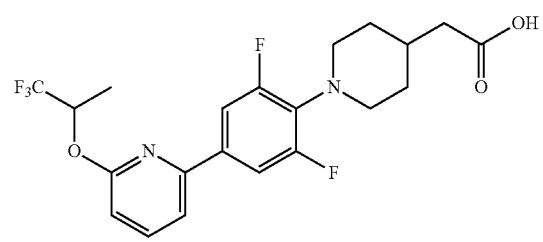 [SMILES: CC(Oc1cccc(-c2cc(F)c(N3CCC(CC(=O)O)CC3)c(F)c2)n1)C(F)(F)F]

2-Chloro-6-(2,2,2-trifluoro-1-methyl-ethoxy)pyridine (0.075 g, 0.33 mmol) obtained in Preparation Example 275 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.127 g, 86%).

$^1$H-NMR (CDCl$_3$) δ 7.67 (1H, t), 7.45 (2H, m), 7.28 (1H, d), 6.74 (1H, d), 5.89 (1H, m), 3.33 (2H, m), 3.16 (2H, m), 2.37 (2H, d), 1.98 (1H, m), 1.83 (2H, m), 1.55 (3H, d), 1.50 (2H, m)

Example 317: 2-[1-[4-(6-cyclopentyl-2-pyridyl)-2,6-difluoro-phenyl]-4-piperidyl]acetic acid

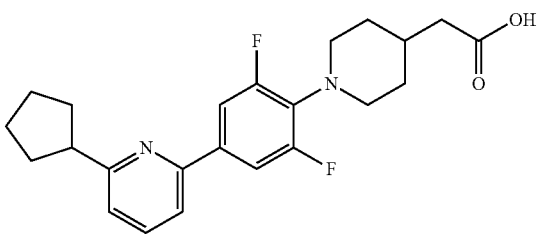 [SMILES: O=C(O)CC1CCN(c2c(F)cc(-c3cccc(C4CCCC4)n3)cc2F)CC1]

2-Bromo-6-cyclopentyl-pyridine (0.067 g, 0.3 mmol) and 2-[1-[2,6-difluoro-4-(4,4,5,5-tetramethyl-1,3,2-dioxaborolan-2-yl)phenyl]-4-piperidyl]acetic acid ethyl ester (0.13 g, 0.32 mmol) obtained in Preparation Example 220 were reacted in the same manner as in Step A of Example 96 and Step B of Example 1 to obtain the title compound (0.06 g, 50%).

$^1$H-NMR (CDCl$_3$) δ 7.61 (1H, t), 7.53 (2H, m), 7.41 (1H, d), 7.09 (1H, d), 3.31 (2H, m), 3.22 (1H, m), 3.15 (2H, m), 2.37 (2H, d), 2.10 (2H, m), 1.97 (1H, m), 1.85 (6H, m), 1.70 (2H, m), 1.50 (2H, m)

Example 318: 2-[1-[4-[6-[cyclopropyl(methoxy)methyl]-2-pyridyl]-2,6-difluoro-phenyl]-4-piperidyl]acetic acid

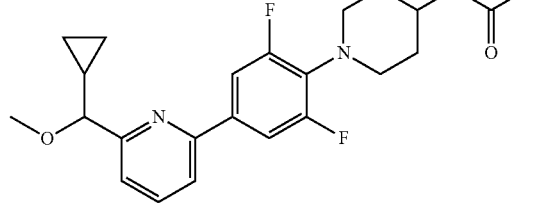

2-[1-[4-[6-[Cyclopropyl](hydroxy)methyl]-2-pyridyl]-2,6-difluoro-phenyl]-4-piperidyl]acetic acid ethyl ester (0.054 g, 0.125 mmol) obtained in Step A of Example 312 was dissolved in 4 mL of CH₃CN. Ag₂O (0.032 g, 0.138 mmol) and iodomethane (0.08 mL, 1.29 mmol) were added thereto, and the mixture was stirred at room temperature for 7 days. After termination of the reaction, solids were filtered through Celite, and the filtrate was purified by column chromatography to obtain 2-[1-[4-[6-[cyclopropyl(methoxy)methyl]-2-pyridyl]-2,6-difluoro-phenyl]-4-piperidyl]acetic acid ethyl ester (0.015 g, 27%). The obtained compound was reacted in the same manner as in Step B of Example 1 to obtain the title compound (0.012 g, 86%).

¹H-NMR (CDCl₃) δ 7.76 (1H, t), 2.52 (3H, m), 7.36 (1H, d), 3.81 (1H, d), 3.35 (3H, s), 3.32 (2H, m), 3.15 (2H, m), 2.36 (2H, d), 1.96 (1H, m), 1.85 (2H, m), 1.49 (2H, m), 1.20 (1H, m), 0.64 (1H, m), 0.50 (3H, m)

Example 319: 2-[1-[2-chloro-4-[6-(cyclobutoxy)-2-pyridyl]-6-fluoro-phenyl]-4-piperidyl]acetic acid

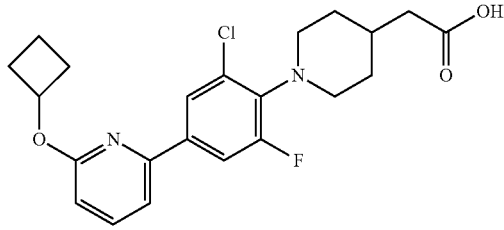 [SMILES: O=C(O)CC1CCN(c2c(F)cc(-c3cccc(OC4CCC4)n3)cc2Cl)CC1]

2-Chloro-6-cyclobutoxy-pyridine (0.23 g, 1.25 mmol) obtained in Preparation Example 29 and 2-chloro-6-fluoro-4-(4,4,5,5-tetramethyl-1,3,2-dioxaborolan-2-yl)aniline (0.374 g, 1.37 mmol) obtained in Preparation Example 225 were reacted in the same manner as in Example 307 to obtain the title compound (0.01 g, 2%).

¹H-NMR (CDCl₃) δ 7.78 (1H, m), 7.60 (2H, m), 7.21 (1H, m), 6.63 (1H, m), 5.25 (1H, m), 3.23 (2H, m), 3.17 (2H, m), 2.53 (2H, m), 2.38 (2H, d), 2.19 (2H, m), 1.99 (1H, m) 1.88 (1H, m), 1.81 (2H, m), 1.74 (1H, m), 1.50 (2H, m)

Example 320: 2-[1-[4-[6-(cyclobutoxy)-2-pyridyl]-2-fluoro-phenyl]-4-piperidyl]acetic acid

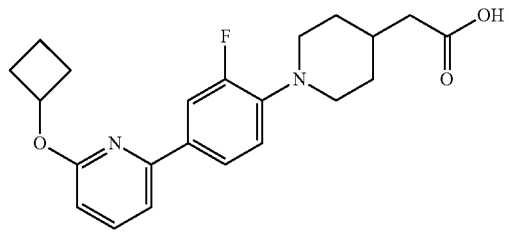 [SMILES: O=C(O)CC1CCN(c2ccc(-c3cccc(OC4CCC4)n3)cc2F)CC1]

2-Chloro-6-cyclobutoxy-pyridine (0.034 g, 0.185 mmol) obtained in Preparation Example 29 and 2-[1-[2-fluoro-4-(4,4,5,5-tetramethyl-1,3,2-dioxaborolan-2-yl)phenyl]-4-piperidyl]acetic acid ethyl ester (0.08 g, 0.2 mmol) obtained in Preparation Example 99 were reacted in the same manner as in Step A of Example 96 and Step B of Example 1 to obtain the title compound (0.009 g, 13%).

¹H-NMR (CDCl₃) δ 7.72 (2H, m), 7.58 (1H, m), 7.24 (1H, m), 7.00 (1H, m), 6.60 (1H, m), 5.27 (1H, m), 3.53 (2H, m), 2.76 (2H, m), 2.53 (2H, m), 2.38 (2H, m), 2.19 (2H, m), 1.98 (1H, m), 1.89 (3H, m), 1.74 (1H, m), 1.58 (2H, m)

Example 321: 2-[1-[4-[6-(cyclobutoxy)-2-pyridyl]-2,6-difluoro-phenyl]azetidin-3-yl]acetic acid

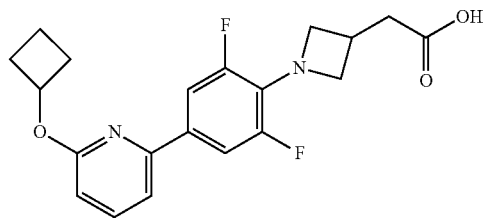 [SMILES: O=C(O)CC1CN(c2c(F)cc(-c3cccc(OC4CCC4)n3)cc2F)C1]

2-Chloro-6-cyclobutoxy-pyridine (0.057 g, 0.31 mmol) obtained in Preparation Example 29 and 2-[1-[2,6-difluoro-4-(4,4,5,5-tetramethyl-1,3,2-dioxaborolan-2-yl)phenyl]azetidin-3-yl]acetic acid ethyl ester (0.13 g, 0.34 mmol) obtained in Preparation Example 88 were reacted in the same manner as in Step A of Example 96 and Step B of Example 1 to obtain the title compound (0.018 g, 16%).

¹H-NMR (CDCl₃) δ 7.56 (1H, t), 7.45 (2H, m), 7.15 (1H, m), 6.56 (1H, m), 5.29 (1H, m), 4.42 (2H, m), 3.95 (2H, m), 3.05 (1H, m), 2.79 (2H, d), 2.51 (2H, m), 2.18 (2H, m), 1.86 (1H, m), 1.74 (1H, m)

Example 322: 2-[1-[4-[6-(cyclopropylmethoxy)-2-pyridyl]-2,6-difluoro-phenyl]azetidin-3-yl]acetic acid

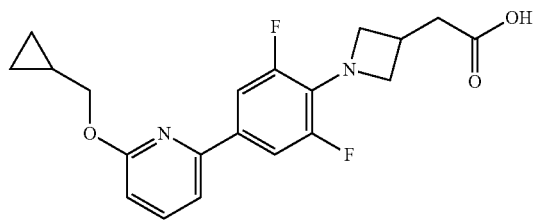 [SMILES: O=C(O)CC1CN(c2c(F)cc(-c3cccc(OCC4CC4)n3)cc2F)C1]

2-Chloro-6-cyclopropylmethoxy-pyridine (0.057 g, 0.31 mmol) obtained in Preparation Example 43 and 2-[1-[2,6-difluoro-4-(4,4,5,5-tetramethyl-1,3,2-dioxaborolan-2-yl)phenyl]azetidin-3-yl]acetic acid ethyl ester (0.13 g, 0.34 mmol) obtained in Preparation Example 88 were reacted in the same manner as in Step A of Example 96 and Step B of Example 1 to obtain the title compound (0.008 g, 7%).

$^1$H-NMR (CDCl$_3$) δ 7.57 (1H, t), 7.45 (2H, m), 7.15 (1H, m), 6.65 (1H, m), 4.43 (2H, m), 4.21 (2H, d), 3.94 (2H, m), 3.05 (1H, m), 2.79 (2H, d), 1.23 (1H, m), 0.63 (2H, m), 0.40 (2H, m)

Example 323: 2-[1-[4-[4-(cyclobutoxy)-6-methyl-pyrimidin-2-yl]-2,6-difluoro-phenyl]-4-piperidyl]acetic acid

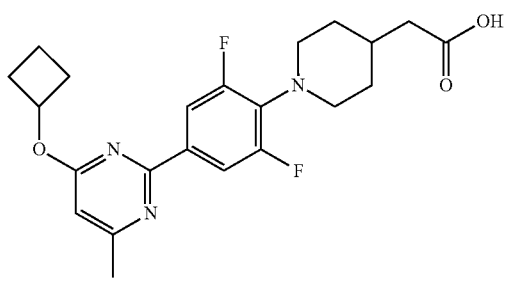 [SMILES: Cc1cc(OC2CCC2)nc(-c2cc(F)c(N3CCC(CC(=O)O)CC3)c(F)c2)n1]

2-Chloro-4-(cyclobutoxy)-6-methyl-pyrimidine (0.079 g, 0.4 mmol) obtained in Preparation Example 228 and 2-[1-[2,6-difluoro-4-(4,4,5,5-tetramethyl-1,3,2-dioxaborolan-2-yl)phenyl]-4-piperidyl]acetic acid ethyl ester (0.165 g, 0.4 mmol) obtained in Preparation Example 220 were reacted in the same manner as in Step A of Example 96 and Step B of Example 1 to obtain the title compound (0.08 g, 48%).

$^1$H-NMR (CDCl$_3$) δ 7.87 (2H, m), 6.39 (1H, s), 5.31 (1H, m), 3.35 (2H, m), 3.17 (2H, m), 2.52 (2H, m), 2.45 (3H, s), 2.36 (2H, d), 2.18 (2H, m), 1.95 (1H, m), 1.90 (1H, m), 1.82 (2H, m), 1.75 (1H, m), 1.50 (2H, m)

Example 324: 2-[1-[4-(6-butoxy-2-pyridyl)-2,6-difluoro-phenyl]-4-piperidyl]acetic acid

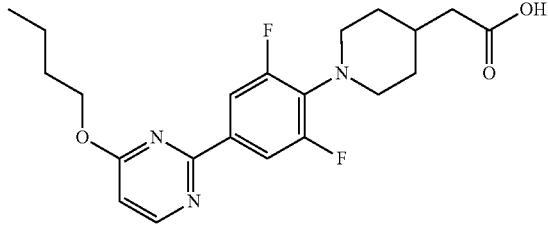 [SMILES: CCCCOc1ccnc(-c2cc(F)c(N3CCC(CC(=O)O)CC3)c(F)c2)n1]

2-Butoxy-6-chloro-pyridine (0.075 g, 0.4 mmol) obtained in Preparation Example 276 and 2-[1-[2,6-difluoro-4-(4,4,5,5-tetramethyl-1,3,2-dioxaborolan-2-yl)phenyl]-4-piperidyl]acetic acid ethyl ester (0.165 g, 0.4 mmol) obtained in Preparation Example 220 were reacted in the same manner as in Step A of Example 96 and Step B of Example 1 to obtain the title compound (0.06 g, 37%).

$^1$H-NMR (CDCl$_3$) δ 7.59 (1H, t), 7.51 (2H, m), 7.19 (1H, m), 6.65 (1H, m), 4.40 (2H, t), 3.32 (2H, m), 3.15 (2H, m), 2.37 (2H, d), 1.97 (1H, m), 1.81 (4H, m), 1.52 (4H, m), 0.99 (3H, t)

Example 325: 2-[1-[4-[2-(cyclobutoxy)-6-methyl-pyrimidin-4-yl]-2,6-difluoro-phenyl]-4-piperidyl]acetic acid

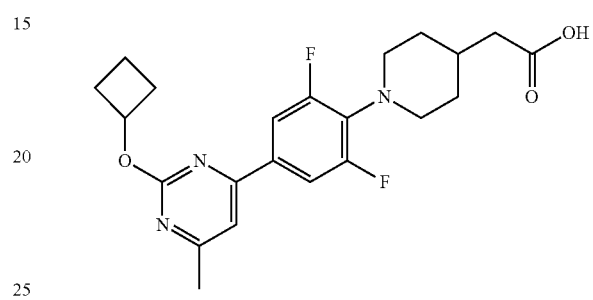

4-Chloro-2-(cyclobutoxy)-6-methyl-pyrimidine (0.051 g, 0.25 mmol) obtained in Preparation Example 229 and 2-[1-[2,6-difluoro-4-(4,4,5,5-tetramethyl-1,3,2-dioxaborolan-2-yl)phenyl]-4-piperidyl]acetic acid ethyl ester (0.116 g, 0.28 mmol) obtained in Preparation Example 220 were reacted in the same manner as in Step A of Example 96 and Step B of Example 1 to obtain the title compound (0.06 g, 57%).

$^1$H-NMR (CDCl$_3$) δ 7.57 (2H, m), 7.07 (1H, s), 5.27 (1H, m), 3.38 (2H, m), 3.16 (2H, m), 2.52 (2H, m), 2.48 (3H, s), 2.36 (2H, d), 2.24 (2H, m), 1.98 (1H, m), 1.86 (3H, m), 1.75 (1H, m), 1.47 (2H, m)

Example 326: 2-[1-[4-[2-(cyclobutoxy)thiazol-4-yl]-2,6-difluoro-phenyl]-4-piperidyl]acetic acid

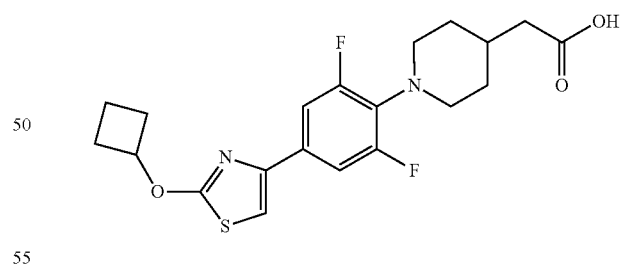

4-Bromo-2-(cyclobutoxy)thiazole (0.062 g, 0.26 mmol) obtained in Preparation Example 289 and 2-[1-[2,6-difluoro-4-(4,4,5,5-tetramethyl-1,3,2-dioxaborolan-2-yl)phenyl]-4-piperidyl]acetic acid ethyl ester (0.12 g, 0.29 mmol) obtained in Preparation Example 220 were reacted in the same manner as in Step A of Example 96 and Step B of Example 1 to obtain the title compound (0.04 g, 38%).

$^1$H-NMR (MeOH-d$_4$) δ 7.33 (2H, m), 7.12 (1H, s), 5.18 (1H, m), 3.21 (2H, m), 3.10 (2H, m), 2.51 (2H, m), 2.24 (4H, m), 1.87 (2H, m), 1.76 (3H, m), 1.41 (2H, m)

Example 327: 2-[1-[4-[6-(cyclobutoxy)-4-methyl-2-pyridyl]-2,6-difluoro-phenyl]-4-piperidyl]acetic acid

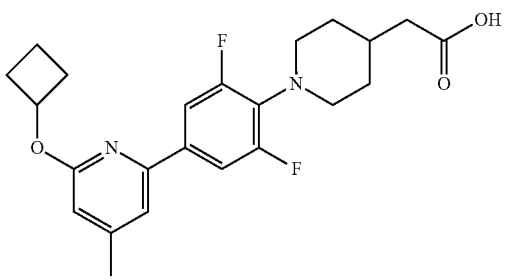 [SMILES: Cc1cc(OC2CCC2)nc(-c2cc(F)c(N3CCC(CC(=O)O)CC3)c(F)c2)c1]

2-Chloro-6-(cyclobutoxy)-4-methyl-pyridine (0.06 g, 0.3 mmol) obtained in Preparation Example 271 and 2-[1-[2,6-difluoro-4-(4,4,5,5-tetramethyl-1,3,2-dioxaborolan-2-yl)phenyl]-4-piperidyl]acetic acid ethyl ester (0.137 g, 0.33 mmol) obtained in Preparation Example 220 were reacted in the same manner as in Step A of Example 96 and Step B of Example 1 to obtain the title compound (0.038 g, 30%).

$^1$H-NMR (CDCl$_3$) δ 7.47 (2H, m), 7.03 (1H, s), 6.44 (1H, s), 5.23 (1H, m), 3.32 (2H, m), 3.14 (2H, m), 2.50 (2H, m), 2.36 (2H, d), 2.32 (3H, s), 2.17 (2H, m), 1.97 (1H, m), 1.84 (3H, m), 1.75 (1H, m), 1.49 (2H, m)

Example 328: 2-[1-[4-[4-(cyclobutoxy)-6-methyl-pyrimidin-2-yl]-2,6-difluoro-phenyl]azetidin-3-yl]acetic acid

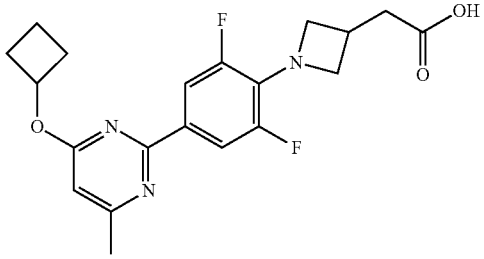 [SMILES: Cc1cc(OC2CCC2)nc(-c2cc(F)c(N3CC(CC(=O)O)C3)c(F)c2)n1]

2-Chloro-4-(cyclobutoxy)-6-methyl-pyrimidine (0.08 g, 0.4 mmol) obtained in Preparation Example 228 and 2-[1-[2,6-difluoro-4-(4,4,5,5-tetramethyl-1,3,2-dioxaborolan-2-yl)phenyl]azetidin-3-yl]acetic acid ethyl ester (0.17 g, 0.44 mmol) obtained in Preparation Example 88 were reacted in the same manner as in Step A of Example 96 and Step B of Example 1 to obtain the title compound (0.124 g, 80%).

$^1$H-NMR (CDCl$_3$) δ 7.82 (2H, m), 6.34 (1H, s), 5.28 (1H, m), 4.46 (2H, m), 3.98 (2H, m), 3.06 (1H, m), 2.79 (2H, d), 2.52 (2H, m), 2.43 (3H, s), 2.18 (2H, m), 1.87 (1H, m), 1.75 (1H, m)

Example 329: 2-[1-[4-[6-(cyclobutoxy)pyrazin-2-yl]-2,6-difluoro-phenyl]-4-piperidyl]acetic acid

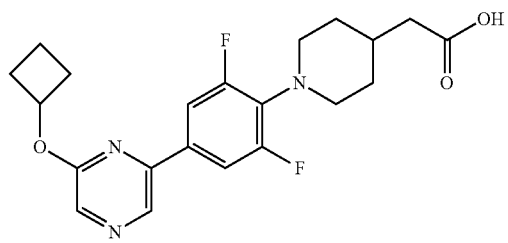 [SMILES: O=C(O)CC1CCN(c2c(F)cc(-c3cncc(OC4CCC4)n3)cc2F)CC1]

2-Chloro-6-(cyclobutoxy)pyrazine (0.07 g, 0.38 mmol) obtained in Preparation Example 232 and 2-[1-[2,6-difluoro-4-(4,4,5,5-tetramethyl-1,3,2-dioxaborolan-2-yl)phenyl]-4-piperidyl]acetic acid ethyl ester (0.17 g, 0.42 mmol) obtained in Preparation Example 220 were reacted in the same manner as in Step A of Example 96 and Step B of Example 1 to obtain the title compound (0.12 g, 78%).

$^1$H-NMR (CDCl$_3$) δ 8.46 (1H, s), 8.08 (1H, s), 7.48 (2H, m), 5.26 (1H, m), 3.36 (2H, m), 3.17 (2H, m), 2.53 (2H, m), 2.37 (2H, d), 2.22 (2H, m), 1.99 (1H, m), 1.91 (1H, m), 1.84 (2H, m), 1.76 (1H, m), 1.50 (2H, m)

Example 330: 2-[1-[4-[4-(cyclobutoxy)pyrimidin-2-yl]-2,6-difluoro-phenyl]-4-piperidyl]acetic acid

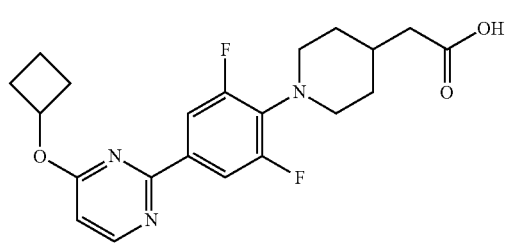 [SMILES: O=C(O)CC1CCN(c2c(F)cc(-c3nccc(OC4CCC4)n3)cc2F)CC1]

2-Chloro-4-(cyclobutoxy)pyrimidine (0.07 g, 0.38 mmol) obtained in Preparation Example 230 and 2-[1-[2,6-difluoro-4-(4,4,5,5-tetramethyl-1,3,2-dioxaborolan-2-yl)phenyl]-4-piperidyl]acetic acid ethyl ester (0.17 g, 0.42 mmol) obtained in Preparation Example 220 were reacted in the same manner as in Step A of Example 96 and Step B of Example 1 to obtain the title compound (0.135 g, 88%).

$^1$H-NMR (CDCl$_3$) δ 8.45 (1H, d), 7.87 (2H, m), 6.54 (1H, d), 5.32 (1H, m), 3.37 (2H, m), 3.18 (2H, m), 2.54 (2H, m), 2.37 (2H, d), 2.20 (2H, m), 1.99 (1H, m), 1.89 (1H, m), 1.83 (2H, m), 1.77 (1H, m), 1.49 (2H, m)

Example 331: 2-[1-[4-[4-(cyclopropylmethoxy)-6-methyl-pyrimidin-2-yl]-2,6-difluoro-phenyl]-4-piperidyl]acetic acid

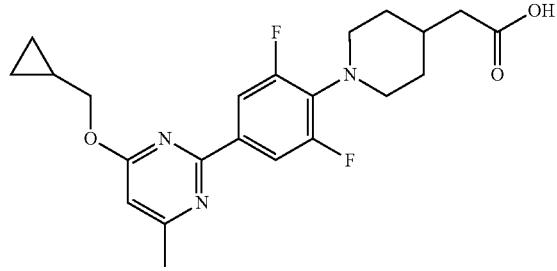 [SMILES: Cc1cc(OCC2CC2)nc(-c2cc(F)c(N3CCC(CC(=O)O)CC3)c(F)c2)n1]

2-Chloro-4-(cyclopropylmethoxy)-6-methyl-pyrimidine (0.073 g, 0.367 mmol) obtained in Preparation Example 227 and 2-[1-[2,6-difluoro-4-(4,4,5,5-tetramethyl-1,3,2-dioxaborolan-2-yl)phenyl]-4-piperidyl]acetic acid ethyl ester (0.165 g, 0.40 mmol) obtained in Preparation Example 220 were reacted in the same manner as in Step A of Example 96 and Step B of Example 1 to obtain the title compound (0.13 g, 85%).

$^1$H-NMR (CDCl$_3$) δ 7.88 (2H, m), 6.46 (1H, s), 4.27 (2H, d), 3.35 (2H, m), 3.16 (2H, m), 2.46 (3H, s), 2.36 (2H, d), 1.99 (1H, m), 1.82 (2H, m), 1.48 (2H, m), 1.31 (1H, m), 0.64 (2H, m), 0.40 (2H, m)

Example 332: 2-[1-[4-[4-(cyclopropylmethoxy)pyrimidin-2-yl]-2,6-difluoro-phenyl]-4-piperidyl]acetic acid

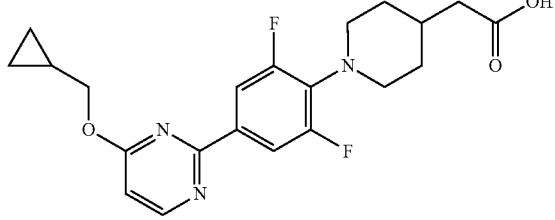

2-Chloro-4-(cyclopropylmethoxy)pyrimidine (0.07 g, 0.38 mmol) obtained in Preparation Example 231 and 2-[1-[2,6-difluoro-4-(4,4,5,5-tetramethyl-1,3,2-dioxaborolan-2-yl)phenyl]-4-piperidyl]acetic acid ethyl ester (0.17 g, 0.42 mmol) obtained in Preparation Example 220 were reacted in the same manner as in Step A of Example 96 and Step B of Example 1 to obtain the title compound (0.12 g, 78%).

$^1$H-NMR (CDCl$_3$) δ 8.45 (1H, d), 7.87 (2H, m), 6.62 (1H, d), 4.30 (2H, d), 3.38 (2H, m), 3.18 (2H, m), 2.37 (2H, d), 1.99 (1H, m), 1.83 (2H, m), 1.50 (2H, m), 1.33 (1H, m), 0.66 (2H, m), 0.41 (2H, m)

Example 333: 2-[1-[4-[6-(cyclopropylmethoxy)pyrazin-2-yl]-2,6-difluoro-phenyl]-4-piperidyl]acetic acid

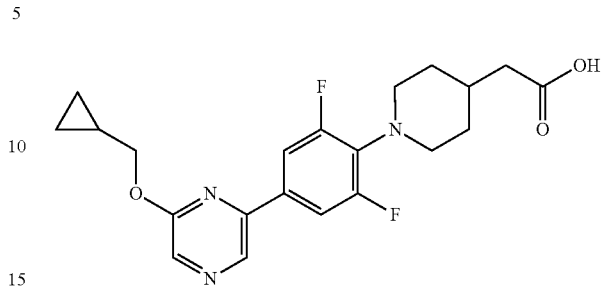

2-Chloro-6-(cyclopropylmethoxy)pyrazine (0.07 g, 0.38 mmol) obtained in Preparation Example 233 and 2-[1-[2,6-difluoro-4-(4,4,5,5-tetramethyl-1,3,2-dioxaborolan-2-yl)phenyl]-4-piperidyl]acetic acid ethyl ester (0.17 g, 0.42 mmol) obtained in Preparation Example 220 were reacted in the same manner as in Step A of Example 96 and Step B of Example 1 to obtain the title compound (0.13 g, 85%).

$^1$H-NMR (CDCl$_3$) δ 8.46 (1H, s), 8.15 (1H, s), 7.50 (2H, m), 4.25 (2H, d), 3.35 (2H, m), 3.16 (2H, m), 2.37 (2H, d), 1.99 (1H, m), 1.84 (2H, m), 1.51 (2H, m), 1.33 (1H, m), 0.66 (2H, m), 0.41 (2H, m)

Example 334: 2-[1-[4-[6-(cyclobutoxy)pyrazin-2-yl]-2,6-difluoro-phenyl]azetidin-3-yl]acetic acid

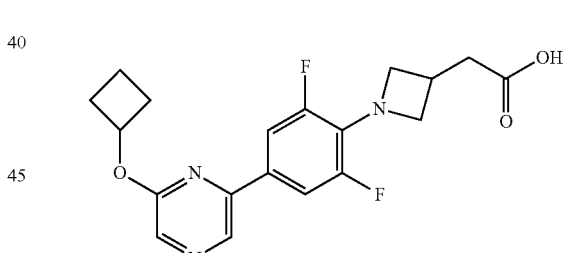

2-Chloro-6-(cyclobutoxy)pyrazine (0.048 g, 0.26 mmol) obtained in Preparation Example 232 and 2-[1-[2,6-difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 were reacted in the same manner as in Step A of Example 96 and Step B of Example 1 to obtain the title compound (0.06 g, 61%).

$^1$H-NMR (CDCl$_3$) δ 8.41 (1H, s), 8.02 (1H, s), 7.44 (2H, m), 5.25 (1H, m), 4.46 (2H, m), 3.98 (2H, m), 3.07 (1H, m), 2.80 (2H, d), 2.52 (2H, m), 2.21 (2H, m), 1.90 (1H, m), 1.77 (1H, m)

Example 335: 2-[1-[4-[6-(cyclopropylmethoxy)pyrazin-2-yl]-2,6-difluoro-phenyl]azetidin-3-yl]acetic acid

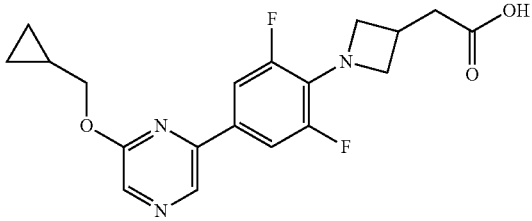 [SMILES: O=C(O)CC1CN(c2c(F)cc(-c3cncc(OCC4CC4)n3)cc2F)C1]

2-Chloro-6-(cyclopropylmethoxy)pyrazine (0.048 g, 0.26 mmol) obtained in Preparation Example 233 and 2-[1-[2,6-difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 were reacted in the same manner as in Step A of Example 96 and Step B of Example 1 to obtain the title compound (0.058 g, 59%).

$^1$H-NMR (CDCl$_3$) δ 8.41 (1H, s), 8.09 (1H, s), 7.45 (2H, m), 4.45 (2H, m), 4.24 (2H, d), 3.98 (2H, m), 3.06 (1H, m), 2.80 (2H, d), 1.33 (1H, m), 0.66 (2H, m), 0.40 (2H, m)

Example 336: 2-[1-[4-[4-(cyclobutoxy)pyrimidin-2-yl]-2,6-difluoro-phenyl]azetidin-3-yl]acetic acid

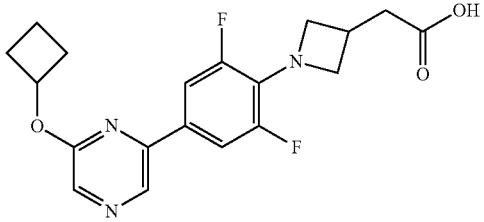 [SMILES: O=C(O)CC1CN(c2c(F)cc(-c3cncc(OC4CCC4)n3)cc2F)C1]

2-Chloro-4-(cyclobutoxy)pyrimidine (0.048 g, 0.26 mmol) obtained in Preparation Example 230 and 2-[1-[2,6-difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 were reacted in the same manner as in Step A of Example 96 and Step B of Example 1 to obtain the title compound (0.024 g, 25%).

$^1$H-NMR (CDCl$_3$) δ 8.41 (1H, d), 7.81 (2H, m), 6.49 (1H, d), 5.31 (1H, m), 4.48 (2H, m), 3.99 (2H, m), 3.08 (1H, m), 2.79 (2H, d), 2.53 (2H, m), 2.20 (2H, m), 1.90 (1H, m), 1.78 (1H, m)

Example 337: 2-[1-[4-[4-(cyclopropylmethoxy)pyrimidin-2-yl]-2,6-difluoro-phenyl]azetidin-3-yl]acetic acid

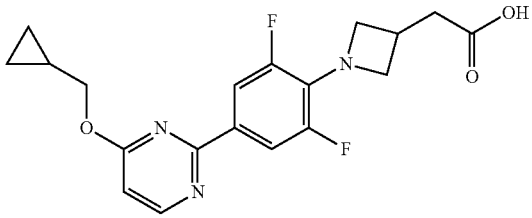 [SMILES: O=C(O)CC1CN(c2c(F)cc(-c3nccc(OCC4CC4)n3)cc2F)C1]

2-Chloro-4-(cyclopropylmethoxy)pyrimidine (0.048 g, 0.26 mmol) obtained in Preparation Example 231 and 2-[1-[2,6-difluoro-4-(4,4,5,5-tetramethyl-1,3,2-dioxaborolan-2-yl)phenyl]azetidin-3-yl]acetic acid ethyl ester (0.10 g, 0.26 mmol) obtained in Preparation Example 88 were reacted in the same manner as in Step A of Example 96 and Step B of Example 1 to obtain the title compound (0.054 g, 55%).

$^1$H-NMR (CDCl$_3$) δ 8.41 (1H, d), 7.82 (2H, m), 6.56 (1H, d), 4.47 (2H, m), 4.28 (2H, d), 3.99 (2H, m), 3.07 (1H, m), 2.79 (2H, d), 1.32 (1H, m), 0.64 (2H, m), 0.40 (2H, m)

Example 338: 2-[1-[4-(6-ethoxypyrazin-2-yl)-2,6-difluoro-phenyl]-4-piperidyl]acetic acid

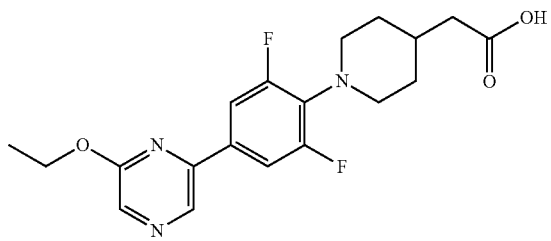 [SMILES: CCOc1cncc(-c2cc(F)c(N3CCC(CC(=O)O)CC3)c(F)c2)n1]

2-Chloro-6-ethoxy-pyrazine (0.051 g, 0.32 mmol) obtained in Preparation Example 302 and 2-[1-[2,6-difluoro-4-(4,4,5,5-tetramethyl-1,3,2-dioxaborolan-2-yl)phenyl]-4-piperidyl]acetic acid ethyl ester (0.144 g, 0.35 mmol) obtained in Preparation Example 220 were reacted in the same manner as in Step A of Example 96 and Step B of Example 1 to obtain the title compound (0.083 g, 69%).

$^1$H-NMR (CDCl$_3$) δ 8.46 (1H, s), 8.11 (1H, s), 7.51 (2H, m), 4.48 (2H, q), 3.35 (2H, m), 3.16 (2H, m), 2.37 (2H, d), 1.98 (1H, m), 1.83 (2H, m), 1.45 (5H, m)

Example 339: 2-[1-[2,6-difluoro-4-(6-isopropoxy-pyrazin-2-yl)phenyl]-4-piperidyl]acetic acid

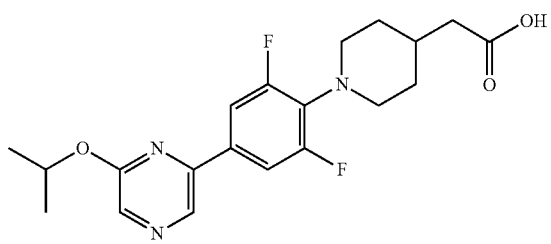 [SMILES: CC(C)Oc1cncc(-c2cc(F)c(N3CCC(CC(=O)O)CC3)c(F)c2)n1]

2-Chloro-6-isopropoxy-pyrazine (0.055 g, 0.32 mmol) obtained in Preparation Example 301 and 2-[1-[2,6-difluoro-4-(4,4,5,5-tetramethyl-1,3,2-dioxaborolan-2-yl)phenyl]-4-piperidyl]acetic acid ethyl ester (0.144 g, 0.35 mmol) obtained in Preparation Example 220 were reacted in the same manner as in Step A of Example 96 and Step B of Example 1 to obtain the title compound (0.108 g, 87%).

$^1$H-NMR (CDCl$_3$) δ 8.44 (1H, s), 8.06 (1H, s), 7.49 (2H, m), 5.43 (1H, m), 3.35 (2H, m), 3.16 (2H, m), 2.37 (2H, d), 1.99 (1H, m), 1.84 (2H, m), 1.51 (2H, m), 1.42 (6H, d)

Example 340: 2-[1-[2,6-difluoro-4-(6-methoxy-pyrazin-2-yl)phenyl]-4-piperidyl]acetic acid

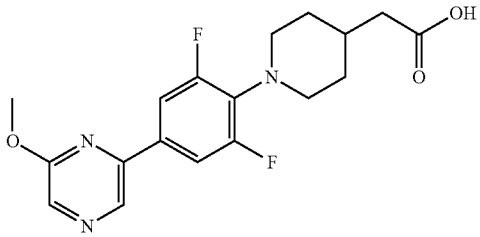 [SMILES: COc1cncc(-c2cc(F)c(N3CCC(CC(=O)O)CC3)c(F)c2)n1]

2-Chloro-6-methoxy-pyrazine (0.044 g, 0.3 mmol) obtained in Preparation Example 234 and 2-[1-[2,6-difluoro-4-(4,4,5,5-tetramethyl-1,3,2-dioxaborolan-2-yl)phenyl]-4-piperidyl]acetic acid ethyl ester (0.135 g, 0.33 mmol) obtained in Preparation Example 220 were reacted in the same manner as in Step A of Example 96 and Step B of Example 1 to obtain the title compound (0.053 g, 49%).

$^1$H-NMR (CDCl$_3$) δ 8.48 (1H, s), 8.14 (1H, s), 7.52 (2H, m), 4.05 (3H, s), 3.35 (2H, m), 3.17 (2H, m), 2.36 (2H, d), 1.99 (1H, m), 1.83 (2H, m), 1.50 (2H, m)

Example 341: 2-[1-[2,6-difluoro-4-(6-propoxy-pyrazin-2-yl)phenyl]-4-piperidyl]acetic acid

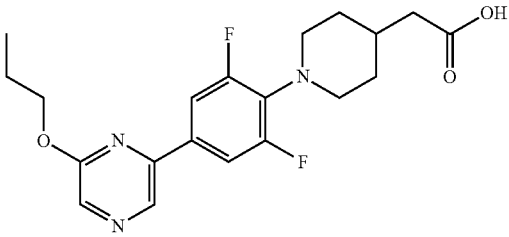 [SMILES: CCCOc1cncc(-c2cc(F)c(N3CCC(CC(=O)O)CC3)c(F)c2)n1]

2-Chloro-6-propoxy-pyrazine (0.052 g, 0.3 mmol) obtained in Preparation Example 235 and 2-[1-[2,6-difluoro-4-(4,4,5,5-tetramethyl-1,3,2-dioxaborolan-2-yl)phenyl]-4-piperidyl]acetic acid ethyl ester (0.135 g, 0.33 mmol) obtained in Preparation Example 220 were reacted in the same manner as in Step A of Example 96 and Step B of Example 1 to obtain the title compound (0.057 g, 51%).

$^1$H-NMR (CDCl$_3$) δ 8.46 (1H, s), 8.12 (1H, s), 7.50 (2H, m), 4.38 (2H, t), 3.35 (2H, m), 3.16 (2H, m), 2.37 (2H, d), 1.99 (1H, m), 1.86 (4H, m), 1.48 (2H, m), 1.06 (3H, t)

Example 342: 2-[1-[2,6-difluoro-4-(6-isobutoxy-pyrazin-2-yl)phenyl]-4-piperidyl]acetic acid

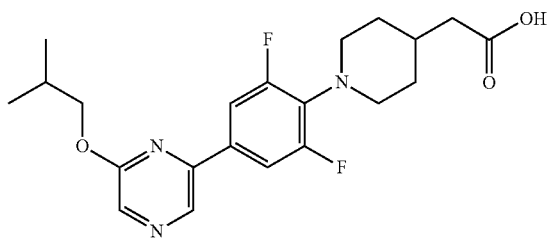 [SMILES: CC(C)COc1cncc(-c2cc(F)c(N3CCC(CC(=O)O)CC3)c(F)c2)n1]

2-Chloro-6-isobutoxy-pyrazine (0.056 g, 0.3 mmol) obtained in Preparation Example 237 and 2-[1-[2,6-difluoro-4-(4,4,5,5-tetramethyl-1,3,2-dioxaborolan-2-yl)phenyl]-4-piperidyl]acetic acid ethyl ester (0.135 g, 0.33 mmol) obtained in Preparation Example 220 were reacted in the same manner as in Step A of Example 96 and Step B of Example 1 to obtain the title compound (0.053 g, 44%).

$^1$H-NMR (CDCl$_3$) δ 8.45 (1H, s), 8.12 (1H, s), 7.49 (2H, m), 4.18 (2H, d), 3.35 (2H, m), 3.16 (2H, m), 2.37 (2H, d), 2.15 (1H, m), 1.99 (1H, m), 1.83 (2H, m), 1.50 (2H, m), 1.06 (6H, d)

Example 343: 2-[1-[4-(6-butoxypyrazin-2-yl)-2,6-difluoro-phenyl]-4-piperidyl]acetic acid

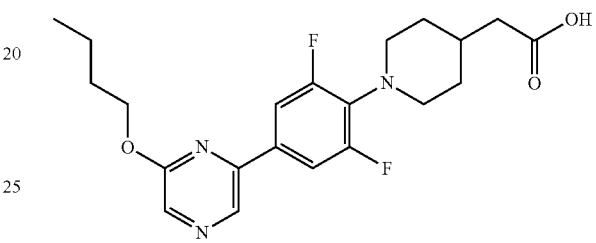

2-Butoxy-6-chloro-pyrazine (0.056 g, 0.3 mmol) obtained in Preparation Example 236 and 2-[1-[2,6-difluoro-4-(4,4,5,5-tetramethyl-1,3,2-dioxaborolan-2-yl)phenyl]-4-piperidyl]acetic acid ethyl ester (0.135 g, 0.33 mmol) obtained in Preparation Example 220 were reacted in the same manner as in Step A of Example 96 and Step B of Example 1 to obtain the title compound (0.044 g, 36%).

$^1$H-NMR (CDCl$_3$) δ 8.45 (1H, s), 8.10 (1H, s), 7.50 (2H, m), 4.41 (2H, t), 3.33 (2H, m), 3.15 (2H, m), 2.36 (2H, d), 1.98 (1H, m), 1.80 (4H, m), 1.49 (4H, m), 1.00 (3H, t)

Example 344: 2-[1-[4-[6-(cyclopentoxy)pyrazin-2-yl]-2,6-difluoro-phenyl]-4-piperidyl]acetic acid

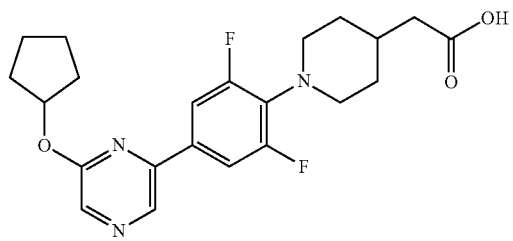 [SMILES: O=C(O)CC1CCN(c2c(F)cc(-c3cncc(OC4CCCC4)n3)cc2F)CC1]

2-Chloro-6-(cyclopentoxy)pyrazine (0.06 g, 0.3 mmol) obtained in Preparation Example 238 and 2-[1-[2,6-difluoro-4-(4,4,5,5-tetramethyl-1,3,2-dioxaborolan-2-yl)phenyl]-4-piperidyl]acetic acid ethyl ester (0.135 g, 0.33 mmol) obtained in Preparation Example 220 were reacted in the same manner as in Step A of Example 96 and Step B of Example 1 to obtain the title compound (0.061 g, 49%).

$^1$H-NMR (CDCl$_3$) δ 8.43 (1H, s), 8.06 (1H, s), 7.50 (2H, m), 5.50 (1H, m), 3.34 (2H, m), 3.16 (2H, m), 2.37 (2H, d), 2.02 (2H, m), 1.99 (1H, m), 1.82 (6H, m), 1.67 (2H, m), 1.50 (2H, m)

Example 345: 2-[1-[4-(4-ethoxypyrimidin-2-yl)-2,6-difluoro-phenyl]-4-piperidyl]acetic acid

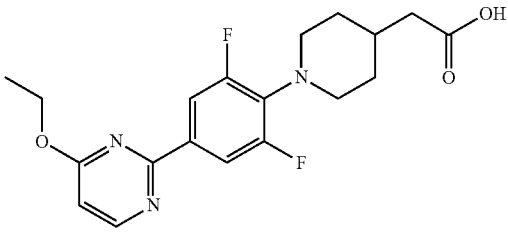 [SMILES: CCOc1ccnc(-c2cc(F)c(N3CCC(CC(=O)O)CC3)c(F)c2)n1]

2-Chloro-4-ethoxy-pyrimidine (0.049 g, 0.31 mmol) obtained in Preparation Example 239 and 2-[1-[2,6-difluoro-4-(4,4,5,5-tetramethyl-1,3,2-dioxaborolan-2-yl)phenyl]-4-piperidyl]acetic acid ethyl ester (0.156 g, 0.38 mmol) obtained in Preparation Example 220 were reacted in the same manner as in Step A of Example 96 and Step B of Example 1 to obtain the title compound (0.074 g, 64%).

$^1$H-NMR (CDCl$_3$) δ 8.44 (1H, d), 7.87 (2H, m), 6.57 (1H, d), 4.52 (2H, q), 3.37 (2H, m), 3.16 (2H, m), 2.36 (2H, d), 1.98 (1H, m), 1.82 (2H, m), 1.48 (2H, m), 1.45 (3H, t)

Example 346: 2-[1-[2,6-difluoro-4-(4-isopropoxypyrimidin-2-yl)phenyl]-4-piperidyl]acetic acid

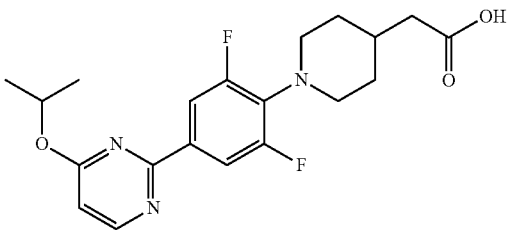 [SMILES: CC(C)Oc1ccnc(-c2cc(F)c(N3CCC(CC(=O)O)CC3)c(F)c2)n1]

2-Chloro-4-isopropoxy-pyrimidine (0.059 g, 0.34 mmol) obtained in Preparation Example 240 and 2-[1-[2,6-difluoro-4-(4,4,5,5-tetramethyl-1,3,2-dioxaborolan-2-yl)phenyl]-4-piperidyl]acetic acid ethyl ester (0.156 g, 0.38 mmol) obtained in Preparation Example 220 were reacted in the same manner as in Step A of Example 96 and Step B of Example 1 to obtain the title compound (0.089 g, 67%).

$^1$H-NMR (CDCl$_3$) δ 8.43 (1H, d), 7.86 (2H, m), 6.53 (1H, d), 5.52 (1H, m), 3.37 (2H, m), 3.17 (2H, m), 2.36 (2H, d), 1.98 (1H, m), 1.83 (2H, m), 1.48 (2H, m), 1.41 (6H, d)

Example 347: 2-[1-[2,6-difluoro-4-(4-propoxypyrimidin-2-yl)phenyl]-4-piperidyl]acetic acid

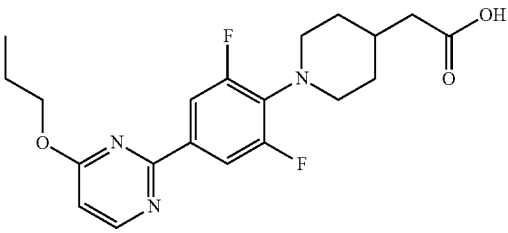 [SMILES: CCCOc1ccnc(-c2cc(F)c(N3CCC(CC(=O)O)CC3)c(F)c2)n1]

2-Chloro-4-propoxy-pyrimidine (0.055 g, 0.32 mmol) obtained in Preparation Example 241 and 2-[1-[2,6-difluoro-4-(4,4,5,5-tetramethyl-1,3,2-dioxaborolan-2-yl)phenyl]-4-piperidyl]acetic acid ethyl ester (0.156 g, 0.38 mmol) obtained in Preparation Example 220 were reacted in the same manner as in Step A of Example 96 and Step B of Example 1 to obtain the title compound (0.079 g, 63%).

$^1$H-NMR (CDCl$_3$) δ 8.45 (1H, d), 7.88 (2H, m), 6.58 (1H, d), 4.42 (2H, t), 3.37 (2H, m), 3.16 (2H, m), 2.36 (2H, d), 1.98 (1H, m), 1.83 (4H, m), 1.48 (2H, m), 1.06 (3H, t)

Example 348: 2-[1-[2,6-difluoro-4-(4-isobutoxypyrimidin-2-yl)phenyl]-4-piperidyl]acetic acid

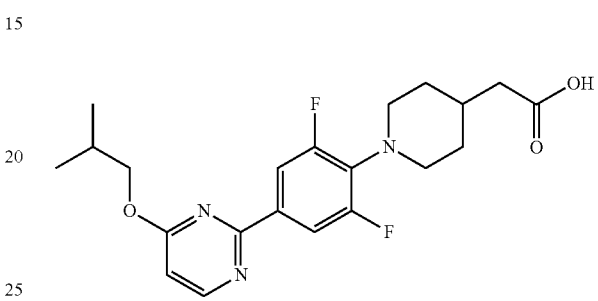

2-Chloro-4-isobutoxy-pyrimidine (0.059 g, 0.31 mmol) obtained in Preparation Example 242 and 2-[1-[2,6-difluoro-4-(4,4,5,5-tetramethyl-1,3,2-dioxaborolan-2-yl)phenyl]-4-piperidyl]acetic acid ethyl ester (0.156 g, 0.38 mmol) obtained in Preparation Example 220 were reacted in the same manner as in Step A of Example 96 and Step B of Example 1 to obtain the title compound (0.066 g, 52%).

$^1$H-NMR (CDCl$_3$) δ 8.44 (1H, d), 7.88 (2H, m), 6.59 (1H, d), 4.23 (2H, d), 3.37 (2H, m), 3.18 (2H, m), 2.37 (2H, d), 2.15 (1H, m), 1.99 (1H, m), 1.83 (2H, m), 1.48 (2H, m), 1.04 (6H, d)

Example 349: 2-[1-[4-(4-ethoxy-6-methyl-pyrimidin-2-yl)-2,6-difluoro-phenyl]-4-piperidyl]acetic acid

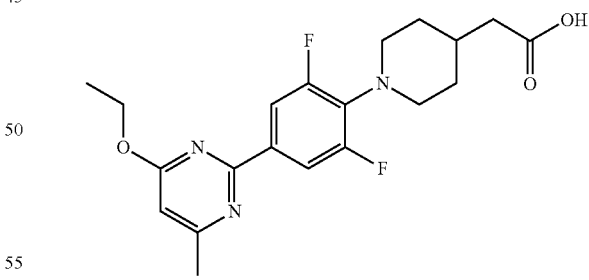

2-Chloro-4-ethoxy-6-methyl-pyrimidine (0.056 g, 0.32 mmol) obtained in Preparation Example 243 and 2-[1-[2,6-difluoro-4-(4,4,5,5-tetramethyl-1,3,2-dioxaborolan-2-yl)phenyl]-4-piperidyl]acetic acid ethyl ester (0.148 g, 0.36 mmol) obtained in Preparation Example 220 were reacted in the same manner as in Step A of Example 96 and Step B of Example 1 to obtain the title compound (0.085 g, 67%).

$^1$H-NMR (CDCl$_3$) δ 7.89 (2H, m), 6.42 (1H, s), 4.50 (2H, q), 3.36 (2H, m), 3.16 (2H, m), 2.46 (3H, s), 2.36 (2H, d), 1.98 (1H, m), 1.82 (2H, m), 1.48 (2H, m), 1.42 (3H, t)

Example 350: 2-[1-[2,6-difluoro-4-(4-isopropoxy-6-methyl-pyrimidin-2-yl)phenyl]-4-piperidyl]acetic acid

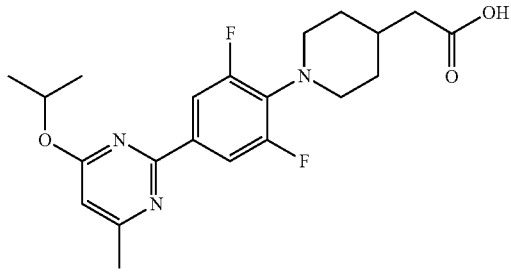 [SMILES: Cc1cc(OC(C)C)nc(-c2cc(F)c(N3CCC(CC(=O)O)CC3)c(F)c2)n1]

2-Chloro-4-isopropoxy-6-methyl-pyrimidine (0.06 g, 0.32 mmol) obtained in Preparation Example 244 and 2-[1-[2,6-difluoro-4-(4,4,5,5-tetramethyl-1,3,2-dioxaborolan-2-yl)phenyl]-4-piperidyl]acetic acid ethyl ester (0.148 g, 0.36 mmol) obtained in Preparation Example 220 were reacted in the same manner as in Step A of Example 96 and Step B of Example 1 to obtain the title compound (0.09 g, 69%).

$^1$H-NMR (CDCl$_3$) δ 7.88 (2H, m), 6.38 (1H, s), 5.50 (1H, m), 3.36 (2H, m), 3.16 (2H, m), 2.45 (3H, s), 2.36 (2H, d), 1.98 (1H, m), 1.82 (2H, m), 1.49 (2H, m), 1.39 (6H, d)

Example 351: 2-[1-[2,6-difluoro-4-(4-methyl-6-propoxy-pyrimidin-2-yl)phenyl]-4-piperidyl]acetic acid

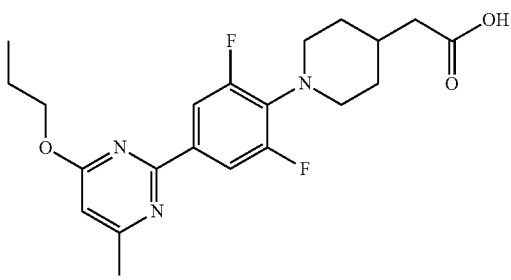 [SMILES: CCCOc1cc(C)nc(-c2cc(F)c(N3CCC(CC(=O)O)CC3)c(F)c2)n1]

2-Chloro-4-methyl-6-propoxy-pyrimidine (0.061 g, 0.32 mmol) obtained in Preparation Example 245 and 2-[1-[2,6-difluoro-4-(4,4,5,5-tetramethyl-1,3,2-dioxaborolan-2-yl)phenyl]-4-piperidyl]acetic acid ethyl ester (0.147 g, 0.36 mmol) obtained in Preparation Example 220 were reacted in the same manner as in Step A of Example 96 and Step B of Example 1 to obtain the title compound (0.085 g, 66%).

$^1$H-NMR (CDCl$_3$) δ 7.88 (2H, m), 6.42 (1H, s), 4.39 (2H, t), 3.36 (2H, m), 3.15 (2H, m), 2.45 (3H, s), 2.36 (2H, d), 1.98 (1H, m), 1.81 (4H, m), 1.48 (2H, m), 1.03 (3H, t)

Example 352: 2-[1-[2,6-difluoro-4-(4-isobutoxy-6-methyl-pyrimidin-2-yl)phenyl]-4-piperidyl]acetic acid

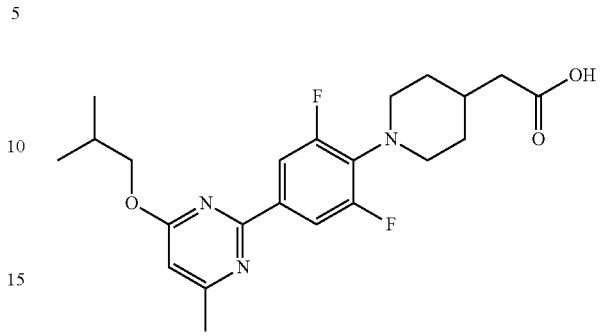

2-Chloro-4-isobutoxy-6-methyl-pyrimidine (0.058 g, 0.29 mmol) obtained in Preparation Example 246 and 2-[1-[2,6-difluoro-4-(4,4,5,5-tetramethyl-1,3,2-dioxaborolan-2-yl)phenyl]-4-piperidyl]acetic acid ethyl ester (0.149 g, 0.36 mmol) obtained in Preparation Example 220 were reacted in the same manner as in Step A of Example 96 and Step B of Example 1 to obtain the title compound (0.079 g, 65%).

$^1$H-NMR (CDCl$_3$) δ 7.88 (2H, m), 6.44 (1H, s), 4.21 (2H, d), 3.36 (2H, m), 3.16 (2H, m), 2.46 (3H, s), 2.36 (2H, d), 2.11 (1H, m), 1.98 (1H, m), 1.82 (2H, m), 1.48 (2H, m), 1.03 (6H, d)

Example 353: 2-[1-[2,6-difluoro-4-(6-pyrrolidin-1-ylpyrazin-2-yl)phenyl]-4-piperidyl]acetic acid

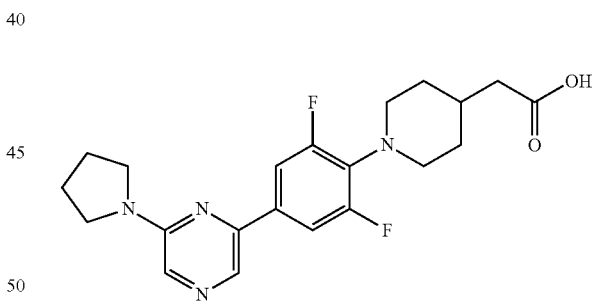

2-Chloro-6-pyrrolidin-1-yl-pyrazine (0.061 g, 0.33 mmol) obtained in Preparation Example 249 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.098 g, 74%).

$^1$H-NMR (CDCl$_3$) δ 8.12 (1H, s), 7.77 (1H, s), 7.52 (2H, m), 3.56 (4H, m), 3.32 (2H, m), 3.15 (2H, m), 2.32 (2H, d), 2.05 (4H, m), 1.96 (1H, m), 1.82 (2H, m), 1.47 (2H, m)

Example 354: 2-[1-[2,6-difluoro-4-[6-(isopropylamino)pyrazin-2-yl]phenyl]-4-piperidyl]acetic acid

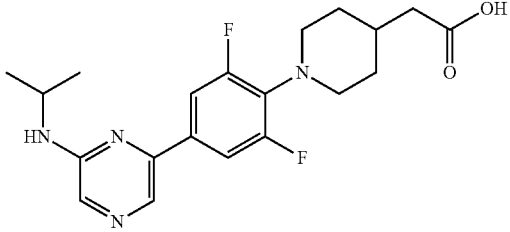 [SMILES: CC(C)Nc1cncc(-c2cc(F)c(N3CCC(CC(=O)O)CC3)c(F)c2)n1]

6-Chloro-N-isopropyl-pyrazin-2-amine (0.057 g, 0.33 mmol) obtained in Preparation Example 250 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.051 g, 40%).

$^1$H-NMR (CDCl$_3$) δ 8.11 (1H, s), 7.75 (1H, s), 7.46 (2H, m), 4.72 (1H, brs), 4.12 (1H, m), 3.33 (2H, m), 3.15 (2H, m), 2.32 (2H, d), 1.96 (1H, m), 1.83 (2H, m), 1.48 (2H, m), 1.29 (6H, d)

Example 355: 2-[1-[4-[6-(diethylamino)pyrazin-2-yl]-2,6-difluoro-phenyl]-4-piperidyl]acetic acid

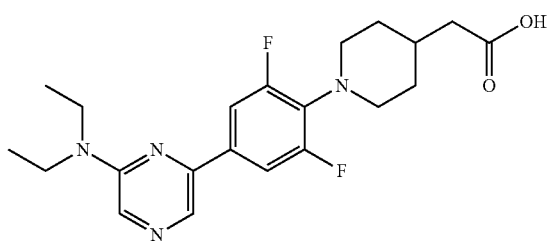 [SMILES: CCN(CC)c1cncc(-c2cc(F)c(N3CCC(CC(=O)O)CC3)c(F)c2)n1]

6-Chloro-N,N-diethyl-pyrazin-2-amine (0.055 g, 0.3 mmol) obtained in Preparation Example 253 and 2-[1-[2,6-difluoro-4-(4,4,5,5-tetramethyl-1,3,2-dioxaborolan-2-yl)phenyl]-4-piperidyl]acetic acid ethyl ester (0.17 g, 0.41 mmol) obtained in Preparation Example 220 were reacted in the same manner as in Step A of Example 96 and Step B of Example 1 to obtain the title compound (0.1 g, 82%).

$^1$H-NMR (CDCl$_3$) δ 8.11 (1H, s), 7.89 (1H, s), 7.48 (2H, m), 3.60 (4H, q), 3.33 (2H, m), 3.16 (2H, m), 2.36 (2H, d), 1.99 (1H, m), 1.83 (2H, m), 1.50 (2H, m), 1.25 (6H, t)

Example 356: 2-[1-[2,6-difluoro-4-[6-(isobutylamino)pyrazin-2-yl]phenyl]-4-piperidyl]acetic acid

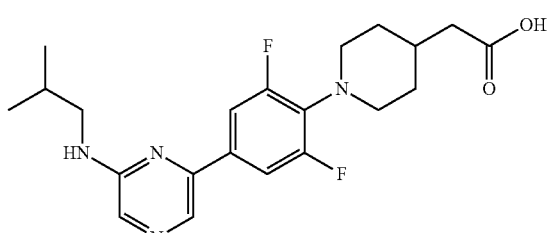

6-Chloro-N-isobutyl-pyrazin-2-amine (0.052 g, 0.28 mmol) obtained in Preparation Example 251 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.08 g, 72%).

$^1$H-NMR (CDCl$_3$) δ 8.15 (1H, s), 7.80 (1H, s), 7.45 (2H, m), 4.75 (1H, m), 3.32 (2H, m), 3.25 (2H, t), 3.15 (2H, m), 2.36 (2H, d), 1.95 (2H, m), 1.83 (2H, m), 1.48 (2H, m), 1.02 (6H, d)

Example 357: 2-[1-[4-[6-(cyclopentylamino)pyrazin-2-yl]-2,6-difluoro-phenyl]-4-piperidyl]acetic acid

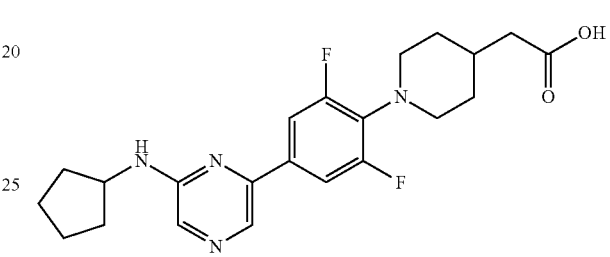

6-Chloro-N-cyclopentyl-pyrazin-2-amine (0.056 g, 0.28 mmol) obtained in Preparation Example 252 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.085 g, 72%).

$^1$H-NMR (CDCl$_3$) δ 8.15 (1H, s), 7.79 (1H, s), 7.47 (2H, m), 4.71 (1H, brs), 4.17 (1H, m), 3.32 (2H, m), 3.15 (2H, m), 2.36 (2H, d), 2.12 (2H, m), 1.97 (1H, m), 1.82-1.46 (10H, m)

Example 358: 2-[1-[4-[6-(cyclopentylamino)-2-pyridyl]-2,6-difluoro-phenyl]-4-piperidyl]acetic acid

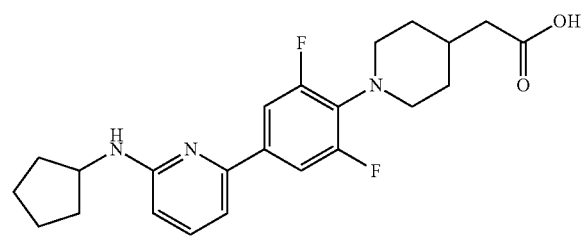 [SMILES: O=C(O)CC1CCN(c2c(F)cc(-c3cccc(NC4CCCC4)n3)cc2F)CC1]

6-Chloro-N-cyclopentyl-pyridin-2-amine (0.065 g, 0.33 mmol) and 2-[1-[2,6-difluoro-4-(4,4,5,5-tetramethyl-1,3,2-dioxaborolan-2-yl)phenyl]-4-piperidyl]acetic acid ethyl ester (0.149 g, 0.36 mmol) obtained in Preparation Example 220 were reacted in the same manner as in Step A of Example 96 and Step B of Example 1 to obtain the title compound (0.048 g, 34%).

$^1$H-NMR (CDCl$_3$) δ 7.49 (1H, t), 7.34 (2H, m), 6.82 (1H, d), 6.37 (1H, d), 3.95 (1H, m), 3.28 (2H, m), 3.13 (2H, m), 2.31 (2H, d), 2.05 (2H, m), 1.93 (1H, m), 1.79 (4H, m), 1.64 (2H, m), 1.57 (2H, m), 1.45 (2H, m)

Example 359: 2-[1-[4-[6-(dimethylamino)pyrazin-2-yl]-2,6-difluoro-phenyl]-4-piperidyl]acetic acid

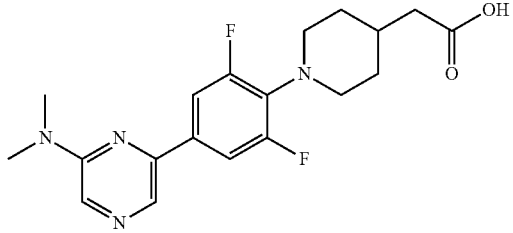 [SMILES: CN(C)c1cncc(-c2cc(F)c(N3CCC(CC(=O)O)CC3)c(F)c2)n1]

6-Chloro-N,N-dimethyl-pyrazin-2-amine (0.053 g, 0.33 mmol) obtained in Preparation Example 254 and 2-[1-[2,6-difluoro-4-(4,4,5,5-tetramethyl-1,3,2-dioxaborolan-2-yl)phenyl]-4-piperidyl]acetic acid ethyl ester (0.19 g, 0.47 mmol) obtained in Preparation Example 220 were reacted in the same manner as in Step A of Example 96 and Step B of Example 1 to obtain the title compound (0.06 g, 47%).

$^1$H-NMR (CDCl$_3$+MeOH-d$_4$) δ 8.13 (1H, m), 7.91 (1H, m), 7.51 (2H, m), 3.32 (2H, m), 3.19 (6H, s), 3.15 (2H, m), 2.31 (2H, d), 1.96 (1H, m), 1.82 (2H, m), 1.48 (2H, m)

Example 360: 2-[1-[2,6-difluoro-4-[4-(isobutylamino)pyrimidin-2-yl]phenyl]-4-piperidyl]acetic acid

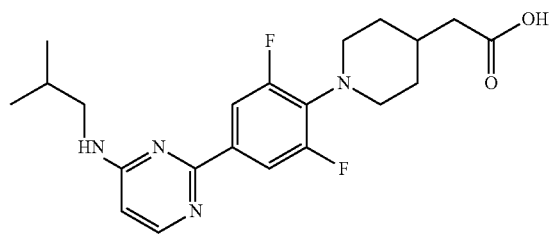 [SMILES: CC(C)CNc1ccnc(-c2cc(F)c(N3CCC(CC(=O)O)CC3)c(F)c2)n1]

2-Chloro-N-isobutyl-pyrimidin-4-amine (0.054 g, 0.29 mmol) obtained in Preparation Example 255 and 2-[1-[2,6-difluoro-4-(4,4,5,5-tetramethyl-1,3,2-dioxaborolan-2-yl)phenyl]-4-piperidyl]acetic acid ethyl ester (0.166 g, 0.4 mmol) obtained in Preparation Example 220 were reacted in the same manner as in Step A of Example 96 and Step B of Example 1 to obtain the title compound (0.035 g, 35%).

$^1$H-NMR (CDCl$_3$) δ 8.24 (1H, m), 7.80 (2H, m), 6.21 (1H, d), 3.35 (2H, m), 3.15 (4H, m), 2.35 (2H, d), 1.94 (2H, m), 1.82 (2H, m), 1.48 (2H, m), 1.00 (6H, d)

Example 361: 2-[1-[4-[6-(cyclobutoxy)-5-methyl-pyrazin-2-yl]-2,6-difluoro-phenyl]-4-piperidyl]acetic acid

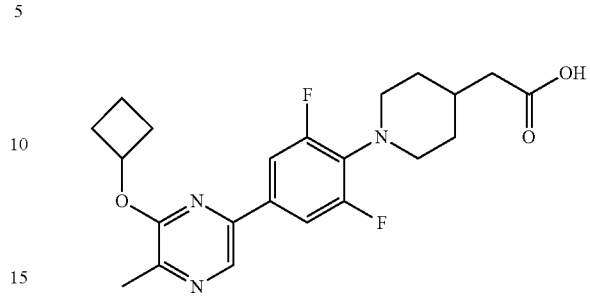

5-Chloro-3-(cyclobutoxy)-2-methyl-pyrazine (0.061 g, 0.3 mmol) obtained in Preparation Example 256 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.064 g, 48%).

$^1$H-NMR (CDCl$_3$) δ 8.33 (1H, s), 7.46 (2H, m), 5.27 (1H, m), 3.31 (2H, m), 3.16 (2H, m), 2.53 (2H, m), 2.49 (3H, s), 2.37 (2H, d), 2.23 (2H, m), 1.99 (1H, m), 1.81 (4H, m), 1.48 (2H, m)

Example 362: 2-[1-[2,6-difluoro-4-(6-phenylpyrazin-2-yl)phenyl]-4-piperidyl]acetic acid

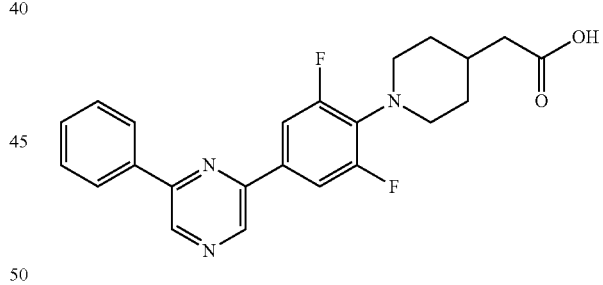

2-Chloro-6-phenyl-pyrazine (0.058 g, 0.3 mmol) and 2-[1-[2,6-difluoro-4-(4,4,5,5-tetramethyl-1,3,2-dioxaborolan-2-yl)phenyl]-4-piperidyl]acetic acid ethyl ester (0.15 g, 0.36 mmol) obtained in Preparation Example 220 were reacted in the same manner as in Step A of Example 96 and Step B of Example 1 to obtain the title compound (0.12 g, 98%).

$^1$H-NMR (CDCl$_3$) δ 8.95 (1H, s), 8.86 (1H, s), 8.13 (2H, m), 7.66 (2H, m), 7.54 (3H, m), 3.37 (2H, m), 3.19 (2H, m), 2.38 (2H, d), 1.99 (1H, m), 1.82 (2H, m), 1.48 (2H, m)

Example 363: 2-[1-[4-(6-cyclopentylpyrazin-2-yl)-2,6-difluoro-phenyl]-4-piperidyl]acetic acid

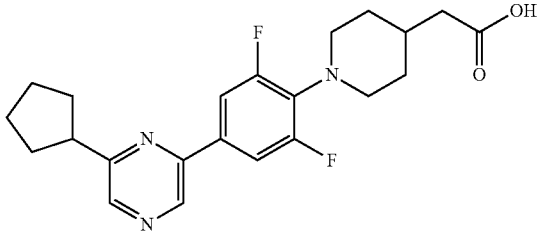 [SMILES: O=C(O)CC1CCN(c2c(F)cc(-c3cncc(C4CCCC4)n3)cc2F)CC1]

2-Chloro-6-cyclopentyl-pyrazine (0.058 g, 0.32 mmol) obtained in Preparation Example 258 and 2-[1-[2,6-difluoro-4-(4,4,5,5-tetramethyl-1,3,2-dioxaborolan-2-yl)phenyl]-4-piperidyl]acetic acid ethyl ester (0.155 g, 0.38 mmol) obtained in Preparation Example 220 were reacted in the same manner as in Step A of Example 96 and Step B of Example 1 to obtain the title compound (0.087 g, 66%).

$^1$H-NMR (CDCl$_3$) δ 8.71 (1H, s), 8.37 (1H, s), 7.55 (2H, m), 3.35 (2H, m), 3.26 (1H, m), 3.17 (2H, m), 2.37 (2H, d), 2.10 (2H, m), 1.99 (1H, m), 1.88 (6H, m), 1.74 (2H, m), 1.49 (2H, m)

Example 364: 2-[1-[2,6-difluoro-4-(6-isobutylpyrazin-2-yl)phenyl]-4-piperidyl]acetic acid

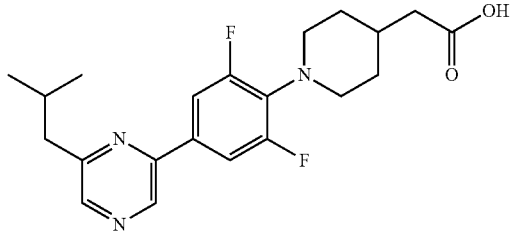 [SMILES: CC(C)Cc1cncc(-c2cc(F)c(N3CCC(CC(=O)O)CC3)c(F)c2)n1]

2-Chloro-6-isobutyl-pyrazine (0.055 g, 0.32 mmol) obtained in Preparation Example 257 and 2-[1-[2,6-difluoro-4-(4,4,5,5-tetramethyl-1,3,2-dioxaborolan-2-yl)phenyl]-4-piperidyl]acetic acid ethyl ester (0.158 g, 0.38 mmol) obtained in Preparation Example 220 were reacted in the same manner as in Step A of Example 96 and Step B of Example 1 to obtain the title compound (0.10 g, 80%).

$^1$H-NMR (CDCl$_3$) δ 8.73 (1H, s), 8.31 (1H, s), 7.54 (2H, m), 3.35 (2H, m), 3.17 (2H, m), 2.71 (2H, d), 2.37 (2H, d), 2.20 (1H, m), 1.99 (1H, m), 1.83 (2H, m), 1.48 (2H, m), 0.98 (6H, d)

Example 365: 2-[1-[2,6-difluoro-4-(4-isobutylpyrimidin-2-yl)phenyl]-4-piperidyl]acetic acid

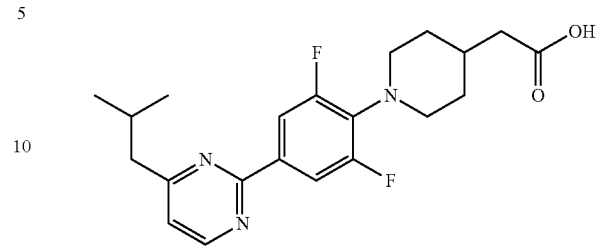

2-Chloro-4-isobutyl-pyrimidine (0.055 g, 0.32 mmol) obtained in Preparation Example 259 and 2-[1-[2,6-difluoro-4-(4,4,5,5-tetramethyl-1,3,2-dioxaborolan-2-yl)phenyl]-4-piperidyl]acetic acid ethyl ester (0.158 g, 0.38 mmol) obtained in Preparation Example 220 were reacted in the same manner as in Step A of Example 96 and Step B of Example 1 to obtain the title compound (0.102 g, 82%).

$^1$H-NMR (CDCl$_3$) δ 8.60 (1H, d), 7.94 (2H, m), 6.97 (1H, d), 3.37 (2H, m), 3.17 (2H, m), 2.65 (2H, d), 2.37 (2H, d), 2.22 (1H, m), 1.98 (1H, m), 1.83 (2H, m), 1.49 (2H, m), 0.97 (6H, d)

Example 366: 2-[1-[4-[5-(cyclobutoxy)-3-methyl-isothiazol-4-yl]-2,6-difluoro-phenyl]-4-piperidyl]acetic acid

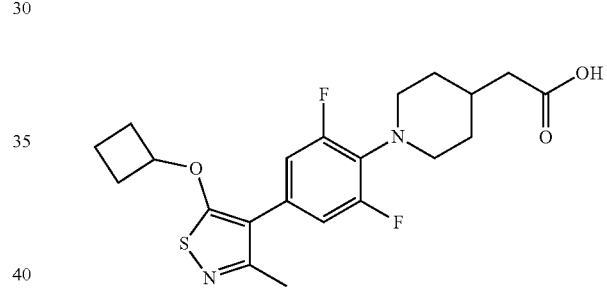

4-Bromo-5-(cyclobutoxy)-3-methyl-isothiazole (0.046 g, 0.19 mmol) obtained in Preparation Example 292 and 2-[1-[2,6-difluoro-4-(4,4,5,5-tetramethyl-1,3,2-dioxaborolan-2-yl)phenyl]-4-piperidyl]acetic acid ethyl ester (0.091 g, 0.22 mmol) obtained in Preparation Example 220 were reacted in the same manner as in Step A of Example 96 and Step B of Example 1 to obtain the title compound (0.05 g, 62%).

$^1$H-NMR (CDCl$_3$) δ 6.83 (2H, m), 4.60 (1H, m), 3.30 (2H, m), 3.15 (2H, m), 2.47 (2H, m), 2.37 (5H, m), 2.24 (2H, m), 1.97 (1H, m), 1.84 (3H, m), 1.67 (1H, m), 1.48 (2H, m)

Example 367: {1-[4-(4-ethoxy-thiazol-2-yl)-2,6-difluoro-phenyl]-piperidin-4-yl}acetic acid

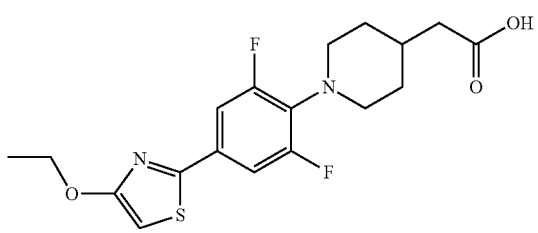 [SMILES: CCOc1csc(-c2cc(F)c(N3CCC(CC(=O)O)CC3)c(F)c2)n1]

Step A: {1-[4-(4-ethoxy-thiazol-2-yl)-2,6-difluorophenyl]-piperidin-4-yl}acetic acid ethyl ester

[1-(2,6-Difluoro-4-thiocarbamoyl-phenyl)-piperidin-4-yl]acetic acid ethyl ester (0.160 g, 0.47 mmol) obtained in Preparation Example 224 and chloroacetic acid ethyl ester (0.115 g, 0.93 mmol) were dissolved in EtOH and stirred for 5 hours under reflux. The reaction solution was cooled to room temperature, concentrated under reduced pressure and purified by column chromatography to obtain the title compound (0.061 g, 32%).

$^1$H-NMR (CDCl$_3$) δ 7.42 (2H, m), 6.07 (1H, s), 4.24-4.15 (4H, m), 3.35 (2H, m), 3.16 (2H, m), 2.32 (2H, d), 1.99 (1H, m), 1.80 (2H, m), 1.49 (3H, t), 1.43 (2H, m), 1.30 (3H, t)

Step B: {1-[4-(4-ethoxy-thiazol-2-yl)-2,6-difluorophenyl]-piperidin-4-yl}acetic acid {1-[4-(4-Ethoxy-thiazol-2-yl)-2,6-difluoro-phenyl]-piperidin-4-yl}acetic acid ethyl ester (0.061 g, 0.15 mmol) obtained in Step A was reacted in the same manner as in Step B of Example 1 to obtain the title compound (0.046 g, 81%).

$^1$H-NMR (CDCl$_3$) δ 7.43 (2H, m), 6.09 (1H, s), 4.22 (2H, q), 3.37 (2H, m), 3.18 (2H, m), 2.40 (2H, d), 2.01 (1H, m), 1.86 (2H, m), 1.52-1.47 (5H, m)

Example 368: {1-[4-(4-ethoxy-5-methyl-thiazol-2-yl)-2,6-difluoro-phenyl]-piperidin-4-yl}acetic acid

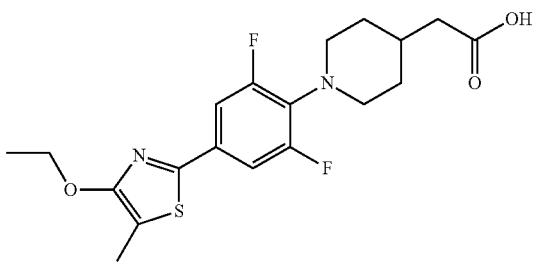 [SMILES: CCOc1nc(-c2cc(F)c(N3CCC(CC(=O)O)CC3)c(F)c2)sc1C]

Step A: {1-[4-(4-ethoxy-5-methyl-thiazol-2-yl)-2,6-difluoro-phenyl]-piperidin-4-yl}acetic acid ethyl ester

[1-(2,6-Difluoro-4-thiocarbamoyl-phenyl)-piperidin-4-yl]acetic acid ethyl ester (0.089 g, 0.26 mmol) obtained in Preparation Example 224 and 2-bromopropanoic acid ethyl ester (0.095 g, 0.52 mmol) were reacted in the same manner as in Step A of Example 367 to obtain the title compound (0.059 g, 53%).

$^1$H-NMR (CDCl$_3$) δ 7.33 (2H, m), 4.41 (2H, q), 4.19 (2H, q), 3.33 (2H, m), 3.15 (2H, m), 2.32 (2H, d), 2.31 (3H, s), 1.99 (1H, m), 1.80 (2H, m), 1.49 (2H, m), 1.39 (3H, t), 1.29 (3H, t)

Step B: {1-[4-(4-ethoxy-5-methyl-thiazol-2-yl)-2,6-difluoro-phenyl]-piperidin-4-yl}acetic acid {1-[4-(4-Ethoxy-5-methyl-thiazol-2-yl)-2,6-difluoro-phenyl]-piperidin-4-yl}acetic acid ethyl ester (0.059 g, 0.14 mmol) obtained in Step A was reacted in the same manner as in Step B of Example 1 to obtain the title compound (0.045 g, 82%).

$^1$H-NMR (CDCl$_3$) δ 7.35 (2H, m), 4.41 (2H, q), 3.34 (2H, m), 3.17 (2H, m), 2.40 (2H, d), 2.32 (3H, s), 2.01 (1H, m), 1.86 (2H, m), 1.52 (2H, m), 1.42 (3H, t)

Example 369: 2-[1-[4-(6-butylpyrazin-2-yl)-2,6-difluoro-phenyl]-4-piperidyl]acetic acid

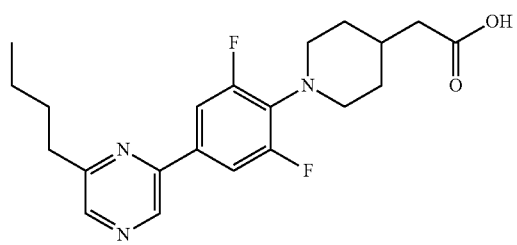 [SMILES: CCCCc1cncc(-c2cc(F)c(N3CCC(CC(=O)O)CC3)c(F)c2)n1]

2-Butyl-6-chloro-pyrazine (0.06 g, 0.35 mmol) obtained in Preparation Example 260 and 2-[1-[2,6-difluoro-4-(4,4,5,5-tetramethyl-1,3,2-dioxaborolan-2-yl)phenyl]-4-piperidyl]acetic acid ethyl ester (0.158 g, 0.39 mmol) obtained in Preparation Example 220 were reacted in the same manner as in Step A of Example 96 and Step B of Example 1 to obtain the title compound (0.11 g, 81%).

$^1$H-NMR (CDCl$_3$) δ 8.72 (1H, s), 8.35 (1H, s), 7.55 (2H, m), 3.34 (2H, m), 3.16 (2H, m), 2.84 (2H, t), 2.37 (2H, d), 2.00 (1H, m), 1.80 (4H, m), 1.44 (4H, m), 0.97 (3H, t)

Example 370: 2-[1-[2,6-difluoro-4-(6-isopentylpyrazin-2-yl)phenyl]-4-piperidyl]acetic acid

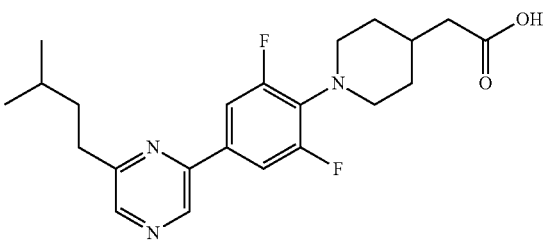 [SMILES: CC(C)CCc1cncc(-c2cc(F)c(N3CCC(CC(=O)O)CC3)c(F)c2)n1]

2-Chloro-6-isopentyl-pyrazine (0.06 g, 0.32 mmol) obtained in Preparation Example 261 and 2-[1-[2,6-difluoro-4-(4,4,5,5-tetramethyl-1,3,2-dioxaborolan-2-yl)phenyl]-4-piperidyl]acetic acid ethyl ester (0.146 g, 0.36 mmol) obtained in Preparation Example 220 were reacted in the same manner as in Step A of Example 96 and Step B of Example 1 to obtain the title compound (0.11 g, 88%).

$^1$H-NMR (CDCl$_3$) δ 8.72 (1H, s), 8.35 (1H, s), 7.54 (2H, m), 3.35 (2H, m), 3.17 (2H, m), 2.85 (2H, m), 2.37 (2H, d), 2.00 (1H, m), 1.83 (2H, m), 1.68 (3H, m), 1.52 (2H, m), 0.98 (6H, d)

Example 371: 2-[1-[4-[4-(cyclobutoxy)-5-fluoro-pyrimidin-2-yl]-2,6-difluoro-phenyl]-4-piperidyl]acetic acid

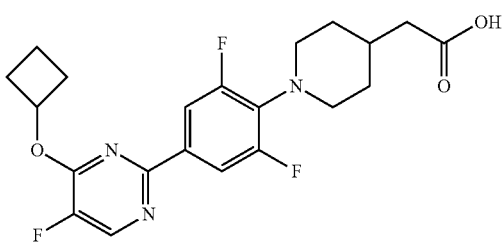 [SMILES: O=C(O)CC1CCN(c2c(F)cc(-c3ncc(F)c(OC4CCC4)n3)cc2F)CC1]

2-Chloro-4-(cyclobutoxy)-5-fluoro-pyrimidine (0.05 g, 0.25 mmol) obtained in Preparation Example 329 and 2-[1-[2,6-difluoro-4-(4,4,5,5-tetramethyl-1,3,2-dioxaborolan-2-yl)phenyl]-4-piperidyl]acetic acid ethyl ester (0.11 g, 0.27 mmol) obtained in Preparation Example 220 were reacted in the same manner as in Step A of Example 96 and Step B of Example 1 to obtain the title compound (0.072 g, 69%).

$^1$H-NMR (CDCl$_3$) δ 8.31 (1H, m), 7.78 (2H, m), 5.40 (1H, m), 3.37 (2H, m), 3.16 (2H, m), 2.55 (2H, m), 2.37 (2H, d), 2.23 (2H, m), 1.95 (2H, m), 1.83 (3H, m), 1.49 (2H, m)

Example 372: 2-[1-[4-[4-(cyclopropylmethoxy)-5-fluoro-pyrimidin-2-yl]-2,6-difluoro-phenyl]-4-piperidyl]acetic acid

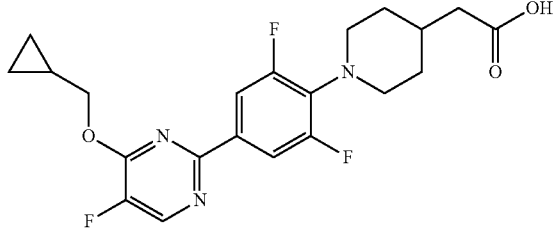 [SMILES: O=C(O)CC1CCN(c2c(F)cc(-c3ncc(F)c(OCC4CC4)n3)cc2F)CC1]

2-Chloro-4-(cyclopropylmethoxy)-5-fluoro-pyrimidine (0.05 g, 0.25 mmol) obtained in Preparation Example 330 and 2-[1-[2,6-difluoro-4-(4,4,5,5-tetramethyl-1,3,2-dioxaborolan-2-yl)phenyl]-4-piperidyl]acetic acid ethyl ester (0.11 g, 0.27 mmol) obtained in Preparation Example 220 were reacted in the same manner as in Step A of Example 96 and Step B of Example 1 to obtain the title compound (0.08 g, 77%).

$^1$H-NMR (CDCl$_3$) δ 8.32 (1H, m), 7.79 (2H, m), 4.39 (2H, d), 3.36 (2H, m), 3.16 (2H, m), 2.36 (2H, d), 1.99 (1H, m), 1.82 (2H, m), 1.48 (2H, m), 1.39 (1H, m), 0.68 (2H, m), 0.44 (2H, m)

Example 373: 2-[1-[4-(6-cyclobutyl-2-pyridyl)-2,6-difluoro-phenyl]-4-piperidyl]acetic acid

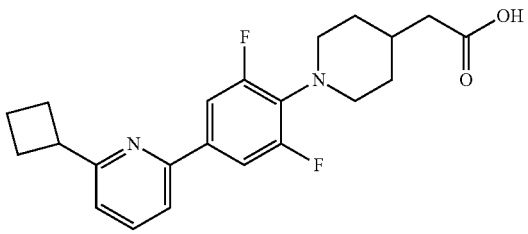 [SMILES: O=C(O)CC1CCN(c2c(F)cc(-c3cccc(C4CCC4)n3)cc2F)CC1]

2-Chloro-6-cyclobutyl-pyridine (0.05 g, 0.3 mmol) obtained in Preparation Example 277 and 2-[1-[2,6-difluoro-4-(4,4,5,5-tetramethyl-1,3,2-dioxaborolan-2-yl)phenyl]-4-piperidyl]acetic acid ethyl ester (0.134 g, 0.33 mmol) obtained in Preparation Example 220 were reacted in the same manner as in Step A of Example 96 and Step B of Example 1 to obtain the title compound (0.093 g, 80%).

$^1$H-NMR (CDCl$_3$) δ 7.63 (1H, t), 7.56 (2H, m), 7.42 (1H, d), 7.08 (1H, d), 3.70 (1H, m), 3.31 (2H, m), 3.16 (2H, m), 2.36 (6H, m), 2.09 (1H, m), 1.97 (2H, m), 1.82 (2H, m), 1.51 (2H, m)

Example 374: 2-[1-[4-(6-cyclobutylpyrazin-2-yl)-2,6-difluoro-phenyl]-4-piperidyl]acetic acid

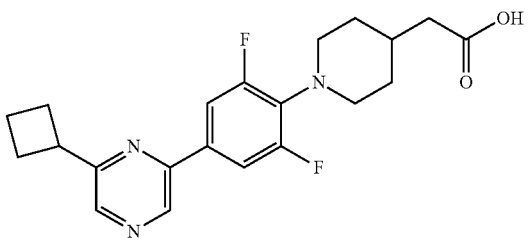 [SMILES: O=C(O)CC1CCN(c2c(F)cc(-c3cncc(C4CCC4)n3)cc2F)CC1]

2-Chloro-6-cyclobutyl-pyrazine (0.05 g, 0.3 mmol) obtained in Preparation Example 262 and 2-[1-[2,6-difluoro-4-(4,4,5,5-tetramethyl-1,3,2-dioxaborolan-2-yl)phenyl]-4-piperidyl]acetic acid ethyl ester (0.134 g, 0.33 mmol) obtained in Preparation Example 220 were reacted in the same manner as in Step A of Example 96 and Step B of Example 1 to obtain the title compound (0.042 g, 36%).

$^1$H-NMR (CDCl$_3$) δ 8.72 (1H, s), 8.33 (1H, s), 7.59 (2H, m), 3.74 (1H, m), 3.35 (2H, m), 3.17 (2H, m), 2.38 (6H, m), 2.11 (1H, m), 1.99 (2H, m), 1.84 (2H, m), 1.48 (2H, m)

Example 375: 2-[1-[4-[6-(cyclobutylmethyl)-2-pyridyl]-2,6-difluoro-phenyl]-4-piperidyl]acetic acid

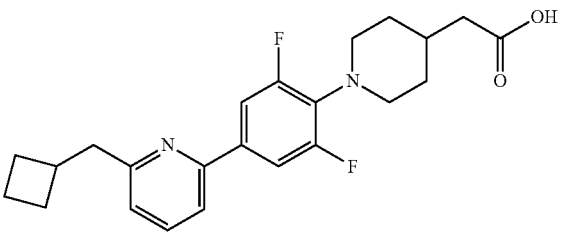 [SMILES: O=C(O)CC1CCN(c2c(F)cc(-c3cccc(CC4CCC4)n3)cc2F)CC1]

2-Bromo-6-(cyclobutylidenemethyl)pyridine (0.074 g, 0.33 mmol) obtained in Preparation Example 278 and 2-[1-[2,6-difluoro-4-(4,4,5,5-tetramethyl-1,3,2-dioxaborolan-2-yl)phenyl]-4-piperidyl]acetic acid ethyl ester (0.150 g, 0.366 mmol) obtained in Preparation Example 220 were reacted in the same manner as in Step A of Example 96 to obtain 2-[1-[4-[6-(cyclobutylidenemethyl)-2-pyridyl]-2,6-difluoro-phenyl]-4-piperidyl]acetic acid ethyl ester (0.128 g, 0.3 mmol). 3 mL of MeOH and catalytic amount of Pd/C were added thereto, and the mixture was stirred for 150 minutes under hydrogen atmosphere. Solids were filtered through Celite to obtain 2-[1-[4-[6-(cyclobutylmethyl)-2-pyridyl]-2,6-difluoro-phenyl]-4-piperidyl]acetic acid ethyl ester. The obtained compound was reacted in the same manner as in Step B of Example 1 to obtain the title compound (0.108 g, 89%).

$^1$H-NMR (CDCl$_3$) δ 7.61 (1H, t), 7.51 (2H, m), 7.41 (1H, d), 7.02 (1H, d), 3.31 (2H, m), 3.16 (2H, m), 2.93 (2H, d), 2.79 (1H, m), 2.37 (2H, d), 2.10 (2H, m), 1.98 (1H, m), 1.87 (2H, m), 1.81 (4H, m), 1.48 (2H, m)

Example 376: 2-[1-[4-[6-(cyclopentylmethyl)-2-pyridyl]-2,6-difluoro-phenyl]-4-piperidyl]acetic acid

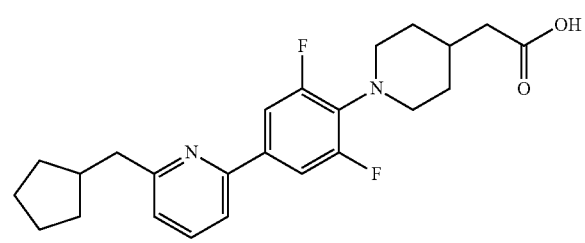 [SMILES: O=C(O)CC1CCN(c2c(F)cc(-c3cccc(CC4CCCC4)n3)cc2F)CC1]

2-Bromo-6-(cyclopentylidenemethyl)pyridine (0.080 g, 0.33 mmol) obtained in Preparation Example 279 and 2-[1-[2,6-difluoro-4-(4,4,5,5-tetramethyl-1,3,2-dioxaborolan-2-yl)phenyl]-4-piperidyl]acetic acid ethyl ester (0.150 g, 0.366 mmol) obtained in Preparation Example 220 were reacted in the same manner as in Step A of Example 96 to obtain 2-[1-[4-[6-(cyclopentylidenemethyl)-2-pyridyl]-2,6-difluoro-phenyl]-4-piperidyl]acetic acid ethyl ester (0.128 g, 0.29 mmol). 3 mL of MeOH and catalytic amount of Pd/C were added thereto, and the mixture was stirred for 150 minutes under hydrogen atmosphere. Solids were filtered through Celite to obtain 2-[1-[4-[6-(cyclopentylmethyl)-2-pyridyl]-2,6-difluoro-phenyl]-4-piperidyl]acetic acid ethyl ester. The obtained compound was reacted in the same manner as in Step B of Example 1 to obtain the title compound (0.106 g, 88%).

$^1$H-NMR (CDCl$_3$) δ 7.61 (1H, t), 7.50 (2H, m), 7.41 (1H, d), 7.05 (1H, d), 3.30 (2H, m), 3.15 (2H, m), 2.83 (2H, d), 2.36 (2H, d), 2.32 (1H, m), 1.97 (1H, m), 1.82 (2H, m), 1.74 (2H, m), 1.65 (2H, m), 1.54 (2H, m), 1.48 (2H, m), 1.26 (2H, m)

Example 377: {1-[4-(4-cyclopropylmethoxy-thiazol-2-yl)-2,6-difluoro-phenyl]-piperidin-4-yl}acetic acid

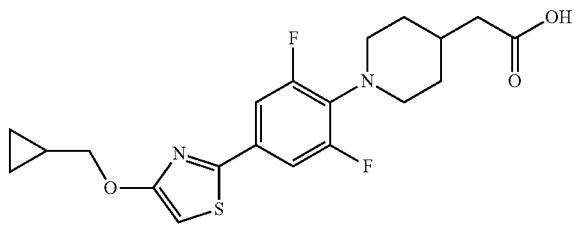 [SMILES: O=C(O)CC1CCN(c2c(F)cc(-c3nc(OCC4CC4)cs3)cc2F)CC1]

Step A: {1-[4-(4-cyclopropylmethoxy-thiazol-2-yl)-2,6-difluoro-phenyl]-piperidin-4-yl}acetic acid ethyl ester

[1-(2,6-Difluoro-4-thiocarbamoyl-phenyl)-piperidin-4-yl]acetic acid ethyl ester (0.137 g, 0.40 mmol) obtained in Preparation Example 224 and chloroacetic acid cyclopropylmethyl ester (0.119 g, 0.80 mmol) were reacted in the same manner as in Step A of Example 367 to obtain the title compound (0.090 g, 52%).

$^1$H-NMR (CDCl$_3$) δ 7.44 (2H, m), 6.08 (1H, s), 4.18 (2H, q), 3.98 (2H, d), 3.35 (2H, m), 3.16 (2H, m), 2.32 (2H, d), 1.99 (1H, m), 1.80 (2H, m), 1.47 (2H, m), 1.35 (1H, m), 1.31 (3H, t), 0.69 (2H, m), 0.41 (2H, m)

Step B: {1-[4-(4-cyclopropylmethoxy-thiazol-2-yl)-2,6-difluoro-phenyl]-piperidin-4-yl}acetic acid {1-[4-(4-Cyclopropylmethoxy-thiazol-2-yl)-2,6-difluoro-phenyl]-piperidin-4-yl}acetic acid ethyl ester (0.090 g, 0.21 mmol) obtained in Step A was reacted in the same manner as in Step B of Example 1 to obtain the title compound (0.071 g, 83%).

$^1$H-NMR (CDCl$_3$) δ 7.45 (2H, m), 6.09 (1H, s), 4.02 (2H, d), 3.37 (2H, m), 3.18 (2H, m), 2.40 (2H, d), 2.01 (1H, m), 1.86 (2H, m), 1.52 (2H, m), 1.37 (1H, m), 0.69 (2H, m), 0.42 (2H, m)

Example 378: (1-{2,6-difluoro-4-[4-(4-fluoro-phenyl)-thiazol-2-yl]-phenyl}-piperidin-4-yl)-acetic acid

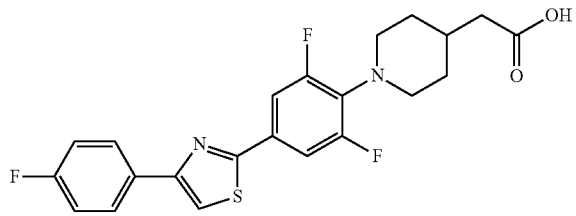 [SMILES: O=C(O)CC1CCN(c2c(F)cc(-c3nc(-c4ccc(F)cc4)cs3)cc2F)CC1]

Step A: (1-{2,6-difluoro-4-[4-(4-fluoro-phenyl)-thiazol-2-yl]-phenyl}-piperidin-4-yl)-acetic acid ethyl ester

[1-(2,6-Difluoro-4-thiocarbamoyl-phenyl)-piperidin-4-yl]acetic acid ethyl ester (0.123 g, 0.36 mmol) obtained in Preparation Example 224 and 2-chloro-1-(4-fluoro-phenyl)- ethanone (0.052 g, 0.30 mmol) were reacted in the same manner as in Step A of Example 367 to obtain the title compound (0.107 g, 77%).

$^1$H-NMR (CDCl$_3$) δ 7.97 (2H, m), 7.52 (2H, m), 7.42 (1H, s), 7.17 (2H, m), 4.20 (2H, q), 3.39 (2H, m), 3.19 (2H, m), 2.34 (2H, d), 2.02 (1H, m), 1.83 (2H, m), 1.50 (2H, m), 1.32 (3H, t)

Step B: (1-{2,6-difluoro-4-[4-(4-fluoro-phenyl)-thiazol-2-yl]-phenyl}-piperidin-4-yl)-acetic acid (1-{2,6-Difluoro-4-[4-(4-fluoro-phenyl)-thiazol-2-yl]-phenyl}-piperidin-4-yl)-acetic acid ethyl ester (0.107 g, 0.23 mmol) obtained in Step A was reacted in the same manner as in Step B of Example 1 to obtain the title compound (0.063 g, 63%).

$^1$H-NMR (DMSO-d$_6$) δ 8.19 (1H, s), 8.11 (2H, m), 7.67 (2H, m), 7.32 (2H, t), 3.34 (2H, m), 3.10 (2H, m), 2.23 (2H, d), 1.85 (1H, m), 1.76 (2H, m), 1.34 (2H, m)

Example 379: {1-[4-(4-cyclobutoxy-thiazol-2-yl)-2,6-difluoro-phenyl]-piperidin-4-yl}acetic acid

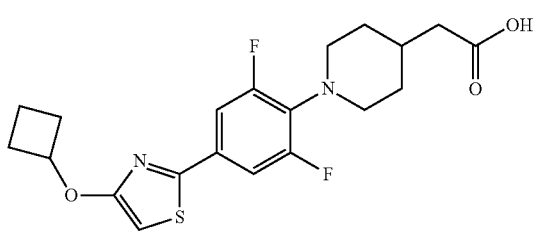 [SMILES: O=C(O)CC1CCN(c2c(F)cc(-c3nc(OC4CCC4)cs3)cc2F)CC1]

Step A: {1-[4-(4-cyclobutoxy-thiazol-2-yl)-2,6-difluoro-phenyl]-piperidin-4-yl}acetic acid ethyl ester

[1-(2,6-Difluoro-4-thiocarbamoyl-phenyl)-piperidin-4-yl]acetic acid ethyl ester (0.103 g, 0.30 mmol) obtained in Preparation Example 224 and chloroacetic acid cyclobutyl ester (0.09 g, 0.60 mmol) were reacted in the same manner as in Step A of Example 367 to obtain the title compound (0.072 g, 55%).

$^1$H-NMR (CDCl$_3$) δ 7.42 (2H, m), 5.99 (1H, s), 4.80 (1H, m), 4.18 (2H, q), 3.36 (2H, m), 3.16 (2H, m), 2.50 (2H, m), 2.32 (2H, d), 2.29 (2H, m), 1.96-1.45 (5H, m), 1.47 (2H, m), 1.31 (3H, t)

Step B: {1-[4-(4-cyclobutoxy-thiazol-2-yl)-2,6-difluoro-phenyl]-piperidin-4-yl}acetic acid {1-[4-(4-Cyclobutoxy-thiazol-2-yl)-2,6-difluoro-phenyl]-piperidin-4-yl}acetic acid ethyl ester (0.090 g, 0.21 mmol) obtained in Step A was reacted in the same manner as in Step B of Example 1 to obtain the title compound (0.071 g, 83%).

$^1$H-NMR (CDCl$_3$) δ 7.45 (2H, m), 6.00 (1H, s), 4.80 (1H, m), 3.37 (2H, m), 3.18 (2H, m), 2.50 (2H, m), 2.40 (2H, d), 2.29 (2H, m), 1.94-1.84 (4H, m), 1.73 (1H, m), 1.51 (2H, m)

Example 380: {1-[4-(4-butoxy-thiazol-2-yl)-2,6-difluoro-phenyl]-piperidin-4-yl}acetic acid

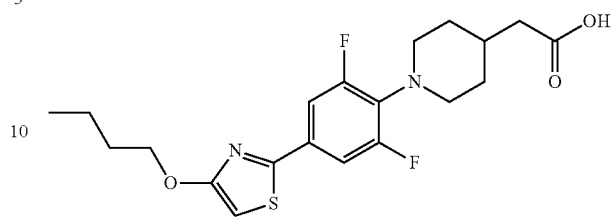

Step A: {1-[4-(4-butoxy-thiazol-2-yl)-2,6-difluoro-phenyl]-piperidin-4-yl}acetic acid ethyl ester

[1-(2,6-Difluoro-4-thiocarbamoyl-phenyl)-piperidin-4-yl]acetic acid ethyl ester (0.103 g, 0.30 mmol) obtained in Preparation Example 224 and chloroacetic acid butyl ester (0.091 g, 0.60 mmol) were reacted in the same manner as in Step A of Example 367 to obtain the title compound (0.061 g, 46%).

$^1$H-NMR (CDCl$_3$) δ 7.42 (2H, m), 6.07 (1H, s), 4.32 (2H, t), 4.19 (2H, q), 3.42 (2H, m), 3.16 (2H, m), 2.32 (2H, d), 2.03 (1H, m), 1.86-1.78 (4H, m), 1.56-1.42 (4H, m), 1.30 (3H, t), 1.01 (3H, t)

Step B: {1-[4-(4-butoxy-thiazol-2-yl)-2,6-difluoro-phenyl]-piperidin-4-yl}acetic acid {1-[4-(4-Butoxy-thiazol-2-yl)-2,6-difluoro-phenyl]-piperidin-4-yl}acetic acid ethyl ester (0.061 g, 0.14 mmol) obtained in Step A was reacted in the same manner as in Step B of Example 1 to obtain the title compound (0.044 g, 77%).

$^1$H-NMR (CDCl$_3$) δ 7.45 (2H, m), 6.08 (1H, s), 4.15 (2H, t), 3.37 (2H, m), 3.18 (2H, m), 2.40 (2H, d), 2.01 (1H, m), 1.87-1.82 (4H, m), 1.61-1.47 (4H, m), 1.02 (3H, t)

Example 381: 2-(1-{2,6-difluoro-4-[7-(propan-2-yl)-7H-pyrrolo[2,3-d]pyrimidin-4-yl]phenyl}piperidin-4-yl)acetic acid

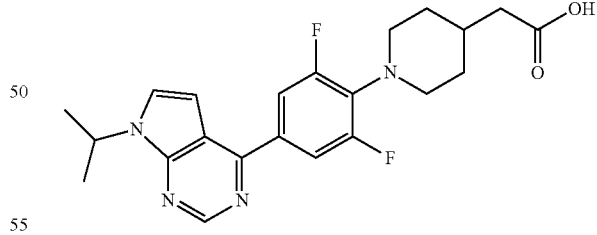

Step A: 2-(1-{2,6-difluoro-4-[7-(propan-2-yl)-7H-pyrrolo[2,3-d]pyrimidin-4-yl]phenyl}piperidin-4-yl) acetic acid ethyl ester 4-Chloro-7H-pyrrolo[2,3-d]pyrimidine (0.097 g, 0.63 mmol) and 2-[1-[2,6-difluoro-4-(4,4,5,5-tetramethyl-1,3,2-dioxaborolan-2-yl)phenyl]-4-piperidyl]acetic acid ethyl ester (0.284 g, 0.69 mmol) obtained in Preparation Example 220 were reacted in the same manner as in Step A of Example 96 to obtain 2-[1-[2,6-difluoro-4-(7H-pyrrolo[2,3- d]pyrimidin-4-yl)phenyl]-4-piperidyl]acetic acid ethyl ester. The obtained compound was dissolved in 1.6 mL of CH₃CN. Cs₂CO₃ (0.244 g, 0.75 mmol) and 2-iodopropane (0.075 mL, 0.75 mmol) were added thereto, and the mixture was stirred for 1 hour under reflux. The reaction solution was purified by column chromatography to obtain the title compound (0.16 g, 58%).

¹H-NMR (CDCl₃) δ 8.90 (1H, s), 7.66 (2H, m), 7.38 (1H, m), 6.80 (1H, m), 5.20 (1H, m), 4.15 (2H, m), 3.38 (2H, m), 3.18 (2H, m), 2.30 (2H, d), 1.98 (1H, m), 1.79 (2H, m), 1.55 (6H, d), 1.47 (2H, m), 1.28 (3H, t)

Step B: 2-(1-{2,6-difluoro-4-[7-(propan-2-yl)-7H-pyrrolo[2,3-d]pyrimidin-4-yl]phenyl}piperidin-4-yl)acetic acid 2-(1-{2,6-Difluoro-4-[7-(propan-2-yl)-7H-pyrrolo[2,3-d]pyrimidin-4-yl]phenyl}piperidin-4-yl)acetic acid ethyl ester (0.16 g, 0.36 mmol) obtained in Step A was reacted in the same manner as in Step B of Example 1 to obtain the title compound (0.135 g, 95%).

¹H-NMR (CDCl₃) δ 8.90 (1H, s), 7.65 (2H, m), 7.40 (1H, m), 6.81 (1H, m), 5.19 (1H, m), 3.39 (2H, m), 3.19 (2H, m), 2.34 (2H, d), 1.99 (1H, m), 1.83 (2H, m), 1.56 (6H, d), 1.51 (2H, m)

Example 382: 2-[1-[4-(6,7-dihydro-5H-cyclopenta[d]pyrimidin-4-yl)-2,6-difluoro-phenyl]-4-piperidyl]acetic acid

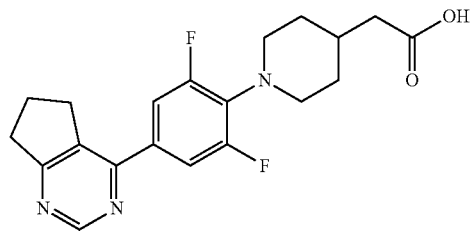 [SMILES: O=C(O)CC1CCN(c2c(F)cc(-c3ncnc4c3CCC4)cc2F)CC1]

4-Chloro-6,7-dihydro-5H-cyclopenta[d]pyrimidine (0.052 g, 0.33 mmol) obtained in Preparation Example 263 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.366 mmol) obtained in Preparation Example 220 were reacted in the same manner as in Step A of Example 96 and Step B of Example 1 to obtain the title compound (0.016 g, 12%).

¹H-NMR (CDCl₃) δ 9.00 (1H, s), 7.48 (2H, m), 3.39 (2H, m), 3.21 (2H, t), 3.17 (2H, m), 3.07 (2H, t), 2.36 (2H, d), 2.18 (2H, m), 1.99 (1H, m), 1.84 (2H, m), 1.48 (2H, m)

Example 383: 2-[1-[4-[4-(cyclobutoxy)-6,7-dihydro-5H-cyclopenta[d]pyrimidin-2-yl]-2,6-difluoro-phenyl]-4-piperidyl]acetic acid

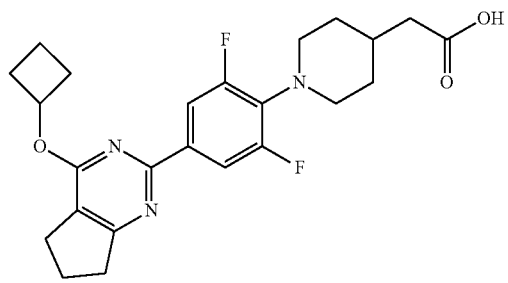 [SMILES: O=C(O)CC1CCN(c2c(F)cc(-c3nc4c(c(OC5CCC5)n3)CCC4)cc2F)CC1]

2-Chloro-4-(cyclobutoxy)-6,7-dihydro-5H-cyclopenta[d]pyrimidine (0.052 g, 0.33 mmol) obtained in Preparation Example 264 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.366 mmol) obtained in Preparation Example 220 were reacted in the same manner as in Step A of Example 96 and Step B of Example 1 to obtain the title compound (0.12 g, 82%).

¹H-NMR (CDCl₃) δ 7.84 (2H, m), 5.35 (1H, m), 3.34 (2H, m), 3.15 (2H, m), 2.97 (2H, t), 2.85 (2H, t), 2.53 (2H, m), 2.35 (2H, d), 2.19 (2H, m), 2.12 (2H, m), 1.97 (1H, m), 1.87 (1H, m), 1.81 (2H, m), 1.75 (1H, m), 1.47 (2H, m)

Example 384: 2-[1-[4-[4-(cyclobutoxy)-5,6-dimethyl-pyrimidin-2-yl]-2,6-difluoro-phenyl]-4-piperidyl]acetic acid

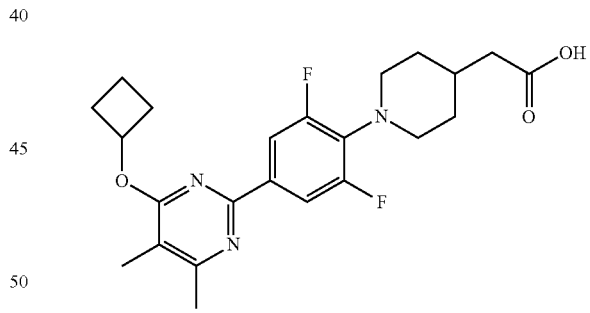

2-Chloro-4-(cyclobutoxy)-5,6-dimethyl-pyrimidine (0.052 g, 0.33 mmol) obtained in Preparation Example 265 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.366 mmol) obtained in Preparation Example 220 were reacted in the same manner as in Step A of Example 96 and Step B of Example 1 to obtain the title compound (0.105 g, 74%).

¹H-NMR (CDCl₃) δ 7.84 (2H, m), 5.31 (1H, m), 3.33 (2H, m), 3.16 (2H, m), 2.54 (2H, m), 2.45 (3H, s), 2.36 (2H, d), 2.18 (2H, m), 2.13 (3H, s), 1.97 (1H, m), 1.87 (1H, m), 1.82 (2H, m), 1.77 (1H, m), 1.49 (2H, m)

Example 385: 4-[2-chloro-4-[6-(cyclobutoxy)-2-pyridyl]-6-fluoro-phenoxy]butanoic acid

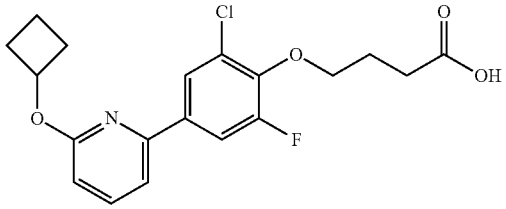 [SMILES: O=C(O)CCCOc1c(F)cc(-c2cccc(OC3CCC3)n2)cc1Cl]

4-[2-Chloro-6-fluoro-4-(4,4,5,5-tetramethyl-1,3,2-dioxaborolan-2-yl)phenoxy]butanoic acid ethyl ester (0.255 g, 0.66 mmol) obtained in Preparation Example 221 and 2-chloro-6-cyclobutoxy-pyridine (0.11 g, 0.60 mmol) obtained in Preparation Example 29 were reacted in the same manner as in Step A of Example 96 and Step B of Example 1 to obtain the title compound (0.136 g, 60%).

$^1$H-NMR (CDCl$_3$) δ 7.79 (1H, m), 7.70 (1H, m), 7.61 (1H, t), 7.22 (1H, m), 6.65 (1H, d), 5.25 (1H, m), 4.21 (2H, t), 2.72 (2H, t), 2.53 (2H, m), 2.18 (4H, m), 1.87 (1H, m), 1.76 (1H, m)

Example 386: 4-[2,6-dichloro-4-[6-(cyclobutoxy)-2-pyridyl]phenoxy]butanoic acid

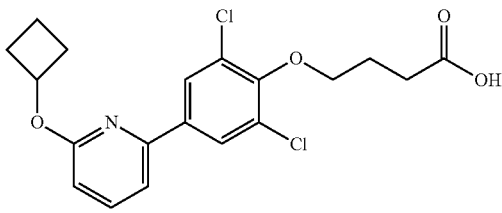 [SMILES: O=C(O)CCCOc1c(Cl)cc(-c2cccc(OC3CCC3)n2)cc1Cl]

4-[2,6-Dichloro-4-(4,4,5,5-tetramethyl-1,3,2-dioxaborolan-2-yl)phenoxy]butanoic acid ethyl ester (0.222 g, 0.55 mmol) obtained in Preparation Example 222 and 2-chloro-6-cyclobutoxy-pyridine (0.092 g, 0.50 mmol) obtained in Preparation Example 29 were reacted in the same manner as in Step A of Example 96 and Step B of Example 1 to obtain the title compound (0.038 g, 19%).

$^1$H-NMR (CDCl$_3$) δ 7.92 (2H, s), 7.62 (1H, t), 7.22 (1H, m), 6.66 (1H, m), 5.25 (1H, m), 4.12 (2H, t), 2.77 (2H, t), 2.53 (2H, m), 2.20 (4H, m), 1.88 (1H, m), 1.77 (1H, m)

Example 387: 4-[4-[3-(cyclopropylmethoxymethyl)-2-furyl]-2,6-difluoro-phenoxy]butanoic acid

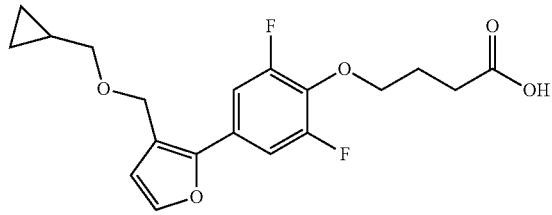 [SMILES: O=C(O)CCCOc1c(F)cc(-c2occc2COCC2CC2)cc1F]

Step A: 4-[2,6-difluoro-4-(3-formyl-2-furyl)phenoxy]butanoic acid ethyl ester 4-[2,6-Difluoro-4-(4,4,5,5-tetramethyl-1,3,2-dioxaborolan-2-yl)phenoxy]butanoic acid ethyl ester (0.26 g, 0.8 mmol) obtained in Preparation Example 16 and (3-formyl-2-furyl)boronic acid (0.168 g, 1.2 mmol) were reacted in the same manner as in Step A of Example 96 to obtain the title compound (0.191 g, 71%).

$^1$H-NMR (CDCl$_3$) δ 10.07 (1H, s), 7.41 (3H, m), 6.90 (1H, m), 4.26 (2H, t), 4.14 (2H, q), 2.58 (2H, t), 2.12 (2H, m), 1.26 (3H, t)

Step B: 4-[2,6-difluoro-4-[3-(hydroxymethyl)-2-furyl]phenoxy]butanoic acid ethyl ester 4-[2,6-Difluoro-4-(3-formyl-2-furyl)phenoxy]butanoic acid ethyl ester (0.191 g, 0.56 mmol) obtained in Step A was dissolved in 10 mL of MeOH and cooled to 0° C. NaBH$_4$ (0.022 g, 0.58 mmol) was added thereto, and the mixture was stirred at room temperature for 30 minutes. After addition of water, the reaction solution was extracted with EtOAc. The organic layer was dried with anhydrous magnesium sulfate and purified by column chromatography to obtain the title compound (0.189 g, 99%).

$^1$H-NMR (CDCl$_3$) δ 7.40 (1H, d), 7.26 (2H, m), 6.53 (1H, d), 4.70 (2H, d), 4.20 (2H, t), 4.14 (2H, q), 2.58 (2H, t), 2.10 (2H, m), 1.63 (1H, t), 1.26 (3H, t)

Step C: 4-[4-[3-(cyclopropylmethoxymethyl)-2-furyl]-2,6-difluoro-phenoxy]butanoic acid 4-[2,6-Difluoro-4-[3-(hydroxymethyl)-2-furyl]phenoxy]butanoic acid ethyl ester (0.189 g, 0.55 mmol) obtained in Step B and bromomethylcyclopropane (0.082 g, 0.61 mmol) were reacted in the same manner as in Preparation Example 267 to obtain 4-[4-[3-(cyclopropylmethoxymethyl)-2-furyl]-2,6-difluoro-phenoxy]butanoic acid ethyl ester (0.105 g, 48%). The obtained compound was reacted in the same manner as in Step B of Example 1 to obtain the title compound (0.087 g, 89%).

$^1$H-NMR (CDCl$_3$) δ 7.40 (1H, d), 7.28 (2H, m), 6.49 (1H, d), 4.46 (2H, s), 4.21 (2H, t), 3.37 (2H, d), 2.66 (2H, t), 2.10 (2H, m), 1.13 (1H, m), 0.56 (2H, m), 0.25 (2H, m)

Example 388: 4-[4-[6-(cyclopropylmethoxymethyl)-2-pyridyl]-2,6-difluoro-phenoxy]butanoic acid

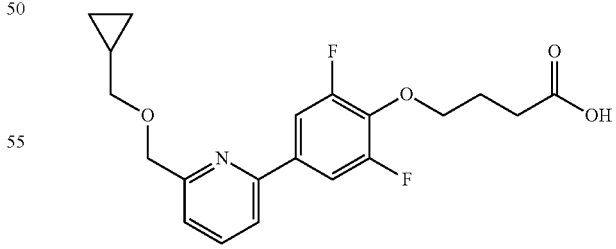

4-[2,6-Difluoro-4-(4,4,5,5-tetramethyl-1,3,2-dioxaborolan-2-yl)phenoxy]butanoic acid ethyl ester (0.163 g, 0.44 mmol) obtained in Preparation Example 16 and 2-bromo-6-(cyclopropylmethoxymethyl)pyridine (0.097 g, 0.40 mmol) obtained in Preparation Example 267 were reacted in the same manner as in Step A of Example 96 and Step B of Example 1 to obtain the title compound (0.133 g, 88%).

¹H-NMR (CDCl₃) δ 7.76 (1H, t), 7.57 (2H, m), 7.51 (1H, m), 7.45 (1H, m), 4.72 (2H, s), 4.24 (2H, t), 3.44 (2H, d), 2.67 (2H, t), 2.11 (2H, m), 2.08 (1H, m), 0.58 (2H, m), 0.26 (2H, m)

Example 389: 4-[2-chloro-4-[3-(cyclobutoxy)-5-fluoro-phenyl]-6-fluoro-phenoxy]butanoic acid

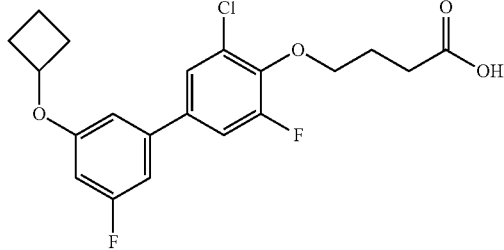 [SMILES: O=C(O)CCCOc1c(F)cc(-c2cc(F)cc(OC3CCC3)c2)cc1Cl]

4-[2-Chloro-6-fluoro-4-(4,4,5,5-tetramethyl-1,3,2-dioxaborolan-2-yl)phenoxy]butanoic acid ethyl ester (1.55 g, 4.0 mmol) obtained in Preparation Example 221 and 1-bromo-3-(cyclobutoxy)-5-fluoro-benzene (1.08 g, 4.4 mmol) obtained in Preparation Example 284 were reacted in the same manner as in Step A of Example 96 and Step B of Example 1 to obtain the title compound (1.25 g, 79%).

¹H-NMR (CDCl₃) δ 7.34 (1H, m), 7.18 (1H, m), 6.78 (1H, m), 6.77 (1H, m), 6.51 (1H, m), 4.64 (1H, m), 4.20 (2H, t), 2.72 (2H, t), 2.58 (2H, m), 2.19 (4H, m), 1.89 (1H, m), 1.72 (1H, m)

Example 390: 4-[4-[3-(cyclopropylmethoxymethyl)-5-methyl-isoxazol-4-yl]-2,6-difluoro-phenoxy]butanoic acid

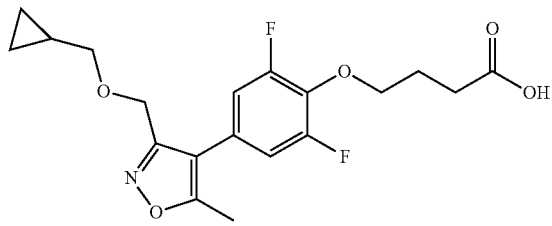 [SMILES: Cc1onc(COCC2CC2)c1-c1cc(F)c(OCCCC(=O)O)c(F)c1]

4-Bromo-3-(cyclopropylmethoxymethyl)-5-methyl-isoxazole (0.058 g, 0.24 mmol) obtained in Preparation Example 291 and 4-[2,6-difluoro-4-(4,4,5,5-tetramethyl-1,3,2-dioxaborolan-2-yl)phenoxy]butanoic acid ethyl ester (0.098 g, 0.26 mmol) obtained in Preparation Example 16 were reacted in the same manner as in Step A of Example 96 and Step B of Example 1 to obtain the title compound (0.015 g, 16%).

¹H-NMR (CDCl₃) δ 7.05 (2H, m), 4.50 (2H, s), 4.24 (2H, t), 3.35 (2H, d), 2.67 (2H, t), 2.47 (3H, s), 2.12 (2H, m), 1.06 (1H, m), 0.55 (2H, m), 0.20 (2H, m)

Example 391: 4-[2-chloro-4-[4-(cyclobutoxy)-6-methyl-pyrimidin-2-yl]-6-fluoro-phenoxy]butanoic acid

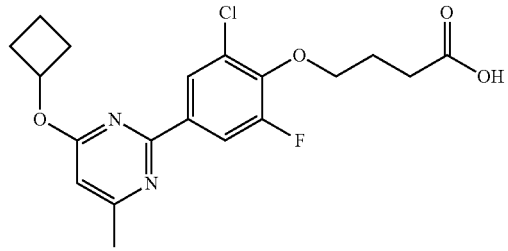 [SMILES: Cc1cc(OC2CCC2)nc(-c2cc(F)c(OCCCC(=O)O)c(Cl)c2)n1]

4-[2-Chloro-6-fluoro-4-(4,4,5,5-tetramethyl-1,3,2-dioxaborolan-2-yl)phenoxy]butanoic acid ethyl ester (0.193 g, 0.5 mmol) obtained in Preparation Example 221 and 2-chloro-4-(cyclobutoxy)-6-methyl-pyrimidine (0.10 g, 0.5 mmol) obtained in Preparation Example 228 were reacted in the same manner as in Step A of Example 96 and Step B of Example 1 to obtain the title compound (0.081 g, 41%).

¹H-NMR (CDCl₃) δ 8.27 (1H, d), 8.11 (1H, m), 6.46 (1H, s), 5.34 (1H, m), 4.27 (2H, t), 2.76 (2H, t), 2.56 (2H, m), 2.51 (3H, s), 2.24 (4H, m), 1.93 (1H, m), 1.80 (1H, m)

Example 392: 4-[2-chloro-4-[2-(cyclobutoxy)-6-methyl-pyrimidin-4-yl]-6-fluoro-phenoxy]butanoic acid

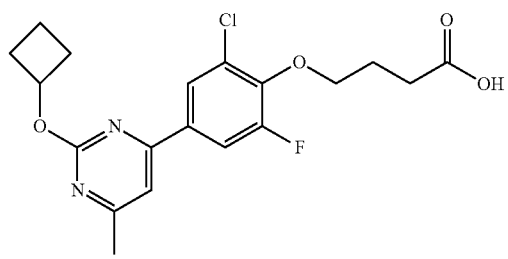 [SMILES: Cc1cc(-c2cc(F)c(OCCCC(=O)O)c(Cl)c2)nc(OC2CCC2)n1]

4-[2-Chloro-6-fluoro-4-(4,4,5,5-tetramethyl-1,3,2-dioxaborolan-2-yl)phenoxy]butanoic acid ethyl ester (0.193 g, 0.5 mmol) obtained in Preparation Example 221 and 4-chloro-2-(cyclobutoxy)-6-methyl-pyrimidine (0.10 g, 0.5 mmol) obtained in Preparation Example 229 were reacted in the same manner as in Step A of Example 96 and Step B of Example 1 to obtain the title compound (0.166 g, 84%).

¹H-NMR (CDCl₃) δ 7.92 (1H, d), 7.80 (1H, m), 7.14 (1H, s), 5.30 (1H, m), 4.29 (2H, t), 2.75 (2H, t), 2.54 (5H, m), 2.29 (2H, m), 2.19 (2H, m), 1.91 (1H, m), 1.77 (1H, m)

Example 393: 4-[4-[6-chloro-4-(cyclobutoxy)-2-pyridyl]-2,6-difluoro-phenoxy]butanoic acid

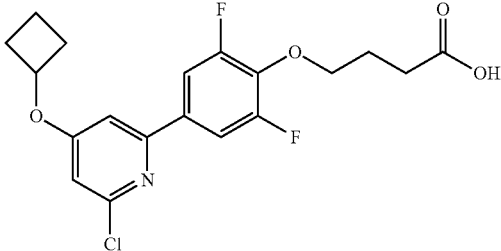 [SMILES: O=C(O)CCCOc1c(F)cc(-c2cc(OC3CCC3)cc(Cl)n2)cc1F]

2,6-Dichloro-4-(cyclobutoxy)pyridine (0.06 g, 0.27 mmol) obtained in Preparation Example 270 and 4-[2,6-difluoro-4-(4,4,5,5-tetramethyl-1,3,2-dioxaborolan-2-yl)phenoxy]butanoic acid ethyl ester (0.122 g, 0.33 mmol) obtained in Preparation Example 16 were reacted in the same manner as in Step A of Example 96 and Step B of Example 1 to obtain the title compound (0.021 g, 20%).
¹H-NMR (CDCl₃) δ 7.51 (2H, m), 6.97 (1H, m), 6.66 (1H, m), 4.73 (1H, m), 4.25 (2H, t), 2.66 (2H, m), 2.52 (2H, m), 2.22 (2H, m), 2.11 (2H, m), 1.95 (1H, m), 1.77 (1H, m)

Example 394: 4-[4-[2-(cyclobutoxy)thiazol-4-yl]-2,6-difluoro-phenoxy]butanoic acid

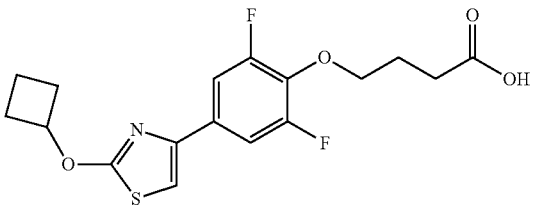 [SMILES: O=C(O)CCCOc1c(F)cc(-c2csc(OC3CCC3)n2)cc1F]

4-Bromo-2-(cyclobutoxy)thiazole (0.07 g, 0.3 mmol) obtained in Preparation Example 289 and 4-[2,6-difluoro-4-(4,4,5,5-tetramethyl-1,3,2-dioxaborolan-2-yl)phenoxy]butanoic acid ethyl ester (0.122 g, 0.33 mmol) obtained in Preparation Example 16 were reacted in the same manner as in Step A of Example 96 and Step B of Example 1 to obtain the title compound (0.91 g, 82%).
¹H-NMR (CDCl₃) δ 7.34 (2H, m), 6.78 (1H, s), 5.18 (1H, m), 4.20 (2H, t), 2.65 (2H, t), 2.54 (2H, m), 2.25 (2H, m), 2.10 (2H, m), 1.88 (1H, m), 1.70 (1H, m)

Example 395: 4-[4-[6-(cyclobutoxy)-4-methyl-2-pyridyl]-2,6-difluoro-phenoxy]butanoic acid

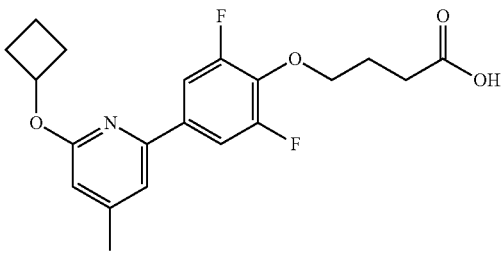 [SMILES: Cc1cc(OC2CCC2)nc(-c2cc(F)c(OCCCC(=O)O)c(F)c2)c1]

2-Chloro-6-(cyclobutoxy)-4-methyl-pyridine (0.06 g, 0.3 mmol) obtained in Preparation Example 271 and 4-[2,6-difluoro-4-(4,4,5,5-tetramethyl-1,3,2-dioxaborolan-2-yl)phenoxy]butanoic acid ethyl ester (0.124 g, 0.33 mmol) obtained in Preparation Example 16 were reacted in the same manner as in Step A of Example 96 and Step B of Example 1 to obtain the title compound (0.04 g, 35%).
¹H-NMR (CDCl₃) δ 7.56 (2H, m), 7.04 (1H, s), 6.47 (1H, s), 5.23 (1H, m), 4.23 (2H, t), 2.67 (2H, m), 2.51 (2H, m), 2.33 (3H, s), 2.14 (4H, m), 1.85 (1H, m), 1.74 (1H, m)

Example 396: 4-[2-chloro-4-[4-(cyclopropyl-methoxy)-6-methyl-pyrimidin-2-yl]-6-fluoro-phenoxy]butanoic acid

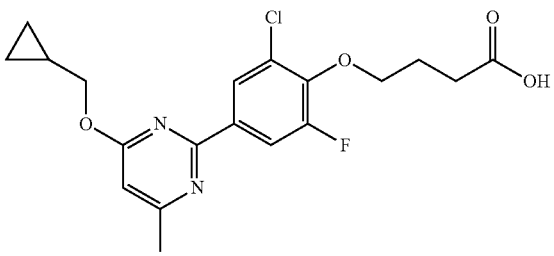 [SMILES: Cc1cc(OCC2CC2)nc(-c2cc(F)c(OCCCC(=O)O)c(Cl)c2)n1]

2-Chloro-4-(cyclopropylmethoxy)-6-methyl-pyrimidine (0.065 g, 0.33 mmol) obtained in Preparation Example 227 and 4-[2-chloro-6-fluoro-4-(4,4,5,5-tetramethyl-1,3,2-dioxaborolan-2-yl)phenoxy]butanoic acid ethyl ester (0.139 g, 0.36 mmol) obtained in Preparation Example 221 were reacted in the same manner as in Step A of Example 96 and Step B of Example 1 to obtain the title compound (0.10 g, 72%).
¹H-NMR (CDCl₃) δ 8.24 (1H, d), 8.07 (1H, m), 6.49 (1H, s), 4.28 (2H, d), 4.23 (2H, t), 2.72 (2H, t), 2.47 (3H, s), 2.15 (2H, m), 1.31 (1H, m), 0.66 (2H, m), 0.40 (2H, m)

Example 397: 4-[4-[2-(cyclopropylmethoxy)thiazol-4-yl]-2,6-difluoro-phenoxy]butanoic acid

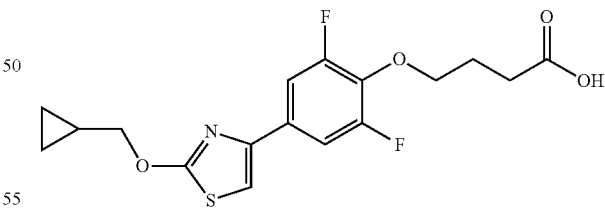

4-Bromo-2-(cyclopropylmethoxy)thiazole (0.07 g, 0.3 mmol) obtained in Preparation Example 290 and 4-[2,6-difluoro-4-(4,4,5,5-tetramethyl-1,3,2-dioxaborolan-2-yl)phenoxy]butanoic acid ethyl ester (0.122 g, 0.33 mmol) obtained in Preparation Example 16 were reacted in the same manner as in Step A of Example 96 and Step B of Example 1 to obtain the title compound (0.073 g, 66%).
¹H-NMR (CDCl₃) δ 7.34 (2H, m), 6.78 (1H, s), 4.30 (2H, d), 4.20 (2H, t), 2.66 (2H, m), 2.10 (2H, m), 1.35 (1H, m), 0.67 (2H, m), 0.42 (2H, m)

Example 398: 4-[4-[6-(cyclobutoxy)pyrazin-2-yl]-2,6-difluoro-phenoxy]butanoic acid

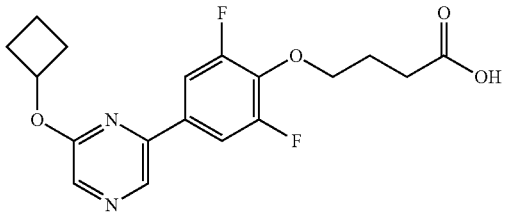 [SMILES: O=C(O)CCCOc1c(F)cc(-c2cncc(OC3CCC3)n2)cc1F]

2-Chloro-6-(cyclobutoxy)pyrazine (0.07 g, 0.38 mmol) obtained in Preparation Example 232 and 4-[2,6-difluoro-4-(4,4,5,5-tetramethyl-1,3,2-dioxaborolan-2-yl)phenoxy]butanoic acid ethyl ester (0.154 g, 0.42 mmol) obtained in Preparation Example 16 were reacted in the same manner as in Step A of Example 96 and Step B of Example 1 to obtain the title compound (0.12 g, 87%).

$^1$H-NMR (CDCl$_3$) δ 8.48 (1H, s), 8.12 (1H, s), 7.57 (2H, m), 5.26 (1H, m), 4.27 (2H, t), 2.68 (2H, t), 2.53 (2H, m), 2.22 (2H, m), 2.14 (2H, m), 1.91 (1H, m), 1.77 (1H, m)

Example 399: 5-[4-[6-(cyclobutoxy)pyrazin-2-yl]-2,6-difluoro-phenyl]hexanoic acid

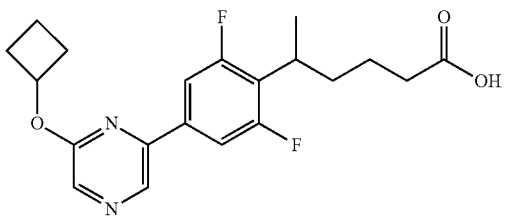 [SMILES: CC(CCCC(=O)O)c1c(F)cc(-c2cncc(OC3CCC3)n2)cc1F]

2-Chloro-6-(cyclobutoxy)pyrazine (0.053 g, 0.28 mmol) obtained in Preparation Example 232 and 5-[2,6-difluoro-4-(4,4,5,5-tetramethyl-[1,3,2]dioxaborolan-2-yl)phenyl]hexanoic acid ethyl ester (0.12 g, 0.31 mmol) obtained in Preparation Example 32 were reacted in the same manner as in Step A of Example 96 and Step B of Example 1 to obtain the title compound (0.10 g, 98%).

$^1$H-NMR (CDCl$_3$) δ 8.50 (1H, s), 8.14 (1H, s), 7.48 (2H, m), 5.27 (1H, m), 3.26 (1H, m), 2.55 (2H, m), 2.38 (2H, m), 2.21 (2H, m), 1.90 (2H, m), 1.75 (2H, m), 1.64 (2H, m), 1.37 (3H, d)

Example 400: 4-[2-chloro-4-(6-cyclopentyloxy-pyridin-2-yl)-6-fluoro-phenoxy]-butyric acid

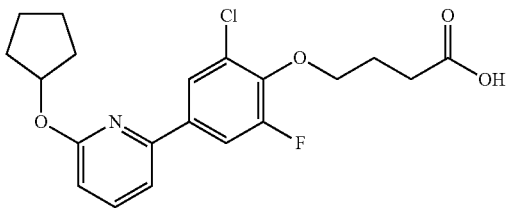 [SMILES: O=C(O)CCCOc1c(F)cc(-c2cccc(OC3CCCC3)n2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-cyclopentyloxy-pyridine (0.077 g, 0.39 mmol) obtained in Preparation Example 12 were sequentially reacted in the same manner as in Steps A and B of Example 1 to obtain the title compound (0.059 g, 57%).

1H-NMR (CDCl3) δ 7.80 (1H, s), 7.70 (1H, dd), 7.58 (1H, t), 7.20 (1H, d), 6.63 (1H, d), 5.49 (1H, m), 4.20 (2H, t), 2.72 (2H, t), 2.15 (2H, t), 2.04 (2H, m), 1.81 (4H, m), 1.64 (2H, m).

Example 401: 4-[2-chloro-4-(6-cyclopropyl-methoxy-pyridin-2-yl)-6-fluoro-phenoxy]-butyric acid

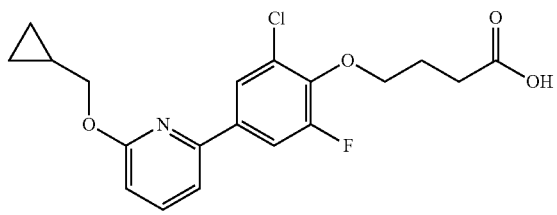 [SMILES: O=C(O)CCCOc1c(F)cc(-c2cccc(OCC3CC3)n2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-cyclopropylmethoxy-pyridine (0.07 g, 0.39 mmol) obtained in Preparation Example 43 were sequentially reacted in the same manner as in Steps A and B of Example 1 to obtain the title compound (0.053 g, 53%).

$^1$H-NMR (CDCl$_3$) δ 7.78 (1H, s), 7.69 (1H, dd), 7.61 (1H, t), 7.22 (1H, d), 6.71 (1H, d), 4.21 (4H, m), 2.71 (2H, t), 2.13 (2H, m), 1.32 (1H, m), 0.62 (2H, m), 0.38 (2H, m).

Example 402: 4-[2-chloro-6-fluoro-4-(6-isopropoxy-pyridin-2-yl)-phenoxy]-butyric acid

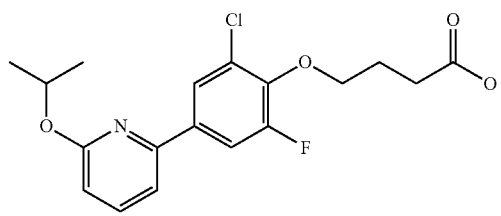 [SMILES: CC(C)Oc1cccc(-c2cc(F)c(OCCCC(=O)O)c(Cl)c2)n1]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-isopropoxy-pyridine (0.066 g, 0.39 mmol) obtained in Preparation Example 46 were sequentially reacted in the same manner as in Steps A and B of Example 1 to obtain the title compound (0.053 g, 55%).

$^1$H-NMR (CDCl$_3$) δ 7.79 (1H, s), 7.69 (1H, dd), 7.59 (1H, t), 7.18 (1H, d), 6.64 (1H, d), 5.43 (1H, m), 4.20 (2H, t), 2.72 (2H, t), 2.15 (2H, m), 1.39 (6H, d).

Example 403: 4-[2-chloro-4-(6-cyclobutylsulfanyl-pyridin-2-yl)-6-fluoro-phenoxy]-butyric acid

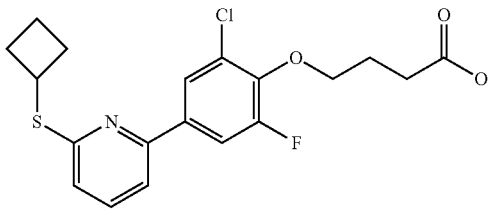

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-cyclobutylsulfanyl-pyridine (0.077 g, 0.39 mmol) obtained in Preparation Example 299 were sequentially reacted in the same manner as in Steps A and B of Example 1 to obtain the title compound (0.04 g, 39%).

$^1$H-NMR (CDCl$_3$) δ 7.81 (1H, s), 7.71 (1H, dd), 7.51 (1H, t), 7.31 (1H, d), 7.02 (1H, d), 4.40 (1H, m), 4.21 (2H, t), 2.72 (2H, t), 2.59 (2H, m), 2.14 (6H, m).

Example 404: 4-[2-chloro-6-fluoro-4-(6-isopropylsulfanyl-pyridin-2-yl)-phenoxy]-butyric acid

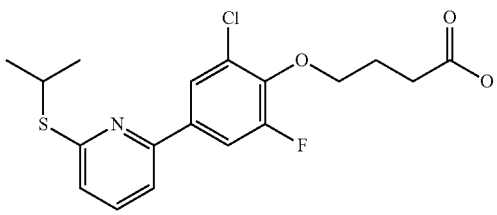 [SMILES: CC(C)Sc1cccc(-c2cc(F)c(OCCCC(=O)O)c(Cl)c2)n1]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-isopropylsulfanyl-pyridine (0.073 g, 0.39 mmol) obtained in Preparation Example 10 were sequentially reacted in the same manner as in Steps A and B of Example 1 to obtain the title compound (0.038 g, 38%).

$^1$H-NMR (CDCl$_3$) δ 7.81 (1H, s), 7.70 (1H, dd), 7.51 (1H, t), 7.31 (1H, d), 7.08 (1H, d), 4.22 (2H, t), 4.11 (1H, m), 2.72 (2H, t), 2.14 (2H, m), 1.48 (6H, d).

Example 405: 4-(5-chloro-3'-cyclobutoxy-3-fluoro-biphenyl-4-yloxy)-butyric acid

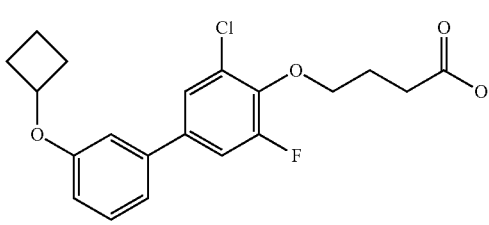 [SMILES: O=C(O)CCCOc1c(F)cc(-c2cccc(OC3CCC3)c2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 1-bromo-3-cyclobutoxy-benzene (0.088 g, 0.39 mmol) obtained in Step A of Preparation Example 121 were sequentially reacted in the same manner as in Steps A and B of Example 1 to obtain the title compound (0.059 g, 60%).

$^1$H-NMR (CDCl$_3$) δ 7.35 (1H, s), 7.30 (1H, t), 7.21 (1H, m), 7.05 (1H, m), 6.93 (1H, s), 6.79 (1H, m), 4.68 (1H, m), 4.18 (2H, t), 2.71 (2H, t), 2.46 (2H, m), 2.15 (4H, m), 1.86 (1H, m), 1.71 (1H, m).

Example 406: 4-(5-chloro-3'-cyclopropylmethoxy-3-fluoro-biphenyl-4-yloxy)-butyric acid

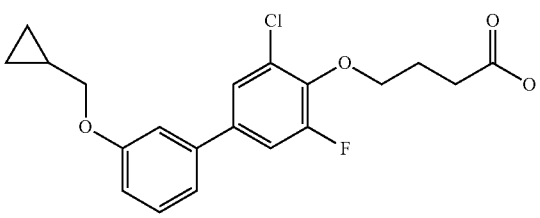 [SMILES: O=C(O)CCCOc1c(F)cc(-c2cccc(OCC3CC3)c2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 1-bromo-3-(cyclopropylmethoxy)benzene (0.088 g, 0.39 mmol) obtained in Preparation Example 280 were sequentially reacted in the same manner as in Steps A and B of Example 1 to obtain the title compound (0.051 g, 52%).

$^1$H-NMR (CDCl$_3$) δ 7.37 (1H, s), 7.32 (1H, t), 7.22 (1H, m), 7.04 (1H, m), 7.01 (1H, s), 6.89 (1H, m), 4.18 (2H, t), 3.83 (2H, d), 2.71 (2H, t), 2.14 (2H, m), 1.28 (1H, m), 0.65 (2H, m), 0.37 (2H, m).

Example 407: 4-(5-chloro-3'-cyclopropylmethoxy-3-fluoro-4'-methoxy-biphenyl-4-yloxy)-butyric acid

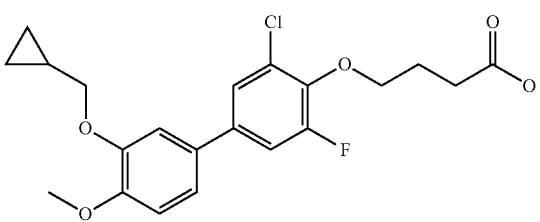 [SMILES: COc1ccc(-c2cc(F)c(OCCCC(=O)O)c(Cl)c2)cc1OCC1CC1]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 4-bromo-2-(cyclopropylmethoxy)-1-methoxy-benzene (0.1 g, 0.39 mmol) obtained in Preparation Example 282 were sequentially reacted in the same manner as in Steps A and B of Example 1 to obtain the title compound (0.055 g, 52%).

$^1$H-NMR (CDCl$_3$) δ 7.31 (1H, s), 7.16 (1H, m), 7.03 (1H, m), 6.98 (1H, m), 6.92 (1H, d), 4.17 (2H, t), 3.90 (5H, m), 2.71 (2H, t), 2.14 (2H, m), 1.36 (1H, m), 0.65 (2H, m), 0.38 (2H, m).

Example 408: 4-(5-chloro-3'-cyclopropylmethoxy-3, 4'-difluoro-biphenyl-4-yloxy)-butyric acid

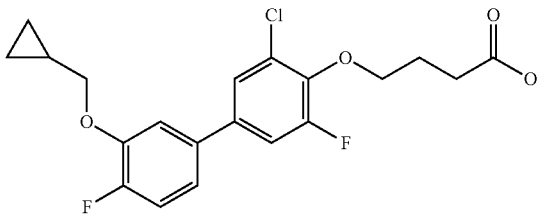 [SMILES: O=C(O)CCCOc1c(F)cc(-c2ccc(F)c(OCC3CC3)c2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 4-bromo-2-(cyclopropylmethoxy)-1-fluoro-benzene (0.095 g, 0.39 mmol) obtained in Preparation Example 283 were sequentially reacted in the same manner as in Steps A and B of Example 1 to obtain the title compound (0.048 g, 46%).

$^1$H-NMR (CDCl$_3$) δ 7.30 (1H, s), 7.13 (2H, m), 7.02 (2H, m), 4.18 (2H, t), 3.93 (2H, d), 2.71 (2H, t), 2.13 (2H, m), 1.32 (1H, m), 0.66 (2H, m), 0.37 (2H, m).

Example 409: 4-(3'-cyclobutylsulfanyl-3,5-difluoro-biphenyl-4-yloxy)-butyric acid

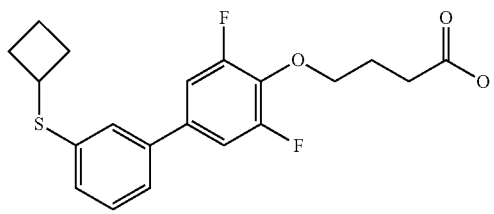 [SMILES: O=C(O)CCCOc1c(F)cc(-c2cccc(SC3CCC3)c2)cc1F]

4-[2,6-Difluoro-4-(4,4,5,5-tetramethyl-1,3,2-dioxaborolan-2-yl)phenoxy]butyric acid ethyl ester (0.1 g, 0.27 mmol) obtained in Preparation Example 16 and 1-bromo-3-cyclobutylsulfanyl-benzene (0.098 g, 0.40 mmol) obtained in Preparation Example 293 were sequentially reacted in the same manner as in Steps A and B of Example 1 to obtain the title compound (0.036 g, 35%).

$^1$H-NMR (CDCl$_3$) δ 7.33 (2H, m), 7.25 (2H, m), 7.07 (2H, m), 4.22 (2H, t), 3.93 (1H, m), 2.66 (2H, t), 2.48 (2H, m), 2.10 (6H, m).

Example 410: 5-(3'-cyclobutoxy-3,5-difluoro-biphenyl-4-yl)-hexanoic acid

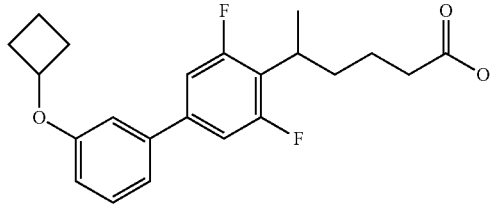

5-[2,6-Difluoro-4-(4,4,5,5-tetramethyl-[1,3,2]dioxaborolan-2-yl)phenyl]hexanoic acid ethyl ester (0.1 g, 0.26 mmol) obtained in Preparation Example 32 and 1-bromo-3-cyclobutoxy-benzene (0.089 g, 0.39 mmol) obtained in Step A of Preparation Example 121 were sequentially reacted in the same manner as in Steps A and B of Example 1 to obtain the title compound (0.058 g, 59%).

$^1$H-NMR (CDCl$_3$) δ 7.30 (1H, t), 7.08 (1H, m), 7.03 (2H, m), 6.95 (1H, s), 6.82 (1H, m), 4.68 (1H, m), 3.21 (1H, m), 2.46 (2H, m), 2.35 (2H, m), 2.19 (2H, m), 1.86 (2H, m), 1.72 (2H, m), 1.65 (1H, m), 1.52 (1H, m), 1.35 (3H, d).

Example 411: 5-(5'-cyclobutoxy-3,5,3'-trifluoro-biphenyl-4-yl)-hexanoic acid

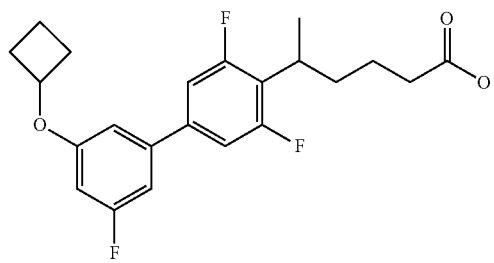 [SMILES: CC(CCCC(=O)O)c1c(F)cc(-c2cc(F)cc(OC3CCC3)c2)cc1F]

5-[2,6-Difluoro-4-(4,4,5,5-tetramethyl-[1,3,2]dioxaborolan-2-yl)phenyl]hexanoic acid ethyl ester (0.1 g, 0.26 mmol) obtained in Preparation Example 32 and 1-bromo-3-(cyclobutoxy)-5-fluoro-benzene (0.096 g, 0.39 mmol) obtained in Preparation Example 284 were sequentially reacted in the same manner as in Steps A and B of Example 1 to obtain the title compound (0.058 g, 56%).

$^1$H-NMR (CDCl$_3$) δ 7.00 (2H, m), 6.77 (1H, m), 6.74 (1H, s), 6.52 (1H, m), 4.65 (1H, m), 3.21 (1H, m), 2.46 (2H, m), 2.36 (2H, m), 2.18 (2H, m), 1.87 (2H, m), 1.73 (2H, m), 1.65 (1H, m), 1.52 (1H, m), 1.35 (3H, d).

Example 412: 5-(3'-cyclopropylmethoxy-3,5-difluoro-4'-methoxy-biphenyl-4-yl)-hexanoic acid

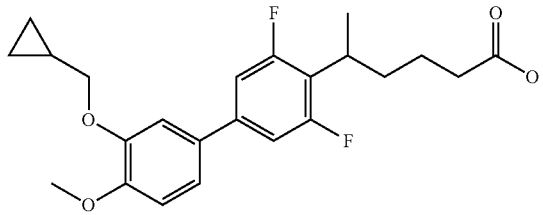 [SMILES: COc1ccc(-c2cc(F)c(C(C)CCCC(=O)O)c(F)c2)cc1OCC1CC1]

5-[2,6-Difluoro-4-(4,4,5,5-tetramethyl-[1,3,2]dioxaborolan-2-yl)phenyl]hexanoic acid ethyl ester (0.1 g, 0.26 mmol) obtained in Preparation Example 32 and 4-bromo-2-(cyclopropylmethoxy)-1-methoxy-benzene (0.1 g, 0.39 mmol) obtained in Preparation Example 282 were sequentially reacted in the same manner as in Steps A and B of Example 1 to obtain the title compound (0.046 g, 43%).

$^1$H-NMR (CDCl$_3$) δ 7.08 (1H, m), 7.00 (3H, m), 6.92 (1H, d), 3.91 (5H, m), 3.20 (1H, m), 2.34 (2H, m), 1.82 (1H, m), 1.71 (1H, m), 1.62 (1H, m), 1.52 (1H, m), 1.33 (4H, m), 0.65 (2H, m), 0.37 (2H, m).

Example 413: 5-(3'-cyclopropylmethoxy-3,5-difluoro-biphenyl-4-yl)-hexanoic acid

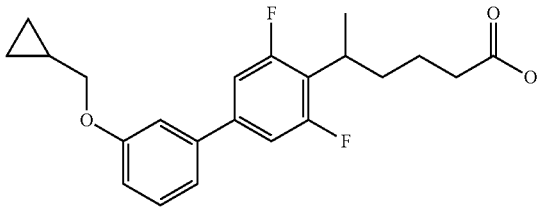 [SMILES: CC(CCCC(=O)O)c1c(F)cc(-c2cccc(OCC3CC3)c2)cc1F]

5-[2,6-Difluoro-4-(4,4,5,5-tetramethyl-[1,3,2]dioxaborolan-2-yl)phenyl]hexanoic acid ethyl ester (0.1 g, 0.26 mmol) obtained in Preparation Example 32 and 1-bromo-3-(cyclopropylmethoxy)benzene (0.089 g, 0.39 mmol) obtained in Preparation Example 280 were sequentially reacted in the same manner as in Steps A and B of Example 1 to obtain the title compound (0.028 g, 28%).
$^1$H-NMR (CDCl$_3$) δ 7.32 (1H, t), 7.09 (1H, m), 7.03 (3H, m), 6.90 (1H, m), 3.85 (2H, d), 3.21 (1H, m), 2.36 (2H, m), 1.83 (1H, m), 1.71 (1H, m), 1.63 (1H, m), 1.52 (1H, m), 1.34 (3H, d), 1.29 (1H, m), 0.66 (2H, m), 0.37 (2H, m).

Example 414: 5-(5'-cyclobutoxy-3'-fluoro-biphenyl-4-yl)-5,5-difluoro-pentanoic acid

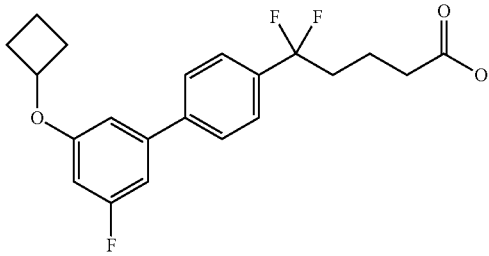 [SMILES: O=C(O)CCCC(F)(F)c1ccc(-c2cc(F)cc(OC3CCC3)c2)cc1]

5,5-Difluoro-5-[4-(4,4,5,5-tetramethyl-[1,3,2]dioxaborolan-2-yl)-phenyl]-pentanoic acid methyl ester (0.1 g, 0.28 mmol) obtained in Preparation Example 169 and 1-bromo-3-(cyclobutoxy)-5-fluoro-benzene (0.104 g, 0.42 mmol) obtained in Preparation Example 284 were sequentially reacted in the same manner as in Steps A and B of Example 1 to obtain the title compound (0.038 g, 35%).
$^1$H-NMR (CDCl$_3$) δ 7.58 (2H, d), 7.53 (2H, d), 6.84 (1H, m), 6.81 (1H, s), 6.51 (1H, m), 4.66 (1H, m), 2.43 (4H, m), 2.21 (4H, m), 1.83 (3H, m), 1.71 (1H, m).

Example 415: 5-[4-(5-chloro-6-cyclobutoxy-pyridin-2-yl)-2,6-difluoro-phenyl]-hexanoic acid

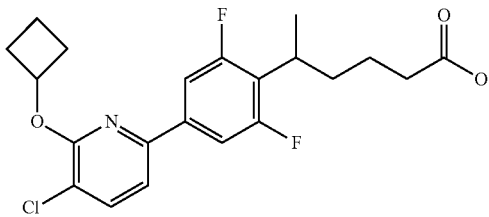

5-[2,6-Difluoro-4-(4,4,5,5-tetramethyl-[1,3,2]dioxaborolan-2-yl)phenyl]hexanoic acid ethyl ester (0.08 g, 0.21 mmol) obtained in Preparation Example 32 and 3,6-dichloro-2-cyclobutoxy-pyridine (0.068 g, 0.31 mmol) obtained in Preparation Example 298 were sequentially reacted in the same manner as in Steps A and B of Example 1 to obtain the title compound (0.032 g, 37%).
$^1$H-NMR (CDCl$_3$) δ 7.66 (1H, d), 7.43 (2H, m), 67.18 (1H, d), 5.31 (1H, m), 3.24 (1H, m), 2.54 (2H, m), 2.35 (2H, m), 2.25 (2H, m), 1.88-1.52 (6H, m), 1.35 (3H, d).

Example 416: 4-(3'-cyclobutanesulfonyl-3,5-difluoro-biphenyl-4-yloxy)-butyric acid

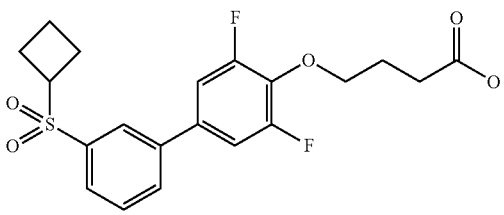 [SMILES: O=C(O)CCCOc1c(F)cc(-c2cccc(S(=O)(=O)C3CCC3)c2)cc1F]

2,6-Difluoro-4-(4,4,5,5-tetramethyl-1,3,2-dioxaborolan-2-yl)phenol (0.1 g, 0.27 mmol) obtained in Step B of Preparation Example 16 and 1-bromo-3-cyclobutylsulfonyl-benzene (0.111 g, 0.40 mmol) obtained in Preparation Example 285 were sequentially reacted in the same manner as in Steps A and B of Example 1 to obtain the title compound (0.052 g, 47%).
$^1$H-NMR (CDCl$_3$) δ 8.00 (1H, s), 7.86 (1H, d), 7.76 (1H, d), 7.64 (1H, t), 7.17 (2H, m), 4.26 (2H, t), 3.83 (1H, m), 2.63 (4H, m), 2.16 (4H, m), 2.02 (2H, m).

Example 417: 5-({[4-(6-cyclobutoxy-pyridin-2-yl)-phenyl]-methyl-amino}-methyl)-isoxazol-3-ol

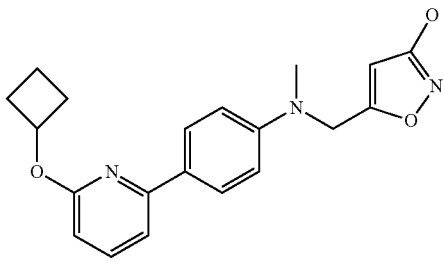 [SMILES: CN(Cc1cc(O)no1)c1ccc(-c2cccc(OC3CCC3)n2)cc1]

4-(6-Cyclobutoxy-pyridin-2-yl)-phenyl]-[3-(4-methoxyphenoxy)-isoxazol-5-ylmethyl]-amine (0.07 g, 0.15 mmol) obtained in Preparation Example 296 was dissolved in 2 mL of methanol. 0.3 ml of 37% formaldehyde solution and 0.3 ml of HCl were added thereto. Sodium cyanoborohydride (0.014 g, 0.23 mmol) was added thereto at 0° C., and the mixture was stirred at room temperature for 30 minutes. The reaction solution was diluted with water and extracted with ethyl acetate. The organic layer was dried with anhydrous magnesium sulfate and purified by column chromatography to obtain the title compound (0.02 g, 37%).
$^1$H-NMR (CDCl$_3$) δ 7.94 (2H, d), 7.54 (1H, t), 7.22 (1H, d), 6.79 (2H, d), 6.53 (1H, d), 5.73 (1H, s), 5.26 (1H, m), 4.52 (2H, s), 3.07 (3H, s), 2.52 (2H, m), 2.18 (2H, m), 1.83 (1H, m), 1.69 (1H, m).

Example 418: 5-[4-(2-cyclobutoxy-6-methyl-pyrimidin-4-yl)-2,6-difluoro-phenyl]-hexanoic acid

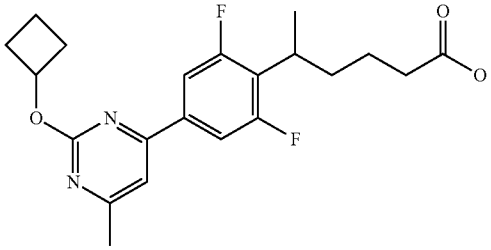 [SMILES: Cc1cc(-c2cc(F)c(C(C)CCCC(=O)O)c(F)c2)nc(OC2CCC2)n1]

5-[2,6-Difluoro-4-(4,4,5,5-tetramethyl-[1,3,2]dioxaborolan-2-yl)phenyl]hexanoic acid ethyl ester (0.1 g, 0.26 mmol) obtained in Preparation Example 32 and 4-chloro-2-(cyclobutoxy)-6-methyl-pyrimidine (0.062 g, 0.39 mmol) obtained in Preparation Example 229 were sequentially reacted in the same manner as in Steps A and B of Example 1 to obtain the title compound (0.056 g, 54%).

$^1$H-NMR (CDCl$_3$) δ 7.54 (2H, d), 7.12 (1H, s), 5.28 (1H, m), 3.25 (1H, m), 2.51 (5H, m), 2.26 (4H, m), 1.86 (2H, m), 1.73 (2H, m), 1.55 (1H, m), 1.45 (1H, m), 1.35 (3H, d).

Example 419: 5-[4-(4-cyclobutoxy-6-methyl-pyrimidin-2-yl)-2,6-difluoro-phenyl]-hexanoic acid

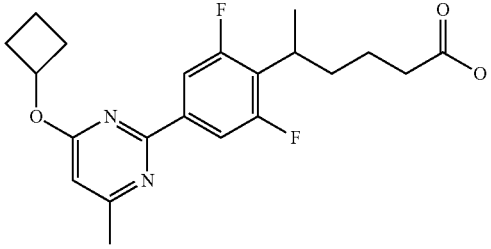 [SMILES: Cc1cc(OC2CCC2)nc(-c2cc(F)c(C(C)CCCC(=O)O)c(F)c2)n1]

5-[2,6-Difluoro-4-(4,4,5,5-tetramethyl-[1,3,2]dioxaborolan-2-yl)phenyl]hexanoic acid ethyl ester (0.1 g, 0.26 mmol) obtained in Preparation Example 32 and 2-chloro-4-(cyclobutoxy)-6-methyl-pyrimidine (0.062 g, 0.39 mmol) obtained in Preparation Example 228 were sequentially reacted in the same manner as in Steps A and B of Example 1 to obtain the title compound (0.042 g, 41%).

$^1$H-NMR (CDCl$_3$) δ 7.86 (2H, d), 6.44 (1H, s), 5.30 (1H, m), 3.25 (1H, m), 2.53 (2H, m), 2.47 (3H, s), 2.34 (2H, t), 2.19 (2H, m), 1.87 (2H, m), 1.74 (2H, m), 1.63 (1H, m), 1.51 (1H, m), 1.35 (3H, d).

Example 420: 4-[4-(4-cyclobutoxy-pyrimidin-2-yl)-2,6-difluoro-phenoxy]-butyric acid

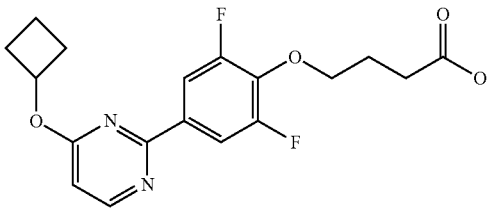 [SMILES: O=C(O)CCCOc1c(F)cc(-c2nccc(OC3CCC3)n2)cc1F]

4-[2,6-Difluoro-4-(4,4,5,5-tetramethyl-1,3,2-dioxaborolan-2-yl)phenoxy]butyric acid ethyl ester (0.2 g, 0.54 mmol) obtained in Preparation Example 16, and the mixture (0.11 g, 0.59 mmol) of 2-chloro-4-(cyclobutoxy)pyrimidine obtained in Preparation Example 230 and 4-chloro-2-cyclobutoxy-pyrimidine were sequentially reacted in the same manner as in Steps A and B of Example 1 to obtain 4-[4-(4-cyclobutoxy-pyrimidin-2-yl)-2,6-difluoro-phenoxy]-butyric acid (0.015 g, 7%) and 4-[4-(2-cyclobutoxy-pyrimidin-4-yl)-2,6-difluoro-phenoxy]-butyric acid (0.088 g, 44%).

$^1$H-NMR (CDCl$_3$) δ 8.48 (1H, d), 7.97 (2H, m), 6.58 (1H, d), 5.33 (1H, m), 4.28 (2H, t), 2.67 (2H, t), 2.53 (2H, m), 2.22 (2H, m), 2.14 (2H, m), 1.89 (1H, m), 1.76 (1H, m).

Example 421: 4-[4-(2-cyclobutoxy-pyrimidin-4-yl)-2,6-difluoro-phenoxy]-butyric acid

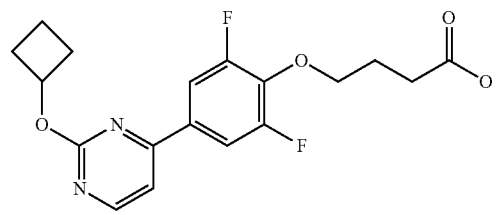 [SMILES: O=C(O)CCCOc1c(F)cc(-c2ccnc(OC3CCC3)n2)cc1F]

4-[2,6-Difluoro-4-(4,4,5,5-tetramethyl-1,3,2-dioxaborolan-2-yl)phenoxy]butyric acid ethyl ester (0.2 g, 0.54 mmol) obtained in Preparation Example 16, and the mixture (0.11 g, 0.59 mmol) of 2-chloro-4-(cyclobutoxy)pyrimidine obtained in Preparation Example 230 and 4-chloro-2-cyclobutoxy-pyrimidine were sequentially reacted in the same manner as in Steps A and B of Example 1 to obtain 4-[4-(4-cyclobutoxy-pyrimidin-2-yl)-2,6-difluoro-phenoxy]-butyric acid (0.015 g, 7%) and 4-[4-(2-cyclobutoxy-pyrimidin-4-yl)-2,6-difluoro-phenoxy]-butyric acid (0.088 g, 44%).

$^1$H-NMR (CDCl$_3$) δ 8.54 (1H, d), 7.65 (2H, m), 7.21 (1H, d), 5.27 (1H, m), 4.29 (2H, t), 2.66 (2H, t), 2.50 (2H, m), 2.27 (2H, m), 2.12 (2H, m), 1.87 (1H, m), 1.73 (1H, m).

Example 422: 4-[2-chloro-4-(4-cyclobutoxy-pyrimidin-2-yl)-6-fluoro-phenoxy]-butyric acid

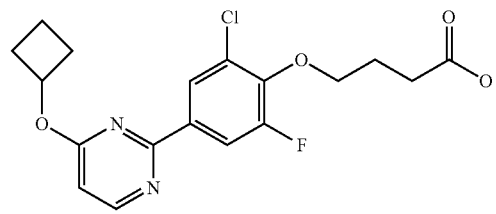 [SMILES: O=C(O)CCCOc1c(F)cc(-c2nccc(OC3CCC3)n2)cc1Cl]

4-[2-Chloro-6-fluoro-4-(4,4,5,5-tetramethyl-1,3,2-dioxaborolan-2-yl)phenoxy]butanoic acid ethyl ester (0.2 g, 0.52 mmol) obtained in Preparation Example 221, and the mixture (0.105 g, 0.57 mmol) of 2-chloro-4-(cyclobutoxy)pyrimidine obtained in Preparation Example 230 and 4-chloro-2-cyclobutoxy-pyrimidine were sequentially reacted in the same manner as in Steps A and B of Example 1 to obtain 4-[2-chloro-4-(4-cyclobutoxy-pyrimidin-2-yl)-6-fluorophenoxy]-butyric acid (0.012 g, 6%) and 4-[2-chloro-4-(2-cyclobutoxy-pyrimidin-4-yl)-6-fluoro-phenoxy]-butyric acid (0.083 g, 42%).

$^1$H-NMR (CDCl$_3$) δ 8.46 (1H, d), 8.22 (1H, s), 8.04 (1H, m), 6.58 (1H, d), 5.33 (1H, m), 4.24 (2H, t), 2.72 (2H, t), 2.54 (2H, m), 2.18 (4H, m), 1.89 (1H, m), 1.79 (1H, m).

Example 423: 4-[2-chloro-4-(2-cyclobutoxy-pyrimidin-4-yl)-6-fluoro-phenoxy]-butyric acid

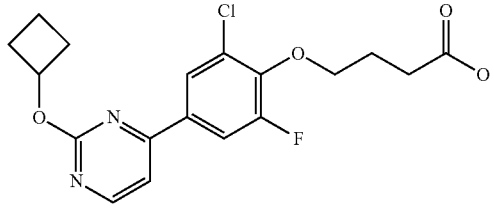 [SMILES: O=C(O)CCCOc1c(F)cc(-c2ccnc(OC3CCC3)n2)cc1Cl]

4-[2-Chloro-6-fluoro-4-(4,4,5,5-tetramethyl-1,3,2-dioxaborolan-2-yl)phenoxy]butanoic acid ethyl ester (0.2 g, 0.52 mmol) obtained in Preparation Example 221, and the mixture (0.105 g, 0.57 mmol) of 2-chloro-4-(cyclobutoxy)pyrimidine obtained in Preparation Example 230 and 4-chloro-2-cyclobutoxy-pyrimidine were sequentially reacted in the same manner as in Steps A and B of Example 1 to obtain 4-[2-chloro-4-(4-cyclobutoxy-pyrimidin-2-yl)-6-fluoro-phenoxy]-butyric acid (0.012 g, 6%) and 4-[2-chloro-4-(2-cyclobutoxy-pyrimidin-4-yl)-6-fluoro-phenoxy]-butyric acid (0.083 g, 42%).

$^1$H-NMR (CDCl$_3$) δ 8.54 (1H, d), 7.90 (1H, s), 7.77 (1H, m), 7.24 (1H, d), 5.27 (1H, m), 4.27 (2H, t), 2.70 (2H, t), 2.51 (2H, m), 2.28 (2H, m), 2.17 (2H, m), 1.88 (1H, m), 1.74 (1H, m).

Example 424: 4-[2-chloro-4-(6-chloro-4-cyclobutoxy-pyridin-2-yl)-6-fluoro-phenoxy]-butyric acid

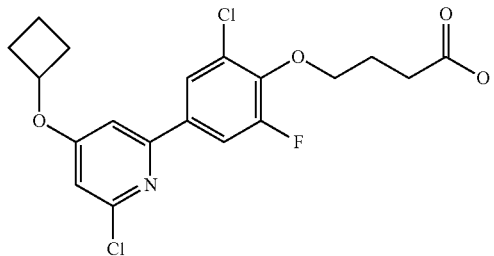 [SMILES: O=C(O)CCCOc1c(F)cc(-c2cc(OC3CCC3)cc(Cl)n2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2,6-dichloro-4-(cyclobutoxy)pyridine (0.068 g, 0.31 mmol) obtained in Preparation Example 270 were sequentially reacted in the same manner as in Steps A and B of Example 1 to obtain the title compound (0.028 g, 26%).

$^1$H-NMR (CDCl$_3$) δ 7.49 (1H, s), 7.64 (1H, m), 6.97 (1H, s), 6.66 (1H, s), 4.73 (1H, m), 4.21 (2H, t), 2.71 (2H, t), 2.50 (2H, m), 2.15 (4H, m), 1.94 (1H, m), 1.76 (1H, m).

Example 425: 4-[4-(4-cyclobutoxy-6-methyl-pyrimidin-2-yl)-2,6-difluoro-phenoxy]-butyric acid

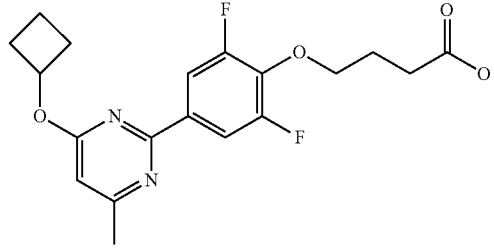 [SMILES: Cc1cc(OC2CCC2)nc(-c2cc(F)c(OCCCC(=O)O)c(F)c2)n1]

4-[2,6-Difluoro-4-(4,4,5,5-tetramethyl-1,3,2-dioxaborolan-2-yl)phenoxy]butyric acid ethyl ester (0.1 g, 0.27 mmol) obtained in Preparation Example 16 and 2-chloro-4-(cyclobutoxy)-6-methyl-pyrimidine (0.059 g, 0.3 mmol) obtained in Preparation Example 228 were sequentially reacted in the same manner as in Steps A and B of Example 1 to obtain the title compound (0.042 g, 41%).

$^1$H-NMR (CDCl$_3$) δ 7.98 (2H, m), 6.42 (1H, s), 5.30 (1H, m), 4.27 (2H, t), 2.67 (2H, t), 2.52 (2H, m), 2.46 (3H, s), 2.15 (4H, m), 1.87 (1H, m), 1.74 (1H, m).

Example 426: 4-[2-chloro-4-(2-cyclobutoxy-thiazol-4-yl)-6-fluoro-phenoxy]-butyric acid

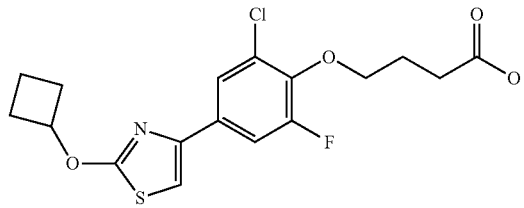 [SMILES: O=C(O)CCCOc1c(F)cc(-c2csc(OC3CCC3)n2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 4-bromo-2-(cyclobutoxy)thiazole (0.073 g, 0.31 mmol) obtained in Preparation Example 289 were sequentially reacted in the same manner as in Steps A and B of Example 1 to obtain the title compound (0.037 g, 37%).

$^1$H-NMR (CDCl$_3$) δ 7.58 (1H, s), 7.43 (1H, m), 6.78 (1H, s), 5.16 (1H, m), 4.16 (2H, t), 2.68 (2H, t), 2.51 (2H, m), 2.24 (2H, m), 2.12 (2H, m), 1.86 (1H, m), 1.68 (1H, m).

Example 427: 4-[2-chloro-4-(2-cyclopropyl-methoxy-thiazol-4-yl)-6-fluoro-phenoxy]-butyric acid

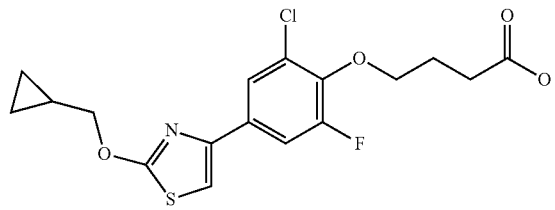 [SMILES: O=C(O)CCCOc1c(F)cc(-c2csc(OCC3CC3)n2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 4-bromo-2-(cyclopropylmethoxy)thiazole (0.073 g, 0.31 mmol) obtained in Preparation Example 290 were sequentially reacted in the same manner as in Steps A and B of Example 1 to obtain the title compound (0.033 g, 33%).

$^1$H-NMR (CDCl$_3$) δ 7.59 (1H, s), 7.43 (1H, m), 6.78 (1H, s), 4.28 (2H, d), 4.16 (2H, t), 2.70 (2H, t), 2.13 (2H, m), 1.34 (1H, m), 0.65 (2H, m), 0.40 (2H, m).

Example 428: 4-[2-chloro-4-(4-cyclopropyl-methoxy-pyrimidin-2-yl)-6-fluoro-phenoxy]-butyric acid

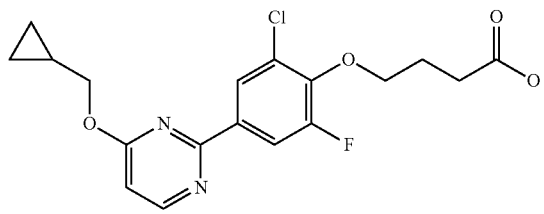

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-4-(cyclopropylmethoxy)pyrimidine (0.057 g, 0.31 mmol) obtained in Preparation Example 231 were sequentially reacted in the same manner as in Steps A and B of Example 1 to obtain the title compound (0.038 g, 38%).

$^1$H-NMR (CDCl$_3$) δ 8.46 (1H, d), 8.22 (1H, s), 8.04 (1H, m), 6.64 (1H, d), 4.29 (2H, d), 4.24 (2H, t), 2.71 (2H, t), 2.14 (2H, m), 1.32 (1H, m), 0.65 (2H, m), 0.40 (2H, m).

Example 429: 4-[2-chloro-4-(6-cyclobutoxy-4-methyl-pyridin-2-yl)-6-fluoro-phenoxy]-butyric acid

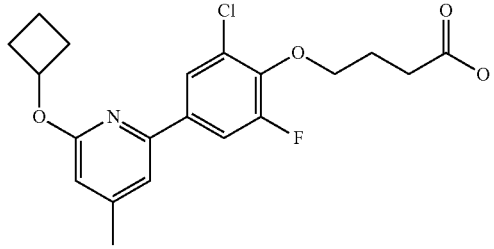

4-[2-Chloro-6-fluoro-4-(4,4,5,5-tetramethyl-1,3,2-dioxaborolan-2-yl)phenoxy]butanoic acid ethyl ester (1 g, 2.59 mmol) obtained in Preparation Example 221 and 2-chloro-6-(cyclobutoxy)-4-methyl-pyridine (0.613 g, 3.10 mmol) obtained in Preparation Example 271 were sequentially reacted in the same manner as in Steps A and B of Example 1 to obtain the title compound (0.8 g, 78%).

$^1$H-NMR (CDCl$_3$) δ 7.77 (1H, s), 7.65 (1H, m), 7.04 (1H, s), 6.46 (1H, s), 5.22 (1H, m), 4.19 (2H, t), 2.71 (2H, t), 2.51 (2H, m), 2.32 (3H, s), 2.16 (4H, m), 1.84 (1H, m), 1.73 (1H, m).

Example 430: 4-[2-chloro-4-(6-cyclobutoxy-pyrazin-2-yl)-6-fluoro-phenoxy]-butyric acid

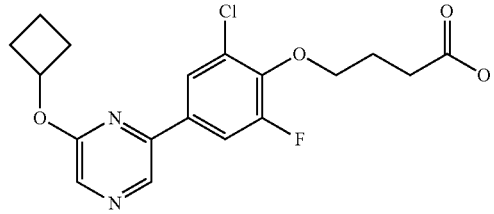 [SMILES: O=C(O)CCCOc1c(F)cc(-c2cncc(OC3CCC3)n2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-(cyclobutoxy)pyrazine (0.057 g, 0.31 mmol) obtained in Preparation Example 232 were sequentially reacted in the same manner as in Steps A and B of Example 1 to obtain the title compound (0.036 g, 36%).

$^1$H-NMR (CDCl$_3$) δ 8.48 (1H, s), 8.11 (1H, s), 7.79 (1H, s), 7.65 (1H, m), 5.26 (1H, m), 4.24 (2H, t), 2.70 (2H, t), 2.51 (2H, m), 2.20 (4H, m), 1.90 (1H, m), 1.75 (1H, m).

Example 431: 4-[2-chloro-4-(6-cyclopropyl-methoxy-pyrazin-2-yl)-6-fluoro-phenoxy]-butyric acid

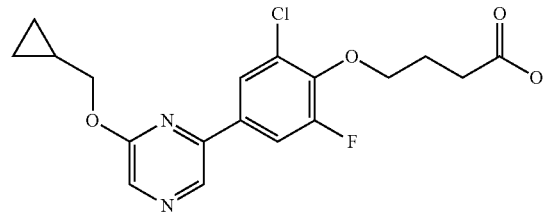 [SMILES: O=C(O)CCCOc1c(F)cc(-c2cncc(OCC3CC3)n2)cc1Cl]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-(cyclopropylmethoxy)pyrazine (0.057 g, 0.31 mmol) obtained in Preparation Example 233 were sequentially reacted in the same manner as in Steps A and B of Example 1 to obtain the title compound (0.028 g, 28%).

$^1$H-NMR (CDCl$_3$) δ 8.46 (1H, s), 8.18 (1H, s), 7.80 (1H, s), 7.65 (1H, m), 4.24 (4H, m), 2.71 (2H, t), 2.14 (2H, m), 1.32 (1H, m), 0.65 (2H, m), 0.39 (2H, m).

Example 432: 4-[4-(4-cyclopropylmethoxy-6-methyl-pyrimidin-2-yl)-2,6-difluoro-phenoxy]-butyric acid

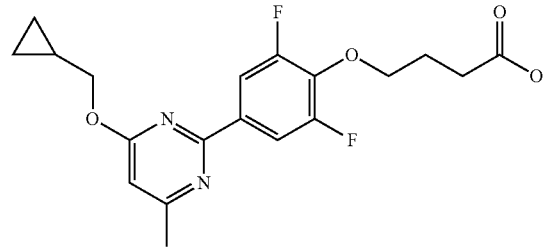 [SMILES: Cc1cc(OCC2CC2)nc(-c2cc(F)c(OCCCC(=O)O)c(F)c2)n1]

4-[2,6-Difluoro-4-(4,4,5,5-tetramethyl-1,3,2-dioxaborolan-2-yl)phenoxy]butyric acid ethyl ester (0.1 g, 0.27 mmol) obtained in Preparation Example 16 and 2-chloro-4-(cyclopropylmethoxy)-6-methyl-pyrimidine (0.064 g, 0.32 mmol) obtained in Preparation Example 227 were sequentially reacted in the same manner as in Steps A and B of Example 1 to obtain the title compound (0.045 g, 44%).

$^1$H-NMR (CDCl$_3$) δ 7.99 (2H, m), 6.49 (1H, s), 4.27 (4H, m), 2.67 (2H, t), 2.47 (3H, s), 2.12 (2H, m), 1.32 (1H, m), 0.64 (2H, m), 0.39 (2H, m).

Example 433: 4-[4-(4-cyclopropylmethoxy-pyrimidin-2-yl)-2,6-difluoro-phenoxy]-butyric acid

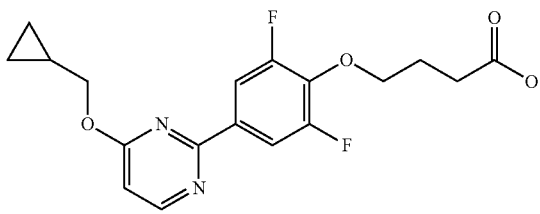

4-[2,6-Difluoro-4-(4,4,5,5-tetramethyl-1,3,2-dioxaborolan-2-yl)phenoxy]butyric acid ethyl ester (0.1 g, 0.27 mmol) obtained in Preparation Example 16 and 2-chloro-4-(cyclopropylmethoxy)pyrimidine (0.06 g, 0.32 mmol) obtained in Preparation Example 231 were sequentially reacted in the same manner as in Steps A and B of Example 1 to obtain the title compound (0.048 g, 48%).

$^1$H-NMR (CDCl$_3$) δ 8.46 (1H, d), 7.98 (2H, m), 6.64 (1H, d), 4.28 (4H, m), 2.67 (2H, t), 2.12 (2H, m), 1.33 (1H, m), 0.67 (2H, m), 0.41 (2H, m).

Example 434: 4-[4-(6-cyclopropylmethoxy-pyrazin-2-yl)-2,6-difluoro-phenoxy]-butyric acid

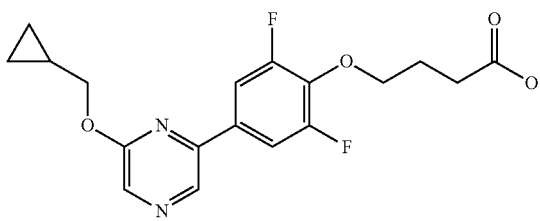 [SMILES: O=C(O)CCCOc1c(F)cc(-c2cncc(OCC3CC3)n2)cc1F]

4-[2,6-Difluoro-4-(4,4,5,5-tetramethyl-1,3,2-dioxaborolan-2-yl)phenoxy]butyric acid ethyl ester (0.1 g, 0.27 mmol) obtained in Preparation Example 16 and 2-chloro-6-(cyclopropylmethoxy)pyrazine (0.06 g, 0.32 mmol) obtained in Preparation Example 233 were sequentially reacted in the same manner as in Steps A and B of Example 1 to obtain the title compound (0.047 g, 47%).

$^1$H-NMR (CDCl$_3$) δ 8.48 (1H, s), 8.18 (1H, s), 7.56 (2H, m), 4.26 (4H, m), 2.67 (2H, t), 2.14 (2H, m), 1.33 (1H, m), 0.67 (2H, m), 0.40 (2H, m).

Example 435: 4-[2-chloro-4-(6-cyclopropylmethoxy-4-methyl-pyridin-2-yl)-6-fluoro-phenoxy]-butyric acid

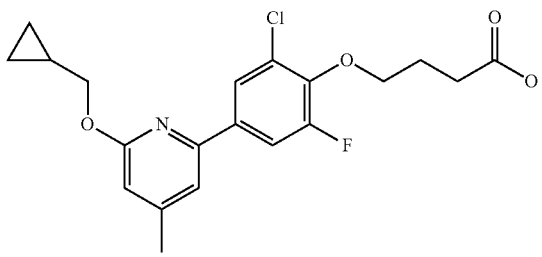

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-cyclopropylmethoxy-4-methyl-pyridine (0.061 g, 0.31 mmol) obtained in Preparation Example 300 were sequentially reacted in the same manner as in Steps A and B of Example 1 to obtain the title compound (0.053 g, 52%).

$^1$H-NMR (CDCl$_3$) δ 7.77 (1H, s), 7.66 (1H, m), 7.05 (1H, s), 6.54 (1H, s), 4.19 (4H, m), 2.71 (2H, t), 2.33 (3H, s), 2.12 (2H, m), 1.30 (1H, m), 0.61 (2H, m), 0.36 (2H, m).

Example 436: 4-[2-chloro-6-fluoro-4-(6-isopropoxy-pyrazin-2-yl)-phenoxy]-butyric acid

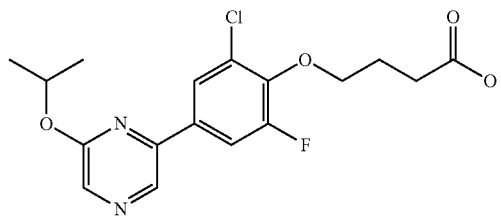 [SMILES: CC(C)Oc1cncc(-c2cc(F)c(OCCCC(=O)O)c(Cl)c2)n1]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-isopropoxy-pyrazine (0.053 g, 0.31 mmol) obtained in Preparation Example 301 were sequentially reacted in the same manner as in Steps A and B of Example 1 to obtain the title compound (0.043 g, 45%).

$^1$H-NMR (CDCl$_3$) δ 8.48 (1H, s), 8.09 (1H, s), 7.79 (1H, s), 7.67 (1H, m), 5.42 (1H, m), 4.23 (2H, t), 2.71 (2H, t), 2.15 (2H, m), 1.40 (6H, d).

Example 437: 4-[2-chloro-4-(6-ethoxy-pyrazin-2-yl)-6-fluoro-phenoxy]-butyric acid

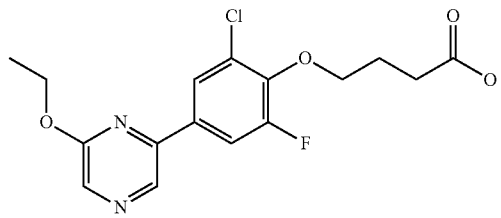 [SMILES: CCOc1cncc(-c2cc(F)c(OCCCC(=O)O)c(Cl)c2)n1]

4-[2-Chloro-6-fluoro-4-(4,4,5,5-tetramethyl-1,3,2-dioxaborolan-2-yl)phenoxy]butanoic acid ethyl ester (0.1 g, 0.26 mmol) obtained in Preparation Example 221 and 2-chloro-6-ethoxy-pyrazine (0.049 g, 0.31 mmol) obtained in Preparation Example 302 were sequentially reacted in the same manner as in Steps A and B of Example 1 to obtain the title compound (0.032 g, 32%).

$^1$H-NMR (CDCl$_3$) δ 8.48 (1H, s), 8.14 (1H, s), 7.81 (1H, s), 7.69 (1H, m), 4.49 (2H, q), 4.23 (2H, t), 2.71 (2H, t), 2.14 (2H, m), 1.45 (3H, t).

Example 438: {(R)-1-[4-(6-cyclopropylmethoxy-pyridin-2-yl)-2,6-difluoro-phenyl]-pyrrolidin-3-yl}-acetic acid

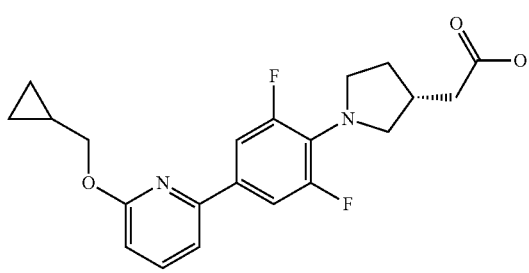 [SMILES: O=C(O)C[C@H]1CCN(c2c(F)cc(-c3cccc(OCC4CC4)n3)cc2F)C1]

{(R)-1-[2,6-difluoro-4-(4,4,5,5-tetramethyl-[1,3,2]dioxaborolan-2-yl)-phenyl]-pyrrolidin-3-yl}-acetic acid methyl ester (0.090 g, 0.23 mmol) obtained in Preparation Example 303 and 2-chloro-6-cyclopropylmethoxy-pyridine (0.084 g, 0.45 mmol) obtained in Preparation Example 43 were sequentially reacted in the same manner as in Steps A and B of Example 1 to obtain the title compound (0.017 g, 19%).

$^1$H-NMR (CDCl$_3$) δ 7.58 (1H, t), 7.48 (2H, m), 7.16 (1H, d), 6.65 (1H, d), 4.23 (2H, d), 3.74 (2H, m), 3.61 (1H, m), 3.36 (1H, m), 2.65 (1H, m), 2.53 (2H, m), 2.16 (1H, m), 1.65 (1H, m), 1.32 (1H, m), 0.63 (2H, m), 0.37 (2H, m).

Example 439: {1-[4-(2,2-difluoro-benzo[1,3]dioxol-4-yl)-2,6-difluoro-phenyl]-piperidin-4-yl}-acetic acid

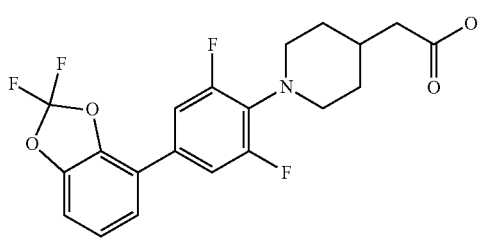 [SMILES: O=C(O)CC1CCN(c2c(F)cc(-c3cccc4c3OC(F)(F)O4)cc2F)CC1]

2-[1-[2,6-Difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 and 4-bromo-2,2-difluoro-benzo[1,3]dioxole (0.081 ml, 0.59 mmol) were sequentially reacted in the same manner as in Steps A and B of Example 1 to obtain the title compound (0.090 g, 44%).

$^1$H-NMR (CDCl$_3$) δ 7.20 (3H, m), 7.12 (1H, t), 7.02 (1H, d), 3.31 (2H, m), 3.13 (2H, m), 2.35 (2H, d), 1.98 (1H, m), 1.81 (2H, m), 1.49 (2H, m).

Example 440: 3-[8-fluoro-6-(2-isopropylsulfanyl-3-pyridyl)thiochroman-2-yl]propanoic acid

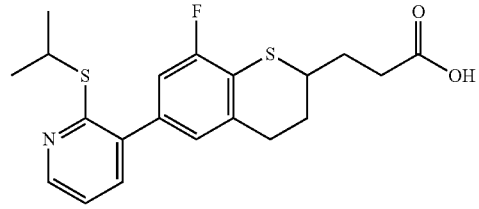 [SMILES: CC(C)Sc1ncccc1-c1cc(F)c2c(c1)CCC(CCC(=O)O)S2]

3-Iodo-2-isopropylsulfanyl-pyridine (0.033 g, 0.12 mmol) obtained in Preparation Example 9 and 3-[8-fluoro-6-(4,4,5,5-tetramethyl-1,3,2-dioxaborolan-2-yl)thiochroman-2-yl]propanoic acid ethyl ester (0.046 g, 0.12 mmol) obtained in Preparation Example 304 were reacted in the same manner as in Steps A and B of Example 1 to obtain the title compound (0.027 g, 57%).

$^1$H-NMR (CDCl$_3$) δ 8.43 (1H, m), 7.34 (1H, m), 7.02 (1H, m), 6.97 (1H, m), 6.92 (1H, m), 4.09 (1H, m), 3.36 (1H, m), 2.94 (2H, m), 2.61 (2H, m), 2.24 (1H, m), 2.07 (1H, m), 1.87 (1H, m), 1.36 (6H, d)

Example 441: 3-[6-[6-(cyclobutoxy)-2-pyridyl]thiochroman-2-yl]propanoic acid

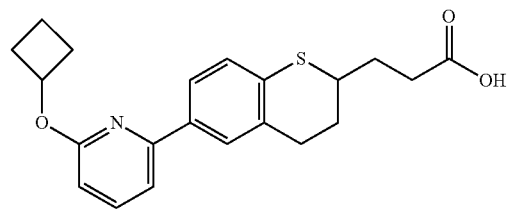 [SMILES: O=C(O)CCC1CCc2cc(-c3cccc(OC4CCC4)n3)ccc2S1]

2-Chloro-6-cyclobutoxy-pyridine (0.062 g, 0.34 mmol) obtained in Preparation Example 29 and 3-[6-(4,4,5,5-tetramethyl-[1,3,2]dioxaborolan-2-yl)-thiochroman-2-yl]-propionic acid ethyl ester (0.13 g, 0.34 mmol) obtained in Preparation Example 5 were reacted in the same manner as in Step A of Example 96 and Step B of Example 1 to obtain the title compound (0.067 g, 53%).

$^1$H-NMR (CDCl$_3$) δ 7.71 (2H, m), 7.58 (1H, t), 7.25 (1H, d), 7.15 (1H, d), 6.59 (1H, d), 5.25 (1H, m), 3.38 (1H, m), 2.94 (2H, m), 2.62 (2H, m), 2.52 (2H, m), 2.24 (3H, m), 2.05 (2H, m), 1.85 (2H, m), 1.72 (1H, m)

Example 442: 3-[2-[2,6-difluoro-4-(7-methoxy-2,2-dimethyl-3H-benzofuran-4-yl)phenyl]cyclopropyl]propanoic acid

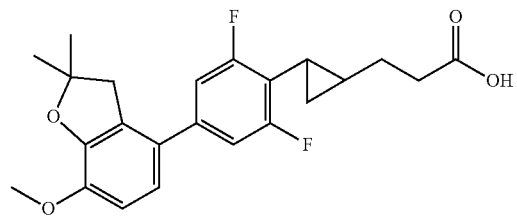 [SMILES: COc1ccc(-c2cc(F)c(C3CC3CCC(=O)O)c(F)c2)c2c1OC(C)(C)C2]

4-Bromo-7-methoxy-2,2-dimethyl-2,3-dihydro-benzofuran (0.067 g, 0.26 mmol) obtained in Preparation Example 211 and 4-{1-[2,6-difluoro-4-(4,4,5,5-tetramethyl-[1,3,2]dioxaborolan-2-yl)-phenyl]-cyclopropyl}-butyric acid ethyl ester (0.099 g, 0.26 mmol) obtained in Preparation Example 155 were reacted in the same manner as in Steps A and B of Example 1 to obtain the title compound (0.07 g, 67%).

$^1$H-NMR (CDCl$_3$) δ 6.85 (4H, m), 3.90 (3H, s), 3.12 (2H, s), 2.59 (2H, t), 1.84 (1H, m), 1.65 (2H, m), 1.52 (6H, s), 1.38 (1H, m), 1.22 (1H, m), 0.82 (1H, m)

Example 443: 3-[2-(2,6-difluoro-4-spiro[3H-benzofuran-2,1'-cyclopentan]-7-yl-phenyl)cyclopropyl]propanoic acid

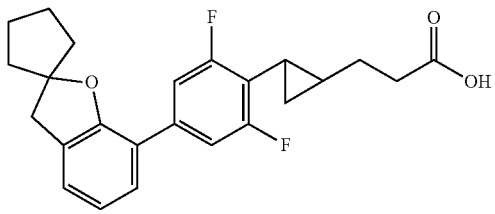 [SMILES: O=C(O)CCC1CC1c1c(F)cc(-c2cccc3c2OC2(CCCC2)C3)cc1F]

7-Bromospiro[3H-benzofuran-2,1'-cyclopentane] (0.067 g, 0.26 mmol) obtained in Preparation Example 212 and 4-{1-[2,6-difluoro-4-(4,4,5,5-tetramethyl-[1,3,2]dioxaborolan-2-yl)-phenyl]-cyclopropyl}-butyric acid ethyl ester (0.099 g, 0.26 mmol) obtained in Preparation Example 155 were reacted in the same manner as in Steps A and B of Example 1 to obtain the title compound (0.056 g, 54%).

$^1$H-NMR (CDCl$_3$) δ 7.22 (3H, m), 7.12 (1H, m), 6.88 (1H, t), 3.20 (2H, s), 2.59 (2H, t), 2.12 (2H, m), 1.93-1.60 (9H, m), 1.37 (1H, m), 1.22 (1H, m), 0.81 (1H, m)

Example 444: 3-[6-[6-(cyclobutoxy)-2-pyridyl]chroman-2-yl]propanoic acid

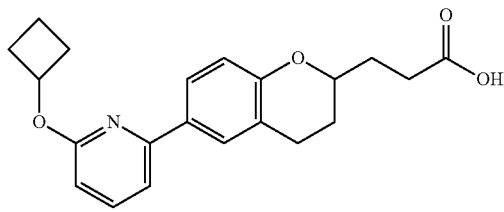

2-Chloro-6-cyclobutoxy-pyridine (0.069 g, 0.37 mmol) obtained in Preparation Example 29 and 3-[6-(4,4,5,5-tetramethyl-[1,3,2]dioxaborolan-2-yl)-chroman-2-yl]-propionic acid ethyl ester (0.133 g, 0.37 mmol) obtained in Preparation Example 4 were reacted in the same manner as in Step A of Example 96 and Step B of Example 1 to obtain the title compound (0.050 g, 38%).

$^1$H-NMR (CDCl$_3$) δ 7.73 (2H, m), 7.55 (1H, t), 7.21 (1H, d), 6.85 (1H, d), 6.65 (1H, d), 5.25 (1H, m), 4.09 (1H, m), 2.87 (3H, m), 2.66 (2H, m), 2.20 (2H, m), 2.03 (4H, m), 1.78 (3H, m)

Example 445: 3-[6-[6-(cyclopropylmethoxy)-2-pyridyl]chroman-2-yl]propanoic acid

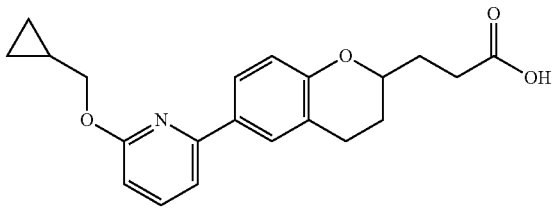 [SMILES: O=C(O)CCC1CCc2cc(-c3cccc(OCC4CC4)n3)ccc2O1]

2-Chloro-6-cyclopropylmethoxy-pyridine (0.090 g, 0.49 mmol) obtained in Preparation Example 43 and 3-[6-(4,4,5,5-tetramethyl-[1,3,2]dioxaborolan-2-yl)-chroman-2-yl]-propionic acid ethyl ester (0.176 g, 0.49 mmol) obtained in Preparation Example 4 were reacted in the same manner as in Step A of Example 96 and Step B of Example 1 to obtain the title compound (0.080 g, 46%).

$^1$H-NMR (CDCl$_3$) δ 7.72 (2H, m), 7.57 (1H, t), 7.21 (1H, d), 6.85 (1H, d), 6.63 (1H, d), 4.24 (2H, d), 4.10 (1H, m), 2.87 (2H, m), 2.65 (2H, m), 2.04 (3H, m), 1.78 (1H, m), 1.33 (1H, m), 0.62 (2H, m), 0.38 (2H, m)

Example 446: 4-[4-(2,3-dimethoxyphenyl)-2,6-difluoro-phenoxy]butanoic acid

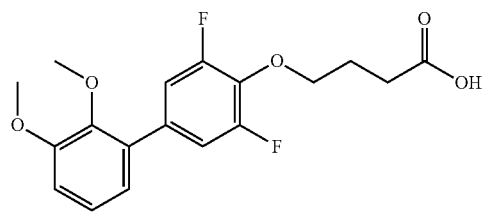 [SMILES: COc1cccc(-c2cc(F)c(OCCCC(=O)O)c(F)c2)c1OC]

1-Iodo-2,3-dimethoxy-benzene (0.054 g, 0.20 mmol) obtained in Step A of Preparation Example 215 and 4-[2,6-difluoro-4-(4,4,5,5-tetramethyl-1,3,2-dioxaborolan-2-yl)phenoxy]butyric acid ethyl ester (0.075 g, 0.20 mmol) obtained in Preparation Example 16 were reacted in the same manner as in Steps A and B of Example 1 to obtain the title compound (0.030 g, 43%).

$^1$H-NMR (CDCl$_3$) δ 7.11 (3H, m), 6.93 (1H, m), 6.88 (1H, m), 4.23 (2H, t), 3.90 (3H, s), 3.63 (3H, s), 2.68 (2H, t), 2.12 (2H, m)

Example 447: 3-[6-[3-(cyclopropylmethoxy)phenyl]chroman-2-yl]propanoic acid

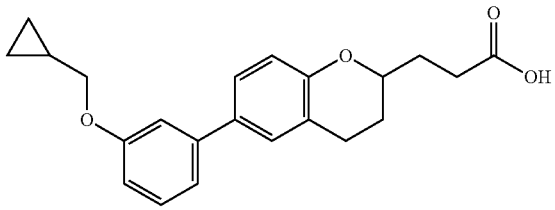 [SMILES: O=C(O)CCC1CCc2cc(-c3cccc(OCC4CC4)c3)ccc2O1]

1-Bromo-3-(cyclopropylmethoxy)benzene (0.098 g, 0.43 mmol) obtained in Preparation Example 280 and 3-[6-(4,4,5,5-tetramethyl-[1,3,2]dioxaborolan-2-yl)-chroman-2-yl]-propionic acid ethyl ester (0.154 g, 0.43 mmol) obtained in Preparation Example 4 were reacted in the same manner as in Steps A and B of Example 1 to obtain the title compound (0.056 g, 37%).

¹H-NMR (CDCl₃) δ 7.30 (3H, m), 7.14 (1H, m), 7.11 (1H, m), 6.88 (2H, m), 4.13 (1H, m), 3.89 (2H, d), 2.96 (1H, m), 2.86 (1H, m), 2.70 (2H, m), 2.08 (3H, m), 1.87 (1H, m), 1.35 (1H, m), 0.70 (2H, m), 0.41 (2H, m)

Example 448: 3-[6-[3-(cyclopentoxy)phenyl]chroman-2-yl]propanoic acid

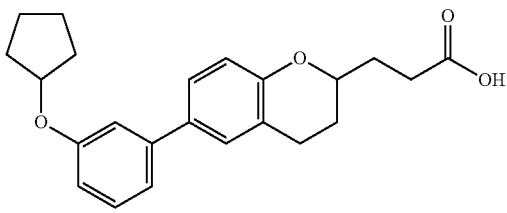 [SMILES: O=C(O)CCC1CCc2cc(-c3cccc(OC4CCCC4)c3)ccc2O1]

1-Bromo-3-(cyclopentoxy)benzene (0.097 g, 0.40 mmol) obtained in Preparation Example 297 and 3-[6-(4,4,5,5-tetramethyl-[1,3,2]dioxaborolan-2-yl)-chroman-2-yl]-propionic acid ethyl ester (0.144 g, 0.40 mmol) obtained in Preparation Example 4 were reacted in the same manner as in Steps A and B of Example 1 to obtain the title compound (0.064 g, 44%).

¹H-NMR (CDCl₃) δ 7.28 (3H, m), 7.07 (1H, d), 7.03 (1H, m), 6.84 (1H, d), 6.80 (1H, m), 4.81 (1H, m), 4.08 (1H, m), 2.91 (1H, m), 2.81 (1H, m), 2.64 (2H, m), 2.03 (3H, m), 1.86 (7H, m), 1.62 (2H, m)

Example 449: 4-(2,6-difluoro-N-methyl-4-spiro[1,3-benzodioxol-2,1'-cyclopentan]-4-yl-anilino)butanoic acid

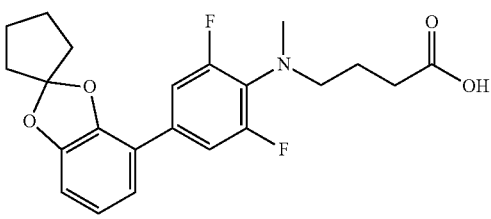 [SMILES: CN(CCCC(=O)O)c1c(F)cc(-c2cccc3c2OC2(CCCC2)O3)cc1F]

4-Iodospiro[1,3-benzodioxol-2,1'-cyclopentane] (0.089 g, 0.29 mmol) obtained in Preparation Example 215 and 4-{[2,6-difluoro-4-(4,4,5,5-tetramethyl-[1,3,2]dioxaborolan-2-yl)-phenyl]-methyl-amino}-butyric acid methyl ester (0.111 g, 0.29 mmol) obtained in Preparation Example 183 were reacted in the same manner as in Steps A and B of Example 1 to obtain the title compound (0.031 g, 26%).

¹H-NMR (CDCl₃) δ 7.27 (2H, m), 6.92 (1H, d), 6.84 (1H, t), 6.72 (1H, d), 3.18 (2H, t), 2.87 (3H, s), 2.48 (2H, t), 2.13 (4H, m), 1.87 (6H, m)

Example 450: 5-(2,6-difluoro-4-spiro[1,3-benzodioxol-2,1'-cyclopentan]-4-yl-phenyl)hexanoic acid

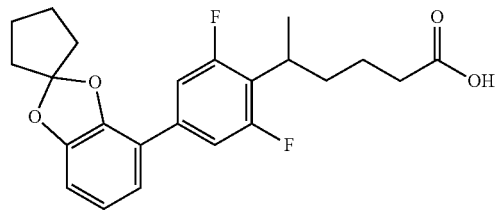 [SMILES: CC(CCCC(=O)O)c1c(F)cc(-c2cccc3c2OC2(CCCC2)O3)cc1F]

4-Iodospiro[1,3-benzodioxol-2,1'-cyclopentane] (0.107 g, 0.35 mmol) obtained in Preparation Example 215 and 5-[2,6-difluoro-4-(4,4,5,5-tetramethyl-[1,3,2]dioxaborolan-2-yl)phenyl]hexanoic acid ethyl ester (0.107 g, 0.35 mmol) obtained in Preparation Example 32 were reacted in the same manner as in Steps A and B of Example 1 to obtain the title compound (0.065 g, 46%).

¹H-NMR (CDCl₃) δ 7.23 (2H, m), 6.96 (1H, d), 6.85 (1H, t), 6.73 (1H, d), 3.23 (1H, m), 2.36 (2H, t), 2.15 (4H, m), 1.86 (5H, m), 1.72 (1H, m), 1.64 (1H, m), 1.56 (1H, m), 1.35 (3H, d)

Example 451: 3-[6-(6-tert-butylsulfanyl-2-pyridyl)chroman-2-yl]propanoic acid

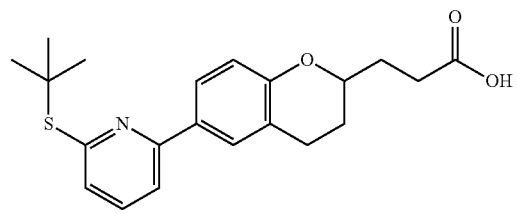 [SMILES: CC(C)(C)Sc1cccc(-c2ccc3c(c2)CCC(CCC(=O)O)O3)n1]

2-Tert-butylsulfanyl-6-chloro-pyridine (0.092 g, 0.45 mmol) and 3-[6-(4,4,5,5-tetramethyl-[1,3,2]dioxaborolan-2-yl)-chroman-2-yl]-propionic acid ethyl ester (0.162 g, 0.45 mmol) obtained in Preparation Example 4 were reacted in the same manner as in Step A of Example 96 and Step B of Example 1 to obtain the title compound (0.045 g, 27%).

¹H-NMR (CDCl₃) δ 7.75 (2H, m), 7.53 (1H, m), 7.43 (1H, m), 7.17 (1H, m), 6.86 (1H, m), 4.11 (1H, m), 2.90 (2H, m), 2.66 (2H, m), 2.03 (3H, m), 1.81 (1H, m), 1.60 (9H, s)

Example 452: 3-[6-(6-isopropoxy-2-pyridyl)chroman-2-yl]propanoic acid

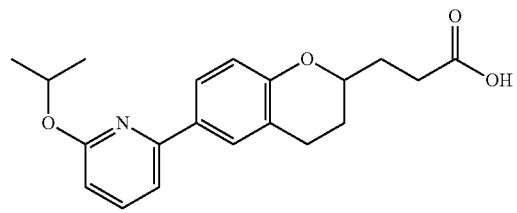 [SMILES: CC(C)Oc1cccc(-c2ccc3c(c2)CCC(CCC(=O)O)O3)n1]

2-Chloro-6-isopropoxy-pyridine (0.084 g, 0.48 mmol) obtained in Preparation Example 46 and 3-[6-(4,4,5,5-tetramethyl-[1,3,2]dioxaborolan-2-yl)-chroman-2-yl]-propionic acid ethyl ester (0.172 g, 0.48 mmol) obtained in Preparation Example 4 were reacted in the same manner as in Step A of Example 96 and Step B of Example 1 to obtain the title compound (0.065 g, 39%).

$^1$H-NMR (CDCl$_3$) δ 7.73 (2H, m), 7.60 (1H, t), 7.20 (1H, d), 6.85 (1H, d), 6.58 (1H, d), 5.42 (1H, m), 4.09 (1H, m), 2.88 (2H, m), 2.65 (2H, m), 2.04 (3H, m), 1.80 (1H, m), 1.41 (6H, d)

Example 453: 2-[1-(2,6-difluoro-4-spiro[1,3-benzodioxol-2,1'-cyclopentan]-4-yl-phenyl)-4-piperidyl]acetic acid

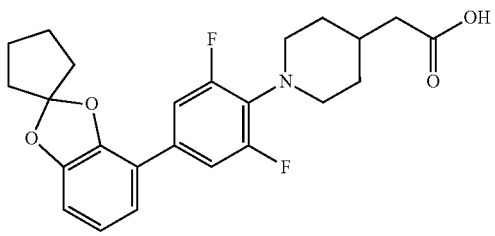 [SMILES: O=C(O)CC1CCN(c2c(F)cc(-c3cccc4c3OC3(CCCC3)O4)cc2F)CC1]

4-Iodospiro[1,3-benzodioxol-2,1'-cyclopentane] (0.80 g, 0.26 mmol) obtained in Preparation Example 215 and 2-[1-[2,6-difluoro-4-(4,4,5,5-tetramethyl-1,3,2-dioxaborolan-2-yl)phenyl]-4-piperidyl]acetic acid ethyl ester (0.106 g, 0.26 mmol) obtained in Preparation Example 220 were reacted in the same manner as in Steps A and B of Example 1 to obtain the title compound (0.057 g, 51%).

$^1$H-NMR (CDCl$_3$) δ 7.26 (2H, m), 6.93 (1H, d), 6.84 (1H, t), 6.72 (1H, d), 3.35 (2H, m), 3.21 (2H, m), 2.38 (2H, d), 2.12 (4H, m), 1.99 (1H, m), 1.86 (6H, m), 1.62 (2H, m)

Example 454: 4-[4-(2,3-dipropoxyphenyl)-2,6-difluoro-phenoxy]butanoic acid

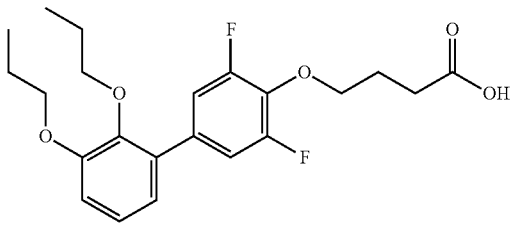 [SMILES: CCCOc1cccc(-c2cc(F)c(OCCCC(=O)O)c(F)c2)c1OCCC]

1-Iodo-2,3-dipropoxy-benzene (0.086 g, 0.26 mmol) obtained in Preparation Example 305 and 4-[2,6-difluoro-4-(4,4,5,5-tetramethyl-1,3,2-dioxaborolan-2-yl)phenoxy]butyric acid ethyl ester (0.096 g, 0.26 mmol) obtained in Preparation Example 16 were reacted in the same manner as in Steps A and B of Example 1 to obtain the title compound (0.041 g, 39%).

$^1$H-NMR (CDCl$_3$) δ 7.14 (2H, m), 7.06 (1H, t), 6.91 (1H, m), 6.87 (1H, m), 4.22 (2H, t), 3.98 (2H, t), 3.70 (2H, t), 2.68 (2H, t), 2.11 (2H, m), 1.88 (2H, m), 1.57 (2H, m), 1.07 (3H, t), 0.84 (3H, t)

Example 455: 4-[4-[6-(cyclobutoxy)-5-methoxy-2-pyridyl]-2,6-difluoro-phenoxy]butanoic acid

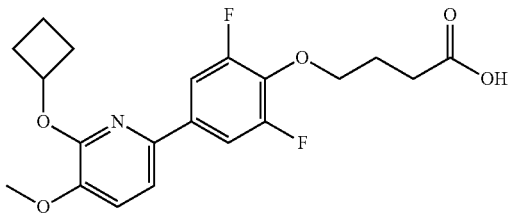 [SMILES: COc1ccc(-c2cc(F)c(OCCCC(=O)O)c(F)c2)nc1OC1CCC1]

2-(Cyclobutoxy)-6-iodo-3-methoxy-pyridine (0.095 g, 0.31 mmol) obtained in Preparation Example 307 and 4-[2,6-difluoro-4-(4,4,5,5-tetramethyl-1,3,2-dioxaborolan-2-yl)phenoxy]butyric acid ethyl ester (0.115 g, 0.31 mmol) obtained in Preparation Example 16 were reacted in the same manner as in Steps A and B of Example 1 to obtain the title compound (0.046 g, 38%).

$^1$H-NMR (CDCl$_3$) δ 7.48 (2H, m), 7.18 (1H, d), 7.06 (1H, d), 5.32 (1H, m), 4.22 (2H, t), 3.89 (3H, s), 2.67 (2H, t), 2.55 (2H, m), 2.27 (2H, m), 2.11 (2H, m), 1.88 (1H, m), 1.77 (1H, m)

Example 456: 4-[4-[6-(cyclobutoxy)-5-methoxy-2-pyridyl]-2,6-difluoro-N-methyl-anilino]butanoic acid

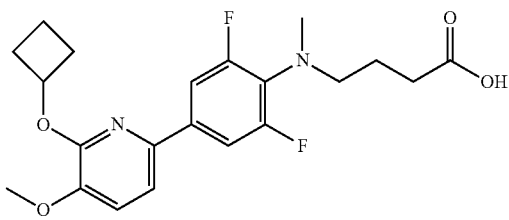 [SMILES: COc1ccc(-c2cc(F)c(N(C)CCCC(=O)O)c(F)c2)nc1OC1CCC1]

2-(Cyclobutoxy)-6-iodo-3-methoxy-pyridine (0.076 g, 0.25 mmol) obtained in Preparation Example 307 and 4-{[2,6-difluoro-4-(4,4,5,5-tetramethyl-[1,3,2]dioxaborolan-2-yl)-phenyl]-methyl-amino}-butyric acid methyl ester (0.096 g, 0.25 mmol) obtained in Preparation Example 183 were reacted in the same manner as in Steps A and B of Example 1 to obtain the title compound (0.059 g, 58%).

$^1$H-NMR (CDCl$_3$) δ 7.43 (2H, m), 7.19 (1H, m), 7.07 (1H, m), 5.33 (1H, m), 3.90 (3H, s), 3.17 (2H, t), 2.88 (3H, s), 2.57 (2H, m), 2.46 (2H, t), 2.27 (2H, m), 1.86 (3H, m), 1.76 (1H, m)

Example 457: 2-[1-[4-[6-(cyclobutoxy)-5-methoxy-2-pyridyl]-2,6-difluoro-phenyl]-4-piperidyl]acetic acid

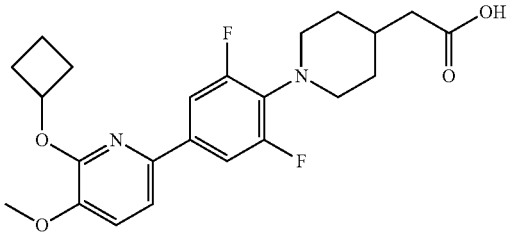 [SMILES: COc1ccc(-c2cc(F)c(N3CCC(CC(=O)O)CC3)c(F)c2)nc1OC1CCC1]

2-(Cyclobutoxy)-6-iodo-3-methoxy-pyridine (0.088 g, 0.29 mmol) obtained in Preparation Example 307 and 2-[1-[2,6-difluoro-4-(4,4,5,5-tetramethyl-1,3,2-dioxaborolan-2-yl)phenyl]-4-piperidyl]acetic acid ethyl ester (0.118 g, 0.29 mmol) obtained in Preparation Example 220 were reacted in the same manner as in Steps A and B of Example 1 to obtain the title compound (0.076 g, 60%).

$^1$H-NMR (CDCl$_3$) δ 7.41 (2H, m), 7.17 (1H, d), 7.06 (1H, d), 5.33 (1H, m), 3.89 (3H, s), 3.29 (2H, m), 3.14 (2H, m), 2.57 (2H, m), 2.33 (2H, d), 2.27 (2H, m), 1.97 (1H, m), 1.81 (4H, m), 1.50 (2H, m)

Example 458: 2-[1-[4-(2,3-dipropoxyphenyl)-2,6-difluoro-phenyl]-4-piperidyl]acetic acid

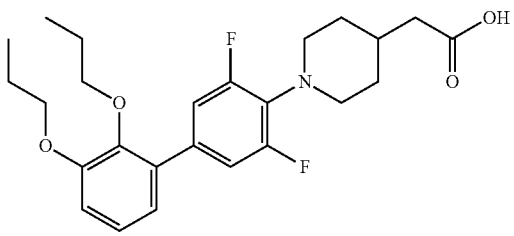 [SMILES: CCCOc1cccc(-c2cc(F)c(N3CCC(CC(=O)O)CC3)c(F)c2)c1OCCC]

1-Iodo-2,3-dipropoxy-benzene (0.091 g, 0.28 mmol) obtained in Preparation Example 305 and 2-[1-[2,6-difluoro-4-(4,4,5,5-tetramethyl-1,3,2-dioxaborolan-2-yl)phenyl]-4-piperidyl]acetic acid ethyl ester (0.115 g, 0.28 mmol) obtained in Preparation Example 220 were reacted in the same manner as in Steps A and B of Example 1 to obtain the title compound (0.069 g, 55%).

$^1$H-NMR (CDCl$_3$) δ 7.08 (2H, m), 7.05 (1H, t), 6.88 (2H, m), 3.98 (2H, t), 3.71 (2H, t), 3.30 (2H, m), 3.15 (2H, m), 2.37 (2H, d), 1.98 (1H, m), 1.83 (4H, m), 1.58 (2H, m), 1.49 (2H, m), 1.07 (3H, t), 0.86 (3H, t)

Example 459: 4-[4-[6-(cyclopropylmethoxy)-5-methoxy-2-pyridyl]-2,6-difluoro-phenoxy]butanoic acid

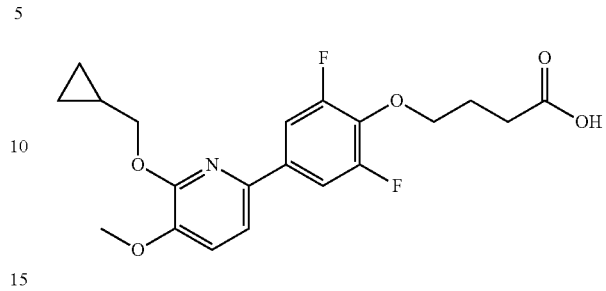

2-(Cyclopropylmethoxy)-6-iodo-3-methoxy-pyridine (0.085 g, 0.28 mmol) obtained in Preparation Example 306 and 4-[2,6-difluoro-4-(4,4,5,5-tetramethyl-1,3,2-dioxaborolan-2-yl)phenoxy]butyric acid ethyl ester (0.104 g, 0.28 mmol) obtained in Preparation Example 16 were reacted in the same manner as in Steps A and B of Example 1 to obtain the title compound (0.07 g, 57%).

$^1$H-NMR (CDCl$_3$) δ 7.49 (2H, m), 7.19 (1H, d), 7.08 (1H, d), 4.32 (2H, d), 4.22 (2H, t), 3.91 (3H, s), 2.67 (2H, t), 2.10 (2H, m), 1.43 (1H, m), 0.64 (2H, m), 0.42 (2H, m)

Example 460: 4-[4-(2,3-dipropoxyphenyl)-2,6-difluoro-N-methyl-anilino]butanoic acid

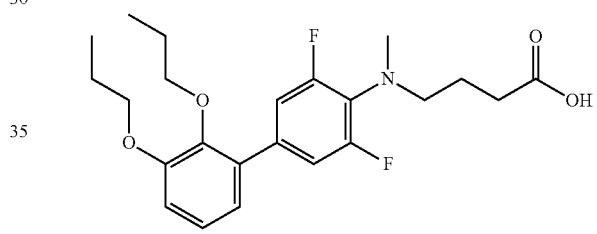

1-Iodo-2,3-dipropoxy-benzene (0.10 g, 0.31 mmol) obtained in Preparation Example 305 and 4-{[2,6-difluoro-4-(4,4,5,5-tetramethyl-[1,3,2]dioxaborolan-2-yl)-phenyl]-methyl-amino}-butyric acid methyl ester (0.118 g, 0.31 mmol) obtained in Preparation Example 183 were reacted in the same manner as in Steps A and B of Example 1 to obtain the title compound (0.045 g, 34%).

$^1$H-NMR (CDCl$_3$) δ 7.10 (2H, m), 7.06 (1H, t), 6.88 (2H, m), 3.98 (2H, t), 3.72 (2H, t), 3.18 (2H, m), 2.89 (3H, s), 2.48 (2H, t), 1.87 (4H, m), 1.58 (2H, m), 1.08 (3H, t), 0.84 (3H, t)

Example 461: 4-[4-[6-(cyclopropylmethoxy)-5-methoxy-2-pyridyl]-2,6-difluoro-N-methyl-anilino]butanoic acid

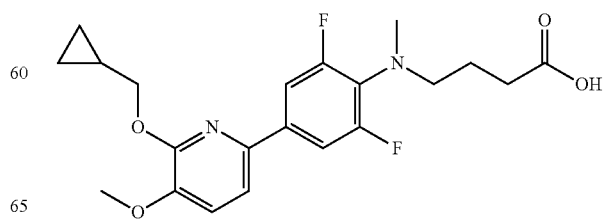

2-(Cyclopropylmethoxy)-6-iodo-3-methoxy-pyridine (0.09 g, 0.29 mmol) obtained in Preparation Example 306 and 4-{[2,6-difluoro-4-(4,4,5,5-tetramethyl-[1,3,2]dioxaborolan-2-yl)-phenyl]-methyl-amino}-butyric acid methyl ester (0.111 g, 0.29 mmol) obtained in Preparation Example 183 were reacted in the same manner as in Steps A and B of Example 1 to obtain the title compound (0.076 g, 64%).

¹H-NMR (CDCl₃) δ 7.45 (2H, m), 7.20 (1H, d), 7.08 (1H, d), 4.32 (2H, d), 3.91 (3H, s), 3.19 (2H, t), 2.88 (3H, s), 2.48 (2H, t), 1.88 (2H, m), 1.45 (1H, m), 0.54 (2H, m), 0.42 (2H, m)

Example 462: 2-[1-[4-[6-(cyclopropylmethoxy)-5-methoxy-2-pyridyl]-2,6-difluoro-phenyl]-4-piperidyl]acetic acid

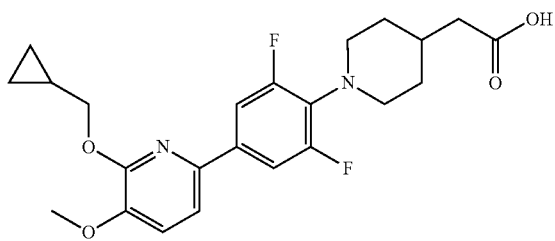 [SMILES: COc1ccc(-c2cc(F)c(N3CCC(CC(=O)O)CC3)c(F)c2)nc1OCC1CC1]

2-(Cyclopropylmethoxy)-6-iodo-3-methoxy-pyridine (0.097 g, 0.31 mmol) obtained in Preparation Example 306 and 2-[1-[2,6-difluoro-4-(4,4,5,5-tetramethyl-1,3,2-dioxaborolan-2-yl)phenyl]-4-piperidyl]acetic acid ethyl ester (0.126 g, 0.31 mmol) obtained in Preparation Example 220 were reacted in the same manner as in Steps A and B of Example 1 to obtain the title compound (0.064 g, 47%).

¹H-NMR (CDCl₃) δ 7.41 (2H, m), 7.17 (1H, d), 7.07 (1H, d), 4.32 (2H, d), 3.90 (3H, s), 3.29 (2H, m), 3.14 (2H, m), 2.36 (2H, d), 1.97 (1H, m), 1.83 (2H, m), 1.47 (3H, m), 0.63 (2H, m), 0.42 (2H, m)

Example 463: 4-[4-(6-chloroindol-1-yl)-2,6-difluoro-phenoxy]butanoic acid

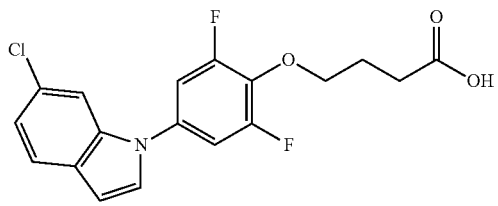 [SMILES: O=C(O)CCCOc1c(F)cc(-n2ccc3ccc(Cl)cc32)cc1F]

Step A: 4-[4-(6-chloroindol-1-yl)-2,6-difluoro-phenoxy]butanoic acid ethyl ester 6-Chloro-1H-indole (0.042 g, 0.28 mmol), 4-(4-bromo-2,6-difluoro-phenoxy)butanoic acid ethyl ester (0.18 g, 0.56 mmol) obtained in Preparation Example 339, copper iodide (0.006 g, 0.028 mmol), potassium phosphate (0.12 g, 0.56 mmol), cyclohexane-1,2-diamine (0.007 mL, 0.056 mmol) and dodecane (0.007 mL, 0.028 mmol) were added to a seal tube. 1,4-Dioxane (1 mL) were added thereto, and the mixture was stirred at 110° C. for 18 hours. After termination of the reaction, the reaction solution was cooled and filtered through Celite. The organic layer was concentrated under reduced pressure and purified by column chromatography to obtain the title compound (0.083 g, 75%).

¹H-NMR (CDCl₃) δ 7.57 (1H, d), 7.50 (1H, d), 7.22 (1H, d), 7.15 (1H, m), 7.05 (2H, m), 6.65 (1H, d), 4.26 (2H, t) 4.18 (2H, q), 2.60 (2H, t), 2.15 (2H, m), 1.28 (3H, t)

Step B: 4-[4-(6-chloroindol-1-yl)-2,6-difluoro-phenoxy]butanoic acid

4-[4-(6-Chloroindol-1-yl)-2,6-difluoro-phenoxy]butanoic acid ethyl ester (0.083 g, 0.21 mmol) obtained in Step A was reacted in the same manner as in Step B of Example 1 to obtain the title compound (0.067 g, 65%).

¹H-NMR (CDCl₃) δ 7.57 (1H, d), 7.50 (1H, d), 7.22 (1H, d), 7.15 (1H, m), 7.05 (2H, m), 6.65 (1H, d), 4.26 (2H, t), 2.70 (2H, t), 2.15 (2H, m)

Example 464: 5-[4-[6-(cyclobutoxy)-5-methoxy-2-pyridyl]phenyl]-5,5-difluoro-pentanoic acid

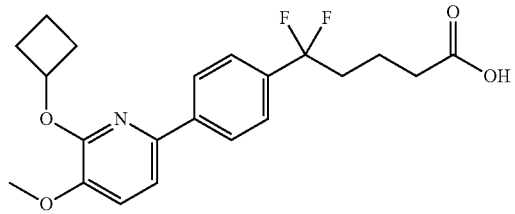 [SMILES: COc1ccc(-c2ccc(C(F)(F)CCCC(=O)O)cc2)nc1OC1CCC1]

2-(Cyclobutoxy)-6-iodo-3-methoxy-pyridine (0.088 g, 0.29 mmol) obtained in Preparation Example 307 and 5,5-difluoro-5-[4-(4,4,5,5-tetramethyl-[1,3,2]dioxaborolan-2-yl)-phenyl]-pentanoic acid methyl ester (0.101 g, 0.29 mmol) obtained in Preparation Example 169 were reacted in the same manner as in Steps A and B of Example 1 to obtain the title compound (0.023 g, 20%).

¹H-NMR (CDCl₃) δ 8.00 (2H, d), 7.52 (2H, d), 7.32 (1H, d), 7.10 (1H, d), 5.35 (1H, m), 3.91 (3H, s), 2.57 (2H, m), 2.42 (2H, t), 2.26 (4H, m), 1.80 (4H, m)

Example 465: 4-[2,6-difluoro-4-(5-fluoroindol-1-yl)phenoxy]butanoic acid

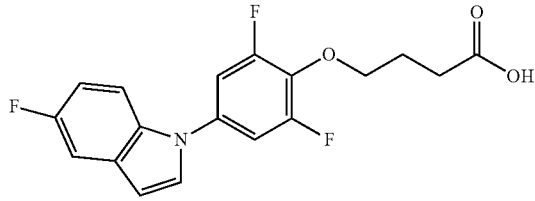 [SMILES: O=C(O)CCCOc1c(F)cc(-n2ccc3cc(F)ccc32)cc1F]

5-Fluoro-1H-indole (0.042 g, 0.31 mmol) and 4-(4-bromo-2,6-difluoro-phenoxy)butanoic acid ethyl ester (0.20 g, 0.62 mmol) obtained in Preparation Example 339 were reacted in the same manner as in Step A of Example 463 and Step B of Example 1 to obtain the title compound (0.05 g, 46%).

¹H-NMR (CDCl₃) δ 7.44 (1H, m), 7.30 (1H, m), 7.27 (1H, d), 7.05 (2H, m), 6.99 (1H, m), 6.63 (1H, d), 4.25 (2H, t), 2.69 (2H, t), 2.14 (2H, m)

Example 466: 4-[4-[3-(cyclopropylmethylamino)phenyl]-2,6-difluoro-N-methyl-anilino]butanoic acid

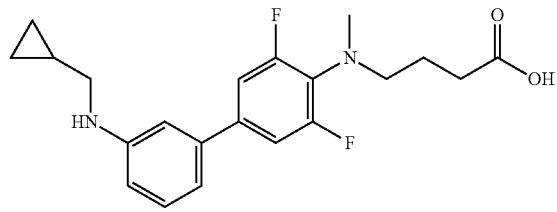 [SMILES: CN(CCCC(=O)O)c1c(F)cc(-c2cccc(NCC3CC3)c2)cc1F]

3-Bromo-N-(cyclopropylmethyl)aniline (0.087 g, 0.38 mmol) and 4-{[2,6-difluoro-4-(4,4,5,5-tetramethyl-[1,3,2]dioxaborolan-2-yl)-phenyl]-methyl-amino}-butyric acid methyl ester (0.146 g, 0.38 mmol) obtained in Preparation Example 183 were reacted in the same manner as in Steps A and B of Example 1 to obtain the title compound (0.057 g, 40%).

$^1$H-NMR (CDCl$_3$) δ 7.26 (1H, t), 7.03 (2H, m), 6.96 (2H, m), 6.83 (1H, m), 3.16 (2H, t), 3.05 (2H, d), 2.86 (3H, s), 2.45 (2H, t), 1.85 (2H, m), 1.12 (1H, m), 0.57 (2H, m), 0.28 (2H, m)

Example 467: 4-[2,6-difluoro-N-methyl-4-(6-pyrrolidin-1-yl-2-pyridyl)anilino]butanoic acid

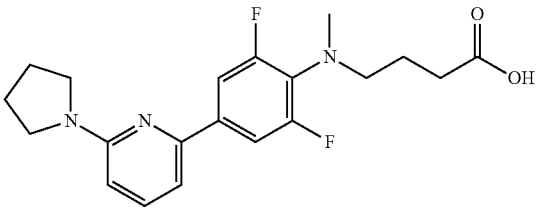 [SMILES: CN(CCCC(=O)O)c1c(F)cc(-c2cccc(N3CCCC3)n2)cc1F]

2-Chloro-6-pyrrolidin-1-yl-pyridine (0.099 g, 0.54 mmol) and 4-{[2,6-difluoro-4-(4,4,5,5-tetramethyl-[1,3,2]dioxaborolan-2-yl)-phenyl]-methyl-amino}-butyric acid methyl ester (0.206 g, 0.54 mmol) obtained in Preparation Example 183 were reacted in the same manner as in Steps A and B of Example 1 to obtain the title compound (0.108 g, 53%).

$^1$H-NMR (CDCl$_3$) δ 7.53 (2H, m), 7.46 (1H, t), 6.88 (1H, d), 6.31 (1H, d), 3.52 (4H, m), 3.16 (2H, t), 2.88 (3H, s), 2.45 (2H, t), 2.02 (4H, m), 1.85 (2H, m)

Example 468: 4-[2,6-difluoro-4-(5-methoxyindol-1-yl)phenoxy]butanoic acid

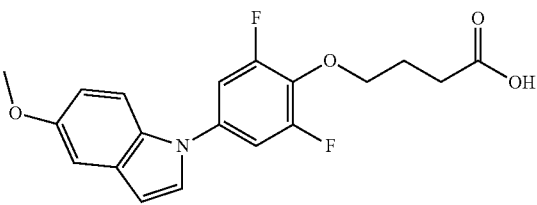 [SMILES: COc1ccc2c(ccn2-c2cc(F)c(OCCCC(=O)O)c(F)c2)c1]

5-Methoxy-1H-indole (0.046 g, 0.31 mmol) and 4-(4-bromo-2,6-difluoro-phenoxy)butanoic acid ethyl ester (0.20 g, 0.62 mmol) obtained in Preparation Example 339 were reacted in the same manner as in Step A of Example 463 and Step B of Example 1 to obtain the title compound (0.019 g, 17%).

$^1$H-NMR (CDCl$_3$) δ 7.44 (1H, d), 7.21 (1H, d), 7.11 (1H, d), 7.06 (2H, m), 6.90 (1H, m), 6.60 (1H, d), 4.24 (2H, t), 3.87 (3H, s), 2.69 (2H, t), 2.13 (2H, m)

Example 469: 4-[4-(5-cyanoindol-1-yl)-2,6-difluoro-phenoxy]butanoic acid

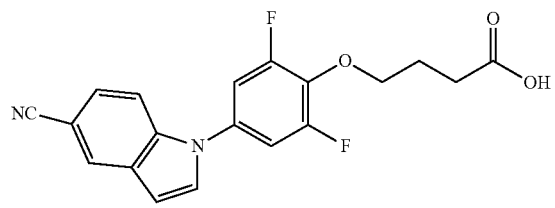 [SMILES: N#Cc1ccc2c(ccn2-c2cc(F)c(OCCCC(=O)O)c(F)c2)c1]

1H-Indol-5-carbonitrile (0.044 g, 0.31 mmol) and 4-(4-bromo-2,6-difluoro-phenoxy)butanoic acid ethyl ester (0.20 g, 0.62 mmol) obtained in Preparation Example 339 were reacted in the same manner as in Step A of Example 463 and Step B of Example 1 to obtain the title compound (0.034 g, 31%).

$^1$H-NMR (CDCl$_3$) δ 8.02 (1H, m), 7.55 (1H, d), 7.48 (1H, m), 7.36 (1H, m), 7.06 (2H, m), 6.76 (1H, m), 4.28 (2H, t), 2.69 (2H, t), 2.14 (2H, m)

Example 470: 4-[4-[3-(cyclopropylmethoxymethyl)-2-furyl]-2,6-difluoro-N-methyl-anilino]butanoic acid

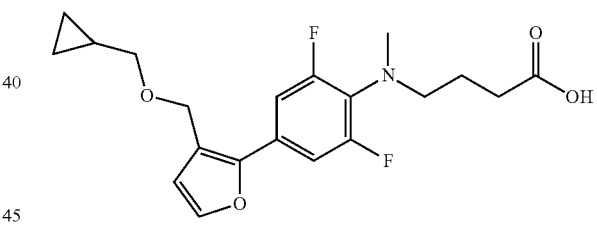

Step A: 4-[2,6-difluoro-4-(3-formyl-2-furyl)-N-methyl-anilino]butanoic acid methyl ester (3-Formyl-2-furyl)boronic acid (0.05 g, 0.36 mmol) and 4-(4-bromo-2,6-difluoro-N-methyl-anilino)butanoic acid methyl ester (0.11 g, 0.32 mmol) were reacted in the same manner as in Step A of Example 1 to obtain the title compound (0.027 g, 22%).

$^1$H-NMR (CDCl$_3$) δ 10.10 (1H, s), 7.45 (1H, d), 7.35 (2H, m), 6.89 (1H, d), 3.66 (3H, s), 3.22 (2H, t), 2.94 (3H, t), 2.39 (2H, t), 1.89 (2H, m)

Step B: 4-[2,6-difluoro-4-[3-(hydroxymethyl)-2-furyl]-N-methyl-anilino]butanoic acid methyl ester 4-[2,6-Difluoro-4-(3-formyl-2-furyl)-N-methyl-anilino]butanoic acid methyl ester (0.027 g, 0.08 mmol) obtained in Step A was dissolved in 3 mL of MeOH. NaBH$_4$ (0.003 g, 0.08 mmol) were added thereto at 0° C., and the mixture was stirred at room temperature for 2 hours. After addition of water, the reaction solution was extracted with EtOAc. The organic layer was dried with MgSO$_4$ and purified by column chromatography to obtain the title compound (0.027 g, 99%).

$^1$H-NMR (CDCl$_3$) δ 7.39 (1H, d), 7.17 (2H, m), 6.52 (1H, d), 4.69 (2H, s), 3.65 (3H, s), 3.13 (2H, t), 2.87 (3H, s), 2.38 (2H, t), 1.84 (2H, m), 1.70 (1H, brs)

Step C: 4-[4-[3-(cyclopropylmethoxyoxethyl)-2-furyl]-2,6-difluoro-N-methyl-anilino]butanoic acid cyclopropylmethyl ester 4-[2,6-Difluoro-4-[3-(hydroxymethyl)-2-furyl]-N-methyl-anilino]butanoic acid methyl ester (0.027 g, 0.08 mmol) obtained in Step B was dissolved in 3 mL of DMF and cooled to 0° C. NaH (60%)(0.004 g, 0.09 mmol) and 18-crown-6 (0.024 g, 0.09 mmol) were added thereto, and the mixture was stirred for 0.5 hour. Bromomethyl-cyclopropane (0.014 g, 0.10 mmol) was added thereto, and the mixture was stirred at room temperature for 18 hours. The reaction solution was extracted with EtOAc, dried with MgSO$_4$ and purified by column chromatography to obtain the title compound (0.005 g, 14%).

$^1$H-NMR (CDCl$_3$) δ 7.40 (1H, d), 7.20 (2H, m), 6.50 (1H, d), 4.47 (2H, s), 3.89 (2H, d), 3.38 (2H, d), 3.15 (2H, t), 2.89 (3H, s), 2.40 (2H, t), 1.86 (2H, m), 1.12 (2H, m), 0.56 (4H, m), 0.25 (4H, m)

Step D: 4-[4-[3-(cyclopropylmethoxymethyl)-2-furyl]-2,6-difluoro-N-methyl-anilino]butanoic acid 4-[4-[3-(Cyclopropylmethoxymethyl)-2-furyl]-2,6-difluoro-N-methyl-anilino]butanoic acid cyclopropylmethyl ester (0.005 g, 0.01 mmol) obtained in Step C was reacted in the same manner as in Step B of Example 1 to obtain the title compound (0.003 g, 79%).

$^1$H-NMR (CDCl$_3$) δ 7.35 (1H, d), 7.22 (2H, m), 6.50 (1H, d), 4.47 (2H, s), 3.38 (2H, d), 3.17 (2H, t), 2.87 (3H, s), 2.46 (2H, t), 1.86 (2H, m), 1.14 (1H, m), 0.57 (2H, m), 0.25 (2H, m)

Example 471: 4-[2,6-difluoro-4-(4-fluoroindol-1-yl)phenoxy]butanoic acid

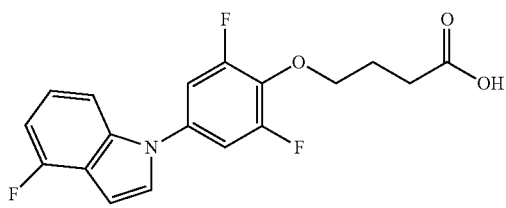 [SMILES: O=C(O)CCCOc1c(F)cc(-n2ccc3c(F)cccc32)cc1F]

4-Fluoro-1H-indole (0.05 g, 0.37 mmol) and 4-(4-bromo-2,6-difluoro-phenoxy)butanoic acid ethyl ester (0.18 g, 0.55 mmol) obtained in Preparation Example 339 were reacted in the same manner as in Step A of Example 463 and Step B of Example 1 to obtain the title compound (0.056 g, 43%).

$^1$H-NMR (CDCl$_3$) δ 7.30 (1H, m), 7.21 (1H, m), 7.17 (1H, m), 7.01 (2H, m), 6.86 (1H, m), 6.77 (1H, m), 4.26 (2H, t), 2.69 (2H, t), 2.15 (2H, m)

Example 472: 4-[4-(7-chloroindol-1-yl)-2,6-difluoro-phenoxy]butanoic acid

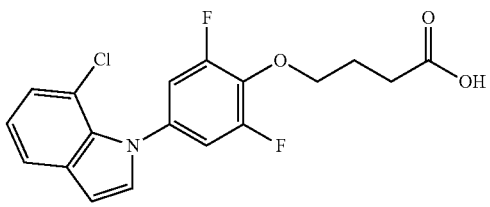 [SMILES: O=C(O)CCCOc1c(F)cc(-n2ccc3cccc(Cl)c32)cc1F]

7-Chloro-1H-indole (0.05 g, 0.37 mmol) and 4-(4-bromo-2,6-difluoro-phenoxy)butanoic acid ethyl ester (0.18 g, 0.55 mmol) obtained in Preparation Example 339 were reacted in the same manner as in Step A of Example 463 and Step B of Example 1 to obtain the title compound (0.049 g, 36%).

$^1$H-NMR (CDCl$_3$) δ7.57 (1H, m), 7.19 (1H, m), 7.10 (2H, m), 6.98 (2H, m), 6.65 (1H, d), 4.28 (2H, t), 2.69 (2H, t), 2.15 (2H, m)

Example 473: 4-[4-[5-(cyclopropylmethoxymethyl)-2-furyl]-2,6-difluoro-N-methyl-anilino]butanoic acid

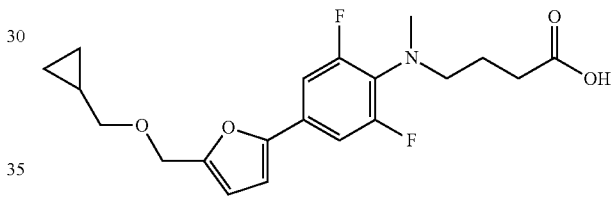

Step A: 4-[2,6-difluoro-4-(5-formyl-2-furyl)-N-methyl-anilino]butanoic acid methyl ester (5-Formyl-2-furyl)boronic acid (0.05 g, 0.36 mmol) and 4-(4-bromo-2,6-difluoro-N-methyl-anilino)butanoic acid methyl ester (0.11 g, 0.32 mmol) were reacted in the same manner as in Step A of Example 96 to obtain the title compound (0.025 g, 22%).

Step B: 4-[2,6-difluoro-4-[5-(hydroxymethyl)-2-furyl]-N-methyl-anilino]butanoic acid methyl ester 4-[2,6-Difluoro-4-(5-formyl-2-furyl)-N-methyl-anilino]butanoic acid methyl ester (0.025 g, 0.074 mmol) obtained in Step A was dissolved in 3 mL of MeOH. NaBH$_4$ (0.003 g, 0.074 mmol) was added thereto at 0° C., and the mixture was stirred at room temperature for 30 minutes. After addition of acetic acid, the reaction solution was extracted with EtOAc. The organic layer was dried with MgSO$_4$ and purified by column chromatography to obtain the title compound (0.018 g, 72%).

Step C: 4-[4-[5-(cyclopropylmethoxymethyl)-2-furyl]-2,6-difluoro-N-methyl-anilino]butanoic acid methyl ester 4-[2,6-Difluoro-4-[5-(hydroxymethyl)-2-furyl]-N-methyl-anilino]butanoic acid methyl ester (0.018 g, 0.053 mmol) obtained in Step B was dissolved in 5 mL of DCM and cooled to 0° C. PBr₃ (0.016 g, 0.058 mmol) was added thereto, and the mixture was stirred for 0.5 hour. The reaction solution was extracted with DCM, dried with MgSO₄ and dissolved in 5 mL of DMF. Cyclopropylmethanol and K₂CO₃ were added thereto, and the mixture was stirred at 50° C. for 18 hours. After addition of water, the reaction solution extracted with EtOAc. The organic layer was dried with MgSO₄ and purified by column chromatography to obtain the title compound (0.003 g, 14%).

¹H-NMR (CDCl₃) δ 7.14 (2H, m), 6.52 (1H, d), 6.38 (1H, d), 4.50 (2H, s), 3.65 (3H, s), 3.34 (2H, d), 3.12 (2H, t), 2.86 (3H, s), 2.38 (2H, t), 1.86 (2H, m), 1.09 (1H, m), 0.55 (2H, m), 0.22 (2H, m)

Step D: 4-[4-[5-(cyclopropylmethoxymethyl)-2-furyl]-2,6-difluoro-N-methyl-anilino]butanoic acid 4-[4-[5-(Cyclopropylmethoxymethyl)-2-furyl]-2,6-difluoro-N-methyl-anilino]butanoic acid methyl ester obtained in Step C was reacted in the same manner as in Step B of Example 1 to obtain the title compound (0.002 g, 69%).

¹H-NMR (CDCl₃) δ 7.14 (2H, m), 6.53 (1H, d), 6.38 (1H, d), 4.51 (2H, s), 3.35 (2H, d), 3.15 (2H, t), 2.86 (3H, s), 2.46 (2H, t), 1.86 (2H, m), 1.09 (1H, m), 0.55 (2H, m), 0.22 (2H, m)

Example 474: 4-[4-[6-(cyclopropylmethoxy)indol-1-yl]-2,6-difluoro-phenoxy]butanoic acid

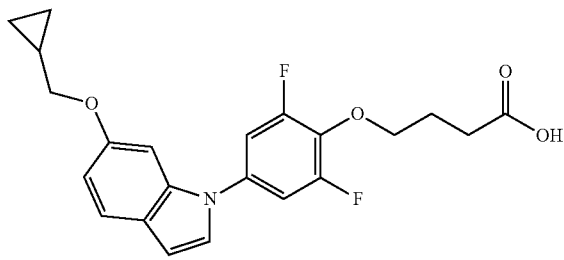 [SMILES: O=C(O)CCCOc1c(F)cc(-n2ccc3ccc(OCC4CC4)cc32)cc1F]

6-(Cyclopropylmethoxy)-1H-indole (0.017 g, 0.09 mmol) obtained in Preparation Example 311 and 4-(4-bromo-2,6-difluoro-phenoxy)butanoic acid ethyl ester (0.060 g, 0.18 mmol) obtained in Preparation Example 339 were reacted in the same manner as in Step A of Example 463 and Step B of Example 1 to obtain the title compound (0.004 g, 11%).

¹H-NMR (CDCl₃) δ 7.52 (1H, m), 7.11 (1H, m), 7.05 (2H, m), 7.01 (1H, m), 6.87 (1H, m), 6.59 (1H, m), 4.25 (2H, t), 3.82 (2H, d), 2.70 (2H, t), 2.15 (2H, m), 1.26 (1H, m), 0.65 (2H, m), 0.37 (2H, m)

Example 475: 4-[4-(7-chloroindol-1-yl)-2,6-difluoro-N-methyl-anilino]butanoic acid

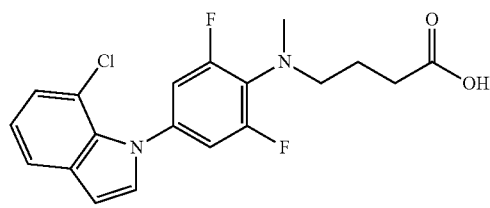 [SMILES: CN(CCCC(=O)O)c1c(F)cc(-n2ccc3cccc(Cl)c32)cc1F]

7-Chloro-1H-indole (0.047 g, 0.31 mmol) and 4-(4-bromo-2,6-difluoro-N-methyl-anilino)butanoic acid methyl ester (0.1 g, 0.31 mmol) were reacted in the same manner as in Step A of Example 463 and Step B of Example 1 to obtain the title compound (0.042 g, 36%).

¹H-NMR (CDCl₃) δ 7.57 (1H, m), 7.19 (1H, m), 7.12 (1H, m), 7.08 (1H, t), 6.93 (2H, m), 6.65 (1H, m), 3.21 (2H, m), 2.92 (3H, s), 2.50 (2H, m), 1.90 (2H, m)

Example 476: 4-[4-[6-(cyclobutoxy)indol-1-yl]-2,6-difluoro-phenoxy]butanoic acid

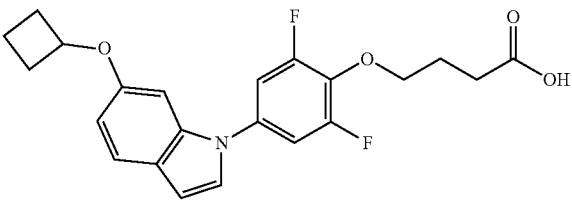

6-(Cyclobutoxy)-1H-indole (0.026 g, 0.14 mmol) obtained in Preparation Example 308 and 4-(4-bromo-2,6-difluoro-phenoxy)butanoic acid ethyl ester (0.068 g, 0.21 mmol) obtained in Preparation Example 339 were reacted in the same manner as in Step A of Example 463 and Step B of Example 1 to obtain the title compound (0.008 g, 14%).

¹H-NMR (CDCl₃) δ 7.50 (1H, m), 7.11 (1H, m), 7.06 (2H, m), 6.94 (1H, m), 6.77 (1H, m), 6.58 (1H, m), 4.66 (1H, m), 4.24 (2H, t), 2.69 (2H, t), 2.45 (2H, m), 2.16 (4H, m), 1.86 (1H, m), 1.70 (1H, m)

Example 477: 4-[4-[5-(cyclobutoxy)indol-1-yl]-2,6-difluoro-phenoxy]butanoic acid

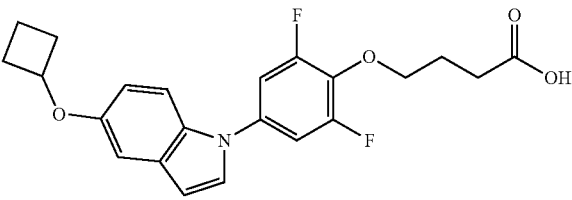 [SMILES: O=C(O)CCCOc1c(F)cc(-n2ccc3cc(OC4CCC4)ccc32)cc1F]

5-(Cyclobutoxy)-1H-indole (0.021 g, 0.14 mmol) obtained in Preparation Example 310 and 4-(4-bromo-2,6-difluoro-phenoxy)butanoic acid ethyl ester (0.068 g, 0.21 mmol) obtained in Preparation Example 339 were reacted in the same manner as in Step A of Example 463 and Step B of Example 1 to obtain the title compound (0.002 g, 3%).

¹H-NMR (CDCl₃) δ 7.41 (1H, m), 7.21 (1H, m), 7.02 (3H, m), 6.85 (1H, m), 6.58 (1H, m), 4.68 (1H, m), 4.24 (2H, t), 2.67 (2H, m), 2.48 (2H, m), 2.17 (4H, m), 1.81 (1H, m), 1.69 (1H, m)

Example 478: 4-[2,6-difluoro-4-(4-methoxyindol-1-yl)phenoxy]butanoic acid

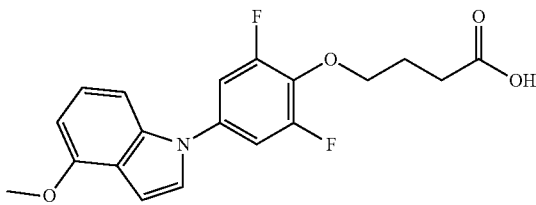 [SMILES: COc1cccc2c1ccn2-c1cc(F)c(OCCCC(=O)O)c(F)c1]

4-Methoxy-1H-indole (0.055 g, 0.37 mmol) and 4-(4-bromo-2,6-difluoro-phenoxy)butanoic acid ethyl ester (0.180 g, 0.55 mmol) obtained in Preparation Example 339 were reacted in the same manner as in Step A of Example 463 and Step B of Example 1 to obtain the title compound (0.011 g, 8%).

$^1$H-NMR (CDCl$_3$) δ 7.15 (3H, m), 7.08 (2H, m), 6.78 (1H, m), 6.59 (1H, m), 4.24 (2H, t), 3.97 (3H, s), 2.68 (2H, t), 2.14 (2H, m)

Example 479: 4-[2,6-difluoro-4-(7-methoxyindol-1-yl)phenoxy]butanoic acid

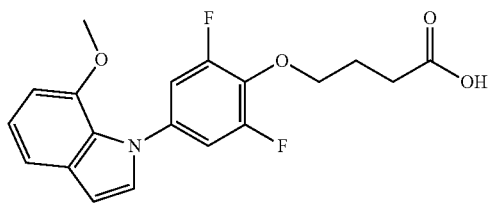 [SMILES: COc1cccc2ccn(-c3cc(F)c(OCCCC(=O)O)c(F)c3)c12]

7-Methoxy-1H-indole (0.055 g, 0.37 mmol) and 4-(4-bromo-2,6-difluoro-phenoxy)butanoic acid ethyl ester (0.180 g, 0.55 mmol) obtained in Preparation Example 339 were reacted in the same manner as in Step A of Example 463 and Step B of Example 1 to obtain the title compound (0.045 g, 34%).

$^1$H-NMR (CDCl$_3$) δ 7.26 (1H, m), 7.08 (2H, m), 6.96 (2H, m), 6.69 (1H, m), 6.62 (1H, m), 4.24 (2H, t), 3.76 (3H, s), 2.69 (2H, t), 2.14 (2H, m)

Example 480: 4-[2,6-difluoro-4-[5-(methoxymethyl)indazol-1-yl]phenoxy]butanoic acid

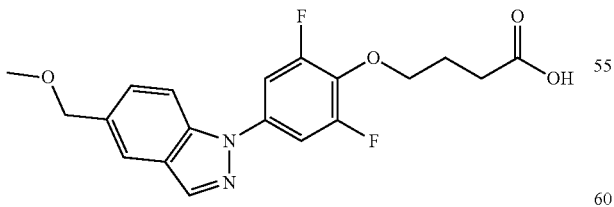

Step A: 4-[2,6-difluoro-4-(5-formylindazol-1-yl)phenoxy]butanoic acid ethyl ester 1H-indazol-5-carbaldehyde (0.054 g, 0.37 mmol) and 4-(4-bromo-2,6-difluoro-phenoxy)butanoic acid ethyl ester (0.180 g, 0.55 mmol) obtained in Preparation Example 339 were reacted in the same manner as in Step A of Example 463 to obtain the title compound (0.022 g, 15%).

$^1$H-NMR (CDCl$_3$) δ 10.10 (1H, s), 8.35 (2H, m), 8.04 (1H, m), 7.81 (1H, m), 7.34 (2H, m), 4.26 (2H, t), 4.17 (2H, q), 2.61 (2H, t), 2.14 (2H, m), 1.28 (3H, t)

Step B: 4-[2,6-difluoro-4-[5-(hydroxymethyl)indazol-1-yl]phenoxy]butanoic acid ethyl ester 4-[2,6-Difluoro-4-(5-formylindazol-1-yl)phenoxy]butanoic acid ethyl ester (0.022 g, 0.057 mmol) obtained in Step A was dissolved in 3 mL of MeOH. NaBH$_4$ (0.003 g, 0.057 mmol) was added thereto at 0° C., and the mixture was stirred at room temperature for 30 minutes. After addition of acetic acid, the reaction solution was extracted with EtOAc. The organic layer was dried with MgSO$_4$ and purified by column chromatography to obtain the title compound (0.020 g, 98%).

$^1$H-NMR (CDCl$_3$) δ 8.18 (1H, s), 7.79 (1H, m), 7.73 (1H, m), 7.50 (1H, m), 7.34 (2H, m), 4.83 (2H, s), 4.23 (2H, t), 4.17 (2H, q), 2.60 (2H, t), 2.12 (2H, m), 1.78 (1H, brs), 1.28 (3H, t)

Step C: 4-[2,6-difluoro-4-[5-(methoxymethyl)indazol-1-yl]phenoxy]butanoic acid ethyl ester 4-[2,6-Difluoro-4-[5-(hydroxymethyl)indazol-1-yl]phenoxy]butanoic acid ethyl ester (0.020 g, 0.057 mmol) obtained in Step B was dissolved in 1 mL of DMF and cooled to 0° C. NaH (60%)(0.003 g, 0.007 mmol) and tetrabutylammonium iodide (0.021 g, 0.057 mmol) were added thereto, and the mixture was stirred for 0.5 hour. Methyl iodide (0.012 g, 0.086 mmol) was added thereto, and the mixture was stirred at room temperature for 18 hours. The reaction solution was extracted with EtOAc, dried with MgSO$_4$ and purified by column chromatography to obtain the title compound (0.002 g, 9%).

Step D: 4-[2,6-difluoro-4-[5-(methoxymethyl)indazol-1-yl]phenoxy]butanoic acid

4-[2,6-Difluoro-4-[5-(methoxymethyl)indazol-1-yl]phenoxy]butanoic acid ethyl ester (0.002 g, 0.005 mmol) obtained in Step C was reacted in the same manner as in Step B of Example 1 to obtain the title compound (0.0007 g, 37%).

$^1$H-NMR (CDCl$_3$) δ 8.16 (1H, m), 7.50 (2H, m), 7.47 (1H, m), 7.34 (2H, m), 4.58 (2H, s), 4.25 (2H, t), 3.42 (3H, s), 2.69 (2H, t), 2.14 (2H, m)

Example 481: 2-[1-[4-(7-chloroindol-1-yl)-2,6-difluoro-phenyl]-4-piperidyl]acetic acid

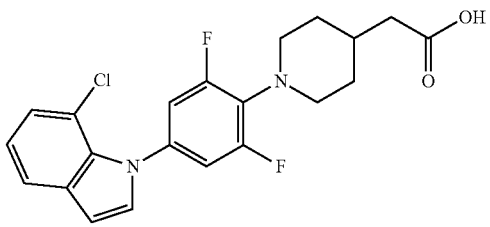 [SMILES: O=C(O)CC1CCN(c2c(F)cc(-n3ccc4cccc(Cl)c43)cc2F)CC1]

7-Chloro-1H-indole (0.042 g, 0.28 mmol) and 2-[1-(4-bromo-2,6-difluoro-phenyl)-4-piperidyl]acetic acid ethyl ester (0.1 g, 0.28 mmol) obtained in Step A of Preparation Example 220 were reacted in the same manner as in Step A of Example 463 and Step B of Example 1 to obtain the title compound (0.045 g, 40%).

$^1$H-NMR (CDCl$_3$) δ 7.56 (1H, m), 7.18 (1H, m), 7.08 (2H, m), 6.91 (2H, m), 6.63 (1H, m), 3.32 (2H, m), 3.18 (2H, m), 2.40 (2H, m), 2.00 (1H, m), 1.90 (2H, m), 1.52 (2H, m)

Example 482: 4-[4-[6-(cyclobutoxy)indazol-1-yl]-2,6-difluoro-phenoxy]butanoic acid

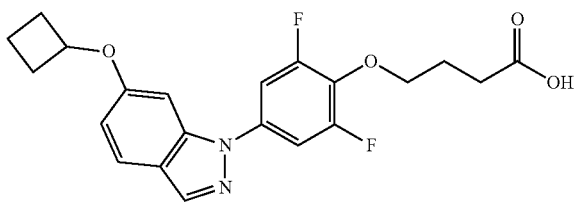

6-(Cyclobutoxy)-1H-indazole (0.04 g, 0.21 mmol) obtained in Preparation Example 309 and 4-(4-bromo-2,6-difluoro-phenoxy)butanoic acid ethyl ester (0.103 g, 0.32 mmol) obtained in Preparation Example 339 were reacted in the same manner as in Step A of Example 463 and Step B of Example 1 to obtain the title compound (0.05 g, 59%).

$^1$H-NMR (CDCl$_3$) δ 8.06 (1H, m), 7.63 (1H, m), 7.29 (2H, m), 6.96 (1H, m), 6.84 (1H, m), 4.72 (1H, m), 4.25 (2H, m), 2.68 (2H, m), 2.50 (2H, m), 2.23 (2H, m), 2.16 (2H, m), 1.90 (1H, m), 1.75 (1H, m)

Example 483: 4-[2-chloro-4-[6-(cyclobutoxy)indazol-1-yl]-6-fluoro-phenoxy]butanoic acid

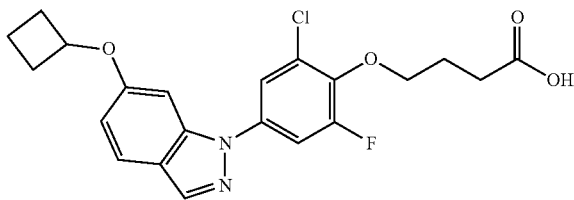 [SMILES: O=C(O)CCCOc1c(F)cc(-n2ncc3ccc(OC4CCC4)cc32)cc1Cl]

6-(Cyclobutoxy)-1H-indazole (0.1 g, 0.53 mmol) obtained in Preparation Example 309 and 4-(4-bromo-2-chloro-6-fluoro-phenoxy)butanoic acid ethyl ester (0.2 g, 0.58 mmol) obtained in Step A of Preparation Example 221 were reacted in the same manner as in Step A of Example 463 and Step B of Example 1 to obtain the title compound (0.048 g, 22%).

$^1$H-NMR (CDCl$_3$) δ 8.06 (1H, m), 7.63 (1H, m), 7.54 (1H, m), 7.41 (1H, m), 6.96 (1H, m), 6.84 (1H, m), 4.72 (1H, m), 4.22 (2H, t), 2.74 (2H, t), 2.48 (2H, m), 2.19 (4H, m), 1.91 (1H, m), 1.76 (1H, m)

Example 484: 4-[4-[4-(cyclobutoxy)-6-methyl-pyrimidin-2-yl]-2,6-difluoro-N-methyl-anilino]butanoic acid

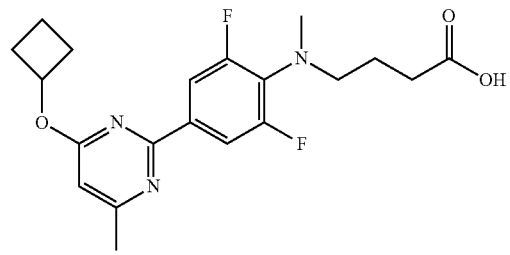 [SMILES: Cc1cc(OC2CCC2)nc(-c2cc(F)c(N(C)CCCC(=O)O)c(F)c2)n1]

2-Chloro-4-(cyclobutoxy)-6-methyl-pyrimidine (0.082 g, 0.41 mmol) obtained in Preparation Example 228 and 4-{[2,6-difluoro-4-(4,4,5,5-tetramethyl-[1,3,2]dioxaborolan-2-yl)-phenyl]-methyl-amino}-butyric acid methyl ester (0.157 g, 0.41 mmol) obtained in Preparation Example 183 were reacted in the same manner as in Step A of Example 96 and Step B of Example 1 to obtain the title compound (0.118 g, 73%).

$^1$H-NMR (CDCl$_3$) δ 7.88 (2H, m), 6.40 (1H, s), 5.29 (1H, m), 3.21 (2H, t), 2.92 (3H, s), 2.53 (2H, m), 2.45 (3H, s), 2.43 (2H, m), 2.19 (2H, m), 1.87 (3H, m), 1.73 (1H, m)

Example 485: 4-[4-[4-(cyclobutoxy)pyrimidin-2-yl]-2,6-difluoro-N-methyl-anilino]butanoic acid

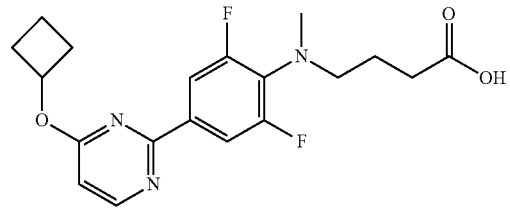 [SMILES: CN(CCCC(=O)O)c1c(F)cc(-c2nccc(OC3CCC3)n2)cc1F]

2-Chloro-4-(cyclobutoxy)pyrimidine (0.081 g, 0.44 mmol) obtained in Preparation Example 230 and 4-{[2,6-difluoro-4-(4,4,5,5-tetramethyl-[1,3,2]dioxaborolan-2-yl)-phenyl]-methyl-amino}-butanoic acid methyl ester (0.168 g, 0.44 mmol) obtained in Preparation Example 183 were reacted in the same manner as in Step A of Example 96 and Step B of Example 1 to obtain the title compound (0.119 g, 72%).

$^1$H-NMR (CDCl$_3$) δ 8.46 (1H, d), 7.87 (2H, m), 6.56 (1H, d), 5.32 (1H, m), 3.22 (2H, t), 2.93 (3H, s), 2.53 (2H, m), 2.44 (2H, t), 2.20 (2H, m), 1.88 (3H, m), 1.78 (1H, m)

Example 486: 4-[4-[2-(cyclobutoxy)thiazol-4-yl]-2,6-difluoro-N-methyl-anilino]butanoic acid

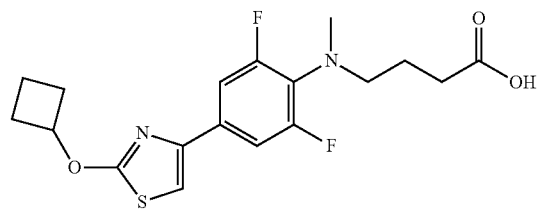 [SMILES: CN(CCCC(=O)O)c1c(F)cc(-c2csc(OC3CCC3)n2)cc1F]

4-Bromo-2-(cyclobutoxy)thiazole (0.083 g, 0.35 mmol) obtained in Preparation Example 289 and 4-{[2,6-difluoro-4-(4,4,5,5-tetramethyl-[1,3,2]dioxaborolan-2-yl)-phenyl]-methyl-amino}-butyric acid methyl ester (0.134 g, 0.35 mmol) obtained in Preparation Example 183 were reacted in the same manner as in Step A of Example 96 and Step B of Example 1 to obtain the title compound (0.085 g, 63%).

¹H-NMR (CDCl₃) δ 7.28 (2H, m), 6.77 (1H, s), 5.18 (1H, m), 3.15 (2H, t), 2.86 (3H, s), 2.54 (2H, m), 2.45 (2H, t), 2.25 (2H, m), 1.85 (3H, m), 1.67 (1H, m)

Example 487: 2-[1-[4-[6-(cyclobutoxy)indazol-1-yl]-2,6-difluoro-phenyl]-4-piperidyl]acetic acid

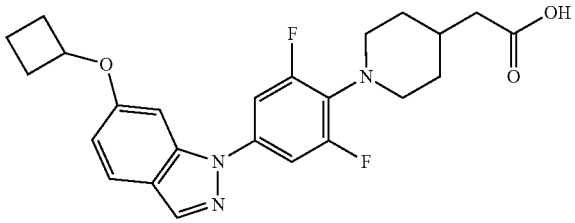 [SMILES: O=C(O)CC1CCN(c2c(F)cc(-n3ncc4ccc(OC5CCC5)cc43)cc2F)CC1]

6-(Cyclobutoxy)-1H-indazole (0.1 g, 0.53 mmol) obtained in Preparation Example 309 and 2-[1-(4-bromo-2,6-difluoro-phenyl)-4-piperidyl]acetic acid ethyl ester (0.21 g, 0.58 mmol) obtained in Step A of Preparation Example 220 were reacted in the same manner as in Step A of Example 463 and Step B of Example 1 to obtain the title compound (0.026 g, 11%).

¹H-NMR (CDCl₃) δ 8.09 (1H, s), 7.67 (1H, d), 7.26 (2H, m), 7.00 (1H, m), 6.87 (1H, m), 4.76 (1H, m), 3.34 (2H, m), 3.22 (2H, t), 2.53 (2H, m), 2.42 (2H, d), 2.27 (2H, m), 2.03 (1H, m), 1.93 (3H, m), 1.80 (1H, m), 1.56 (2H, m)

Example 488: 4-[4-[6-(cyclobutoxy)pyrazin-2-yl]-2,6-difluoro-N-methyl-anilino]butanoic acid

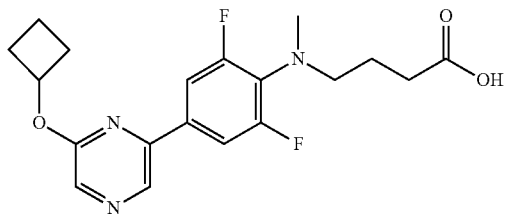 [SMILES: CN(CCCC(=O)O)c1c(F)cc(-c2cncc(OC3CCC3)n2)cc1F]

2-Chloro-6-(cyclobutoxy)pyrazine (0.06 g, 0.32 mmol) obtained in Preparation Example 232 and 4-{[2,6-difluoro-4-(4,4,5,5-tetramethyl-[1,3,2]dioxaborolan-2-yl)-phenyl]-methyl-amino}-butyric acid methyl ester (0.123 g, 0.32 mmol) obtained in Preparation Example 183 were reacted in the same manner as in Step A of Example 96 and Step B of Example 1 to obtain the title compound (0.079 g, 65%).

¹H-NMR (CDCl₃) δ 8.46 (1H, s), 8.09 (1H, s), 7.50 (2H, m), 5.26 (1H, m), 3.21 (2H, t), 2.92 (3H, s), 2.54 (2H, m), 2.44 (2H, t), 2.21 (2H, m), 1.89 (3H, m), 1.75 (1H, m)

Example 489: 4-[4-[4-(cyclopropylmethoxy)-6-methyl-pyrimidin-2-yl]-2,6-difluoro-N-methyl-anilino]butanoic acid

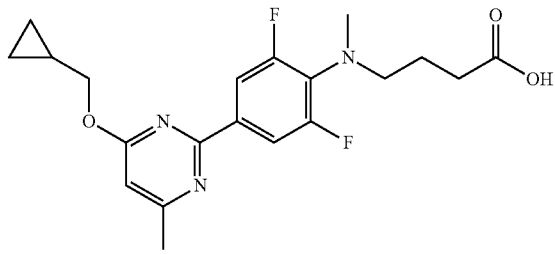 [SMILES: Cc1cc(OCC2CC2)nc(-c2cc(F)c(N(C)CCCC(=O)O)c(F)c2)n1]

2-Chloro-4-(cyclopropylmethoxy)-6-methyl-pyrimidine (0.067 g, 0.34 mmol) obtained in Preparation Example 227 and 4-{[2,6-difluoro-4-(4,4,5,5-tetramethyl-[1,3,2]dioxaborolan-2-yl)-phenyl]-methyl-amino}-butyric acid methyl ester (0.13 g, 0.34 mmol) obtained in Preparation Example 183 were reacted in the same manner as in Step A of Example 96 and Step B of Example 1 to obtain the title compound (0.086 g, 64%).

¹H-NMR (CDCl₃) δ 7.89 (2H, m), 6.46 (1H, s), 4.27 (2H, d), 3.21 (2H, t), 2.92 (3H, s), 2.46 (3H, s), 2.43 (2H, t), 1.88 (2H, m), 1.32 (1H, m), 0.63 (2H, m), 0.39 (2H, m)

Example 490: 4-[4-[4-(cyclopropylmethoxy)pyrimidin-2-yl]-2,6-difluoro-N-methyl-anilino]butanoic acid

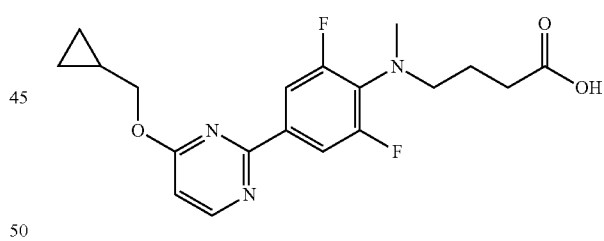

2-Chloro-4-(cyclopropylmethoxy)pyrimidine (0.073 g, 0.39 mmol) obtained in Preparation Example 231 and 4-{[2,6-difluoro-4-(4,4,5,5-tetramethyl-[1,3,2]dioxaborolan-2-yl)-phenyl]-methyl-amino}-butyric acid methyl ester (0.15 g, 0.39 mmol) obtained in Preparation Example 183 were reacted in the same manner as in Step A of Example 96 and Step B of Example 1 to obtain the title compound (0.097 g, 66%).

¹H-NMR (CDCl₃) δ 8.46 (1H, d), 7.88 (2H, m), 6.62 (1H, d), 4.30 (2H, d), 3.22 (2H, t), 2.92 (3H, s), 2.44 (2H, t), 1.89 (2H, m), 1.33 (1H, m), 0.65 (2H, m), 0.41 (2H, m)

Example 491: 4-[4-[6-(cyclopropylmethoxy)pyrazin-2-yl]-2,6-difluoro-N-methyl-anilino]butanoic acid

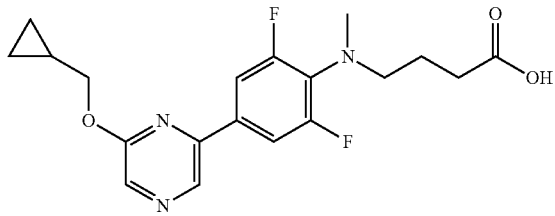 [SMILES: CN(CCCC(=O)O)c1c(F)cc(-c2cncc(OCC3CC3)n2)cc1F]

2-Chloro-6-(cyclopropylmethoxy)pyrazine (0.065 g, 0.35 mmol) obtained in Preparation Example 233 and 4-{[2,6-difluoro-4-(4,4,5,5-tetramethyl-[1,3,2]dioxaborolan-2-yl)-phenyl]-methyl-amino}-butyric acid methyl ester (0.134 g, 0.35 mmol) obtained in Preparation Example 183 were reacted in the same manner as in Step A of Example 96 and Step B of Example 1 to obtain the title compound (0.071 g, 53%).

$^1$H-NMR (CDCl$_3$) δ 8.47 (1H, s), 8.16 (1H, s), 7.50 (2H, m), 4.25 (2H, d), 3.21 (2H, t), 2.92 (3H, s), 2.44 (2H, t), 1.89 (2H, m), 1.33 (1H, m), 0.66 (2H, m), 0.40 (2H, m)

Example 492: 4-[4-[6-(cyclobutoxy)indazol-1-yl]-2,6-difluoro-N-methyl-anilino]butanoic acid

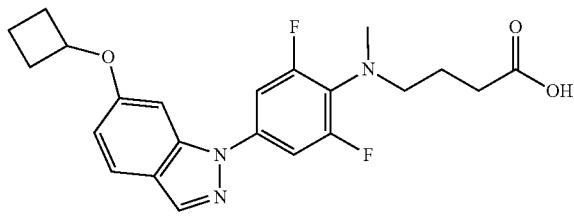 [SMILES: CN(CCCC(=O)O)c1c(F)cc(-n2ncc3ccc(OC4CCC4)cc32)cc1F]

6-(Cyclobutoxy)-1H-indazole (0.1 g, 0.53 mmol) obtained in Preparation Example 309 and 4-(4-bromo-2,6-difluoro-N-methyl-anilino)butanoic acid methyl ester (0.187 g, 0.58 mmol) were reacted in the same manner as in Step A of Example 463 and Step B of Example 1 to obtain the title compound (0.079 g, 35%).

$^1$H-NMR (CDCl$_3$) δ 8.05 (1H, m), 7.63 (1H, d), 7.25 (2H, m), 6.99 (1H, m), 6.83 (1H, m), 4.73 (1H, m), 3.18 (2H, t), 2.90 (3H, s), 2.50 (4H, m), 2.22 (2H, m), 1.88 (3H, m), 1.77 (1H, m)

Example 493: 4-[4-[6-(cyclopropylmethoxy)-2-pyridyl]-2,6-difluoro-N-methyl-anilino]butanoic acid

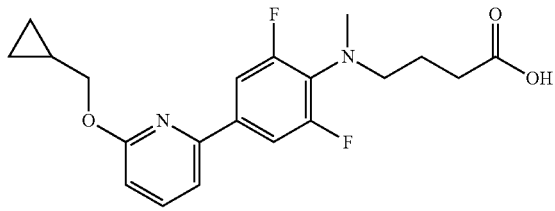 [SMILES: CN(CCCC(=O)O)c1c(F)cc(-c2cccc(OCC3CC3)n2)cc1F]

2-Chloro-6-cyclopropylmethoxy-pyridine (0.083 g, 0.45 mmol) obtained in Preparation Example 43 and 4-{[2,6-difluoro-4-(4,4,5,5-tetramethyl-[1,3,2]dioxaborolan-2-yl)-phenyl]-methyl-amino}-butyric acid methyl ester (0.172 g, 0.45 mmol) obtained in Preparation Example 183 were reacted in the same manner as in Step A of Example 96 and Step B of Example 1 to obtain the title compound (0.14 g, 82%).

$^1$H-NMR (CDCl$_3$) δ 7.60 (1H, t), 7.50 (2H, m), 7.20 (1H, d), 6.70 (1H, d), 4.23 (2H, d), 3.17 (2H, t), 2.89 (3H, s), 2.45 (2H, t), 1.87 (2H, m), 1.32 (1H, m), 0.61 (2H, m), 0.39 (2H, m)

Example 494: 2-[1-[4-[6-(cyclobutoxy)indazol-1-yl]-2,6-difluoro-phenyl]pyrrolidin-3-yl]acetic acid

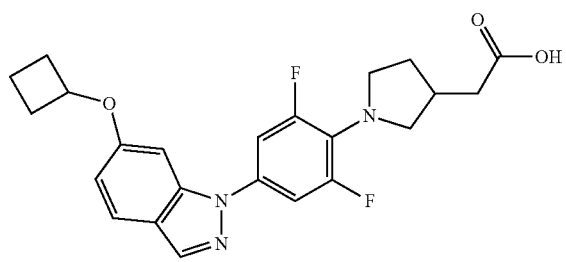 [SMILES: O=C(O)CC1CCN(c2c(F)cc(-n3ncc4ccc(OC5CCC5)cc43)cc2F)C1]

6-(Cyclobutoxy)-1H-indazole (0.15 g, 0.79 mmol) obtained in Preparation Example 309 and 2-[1-(4-bromo-2,6-difluoro-phenyl)pyrrolidin-3-yl]acetic acid ethyl ester (0.302 g, 0.87 mmol) obtained in Step F of Preparation Example 91 were reacted in the same manner as in Step A of Example 463 and Step B of Example 1 to obtain the title compound (0.05 g, 15%).

$^1$H-NMR (CDCl$_3$) δ 8.04 (1H, m), 7.61 (1H, d), 7.17 (2H, m), 6.92 (1H, m), 6.82 (1H, m), 4.71 (1H, m), 3.77 (1H, m), 3.62 (2H, m), 3.36 (1H, m), 2.70 (1H, m), 2.57 (2H, m), 2.48 (2H, m), 2.27 (3H, m), 1.89 (1H, m), 1.71 (2H, m)

Example 495: 2-{1-[2,6-difluoro-4-(6-propoxy-pyrazin-2-yl)phenyl]pyrrolidin-3-yl}acetic acid

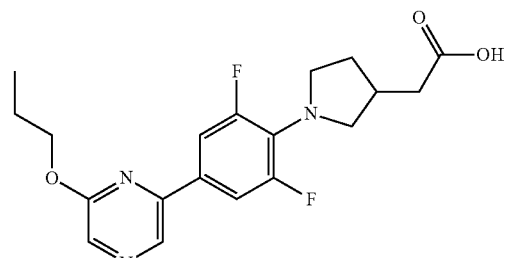

2-Chloro-6-propoxy-pyrazine (0.063 g, 0.36 mmol) obtained in Preparation Example 235 and 2-[1-[2,6-difluoro-4-(4,4,5,5-tetramethyl-1,3,2-dioxaborolan-2-yl)phenyl]pyrrolidin-3-yl]acetic acid ethyl ester (0.119 g, 0.30 mmol) obtained in Preparation Example 91 were reacted in the same manner as in Step A of Example 96 and Step B of Example 1 to obtain the title compound (0.029 g, 21%).

¹H-NMR (CDCl₃) δ 8.44 (1H, s), 8.07 (1H, s), 7.49 (2H, m), 4.37 (2H, t), 3.79 (2H, m), 3.64 (1H, m), 3.41 (1H, m), 2.67 (1H, m), 2.55 (2H, m), 2.19 (1H, m), 1.83 (2H, q), 1.65 (1H, m), 1.06 (3H, t)

Example 496: 2-{1-[2,6-difluoro-4-(6-isobutoxy-pyrazin-2-yl)phenyl]pyrrolidin-3-yl}acetic acid

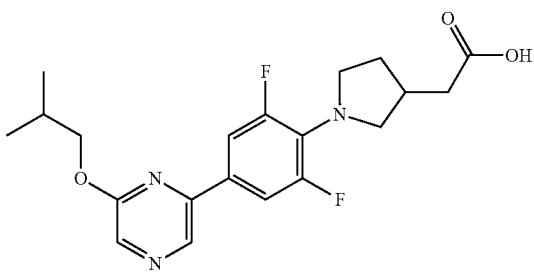 [SMILES: CC(C)COc1cncc(-c2cc(F)c(N3CCC(CC(=O)O)C3)c(F)c2)n1]

2-Chloro-6-isobutoxy-pyrazine (0.061 g, 0.33 mmol) obtained in Preparation Example 237 and 2-[1-[2,6-difluoro-4-(4,4,5,5-tetramethyl-1,3,2-dioxaborolan-2-yl)phenyl]pyrrolidin-3-yl]acetic acid ethyl ester (0.107 g, 0.27 mmol) obtained in Preparation Example 91 were reacted in the same manner as in Step A of Example 96 and Step B of Example 1 to obtain the title compound (0.049 g, 38%).

¹H-NMR (DMSO-d₆) δ8.77 (1H, s), 8.17 (1H, s), 7.74 (2H, m), 4.19 (2H, d), 3.69 (2H, m), 3.57 (1H, m), 3.34 (1H, m), 2.49 (1H, m), 2.41 (2H, m), 2.10 (2H, m), 1.60 (1H, m), 1.02 (6H, d)

Example 497: 2-{1-[2,6-difluoro-4-(6-cyclopentoxy-pyrazin-2-yl)phenyl]pyrrolidin-3-yl}acetic acid

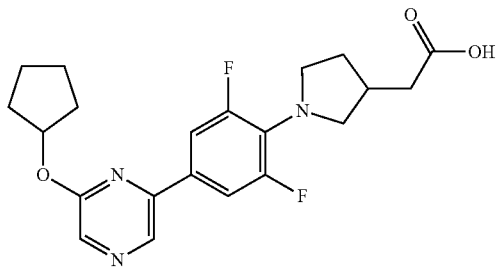 [SMILES: O=C(O)CC1CCN(c2c(F)cc(-c3cncc(OC4CCCC4)n3)cc2F)C1]

2-Chloro-6-cyclopentoxy-pyrazine (0.075 g, 0.38 mmol) obtained in Preparation Example 238 and 2-[1-[2,6-difluoro-4-(4,4,5,5-tetramethyl-1,3,2-dioxaborolan-2-yl)phenyl]pyrrolidin-3-yl]acetic acid ethyl ester (0.123 g, 0.31 mmol) obtained in Preparation Example 91 were reacted in the same manner as in Step A of Example 96 and Step B of Example 1 to obtain the title compound (0.056 g, 36%).

¹H-NMR (DMSO-d₆) δ8.75 (1H, s), 8.11 (1H, s), 7.74 (2H, m), 5.49 (1H, m), 3.69 (2H, m), 3.57 (1H, m), 3.34 (1H, m), 2.51 (1H, m), 2.41 (2H, m), 2.04 (3H, m), 1.81-1.52 (7H, m)

Example 498: 2-{1-[2,6-difluoro-4-(6-butoxy-pyrazin-2-yl)phenyl]pyrrolidin-3-yl}acetic acid

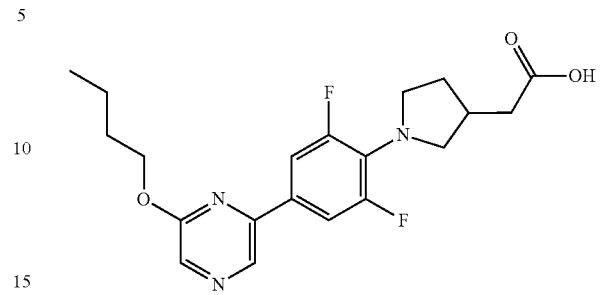

2-Butoxy-6-chloro-pyrazine (0.071 g, 0.38 mmol) obtained in Preparation Example 236 and 2-[1-[2,6-difluoro-4-(4,4,5,5-tetramethyl-1,3,2-dioxaborolan-2-yl)phenyl]pyrrolidin-3-yl]acetic acid ethyl ester (0.123 g, 0.31 mmol) obtained in Preparation Example 91 was reacted in the same manner as in Step A of Example 96 and Step B of Example 1 to obtain the title compound (0.1 g, 67%).

¹H-NMR (DMSO-d₆) δ8.77 (1H, s), 8.16 (1H, s), 7.74 (2H, m), 4.41 (2H, t), 3.69 (2H, m), 3.57 (1H, m), 3.34 (1H, m), 2.49 (1H, m), 2.41 (2H, m), 2.09 (1H, m), 1.77 (2H, m), 1.59 (1H, m), 1.47 (2H, m), 0.96 (3H, t)

Example 499: 2-{1-[2,6-difluoro-4-(4-propoxy-pyrimidin-2-yl)phenyl]pyrrolidin-3-yl}acetic acid

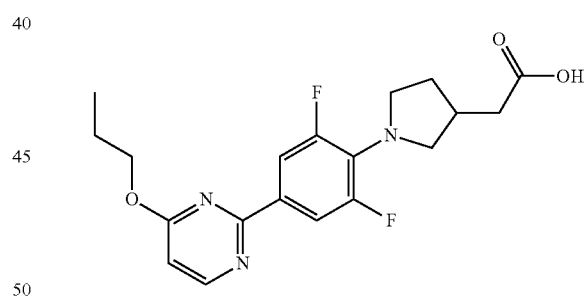

2-Chloro-4-propoxy-pyrimidine (0.068 g, 0.39 mmol) obtained in Preparation Example 241 and 2-[1-[2,6-difluoro-4-(4,4,5,5-tetramethyl-1,3,2-dioxaborolan-2-yl)phenyl]pyrrolidin-3-yl]acetic acid ethyl ester (0.130 g, 0.33 mmol) obtained in Preparation Example 91 were reacted in the same manner as in Step A of Example 96 and Step B of Example 1 to obtain the title compound (0.034 g, 23%).

¹H-NMR (DMSO-d₆) δ8.53 (1H, d), 7.82 (2H, m), 6.77 (1H, d), 4.41 (2H, t), 3.71 (2H, m), 3.59 (1H, m), 3.34 (1H, m), 2.49 (1H, m), 2.41 (2H, m), 2.07 (1H, m), 1.80 (2H, q), 1.59 (1H, m), 1.00 (3H, t)

Example 500: 2-{1-[2,6-difluoro-4-(4-isopropoxy-pyrimidin-2-yl)phenyl]pyrrolidin-3-yl}acetic acid

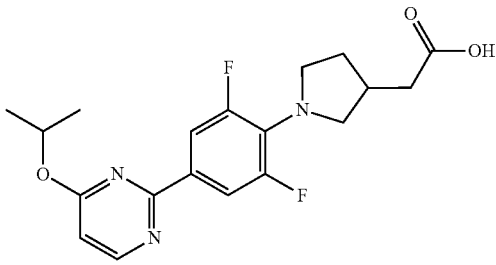 [SMILES: CC(C)Oc1ccnc(-c2cc(F)c(N3CCC(CC(=O)O)C3)c(F)c2)n1]

2-Chloro-4-isopropoxy-pyrimidine (0.073 g, 0.42 mmol) obtained in Preparation Example 240 and 2-[1-[2,6-difluoro-4-(4,4,5,5-tetramethyl-1,3,2-dioxaborolan-2-yl)phenyl]pyrrolidin-3-yl]acetic acid ethyl ester (0.138 g, 0.35 mmol) obtained in Preparation Example 91 were reacted in the same manner as in Step A of Example 96 and Step B of Example 1 to obtain the title compound (0.042 g, 26%).

$^1$H-NMR (DMSO-$d_6$) δ8.52 (1H, d), 7.83 (2H, m), 6.72 (1H, d), 5.49 (1H, m), 3.71 (2H, m), 3.59 (1H, m), 3.34 (1H, m), 2.50 (1H, m), 2.41 (2H, m), 2.07 (1H, m), 1.59 (1H, m), 1.37 (6H, d)

Example 501: 2-{1-[2,6-difluoro-4-(4-ethoxy-pyrimidin-2-yl)phenyl]pyrrolidin-3-yl}acetic acid

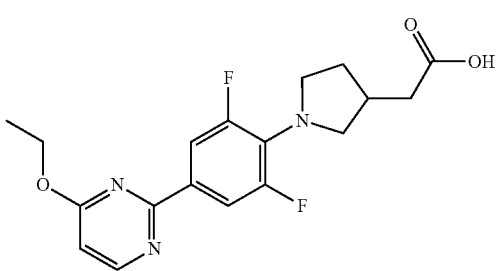 [SMILES: CCOc1ccnc(-c2cc(F)c(N3CCC(CC(=O)O)C3)c(F)c2)n1]

2-Chloro-4-ethoxy-pyrimidine (0.098 g, 0.61 mmol) obtained in Preparation Example 239 and 2-[1-[2,6-difluoro-4-(4,4,5,5-tetramethyl-1,3,2-dioxaborolan-2-yl)phenyl]pyrrolidin-3-yl]acetic acid ethyl ester (0.197 g, 0.50 mmol) obtained in Preparation Example 91 were reacted in the same manner as in Step A of Example 96 and Step B of Example 1 to obtain the title compound (0.071 g, 32%).

$^1$H-NMR (DMSO-$d_6$) δ8.52 (1H, d), 7.84 (2H, m), 6.76 (1H, d), 4.51 (2H, q), 3.70 (2H, m), 3.59 (1H, m), 3.34 (1H, m), 2.51 (1H, m), 2.41 (2H, m), 2.09 (1H, m), 1.58 (1H, m), 1.37 (3H, t)

Example 502: 2-{1-[2,6-difluoro-4-(4-isobutoxy-pyrimidin-2-yl)phenyl]pyrrolidin-3-yl}acetic acid

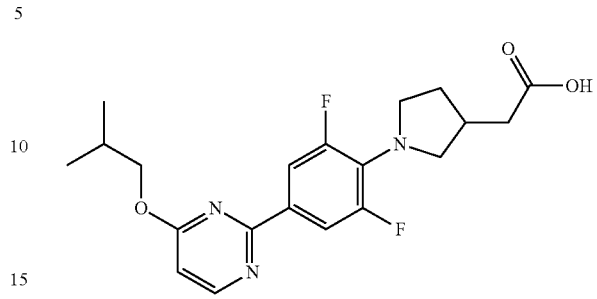

2-Chloro-4-isobutoxy-pyrimidine (0.083 g, 0.44 mmol) obtained in Preparation Example 242 and 2-[1-[2,6-difluoro-4-(4,4,5,5-tetramethyl-1,3,2-dioxaborolan-2-yl)phenyl]pyrrolidin-3-yl]acetic acid ethyl ester (0.146 g, 0.37 mmol) obtained in Preparation Example 91 were reacted in the same manner as in Step A of Example 96 and Step B of Example 1 to obtain the title compound (0.059 g, 34%).

$^1$H-NMR (DMSO-$d_6$) δ8.53 (1H, d), 7.82 (2H, m), 6.78 (1H, d), 4.24 (2H, d), 3.70 (2H, m), 3.60 (1H, m), 3.35 (1H, m), 2.51 (1H, m), 2.42 (2H, m), 2.09 (2H, m), 1.59 (1H, m), 1.01 (6H, d)

Example 503: 2-{1-[2,6-difluoro-4-(6-isobutylamino-pyrazin-2-yl)phenyl]pyrrolidin-3-yl}acetic acid

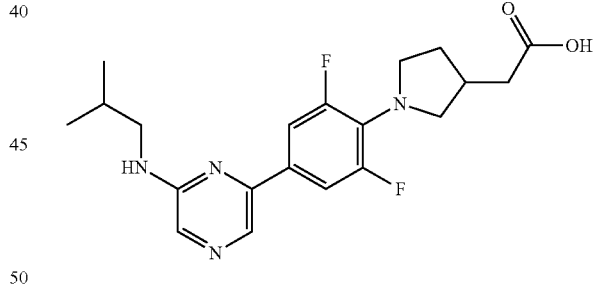

6-Chloro-N-isobutyl-pyrazin-2-amine (0.278 g, 1.50 mmol) obtained in Preparation Example 251 and 2-[1-[2,6-difluoro-4-(4,4,5,5-tetramethyl-1,3,2-dioxaborolan-2-yl)phenyl]pyrrolidin-3-yl]acetic acid ethyl ester (0.3 g, 0.75 mmol) obtained in Preparation Example 91 were reacted in the same manner as in Step A of Example 96 and Step B of Example 1 to obtain the title compound (0.172 g, 58%).

$^1$H-NMR (CDCl$_3$) δ 8.10 (1H, s), 7.75 (1H, s), 7.43 (2H, m), 4.89 (1H, brs), 3.71 (2H, m), 3.61 (1H, m), 3.39 (1H, m), 3.22 (2H, d), 2.64 (1H, m), 2.52 (2H, m), 2.16 (1H, m), 1.93 (1H, m), 1.65 (1H, m), 0.99 (6H, d)

Example 504: 2-{1-[2,6-difluoro-4-(6-cyclopenty-lamino-pyrazin-2-yl)phenyl]pyrrolidin-3-yl}acetic acid

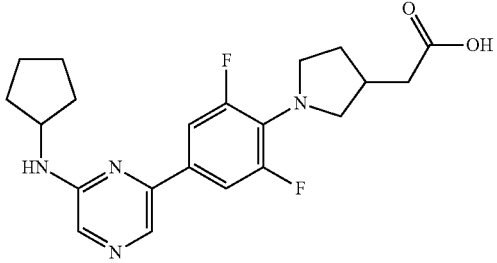

6-Chloro-N-cyclopentyl-pyrazin-2-amine (0.297 g, 1.50 mmol) obtained in Preparation Example 252 and 2-[1-[2,6-difluoro-4-(4,4,5,5-tetramethyl-1,3,2-dioxaborolan-2-yl)phenyl]pyrrolidin-3-yl]acetic acid ethyl ester (0.3 g, 0.75 mmol) obtained in Preparation Example 91 were reacted in the same manner as in Step A of Example 96 and Step B of Example 1 to obtain the title compound (0.17 g, 56%).

$^1$H-NMR (DMSO-$d_6$) δ8.17 (1H, s), 7.75 (1H, s), 7.60 (2H, m), 7.07 (1H, d), 4.14 (1H, m), 3.61 (2H, m), 3.49 (1H, m), 3.29 (1H, m), 2.47 (1H, m), 2.36 (2H, m), 2.03 (1H, m), 1.94 (2H, m), 1.66 (2H, m), 1.54 (3H, m), 1.44 (2H, m)

Example 505: 2-{1-[2,6-difluoro-4-(6-isopropy-lamino-pyrazin-2-yl)phenyl]pyrrolidin-3-yl}acetic acid

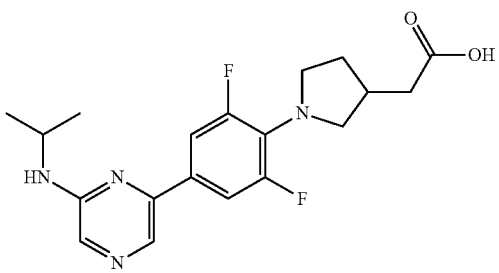 [SMILES: CC(C)Nc1cncc(-c2cc(F)c(N3CCC(CC(=O)O)C3)c(F)c2)n1]

6-Chloro-N-isopropyl-pyrazin-2-amine (0.257 g, 1.50 mmol) obtained in Preparation Example 250 and 2-[1-[2,6-difluoro-4-(4,4,5,5-tetramethyl-1,3,2-dioxaborolan-2-yl)phenyl]pyrrolidin-3-yl]acetic acid ethyl ester (0.3 g, 0.75 mmol) obtained in Preparation Example 91 were reacted in the same manner as in Step A of Example 96 and Step B of Example 1 to obtain the title compound (0.12 g, 42%).

$^1$H-NMR (DMSO-$d_6$) δ8.21 (1H, s), 7.78 (1H, s), 7.64 (2H, m), 6.99 (1H, d), 4.11 (1H, m), 3.65 (2H, m), 3.53 (1H, m), 3.33 (1H, m), 2.51 (1H, m), 2.40 (2H, m), 2.09 (1H, m), 1.58 (1H, m), 1.21 (6H, d)

Example 506: 2-{1-[2,6-difluoro-4-(6-diethylamino-pyrazin-2-yl)phenyl]pyrrolidin-3-yl}acetic acid

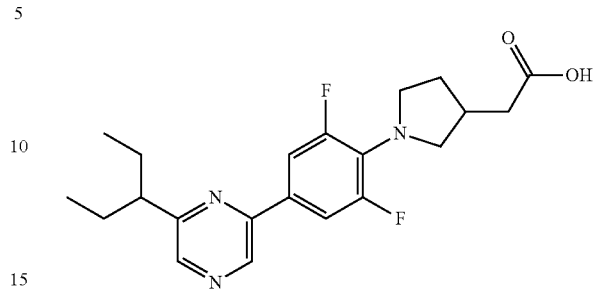

6-Chloro-N,N-diethyl-pyrazin-2-amine (0.278 g, 1.50 mmol) obtained in Preparation Example 253 and 2-[1-[2,6-difluoro-4-(4,4,5,5-tetramethyl-1,3,2-dioxaborolan-2-yl)phenyl]pyrrolidin-3-yl]acetic acid ethyl ester (0.3 g, 0.75 mmol) obtained in Preparation Example 91 were reacted in the same manner as in Step A of Example 96 and Step B of Example 1 to obtain the title compound (0.17 g, 58%).

$^1$H-NMR (DMSO-$d_6$) δ8.31 (1H, s), 8.00 (1H, s), 7.66 (2H, m), 3.67 (2H, m), 3.59 (4H, q), 3.56 (1H, m), 3.33 (1H, m), 2.50 (1H, m), 2.41 (2H, m), 2.09 (1H, m), 1.58 (1H, m), 1.17 (6H, t)

Example 507: 3-[6-(6-cyclobutoxy-pyrazin-2-yl)-thiochroman-2-yl]-propionic acid

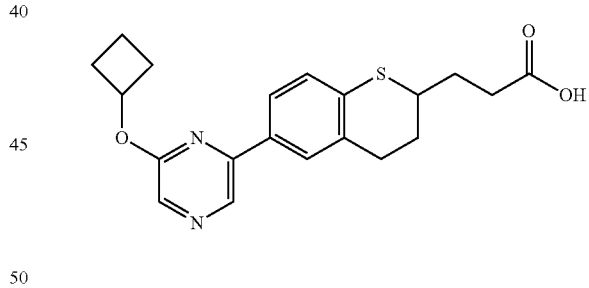

2-Chloro-6-(cyclobutoxy)pyrazine (0.137 g, 0.74 mmol) obtained in Preparation Example 232 and 3-[6-(4,4,5,5-tetramethyl-[1,3,2]dioxaborolan-2-yl)-thiochroman-2-yl]-propionic acid ethyl ester (0.14 g, 0.37 mmol) obtained in Preparation Example 5 were reacted in the same manner as in Step A of Example 96 and Step B of Example 1 to obtain the title compound (0.085 g, 62%).

$^1$H-NMR (CDCl$_3$) δ 8.51 (1H, s), 8.05 (1H, s), 7.70 (2H, m), 7.18 (1H, d), 5.26 (1H, m), 3.43 (1H, m), 2.97 (2H, m), 2.60 (2H, m), 2.51 (2H, m), 2.26-2.18 (3H, m), 2.07 (2H, m), 1.91-1.70 (3H, m)

Example 508: 2-[1-[4-[4-(4-chlorophenoxy)pyrimidin-2-yl]-2,6-difluoro-phenyl]-4-piperidyl]acetic acid

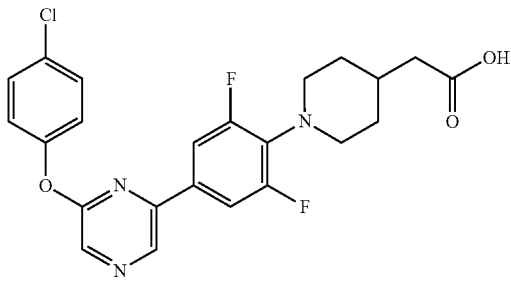

2-Chloro-4-(4-chloro-phenoxy)-pyrimidine (0.235 g, 0.98 mmol) obtained in Preparation Example 312 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.014 g, 6%).

$^1$H-NMR (CDCl$_3$) δ 8.60 (1H, d), 7.71 (2H, m), 7.41 (2H, m), 7.15 (2H, m), 6.73 (1H, d), 3.35 (2H, m), 3.13 (2H, m), 2.35 (2H, d), 1.97 (1H, m), 1.80 (2H, m), 1.47 (2H, m)

Example 509: 2-[1-[4-[4-(4-chlorophenoxy)pyrimidin-2-yl]-2,6-difluoro-phenyl]-pyrrolidin-3-yl]acetic acid

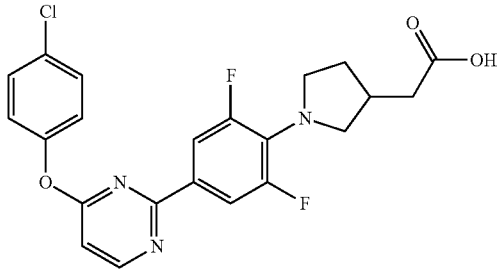 [SMILES: O=C(O)CC1CCN(c2c(F)cc(-c3nccc(Oc4ccc(Cl)cc4)n3)cc2F)C1]

2-Chloro-4-(4-chloro-phenoxy)-pyrimidine (0.145 g, 0.60 mmol) obtained in Preparation Example 312 and 2-[1-[2,6-difluoro-4-(4,4,5,5-tetramethyl-1,3,2-dioxaborolan-2-yl)phenyl]pyrrolidin-3-yl]acetic acid ethyl ester (0.2 g, 0.50 mmol) obtained in Preparation Example 91 were reacted in the same manner as in Step A of Example 96 and Step B of Example 1 to obtain the title compound (0.014 g, 10%).

$^1$H-NMR (CDCl$_3$) δ 8.56 (1H, d), 7.68 (2H, m), 7.42 (2H, m), 7.15 (2H, m), 6.67 (1H, d), 3.76 (2H, m), 3.64 (1H, m), 3.42 (1H, m), 2.63 (1H, m), 2.52 (2H, m), 2.16 (1H, m), 1.64 (1H, m)

Example 510: 2-[1-[4-[4-phenoxy-pyrimidin-2-yl]-2,6-difluoro-phenyl]-4-piperidyl]acetic acid

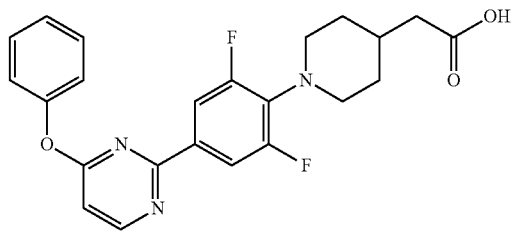 [SMILES: O=C(O)CC1CCN(c2c(F)cc(-c3nccc(Oc4ccccc4)n3)cc2F)CC1]

2-Chloro-4-phenoxy-pyrimidine (0.122 g, 0.59 mmol) obtained in Preparation Example 313 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.075 g, 36%).

$^1$H-NMR (CDCl$_3$) δ 8.58 (1H, d), 7.74 (2H, m), 7.46 (2H, m), 7.30 (1H, m), 7.20 (2H, m), 6.69 (1H, d), 3.36 (2H, m), 3.13 (2H, m), 2.34 (2H, d), 1.96 (1H, m), 1.80 (2H, m), 1.45 (2H, m)

Example 511: 2-[1-[4-[4-(4-fluorophenoxy)pyrimidin-2-yl]-2,6-difluoro-phenyl]-4-piperidyl]acetic acid

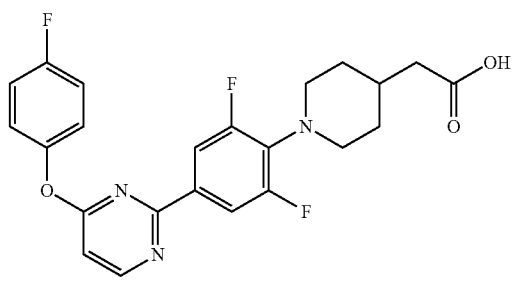 [SMILES: O=C(O)CC1CCN(c2c(F)cc(-c3nccc(Oc4ccc(F)cc4)n3)cc2F)CC1]

2-Chloro-4-(4-fluoro-phenoxy)-pyrimidine (0.133 g, 0.59 mmol) obtained in Preparation Example 314 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.061 g, 28%).

$^1$H-NMR (DMSO-d$_6$) δ 8.70 (1H, d), 7.60 (2H, m), 7.31 (4H, m), 6.98 (1H, d), 3.35 (2H, m), 3.01 (2H, m), 2.16 (2H, d), 1.78 (1H, m), 1.68 (2H, m), 1.27 (2H, m)

Example 512: 2-[1-[4-[4-(4-pyridin-3-yloxy-pyrimidin-2-yl]-2,6-difluoro-phenyl]-4-piperidyl]acetic acid

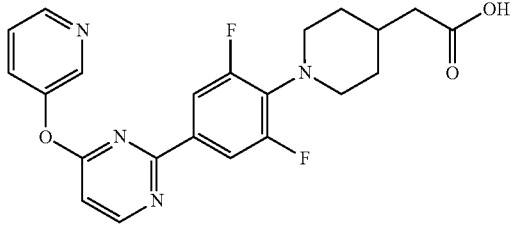

2-Chloro-4-(4-pyridin-3-yloxy)-pyrimidine (0.122 g, 0.59 mmol) obtained in Preparation Example 315 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.081 g, 38%).

$^1$H-NMR (CDCl$_3$) δ 8.64 (2H, m), 8.57 (1H, d), 7.65 (2H, m), 7.62 (1H, m), 7.45 (1H, m), 6.83 (1H, d), 3.34 (2H, m), 3.11 (2H, m), 2.33 (2H, d), 1.96 (1H, m), 1.80 (2H, m), 1.45 (2H, m)

Example 513: 2-[1-[2,6-difluoro-4-[6-(4-fluorophenoxy)pyrazin-2-yl]phenyl]-4-piperidyl]acetic acid

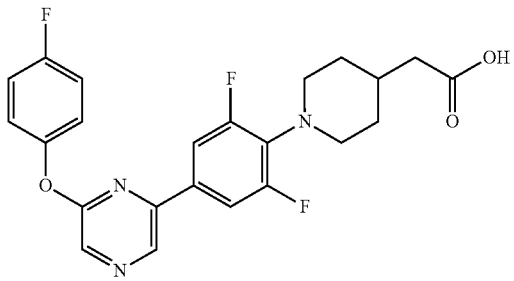 [SMILES: O=C(O)CC1CCN(c2c(F)cc(-c3cncc(Oc4ccc(F)cc4)n3)cc2F)CC1]

2-Chloro-4-(4-fluoro-phenoxy)-pyrazine (0.133 g, 0.59 mmol) obtained in Preparation Example 316 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.143 g, 65%).

$^1$H-NMR (CDCl$_3$) δ 8.62 (1H, s), 8.28 (1H, s), 7.34 (2H, m), 7.20-7.11 (4H, m), 3.33 (2H, m), 3.13 (2H, m), 2.35 (2H, d), 1.97 (1H, m), 1.82 (2H, m), 1.45 (2H, m)

Example 514: 2-[1-[4-[4-(4-methoxyphenoxy)pyrimidin-2-yl]-2,6-difluoro-phenyl]-4-piperidyl]acetic acid

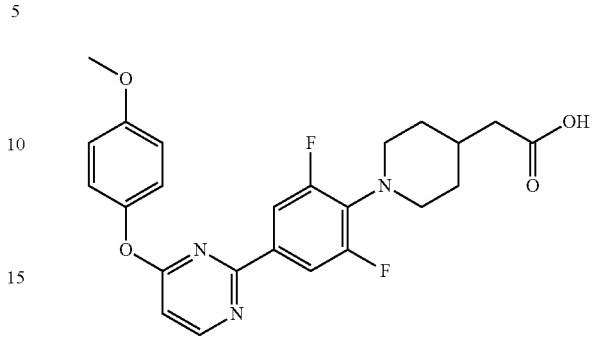

2-Chloro-4-(4-methoxy-phenoxy)-pyrimidine (0.140 g, 0.59 mmol) obtained in Preparation Example 317 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.059 g, 26%).

$^1$H-NMR (CDCl$_3$) δ 8.56 (1H, d), 7.75 (2H, m), 7.11 (2H, m), 6.96 (2H, m), 6.65 (1H, d), 3.85 (3H, s), 3.36 (2H, m), 3.13 (2H, m), 2.35 (2H, d), 1.97 (1H, m), 1.80 (2H, m), 1.47 (2H, m)

Example 515: 2-[1-[2,6-difluoro-4-[4-(4-fluorophenoxy)-6-methyl-pyrimidin-2-yl]phenyl]-4-piperidyl]acetic acid

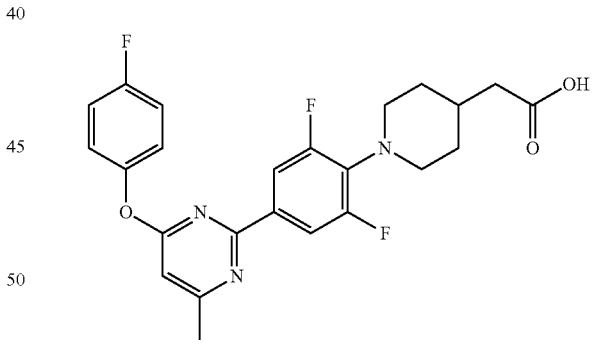

2-Chloro-4-(4-fluoro-phenoxy)-6-methyl-pyrimidine (0.140 g, 0.59 mmol) obtained in Preparation Example 318 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.097 g, 43%).

$^1$H-NMR (CDCl$_3$) δ 7.74 (2H, m), 7.13 (4H, m), 6.52 (1H, s), 3.34 (2H, m), 3.13 (2H, m), 2.51 (3H, s), 2.34 (2H, d), 1.96 (1H, m), 1.80 (2H, m), 1.47 (2H, m)

Example 516: 2-[1-[4-[4-(p-tolyloxy)pyrimidin-2-yl]-2,6-difluoro-phenyl]-4-piperidyl]acetic acid

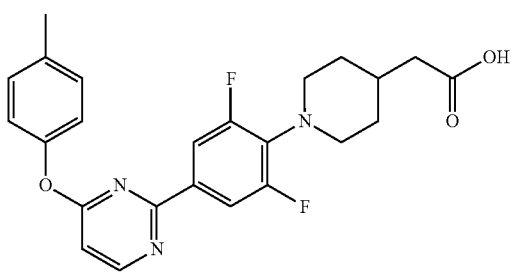 [SMILES: Cc1ccc(Oc2ccnc(-c3cc(F)c(N4CCC(CC(=O)O)CC4)c(F)c3)n2)cc1]

2-Chloro-4-p-tolyloxypyrimidine (0.130 g, 0.59 mmol) obtained in Preparation Example 319 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.07 g, 32%).

$^1$H-NMR (CDCl$_3$) δ 8.56 (1H, d), 7.76 (2H, m), 7.24 (2H, d), 7.08 (2H, d), 6.66 (1H, d), 3.36 (2H, m), 3.13 (2H, m), 2.40 (3H, s), 2.35 (2H, d), 1.97 (1H, m), 1.80 (2H, m), 1.47 (2H, m)

Example 517: 2-[1-[4-[4-(3,4-difluorophenoxy)pyrimidin-2-yl]-2,6-difluoro-phenyl]-4-piperidyl]acetic acid

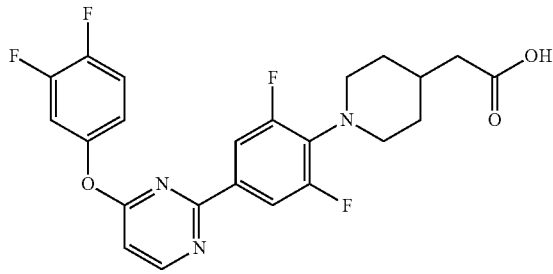 [SMILES: O=C(O)CC1CCN(c2c(F)cc(-c3nccc(Oc4ccc(F)c(F)c4)n3)cc2F)CC1]

2-Chloro-4-(3,4-difluoro-phenoxy)-pyrimidine (0.143 g, 0.59 mmol) obtained in Preparation Example 320 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.08 g, 35%).

$^1$H-NMR (CDCl$_3$) δ 8.61 (1H, d), 7.69 (2H, m), 7.24 (1H, m), 7.09 (1H, m), 6.96 (1H, m), 6.76 (1H, d), 3.36 (2H, m), 3.14 (2H, m), 2.35 (2H, d), 1.97 (1H, m), 1.80 (2H, m), 1.47 (2H, m)

Example 518: 4-[4-(5-chloro-2-methyl-benzofuran-7-yl)-2,6-difluoro-phenoxy]-butyric acid

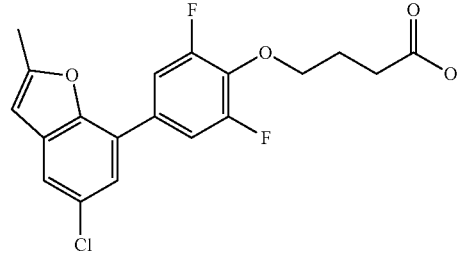 [SMILES: Cc1cc2cc(Cl)cc(-c3cc(F)c(OCCCC(=O)O)c(F)c3)c2o1]

7-Bromo-5-chloro-2-methyl-benzofuran (0.030 g, 0.12 mmol) obtained in Preparation Example 328 and 4-[2,6-difluoro-4-(4,4,5,5-tetramethyl-1,3,2-dioxaborolan-2-yl)phenoxy]butyric acid ethyl ester (0.045 g, 0.12 mmol) obtained in Preparation Example 16 were reacted in the same manner as in Example 1 to obtain the title compound (0.023 g, 49%).

$^1$H-NMR (CDCl$_3$) δ 7.41 (3H, m), 7.24 (1H, s), 6.38 (1H, s), 4.27 (2H, t), 2.70 (2H, t), 2.49 (3H, s), 2.14 (2H, m)

Example 519: 5-[4-(5-chloro-2-methyl-benzofuran-7-yl)-2,6-difluoro-phenyl]-hexanoic acid

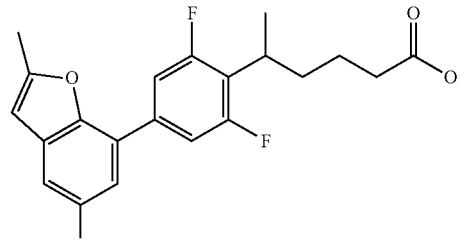

7-Bromo-5-chloro-2-methyl-benzofuran (0.030 g, 0.12 mmol) obtained in Preparation Example 328 and 5-[2,6-difluoro-4-(4,4,5,5-tetramethyl-[1,3,2]dioxaborolan-2-yl)phenyl]hexanoic acid ethyl ester (0.047 g, 0.12 mmol) obtained in Preparation Example 32 were reacted in the same manner as in Example 1 to obtain the title compound (0.025 g, 53%).

$^1$H-NMR (CDCl$_3$) δ 7.41 (1H, s), 7.32 (2H, d), 7.29 (1H, s), 6.38 (1H, s), 3.27 (1H, m), 2.89 (3H, s), 2.38 (2H, t), 1.86 (1H, m), 1.75 (1H, m), 1.66 (1H, m), 1.55 (1H, m), 1.38 (3H, d)

Example 520: 4-[(3'-cyclobutylmethoxy-3,5-difluoro-biphenyl-4-yl)-methyl-amino]-butyric acid

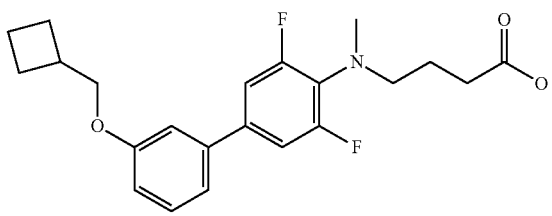 [SMILES: CN(CCCC(=O)O)c1c(F)cc(-c2cccc(OCC3CCC3)c2)cc1F]

1-Bromo-3-cyclobutylmethoxy-benzene (0.050 g, 0.21 mmol) obtained in Preparation Example 323 and 4-{[2,6-difluoro-4-(4,4,5,5-tetramethyl-[1,3,2]dioxaborolan-2-yl)-phenyl]-methyl-amino}-butyric acid methyl ester (0.077 g, 0.21 mmol) obtained in Preparation Example 183 were reacted in the same manner as in Example 1 to obtain the title compound (0.025 g, 31%).

$^1$H-NMR (CDCl$_3$) δ 7.43 (1H, t), 7.08 (4H, m), 6.90 (1H, m), 3.97 (2H, d), 3.18 (2H, t), 2.87 (3H, s), 2.81 (1H, m), 2.48 (2H, t), 2.16 (2H, m), 1.91 (6H, m)

Example 521: 4-(3'-cyclobutylmethoxy-3,5-difluoro-biphenyl-4-yloxy)-butyric acid

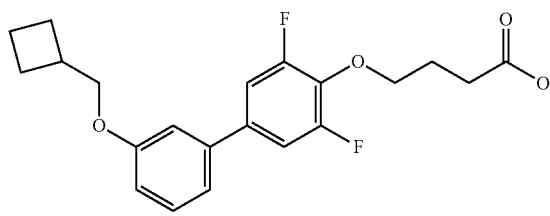 [SMILES: O=C(O)CCCOc1c(F)cc(-c2cccc(OCC3CCC3)c2)cc1F]

1-Bromo-3-cyclobutylmethoxy-benzene (0.030 g, 0.12 mmol) obtained in Preparation Example 323 and 4-[2,6-difluoro-4-(4,4,5,5-tetramethyl-1,3,2-dioxaborolan-2-yl)phenoxy]butyric acid ethyl ester (0.046 g, 0.12 mmol) obtained in Preparation Example 16 were reacted in the same manner as in Example 1 to obtain the title compound (0.015 g, 32%).

$^1$H-NMR (CDCl$_3$) δ 7.32 (1H, t), 7.12 (2H, m), 7.16 (1H, m), 7.02 (1H, m), 6.90 (1H, m), 4.23 (2H, t), 3.97 (2H, d), 2.80 (1H, m), 2.69 (2H, t), 2.16 (4H, m), 1.91 (4H, m)

Example 522: 4-{[4-(6-cyclobutylmethoxy-pyridin-2-yl)-2,6-difluoro-phenyl]-methyl-amino}-butyric acid

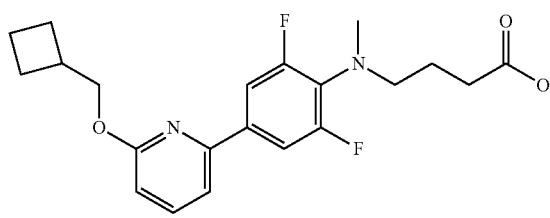 [SMILES: CN(CCCC(=O)O)c1c(F)cc(-c2cccc(OCC3CCC3)n2)cc1F]

2-Chloro-6-cyclobutylmethoxy-pyridine (0.050 g, 0.25 mmol) obtained in Preparation Example 324 and 4-{[2,6-difluoro-4-(4,4,5,5-tetramethyl-[1,3,2]dioxaborolan-2-yl)-phenyl]-methyl-amino}-butyric acid methyl ester (0.093 g, 0.25 mmol) obtained in Preparation Example 183 were reacted in the same manner as in Example 1 to obtain the title compound (0.030 g, 30%).

$^1$H-NMR (CDCl$_3$) δ 7.61 (1H, t), 7.53 (2H, m), 7.20 (1H, d), 6.68 (1H, d), 4.37 (2H, d), 3.20 (2H, t), 2.89 (3H, s), 2.81 (1H, m), 2.47 (2H, t), 2.15 (2H, m), 1.92 (6H, m)

Example 523: 4-[4-(6-cyclobutylmethoxy-pyridin-2-yl)-2,6-difluoro-phenoxy]-butyric acid

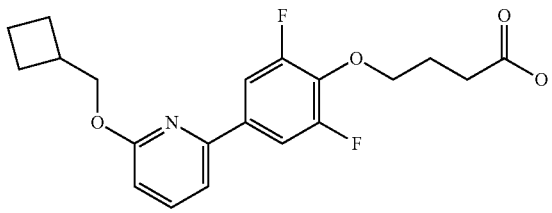 [SMILES: O=C(O)CCCOc1c(F)cc(-c2cccc(OCC3CCC3)n2)cc1F]

2-Chloro-6-cyclobutylmethoxy-pyridine (0.030 g, 0.15 mmol) obtained in Preparation Example 324 and 4-[2,6-difluoro-4-(4,4,5,5-tetramethyl-1,3,2-dioxaborolan-2-yl)phenoxy]butyric acid ethyl ester (0.056 g, 0.15 mmol) obtained in Preparation Example 16 were reacted in the same manner as in Example 1 to obtain the title compound (0.018 g, 31%).

$^1$H-NMR (CDCl$_3$) δ 7.60 (3H, m), 7.21 (1H, d), 6.69 (1H, d), 4.36 (2H, d), 4.24 (2H, t), 2.81 (1H, m), 2.69 (2H, t), 2.14 (4H, m), 1.92 (4H, m)

Example 524: 4-[(3'-cyclopropylmethoxy-3,5-difluoro-biphenyl-4-yl)-methyl-amino]-butyric acid

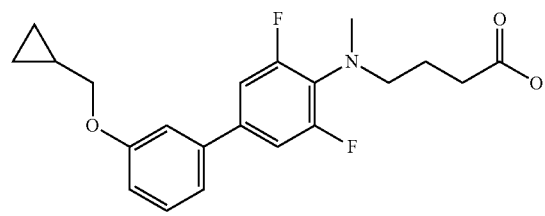 [SMILES: CN(CCCC(=O)O)c1c(F)cc(-c2cccc(OCC3CC3)c2)cc1F]

1-Bromo-3-cyclopropylmethoxy-benzene (0.050 g, 0.22 mmol) obtained in Preparation Example 280 and 4-{[2,6-difluoro-4-(4,4,5,5-tetramethyl-[1,3,2]dioxaborolan-2-yl)-phenyl]-methyl-amino}-butyric acid methyl ester (0.081 g, 0.22 mmol) obtained in Preparation Example 183 were reacted in the same manner as in Example 1 to obtain the title compound (0.025 g, 30%).

$^1$H-NMR (CDCl$_3$) δ 7.32 (1H, t), 7.07 (4H, m), 6.89 (1H, m), 3.85 (2H, d), 3.16 (2H, t), 2.87 (3H, s), 2.48 (2H, t), 1.87 (2H, m), 1.31 (1H, m), 0.66 (2H, m), 0.38 (2H, m)

Example 525: 4-[(3'-cyclopentyloxy-3,5-difluoro-biphenyl-4-yl)-methyl-amino]-butyric acid

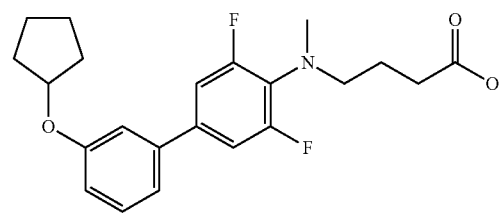 [SMILES: CN(CCCC(=O)O)c1c(F)cc(-c2cccc(OC3CCCC3)c2)cc1F]

1-Bromo-3-cyclopentyloxy-benzene (0.050 g, 0.21 mmol) obtained in Preparation Example 297 and 4-{[2,6- difluoro-4-(4,4,5,5-tetramethyl-[1,3,2]dioxaborolan-2-yl)-phenyl]-methyl-amino}-butyric acid methyl ester (0.077 g, 0.21 mmol) obtained in Preparation Example 183 were reacted in the same manner as in Example 1 to obtain the title compound (0.026 g, 32%).

¹H-NMR (CDCl₃) δ 7.32 (1H, t), 7.07 (3H, m), 7.00 (1H, m), 6.85 (1H, m), 4.81 (1H, m), 3.16 (2H, t), 2.87 (3H, s), 2.48 (2H, t), 1.92 (8H, m), 1.64 (2H, m)

Example 526: 4-(3'-cyclopropylmethoxy-3,5-difluoro-4'-methoxy-biphenyl-4-yloxy)-butyric acid

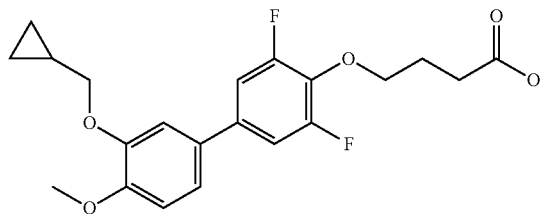 [SMILES: COc1ccc(-c2cc(F)c(OCCCC(=O)O)c(F)c2)cc1OCC1CC1]

4-Bromo-2-cyclopropylmethoxy-1-methoxy-benzene (0.050 g, 0.19 mmol) obtained in Preparation Example 282 and 4-[2,6-difluoro-4-(4,4,5,5-tetramethyl-1,3,2-dioxaborolan-2-yl)phenoxy]butyric acid ethyl ester (0.072 g, 0.19 mmol) obtained in Preparation Example 16 were reacted in the same manner as in Example 1 to obtain the title compound (0.032 g, 42%).

¹H-NMR (CDCl₃) δ 7.06 (3H, m), 6.99 (1H, m), 6.93 (1H, d), 4.21 (2H, t), 3.94 (5H, m), 2.68 (2H, t), 2.13 (2H, m), 1.37 (1H, m), 0.67 (2H, m), 0.39 (2H, m)

Example 527: 4-(3'-cyclopropylmethoxy-3,5,4'-trifluoro-biphenyl-4-yloxy)-butyric acid

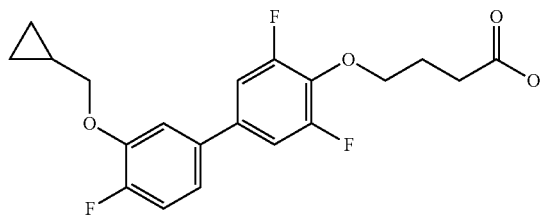 [SMILES: O=C(O)CCCOc1c(F)cc(-c2ccc(F)c(OCC3CC3)c2)cc1F]

4-Bromo-2-cyclopropylmethoxy-1-fluoro-benzene (0.050 g, 0.20 mmol) obtained in Preparation Example 283 and 4-[2,6-difluoro-4-(4,4,5,5-tetramethyl-1,3,2-dioxaborolan-2-yl)phenoxy]butyric acid ethyl ester (0.076 g, 0.20 mmol) obtained in Preparation Example 16 were reacted in the same manner as in Example 1 to obtain the title compound (0.025 g, 32%).

¹H-NMR (CDCl₃) δ 7.13 (1H, m), 7.05 (4H, m), 4.21 (2H, t), 3.93 (2H, d), 2.68 (2H, t), 2.12 (2H, m), 1.34 (1H, m), 0.67 (2H, m), 0.39 (2H, m)

Example 528: 4-(5'-cyclobutoxy-3,5,3'-trifluoro-biphenyl-4-yloxy)-butyric acid

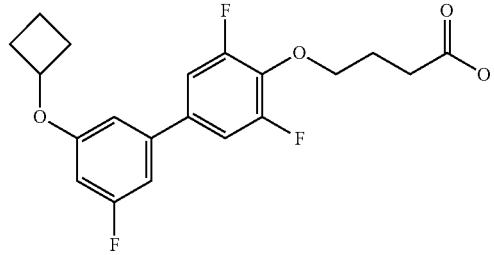 [SMILES: O=C(O)CCCOc1c(F)cc(-c2cc(F)cc(OC3CCC3)c2)cc1F]

1-Bromo-3-cyclobutoxy-5-fluoro-benzene (0.050 g, 0.20 mmol) obtained in Preparation Example 284 and 4-[2,6-difluoro-4-(4,4,5,5-tetramethyl-1,3,2-dioxaborolan-2-yl)phenoxy]butyric acid ethyl ester (0.076 g, 0.20 mmol) obtained in Preparation Example 16 were reacted in the same manner as in Example 1 to obtain the title compound (0.030 g, 39%).

¹H-NMR (CDCl₃) δ 7.08 (2H, m), 6.77 (1H, m), 6.72 (1H, m), 6.51 (1H, m), 4.66 (1H, m), 4.24 (2H, t), 2.68 (2H, t), 2.47 (2H, m), 2.12 (4H, m), 1.89 (1H, m), 1.74 (1H, m)

Example 529: 4-[(5'-cyclobutylmethoxy-3,5-difluoro-2'-methyl-biphenyl-4-yl)-methyl-amino]-butyric acid

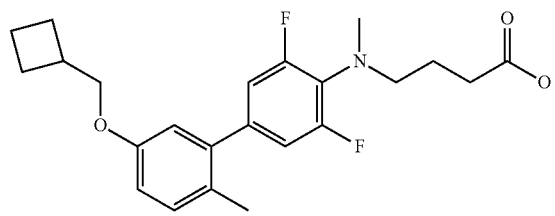 [SMILES: Cc1ccc(OCC2CCC2)cc1-c1cc(F)c(N(C)CCCC(=O)O)c(F)c1]

2-Bromo-4-cyclobutylmethoxy-1-methyl-benzene (0.050 g, 0.20 mmol) obtained in Preparation Example 325 and 4-{[2,6-difluoro-4-(4,4,5,5-tetramethyl-[1,3,2]dioxaborolan-2-yl)-phenyl]-methyl-amino}-butyric acid methyl ester (0.072 g, 0.20 mmol) obtained in Preparation Example 183 were reacted in the same manner as in Example 1 to obtain the title compound (0.024 g, 30%).

¹H-NMR (CDCl₃) δ 7.14 (1H, d), 6.83 (3H, m), 6.74 (1H, m), 3.92 (2H, d), 3.19 (2H, t), 2.88 (3H, s), 2.76 (1H, m), 2.51 (2H, t), 2.20 (3H, s), 2.14 (2H, m), 1.95 (6H, m)

Example 530: 4-(5'-cyclobutylmethoxy-3,5-difluoro-2'-methyl-biphenyl-4-yloxy)-butyric acid

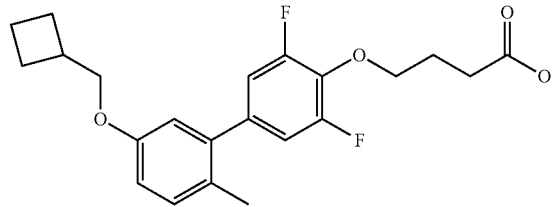 [SMILES: Cc1ccc(OCC2CCC2)cc1-c1cc(F)c(OCCCC(=O)O)c(F)c1]

2-Bromo-4-cyclobutylmethoxy-1-methyl-benzene (0.025 g, 0.10 mmol) obtained in Preparation Example 325 and 4-[2,6-difluoro-4-(4,4,5,5-tetramethyl-1,3,2-dioxaborolan-2-yl)phenoxy]butyric acid ethyl ester (0.036 g, 0.10 mmol) obtained in Preparation Example 16 were reacted in the same manner as in Example 1 to obtain the title compound (0.020 g, 52%).

¹H-NMR (CDCl₃) δ 7.14 (1H, d), 6.86 (3H, m), 6.73 (1H, m), 4.24 (2H, t), 3.91 (2H, d), 2.75 (1H, m), 2.70 (2H, t), 2.18 (3H, s), 2.14 (4H, m), 1.95 (4H, m)

Example 531: 4-{[4-(5-chloro-6-cyclobutoxy-pyridin-2-yl)-2,6-difluoro-phenyl]-methyl-amino}-butyric acid

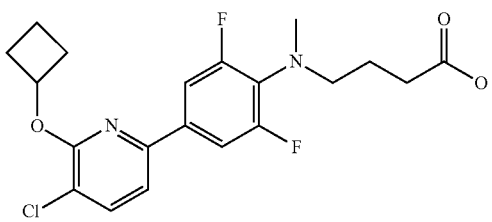

3,6-Dichloro-2-cyclobutoxy-pyridine (0.050 g, 0.23 mmol) obtained in Preparation Example 298 and 4-{[2,6-difluoro-4-(4,4,5,5-tetramethyl-[1,3,2]dioxaborolan-2-yl)-phenyl]-methyl-amino}-butyric acid methyl ester (0.085 g, 0.23 mmol) obtained in Preparation Example 183 were reacted in the same manner as in Example 1 to obtain the title compound (0.015 g, 16%).

¹H-NMR (CDCl₃) δ 7.64 (1H, d), 7.46 (2H, m), 7.16 (1H, d), 5.33 (1H, m), 3.19 (2H, t), 2.89 (3H, s), 2.54 (2H, m), 2.46 (2H, t), 2.28 (2H, m), 1.89 (3H, m), 1.77 (1H, m)

Example 532: 4-(3'-cyclopropylmethoxy-3,5-difluoro-4'-methyl-biphenyl-4-yloxy)-butyric acid

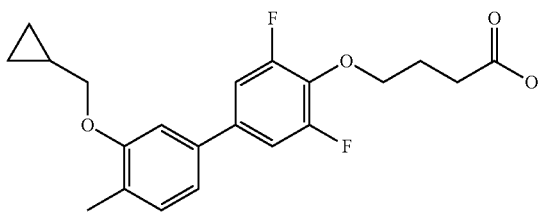 [SMILES: Cc1ccc(-c2cc(F)c(OCCCC(=O)O)c(F)c2)cc1OCC1CC1]

4-Bromo-2-cyclopropylmethoxy-1-methyl-benzene (0.050 g, 0.21 mmol) obtained in Preparation Example 327 and 4-[2,6-difluoro-4-(4,4,5,5-tetramethyl-1,3,2-dioxaborolan-2-yl)phenoxy]butyric acid ethyl ester (0.077 g, 0.21 mmol) obtained in Preparation Example 16 were reacted in the same manner as in Example 1 to obtain the title compound (0.025 g, 32%).

¹H-NMR (CDCl₃) δ 7.18 (1H, d), 7.09 (2H, m), 6.99 (1H, d), 6.88 (1H, s), 4.22 (2H, t), 3.88 (2H, d), 2.68 (2H, t), 2.27 (3H, s), 2.12 (2H, m), 1.29 (1H, m), 0.64 (2H, m), 0.39 (2H, m)

Example 533: 4-[4-(5-chloro-6-cyclobutoxy-pyridin-2-yl)-2,6-difluoro-phenoxy]-butyric acid

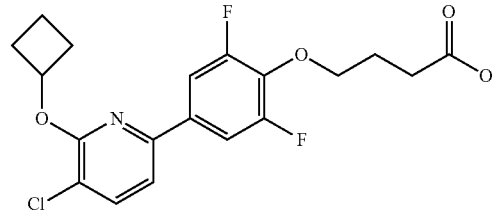 [SMILES: O=C(O)CCCOc1c(F)cc(-c2ccc(Cl)c(OC3CCC3)n2)cc1F]

3,6-Dichloro-2-cyclobutoxy-pyridine (0.050 g, 0.23 mmol) obtained in Preparation Example 298 and 4-[2,6-difluoro-4-(4,4,5,5-tetramethyl-1,3,2-dioxaborolan-2-yl)phenoxy]butyric acid ethyl ester (0.085 g, 0.23 mmol) obtained in Preparation Example 16 were reacted in the same manner as in Example 1 to obtain the title compound (0.020 g, 22%).

¹H-NMR (CDCl₃) δ 7.65 (1H, d), 7.53 (2H, m), 7.16 (1H, d), 5.33 (1H, m), 4.25 (2H, t), 2.68 (2H, t), 2.55 (2H, m), 2.26 (2H, m), 2.12 (2H, m), 1.90 (1H, m), 1.77 (1H, m)

Example 534: 4-(4'-chloro-3'-cyclopropylmethoxy-3,5-difluoro-biphenyl-4-yloxy)-butyric acid

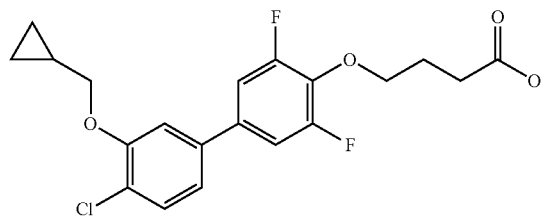 [SMILES: O=C(O)CCCOc1c(F)cc(-c2ccc(Cl)c(OCC3CC3)c2)cc1F]

4-Bromo-1-chloro-2-cyclopropylmethoxy-benzene (0.050 g, 0.19 mmol) obtained in Preparation Example 326 and 4-[2,6-difluoro-4-(4,4,5,5-tetramethyl-1,3,2-dioxaborolan-2-yl)phenoxy]butyric acid ethyl ester (0.071 g, 0.19 mmol) obtained in Preparation Example 16 were reacted in the same manner as in Example 1 to obtain the title compound (0.015 g, 20%).

¹H-NMR (CDCl₃) δ 7.40 (1H, d), 7.08 (2H, m), 6.99 (2H, m), 4.23 (2H, t), 3.95 (2H, d), 2.68 (2H, t), 2.13 (2H, m), 1.35 (1H, m), 0.68 (2H, m), 0.42 (2H, m)

Example 535: 5-(5'-cyclobutoxy-3,3'-difluoro-biphenyl-4-yl)-pentanoic acid

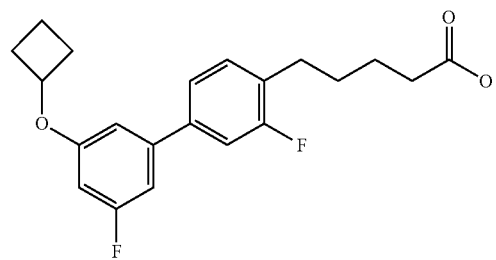 [SMILES: O=C(O)CCCCc1ccc(-c2cc(F)cc(OC3CCC3)c2)cc1F]

1-Bromo-3-cyclobutoxy-5-fluoro-benzene (0.050 g, 0.20 mmol) obtained in Preparation Example 284 and 5-[2-fluoro-4-(4,4,5,5-tetramethyl-[1,3,2]dioxaborolan-2-yl)-phenyl]-pentanoic acid ethyl ester (0.072 g, 0.20 mmol) obtained in Preparation Example 201 were reacted in the same manner as in Example 1 to obtain the title compound (0.025 g, 34%).

$^1$H-NMR (CDCl$_3$) δ 7.22 (3H, m), 6.78 (2H, m), 6.51 (1H, m), 4.67 (1H, m), 2.70 (2H, t), 2.46 (4H, m), 2.21 (2H, m), 1.89 (1H, m), 1.71 (5H, m)

Example 536: 4-(5'-cyclobutoxy-3,3'-difluoro-biphenyl-4-yloxy)-butyric acid

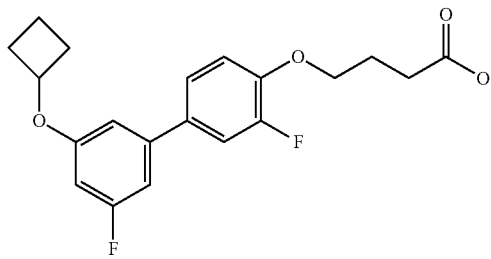 [SMILES: O=C(O)CCCOc1ccc(-c2cc(F)cc(OC3CCC3)c2)cc1F]

1-Bromo-3-cyclobutoxy-5-fluoro-benzene (0.025 g, 0.10 mmol) obtained in Preparation Example 284 and 4-[2-fluoro-4-(4,4,5,5-tetramethyl-1,3,2-dioxaborolan-2-yl)phenoxy]butyric acid ethyl ester (0.036 g, 0.10 mmol) obtained in Preparation Example 198 were reacted in the same manner as in Example 1 to obtain the title compound (0.021 g, 57%).

$^1$H-NMR (CDCl$_3$) δ 7.52 (2H, m), 7.01 (1H, t), 6.75 (2H, m), 6.48 (1H, m), 4.66 (1H, m), 4.14 (2H, t), 2.65 (2H, t), 2.47 (2H, m), 2.19 (4H, m), 1.89 (1H, m), 1.71 (1H, m)

Example 537: 5-[4-(6-cyclobutoxy-pyridin-2-yl)-2-fluoro-phenyl]-pentanoic acid

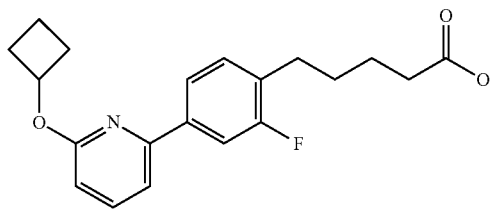 [SMILES: O=C(O)CCCCc1ccc(-c2cccc(OC3CCC3)n2)cc1F]

2-Chloro-6-cyclobutoxy-pyridine (0.050 g, 0.27 mmol) obtained in Preparation Example 29 and 5-[2-fluoro-4-(4,4,5,5-tetramethyl-[1,3,2]dioxaborolan-2-yl)-phenyl]-pentanoic acid ethyl ester (0.095 g, 0.27 mmol) obtained in Preparation Example 201 were reacted in the same manner as in Example 1 to obtain the title compound (0.019 g, 20%).

$^1$H-NMR (CDCl$_3$) δ 7.70 (2H, m), 7.51 (1H, t), 7.36 (1H, d), 7.25 (1H, m), 7.03 (1H, d), 4.46 (1H, m), 2.72 (2H, m), 2.61 (2H, m), 2.42 (2H, m), 2.20 (4H, m), 1.72 (4H, m)

Example 538: 4-[4-(6-cyclobutoxy-pyridin-2-yl)-2-fluoro-phenoxy]-butyric acid

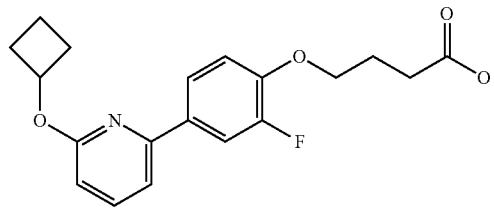 [SMILES: O=C(O)CCCOc1ccc(-c2cccc(OC3CCC3)n2)cc1F]

2-Chloro-6-cyclobutoxy-pyridine (0.035 g, 0.19 mmol) obtained in Preparation Example 29 and 4-[2-fluoro-4-(4,4,5,5-tetramethyl-1,3,2-dioxaborolan-2-yl)phenoxy]butyric acid ethyl ester (0.067 g, 0.19 mmol) obtained in Preparation Example 198 were reacted in the same manner as in Example 1 to obtain the title compound (0.030 g, 46%).

$^1$H-NMR (CDCl$_3$) δ 7.81 (1H, m), 7.73 (1H, d), 7.49 (1H, t), 7.32 (1H, d), 7.01 (2H, m), 4.44 (1H, m), 4.17 (2H, t), 2.65 (4H, m), 2.20 (6H, m)

Example 539: 4-[4-(6-cyclobutylmethoxy-pyridin-2-yl)-2-fluoro-phenoxy]-butyric acid

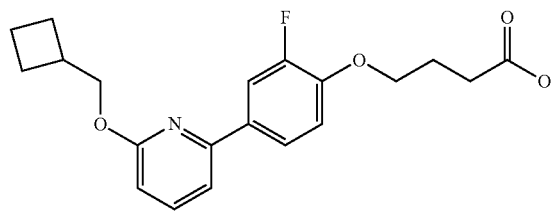 [SMILES: O=C(O)CCCOc1ccc(-c2cccc(OCC3CCC3)n2)cc1F]

2-Chloro-6-cyclobutylmethoxy-pyridine (0.030 g, 0.15 mmol) obtained in Preparation Example 324 and 4-[2-fluoro-4-(4,4,5,5-tetramethyl-1,3,2-dioxaborolan-2-yl)phenoxy]butyric acid ethyl ester (0.054 g, 0.15 mmol) obtained in Preparation Example 198 were reacted in the same manner as in Example 1 to obtain the title compound (0.024 g, 44%).

$^1$H-NMR (CDCl$_3$) δ 7.81 (1H, m), 7.70 (1H, d), 7.59 (1H, t), 7.22 (1H, d), 7.02 (1H, t), 6.64 (1H, d), 4.37 (2H, d), 4.15 (2H, t), 2.82 (1H, m), 2.65 (2H, t), 2.20 (4H, m), 1.92 (4H, m)

Example 540: 4-[4-(6-cyclobutylsulfanyl-pyridin-2-yl)-2-fluoro-phenoxy]-butyric acid

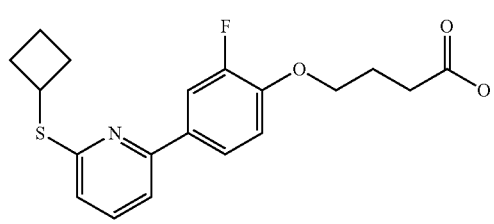 [SMILES: O=C(O)CCCOc1ccc(-c2cccc(SC3CCC3)n2)cc1F]

2-Chloro-6-cyclobutylsulfanyl-pyridine (0.030 g, 0.15 mmol) obtained in Preparation Example 299 and 4-[2- fluoro-4-(4,4,5,5-tetramethyl-1,3,2-dioxaborolan-2-yl)phe-noxy]butyric acid ethyl ester (0.053 g, 0.15 mmol) obtained in Preparation Example 198 were reacted in the same manner as in Example 1 to obtain the title compound (0.025 g, 46%).

¹H-NMR (CDCl₃) δ 7.81 (1H, m), 7.73 (1H, d), 7.49 (1H, t), 7.31 (1H, d), 7.01 (2H, m), 4.44 (1H, m), 4.17 (2H, t), 2.65 (4H, m), 2.20 (6H, m)

Example 541: 2-(3'-cyclobutoxy-3,5,5'-trifluoro-biphenyl-4-yloxymethyl)-cyclopropanecarboxylic acid

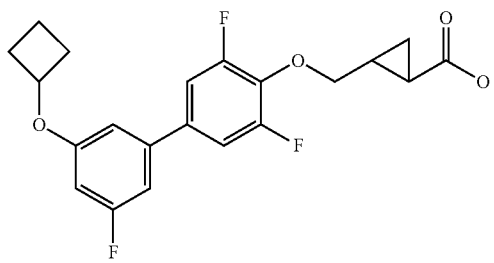 [SMILES: O=C(O)C1CC1COc1c(F)cc(-c2cc(F)cc(OC3CCC3)c2)cc1F]

Step A: 5'-cyclobutoxy-3,5,3'-trifluoro-biphenyl-4-ol

1-Bromo-3-cyclobutoxy-5-fluoro-benzene (1.0 g, 4.08 mmol) obtained in Preparation Example 284 and 2,6-difluoro-4-(4,4,5,5-tetramethyl-1,3,2-dioxaborolan-2-yl)phe-nol (1.04 g, 4.08 mmol) obtained in Step B of Preparation Example 16 were reacted in the same manner as in Step A of Example 1 to obtain the title compound (0.50 g, 42%).

¹H-NMR (CDCl₃) δ 7.10 (2H, m), 6.72 (2H, m), 6.51 (1H, m), 5.21 (1H, s), 4.67 (1H, m), 2.47 (2H, m), 2.19 (2H, m), 1.89 (1H, m), 1.72 (1H, m)

Step B: 2-(3'-cyclobutoxy-3,5,5'-trifluoro-biphenyl-4-yloxymethyl)-cyclopropanecarboxylic acid 5'-Cyclobutoxy-3,5,3'-trifluoro-biphenyl-4-ol (0.045 g, 0.15 mmol) obtained in Step A and 2-hydroxymethyl-cyclopropanecarboxylic acid ethyl ester (0.033 g, 0.23 mmol) were sequentially reacted in the same manner as in Preparation Example 62 and Step B of Example 1 to obtain the title compound (0.035 g, 58%).

¹H-NMR (CDCl₃) δ 7.08 (2H, m), 6.77 (1H, d), 6.72 (1H, s), 6.51 (1H, m), 4.67 (1H, m), 4.17 (1H, m), 4.03 (1H, m), 2.48 (2H, m), 2.20 (2H, m), 1.96 (1H, m), 1.90 (1H, m), 1.72 (2H, m), 1.36 (1H, m), 1.06 (1H, m)

Example 542: 2-[4-(4-cyclobutoxy-6-methyl-pyrimidin-2-yl)-2,6-difluoro-phenoxymethyl]-cyclopropanecarboxylic acid

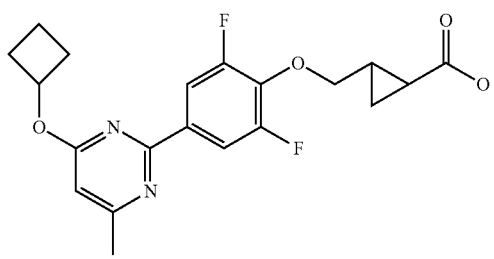 [SMILES: Cc1cc(OC2CCC2)nc(-c2cc(F)c(OCC3CC3C(=O)O)c(F)c2)n1]

2-Chloro-4-cyclobutoxy-6-methyl-pyrimidine (0.050 g, 0.25 mmol) obtained in Preparation Example 228 and 2-[2,6-difluoro-4-(4,4,5,5-tetramethyl-[1,3,2]dioxaborolan-2-yl)-phenoxymethyl]-cyclopropanecarboxylic acid ethyl ester (0.096 g, 0.25 mmol) obtained in Preparation Example 321 were reacted in the same manner as in Example 1 to obtain the title compound (0.030 g, 31%).

¹H-NMR (CDCl₃) δ 7.99 (2H, m), 6.42 (1H, s), 5.31 (1H, m), 4.12 (2H, m), 2.51 (2H, m), 2.46 (3H, s), 2.20 (2H, m), 1.96 (1H, m), 1.89 (1H, m), 1.72 (2H, m), 1.35 (1H, m), 1.08 (1H, m)

Example 543: 2-[4-(4-cyclobutoxy-pyrimidin-2-yl)-2,6-difluoro-phenoxymethyl]-cyclopropanecarboxylic acid

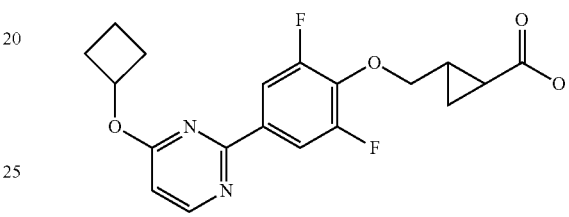

2-Chloro-4-cyclobutoxy-pyrimidine (0.050 g, 0.27 mmol) obtained in Preparation Example 230 and 2-[2,6-difluoro-4-(4,4,5,5-tetramethyl-[1,3,2]dioxaborolan-2-yl)-phe-noxymethyl]-cyclopropanecarboxylic acid ethyl ester (0.104 g, 0.27 mmol) obtained in Preparation Example 321 were reacted in the same manner as in Example 1 to obtain the title compound (0.022 g, 22%).

¹H-NMR (CDCl₃) δ 8.46 (1H, d), 7.98 (2H, m), 6.59 (1H, d), 5.34 (1H, m), 4.17 (1H, m), 4.10 (1H, m), 2.55 (2H, m), 2.23 (2H, m), 1.88 (2H, m), 1.78 (2H, m), 1.35 (1H, m), 1.07 (1H, m)

Example 544: 2-[4-(6-cyclobutoxy-pyridin-2-yl)-2,6-difluoro-phenoxymethyl]-cyclopropanecarboxylic acid

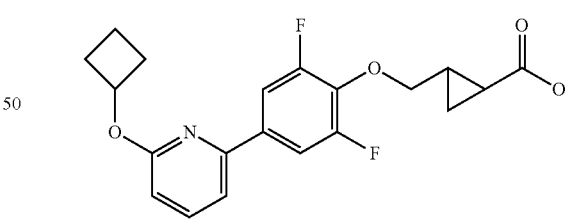

2-Chloro-6-cyclobutoxy-pyridine (0.030 g, 0.16 mmol) obtained in Preparation Example 29 and 2-[2,6-difluoro-4-(4,4,5,5-tetramethyl-[1,3,2]dioxaborolan-2-yl)-phenoxymethyl]-cyclopropanecarboxylic acid ethyl ester (0.062 g, 0.16 mmol) obtained in Preparation Example 321 were reacted in the same manner as in Example 1 to obtain the title compound (0.026 g, 42%).

¹H-NMR (CDCl₃) δ 7.60 (3H, m), 7.21 (1H, d), 6.65 (1H, d), 5.26 (1H, m), 4.14 (1H, m), 4.06 (1H, m), 2.52 (2H, m), 2.20 (2H, m), 2.01 (1H, m), 1.85 (1H, m), 1.75 (2H, m), 1.35 (1H, m), 1.06 (1H, m)

Example 545: 2-[4-(4-cyclopropylmethoxy-pyrimidin-2-yl)-2,6-difluoro-phenoxymethyl]-cyclopropanecarboxylic acid

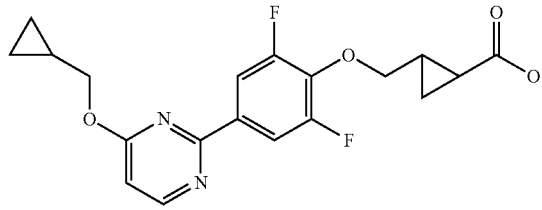 [SMILES: O=C(O)C1CC1COc1c(F)cc(-c2nccc(OCC3CC3)n2)cc1F]

2-Chloro-4-cyclopropylmethoxy-pyrimidine (0.035 g, 0.19 mmol) obtained in Preparation Example 231 and 2-[2,6-difluoro-4-(4,4,5,5-tetramethyl-[1,3,2]dioxaborolan-2-yl)-phenoxymethyl]-cyclopropanecarboxylic acid ethyl ester (0.073 g, 0.16 mmol) obtained in Preparation Example 321 were reacted in the same manner as in Example 96 to obtain the title compound (0.030 g, 42%).

$^1$H-NMR (CDCl$_3$) δ 8.47 (1H, d), 7.99 (2H, m), 6.65 (1H, d), 4.30 (2H, d), 4.18 (1H, m), 4.12 (1H, m), 1.97 (1H, m), 1.71 (1H, m), 1.36 (2H, m), 1.07 (1H, m), 0.66 (2H, m), 0.41 (2H, m)

Example 546: 2-[4-(4-cyclopropylmethoxy-6-methyl-pyrimidin-2-yl)-2,6-difluoro-phenoxymethyl]-cyclopropanecarboxylic acid

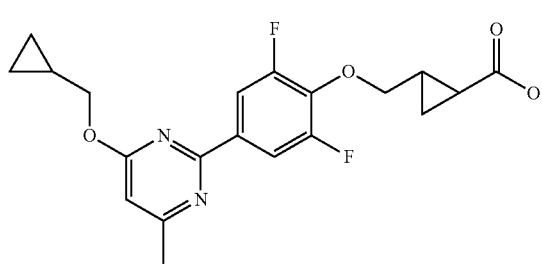 [SMILES: Cc1cc(OCC2CC2)nc(-c2cc(F)c(OCC3CC3C(=O)O)c(F)c2)n1]

2-Chloro-4-cyclopropylmethoxy-6-methyl-pyrimidine (0.030 g, 0.15 mmol) obtained in Preparation Example 227 and 2-[2,6-difluoro-4-(4,4,5,5-tetramethyl-[1,3,2]dioxaborolan-2-yl)-phenoxymethyl]-cyclopropanecarboxylic acid ethyl ester (0.058 g, 0.25 mmol) obtained in Preparation Example 321 were reacted in the same manner as in Example 96 to obtain the title compound (0.026 g, 44%).

$^1$H-NMR (CDCl$_3$) δ 7.99 (2H, m), 6.50 (1H, s), 4.28 (2H, d), 4.12 (2H, m), 2.47 (3H, s), 1.98 (1H, m), 1.71 (1H, m), 1.34 (2H, m), 1.07 (1H, m), 0.65 (2H, m), 0.40 (2H, m)

Example 547: 2-[4-(6-cyclopropylmethoxy-pyrazin-2-yl)-2,6-difluoro-phenoxymethyl]-cyclopropanecarboxylic acid

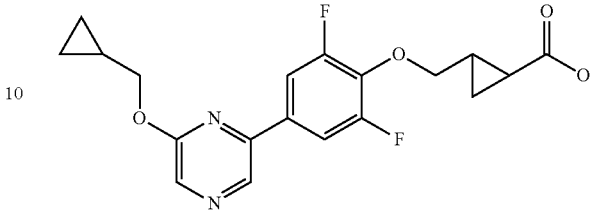

2-Chloro-6-cyclopropylmethoxy-pyrazine (0.030 g, 0.16 mmol) obtained in Preparation Example 233 and 2-[2,6-difluoro-4-(4,4,5,5-tetramethyl-[1,3,2]dioxaborolan-2-yl)-phenoxymethyl]-cyclopropanecarboxylic acid ethyl ester (0.062 g, 0.25 mmol) obtained in Preparation Example 321 were reacted in the same manner as in Example 96 to obtain the title compound (0.015 g, 25%).

$^1$H-NMR (CDCl$_3$) δ 8.48 (1H, s), 8.19 (1H, s), 7.59 (2H, m), 4.26 (2H, d), 4.19 (1H, m), 4.06 (1H, m), 1.98 (1H, m), 1.72 (1H, m), 1.36 (2H, m), 1.06 (1H, m), 0.67 (2H, m), 0.41 (2H, m)

Example 548: 2-[4-(6-cyclobutoxy-4-methyl-pyridin-2-yl)-2,6-difluoro-phenoxymethyl]-cyclopropanecarboxylic acid

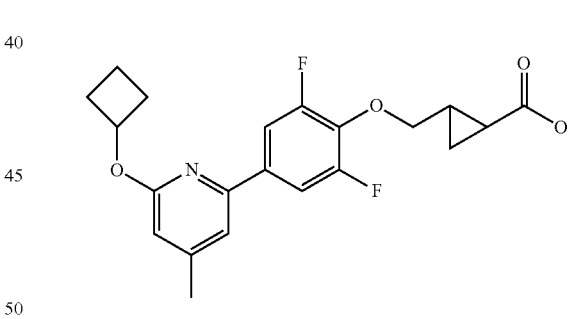

2-Chloro-6-cyclobutoxy-4-methyl-pyridine (0.030 g, 0.15 mmol) obtained in Preparation Example 271 and 2-[2,6-difluoro-4-(4,4,5,5-tetramethyl-[1,3,2]dioxaborolan-2-yl)-phenoxymethyl]-cyclopropanecarboxylic acid ethyl ester (0.058 g, 0.15 mmol) obtained in Preparation Example 321 were reacted in the same manner as in Example 96 to obtain the title compound (0.025 g, 42%).

$^1$H-NMR (CDCl$_3$) δ 7.58 (2H, m), 7.05 (1H, s), 6.47 (1H, s), 5.25 (1H, m), 4.14 (1H, m), 4.04 (1H, m), 2.51 (2H, m), 2.33 (3H, s), 2.17 (1H, m), 1.98 (1H, m), 1.87 (1H, m), 1.72 (2H, m), 1.35 (1H, m), 1.07 (1H, m)

Example 549: 2-[4-(6-cyclopropylmethoxy-pyridin-2-yl)-2,6-difluoro-phenoxymethyl]-cyclopropanecarboxylic acid

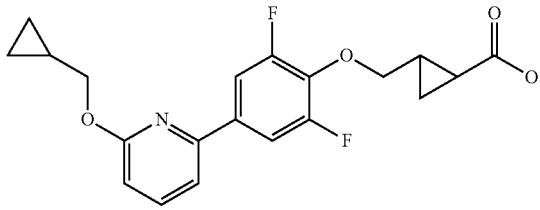 [SMILES: O=C(O)C1CC1COc1c(F)cc(-c2cccc(OCC3CC3)n2)cc1F]

2-Chloro-6-cyclopropylmethoxy-pyridine (0.030 g, 0.16 mmol) obtained in Preparation Example 43 and 2-[2,6-difluoro-4-(4,4,5,5-tetramethyl-[1,3,2]dioxaborolan-2-yl)-phenoxymethyl]-cyclopropanecarboxylic acid ethyl ester (0.062 g, 0.15 mmol) obtained in Preparation Example 321 were reacted in the same manner as in Example 96 to obtain the title compound (0.024 g, 36%).

$^1$H-NMR (CDCl$_3$) δ 7.62 (3H, m), 7.22 (1H, d), 6.73 (1H, d), 4.24 (1H, d), 4.15 (1H, m), 4.04 (1H, m), 1.98 (2H, m), 1.72 (1H, m), 1.35 (2H, m), 1.07 (1H, m), 0.65 (2H, m), 0.39 (2H, m)

Example 550: 2-[4-(6-cyclobutoxy-pyrazin-2-yl)-2,6-difluoro-phenoxymethyl]-cyclopropanecarboxylic acid

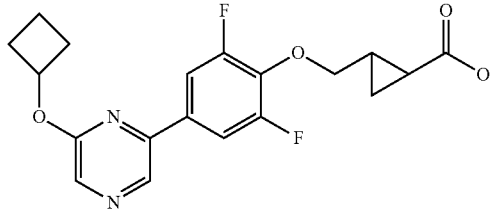 [SMILES: O=C(O)C1CC1COc1c(F)cc(-c2cncc(OC3CCC3)n2)cc1F]

2-Chloro-6-cyclobutoxy-pyrazine (0.030 g, 0.16 mmol) obtained in Preparation Example 232 and 2-[2,6-difluoro-4-(4,4,5,5-tetramethyl-[1,3,2]dioxaborolan-2-yl)-phenoxymethyl]-cyclopropanecarboxylic acid ethyl ester (0.062 g, 0.15 mmol) obtained in Preparation Example 321 were reacted in the same manner as in Example 96 to obtain the title compound (0.026 g, 40%).

$^1$H-NMR (CDCl$_3$) δ 8.52 (1H, s), 8.17 (1H, s), 7.57 (2H, m), 5.28 (1H, d), 4.18 (1H, m), 4.07 (1H, m), 2.54 (2H, m), 2.23 (2H, m), 1.98 (2H, m), 1.77 (2H, m), 1.36 (1H, m), 1.07 (1H, m)

Example 551: 2-[4-(2-cyclobutoxy-thiazol-4-yl)-2,6-difluoro-phenoxymethyl]-cyclopropanecarboxylic acid

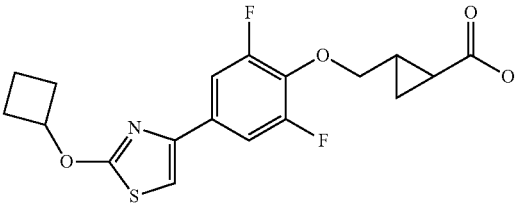 [SMILES: O=C(O)C1CC1COc1c(F)cc(-c2csc(OC3CCC3)n2)cc1F]

4-Bromo-2-cyclobutoxy-thiazole (0.030 g, 0.13 mmol) obtained in Preparation Example 289 and 2-[2,6-difluoro-4-(4,4,5,5-tetramethyl-[1,3,2]dioxaborolan-2-yl)-phenoxymethyl]-cyclopropanecarboxylic acid ethyl ester (0.049 g, 0.13 mmol) obtained in Preparation Example 321 were reacted in the same manner as in Example 96 to obtain the title compound (0.023 g, 44%).

$^1$H-NMR (CDCl$_3$) δ 7.35 (2H, m), 6.78 (1H, s), 5.19 (1H, d), 4.12 (1H, m), 4.02 (1H, m), 2.53 (2H, m), 2.27 (2H, m), 1.95 (1H, m), 1.89 (1H, m), 1.70 (2H, m), 1.31 (1H, m), 1.04 (1H, m)

Example 552: 2-[2-chloro-4-(6-cyclopropylmethoxy-pyridin-2-yl)-6-fluoro-phenoxymethyl]-cyclopropanecarboxylic acid

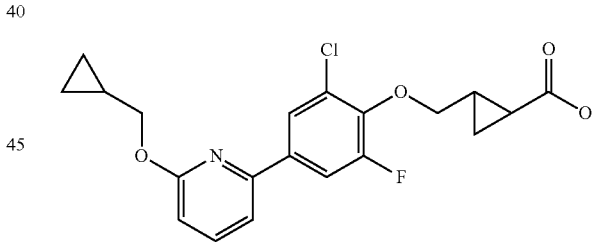

2-Chloro-6-cyclopropylmethoxy-pyridine (0.030 g, 0.16 mmol) obtained in Preparation Example 43 and 2-[2-chloro-6-fluoro-4-(4,4,5,5-tetramethyl-[1,3,2]dioxaborolan-2-yl)-phenoxymethyl]-cyclopropanecarboxylic acid ethyl ester (0.065 g, 0.16 mmol) obtained in Preparation Example 322 were reacted in the same manner as in Example 96 to obtain the title compound (0.021 g, 33%).

$^1$H-NMR (CDCl$_3$) δ 7.80 (1H, s), 7.70 (1H, m), 7.62 (1H, t), 7.23 (1H, d), 6.73 (1H, d), 4.24 (2H, d), 4.15 (1H, m), 4.01 (1H, m), 2.00 (1H, m), 1.75 (1H, m), 1.36 (2H, m), 1.09 (1H, m), 0.65 (2H, m), 0.44 (2H, m)

Example 553: 2-[2-chloro-4-(4-cyclobutoxy-6-methyl-pyrimidin-2-yl)-6-fluoro-phenoxymethyl]-cyclopropanecarboxylic acid

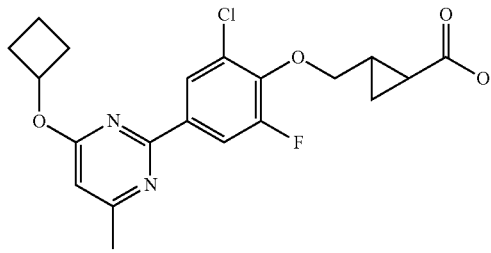 [SMILES: Cc1cc(OC2CCC2)nc(-c2cc(F)c(OCC3CC3C(=O)O)c(Cl)c2)n1]

2-Chloro-4-cyclobutoxy-6-methyl-pyrimidine (0.030 g, 0.15 mmol) obtained in Preparation Example 228 and 2-[2-chloro-6-fluoro-4-(4,4,5,5-tetramethyl-[1,3,2]dioxaborolan-2-yl)-phenoxymethyl]-cyclopropanecarboxylic acid ethyl ester (0.060 g, 0.15 mmol) obtained in Preparation Example 322 were reacted in the same manner as in Example 96 to obtain the title compound (0.020 g, 33%).

$^1$H-NMR (CDCl$_3$) δ 8.24 (1H, s), 8.08 (1H, d), 6.42 (1H, s), 5.31 (1H, m), 4.17 (1H, m), 4.06 (1H, m), 2.51 (2H, m), 2.46 (3H, s), 2.21 (2H, m), 2.02 (1H, m), 1.91 (1H, m), 1.77 (2H, m), 1.36 (1H, m), 1.09 (1H, m)

Example 554: 2-[2-chloro-4-(6-cyclobutoxy-pyridin-2-yl)-6-fluoro-phenoxymethyl]-cyclopropanecarboxylic acid

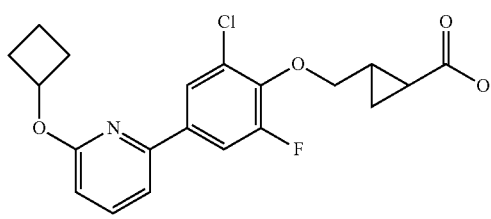 [SMILES: O=C(O)C1CC1COc1c(F)cc(-c2cccc(OC3CCC3)n2)cc1Cl]

2-Chloro-6-cyclobutoxy-pyridine (0.030 g, 0.16 mmol) obtained in Preparation Example 29 and 2-[2-chloro-6-fluoro-4-(4,4,5,5-tetramethyl-[1,3,2]dioxaborolan-2-yl)-phenoxymethyl]-cyclopropanecarboxylic acid ethyl ester (0.065 g, 0.16 mmol) obtained in Preparation Example 322 were reacted in the same manner as in Example 96 to obtain the title compound (0.024 g, 37%).

$^1$H-NMR (CDCl$_3$) δ 7.79 (1H, s), 7.70 (1H, m), 7.60 (1H, t), 7.22 (1H, d), 6.66 (1H, d), 5.26 (1H, m), 4.18 (1H, m), 4.02 (1H, m), 2.53 (2H, m), 2.19 (2H, m), 2.04 (1H, m), 1.89 (1H, m), 1.76 (2H, m), 1.36 (1H, m), 1.09 (1H, m)

Example 555: 3-[6-(3-cyclobutoxy-phenyl)-chroman-2-yl]-propionic acid

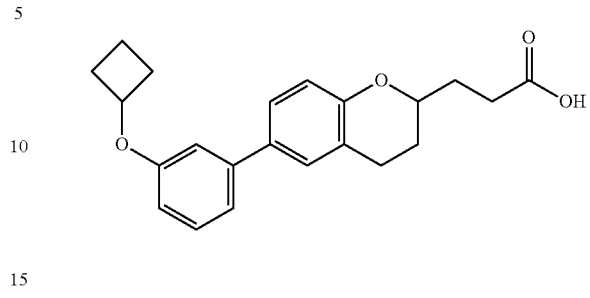

Step A: 3-[6-(3-cyclobutoxy-phenyl)-chroman-2-yl]-propionic acid ethyl ester 3-[6-(4,4,5,5-Tetramethyl-[1,3,2]dioxaborolan-2-yl)-chroman-2-yl]-propionic acid ethyl ester (0.069 g, 0.19 mmol) obtained in Preparation Example 4 and 1-cyclobutoxy-3-iodo-benzene (0.058 g, 0.21 mmol) obtained in Preparation Example 21 were reacted in the same manner as in Step A of Example 1 to obtain the title compound (0.048 g, 66%).

$^1$H-NMR (400 HMz, CDCl$_3$); δ 7.33-7.27 (m, 3H), 7.10-7.08 (m, 1H), 6.98-6.97 (m, 1H), 6.85-6.83 (d, 1H), 6.75-6.72 (m, 1H), 4.72-4.65 (m, 1H), 4.18-4.13 (q, 2H), 4.09-4.03 (m, 1H), 2.93-2.79 (m, 2H), 2.64-2.43 (m, 4H), 2.24-2.17 (m, 2H), 2.04-2.00 (m, 3H), 1.88-1.58 (m, 3H), 1.29-1.25 (t, 3H)

Step B: 3-[6-(3-cyclobutoxy-phenyl)-chroman-2-yl]-propionic acid

3-[6-(3-Cyclobutoxy-phenyl)-chroman-2-yl]-propionic acid ethyl ester (0.048 g, 0.126 mmol) obtained in Step A was reacted in the same manner as in Step B of Example 1 to obtain the title compound (0.042 g, 94%).

$^1$H-NMR (400 HMz, CDCl$_3$); δ 7.31-7.27 (m, 3H), 7.10-7.08 (m, 1H), 6.98-3.97 (m, 1H), 6.85-6.83 (d, 1H), 6.75-6.73 (m, 1H), 4.73-7.65 (m, 1H), 4.09-4.06 (m, 1H), 2.94-2.72 (m, 2H), 2.69-2.61 (m, 2H), 2.50-2.43 (m, 2H), 2.22-2.17 (m, 2H), 2.06-2.01 (m, 3H), 1.88-1.66 (m, 3H)

Example 556: 3-[6-(6-propoxy-pyridin-2-yl)-chroman-2-yl]-propionic acid

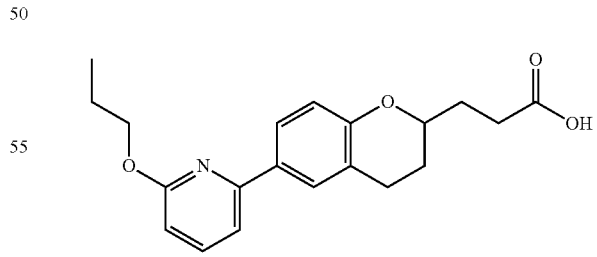

Step A: 3-[6-(6-propoxy-pyridin-2-yl)-chroman-2-yl]-propionic acid ethyl ester 3-[6-(4,4,5,5-Tetramethyl-[1,3,2]dioxaborolan-2-yl)-chroman-2-yl]-propionic acid ethyl ester (0.09 g, 0.24 mmol) obtained in Preparation Example 4 and 2-chloro-6- propoxy-pyridine (0.044 g, 0.26 mmol) were reacted in the same manner as in Step A of Example 1 to obtain the title compound (0.023 g, 27%).

¹H-NMR (500 HMz, CDCl₃); δ 7.75-7.73 (m, 2H), 7.58-7.55 (t, 1H), 7.22-7.20 (d, 1H), 6.85-6.83 (d, 1H), 6.60-6.58 (d, 1H), 4.37-4.34 (t, 2H), 4.18-4.13 (q, 2H), 4.09-4.02 (m, 1H), 2.92-2.81 (m, 2H), 2.65-2.52 (m, 2H), 2.06-2.00 (m, 3H), 1.88-1.74 (m, 3H), 1.28-1.25 (t, 3H), 1.06-1.03 (t, 3H)

Step B: 3-[6-(6-propoxy-pyridin-2-yl)-chroman-2-yl]-propionic acid

3-[6-(6-Propoxy-pyridin-2-yl)-chroman-2-yl]-propionic acid ethyl ester (0.048 g, 0.126 mmol) obtained in Step A was reacted in the same manner as in Step B of Example 1 to obtain the title compound (0.042 g, 94%).

¹H-NMR (400 HMz, CDCl₃); δ 7.75-7.73 (m, 2H), 7.58-7.52 (m, 1H), 7.22-7.20 (d, 1H0, 6.86-6.84 (m, 1H), 6.61-6.59 (m, 1H), 4.38-4.34 (t, 2H), 4.11-4.09 (m, 1H), 2.93-2.83 (m, 2H), 2.72-2.60 (m, 2H), 2.06-2.01 (m, 3H), 1.88-1.80 (m, 3H), 1.07-1.03 (t, 3H)

Example 557: 4-[2,6-difluoro-4-(1H-indol-6-yl)-phenoxy]-butanoic acid

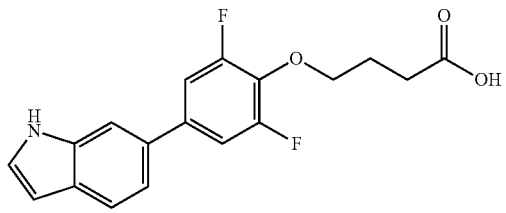 [SMILES: O=C(O)CCCOc1c(F)cc(-c2ccc3cc[nH]c3c2)cc1F]

Step A: 4-[2,6-difluoro-4-(1H-indol-6-yl)-phenoxy]-butanoic acid ethyl ester 4-(4-Bromo-2,6-difluoro-phenoxy)-butanoic acid ethyl ester (0.20 g, 0.62 mmol) obtained in Preparation Example 339 and 6-indolylboronic acid (0.11 g, 0.68 mmol) were reacted in the same manner as in Step A of Example 1 to obtain the title compound (0.21 g, 94%).

¹H-NMR (400 HMz, CDCl₃); δ 8.23 (br s, 1H), 7.69-7.67 (d, 1H), 7.52 (s, 1H), 7.28-7.27 (m, 2H), 7.20-7.13 (m, 2H), 6.58-6.57 (m, 1H), 4.21-4.13 (m, 4H), 2.61-2.58 (t, 2H), 2.13-2.09 (m, 2H), 1.28-1.25 (t, 3H)

Step B: 4-[2,6-difluoro-4-(1H-indol-6-yl)-phenoxy]-butanoic acid

4-[2,6-Difluoro-4-(1H-indol-6-yl)-phenoxy]-butanoic acid ethyl ester (0.025 g, 0.07 mmol) obtained in Step A was reacted in the same manner as in Step B of Example 1 to obtain the title compound (0.019 g, 84%).

¹H-NMR (400 HMz, MeOD-d₄); δ 7.63-7.61 (m, 2H), 7.33-7.26 (m, 4H), 6.48-6.47 (m, 1H), 4.22-4.19 (t, 2H), 2.60-2.56 (t, 2H), 2.10-2.03 (m, 2H)

Example 558: 4-[2,6-difluoro-4-(1-isopropyl-1H-indol-6-yl)-phenoxy]-butanoic acid

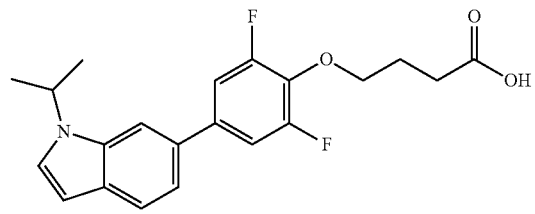 [SMILES: CC(C)n1ccc2ccc(-c3cc(F)c(OCCCC(=O)O)c(F)c3)cc21]

Step A: 4-[2,6-difluoro-4-(1-isopropyl-1H-indol-6-yl)-phenoxy]-butanoic acid ethyl ester 4-[2,6-Difluoro-4-(1H-indol-6-yl)-phenoxy]-butanoic acid ethyl ester (0.05 g, 0.14 mmol) obtained in Step A of Example 557 was dissolved in N,N-dimethylformamide (5 ml) and cooled to 0° C. NaH (60%)(0.003 g, 0.21 mmol) and 2-iodopropane (0.02 ml, 0.21 mmol) were added thereto, and the mixture was stirred at room temperature for 16 hours. After addition of water, the reaction solution was extracted to separate an organic layer. The organic layer was dried with MgSO₄ and purified by column chromatography to obtain the title compound (0.03 g, 54%).

¹H-NMR (400 HMz, CDCl₃); δ 7.67-7.65 (d, 1H), 7.47 (s, 1H), 7.28-7.17 (m, 4H), 6.53-6.52 (d, 1H), 4.75-4.73 (m, 1H), 4.21-4.14 (m, 4H), 2.61-2.59 (t, 2H), 2.14-2.10 (m, 2H), 1.56-1.55 (dd, 6H), 1.29-1.26 (t, 3H)

Step B: 4-[2,6-difluoro-4-(1-isopropyl-1H-indol-6-yl)-phenoxy]l-butanoic acid 4-[2,6-difluoro-4-(1-isopropyl-1H-indol-6-yl)-phenoxy]-butanoic acid ethyl ester (0.03 g, 0.075 mmol) obtained in Step A was reacted in the same manner as in Step B of Example 1 to obtain the title compound (0.02 g, 72%).

¹H-NMR (400 HMz, CDCl₃); δ 7.67-7.65 (d, 1H), 7.47 (s, 1H), 7.28-7.17 (m, 4H), 6.54-6.53 (d, 1H), 4.78-4.71 (m, 1H), 4.24-4.21 (t, 2H), 2.71-2.67 (t, 2H), 2.16-2.09 (m, 2H), 1.57-1.55 (d, 6H)

Example 559: 4-[4-(1-cyclopropylmethyl-1H-indol-6-yl)-2,6-difluoro-phenoxy]-butanoic acid

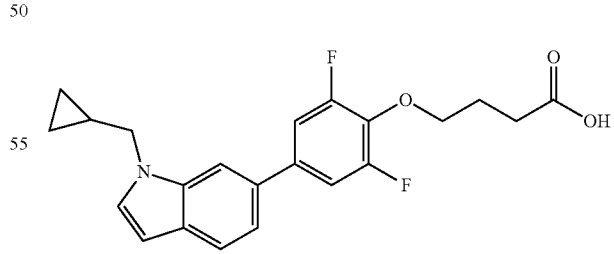

Step A: 4-[4-(1-cyclopropylmethyl-1H-indol-6-yl)-2,6-difluoro-phenoxy]-butanoic acid ethyl ester 4-[2,6-Difluoro-4-(1H-indol-6-yl)-phenoxy]-butanoic acid ethyl ester (0.05 g, 0.14 mmol) obtained in Step A of Example 557 and iodomethyl-cyclopropane (0.02 ml, 0.21 mmol) were reacted in the same manner as in Step A of Example 1 to obtain the title compound (0.03 g, 52%).

¹H-NMR (400 HMz, CDCl₃); δ 7.68-7.66 (d, 1H), 7.47 (s, 1H), 7.28-7.24 (m, 2H), 7.22-7.16 (m, 2H), 6.52-6.51 (m, 1H), 4.22-4.19 (t, 2H), 4.04-4.02 (d, 2H), 3.71 (s, 3H), 2.64-2.60 (t, 2H), 2.15-2.08 (m, 2H), 1.32-1.25 (m, 1H), 0.68-0.63 (m, 2H), 0.41-0.37 (m, 2H)

Step B: 4-[4-(1-cyclopropylmethyl-1H-indol-6-yl)-2,6-difluoro-phenoxy]-butanoic acid 4-[4-(1-Cyclopropylmethyl-1H-indol-6-yl)-2,6-difluoro-phenoxy]-butanoic acid ethyl ester (0.03 g, 0.073 mmol) obtained in Step A was reacted in the same manner as in Step B of Example 1 to obtain the title compound (0.02 g, 72%).

¹H-NMR (400 HMz, CDCl₃); δ 7.67-7.65 (d, 1H), 7.47 (s, 1H), 7.27-7.24 (m, 2H), 7.23-7.16 (m, 2H), 6.52-6.51 (m, 1H), 4.24-4.21 (t, 2H), 4.03-4.02 (d, 2H), 2.71-2.67 (t, 2H), 2.16-2.09 (m, 2H), 1.35-1.23 (m, 1H), 0.69-0.64 (m, 2H), 0.45-0.37 (m, 2H)

Example 560: {1-[4-(6-cyclopropylmethoxy-pyridin-2-yl)-2,6-difluoro-phenyl]-pyrrolidin-3-yl}-acetic acid

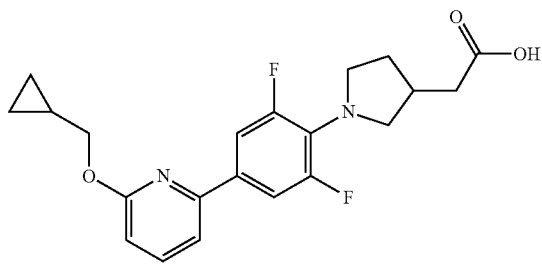 [SMILES: O=C(O)CC1CCN(c2c(F)cc(-c3cccc(OCC4CC4)n3)cc2F)C1]

Step A: {1-[4-(6-cyclopropylmethoxy-pyridin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.09 g, 0.23 mmol) obtained in Preparation Example 91 and 2-chloro-6-cyclopropylmethoxy-pyridine (0.046 g, 0.25 mmol) obtained in Preparation Example 43 were reacted in the same manner as in Step A of Example 1 to obtain the title compound (0.043 g, 45%).

¹H-NMR (400 HMz, CDCl₃); δ 7.60-7.56 (t, 1H), 7.53-7.45 (m, 2H), 7.18-7.16 (d, 1H), 6.66-6.64 (d, 1H), 4.24-4.22 (d, 2H), 4.19-4.13 (q, 2H), 3.76-3.60 (m, 3H), 3.37 (m, 1H), 2.68-2.63 (m, 1H), 2.53-2.47 (m, 2H), 2.18-2.14 (m, 1H), 1.68-1.63 (m, 1H), 1.35-1.30 (m, 1H), 1.28-1.24 (t, 3H), 0.66-0.61 (m, 2H), 0.41-0.37 (m, 2H)

Step B: {1-[4-(6-cyclopropylmethoxy-pyridin-2-yl)-2,6-difluoro-phenyl]-pyrrolidin-3-yl}-acetic acid {1-[4-(6-Cyclopropylmethoxy-pyridin-2-yl)-2,6-difluoro-phenyl]-pyrrolidin-3-yl}-acetic acid ethyl ester (0.043 g, 0.10 mmol) obtained in Step A was reacted in the same manner as in Step B of Example 1 to obtain the title compound (0.037 g, 93%).

¹H-NMR (400 HMz, CDCl₃); δ 7.60-7.56 (t, 1H), 7.52-7.44 (m, 2H), 7.18-7.16 (d, 1H), 6.66-6.64 (d, 1H), 4.24-4.22 (d, 2H), 3.77-3.61 (m, 3H), 3.40-3.36 (m, 1H), 2.68-2.63 (m, 1H), 2.56-2.52 (m, 2H), 2.21-2.17 (m, 1H), 1.69-1.64 (m, 1H), 1.35-1.31 (m, 1H), 0.66-0.61 (m, 2H), 0.41-0.37 (m, 2H)

Example 561: {1-[4-(6-cyclobutoxy-pyridin-2-yl)-2,6-difluoro-phenyl]-pyrrolidin-3-yl}-acetic acid

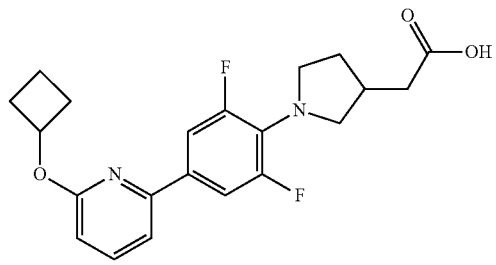 [SMILES: O=C(O)CC1CCN(c2c(F)cc(-c3cccc(OC4CCC4)n3)cc2F)C1]

Step A: {1-[4-(6-cyclobutoxy-pyridin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.09 g, 0.23 mmol) obtained in Preparation Example 91 and 2-chloro-6-cyclobutoxy-pyridine (0.046 g, 0.25 mmol) obtained in Preparation Example 29 were reacted in the same manner as in Step A of Example 1 to obtain the title compound (0.05 g, 53%).

¹H-NMR (400 HMz, CDCl₃); δ 7.59-7.55 (t, 1H), 7.52-7.46 (m, 2H), 7.17-7.15 (d, 1H), 6.59-6.57 (d, 1H), 5.28-5.24 (m, 1H), 4.19-4.14 (q, 2H), 3.76-3.60 (m, 3H), 3.39-3.35 (m, 1H), 2.68-2.56 (m, 1H), 2.53-2.47 (m, 4H), 2.21-2.14 (m, 3H), 1.88-1.62 (m, 3H), 1.30-1.26 (t, 3H)

Step B: {1-[4-(6-cyclobutoxy-pyridin-2-yl)-2,6-difluoro-phenyl]-pyrrolidin-3-yl}-acetic acid {1-[4-(6-Cyclobutoxy-pyridin-2-yl)-2,6-difluoro-phenyl]-pyrrolidin-3-yl}-acetic acid ethyl ester (0.05 g, 0.12 mmol) obtained in Step A was reacted in the same manner as in Step B of Example 1 to obtain the title compound (0.048 g, 96%).

¹H-NMR (400 HMz, CDCl₃); δ 7.59-7.55 (t, 1H), 7.52-7.46 (m, 2H), 7.17-7.16 (d, 1H), 6.59-6.57 (d, 1H), 5.30-5.24 (m, 1H), 3.78-3.61 (m, 3H), 3.40-3.36 (m, 1H), 2.69-2.61 (m, 1H), 2.57-2.49 (m, 4H), 2.21-2.16 (m, 3H), 1.88-1.64 (m, 3H)

Example 562: 4-[4-(3-chloro-1-isopropyl-1H-indol-6-yl)-2,6-difluoro-phenoxy]-butanoic acid

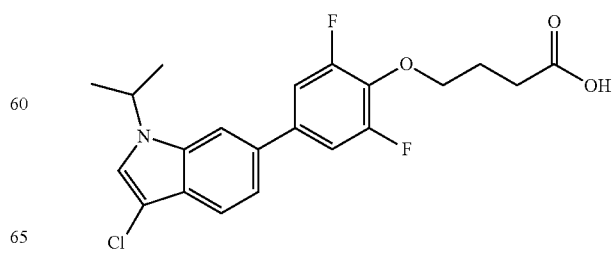

Step A: 4-[4-(3-chloro-1-isopropyl-1H-indol-6-yl)-2,6-difluoro-phenoxy]-butanoic acid ethyl ester 4-[2,6-Difluoro-4-(1-isopropyl-1H-indol-6-yl)-phenoxy]butanoic acid ethyl ester (0.048 g, 0.12 mmol) obtained in Step A of Example 558 and NCS (0.018 g, 0.13 mmol) were reacted in the same manner as in Step E of Preparation Example 4 to obtain the title compound (0.031 g, 59%).

¹H-NMR (400 HMz, CDCl₃); δ 7.66-7.64 (d, 1H), 7.45 (s, 1H), 7.33-7.30 (m, 1H), 7.23 (s, 1H), 7.21-7.14 (m, 2H), 4.75-4.67 (m, 1H), 4.23-4.20 (t, 2H), 4.19-4.14 (q, 2H), 2.62-2.58 (t, 2H), 2.15-2.04 (m, 2H), 1.55-1.53 (d, 6H), 1.29-1.26 (t, 3H)

Step B: 4-[4-(3-chloro-1-isopropyl-1H-indol-6-yl)-2,6-difluoro-phenoxy]-butanoic acid 4-[4-(3-Chloro-1-isopropyl-1H-indol-6-yl)-2,6-difluoro-phenoxy]-butanoic acid ethyl ester (0.031 g, 0.071 mmol) obtained in Step A was reacted in the same manner as in Step B of Example 1 to obtain the title compound (0.018 g, 63%).

¹H-NMR (500 HMz, CDCl₃); δ 7.66-7.64 (d, 1H), 7.44 (s, 1H), 7.32-7.30 (m, 1H), 7.22 (s, 1H), 7.21-7.15 (m, 2H), 4.73-4.69 (m, 1H), 4.24-4.21 (t, 2H), 2.70-2.67 (t, 2H), 2.15-2.11 (m, 2H), 1.56-1.53 (d, 6H)

Example 563: {1-[2,6-difluoro-4-(6-isopropoxy-pyridin-2-yl)-phenyl]-pyrrolidin-3-yl}-acetic acid

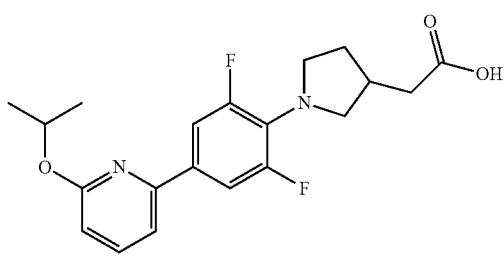 [SMILES: CC(C)Oc1cccc(-c2cc(F)c(N3CCC(CC(=O)O)C3)c(F)c2)n1]

Step A: {1-[2,6-difluoro-4-(6-isopropoxy-pyridin-2-yl)-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.16 g, 0.40 mmol) obtained in Preparation Example 91 and 2-chloro-6-isopropoxy-pyridine (0.076 g, 0.44 mmol) obtained in Preparation Example 46 were reacted in the same manner as in Step A of Example 1 to obtain the title compound (0.071 g, 44%).

¹H-NMR (400 HMz, MeOD-d₄); δ 7.64-7.60 (t, 1H), 7.58-7.48 (m, 2H), 7.28-7.26 (d, 1H), 6.58-6.56 (d, 1H), 5.46-5.37 (m, 1H), 4.19-4.13 (q, 2H), 3.70-3.66 (m, 2H), 3.64-3.54 (m, 1H), 3.36-3.30 (m, 1H), 2.64-2.56 (m, 1H), 2.50-2.48 (d, 2H), 2.18-2.10 (m, 1H), 1.67-1.58 (m, 1H), 1.40-1.38 (d, 6H), 1.29-1.26 (t, 3H)

Step B: {1-[2,6-difluoro-4-(6-isopropoxy-pyridin-2-yl)-phenyl]-pyrrolidin-3-yl}-acetic acid {1-[2,6-Difluoro-4-(6-isopropoxy-pyridin-2-yl)-phenyl]-pyrrolidin-3-yl}-acetic acid ethyl ester (0.071 g, 0.18 mmol) Obtained in Step A was reacted in the same manner as in Step B of Example 1 to obtain the title compound (0.060 g, 90%).

¹H-NMR (500 HMz, CDCl₃); δ 7.58-7.54 (t, 1H), 7.53-7.44 (m, 2H), 7.15-7.13 (d, 1H), 6.58-6.55 (d, 1H), 5.48-5.42 (m, 1H), 3.77-3.61 (m, 3H), 3.40-3.36 (m, 1H), 2.70-2.63 (m, 1H), 2.60-2.50 (m, 2H), 2.21-2.17 (m, 1H), 1.71-1.62 (m, 1H), 1.40-1.38 (d, 6H)

Example 564: {1-[4-(6-cyclobutylmethoxy-pyridin-2-yl)-2,6-difluoro-phenyl]-pyrrolidin-3-yl}-acetic acid

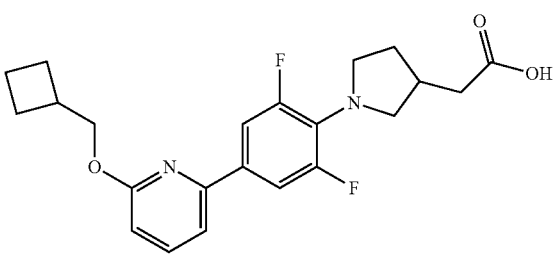 [SMILES: O=C(O)CC1CCN(c2c(F)cc(-c3cccc(OCC4CCC4)n3)cc2F)C1]

Step A: {1-[4-(6-cyclobutylmethoxy-pyridin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.16 g, 0.4 mmol) obtained in Preparation Example 91 and 2-chloro-6-cyclobutylmethoxy-pyridine (0.087 g, 0.44 mmol) obtained in Preparation Example 324 were reacted in the same manner as in Step A of Example 1 to obtain the title compound (0.053 g, 31%).

¹H-NMR (500 HMz, CDCl₃); δ 7.57-7.54 (t, 1H), 7.52-7.45 (m, 2H), 7.16-7.14 (d, 1H), 6.61-6.60 (d, 1H), 4.37-4.35 (d, 2H), 4.18-4.13 (q, 2H), 3.72-3.67 (m, 2H), 3.61-3.57 (m, 1H), 3.36-3.33 (m, 1H), 2.83-2.78 (m, 1H), 2.67-2.62 (m, 1H), 2.51-2.43 (m, 2H), 2.18-2.12 (m, 3H), 1.96-1.86 (m, 4H), 1.65-1.59 (m, 1H), 1.29-1.26 (t, 3H)

Step B: {1-[4-(6-cyclobutylmethoxy-pyridin-2-yl)-2,6-difluoro-phenyl]-pyrrolidin-3-yl}-acetic acid {1-[4-(6-Cyclobutylmethoxy-pyridin-2-yl)-2,6-difluoro-phenyl]-pyrrolidin-3-yl}-acetic acid ethyl ester (0.053 g, 0.12 mmol) obtained in Step A was reacted in the same manner as in Step B of Example 1 to obtain the title compound (0.029 g, 59%).

¹H-NMR (400 HMz, CDCl₃); δ 7.59-7.55 (t, 1H), 7.53-7.46 (m, 2H), 7.17-7.15 (d, 1H), 6.63-6.61 (d, 1H), 4.38-1.36 (d, 2H), 3.78-3.61 (m, 3H), 3.40-3.36 (m, 1H), 2.84-2.71 (m, 1H), 2.69-2.61 (m, 1H), 2.57-2.50 (m, 2H), 2.21-2.12 (m, 3H), 2.00-1.88 (m, 4H), 1.71-1.62 (m, 1H)

Example 565: 4-[4-(5-cyclopropylmethoxymethyl-thiophen-2-yl)-2,6-difluoro-phenoxy]-butanoic acid

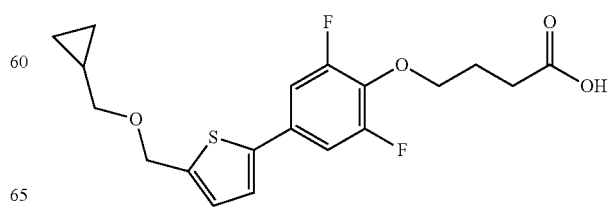

Step A: 4-[2,6-difluoro-4-(5-formyl-thiophen-2-yl)-phenoxyl]-butanoic acid ethyl ester 4-[2,6-Difluoro-4-(4,4,5,5-tetramethyl-1,3,2-dioxaborolan-2-yl)phenoxy]butanoic acid ethyl ester (0.11 g, 0.40 mmol) obtained in Preparation Example 16 and 5-bromothiophen-2-carbaldehyde (0.084 g, 0.44 mmol) were reacted in the same manner as in Step A of Example 1 to obtain the title compound (0.052 g, 37%).

$^1$H-NMR (400 HMz CDCl$_3$); δ 9.89 (s, 1H), 7.73-7.72 (d, 1H), 7.32-7.31 (d, 1H), 7.22-7.19 (m, 2H), 4.26-4.23 (t, 2H), 4.19-4.13 (q, 2H), 2.59-2.56 (t, 2H0, 2.14-2.07 (m, 2H), 1.29-1.25 (t, 3H)

Step B: 4-[2,6-difluoro-4-(5-hydroxymethyl-thiophen-2-yl)-phenoxy]-butanoic acid ethylester 4-[2,6-Difluoro-4-(5-formyl-thiophen-2-yl)-phenoxy]-butanoic acid ethyl ester (0.052 g, 0.15 mmol) obtained in Step A was dissolved in MeOH (5 ml). NaBH$_4$ (0.006 g, 0.15 mmol) was added thereto, and the mixture was stirred for 30 minutes. After addition of water, the reaction solution was extracted with EtOAc. The organic layer was dried with MgSO$_4$ and purified by column chromatography to obtain the title compound (0.052 g, 99%).

$^1$H-NMR (400 HMz CDCl$_3$); δ 7.13-7.04 (m, 3H), 6.96-6.95 (d, 1H), 4.82 (s, 2H), 4.20-4.02 (m, 4H), 2.59-2.55 (t, 2H), 2.12-2.05 (m, 2H), 1.94 (br s, 1H), 1.28-1.26 (t, 3H)

Step C: 4-[4-(5-cyclopropylmethoxymethyl-thiophen-2-yl)-2,6-difluoro-phenoxy]-butanoic acid ethyl ester 4-[2,6-Difluoro-4-(5-hydroxymethyl-thiophen-2-yl)-phenoxy]-butanoic acid ethyl ester (0.052 g, 0.15 mmol) obtained in Step B was dissolved in THF (5 ml). NaH (60%)(0.009 mg, 0.22 mmol) was added thereto at 0° C., and the mixture was stirred for 10 minutes. Bromomethylcyclopropane (0.029 ml, 0.29 mmol) and tetrabutylammonium iodide (0.054 g, 0.15 mmol) were sequentially added thereto, and the mixture was stirred at 50° C. for 16 hours. After addition of water, the reaction solution was extracted with EtOAc. The organic layer was dried with MgSO$_4$ and purified by column chromatography to obtain the title compound (0.015 g, 25%).

$^1$H-NMR (400 HMz CDCl$_3$); δ 7.13-7.07 (m, 3H), 6.94-6.93 (d, 1H), 4.67 (s, 2H), 4.20-4.13 (m, 4H), 3.36-3.34 (d, 2H), 2.60-2.56 (t, 2H), 2.12-2.05 (m, 2H), 1.29-1.25 (t, 3H), 1.13-1.07 (m, 1H), 0.59-0.54 (m, 2H), 0.28-0.20 (m, 2H)

Step D: 4-[4-(5-cyclopropylmethoxymethyl-thiophen-2-yl)-2,6-difluoro-phenoxy]-butanoic acid 4-[4-(5-Cyclopropylmethoxymethyl-thiophen-2-yl)-2,6-difluoro-phenoxy]-butanoic acid ethyl ester (0.015 g, 0.037 mmol) obtained in Step C was reacted in the same manner as in Step B of Example 1 to obtain the title compound (0.014 g, 97%).

$^1$H-NMR (400 HMz CDCl$_3$); δ 7.11-7.07 (m, 3H), 6.94-6.93 (d, 1H), 4.67 (s, 2H), 4.22-4.19 (t, 2H), 3.36-3.34 (d, 2H), 2.68-2.66 (t, 2H), 2.10-2.04 (m, 2H), 1.10 (m, 1H), 0.58-0.54 (m, 2H), 0.24-0.22 (m, 2H)

Example 566: 4-[4-(5-cyclopropylmethoxymethyl-thiophen-3-yl)-2,6-difluoro-phenoxy]-butanoic acid

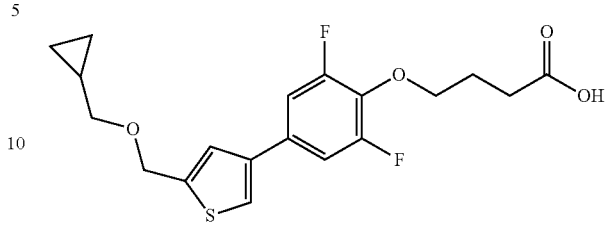

Step A: 4-[2,6-difluoro-4-(5-formyl-thiophen-3-yl)-phenoxy]-butanoic acid ethyl ester 4-[2,6-Difluoro-4-(4,4,5,5-tetramethyl-1,3,2-dioxaborolan-2-yl)phenoxy]butanoic acid ethyl ester (0.19 g, 0.50 mmol) obtained in Preparation Example 16 and 4-bromothiophen-carbaldehyde (0.11 g, 0.55 mmol) were reacted in the same manner as in Step A of Example 565 to obtain the title compound (0.11 g, 62%).

$^1$H-NMR (400 HMz CDCl$_3$); δ 9.97 (s, 1H), 7.93 (s, 1H), 7.79 (s, 1H), 7.15-7.09 (m, 2H), 4.24-4.21 (t, 2H), 4.19-4.13 (q, 2H), 2.60-2.56 (t, 2H), 2.14-2.09 (m, 2H), 1.29-1.25 (t, 3H)

Step B: 4-[2,6-difluoro-4-(5-hydroxymethyl-thiophen-3-yl)-phenoxy]-butanoic acid ethylester 4-[2,6-Difluoro-4-(5-formyl-thiophen-3-yl)-phenoxy]-butanoic acid ethyl ester (0.11 g, 0.21 mmol) obtained in Step A was reacted in the same manner as in Step B of Example 565 to obtain the title compound (0.10 g, 90%).

$^1$H-NMR (500 HMz CDCl$_3$); δ 7.31 (s, 1H), 7.17 (s, 1H), 7.09-7.04 (m, 2H), 4.84-4.83 (d, 2H), 4.19-4.09 (m, 4H), 2.58-2.55 (t, 2H), 2.10-2.05 (m, 2H), 1.98 (br s, 1H), 1.27-1.24 (t, 3H)

Step C: 4-[4-(5-cyclopropylmethoxymethyl-thiophen-3-yl)-2,6-difluoro-phenoxy]-butanoic acid ethyl ester 4-[2,6-Difluoro-4-(5-hydroxymethyl-thiophen-3-yl)-phenoxy]-butanoic acid ethylester (0.10 g, 0.28 mmol) obtained in Step B and bromomethyl-cyclopropane (0.055 ml, 0.56 mmol) were reacted in the same manner as in Step C of Example 565 to obtain the title compound (0.027 g, 23%).

$^1$H-NMR (400 HMz CDCl$_3$); δ 7.32 (d, 1H), 7.17 (m, 1H), 7.11-7.04 (m, 2H), 4.69 (s, 2H), 4.20-4.13 (m, 4H), 3.37-3.35 (d, 2H), 2.60-2.56 (t, 2H), 2.14-2.05 (m, 2H), 1.29-1.25 (t, 3H), 1.14-1.07 (m, 1H), 0.58-0.54 (m, 2H), 0.24-0.21 (m, 2H)

Step D: 4-[4-(5-cyclopropylmethoxymethyl-thiophen-3-yl)-2,6-difluoro-phenoxy]-butanoic acid 4-[4-(5-Cyclopropylmethoxymethyl-thiophen-3-yl)-2,6-difluoro-phenoxy]-butanoic acid ethyl ester (0.027 g, 0.066 mmol) obtained in Step C was reacted in the same manner as in Step D of Example 565 to obtain the title compound (0.015 g, 61%).

$^1$H-NMR (400 HMz CDCl$_3$); δ 7.33-7.32 (d, 1H), 7.17-7.16 (m, 1H), 7.11-7.05 (m, 2H), 4.70-4.69 (d, 2H), 4.21-

4.18 (t, 2H), 3.37-3.35 (d, 2H), 2.68-2.64 (t, 2H), 2.13-2.04 (m, 2H), 1.15-1.07 (m, 1H), 0.58-0.54 (m, 2H), 0.24-0.21 (m, 2H)

Example 567: {1-[4-(5-cyclopropylmethoxymethyl-thiophen-3-yl)-2,6-difluoro-phenyl]-piperidin-4-yl}-acetic acid

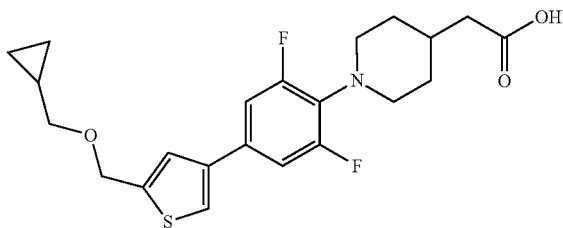 [SMILES: O=C(O)CC1CCN(c2c(F)cc(-c3csc(COCC4CC4)c3)cc2F)CC1]

Step A: {1-[2,6-difluoro-4-(5-formyl-thiophen-3-yl)-phenyl]-piperidin-4-yl}-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.21 g, 0.50 mmol) obtained in Preparation Example 220 and 4-bromo-thiophen-carbaldehyde (0.11 g, 0.55 mmol) were reacted in the same manner as in Step A of Example 565 to obtain the title compound (0.053 g, 27%).

$^1$H-NMR (400 HMz CDCl$_3$); δ 9.96-9.95 (d, 1H), 7.93-7.92 (d, 1H), 7.77-7.76 (t, 1H), 7.08-7.03 (m, 2H), 4.18-4.13 (q, 2H), 3.30-3.27 (m, 2H), 3.16-3.11 (m, 2H), 2.31-2.29 (d, 2H), 1.97-1.95 (m, 1H), 1.80-1.77 (m, 2H), 1.50-1.41 (m, 2H), 1.29-1.26 (t, 3H)

Step B: {1-[2,6-difluoro-4-(5-hydroxymethyl-thiophen-3-yl)-phenyl]-piperidin-4-yl}-acetic acid ethyl ester {1-[2,6-Difluoro-4-(5-formyl-thiophen-3-yl)-phenyl]-piperidin-4-yl}-acetic acid ethyl ester (0.053 g, 0.14 mmol) obtained in Step A was reacted in the same manner as in Step B of Example 565 to obtain the title compound (0.053 g, 99%).

$^1$H-NMR (400 HMz CDCl$_3$); δ 7.31-7.30 (d, 1H), 7.19 (s, 1H), 7.05-6.98 (m, 2H), 4.84 (s, 2H), 4.18-4.12 (q, 2H), 3.26-3.23 (m, 2H), 3.15-3.09 (m, 2H), 2.30-2.28 (d, 2H), 2.00-1.90 (m, 2H), 1.78-1.75 (m, 2H), 1.50-1.40 (m, 2H), 1.29-1.26 (t, 3H)

Step C: {1-[4-(5-cyclopropylmethoxymethyl-thiophen-3-yl)-2,6-difluoro-phenyl]-piperidin-4-yl}-acetic acid ethyl ester {1-[2,6-Difluoro-4-(5-hydroxymethyl-thiophen-3-yl)-phenyl]-piperidin-4-yl}-acetic acid ethyl ester (0.053 g, 0.13 mmol) obtained in Step B and bromomethyl-cyclopropane (0.026 ml, 0.27 mmol) were reacted in the same manner as in Step C of Example 565 to obtain the title compound (0.046 g, 76%).

$^1$H-NMR (400 HMz CDCl$_3$); δ 7.31-7.30 (d, 1H), 7.17 (s, 1H), 7.05-6.98 (m, 2H), 4.69 (s, 2H), 4.18-4.12 (q, 2H), 3.41-3.36 (d, 2H), 3.26-3.23 (m, 2H), 3.14-3.08 (m, 2H), 2.30-2.28 (d, 2H), 1.98-1.93 (m, 1H), 1.78-1.75 (m, 2H), 1.58-1.43 (m, 2H), 1.29-1.26 (t, 3H), 1.12-1.08 (m, 1H), 0.58-0.53 (m, 2H), 0.24-0.20 (m, 2H)

Step D: {1-[4-(5-cyclopropylmethoxymethyl-thiophen-3-yl)-2,6-difluoro-phenyl]-piperidin-4-yl}-acetic acid {1-[4-(5-Cyclopropylmethoxymethyl-thiophen-3-yl)-2,6-difluoro-phenyl]-piperidin-4-yl}-acetic acid ethyl ester (0.046 g, 0.10 mmol) obtained in Step C was reacted in the same manner as in Step B of Example 1 to obtain the title compound (0.040 g, 92%).

$^1$H-NMR (400 HMz CDCl$_3$); δ 7.31 (d, 1H), 7.18 (s, 1H), 7.05-7.00 (m, 2H), 4.69 (s, 2H), 3.36-3.34 (d, 2H), 3.28-3.25 (m, 2H), 3.16-3.10 (m, 2H), 2.37-2.35 (d, 2H), 1.96-1.95 (m, 1H), 1.83-1.80 (m, 2H), 1.52-1.44 (m, 2H), 1.12-1.08 (m, 1H), 0.58-0.54 (m, 2H), 0.24-0.20 (m, 2H)

Example 568: 4-[4-(4-cyclopropylmethoxymethyl-2-methyl-thiazol-5-yl)-2,6-difluoro-phenoxy]-butanoic acid

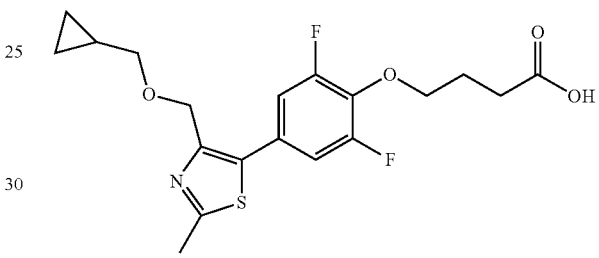

Step A: 4-[4-(4-cyclopropylmethoxymethyl-2-methyl-thiazol-5-yl)-2,6-difluoro-phenoxy]l-butanoic acid ethyl ester 4-[2,6-Difluoro-4-(4,4,5,5-tetramethyl-1,3,2-dioxaborolan-2-yl)phenoxy]butanoic acid ethyl ester (0.15 g, 0.40 mmol) obtained in Preparation Example 16 and 5-bromo-4-cyclopropylmethoxymethyl-2-methyl-thiazole (0.12 g, 0.44 mmol) obtained in Preparation Example 337 were reacted in the same manner as in Step A of Example 1 to obtain the title compound (0.077 g, 45%).

$^1$H-NMR (400 HMz CDCl$_3$); δ 7.22-7.09 (m, 2H), 4.49 (s, 2H), 4.23.-4.21 (t, 2H), 4.19-4.10 (q, 2H), 3.45-3.43 (d, 2H), 2.70 (s, 3H), 2.60-2.57 (t, 2H), 2.18-2.07 (m, 2H), 1.29-1.26 (t, 3H), 1.21-1.12 (m, 1H), 0.61-0.52 (m, 2H), 0.31-0.25 (m, 2H)

Step B: 4-[4-(4-cyclopropylmethoxymethyl-2-methyl-thiazol-5-yl)-2,6-difluoro-phenoxy]l-butanoic acid 4-[4-(4-Cyclopropylmethoxymethyl-2-methyl-thiazol-5-yl)-2,6-difluoro-phenoxy]-butanoic acid ethyl ester (0.077 g, 0.18 mmol) obtained in Step A was reacted in the same manner as in Step B of Example 1 to obtain the title compound (0.063 g, 88%).

$^1$H-NMR (400 HMz CDCl$_3$); δ 7.19-7.13 (m, 2H), 4.49 (s, 2H), 4.25-4.22 (t, 2H), 3.44-3.42 (d, 2H), 2.70 (s, 3H), 2.68-2.65 (t, 2H), 2.15-2.08 (m, 2H), 1.18-1.14 (m, 1H), 0.60-0.56 (m, 2H), 0.28-0.24 (m, 2H)

Example 569: {1-[4-(5-cyclomethoxymethyl-thiophen-2-yl)-2,6-difluoro-phenyl]-piperidin-4-yl}-acetic acid

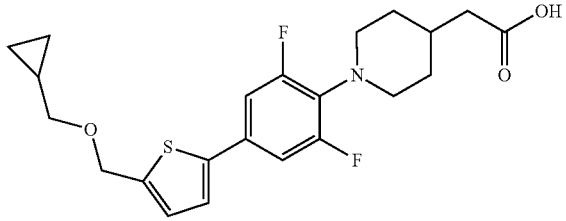 [SMILES: O=C(O)CC1CCN(c2c(F)cc(-c3ccc(COCC4CC4)s3)cc2F)CC1]

Step A: {1-[2,6-difluoro-4-(5-formyl-thiophen-2-yl)-phenyl]-piperidin-4-yl}-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.33 g, 0.80 mmol) obtained in Preparation Example 220 and 5-bromo-thiophen-2-carbaldehyde (0.17 g, 0.88 mmol) were reacted in the same manner as in Step A of Example 1 to obtain the title compound (0.16 g, 51%).

¹H-NMR (400 HMz CDCl₃); δ 9.98 (s, 1H), 7.72-7.71 (d, 1H), 7.30-7.29 (d, 1H0, 7.16-7.10 (m, 2H), 4.18-4.13 (q, 2H), 3.34-3.31 (m, 2H), 3.17-3.11 (m, 2H), 2.30-2.29 (d, 2H), 1.97-1.80 (m, 1H), 1.97-1.77 (m, 2H), 1.55-1.40 (m, 2H), 1.28-1.26 (t, 3H)

Step B: {1-[2,6-difluoro-4-(5-hydroxymethyl-thiophen-2-yl)-phenyl]-piperidin-4-yll}-acetic acid ethyl ester {1-[2,6-Difluoro-4-(5-formyl-thiophen-2-yl)-phenyl]-piperidin-4-yl}-acetic acid ethyl ester (0.16 g, 0.40 mmol) obtained in Step A was reacted in the same manner as in Step B of Example 565 to obtain the title compound (0.14 g, 89%).

¹H-NMR (400 HMz CDCl₃); δ 7.08-7.03 (m, 3H), 6.96-9.95 (d, 1H), 4.82 (s, 2H), 4.18-4.12 (q, 2H), 3.28-3.26 (m, 2H), 3.16-3.10 (m, 2H), 2.30-2.28 (d, 2H), 1.79-1.76 (m, 1H), 1.79-1.76 (m, 2H), 1.49-1.46 (m, 2H), 1.29-1.26 (t, 3H)

Step C: {1-[4-(5-cyclomethoxymethyl-thiophen-2-yl)-2,6-difluoro-phenyl]-piperidin-4-yl}-acetic acid ethyl ester {1-[2,6-Difluoro-4-(5-hydroxymethyl-thiophen-2-yl)-phenyl]-piperidin-4-yll}-acetic acid ethyl ester (0.14 g, 0.36 mmol) obtained in Step B and bromomethyl-cyclopropane (0.070 ml, 0.54 mmol) were reacted in the same manner as in Step C of Example 565 to obtain the title compound (0.12 g, 75%).

¹H-NMR (400 HMz CDCl₃); δ 7.06-7.00 (m, 3H), 6.92-6.91 (d, 1H), 4.67 (s, 2H), 4.18-4.12 (q, 2H), 3.35-3.33 (d, 2H), 3.27-3.24 (m, 2H), 3.14-3.09 (m, 2H), 2.30-2.28 (d, 2H), 1.95 (m, 1H), 1.78-1.75 (m, 2H0, 1.48-1.40 (m, 2H), 1.29-1.26 (t, 3H), 1.11-1.08 (m, 1H), 0.58-0.53 (m, 2H), 0.24-0.20 (m, 2H)

Step D: {1-[4-(5-cyclomethoxymethyl-thiophen-2-yl)-2,6-difluoro-phenyl]-piperidin-4-yl}-acetic acid {1-[4-(5-Cyclomethoxymethyl-thiophen-2-yl)-2,6-difluoro-phenyl]-piperidin-4-yl}-acetic acid ethyl ester (0.12 g, 0.27 mmol) obtained in Step C was reacted in the same manner as in Step B of Example 1 to obtain the title compound (0.10 g, 89%).

¹H-NMR (400 HMz CDCl₃); δ 7.07-7.01 (m, 3H), 6.93-6.92 (d, 1H), 4.67 (s, 2H), 3.35-3.34 (d, 2H), 3.28-3.25 (m, 2H), 3.15-3.10 (m, 2H), 3.67-3.35 (d, 2H), 1.96 (m, 1H), 1.83-1.80 (m, 2H), 1.51-1.43 (m, 2H), 1.15-1.08 (m, 1H), 0.58-0.53 (m, 2H), 0.24-0.20 (m, 2H)

Example 570: {1-[4-(4-cyclopropylmethoxymethyl-2-methyl-thiazol-5-yl)-2,6-difluoro-phenyl]-piperidin-4-yl}-acetic acid

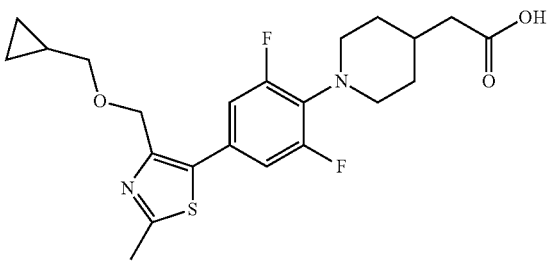 [SMILES: Cc1nc(COCC2CC2)c(-c2cc(F)c(N3CCC(CC(=O)O)CC3)c(F)c2)s1]

Step A: {1-[4-(4-cyclopropylmethoxymethyl-2-methyl-thiazol-5-yl)-2,6-difluoro-phenyl]-piperidin-4-yl}-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 5-bromo-4-cyclopropylmethoxymethyl-2-methyl-thiazole (0.12 g, 0.44 mmol) obtained in Preparation Example 337 were reacted in the same manner as in Step A of Example 1 to obtain the title compound (0.059 g, 32%).

¹H-NMR (400 HMz CDCl₃); δ 7.11-7.01 (m, 2H), 4.49 (s, 2H), 4.20-4.13 (q, 2H), 3.45-3.42 (d, 2H), 3.31-3.28 (m, 2H), 3.16-3.10 (m, 2H), 2.75 (s, 3H), 2.30-2.28 (d, 2H), 1.98-1.94 (m, 1H), 1.79-1.76 (m, 2H), 1.49-1.43 (m, 2H), 1.29-1.26 (t, 3H), 1.18-1.14 (m, 1H), 0.60-0.55 (m, 2H), 0.28-0.24 (m, 2H)

Step B: {1-[4-(4-cyclopropylmethoxymethyl-2-methyl-thiazol-5-yl)-2,6-difluoro-phenyl]-piperidin-4-yl}-acetic acid {1-[4-(4-Cyclopropylmethoxymethyl-2-methyl-thiazol-5-yl)-2,6-difluoro-phenyl]-piperidin-4-yl}-acetic acid ethyl ester (0.059 g, 0.13 mmol) obtained in Step A was reacted in the same manner as in Step B of Example 1 to obtain the title compound (0.050 g, 88%).

¹H-NMR (500 HMz CDCl₃); δ 7.08-7.06 (m, 2H), 4.48 (s, 2H), 3.43-3.42 (d, 2H), 3.31-3.28 (m, 2H), 3.16-3.11 (m, 2H), 2.69 (s, 3H), 2.36-2.35 (d, 2H), 1.98 (m, 1H), 1.83-1.81 (m, 2H), 1.49-1.46 (m, 2H), 1.16 (m, 1H), 0.59-0.54 (m, 2H), 0.27-0.25 (m, 2H)

Example 571: 4-[4-(5-cyclobutylmethoxymethyl-thiophen-3-yl)-2,6-difluoro-phenoxy]-butanoic acid

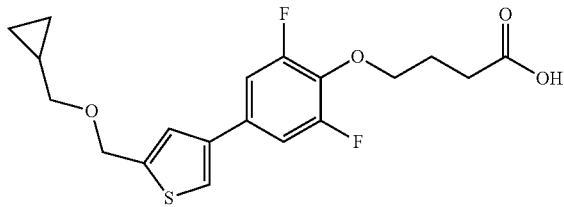 [SMILES: O=C(O)CCCOc1c(F)cc(-c2csc(COCC3CC3)c2)cc1F]

Step A: 4-[4-(5-cyclobutylmethoxymethyl-thiophen-3-yl)-2,6-difluoro-phenoxy]-butanoic acid ethyl ester 4-[2,6-Difluoro-4-(5-hydroxymethyl-thiophen-3-yl)-phenoxy]-butanoic acid ethylester (0.10 g, 0.29 mmol) obtained in Step B of Example 566 and bromomethyl-cyclobutane (0.062 ml, 0.58 mmol) were reacted in the same manner as in Step C of Example 565 to obtain the title compound (0.016 g, 13%).
$^1$H-NMR (400 HMz CDCl$_3$); δ 7.32 (d, 1H), 7.16 (m, 1H), 7.11-7.05 (m, 2H), 4.66 (s, 2H), 4.20-4.15 (q, 2H), 3.49-3.48 (d, 2H), 2.65-2.56 (m, 3H), 2.27-2.03 (m, 4H), 1.96-1.73 (m, 4H), 1.29-1.27 (t, 3H)

Step B: 4-[4-(5-cyclobutylmethoxymethyl-thiophen-3-yl)-2,6-difluoro-phenoxy]-butanoic acid 4-[4-(5-Cyclobutylmethoxymethyl-thiophen-3-yl)-2,6-difluoro-phenoxy]-butanoic acid ethyl ester (0.016 g, 0.038 mmol) obtained in Step A was reacted in the same manner as in Step B of Example 1 to obtain the title compound (0.014 g, 92%).
$^1$H-NMR (400 HMz CDCl$_3$); δ 7.32 (d, 1H), 7.16 (m, 1H), 7.17-7.05 (m, 2H), 4.66 (s, 2H), 4.21-4.10 (t, 2H), 2.68-2.64 (t, 2H), 2.63-2.57 (m, 1H), 2.13-2.03 (m, 4H), 1.96-1.73 (m, 4H)

Example 572: 4-[2,6-difluoro-4-(5-isobutoxymethyl-thiophen-3-yl)-phenoxy]-butanoic acid

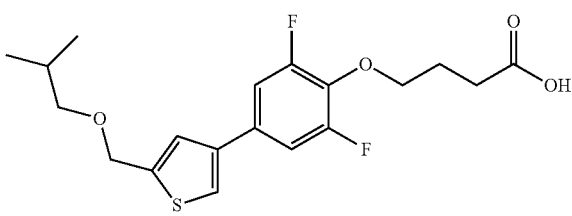 [SMILES: CC(C)COCc1cc(-c2cc(F)c(OCCCC(=O)O)c(F)c2)cs1]

Step A: 4-[2,6-difluoro-4-(5-isobutoxymethyl-thiophen-3-yl)-phenoxy]-butanoic acid ethyl ester 4-[2,6-Difluoro-4-(5-hydroxymethyl-thiophen-3-yl)-phenoxy]-butanoic acid ethylester (0.12 g, 0.34 mmol) obtained in Step B of Example 566 and 1-iodo-2-methyl-propane (0.090 ml, 0.67 mmol) were reacted in the same manner as in Step C of Example 565 to obtain the title compound (0.014 g, 10%).
$^1$H-NMR (400 HMz CDCl$_3$); δ 7.32 (d, 1H), 7.15 (m, 1H), 7.09-7.05 (m, 2H), 4.66 (s, 2H), 4.20-4.15 (q, 2H), 3.29-3.27 (d, 2H), 2.58-2.56 (t, 2H), 2.12-2.06 (m, 2H), 1.96-1.86 (m, 1H), 1.29-1.25 (t, 3H), 0.94-0.92 (t, 3H)

Step B: 4-[2,6-difluoro-4-(5-isobutoxymethyl-thiophen-3-yl)-phenoxy]-butanoic acid 4-[2,6-Difluoro-4-(5-isobutoxymethyl-thiophen-3-yl)-phenoxy]-butanoic acid ethyl ester (0.014 g, 0.034 mmol) obtained in Step A was reacted in the same manner as in Step B of Example 1 to obtain the title compound (0.006 g, 42%).
$^1$H-NMR (400 HMz CDCl$_3$); δ 7.32 (d, 1H), 7.15 (m, 1H), 7.10-7.07 (m, 2H), 4.66 (s, 2H), 4.22-4.19 (t, 2H), 3.29-3.27 (d, 2H), 2.68-2.65 (t, 2H), 2.14-2.05 (m, 2H), 1.94-1.87 (m, 1H), 0.94-0.92 (d, 6H)

Example 573: 4-[4-(5-cyclobutoxymethyl-thiophen-3-yl)-2,6-difluoro-phenoxy]-butanoic acid

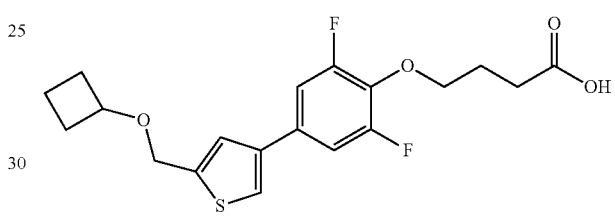

Step A: 4-[4-(5-cyclobutoxymethyl-thiophen-3-yl)-2,6-difluoro-phenoxy]-butanoic acid ethyl ester 4-[2,6-Difluoro-4-(4,4,5,5-tetramethyl-1,3,2-dioxaborolan-2-yl)phenoxy]butyric acid ethyl ester (0.10 g, 0.28 mmol) obtained in Preparation Example 16 and 4-bromo-2-cyclobutoxymethyl-thiophene (0.069 ml, 0.28 mmol) obtained in Preparation Example 338 were reacted in the same manner as in Step A of Example 1 to obtain the title compound (0.035 g, 30%).
$^1$H-NMR (500 HMz CDCl$_3$); δ 7.31-7.30 (d, 1H), 7.15 (m, 1H), 7.09-7.05 (m, 2H), 4.56 (s, 2H), 4.19-4.12 (m, 4H), 4.09-4.03 (m, 1H), 2.58-2.55 (t, 2H), 2.25-1.98 (m, 2H), 2.11-2.06 (m, 2H), 2.05-1.95 (m, 2H), 1.78-1.68 (m, 1H), 1.56-1.48 (m, 1H), 1.27-1.25 (t, 3H)

Step B: 4-[4-(5-cyclobutoxymethyl-thiophen-3-yl)-2,6-difluoro-phenoxy]-butanoic acid 4-[4-(5-Cyclobutoxymethyl-thiophen-3-yl)-2,6-difluoro-phenoxy]-butanoic acid ethyl ester (0.035 g, 0.085 mmol) obtained in Step A was reacted in the same manner as in Step B of Example 1 to obtain the title compound (0.030 g, 90%).
$^1$H-NMR (400 HMz CDCl$_3$); δ 7.31 (d, 1H), 7.16 (m, 1H), 7.10-7.05 (m, 2H), 4.57 (s, 2H), 4.22-4.19 (t, 2H), 4.10-4.03 (m, 1H), 2.68-2.65 (t, 2H), 2.26-2.19 (m, 2H), 2.14-1.97 (m, 4H), 1.76-1.69 (m, 1H), 1.58-1.48 (m, 1H)

Example 574: 4-[4-(3-cyclopropylmethoxymethyl-thiophen-2-yl)-2,6-difluoro-phenoxy]-butanoic acid

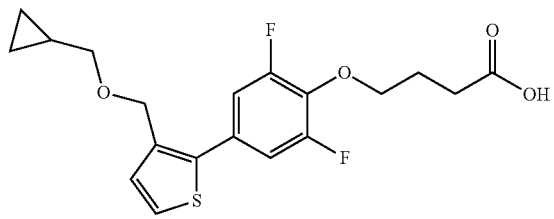

Step A: 4-[2,6-difluoro-4-(3-formyl-thiophen-2-yl)-phenoxy]-butanoic acid ethyl ester 4-(4-Bromo-2,6-difluoro-phenoxy)-butanoic acid ethyl ester (0.23 g, 0.70 mmol) obtained in Preparation Example 339 and 3-formyl-2-thiopheneboronic acid (0.11 g, 0.70 mmol) were reacted in the same manner as in Step A of Example 565 to obtain the title compound (0.16 g, 66%).

$^1$H-NMR (400 HMz CDCl$_3$); δ 9.90-9.89 (d, 1H), 7.76-7.75 (d, 1H), 7.18-7.16 (d, 1H), 7.04-7.00 (m, 2H), 4.28-4.25 (t, 2H), 4.19-4.14 (q, 2H), 2.61-2.57 (t, 2H), 2.16-2.09 (m, 2H), 1.29-1.26 (t, 3H)

Step B: 4-[2,6-difluoro-4-(3-hydroxymethyl-thiophen-2-yl)-phenoxy]-butanoic acid ethyl ester 4-[2,6-Difluoro-4-(3-formyl-thiophen-2-yl)-phenoxy]-butanoic acid ethyl ester (0.16 g, 0.46 mmol) obtained in Step A was reacted in the same manner as in Step B of Example 565 to obtain the title compound (0.15 g, 92%).

$^1$H-NMR (500 HMz CDCl$_3$); δ 7.32-7.30 (d, 1H), 7.08-7.01 (m, 3H), 4.81-4.80 (d, 2H), 4.23-4.20 (t, 2H), 4.19-4.13 (q, 2H), 2.61-2.57 (t, 2H), 2.14-2.07 (m, 2H), 1.87-1.84 (t, 1H), 1.29-1.25 (t, 3H)

Step C: 4-[4-(3-cyclopropylmethoxymethyl-thiophen-2-yl)-2,6-difluoro-phenoxy]-butanoic acid ethyl ester 4-[2,6-Difluoro-4-(3-hydroxymethyl-thiophen-2-yl)-phenoxy]-butanoic acid ethyl ester (0.15 g, 0.43 mmol) obtained in Step B and bromomethyl-cyclopropane (0.16 ml, 0.43 mmol) were reacted in the same manner as in Step C of Example 565 to obtain the title compound (0.082 g, 47%).

$^1$H-NMR (400 HMz CDCl$_3$); δ 7.29-7.28 (d, 1H), 7.10-7.04 (m, 3H), 4.57 (s, 2H), 4.21-4.14 (m, 4H), 3.39-3.37 (d, 2H), 2.61-2.57 (t, 2H), 2.11-2.08 (m, 2H), 1.28-1.25 (t, 2H), 1.14-1.11 (m, 1H), 0.58-0.55 (m, 2H), 0.26-0.24 (m, 2H)

Step D: 4-[4-(3-cyclopropylmethoxymethyl-thiophen-2-yl)-2,6-difluoro-phenoxy]-butanoic acid 4-[4-(3-Cyclopropylmethoxymethyl-thiophen-2-yl)-2,6-difluoro-phenoxy]-butanoic acid ethyl ester (0.082 g, 0.20 mmol) obtained in Step C was reacted in the same manner as in Step D of Example 565 to obtain the title compound (0.074 g, 97%).

$^1$H-NMR (400 HMz CDCl$_3$); δ 7.29-7.28 (d, 1H), 7.10-7.04 (m, 3H), 4.57 (s, 2H), 4.23-4.21 (t, 2H), 3.39-3.37 (d, 2H), 2.68-2.66 (t, 2H), 2.12-2.09 (m, 2H), 1.13-1.11 (m, 1H), 0.58-0.55 (m, 2H), 0.25-0.23 (m, 2H)

Example 575: {1-[4-(4-cyclobutoxy-6-methyl-pyrimidin-2-yl)-2,6-difluoro-phenyl]-pyrrolidin-3-yl}-acetic acid

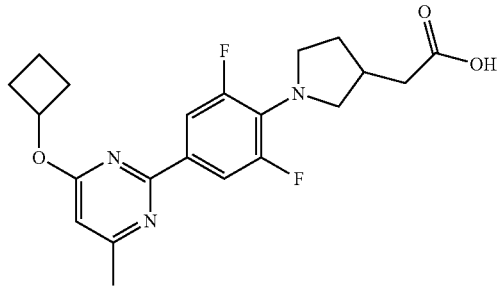 [SMILES: Cc1cc(OC2CCC2)nc(-c2cc(F)c(N3CCC(CC(=O)O)C3)c(F)c2)n1]

Step A: {1-[4-(4-cyclobutoxy-6-methyl-pyrimidin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-4-(cyclobutoxy)-6-methyl-pyrimidine (0.099 g, 0.50 mmol) obtained in Preparation Example 228 were reacted in the same manner as in Step A of Example 1 to obtain the title compound (0.057 g, 53%).

$^1$H-NMR (400 HMz, CDCl$_3$); δ 7.86-7.81 (m, 2H), 6.34 (s, 1H), 5.33-5.26 (m, 1H), 4.19-4.14 (q, 2H), 3.79-3.64 (m, 3H), 3.42-3.38 (m, 1H), 2.68-2.55 (m, 1H), 2.53-2.46 (m, 4H), 2.44 (s, 3H), 2.23-2.14 (m, 3H), 1.91-1.55 (m, 3H), 1.30-1.26 (t, 3H)

Step B: {1-[4-(4-cyclobutoxy-6-methyl-pyrimidin-2-yl)-2,6-difluoro-phenyl]-pyrrolidin-3-yl}-acetic acid {1-[4-(4-Cyclobutoxy-6-methyl-pyrimidin-2-yl)-2,6-difluoro-phenyl]-pyrrolidin-3-yl}-acetic acid ethyl ester (0.053 g, 0.13 mmol) obtained in Step A was reacted in the same manner as in Step B of Example 1 to obtain the title compound (0.048 g, 90%).

$^1$H-NMR (400 HMz, CDCl$_3$); δ 7.88-7.81 (m, 2H), 6.34 (s, 1H), 5.33-5.26 (m, 1H), 3.79-3.64 (m, 3H), 3.44-3.39 (m, 1H), 2.67-2.59 (m, 1H), 2.56-2.48 (m, 4H), 2.44 (s, 3H), 2.21-2.16 (m, 3H), 1.91-1.63 (m, 3H)

Example 576: {1-[4-(4-cyclopropylmethoxy-6-methyl-pyrimidin-2-yl)-2,6-difluoro-phenyl]-pyrrolidin-3-yl}-acetic acid

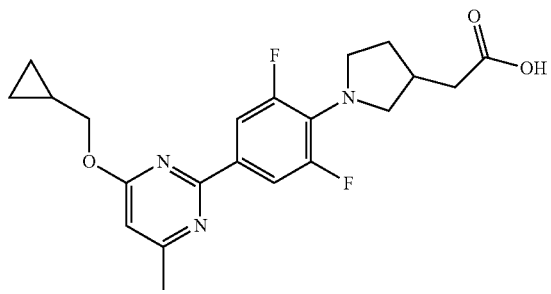 [SMILES: Cc1cc(OCC2CC2)nc(-c2cc(F)c(N3CCC(CC(=O)O)C3)c(F)c2)n1]

Step A: {1-[4-(4-cyclopropylmethoxy-6-methyl-pyrimidin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-4-(cyclopropylmethoxy)-6-methyl-pyrimidine (0.099 g, 0.50 mmol) obtained in Preparation Example 227 were reacted in the same manner as in Step A of Example 1 to obtain the title compound (0.068 g, 63%).

$^1$H-NMR (400 HMz, CDCl$_3$); δ 7.90-7.81 (m, 2H), 6.41 (s, 1H), 4.28-4.26 (d, 2H), 4.19-4.14 (q, 2H), 3.79-3.70 (m, 2H), 3.65-3.63 (m, 1H), 3.43-3.37 (m, 1H), 2.68-2.60 (m, 1H), 2.52-2.46 (m, 2H), 2.45 (s, 3H), 2.18-2.11 (m, 1H), 1.67-1.58 (m, 1H), 1.35-1.31 (m, 1H), 1.30-1.26 (t, 3H), 0.66-0.61 (m, 2H), 0.41-0.37 (m, 2H)

Step B: {1-[4-(4-cyclopropylmethoxy-6-methyl-pyrimidin-2-yl)-2,6-difluoro-phenyl]-pyrrolidin-3-yl}-acetic acid {1-[4-(4-Cyclopropylmethoxy-6-methyl-pyrimidin-2-yl)-2,6-difluoro-phenyl]-pyrrolidin-3-yl}-acetic acid ethyl ester (0.068 g, 0.016 mmol) obtained in Step A was reacted in the same manner as in Step B of Example 1 to obtain the title compound (0.062 g, 97%).

$^1$H-NMR (400 HMz, CDCl$_3$); δ 7.87-7.84 (m, 2H), 6.41 (s, 1H), 4.28-4.26 (d, 2H), 3.79-3.65 (m, 3H), 3.41 (m, 1H), 2.67-2.64 (m, 1H), 2.56-2.53 (m, 2H), 2.45 (s, 3H), 2.17 (m, 1H), 1.68-1.63 (m, 1H), 1.31-1.29 (m, 1H), 0.66-0.61 (m, 2H), 0.41-0.38 (m, 2H)

Example 577: {1-[4-(6-cyclobutoxy-4-methyl-pyridin-2-yl)-2,6-difluoro-phenyl]-pyrrolidin-3-yl}-acetic acid

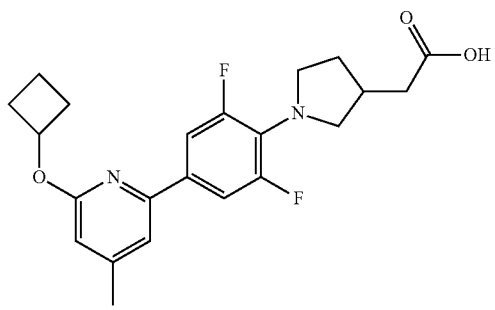 [SMILES: Cc1cc(OC2CCC2)nc(-c2cc(F)c(N3CCC(CC(=O)O)C3)c(F)c2)c1]

Step A: {1-[4-(6-cyclobutoxy-4-methyl-pyridin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-6-(cyclobutoxy)-4-methyl-pyridine (0.099 g, 0.50 mmol) obtained in Preparation Example 271 were reacted in the same manner as in Step A of Example 1 to obtain the title compound (0.075 g, 69%).

$^1$H-NMR (400 HMz, CDCl$_3$); δ 7.51-7.42 (m, 2H), 7.00 (s, 1H), 6.40 (s, 1H), 5.27-5.20 (m, 1H), 4.19-7.13 (q, 2H), 3.74-3.67 (m, 2H), 3.62-3.58 (m, 1H), 3.37-3.33 (m, 1H), 2.67-2.63 (m, 1H), 2.55-2.46 (m, 4H), 2.31 (s, 3H), 2.19-2.12 (m, 3H), 1.46-1.42 (m, 3H), 1.29-1.26 (t, 3H)

Step B: {1-[4-(6-cyclobutoxy-4-methyl-pyridin-2-yl)-2,6-difluoro-phenyl]-pyrrolidin-3-yl}-acetic acid {1-[4-(6-Cyclobutoxy-4-methyl-pyridin-2-yl)-2,6-difluoro-phenyl]-pyrrolidin-3-yl}-acetic acid ethyl ester (0.075 g, 0.17 mmol) obtained in Step A was reacted in the same manner as in Step B of Example 1 to obtain the title compound (0.069 g, 98%).

$^1$H-NMR (400 HMz, CDCl$_3$); δ 7.51-7.43 (m, 2H), 7.00 (s, 1H), 6.40 (s, 1H), 5.27-5.20 (m, 1H), 3.77-3.60 (m, 3H), 3.39-3.35 (m, 1H), 2.68-2.60 (m, 1H), 2.56-2.48 (m, 4H), 2.31 (s, 3H), 2.19-2.12 (m, 3H), 1.86-1.64 (m, 3H)

Example 578: {1-[4-(6-cyclobutoxy-pyrazin-2-yl)-2,6-difluoro-phenyl]-pyrrolidin-3-yll}-acetic acid

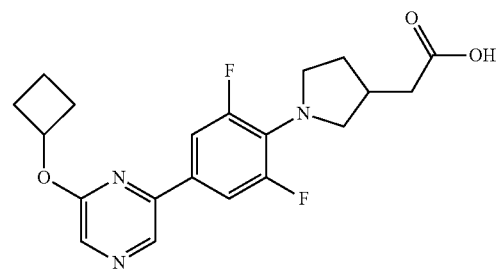 [SMILES: O=C(O)CC1CCN(c2c(F)cc(-c3cncc(OC4CCC4)n3)cc2F)C1]

Step A: {1-[4-(6-cyclobutoxy-pyrazin-2-yl)-2,6-difluoro-phenyl]-pyrrolidin-3-yll}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-6-(cyclobutoxy)pyrazine (0.099 g, 0.50 mmol) obtained in Preparation Example 232 were reacted in the same manner as in Step A of Example 1 to obtain the title compound (0.083 g, 80%).

$^1$H-NMR (400 HMz, CDCl$_3$); δ 8.43 (s, 1H), 8.02 (s, 1H), 7.50-7.42 (m, 2H), 5.30-5.23 (m, 1H), 4.19-4.14 (q, 2H), 3.78-3.63 (m, 3H), 3.41-3.37 (m, 1H), 2.69-2.61 (m, 1H), 2.57-2.46 (m, 4H), 2.26-2.14 (m, 3H), 1.96-1.59 (m, 3H), 1.30-1.26 (t, 3H)

Step B: {1-[4-(6-cyclobutoxy-pyrazin-2-yl)-2,6-difluoro-phenyl]-pyrrolidin-3-yll}-acetic acid {1-[4-(6-Cyclobutoxy-pyrazin-2-yl)-2,6-difluoro-phenyl]-pyrrolidin-3-yll}-acetic acid (0.083 g, 0.20 mmol) obtained in Step A was reacted in the same manner as in Step B of Example 1 to obtain the title compound (0.067 g, 86%).

$^1$H-NMR (500 HMz, MeOD-d$_4$); δ 8.73 (s, 1H), 8.09 (s, 1H), 7.69-7.67 (m, 2H), 5.23-5.19 (m, 1H), 3.65 (m, 2H), 3.53 (m, 1H), 3.29 (m, 1H), 2.45-2.41 (m, 34H), 2.38 (m, 2H), 2.11-2.21 (m, 3H), 1.82-1.68 (m, 2H), 1.59-1.51 (m, 1H)

Example 579: {1-[4-(4-cyclobutoxy-pyrimidin-2-yl)-2,6-difluoro-phenyl]-pyrrolidin-3-yl}-acetic acid

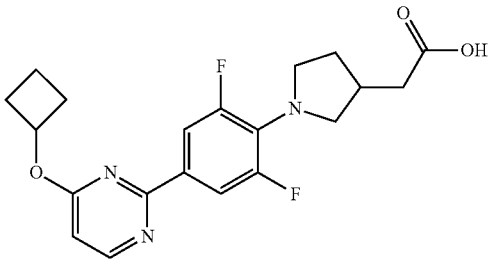 [SMILES: O=C(O)CC1CCN(c2c(F)cc(-c3nccc(OC4CCC4)n3)cc2F)C1]

Step A: {1-[4-(4-cyclobutoxy-pyrimidin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-4-(cyclobutoxy)pyrimidine (0.099 g, 0.50 mmol) obtained in Preparation Example 230 were reacted in the same manner as in Step A of Example 1 to obtain the title compound (0.047 g, 44%).
$^1$H-NMR (400 HMz, CDCl$_3$); δ 8.42-8.40 (d, 1H), 7.88-7.78 (m, 2H), 6.50-6.48 (d, 1H), 5.36-5.29 (m, 1H), 4.19-4.14 (q, 2H), 3.80-3.64 (m, 2H), 3.44-3.38 (m, 2H), 2.68-2.46 (m, 5H), 2.23-2.13 (m, 3H), 1.90-1.61 (m, 3H), 1.30-1.26 (t, 3H)

Step B: {1-[4-(4-cyclobutoxy-pyrimidin-2-yl)-2,6-difluoro-phenyl]-pyrrolidin-3-yl}-acetic acid {1-[4-(4-Cyclobutoxy-pyrimidin-2-yl)-2,6-difluoro-phenyl]-pyrrolidin-3-yl}-acetic acid ethyl ester (0.047 g, 0.11 mmol) obtained in Step A was reacted in the same manner as in Step B of Example 1 to obtain the title compound (0.042 g, 99%).
$^1$H-NMR (500 HMz, CDCl$_3$); δ 8.43-8.42 (d, 1H), 7.86-7.79 (m, 2H), 6.50-6.49 (d, 1H), 5.35-5.29 (m, 1H), 3.83-3.71 (m, 2H), 3.65 (m, 1H), 3.45-3.41 (m, 1H), 2.68-2.61 (m, 1H), 2.59-2.49 (m, 4H), 2.24-2.15 (m, 3H), 1.89-1.63 (m, 3H)

Example 580: {1-[4-(6-cyclopropylmethoxy-pyrazin-2-yl)-2,6-difluoro-phenyl]-pyrrolidin-3-yl}-acetic acid

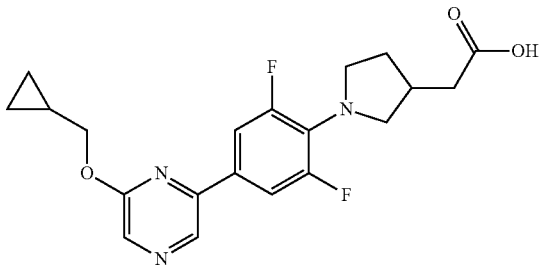 [SMILES: O=C(O)CC1CCN(c2c(F)cc(-c3cncc(OCC4CC4)n3)cc2F)C1]

Step A: {1-[4-(6-cyclopropylmethoxy-pyrazin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-6-(cyclopropylmethoxy)pyrazine (0.099 g, 0.50 mmol) obtained in Preparation Example 233 were reacted in the same manner as in Step A of Example 1 to obtain the title compound (0.041 g, 38%).
$^1$H-NMR (400 HMz, CDCl$_3$); δ 8.43 (s, 1H), 8.09 (s, 1H), 7.52-7.42 (m, 2H), 4.26-4.24 (d, 2H), 4.19-1.14 (q, 2H), 3.78-3.71 (m, 2H), 3.64-3.63 (m, 1H), 3.42-3.37 (m, 1H), 2.69-2.52 (m, 1H), 2.51-2.42 (m, 2H), 2.19-2.12 (m, 1H), 1.68-1.61 (m, 1H), 1.39-1.32 (m, 1H), 1.30-1.26 (t, 3H), 0.68-0.64 (m, 2H), 0.46-0.39 (m, 2H)

Step B: {1-[4-(6-cyclopropylmethoxy-pyrazin-2-yl)-2,6-difluoro-phenyl]-pyrrolidin-3-yl}-acetic acid {1-[4-(6-Cyclopropylmethoxy-pyrazin-2-yl)-2,6-difluoro-phenyl]-pyrrolidin-3-yl}-acetic acid ethyl ester (0.041 g, 0.095 mmol) obtained in Step A was reacted in the same manner as in Step B of Example 1 to obtain the title compound (0.036 g, 98%).
$^1$H-NMR (400 HMz, MeOD-d$_4$); δ 8.75 (s, 1H), 8.17 (s, 1H), 7.75-7.72 (m, 2H), 4.26-4.24 (d, 2H), 3.68 (m, 2H), 3.56 (m, 1H), 3.32 (m, 1H), 2.47 (m, 1H), 2.41-2.39 (m, 2H), 2.07 (m, 1H), 1.60-1.55 (m, 1H), 1.29-1.23 (m, 1H), 0.61-0.57 (m, 2H), 0.41-0.38 (m, 2H)

Example 581: {1-[4-(4-cyclopropylmethoxy-pyrimidin-2-yl)-2,6-difluoro-phenyl]-pyrrolidin-3-yl}-acetic acid

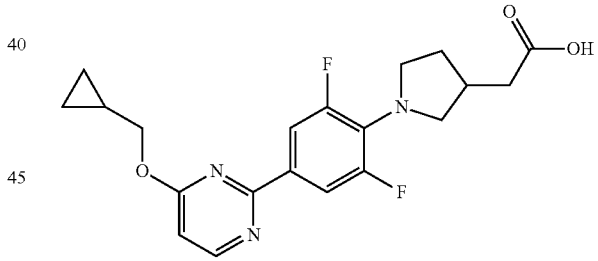

Step A: {1-[4-(4-cyclopropylmethoxy-pyrimidin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-4-(cyclopropylmethoxy)pyrimidine (0.099 g, 0.50 mmol) obtained in Preparation Example 231 were reacted in the same manner as in Step A of Example 1 to obtain the title compound (0.039 g, 36%).
$^1$H-NMR (500 HMz, CDCl$_3$); δ 8.41-8.40 (d, 1H), 7.86-7.81 (m, 2H), 6.55-6.54 (d, 1H), 4.29-4.27 (d, 2H), 4.16-4.13 (q, 2H), 3.79-3.63 (m, 3H), 3.42-3.38 (m, 1H), 2.69-2.59 (m, 1H), 2.49-2.42 (m, 2H), 2.18-2.12 (m, 1H), 1.67-1.62 (m, 1H), 1.35-1.29 (m, 1H), 1.28-1.25 (t, 3H), 0.66-0.63 (m, 2H), 0.41-0.38 (m, 2H)

Step B: {1-[4-(4-cyclopropylmethoxy-pyrimidin-2-yl)-2,6-difluoro-phenyl]-pyrrolidin-3-yl}-acetic acid {1-[4-(4-Cyclopropylmethoxy-pyrimidin-2-yl)-2,6-difluoro-phenyl]-pyrrolidin-3-yl}-acetic acid ethyl ester (0.039 g, 0.090 mmol) Obtained in Step A was reacted in the same manner as in Step B of Example 1 to obtain the title compound (0.035 g, 98%).

$^1$H-NMR (400 HMz, MeOD-d$_4$); δ 8.53-8.51 (d, 1H), 7.83-7.80 (m, 2H), 6.79-6.77 (d, 1H), 4.30-4.28 (d, 2H), 3.70 (m, 2H), 3.58 (m, 1H), 3.32 (m, 1H), 2.49 (m, 1H), 2.41-2.39 (m, 2H), 2.07 (m, 1H), 1.60-1.55 (m, 1H), 1.29-1.27 (m, 1H), 0.61-0.56 (m, 2H), 0.42-0.39 (m, 2H)

Example 582: {1-[4-(2-cyclobutoxy-thiazol-4-yl)-2,6-difluoro-phenyl]-pyrrolidin-3-yll}-acetic acid

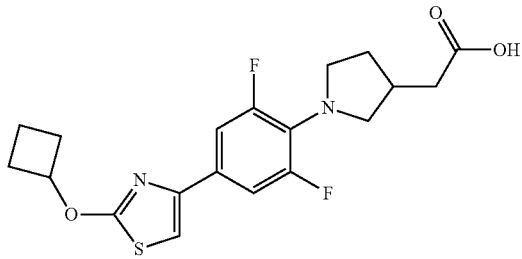 [SMILES: O=C(O)CC1CCN(c2c(F)cc(-c3csc(OC4CCC4)n3)cc2F)C1]

Step A: {1-[4-(2-cyclobutoxy-thiazol-4-yl)-2,6-difluoro-phenyl]-pyrrolidin-3-yll}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 4-bromo-2-(cyclobutoxy)thiazole (0.099 g, 0.50 mmol) obtained in Preparation Example 289 were reacted in the same manner as in Step A of Example 1 to obtain the title compound (0.041 g, 39%).

$^1$H-NMR (400 HMz, CDCl$_3$); δ 7.28-7.19 (m, 2H), 6.67 (s, 1H), 5.21-5.14 (m, 1H), 4.18-4.11 (q, 2H), 3.70-3.61 (m, 2H), 3.57-3.54 (m, 1H), 3.34-3.28 (m, 1H), 2.66-2.62 (m, 1H), 2.55-2.45 (m, 4H), 2.28-2.22 (m, 2H), 2.16-2.12 (m, 1H), 1.89-1.86 (m, 1H), 1.73-1.57 (m, 2H), 1.29-1.25 (t, 3H)

Step B: {11-[4-(2-cyclobutoxy-thiazol-4-yl)-2,6-difluoro-phenyl]-pyrrolidin-3-yll}-acetic acid {1-[4-(2-Cyclobutoxy-thiazol-4-yl)-2,6-difluoro-phenyl]-pyrrolidin-3-yll}-acetic acid ethyl ester (0.041 g, 0.097 mmol) obtained in Step A was reacted in the same manner as in Step B of Example 1 to obtain the title compound (0.033 g, 87%).

$^1$H-NMR (400 HMz, CDCl$_3$); δ 7.25-7.20 (m, 2H), 6.68 (s, 1H), 5.19-5.14 (m, 1H), 3.72-3.56 (m, 3H), 3.35-3.31 (m, 1H), 2.67-2.59 (m, 1H), 2.55-2.49 (m, 4H), 2.30-2.16 (m, 3H), 1.89-1.86 (m, 1H), 1.75-1.63 (m, 2H)

Example 583: {1-[4-(2-cyclopropylmethoxy-thiazol-4-yl)-2,6-difluoro-phenyl]-pyrrolidin-3-yl}-acetic acid

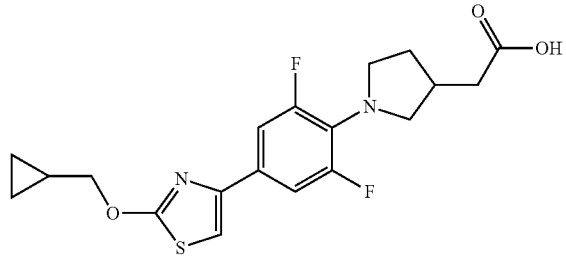 [SMILES: O=C(O)CC1CCN(c2c(F)cc(-c3csc(OCC4CC4)n3)cc2F)C1]

Step A: {1-[4-(2-cyclopropylmethoxy-thiazol-4-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 4-bromo-2-(cyclopropylmethoxy)thiazole (0.099 g, 0.50 mmol) obtained in Preparation Example 290 were reacted in the same manner as in Step A of Example 1 to obtain the title compound (0.048 g, 45%).

$^1$H-NMR (500 HMz, CDCl$_3$); δ 7.25-7.20 (m, 2H), 6.66 (s, 1H), 4.29-4.28 (d, 2H), 4.18-4.12 (q, 2H), 3.69-3.51 (m, 4H), 3.32-3.28 (m, 1H), 2.62-2.59 (m, 1H), 2.47-2.44 (m, 2H), 2.14-2.11 (m, 1H), 1.63-1.59 (m, 1H), 1.38-1.31 (m, 1H), 1.28-1.25 (t, 3H), 0.68-0.63 (m, 2H), 0.41-0.39 (m, 2H)

Step B: {1-[4-(2-cyclopropylmethoxy-thiazol-4-yl)-2,6-difluoro-phenyl]-pyrrolidin-3-yl}-acetic acid {1-[4-(2-Cyclopropylmethoxy-thiazol-4-yl)-2,6-difluoro-phenyl]-pyrrolidin-3-yl}-acetic acid ethyl ester (0.048 g, 0.11 mmol) obtained in Step was reacted in the same manner as in Step B of Example 1 to obtain the title compound (0.031 g, 70%).

$^1$H-NMR (400 HMz, CDCl$_3$); δ 7.26-7.23 (m, 2H), 6.69 (s, 1H), 4.30-4.29 (d, 2H), 3.73-3.56 (m, 3H), 3.34 (m, 1H), 2.68-2.60 (m, 1H), 2.56-2.53 (m, 2H), 2.19-2.16 (m, 1H), 1.69-1.64 (m, 1H), 1.37-1.32 (m, 1H), 0.69-0.64 (m, 2H), 0.43-0.39 (m, 2H)

Example 584: {1-[2,6-difluoro-4-(6-methoxy-pyrazin-2-yl)-phenyl]-pyrrolidin-3-yl}-acetic acid

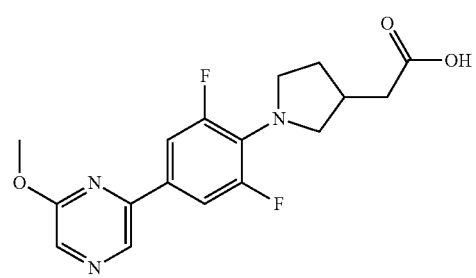 [SMILES: COc1cncc(-c2cc(F)c(N3CCC(CC(=O)O)C3)c(F)c2)n1]

Step A: {1-[2,6-difluoro-4-(6-methoxy-pyrazin-2-yl)-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 2-chloro-6-methoxy-pyrazine (0.072 g, 0.50 mmol) obtained in Preparation Example 234 were reacted in the same manner as in Step A of Example 1 to obtain the title compound (0.069 g, 73%).

$^1$H-NMR (400 HMz, CDCl$_3$); δ 8.45 (s, 1H), 8.08 (s, 1H), 7.52 (m, 2H), 4.19-4.14 (q, 2H), 4.05 (s, 3H), 3.76-3.64 (m, 3H), 3.40 (m, 1H), 2.67-2.61 (m, 1H), 2.49-2.47 (m, 2H), 2.17-2.15 9 m, 1H), 1.67-1.61 (m, 1H), 1.30-1.26 (t, 3H)

Step B: {1-[2,6-difluoro-4-(6-methoxy-pyrazin-2-yl)-phenyl]-pyrrolidin-3-yl}-acetic acid {1-[2,6-Difluoro-4-(6-methoxy-pyrazin-2-yl)-phenyl]-pyrrolidin-3-yl}-acetic acid ethyl ester (0.069 g, 0.18 mmol) obtained in Step A was reacted in the same manner as in Step B of Example 1 to obtain the title compound (0.048 g, 75%).

$^1$H-NMR (400 HMz, CDCl$_3$+MeOD-d$_4$); δ 8.43 (s, 1H), 8.04 (s, 1H), 7.55-7.50 (m, 2H), 4.06 (s, 3H), 3.79-3.64 (m, 3H), 3.41 (m, 1H), 2.67-2.63 (m, 1H), 2.49-2.48 (m, 2H), 2.20-2.16 (m, 1H), 1.70-1.63 (m, 1H)

Example 585: {1-[4-(6-ethoxy-pyrazin-2-yl)-2,6-difluoro-phenyl]-pyrrolidin-3-yl}-acetic acid

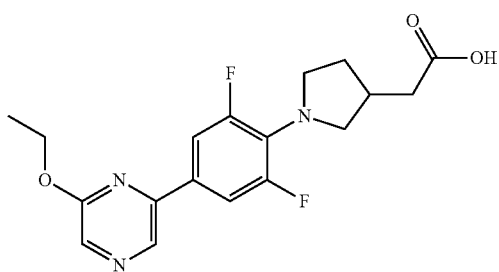 [SMILES: CCOc1cncc(-c2cc(F)c(N3CCC(CC(=O)O)C3)c(F)c2)n1]

Step A: {1-[4-(6-ethoxy-pyrazin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-6-ethoxy-pyrazine (0.079 g, 0.50 mmol) obtained in Preparation Example 302 were reacted in the same manner as in Step A of Example 1 to obtain the title compound (0.031 g, 32%).

$^1$H-NMR (400 HMz, CDCl$_3$); δ 8.43 (s, 1H), 8.05 (s, 1H), 7.52-7.44 (m, 2H), 4.51-4.46 (q, 2H), 4.19-4.14 (q, 2H), 3.78-3.71 (m, 3H), 3.41-3.37 (m, 1H), 2.67-2.61 (m, 1H), 2.48-2.46 (m, 2H), 2.18-2.13 (m, 1H), 1.68-1.61 (m, 1H), 1.47-1.44 (t, 3H), 1.30-1.25 (t, 3H)

Step B: {1-[4-(6-ethoxy-pyrazin-2-yl)-2,6-difluoro-phenyl]-pyrrolidin-3-yl}-acetic acid {1-[4-(6-Ethoxy-pyrazin-2-yl)-2,6-difluoro-phenyl]-pyrrolidin-3-yl}-acetic acid (0.031 g, 0.079 mmol) obtained in Step A was reacted in the same manner as in Step B of Example 1 to obtain the title compound (0.023 g, 80%).

$^1$H-NMR (400 MHz, DMSO-d$_6$) δ 8.77 (s, 1H), 8.15 (s, 1H), 7.77-7.73 (m, 2H), 4.49-4.44 (q, 2H), 3.69-3.57 (m, 3H), 3.33 (m, 1H), 2.47 (m, 1H), 2.43-2.41 (m, 2H), 2.08 (m, 1H), 1.62-1.56 (m, 1H), 1.41-1.38 (t, 3H)

Example 586: {1-[2,6-difluoro-4-(6-isopropoxy-pyrazin-2-yl)-phenyl]-pyrrolidin-3-yl}-acetic acid

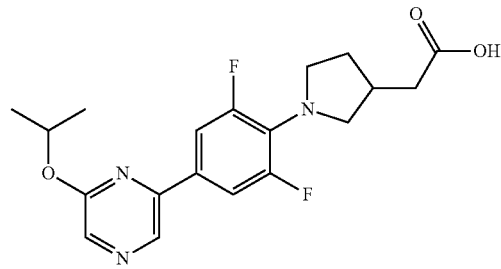 [SMILES: CC(C)Oc1cncc(-c2cc(F)c(N3CCC(CC(=O)O)C3)c(F)c2)n1]

Step A: {1-[2,6-difluoro-4-(6-isopropoxy-pyrazin-2-yl)-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0099 g, 0.25 mmol) obtained in Preparation Example 91 and 2-chloro-6-isopropoxy-pyrazine (0.086 g, 0.50 mmol) obtained in Preparation Example 301 were reacted in the same manner as in Step A of Example 1 to obtain the title compound (0.076 g, 75%).

$^1$H-NMR (400 HMz, CDCl$_3$); δ 8.40 (s, 1H), 8.00 (s, 1H), 7.48-7.45 (m, 1H), 5.45-5.39 (m, 1H), 4.19-4.14 (q, 2H), 3.76-3.63 (m, 3H), 3.39-3.37 (m, 1H), 2.67-2.63 (m, 1H). 2.48-2.46 (m, 2H), 2.15 (m, 1H), 1.66-1.61 (m, 1H), 1.42-1.40 (d, 6H), 1.30-1.26 (t, 3H)

Step B: {1-[2,6-difluoro-4-(6-isopropoxy-pyrazin-2-yl)-phenyl]-pyrrolidin-3-yl}-acetic acid {1-[2,6-Difluoro-4-(6-isopropoxy-pyrazin-2-yl)-phenyl]-pyrrolidin-3-yl}-acetic acid ethyl ester (0.076 g, 0.19 mmol) obtained in Step A was reacted in the same manner as in Step B of Example 1 to obtain the title compound (0.067 g, 95%).

$^1$H-NMR (400 MHz, DMSO-d$_6$) δ 8.73 (s, 1H), 8.09 (s, 1H), 7.74-7.70 (m, 2H), 5.40-5.35 (m, 1H), 3.68-3.56 (m, 2H), 3.33 (m, 1H), 2.45 (m, 1H), 2.41-2.40 (m, 2H), 2.07 (m, 1H), 1.60-1.55 (m, 1H), 1.37-1.36 (d, 6H)

Example 587: {1-[2,6-difluoro-4-(4-isopropoxy-6-methyl-pyrimidin-2-yl)-phenyl]-pyrrolidin-3-yl}-acetic acid

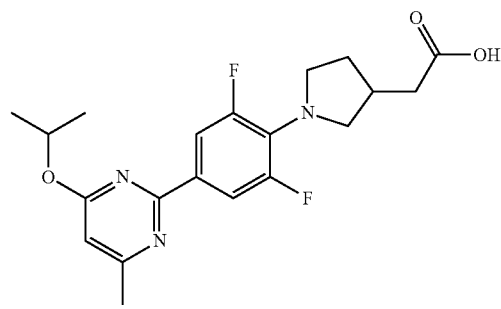 [SMILES: Cc1cc(OC(C)C)nc(-c2cc(F)c(N3CCC(CC(=O)O)C3)c(F)c2)n1]

Step A: {1-[2,6-difluoro-4-(4-isopropoxy-6-methyl-pyrimidin-2-yl)-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.30 g, 0.75 mmol) obtained in Preparation Example 91 and 2-chloro-4-isopropoxy-6-methyl-pyrimidine (0.28 g, 1.50 mmol) obtained in Preparation Example 244 were reacted in the same manner as in Step A of Example 1 to obtain the title compound (0.254 g, 81%).
$^1$H-NMR (400 HMz, CDCl$_3$); δ 7.90-7.80 (m, 2H), 6.33 (s, 1H), 5.53-5.46 (m, 1H), 4.19-4.14 (q, 2H), 3.79-3.70 (m, 2H), 3.64 (m, 1H), 3.42-3.37 (m, 1H), 2.68 (m, 1H), 2.48-2.46 (m, 2H), 2.43 (s, 3H), 2.18-2.13 (m, 1H), 1.68-1.60 (m, 1H), 1.40-1.38 (d, 6H), 1.30-1.26 (t, 3H)

Step B: {1-[2,6-difluoro-4-(4-isopropoxy-6-methyl-pyrimidin-2-yl)-phenyl]-pyrrolidin-3-yl}-acetic acid {1-[2,6-Difluoro-4-(4-isopropoxy-6-methyl-pyrimidin-2-yl)-phenyl]-pyrrolidin-3-yl}-acetic acid ethyl ester (0.254 g, 0.61 mmol) obtained in Step A was reacted in the same manner as in Step B of Example 1 to obtain the title compound (0.235 g, 99%).
$^1$H-NMR (400 HMz, CDCl$_3$); δ 7.90-7.81 (m, 2H), 6.34-6.33 (d, 1H), 5.53-5.46 (m, 1H), 3.81-3.65 (m, 3H), 3.44-3.40 (m, 1H), 2.69-2.61 (m, 1H), 2.55-2.51 (m, 2H), 2.44 (s, 3H), 2.20-2.16 (m, 1H), 1.70-1.61 (m, 1H), 1.40-1.38 (d, 6H)

Example 588: {1-[2,6-difluoro-4-(4-isobutoxy-6-methyl-pyrimidin-2-yl)-phenyl]-pyrrolidin-3-yl}-acetic acid

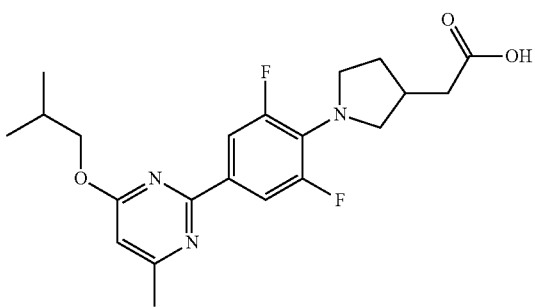 [SMILES: Cc1cc(OCC(C)C)nc(-c2cc(F)c(N3CCC(CC(=O)O)C3)c(F)c2)n1]

Step A: {1-[2,6-difluoro-4-(4-isobutoxy-6-methyl-pyrimidin-2-yl)-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.30 g, 0.75 mmol) obtained in Preparation Example 91 and 2-chloro-4-isobutoxy-6-methyl-pyrimidine (0.30 g, 1.50 mmol) obtained in Preparation Example 246 were reacted in the same manner as in Step A of Example 1 to obtain the title compound (0.176 g, 54%).
$^1$H-NMR (400 HMz, CDCl$_3$); δ 7.88-7.84 (m, 2H), 6.39 (s, 1H), 4.21-4.14 (m, 4H), 3.76-3.63 (m, 3H), 3.40 (m, 1H), 2.66-2.63 (m, 1H), 2.48-2.46 (m, 2H), 2.45 (s, 3H), 2.15-2.08 (m, 2H), 1.66-1.61 (m, 1H), 1.30-1.26 (t, 3H), 1.04-1.03 (d, 6H)

Step B: {1-[2,6-difluoro-4-(4-isobutoxy-6-methyl-pyrimidin-2-yl)-phenyl]-pyrrolidin-3-yl}-acetic acid {1-[2,6-Difluoro-4-(4-isobutoxy-6-methyl-pyrimidin-2-yl)-phenyl]-pyrrolidin-3-yl}-acetic acid ethyl ester (0.176 g, 0.41 mmol) obtained in Step A was reacted in the same manner as in Step B of Example 1 to obtain the title compound (0.164 g, 99%).
$^1$H-NMR (400 HMz, CDCl$_3$); δ 7.89-7.85 (m, 2H), 6.40 (s, 1H), 4.21-4.20 (d, 2H), 3.79-3.65 (m, 3H), 3.44-3.42 (m, 1H), 2.68-2.62 (m, 1H), 2.56-2.51 (m, 2H), 2.46 (s, 3H), 2.17-2.08 (m, 2H), 1.68-1.63 (m, 1H), 1.04-1.03 (d, 6H)

Example 589: {1-[2,6-difluoro-4-(4-methyl-6-propoxy-pyrimidin-2-yl)-phenyl]-pyrrolidin-3-yl}-acetic acid

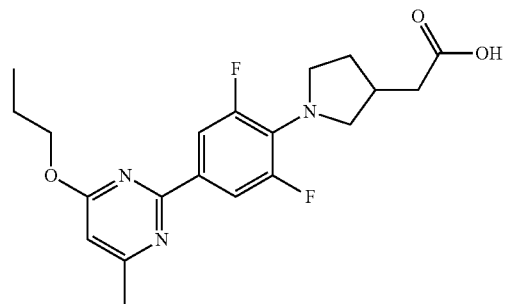 [SMILES: CCCOc1cc(C)nc(-c2cc(F)c(N3CCC(CC(=O)O)C3)c(F)c2)n1]

Step A: {1-[2,6-difluoro-4-(4-methyl-6-propoxy-pyrimidin-2-yl)-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.30 g, 0.75 mmol) obtained in Preparation Example 91 and 2-chloro-4-methyl-6-propoxy-pyrimidine (0.28 g, 1.50 mmol) obtained in Preparation Example 245 were reacted in the same manner as in Step A of Example 1 to obtain the title compound (0.281 g, 89%).
$^1$H-NMR (400 HMz, CDCl$_3$); δ 7.89-7.85 (m, 2H), 6.40 (s, 1H), 4.21-4.20 (d, 2H), 3.79-3.65 (m, 3H), 3.44-3.42 (m, 1H), 2.68-2.62 (m, 1H), 2.56-2.51 (m, 2H), 2.46 (s, 3H), 2.17-2.08 (m, 2H), 1.68-1.63 (m, 1H), 1.04-1.03 (d, 6H)

Step B: {1-[2,6-difluoro-4-(4-methyl-6-propoxy-pyrimidin-2-yl)-phenyl]-pyrrolidin-3-yl}-acetic acid {1-[2,6-Difluoro-4-(4-methyl-6-propoxy-pyrimidin-2-yl)-phenyl]-pyrrolidin-3-yl}-acetic acid ethyl ester (0.281 g, 0.67 mmol) obtained in Step A was reacted in the same manner as in Step B of Example 1 to obtain the title compound (0.183 g, 70%).
$^1$H-NMR (400 HMz, CDCl$_3$); δ 7.90-7.85 (m, 2H), 6.39 (s, 1H), 4.41-4.37 (t, 2H), 3.82-3.65 (m, 3H), 3.44-3.40 (m, 1H), 2.69-2.59 (m, 1H), 2.55-2.51 (m, 2H), 2.45 (s, 3H), 2.20-2.16 (m, 1H), 1.87-1.78 (m, 2H), 1.68-1.61 (m, 1H), 1.06-1.03 (t, 2H)

Example 590: {1-[4-(4-ethoxy-6-methyl-pyrimidin-2-yl)-2,6-difluoro-phenyl]-pyrrolidin-3-yl}-acetic acid

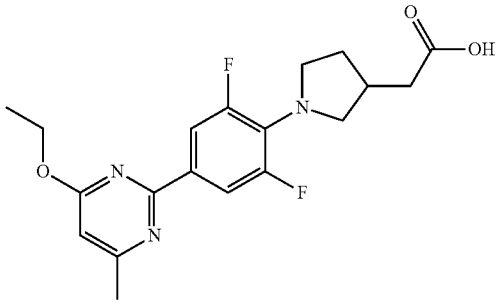 [SMILES: CCOc1cc(C)nc(-c2cc(F)c(N3CCC(CC(=O)O)C3)c(F)c2)n1]

Step A: {1-[4-(4-ethoxy-6-methyl-pyrimidin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.30 g, 0.75 mmol) obtained in Preparation Example 91 and 2-chloro-4-ethoxy-6-methyl-pyrimidine (0.259 g, 1.50 mmol) obtained in Preparation Example 243 were reacted in the same manner as in Step A of Example 1 to obtain the title compound (0.266 g, 88%).

$^{1}$H-NMR (400 HMz, CDCl$_{3}$); δ 7.88-7.85 (m, 2H), 6.37 (s, 1H), 4.52-4.47 (t, 2H), 4.19-4.14 (q, 2H), 3.77-3.64 (m, 3H), 3.40 (m, 1H), 2.66-2.61 (m, 1H), 2.48-2.46 (m, 2H), 2.45 (s, 3H), 2.05 (m, 1H) 1.65-1.60 (m, 1H), 1.44-1.41 (t, 3H), 1.30-1.26 (t, 3H)

Step B: {1-[4-(4-ethoxy-6-methyl-pyrimidin-2-yl)-2,6-difluoro-phenyl]-pyrrolidin-3-yl}-acetic acid {1-[4-(4-Ethoxy-6-methyl-pyrimidin-2-yl)-2,6-difluoro-phenyl]-pyrrolidin-3-yl}-acetic acid ethyl ester (0.266 g, 0.66 mmol) obtained in Step A was reacted in the same manner as in Step B of Example 1 to obtain the title compound (0.234 g, 94%).

$^{1}$H-NMR (400 HMz, CDCl$_{3}$); δ 7.90-7.82 (m, 2H), 6.37 (s, 1H), 4.52-4.47 (q, 2H), 3.79-3.64 (m, 3H), 3.49-3.40 (m, 1H), 2.69-2.62 (m, 1H), 2.55-2.51 (m, 2H), 2.45 (s, 3H), 2.20-2.16 (m, 1H), 1.70-1.63 (m, 1H), 1.44-1.41 (t, 3H)

Example 591: {1-[4-(5-cyclobutoxy-3-methyl-isothiazol-4-yl)-2,6-difluoro-phenyl]-pyrrolidin-3-yl}-acetic acid

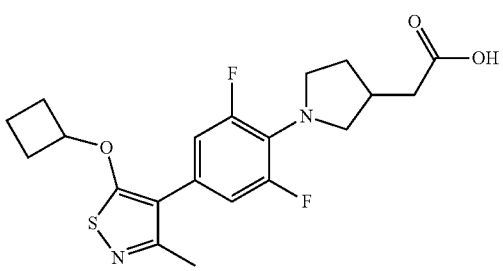 [SMILES: Cc1nsc(OC2CCC2)c1-c1cc(F)c(N2CCC(CC(=O)O)C2)c(F)c1]

Step A: {1-[4-(5-cyclobutoxy-3-methyl-isothiazol-4-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.094 g, 0.24 mmol) obtained in Preparation Example 91 and 4-bromo-5-(cyclobutoxy)-3-methyl-isothiazole (0.060 g, 0.24 mmol) obtained in Preparation Example 292 were reacted in the same manner as in Step A of Example 1 to obtain the title compound (0.048 g, 46%).

$^{1}$H-NMR (400 HMz, CDCl$_{3}$); δ 6.82-6.77 (m, 2H), 4.62-4.57 (m, 1H), 4.19-4.13 (q, 2H), 3.72-3.58 (m, 3H), 3.34-3.30 (m, 1H), 2.67-2.62 (m, 1H), 2.48-2.46 (m, 4H), 2.36 (s, 3H), 2.26-2.13 (m, 3H), 1.87-1.82 (m, 1H), 1.69-1.63 (m, 2H), 1.30-1.26 (t, 3H)

Step B: {1-[4-(5-cyclobutoxy-3-methyl-isothiazol-4-yl)-2,6-difluoro-phenyl]-pyrrolidin-3-yl}-acetic acid {1-[4-(5-Cyclobutoxy-3-methyl-isothiazol-4-yl)-2,6-difluoro-phenyl]-pyrrolidin-3-yl}-acetic acid ethyl ester (0.048 g, 0.11 mmol) obtained in Step A was reacted in the same manner as in Step B of Example 1 to obtain the title compound (0.038 g, 80%).

$^{1}$H-NMR (400 HMz, CDCl$_{3}$); δ 6.82-6.79 (m, 2H), 4.61-4.58 (m, 1H), 3.72-3.58 (m, 3H), 3.34 (m, 1H), 2.69-2.65 (m, 1H), 2.55-2.53 (m, 2H), 2.49-2.43 (m, 2H), 2.36 (s, 3H), 2.26-2.18 (m, 3H), 1.87-1.85 (m, 1H), 1.69-1.62 (m, 2H)

Example 592: {1-[4-(4-cyclobutoxy-5-fluoro-pyrimidin-2-yl)-2,6-difluoro-phenyl]-pyrrolidin-3-yl}-acetic acid

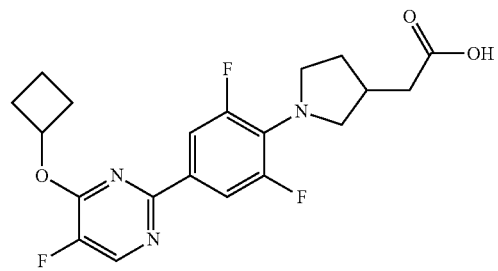 [SMILES: O=C(O)CC1CCN(c2c(F)cc(-c3ncc(F)c(OC4CCC4)n3)cc2F)C1]

Step A: {1-[4-(4-cyclobutoxy-5-fluoro-pyrimidin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.20 g, 0.5 mmol) obtained in Preparation Example 91 and 2-chloro-4-cyclobutoxy-5-fluoropyrimidine (0.15 g, 0.75 mmol) obtained in Preparation Example 329 were reacted in the same manner as in Step A of Example 1 to obtain the title compound (0.16 g, 72%).

$^{1}$H-NMR (400 HMz, CDCl$_{3}$); δ 8.29-8.27 (d, 1H), 7.78-7.72 (m, 2H), 5.42-5.38 (m, 1H), 4.19-4.4 (q, 2H), 3.77-3.75 (m, 2H), 6.64 (m, 2H), 3.42-3.38 (m, 1H), 2.66-2.53 (m, 3H0, 2.48-2.46 (m, 2H), 2.31-2.26 (m, 2H), 2.17-2.13 (m, 1H), 1.94-1.91 (m, 1H), 1.82-1.75 (m, 1H), 1.66-1.61 (m, 1H), 1.30-1.26 (t, 3H)

Step B: {1-[4-(4-cyclobutoxy-5-fluoro-pyrimidin-2-yl)-2,6-difluoro-phenyl]-pyrrolidin-3-yl}-acetic acid {1-[4-(4-Cyclobutoxy-5-fluoro-pyrimidin-2-yl)-2,6-difluoro-phenyl]-pyrrolidin-3-yl}-acetic acid ethyl ester (0.14 g, 0.31 mmol) obtained in Step A was reacted in the same manner as in Step B of Example 1 to obtain the title compound (0.10 g, 78%).

$^1$H-NMR (400 HMz, CDCl$_3$); δ 8.28-8.27 (d, 1H), 7.74-7.71 (m, 2H), 5.40-5.37 (m, 1H), 3.79-3.64 (m, 3H), 4.43-3.39 (m, 1H), 2.69-2.62 (m, 1H), 2.61-2.52 (m, 4H), 2.31-2.23 (m, 2H), 2.19-2.15 (m, 1H), 1.93-1.90 (m, 1H), 1.80-1.73 (m, 1H), 1.69-1.62 (m, 1H)

Example 593: {1-[4-(4-cyclopropylmethoxy-5-fluoro-pyrimidin-2-yl)-2,6-difluoro-phenyl]-pyrrolidin-3-yl}-acetic acid

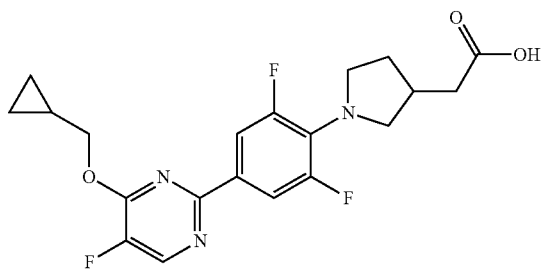 [SMILES: O=C(O)CC1CCN(c2c(F)cc(-c3ncc(F)c(OCC4CC4)n3)cc2F)C1]

Step A: {1-[4-(4-cyclopropylmethoxy-5-fluoro-pyrimidin-2-yl)-2,6-difluoro-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.2 g, 0.5 mmol) obtained in Preparation Example 91 and 2-chloro-4-cyclopropylmethoxy-5-fluoro-pyrimidine (0.15 g, 0.75 mmol) obtained in Preparation Example 330 were reacted in the same manner as in Step A of Example 1 to obtain the title compound (0.16 g, 69%).

$^1$H-NMR (400 HMz, CDCl$_3$); δ 8.29-8.28 (d, 1H), 7.79-7.71 (m, 2H), 4.39-7.37 (d, 2H), 4.19-4.14 (q, 2H), 3.77-3.64 (m, 3H), 3.42-3.38 (m, 1H), 2.66-2.62 (m, 1H), 2.48-2.46 (m, 2H), 2.17-2.13 (m, 1H), 1.68-1.61 (m, 1H), 1.40-1.37 (m, 1H), 1.30-1.26 (t, 3H), 0.70-0.66 (m, 2H), 0.46-0.42 (m, 2H)

Step B: {1-[4-(4-cyclopropylmethoxy-5-fluoro-pyrimidin-2-yl)-2,6-difluoro-phenyl]-pyrrolidin-3-yl}-acetic acid {1-[4-(4-Cyclopropylmethoxy-5-fluoro-pyrimidin-2-yl)-2,6-difluoro-phenyl]-pyrrolidin-3-yl}-acetic acid ethyl ester (0.12 g, 0.27 mmol) obtained in Step A was reacted in the same manner as in Step B of Example 1 to obtain the title compound (0.096 g, 81%).

$^1$H-NMR (400 HMz, CDCl$_3$); δ 8.29-8.28 (d, 1H), 7.74-7.72 (m, 2H), 4.38-4.36 (d, 2H), 3.81-3.63 (m, 3H), 3.48-3.39 (m, 1H), 2.68-2.61 (m, 1H), 2.54-2.50 (m, 2H), 2.18-2.15 (m, 1H), 1.66-1.64 (m, 1H), 1.39-1.36 (m, 1H), 0.69-0.66 (m, 2H), 0.44-0.42 (m, 2H)

Example 594: {1-[2,6-difluoro-4-(5-fluoro-4-isobutoxy-pyrimidin-2-yl)-phenyl]-pyrrolidin-3-yl}-acetic acid

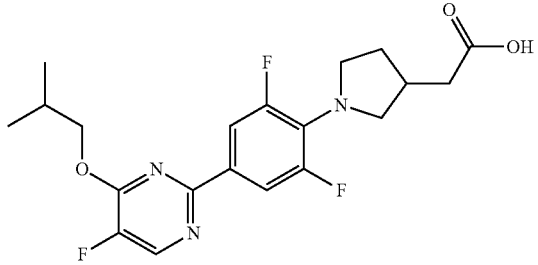 [SMILES: CC(C)COc1nc(-c2cc(F)c(N3CCC(CC(=O)O)C3)c(F)c2)ncc1F]

Step A: {1-[2,6-difluoro-4-(5-fluoro-4-isobutoxy-pyrimidin-2-yl)-phenyl]-pyrrolidin-3-yl}-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.16 g, 0.40 mmol) obtained in Preparation Example 91 and 2-chloro-5-fluoro-4-isobutoxy-pyrimidine (0.12 g, 0.60 mmol) obtained in Preparation Example 331 were reacted in the same manner as in Step A of Example 1 to obtain the title compound (0.12 g, 63%).

$^1$H-NMR (400 HMz, CDCl$_3$); δ 8.28-8.27 (d, 1H), 7.77-7.74 (m, 2H), 4.32-4.30 (d, 2H), 4.19-4.14 (q, 2H), 3.77-3.64 (m, 3H), 3.41 (m, 1H), 2.64-2.63 (m, 1H), 2.48-2.46 (m, 2H), 2.23-2.18 (m, 2H), 1.66-1.61 (m, 1H), 1.30-1.26 (t, 3H), 1.08-1.06 (d, 6H)

Step B: {1-[2,6-difluoro-4-(5-fluoro-4-isobutoxy-pyrimidin-2-yl)-phenyl]-pyrrolidin-3-yl}-acetic acid {1-[2,6-Difluoro-4-(5-fluoro-4-isobutoxy-pyrimidin-2-yl)-phenyl]-pyrrolidin-3-yl}-acetic acid ethyl ester (0.12 g, 0.27 mmol) obtained in Step A were reacted in the same manner as in Step B of Example 1 to obtain the title compound (0.074 g, 68%).

$^1$H-NMR (400 HMz, CDCl$_3$); δ 8.28-8.27 (d, 1H), 7.75-7.73 (m, 2H), 4.30-4.29 (d, 2H), 3.79-3.64 (m, 3H), 3.43-3.41 (m, 1H), 2.64-2.62 (m, 1H), 2.54-2.52 (m, 2H), 2.20-2.17 (m, 2H), 1.67-1.64 (m, 1H), 1.07-1.05 (d, 6H)

Example 595: (1-{2,6-difluoro-4-[6-(3-methoxypropoxy)-pyridin-2-yl]-phenyl}-pyrrolidin-3-yl)-acetic acid

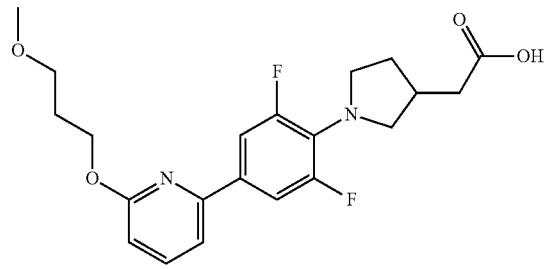 [SMILES: COCCCOc1cccc(-c2cc(F)c(N3CCC(CC(=O)O)C3)c(F)c2)n1]

Step A: (1-{2,6-difluoro-4-[6-(3-methoxy-propoxy)-pyridin-2-yl]-phenyl}-pyrrolidin-3-yl)-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-6-(3-methoxy-propoxy)-pyridine (0.076 g, 0.38 mmol) obtained in Preparation Example 332 were reacted in the same manner as in Step A of Example 1 to obtain the title compound (0.039 g, 34%).

$^1$H-NMR (400 HMz, CDCl$_3$); δ 7.59-7.55 (t, 1H), 7.54-7.45 (m, 2H), 7.18-7.16 (d, 1H), 6.62-6.60 (d, 1H), 4.50-4.47 (t, 2H), 4.19-4.14 (q, 2H), 3.75-3.66 (m, 2H), 3.62-3.55 (m, 3H), 3.38 (s, 3H), 3.36-3.33 (m, 1H), 2.69-2.61 (m, 1H), 2.52-2.42 (m, 2H), 2.17-2.06 (m, 3H), 1.68-1.61 (m, 1H), 1.30-1.26 (t, 3H)

Step B: (1-{2,6-difluoro-4-[6-(3-methoxy-propoxy)-pyridin-2-yl]-phenyl}-pyrrolidin-3-yl)-acetic acid (1-{2,6-Difluoro-4-[6-(3-methoxy-propoxy)-pyridin-2-yl]-phenyl}-pyrrolidin-3-yl)-acetic acid ethyl ester (0.039 g, 0.089 mmol) obtained in Step A was reacted in the same manner as in Step B of Example 1 to obtain the title compound (0.031 g, 85%).

$^1$H-NMR (400 HMz, CDCl$_3$); δ 7.58-7.55 (t, 1H), 7.55-7.47 (m, 2H), 7.17-7.15 (d, 1H), 6.61-6.59 (d, 1H), 4.49-4.46 (t, 2H), 3.74-3.67 (m, 2H), 3.60-3.55 (m, 3H), 3.38-3.35 (m, 4H), 2.66-2.61 (m, 1H), 2.58-2.52 (m, 2H), 2.21-2.14 (m, 1H), 2.11-2.05 (m, 2H), 1.67-1.62 (m, 1H)

Example 596: (1-{2,6-difluoro-4-[6-(tetrahydro-thiopyran-4-yloxy-pyridin-2-yl]-phenyl}-pyrrolidin-3-yl)-acetic acid

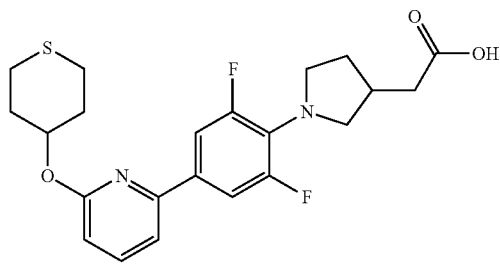 [SMILES: O=C(O)CC1CCN(c2c(F)cc(-c3cccc(OC4CCSCC4)n3)cc2F)C1]

Step A: (1-{2,6-difluoro-4-[6-(tetrahydro-thiopyran-4-yloxy-pyridin-2-yl]-phenyl}-pyrrolidin-3-yl)-acetic acid ethyl ester 2-[1-[2,6-Difluoro-4-(4,4,5,5-tetramethyl-1,3,2-dioxaborolan-2-yl)phenyl]pyrrolidin-3-yl]acetic acid ethyl ester (0.099 g, 0.25 mmol) obtained in Preparation Example 91 and 2-chloro-6-(tetrahydro-thiopyran-4-yloxy)-pyridine (0.086 g, 0.38 mmol) obtained in Preparation Example 333 were reacted in the same manner as in Step A of Example 1 to obtain the title compound (0.063 g, 52%).

$^1$H-NMR (400 HMz, CDCl$_3$); δ 7.60-7.56 (t, 1H), 7.47-7.39 (m, 2H), 7.17-7.15 (d, 1H), 6.61-6.59 (d, 1H), 5.32-5.28 (m, 1H), 4.19-4.14 (q, 2H), 3.75-3.60 (m, 3H), 3.38-3.34 (m, 1H), 2.95-2.90 (m, 2H), 2.70-2.61 (m, 3H), 2.52-2.46 (m, 2H), 2.31-2.25 (m, 2H), 2.17-2.04 (m, 3H), 1.68-1.63 (m, 1H), 1.30-1.26 (t, 3H)

Step B: (1-{2,6-difluoro-4-[6-(tetrahydro-thiopyran-4-yloxy-pyridin-2-yl]-phenyl}-pyrrolidin-3-yl)-acetic acid (1-{2,6-Difluoro-4-[6-(tetrahydro-thiopyran-4-yloxy-pyridin-2-yl]-phenyl}-pyrrolidin-3-yl)-acetic acid ethyl ester (0.063 g, 0.14 mmol) obtained in Step A was reacted in the same manner as in Step B of Example 1 to obtain the title compound (0.052 g, 89%).

$^1$H-NMR (400 HMz, CDCl$_3$); δ 7.60-7.56 (t, 1H), 7.47-7.39 (m, 2H), 7.17-7.15 (d, 1H), 6.62-6.60 (d, 1H), 5.32-5.28 (m, 1H), 3.78-3.61 (m, 3H), 3.40-3.36 (m, 1H), 2.95-2.91 (m, 2H), 2.70-2.65 (m, 3H), 2.56-2.53 (m, 2H), 2.31-2.04 (m, 5H), 1.71-1.64 (m, 1H)

Example 597: {1-[2,6-difluoro-4-(5-fluoro-4-isobutoxy-pyrimidin-2-yl)-phenyl]-piperidin-4-yl}-acetic acid

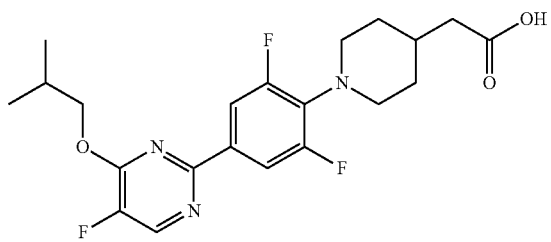 [SMILES: CC(C)COc1nc(-c2cc(F)c(N3CCC(CC(=O)O)CC3)c(F)c2)ncc1F]

Step A: {1-[2,6-difluoro-4-(5-fluoro-4-isobutoxy-pyrimidin-2-yl)-phenyl]-piperidin-4-yl}-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 2-chloro-5-fluoro-4-isobutoxy-pyrimidine (0.12 g, 0.60 mmol) obtained in Preparation Example 331 were reacted in the same manner as in Step A of Example 1 to obtain the title compound (0.11 g, 62%).

$^1$H-NMR (500 HMz, CDCl$_3$); δ 8.30-8.29 (d, 1H), 7.82-7.77 (m, 2H), 4.31-4.30 (d, 2H), 4.17-4.12 (q, 2H), 3.36-3.34 (m, 2H), 3.17-3.12 (m, 2H), 2.30-2.28 (d, 2H), 2.22-2.16 (m, 1H), 1.98-1.94 (m, 1H), 1.79-1.76 (m, 2H), 1.49-1.41 (m, 2H), 1.28-1.24 (t, 3H), 1.08-1.05 (d, 6H)

Step B: {1-[2,6-difluoro-4-(5-fluoro-4-isobutoxy-pyrimidin-2-yl)-phenyl]-piperidin-4-yl}-acetic acid {1-[2,6-Difluoro-4-(5-fluoro-4-isobutoxy-pyrimidin-2-yl)-phenyl]-piperidin-4-yl}-acetic acid ethyl ester (0.11 g, 0.25 mmol) obtained in Step A was reacted in the same manner as in Step B of Example 1 to obtain the title compound (0.095 g, 90%).

$^1$H-NMR (500 HMz, CDCl$_3$); δ 8.31-8.30 (d, 1H), 7.79-7.76 (m, 2H), 4.31-4.30 (d, 2H), 3.37-3.35 (m, 2H), 3.18-3.13 (m, 2H), 2.37-2.35 (d, 2H), 2.21-2.17 (m, 1H), 1.98-1.97 (m, 1H), 1.83-1.81 (m, 2H), 1.51-1.46 (m, 2H), 1.07-1.05 (d, 6H)

449

Example 598: {1-[2,6-difluoro-4-(5-fluoro-4-propoxy-pyrimidin-2-yl)-phenyl]-piperidin-4-yl}-acetic acid

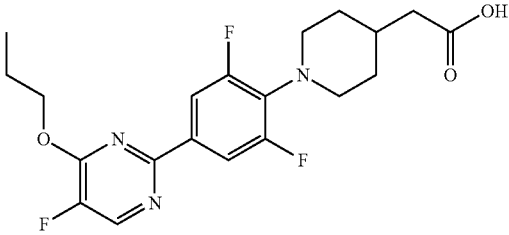 [SMILES: CCCOc1nc(-c2cc(F)c(N3CCC(CC(=O)O)CC3)c(F)c2)ncc1F]

Step A: {1-[2,6-difluoro-4-(5-fluoro-4-propoxy-pyrimidin-2-yl)-phenyl]-piperidin-4-yl}-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 2-chloro-5-fluoro-4-propoxy-pyrimidine (0.11 g, 0.60 mmol) obtained in Preparation Example 334 were reacted in the same manner as in Step A of Example 1 to obtain the title compound (0.11 g, 60%).

$^1$H-NMR (500 HMz, CDCl$_3$); δ 8.30-8.29 (d, 1H), 7.80-7.78 (m, 2H), 4.52-4.49 (t, 2H), 4.15-4.12 (q, 2H), 3.36-3.34 (m, 2H), 3.17-3.12 (m, 2H), 2.30-2.28 (d, 2H), 1.96 (m, 1H), 1.92-1.87 (q, 2H), 1.79-1.76 (m, 2H), 1.51-1.43 (m, 2H), 1.28-1.25 (t, 3H), 1.09-1.06 (t, 3H)

Step B: {1-[2,6-difluoro-4-(5-fluoro-4-propoxy-pyrimidin-2-yl)-phenyl]-piperidin-4-yl}-acetic acid {1-[2,6-Difluoro-4-(5-fluoro-4-propoxy-pyrimidin-2-yl)-phenyl]-piperidin-4-yl}-acetic acid ethyl ester (0.11 g, 0.24 mmol) obtained in Step A was reacted in the same manner as in Step B of Example 1 to obtain the title compound (0.092 g, 93%).

$^1$H-NMR (500 HMz, CDCl$_3$); δ 8.31-8.30 (d, 1H), 7.80-7.78 (m, 2H), 4.51-4.49 (t, 2H), 3.37-3.35 (m, 2H), 3.18-3.13 (m, 2H), 2.37-2.35 (d, 2H), 1.98 (m, 1H), 1.92-1.87 (m, 2H), 1.83-1.81 (m, 2H), 1.49-1.46 (m, 2H), 1.09-1.06 (t, 3H)

Example 599: (1-{2,6-difluoro-4-[4-(3-methyl-butoxy)-pyrimidin-2-yl]-phenyl}-piperidin-4-yl)-acetic acid

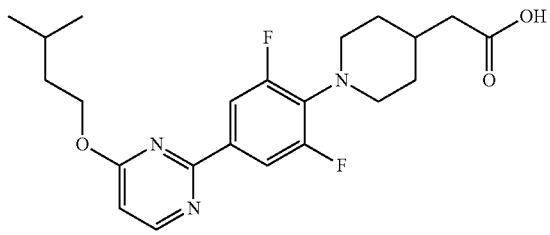 [SMILES: CC(C)CCOc1ccnc(-c2cc(F)c(N3CCC(CC(=O)O)CC3)c(F)c2)n1]

450

Step A: (1-{2,6-difluoro-4-[4-(3-methyl-butoxy)-pyrimidin-2-yl]-phenyl}-piperidin-4-yl)-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.21 g, 0.50 mmol) obtained in Preparation Example 220 and 2-chloro-4-(3-methyl-butoxy)-pyrimidine (0.15 g, 0.75 mmol) obtained in Preparation Example 335 were reacted in the same manner as in Step A of Example 1 to obtain the title compound (0.079 g, 35%).

$^1$H-NMR (500 HMz, CDCl$_3$); δ 8.43-8.42 (d, 1H), 7.90-7.85 (m, 2H), 6.56-6.55 (d, 1H), 4.50-4.47 (t, 2H), 4.15-4.12 (q, 2H), 3.37-3.35 (m, 2H), 3.17-3.14 (m, 2H), 2.29-2.28 (d, 2H), 1.98-1.95 (m, 1H), 1.84-1.80 (m, 1H), 1.79-1.76 (m, 2H), 1.72-1.68 (q, 2H), 1.49-1.42 (m, 2H), 1.29-1.24 (t, 3H), 0.99-0.96 (d, 6H)

Step B: (1-{2,6-difluoro-4-[4-(3-methyl-butoxy)-pyrimidin-2-yl]-phenyl}-piperidin-4-yl)-acetic acid (1-{2,6-Difluoro-4-[4-(3-methyl-butoxy)-pyrimidin-2-yl]-phenyl}-piperidin-4-yl)-acetic acid ethyl ester (0.079 g, 0.18 mmol) obtained in Step A was reacted in the same manner as in Step B of Example 1 to obtain the title compound (0.067 g, 90%).

$^1$H-NMR (500 HMz, CDCl$_3$); δ 8.44-0.43 (d, 1H), 7.90-7.86 (m, 2H), 6.57-6.56 (d, 1H), 4.50-4.48 (t, 2H), 3.39-3.36 (m, 2H), 3.18-3.14 (m, 2H), 2.37-2.35 (d, 2H), 2.0-1.96 (m, 1H), 1.84-1.78 (m, 3H), 1.72-1.68 (m, 2H), 1.52-1.45 (m, 2H), 0.99-0.98 (d, 6H)

Example 600: (1-{2,6-difluoro-4-[4-(3-methoxy-propoxy)-pyrimidin-2-yl]-phenyl}-piperidin-4-yl)-acetic acid

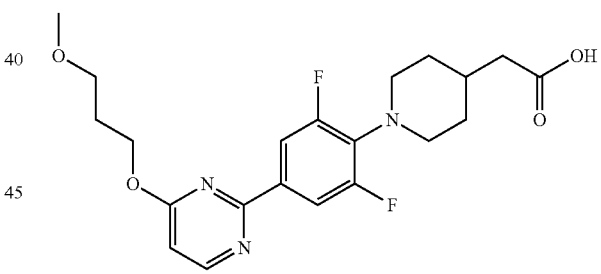

Step A: (1-{2,6-difluoro-4-[4-(3-methoxy-propoxy)-pyrimidin-2-yl]-phenyl}-piperidin-4-yl)-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 2-chloro-4-(3-methoxy-propoxy)-pyrimidine (0.12 g, 0.60 mmol) obtained in Preparation Example 336 were reacted in the same manner as in Step A of Example 1 to obtain the title compound (0.10 g, 56%).

$^1$H-NMR (500 HMz, CDCl$_3$); δ 8.44-8.43 (d, 1H), 7.90-7.88 (m, 2H), 6.58-6.57 (d, 1H), 4.56-4.54 (t, 2H), 4.17-4.13 (q, 2H), 3.56-3.54 (t, 2H), 3.36 (s, 3H), 3.35 (m, 2H), 3.17-3.13 (m, 2H), 2.30-2.28 (d, 2H), 2.11-2.17 (m, 2H), 1.97 (m, 1H), 1.79-1.76 (m, 2H), 1.48-1.42 (m, 2H), 1.28-1.25 (t, 3H)

Step B: (1-{2,6-difluoro-4-[4-(3-methoxy-propoxy)-pyrimidin-2-yl]-phenyl}-piperidin-4-yl)-acetic acid (1-{2,6-Difluoro-4-[4-(3-methoxy-propoxy)-pyrimidin-2-yl]-phenyl}-piperidin-4-yl)-acetic acid ethyl ester (0.10 g, 0.23 mmol) obtained in Step A was reacted in the same manner as in Step B of Example 1 to obtain the title compound (0.086 g, 90%).
$^1$H-NMR (500 HMz, CDCl$_3$); δ 8.45-8.44 (d, 1H), 7.91-7.86 (m, 2H), 6.59-6.58 (d, 1H), 4.57-4.54 (t, 2H), 3.57-3.54 (t, 2H), 3.38-3.34 (m, 5H), 3.18-3.14 (m, 2H), 2.37-2.35 (d, 2H), 2.12-2.07 (m, 2H), 1.99-1.97 (m, 1H), 1.84-1.81 (m, 2H) 1.52-1.44 (m, 2H)

Example 601: (1-{2,6-difluoro-4-[4-(3-methoxy-propoxy)-6-methyl-pyrimidin-2-yl]-phenyl}-piperidin-4-yl)-acetic acid

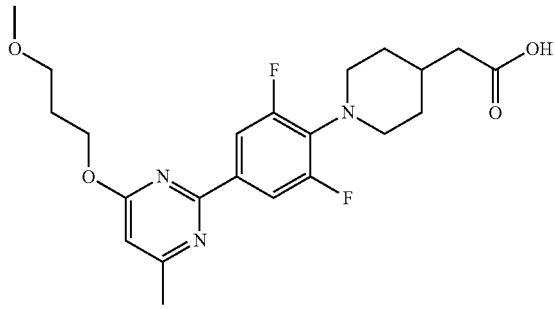 [SMILES: COCCCOc1cc(C)nc(-c2cc(F)c(N3CCC(CC(=O)O)CC3)c(F)c2)n1]

Step A: (1-{2,6-difluoro-4-[4-(3-methoxy-propoxy)-6-methyl-pyrimidin-2-yl]-phenyl}-piperidin-4-yl)-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 2-chloro-4-(3-methoxy-propoxy)-6-methyl-pyrimidine (0.17 g, 0.80 mmol) obtained in Preparation Example 248 were reacted in the same manner as in Step A of Example 1 to obtain the title compound (0.15 g, 82%).
$^1$H-NMR (500 HMz, CDCl$_3$); δ 7.92-7.87 (m, 2H), 6.42 (s, 1H), 4.53-4.51 (t, 2H), 4.17-4.13 (q, 2H), 3.55-3.53 (t, 2H), 3.36 (s, 3H), 3.34 (m, 2H), 3.17-3.12 (m, 2H), 2.45 (s, 3H), 2.30-2.28 (d, 2H), 2.10-2.05 (m, 2H), 1.97-1.95 (m, 1H), 1.78-1.76 (m, 2H), 1.49-1.41 (m, 2H), 1.28-1.24 (t, 3H)

Step B: (1-{2,6-difluoro-4-[4-(3-methoxy-propoxy)-6-methyl-pyrimidin-2-yl]-phenyl}-piperidin-4-yl)-acetic acid (1-{2,6-Difluoro-4-[4-(3-methoxy-propoxy)-6-methyl-pyrimidin-2-yl]-phenyl}-piperidin-4-yl)-acetic acid ethyl ester (0.15 g, 0.33 mmol) obtained in Step A was reacted in the same manner as in Step B of Example 1 to obtain the title compound (0.13 g, 90%).
$^1$H-NMR (500 HMz, CDCl$_3$); δ 7.92-7.87 (m, 2H), 6.43 (s, 1H), 4.54-4.51 (t, 2H), 3.56-3.53 (t, 2H), 3.36 (s, 3H), 3.34-3.33 (m, 2H), 3.18-3.13 (m, 2H), 2.46 (s, 3H), 2.36-2.35 (d, 2H), 2.09-2.05 (m, 2H), 1.99-1.96 (m, 1H), 1.83-1.81 (m, 2H), 1.52-1.46 (m, 2H)

Example 602: (1-{2,6-difluoro-4-[4-(2-methoxy-ethoxy)-6-methyl-pyrimidin-2-yl]-phenyl}-piperidin-4-yl)-acetic acid

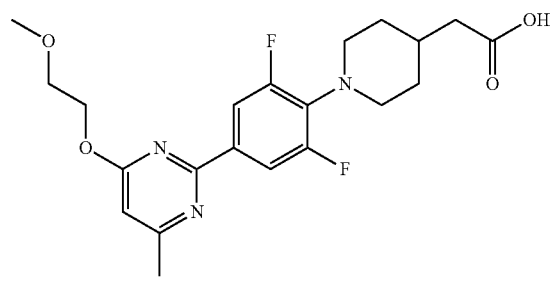 [SMILES: COCCOc1cc(C)nc(-c2cc(F)c(N3CCC(CC(=O)O)CC3)c(F)c2)n1]

Step A: (1-{2,6-difluoro-4-[4-(2-methoxy-ethoxy)-6-methyl-pyrimidin-2-yl]-phenyl}-piperidin-4-yl)-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 2-chloro-4-(2-methoxyethoxy)-6-methyl-pyrimidine (0.16 g, 0.80 mmol) obtained in Preparation Example 247 were reacted in the same manner as in Step A of Example 1 to obtain the title compound (0.15 g, 82%).
$^1$H-NMR (500 HMz, CDCl$_3$); δ 7.89-7.86 (m, 2H), 6.50 (s, 1H), 4.62-4.60 (t, 2H), 4.17-4.13 (q, 2H), 3.78-3.76 (t, 2H), 3.44 (s, 3H), 3.36-3.33 (m, 2H), 3.17-3.12 (m, 2H), 2.46 (s, 3H), 2.30-2.28 (d, 2H), 1.97-1.95 (m, 1H), 1.79-1.76 (m, 2H), 1.51-1.42 (m, 2H), 1.28-1.25 (t, 3H)

Step B: (1-{2,6-difluoro-4-[4-(2-methoxy-ethoxy)-6-methyl-pyrimidin-2-yl]-phenyl}-piperidin-4-yl)-acetic acid (1-{2,6-Difluoro-4-[4-(2-methoxy-ethoxy)-6-methyl-pyrimidin-2-yl]-phenyl}-piperidin-4-yl)-acetic acid ethyl ester (0.15 g, 0.33 mmol) obtained in Step A was reacted in the same manner as in Step B of Example 1 to obtain the title compound (0.13 g, 90%).
$^1$H-NMR (500 HMz, CDCl$_3$); δ 7.91-7.86 (m, 2H), 6.50 (s, 1H), 4.62-4.60 (t, 2H), 3.78-3.76 (t, 2H), 3.44 (s, 3H), 3.37-3.34 (m, 2H), 3.18-3.13 (m, 2H), 2.46 (s, 3H), 2.36-2.35 (d, 2H), 1.99-1.95 (m, 1H), 1.83-1.81 (m, 2H), 1.52-1.46 (m, 2H)

Example 603: (1-{2,6-difluoro-4-[6-(3-methoxy-propoxy)-pyridin-2-yl]-phenyl}-piperidin-4-yl)-acetic acid

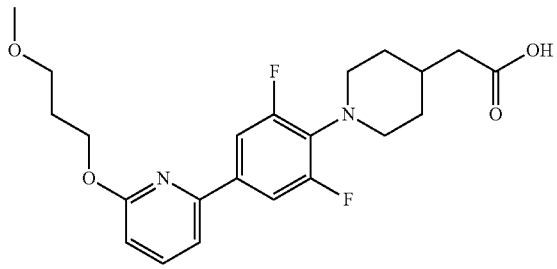 [SMILES: COCCCOc1cccc(-c2cc(F)c(N3CCC(CC(=O)O)CC3)c(F)c2)n1]

Step A: (1-{2,6-difluoro-4-[6-(3-methoxy-propoxy)-pyridin-2-yl]-phenyl}-piperidin-4-yl)-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 2-chloro-6-(3-methoxy-propoxy)-pyridine (0.16 g, 0.80 mmol) obtained in Preparation Example 332 were reacted in the same manner as in Step A of Example 1 to obtain the title compound (0.14 g, 76%).

$^1$H-NMR (400 HMz, CDCl$_3$); δ 7.61-7.58 (t, 1H), 7.54-7.49 (m, 2H), 7.21-7.19 (d, 1H), 6.66-6.64 (d, 1H), 4.49-4.47 (t, 2H), 4.17-4.13 (q, 2H), 3.58-3.55 (t, 2H), 3.37 (s, 3H), 3.34-3.30 (m, 2H), 3.17-3.12 (m, 2H), 2.30-2.28 (d, 2H), 2.11-2.06 (m, 2H), 1.97-1.94 (m, 1H), 1.79-1.76 (m, 2H), 1.51-1.43 (m, 2H), 1.28-1.26 (t, 3H)

Step B: (1-{2,6-difluoro-4-[6-(3-methoxy-propoxy)-pyridin-2-yl]-phenyl}-piperidin-4-yl)-acetic acid (1-{2,6-Difluoro-4-[6-(3-methoxy-propoxy)-pyridin-2-yl]-phenyl}-piperidin-4-yl)-acetic acid ethyl ester (0.14 g, 0.31 mmol) obtained in Step A was reacted in the same manner as in Step B of Example 1 to obtain the title compound (0.12 g, 90%).

$^1$H-NMR (400 HMz, CDCl$_3$); δ 7.61-7.58 (t, 1H), 7.54-7.50 (m, 2H), 7.21-7.19 (d, 1H), 6.66-6.65 (d, 1H), 4.49-4.47 (t, 2H), 3.58-3.56 (t, 2H), 3.37 (s, 3H), 3.33-3.31 (m, 2H), 3.18-3.13 (m, 2H), 2.37-2.35 (d, 2H), 2.11-2.06 (m, 2H), 1.98-1.95 (m, 1H), 1.83-1.81 (m, 2H), 1.53-1.46 (m, 2H)

Example 604: {(S)-1-[4-(6-cyclopropylmethoxy-pyridin-2-yll)-2,6-difluoro-phenyl]-pyrrolidin-3-yl}-acetic acid

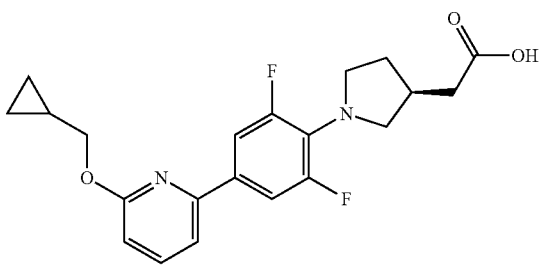 [SMILES: O=C(O)C[C@@H]1CCN(c2c(F)cc(-c3cccc(OCC4CC4)n3)cc2F)C1]

Step A: {(S)-1-[4-(6-cyclopropylmethoxy-pyridin-2-yll)-2,6-difluoro-phenyl]-pyrrolidin-3-yl}-acetic acid methyl ester 2-[(3S)-1-[2,6-difluoro-4-(4,4,5,5-tetramethyl-1,3,2-dioxaborolan-2-yl)phenyl]pyrrolidin-3-yl]acetic acid methyl ester (0.02 g, 0.53 mmol) obtained in Preparation Example 97 and 2-chloro-6-cyclopropylmethoxy-pyridine (0.19 g, 1.05 mmol) obtained in Preparation Example 43 were reacted in the same manner as in Step A of Example 1 to obtain the title compound (0.15 g, 70%).

$^1$H-NMR (400 HMz, CDCl$_3$); δ 7.60-7.56 (t, 1H), 7.53-7.45 (m, 2H), 7.18-7.16 (d, 1H), 6.67-6.65 (d, 1H), 4.24-4.22 (d, 2H), 3.76-3.61 (m, 6H), 3.39-3.35 (m, 1H), 2.69-2.64 (m, 1H), 2.51-2.46 (m, 2H), 2.18-2.14 (m, 1H), 1.68-1.63 (m, 1H), 1.36-1.30 (m, 1H), 0.66-0.61 (m, 2H), 0.41-0.37 (m, 2H)

Step B: {(S)-1-[4-(6-cyclopropylmethoxy-pyridin-2-yll)-2,6-difluoro-phenyl]-pyrrolidin-3-yl}-acetic acid {(S)-1-[4-(6-cyclopropylmethoxy-pyridin-2-yll)-2,6-difluoro-phenyl]-pyrrolidin-3-yl}-acetic acid methyl ester (0.15 g, 0.37 mmol) obtained in Step A was reacted in the same manner as in Step B of Example 1 to obtain the title compound (0.14 g, 97%).

$^1$H-NMR (400 HMz, CDCl$_3$); δ 7.60-7.56 (t, 1H), 7.52-7.44 (m, 2H), 7.18-7.16 (d, 1H), 6.67-6.64 (d, 1H), 4.24-4.22 (d, 2H), 3.77-3.61 (m, 3H), 3.40-3.36 (m, 1H), 2.70-2.63 (m, 1H), 2.56-2.50 (m, 2H), 2.23-2.17 (m, 1H), 1.71-1.62 (m, 1H), 1.35-1.30 (m, 1H), 0.66-0.61 (m, 2H), 0.41-0.37 (m, 2H)

Example 605: 2-[1-[2,6-difluoro-4-[4-[(6-methyl-3-pyridyl)oxy]pyrimidin-2-yl]phenyl]-4-piperidyl]acetic acid

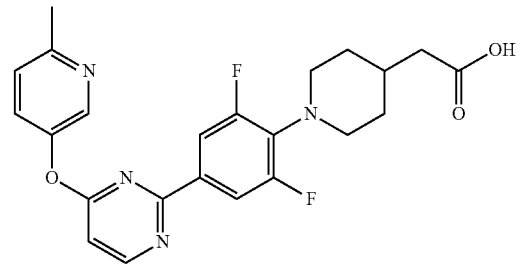

2-Chloro-4-(6-methyl-pyridin-3-yloxy)-pyrimidine (0.131 g, 0.59 mmol) obtained in Preparation Example 340 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.037 g, 17%).

$^1$H-NMR (CDCl$_3$) δ 8.63 (1H, d), 8.56 (1H, d), 7.70 (2H, m), 7.50 (1H, dd), 7.27 (1H, d), 6.81 (1H, d), 3.34 (2H, m), 3.12 (2H, m), 2.64 (3H, s), 2.34 (2H, d), 1.97 (1H, m), 1.81 (2H, m), 1.43 (2H, m)

Example 606: 2-[1-[2,6-difluoro-4-[6-(4-ethylphenoxy)pyrimidin-2-yl]phenyl]-4-piperidyl]acetic acid

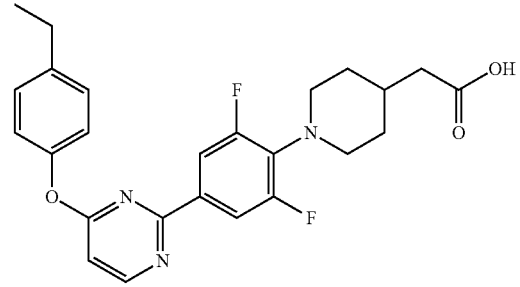

2-Chloro-4-(4-ethyl-phenoxy)-pyrimidine (0.138 g, 0.59 mmol) obtained in Preparation Example 341 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.097 g, 43%).

$^1$H-NMR (CDCl$_3$) δ 8.56 (1H, d), 7.75 (2H, m), 7.27 (2H, m), 7.11 (2H, m), 6.66 (1H, d), 3.35 (2H, m), 3.14 (2H, m), 2.71 (2H, q), 2.35 (2H, d), 1.97 (1H, m), 1.82 (2H, m), 1.45 (2H, m), 1.29 (3H, t)

Example 607: 2-[1-[4-[4-(3-fluorophenoxy)pyrimidin-2-yl]-2,6-difluoro-phenyl]-4-piperidyl]acetic acid

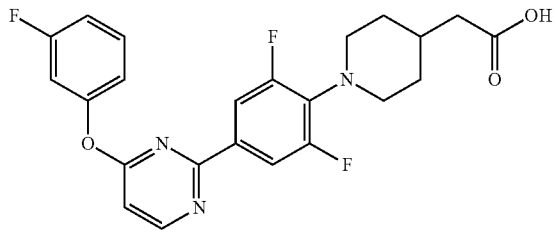 [SMILES: O=C(O)CC1CCN(c2c(F)cc(-c3nccc(Oc4cccc(F)c4)n3)cc2F)CC1]

2-Chloro-4-(3-fluoro-phenoxy)-pyrimidine (0.133 g, 0.59 mmol) obtained in Preparation Example 342 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.091 g, 41%).

$^1$H-NMR (CDCl$_3$) δ 8.62 (1H, d), 7.72 (2H, m), 7.41 (1H, m), 7.05-6.95 (3H, m), 6.74 (1H, d), 3.36 (2H, m), 3.13 (2H, m), 2.35 (2H, d), 1.97 (1H, m), 1.80 (2H, m), 1.45 (2H, m)

Example 608: 2-[1-[2,6-difluoro-4-[4-(3,4-fluoro-phenoxy)-6-methyl-pyrimidin-2-yl]phenyl]-4-piperidyl]acetic acid

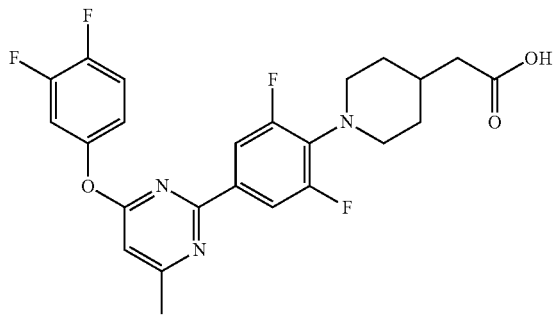 [SMILES: Cc1cc(Oc2ccc(F)c(F)c2)nc(-c2cc(F)c(N3CCC(CC(=O)O)CC3)c(F)c2)n1]

2-Chloro-4-(3,4-difluoro-phenoxy)-6-methyl-pyrimidine (0.151 g, 0.59 mmol) obtained in Preparation Example 343 and 2-[1-[2,6-difluoro-4-(4,4,5,5-tetramethyl-1,3,2-dioxaborolan-2-yl)phenyl]-4-piperidyl]acetic acid ethyl ester (0.2 g, 0.49 mmol) obtained in Preparation Example 220 were reacted in the same manner as in Step A of Example 96 and Step B of Example 1 to obtain the title compound (0.133 g, 57%).

$^1$H-NMR (CDCl$_3$) δ 7.72 (2H, m), 7.23 (1H, m), 7.05 (1H, m), 6.94 (1H, m), 6.57 (1H, s), 3.34 (2H, m), 3.13 (2H, m), 2.53 (3H, s), 2.34 (2H, d), 1.97 (1H, m), 1.80 (2H, m), 1.47 (2H, m)

Example 609: 2-[1-[2,6-difluoro-4-[4-(2-pyridyloxy)pyrimidin-2-yl]phenyl]-4-piperidyl]acetic acid

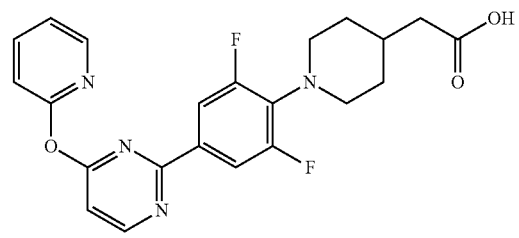 [SMILES: O=C(O)CC1CCN(c2c(F)cc(-c3nccc(Oc4ccccn4)n3)cc2F)CC1]

2-Chloro-4-(pyridin-2-yloxy)-pyrimidine (0.10 g, 0.48 mmol) obtained in Preparation Example 344 and 2-[1-[2,6-difluoro-4-(4,4,5,5-tetramethyl-1,3,2-dioxaborolan-2-yl)phenyl]-4-piperidyl]acetic acid ethyl ester (0.164 g, 0.40 mmol) obtained in Preparation Example 220 were reacted in the same manner as in Step A of Example 96 and Step B of Example 1 to obtain the title compound (0.037 g, 21%).

$^1$H-NMR (CDCl$_3$) δ 8.56 (1H, d), 8.41 (1H, m), 7.87 (1H, m), 7.72 (2H, m), 7.27 (1H, m), 7.19 (1H, d), 6.90 (1H, d), 3.35 (2H, m), 3.12 (2H, m), 2.34 (2H, d), 1.95 (1H, m), 1.80 (2H, m), 1.43 (2H, m)

Example 610: 2-[1-[2,6-difluoro-4-[4-[4-(trifluoromethyl)phenoxy]pyrimidin-2-yl]phenyl]-4-piperidyl]acetic acid

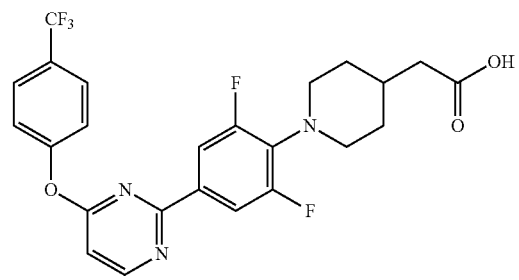 [SMILES: O=C(O)CC1CCN(c2c(F)cc(-c3nccc(Oc4ccc(C(F)(F)F)cc4)n3)cc2F)CC1]

2-Chloro-4-[4-(trifluoromethyl)phenoxy]pyrimidine (0.088 g, 0.32 mmol) obtained in Preparation Example 345 and 2-[1-[2,6-difluoro-4-(4,4,5,5-tetramethyl-1,3,2-dioxaborolan-2-yl)phenyl]-4-piperidyl]acetic acid ethyl ester (0.144 g, 0.35 mmol) obtained in Preparation Example 220 were reacted in the same manner as in Step A of Example 96 and Step B of Example 1 to obtain the title compound (0.12 g, 76%).

$^1$H-NMR (CDCl$_3$) δ 8.54 (1H, d), 7.70 (4H, m), 7.35 (2H, d), 6.80 (1H, d), 3.36 (2H, m), 3.13 (2H, m), 2.34 (2H, d), 1.97 (1H, m), 1.81 (2H, m), 1.47 (2H, m)

Example 611: 2-[1-[2,6-difluoro-4-[4-[3-(trifluoromethyl)phenoxy]pyrimidin-2-yl]phenyl]-4-piperidyl]acetic acid

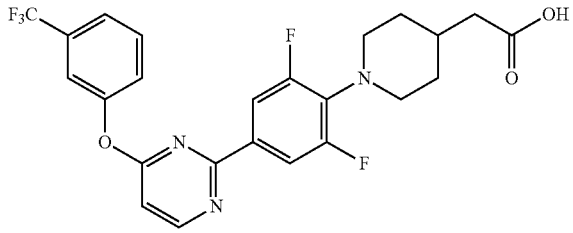 [SMILES: O=C(O)CC1CCN(c2c(F)cc(-c3nccc(Oc4cccc(C(F)(F)F)c4)n3)cc2F)CC1]

2-Chloro-4-[3-(trifluoromethyl)phenoxy]pyrimidine (0.092 g, 0.33 mmol) obtained in Preparation Example 346 and 2-[1-[2,6-difluoro-4-(4,4,5,5-tetramethyl-1,3,2-dioxaborolan-2-yl)phenyl]-4-piperidyl]acetic acid ethyl ester (0.15 g, 0.37 mmol) obtained in Preparation Example 220 were reacted in the same manner as in Step A of Example 96 and Step B of Example 1 to obtain the title compound (0.07 g, 51%).

$^1$H-NMR (CDCl$_3$) δ 8.64 (1H, d), 7.68 (2H, m), 7.58 (3H, m), 7.43 (1H, m), 6.80 (1H, d), 3.36 (2H, m), 3.13 (2H, m), 2.34 (2H, d), 1.97 (1H, m), 1.80 (2H, m), 1.45 (2H, m)

Example 612: 2-[1-[2,6-difluoro-4-[4-methyl-6-[4-(trifluoromethyl)phenoxy]pyrimidin-2-yl]phenyl]-4-piperidyl]acetic acid

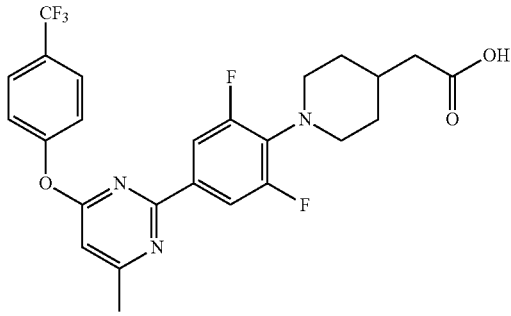 [SMILES: Cc1cc(Oc2ccc(C(F)(F)F)cc2)nc(-c2cc(F)c(N3CCC(CC(=O)O)CC3)c(F)c2)n1]

2-Chloro-4-methyl-6-[4-(trifluoromethyl)phenoxy]pyrimidine (0.088 g, 0.3 mmol) obtained in Preparation Example 347 and 2-[1-[2,6-difluoro-4-(4,4,5,5-tetramethyl-1,3,2-dioxaborolan-2-yl)phenyl]-4-piperidyl]acetic acid ethyl ester (0.135 g, 0.33 mmol) obtained in Preparation Example 220 were reacted in the same manner as in Step A of Example 96 and Step B of Example 1 to obtain the title compound (0.118 g, 77%).

$^1$H-NMR (CDCl$_3$) δ 7.72 (4H, m), 7.32 (2H, d), 6.61 (1H, s), 3.35 (2H, m), 3.13 (2H, m), 2.55 (3H, s), 2.35 (2H, d), 1.97 (1H, m), 1.80 (2H, m), 1.46 (2H, m)

Example 613: 2-[1-[2,6-difluoro-4-[4-methyl-6-[3-(trifluoromethyl)phenoxy]pyrimidin-2-yl]phenyl]-4-piperidyl]acetic acid

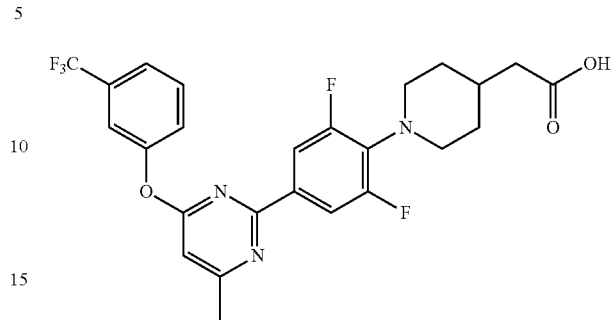

2-Chloro-4-methyl-6-[3-(trifluoromethyl)phenoxy]pyrimidine (0.087 g, 0.3 mmol) obtained in Preparation Example 348 and 2-[1-[2,6-difluoro-4-(4,4,5,5-tetramethyl-1,3,2-dioxaborolan-2-yl)phenyl]-4-piperidyl]acetic acid ethyl ester (0.135 g, 0.33 mmol) obtained in Preparation Example 220 was reacted in the same manner as in Step A of Example 96 and Step B of Example 1 to obtain the title compound (0.124 g, 81%).

$^1$H-NMR (CDCl$_3$) δ 7.71 (2H, m), 7.56 (3H, m), 7.39 (1H, m), 6.62 (1H, s), 3.35 (2H, m), 3.13 (2H, m), 2.55 (3H, s), 2.35 (2H, d), 1.97 (1H, m), 1.80 (2H, m), 1.46 (2H, m)

Example 614: {1-[4-(6-cyclobutoxy-4-trifluoromethyl-pyridin-2-yl)-2,6-difluoro-phenyl]-piperidin-4-yl}-acetic acid

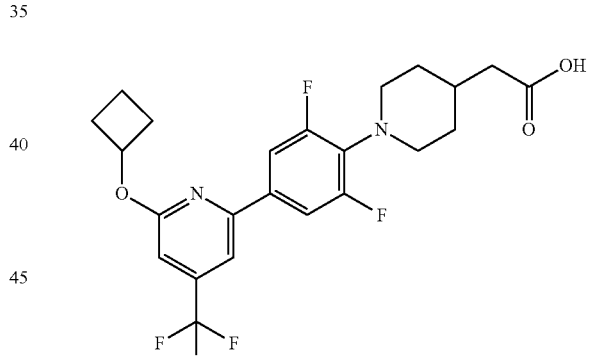

Step A: {1-[4-(6-cyclobutoxy-4-trifluoromethyl-pyridin-2-yl)-2,6-difluoro-phenyl]-piperidin-4-yl}-acetic acid ethyl ester 2-[1-[2,6-Difluoro-4-(4,4,5,5-tetramethyl-1,3,2-dioxaborolan-2-yl)phenyl]-4-piperidyl]acetic acid ethyl ester (0.16 g, 0.40 mmol) obtained in Preparation Example 220 and 2-chloro-4-cyclobutoxy-6-trifluoromethyl-pyrimidine (0.15 g, 0.60 mmol) obtained in Preparation Example 349 were reacted in the same manner as in Step A of Example 1 to obtain the title compound (0.09 g, 45%).

$^1$H-NMR (400 HMz, CDCl$_3$); δ 7.54-7.47 (m, 2H), 7.35 (s, 1H), 6.84 (s, 1H), 5.33-5.26 (m, 1H), 4.18-4.11 (q, 2H), 3.36-3.33 (m, 2H), 3.19-3.13 (m, 2H), 2.57-2.50 (m, 2H), 2.33-2.30 (d, 2H), 2.22-2.19 (m, 2H), 2.05-1.88 (m, 2H), 1.80-1.75 (m, 3H), 1.51-1.42 (m, 2H), 1.30-1.26 (t, 3H)

Step B: {1-[4-(6-cyclobutoxy-4-trifluoromethyl-pyridin-2-yl)-2,6-difluoro-phenyl]-piperidin-4-yl}-acetic acid {1-[4-(6-Cyclobutoxy-4-trifluoromethyl-pyridin-2-yl)-2,6-difluoro-phenyl]-piperidin-4-yl}-acetic acid ethyl ester (0.09 g, 0.18 mmol) obtained in Step A was reacted in the same manner as in Step B of Example 1 to obtain the title compound (0.076 g, 89%).

$^1$H-NMR (400 HMz, CDCl$_3$); δ 7.52-7.43 (m, 2H), 7.35 (s, 1H), 6.84 (s, 1H), 5.33-5.25 (m, 1H), 3.37-3.34 (m, 2H), 3.19-3.14 (m, 2H), 2.56-2.50 (m, 2H), 2.38-2.36 (d, 2H), 2.22-2.17 (m, 2H), 1.99 (m, 1H), 1.94-1.73 (m, 4H), 1.53-1.43 (m, 2H)

Example 615: (1-{2,6-difluoro-4-[2-(4-fluoro-phenyl)-benzo[b]thiophen-4-yl]-phenyl}-piperidin-4-yl)-acetic acid

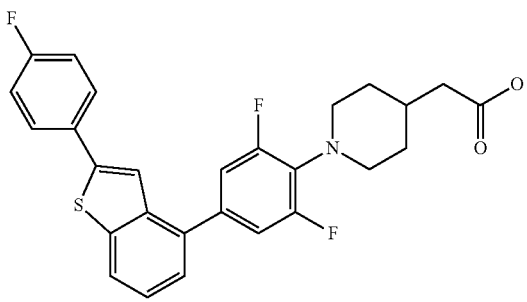 [SMILES: O=C(O)CC1CCN(c2c(F)cc(-c3cccc4sc(-c5ccc(F)cc5)cc34)cc2F)CC1]

[1-(4-Benzo[b]thiophen-4-yl-2,6-difluoro-phenyl)-piperidin-4-yl]-acetic acid ethyl ester (0.11 g, 0.26 mmol) obtained in Preparation Example 351 was dissolved in 2 mL of DMF. 1-Bromo-4-fluoro-benzene (0.03 g, 0.17 mmol), Pd(OAc)$_2$ (0.5 mol %) and KOAc (0.034 g, 0.34 mmol) were added thereto, and the mixture was stirred at 140° C. for 24 hours. Solids were filtered, and the reaction solution was concentrated under reduced pressure and purified by column chromatography to obtain (1-{2,6-difluoro-4-[2-(4-fluoro-phenyl)-benzo[b]thiophen-4-yl]-phenyl-piperidin-4-yl)-acetic acid ethyl ester. The obtained compound was reacted in the same manner as in Step B of Example 1 to obtain the title compound (0.008 g, 9%).

$^1$H-NMR (CDCl$_3$) δ 7.82 (1H, d), 7.65 (2H, m), 7.55 (1H, s), 7.35 (1H, t), 7.27 (1H, m), 7.08 (4H, m), 3.36 (2H, m), 3.21 (2H, m), 2.37 (2H, d), 1.99 (1H, m), 1.84 (2H, m), 1.52 (2H, m).

Example 616: {1-[2,6-difluoro-4-(2-m-tolyl-benzo[b]thiophen-4-yl)-phenyl]-piperidin-4-yl}-acetic acid

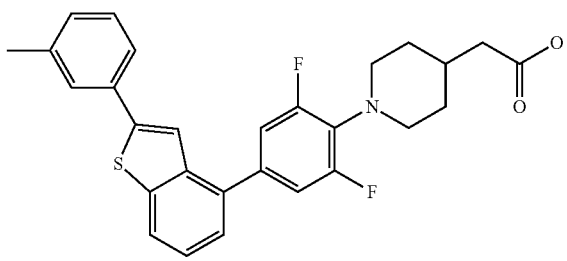 [SMILES: Cc1cccc(-c2cc3c(-c4cc(F)c(N5CCC(CC(=O)O)CC5)c(F)c4)cccc3s2)c1]

[1-(4-Benzo[b]thiophen-4-yl-2,6-difluoro-phenyl)-piperidin-4-yl]-acetic acid ethyl ester (0.07 g, 0.17 mmol) obtained in Preparation Example 351, 1-bromo-3-methyl-benzene (0.029 g, 0.17 mmol), Pd(OAc)$_2$ (0.5 mol %) and KOAc (0.034 g, 0.34 mmol) were reacted in the same manner as in Example 615 to obtain the title compound (0.004 g, 5%).

$^1$H-NMR (CDCl$_3$) δ 7.81 (1H, d), 7.61 (1H, s), 7.48 (2H, m), 7.29 (3H, m), 7.14 (1H, d), 7.08 (2H, m), 3.36 (2H, m), 3.20 (2H, m), 2.41 (3H, s), 2.39 (2H, d), 2.00 (1H, m), 1.84 (2H, m), 1.53 (2H, m).

Example 617: {1-[4-(4-cyclobutoxy-6-trifluoromethyl-pyrimidin-2-yl)-2,6-difluoro-phenyl]-piperidin-4-yl}-acetic acid

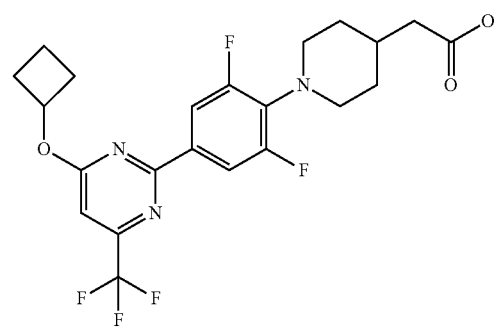 [SMILES: O=C(O)CC1CCN(c2c(F)cc(-c3nc(OC4CCC4)cc(C(F)(F)F)n3)cc2F)CC1]

2-[1-[2,6-Difluoro-4-(4,4,5,5-tetramethyl-1,3,2-dioxaborolan-2-yl)phenyl]-4-piperidyl]acetic acid ethyl ester (0.1 g, 0.24 mmol) obtained in Preparation Example 220 and 2-chloro-4-cyclobutoxy-6-trifluoromethyl-pyrimidine (0.074 g, 0.29 mmol) obtained in Preparation Example 352 were reacted in the same manner as in Step A of Example 1 to obtain 1-[4-(4-cyclobutoxy-6-trifluoromethyl-pyrimidin-2-yl)-2,6-difluoro-phenyl]-piperidin-4-yl}-acetic acid ethyl ester. The obtained compound was dissolved in 2 ml of 1,4-dioxane. 0.45 ml of 1N NaOH was added thereto, and the mixture was stirred at 60° C. for 4 hours. The organic solvent was removed, and the reaction product was adjusted to pH 3 by the use of 1N HCl aqueous solution and extracted with EtOAc to separate an organic layer. The organic layer was dried with anhydrous magnesium sulfate and concentrated under reduced pressure to obtain the title compound (0.072 g, 62%).

$^1$H-NMR (CDCl$_3$) δ 7.90 (2H, m), 6.84 (1H, s), 5.38 (1H, m), 3.40 (2H, m), 3.16 (2H, m), 2.53 (2H, m), 2.37 (2H, d), 2.21 (2H, m), 2.04 (1H, m), 1.89 (1H, m), 1.81 (3H, m), 1.47 (2H, m).

Example 618: {1-[2,6-difluoro-4-(4-propoxy-6-trifluoromethyl-pyrimidin-2-yl)-phenyl]-piperidin-4-yl}-acetic acid

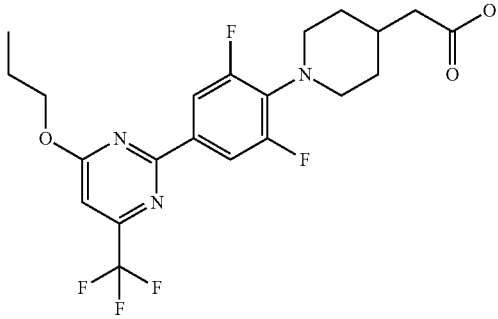 [SMILES: CCCOc1cc(C(F)(F)F)nc(-c2cc(F)c(N3CCC(CC(=O)O)CC3)c(F)c2)n1]

2-[1-[2,6-Difluoro-4-(4,4,5,5-tetramethyl-1,3,2-dioxaborolan-2-yl)phenyl]-4-piperidyl]acetic acid ethyl ester (0.1 g, 0.24 mmol) obtained in Preparation Example 220 and 2-chloro-4-propoxy-6-trifluoromethyl-pyrimidine (0.07 g, 0.29 mmol) obtained in Preparation Example 353 were reacted in the same manner as in Example 617 to obtain the title compound (0.064 g, 57%).

¹H-NMR (CDCl₃) δ 7.90 (2H, m), 6.88 (1H, s), 4.47 (2H, t), 3.40 (2H, m), 3.16 (2H, m), 2.37 (2H, d), 2.04 (1H, m), 1.85 (4H, m), 1.47 (2H, m), 1.06 (3H, t).

Example 619: (1-{2,6-difluoro-4-[4-(4-fluoro-phenoxy)-6-trifluoromethyl-pyrimidin-2-yl]-phenyl}-piperidin-4-yl)-acetic acid

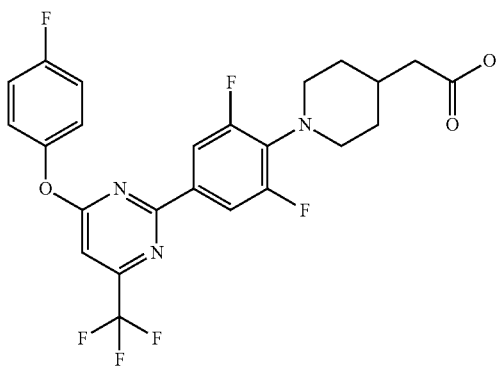 [SMILES: O=C(O)CC1CCN(c2c(F)cc(-c3nc(Oc4ccc(F)cc4)cc(C(F)(F)F)n3)cc2F)CC1]

2-[1-[2,6-Difluoro-4-(4,4,5,5-tetramethyl-1,3,2-dioxaborolan-2-yl)phenyl]-4-piperidyl]acetic acid ethyl ester (0.1 g, 0.24 mmol) obtained in Preparation Example 220 and 2-chloro-4-(4-fluoro-phenoxy)-6-trifluoromethyl-pyrimidine (0.086 g, 0.29 mmol) obtained in Preparation Example 354 were reacted in the same manner as in Example 617 to obtain the title compound (0.039 g, 31%).

¹H-NMR (CDCl₃) δ 7.71 (2H, m), 7.17 (4H, d), 7.04 (1H, s), 3.38 (2H, m), 3.13 (2H, m), 2.35 (2H, d), 1.96 (1H, m), 1.79 (2H, m), 1.45 (2H, m).

Example 620: 3-{1-[2,6-difluoro-4-(6-propoxy-pyridin-2-yl)-phenyl]-piperidin-4-yl}-propionic acid

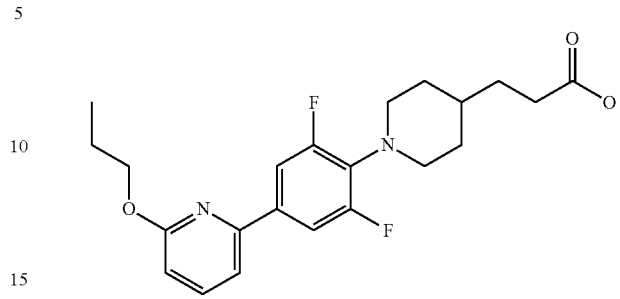

3-[1-[2,6-Difluoro-4-(4,4,5,5-tetramethyl-1,3,2-dioxaborolan-2-yl)phenyl]-4-piperidyl]propanoic acid ethyl ester (0.059 g, 0.14 mmol) obtained in Preparation Example 92 and 2-bromo-6-propoxy-pyridine (0.030 g, 0.14 mmol) obtained in Preparation Example 45 were reacted in the same manner as in Example 96 to obtain the title compound (0.025 g, 45%).

¹H-NMR (CDCl₃) δ 7.59 (1H, t), 7.51 (2H, m), 7.20 (1H, d), 6.66 (1H, d), 4.36 (2H, t), 3.32 (2H, d), 3.12 (2H, t), 2.44 (2H, t), 1.84 (2H, m), 1.76 (2H, d), 1.67 (2H, m), 1.43 (3H, m), 1.06 (3H, t)

Example 621: 3-{1-[4-(6-cyclobutyl-pyridin-2-yl)-2,6-difluoro-phenyl]-piperidin-4-yl}-propionic acid

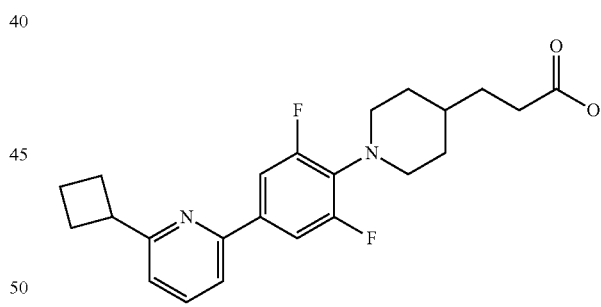

3-[1-[2,6-Difluoro-4-(4,4,5,5-tetramethyl-1,3,2-dioxaborolan-2-yl)phenyl]-4-piperidyl]propanoic acid ethyl ester (0.076 g, 0.18 mmol) obtained in Preparation Example 92 and 2-chloro-6-cyclobutyl-pyridine (0.030 g, 0.18 mmol) obtained in Preparation Example 277 were reacted in the same manner as in Example 96 to obtain the title compound (0.025 g, 35%).

¹H-NMR (CDCl₃) δ 7.63 (1H, t), 7.56 (2H, m), 7.42 (1H, d), 7.08 (1H, d), 3.71 (1H, m), 3.32 (2H, d), 3.12 (2H, t), 2.43 (6H, m), 2.07 (1H, m), 1.94 (1H, m), 1.76-1.40 (7H, m)

Example 622: 3-{1-[4-(6-ethoxy-pyridin-2-yl)-2,6-difluoro-phenyl]-piperidin-4-yl}-propionic acid

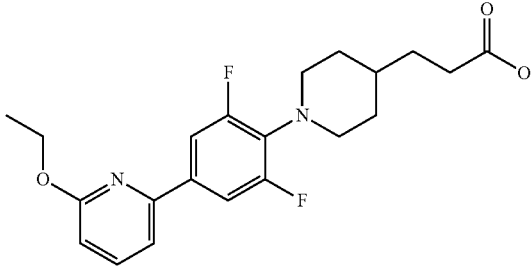 [SMILES: CCOc1cccc(-c2cc(F)c(N3CCC(CCC(=O)O)CC3)c(F)c2)n1]

3-[1-[2,6-Difluoro-4-(4,4,5,5-tetramethyl-1,3,2-dioxaborolan-2-yl)phenyl]-4-piperidyl]propanoic acid ethyl ester (0.081 g, 0.19 mmol) obtained in Preparation Example 92 and 2-chloro-6-ethoxy-pyridine (0.030 g, 0.19 mmol) obtained in Preparation Example 273 were reacted in the same manner as in Example 96 to obtain the title compound (0.030 g, 40%).

$^1$H-NMR (CDCl$_3$) δ 7.59 (1H, t), 7.51 (2H, m), 7.20 (1H, d), 6.65 (1H, d), 4.46 (2H, m), 3.32 (2H, d), 3.12 (2H, t), 2.44 (2H, t), 1.76 (2H, d), 1.67 (2H, m), 1.44 (6H, m)

Experimental Example: Measurement of Activity of GPR120 Agonist (Cell-Based Assay)

CHO-K1 cells expressing Ga16 and hGPR120 were dispensed into each well of a 96-well plate (3×10$^4$ cells/100 μl/well) and then incubated in 5% CO$_2$, 37° C. incubator for 18 hours. Each well was treated with 100 μl of Calcium 5 dye (Molecular Devices) solution including 2% DMSO and then incubated in 5% CO$_2$, 37° C. incubator for 1 hour. Serially diluted GPR120 agonists were prepared to a final concentration of 0.5% DMSO in a 96-well plate. Each well was treated with 50 μl of the agonist compounds using Plexstation II, and then fluorescence was measured at Ex 485 nm and Em 525 nm.

Fluorescence increased by the serially diluted GPR120 agonists is calculated as a relative percent (%) value based on the fluorescence represented by the treatment of 1% DMSO only. EC$_{50}$ refers to the concentration of agonist which shows 50% of maximum fluorescence increased by the treatment of agonist. The calculation of measurement was carried out by using statistical software (Prizm).

The agonistic effects of the Example compounds obtained by the above experiment are shown in the following Table 1 with EC$_{50}$ unit (μM). Activity is denoted based on the following criteria:

A=>20 μM, B=20-2 μM, C=2-0.2 μM, D=<0.2 μM

As shown in the table, most of the novel compounds according to the present invention have superior GPR120 agonistic effects (EC$_{50}$), less than 0.2 μM.

TABLE 1

| Example | EC$_{50}$ |
|---|---|
| 1 | C |
| 2 | C |
| 3 | C |
| 4 | B |
| 5 | C |
| 7 | D |

TABLE 1-continued

| Example | EC$_{50}$ |
|---|---|
| 8 | D |
| 9 | D |
| 10 | D |
| 11 | C |
| 12 | C |
| 17 | B |
| 18 | D |
| 19 | D |
| 20 | D |
| 21 | D |
| 22 | D |
| 23 | D |
| 25 | C |
| 26 | C |
| 27 | D |
| 28 | D |
| 29 | D |
| 31 | D |
| 32 | D |
| 33 | D |
| 34 | D |
| 35 | D |
| 36 | D |
| 37 | D |
| 38 | C |
| 39 | D |
| 40 | D |
| 41 | D |
| 42 | D |
| 43 | D |
| 46 | D |
| 47 | D |
| 48 | D |
| 49 | D |
| 50 | D |
| 51 | D |
| 52 | D |
| 53 | D |
| 54 | D |
| 55 | D |
| 56 | D |
| 59 | D |
| 60 | D |
| 61 | D |
| 63 | B |
| 64 | B |
| 65 | D |
| 66 | D |
| 67 | D |
| 68 | D |
| 69 | D |
| 70 | D |
| 71 | D |
| 72 | D |
| 73 | D |
| 74 | D |
| 76 | D |
| 77 | D |
| 78 | D |
| 79 | B |
| 81 | D |
| 83 | D |
| 84 | D |
| 86 | D |
| 87 | D |
| 88 | D |
| 89 | D |
| 90 | C |
| 93 | B |
| 94 | D |
| 95 | C |
| 96 | C |
| 97 | D |
| 98 | D |
| 99 | D |
| 100 | D |
| 101 | D |
| 102 | D |

TABLE 1-continued

| Example | EC$_{50}$ |
|---------|-----------|
| 103 | C |
| 104 | D |
| 105 | D |
| 106 | D |
| 108 | B |
| 109 | D |
| 110 | C |
| 111 | B |
| 112 | D |
| 113 | D |
| 114 | D |
| 115 | D |
| 116 | D |
| 117 | D |
| 118 | C |
| 119 | C |
| 120 | C |
| 121 | D |
| 122 | B |
| 123 | C |
| 124 | D |
| 125 | D |
| 126 | D |
| 128 | D |
| 131 | B |
| 132 | D |
| 133 | C |
| 134 | D |
| 135 | D |
| 136 | D |
| 137 | D |
| 138 | C |
| 139 | C |
| 140 | C |
| 141 | D |
| 142 | C |
| 143 | B |
| 144 | D |
| 146 | C |
| 147 | D |
| 148 | C |
| 149 | D |
| 150 | D |
| 151 | B |
| 152 | C |
| 153 | D |
| 154 | D |
| 155 | D |
| 156 | C |
| 157 | D |
| 158 | C |
| 159 | D |
| 160 | D |
| 161 | C |
| 162 | C |
| 163 | C |
| 164 | C |
| 165 | D |
| 166 | D |
| 167 | C |
| 168 | D |
| 169 | C |
| 170 | D |
| 171 | D |
| 172 | B |
| 173 | B |
| 174 | C |
| 175 | D |
| 176 | D |
| 177 | D |
| 178 | D |
| 179 | D |
| 180 | D |
| 181 | D |
| 182 | D |
| 183 | D |
| 184 | D |
| 185 | D |

TABLE 1-continued

| Example | EC$_{50}$ |
|---------|-----------|
| 186 | D |
| 187 | C |
| 188 | D |
| 189 | D |
| 190 | C |
| 191 | D |
| 192 | D |
| 193 | D |
| 194 | D |
| 195 | D |
| 196 | D |
| 197 | D |
| 198 | D |
| 199 | D |
| 200 | C |
| 201 | C |
| 202 | D |
| 203 | D |
| 204 | D |
| 205 | D |
| 206 | D |
| 207 | D |
| 208 | D |
| 209 | D |
| 210 | D |
| 211 | C |
| 212 | D |
| 213 | D |
| 214 | C |
| 215 | D |
| 216 | D |
| 217 | D |
| 218 | D |
| 219 | B |
| 221 | D |
| 222 | C |
| 223 | D |
| 224 | C |
| 225 | C |
| 226 | C |
| 227 | D |
| 228 | D |
| 229 | D |
| 230 | D |
| 231 | D |
| 232 | C |
| 233 | C |
| 234 | D |
| 235 | D |
| 236 | D |
| 237 | D |
| 238 | D |
| 239 | D |
| 240 | C |
| 241 | D |
| 244 | D |
| 245 | D |
| 246 | D |
| 247 | D |
| 248 | D |
| 249 | D |
| 250 | D |
| 251 | D |
| 252 | D |
| 253 | C |
| 254 | C |
| 255 | D |
| 256 | C |
| 257 | D |
| 258 | D |
| 259 | D |
| 260 | D |
| 261 | D |
| 262 | D |
| 263 | D |
| 264 | C |
| 265 | C |
| 266 | C |

TABLE 1-continued

| Example | EC$_{50}$ |
|---|---|
| 268 | C |
| 269 | C |
| 270 | D |
| 271 | D |
| 272 | D |
| 273 | B |
| 274 | C |
| 275 | D |
| 276 | C |
| 277 | C |
| 278 | D |
| 279 | D |
| 280 | D |
| 281 | D |
| 282 | C |
| 283 | C |
| 284 | C |
| 285 | B |
| 286 | D |
| 287 | D |
| 288 | D |
| 289 | C |
| 290 | D |
| 291 | D |
| 292 | B |
| 293 | C |
| 294 | D |
| 295 | D |
| 296 | D |
| 297 | C |
| 298 | C |
| 299 | C |
| 300 | C |
| 301 | C |
| 302 | C |
| 303 | C |
| 304 | C |
| 305 | C |
| 306 | C |
| 307 | C |
| 308 | C |
| 309 | C |
| 310 | B |
| 311 | C |
| 312 | C |
| 313 | A |
| 314 | C |
| 315 | C |
| 316 | C |
| 317 | C |
| 318 | B |
| 319 | C |
| 320 | C |
| 321 | D |
| 322 | D |
| 323 | C |
| 324 | C |
| 325 | C |
| 326 | C |
| 327 | C |
| 328 | C |
| 329 | D |
| 330 | D |
| 331 | C |
| 332 | D |
| 333 | D |
| 334 | D |
| 335 | D |
| 336 | D |
| 337 | D |
| 338 | D |
| 339 | D |
| 340 | C |
| 341 | D |
| 342 | D |
| 343 | D |
| 344 | D |
| 345 | D |

TABLE 1-continued

| Example | EC$_{50}$ |
|---|---|
| 346 | D |
| 347 | D |
| 348 | D |
| 349 | D |
| 350 | C |
| 351 | D |
| 352 | C |
| 353 | B |
| 354 | C |
| 355 | B |
| 356 | C |
| 357 | C |
| 358 | C |
| 360 | C |
| 361 | C |
| 363 | D |
| 364 | C |
| 365 | C |
| 366 | C |
| 367 | C |
| 368 | C |
| 369 | D |
| 370 | C |
| 371 | D |
| 372 | D |
| 373 | C |
| 374 | D |
| 375 | C |
| 376 | C |
| 377 | D |
| 379 | D |
| 380 | C |
| 382 | A |
| 384 | B |
| 385 | D |
| 386 | D |
| 387 | D |
| 388 | C |
| 389 | D |
| 390 | A |
| 391 | D |
| 392 | D |
| 393 | D |
| 394 | D |
| 395 | D |
| 396 | D |
| 397 | D |
| 398 | D |
| 399 | D |
| 400 | D |
| 401 | D |
| 402 | D |
| 403 | D |
| 404 | D |
| 405 | D |
| 406 | D |
| 407 | D |
| 408 | D |
| 409 | D |
| 410 | D |
| 411 | D |
| 412 | D |
| 413 | D |
| 414 | D |
| 415 | D |
| 416 | C |
| 417 | D |
| 418 | D |
| 419 | D |
| 420 | D |
| 421 | D |
| 422 | D |
| 423 | D |
| 424 | D |
| 425 | D |
| 426 | D |
| 427 | D |
| 428 | D |

TABLE 1-continued

| Example | EC$_{50}$ |
|---|---|
| 429 | D |
| 430 | D |
| 431 | D |
| 432 | D |
| 433 | D |
| 434 | D |
| 435 | D |
| 436 | D |
| 437 | D |
| 438 | D |
| 439 | C |
| 440 | C |
| 441 | D |
| 442 | C |
| 443 | C |
| 444 | D |
| 445 | D |
| 446 | C |
| 447 | D |
| 448 | D |
| 449 | D |
| 450 | D |
| 451 | D |
| 452 | D |
| 453 | C |
| 454 | D |
| 455 | D |
| 456 | D |
| 457 | C |
| 458 | C |
| 459 | D |
| 460 | C |
| 461 | C |
| 462 | C |
| 463 | D |
| 464 | D |
| 465 | D |
| 466 | D |
| 467 | C |
| 468 | D |
| 469 | B |
| 470 | C |
| 471 | D |
| 472 | D |
| 473 | C |
| 474 | D |
| 475 | D |
| 476 | D |
| 477 | C |
| 478 | C |
| 479 | D |
| 480 | B |
| 481 | B |
| 482 | D |
| 483 | D |
| 484 | D |
| 485 | D |
| 486 | D |
| 487 | C |
| 488 | D |
| 489 | D |
| 490 | D |
| 491 | D |
| 492 | D |
| 493 | D |
| 494 | C |
| 495 | D |
| 496 | C |
| 497 | C |
| 498 | D |
| 499 | D |
| 500 | D |
| 501 | D |
| 502 | C |
| 503 | C |
| 504 | C |
| 505 | C |
| 506 | C |

TABLE 1-continued

| Example | EC$_{50}$ |
|---|---|
| 507 | C |
| 508 | D |
| 509 | C |
| 510 | D |
| 511 | D |
| 512 | C |
| 513 | D |
| 514 | C |
| 515 | C |
| 516 | D |
| 517 | D |
| 518 | D |
| 519 | C |
| 520 | C |
| 521 | D |
| 522 | D |
| 523 | D |
| 524 | D |
| 525 | D |
| 526 | D |
| 527 | D |
| 528 | D |
| 529 | C |
| 530 | D |
| 531 | C |
| 532 | D |
| 533 | C |
| 534 | C |
| 535 | D |
| 536 | D |
| 537 | D |
| 538 | D |
| 539 | C |
| 540 | D |
| 541 | D |
| 542 | D |
| 543 | D |
| 544 | D |
| 545 | C |
| 546 | C |
| 547 | C |
| 548 | D |
| 549 | D |
| 550 | D |
| 551 | C |
| 552 | C |
| 553 | C |
| 554 | D |
| 555 | D |
| 556 | D |
| 557 | B |
| 558 | D |
| 559 | D |
| 560 | D |
| 561 | D |
| 562 | B |
| 563 | D |
| 564 | C |
| 565 | D |
| 566 | D |
| 567 | C |
| 568 | B |
| 569 | B |
| 570 | C |
| 571 | D |
| 572 | D |
| 573 | D |
| 574 | D |
| 575 | C |
| 576 | D |
| 577 | C |
| 578 | D |
| 579 | D |
| 580 | D |
| 581 | D |
| 582 | C |
| 583 | C |
| 584 | C |

TABLE 1-continued

| Example | EC50 |
|---|---|
| 585 | D |
| 586 | D |
| 587 | C |
| 588 | C |
| 589 | D |
| 590 | D |
| 591 | D |
| 592 | C |
| 593 | C |
| 594 | C |
| 595 | C |
| 596 | C |
| 597 | C |
| 598 | D |
| 599 | C |
| 600 | C |
| 601 | C |
| 602 | C |
| 603 | C |
| 604 | D |
| 605 | C |
| 606 | C |
| 607 | D |
| 608 | C |
| 609 | C |
| 610 | C |
| 611 | C |
| 612 | B |
| 613 | B |
| 614 | B |
| 615 | B |
| 616 | C |
| 617 | A |
| 618 | B |
| 619 | B |
| 620 | C |
| 621 | C |
| 622 | C |

The invention claimed is:

1. A compound selected from the group consisting of:
2-[1-[4-[4-(cyclobutoxy)-6-methyl-pyrimidin-2-yl]-2,6-difluoro-phenyl]-4-piperidyl]acetic acid,
2-[1-[4-[2-(cyclobutoxy)-6-methyl-pyrimidin-4-yl]-2,6-difluoro-phenyl]-4-piperidyl]acetic acid,
2-[1-[4-[4-(cyclobutoxy)-6-methyl-pyrimidin-2-yl]-2,6-difluoro-phenyl]azetidin-3-yl]acetic acid,
2-[1-[4-[6-(cyclobutoxy)pyrazin-2-yl]-2,6-difluoro-phenyl]-4-piperidyl]acetic acid,
2-[1-[4-[4-(cyclobutoxy)pyrimidin-2-yl]-2,6-difluoro-phenyl]-4-piperidyl]acetic acid,
2-[1-[4-[4-(cyclopropylmethoxy)-6-methyl-pyrimidin-2-yl]-2,6-difluoro-phenyl]-4-piperidyl]acetic acid,
2-[1-[4-[4-(cyclopropylmethoxy)pyrimidin-2-yl]-2,6-difluoro-phenyl]-4-piperidyl]acetic acid,
2-[1-[4-[6-(cyclopropylmethoxy)pyrazin-2-yl]-2,6-difluoro-phenyl]-4-piperidyl]acetic acid,
2-[1-[4-[6-(cyclobutoxy)pyrazin-2-yl]-2,6-difluoro-phenyl]azetidin-3-yl]acetic acid,
2-[1-[4-[6-(cyclopropylmethoxy)pyrazin-2-yl]-2,6-difluoro-phenyl]azetidin-3-yl]acetic acid,
2-[1-[4-[4-(cyclobutoxy)pyrimidin-2-yl]-2,6-difluoro-phenyl]azetidin-3-yl]acetic acid,
2-[1-[4-[4-(cyclopropylmethoxy)pyrimidin-2-yl]-2,6-difluoro-phenyl]azetidin-3-yl]acetic acid,
2-[1-[4-(6-ethoxypyrazin-2-yl)-2,6-difluoro-phenyl]-4-piperidyl]acetic acid,
2-[1-[2,6-difluoro-4-(6-isopropoxypyrazin-2-yl)phenyl]-4-piperidyl]acetic acid,
2-[1-[2,6-difluoro-4-(6-methoxypyrazin-2-yl)phenyl]-4-piperidyl]acetic acid,
2-[1-[2,6-difluoro-4-(6-propoxypyrazin-2-yl)phenyl]-4-piperidyl]acetic acid,
2-[1-[2,6-difluoro-4-(6-isobutoxypyrazin-2-yl)phenyl]-4-piperidyl]acetic acid,
2-[1-[4-(6-butoxypyrazin-2-yl)-2,6-difluoro-phenyl]-4-piperidyl]acetic acid,
2-[1-[4-[6-(cyclopentoxy)pyrazin-2-yl]-2,6-difluoro-phenyl]-4-piperidyl]acetic acid,
2-[1-[4-(4-ethoxypyrimidin-2-yl)-2,6-difluoro-phenyl]-4-piperidyl]acetic acid,
2-[1-[2,6-difluoro-4-(4-isopropoxypyrimidin-2-yl)phenyl]-4-piperidyl]acetic acid,
2-[1-[2,6-difluoro-4-(4-propoxypyrimidin-2-yl)phenyl]-4-piperidyl]acetic acid,
2-[1-[2,6-difluoro-4-(4-isobutoxypyrimidin-2-yl)phenyl]-4-piperidyl]acetic acid,
2-[1-[4-(4-ethoxy-6-methyl-pyrimidin-2-yl)-2,6-difluoro-phenyl]-4-piperidyl]acetic acid,
2-[1-[2,6-difluoro-4-(4-isopropoxy-6-methyl-pyrimidin-2-yl)phenyl]-4-piperidyl]acetic acid,
2-[1-[2,6-difluoro-4-(4-methyl-6-propoxy-pyrimidin-2-yl)phenyl]-4-piperidyl]acetic acid,
2-[1-[2,6-difluoro-4-(4-isobutoxy-6-methyl-pyrimidin-2-yl)phenyl]-4-piperidyl]acetic acid,
2-[1-[2,6-difluoro-4-(6-pyrrolidin-1-ylpyrazin-2-yl)phenyl]-4-piperidyl]acetic acid,
2-[1-[2,6-difluoro-4-[6-(isopropylamino)pyrazin-2-yl]phenyl]-4-piperidyl]acetic acid,
2-[1-[4-[6-(diethylamino)pyrazin-2-yl]-2,6-difluoro-phenyl]-4-piperidyl]acetic acid,
2-[1-[2,6-difluoro-4-[6-(isobutylamino)pyrazin-2-yl]phenyl]-4-piperidyl]acetic acid,
2-[1-[4-[6-(cyclopentylamino)pyrazin-2-yl]-2,6-difluoro-phenyl]-4-piperidyl]acetic acid,
2-[1-[4-[6-(dimethylamino)pyrazin-2-yl]-2,6-difluoro-phenyl]-4-piperidyl]acetic acid,
2-[1-[2,6-difluoro-4-[4-(isobutylamino)pyrimidin-2-yl]phenyl]-4-piperidyl]acetic acid,
2-[1-[4-[6-(cyclobutoxy)-5-methyl-pyrazin-2-yl]-2,6-difluoro-phenyl]-4-piperidyl]acetic acid,
2-[1-[2,6-difluoro-4-(6-phenylpyrazin-2-yl)phenyl]-4-piperidyl]acetic acid,
2-[1-[4-(6-cyclopentylpyrazin-2-yl)-2,6-difluoro-phenyl]-4-piperidyl]acetic acid,
2-[1-[2,6-difluoro-4-(6-isobutylpyrazin-2-yl)phenyl]-4-piperidyl]acetic acid,
2-[1-[2,6-difluoro-4-(4-isobutylpyrimidin-2-yl)phenyl]-4-piperidyl]acetic acid,
2-[1-[4-(6-butylpyrazin-2-yl)-2,6-difluoro-phenyl]-4-piperidyl]acetic acid,
2-[1-[2,6-difluoro-4-(6-isopentylpyrazin-2-yl)phenyl]-4-piperidyl]acetic acid,
2-[1-[4-[4-(cyclobutoxy)-5-fluoro-pyrimidin-2-yl]-2,6-difluoro-phenyl]-4-piperidyl]acetic acid,
2-[1-[4-[4-(cyclopropylmethoxy)-5-fluoro-pyrimidin-2-yl]-2,6-difluoro-phenyl]-4-piperidyl]acetic acid,
2-[1-[4-(6-cyclobutylpyrazin-2-yl)-2,6-difluoro-phenyl]-4-piperidyl]acetic acid,
2-[1-[4-[4-(cyclobutoxy)-6,7-dihydro-5H-cyclopenta[d]pyrimidin-2-yl]-2,6-difluoro-phenyl]-4-piperidyl]acetic acid,
2-[1-[4-[4-(cyclobutoxy)-5,6-dimethyl-pyrimidin-2-yl]-2,6-difluoro-phenyl]-4-piperidyl]acetic acid,
4-[2-chloro-4-[4-(cyclobutoxy)-6-methyl-pyrimidin-2-yl]-6-fluoro-phenoxy]butanoic acid, 4-[2-chloro-4-[2-(cyclobutoxy)-6-methyl-pyrimidin-4-yl]-6-fluoro-phenoxy]butanoic acid,
4-[2-chloro-4-[4-(cyclopropylmethoxy)-6-methyl-pyrimidin-2-yl]-6-fluoro-phenoxy]butanoic acid,
4-[4-[6-(cyclobutoxy)pyrazin-2-yl]-2,6-difluoro-phenoxy]butanoic acid,
5-[4-[6-(cyclobutoxy)pyrazin-2-yl]-2,6-difluoro-phenyl]hexanoic acid,
5-[4-(2-cyclobutoxy-6-methyl-pyrimidin-4-yl)-2,6-difluoro-phenyl]-hexanoic acid,
5-[4-(4-cyclobutoxy-6-methyl-pyrimidin-2-yl)-2,6-difluoro-phenyl]-hexanoic acid,
4-[4-(4-cyclobutoxy-pyrimidin-2-yl)-2,6-difluoro-phenoxy]-butyric acid,
4-[4-(2-cyclobutoxy-pyrimidin-4-yl)-2,6-difluoro-phenoxy]-butyric acid,
4-[2-chloro-4-(4-cyclobutoxy-pyrimidin-2-yl)-6-fluoro-phenoxy]-butyric acid,
4-[2-chloro-4-(2-cyclobutoxy-pyrimidin-4-yl)-6-fluoro-phenoxy]-butyric acid,
4-[4-(4-cyclobutoxy-6-methyl-pyrimidin-2-yl)-2,6-difluoro-phenoxy]-butyric acid,
4-[2-chloro-4-(4-cyclopropylmethoxy-pyrimidin-2-yl)-6-fluoro-phenoxy]-butyric acid,
4-[2-chloro-4-(6-cyclobutoxy-pyrazin-2-yl)-6-fluoro-phenoxy]-butyric acid,
4-[2-chloro-4-(6-cyclopropylmethoxy-pyrazin-2-yl)-6-fluoro-phenoxy]-butyric acid,
4-[4-(4-cyclopropylmethoxy-6-methyl-pyrimidin-2-yl)-2,6-difluoro-phenoxy]-butyric acid,
4-[4-(4-cyclopropylmethoxy-pyrimidin-2-yl)-2,6-difluoro-phenoxy]-butyric acid,
4-[4-(6-cyclopropylmethoxy-pyrazin-2-yl)-2,6-difluoro-phenoxy]-butyric acid,
4-[2-chloro-6-fluoro-4-(6-isopropoxy-pyrazin-2-yl)-phenoxy]-butyric acid,
4-[2-chloro-4-(6-ethoxy-pyrazin-2-yl)-6-fluoro-phenoxy]-butyric acid,
4-[4-[4-(cyclobutoxy)-6-methyl-pyrimidin-2-yl]-2,6-difluoro-N-methyl-anilino]butanoic acid,
4-[4-[4-(cyclobutoxy)pyrimidin-2-yl]-2,6-difluoro-N-methyl-anilino]butanoic acid,
4-[4-[6-(cyclobutoxy)pyrazin-2-yl]-2,6-difluoro-N-methyl-anilino]butanoic acid,
4-[4-[4-(cyclopropylmethoxy)-6-methyl-pyrimidin-2-yl]-2,6-difluoro-N-methyl-anilino]butanoic acid,
4-[4-[4-(cyclopropylmethoxy)pyrimidin-2-yl]-2,6-difluoro-N-methyl-anilino]butanoic acid,
4-[4-[6-(cyclopropylmethoxy)pyrazin-2-yl]-2,6-difluoro-N-methyl-anilino]butanoic acid,
2-{1-[2,6-difluoro-4-(6-propoxy-pyrazin-2-yl)phenyl]pyrrolidin-3-yl}acetic acid,
2-{1-[2,6-difluoro-4-(6-isobutoxy-pyrazin-2-yl)phenyl]pyrrolidin-3-yl}acetic acid,
2-{1-[2,6-difluoro-4-(6-cyclopentoxy-pyrazin-2-yl)phenyl]pyrrolidin-3-yl}acetic acid,
2-{1-[2,6-difluoro-4-(6-butoxy-pyrazin-2-yl)phenyl]pyrrolidin-3-yl}acetic acid,
2-{1-[2,6-difluoro-4-(4-propoxy-pyrimidin-2-yl)phenyl]pyrrolidin-3-yl}acetic acid,
2-{1-[2,6-difluoro-4-(4-isopropoxy-pyrimidin-2-yl)phenyl]pyrrolidin-3-yl}acetic acid,
2-{1-[2,6-difluoro-4-(4-ethoxy-pyrimidin-2-yl)phenyl]pyrrolidin-3-yl}acetic acid,
2-{1-[2,6-difluoro-4-(4-isobutoxy-pyrimidin-2-yl)phenyl]pyrrolidin-3-yl}acetic acid,
2-{1-[2,6-difluoro-4-(6-isobutylamino-pyrazin-2-yl)phenyl]pyrrolidin-3-yl}acetic acid,
2-{1-[2,6-difluoro-4-(6-cyclopentylamino-pyrazin-2-yl)phenyl]pyrrolidin-3-yl}acetic acid,
2-{1-[2,6-difluoro-4-(6-isopropylamino-pyrazin-2-yl)phenyl]pyrrolidin-3-yl}acetic acid,
2-{1-[2,6-difluoro-4-(6-diethylamino-pyrazin-2-yl)phenyl]pyrrolidin-3-yl}acetic acid,
3-[6-(6-cyclobutoxy-pyrazin-2-yl)-thiochroman-2-yl]-propionic acid,
2-[1-[4-[4-(chlorophenoxy)pyrimidin-2-yl]-2,6-difluoro-phenyl]-4-piperidyl]acetic acid,
2-[1-[4-[4-(chlorophenoxy)pyrimidin-2-yl]-2,6-difluoro-phenyl]-pyrrolidin-3-yl]acetic acid,
2-[1-[4-[4-phenoxy-pyrimidin-2-yl]-2,6-difluoro-phenyl]-4-piperidyl]acetic acid,
2-[1-[4-[4-(4-fluorophenoxy)pyrimidin-2-yl]-2,6-difluoro-phenyl]-4-piperidyl]acetic acid,
2-[1-[4-[4-(4-pyridin-3-yloxy-pyrimidin-2-yl]-2,6-difluoro-phenyl]-4-piperidyl]acetic acid,
2-[1-[2,6-difluoro-4-[6-(4-fluorophenoxy)pyrazin-2-yl]phenyl]-4-piperidyl]acetic acid,
2-[1-[4-[4-(4-methoxyphenoxy)pyrimidin-2-yl]-2,6-difluoro-phenyl]-4-piperidyl]acetic acid,
2-[1-[2,6-difluoro-4-[4-(4-fluorophenoxy)-6-methyl-pyrimidin-2-yl]phenyl]-4-piperidyl]acetic acid,
2-[1-[4-[4-(p-tolyloxy)pyrimidin-2-yl]-2,6-difluoro-phenyl]-4-piperidyl]acetic acid,
2-[1-[4-[4-(3,4-difluorophenoxy)pyrimidin-2-yl]-2,6-difluoro-phenyl]-4-piperidyl]acetic acid,
2-[4-(4-cyclobutoxy-6-methyl-pyrimidin-2-yl)-2,6-difluoro-phenoxymethyl]-cyclopropane carboxylic acid,
2-[4-(4-cyclobutoxy-pyrimidin-2-yl)-2,6-difluoro-phenoxymethyl]-cyclopropane carboxylic acid,
2-[4-(4-cyclopropylmethoxy-pyrimidin-2-yl)-2,6-difluoro-phenoxymethyl]-cyclopropane carboxylic acid,
2-[4-(4-cyclopropylmethoxy-6-methyl-pyrimidin-2-yl)-2,6-difluoro-phenoxymethyl]-cyclopropane carboxylic acid,
2-[4-(6-cyclopropylmethoxy-pyrazin-2-yl)-2,6-difluoro-phenoxymethyl]-cyclopropane carboxylic acid,
2-[4-(6-cyclobutoxy-pyrazin-2-yl)-2,6-difluoro-phenoxymethyl]-cyclopropane carboxylic acid,
2-[2-chloro-4-(4-cyclobutoxy-6-methyl-pyrimidin-2-yl)-6-fluoro-phenoxymethyl]-cyclopropane carboxylic acid,
{1-[4-(4-cyclobutoxy-6-methyl-pyrimidin-2-yl)-2,6-difluoro-phenyl]-pyrrolidin-3-yl}-acetic acid,
{1-[4-(4-cyclopropylmethoxy-6-methyl-pyrimidin-2-yl)-2,6-difluoro-phenyl]-pyrrolidin-3-yl}-acetic acid,
{1-[4-(6-cyclobutoxy-pyrazin-2-yl)-2,6-difluoro-phenyl]-pyrrolidin-3-yll}-acetic acid,
{1-[4-(4-cyclobutoxy-pyrimidin-2-yl)-2,6-difluoro-phenyl]-pyrrolidin-3-yl}-acetic acid,
{1-[4-(6-cyclopropylmethoxy-pyrazin-2-yl)-2,6-difluoro-phenyl]-pyrrolidin-3-yl}-acetic acid,
{1-[4-(4-cyclopropylmethoxy-pyrimidin-2-yl)-2,6-difluoro-phenyl]-pyrrolidin-3-yl}-acetic acid,
{1-[2,6-difluoro-4-(6-methoxy-pyrazin-2-yl)-phenyl]-pyrrolidin-3-yl}-acetic acid,
{1-[4-(6-ethoxy-pyrazin-2-yl)-2,6-difluoro-phenyl]-pyrrolidin-3-yl}-acetic acid,
{1-[2,6-difluoro-4-(6-isopropoxy-pyrazin-2-yl)-phenyl]-pyrrolidin-3-yl}-acetic acid,
{1-[2,6-difluoro-4-(4-isopropoxy-6-methyl-pyrimidin-2-yl)-phenyl]-pyrrolidin-3-yl]-acetic acid, {1-[2,6-difluoro-4-(4-isobutoxy-6-methyl-pyrimidin-2-yl)-phenyl]-pyrrolidin-3-yl}-acetic acid,
{1-[2,6-difluoro-4-(4-methyl-6-propoxy-pyrimidin-2-yl)-phenyl]-pyrrolidin-3-yl}-acetic acid,
{1-[4-(4-ethoxy-6-methyl-pyrimidin-2-yl)-2,6-difluoro-phenyl]-pyrrolidin-3-yl}-acetic acid,
{1-[4-(4-cyclobutoxy-5-fluoro-pyrimidin-2-yl)-2,6-difluoro-phenyl]-pyrrolidin-3-yl}-acetic acid,
{1-[4-(4-cyclopropylmethoxy-5-fluoro-pyrimidin-2-yl)-2,6-difluoro-phenyl]-pyrrolidin-3-yl}-acetic acid,
{1-[2,6-difluoro-4-(5-fluoro-4-isobutoxy-pyrimidin-2-yl)-phenyl]-piperidin-4-yl}-acetic acid,
{1-[2,6-difluoro-4-(5-fluoro-4-propoxy-pyrimidin-2-yl)-phenyl]-piperidin-4-yl}-acetic acid,
(1-{2,6-difluoro-4-[4-(3-methyl-butoxy)-pyrimidin-2-yl]-phenyl}-piperidin-4-yl)-acetic acid,
(1-{2,6-difluoro-4-[4-(3-methoxy-propoxy)-pyrimidin-2-yl]-phenyl}-piperidin-4-yl)-acetic acid,
(1-{2,6-difluoro-4-[4-(3-methoxy-propoxy)-6-methyl-pyrimidin-2-yl]-phenyl}-piperidin-4-yl)-acetic acid,
(1-{2,6-difluoro-4-[4-(2-methoxy-ethoxy)-6-methyl-pyrimidin-2-yl]-phenyl}-piperidin-4-yl)-acetic acid,
2-[1-[2,6-difluoro-4-[4-[(6-methyl-3-pyridyl)oxy]pyrimidin-2-yl]phenyl]-4-piperidyl]acetic acid,
2-[1-[2,6-difluoro-4-[6-(4-ethylphenoxy)pyrimidin-2-yl]phenyl]-4-piperidyl]acetic acid,
2-[1-[4-[4-(3-fluorophenoxy)pyrimidin-2-yl]-2,6-difluoro-phenyl]-4-piperidyl]acetic acid,
2-[1-[2,6-difluoro-4-[4-(3,4-fluorophenoxy)-6-methyl-pyrimidin-2-yl]phenyl]-4-piperidyl]acetic acid,
2-[1-[2,6-difluoro-4-[4-(2-pyridyloxy)pyrimidin-2-yl]phenyl]-4-piperidyl]acetic acid,
2-[1-[2,6-difluoro-4-[4-[4-(trifluoromethyl)phenoxy]pyrimidin-2-yl]phenyl]-4-piperidyl]acetic acid,
2-[1-[2,6-difluoro-4-[4-[3-(trifluoromethyl)phenoxy]pyrimidin-2-yl]phenyl]-4-piperidyl]acetic acid,
2-[1-[2,6-difluoro-4-[4-methyl-6-[4-(trifluoromethyl)phenoxy]pyrimidin-2-yl]phenyl]-4-piperidyl]acetic acid,
2-[1-[2,6-difluoro-4-[4-methyl-6-[3-(trifluoromethyl)phenoxy]pyrimidin-2-yl]phenyl]-4-piperidyl]acetic acid,
{1-[4-(4-cyclobutoxy-6-trifluoromethyl-pyrimidin-2-yl)-2,6-difluoro-phenyl]-piperidin-4-yl}-acetic acid,
{1-[2,6-difluoro-4-(4-propoxy-6-trifluoromethyl-pyrimidin-2-yl)-phenyl]-piperidin-4-yl}-acetic acid, and
(1-{2,6-difluoro-4-[4-(4-fluoro-phenoxy)-6-trifluoromethyl-pyrimidin-2-yl]-phenyl}-piperidin-4-yl)-acetic acid,
or a pharmaceutically acceptable salt or stereoisomer thereof.

2. A pharmaceutical composition as a GPR120 agonist, comprising the compound, pharmaceutically acceptable salt or stereoisomer thereof as defined in claim 1 as an active ingredient and a pharmaceutically acceptable carrier.

* * * * *